US012679834B2

(12) United States Patent
Bordas et al.

(10) Patent No.: US 12,679,834 B2
(45) Date of Patent: Jul. 14, 2026

(54) BICYCLIC COMPOUNDS AND THEIR USES

(71) Applicant: Novartis AG, Basel (CH)

(72) Inventors: Vincent Bordas, Village-Neuf (FR); Jvan Brun, Muttenz (CH); Markus Furegati, Allschwil (CH); Wanben Gong, Suzhou (CN); Jacques Hamon, Habsheim (FR); Jürgen Hans-Hermann Hinrichs, Schopfheim (DE); Philipp Holzer, Sissach (CH); Fatma Limam, Strasbourg (FR); Henrik Möbitz, Arlesheim (CH); Sandro Nocito, Wölflinswil (CH); Simone Plattner, Weil am Rhein (DE); Niko Schmiedeberg, Riehen (CH); Joseph Schoepfer, Riehen (CH); Ross Sinclair Strang, Hagenthal-le-Bas (FR); Shuping Yao, Suzhou (CN); Huangchao Yu, Suzhou (CN); Frédéric Zecri, Brookline, MA (US); Sisi Zhang, Suzhou (CN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 18/506,164

(22) Filed: Nov. 10, 2023

(65) Prior Publication Data

US 2024/0360118 A1 Oct. 31, 2024

Related U.S. Application Data

(62) Division of application No. 17/824,407, filed on May 25, 2022, now Pat. No. 11,878,973.

(51) Int. Cl.

| | |
|---|---|
| ***C07D 413/14*** | (2006.01) |
| ***C07D 401/14*** | (2006.01) |
| ***C07D 405/14*** | (2006.01) |

(52) U.S. Cl.

CPC ......... *C07D 413/14* (2013.01); *C07D 401/14* (2013.01); *C07D 405/14* (2013.01); *C07B 2200/13* (2013.01)

(58) Field of Classification Search

CPC .. C07D 413/14; C07D 401/14; C07D 405/14; C07D 487/04; C07B 2200/13; A61P 35/00

See application file for complete search history.

(56) References Cited

U.S. PATENT DOCUMENTS

| | | | |
|---|---|---|---|
| 11,878,973 | B2 | 1/2024 | Bordas et al. |
| 2016/0002247 | A1* | 1/2016 | Nagano et al. |
| 2023/0046859 | A1 | 2/2023 | Bordas et al. |

FOREIGN PATENT DOCUMENTS

| | | | |
|---|---|---|---|
| CN | 112409331 | A | 2/2021 |
| CN | 112778311 | A | 5/2021 |

(Continued)

OTHER PUBLICATIONS

Aggarwal, et al., Inhibition of helicase activity by a small molecule impairs Werner syndrome helicase (WRN) function in the cellular response to DNA damage or replication stress, PNAS, Jan. 25, 2011, 1525-1530, 108(4).

(Continued)

*Primary Examiner* — Sarah Pihonak

*Assistant Examiner* — Jackson J Hernandez

(74) *Attorney, Agent, or Firm* — Elizabeth T. Karnas

(57) ABSTRACT

The present invention provides a compound, or a pharmaceutically acceptable salt thereof, of formula (I):

(Continued)

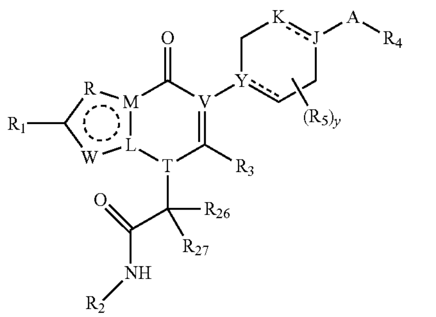

(I)

wherein $R_1$, $R_2$, $R_3$, $R_4$, $R_5$, $R_{26}$, $R_{27}$, y, R, M, W, L, V, T, Y, J, K and A are as described herein, therapeutic uses of said compounds, uses of said compounds as research chemicals, a pharmaceutical composition and combinations comprising said compounds, and methods for manufacturing the compounds of the invention.

16 Claims, 11 Drawing Sheets

Specification includes a Sequence Listing.

(56) References Cited

FOREIGN PATENT DOCUMENTS

| | | | |
|---|---|---|---|
| WO | 2008027990 | A1 | 3/2008 |
| WO | 2008057601 | A2 | 5/2008 |
| WO | 2010093436 | A2 | 8/2010 |
| WO | 2013174931 | A1 | 11/2013 |
| WO | 2017025416 | A1 | 2/2017 |
| WO | 2018229683 | A1 | 12/2018 |
| WO | 2019016772 | A2 | 1/2019 |
| WO | 2019236448 | A1 | 12/2019 |
| WO | 2019241802 | A2 | 12/2019 |
| WO | 2020033413 | A2 | 2/2020 |
| WO | 2020041756 | A1 | 2/2020 |
| WO | 2022008419 | A1 | 1/2022 |
| WO | 2022076403 | A1 | 4/2022 |
| WO | 2022249060 | A1 | 12/2022 |

OTHER PUBLICATIONS

Lizardo, et al., Immunotherapy efficacy on mismatch repair-deficient colorectal cancer: From bench to bedside, BBA—Reviews on Cancer, Oct. 6, 2020, 188447, 1874.

Lorenzi, et al., Epidemiology of Microsatellite Instability High (MSI-H) and Deficient Mismatch Repair (dMMR) in Solid Tumors: A Structured Literature Review, Journal of Oncology, 2020, Article ID 1807929, 2020.

Picco, et al., Werner Helicase Is a Synthetic-Lethal Vulnerability in Mismatch Repair-Deficient Colorectal Cancer Refractory to Targeted Therapies, Chemotherapy, and Immunotherapy, Cancer Discovery, Aug. 2021, 1923-1937, 11(8).

Aguiar, et al., Effect of polymorphism on the absorption of Chloramphenicol from Chloramphenicol Palmitate, Journal of Pharmaceutical Sciences, 56(7), 847-853, 1967.

Akhapkina, et al., Fundamental Principles of the Modulator Concept and Classification of Modulator Drugs, RMZh, 19, 933-951, 2012.

Belikov, Relationship between the chemical structure, properties of compounds and their action on the body, Pharmaceutical Chemistry, chapters 1.1, 1.2, 2.5, 2.6, 2.7, 11, 27-29, 2007.

Byrn, et al., Pharmaceutical Solids: A Strategic Approach to Regulatory Considerations, Pharmaceutical Research, 12(7), 945-954, 1995.

Caira, Crystalline Polymorphism of Organic Compounds, Topics in Current Chemistry, 198, 163-208, 1998.

Chou, Drug Combination Studies and their Synergy Quantification using the Chou-Talalay Method, Cancer Research, 70(2), 440-446, Jan. 15, 2010.

Dyson, et al., Chemistry of Synthetic Drugs, 12-19, 1964.

Einfalt, et al., Methods of amorphization and investigation of the amorphous state, Acta Pharmaceutica, 63, 305-334, 2013.

Gavrilov, Pharmaceutical Engineering. Manufacture of Drugs, 20, 2010.

Kearns, et al., Developmental Pharmacology—Drug Disposition, Action, and Therapy in Infants and Children, The New England Journal of Medicine, 349(12), 1157-1167, Sep. 18, 2003.

Kharkevich, Doses and concentrations, Pharmacology, 10, 72-82, 2010.

Kholodov L.E., Clinical Pharmacokinetics, Medicine, 83-98; 134-138; 160; 378-380, 1985, Moscow.

Knunyants, Chemical Encyclopedia, 167, 1990.

Kuznetsova, High-resolution X-Ray Analysis, Irkutsk State University, 2005.

Pokrovsky, Antitumor Agents, Small Medical Encyclopedia, 5, 90-96, 1996.

Sergeev, A concise course in molecular biology, 10, 1975.

Smith, et al., Organic synthesis, Science and Art, 64, 2001.

Yu, Amorphous pharmaceutical solids: preparation, characterization and stabilization, Advanced Drug Delivery Reviews, 48, 27-42, 2001.

* cited by examiner

BICYCLIC COMPOUNDS AND THEIR USES

SEQUENCE LISTING

The instant application contains a Sequence Listing, which has been submitted electronically in XML format and is hereby incorporated by reference in its entirety. Said XML copy, created on Nov. 9, 2023, is named PAT059096-US-DIV_ST26 SQL.xml and is 26953 bytes in size.

FIELD OF INVENTION

The invention provides bicyclic compounds, such as 7-oxo-[1,2,4]triazolo[1,5-a]pyrimidin-4 (7H)-yl) compounds, and analogues and derivatives thereof, the use thereof for inhibiting Werner Syndrome RecQ DNA helicase (WRN) and methods of treating disease using said compounds, in particular the use in treating cancer, and in particular the treatment of cancer characterized as microsatellite instability-high (MSI-H) or mismatch repair deficient (dMMR), including colorectal, gastric and endometrial cancer. The invention also provides the use of said compounds as research chemicals, intermediate compounds, combinations, processes and formulations.

BACKGROUND OF THE INVENTION

Loss of DNA mismatch repair is a common initiating event in cancer development occurring in 10-30% of colorectal, endometrial, ovarian and gastric cancers (Aaltonen, L. A. et al. Clues to the pathogenesis of familial colorectal cancer, Science 260, 812-816 (1993), Bonneville R et al., Landscape of Microsatellite Instability Across 39 Cancer Types. JCO Precis Oncol. 1: PO.17.00073 (2017)). Cancers that have lost competence in mismatch repair (MMR) have a high mutational burden, and frequent deletion and insertion events in repetitive DNA tracts, a phenotype known as microsatellite instability (MSI). While progress has been made in the treatment of microsatellite instability high (MSI-H) cancers, and the demonstration that pembrolizumab (anti-PD1) treatment led to significantly longer progression-free survival than chemotherapy when received as first-line therapy for MSI-H-dMMR metastatic colorectal cancer resulted in the recent approval of pembrolizumab as first-line treatment of these cancers, there is still a significant unmet medical need in CRC and other MSI-H indications (Andre T., et al. Pembrolizumab in Microsatellite-Instability-High Advanced Colorectal Cancer. N Engl J Med 383 (23):2207-2218 (2020)). Several large-scale functional genomics screens across large panels of cell lines, including Novartis with 398 cell lines from the Cancer Cell Line Encyclopedia (CCLE) (McDonald E. R. et al., Project DRIVE: A Compendium of Cancer Dependencies and Synthetic Lethal Relationships Uncovered by Large-Scale, Deep RNAi Screening. Cell 170(3):577-592 (2017)), have identified the Werner Syndrome RecQ helicase (WRN) as being selectively required for the survival of cell lines with defective mismatch repair that have become MSI-H (Behan, F. M. et al. Prioritization of cancer therapeutic targets using CRISPR-Cas9 screens. Nature 568, 511-516 (2019), Chan, E. M. et al. WRN helicase is a synthetic lethal target in microsatellite unstable cancers. Nature 568, 551-556 (2019). Kategaya, L., Perumal, S. K., Hager, J. H. & Belmont, L. D. Werner syndrome helicase is required for the survival of cancer cells with microsatellite instability. iScience 13, 488-497 (2019), Lieb, S. et al. Werner syndrome helicase is a selective vulnerability of microsatellite instability-high tumor cells. eLife 8, e43333 (2019)). WRN is synthetic lethal with MSI cancers. Depletion of WRN leads to anti-proliferative effects and results in activation of multiple DNA damage signaling markers, induction of cell cycle arrest and apoptosis in MMR cancer models but not cancer cells with an intact MMR pathway. These findings indicate that WRN provides a DNA repair and maintenance function that is essential for cell survival in MSI cancers. Recently, the mechanism of WRN dependence has been elucidated. It has been shown that dinucleotide TA repeats are selectively unstable in MSI cells and undergo large scale expansions. These expanded TA repeats form secondary DNA structures that require the WRN helicase for unwinding (van Wietmarschen, N. et al. Repeat expansions confer WRN dependence in microsatellite-unstable cancers. Nature 586, 292-298, 2020). In the absence of WRN (or upon WRN helicase inhibition), expanded TA repeats in MSI cells are subject to nuclease cleavage and chromosome breakage. Thus, inhibiting the WRN helicase is an attractive strategy for the treatment of mismatch repair defective cancers.

SUMMARY OF THE INVENTION

There remains a need for new treatments and therapies for the treatment of cancer, and in particular cancers characterized as microsatellite instability-high (MSI-H) or mismatch repair deficient (dMMR), including colorectal, gastric or endometrial cancer. The invention provides compounds, pharmaceutically acceptable salts thereof, pharmaceutical compositions thereof and combinations thereof, said compounds being inhibitors of Werner Syndrome RecQ DNA Helicase (WRN). The invention further provides methods of treating, preventing, or ameliorating a disease or condition, comprising administering to a subject in need thereof an effective amount of a WRN inhibitor. The invention also provides compounds, pharmaceutically acceptable salts thereof, pharmaceutical compositions thereof and combinations thereof, said compounds being useful for the treatment of cancer, in particular cancers characterized as microsatellite instability-high (MSI-H) or mismatch repair deficient (dMMR). Also provided are compounds that bind to, and/or inhibit WRN, and are therefore useful as research chemicals, e.g. as a chemical probe, and as tool compounds. Various embodiments of the invention are described herein.

Within certain aspects, provided herein is a compound of formula (I) or a pharmaceutically acceptable salt thereof:

(I)

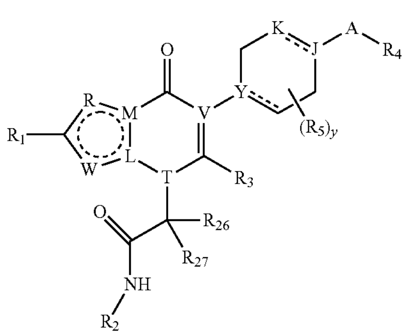

wherein

R, M, W, L, V and T are independently selected from C, CH and N, to form subformulae 1a, 1b, 1c, 1d, 1e and 1f:

1a

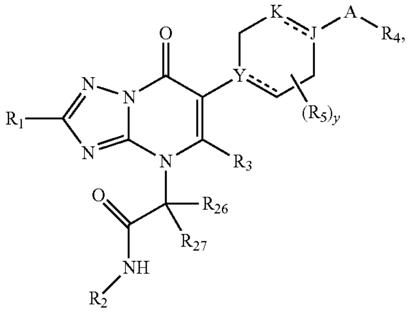

1b

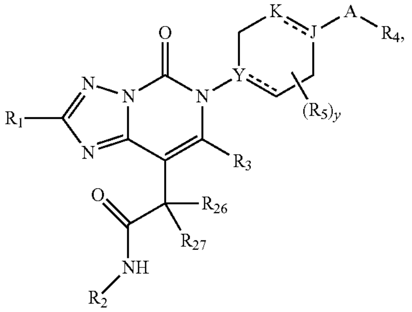

1c

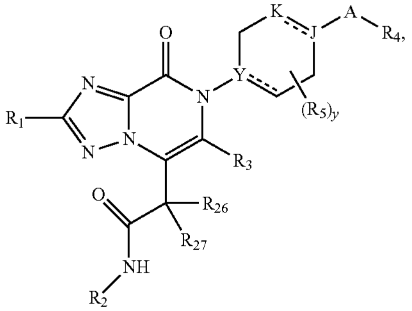

1d

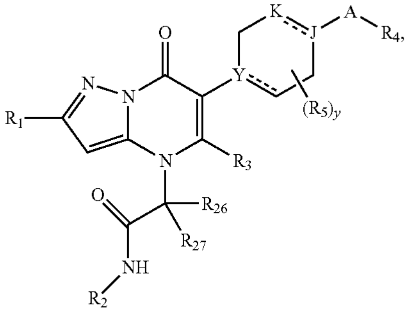

-continued

1e

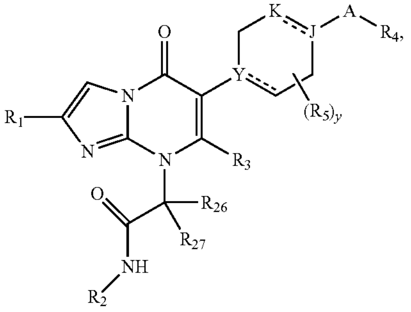

and

1f

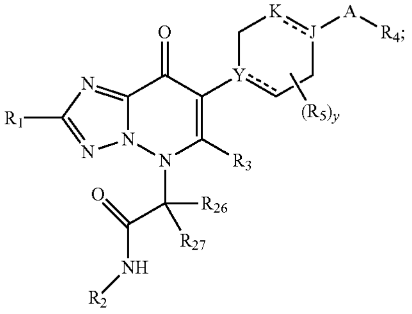

A is a linker selected from —C(O)—, —S(O)—, —S(O)$_2$—, and

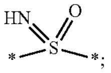

Y is N, C or CH;

y is 0, 1, 2, 3 or 4;

Y--- means Y is linked via a single bond to the adjacent carbon atom when Y is CH, or Y is linked via a double bond to the adjacent atom when Y is C, and when Y --- is a single bond, Y is carbon unsubstituted or substituted by OH or F;

when Y is N, Y--- is a single bond;

K--- means K is linked via a single or double bond to the adjacent atom;

wherein:

when K--- is a double bond, Y--- is a single bond, K is CH, J is C, and A is a linker selected from —C(O)—, —S(O)—, —S(O)$_2$—, and

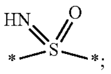

or when K--- is a single bond, K is selected from —CH$_2$—, —CH$_2$CH$_2$—, —NH— and a bond (to form a 5-membered ring:

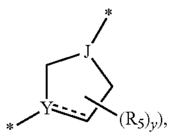

J is N, and A is a linker selected from —C(O)—, —S(O)—, —$S(O)_2$—, and

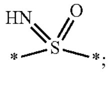

when K--- is a single bond, K is —$CH_2$—, J is CH, and A is a linker selected from —S(O)—, —S(O) $_2$—, and

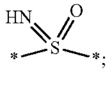

$R_5$ is independently selected from:

—($C_1$-$C_4$)alkyl,

—($C_3$-$C_5$)cycloalkyl, and wherein two $R_5$ substituents on the same ring carbon atom may join, together with the carbon atom to which they are attached, to form a ($C_3$-$C_4$)cycloalkyl spiro ring or a 3 or 4-membered heterocyclyl spiro ring, wherein said heterocyclyl spiro ring contains ring carbon ring atoms and one ring heteroatom selected from O, N and S, when K---J is a carbon-nitrogen single bond, a $R_5$ substituent on K and on the adjacent carbon atom may join to form ring C:

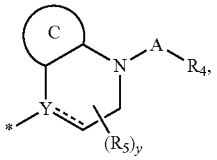

wherein ring C is a fused ($C_3$-$C_6$)cycloalkyl ring, a fused ($C_3$-$C_6$)heterocyclyl ring or a fused phenyl ring, wherein said fused ($C_3$-$C_6$)heterocyclyl ring contains ring carbon atoms and one ring heteroatom selected from O, N and S, when K---J is a carbon-carbon single bond, Y is N and Y--- is a single bond, and A is a linker selected from —S(O)—, —$S(O)_2$—, and

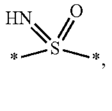

a $R_5$ substituent on K and on the adjacent carbon atom may join to form ring C:

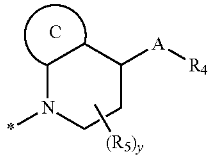

and wherein when K is —$CH_2$— and J is N, two $R_5$ substituents may join to form a ($C_1$-$C_3$)alkylene bridge or a heteroalkylene bridge, wherein said heteroalkylene bridge is one heteroatom selected from N and O, or is —$CH_2$—O—$CH_2$—;

and wherein one or more H atoms on the ring:

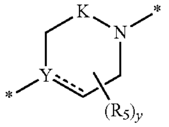

may be replaced by deuterium;

$R_1$ is:

cycloalkenyl, wherein said cycloalkenyl is a partially unsaturated monocyclic ring containing 5 or 6 ring carbon atoms, and said cycloalkenyl is unsubstituted or substituted by 1, 2, 3 or 4, preferably 1 or 2, $R_{33}$, wherein $R_{33}$ is halo, and wherein said cycloalkenyl or halo-substituted cycloalkenyl is substituted by 0, 1 or 2 $R_{15}$ substituents, or $R_1$ is heterocyclyl, wherein said heterocyclyl is a 5 or 6 membered fully saturated or partially unsaturated group comprising ring carbon atoms and 1 or 2 ring heteroatoms independently selected from N, O and S, and wherein said heterocyclyl is unbridged or bridged, and said bridge is 1 or 2 carbon atoms, wherein said heterocyclyl is unsubstituted or substituted by 1, 2, 3 or 4, preferably 1 or 2, $R_{33}$, wherein $R_{33}$ is halo, and wherein said heterocyclyl or halo-substituted heterocyclyl is substituted by 0, 1 or 2 substituents independently selected from $R_{15}$, $R_{16}$, $R_{17}$, $R_{18}$, $R_{19}$, $R_{20}$, $R_{22}$ and $R_{23}$, or said heterocyclyl or halo-substituted heterocyclyl is fused to a cyclopropyl ring, wherein said cyclopropyl ring is unsubstituted or substituted by 1, 2 or 3 F, or said heterocyclyl or halo-substituted heterocyclyl has 2 substitutents at the same ring carbon atom which join to form a cyclopropyl spiro ring, or said heterocyclyl or halo-substituted heterocyclyl is fused with a ($C_3$-$C_5$)heterocycloalkyl ring, wherein said ($C_3$-$C_5$)heterocycloalkyl ring contains ring carbon atoms and 1 ring 0 atom;

or $R_1$ is heteroaryl, wherein said heteroaryl is a 5 or 6 membered fully unsaturated monocyclic group comprising ring carbon atoms and 1, 2, 3 or 4 ring heteroatoms independently selected from N, O and S, preferably 1 or 2 ring heteroatoms, wherein the total number of ring S atoms does not exceed 1, and the total number of ring O atoms does not exceed 1, wherein said heteroaryl is unsubstituted or substituted by 1, 2 or 3 substituents independently selected from $R_{21}$ and $R_{30}$, wherein $R_{21}$ and $R_{30}$ are independently selected from halo and ($C_1$-$C_4$)alkyl, wherein said ($C_1$-$C_4$)alkyl is unsubstituted or substituted by 1, 2 or 3 halo, or $R_1$ is phenyl, wherein said phenyl is unsubstituted or substituted by 1, 2, 3 or 4, preferably 1 or 2, $R_{33}$, wherein $R_{33}$ is halo, and wherein said phenyl or halo-substituted phenyl is substituted by 0, 1 or 2 $R_{15}$ substituents, or $R_1$ is $(C_2\text{-}C_4)$alkynyl or $(C_2\text{-}C_4)$alkenyl, wherein said $(C_2\text{-}C_4)$alkynyl and $(C_2\text{-}C_4)$alkenyl are unsubstituted or substituted by $(C_1\text{-}C_4)$alkyl-O—C(O)—, or morpholinyl;

each $R_{15}$, $R_{16}$, $R_{17}$, $R_{18}$, $R_{19}$, $R_{20}$, $R_{22}$ and $R_{23}$ is independently selected from:

halo $(C_1\text{-}C_4)$alkyl-O— unsubstituted or substituted by 1, 2 or 3 halo;

$(C_1\text{-}C_4)$alkyl unsubstituted or substituted by OH, —O—$(C_1\text{-}C_2)$alkyl or 1, 2 or 3 halo, HOC(O)—$(CH_2)_n$—, $H_3C$—C(O)$(CH_2)_n$—, $(C_1\text{-}C_4)$alkyl-O—C(O)$(CH_2)_n$,

=O azetidinyl or pyrrolidinyl, wherein said azetidinyl and pyrrolidinyl are linked to the rest of the molecule via the N atom, and are each unsubstituted or substituted by 1 or 2 F, $R_{25}(R_{24})$N—, wherein $R_{24}$ is H or $(C_1\text{-}C_4)$alkyl unsubstituted or substituted by 1, 2 or 3 halo, $R_{25}$ is H or $(C_1\text{-}C_4)$alkyl unsubstituted or substituted by 1, 2 or 3 halo,

OH wherein n is 0, 1 or 2, $R_{26}$ is $CH_3$, H or deuterium;

$R_{27}$ is $CH_3$, H or deuterium;

or $R_{26}$ and $R_{27}$ join, together with the carbon atom to which they are attached, to form a cyclopropyl ring;

$R_2$ is the moiety:

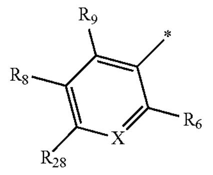

$R_6$ is selected from:

H, halo, $(C_1\text{-}C_4)$alkyl unsubstituted or substituted by 1, 2 or 3 halo, $(C_3\text{-}C_5)$cycloalkyl unsubstituted or substituted by 1, 2 or 3 halo, —O—$(C_1\text{-}C_4)$alkyl unsubstituted or substituted by 1, 2 or 3 halo, OH, and

CN;

$R_6$ is selected from H, halo, and $(C_1\text{-}C_4)$alkyl unsubstituted or substituted by 1, 2 or 3 halo, $R_9$ is selected from H, O—$CH_3$, OH, CN, $CH_3$ and halo;

$R_{28}$ is selected from:

$SF_5$,

H,

—C(O)H, halo, $(C_1\text{-}C_4)$alkyl unsubstituted or substituted by 1, 2 or 3 halo, $(C_1\text{-}C_4)$alkynyl, $(C_1\text{-}C_4)$alkenyl, $(C_3\text{-}C_5)$cycloalkyl unsubstituted or substituted by 1, 2 or 3 halo, and $OCF_3$;

X is selected from C—$R_7$ and N, wherein $R_7$ is H or halo, or $R_7$ can join, together with $R_{28}$ or $R_6$, and the atoms to which they are attached, to form a fused $(C_4\text{-}C_6)$ cycloalkyl ring, wherein said fused $(C_4\text{-}C_6)$cycloalkyl ring is unsubstituted or substituted by 1, 2 or 3 halo, or $R_2$ is selected from:

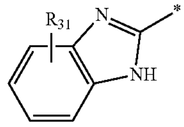

and

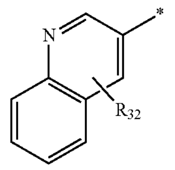

wherein $R_{31}$ is selected from H, halo and $CH_3$, $R_{32}$ is selected from H, halo and $CH_3$, $R_3$ is:

cyclopropyl,

O—$CH_3$, $N(CH_3)_2$,

S—$CH_3$, $(C_1\text{-}C_4)$alkyl unsubstituted or substituted by 1, 2 or 3 substituents independently selected from halo and OH;

$R_4$ is selected from:

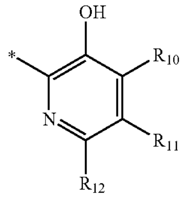

and

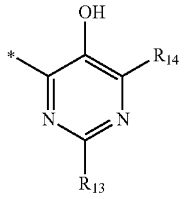

wherein $R_{10}$, $R_{11}$, $R_{12}$, $R_{13}$ and $R_{14}$ are independently selected from:

H, halo, $(C_1\text{-}C_4)$alkyl unsubstituted or substituted by 1, 2 or 3 halo substituents, $(C_1\text{-}C_2)$alkyl substituted by —O—$(C_1\text{-}C_2)$alkyl or OH, —S—$(C_1\text{-}C_3)$alkyl, —O—$(C_1\text{-}C_4)$alkyl unsubstituted or substituted by 1, 2 or 3 halo substituents,

OH, $(C_3\text{-}C_5)$cycloalkyl, wherein said $(C_3\text{-}C_5)$cycloalkyl is unsubstituted or substituted by 1 or 2 halo, —O—$(C_3\text{-}C_5)$cycloalkyl, —$NR_{34}R_{35}$ wherein $R_{34}$ and $R_{35}$ are independently selected from:

H, $(C_1\text{-}C_4)$alkyl, wherein said $(C_1\text{-}C_4)$alkyl is unsubstituted or substituted by OH or —O$(C_1\text{-}C_2)$alkyl, and wherein $R_{34}$ and $R_{35}$ can join, together with the atom to which they are attached, to form an azetidine, pyrrolidinyl or piperidine ring, wherein said azetidine, pyrrolidinyl and piperidine are unsubstituted or substituted with $CH_3$;

CN,

—$(C_2$-$C_4)$alkenyl,

—$(C_2$-$C_4)$alkynyl,

—C(O)H, and

—$C(O)(C_1$-$C_4)$alkyl;

and

* indicates a point of attachment.

In another aspect, the invention provides a pharmaceutical composition comprising a compound of formula (I) of the present invention and one or more pharmaceutically acceptable carriers.

In another aspect, the invention provides a combination, in particular a pharmaceutical combination, comprising a compound of formula (I) of the present invention and one or more therapeutically active agents.

In another aspect, the invention provides a compound of formula (I) of the present invention for use as a medicament, in particular for the treatment of a disorder or disease which can be treated by WRN inhibition.

In another aspect, the invention provides a compound of formula (I) of the present invention for use in the treatment of cancer, particularly wherein the cancer is characterized as microsatellite instability-high (MSI-H) or mismatch repair deficient (dMMR).

In another aspect, the invention provides a method of treating a disorder or disease which can be treated by WRN inhibition in a subject, comprising administering to the subject a therapeutically effective amount of a compound of formula (I) of the present invention.

In another aspect, the invention provides a method of treating cancer in a subject, more particularly wherein the cancer is characterized as microsatellite instability-high (MSI-H) or mismatch repair deficient (dMMR), comprising administering to the subject a therapeutically effective amount of a compound of formula (I) of the present invention.

In another aspect, the invention provides the use of a compound of formula (I) of the present invention in the manufacture of a medicament for the treatment of a disorder or disease which can be treated by WRN inhibition.

In another aspect, the invention provides a compound of formula (I) of the present invention for use as a research chemical, for example as a chemical probe or as a tool compound.

In another aspect, the invention provides a solid form, process or intermediate as described herein.

DETAILED DESCRIPTION

Figure 1:
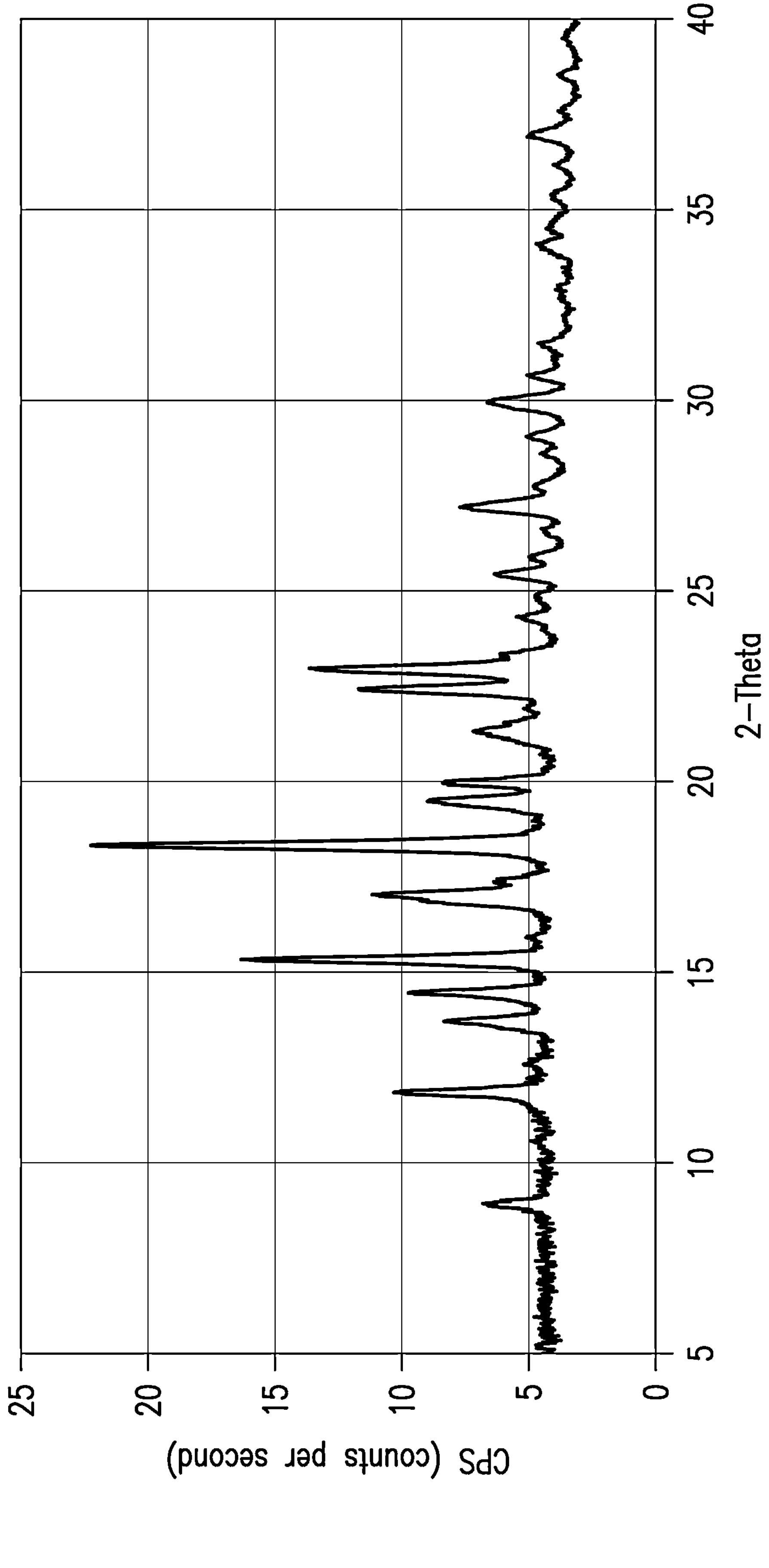
FIG. 1 shows a X-ray powder diffractogram for example 42.

The invention therefore provides a compound of formula (I):

(I)

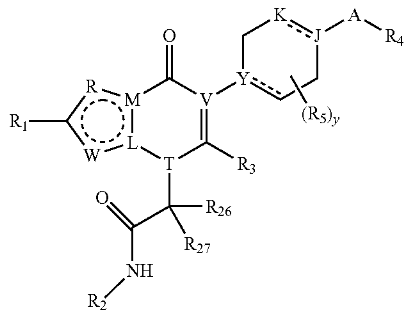

wherein $R_1$, $R_2$, $R_3$, $R_4$, $R_5$, $R_{26}$, $R_{27}$, y, R, M, W, L, V, T, Y, J, K and A are as described in the Summary of the Invention, supra.

Unless specified otherwise, the term "compounds of the present invention" or "compound of the present invention" or "a compound of formula (I)", refers to a compound or compounds of formula (I), subformulae thereof, exemplified compounds, and salts thereof, as well as all zwitterions, stereoisomers (including diastereoisomers and enantiomers), rotamers, tautomers and isotopically labeled compounds (including deuterium substitutions), as well as inherently formed moieties, and combinations or mixtures of the above-mentioned aspects thereof.

Various (enumerated) embodiments of the invention are described herein. It will be recognized that features specified in each embodiment may be combined with other specified features to provide further embodiments of the present invention.

Embodiment 1. A compound of formula (I) or a pharmaceutically acceptable salt thereof, as described above.

Embodiment 2: A compound of formula (I) or a pharmaceutically acceptable salt thereof, according to Embodiment 1, wherein when $R_1$ is a ring, then:

each $R_1$ ring atom adjacent to the $R_1$ ring atom to which said $R_1$ ring is joined to the remainder of the molecule, is independently unsubstituted or substituted by halo only, in particular, independently unsubstituted or substituted with one F substituent, and preferably, said $R_1$ ring is linked to the remainder of the molecule via a $R_1$ ring nitrogen atom, or a $R_1$ ring carbon atom which is double-bonded to an adjacent ring atom.

Embodiment 3. A compound of formula (I) or a pharmaceutically acceptable salt thereof, according to Embodiments 1 or 2, wherein $R_1$ is:

cycloalkenyl, wherein said cycloalkenyl is a partially unsaturated monocyclic ring containing 5 or 6 ring carbon atoms, and said cycloalkenyl is unsubstituted or substituted by 1, 2, 3 or 4, preferably 1 or 2, $R_{33}$, wherein $R_{33}$ is halo, and wherein said cycloalkenyl or halo-substituted cycloalkenyl is substituted by 0, 1 or 2 $R_{15}$ substituents, or $R_1$ is heterocyclyl, wherein said heterocyclyl is a 5 or 6 membered fully saturated or partially unsaturated group comprising ring carbon atoms and 1 or 2 ring heteroatoms independently selected from N, O and S, and wherein said heterocyclyl is unbridged or bridged, and said bridge is 1 or 2 carbon atoms, wherein said heterocyclyl is unsubstituted or substituted by 1, 2, 3 or 4, preferably 1 or 2, $R_{33}$, wherein $R_{33}$ is halo, and wherein said heterocyclyl or halo-substituted heterocyclyl is substituted by 0, 1 or 2 substituents independently selected from $R_{15}$, $R_{16}$, $R_{17}$, $R_{18}$, $R_{19}$, $R_{20}$, $R_{22}$ and $R_{23}$, or $R_1$ is heteroaryl, wherein said heteroaryl is a 5 or 6 membered fully unsaturated monocyclic group comprising ring carbon atoms and 1, 2, 3 or 4 ring heteroatoms independently selected from N, O and S, preferably 1 or 2 ring heteroatoms, wherein the total number of ring S atoms does not exceed 1, and the total number of ring O atoms does not exceed 1, wherein said heteroaryl is unsubstituted or substituted by 1, 2 or 3 substituents independently selected from $R_2$, and $R_{30}$, wherein $R_{21}$ and $R_{30}$ are independently selected from halo and $(C_1\text{-}C_4)$alkyl, wherein said $(C_1\text{-}C_4)$alkyl is unsubstituted or substituted by 1, 2 or 3 halo, and each $R_{15}$, $R_{16}$, $R_{17}$, $R_{18}$, $R_{19}$, $R_{20}$, $R_{22}$ and $R_{23}$ is independently selected from:

halo $(C_1\text{-}C_4)$alkyl-O— unsubstituted or substituted by 1, 2 or 3 halo;

$(C_1\text{-}C_4)$alkyl unsubstituted or substituted by OH, —O—$(C_1\text{-}C_2)$alkyl or 1, 2 or 3 halo, $HOC(O)—(CH_2)_n—$, $H_3C—C(O)(CH_2)_n—$, $(C_1\text{-}C_4)$alkyl-O—$C(O)(CH_2)_n$,

=O azetidinyl or pyrrolidinyl, wherein said azetidinyl and pyrrolidinyl are linked to the rest of the molecule via the N atom, and are each unsubstituted or substituted by 1 or 2 F, $R_{25}(R_{24})N—$, wherein $R_{24}$ is H or $(C_1\text{-}C_4)$alkyl unsubstituted or substituted by 1, 2 or 3 halo, $R_{25}$ is H or $(C_1\text{-}C_4)$alkyl unsubstituted or substituted by 1, 2 or 3 halo,

OH wherein n is 0, 1 or 2,

Embodiment 4. A compound of formula (I) or a pharmaceutically acceptable salt thereof, according to any of Embodiments 1, 2 or 3, wherein $R_1$ is:

cycloalkenyl, wherein said cycloalkenyl is a partially unsaturated monocyclic ring containing 5 or 6 ring carbon atoms, and said cycloalkenyl is unsubstituted or substituted by 1 or 2 $R_{33}$, wherein $R_{33}$ is halo, preferably F, and wherein said cycloalkenyl or halo-substituted cycloalkenyl is substituted by 0 or 1 $R_{15}$ substituents, preferably 1 substituent, wherein $R_{15}$ is selected from:

a) $(C_1\text{-}C_2)$alkyl-O— unsubstituted or substituted by 1, 2 or 3 halo;

b) $(C_1\text{-}C_2)$alkyl unsubstituted or substituted by 1, 2 or 3 halo, c) $HOC(O)—(CH_2)_n—$, d) $H_3C—C(O)(CH_2)_n—$, e) $H_3C—O—C(O)(CH_2)_n$, f) =O, and g) $R_{25}(R_{24})N—$, H, wherein $R_{24}$ is H or $(C_1\text{-}C_2)$alkyl unsubstituted or substituted by 1, 2 or 3 halo, $R_{25}$ is H or $(C_1\text{-}C_2)$alkyl unsubstituted or substituted by 1, 2 or 3 halo, n is 0 or 1, wherein the $R_{15}$ substituent a) to g) of said cycloalkenyl or halo-substituted cycloalkenyl is not present on the ring atoms adjacent to the ring atom to which the cycloalkenyl or halo-substituted cycloalkenyl is joined to the remainder of the molecule, and preferably, said cycloalkenyl or halo-substituted cycloalkenyl is a 6 membered ring, with 1 $R_{15}$ substituent in the ring para position relative to the remainder of the molecule; and said cycloalkenyl or halo-substituted cycloalkenyl is linked to the remainder of the compound via a $R_1$ ring carbon atom which is double bonded to an adjacent $R_1$ ring carbon atom;

or $R_1$ is heterocyclyl, wherein said heterocyclyl is a 5 or 6 membered fully saturated or partially unsaturated group comprising ring carbon atoms and 1 or 2 ring heteroatoms independently selected from N, NH, O and S, and wherein said heterocyclyl is unbridged or bridged, and said bridge is 1 or 2 carbon atoms, wherein said heterocyclyl is unsubstituted or substituted by 1 or 2 $R_{33}$, wherein $R_{33}$ halo, is preferably F, and wherein said heterocyclyl or halo-substituted heterocyclyl is substituted by 0 or 1 substituents independently selected from $R_{15}$, $R_{16}$, $R_{17}$, $R_{18}$, $R_{19}$, $R_{20}$, $R_{22}$ and $R_{23}$, wherein said $R_{15}$, $R_{16}$, $R_{17}$, $R_{18}$, $R_{19}$, $R_{20}$, $R_{22}$ and $R_{23}$ are independently selected from:

a) $(C_1\text{-}C_4)$alkyl-O— unsubstituted or substituted by 1, 2 or 3 halo;

b) $(C_1\text{-}C_4)$alkyl unsubstituted or substituted by OH, —O—$(C_1\text{-}C_2)$alkyl or 1, 2 or 3 halo, c) $HOC(O)—(CH_2)_n—$, d) $H_3C—C(O)(CH_2)_n—$, e) $H_3C—O—C(O)(CH_2)_n$, f) =O g) $R_{25}(R_{24})N—$, wherein $R_{24}$ is H, $(C_1\text{-}C_2)$alkyl unsubstituted or substituted by 1, 2 or 3 halo, $R_{25}$ is H, $(C_1\text{-}C_2)$alkyl unsubstituted or substituted by 1, 2 or 3 halo, h) OH wherein n is 0 or 1, and wherein:

substituent a) to h) of said heterocyclyl or halo-substituted heterocyclyl is not present on the ring atoms adjacent to the ring atom to which the heterocyclyl or halo-substituted heterocyclyl is joined to the remainder of the molecule, and preferably, when said heterocyclyl or halo-substituted heterocyclyl is a 6 membered ring, it has 0 or 1 substituent selected from a) to h) in the meta or para position, preferably para, relative to the remainder of the molecule; and said heterocyclyl is linked to the remainder of the compound via a $R_1$ ring nitrogen atom, or a $R_1$ ring carbon atom which is double bonded to an adjacent ring atom;

or $R_1$ is heteroaryl, wherein said heteroaryl is a 5 or 6 membered fully unsaturated monocyclic group comprising ring carbon atoms and 1 or 2 ring heteroatoms independently selected from N, O and S, preferably N, wherein the total number of ring S atoms does not exceed 1, and the total number of ring O atoms does not exceed 1, wherein said heteroaryl is unsubstituted or substituted by 1 or 2 substituents independently selected from $R_2$, and $R_{30}$, wherein $R_{21}$ and $R_{30}$ are independently selected from $(C_1-C_2)$alkyl, and said $(C_1-C_2)$alkyl is unsubstituted or substituted by 1, 2 or 3 halo, and wherein preferably, said alkyl or halo-alkyl substituent is not present on the $R_1$ ring atoms adjacent to the $R_1$ ring atom to which the heteroaryl is joined to the remainder of the molecule, and more preferably, when heteroaryl is a 6-membered ring, said alkyl or halo-alkyl substituent is in the ring para position relative to the rest of the molecule.

Embodiment 5. A compound of formula (I) or a pharmaceutically acceptable salt thereof, according to any of Embodiments 1 to 3, wherein $R_1$ is selected from:

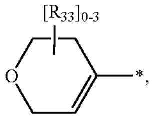
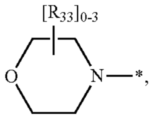
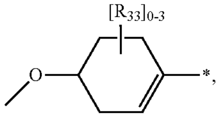
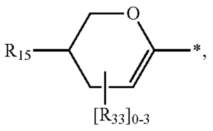
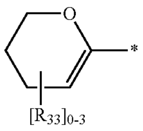
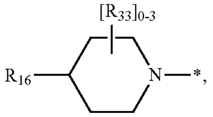
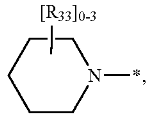
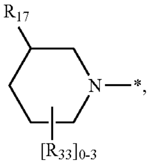
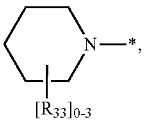
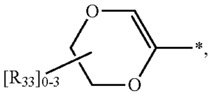
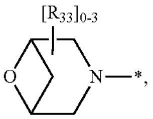
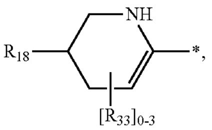
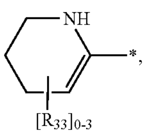
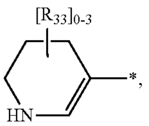
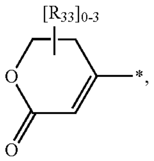
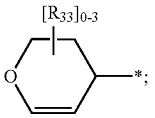
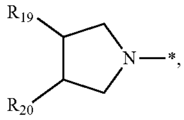
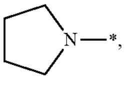

-continued

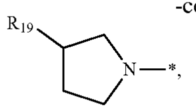
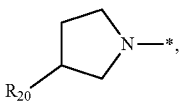
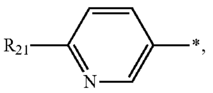
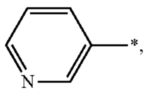
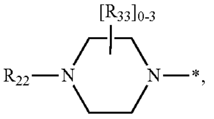
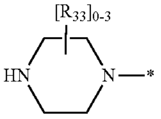
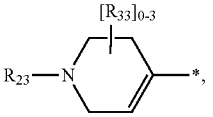
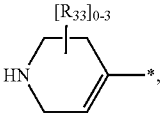
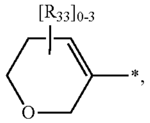
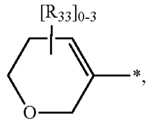
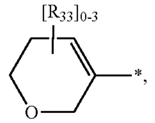
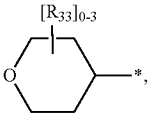
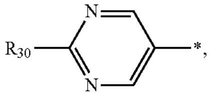
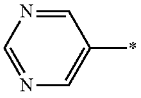
and
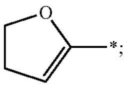

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or $(C_1-C_2)$alkyl, $R_{25}$ is H or $(C_1-C_2)$alkyl unsubstituted or substituted by 1, 2 or 3 halo, in particular F;

$R_{17}$ is halo $R_{18}$ is halo;

$R_{19}$ is halo;

$R_{20}$ is halo;

$R_{21}$ is $(C_1-C_2)$alkyl;

$R_{22}$ and $R_{23}$ are each independently selected from:

$(C_1-C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

Embodiment 6. A compound of formula (I) or a pharmaceutically acceptable salt thereof, according to any of Embodiments 1 to 5, wherein $R_1$ is selected from:

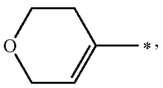
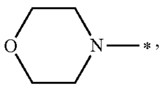

-continued

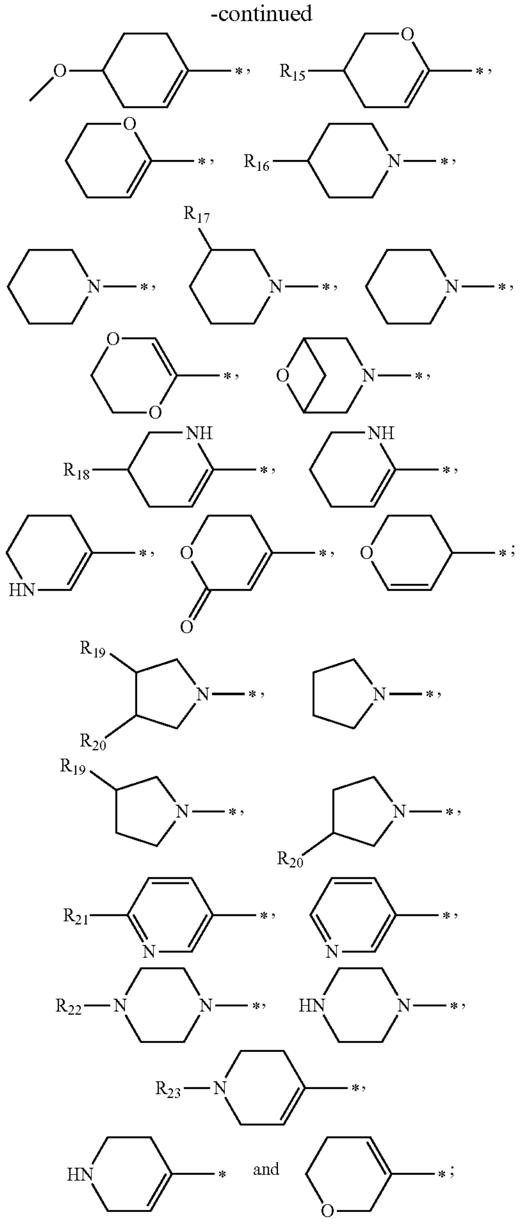

$R_{15}$ is F;

$R_{16}$ is $R_{25}(R_{24})N$—;

$R_{17}$ is F;

$R_{18}$ is F;

$R_{19}$ is F;

$R_{20}$ is F;

$R_{21}$ is $CH_3$;

$R_{22}$ is $CF_3$, $CHF_2CH_2$, $HOC(O)$—$CH_2$—, $H_3C$—$C(O)$—, $(H_3C)_3C$—O—$C(O)$—;

$R_{23}$ is $CF_3$, $CHF_2CH_2$—, $(H_3C)_3C$—O—$C(O)$—;

$R_{24}$ is $CH_3$; and $R_{25}$ is $CHF_2CH_2$—.

Embodiment 7. A compound of formula (I) or a pharmaceutically acceptable salt thereof, according to any of Embodiments 1 to 6, wherein $R_2$ is the moiety:

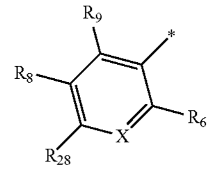

$R_6$ is selected from:
- H,
- halo,
- $(C_1\text{-}C_4)$alkyl unsubstituted or substituted by 1, 2 or 3 halo,
- $(C_3\text{-}C_5)$cycloalkyl unsubstituted or substituted by 1, 2 or 3 halo,
- —O—$(C_1\text{-}C_4)$alkyl unsubstituted or substituted by 1, 2 or 3 halo,
- OH, and
- CN;

$R_8$ is selected from H, halo, and $(C_1\text{-}C_4)$alkyl unsubstituted or substituted by 1, 2 or 3 halo, $R_9$ is selected from H, O—$CH_3$, OH, CN, $CH_3$ and halo;

$R_{28}$ is selected from:
- $SF_5$,
- H,
- —C(O)H,
- halo,
- $(C_1\text{-}C_4)$alkyl unsubstituted or substituted by 1, 2 or 3 halo,
- $(C_1\text{-}C_4)$alkynyl,
- $(C_1\text{-}C_4)$alkenyl,
- $(C_3\text{-}C_5)$cycloalkyl unsubstituted or substituted by 1, 2 or 3 halo, and
- $OCF_3$;

and X is selected from C—$R_7$ and N, wherein $R_7$ is H or halo.

Embodiment 8. A compound of formula (I) or a pharmaceutically acceptable salt thereof, according to any of Embodiments 1 to 7, wherein $R_2$ is the moiety:

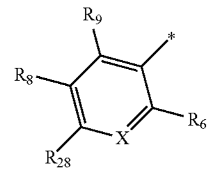

wherein $R_6$ is selected from H, halo, $(C_1\text{-}C_4)$alkyl unsubstituted or substituted by 1, 2 or 3 halo;

$R_8$ is selected from H, halo, $(C_1\text{-}C_4)$alkyl unsubstituted or substituted by 1, 2 or 3 halo;

$R_9$ is selected from H, O—$CH_3$, OH, CN, $CH_3$ and halo;

$R_{28}$ is selected from $SF_5$, halo, $(C_1\text{-}C_4)$alkyl unsubstituted or substituted by 1, 2 or 3 halo and —C(O)H;

X is selected from C—$R_7$ and N; and $R_7$ is selected from H and halo.

Embodiment 9. A compound of formula (I) or a pharmaceutically acceptable salt thereof, according to any of Embodiments 1 to 8, wherein $R_2$ is the moiety:

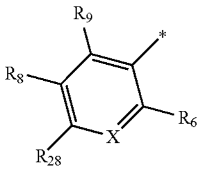

$R_6$ is selected from H, Cl, $CH_3$, F and Br;

$R_8$ is selected from H, Cl, F and $CF_3$;

$R_9$ is selected from H, $CH_3$ and Cl;

$R_{28}$ is selected from $CF_3$, $CF_2H$, $—CH_2CH_3$, Cl, $SF_5$, Br and —C(O)H;

X is selected from C—$R_7$ and N; and $R_7$ is selected from H and F.

Embodiment 10. A compound of formula (I) or a pharmaceutically acceptable salt thereof, according to any of Embodiments 1 to 9, wherein $R_{26}$ is H and $R_{27}$ is H.

Embodiment 11. A compound of formula (I) or a pharmaceutically acceptable salt thereof, according to any of Embodiments 1 to 10, wherein $R_3$ is ($C_1$-$C_4$)alkyl unsubstituted or substituted by 1, 2 or 3 substituents independently selected from halo and OH.

Embodiment 12. A compound of formula (I) or a pharmaceutically acceptable salt thereof, according to any of Embodiments 1 to 11, wherein $R_3$ is ($C_1$-$C_2$)alkyl unsubstituted or substituted by 1, 2 or 3 substituents independently selected from halo and OH, preferably $—CH_2CH_3$ or $CH_3$, more preferably $—CH_2CH_3$.

Embodiment 13. A compound of formula (I) or a pharmaceutically acceptable salt thereof, according to any of Embodiments 1 to 12, wherein Y is N and Y⎓ is Y linked by a single bond.

Embodiment 14. A compound of formula (I) or a pharmaceutically acceptable salt thereof, according to any of Embodiments 1 to 13, wherein K⎓ is K linked by a single bond, and K is selected from $—CH_2—$, $—CH_2CH_2—$, —NH— and a bond (to form a 5-membered ring:

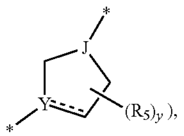

J is N, and A is a linker selected from —C(O)—, —S(O)—, $—S(O)_2—$, and

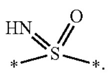

Embodiment 15. A compound of formula (I) or a pharmaceutically acceptable salt thereof, according to any of Embodiments 1 to 14, wherein K⎓ is K linked by a single bond, K is $—CH_2—$, J is N, and A is a linker selected from —C(O)—, —S(O)—, $—S(O)_2—$, and,

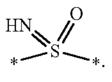

Embodiment 16. A compound of formula (I) or a pharmaceutically acceptable salt thereof, according to any of Embodiments 1 to 15, wherein A is a linker selected from —C(O)— and $—S(O)_2—$, preferably —C(O)—.

Embodiment 17. A compound of formula (I) or a pharmaceutically acceptable salt thereof, according to any of Embodiments 1 to 16, wherein $R_5$ is independently selected from:

—($C_1$-$C_4$)alkyl, preferably methyl, and wherein two $R_5$ substituents on the same ring carbon atom may join, together with the carbon atom to which they are attached, to form a ($C_3$-$C_4$)cycloalkyl spiro ring or a 3 or 4-membered heterocyclyl spiro ring, wherein said heterocyclyl spiro ring contains ring carbon ring atoms and one ring heteroatom selected from O, N and S, when K⎓J is a carbon-nitrogen single bond, a $R_5$ substituent on K and on the adjacent carbon atom may join to form ring C:

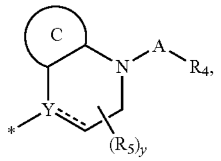

wherein ring C is a fused ($C_3$-$C_6$)cycloalkyl ring, in particular a fused cyclobutyl ring, a fused ($C_3$-$C_6$) heterocyclyl ring or a fused phenyl ring, wherein said fused ($C_3$-$C_6$)heterocyclyl ring contains ring carbon atoms and one ring heteroatom selected from O, N and S, and wherein when K is $—CH_2—$ and J is N, two $R_5$ substituents may join to form a ($C_1$-$C_3$)alkylene bridge or a heteroalkylene bridge, wherein said heteroalkylene bridge is one heteroatom selected from N and O, or is $—CH_2—O—CH_2—$.

Embodiment 18. A compound of formula (I) or a pharmaceutically acceptable salt thereof, according to any of Embodiments 1 to 17, wherein $R_5$ is independently selected from:

—($C_1$-$C_4$)alkyl, preferably methyl, when K⎓J is a carbon-nitrogen single bond, a $R_5$ substituent on K and on the adjacent carbon atom may join to form ring C:

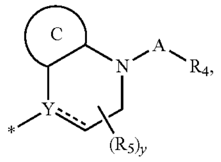

wherein ring C is a fused ($C_3$-$C_6$)cycloalkyl ring, in particular a fused cyclobutyl ring, or a fused ($C_3$-$C_6$) heterocyclyl ring, wherein said fused ($C_3$-$C_6$)heterocyclyl ring contains ring carbon atoms and one ring heteroatom selected from O, N and S, and wherein when K is $—CH_2—$ and J is N, two $R_5$ substituents may join to form a ($C_1$-$C_3$)alkylene bridge or a heteroalkylene bridge, wherein said heteroalkylene bridge is one heteroatom selected from N and O, or is $—CH_2—O—CH_2—$.

Embodiment 19. A compound of formula (I) or a pharmaceutically acceptable salt thereof, according to any of Embodiments 1 to 18, wherein $R_5$ is independently selected from:

—$(C_1\text{-}C_2)$alkyl, preferably methyl, and when K⎓J is a carbon-nitrogen single bond, a $R_5$ substituent on K and on the adjacent carbon atom may join to form ring C:

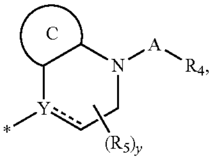

wherein ring C is a fused $(C_3\text{-}C_4)$cycloalkyl ring, in particular a fused cyclobutyl ring.

Embodiment 20. A compound of formula (I) or a pharmaceutically acceptable salt thereof, according to any of Embodiments 1 to 19, wherein $R_5$ is independently selected from:

$CH_3$, and y is 1 or 2, and when K⎓J is a carbon-nitrogen single bond, a $R_5$ substituent on K and on the adjacent carbon atom may join to form ring C:

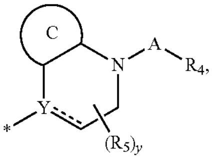

wherein ring C is a fused cyclobutyl ring.

Embodiment 21. A compound of formula (I) or a pharmaceutically acceptable salt thereof, according to any of Embodiments 1 to 20, wherein y is 0, 1, 2 or 3, preferably 0, 1, or 2.

Embodiment 22. A compound of formula (I) or a pharmaceutically acceptable salt thereof, according to any of Embodiments 1 to 21, wherein $R_4$ is selected from:

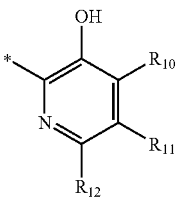 and 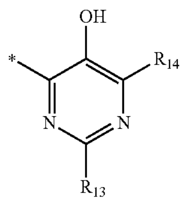

wherein $R_{10}$ is selected from H, halo, $(C_1\text{-}C_2)$alkyl unsubstituted or substituted by 1, 2 or 3 halo substituents, —O—$(C_1\text{-}C_2)$alkyl unsubstituted or substituted by 1, 2 or 3 halo substituents;

$R_{11}$ is selected from H, halo, $(C_1\text{-}C_2)$alkyl unsubstituted or substituted by 1, 2 or 3 halo substituents;

$R_{12}$ is selected from H, halo, $(C_1\text{-}C_2)$alkyl unsubstituted or substituted by 1, 2 or 3 halo substituents;

$R_{13}$ is selected from H, —S—$CH_3$, halo, $(C_1\text{-}C_2)$alkyl unsubstituted or substituted by 1, 2 or 3 halo substituents; and $R_{14}$ is selected from H, halo, $(C_1\text{-}C_2)$alkyl unsubstituted or substituted by 1, 2 or 3 halo substituents, O—$(C_1\text{-}C_2)$alkyl unsubstituted or substituted by 1, 2 or 3 halo substituents, and cyclopropyl.

Embodiment 23. A compound of formula (I) or a pharmaceutically acceptable salt thereof, according to any of Embodiments 1 to 22, wherein $R_4$ is selected from:

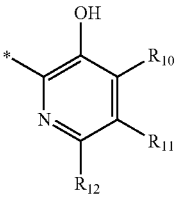 and 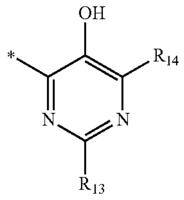

wherein $R_{10}$ is selected from H, F, Cl, $CH_3$ and $OCF_3$;

$R_{11}$ is selected from H, Cl, F, and $CH_3$;

$R_{12}$ is selected from H, Cl and $CH_3$;

$R_{13}$ is selected from H, —S—$CH_3$ and $CH_3$; and $R_{14}$ is selected from H, $CH_3$, —$CH_2CH_3$, cyclopropyl, —$OCHF_2$, $OCF_3$ and Cl.

Embodiment 24. A compound of formula (I) or a pharmaceutically acceptable salt thereof, according to any of Embodiments 1 to 23, wherein formula (I) is formula 1a:

1a

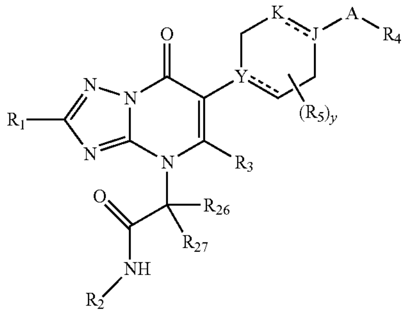

(Preferably, formula (I) is formula 1a)

Embodiment 25. A compound of formula (I) or a pharmaceutically acceptable salt thereof, according to any of Embodiments 1 to 23, wherein formula (I) is formula 1 b:

1b

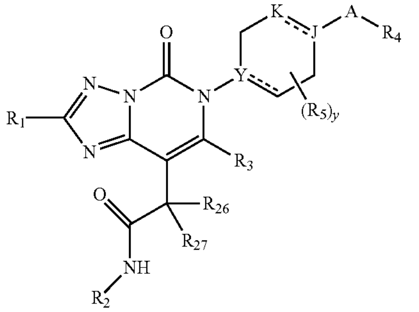

Embodiment 26. A compound of formula (I) or a pharmaceutically acceptable salt thereof, according to any of Embodiments 1 to 23, wherein formula (I) is formula 1c:

1c

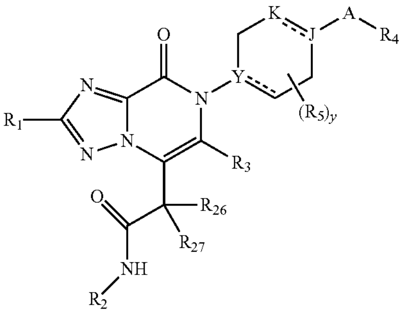

Embodiment 27. A compound of formula (I) or a pharmaceutically acceptable salt thereof, according to any of Embodiments 1 to 23, wherein formula (I) is formula 1d:

1d

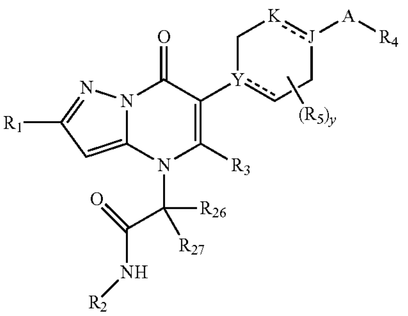

Embodiment 28. A compound of formula (I) or a pharmaceutically acceptable salt thereof, according to any of Embodiments 1 to 23, wherein formula (I) is formula 1e:

1e

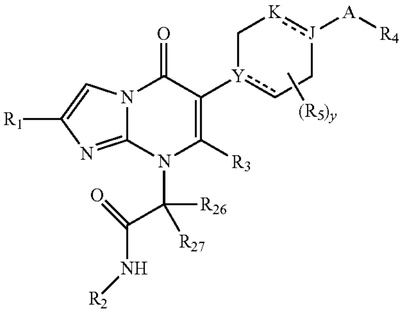

Embodiment 29. A compound of formula (I) or a pharmaceutically acceptable salt thereof, according to any of Embodiments 1 to 23, wherein formula (I) is formula 1f:

1f

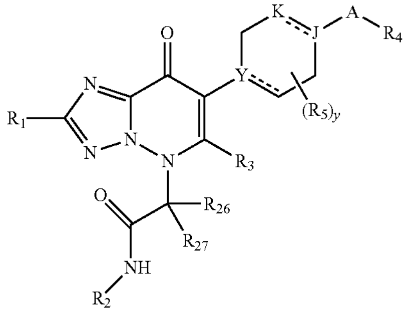

Embodiment 30. A compound of formula (I) or a pharmaceutically acceptable salt thereof, according to any of Embodiments 1 to 24, wherein formula (I) is formula 1g:

1g

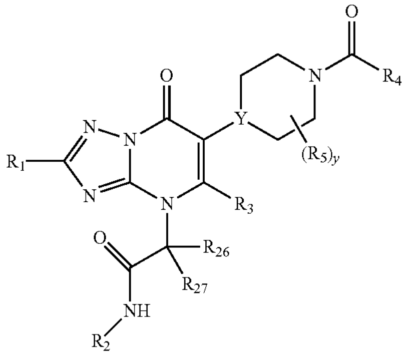

More preferably, formula (I) is formula 1g.

Embodiment 31. A compound of formula (I) or a pharmaceutically acceptable salt thereof, according to any of Embodiments 1 to 24, or 30, wherein formula (I) is formula 1h:

1h

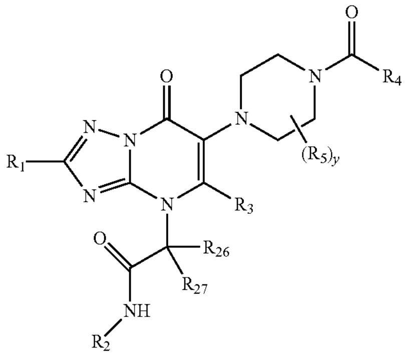

Most preferably, formula (I) is formula 1h.

Embodiment 32. A compound of formula (Ig) or a pharmaceutically acceptable salt thereof, according to any of embodiments 1, 24 or 30,

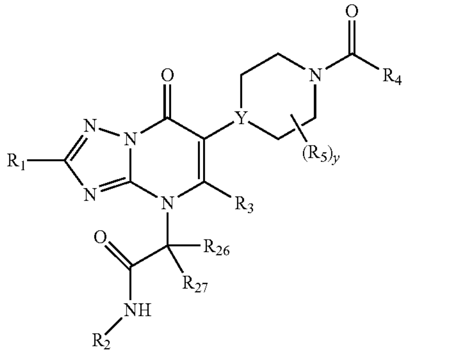

1g wherein $R_1$ is selected from:

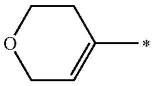, 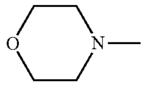,

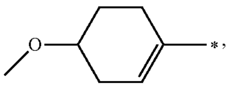, 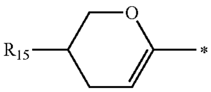,

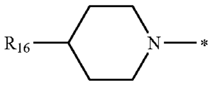,

, 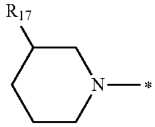, 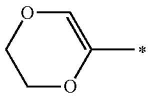,

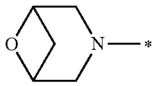, 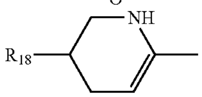,

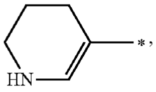, 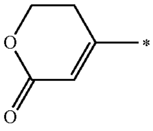, 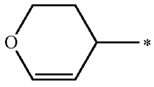;

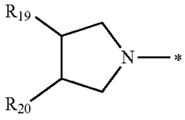, 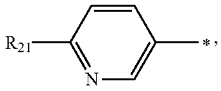,

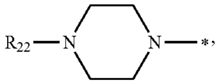,

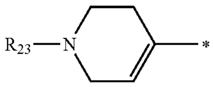 and 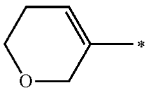;

$R_{15}$ is H or F;
$R_{16}$ is H or $R_{25}(R_{24})N$—;
$R_{17}$ is H or F;
$R_{18}$ is H or F;
$R_{19}$ is H or F;
$R_{20}$ is H or F;
$R_{21}$ is H or $CH_3$;
$R_{22}$ is H, $CF_3$, $CHF_2CH_2$, HOC(O)—$CH_2$—, $H_3C$—C(O)—, $(H_3C)_3C$—O—C(O)—;
$R_{23}$ is H, CF3, $CHF_2CH_2$—, $(H_3C)_3C$—O—C(O)—;
$R_{24}$ is $CH_3$;
$R_{25}$ is $CHF_2CH_2$—;

$R_{26}$ is $CH_3$, H or deuterium;
$R_{27}$ is H or deuterium;
$R_2$ is the moiety:

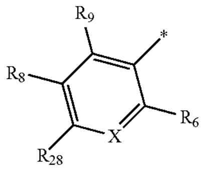

$R_6$ is selected from H, Cl, $CH_3$, F and Br;
$R_8$ is selected from H, Cl, F and $CF_3$;
$R_9$ is selected from H, $CH_3$ and Cl;
$R_{28}$ is selected from $CF_3$, $CF_2H$, —$CH_2CH_3$, Cl, $SF_5$, Br and —C(O)H;
X is selected from C—$R_7$ and N;
$R_7$ is selected from H and F;
$R_3$ is selected from $CH_3$, $CH_2CH_3$, cyclopropyl, hydroxyethyl;
$R_4$ is selected from:

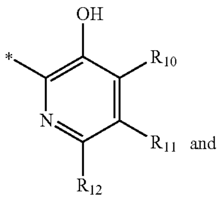 and 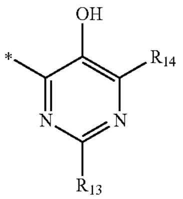

wherein
$R_{10}$ is selected from H, F, Cl, $CH_3$ and $OCF_3$;
$R_{11}$ is selected from H, Cl, F, and $CH_3$;
$R_{12}$ is selected from H, Cl and $CH_3$;
$R_{13}$ is selected from H, —S—$CH_3$ and $CH_3$;
$R_{14}$ is selected from H, $CH_3$, —$CH_2CH_3$, cyclopropyl, —$OCHF_2$, $OCF_3$ and Cl;
Y is N or CH, preferably N,
y is 0, 1 or 2;
$R_5$ is $CH_3$, or alternatively, two $R_5$ groups on adjacent carbon atoms join, along with the carbon atoms to which they are attached, to form a fused cyclobutyl ring:

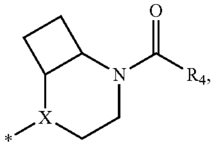

and optionally, wherein one or more H atoms of the ring:

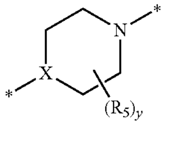

are replaced by deuterium;
* indicates a point of attachment.

Embodiment 33. A compound of formula (I), according to embodiment 1, 24 or 30, or a pharmaceutically acceptable salt thereof:

1h

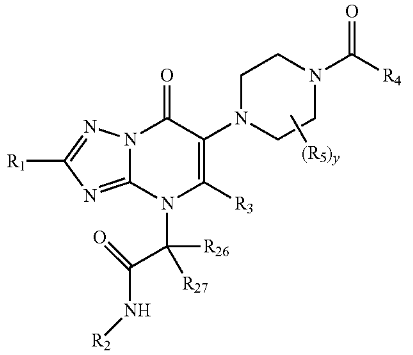

wherein $R_1$ is selected from:

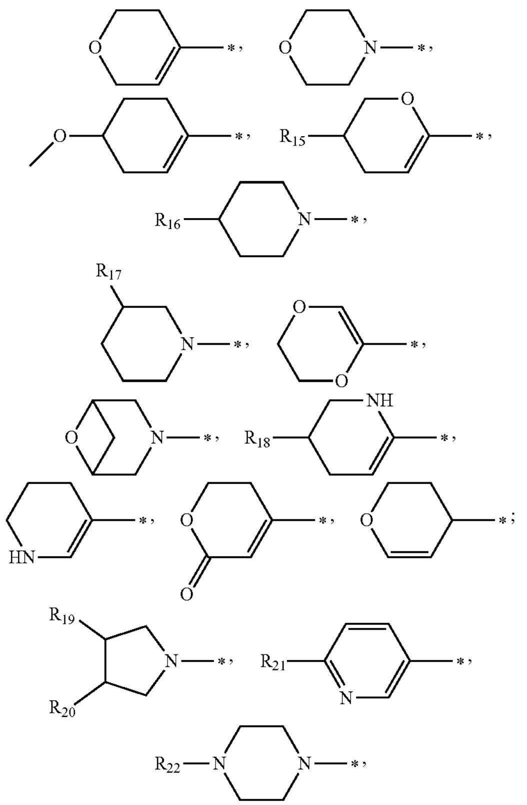

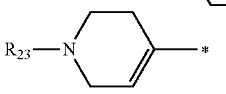 and 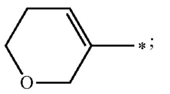

$R_{15}$ is H or F;

$R_{16}$ is H or $R_{25}(R_{24})N$—;

$R_{17}$ is H or F;

$R_{18}$ is H or F;

$R_{19}$ is H or F;

$R_{20}$ is H or F;

$R_{21}$ is H or $CH_3$;

$R_{22}$ is H, $CF_3$, $CHF_2CH_2$, HOC(O)—$CH_2$—, $H_3C$—C(O)—, $(H_3C)_3C$—O—C(O)—;

$R_{23}$ is H, $CF_3$, $CHF_2CH_2$—, $(H_3C)_3C$—O—C(O)—;

$R_{24}$ is $CH_3$;

$R_{25}$ is $CHF_2CH_2$—;

$R_{26}$ is $CH_3$, H or deuterium;

$R_{27}$ is H or deuterium;

$R_2$ is the moiety:

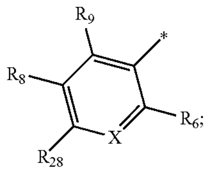

wherein $R_6$ is selected from H, Cl, $CH_3$, F, and Br;

$R_8$ is selected from H, Cl, F and $CF_3$;

$R_8$ is selected from H, $CH_3$ and Cl;

$R_{28}$ is selected from $CF_3$, $CF_2H$, —$CH_2CH_3$, Cl, $SF_5$, Br and —C(O)H;

X is selected from C—$R_7$ and N;

$R_7$ is selected from H and F;

$R_3$ is selected from $CH_3$, $CH_2CH_3$, cyclopropyl and hydroxyethyl;

$R_4$ is selected from:

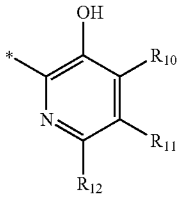 and 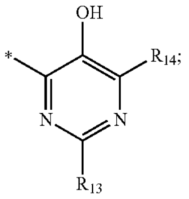

wherein $R_{10}$ is selected from H, F, Cl, $CH_3$ and $OCF_3$;

$R_{11}$ is selected from H, Cl, F, and $CH_3$;

$R_{12}$ is selected from H, Cl and $CH_3$;

$R_{13}$ is selected from H and $CH_3$;

$R_{14}$ is selected from H, $CH_3$, —$CH_2CH_3$, cyclopropyl, —$OCHF_2$, $OCF_3$ and Cl;

y is 0, 1 or 2;

$R_5$ is $CH_3$; or alternatively, two $R_5$ groups on adjacent carbon atoms join, along with the carbon atoms to which they are attached, to form a fused cyclobutyl ring:

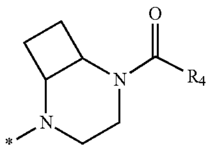

and

* indicates a point of attachment.

Embodiment 34. A compound of formula (I), or a pharmaceutically acceptable salt thereof, according to any of embodiments 1 to 33, wherein $R_1$ is selected from:

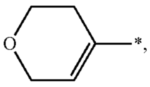, 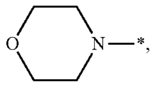, 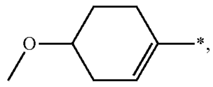,

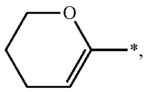, 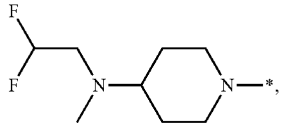,

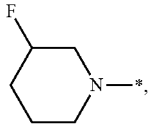, 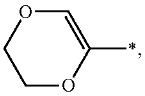, 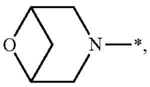,

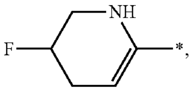, 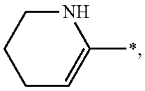, 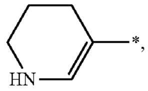,

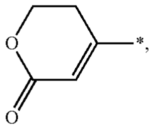, 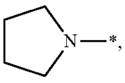, 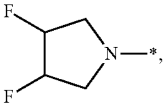,

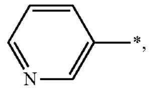, 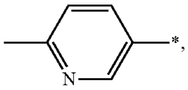,

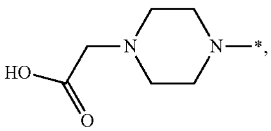, 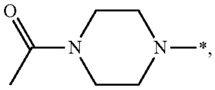,

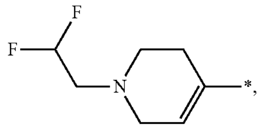,

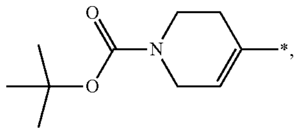, 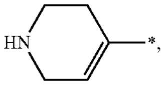,

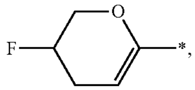, 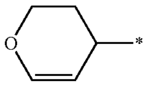 and

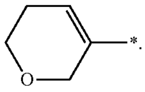.

Embodiment 35. A compound of formula (I), or a pharmaceutically acceptable salt thereof, according to embodiment 34, wherein $R_1$ is selected from:

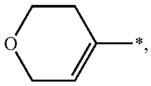, 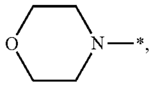,

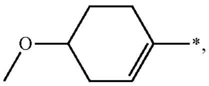, 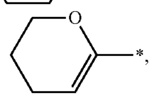,

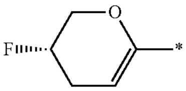 and 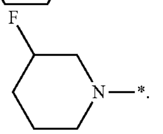.

Embodiment 36. A compound of formula (I), or a pharmaceutically acceptable salt thereof, according to embodiment 35, wherein $R_1$ is selected from:

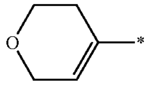 and 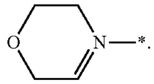.

Embodiment 37. A compound of formula (I), or a pharmaceutically acceptable salt thereof, according to embodiment 36, wherein $R_1$ is:

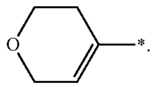.

Embodiment 38. A compound of formula (I), or a pharmaceutically acceptable salt thereof, according to any of embodiments 1-37, wherein $R_{28}$ is selected from $CF_3$, $SF_5$ and Br.

Embodiment 39. A compound of formula (I), or a pharmaceutically acceptable salt thereof, according to embodiments 38, wherein $R_{28}$ is selected from $CF_3$.

Embodiment 40. A compound of formula (I), or a pharmaceutically acceptable salt thereof, according to any of embodiments 1-39, wherein X is $CR_7$.

Embodiment 41. A compound of formula (I), or a pharmaceutically acceptable salt thereof, according to any of embodiments 1-40, wherein $R_7$ is H.

Embodiment 42. A compound of formula (I), or a pharmaceutically acceptable salt thereof, according to any of embodiments 1-41, wherein $R_6$ is Cl or $CH_3$.

Embodiment 43. A compound of formula (I), or a pharmaceutically acceptable salt thereof, according to embodiment 42, wherein $R_6$ is Cl.

Embodiment 44. A compound of formula (I), or a pharmaceutically acceptable salt thereof, according to any of embodiments 1-43, wherein $R_8$ is F or H.

Embodiment 45. A compound of formula (I), or a pharmaceutically acceptable salt thereof, according to embodiment 44, wherein $R_8$ is H.

Embodiment 46. A compound of formula (I), or a pharmaceutically acceptable salt thereof, according to any of embodiments 1-45, wherein $R_9$ is H.

Embodiment 47. A compound of formula (I), or a pharmaceutically acceptable salt thereof, according to any of embodiments 1-46, wherein $R_{26}$ is H.

Embodiment 48 A compound of formula (I), or a pharmaceutically acceptable salt thereof, according to any of embodiments 1-47, wherein $R_{27}$ is H.

Embodiment 49. A compound of formula (I), or a pharmaceutically acceptable salt thereof, according to embodiment 1, wherein $R_{26}$ and $R_{27}$ are both deuterium.

Embodiment 50. A compound of formula (I), or a pharmaceutically acceptable salt thereof, according to any of embodiments 1-49, wherein $R_3$ is $-CH_2-CH_3$.

Embodiment 51. A compound of formula (I), or a pharmaceutically acceptable salt thereof, according to any of embodiments 1-50, wherein y is 0.

Embodiment 52. A compound of formula (I), or a pharmaceutically acceptable salt thereof, according to any of embodiments 1-51, wherein the moiety:

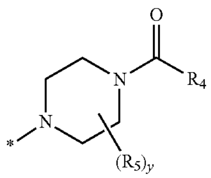
is selected from
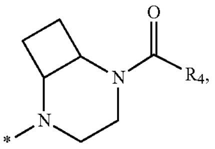
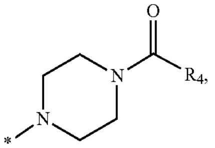
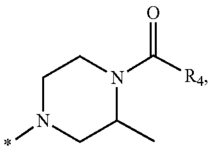
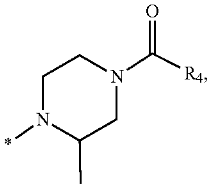
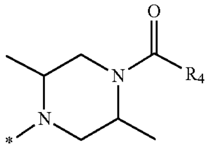
and
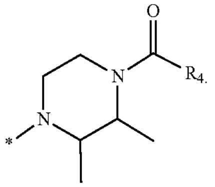
Embodiment 53. A compound of formula (I), or a pharmaceutically acceptable salt thereof, according to embodiment 52, wherein the moiety:
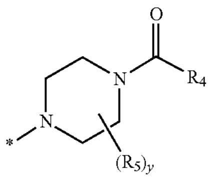
is selected from:
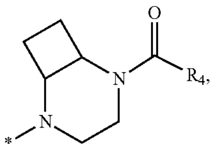
in particular
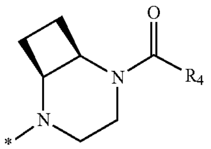
or
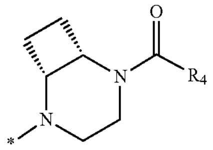
or
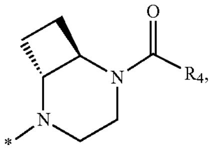
or
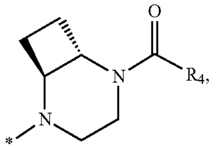
or is selected from:
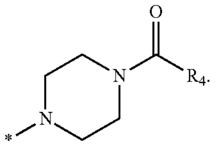
Embodiment 54. A compound of formula (I), or a pharmaceutically acceptable salt thereof, according to embodiments 1-51, wherein the moiety:
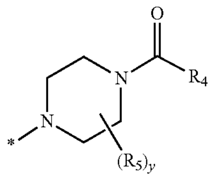
is selected from:
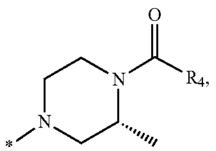

-continued
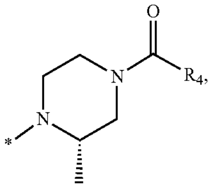
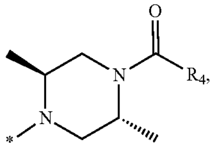
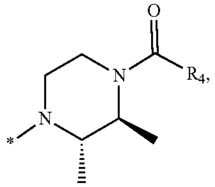
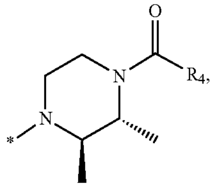
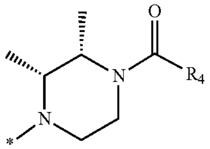
and
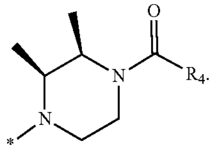
Embodiment 55. A compound of formula (I), or a pharmaceutically acceptable salt thereof, according to any of embodiments 1-54, wherein the moiety:
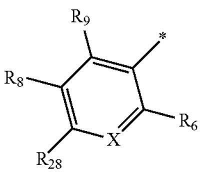
is selected from:
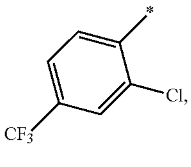
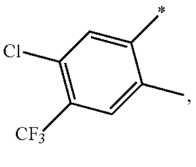
-continued
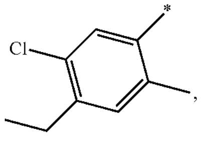
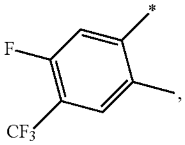
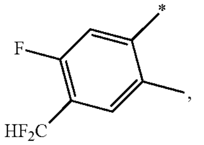
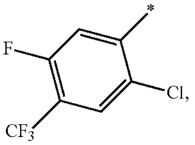
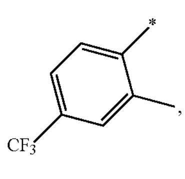
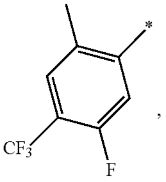
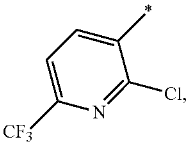
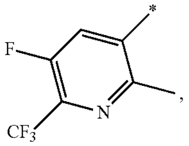
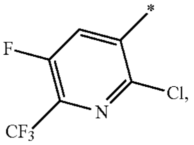
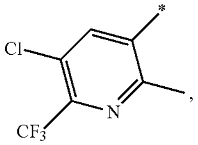
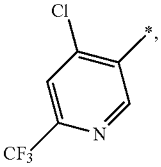
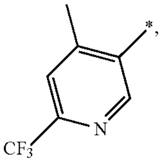
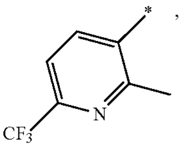
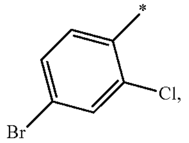
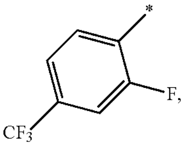
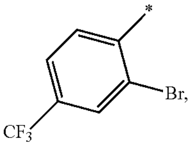
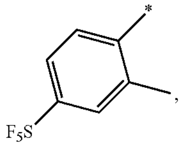
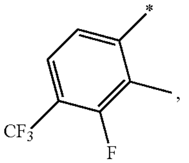
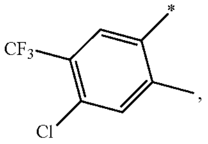
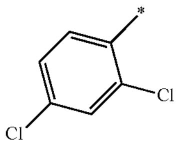
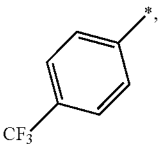
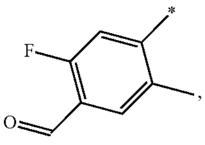
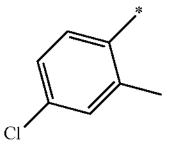
and -continued

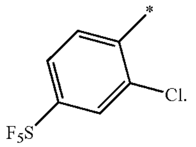

Embodiment 56. A compound of formula (I), or a pharmaceutically acceptable salt thereof, according to embodiment 55, wherein the moiety:

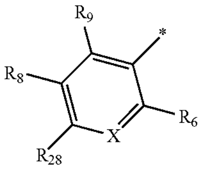

is selected from:

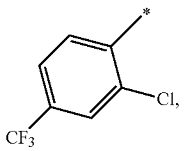

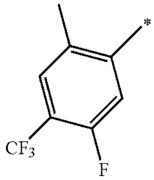
,

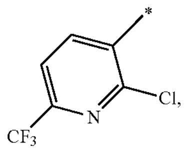

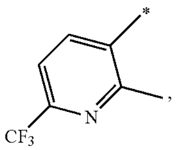

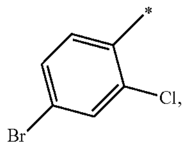

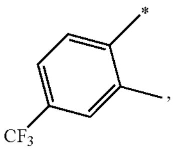

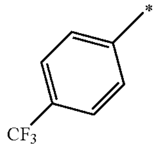
,

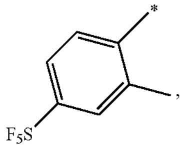

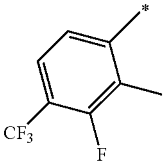
and

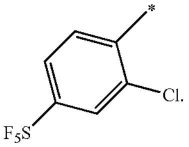

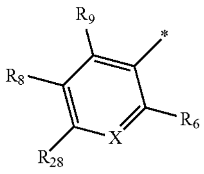

is selected from:

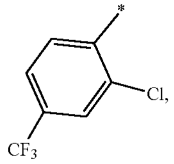

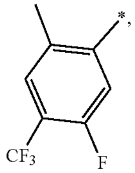

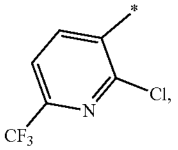

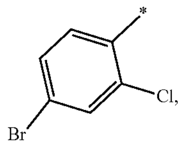

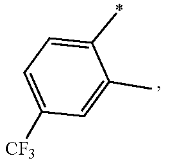

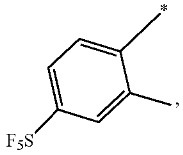

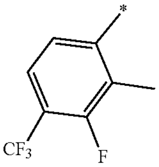
and

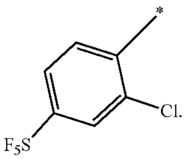

Embodiment 57. A compound of formula (I), or a pharmaceutically acceptable salt thereof, according to embodiment 55, wherein the moiety:

Embodiment 58. A compound of formula (I), or a pharmaceutically acceptable salt thereof, according to embodiment 56, wherein the moiety:

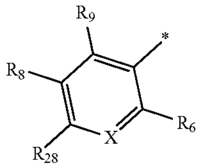

is selected from:

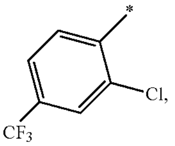 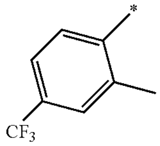 and 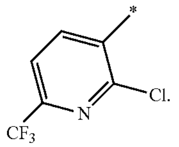

Embodiment 59. A compound of formula (I), or a pharmaceutically acceptable salt thereof, according to any of embodiments 1-58, wherein $R_{10}$ is H, F or Cl.

Embodiment 60. A compound of formula (I), or a pharmaceutically acceptable salt thereof, according to any of embodiments 1-59, wherein $R_{11}$ is H or $CH_3$.

Embodiment 61. A compound of formula (I), or a pharmaceutically acceptable salt thereof, according to any of embodiments 1-60, wherein $R_{12}$ is H.

Embodiment 62. A compound of formula (I), or a pharmaceutically acceptable salt thereof, according to any of embodiments 1-61, wherein $R_{13}$ is H.

Embodiment 63. A compound of formula (I), or a pharmaceutically acceptable salt thereof, according to any of embodiments 1-62, wherein $R_{14}$ is $CH_3$ or H.

Embodiment 64. A compound of formula (I), or a pharmaceutically acceptable salt thereof, according to any of embodiments 1-63, wherein $R_{14}$ is $CH_3$.

Embodiment 65. A compound of formula (I), or a pharmaceutically acceptable salt thereof, according to any of embodiments 1-64, wherein $R_4$ is selected from:

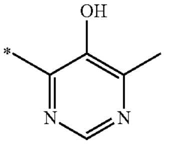 , 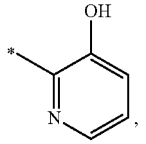 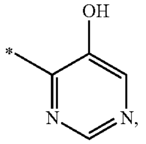

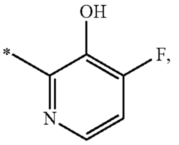 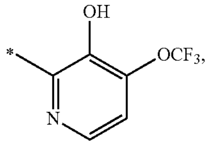

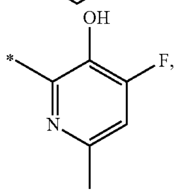 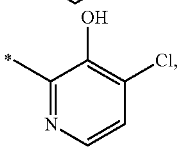

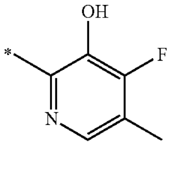 , 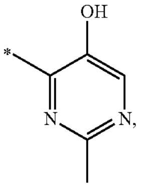 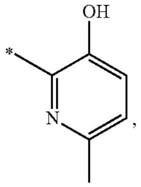

-continued

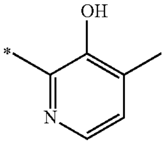 and 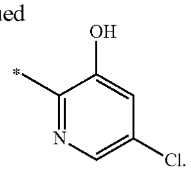

Embodiment 66. A compound of formula (I), or a pharmaceutically acceptable salt thereof, according to embodiment 65, wherein $R_4$ is selected from:

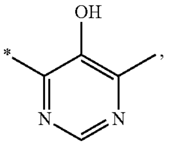 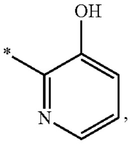 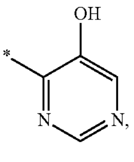

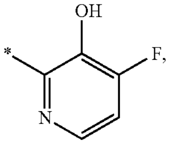 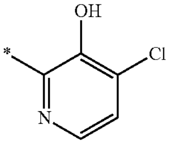 and 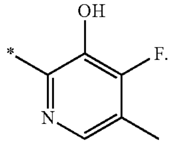

Embodiment 67. A compound of formula (I), or a pharmaceutically acceptable salt thereof, according to embodiment 66, wherein $R_4$ is selected from:

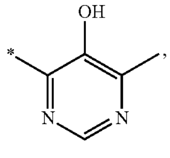 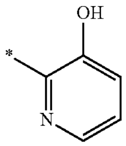 and 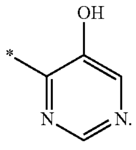

Embodiment 68. A compound of formula (I), or a pharmaceutically acceptable salt thereof, according to any of embodiments 1 and 24 to 31, wherein $R_1$ is selected from:

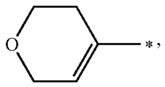 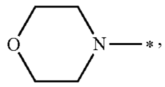

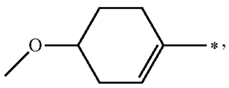 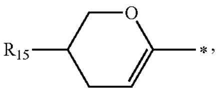

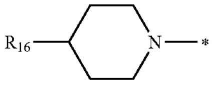

, 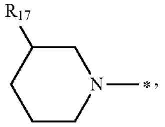 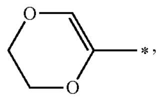

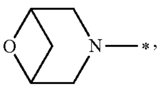 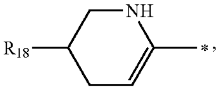

-continued

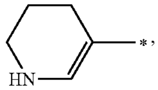
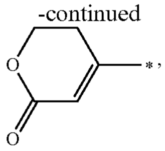
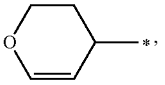
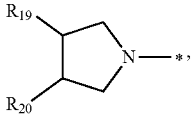
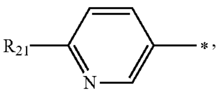
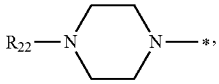
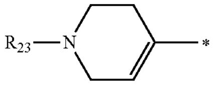
and
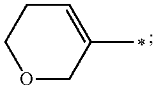

$R_{15}$ is H or F;
$R_{16}$ is H or $R_{25}(R_{24})N$—;
$R_{17}$ is H or F;
$R_{18}$ is H or F;
$R_{19}$ is H or F;
$R_{20}$ is H or F;
$R_{21}$ is H or $CH_3$;
$R_{22}$ is H, $CF_3$, $CHF_2CH_2$, HOC(O)—$CH_2$—, $H_3C$—C(O)—, $(H_3C)_3C$—O—C(O)—;
$R_{23}$ is H, CF3, $CHF_2CH_2$—, $(H_3C)_3C$—O—C(O)—;
$R_{24}$ is $CH_3$;
$R_{25}$ is $CHF_2CH_2$—; and
$R_4$ is selected from:

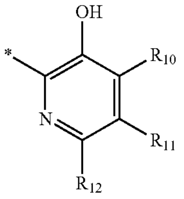
and
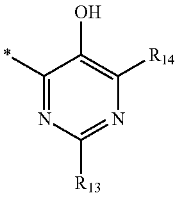

wherein
$R_{10}$ is selected from H, F, Cl, $CH_3$ and $OCF_3$;
$R_{11}$ is selected from H, Cl, F, and $CH_3$;
$R_{12}$ is selected from H, Cl and $CH_3$;
$R_{13}$ is selected from H and $CH_3$;
$R_{14}$ is selected from H, $CH_3$, —$CH_2CH_3$, cyclopropyl, —$OCHF_2$, $OCF_3$ and Cl;
or a pharmaceutically acceptable salt thereof.

Embodiment 69. A compound of formula (I), or a pharmaceutically acceptable salt thereof, according to any of embodiments 1 and 24 to 31, wherein $R_1$ is selected from:

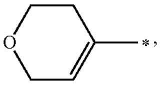
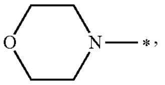
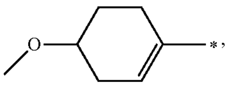
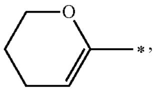
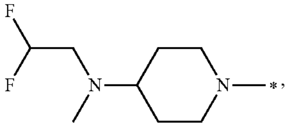

-continued

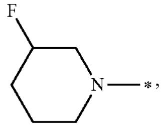
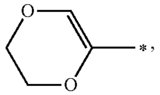
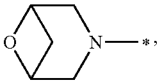
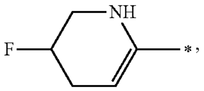
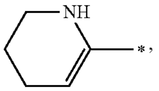
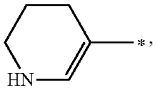
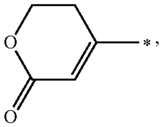
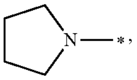
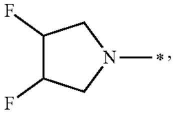
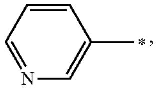
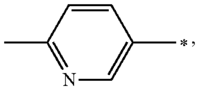
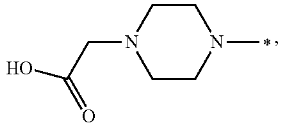
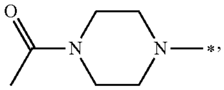
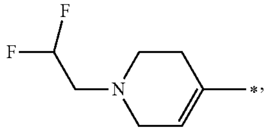
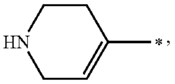
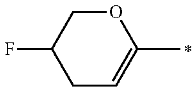
and
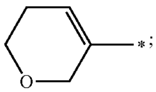

and the moiety:

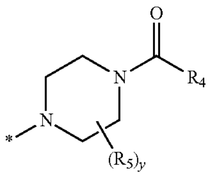

is selected from:

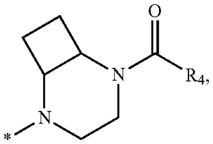
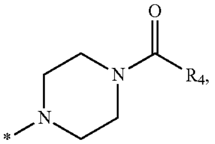
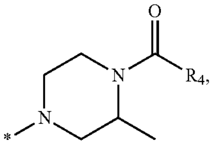
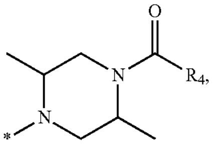

-continued
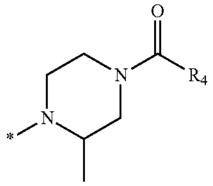 and 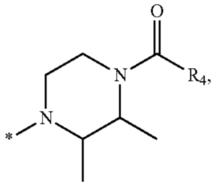
in particular wherein
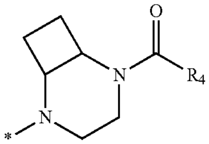 is 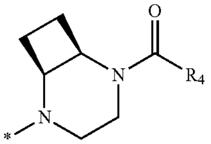 or
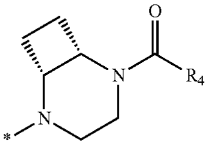 or 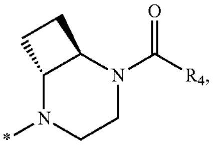 or
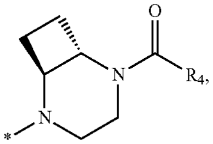 and 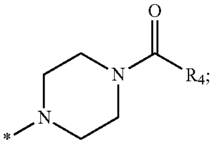
the moiety:
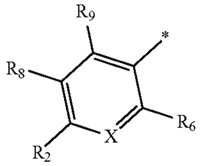
is selected from:
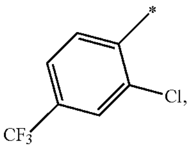 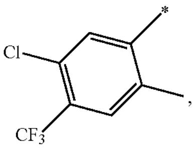
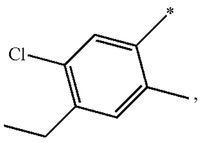 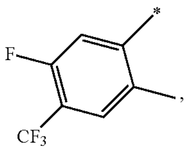
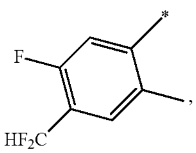 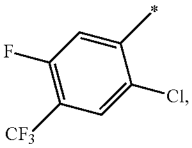
-continued
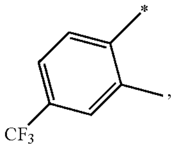 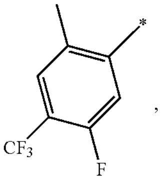
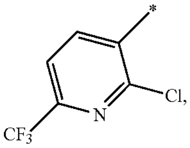 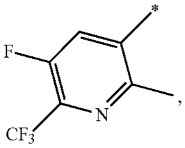
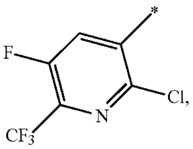 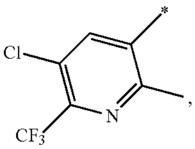
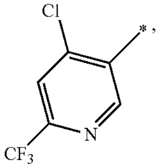 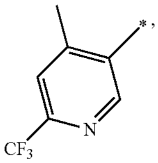
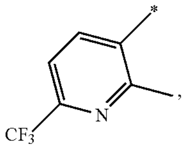 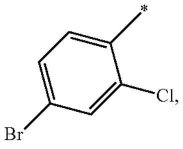
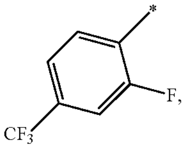 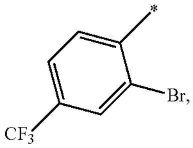
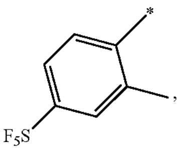 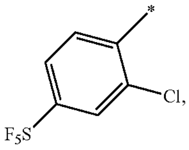
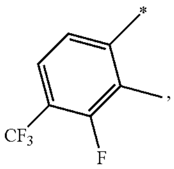 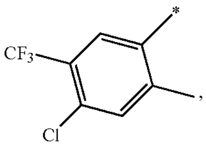
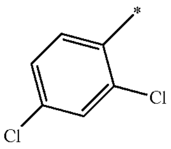 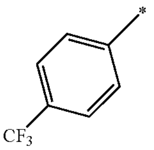 and
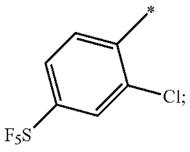

and
$R_4$ is selected from:
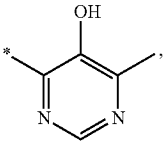
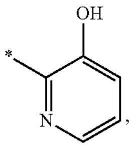
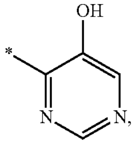
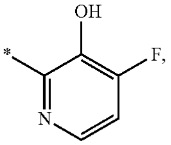
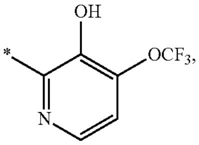
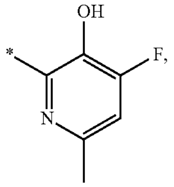
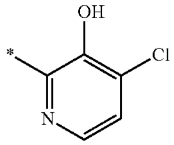
and
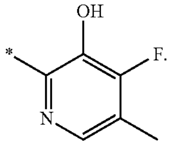
Embodiment 70. A compound of formula (I), or a pharmaceutically acceptable salt thereof, according to any of embodiments 1 and 24 to 31, wherein $R_1$ is selected from:
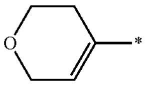
and
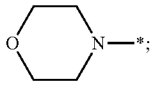
the moiety:
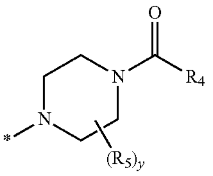
is selected from:
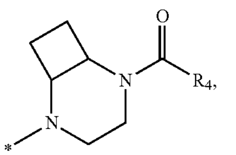
particularly
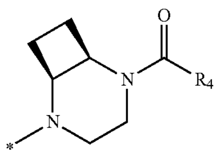
or
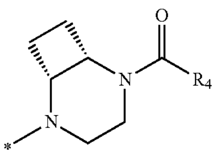
or
-continued
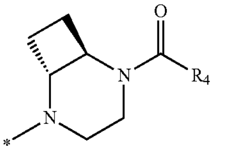
or
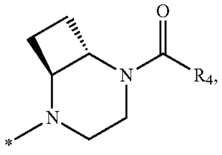
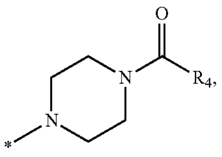
and
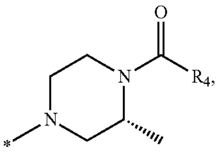
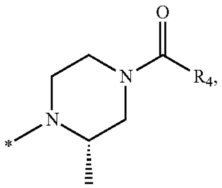
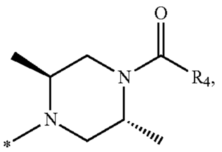
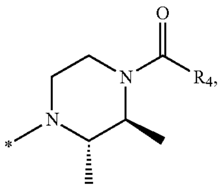
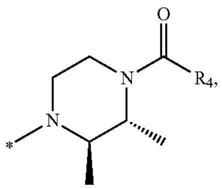
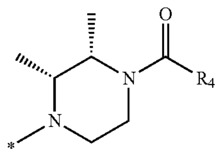
and
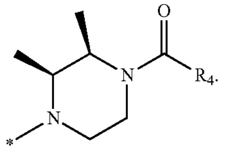
the moiety:
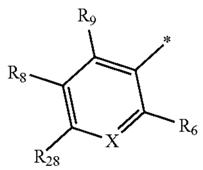
is selected from:
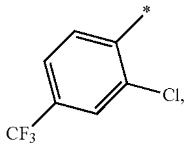
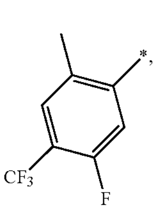
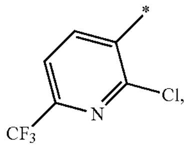

-continued
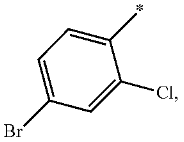 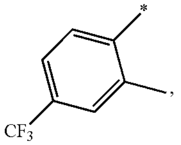 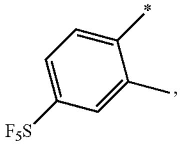
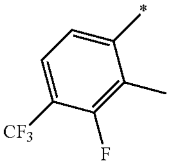 and 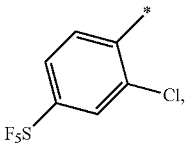 in particular
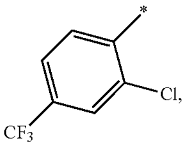 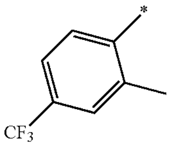 and
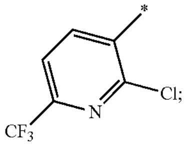
and $R_4$ is selected from:
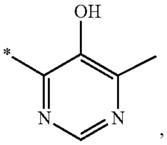 , 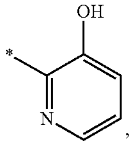 , 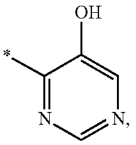
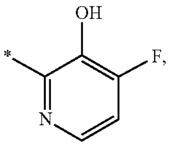 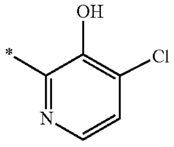 and
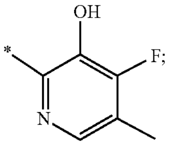
in particular:
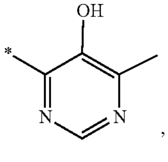 , 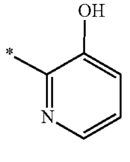 and 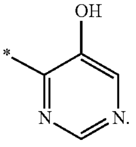
Embodiment 71. A compound of formula (I), or a pharmaceutically acceptable salt thereof, according to any of embodiments 1, 24, 30 and 31, wherein the compound is selected from:
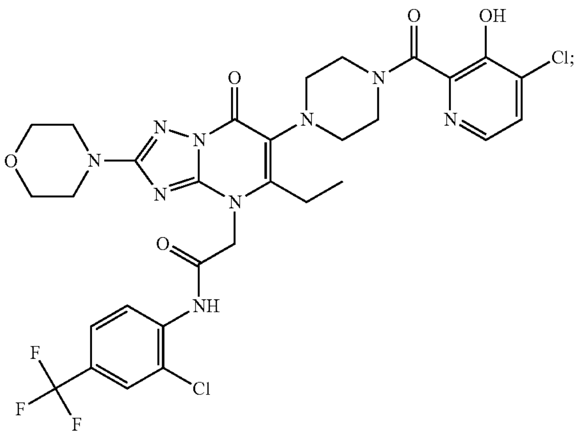
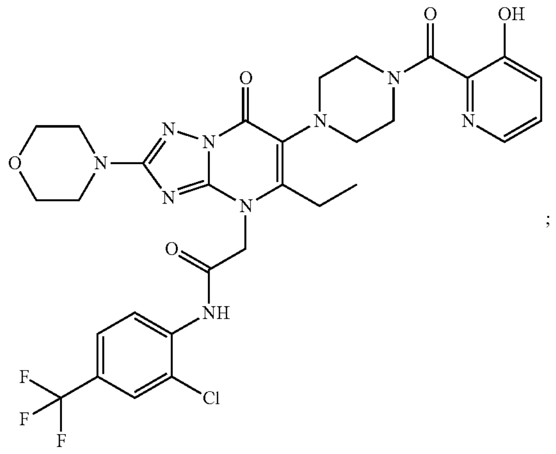
;
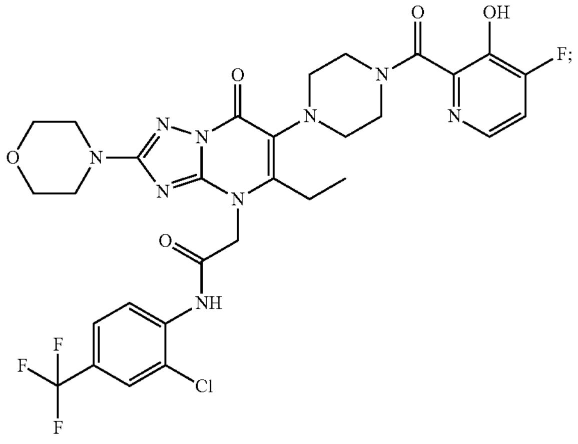

-continued
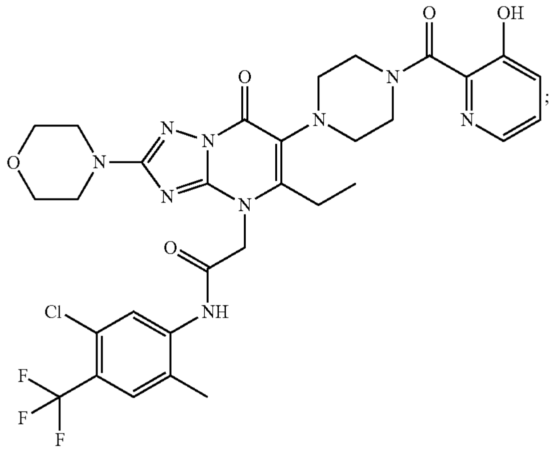
;
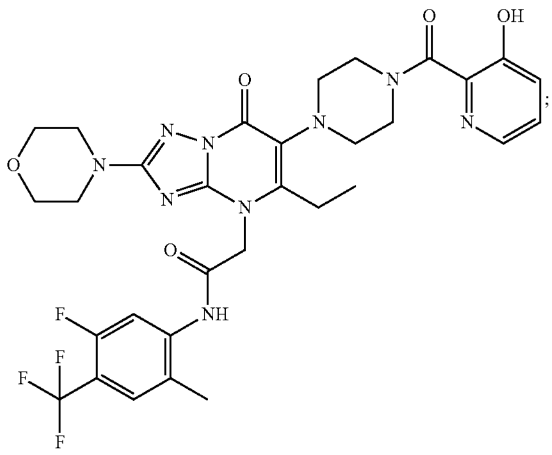
;
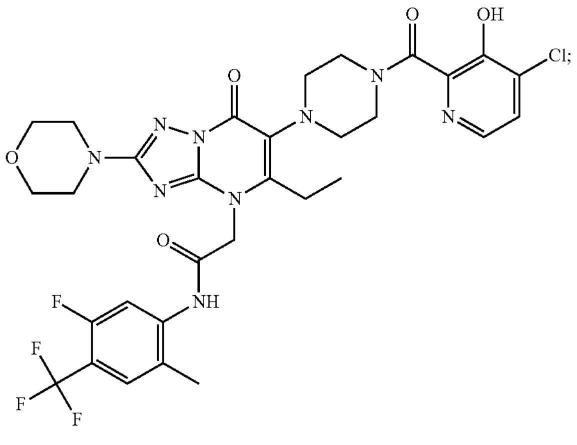
-continued
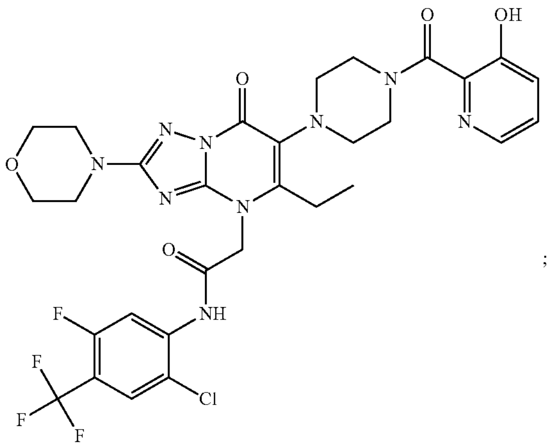
;
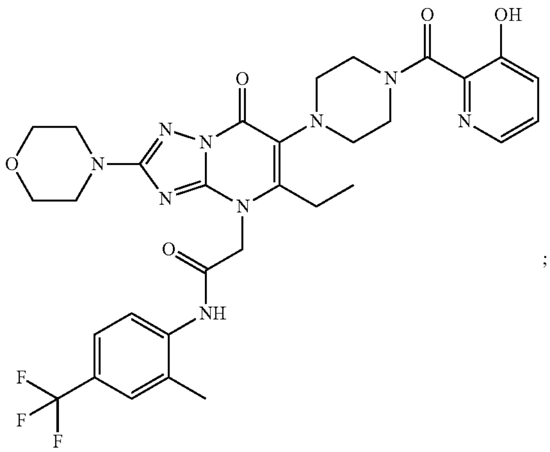
;
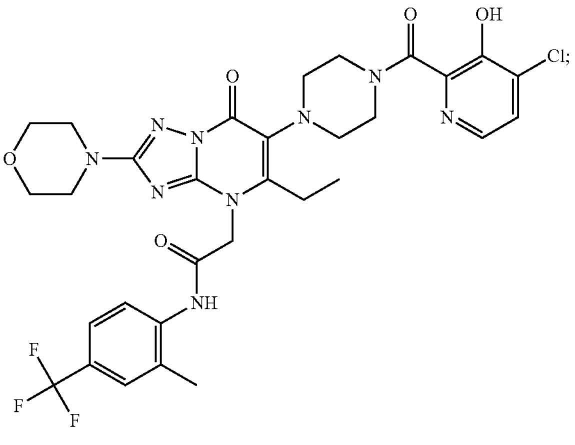

-continued
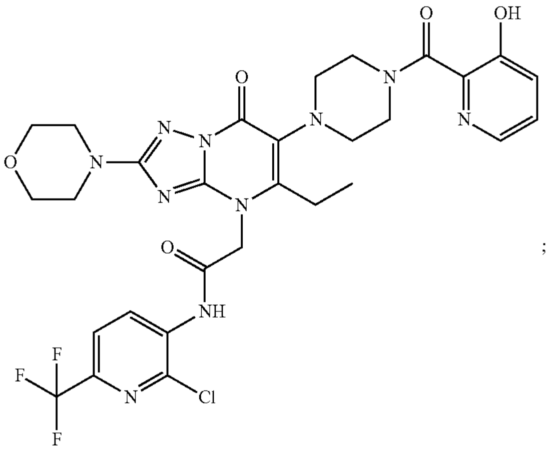
;
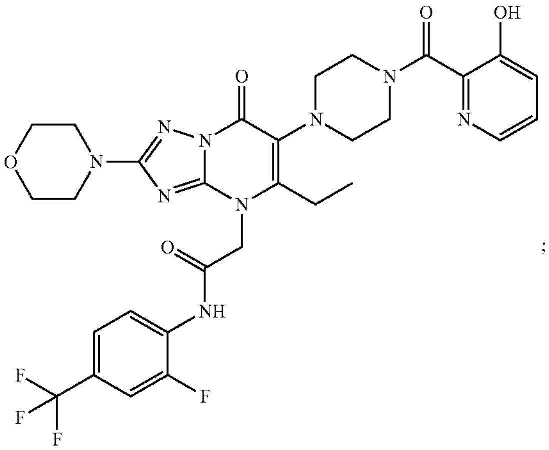
;
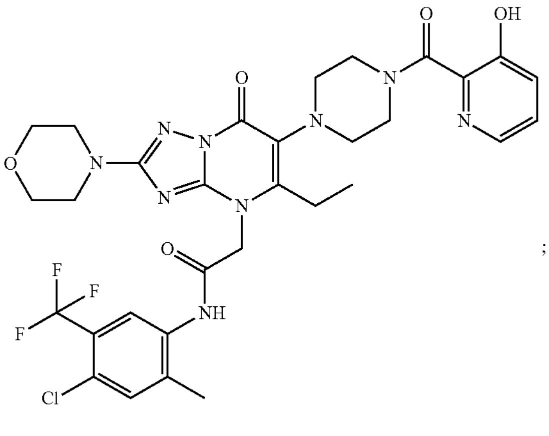
;
-continued
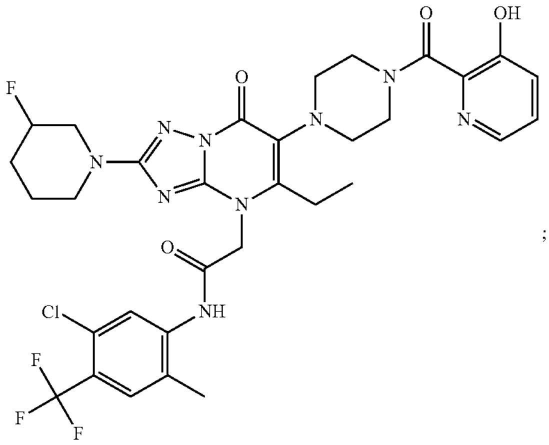
;
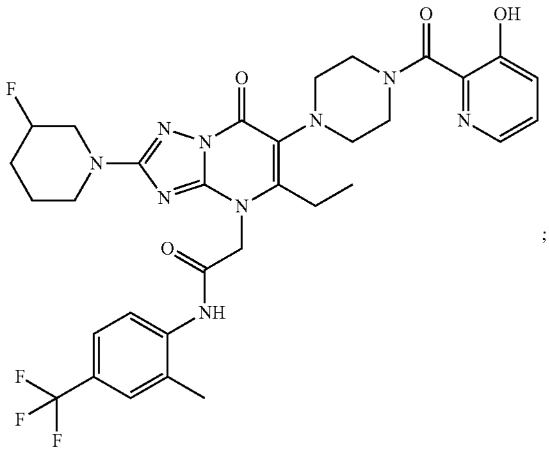
;
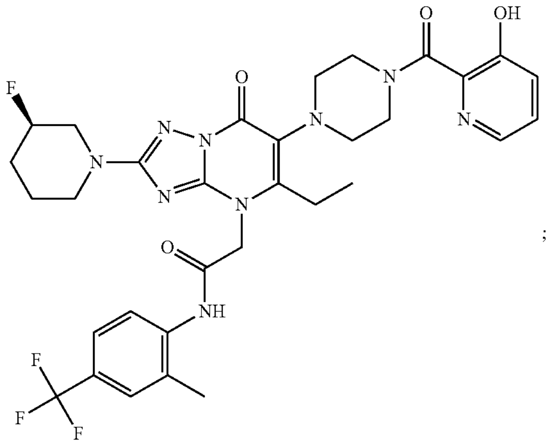
;

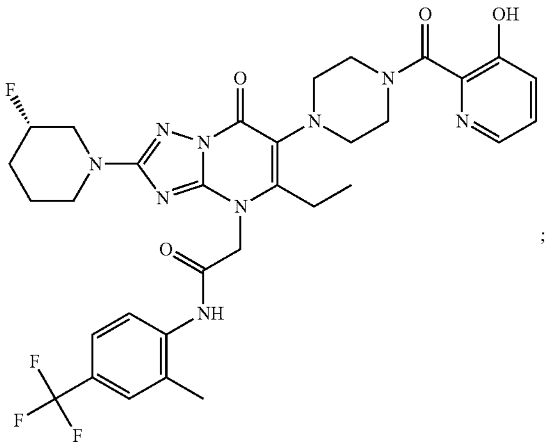
;
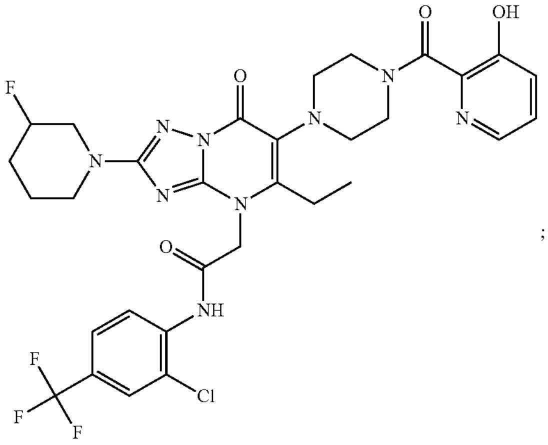
;
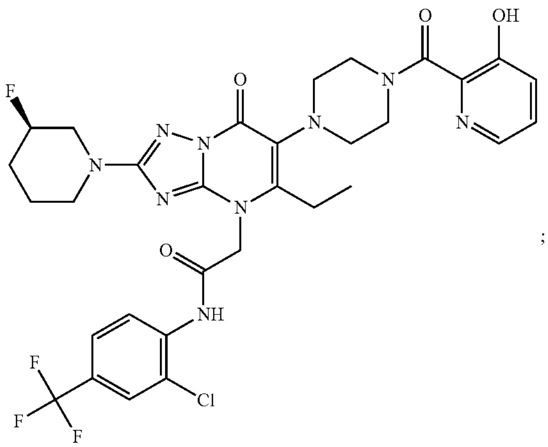
;
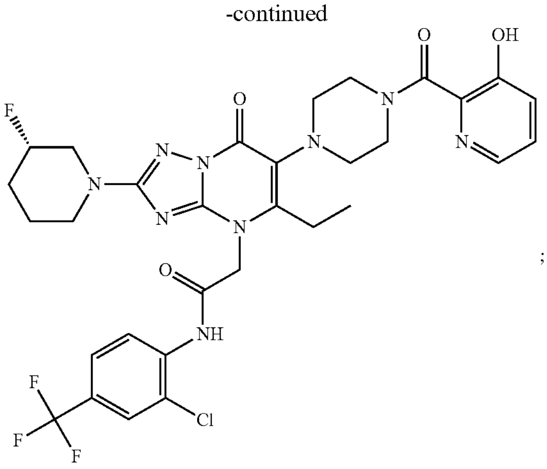
;
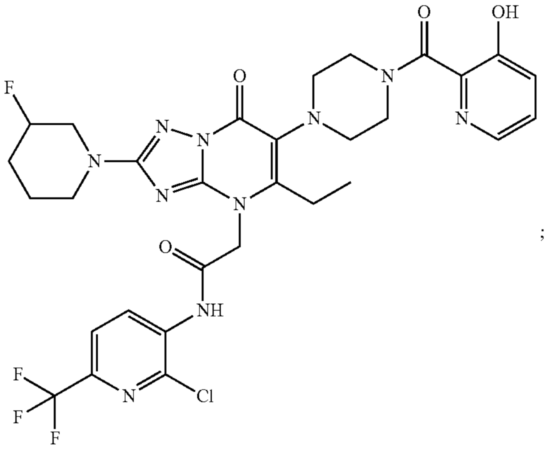
;
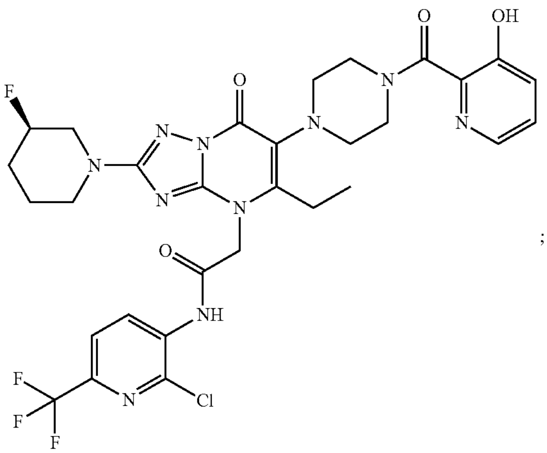
;

-continued
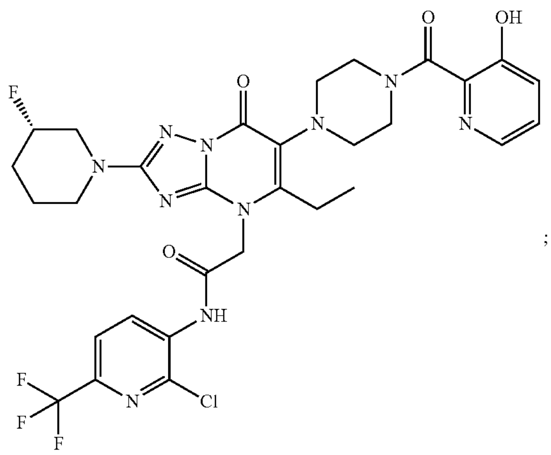
;
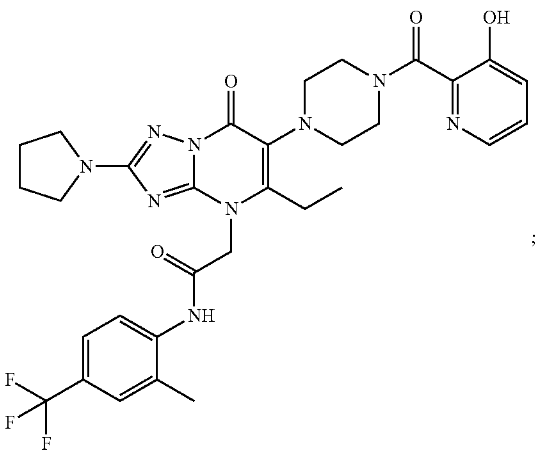
;
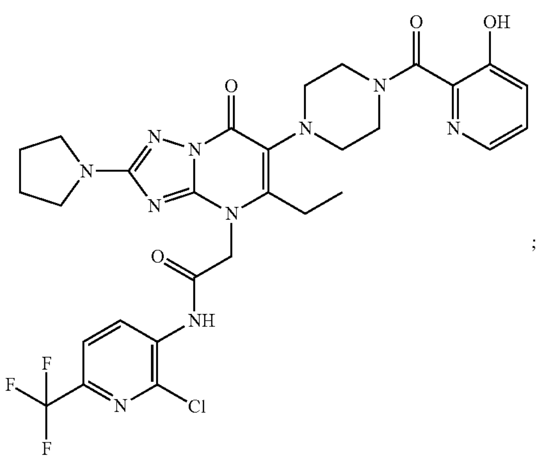
;
-continued
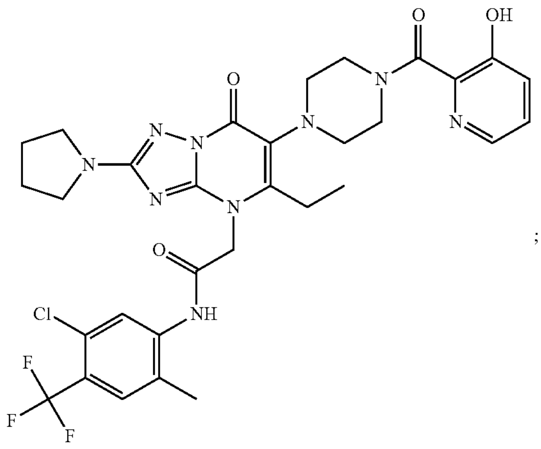
;
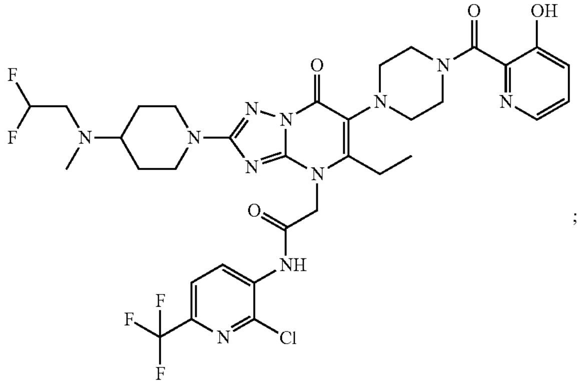
;
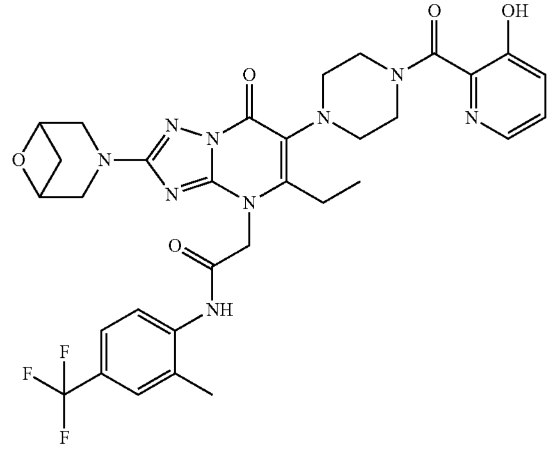
;
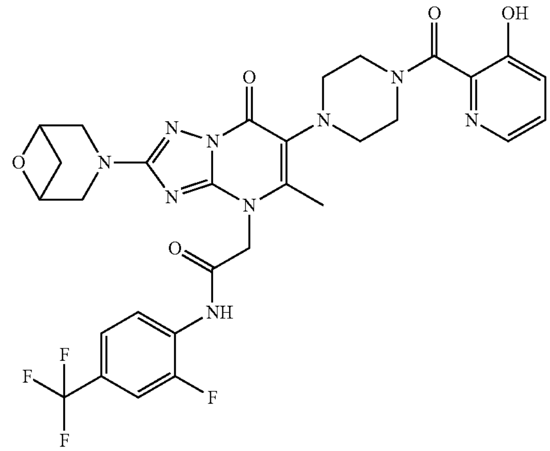
;

-continued
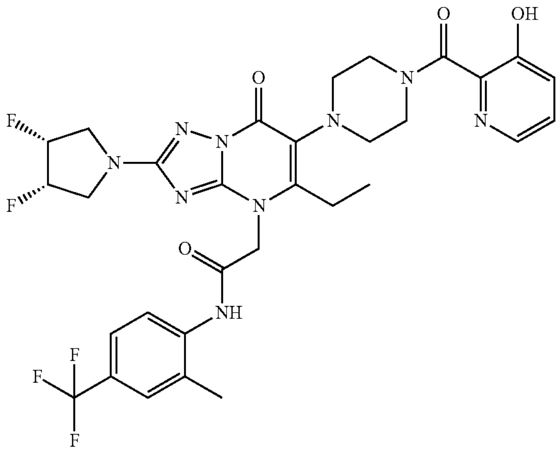
;
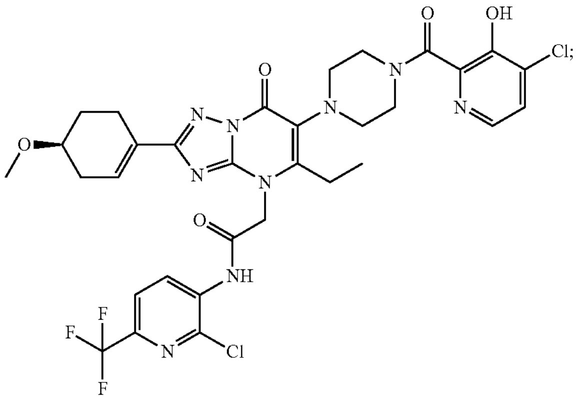
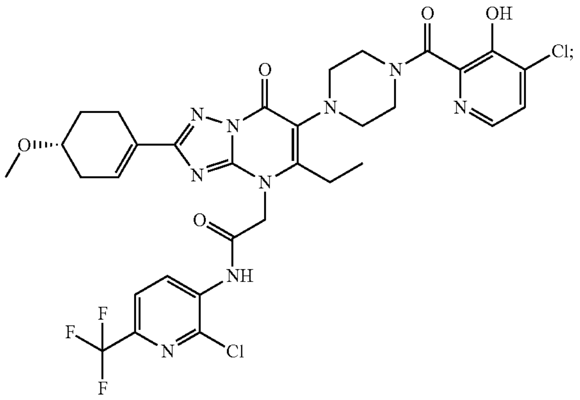
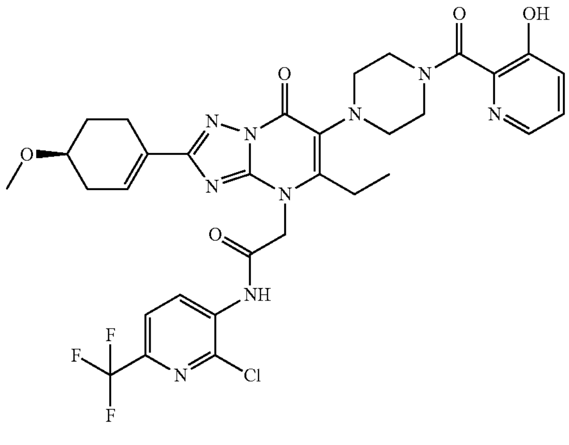
;
-continued
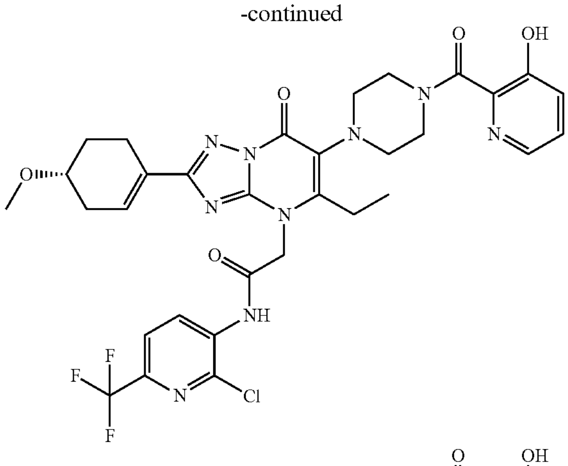
;
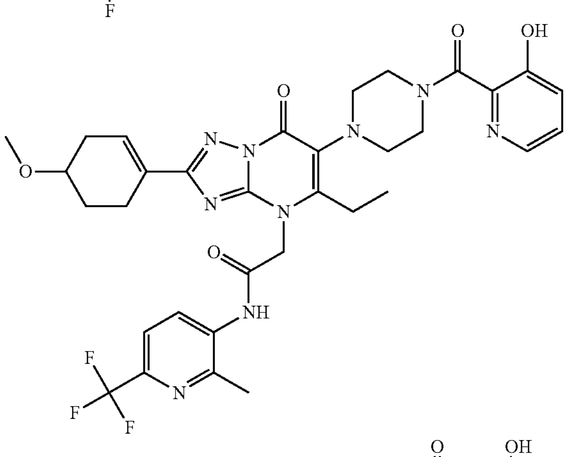
;
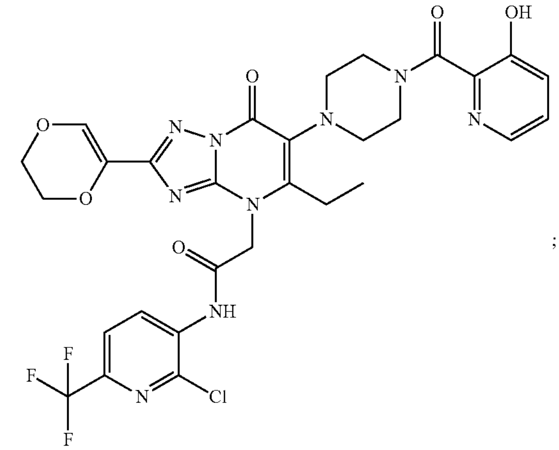
;
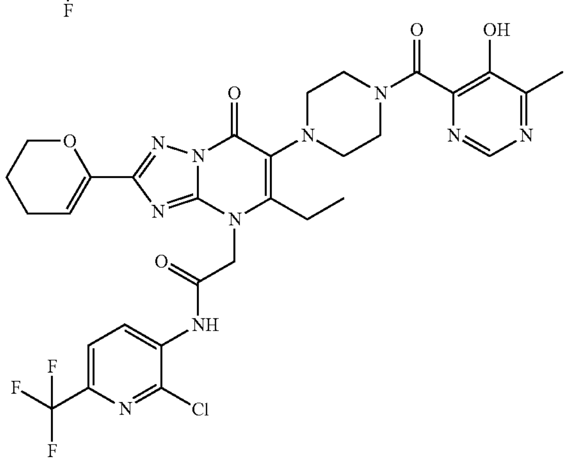
;

-continued
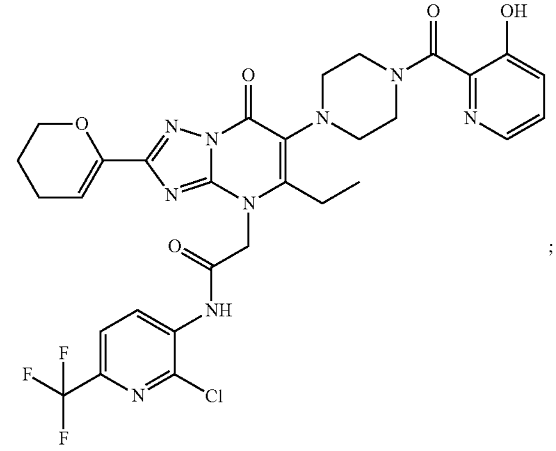
;
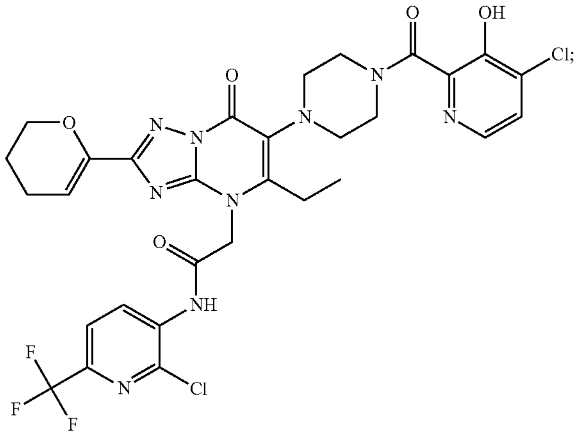
;
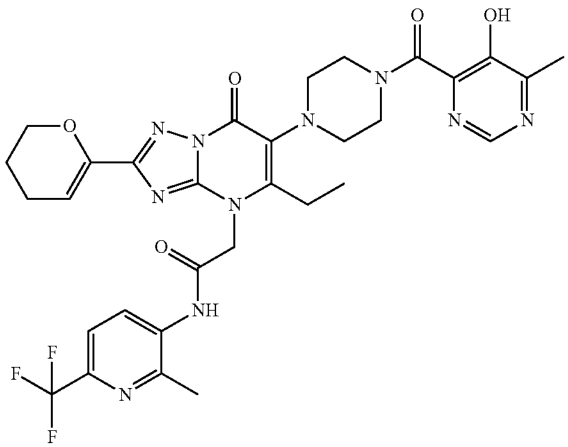
;
-continued
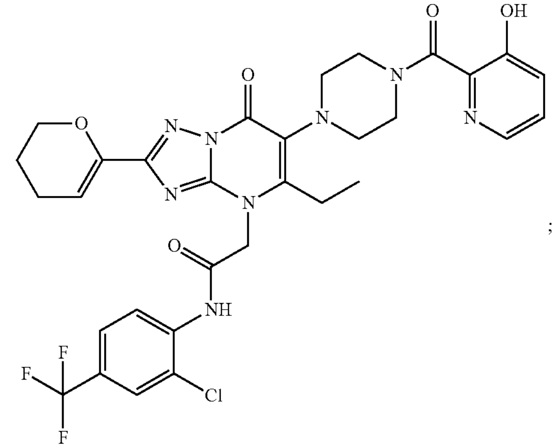
;
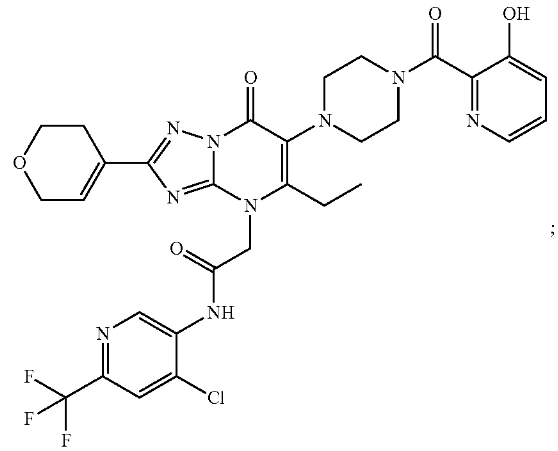
;
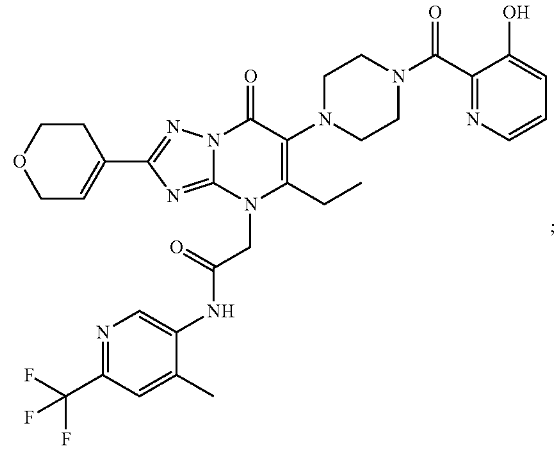
;

-continued
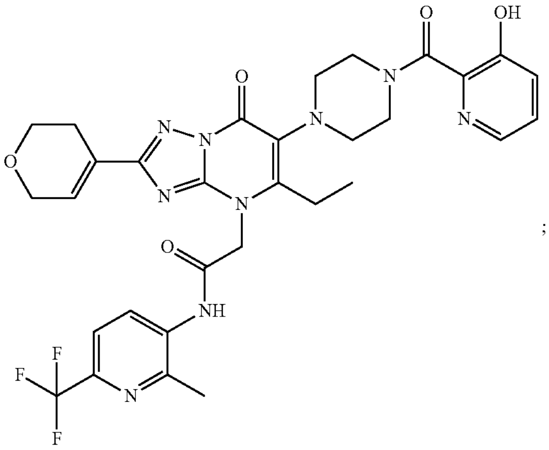
;
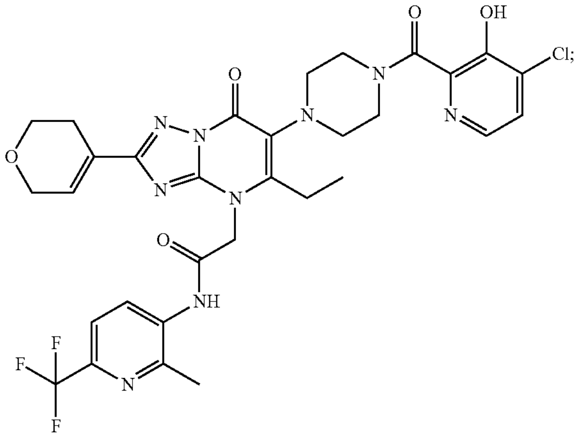
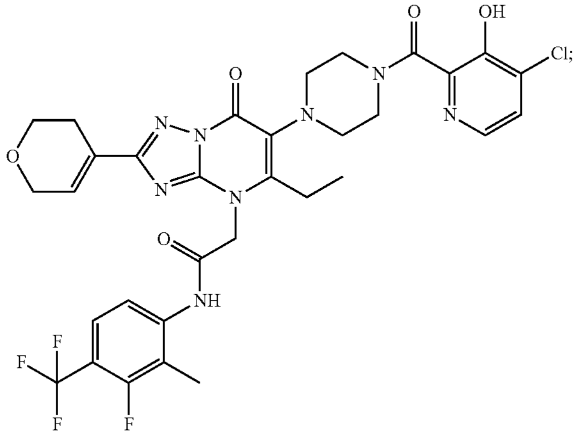
-continued
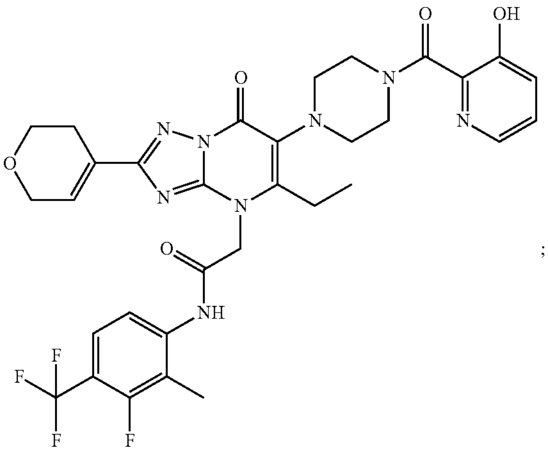
;
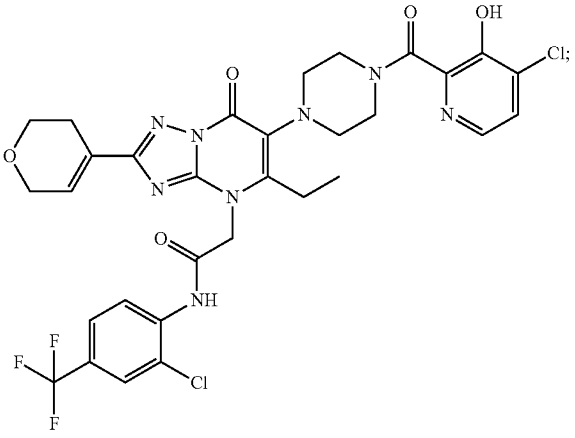
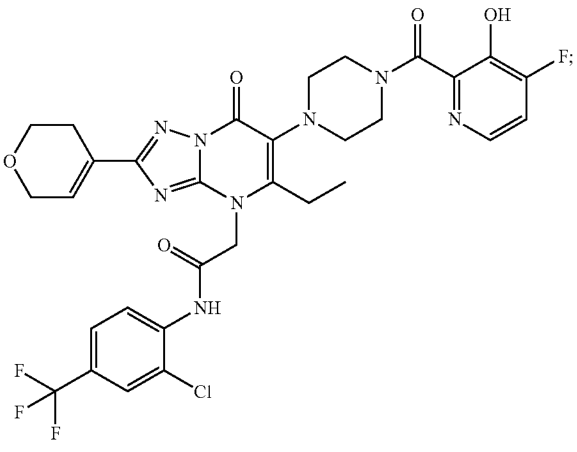

-continued
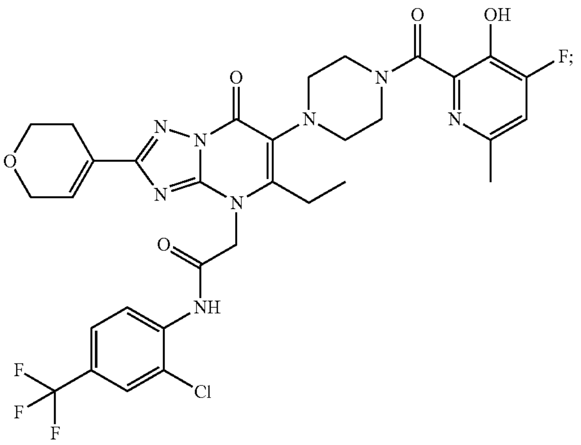
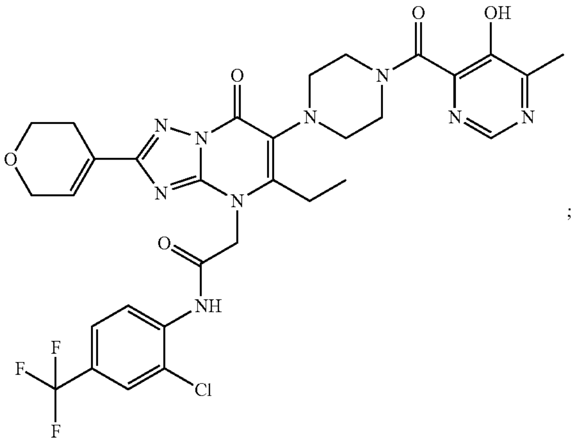
;
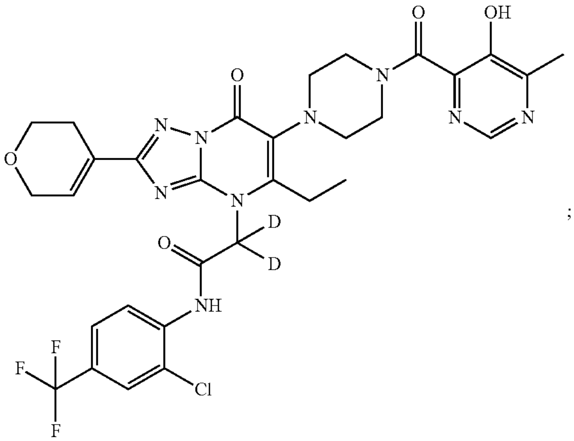
;
-continued
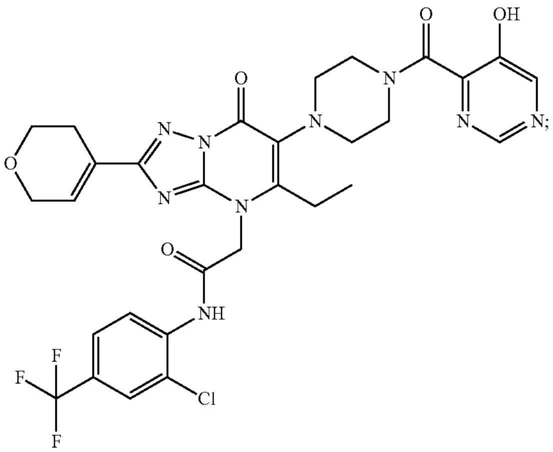
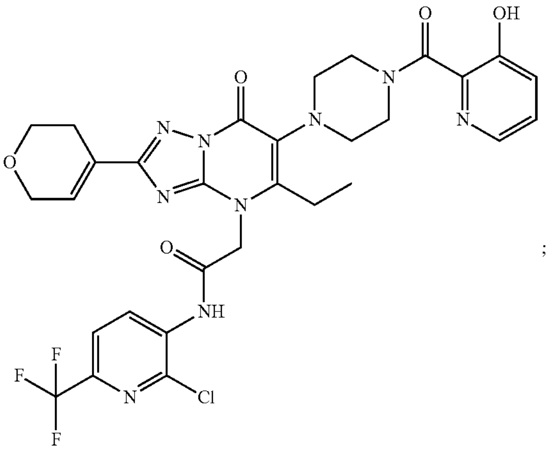
;
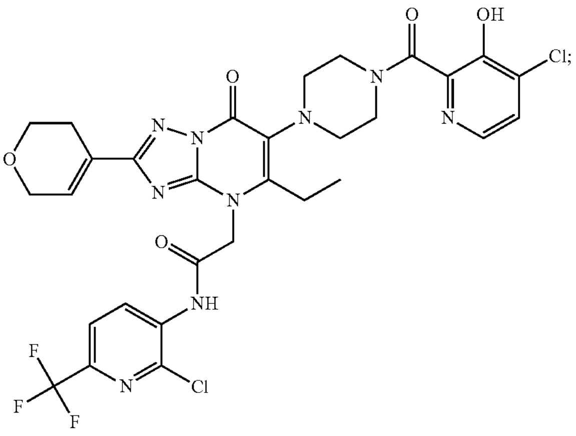

-continued
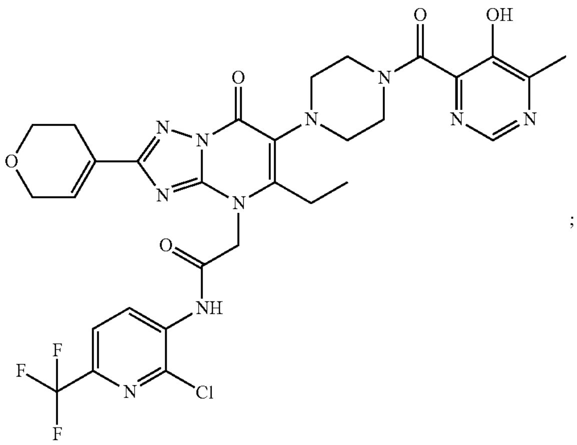
;
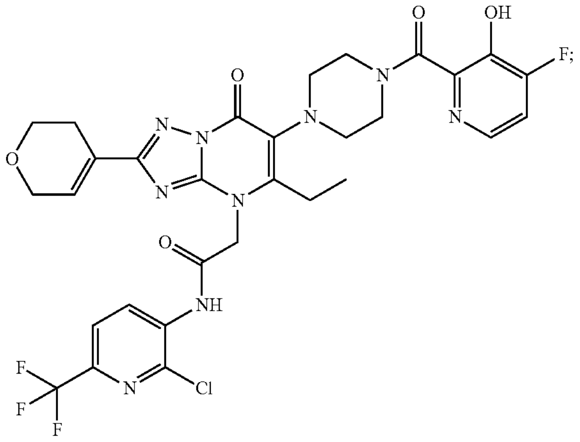
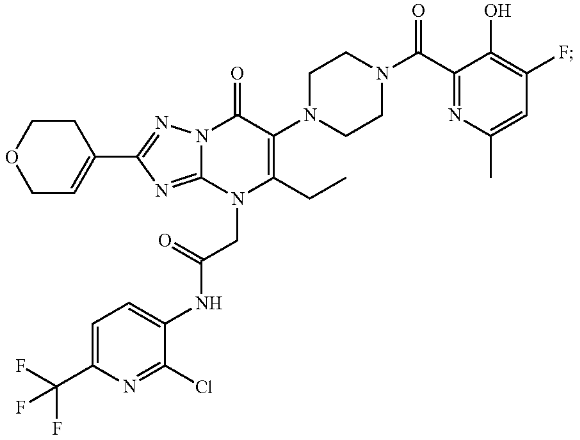
-continued
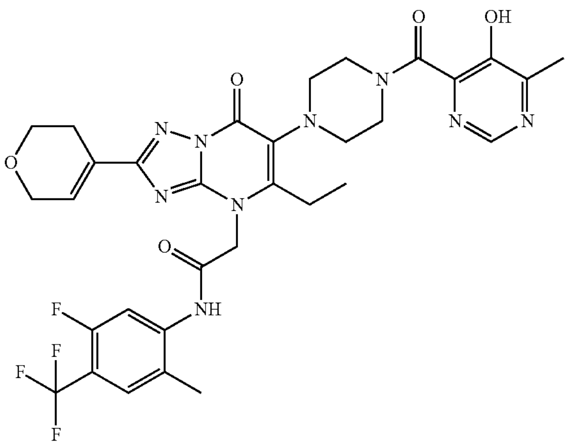
;
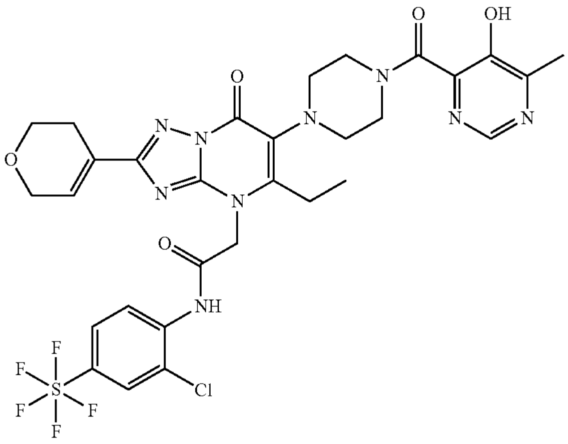
;
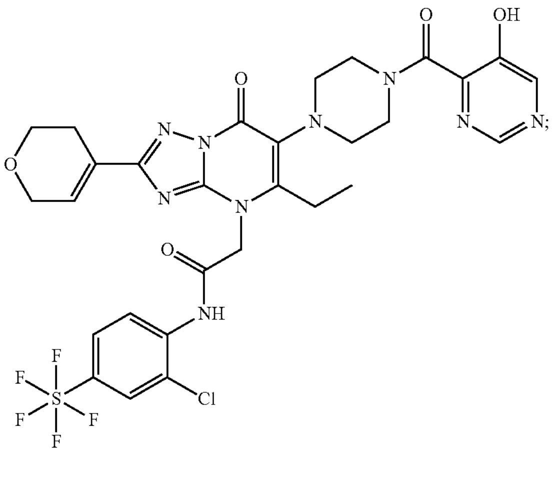

-continued
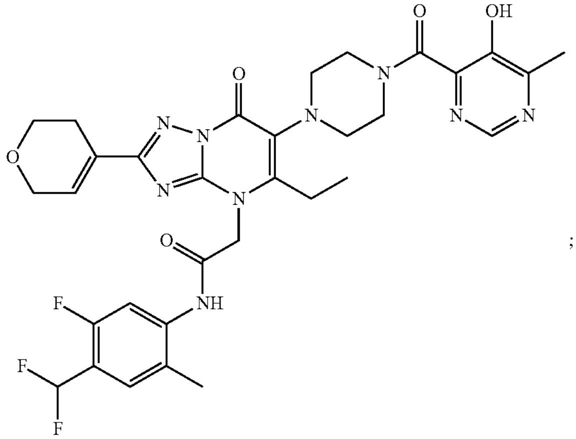
;
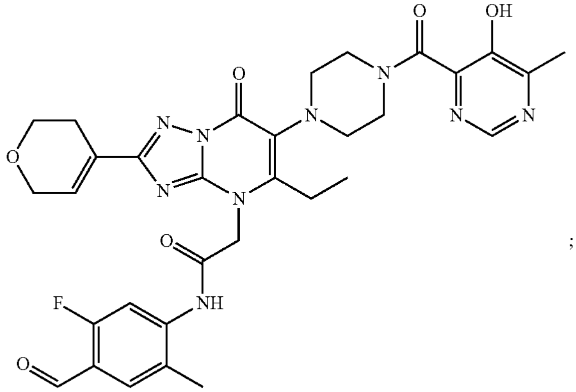
;
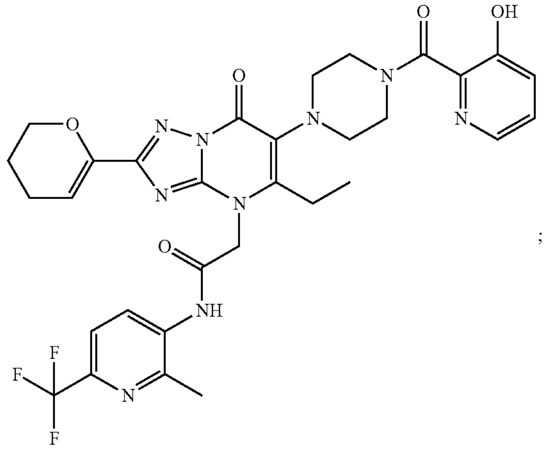
;
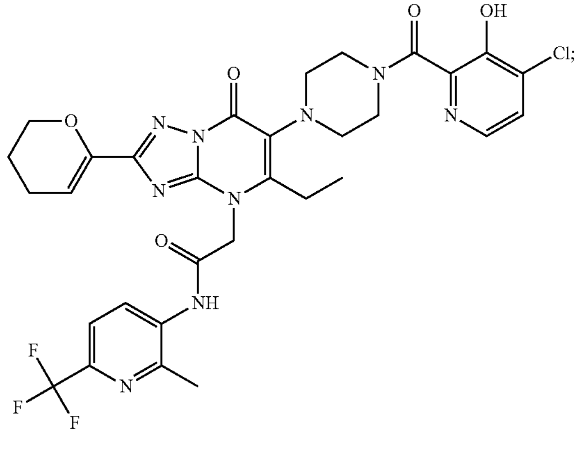
-continued
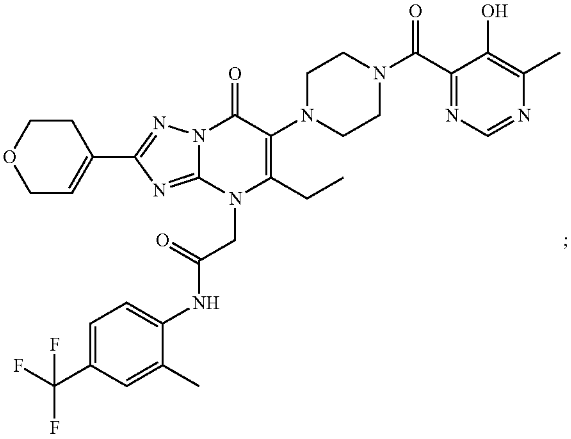
;
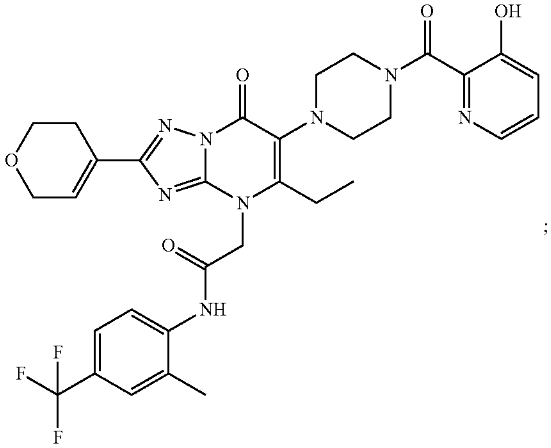
;
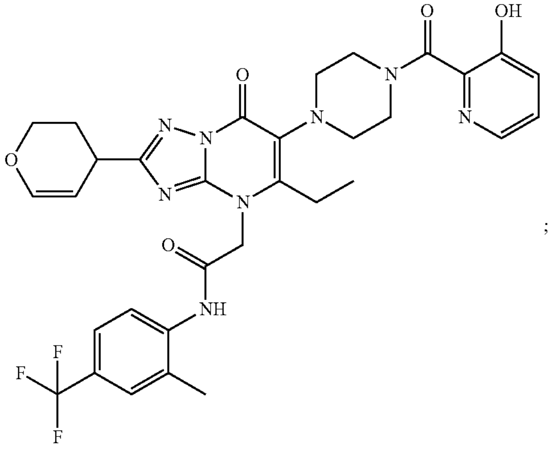
;

-continued
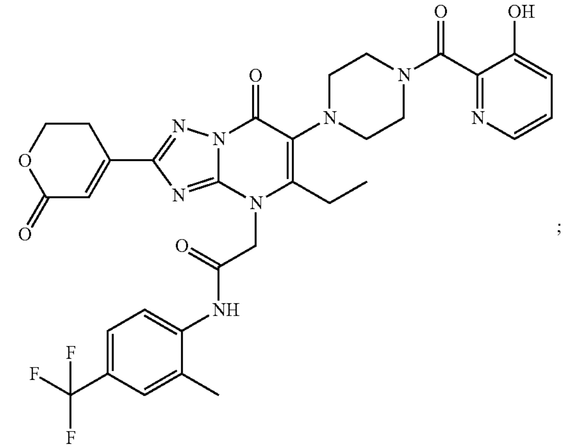
;
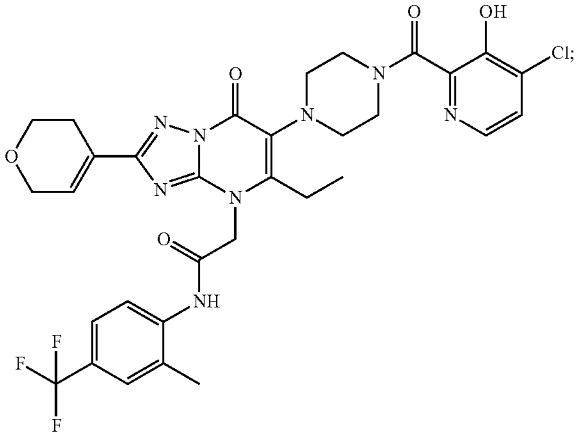
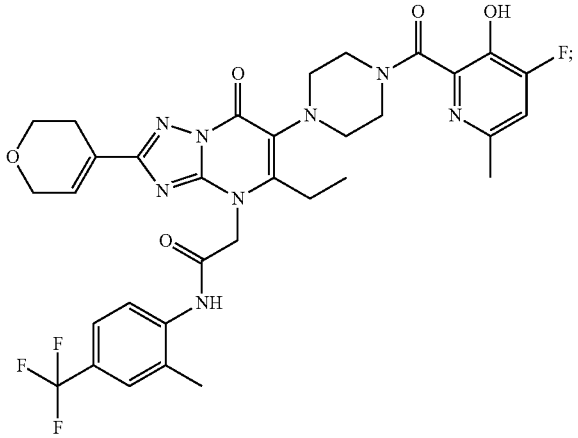
-continued
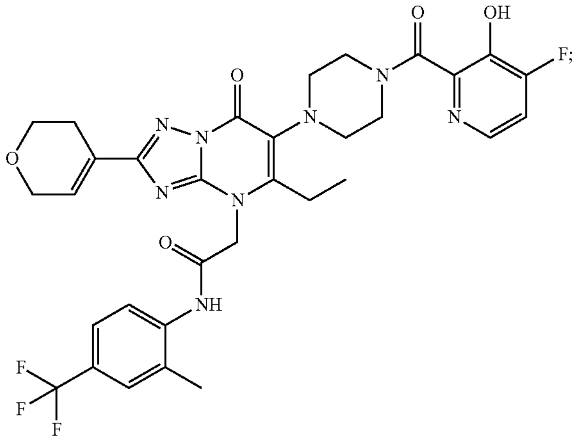
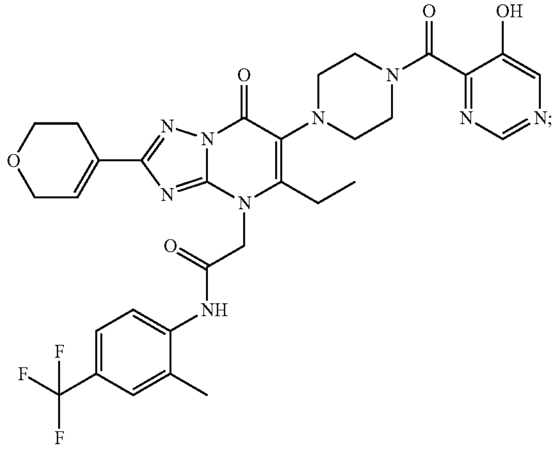
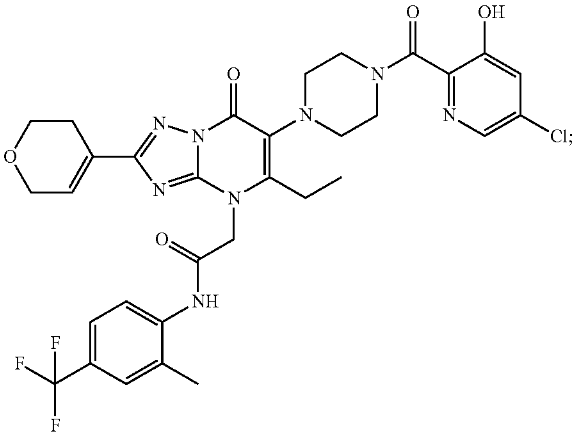

-continued
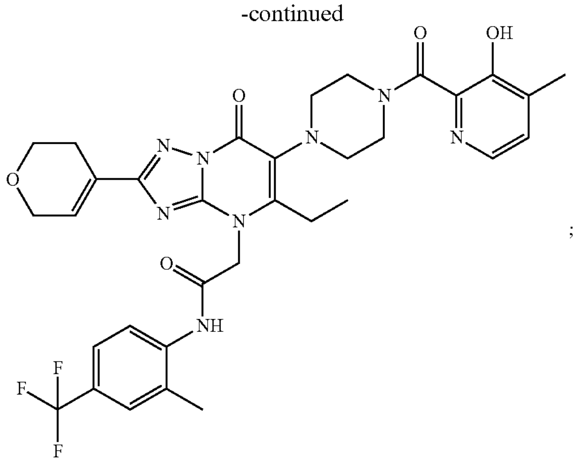
;
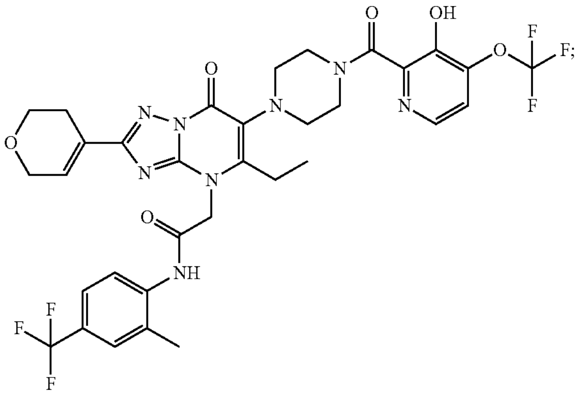
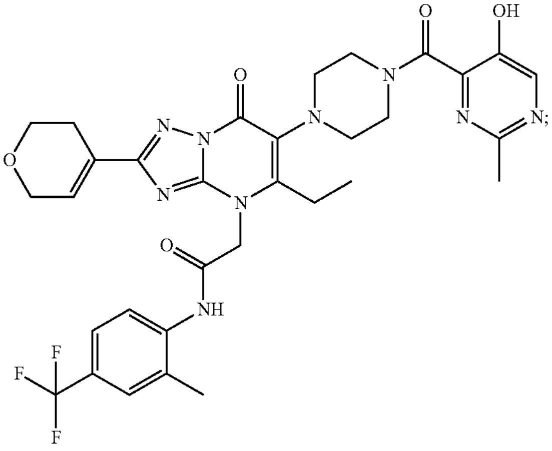
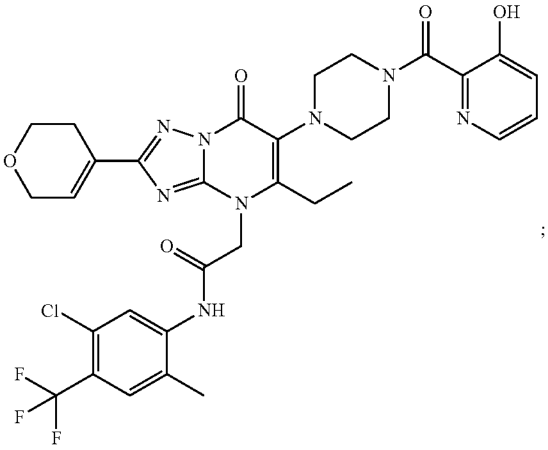
;
-continued
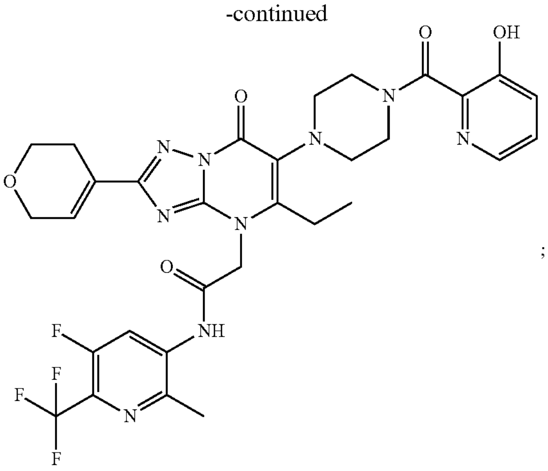
;
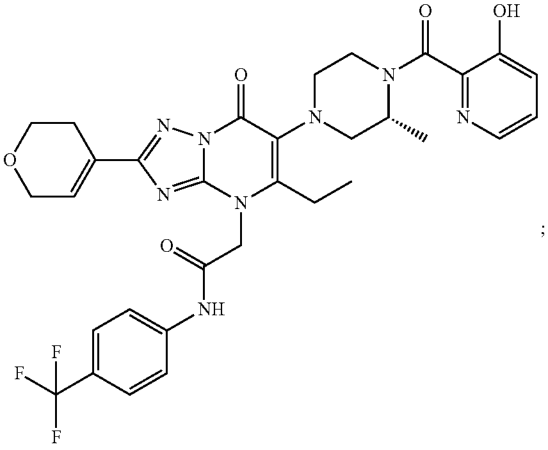
;
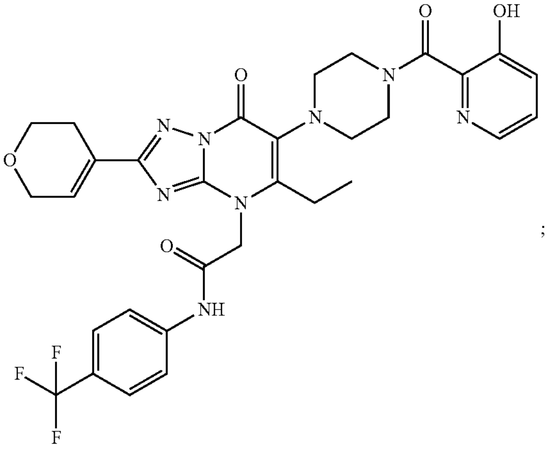
;

-continued
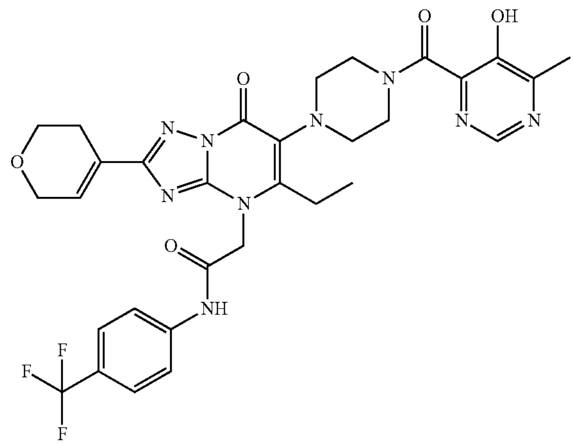
;
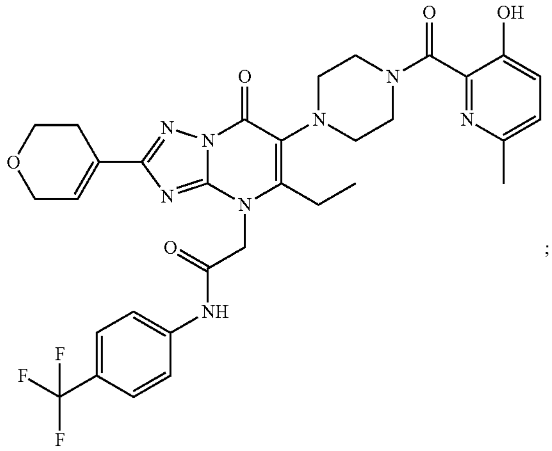
;
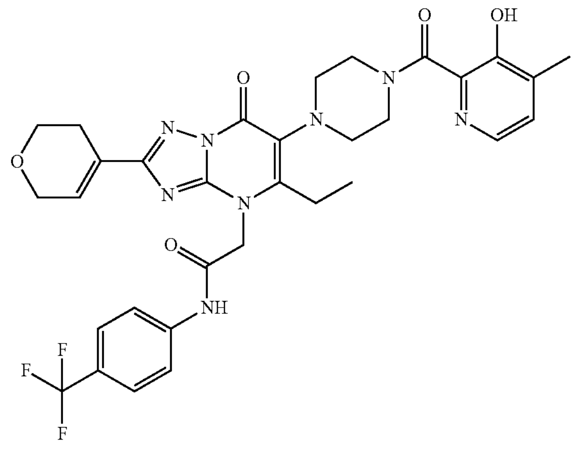
;
-continued
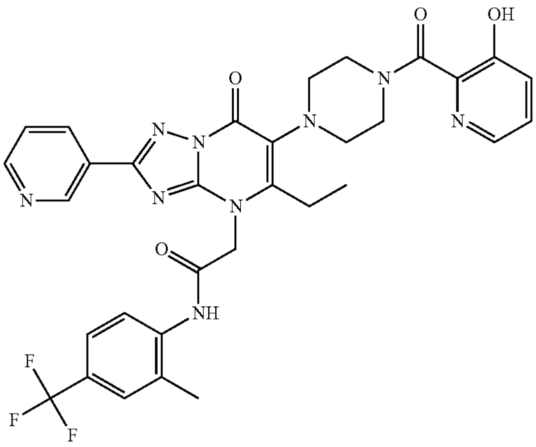
;
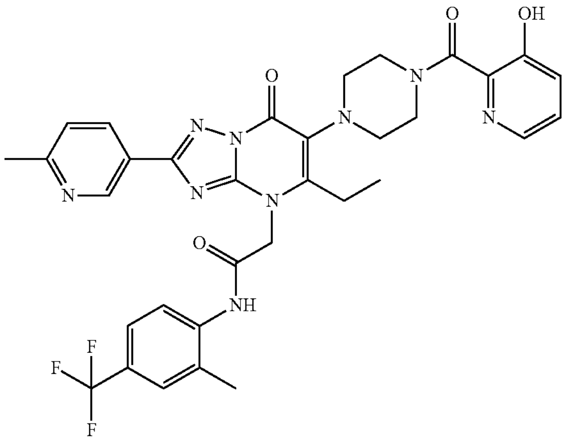
;
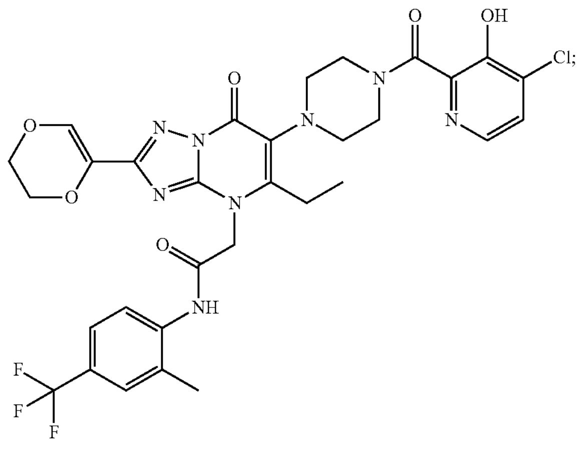

-continued
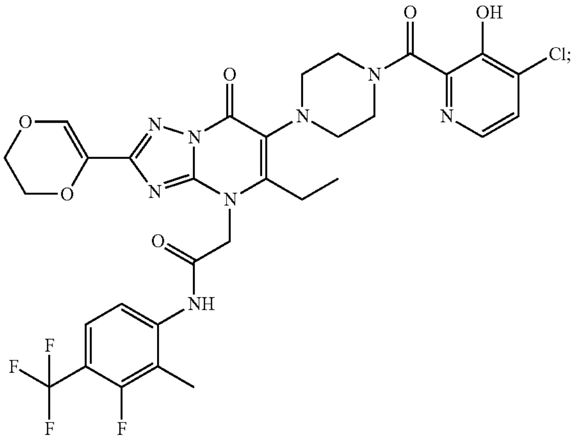
;
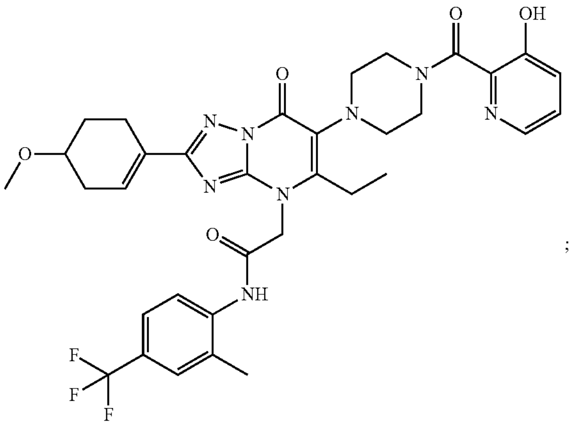
;
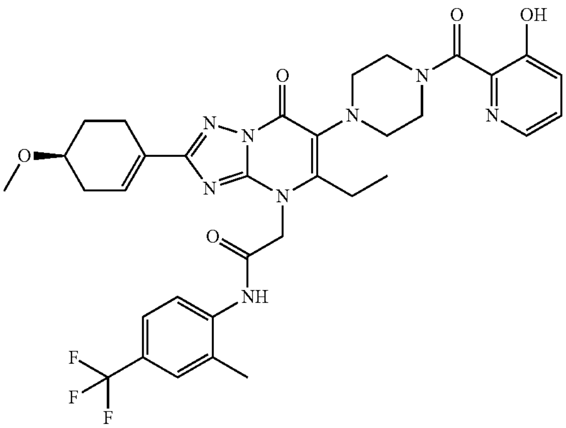
;
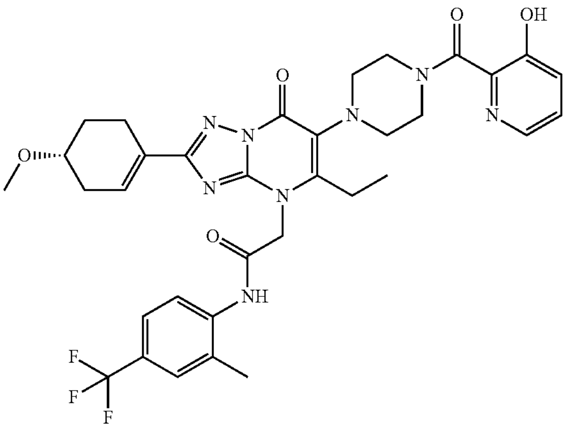
;
-continued
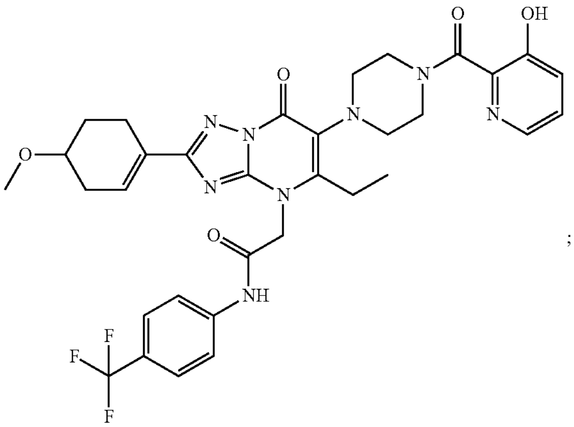
;
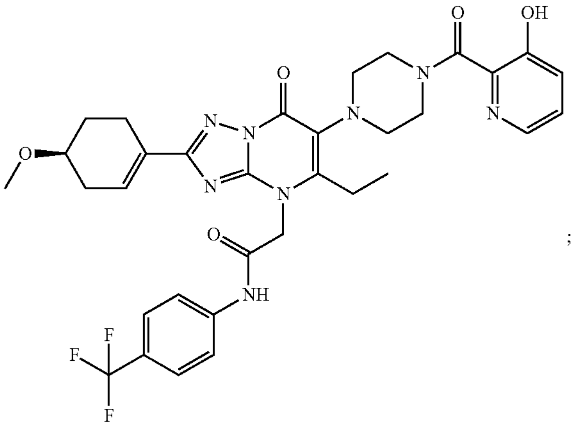
;
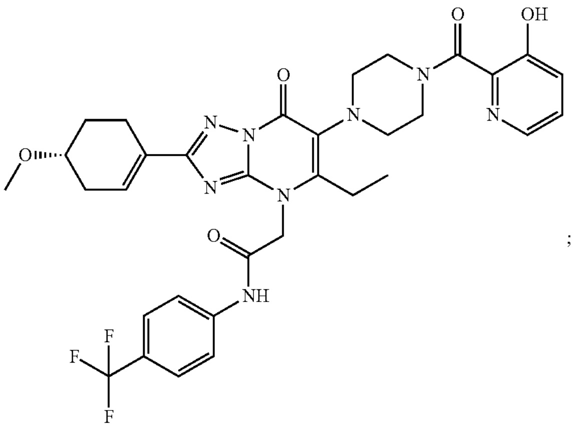
;
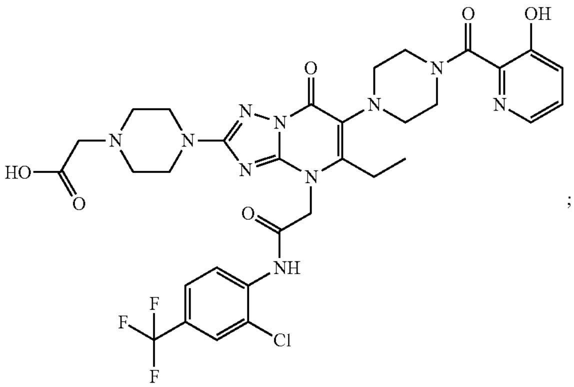
;

-continued
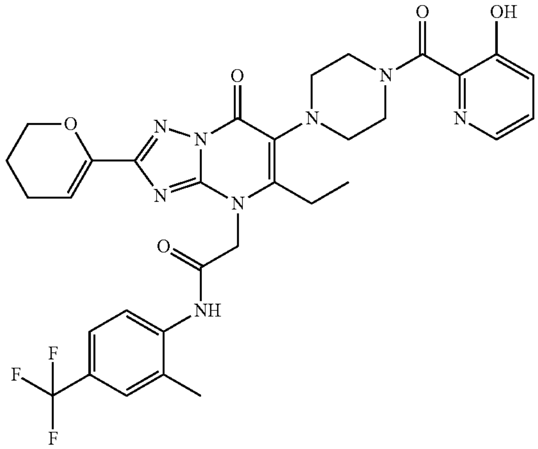
;
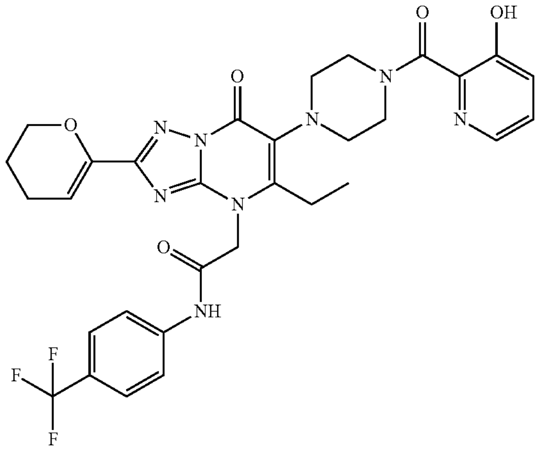
;
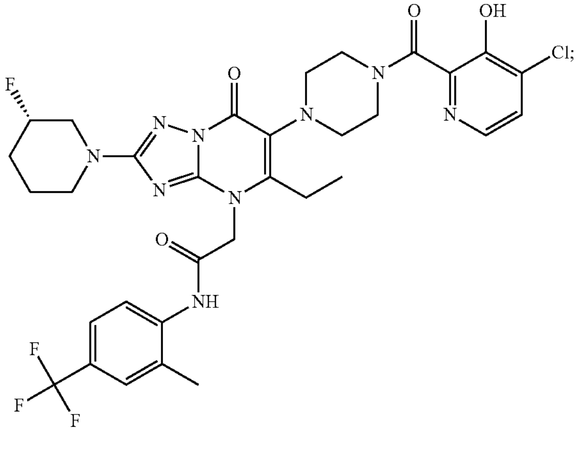
-continued
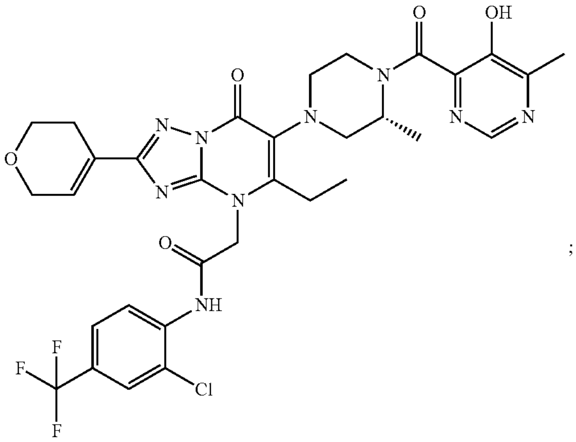
;
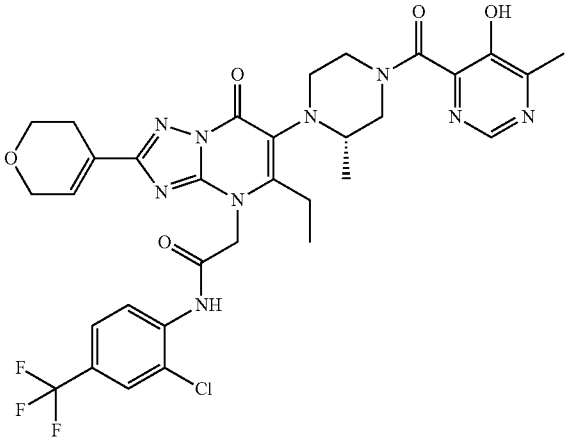
;
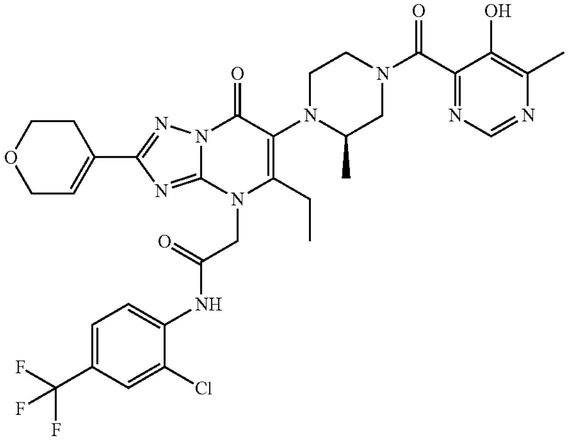
;

-continued
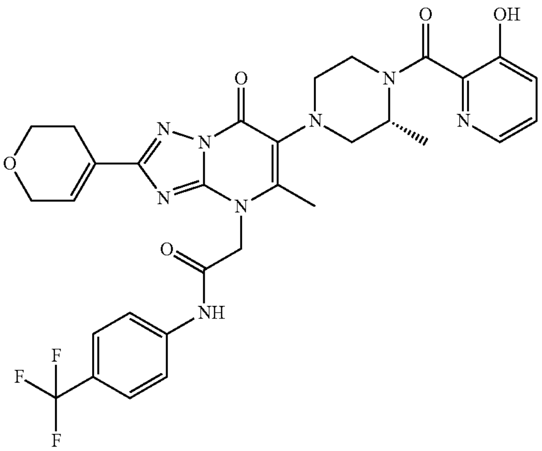
;
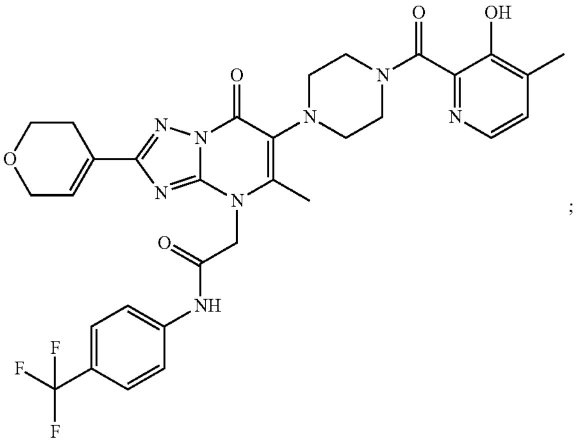
;
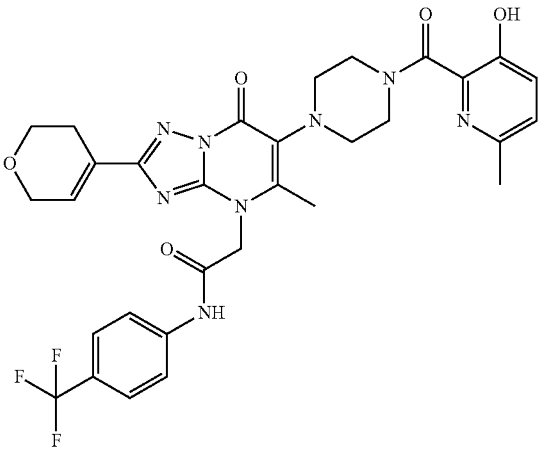
;
-continued
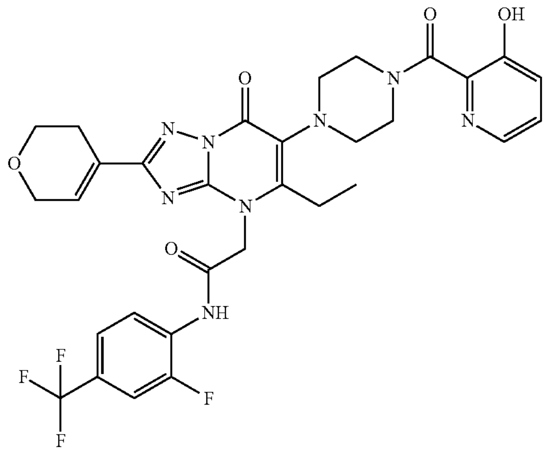
;
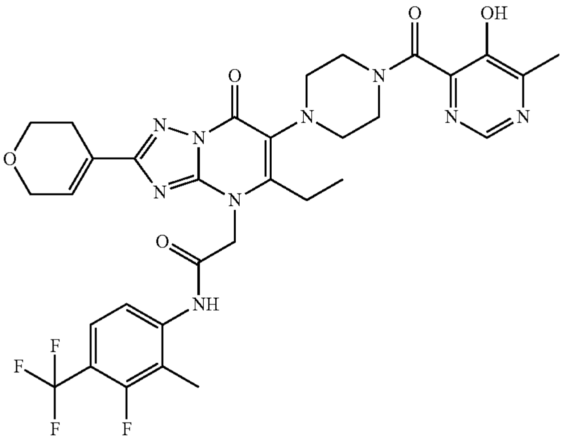
;
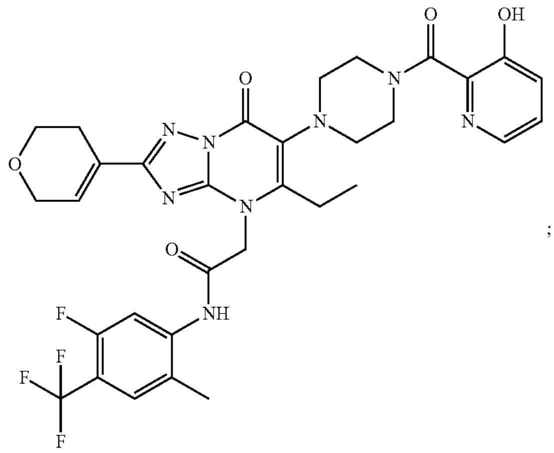
;

-continued
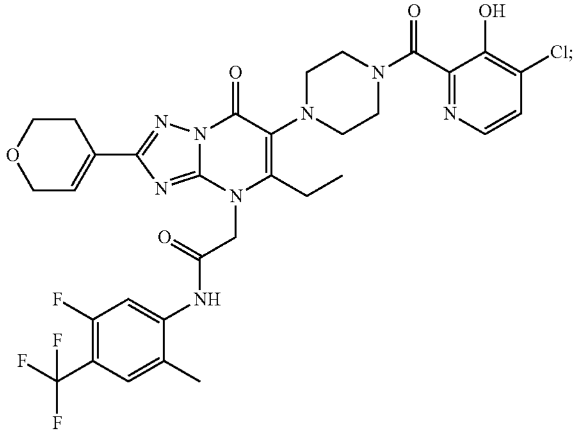
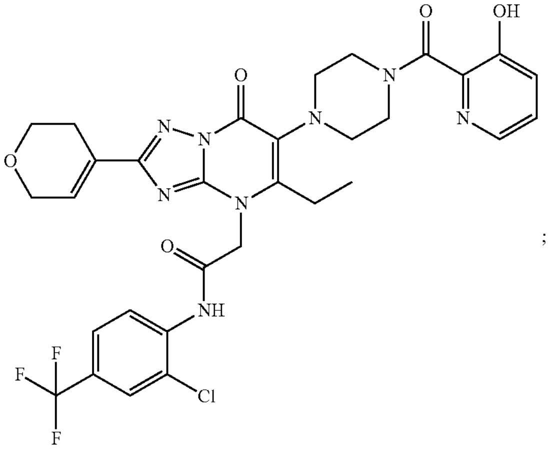
;
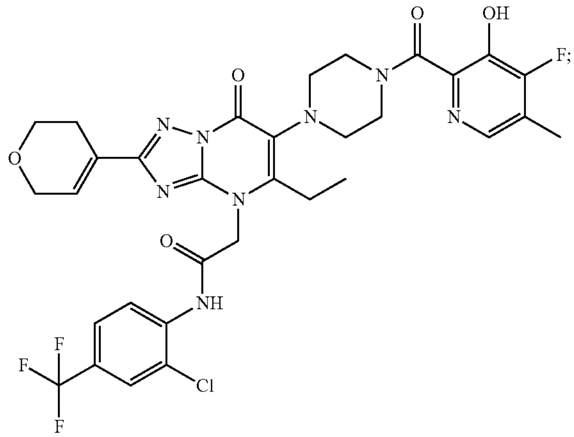
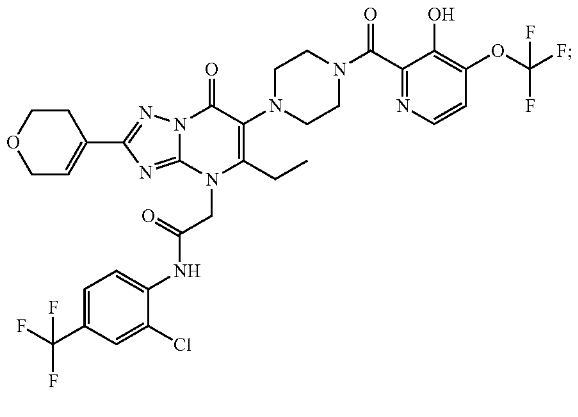
-continued
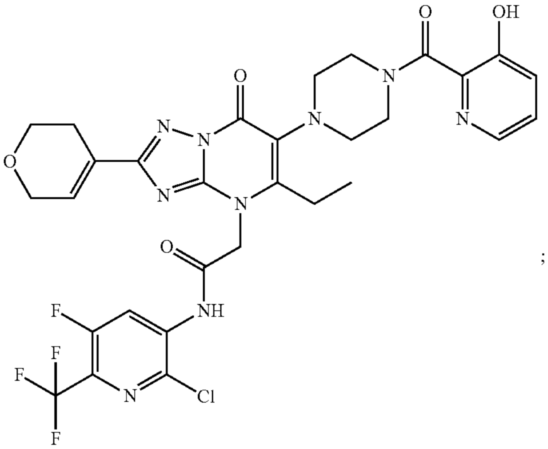
;
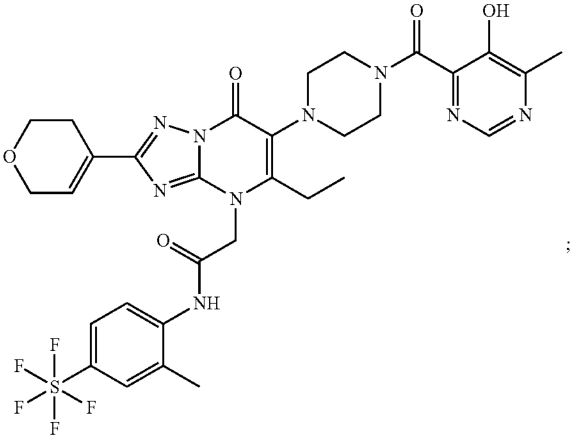
;
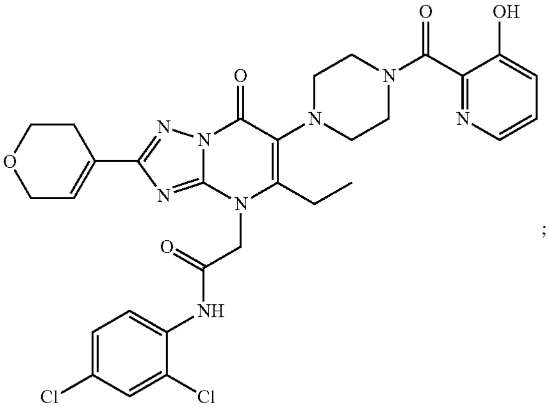
;

-continued
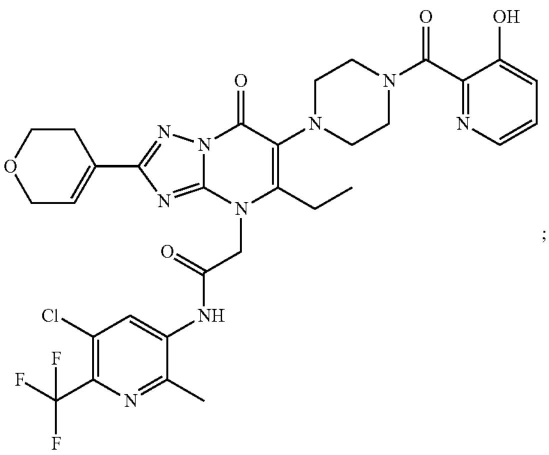
;
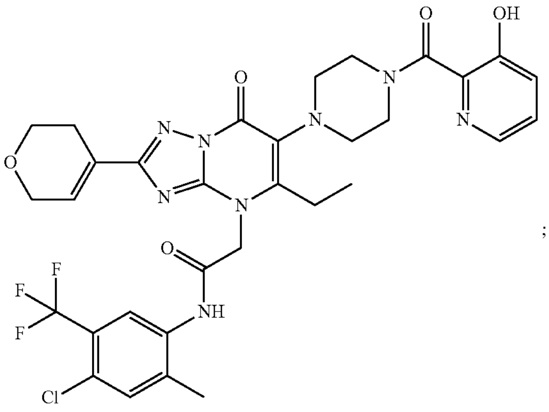
;
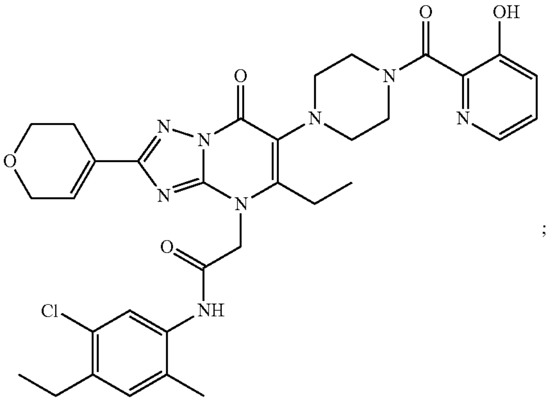
;
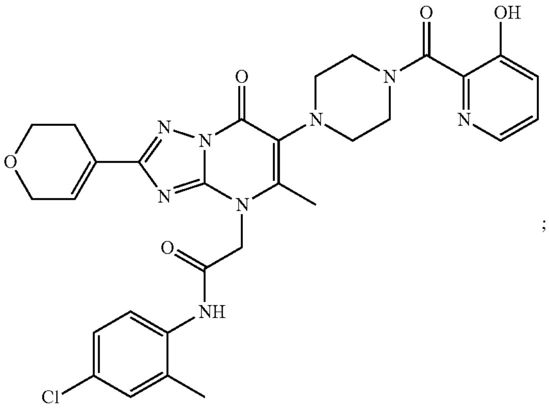
;
-continued
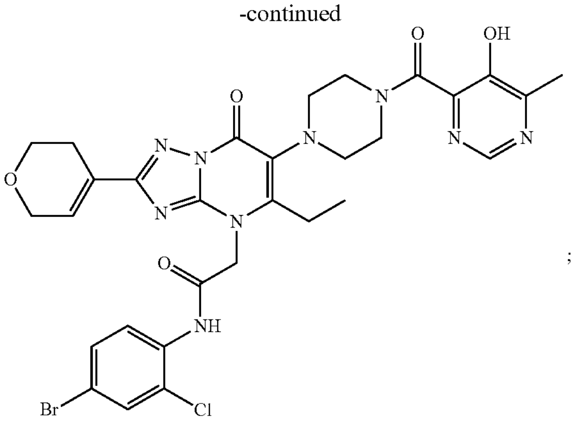
;
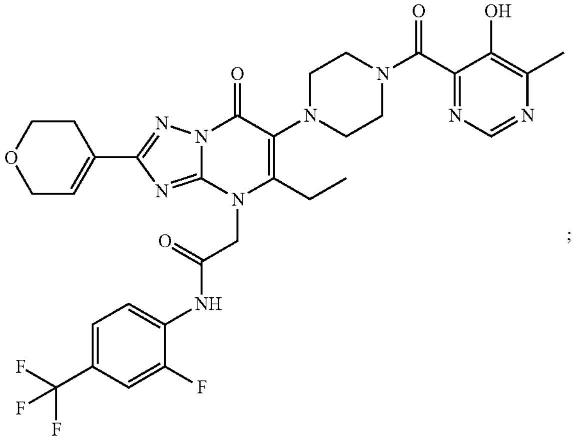
;
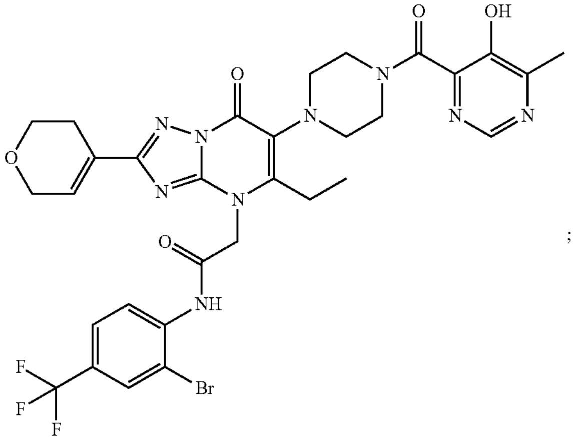
;
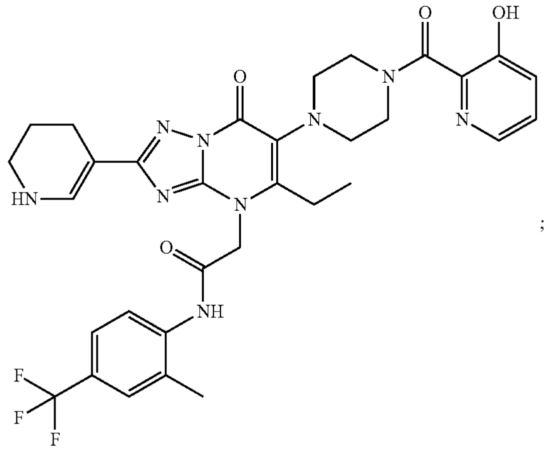
;

-continued
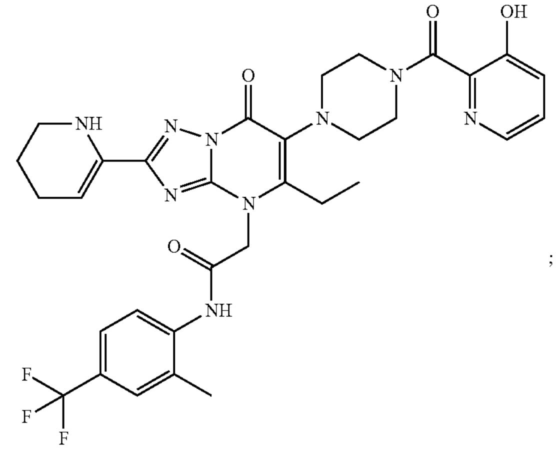
;
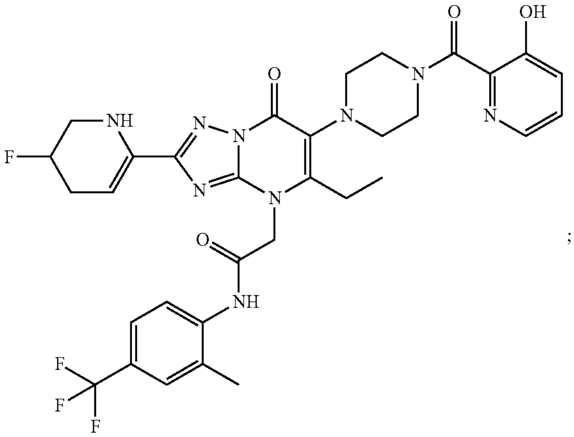
;
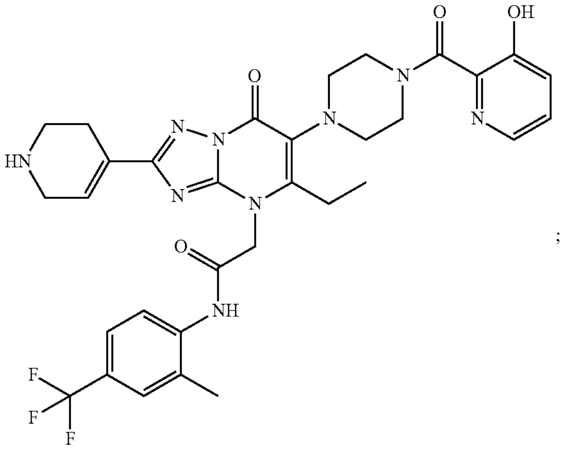
;
-continued
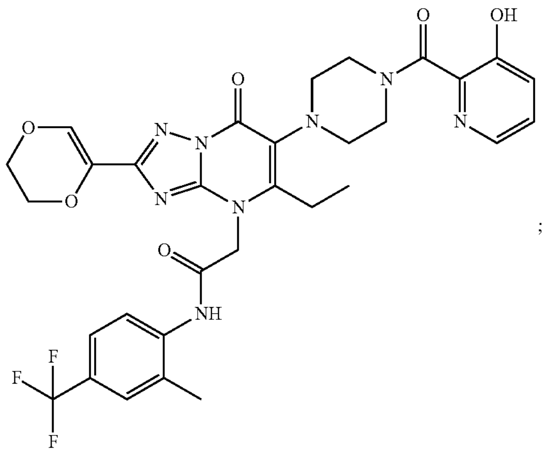
;
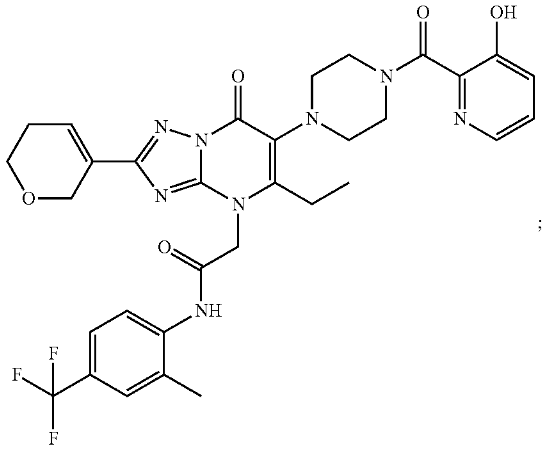
;
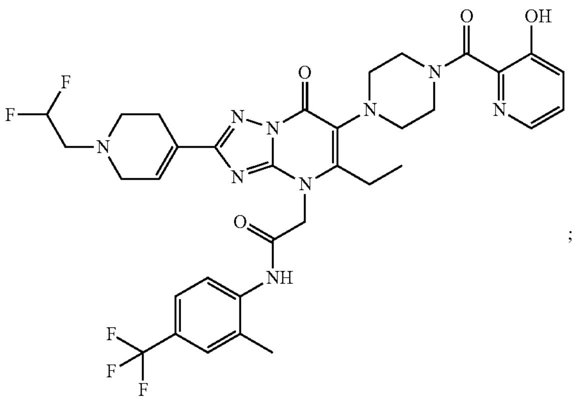
;

-continued
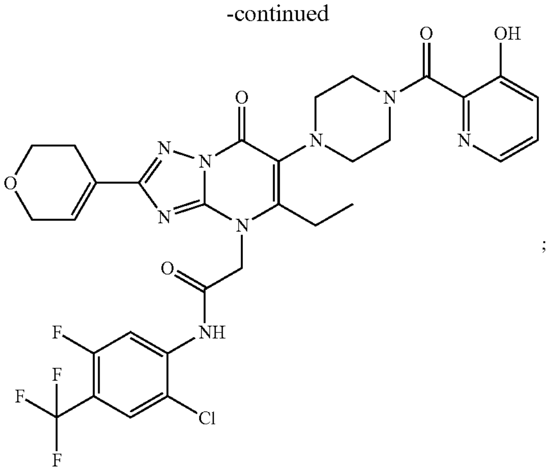
;
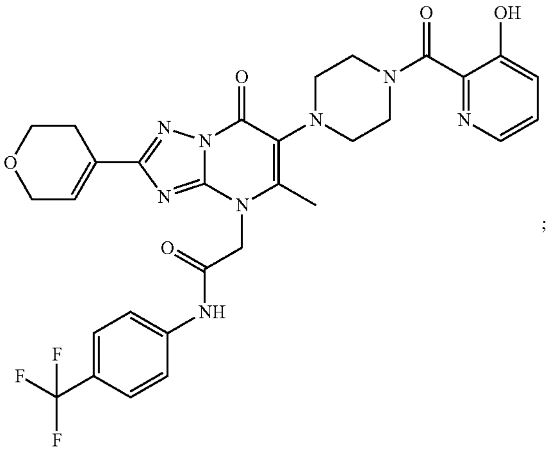
;
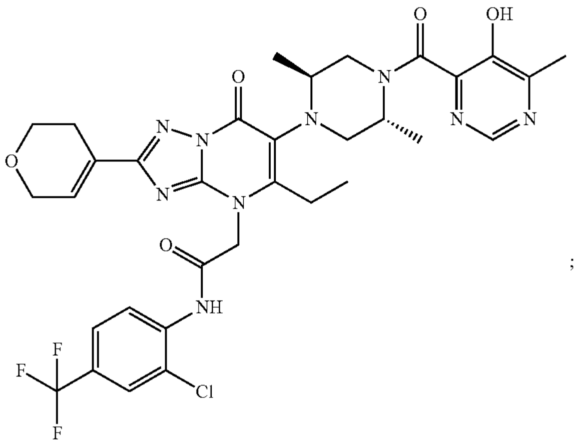
;
-continued
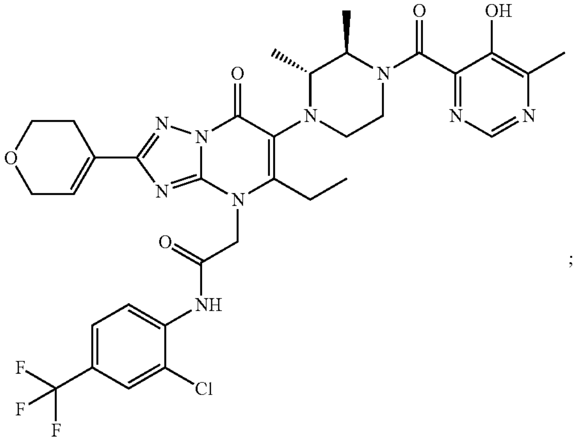
;
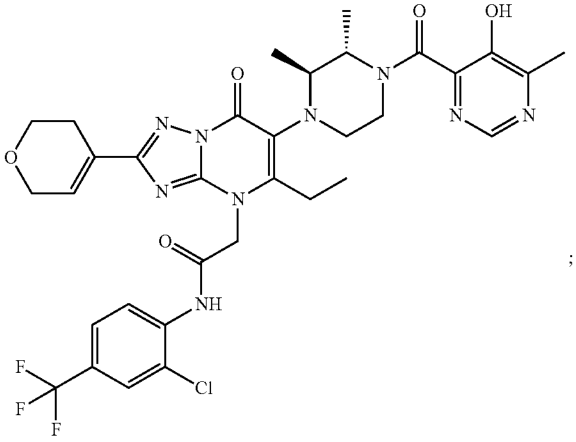
;
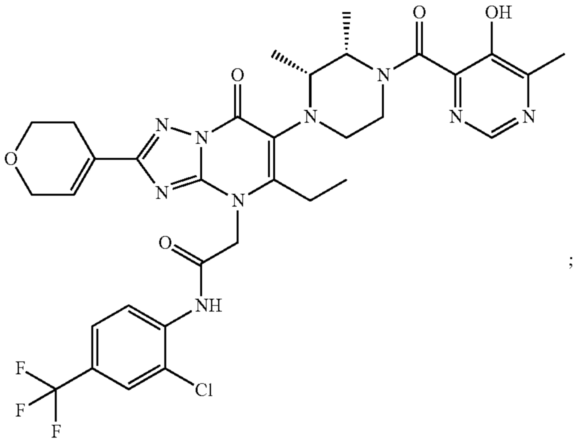
;

-continued
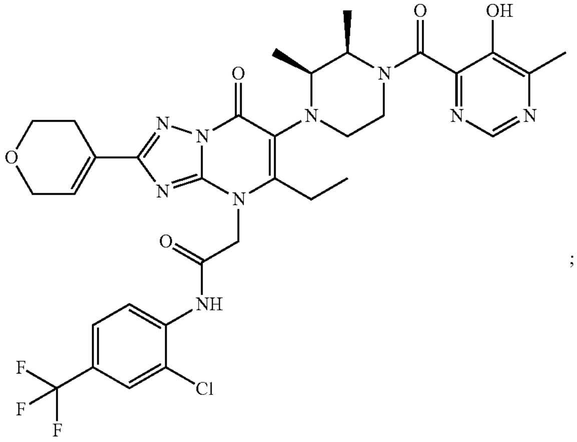
;
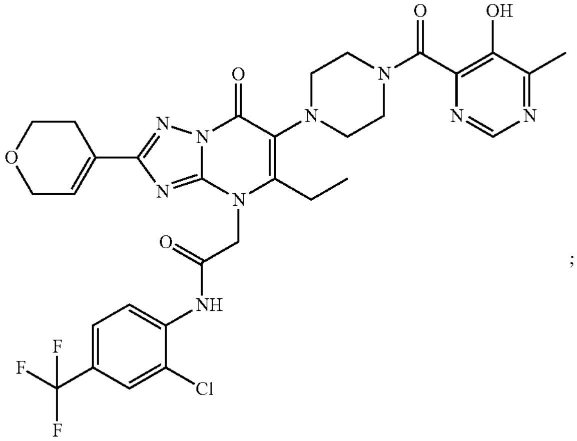
;
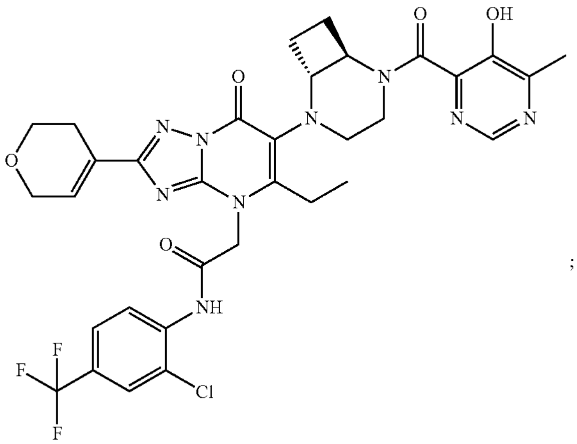
;
-continued
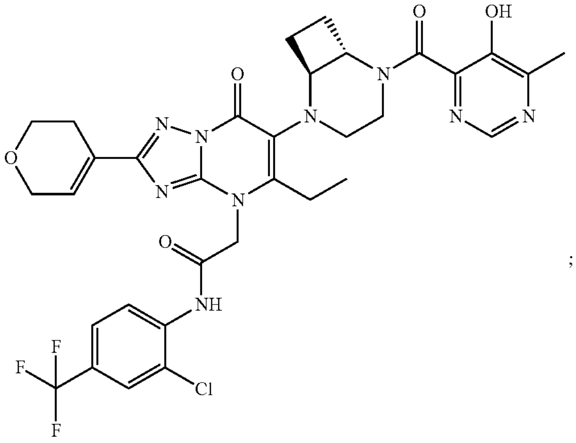
;
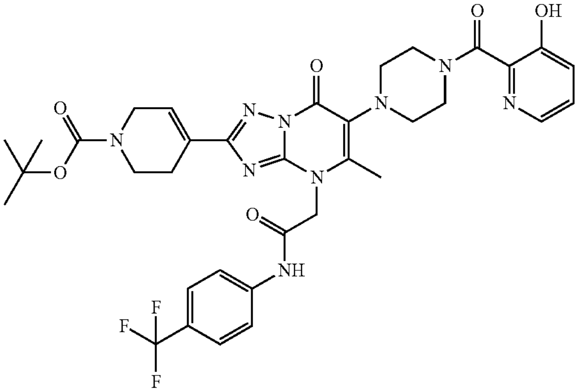
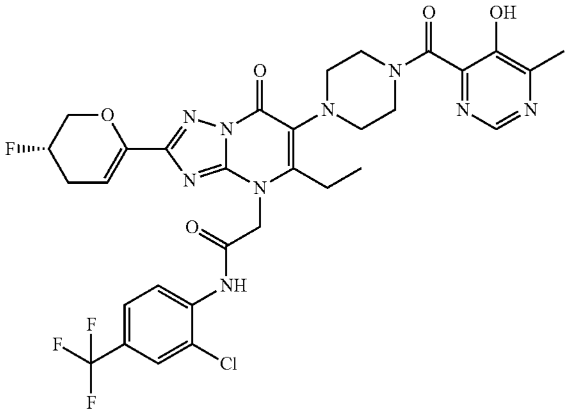
.
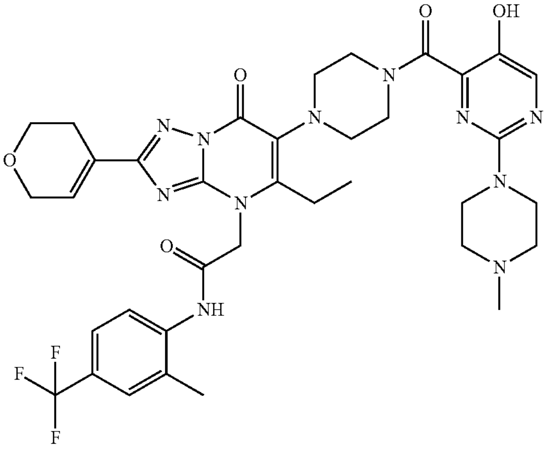

-continued
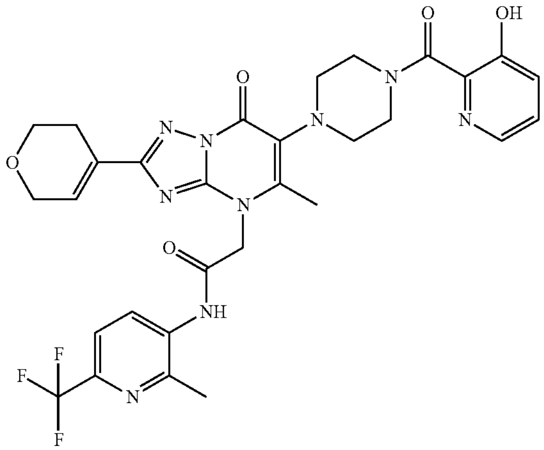
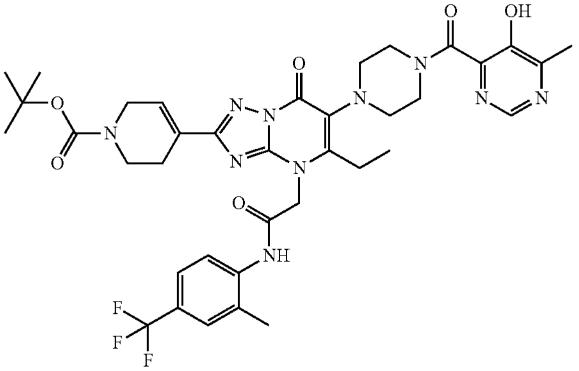
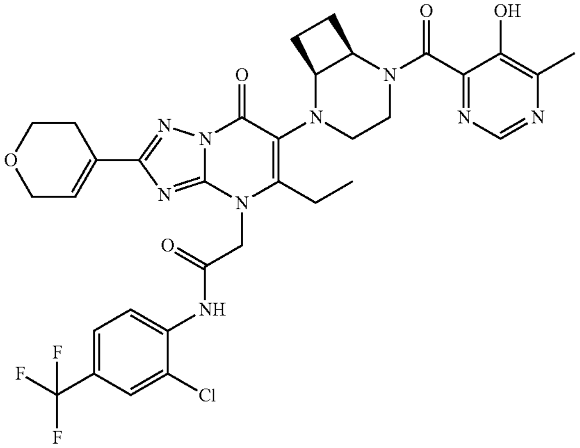
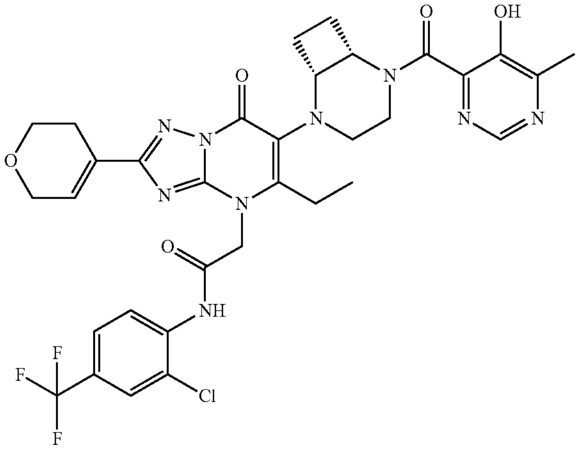
-continued
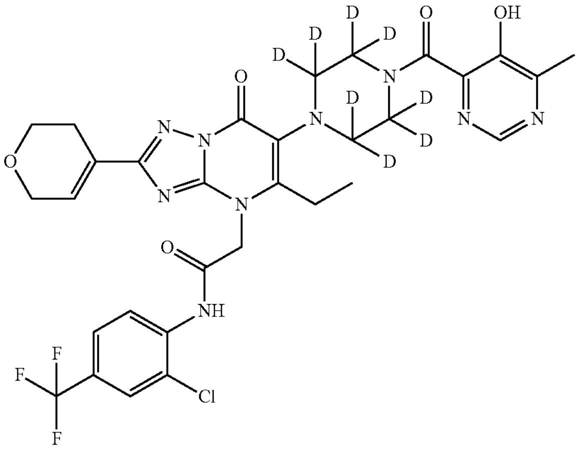
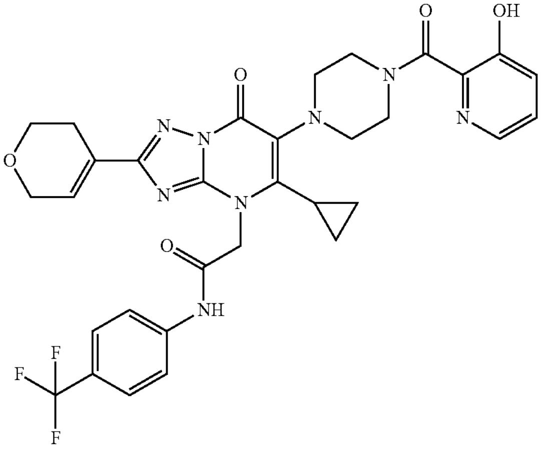
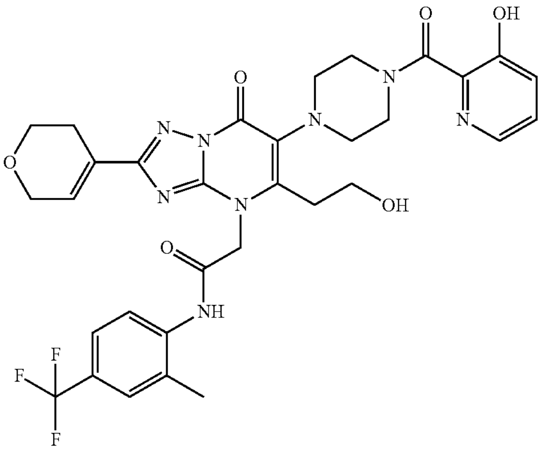

-continued
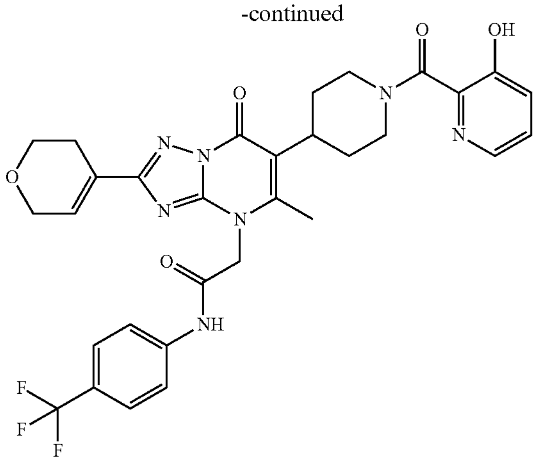
and
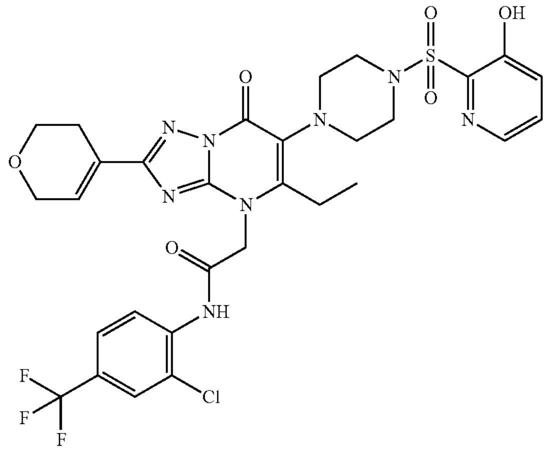 [SMILES: CCc1c(N2CCN(S(=O)(=O)c3ncccc3O)CC2)c(=O)n2nc(C3=CCOCC3)nc2n1CC(=O)Nc1ccc(C(F)(F)F)cc1Cl]
-continued
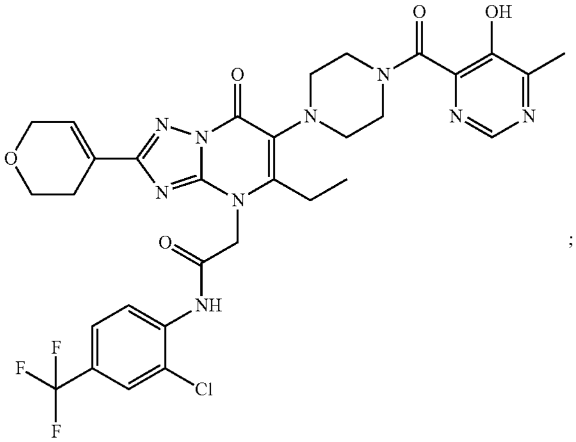
;
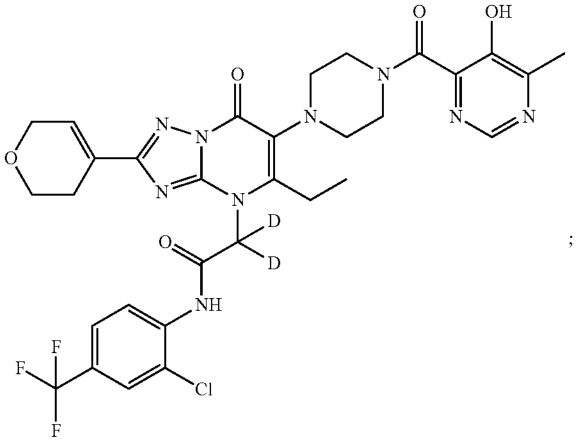
;
Embodiment 72. A compound of formula (1), or a pharmaceutically acceptable salt thereof, according to embodiments 1 or 39, wherein the compound is selected from:
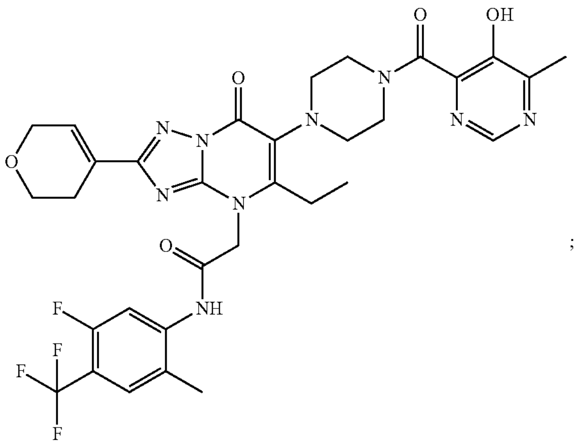
;
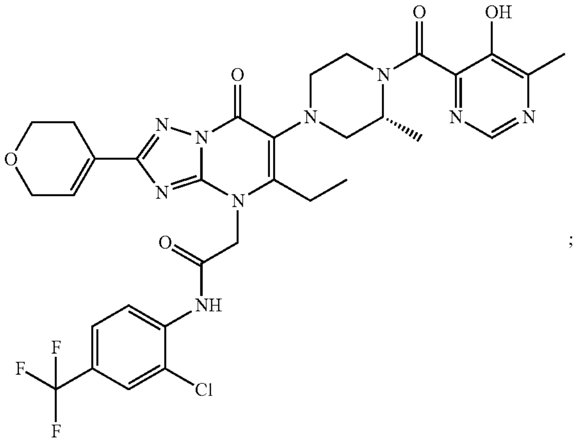
;

-continued
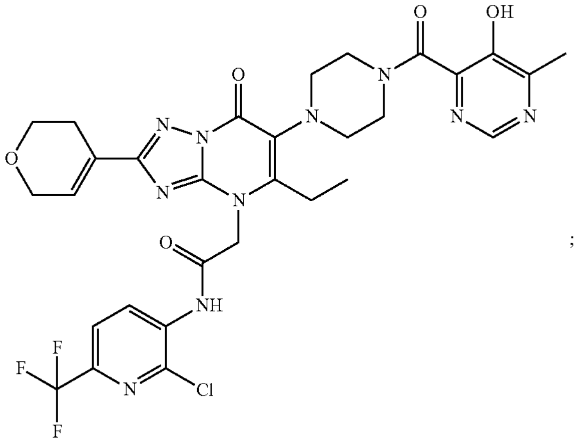
;
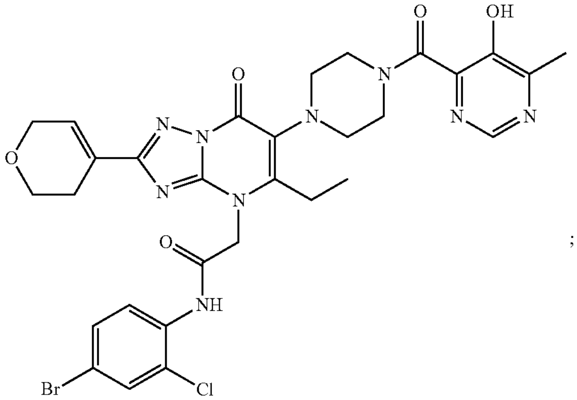
;
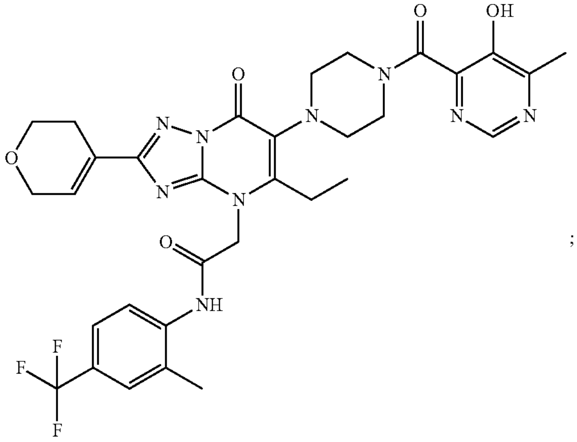
;
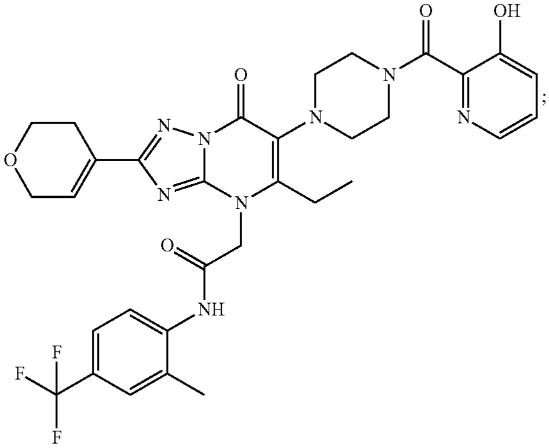
;
-continued
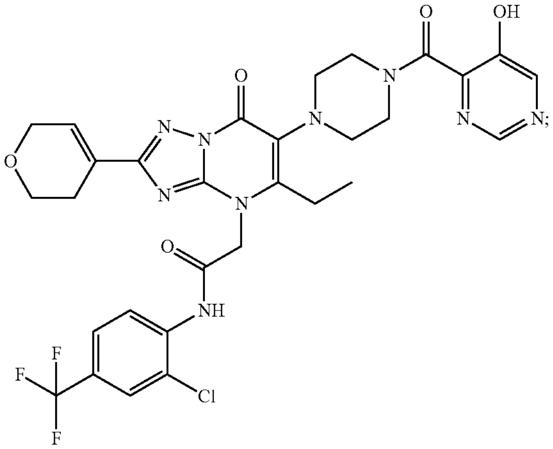
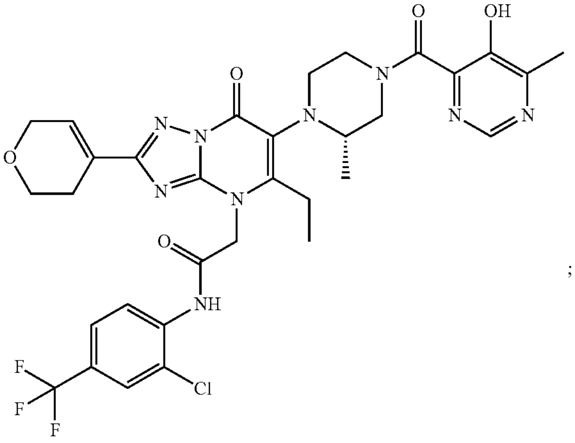
;
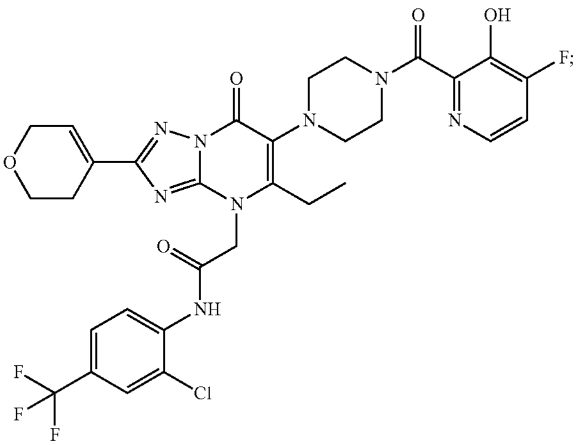

-continued
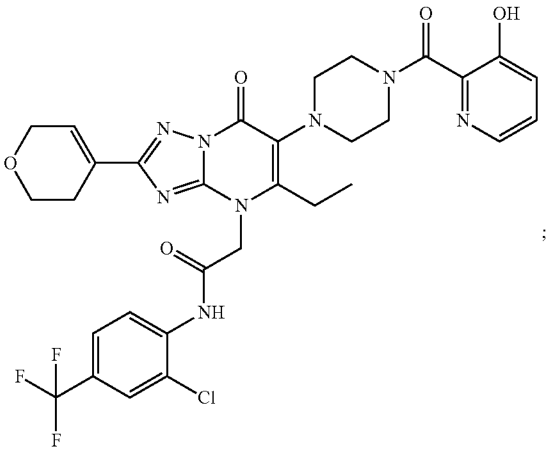
;
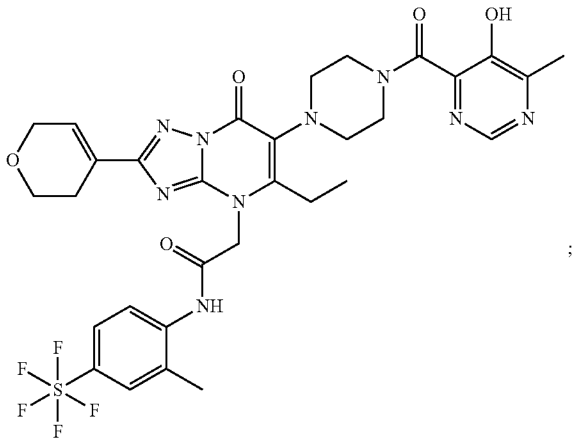
;
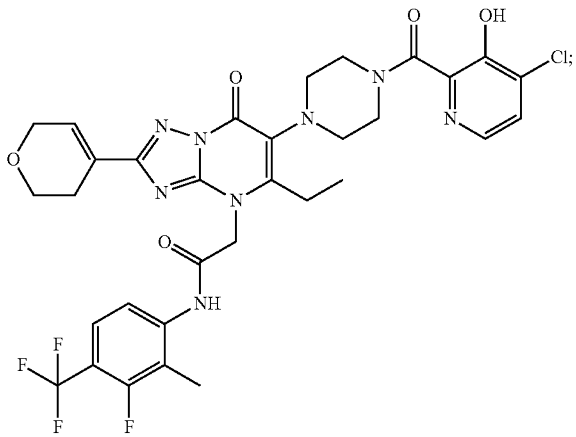
-continued
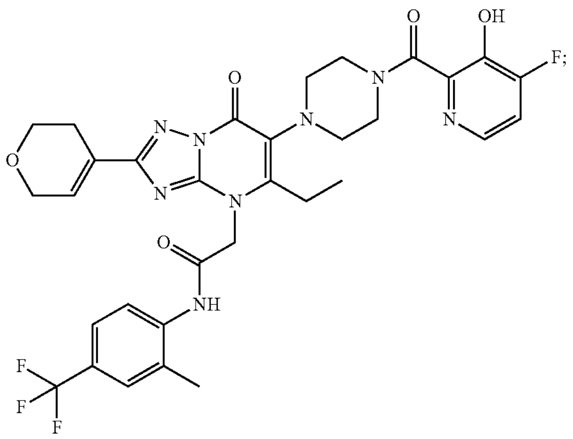
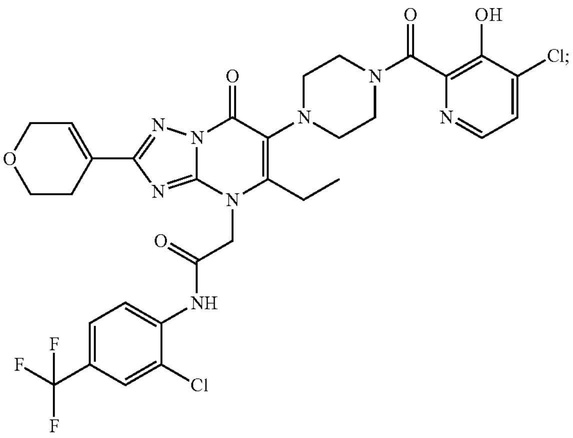
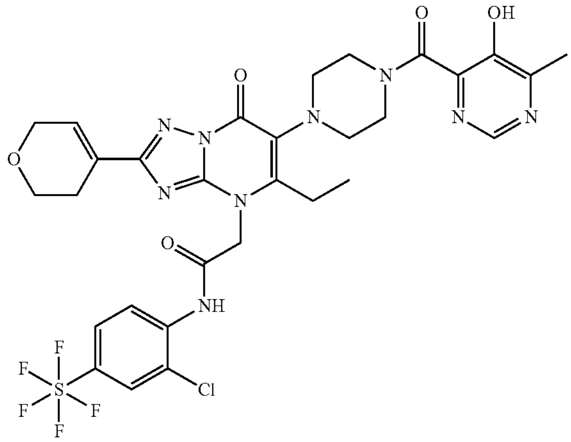
;

-continued
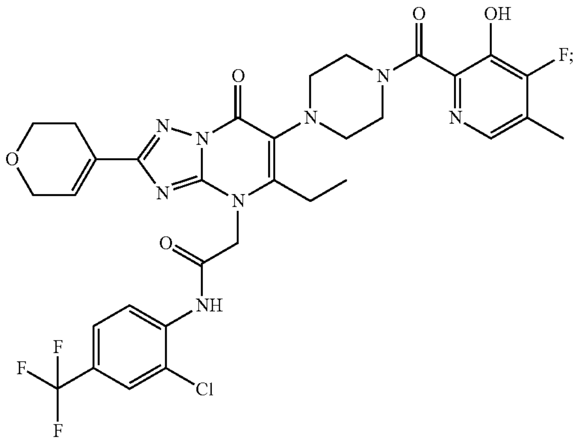
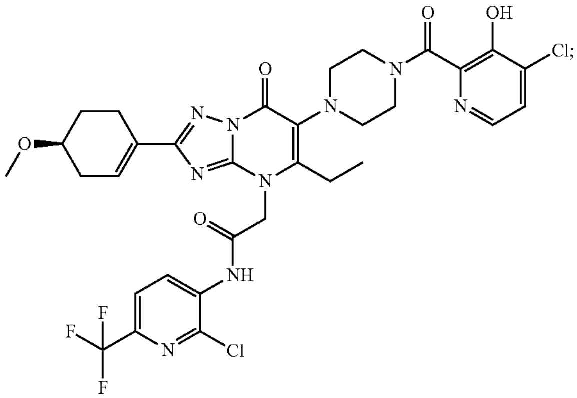
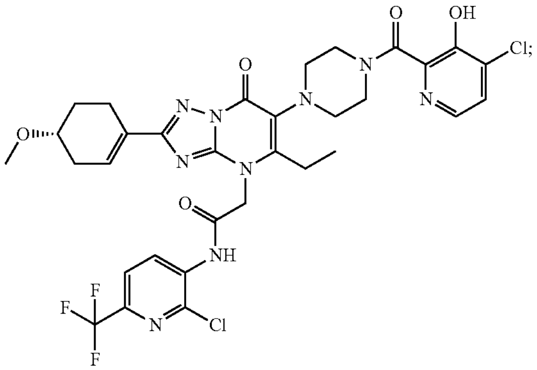
and
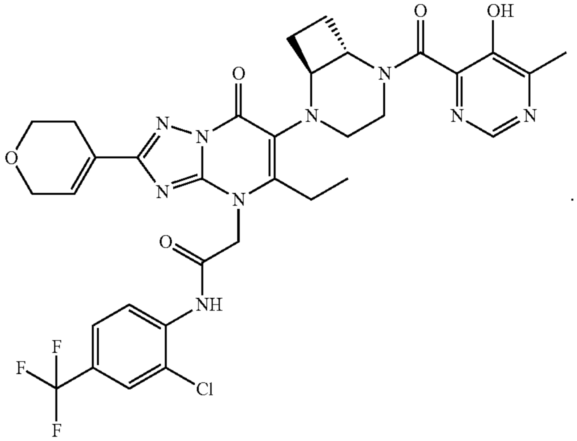 [SMILES: CCc1c(N2CCN(C(=O)c3ncnc(C)c3O)[C@H]3CC[C@@H]32)c(=O)n2nc(C3=CCOCC3)nc2n1CC(=O)Nc1ccc(C(F)(F)F)cc1Cl]
.
Embodiment 73. A compound of formula (1), or a pharmaceutically acceptable salt thereof, according to embodiments 1, 39 or 40, wherein the compound is selected from:
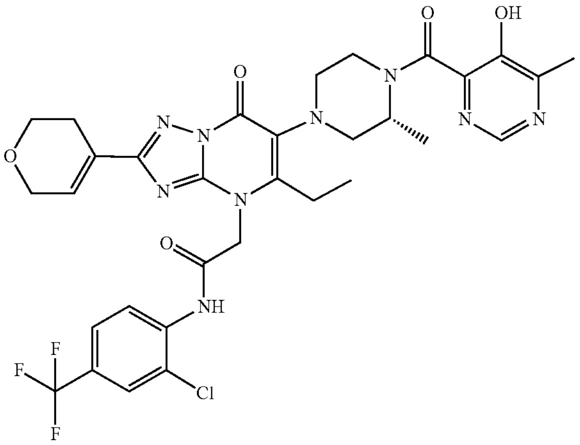
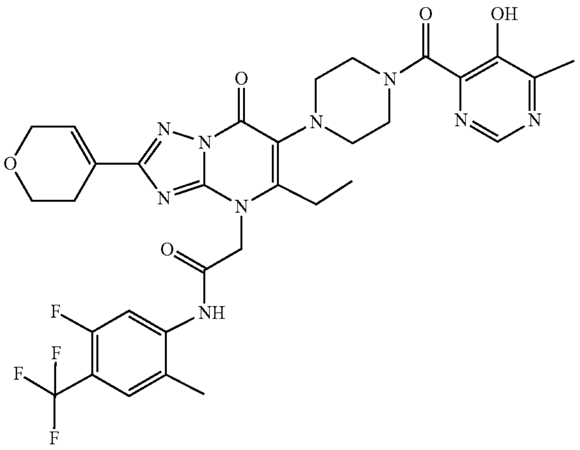
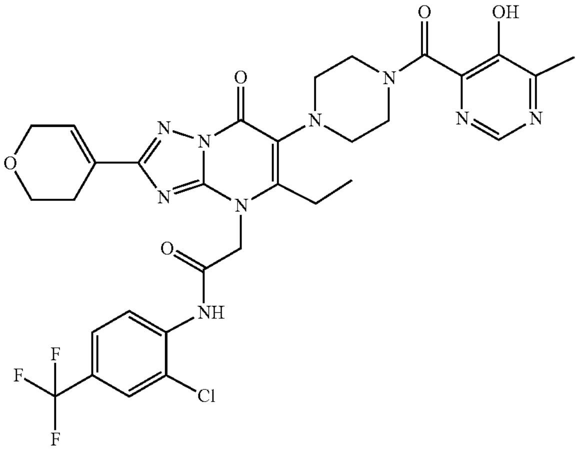

-continued

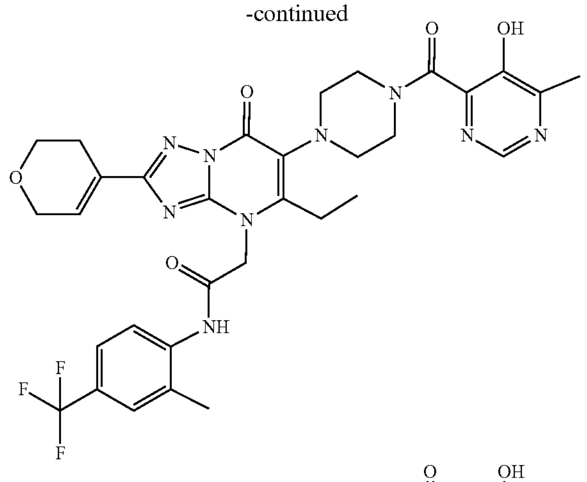

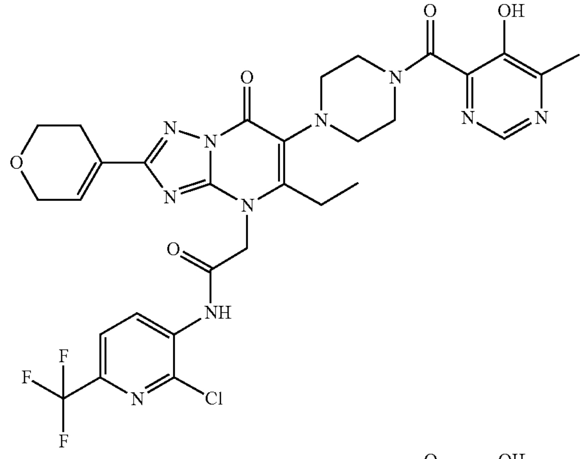

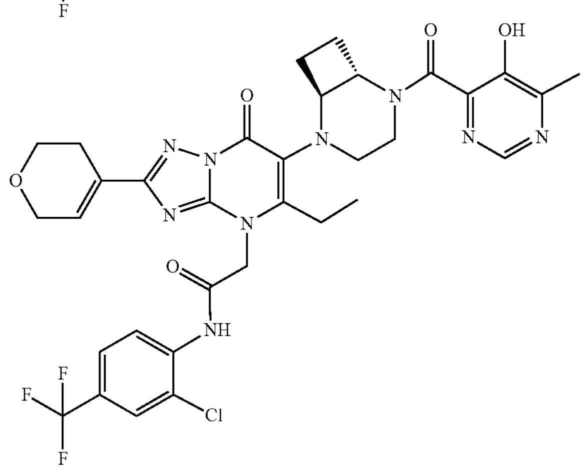

Embodiment 74. A compound of formula (1), or a pharmaceutically acceptable salt thereof, according to any of embodiments 1-73, wherein the compound is in non-zwitterionic form.

Embodiment 75. A compound of formula (1), or a pharmaceutically acceptable salt thereof, according to any of embodiments 1-73, wherein the compound is in zwitterionic form.

Embodiment 76. A compound of formula (1), or a pharmaceutically acceptable salt thereof, according to any of embodiments 1-73, wherein the compound is a mixture of zwitterionic and non-zwitterionic forms.

Embodiment 77. A compound of formula (I), or a pharmaceutically acceptable salt thereof, according to any of embodiments 1-73, wherein the $R_4$ group is present in non-zwitterionic form (d) or (e):

(d)

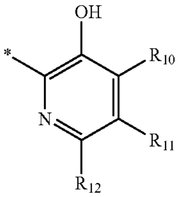

or (e)

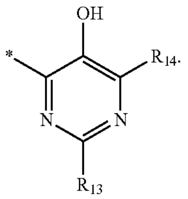

Embodiment 78. A compound of formula (I), or a pharmaceutically acceptable salt thereof, according to any of embodiments 1-73, wherein $R_4$ is present in a zwitterionic form selected from:

(a)

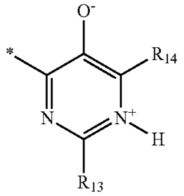

and (b)

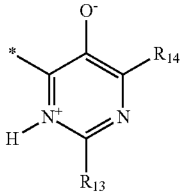

Embodiment 79. A compound of formula (I), or a pharmaceutically acceptable salt thereof, according to any of embodiments 1-73, wherein $R_4$ is present as a mixture of zwitterionic forms (a) and (b) according to embodiment 78.

Embodiment 80. A compound of formula (I), or a pharmaceutically acceptable salt thereof, according to any of embodiments 1-73, wherein $R_4$ is present as a mixture of:

Non-zwitterionic form (e) and zwitterionic forms (a) or (b), (e)

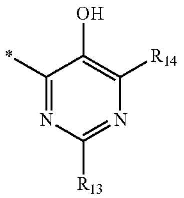

and

-continued (a)

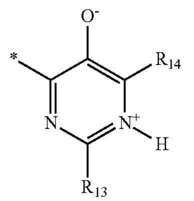

or (b)

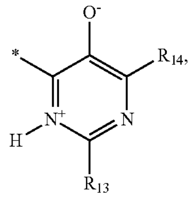

Non-zwitterionic form (e) and zwitterionic forms (a) and (b)

(e)

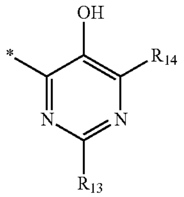

and (a)

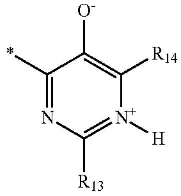

and (b)

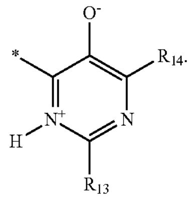

Embodiment 81. A compound of formula (I), or a pharmaceutically acceptable salt thereof, according to any of embodiments 1-73, wherein $R_4$ is in zwitterionic form (c):

(c)

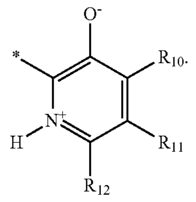

Embodiment 82. A compound of formula (I), or a pharmaceutically acceptable salt thereof, according to any of embodiments 1-73, wherein $R_4$ is present as a mixture of both zwitterionic form (c) and non-zwitterionic form (d):

(c)

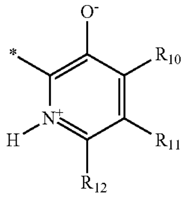

and (d)

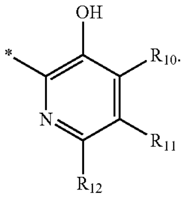

Embodiment 83. A compound of formula (I), according to any of embodiments 1, 24, 30 or 31, wherein the compound N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide is:

in non-zwitterionic form:

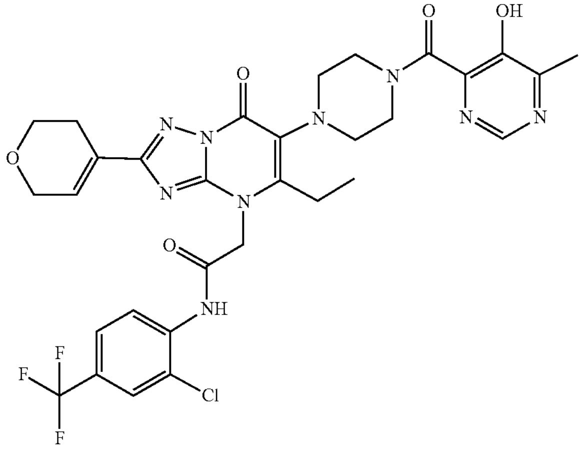 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Cl]

or zwitterionic form:

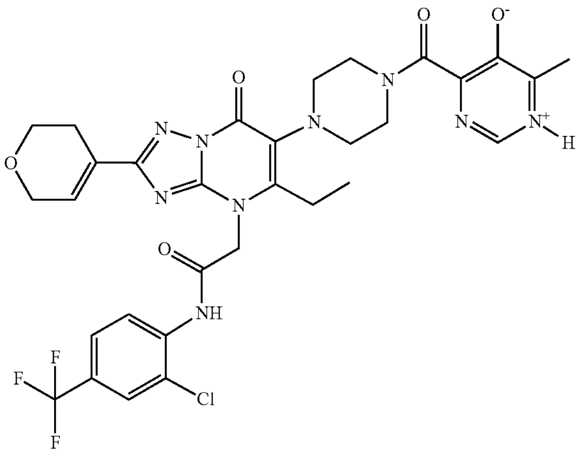 [SMILES: CCc1c(N2CCN(C(=O)c3nc[nH+]c(C)c3[O-])CC2)c(=O)n2nc(C3=CCOCC3)nc2n1CC(=O)Nc1ccc(C(F)(F)F)cc1Cl]

or zwitterionic form:

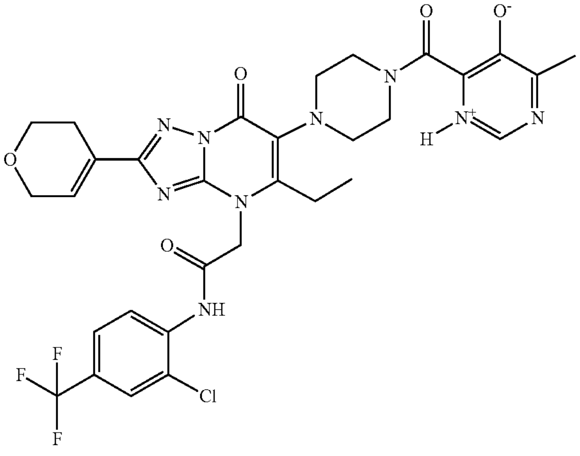 [SMILES: CCc1c(N2CCN(C(=O)c3[nH+]cnc(C)c3[O-])CC2)c(=O)n2nc(C3=CCOCC3)nc2n1CC(=O)Nc1ccc(C(F)(F)F)cc1Cl]

or a mixture of any two or three of said forms.

Embodiment 84. A compound of formula (I), according to any of embodiments 1, 24, 30 or 31, wherein the compound (R)—N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)-3-methylpiperazin-1-yl)-7-oxo-[1,2,4]triazolo[1,5-a]pyrimidin-4 (7H)-yl)acetamide is:

in non-zwitterionic form:

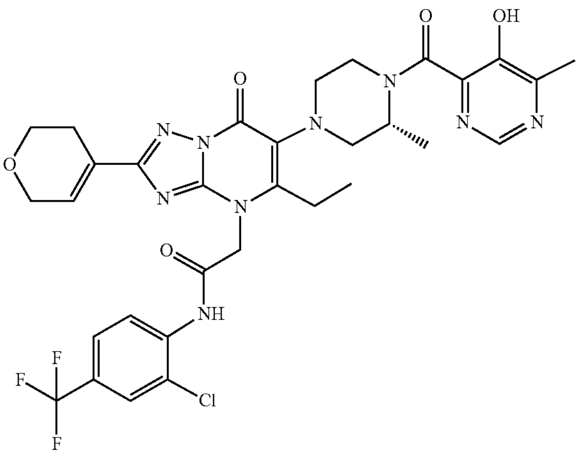 [SMILES: CCc1c(N2CCN(C(=O)c3ncnc(C)c3O)[C@H](C)C2)c(=O)n2nc(C3=CCOCC3)nc2n1CC(=O)Nc1ccc(C(F)(F)F)cc1Cl]

or in zwitterionic form:

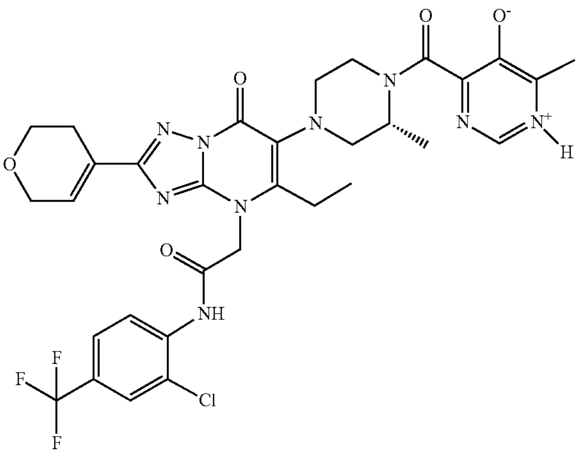 [SMILES: CCc1c(N2CCN(C(=O)c3nc[nH+]c(C)c3[O-])[C@H](C)C2)c(=O)n2nc(C3=CCOCC3)nc2n1CC(=O)Nc1ccc(C(F)(F)F)cc1Cl]

or in zwitterionic form:

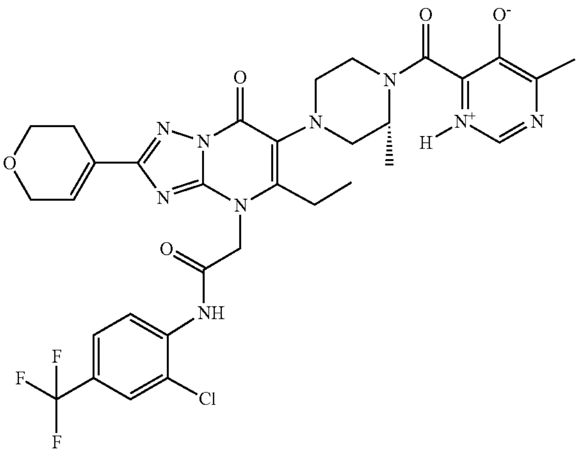 [SMILES: CCc1c(N2CCN(C(=O)c3[nH+]cnc(C)c3[O-])[C@H](C)C2)c(=O)n2nc(C3=CCOCC3)nc2n1CC(=O)Nc1ccc(C(F)(F)F)cc1Cl]

or a mixture of any two or three of said forms.

Embodiment 85. A compound of formula (I), according to any of embodiments 1, 24, 30 or 31, wherein the compound N-(2-chloro-6-(trifluoromethyl)pyridin-3-yl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide is:

in non-zwitterionic form:

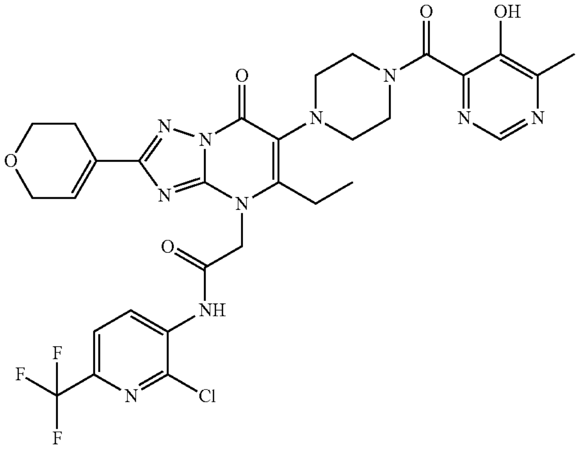

or in zwitterionic form:

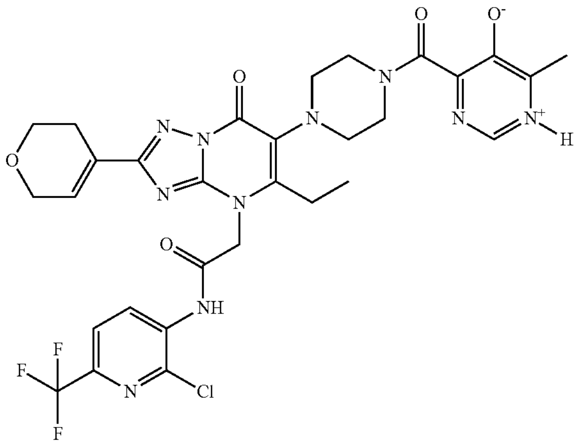 [SMILES: CCc1c(N2CCN(C(=O)c3nc[nH+]c(C)c3[O-])CC2)c(=O)n2nc(C3=CCOCC3)nc2n1CC(=O)Nc1ccc(C(F)(F)F)nc1Cl]

or in zwitterionic form:

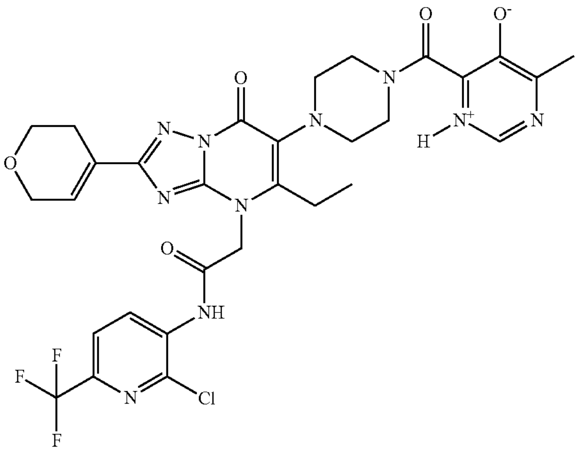 [SMILES: CCc1c(N2CCN(C(=O)c3[nH+]cnc(C)c3[O-])CC2)c(=O)n2nc(C3=CCOCC3)nc2n1CC(=O)Nc1ccc(C(F)(F)F)nc1Cl]

or a mixture of any two or three of said forms.

Embodiment 86. A compound of formula (I), according to any of embodiments 1, 24, 30 or 31, wherein the compound 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide is:

in non-zwitterionic form:

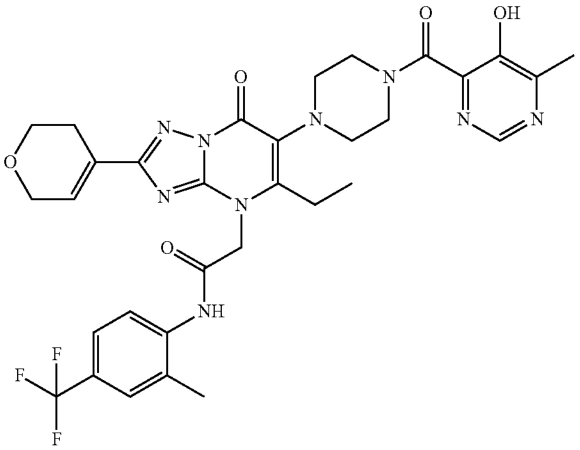 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1C]

or in zwitterionic form:

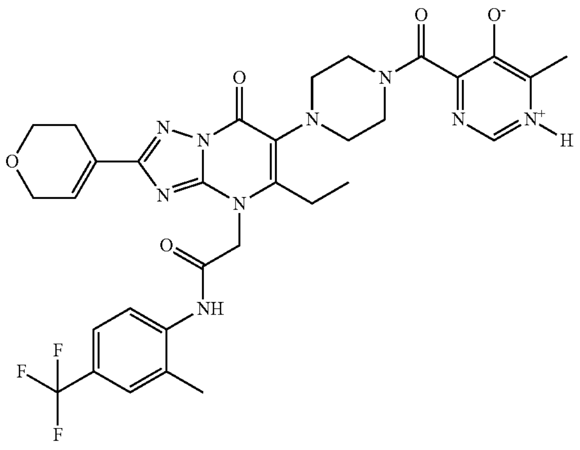 [SMILES: CCc1c(N2CCN(C(=O)c3nc[nH+]c(C)c3[O-])CC2)c(=O)n2nc(C3=CCOCC3)nc2n1CC(=O)Nc1ccc(C(F)(F)F)cc1C]

or in zwitterionic form:

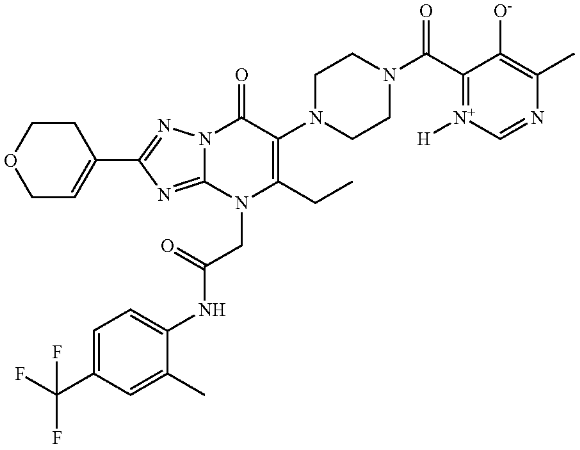 [SMILES: CCc1c(N2CCN(C(=O)c3[nH+]cnc(C)c3[O-])CC2)c(=O)n2nc(C3=CCOCC3)nc2n1CC(=O)Nc1ccc(C(F)(F)F)cc1C]

or a mixture of any two or three of said forms.

Embodiment 87: A compound of formula (I), according to any of embodiments 1, 24, 30 or 31, wherein the compound N-(2-chloro-4-(trifluoromethyl)phenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl) acetamide is:

in non-zwitterionic form:

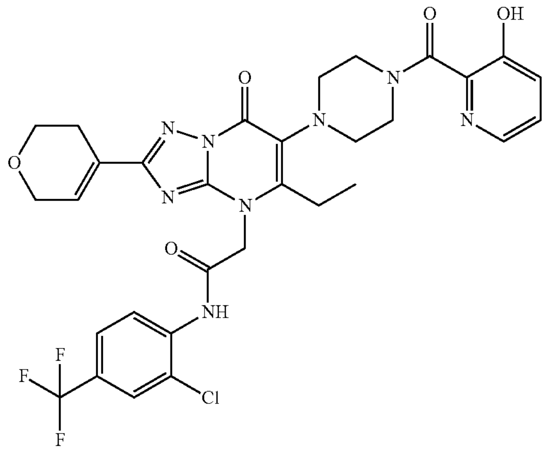

or in zwitterionic form:

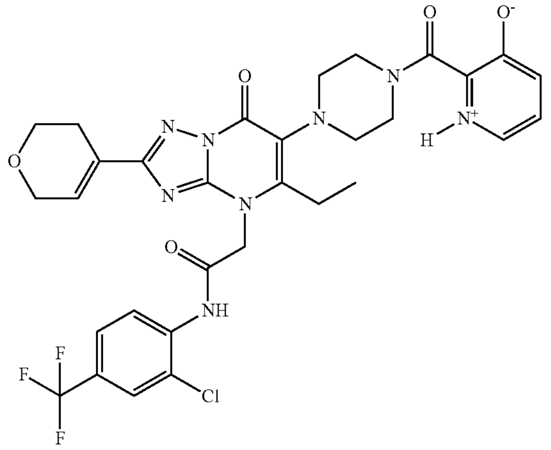 [SMILES: CCc1c(N2CCN(C(=O)c3[nH+]cccc3[O-])CC2)c(=O)n2nc(C3=CCOCC3)nc2n1CC(=O)Nc1ccc(C(F)(F)F)cc1Cl]

or a mixture of said forms.

Embodiment 88. A compound of formula (I), or a pharmaceutically acceptable salt thereof, according to any of embodiments 1-73, wherein the compound is a sodium salt.

Embodiment 89. A compound of formula (I), or a pharmaceutically acceptable salt thereof, according to any of embodiments 1-88, wherein the compound is in amorphous form. For example, the compound is the sodium salt in amorphous form.

Embodiment 90. A compound of formula (I), or a pharmaceutically acceptable salt thereof, according to any of embodiments 1-88, in crystalline form.

Embodiment 91. A compound of formula (I) according to any of embodiments 1, 24, 30 and 31, wherein the compound is:

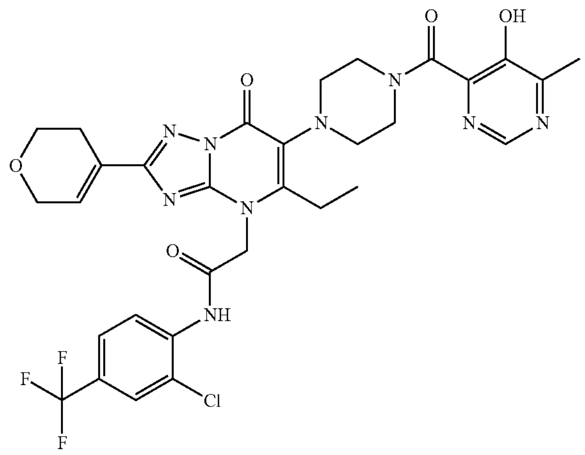 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Cl]

in crystalline form.

Embodiment 92. A compound of formula (I) according to any of embodiments 1, 24, 30 and 31, wherein the compound is:

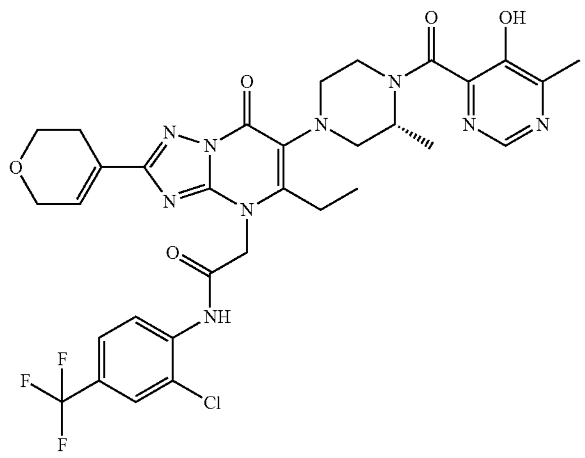 [SMILES: CCc1c(N2CCN(C(=O)c3ncnc(C)c3O)[C@H](C)C2)c(=O)n2nc(C3=CCOCC3)nc2n1CC(=O)Nc1ccc(C(F)(F)F)cc1Cl]

in crystalline form.

Embodiment 93. A compound of formula (I) according to any of embodiments 1, 24, 30 and 31, wherein the compound is:

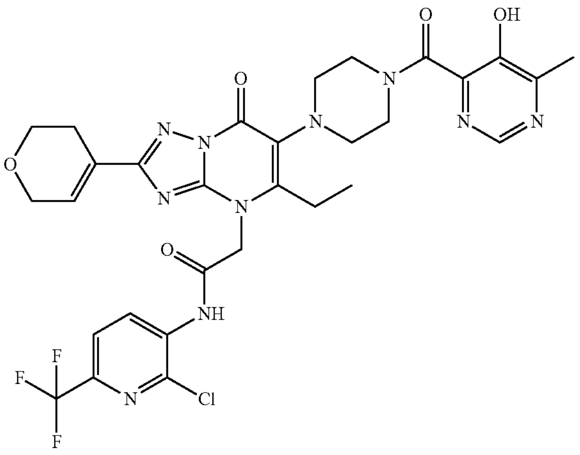 [SMILES: CCc1c(N2CCN(C(=O)c3ncnc(C)c3O)CC2)c(=O)n2nc(C3=CCOCC3)nc2n1CC(=O)Nc1ccc(C(F)(F)F)nc1Cl]

in crystalline form.

Embodiment 94. A compound of formula (I) according to any of embodiments 1, 24, 30 and 31, wherein the compound is:

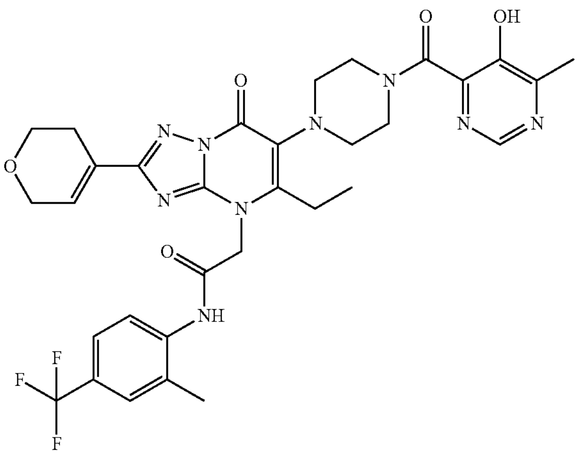 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1C]

in crystalline form.

Embodiment 95. A compound of formula (I) according to any of embodiments 1, 24, 30 and 31, wherein the compound is:

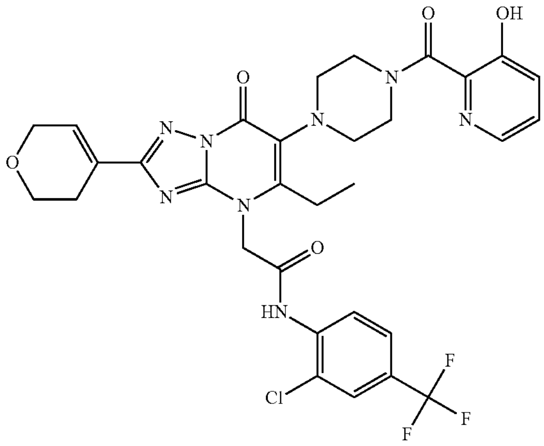 [SMILES: CCc1c(N2CCN(C(=O)c3ncccc3O)CC2)c(=O)n2nc(C3=CCOCC3)nc2n1CC(=O)Nc1ccc(C(F)(F)F)cc1Cl]

in crystalline form.

Embodiment 96. A compound of formula (I) according to embodiments 91-95, wherein the compound is in substantially pure form.

Embodiment 97. A compound of formula (I) according to embodiment 1, wherein the crystalline form according to embodiment 91 is characterized by a X-ray powder diffraction pattern comprising 4 or more 2θ values selected from the group consisting of 11.85±0.2, 13.71±0.2, 14.46±0.2, 15.33±0.2, 17.03±0.2, 18.33±0.2, 19.98±0.2, 22.42±0.2, 22.95±0.2 and 27.20±0.2, at a temperature of about 22° C., or comprising 4 or more 2θ values selected from the group consisting of 6.78±0.2, 8.97±0.2, 11.88±0.2, 13.55±0.2, 13.74±0.2, 14.48±0.2, 15.34±0.2, 16.83±0.2, 17.03±0.2, 18.30±0.2, 19.49±0.2, 19.94±0.2, 21.28±0.2, 21.51±0.2, 22.38±0.2, 22.91±0.2, 23.27±0.2, 25.41±0.2, 27.26±0.2, 29.03±0.2, 29.78±0.2 and 29.96±0.2, at a temperature of about 22° C.

Embodiment 98. A compound of formula (I) according to embodiment 1, wherein the crystalline form according to embodiment 91 is further characterized by a X-ray powder diffraction pattern comprising 5 or more 2θ values selected from the group consisting of 11.85±0.2, 13.71±0.2, 14.46±0.2, 15.33±0.2, 17.03±0.2, 18.33±0.2, 19.98±0.2, 22.42±0.2, 22.95±0.2 and 27.20±0.2, at a temperature of about 22° C., or comprising 5 or more 20 values selected from the group consisting of 6.78±0.2, 8.97±0.2, 11.88±0.2, 13.55±0.2, 13.74±0.2, 14.48±0.2, 15.34±0.2, 16.83±0.2, 17.03±0.2, 18.30±0.2, 19.49±0.2, 19.94±0.2, 21.28±0.2, 21.51±0.2, 22.38±0.2, 22.91±0.2, 23.27±0.2, 25.41±0.2, 27.26±0.2, 29.03±0.2, 29.78±0.2 and 29.96±0.2, at a temperature of about 22° C.

Embodiment 99. A compound of formula (I) according to embodiment 1, wherein the crystalline form according to embodiment 91 is characterized by a X-ray diffraction pattern substantially the same as the X-ray powder diffraction pattern shown in FIG. 1 or FIG. 7.

Embodiment 100. A compound of formula (I) according to embodiment 1, wherein the crystalline form according to embodiment 92 is characterized by a X-ray powder diffraction pattern comprising 4 or more 2θ values selected from the group consisting of 10.29±0.2, 13.31±0.2, 14.01±0.2, 15.26±0.2 and 17.34±0.2 at a temperature of about 22° C.

Embodiment 101. A compound of formula (I) according to embodiment 1, wherein the crystalline form according to embodiment 92 is further characterized by a X-ray powder diffraction pattern comprising 5 2θ values, selected from the group consisting of 10.29±0.2, 13.31±0.2, 14.01±0.2, 15.26±0.2 and 17.34±0.2 at a temperature of about 22° C.

Figure 2:
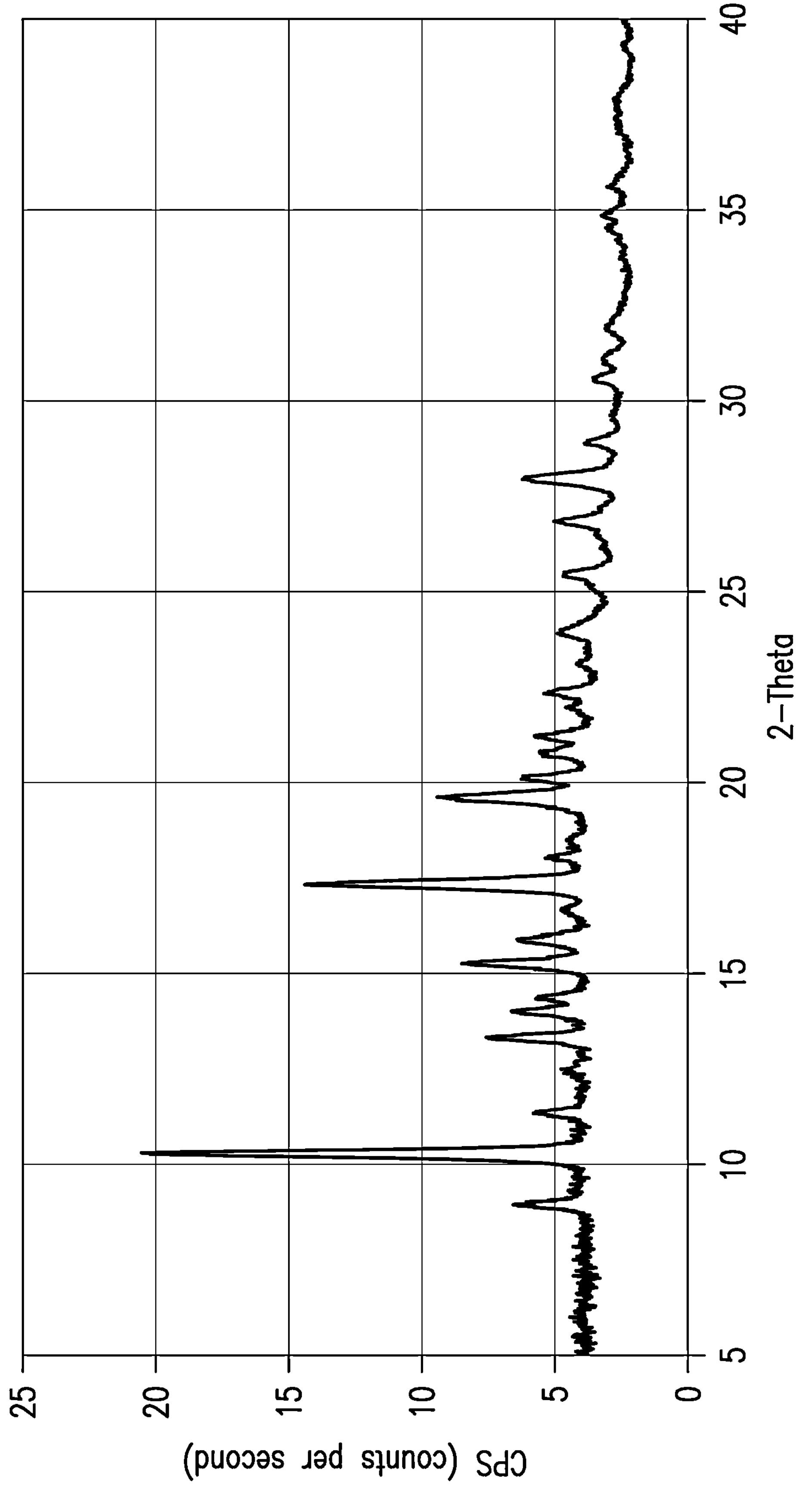
FIG. 2 shows a X-ray powder diffractogram for example 86.

Embodiment 102. A compound of formula (I) according to embodiment 1, wherein the crystalline form according to embodiment 92 is characterized by a X-ray diffraction pattern substantially the same as the X-ray powder diffraction spectrum shown in FIG. 2.

Embodiment 103. A compound of formula (I) according to embodiment 1, wherein the crystalline form according to embodiment 93 is characterized by a X-ray powder diffraction pattern comprising 4 or more 2θ values selected from the group consisting of 9.45±0.2, 12.75±0.2, 13.28±0.2, 21.69±0.2, 25.25±0.2 and 26.85±0.2 at a temperature of about 22° C.

Embodiment 104. A compound of formula (I) according to embodiment 1, wherein the crystalline form according to embodiment 93 is further characterized by a X-ray powder diffraction pattern comprising 5 or more 2θ values selected from the group consisting of 9.45±0.2, 12.75±0.2, 13.28±0.2, 21.69±0.2, 25.25±0.2 and 26.85±0.2 at a temperature of about 22° C.

Figure 3:
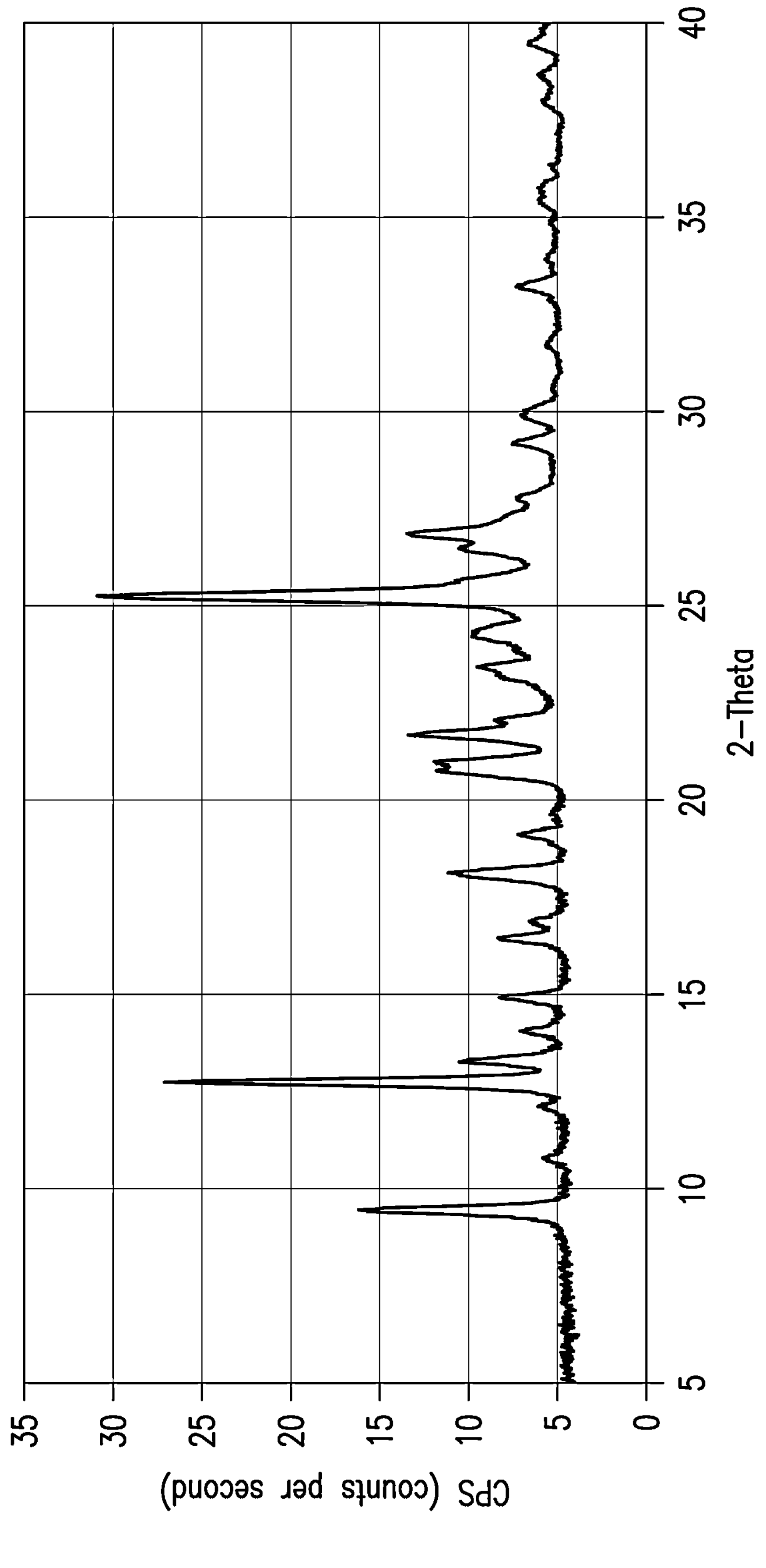
FIG. 3 shows a X-ray powder diffractogram for example 47.

Embodiment 105. A compound of formula (I) according to embodiment 1, wherein the crystalline form according to embodiment 93 is characterized by a X-ray diffraction pattern substantially the same as the X-ray powder diffraction spectrum shown in FIG. 3.

Embodiment 106. A compound of formula (I) according to embodiment 1, wherein the crystalline form according to embodiment 94 is characterized by a X-ray powder diffraction pattern comprising 4 or more 2θ values selected from the group consisting of 11.81±0.2, 13.75±0.2, 14.45±0.2, 15.32±0.2, 17.04±0.2, 17.40±0.2, 18.27±0.2, 19.95±0.2, 22.92±0.2 and 27.13±0.2 at a temperature of about 22° C.

Embodiment 107. A compound of formula (I) according to embodiment 1, wherein the crystalline form according to embodiment 94 is further characterized by a X-ray powder diffraction pattern comprising 5 or more 2θ values selected from the group consisting of 11.81±0.2, 13.75±0.2, 14.45±0.2, 15.32±0.2, 17.04±0.2, 17.40±0.2, 18.27±0.2, 19.95±0.2, 22.92±0.2 and 27.13±0.2 at a temperature of about 22° C.

Figure 4:
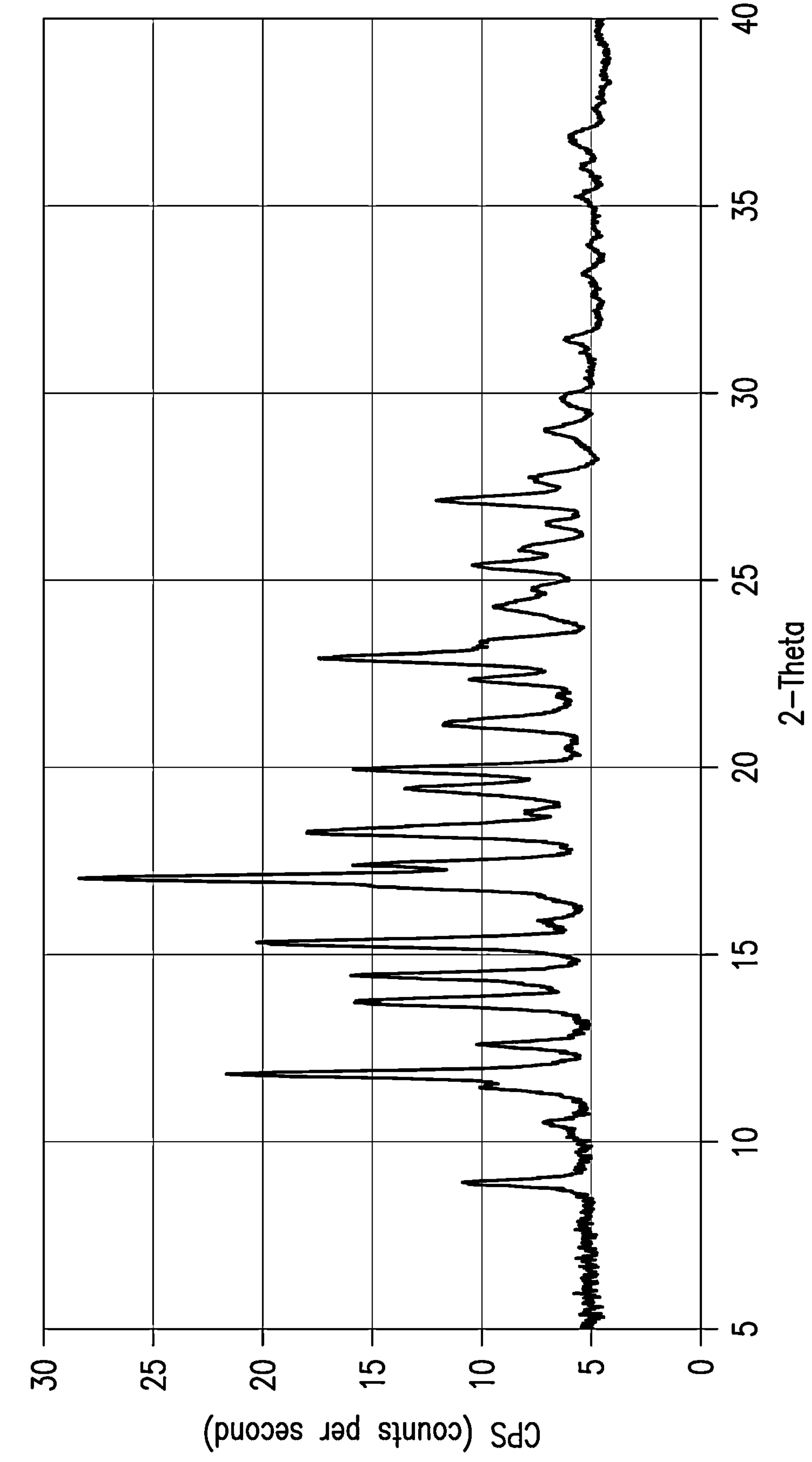
FIG. 4 shows a X-ray powder diffractogram for example 57.

Embodiment 108. A compound of formula (I) according to embodiment 1, wherein the crystalline form according to embodiment 94 is characterized by a X-ray diffraction pattern substantially the same as the X-ray powder diffraction spectrum shown in FIG. 4.

Embodiment 109. A compound of formula (I) according to embodiment 1, wherein the crystalline form according to embodiment 95 is characterized by a X-ray powder diffraction pattern comprising 4 or more 2θ values selected from the group consisting of 13.20±0.2, 14.78±0.2, 15.97±0.2, 16.91±0.2, 19.95±0.2, 20.85±0.2, 24.43±0.2, 25.47±0.2 and 31.06±0.2 at a temperature of about 22° C.

Embodiment 110. A compound of formula (I) according to embodiment 1, wherein the crystalline form according to embodiment 95 is further characterized by a X-ray powder diffraction pattern comprising 5 or more 2θ values selected from the group consisting of 13.20±0.2, 14.78±0.2, 15.97±0.2, 16.91±0.2, 19.95±0.2, 20.85±0.2, 24.43±0.2, 25.47±0.2 and 31.06±0.2 at a temperature of about 22° C.

Figure 5:
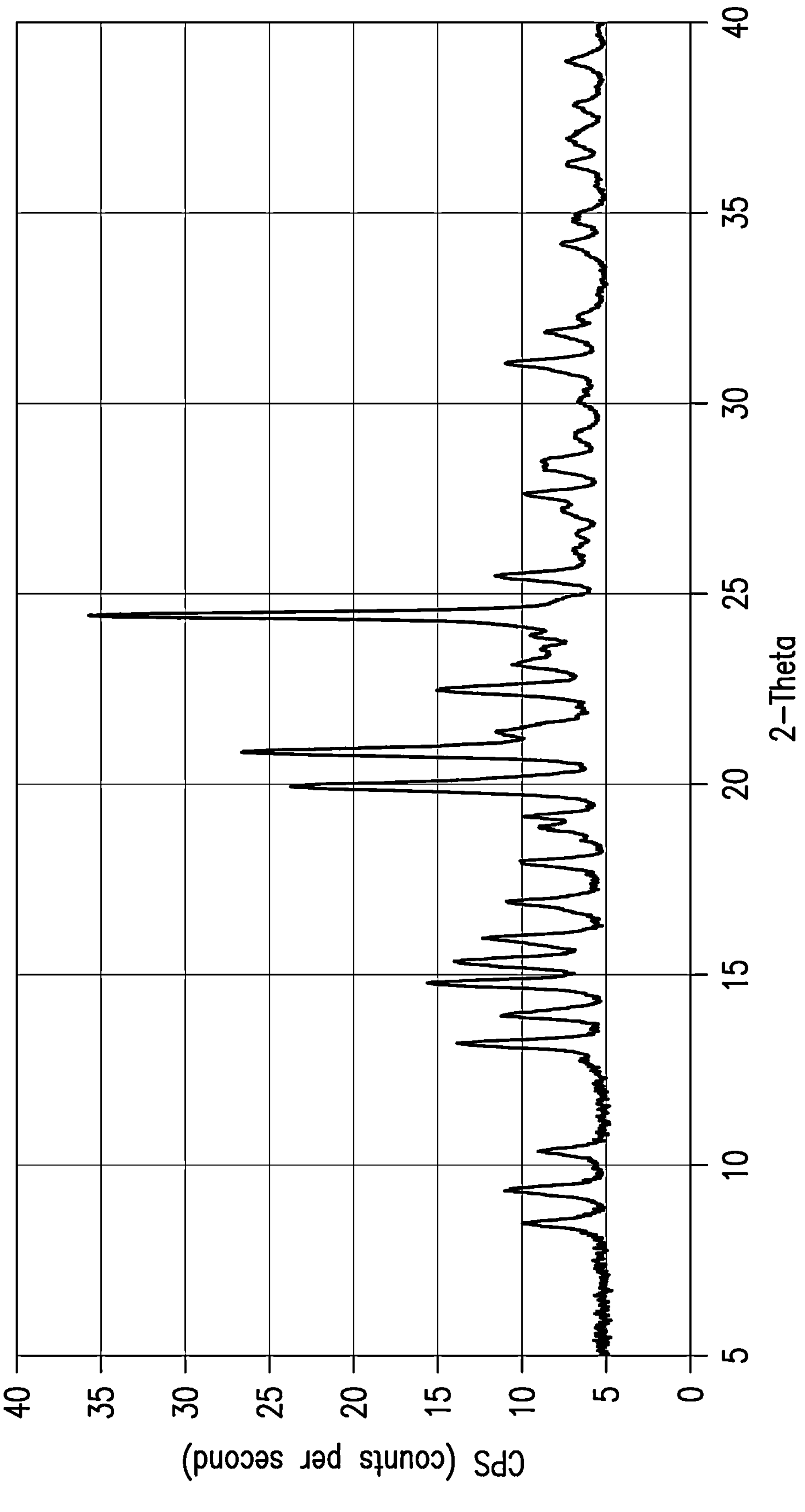
FIG. 5 shows a X-ray powder diffractogram for example 96.

Embodiment 111. A compound of formula (I) according to embodiment 1, wherein the crystalline form according to embodiment 95 is characterized by a X-ray diffraction pattern substantially the same as the X-ray powder diffraction spectrum shown in FIG. 5.

Embodiment 112. A compound of formula (I), or a pharmaceutically acceptable salt thereof, according to embodiment 1, wherein formula (I) is formula 1a:

1a

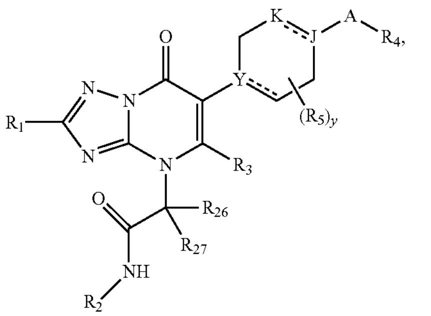

wherein $R_1$ is selected from:

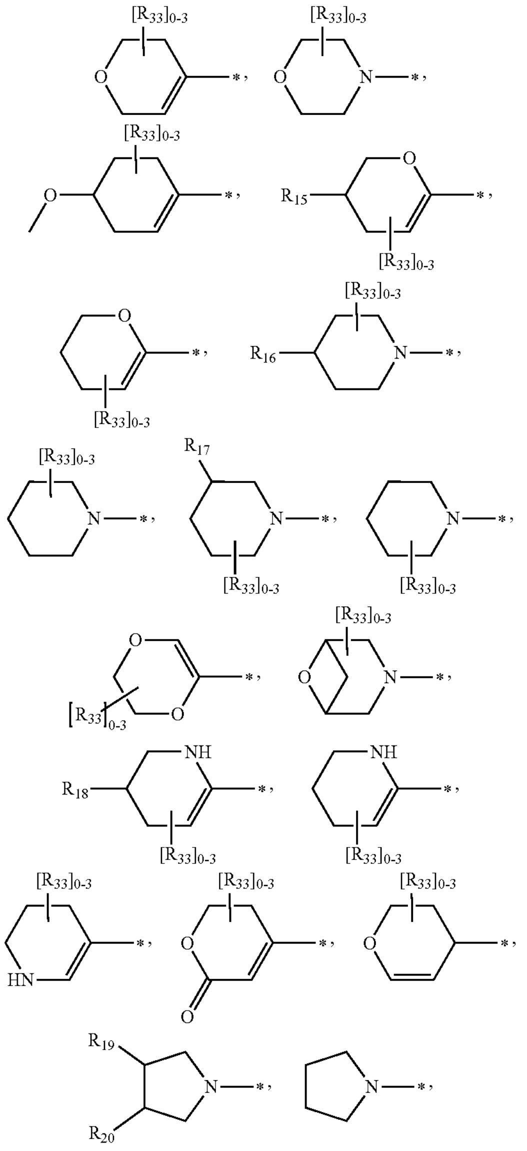

-continued

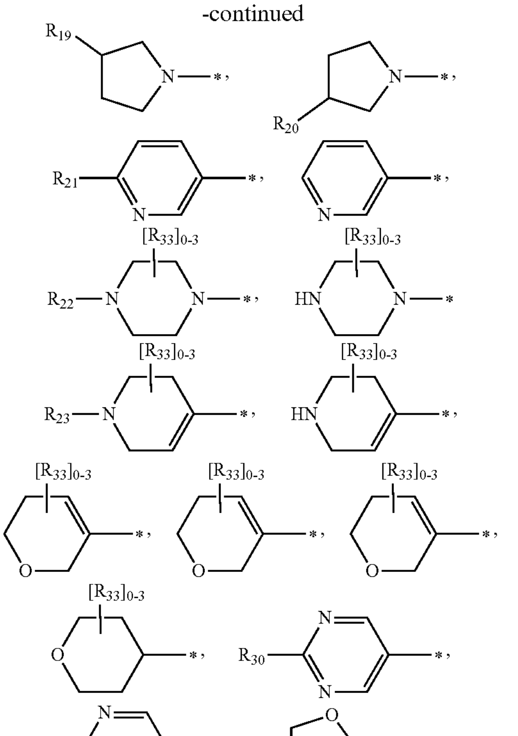

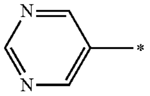 and 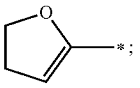;

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or $(C_1\text{-}C_2)$alkyl, $R_{25}$ is H or $(C_1\text{-}C_2)$alkyl;

$R_{17}$ is halo $R_{18}$ is halo;

$R_{19}$ is halo;

$R_{20}$ is halo;

$R_{21}$ is $(C_1\text{-}C_2)$alkyl;

$R_{22}$ and $R_{23}$ are each independently selected from:

$(C_1\text{-}C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

$R_2$ is the moiety:

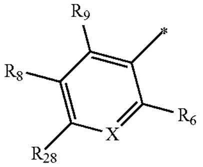

wherein $R_6$ is selected from H, halo, $(C_1\text{-}C_4)$alkyl unsubstituted or substituted by 1, 2 or 3 halo;

$R_8$ is selected from H, halo, ($C_1$-$C_4$)alkyl unsubstituted or substituted by 1, 2 or 3 halo;

$R_9$ is selected from H, halo, ($C_1$-$C_4$)alkyl unsubstituted or substituted by 1, 2 or 3 halo;

$R_{28}$ is selected from $SF_5$, halo, ($C_1$-$C_4$)alkyl unsubstituted or substituted by 1, 2 or 3 halo and —C(O)H;

X is selected from C—$R_7$ and N; and $R_7$ is selected from H and halo;

$R_{26}$ is H and $R_{27}$ is H;

$R_3$ is —$CH_2CH_3$ or $CH_3$;

A is a linker selected from —C(O)— and —$S(O)_2$—, preferably —C(O)—;

and $R_4$ is selected from:

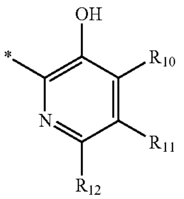 and 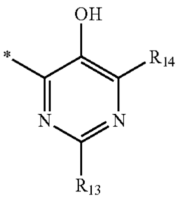

wherein $R_{10}$ is selected from H, halo, ($C_1$-$C_2$)alkyl unsubstituted or substituted by 1, 2 or 3 halo substituents, —O—($C_1$-$C_2$)alkyl unsubstituted or substituted by 1, 2 or 3 halo substituents;

$R_{11}$ is selected from H, halo, ($C_1$-$C_2$)alkyl unsubstituted or substituted by 1, 2 or 3 halo substituents;

$R_{12}$ is selected from H, halo, ($C_1$-$C_2$)alkyl unsubstituted or substituted by 1, 2 or 3 halo substituents;

$R_{13}$ is selected from H, —S—$CH_3$ halo, ($C_1$-$C_2$)alkyl unsubstituted or substituted by 1, 2 or 3 halo substituents; and $R_{14}$ is selected from H, halo, ($C_1$-$C_2$)alkyl unsubstituted or substituted by 1, 2 or 3 halo substituents, O—($C_1$-$C_2$)alkyl unsubstituted or substituted by 1, 2 or 3 halo substituents, cyclopropyl.

Preferably, Formula (I), or 1a, is 1g:

1g

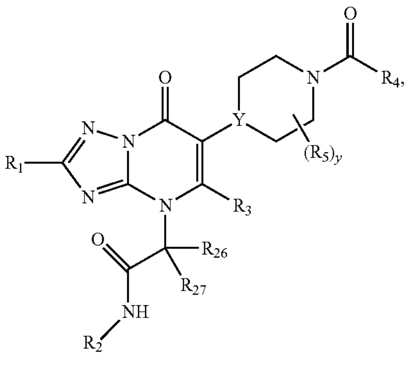

and more preferably 1h:

1h

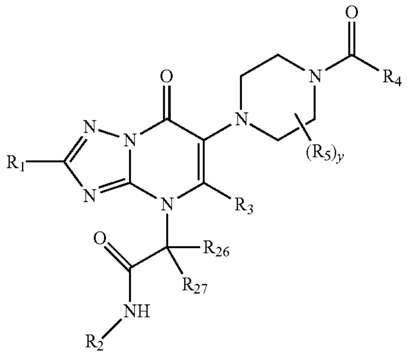

Embodiment 113. A compound of formula (I), or a pharmaceutically acceptable salt thereof, according to embodiment 1, wherein formula (I) is formula 1 b:

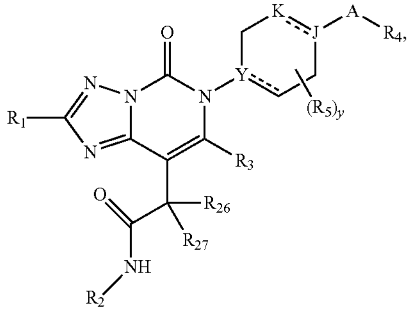

wherein $R_1$ is selected from:

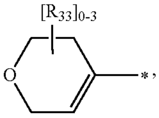, 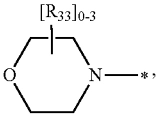,

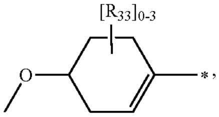, 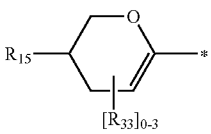,

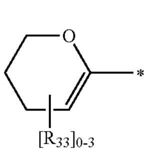 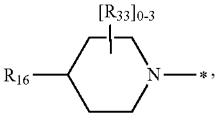,

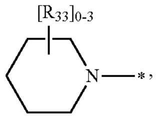, 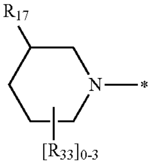, 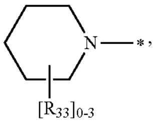,

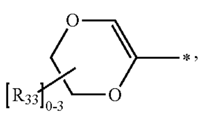, 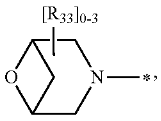,

-continued

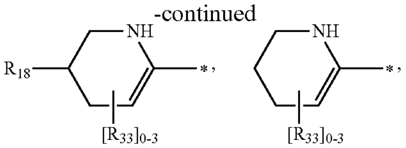
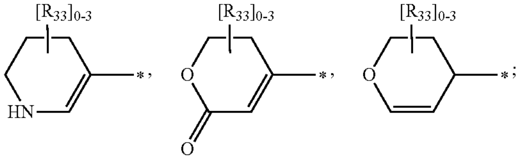
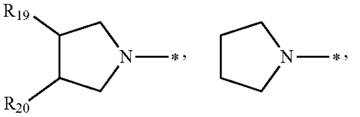
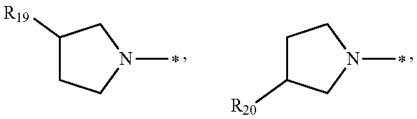
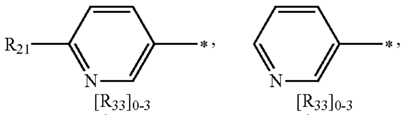
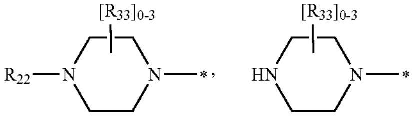
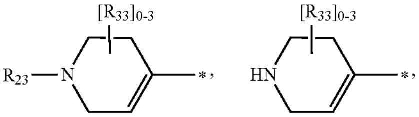
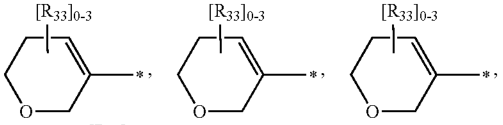
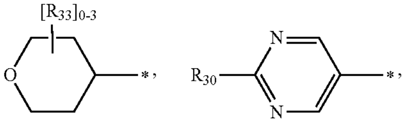
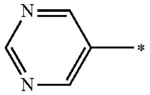 and 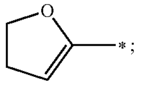

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F; $R_{16}$ is $R_{25}(R_{24})N$—, wherein $R_{24}$ is H or $(C_1\text{-}C_2)$alkyl, $R_{25}$ is H or $(C_1\text{-}C_2)$alkyl;

$R_{17}$ is halo $R_{18}$ is halo;

$R_{19}$ is halo;

$R_{20}$ is halo;

$R_{21}$ is $(C_1\text{-}C_2)$alkyl;

$R_{22}$ and $R_{23}$ are each independently selected from:

$(C_1\text{-}C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

$R_2$ is the moiety:

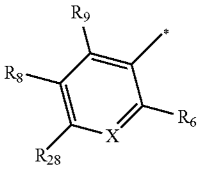

wherein $R_6$ is selected from H, halo, $(C_1\text{-}C_4)$alkyl unsubstituted or substituted by 1, 2 or 3 halo;

$R_8$ is selected from H, halo, $(C_1\text{-}C_4)$alkyl unsubstituted or substituted by 1, 2 or 3 halo;

$R_9$ is selected from H, halo, $(C_1\text{-}C_4)$alkyl unsubstituted or substituted by 1, 2 or 3 halo;

$R_{28}$ is selected from $SF_5$, halo, $(C_1\text{-}C_4)$alkyl unsubstituted or substituted by 1, 2 or 3 halo and —C(O)H;

X is selected from C—$R_7$ and N; and $R_7$ is selected from H and halo;

$R_{26}$ is H and $R_{27}$ is H;

$R_3$ is $—CH_2CH_3$ or $CH_3$;

A is a linker selected from —C(O)— and $—S(O)_2—$, preferably —C(O)—;

and $R_4$ is selected from:

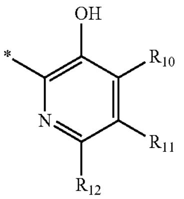 and 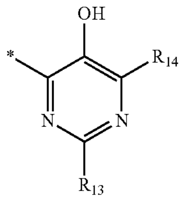

wherein $R_{10}$ is selected from H, halo, $(C_1\text{-}C_2)$alkyl unsubstituted or substituted by 1, 2 or 3 halo substituents, —O—$(C_1\text{-}C_2)$alkyl unsubstituted or substituted by 1, 2 or 3 halo substituents;

$R_{11}$ is selected from H, halo, $(C_1\text{-}C_2)$alkyl unsubstituted or substituted by 1, 2 or 3 halo substituents;

$R_{12}$ is selected from H, halo, $(C_1\text{-}C_2)$alkyl unsubstituted or substituted by 1, 2 or 3 halo substituents;

$R_{13}$ is selected from H, —S—$CH_3$ halo, $(C_1\text{-}C_2)$alkyl unsubstituted or substituted by 1, 2 or 3 halo substituents; and $R_{14}$ is selected from H, halo, $(C_1\text{-}C_2)$alkyl unsubstituted or substituted by 1, 2 or 3 halo substituents, O—$(C_1\text{-}C_2)$alkyl unsubstituted or substituted by 1, 2 or 3 halo substituents, cyclopropyl.

Formula 1b is preferably 1b1:

1b1

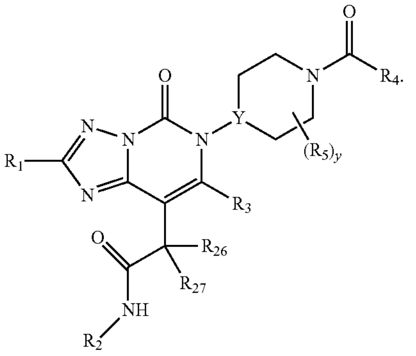

Particularly, where Y is N.

Embodiment 114. A compound of formula (I), or a pharmaceutically acceptable salt thereof, according to embodiment 1, wherein formula (I) is formula 1c:

1c

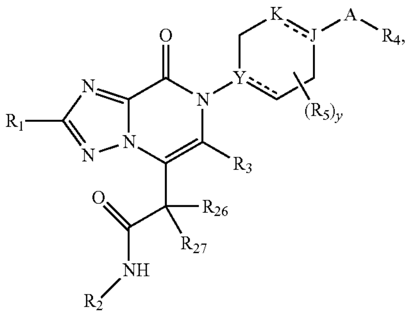

wherein $R_1$ is selected from:

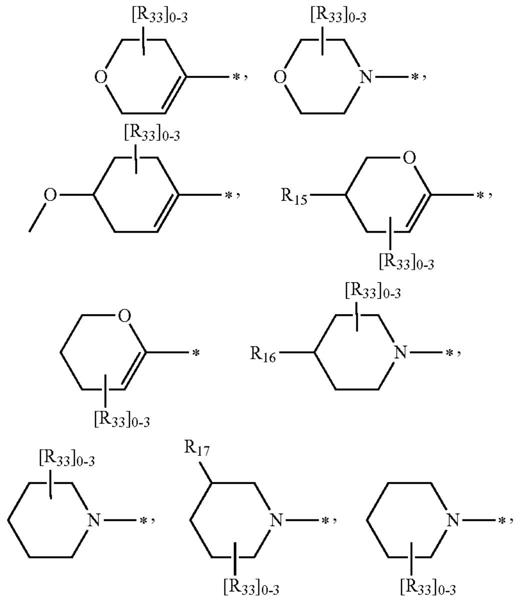

-continued

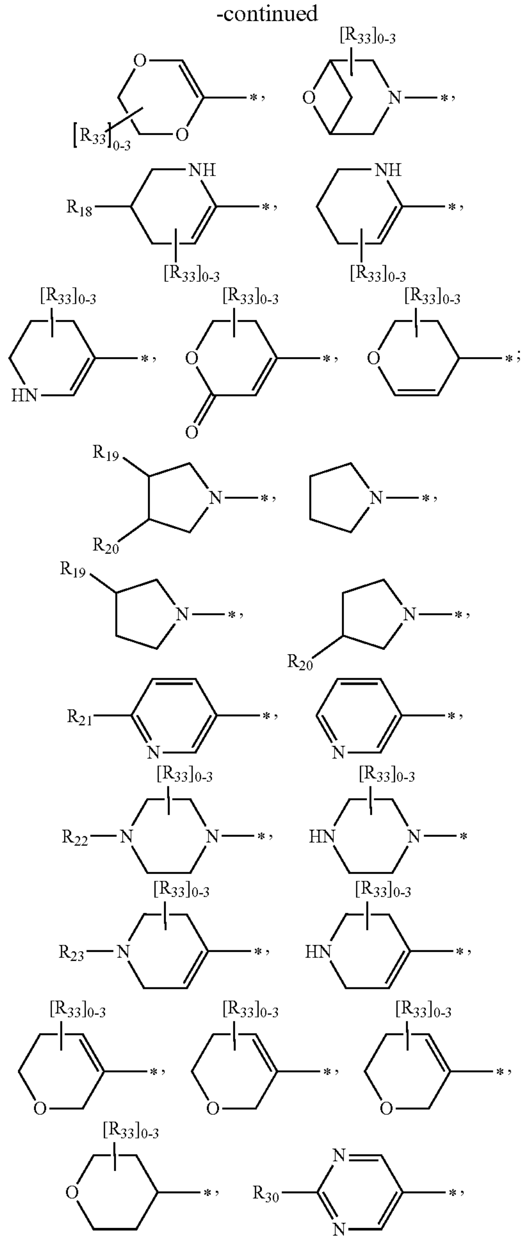

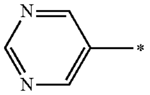 and 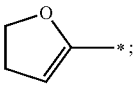

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or $(C_1-C_2)$alkyl, $R_{25}$ is H or $(C_1-C_2)$alkyl;

$R_{17}$ is halo $R_{18}$ is halo;

$R_{19}$ is halo;

$R_{20}$ is halo;

$R_{21}$ is $(C_1-C_2)$alkyl;

$R_{22}$ and $R_{23}$ are each independently selected from:

$(C_1-C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

$R_2$ is the moiety:

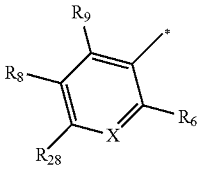

wherein $R_6$ is selected from H, halo, $(C_1-C_4)$alkyl unsubstituted or substituted by 1, 2 or 3 halo;

$R_8$ is selected from H, halo, $(C_1-C_4)$alkyl unsubstituted or substituted by 1, 2 or 3 halo;

$R_9$ is selected from H, halo, $(C_1-C_4)$alkyl unsubstituted or substituted by 1, 2 or 3 halo;

$R_{28}$ is selected from $SF_5$, halo, $(C_1-C_4)$alkyl unsubstituted or substituted by 1, 2 or 3 halo and —C(O)H;

X is selected from C—$R_7$ and N; and $R_7$ is selected from H and halo;

$R_{26}$ is H and $R_{27}$ is H;

$R_3$ is $—CH_2CH_3$ or $CH_3$;

A is a linker selected from —C(O)— and $—S(O)_2—$, preferably —C(O)—;

and $R_4$ is selected from:

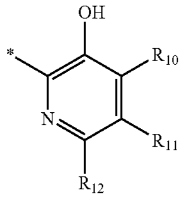

and

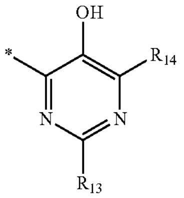

wherein $R_{10}$ is selected from H, halo, $(C_1-C_2)$alkyl unsubstituted or substituted by 1, 2 or 3 halo substituents, —O—$(C_1-C_2)$alkyl unsubstituted or substituted by 1, 2 or 3 halo substituents;

$R_{11}$ is selected from H, halo, $(C_1-C_2)$alkyl unsubstituted or substituted by 1, 2 or 3 halo substituents;

$R_{12}$ is selected from H, halo, $(C_1-C_2)$alkyl unsubstituted or substituted by 1, 2 or 3 halo substituents;

$R_{13}$ is selected from H, $—S—CH_3$ halo, $(C_1-C_2)$alkyl unsubstituted or substituted by 1, 2 or 3 halo substituents; and $R_{14}$ is selected from H, halo, $(C_1-C_2)$alkyl unsubstituted or substituted by 1, 2 or 3 halo substituents, O—$(C_1-C_2)$alkyl unsubstituted or substituted by 1, 2 or 3 halo substituents, cyclopropyl.

Formula 1c, is preferably 1c1:

1c1

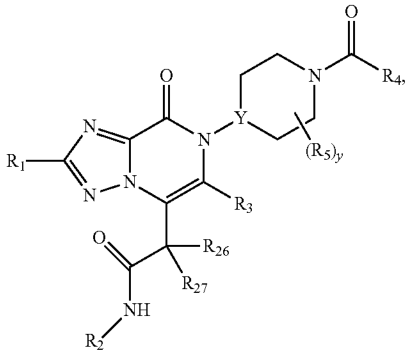

particularly where Y is N.

Embodiment 115. A compound of formula (I), or a pharmaceutically acceptable salt thereof, according to embodiment 1, wherein formula (I) is formula 1d:

1d

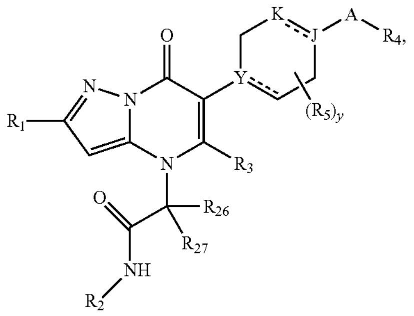

wherein $R_1$ is selected from:

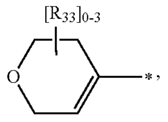

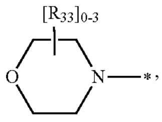

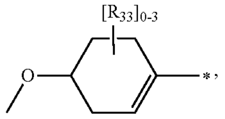

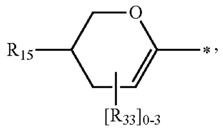

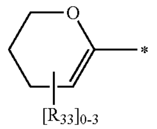

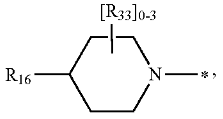

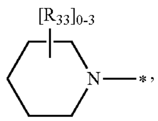

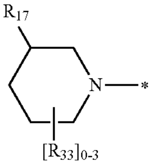

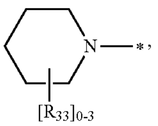

-continued

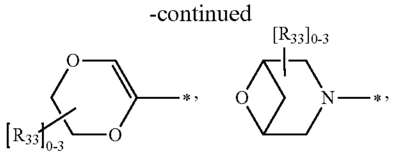
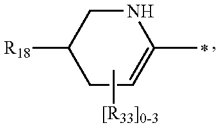
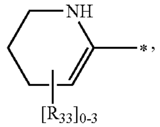
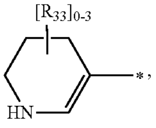
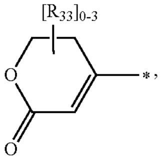
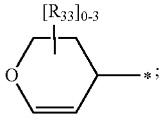
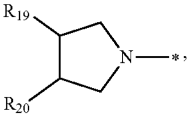
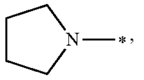
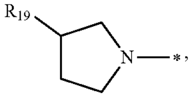
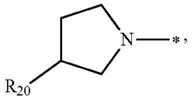
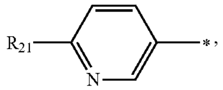
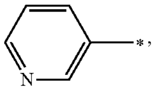
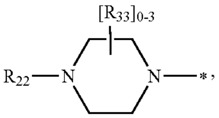
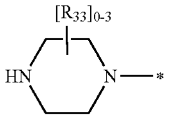
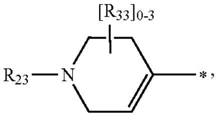
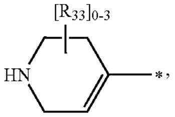
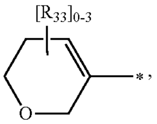
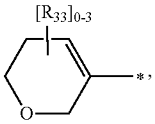
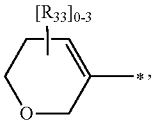
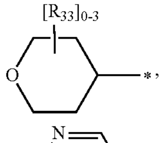
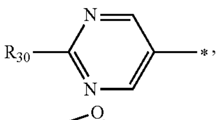
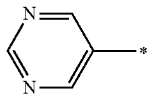 and 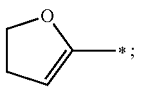

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or $(C_1$-$C_2)$alkyl, $R_{25}$ is H or $(C_1$-$C_2)$alkyl;

$R_{17}$ is halo $R_{18}$ is halo;

$R_{19}$ is halo;

$R_{20}$ is halo;

$R_{21}$ is $(C_1$-$C_2)$alkyl;

$R_{22}$ and $R_{23}$ are each independently selected from:

$(C_1$-$C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

$R_2$ is the moiety:

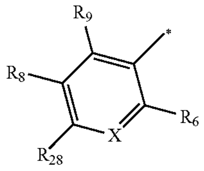

wherein $R_6$ is selected from H, halo, $(C_1$-$C_4)$alkyl unsubstituted or substituted by 1, 2 or 3 halo;

$R_8$ is selected from H, halo, $(C_1$-$C_4)$alkyl unsubstituted or substituted by 1, 2 or 3 halo;

$R_9$ is selected from H, halo, $(C_1$-$C_4)$alkyl unsubstituted or substituted by 1, 2 or 3 halo;

$R_{28}$ is selected from $SF_5$, halo, $(C_1$-$C_4)$alkyl unsubstituted or substituted by 1, 2 or 3 halo and —C(O)H;

X is selected from C—$R_7$ and N; and $R_7$ is selected from H and halo;

$R_{26}$ is H and $R_{27}$ is H;

$R_3$ is —$CH_2CH_3$ or $CH_3$;

A is a linker selected from —C(O)— and —$S(O)_2$—, preferably —C(O)—;

and $R_4$ is selected from:

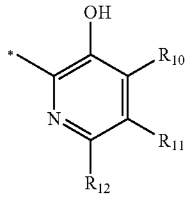 and 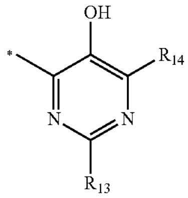

wherein $R_{10}$ is selected from H, halo, $(C_1$-$C_2)$alkyl unsubstituted or substituted by 1, 2 or 3 halo substituents, —O—$(C_1$-$C_2)$alkyl unsubstituted or substituted by 1, 2 or 3 halo substituents;

$R_{11}$ is selected from H, halo, $(C_1$-$C_2)$alkyl unsubstituted or substituted by 1, 2 or 3 halo substituents;

$R_{12}$ is selected from H, halo, $(C_1$-$C_2)$alkyl unsubstituted or substituted by 1, 2 or 3 halo substituents;

$R_{13}$ is selected from H, —S—$CH_3$ halo, $(C_1$-$C_2)$alkyl unsubstituted or substituted by 1, 2 or 3 halo substituents; and $R_{14}$ is selected from H, halo, $(C_1$-$C_2)$alkyl unsubstituted or substituted by 1, 2 or 3 halo substituents, O—$(C_1$-$C_2)$alkyl unsubstituted or substituted by 1, 2 or 3 halo substituents, cyclopropyl.

Formula 1d, is preferably 1d1:

1d1

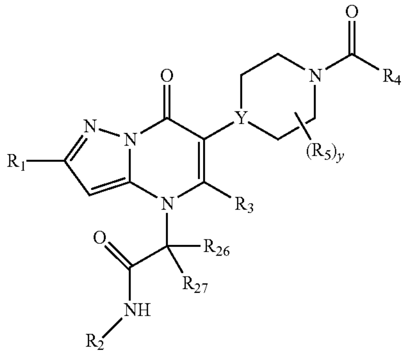

Particularly, where Y is N.

Embodiment 116. A compound of formula (I), or a pharmaceutically acceptable salt thereof, according to embodiment 1, wherein formula (I) is formula 1e:

1e

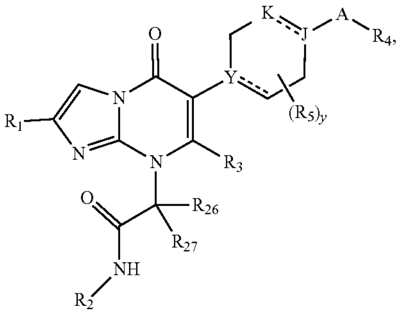

wherein $R_1$ is selected from:

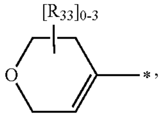
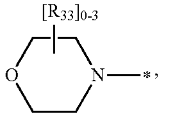
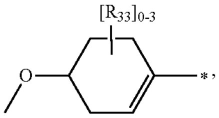
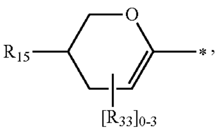
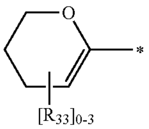
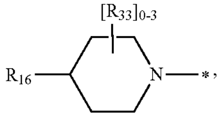
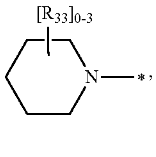
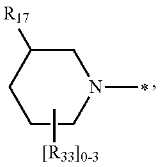
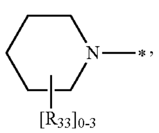

-continued

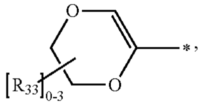
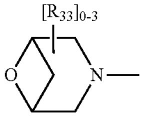
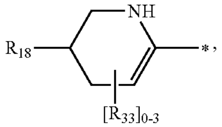
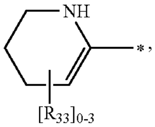
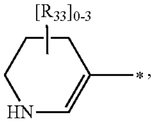
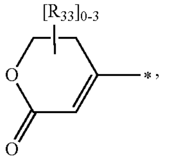
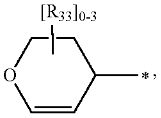
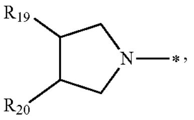
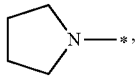
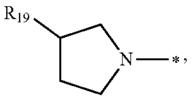
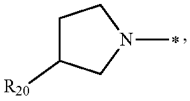
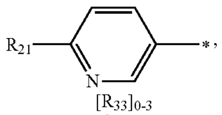
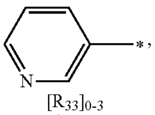
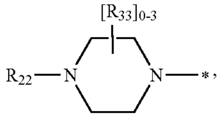
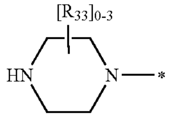
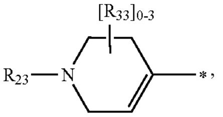
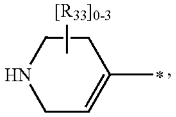
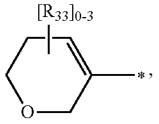
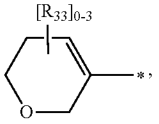
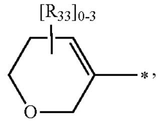
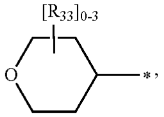
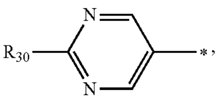
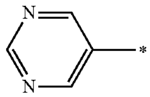
and
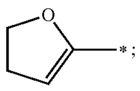

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or $(C_1$-$C_2)$alkyl, $R_{25}$ is H or $(C_1$-$C_2)$alkyl;

$R_{17}$ is halo $R_{18}$ is halo;

$R_{19}$ is halo;

$R_{20}$ is halo;

$R_{21}$ is $(C_1$-$C_2)$alkyl;

$R_{22}$ and $R_{23}$ are each independently selected from:

$(C_1$-$C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

$R_2$ is the moiety:

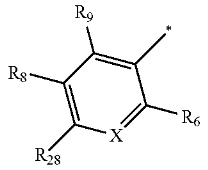

wherein $R_6$ is selected from H, halo, $(C_1$-$C_4)$alkyl unsubstituted or substituted by 1, 2 or 3 halo;

$R_8$ is selected from H, halo, $(C_1$-$C_4)$alkyl unsubstituted or substituted by 1, 2 or 3 halo;

$R_9$ is selected from H, halo, $(C_1$-$C_4)$alkyl unsubstituted or substituted by 1, 2 or 3 halo;

$R_{28}$ is selected from $SF_5$, halo, $(C_1$-$C_4)$alkyl unsubstituted or substituted by 1, 2 or 3 halo and —C(O)H;

X is selected from C—$R_7$ and N; and $R_7$ is selected from H and halo;

$R_{26}$ is H and $R_{27}$ is H;

$R_3$ is $—CH_2CH_3$ or $CH_3$;

A is a linker selected from —C(O)— and $—S(O)_2—$, preferably —C(O)—;

and $R_4$ is selected from:

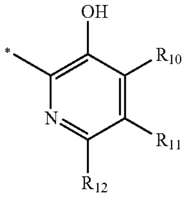

and

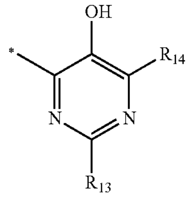

wherein $R_{10}$ is selected from H, halo, $(C_1$-$C_2)$alkyl unsubstituted or substituted by 1, 2 or 3 halo substituents, —O—$(C_1$-$C_2)$alkyl unsubstituted or substituted by 1, 2 or 3 halo substituents;

$R_{11}$ is selected from H, halo, $(C_1$-$C_2)$alkyl unsubstituted or substituted by 1, 2 or 3 halo substituents;

$R_{12}$ is selected from H, halo, $(C_1$-$C_2)$alkyl unsubstituted or substituted by 1, 2 or 3 halo substituents;

$R_{13}$ is selected from H, —S—$CH_3$ halo, $(C_1$-$C_2)$alkyl unsubstituted or substituted by 1, 2 or 3 halo substituents; and $R_{14}$ is selected from H, halo, $(C_1$-$C_2)$alkyl unsubstituted or substituted by 1, 2 or 3 halo substituents, O—$(C_1$-$C_2)$alkyl unsubstituted or substituted by 1, 2 or 3 halo substituents, cyclopropyl.

Formula 1e, is preferably 1e1:

1e1

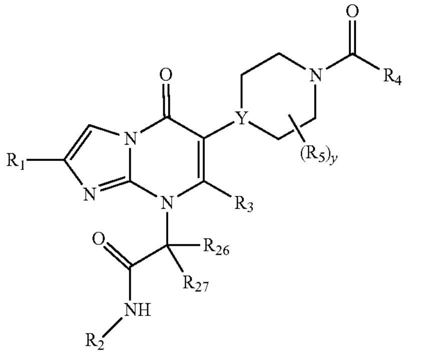

Particularly, where Y is N.

Embodiment 117. A compound of formula (I), or a pharmaceutically acceptable salt thereof, according to embodiment 1, wherein formula (I) is formula 1f:

1f

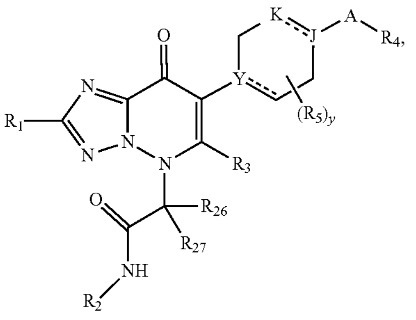

wherein $R_1$ is selected from:

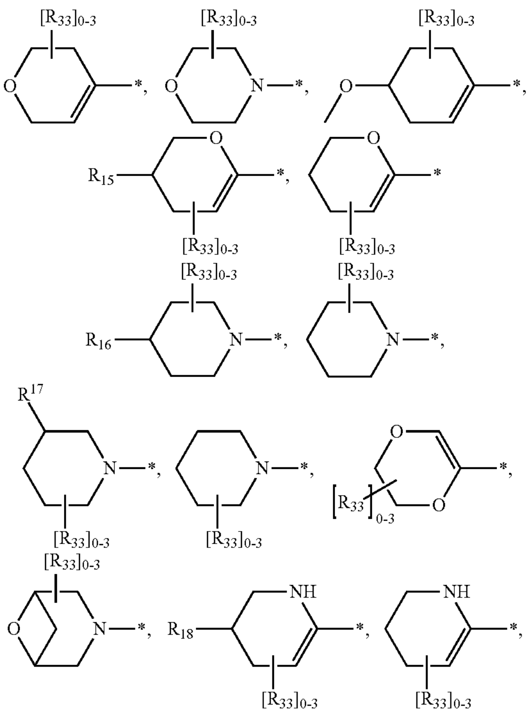

-continued

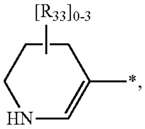, 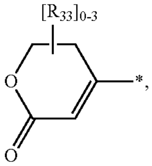, 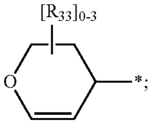;

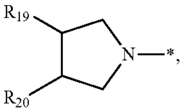, 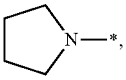, 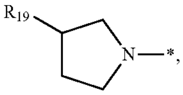,

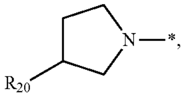, 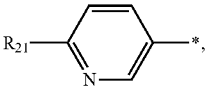,

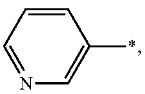, 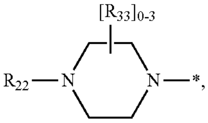,

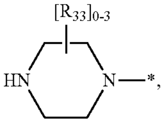, 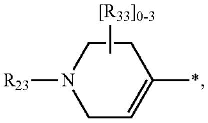,

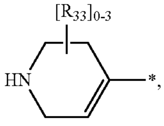, 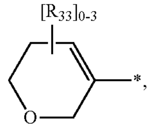, 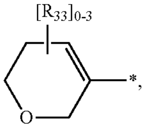,

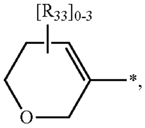, 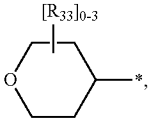, 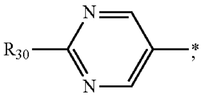

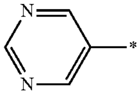 and 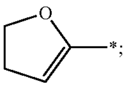;

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or ($C_1$-$C_2$)alkyl, $R_{25}$ is H or ($C_1$-$C_2$)alkyl;

$R_{17}$ is halo $R_{18}$ is halo;

$R_{19}$ is halo;

$R_{20}$ is halo;

$R_{21}$ is ($C_1$-$C_2$)alkyl;

$R_{22}$ and $R_{23}$ are each independently selected from:

($C_1$-$C_4$)alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

$R_2$ is the moiety:

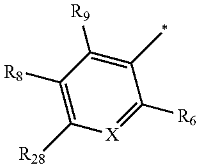

wherein $R_6$ is selected from H, halo, ($C_1$-$C_4$)alkyl unsubstituted or substituted by 1, 2 or 3 halo;

$R_8$ is selected from H, halo, ($C_1$-$C_4$)alkyl unsubstituted or substituted by 1, 2 or 3 halo;

$R_9$ is selected from H, halo, ($C_1$-$C_4$)alkyl unsubstituted or substituted by 1, 2 or 3 halo;

$R_{28}$ is selected from $SF_5$, halo, ($C_1$-$C_4$)alkyl unsubstituted or substituted by 1, 2 or 3 halo and —C(O)H;

X is selected from C—$R_7$ and N; and $R_7$ is selected from H and halo;

$R_{26}$ is H and $R_{27}$ is H;

$R_3$ is $—CH_2CH_3$ or $CH_3$;

A is a linker selected from —C(O)— and $—S(O)_2—$, preferably —C(O)—;

and $R_4$ is selected from:

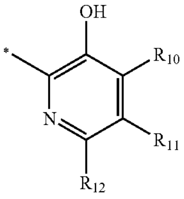 and 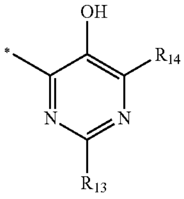

wherein $R_{10}$ is selected from H, halo, ($C_1$-$C_2$)alkyl unsubstituted or substituted by 1, 2 or 3 halo substituents, —O—($C_1$-$C_2$)alkyl unsubstituted or substituted by 1, 2 or 3 halo substituents;

$R_{11}$ is selected from H, halo, ($C_1$-$C_2$)alkyl unsubstituted or substituted by 1, 2 or 3 halo substituents;

$R_{12}$ is selected from H, halo, ($C_1$-$C_2$)alkyl unsubstituted or substituted by 1, 2 or 3 halo substituents;

$R_{13}$ is selected from H, $—S—CH_3$ halo, ($C_1$-$C_2$)alkyl unsubstituted or substituted by 1, 2 or 3 halo substituents; and $R_{14}$ is selected from H, halo, ($C_1$-$C_2$)alkyl unsubstituted or substituted by 1, 2 or 3 halo substituents, O—($C_1$-$C_2$)alkyl unsubstituted or substituted by 1, 2 or 3 halo substituents, cyclopropyl.

Formula 1f, is preferably 1f1:

1f1

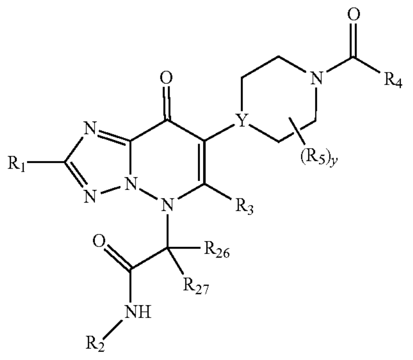

Particularly, where Y is N.

Embodiment 1.1. A compound of formula (I) according to embodiment 1, or a pharmaceutically acceptable salt thereof:

(1g)

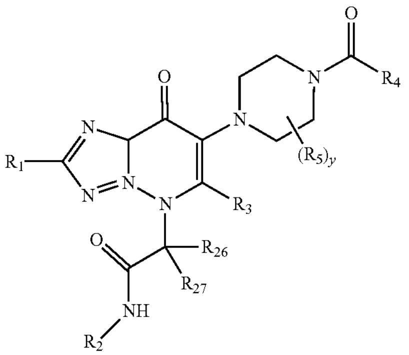

wherein (I) is 1g, and $R_1$ is selected from:

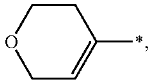, 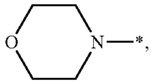,

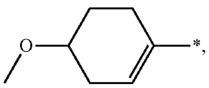, 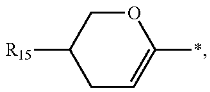,

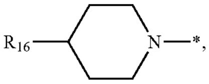, 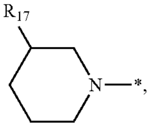,

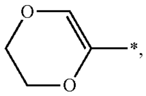, 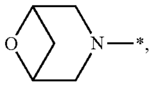, 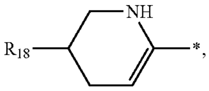,

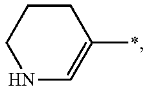, 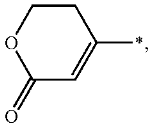, 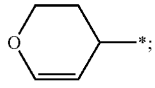;

-continued

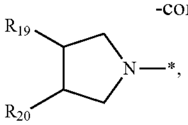, 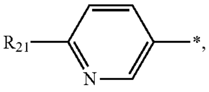,

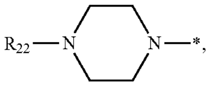, 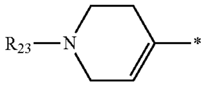 and

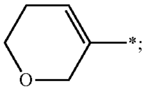;

$R_{15}$ is H or F;
$R_{16}$ is H or $R_{25}(R_{24})N$—;
$R_{17}$ is H or F;
$R_{18}$ is H or F;
$R_{19}$ is H or F;
$R_{20}$ is H or F;
$R_{21}$ is H or $CH_3$;
$R_{22}$ is H, $CF_3$, $CHF_2CH_2$, HOC(O)—$CH_2$—, $H_3C$—C(O)—, $(H_3C)_3C$—O—C(O)—;
$R_{23}$ is H, $CF_3$, $CHF_2CH_2$—, $(H_3C)_3C$—O—C(O)—;
$R_{24}$ is $CH_3$;
$R_{25}$ is $CHF_2CH_2$—;
$R_{26}$ is $CH_3$, H or deuterium;
$R_{27}$ is H or deuterium;
$R_2$ is the moiety:

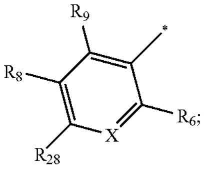;

wherein $R_6$ is selected from H, Cl, $CH_3$, F, and Br;
$R_8$ is selected from H, Cl, F and $CF_3$;
$R_8$ is selected from H, $CH_3$ and Cl;
$R_{28}$ is selected from $CF_3$, $CF_2H$, —$CH_2CH_3$, Cl, $SF_5$, Br and —C(O)H;
X is selected from C—$R_7$ and N;
$R_7$ is selected from H and F;
$R_3$ is selected from $CH_3$, $CH_2CH_3$, cyclopropyl and hydroxyethyl;
$R_4$ is selected from:

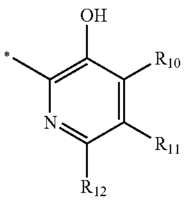 and 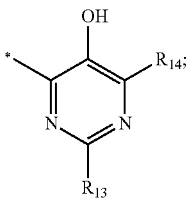;

wherein
$R_{10}$ is selected from H, F, Cl, $CH_3$ and $OCF_3$;
$R_{11}$ is selected from H, Cl, F, and $CH_3$;
$R_{12}$ is selected from H, Cl and $CH_3$;
$R_{13}$ is selected from H and $CH_3$;
$R_{14}$ is selected from H, $CH_3$, —$CH_2CH_3$, cyclopropyl, —$OCHF_2$, $OCF_3$ and Cl;

y is 0, 1 or 2;

$R_5$ is $CH_3$; or alternatively, two $R_5$ groups on adjacent carbon atoms join, along with the carbon atoms to which they are attached, to form a fused cyclobutyl ring:

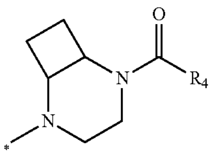

and

* indicates a point of attachment;

or a pharmaceutically acceptable salt thereof.

Embodiment 2.1. A compound of formula (I), or a pharmaceutically acceptable salt thereof, according to embodiment 1, wherein $R_1$ is selected from:

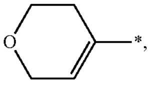, 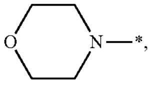, 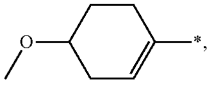,

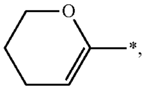, 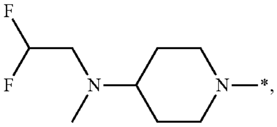,

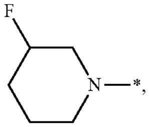, 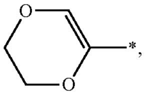, 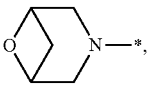,

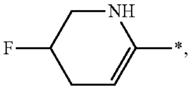, 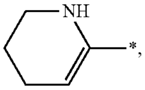, 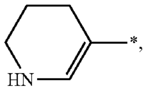,

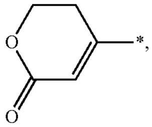, 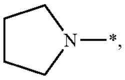, 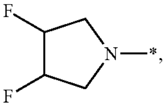,

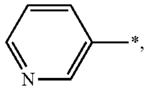, 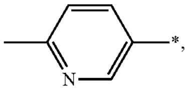,

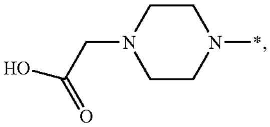, 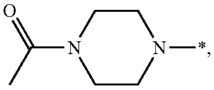,

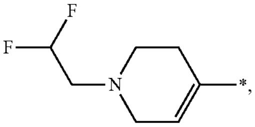,

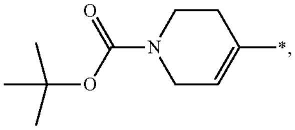, 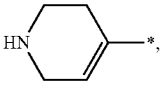,

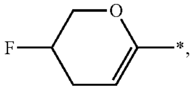, 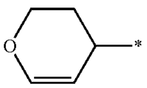 and

-continued

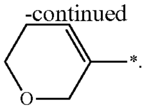

Embodiment 3.1. A compound of formula (I), or a pharmaceutically acceptable salt thereof, according to embodiment 1 or 2, wherein $R_1$ is selected from:

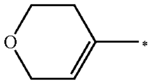, 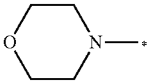,

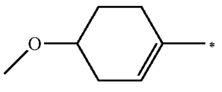, 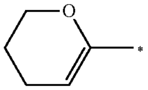,

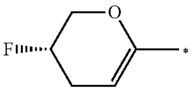 and 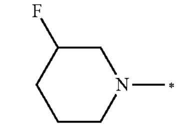

Embodiment 4.1. A compound of formula (I), or a pharmaceutically acceptable salt thereof, according to embodiments 1-3, wherein $R_1$ is selected from:

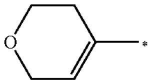 and 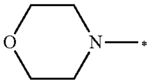.

Embodiment 5.1. A compound of formula (I), or a pharmaceutically acceptable salt thereof, according to embodiments 1-4, wherein $R_1$ is:

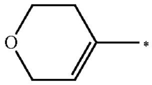.

Embodiment 6.1. A compound of formula (I), or a pharmaceutically acceptable salt thereof, according to embodiments 1-5, wherein $R^{28}$ is selected from $CF_3$, $SF_5$ and Br.

Embodiment 7.1. A compound of formula (I), or a pharmaceutically acceptable salt thereof, according to embodiments 1-6, wherein $R^{28}$ is selected from $CF_3$.

Embodiment 8.1. A compound of formula (I), or a pharmaceutically acceptable salt thereof, according to embodiments 1-7, wherein X is $CR_7$.

Embodiment 9.1. A compound of formula (I), or a pharmaceutically acceptable salt thereof, according to embodiments 1-8, wherein $R_7$ is H.

Embodiment 10.1. A compound of formula (I), or a pharmaceutically acceptable salt thereof, according to embodiments 1-9, wherein $R_6$ is Cl or $CH_3$.

Embodiment 11.1. A compound of formula (I), or a pharmaceutically acceptable salt thereof, according to embodiments 1-10, wherein $R_6$ is Cl.

Embodiment 12.1. A compound of formula (I), or a pharmaceutically acceptable salt thereof, according to embodiments 1-11, wherein $R_8$ is F or H.

Embodiment 13.1. A compound of formula (I), or a pharmaceutically acceptable salt thereof, according to embodiments 1-12, wherein $R_8$ is H.

Embodiment 14.1. A compound of formula (I), or a pharmaceutically acceptable salt thereof, according to embodiments 1-13, wherein $R_9$ is H.

Embodiment 15.1. A compound of formula (I), or a pharmaceutically acceptable salt thereof, according to embodiments 1-14, wherein $R_{26}$ is H.

Embodiment 16.1. A compound of formula (I), or a pharmaceutically acceptable salt thereof, according to embodiments 1-15, wherein $R_{27}$ is H.

Embodiment 17.1. A compound of formula (I), or a pharmaceutically acceptable salt thereof, according to embodiments 1-14, wherein $R_{26}$ and $R_{27}$ are both deuterium.

Embodiment 18.1. A compound of formula (I), or a pharmaceutically acceptable salt thereof, according to embodiments 1-18, wherein $R_3$ is $-CH_2-CH_3$.

Embodiment 19.1. A compound of formula (I), or a pharmaceutically acceptable salt thereof, according to embodiments 1-18, wherein y is 0.

Embodiment 20.1. A compound of formula (I), or a pharmaceutically acceptable salt thereof, according to embodiments 1-18, wherein the moiety:

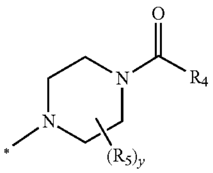

is selected from

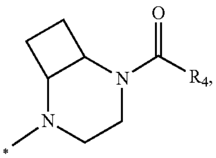,

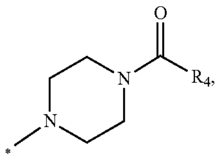,

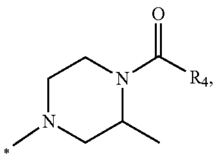,

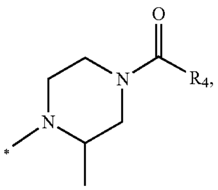,

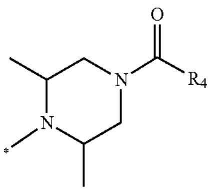 and

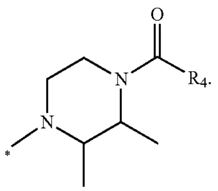.

Embodiment 21.1 A compound of formula (I), or a pharmaceutically acceptable salt thereof, according to embodiments 1-18 and 20, wherein the moiety:

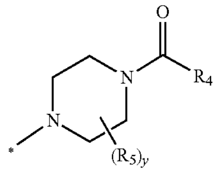

is selected from:

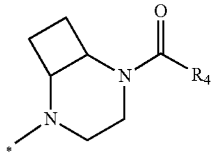 and

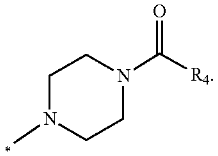.

Embodiment 22.1 A compound of formula (I), or a pharmaceutically acceptable salt thereof, according to embodiments 1-18 and 20, wherein the moiety:

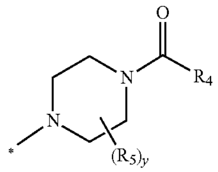

is selected from:

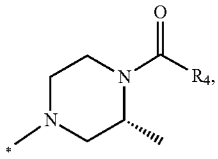,

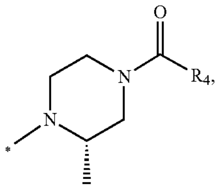,

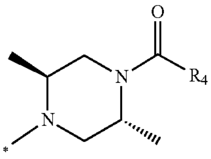 and

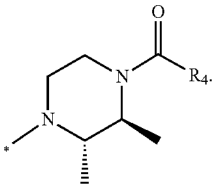.

Embodiment 23.1 A compound of formula (I), or a pharmaceutically acceptable salt thereof, according to embodiments 1-22, wherein the moiety:

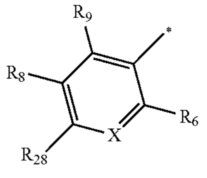

is selected from:
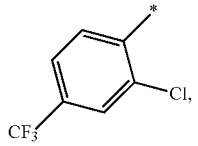
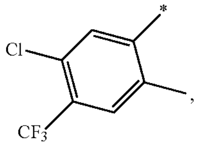
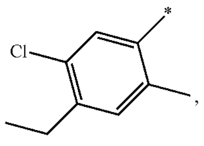
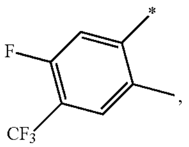
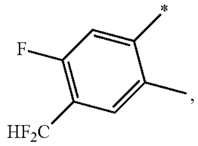
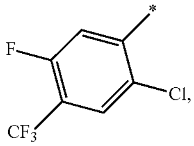
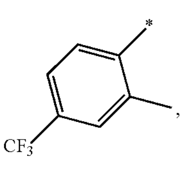
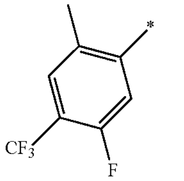
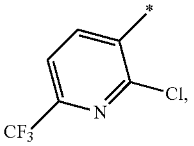
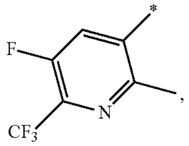
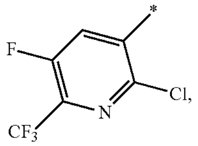
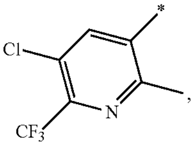
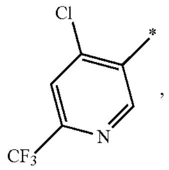
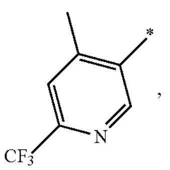
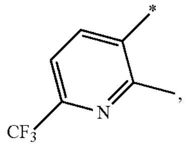
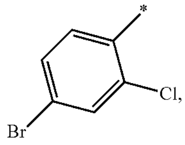
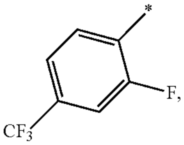
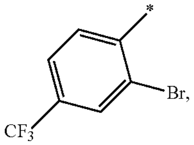
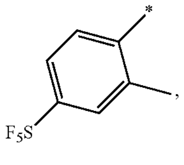
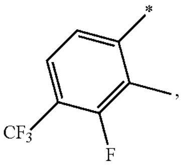
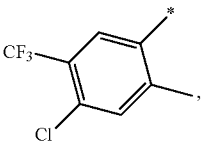
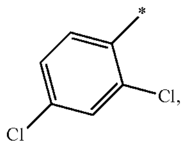
-continued
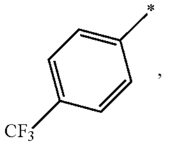
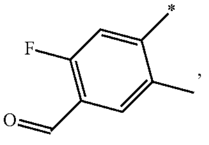
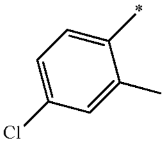
and
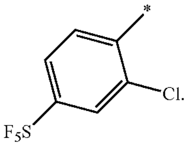
Embodiment 24.1 A compound of formula (I), or a pharmaceutically acceptable salt thereof, according to embodiments 1-23, wherein the moiety:
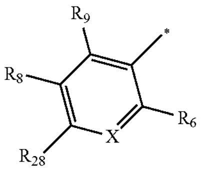
is selected from:
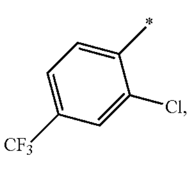
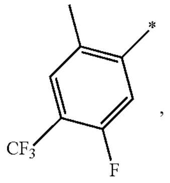
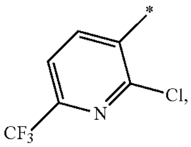
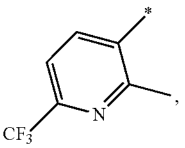
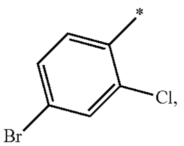
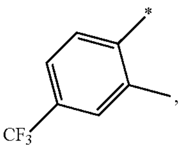
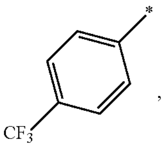
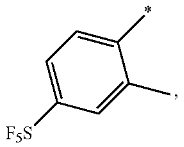
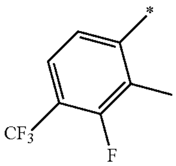
and
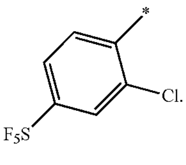
Embodiment 25.1 A compound of formula (I), or a pharmaceutically acceptable salt thereof, according to embodiments 1-24, wherein the moiety:

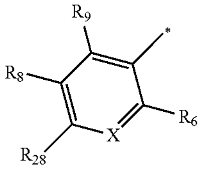

is selected from:

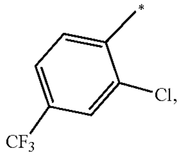
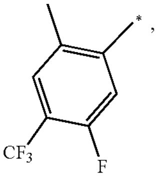
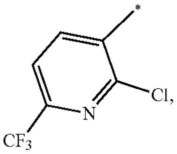
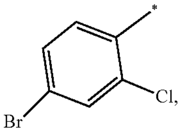
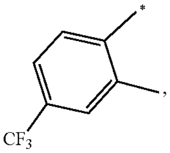
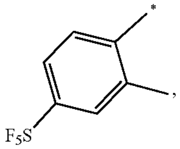
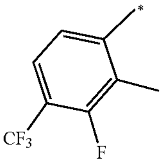
and
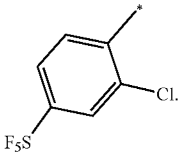

Embodiment 26.1 A compound of formula (I), or a pharmaceutically acceptable salt thereof, according to embodiments 1-25, wherein the moiety:

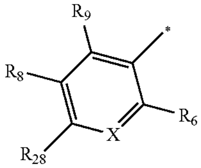

is selected from:

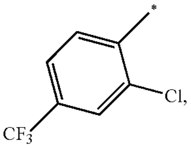
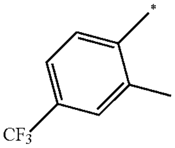
and

-continued

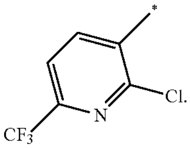

Embodiment 27.1 A compound of formula (I), or a pharmaceutically acceptable salt thereof, according to embodiments 1-26, wherein $R_{10}$ is H, F or Cl.

Embodiment 28.1 A compound of formula (I), or a pharmaceutically acceptable salt thereof, according to embodiments 1-27, wherein $R_{11}$ is H or $CH_3$.

Embodiment 29.1 A compound of formula (I), or a pharmaceutically acceptable salt thereof, according to embodiments 1-28, wherein $R_{12}$ is H.

Embodiment 30.1 A compound of formula (I), or a pharmaceutically acceptable salt thereof, according to embodiments 1-29, wherein $R_{13}$ is H.

Embodiment 31.1 A compound of formula (I), or a pharmaceutically acceptable salt thereof, according to embodiments 1-30, wherein $R_{14}$ is $CH_3$ or H.

Embodiment 32.1 A compound of formula (I), or a pharmaceutically acceptable salt thereof, according to embodiments 1-31, wherein $R_{14}$ is $CH_3$.

Embodiment 33.1 A compound of formula (I), or a pharmaceutically acceptable salt thereof, according to embodiments 1-32, wherein $R_4$ is selected from:

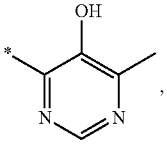
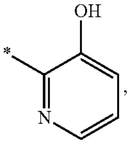
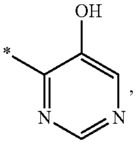
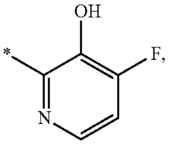
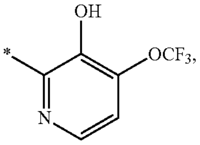
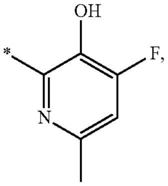
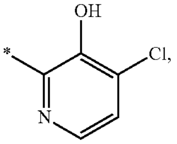
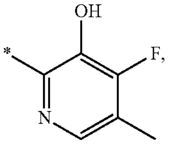
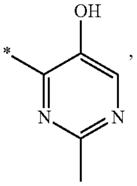
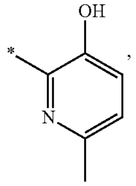
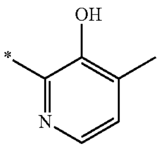
and
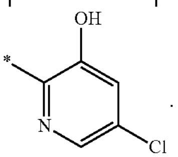

Embodiment 34.1 A compound of formula (I), or a pharmaceutically acceptable salt thereof, according to embodiments 1-33, wherein $R_4$ is selected from:

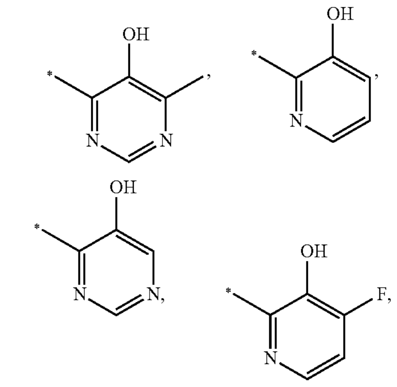

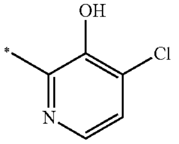
and
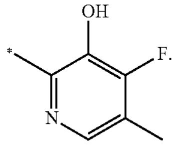

Embodiment 35.1 A compound of formula (I), or a pharmaceutically acceptable salt thereof, according to embodiments 1-34, wherein $R_4$ is selected from:

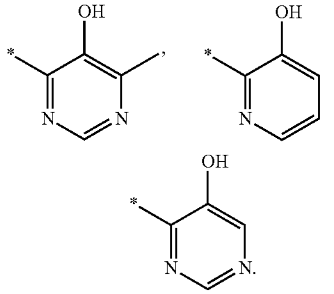
and

Embodiment 36.1 A compound of formula (I), or a pharmaceutically acceptable salt thereof, according to embodiments 1 and 6-26, wherein $R_1$ is selected from:

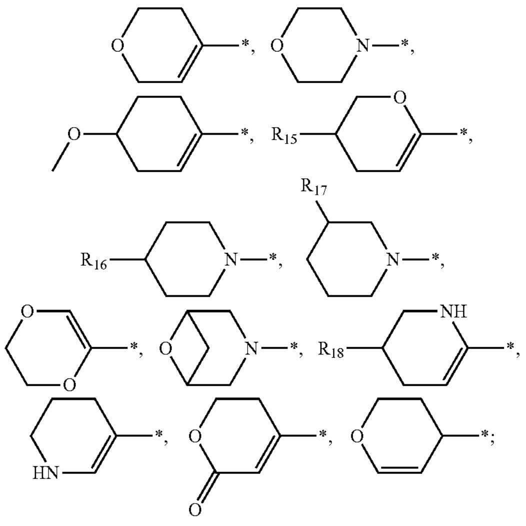

-continued

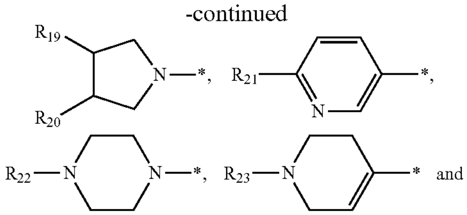
and
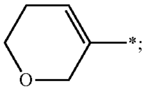

$R_{15}$ is H or F;
$R_{16}$ is H or $R_{25}(R_{24})N$—;
$R_{17}$ is H or F;
$R_{18}$ is H or F;
$R_{19}$ is H or F;
$R_{20}$ is H or F;
$R_{21}$ is H or $CH_3$;
$R_{22}$ is H, $CF_3$, $CHF_2CH_2$, HOC(O)—$CH_2$—, $H_3C$—C(O)—, $(H_3C)_3C$—O—C(O)—;
$R_{23}$ is H, CF3, $CHF_2CH_2$—, $(H_3C)_3C$—O—C(O)—;
$R_{24}$ is $CH_3$;
$R_{25}$ is $CHF_2CH_2$—; and
$R_4$ is selected from:

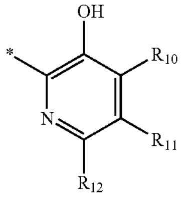
and
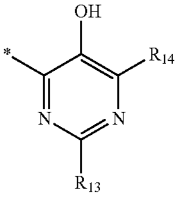

wherein
$R_{10}$ is selected from H, F, Cl, $CH_3$ and $OCF_3$;
$R_{11}$ is selected from H, Cl, F, and $CH_3$;
$R_{12}$ is selected from H, Cl and $CH_3$;
$R_{13}$ is selected from H and $CH_3$;
$R_{14}$ is selected from H, $CH_3$, —$CH_2CH_3$, cyclopropyl, —$OCHF_2$, $OCF_3$ and Cl;
or a pharmaceutically acceptable salt thereof.

Embodiment 37.1 A compound of formula (I), or a pharmaceutically acceptable salt thereof, according to embodiment 1, wherein $R_1$ is selected from:

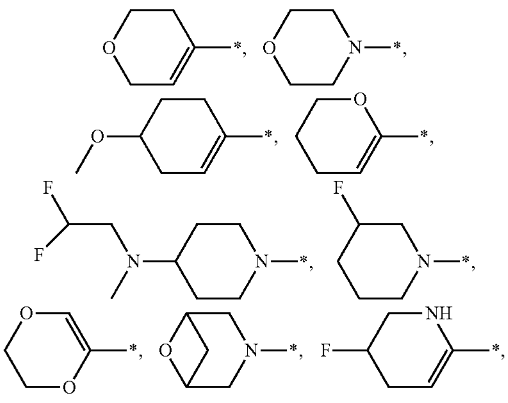

-continued
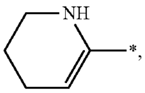, 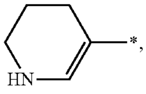, 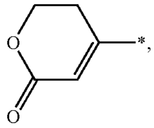,
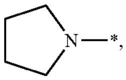, 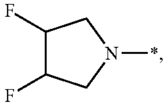, 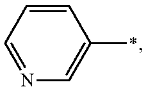,
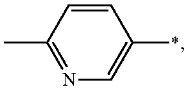, 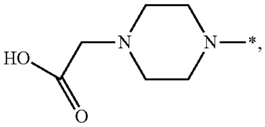,
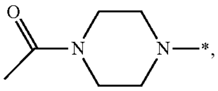, 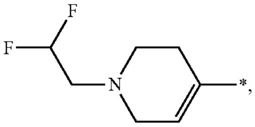,
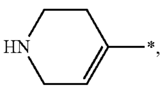, 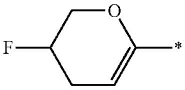 and
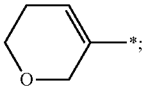;
and the moiety:
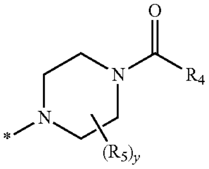
is selected from:
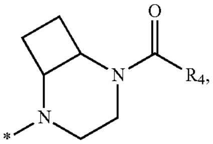 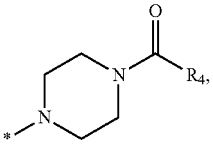
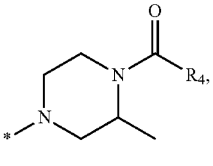 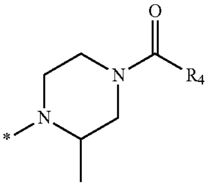 and
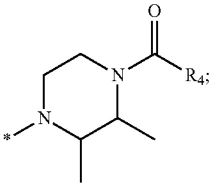
the moiety:
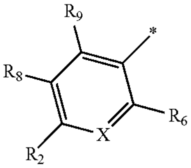
is selected from:
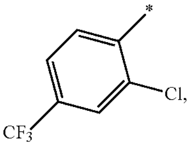 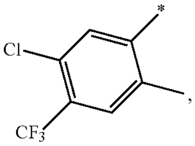
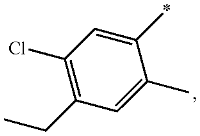 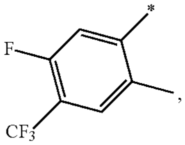
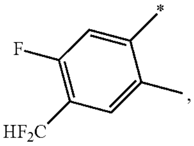 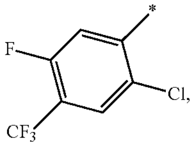
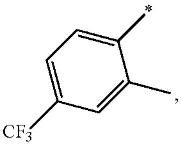 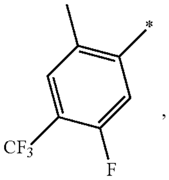
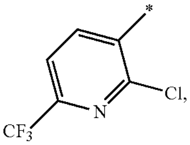 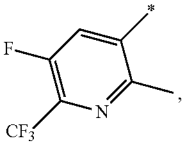
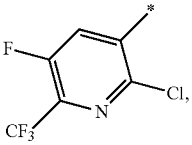 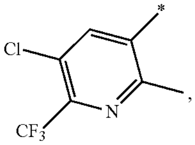
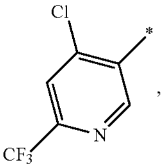 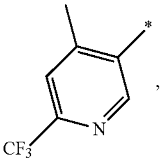
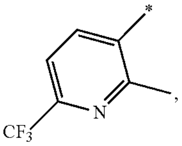 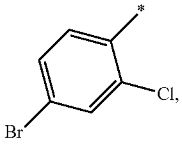
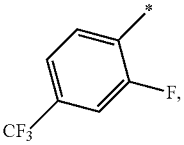 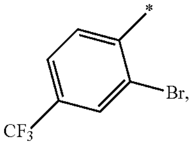

-continued
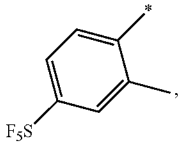 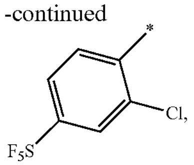
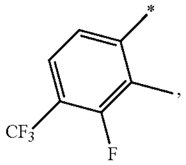 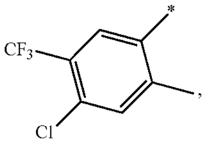
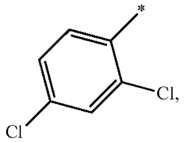 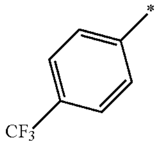 and
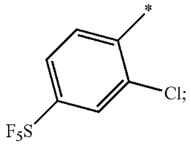
and
$R_4$ is selected from:
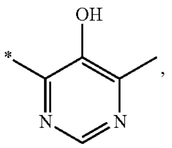 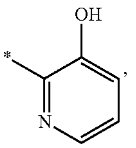 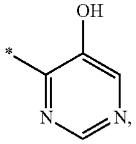
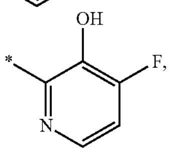 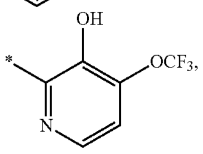
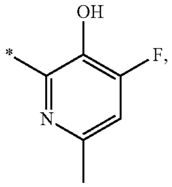 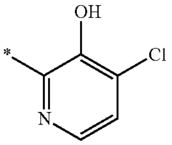 and
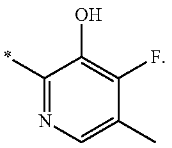
Embodiment 38.1 A compound of formula (I), or a pharmaceutically acceptable salt thereof, according to embodiment 37, wherein $R_1$ is selected from:
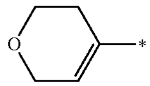 and 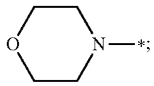
the moiety:
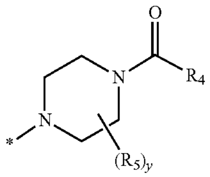
is selected from:
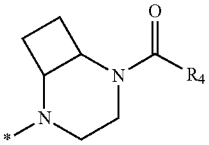 and 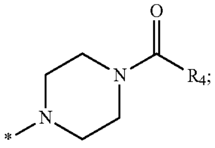
the moiety:
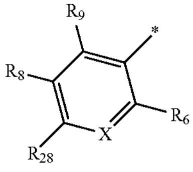
is selected from:
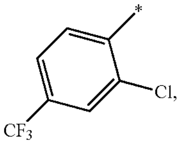 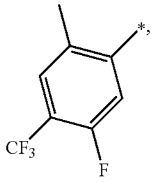 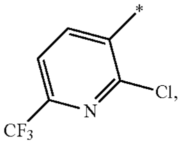
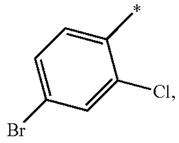 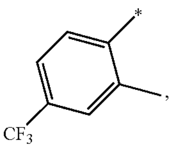
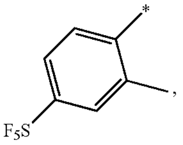 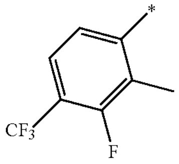 and
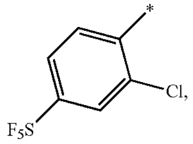 in particular 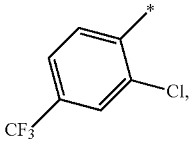

-continued

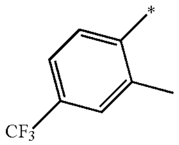

and

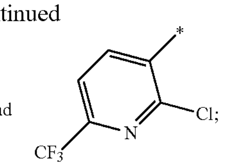

and $R_4$ is selected from:

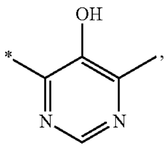,

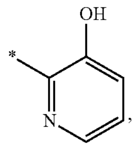,

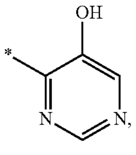,

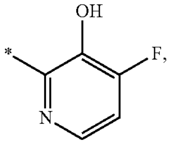,

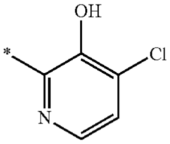

and

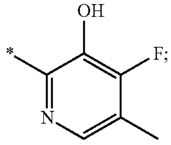

in particular:

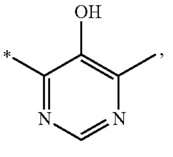,

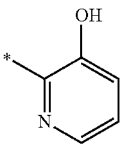

and

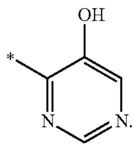

In a further aspect, the invention is as claimed herein.

In one embodiment, there is provided a compound of formula (I) or a pharmaceutically acceptable salt thereof:

(I)

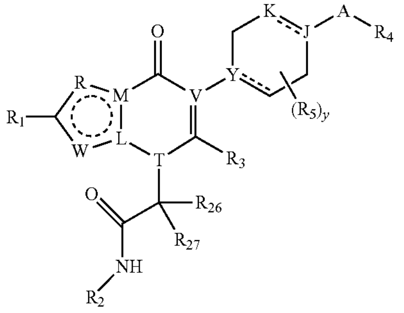

wherein $R_1$ is:

cycloalkenyl, wherein said cycloalkenyl is a partially unsaturated monocyclic ring containing 5 or 6 ring carbon atoms, and said cycloalkenyl is unsubstituted or substituted by 1, 2, 3 or 4, preferably 1 or 2, $R_{33}$, wherein $R_{33}$ is halo, and wherein said cycloalkenyl or halo-substituted cycloalkenyl is substituted by 0, 1 or 2 $R_{15}$ substituents, or $R_1$ is heterocyclyl, wherein said heterocyclyl is a 5 or 6 membered fully saturated or partially unsaturated group comprising ring carbon atoms and 1 or 2 ring heteroatoms independently selected from N, O and S, and wherein said heterocyclyl is unbridged or bridged, and said bridge is 1 or 2 carbon atoms, wherein said heterocyclyl is unsubstituted or substituted by 1, 2, 3 or 4, preferably 1 or 2, $R_{33}$, wherein $R_{33}$ is halo, and wherein said heterocyclyl or halo-substituted heterocyclyl is substituted by 0, 1 or 2 substituents independently selected from $R_{15}$, $R_{16}$, $R_{17}$, $R_{18}$, $R_{19}$, $R_{20}$, $R_{22}$ and $R_{23}$, or $R_1$ is heteroaryl, wherein said heteroaryl is a 5 or 6 membered fully unsaturated monocyclic group comprising ring carbon atoms and 1, 2, 3 or 4 ring heteroatoms independently selected from N, O and S, preferably 1 or 2 ring heteroatoms, wherein the total number of ring S atoms does not exceed 1, and the total number of ring O atoms does not exceed 1, wherein said heteroaryl is unsubstituted or substituted by 1, 2 or 3 substituents independently selected from $R_2$, and $R_{30}$, wherein $R_{21}$ and $R_{30}$ are independently selected from halo and $(C_1\text{-}C_4)$alkyl, wherein said $(C_1\text{-}C_4)$alkyl is unsubstituted or substituted by 1, 2 or 3 halo, and each $R_{15}$, $R_{16}$, $R_{17}$, $R_{18}$, $R_{19}$, $R_{20}$, $R_{22}$ and $R_{23}$ is independently selected from:

halo $(C_1\text{-}C_4)$alkyl-O— unsubstituted or substituted by 1, 2 or 3 halo;

$(C_1\text{-}C_4)$alkyl unsubstituted or substituted by OH, —O—$(C_1\text{-}C_2)$alkyl or 1, 2 or 3 halo, $HOC(O)—(CH_2)_n—$, $H_3C—C(O)(CH_2)_n—$, $(C_1\text{-}C_4)$alkyl-O—$C(O)(CH_2)_n$,

=O azetidinyl or pyrrolidinyl, wherein said azetidinyl and pyrrolidinyl are linked to the rest of the molecule via the N atom, and are each unsubstituted or substituted by 1 or 2 F, $R_{25}(R_{24})N—$, wherein $R_{24}$ is H or $(C_1\text{-}C_4)$alkyl unsubstituted or substituted by 1, 2 or 3 halo, $R_{25}$ is H or $(C_1\text{-}C_4)$alkyl unsubstituted or substituted by 1, 2 or 3 halo,

OH wherein n is 0, 1 or 2.

in particular $R_1$ is:

cycloalkenyl, wherein said cycloalkenyl is a partially unsaturated monocyclic ring containing 5 or 6 ring carbon atoms, and said cycloalkenyl is unsubstituted or substituted by 1 or 2 $R_{33}$, wherein $R_{33}$ is halo, preferably F, and wherein said cycloalkenyl or halo-substituted cycloalkenyl is substituted by 0 or 1 $R_{15}$ substituents, preferably 1 substituent, wherein $R_{15}$ is selected from:

h) $(C_1\text{-}C_2)$alkyl-O— unsubstituted or substituted by 1, 2 or 3 halo;

i) $(C_1\text{-}C_2)$alkyl unsubstituted or substituted by 1, 2 or 3 halo, j) $HOC(O)—(CH_2)_n—$, k) $H_3C—C(O)(CH_2)_n—$, l) $H_3C—O—C(O)(CH_2)_n$, m) =O, and n) $R_{25}(R_{24})N$—, H, wherein $R_{24}$ is H or $(C_1\text{-}C_2)$alkyl unsubstituted or substituted by 1, 2 or 3 halo, $R_{25}$ is H or $(C_1\text{-}C_2)$alkyl unsubstituted or substituted by 1, 2 or 3 halo, n is 0 or 1, wherein the $R_{15}$ substituent a) to g) of said cycloalkenyl or halo-substituted cycloalkenyl is not present on the ring atoms adjacent to the ring atom to which the cycloalkenyl or halo-substituted cycloalkenyl is joined to the remainder of the molecule, and preferably, said cycloalkenyl or halo-substituted cycloalkenyl is a 6 membered ring, with 1 $R_{15}$ substituent in the ring para position relative to the remainder of the molecule; and said cycloalkenyl or halo-substituted cycloalkenyl is linked to the remainder of the compound via a $R_1$ ring carbon atom which is double bonded to an adjacent $R_1$ ring carbon atom;

or $R_1$ is heterocyclyl, wherein said heterocyclyl is a 5 or 6 membered fully saturated or partially unsaturated group comprising ring carbon atoms and 1 or 2 ring heteroatoms independently selected from N, NH, O and S, and wherein said heterocyclyl is unbridged or bridged, and said bridge is 1 or 2 carbon atoms, wherein said heterocyclyl is unsubstituted or substituted by 1 or 2 $R_{33}$, wherein $R_{33}$ halo, is preferably F, and wherein said heterocyclyl or halo-substituted heterocyclyl is substituted by 0 or 1 substituents independently selected from $R_{15}$, $R_{16}$, $R_{17}$, $R_{18}$, $R_{19}$, $R_{20}$, $R_{22}$ and $R_{23}$, wherein said $R_{15}$, $R_{16}$, $R_{17}$, $R_{18}$, $R_{19}$, $R_{20}$, $R_{22}$ and $R_{23}$ are independently selected from:

i) $(C_1\text{-}C_4)$alkyl-O— unsubstituted or substituted by 1, 2 or 3 halo;

j) $(C_1\text{-}C_4)$alkyl unsubstituted or substituted by OH, —O—$(C_1\text{-}C_2)$alkyl or 1, 2 or 3 halo, k) HOC(O)—$(CH_2)_n$—, l) $H_3C$—C(O)$(CH_2)_n$—, m) $H_3C$—O—C(O)$(CH_2)_n$, n) =O o) $R_{25}(R_{24})N$—, wherein $R_{24}$ is H, $(C_1\text{-}C_2)$alkyl unsubstituted or substituted by 1, 2 or 3 halo, $R_{25}$ is H, $(C_1\text{-}C_2)$alkyl unsubstituted or substituted by 1, 2 or 3 halo, p) OH wherein n is 0 or 1, and wherein:

substituent a) to h) of said heterocyclyl or halo-substituted heterocyclyl is not present on the ring atoms adjacent to the ring atom to which the heterocyclyl or halo-substituted heterocyclyl is joined to the remainder of the molecule, and preferably, when said heterocyclyl or halo-substituted heterocyclyl is a 6 membered ring, it has 0 or 1 substituent selected from a) to h) in the meta or para position, preferably para, relative to the remainder of the molecule; and said heterocyclyl is linked to the remainder of the compound via a $R_1$ ring nitrogen atom, or a $R_1$ ring carbon atom which is double bonded to an adjacent ring atom;

or $R_1$ is heteroaryl, wherein said heteroaryl is a 5 or 6 membered fully unsaturated monocyclic group comprising ring carbon atoms and 1 or 2 ring heteroatoms independently selected from N, O and S, preferably N, wherein the total number of ring S atoms does not exceed 1, and the total number of ring O atoms does not exceed 1, wherein said heteroaryl is unsubstituted or substituted by 1 or 2 substituents independently selected from $R_2$, and $R_{30}$, wherein $R_{21}$ and $R_{30}$ are independently selected from $(C_1\text{-}C_2)$alkyl, and said $(C_1\text{-}C_2)$alkyl is unsubstituted or substituted by 1, 2 or 3 halo, and wherein preferably, said alkyl or halo-alkyl substituent is not present on the $R_1$ ring atoms adjacent to the $R_1$ ring atom to which the heteroaryl is joined to the remainder of the molecule, and more preferably, when heteroaryl is a 6-membered ring, said alkyl or halo-alkyl substituent is in the ring para position relative to the rest of the molecule.

More particularly, $R_1$ is selected from:

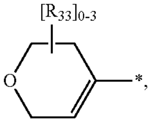,
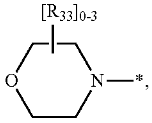,
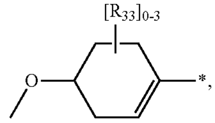,
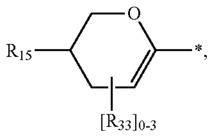,
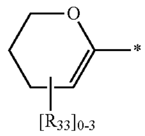
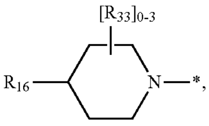,
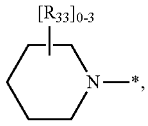,
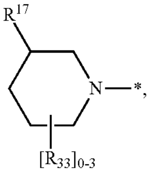,
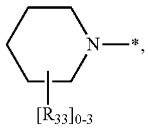,
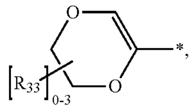,
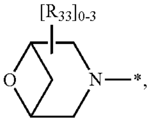,
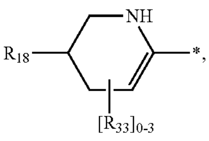,
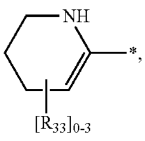,
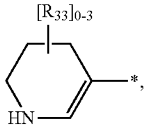,
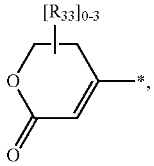,
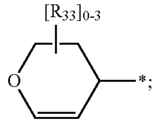;
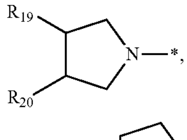,
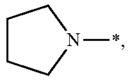,
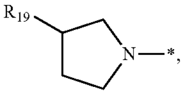,
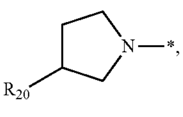,
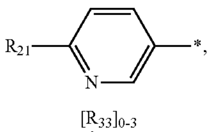,
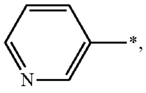,
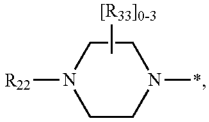,
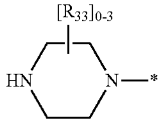
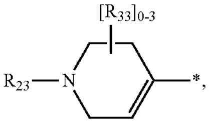, -continued

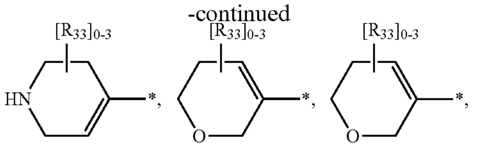
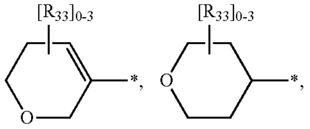
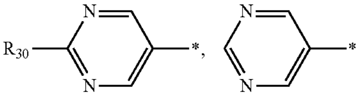
and
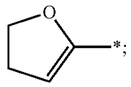

$R_{33}$ is F;

$R_{15}$ is halo, azetidinyl or pyrrolidinyl, wherein said azetidinyl and pyrrolidinyl are linked to the rest of the molecule via the N atom, and are unsubstituted or substituted by 1 or 2 F;

$R_{16}$ is $R_{25}(R_{24})N$—, wherein $R_{24}$ is H or $(C_1\text{-}C_2)$alkyl, $R_{25}$ is H or $(C_1\text{-}C_2)$alkyl unsubstituted or substituted by 1, 2 or 3 halo, in particular F;

$R_{17}$ is halo $R_{18}$ is halo;

$R_{19}$ is halo;

$R_{20}$ is halo;

$R_{21}$ is $(C_1\text{-}C_2)$alkyl;

$R_{22}$ and $R_{23}$ are each independently selected from:

$(C_1\text{-}C_4)$alkyl unsubstituted or substituted by 1, 2 or 3 halo, $HOC(O)—(CH_2)_n—$, $H_3C—C(O)(CH_2)_n—$, $(H_3C)_3C—O—C(O)(CH_2)_n—$;

wherein n is 0, 1 or 2;

and $R_{30}$ is $CH_3$.

Even more particularly, $R_1$ is selected from:

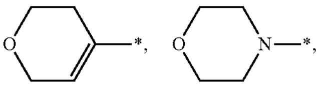
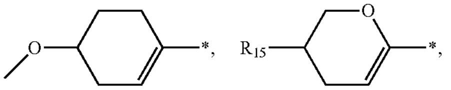
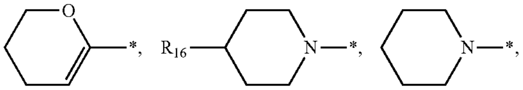
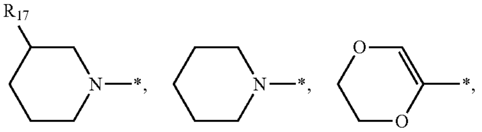
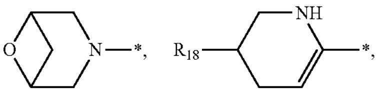
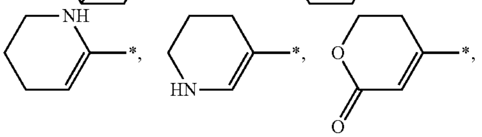

-continued

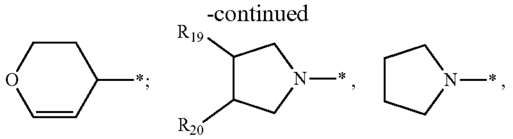
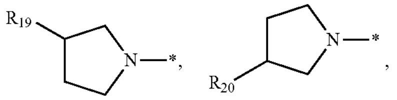
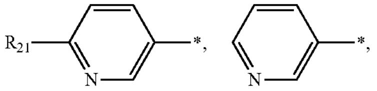
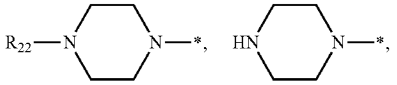
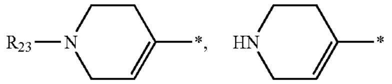
and
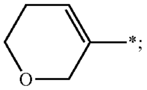

$R_{15}$ is F;

$R_{16}$ is $R_{25}(R_{24})N$—;

$R_{17}$ is F;

$R_{18}$ is F;

$R_{19}$ is F;

$R_{20}$ is F;

$R_{21}$ is $CH_3$;

$R_{22}$ is $CF_3$, $CHF_2CH_2$, $HOC(O)—CH_2—$, $H_3C—C(O)—$, $(H_3C)_3C—O—C(O)—$;

$R_{23}$ is $CF_3$, $CHF_2CH_2—$, $(H_3C)_3C—O—C(O)—$;

$R_{24}$ is $CH_3$; and $R_{25}$ is $CHF_2CH_2—$.

Preferably, $R_1$ is selected from:

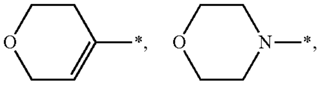
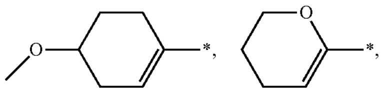
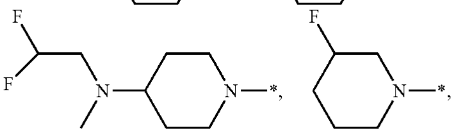
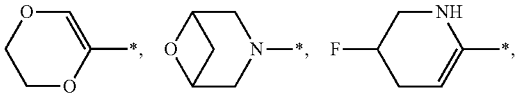
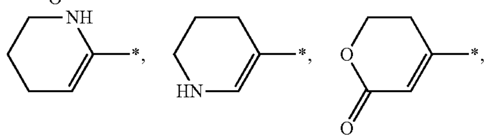
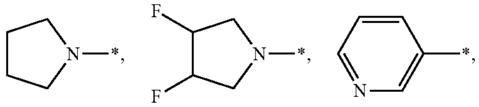

-continued

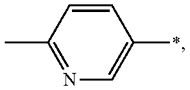

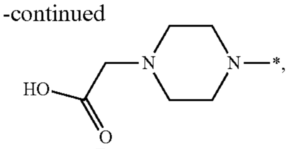

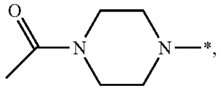

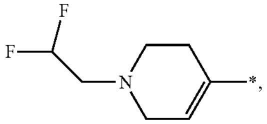

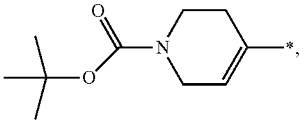

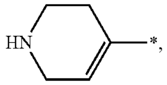

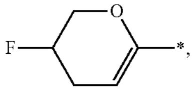

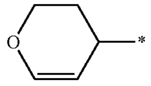

and

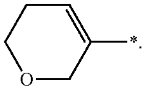

In another embodiment, $R_2$ is the moiety:

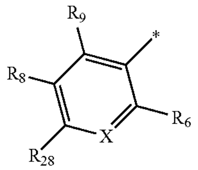

$R_6$ is selected from:

- H,
- halo,
- $(C_1\text{-}C_4)$alkyl unsubstituted or substituted by 1, 2 or 3 halo,
- $(C_3\text{-}C_5)$cycloalkyl unsubstituted or substituted by 1, 2 or 3 halo,
- —O—$(C_1\text{-}C_4)$alkyl unsubstituted or substituted by 1, 2 or 3 halo,
- OH, and
- CN;

$R_8$ is selected from H, halo, and $(C_1\text{-}C_4)$alkyl unsubstituted or substituted by 1, 2 or 3 halo, $R_9$ is selected from H, O—$CH_3$, OH, CN, $CH_3$ and halo;

$R_{28}$ is selected from:

- $SF_5$,
- H,
- —C(O)H,
- halo,
- $(C_1\text{-}C_4)$alkyl unsubstituted or substituted by 1, 2 or 3 halo,
- $(C_1\text{-}C_4)$alkynyl,
- $(C_1\text{-}C_4)$alkenyl,
- $(C_3\text{-}C_5)$cycloalkyl unsubstituted or substituted by 1, 2 or 3 halo, and
- $OCF_3$;

and X is selected from C—$R_7$ and N, wherein $R_7$ is H or halo.

Particularly, $R_2$ is the moiety:

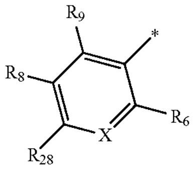

wherein $R_6$ is selected from H, halo, $(C_1\text{-}C_4)$alkyl unsubstituted or substituted by 1, 2 or 3 halo;

$R_8$ is selected from H, halo, $(C_1\text{-}C_4)$alkyl unsubstituted or substituted by 1, 2 or 3 halo;

$R_9$ is selected from H, O—$CH_3$, OH, CN, $CH_3$ and halo;

$R_{28}$ is selected from $SF_5$, halo, $(C_1\text{-}C_4)$alkyl unsubstituted or substituted by 1, 2 or 3 halo and —C(O)H;

X is selected from C—$R_7$ and N; and $R_7$ is selected from H and halo.

More particularly, $R_2$ is the moiety:

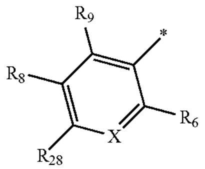

$R_6$ is selected from H, Cl, $CH_3$, F and Br;

$R_8$ is selected from H, Cl, F and $CF_3$;

$R_8$ is selected from H, $CH_3$ and Cl;

$R_{28}$ is selected from $CF_3$, $CF_2H$, —$CH_2CH_3$, Cl, $SF_5$, Br and —C(O)H;

X is selected from C—$R_7$ and N; and $R_7$ is selected from H and F.

Even more particularly, $R_2$ is the moiety selected from:

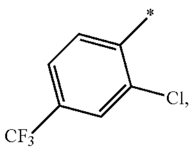

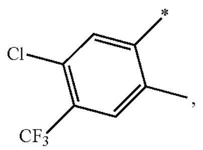

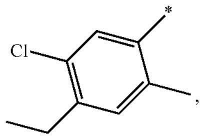

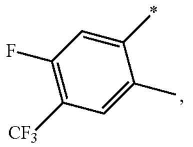

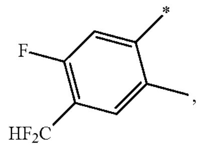

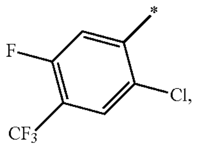

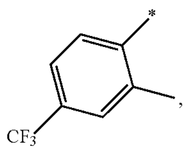

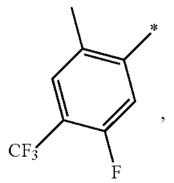

-continued

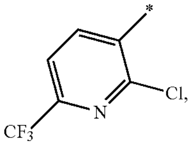,

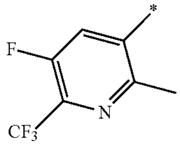,

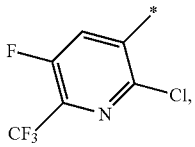,

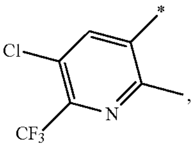,

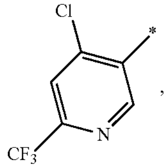,

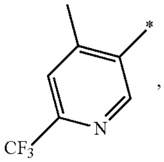,

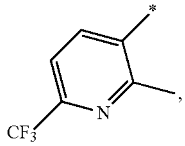,

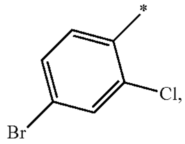,

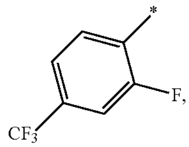,

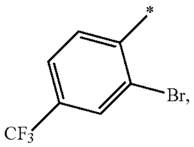,

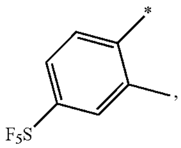,

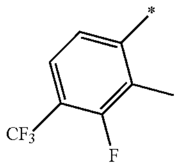,

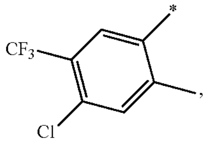,

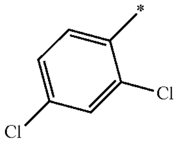

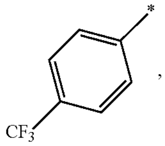,

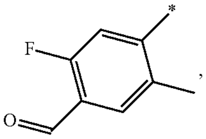,

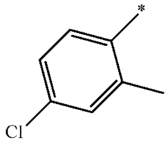

and

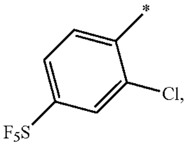, preferably

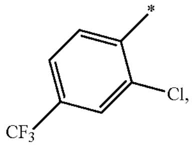,

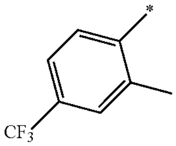

and

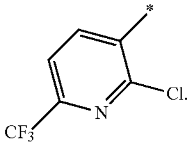.

In another embodiment, $R_{26}$ is H and $R_{27}$ is H.

In another embodiment, $R_3$ is $(C_1\text{-}C_4)$alkyl unsubstituted or substituted by 1, 2 or 3 substituents independently selected from halo and OH, in particular $(C_1\text{-}C_2)$alkyl unsubstituted or substituted by 1, 2 or 3 substituents independently selected from halo and OH, preferably $-CH_2CH_3$ or $CH_3$, more preferably $-CH_2CH_3$.

In another embodiment, Y is N and is Y⎓ linked by a single bond.

In another embodiment, ⎓ is K linked by a single bond, and K is selected from $-CH_2-$, $-CH_2CH_2-$, $-NH-$ and a bond (to form a 5-membered ring:

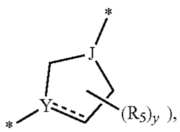),

J is N, and A is a linker selected from $-C(O)-$, $-S(O)-$, $-S(O)_2-$, and

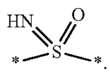.

In particular,

K⎓ is K linked by a single bond, K is $-CH_2-$, J is N, and A is a linker selected from $-C(O)-$, $-S(O)-$, $-S(O)_2-$, and

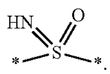.

In another embodiment, A is a linker selected from $-C(O)-$ and $-S(O)_2-$, preferably $-C(O)-$.

In another embodiment, $R_5$ is independently selected from:

$-(C_1\text{-}C_4)$alkyl, preferably methyl, and wherein two $R_5$ substituents on the same ring carbon atom may join, together with the carbon atom to which they are attached, to form a $(C_3\text{-}C_4)$cycloalkyl spiro ring or a 3 or 4-membered heterocyclyl spiro ring, wherein said heterocyclyl spiro ring contains ring carbon ring atoms and one ring heteroatom selected from O, N and S, when K⎓J is a carbon-nitrogen single bond, a $R_5$ substituent on K and on the adjacent carbon atom may join to form ring C:

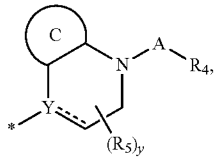, wherein ring C is a fused $(C_3\text{-}C_6)$cycloalkyl ring, in particular a fused cyclobutyl ring, a fused $(C_3\text{-}C_6)$ heterocyclyl ring or a fused phenyl ring, wherein said fused $(C_3\text{-}C_6)$heterocyclyl ring contains ring carbon atoms and one ring heteroatom selected from O, N and S, and wherein when K is —$CH_2$— and J is N, two $R_5$ substituents may join to form a ($C_1$-$C_3$)alkylene bridge or a heteroalkylene bridge, wherein said heteroalkylene bridge is one heteroatom selected from N and O, or is —$CH_2$—O—$CH_2$—.

In particular, $R_5$ is independently selected from:

—($C_1$-$C_4$)alkyl, preferably methyl, when K⋯J is a carbon-nitrogen single bond, a $R_5$ substituent on K and on the adjacent carbon atom may join to form ring C:

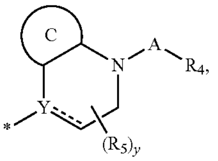

wherein ring C is a fused ($C_3$-$C_6$)cycloalkyl ring, in particular a fused cyclobutyl ring, or a fused ($C_3$-$C_6$) heterocyclyl ring, wherein said fused ($C_3$-$C_6$)heterocyclyl ring contains ring carbon atoms and one ring heteroatom selected from O, N and S, and wherein when K is —$CH_2$— and J is N, two $R_5$ substituents may join to form a ($C_1$-$C_3$)alkylene bridge or a heteroalkylene bridge, wherein said heteroalkylene bridge is one heteroatom selected from N and O, or is —$CH_2$—O—$CH_2$—.

More particularly, $R_5$ is independently selected from:

—($C_1$-$C_2$)alkyl, preferably methyl, and when K⋯J is a carbon-nitrogen single bond, a $R_5$ substituent on K and on the adjacent carbon atom may join to form ring C:

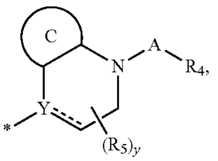

wherein ring C is a fused ($C_3$-$C_4$)cycloalkyl ring, in particular a fused cyclobutyl ring.

Even more particularly, $R_5$ is independently selected from:

$CH_3$, and y is 1 or 2, and when K⋯J is a carbon-nitrogen single bond, a $R_5$ substituent on K and on the adjacent carbon atom may join to form ring C:

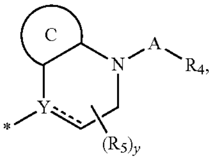

wherein ring C is a fused cyclobutyl ring.

In another embodiment, y is 0, 1, 2 or 3, preferably 0, 1, or 2.

In another embodiment, $R_4$ is selected from:

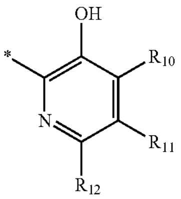 and 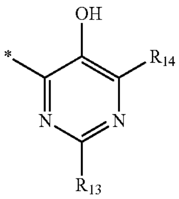

wherein $R_{10}$ is selected from H, halo, ($C_1$-$C_2$)alkyl unsubstituted or substituted by 1, 2 or 3 halo substituents, —O—($C_1$-$C_2$)alkyl unsubstituted or substituted by 1, 2 or 3 halo substituents;

$R_{11}$ is selected from H, halo, ($C_1$-$C_2$)alkyl unsubstituted or substituted by 1, 2 or 3 halo substituents;

$R_{12}$ is selected from H, halo, ($C_1$-$C_2$)alkyl unsubstituted or substituted by 1, 2 or 3 halo substituents;

$R_{13}$ is selected from H, —S—$CH_3$, halo, ($C_1$-$C_2$)alkyl unsubstituted or substituted by 1, 2 or 3 halo substituents; and $R_{14}$ is selected from H, halo, ($C_1$-$C_2$)alkyl unsubstituted or substituted by 1, 2 or 3 halo substituents, O—($C_1$-$C_2$)alkyl unsubstituted or substituted by 1, 2 or 3 halo substituents, and cyclopropyl.

In particular, $R_4$ is selected from:

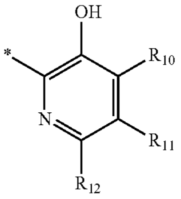 and 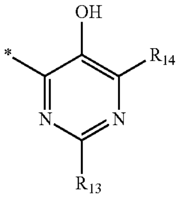

wherein $R_{10}$ is selected from H, F, Cl, $CH_3$ and $OCF_3$;

$R_{11}$ is selected from H, Cl, F, and $CH_3$;

$R_{12}$ is selected from H, Cl and $CH_3$;

$R_{13}$ is selected from H, —S—$CH_3$ and $CH_3$; and $R_{14}$ is selected from H, $CH_3$, —$CH_2CH_3$, cyclopropyl, —$OCHF_2$, $OCF_3$ and Cl.

More particularly, $R_4$ is selected from:

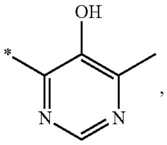, 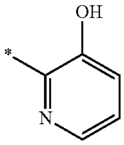, 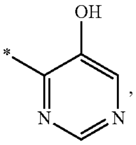,

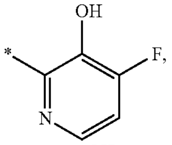 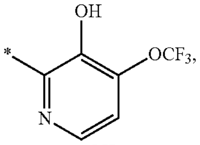

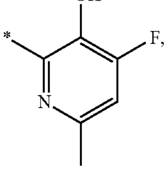 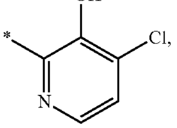

-continued
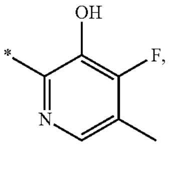, 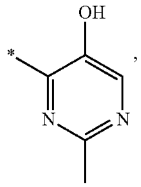, 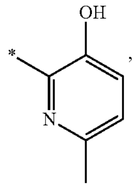,
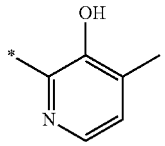 and 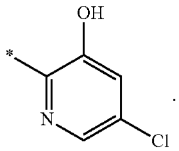.
Even more particularly, $R_4$ is selected from:
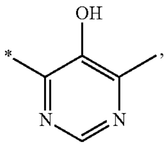, 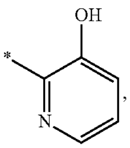, 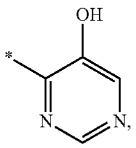,
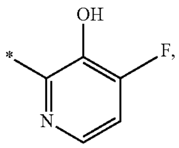, 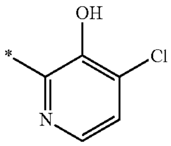 and
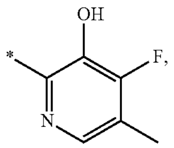,
preferably:
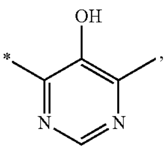, 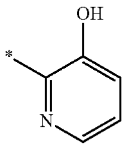 and 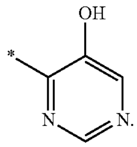.
In another embodiment, formula (I) is formula 1a:
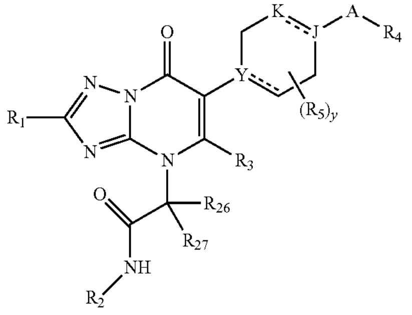
1a
In another embodiment, the moiety:
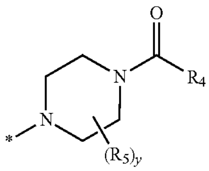
is selected from
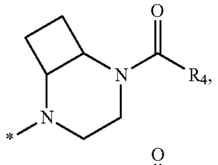, 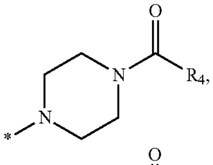,
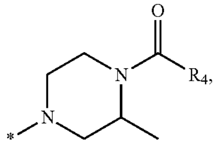, 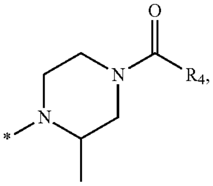,
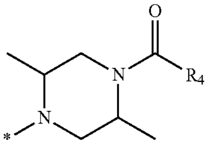 and 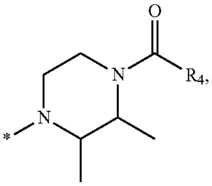,
in particular:
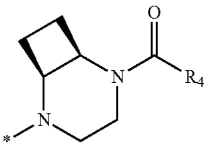 or 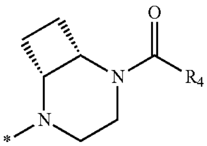 or
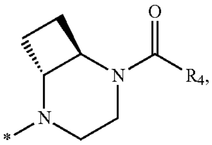, or 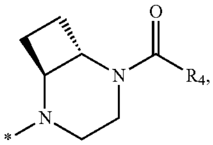, -continued

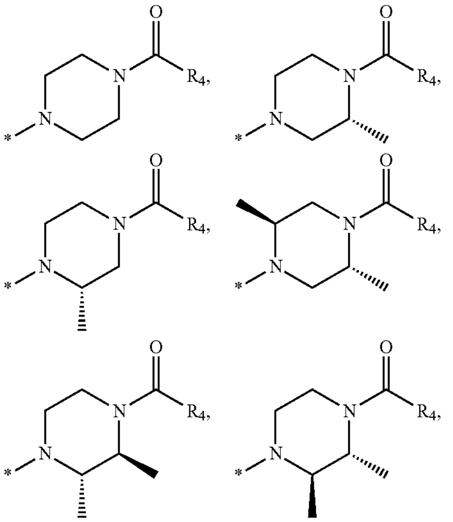

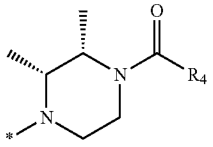

and

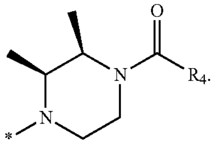

Syntheses

There is also provided a process to manufacture a compound of formula (I) as described herein, in particular 1a, 1b, 1c, 1d, 1e, 1f, 1h or 1g, preferably 1a, more preferably 1g or 1 h, or a pharmaceutically acceptable salt thereof, as described herein.

There is further provided a intermediate compound, used in chemical synthesis of a compound of formula (I) as described herein, for example formula 1a, preferably 1g or 1h, or a pharmaceutically acceptable salt thereof, as described herein.

In another aspect, there is provided an intermediate compound, or a process comprising an intermediate compound, as described below.

In particular, there is provided a compound, or formula, as follows:

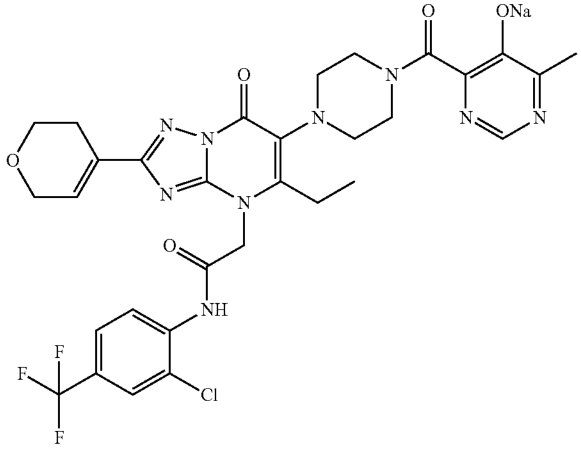

(sodium salt of the compound of Example 42)

A compound, or salt thereof, of formula A:

A

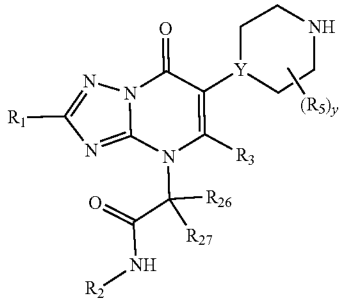

wherein $R_1$, $R_2$, $R_3$, $R_{26}$, $R_{27}$, $R_5$, y and Y are as defined herein.

A compound:

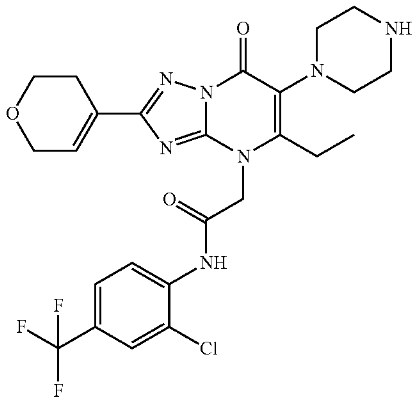

Intermediate AK

A compound, or salt thereof, of Formula B:

B

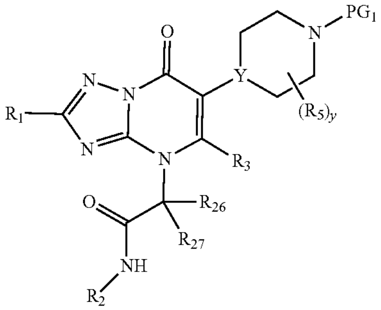

wherein $R_1$, $R_2$, $R_3$, $R_{26}$, $R_{27}$, $R_5$, y and Y are as defined herein, and $PG_1$ is a protecting group. Suitable protecting groups are well-known to the skilled person, and include BOC.

A compound, or salt thereof, which is:

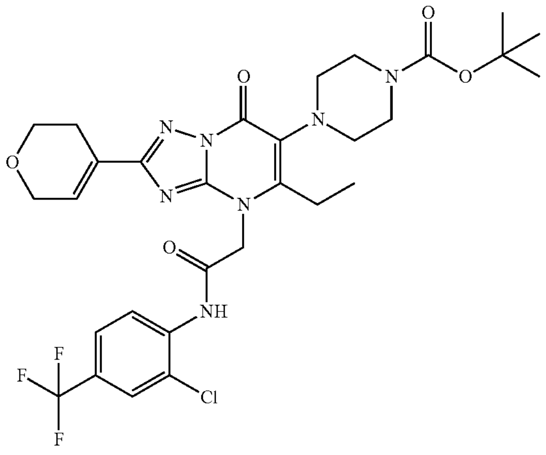 [SMILES: CCc1c(N2CCN(C(=O)OC(C)(C)C)CC2)c(=O)n2nc(C3=CCOCC3)nc2n1CC(=O)Nc1ccc(C(F)(F)F)cc1Cl]

Intermediate AK step 1 product.

A compound, or salt thereof, of Formula C:

C

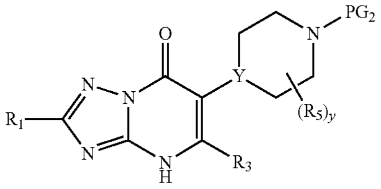

wherein $R_1$, $R_3$, $R_5$, y and Y are as defined herein, and $PG_2$ is a protecting group. Suitable protecting groups are well-known to the skilled person. Such protecting groups $PG_2$ include BOC.

A compound, or salt thereof, which is:

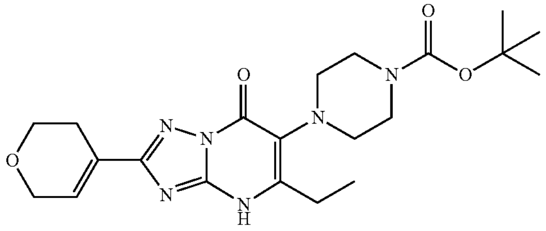 [SMILES: CCc1[nH]c2nc(C3=CCOCC3)nn2c(=O)c1N1CCN(C(=O)OC(C)(C)C)CC1]

Intermediate AF

A compound, or salt thereof, or a tautomer thereof, of Formula D:

D

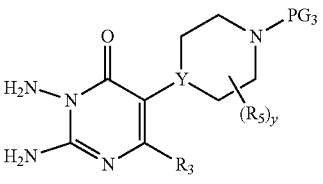

wherein $R_3$, $R_5$, y and Y are as defined herein, and $PG_3$ is a protecting group. Suitable protecting groups are well-known to the skilled person.

A compound, or salt thereof, which is:

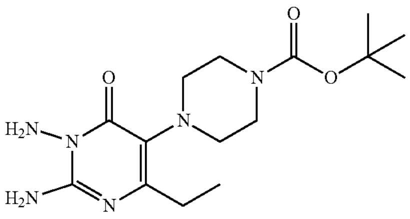 [SMILES: CCc1nc(N)n(N)c(=O)c1N1CCN(C(=O)OC(C)(C)C)CC1]

Intermediate AF step 1 product

A compound, or salt thereof, which is:

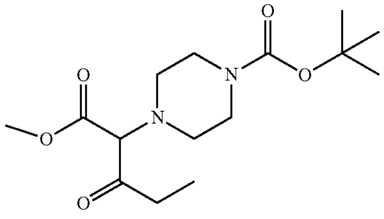 [SMILES: CCC(=O)C(C(=O)OC)N1CCN(C(=O)OC(C)(C)C)CC1]

Intermediate EH

There is also provided a process to make the compound:

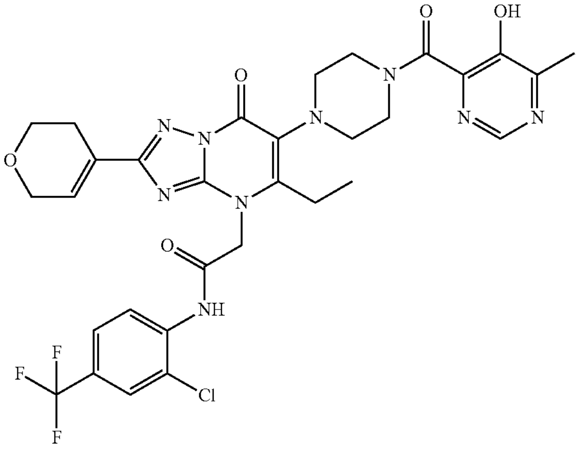 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Cl]

comprising reacting the compound of formula:

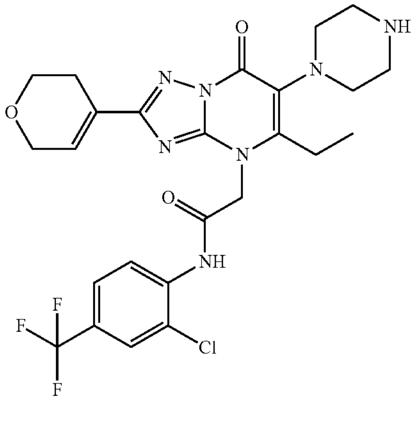

Intermediate AK with a compound of formula:

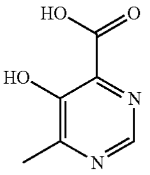

Intermediate DB using coupling reagents and conditions known to the skilled person, in particular HOAt, EDCI and DIPEA. Such reagents have the advantages of being suitable for increased scale, considering their availability and low cost, whilst enabling a robust process with good yields. Protected or unprotected forms can be used as known to the skilled person.

There is also provided a process to make the compound:

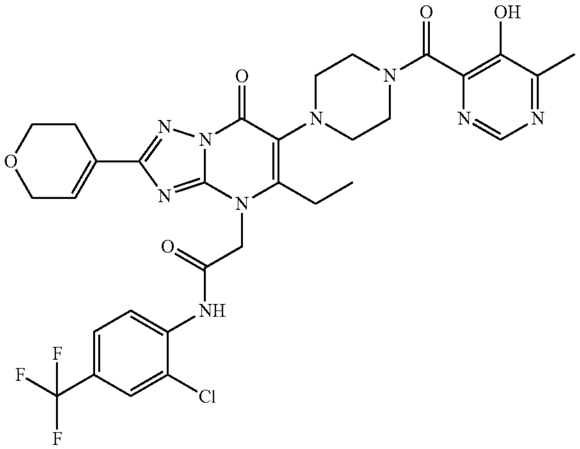 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Cl]

via the intermediates of formula:

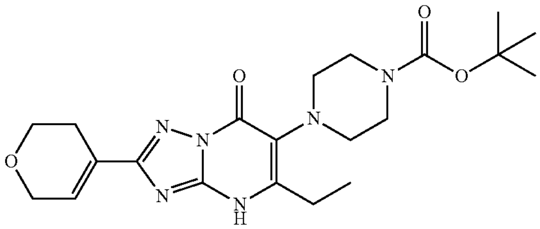 [SMILES: CCc1[nH]c2nc(C3=CCOCC3)nn2c(=O)c1N1CCN(C(=O)OC(C)(C)C)CC1]

intermediate AF, and/or

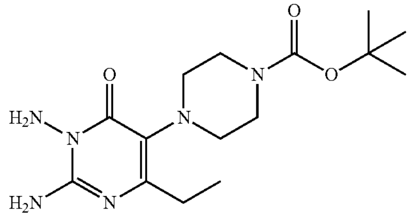 [SMILES: CCc1nc(N)n(N)c(=O)c1N1CCN(C(=O)OC(C)(C)C)CC1]

intermediate AF step 1 product, and/or

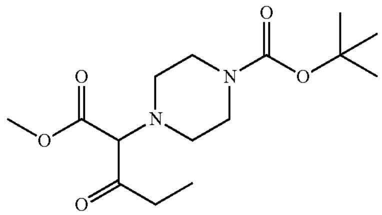 [SMILES: CCC(=O)C(C(=O)OC)N1CCN(C(=O)OC(C)(C)C)CC1]

Intermediate EH.

Formulations

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration, in particular oral administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Compounds intended for parenteral or oral administration can be solubilized using various methods including nano-suspensions, solid dispersions and liposomes (van Hoogevest P., Xiangli L., and Alfred F. "Drug delivery strategies for poorly water-soluble drugs: the industrial perspective" Expert Opinion on Drug Delivery 2011, 8(11), 1481-1500).

Solid dispersion technologies have been used to improve the dissolution characteristics and bioavailability of orally administered drugs (Dhirendra K et al: 'Solid dispersions: A review", Pakistan Journal of Pharmaceutical Sciences, Faculty of Pharmacy, University of Karachi, Pakistan, vol. 22, no. 2. 30 Apr. 200, pages 234-246).

Typical approaches to solubilize compounds for parenteral administration are the optimization of the pH or the use of co-solvents (e.g. PEG300, PEG400, propylene glycol, or ethanol). If these approaches are, for any reason, not feasible, the use of surfactants may be considered (e.g. Tween® 80 or Cremophor EL®). Cyclodextrins are established as safe solubilizing agents. Compounds with a high solubility in natural oils (e.g. propofol) may be solubilized in parenteral fat emulsions.

There is also provided a pharmaceutical composition comprising a compound of formula (I) as described herein, for example formula 1a, preferably 1g or 1h, or a pharmaceutically acceptable salt thereof, and one or more pharmaceutically acceptable carriers.

In another embodiment, there is provided a pharmaceutical composition which is an amorphous solid dispersion comprising the compound N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide, or a pharmaceutically acceptable salt thereof.

In a further embodiment, said pharmaceutical composition comprises the compound N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl) acetamide, or a pharmaceutically acceptable salt thereof, and an amino methacrylate copolymer, in particular Eudragit® E PO.

Uses

The compounds of formula (I) of the present invention in free form or in pharmaceutically acceptable salt form, exhibit valuable pharmacological properties, e.g. WRN inhibiting properties, e.g. as indicated in vitro and in vivo tests as provided in the next sections, and are therefore indicated for therapy, or for use as research chemicals, e.g. as a chemical probe, and as tool compounds.

Also provided is a compound of formula (I), in particular 1a, 1b, 1c, 1d, 1e, 1f, 1h or 1g, as described herein. Said compound can be used as a research chemical, for example a tool compound or chemical probe, in particular for research on WRN. In another embodiment there is provided the use of a compound of formula (I), in particular 1a, 1b, 1c, 1d, 1e, 1f, 1h or 1g, as described herein, as a research chemical, for example tool compound or chemical probe, in particular for research on WRN.

There is also provided a compound of formula (I) as described herein, in particular 1a, 1b, 1c, 1d, 1e, 1f, 1h or 1g, preferably 1a, more preferably 1g or 1h, or a pharmaceutically acceptable salt thereof, for use in the treatment of cancer. Cancers that may be treated by WRN inhibition include cancers that are characterized as microsatellite instability-high (MSI-H) or mismatch repair deficient (dMMR). In particular, a compound of formula (I) as described herein, for example formula 1a, preferably 1g or 1h, or a pharmaceutically acceptable salt thereof, may be useful in the treatment of a cancer that is characterized as microsatellite instability-high (MSI-H) or mismatch repair deficient (dMMR).

There is also provided a compound of formula (I) as described herein, in particular 1a, 1b, 1c, 1d, 1e, 1f, 1h or 1g, preferably 1a, more preferably 1g or 1h, or a pharmaceutically acceptable salt thereof, for use as a medicament. In particular, said use is:

for the treatment of a disease that is treated by WRN inhibition, for the treatment of cancer, for the treatment of cancer that is characterized as microsatellite instability-high (MSI-H) or mismatch repair deficient (dMMR), for the treatment of cancer that is characterized as microsatellite instability-high (MSI-H) or mismatch repair deficient (dMMR), such as colorectal, gastric, prostate, endometrial, adrenocortical, uterine, cervical, esophageal, breast, kidney and ovarian cancer, for the treatment of cancer that is characterized as microsatellite instability-high (MSI-H) or mismatch repair deficient (dMMR) is selected from colorectal, gastric, prostate and endometrial cancer, or for the treatment of cancer wherein the cancer characterized as microsatellite instability-high (MSI-H) or mismatch repair deficient (dMMR) is selected from uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma, prostate cancer and ovarian serous cystadenocarcinoma.

There is also provided a method of:

modulating WRN activity in a subject, wherein the method comprises administering to the subject a therapeutically effective amount of the compound of formula (I) as described herein, in particular 1a, 1b, 1c, 1d, 1e, 1f, 1h or 1g, preferably 1a, more preferably 1g or 1h, or a pharmaceutically acceptable salt thereof, inhibiting WRN in a subject, wherein the method comprises administering to the subject a therapeutically effective amount of the compound of formula (I) as described herein, in particular 1a, 1b, 1c, 1d, 1e, 1f, 1h or 1g, preferably 1a, more preferably 1g or 1h, or a pharmaceutically acceptable salt thereof, treating a disorder or disease which can be treated by WRN inhibition in a subject, comprising administering to the subject a therapeutically effective amount of the compound of formula (I) as described herein, in particular 1a, 1b, 1c, 1d, 1e, 1f, 1h or 1g, preferably 1a, more preferably 1g or 1h, or a pharmaceutically acceptable salt thereof, treating cancer in a subject, comprising administering to the subject a therapeutically effective amount of the compound of formula (I) as described herein, in particular 1a, 1b, 1c, 1d, 1e, 1f, 1h or 1g, preferably 1a, more preferably 1g or 1h, or a pharmaceutically acceptable salt thereof, treating cancer in a subject, comprising administering a compound of formula (I) as described herein, in particular 1a, 1b, 1c, 1d, 1e, 1f, 1h or 1g, preferably 1a, more preferably 1g or 1h, or a pharmaceutically acceptable salt thereof, wherein the cancer is characterized as microsatellite instability-high (MSI-H) or mismatch repair deficient (dMMR). In particular, the cancer characterized as microsatellite instability-high (MSI-H) or mismatch repair deficient (dMMR) is selected from colorectal, gastric, prostate, endometrial, adrenocortical, uterine, cervical, esophageal, breast, kidney and ovarian cancer. More particularly, the cancer characterized as microsatellite instability-high (MSI-H) or mismatch repair deficient (dMMR) is selected from colorectal, gastric, prostate and endometrial cancer. Examples include uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma, prostate cancer and ovarian serous cystadenocarcinoma.

There is also provided the use of a compound of formula (I) as described herein, in particular 1a, 1b, 1c, 1d, 1e, 1f, 1h or 1g, preferably 1a, more preferably 1g or 1h, or a pharmaceutically acceptable salt thereof:

in therapy, in the manufacture of a medicament, in the manufacture of a medicament for the treatment of cancer. In particular, said cancer is characterized as microsatellite instability-high (MSI-H) or mismatch repair deficient (dMMR), in the manufacture of a medicament for treatment of a disease which may be treated by WRN inhibition, wherein in particular, the cancer is characterized by microsatellite instability-high (MSI-H) or mismatch repair deficient (dMMR), for example colorectal, gastric, prostate, endometrial, adrenocortical, uterine, cervical, esophageal, breast, kidney and ovarian cancer, in particular, colorectal, gastric, prostate or endometrial cancer, or uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma and ovarian serous cystadenocarcinoma.

In some embodiments, the subject has or is identified as having a microsatellite instable (MSI-H) cancer, e.g., in reference to a control, e.g., a normal, subject. In one embodiment, the subject has MSI-H advanced solid tumors, a colorectal cancer (CRC), endometrial, uterine, stomach or other MSI-H cancer. In some embodiments, the subject has a colorectal (CRC), endometrial or stomach cancer, which cancer has or is identified as having a microsatellite instability (MSI-H), e.g., in reference to a control, e.g., a normal, subject. Such identification techniques are known in the art.

Forms

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is intended to represent unlabeled forms as well as isotopically labeled forms of the compounds, in addition to the deuteration specifically claimed in formula (I). Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^{2}H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^{3}H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. Accordingly it should be understood that the invention includes compounds that incorporate one or more of any of the aforementioned isotopes, including for example, radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

Deuterated compounds of formula (I) include example 43, a deuterated form of example 42:

Example 42

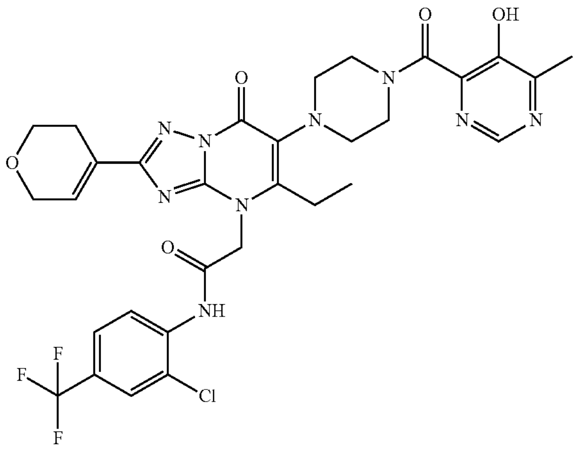

Example 43

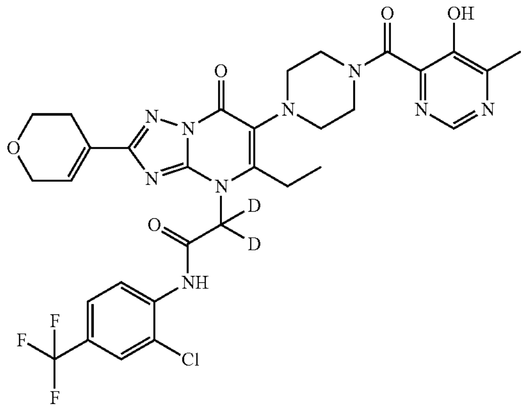

and

Example 133

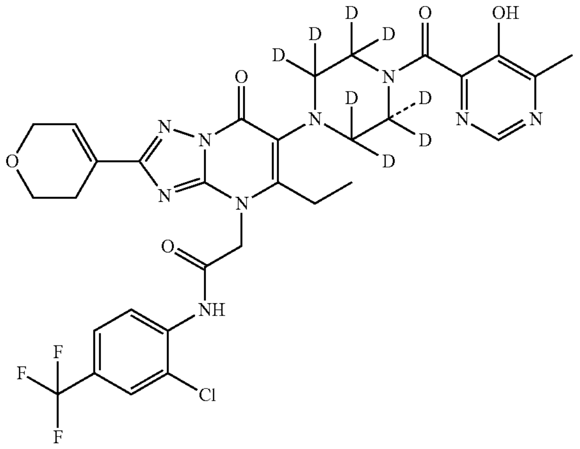

and deuterated forms of the compounds of:

Example 86

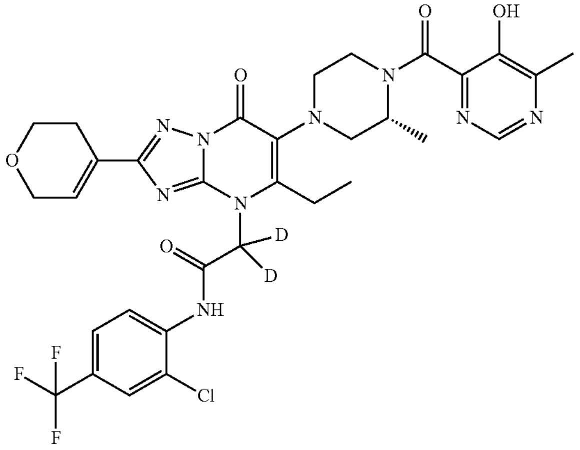 [SMILES: [2H]C([2H])(C(=O)Nc1ccc(C(F)(F)F)cc1Cl)n1c(CC)c(N2CCN(C(=O)c3ncnc(C)c3O)[C@H](C)C2)c(=O)n2nc(C3=CCOCC3)nc12]

Example 50

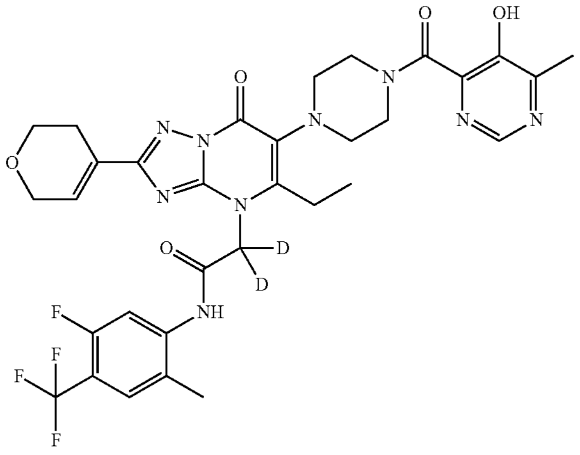 [SMILES: [2H]C([2H])(C(=O)Nc1cc(F)c(C(F)(F)F)cc1C)n1c(CC)c(N2CCN(C(=O)c3ncnc(C)c3O)CC2)c(=O)n2nc(C3=CCOCC3)nc12]

Example 57

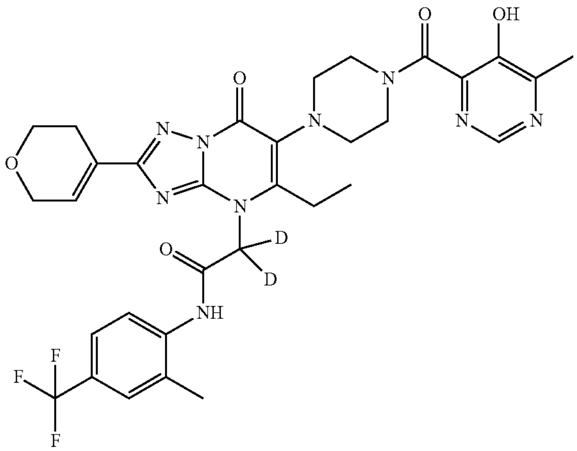 [SMILES: [2H]C([2H])(C(=O)Nc1ccc(C(F)(F)F)cc1C)n1c(CC)c(N2CCN(C(=O)c3ncnc(C)c3O)CC2)c(=O)n2nc(C3=CCOCC3)nc12]

and Example 47

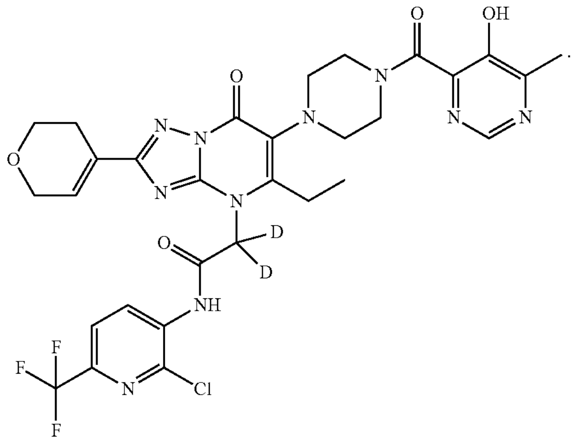 [SMILES: [2H]C([2H])(C(=O)Nc1ccc(C(F)(F)F)nc1Cl)n1c(CC)c(N2CCN(C(=O)c3ncnc(C)c3O)CC2)c(=O)n2nc(C3=CCOCC3)nc12]

Definitions

A 'compound of the present invention' or a 'compound of formula (I)' or a 'compound of formula 1a', or 1g or h etc, includes a zwitterion thereof, a non-zwitterion thereof (non-charged form), or a pharmaceutically acceptable salt of said zwitterionic or non-zwitterionic form thereof.

'zwitterion' or 'zwitterionic form' means a compound containing both positive and negatively charged functional groups.

For example, the compound of formula (I) described herein can include the following forms, wherein $R_4$ is the zwitterionic form (c) or non-zwitterionic form (d), (c)

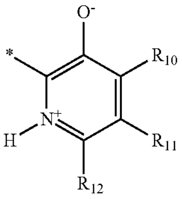

or (d)

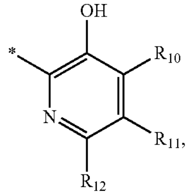

or a mixture thereof.

The compound of formula (I) described herein can also include the following forms, wherein $R_4$ is the zwitterionic form (a) or (b) or the non-zwitterionic form (e), (e)

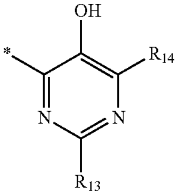

or (a)

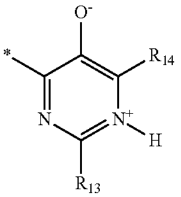

or (b)

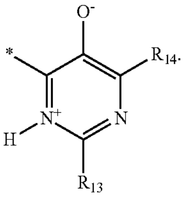

or a mixture of two thereof, or a mixture of all three thereof.

halo means fluoro, chloro or bromo, particularly fluoro or chloro.

Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

'=O' means an oxo substituent.

When $R_1$ is substituted or unsubstituted cycloalkenyl, said cycloalkenyl includes, but is not limited to, groups such as cyclohexenyl, in particular cyclohex-1-en-1-yl.

When $R_1$ is substituted or unsubstituted heterocyclyl, said heterocyclyl includes, but is not limited to, groups such as morpholinyl, piperidinyl, pyrrolidinyl, 6-oxa-3-azabicyclo[3.1.1]heptan-3-yl, 5,6-dihydro-1,4-dioxin-2-yl, dihydropyranyl, in particular 3,4-dihydro-2H-pyran-6-yl, 5,6-dihydro-2H-pyran-3-yl and 3,6-dihydro-2H-pyran-4-yl, piperazinyl, tetrahydropyridinyl, such as 1,4,5,6-tetrahydropyridin-3-yl and 1,2,3,6-tetrahydropyridin-4-yl and dihydropyridinyl, such as 3,6-dihydropyridinyl.

When $R_1$ is substituted or unsubstituted heteroaryl, said heteroaryl includes, but is not limited to, groups such as pyridinyl, in particular pyridin-3-yl.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to colorectal, gastric, endometrial, prostate, adrenocortical, uterine, cervical, esophageal, breast, kidney, ovarian cancer and the like.

The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

'WRN inhibitor' or 'WRN helicase inhibitor' as used herein means a compound that inhibits Werner Syndrome RecQ DNA helicase (WRN). The term "WRN" as used herein refers to the protein of Werner Syndrome RecQ DNA helicase. The term "WRN" includes mutants, fragments, variants, isoforms, and homologs of full-length wild-type WRN. In one embodiment, the protein is encoded by the WRN gene (Entrez gene ID 7486; Ensembl ID ENSG00000165392). Exemplary WRN sequences are available at the Uniprot database under accession number Q14191.

'disease or condition mediated by WRN' includes a disease or condition, such as cancer, which is treated by WRN inhibition. In particular this can include cancers characterized as microsatellite instability-high (MSI-H) or mismatch repair deficient (dMMR).

'microsatellite unstable cancer', microsatellite instability-high cancer', 'microsatellite high cancer' and 'MSI-high cancer' '$MSI^{hi}$' and 'MSI-H' when used herein, are used interchangeably, and describe cancers that have a high number of alterations in the length of simple repetitive genomic sequences within microsatellites.

The determination of MSI-H or dMMR tumor status for patients can be performed using, e.g., polymerase chain reaction (PCR) tests for MSI-H status or immunohistochemistry (IHC) tests for dMMR. Methods for identification of MSI-H or dMMR tumor status are described, e.g., in Ryan et al. Crit Rev Oncol Hematol. 2017; 116:38-57; Dietmaier and Hofstadter. Lab Invest 2001, 81:1453-1456; and Kawakami et al. Curr Treat Options Oncol. 2015; 16(7): 30).

Microsatellite instability can be found in colorectal cancer, gastric cancer and endometrial cancer in particular, but also in adrenocortical, uterine, cervical, esophageal, breast, kidney, prostate and ovarian cancers. Examples of microsatellite high cancers include uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma and ovarian serous cystadenocarcinoma.

A cancer that has "defective mismatch repair" (dMMR) or "dMMR character" includes cancer types associated with documented MLH1, PMS2, MSH2, MSH3, MSH6, MLH3, and PMS1 mutations or epigenetic silencing, microsatellite fragile sites, or other gene inactivation mechanisms, including but not limited to cancers of the lung, breast, kidney, large intestine, ovary, prostate, upper aerodigestive tract, stomach, endometrium, liver, pancreas, haematopoietic and lymphoid tissue, skin, thyroid, pleura, autonomic ganglia, central nervous system, soft tissue, pediatric rhabdoid sarcomas, melanomas and other cancers. A cell or cancer with "defective" mismatch repair has a significantly reduced (e.g., at least about 25%, 30%, 40%, 50%, 60%, 70%, 80% or 90% decrease) amount of mismatch repair. In some cases, a cell or cancer which is defective in mismatch repair will perform no mismatch repair.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22nd Ed. Pharmaceutical Press, 2013, pp. 1049-1070).

The terms "synthetic lethality," and "synthetic lethal" are used to refer to reduced cell viability and/or a reduced rate of cell proliferation caused by a combination of mutations or approaches to cause loss of function (e.g., RNA interference or protein function inhibition) in two or more genes but not by the loss of function of only one of these genes.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In one embodiment, the term "a therapeutically effective amount" refers to the amount of the compound of the present invention that, when administered to a subject, is effective to (1) at least partially alleviate, prevent and/or ameliorate a condition, or a disorder or a disease (i) mediated by WRN, or (ii) associated with WRN activity, or (iii) characterized by activity (normal or abnormal) of WRN; or (2) reduce or inhibit the activity of WRN.

In another embodiment, the term "a therapeutically effective amount" refers to the amount of the compound of the present invention that, when administered to a cell, or a tissue, or a non-cellular biological material, or a medium, is effective to at least partially reducing or inhibiting the activity of WRN, or reducing WRN protein levels.

As used herein, the term "subject" refers to primates (e.g., humans, male or female), dogs, rabbits, guinea pigs, pigs, rats and mice. In certain embodiments, the subject is a primate, a rat or a mouse. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

'May join' means joins or does not join.

'May be replaced by deuterium' means is replaced by deuterium, or is not replaced by deuterium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Isomeric Forms

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Furthermore, the compounds of the present invention, including their salts, can also be obtained in the form of their hydrates, or include other solvents used for their crystallization.

The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Dosage Forms

The pharmaceutical composition or combination of the present invention may, for example, be in unit dosage of about 1-1000 mg of active ingredient(s) for a subject of about 50-70 kg.

Combinations

"Combination" refers to either a fixed combination in one dosage unit form, or a combined administration where a compound of formula (I), or a pharmaceutically acceptable salt thereof, and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage.

The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

The combinations described herein can include a compound of formula (I) and one or more additional therapeutic agents, e.g., one or more anti-cancer agents, cytotoxic or cytostatic agents, hormone treatment, vaccines, and/or other immunotherapies. In other embodiments, the combination is further administered or used in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the treatment.

There is also provided a combination comprising a compound of formula (I) as described herein, in particular 1a, 1b, 1c, 1d, 1e, 1f, 1h or 1g, preferably 1a, more preferably 1g or 1h, or a pharmaceutically acceptable salt thereof, as described herein, and one or more additional therapeutically active agents. The additional therapeutic agent is, for example, a chemical compound, peptide, antibody, antibody fragment or nucleic acid, which is therapeutically active or enhances the therapeutic activity when administered to a patient in combination with a compound of the present disclosure. In particular, an additional therapeutically active agent is:

an anti-cancer agent, a chemotherapy, a chemotherapy selected from anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan@ or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin@, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), in particular fluorouracil (5-FU) and irinotecan (Camptosar®).

a PD-1 inhibitor, an anti-PD-1 antibody molecule, or a PD-1 inhibitor selected from PDR001 (Novartis), Nivolumab (Bristol-Myers Squibb), Pembrolizumab (Merck & Co), Pidilizumab (CureTech), MEDI0680 (Medimmune), Cemiplimab (REGN2810, Regeneron), Dostarlimab (TSR-042, Tesaro), PF-06801591 (Pfizer), Tislelizumab (BGB-A317, Beigene), BGB-108 (Beigene), INCSHR1210 (Incyte), Balstilimab (AGEN2035, Agenus), Sintilimab (InnoVent), Toripalimab (Shanghai Junshi Bioscience), Camrelizumab (Jiangsu Hengrui Medicine Co.), and AMP-224 (Amplimmune), Penpulimab (Akeso Biopharma Inc), Zimberelimab (Arcus Biosciences Inc) and Prolgolimab (Biocad Ltd), in particular PDR001, more particularly Tislelizumab (BGB-A317, Beigene).

In a further embodiment, the additional therapeutically active agent is the chemotherapy irinotecan (Camptosar®).

In another embodiment, the additional therapeutically active agent is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. In another embodiment, the additional therapeutically active agent is an anti-PD-1 antibody molecule.

In a further embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In another embodiment, there is provided a combination of a compound of formula (I) or a pharmaceutically acceptable salt thereof, and a chemotherapy, and a PD-1 inhibitor. In particular, the chemotherapy and PD-1 inhibitor are selected from those described above. More particularly, the chemotherapy is irinotecan (Camptosar®) and the PD-1 inhibitor is PDR001 or Tislelizumab. Tislelizumab can have a heavy chain of SEQ ID NO: 3 and a light chain of SEQ ID NO: 4. In some embodiments, the anti-PD-1 antibody is dosed at 100 mg per week. In some embodiments, tislelizumab and is dosed at 300 mg IV on day 1 of each 28 day cycle. In some embodiments, tislelizumab can be dosed at 500 mg once every four (4) weeks.

In another embodiment, the anti-PD-1 antibody molecule, e.g., tislelizumab, and comprises a heavy chain and/or light chain, VH, VL, HCDR1, HCDR2, HCDR3, LCDR1, LCDR2, and LCDR3 of the following:

| | AMINO ACID SEQUENCE | |
|---|---|---|
| Heavy Chain | QVQLQESGPGLVKPSETLSL TCTVSGFSLTSYGVHWIRQP PGKGLEWIGVIYADGSTNYN PSLKSRVTISKDTSKNQVSL KLSSVTAADTAVYYCARAYG NYWYIDVWGQGTTVTVSSAS TKGPSVFPLAPCSRSTSEST AALGCLVKDYFPEPVTVSWN SGALTSGVHTFPAVLQSSGL YSLSSVVTVPSSSLGTKTYT CNVDHKPSNTKVDKRVESKY GPPCPPCPAPPVAGGPSVFL FPPKPKDTLMISRTPEVTCV VVAVSQEDPEVQFNWYVDGV EVHNAKTKPREEQFNSTYRV VSVLTVVHQDWLNGKEYKCK VSNKGLPSSIEKTISKAKGQ PREPQVYTLPPSQEEMTKNQ VSLTCLVKGFYPSDIAVEWE SNGQPENNYKTTPPVLDSDG SFFLYSKLTVDKSRWQEGNV FSCSVMHEALHNHYTQKSLS LSLGK | SEQ ID NO: 3 |
| Light Chain | DIVMTQSPDSLAVSLGERAT INCKSSESVSNDVAWYQQKP GQPPKLLINYAFHRFTGVPD RFSGSGYGTDFTLTISSLQA EDVAVYYCHQAYSSPYTFGQ GTKLEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | SEQ ID NO: 4 |
| Variable Heavy Chain | QVQLQESGPGLVKPSETLSL TCTVSGFSLTSYGVHWIRQP PGKGLEWIGVIYADGSTNYN PSLKSRVTISKDTSKNQVSL KLSSVTAADTAVYYCARAYG NYWYIDVWGQGTTVTVSS | SEQ ID NO: 5 |
| Variable Light Chain | DIVMTQSPDSLAVSLGERAT INCKSSESVSNDVAWYQQKP GQPPKLLINYAFHRFTGVPD RFSGSGYGTDFTLTISSLQA EDVAVYYCHQAYSSPYTFGQ GTKLEIK | SEQ ID NO: 6 |
| HCDR1 | GFSLTSYGVH | SEQ ID NO: 7 |
| HCDR2 | VIYADGSTNYNPSLKS | SEQ ID NO: 8 |
| HCDR3 | ARAYGNYWYIDV | SEQ ID NO: 9 |
| LCDR1 | KSSESVSNDVA | SEQ ID NO: 10 |
| LCDR2 | YAFHRFT | SEQ ID NO: 11 |
| LCDR3 | HQAYSSPYT | SEQ ID NO: 12 |

In some embodiments, the PD-1 inhibitor comprises the HCDRs and LCDRs of tislelizumab as set forth in SEQ ID NOs: 7-12.

In some embodiments, the PD-1 inhibitor (e.g., tislelizumab) is administered at a flat dose of between about 100 mg to about 600 mg. In some embodiments, the PD-1 inhibitor is administered at a dose of between about 100 mg to about 500 mg. In some embodiments, the PD-1 inhibitor is administered at a dose of between about 100 mg to about 400 mg. In some embodiments, the PD-1 inhibitor is administered at a dose of between about 100 mg to about 300 mg. In some embodiments, the PD-1 inhibitor is administered at a dose of between about 100 mg to about 200 mg. In some embodiments, the PD-1 inhibitor is administered at a dose of between about 200 mg to about 600 mg. In some embodiments, the PD-1 inhibitor is administered at a dose of between about 200 mg to about 500 mg. In some embodiments, the PD-1 inhibitor is administered at a dose of between about 200 mg to about 400 mg. In some embodiments, the PD-1 inhibitor is administered at a dose of between about 200 mg to about 300 mg. In some embodiments, the PD-1 inhibitor is administered at a dose of between about 300 mg to about 600 mg. In some embodiments, the PD-1 inhibitor is administered at a dose of between about 300 mg to about 500 mg. In some embodiments, the PD-1 inhibitor is administered at a dose of between about 300 mg to about 400 mg. In some embodiments, the PD-1 inhibitor is administered at a dose of between about 400 mg to about 600 mg. In some embodiments, the PD-1 inhibitor is administered at a dose of between about 400 mg to about 500 mg. In some embodiments, the PD-1 inhibitor is administered at a dose of between about 500 mg to about 600 mg. In some embodiments, the PD-1 inhibitor is administered at a dose of between about 600 mg to about 700 mg. In some embodiments, the PD-1 inhibitor is administered at a dose of between about 700 mg to about 800 mg. In some embodiments, the PD-1 inhibitor is administered at a dose of between about 800 mg to about 900 mg. In some embodiments, the PD-1 inhibitor is administered at a dose of between about 900 mg to about 1000 mg.

In some embodiments, the PD-1 inhibitor (e.g., tislelizumab) is administered at a flat dose of about 100 mg. In some embodiments, the PD-1 inhibitor is administered at a dose of about 200 mg. In some embodiments, the PD-1 inhibitor is administered at a dose of about 300 mg. In some embodiments, the PD-1 inhibitor is administered at a dose of about 400 mg. In some embodiments, the PD-1 inhibitor is administered at a dose of about 500 mg. In some embodiments, the PD-1 inhibitor is administered at a dose of about 600 mg. In some embodiments, the PD-1 inhibitor is administered at a dose of about 700 mg. In some embodiments, the PD-1 inhibitor is administered at a dose of about 800 mg. In some embodiments, the PD-1 inhibitor is administered at a dose of about 900 mg. In some embodiments, the PD-1 inhibitor is administered at a dose of about 1000 mg.

In some embodiments, the PD-1 inhibitor (e.g., tislelizumab) is administered once every ten weeks. In some embodiments, the PD-1 inhibitor is administered once every nine weeks. In some embodiments, the PD-1 inhibitor is administered once every eight weeks. In some embodiments, the PD-1 inhibitor is administered once every seven weeks. In some embodiments, the PD-1 inhibitor is administered once every six weeks. In some embodiments, the PD-1 inhibitor is administered once every five weeks. In some embodiments, the PD-1 inhibitor is administered once every four weeks. In some embodiments, the PD-1 inhibitor is administered once every three weeks. In some embodiments, the PD-1 inhibitor is administered once every two weeks. In some embodiments, the PD-1 inhibitor is administered once every week.

In some embodiments, the PD-1 inhibitor (e.g., tislelizumab) is administered intravenously.

In some embodiments, the PD-1 inhibitor (e.g., tislelizumab) is administered over a period of about 20 minutes to 40 minutes (e.g., about 30 minutes). In some embodiments, the PD-1 inhibitor is administered over a period of about 30 minutes. In some embodiments, the PD-1 inhibitor is administered over a period of about an hour. In some embodiments, the PD-1 inhibitor is administered over a period of about two hours. In some embodiments, the PD-1 inhibitor is administered over a period of about three hours. In some embodiments, the PD-1 inhibitor is administered over a period of about four hours. In some embodiments, the PD-1 inhibitor is administered over a period of about five hours. In some embodiments, the PD-1 inhibitor is administered over a period of about six hours.

In some embodiments, the PD-1 inhibitor (e.g., tislelizumab) is administered at a dose between about 300 mg to about 500 mg (e.g., about 400 mg), intravenously, once every four weeks. In some embodiments, the PD-1 inhibitor is administered at a dose between about 200 mg to about 400 mg (e.g., about 300 mg), intravenously, once every three weeks. In some embodiments, tislelizumab is administered at a dose of 400 mg, once every four weeks. In some embodiments, tislelizumab is administered at a dose of 300 mg, once every three weeks.

In some embodiments, the PD-1 inhibitor (e.g., tislelizumab) is administered at a dose between about 300 mg to about 500 mg (e.g., about 400 mg), intravenously, over a period of about 20 minutes to about 40 minutes (e.g., about 30 minutes), once every two weeks. In some embodiments, the PD-1 inhibitor is administered at a dose between about 200 mg to about 400 mg (e.g., about 300 mg), intravenously, over a period of about 20 minutes to about 40 minutes (e.g., about 30 minutes), once every three weeks.

In some embodiments, the PD-1 inhibitor (e.g., tislelizumab) is administered at a dose of about 100 mg per week. For example, if a 10-week dose is given to a patient, then the PD-1 inhibitor (e.g., tislelizumab) can be given at 1000 mg. If a 9-week dose is given, then the PD-1 inhibitor (e.g., tislelizumab) can be given at 900 mg. If an 8-week dose is given, then the PD-1 inhibitor (e.g., tislelizumab) can be given at 800 mg. If a 7-week dose is given, then the PD-1 inhibitor (e.g., tislelizumab) can be given at 700 mg. If a 6-week dose is given, then the PD-1 inhibitor (e.g., tislelizumab) can be given at 600 mg. If a 5-week dose is given, then the PD-1 inhibitor (e.g., tislelizumab) can be given at 500 mg. If a 4-week dose is given, then the PD-1 inhibitor (e.g., tislelizumab) can be given at 400 mg. If a 3-week dose is given, then the PD-1 inhibitor (e.g., tislelizumab) can be given at 300 mg. If a 2-week dose is given, then the PD-1 inhibitor (e.g., tislelizumab) can be given at 200 mg. If a 1-week dose is given, then the PD-1 inhibitor (e.g., tislelizumab) can be given at 100 mg.

For example, if an anti-PD-1 antibody, such as tislelizumab is used, it can be administered at a dose of 200 mg as an intravenous infusion, once every three week. Alternatively, tislelizumab can be administered at a dose of 300 mg as an intravenous infusion, once every four weeks. If an anti-PD-1 antibody, such as tislelizumab is used, it can be administered at a dose of 300 mg as an intravenous infusion, once every three week. Alternatively, tislelizumab can be administered at a dose of 400 mg as an intravenous infusion, once every four weeks.

The structure of the active compounds identified by code numbers, generic or trade names may be taken from the actual edition of the standard compendium "The Merck Index" or from databases, e.g. Patents International (e.g. IMS World Publications). The above-mentioned compounds, which can be used in combination with a compound of the present invention, can be prepared and administered as described in the art, such as in the documents cited above.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by WRN. Products provided as a combined preparation include a composition comprising the compound of formula (I) and the other therapeutic agent(s) together in the same pharmaceutical composition, or the compound of the present invention and the other therapeutic agent(s) in separate form, e.g. in the form of a kit.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Accordingly, the invention provides the use of a compound of the present invention for treating a disease or condition mediated by WRN, wherein the medicament is prepared for administration with another therapeutic agent. The invention also provides the use of another therapeutic agent for treating a disease or condition mediated by WRN, wherein the medicament is administered with a compound of the present invention.

The invention also provides a compound of the present invention for use in treating a disease or condition mediated by WRN, wherein the compound of the present invention is prepared for administration with another therapeutic agent. The invention also provides another therapeutic agent for use in treating a disease or condition mediated by WRN, wherein the other therapeutic agent is prepared for administration with a compound of the present invention. The invention also provides a compound of the present invention for use in treating a disease or condition mediated by WRN, wherein the compound of the present invention is administered with another therapeutic agent. The invention also provides another therapeutic agent for use in a method of treating a disease or condition mediated by WRN, wherein the other therapeutic agent is administered with a compound of the present invention.

The invention also provides the use of a compound of the present invention for treating a disease or condition mediated by WRN, wherein the patient has previously (e.g. within 24 hours) been treated with another therapeutic agent. The invention also provides the use of another therapeutic agent for treating a disease or condition mediated by WRN, wherein the patient has previously (e.g. within 24 hours) been treated with compound of the present invention.

Example Formulation

A compound of formula (I) may be formulated as an amorphous solid dispersion tablet, as described below.

A. Amorphous Solid Dispersion:

| Component | Function | Composition % (by weight) |
|---|---|---|
| Example 42 compound (free form) | Active compound | 40 |
| Amino methacrylate copolymer (e.g. Eudragit ® E PO)* | Binder | 15 |
| Copovidone | Binder | 45 |

*Eudragit ® E PO is described in dx.doi.org/10.1021/mp4000635 I *Mol. Pharmaceutics* 2013, 10, 2630-2641 and has a registry CAS Registry Number of 24938-16-7.

Dichloromethane was charged into a vessel, followed by the compound of Example 42 as the free form (not the sodium salt), basic polymethacrylate and copovidone, to obtain a slurry. Dichloromethane was again charged to the vessel and the mixture was stirred until a clear solution was obtained. The solution was spray-dried, then the resulting powder dried in an agitated bed vacuum drier, then sieved.

B. Film Coated Tablet:

| Component | Function | Composition % (by weight) |
|---|---|---|
| Example 42 spray dried powder (from part A, above) | Active compound | 28.98 |
| Mannitol | Filler | 59.41 |
| Croscarmellose sodium (such as Sodium CMC XL | Disintegrant | 5.80 |
| Colloidal silicon dioxide (such as Aerosil ® 200 PH) | Glidant | 0.48 |
| Sodium stearyl fumarate | lubricant | 1.93 |
| Film-coating agent (such as Opadry ®) water | Coating agent | 3.4 |

Mannitol, croscarmellose sodium, colloidal silicon dioxide and sodium stearyl fumarate were added to the Example 42 compound powder obtained in part A above, and the mixture blended then compressed into tablets. The coating agent was dispersed in water to obtain a homogeneous suspension, which was used to coat the tablets.

Biological Assays and Data

The activity of a compound according to the present invention can be assessed by the following in vitro & in vivo methods.

Material and Methods

Molecular Biology and virus production. The DNA encoding human Werner helicase (UniProt Q14191, WRN, amino acids S2-S1432) was designed as four DNA strings which were codon-optimized for expression in *E. coli*. The strings were either ordered from GeneArt (LifeTechnologies, Regensburg, Germany) or made with subcloning overlapping oligonucleotides.

The baculovirus from expression plasmid pLAF1202 (SEQ ID NO: 1) encoding His-ZZ-3C-WRN (aa N517-P1238, encoded by nucleotides 578-2743 in the sequence) was generated with the FlashBac Ultra system (Oxford Expression Technologies 100302) using 540 ng of plasmid DNA, 5.4 μg Flashbac Ultra DNA, and 5.4 microliters Lipofectin (LifeTechnologies 18292-011) for transfection following the manufacturer's instructions. After 5 hours incubation the solution was diluted with 500 microliters TC100 medium (LifeTechnologies 13055-025) and incubated for 7 days at 27° C.

The cells were harvested by centrifugation at 800×g for 10 minutes and the supernatant containing the virus was transferred into a new sterile tube. For the first virus amplification, 500 microliters of the virus was added to 25 mL of SF9 cells at one million cells/mL and incubated for 5 days at 27° C. (200 rpm). The cell viability, density, and diameter was measured and the virus, upon signs of infection, was harvested by centrifugation at 3000 rpm for 15 minutes.

Baculovirus infected insect cells (BIICs) were generated as described by Wasilko et al., 2009, DOI: 10.1016/j.pep.2009.01.002.

In brief, in an Erlenmeyer flask 100 million SF9 cells (one million cells/mL) in 100 mL ESF921 medium (Expression Systems—96-001-01, supplemented with 0.5× Streptomycin/Penicillin) were infected with 300 million baculovirus particles of the respective construct (estimated MOI=3) and incubated at 27° C. for 24 hours at 130 rpm. The infected cells were transferred to 50 mL tubes and harvested by centrifugation at 100×g for 10 minutes at RT.

The cells were resuspended to 10 million/mL in ESF921 (0.5× Streptomycin/Penicillin) medium with BSA (final 10 mg/mL) and 10% DMSO. 500 μL aliquots of cells were transferred to 1.8 mL cryotubes and frozen in Nunc Cryo 1° C. freezing container overnight at −80° C.

SEQ ID NO: 1

```
AACCATCTCGCAAATAAATAAGTATTTTACTGTTTT
CGTAACAGTTTTGTAATAAAAAAACCTATAAATAT
TCCGGATTATTCATACCGTCCCACCATCGGGCGCC
ATGGCTTCTCACCACCATCACCATCACCATCATCA
TCACGCTCAGCACGACGAGGCTGTGGACAACAAGT
TCAACAAGGAGCAGCAGAACGCTTTCTACGAGATC
CTGCACCTCCCTAACCTGAACGAGGAGCAGCGTAA
CGCTTTCATCCAGTCCCTGAAGGACGACCCTTCTC
AGTCTGCTAACCTGCTGGCTGAGGCTAAGAAGCTG
AACGACGCTCAGGCTCCTAAGGTGGACAACAAGTT
CAACAAGGAGCAGCAGAACGCTTTCTACGAGATCC
TGCACCTCCCTAACCTGAACGAGGAGCAGCGTAAC
GCTTTCATCCAGTCCCTGAAGGACGACCCTTCTCA
GTCTGCTAACCTGCTGGCTGAGGCTAAGAAGCTGA
ACGACGCTCAGGCTCCTAAGGTGGACGCTAACGGT
GGCGGCGGTTCCGGCGGTGGTGGCTCTCTCGAGGT
TCTGTTCCAGGGTCCGAATGAAGGCGAGGAAGATG
ATGACAAAGACTTCCTGTGGCCAGCTCCAAACGAA
GAACAGGTGACTTGTCTCAAGATGTACTTCGGTCA
TAGCAGCTTCAAACCAGTGCAGTGGAAAGTTATCC
ACAGCGTTCTTGAAGAACGTCGTGATAATGTGGCT
GTGATGGCTACTGGCTATGGTAAGAGCCTGTGTTT
CCAGTACCCGCCAGTTTACGTTGGTAAGATCGGTC
TGGTGATTAGCCCGCTGATCTCTCTGATGGAAGAC
CAGGTGCTGCAACTTAAGATGAGCAACATCCCGGC
TTGTTTCCTGGGTTCTGCACAAAGCGAGAACGTGC
TCACCGATATCAAGCTGGGTAAGTACCGTATCGTG
```

-continued

```
TACGTGACGCCAGAATACTGTAGCGGCAACATGGG
TCTTCTGCAACAGCTCGAAGCTGATATTGGCATCA
CCCTCATTGCAGTGGACGAAGCTCACTGTATCAGC
GAGTGGGGTCATGATTTCCGCGACTCTTTCCGTAA
ACTGGGTTCTCTGAAGACTGCACTTCCGATGGTTC
CAATTGTGGCACTGACCGCAACTGCTTCTAGCTCT
ATTCGTGAAGACATCGTTCGTTGCCTGAACCTCCG
TAACCCACAAATTACCTGCACCGGCTTTGACCGTC
CGAACCTGTACCTGGAGGTTCGTCGTAAGACCGGT
AATATCCTTCAGGACCTGCAACCATTCCTGGTTAA
GACCAGCAGCCACTGGGAGTTCGAAGGTCCGACTA
TCATCTACTGCCCAAGCCGTAAGATGACCCAGCAG
GTTACTGGTGAACTGCGTAAACTGAACCTGAGCTG
TGGCACTTACCACGCAGGCATGTCTTTCTCTACCC
GTAAAGACATCCATCATCGTTTCGTGCGTGATGAA
ATCCAGTGCGTTATCGCTACCATTGCATTCGGCAT
GGGTATCAACAAAGCTGACATCCGTCAAGTGATTC
ACTACGGTGCACCGAAAGACATGGAAAGCTACTAC
CAGGAAATCGGCCGTGCAGGTCGTGATGGTCTGCA
AAGCTCTTGTCATGTGCTGTGGGCACCAGCAGATA
TTAACCTGAACCGTCACCTGCTGACTGAAATTCGT
AACGAGAAATTCCGTCTGTACAAACTGAAGATGAT
GGCGAAGATGGAGAAATACCTGCATAGCTCCCGTT
GTCGTCGTCAAATCATTCTGAGCCATTTCGAGGAT
AAACAGGTGCAGAAAGCTTCTCTGGGTATCATGGG
CACTGAGAAGTGCTGCGATAACTGTCGTAGCCGTC
TTGATCACTGCTACAGCATGGACGATAGCGAAGAC
ACTTCTTGGGATTTCGGTCCACAAGCATTCAAACT
GCTGAGCGCAGTTGATATCCTGGGTGAGAAATTCG
GCATCGGCCTCCCAATCCTGTTTCTGCGCGGTTCT
AACTCTCAGCGTCTTGCTGATCAATACCGTCGTCA
CTCTCTGTTCGGCACTGGTAAAGACCAGACCGAAT
CTTGGTGGAAAGCATTCAGCCGTCAACTTATCACC
GAAGGCTTTCTGGTGGAAGTGTCTCGTTACAACAA
GTTCATGAAGATCTGCGCACTGACTAAGAAAGGTC
GTAACTGGCTGCACAAGGCAAATACCGAGTCTCAG
TCTCTTATCCTTCAGGCTAACGAAGAACTGTGCCC
GAAGAAGCTTCTGCTGCCATCTTCTAAGACCGTGA
GCTCTGGTACTAAAGAGCATTGCTACAACCAGGTG
CCGGTTGAACTGTCTACCGAGAAGAAGTCCAACCT
GGAGAAGCTGTACTCCTACAAACCGTGCGACAAGA
```

-continued

TCTCCTCCGGTTCTAATATCAGCAAGAAGTCCATC
ATGGTGCAGTCTCCGGAGAAAGCTTACAGCAGCTC
TCAGCCAGTTATCTCTGCACAGGAACAGGAAACTC
AGATTGTGCTGTACGGTAAACTGGTGGAAGCACGT
CAGAAACACGCTAACAAGATGGACGTGCCGCCAGC
AATTCTTGCAACCAACAAGATTCTGGTGGACATGG
CTAAGATGCGCCCAACTACTGTTGAGAACGTGAAA
CGTATCGACGGTGTTAGCGAAGGTAAAGCTGCAAT
GCTGGCACCACTGCTTGAAGTTATCAAGCATTTCT
GCCAGACCAACTCTGTTCAGACCGACCTGTTCTCT
TCTACCAAACCATAATGGTACCGAATTCGCGGCCG
CAGAGCTCGCTCTGGTGCCACGCGGTAGTTCCGCT
TGGAGCCACCCGCAGTTCGAAAAGTAAGTGATTAA
CCTCAGGTTATACATATATTTTGAATTTAATTAAT
TATACATATATTTTATATTATTTTTGTCTTTTATT
ATCGAGGGGCCGTTGTTGGTGTGGGGTTTTGCATA
GAAATAACAATGGGAGTTGGCGACGTTGCTGCGCC
AACACCACCTCCCTTCCCTCCTTTCATCATGTATC
TGTAGATAAAATAAAATATTAAACCTAAAAACAAG
ACCGCGCCTATCAACAAAATGATAGGCATTAACTT
GCCGCTGACGCTGTCACTAACGTTGGACGATTTGC
CGACTAAACCTTCATCGCCCAGTAACCAATCTAGG
TAGCTGAGCGCATGCAAGCTGATCCGGGTTATTAG
TACATTTATTAAGCGCTAGATTCTGTGCGTTGTTG
ATTTACAGACAATTGTTGTACGTATTTTAATAATT
CATTAAATTTATAATCTTTAGGGTGGTATGTTAGA
GCGAAAATCAAATGATTTTCAGCGTCTTTATATCT
GAATTTAAATATTAAATCCTCAATAGATTTGTAAA
ATAGGTTTCGATTAGTTTCAAACAAGGGTTGTTTT
TCCGAACCGATGGCTGGACTATCTAATGGATTTTC
GCTCAACGCCACAAAACTTGCCAAATCTTGTAGCA
GCAATCTAGCTTTGTCGATATTCGTTTGTGTTTTG
TTTTGTAATAAAGGTTCGACGTCGTTCAAAATATT
ATGCGCTTTTGTATTTCTTTCATCACTGTCGTTAG
TGTACAATTGACTCGACGTAAACACGTTAAATAGA
GCTTGGACATATTTAACATCGGGCGTGTTAGCTTT
ATTAGGCCGATTATCGTCGTCGTCCCAACCCTCGT
CGTTAGAAGTTGCTTCCGAAGACGATTTTGCCATA
GCCACACGACGCCTATTAATTGTGTCGGCTAACAC
GTCCGCGATCAAATTTGTAGTTGAGCTTTTTGGAA

-continued

TTATTTCTGATTGCGGGCGTTTTTGGGCGGGTTTC
AATCTAACTGTGCCCGATTTTAATTCAGACAACAC
GTTAGAAAGCGATGGTGCAGGCGGTGGTAACATTT
CAGACGGCAAATCTACTAATGGCGGCGGTGGTGGA
GCTGATGATAAATCTACCATCGGTGGAGGCGCAGG
CGGGGCTGGCGGCGGAGGCGGAGGCGGAGGTGGTG
GCGGTGATGCAGACGGCGGTTTAGGCTCAAATGTC
TCTTTAGGCAACACAGTCGGCACCTCAACTATTGT
ACTGGTTTCGGGCGCCGTTTTTGGTTTGACCGGTC
TAAGACGAGTGCGATTTTTTTCGTTTCTAATAGCT
TCCAACAATTGTTGTCTGTCGTCTAAAGGTGCAGC
GGGTTGAGGTTCCGTCGGCATTGGTGGAGCGGGCG
GCAATTCAGACATCGATGGTGGTGGTGGTGGTGGA
GGCGCTGGAATGTTAGGCACGGGAGAAGGTGGTGG
CGGCGGTGCCGCCGGTATAATTTGTTCTGGTTTAG
TTTGTTCGCGCACGATTGTGGGCACCGGCGCAGGC
GCCGCTGGCTGCACAACGGAAGGTCGTCTGCTTCG
AGGCAGCGCTTGGGGTGGTGGCAATTCAATATTAT
AATTGGAATACAAATCGTAAAAATCTGCTATAAGC
ATTGTAATTTCGCTATCGTTTACCGTGCCGATATT
TAACAACCGCTCAATGTAAGCAATTGTATTGTAAA
GAGATTGTCTCAAGCTCGGATCGATCCCGCACGCC
GATAACAAGCCTTTTCATTTTTACTACAGCATTGT
AGTGGCGAGACACTTCGCTGTCGTCGAGGTTTAAA
CGCTTCCTCGCTCACTGACTCGCTGCGCTCGGTCG
TTCGGCTGCGGCGAGCGGTATCAGCTCACTCAAAG
GCGGTAATACGGTTATCCACAGAATCAGGGGATAA
CGCAGGAAAGAACATGTGAGCAAAAGGCCAGCAAA
AGGCCAGGAACCGTAAAAAGGCCGCGTTGCTGGCG
TTTTTCCATAGGCTCCGCCCCCCTGACGAGCATCA
CAAAAATCGACGCTCAAGTCAGAGGTGGCGAAACC
CGACAGGACTATAAAGATACCAGGCGTTTCCCCCT
GGAAGCTCCCTCGTGCGCTCTCCTGTTCCGACCCT
GCCGCTTACCGGATACCTGTCCGCCTTTCTCCCTT
CGGGAAGCGTGGCGCTTTCTCATAGCTCACGCTGT
AGGTATCTCAGTTCGGTGTAGGTCGTTCGCTCCAA
GCTGGGCTGTGTGCACGAACCCCCCGTTCAGCCCG
ACCGCTGCGCCTTATCCGGTAACTATCGTCTTGAG
TCCAACCCGGTAAGACACGACTTATCGCCACTGGC
AGCAGCCACTGGTAACAGGATTAGCAGAGCGAGGT
ATGTAGGCGGTGCTACAGAGTTCTTGAAGTGGTGG

-continued

CCTAACTACGGCTACACTAGAAGGACAGTATTTGG
TATCTGCGCTCTGCTGAAGCCAGTTACCTTCGGAA
AAAGAGTTGGTAGCTCTTGATCCGGCAAACAAACC
ACCGCTGGTAGCGGTGGTTTTTTTGTTTGCAAGCA
GCAGATTACGCGCAGAAAAAAAGGATCTCAAGAAG
ATCCTTTGATCTTTTCTACGGGGTCTGACGCTCAG
TGGAACGAAAACTCACGTTAAGGGATTTTGGTCAT
GAGATTATCAAAAAGGATCTTCACCTAGATCCTTT
TAAATTAAAAATGAAGTTTTAAATCAATCTAAAGT
ATATATGAGTAAACTTGGTCTGACAGTTACCAATG
CTTAATCAGTGAGGCACCTATCTCAGCGATCTGTC
TATTTCGTTCATCCATAGTTGCCTGACTCCCCGTC
GTGTAGATAACTACGATACGGGAGGGCTTACCATC
TGGCCCCAGTGCTGCAATGATACCGCGAGACCCAC
GCTCACCGGCTCCAGATTTATCAGCAATAAACCAG
CCAGCCGGAAGGGCCGAGCGCAGAAGTGGTCCTGC
AACTTTATCCGCCTCCATCCAGTCTATTAATTGTT
GCCGGGAAGCTAGAGTAAGTAGTTCGCCAGTTAAT
AGTTTGCGCAACGTTGTTGCCATTGCTACAGGCAT
CGTGGTGTCACGCTCGTCGTTTGGTATGGCTTCAT
TCAGCTCCGGTTCCCAACGATCAAGGCGAGTTACA
TGATCCCCCATGTTGTGCAAAAAAGCGGTTAGCTC
CTTCGGTCCTCCGATCGTTGTCAGAAGTAAGTTGG
CCGCAGTGTTATCACTCATGGTTATGGCAGCACTG
CATAATTCTCTTACTGTCATGCCATCCGTAAGATG
CTTTTCTGTGACTGGTGAGTACTCAACCAAGTCAT
TCTGAGAATAGTGTATGCGGCGACCGAGTTGCTCT
TGCCCGGCGTCAATACGGGATAATACCGCGCCACA
TAGCAGAACTTTAAAAGTGCTCATCATTGGAAAAC
GTTCTTCGGGGCGAAAACTCTCAAGGATCTTACCG
CTGTTGAGATCCAGTTCGATGTAACCCACTCGTGC
ACCCAACTGATCTTCAGCATCTTTTACTTTCACCA
GCGTTTCTGGGTGAGCAAAAACAGGAAGGCAAAAT
GCCGCAAAAAAGGGAATAAGGGCGACACGGAAATG
TTGAATACTCATACTCTTCCTTTTTCAATATTATT
GAAGCATTTATCAGGGTTATTGTCTCATGAGCGGA
TACATATTTGAATGTATTTAGAAAAATAAACAAAT
AGGGGTTCCGCGCACATTTCCCCGAAAAGTGCCAC
CTGACGCGCCCTGTAGCGGCGCATTAAGCGCGGCG
GGTGTGGTGGTTACGCGCAGCGTGACCGCTACACT

-continued

TGCCAGCGCCCTAGCGCCCGCTCCTTTCGCTTTCT
TCCCTTCCTTTCTCGCCACGTTCGCCGGCTTTCCC
CGTCAAGCTCTAAATCGGGGGCTCCCTTTAGGGTT
CCGATTTAGTGCTTTACGGCACCTCGACCCCAAAA
AACTTGATTAGGGTGATGGTTCACGTAGTGGGCCA
TCGCCCTGATAGACGGTTTTTCGCCCTTTGACGTT
GGAGTCCACGTTCTTTAATAGTGGACTCTTGTTCC
AAACTGGAACAACACTCAACCCTATCTCGGTCTAT
TCTTTTGATTTATAAGGGATTTTGCCGATTTCGGC
CTATTGGTTAAAAAATGAGCTGATTTAACAAAAAT
TTAACGCGAATTTTAACAAAATATTAACGTTTACA
ATTTCCCATTCGCCATTCAGGCTGCGCAACTGTTG
GGAAGGGCGATCGGTGCGGGCCTCTTCGCTATTAC
GCCAGGAACGGCTCCGCCCACTATTAATGAAATTA
AAAATTCCAATTTTAAAAAACGCAGCAAGAGAAAC
ATTTGTATGAAAGAATGCGTAGAAGGAAAGAAAAA
TGTCGTCGACATGCTGAACAACAAGATTAATATGC
CTCCGTGTATAAAAAAAAATATTGAACGATTTGAAA
GAAAACAATGTACCGCGCGGCGGTATGTACAGGAA
GAGGTTTATACTAAACTGTTACATTGCAAACGTGG
TTTCGTGTGCCAAGTGTGAAAACCGATGTTTAATC
AAGGCTCTGACGCATTTCTACAACCACGACTCCAA
GTGTGTGGGTGAAGTCATGCATCTTTTAATCAAAT
CCCAAGATGTGTATAAACCACCAAACTGCCAAAAA
ATGAAAACTGTCGACAAGCTCTGTCCGTTTGCTGG
CAACTGCAAGGGTCTCAATCCTATTTGTAATTATT
GAATAATAAAACAATTATAAATGCTAAATTTGTTT
TTTATTAACGATACAAACCAAACGCAACAAGAACA
TTTGTAGTATTATCTATAATTGAAAACGCGTAGTT
ATAATCGCTGAGGTAATATTTAAAATCATTTTCAA
ATGATTCACAGTTAATTTGCGACAATATAATTTTA
TTTTCACATAAACTAGACGCCTTGTCGTCTTCTTC
TTCGTATTCCTTCTCTTTTTCATTTTTCTCTTCAT
AAAAATTAACATAGTTATTATCGTATCCATATATG
TATCTATCGTATAGAGTAAATTTTTTTGTTGTCATA
AATATATATGTCTTTTTTAATGGGGTGTATAGTAC
CGCTGCGCATAGTTTTTCTGTAATTTACAACAGTG
CTATTTTCTGGTAGTTCTTCGGAGTGTGTTGCTTT
AATTATTAAATTTATATAATCAATGAATTTGGGAT
CGTCGGTTTTGTACAATATGTTGCCGGCATAGTAC
GCAGCTTCTTCTAGTTCAATTACACCATTTTTTAG

-continued

CAGCACCGGATTAACATAACTTTCCAAAATGTTGT

ACGAACCGTTAAACAAAAACAGTTCACCTCCCTTT

TCTATACTATTGTCTGCGAGCAGTTGTTTGTTGTT

AAAAATAACAGCCATTGTAATAAGACGCACAAACT

AATATCACAAACTGGAAATGTCTATCAATATATAG

TTGCTGATCAGATCTACCCGTAGTGGCTATGGCAG

GGCTTGCCGCCCCGACGTTGGCTGCGAGCCCTGGG

CCTTCACCCGAACTTGGGGGTTGGGGTGGGGAAAA

GGAAGAAACGCGGGCGTATTGGTCCCAATGGGGTC

TCGGTGGGGTATCGACAGAGTGCCAGCCCTGGGAC

CGAACCCCGCGTTTATGAACAAACGACCCAACACC

CGTGCGTTTTATTCTGTCTTTTTATTGCCGTCATA

GCGCGGGTTCCTTCCGGTATTGTCTCCTTCCGTGT

TTCAGTTAGCCTCCCCCATCTCCCGGTACCGCATG

CTATGCATCGGCCGCTTTACTTGTACAGCTCGTCC

ATGCCGAGAGTGATCCCGGCGGCGGTCACGAACTC

CAGCAGGACCATGTGATCGCGCTTCTCGTTGGGGT

CTTTGCTCAGGGCGGACTGGGTGCTCAGGTAGTGG

TTGTCGGGCAGCAGCACGGGGCCGTCGCCGATGGG

GGTGTTCTGCTGGTAGTGGTCGGCGAGCTGCACGC

TGCCGTCCTCGATGTTGTGGCGGATCTTGAAGTTC

ACCTTGATGCCGTTCTTCTGCTTGTCGGCCATGAT

ATAGACGTTGTGGCTGTTGTAGTTGTACTCCAGCT

TGTGCCCCAGGATGTTGCCGTCCTCCTTGAAGTCG

ATGCCCTTCAGCTCGATGCGGTTCACCAGGGTGTC

GCCCTCGAACTTCACCTCGGCGCGGGTCTTGTAGT

TGCCGTCGTCCTTGAAGAAGATGGTGCGCTCCTGG

ACGTAGCCTTCGGGCATGGCGGACTTGAAGAAGTC

GTGCTGCTTCATGTGGTCGGGGTAGCGGCTGAAGC

ACTGCACGCCGTAGGTCAGGGTGGTCACGAGGGTG

GGCCAGGGCACGGGCAGCTTGCCGGTGGTGCAGAT

GAACTTCAGGGTCAGCTTGCCGTAGGTGGCATCGC

CCTCGCCCTCGCCGGACACGCTGAACTTGTGGCCG

TTTACGTCGCCGTCCAGCTCGACCAGGATGGGCAC

CACCCCGGTGAACAGCTCCTCGCCCTTGCTCACCA

TCGTCGAGATCCCGGGCGTTTAAATTGTGTAATTT

ATGTAGCTGTAATTTTTACCTTATTAATATTTTTT

ACGCTTTGCATTCGACGACTGAACTCCCAAATATA

TGTTTAACTCGTCTTGGTCGTTTGAATTTTTGTTG

CTGTGTTTCCTAATATTTTCCATCACCTTAAATAT

-continued

GTTATTGTAATCCTCAATGTTGAACTTGCAATTGG

ACACGGCATAGTTTTCCATAGTCGTGTAAAACATG

GTATTGGCTGCATTGTAATACATCCGACTGAGCGG

GTACGGATCTATGTGTTTGAGCAGCCTGTTCAAAA

ACTCTGCATCGTCGCAAAACGGAATTTGGTACCCG

GGCGTATACTCCGGAATATTAATAGATCATGGAGA

TAATTAAAATGAT

Protein Expression and Purification

BIICs aliquots for Werner helicase protein His-ZZ-3C-WRN (aa N517-P1238, pLAF1202) were diluted 1/100 into ESF921 medium and further diluted 1/100 into the expression/production flasks with Sf21 cells (one million cells/mL) in 1 L ESF921 medium and incubated for protein expression for 96 h (27° C., 130 rpm).

The WRN protein was purified using the following protocol. The cell pellets were thawed and resuspended in 80 mL buffer A (50 mM Tris, 300 mM NaCl, 20 mM imidazole, 1 mM TCEP, 10% glycerol, pH 7.8) supplemented with Turbonuclease (final concentration 40 units/mL, Merck) and cOmplete protease inhibitor tablets (1 tablet/50 mL, Roche). The cells were lysed by three passages through a homogenizer (Avestin, Emulsiflex C3) at 800-1000 bar. The lysed sample was centrifuged at 48000×g for 40 minutes (Sorvall RC5B, SS-34 rotor) and the supernatant was passed through a 0.45 μm filter.

The lysate was loaded onto a HisTrap crude FF 5 mL column (GE Healthcare) mounted on an AKTA Pure 25 chromatography system (GE Healthcare). Contaminating proteins were washed away with buffer A and bound protein was eluted with a linear gradient over 10 column volumes to 100% of buffer B (50 mM Tris, 300 mM NaCl, 300 mM imidazole, 1 mM TCEP, 10% glycerol, pH 7.8). 1% (w/w) HRV 3C protease (His-MBP-tagged, produced in-house) was added to the eluted protein. The N-terminal purification tag was cleaved off by the protease during dialysis overnight at 5° C. against 2 L buffer (50 mM Tris pH 7.0, 150 mM NaCl, 1 mM TCEP, 10% glycerol, 0.02% CHAPS). The protein solution was then carefully diluted with adding two volume parts of 20 mM Tris pH 7.0, 10% glycerol, 0.02% CHAPS. The slightly turbid protein solution was passed over a 0.45 μm filter. The cleaved protein was loaded onto a Resource S 6 mL column (GE Healthcare) pre-equilibrated with 20 mM Tris, 20 mM NaCl, 1 mM TCEP, 10% glycerol, pH 7.0. Cleaved tag and contaminating proteins were washed away with the equilibration buffer. The bound target protein was eluted with a linear gradient over 20 column volumes of the same buffer containing 1 M sodium chloride and then injected onto a HiLoad 16/600 Superdex 75 μg column (GE Healthcare) pre-equilibrated with 50 mM Tris pH 7.4, 300 mM NaCl, 10% glycerol. Fractions containing pure protein were identified by SDS-PAGE and pooled. The purified protein was finally split into aliquots and frozen on dry ice. The purity, quantity, and identity of the protein was determined by RP-HPLC and LC-MS.

In Vitro Enzymatic Activity Assay on WRN Helicase

An ATPase assay was set up to measure the DNA dependent ATP hydrolysis activity of WRN helicase. This assay was used also to assess the inhibition properties of compounds of the invention on DNA dependent WRN ATPase activity.

The core helicase motif of the WRN protein (aa N517-P1238) was produced for this assay (protein production as described above). A 45 oligonucleotide sequence called "FLAP26" as described by Brosh et al., 2009, DOI: 10.1074/jbc.M111446200 (TTTTTTTTTTTTTTTTTTTTTTTC-CAAGTAAAACGACGGCCAGTGC; SEQ ID NO: 2) was purchased from IDT (Integrated DNA Technologies, Leuven, Belgium) and used as single strand DNA substrate. The ADP-Glo assay kit (Promega, Madison, WI) allowing the quantification of ADP produced in ATP hydrolysis reactions was used for setting up this assay.

Time course experiments were first performed in order to determine the best enzymatic assay conditions (including buffer conditions, reaction time and concentrations of protein, ATP and DNA substrates). A typical reaction consists of 10 nM WRN protein, 0.2 nM FLAP26, and 300 micromolar ATP in the following assay buffer: 30 mM Tris pH7.5, 2 mM $MgCl_2$, 0.02% BSA, 50 mM NaCl, 0.1% pluronic F127 prepared in DNAse free water.

To evaluate the inhibition properties of compounds of the invention, serial dilutions were prepared in DMSO (10 half log dilutions from a 10 mM DMSO solution). 50 nanoliters of each concentration was pre-incubated for 3 hours in a 384 small volume assay plate (Greiner #784075) with 2.5 microliters of a 20 nM WRN helicase protein in assay buffer with 600 micromolar ATP. Control wells were included with a "high control" (no inhibition), containing DMSO with no test compound, and "low controls" (maximal inhibition), containing buffer without protein. The reaction was started by addition of 2.5 microliters of FLAP26 at 0.4 nM and incubated for 30 minutes at room temperature. The reaction was stopped with the addition of 5 microliters of the first ADP-Glo reagent and incubated for one hour to remove the excess amount of ATP. Afterwards, 10 microliters of ATP detection reagent was added and incubated for an additional hour before reading. Luminescence output was recorded using Tecan 1000 reader, with 5 minutes delay before reading. Each concentration of compound was tested in duplicates in the assay plate.

Data analysis was carried out using an in-house developed software (Novartis Helios software application, Novartis Institutes for BioMedical Research, unpublished) using the methods described by Formenko et al., 2006, DOI: 10.1016/j.cmpb.2006.01.008. Following normalization of activity values for the wells to % inhibition (% inhibition=[(high control−sample)/(high control−low control)]×100), $IC_{50}$ fitting was carried out from the duplicate determinations present on each plate according to [4]. Data analysis can also be carried out using commercially available software designed to derive $IC_{50}$ values using 4-parameter fits (e.g. GraphPad Prism, XL fit). The reported $IC_{50}$ values are the geometrical means of at least 2 independent replicates.

Method for Detecting Effects on Cellular Proliferation

The colon carcinoma cell lines SW48 (RRID: CVCL_1724), HCT 116 (RRID: CVCL_0291) and SNU-407 (RRID: CVCL_5058) were obtained from ATCC. The WRN-knockdown insensitive colon carcinoma cell line DLD-1 (RRID: CVCL_0248) was obtained from the Korean Cell Line Bank (KCLB), and used to generate a derivative in which the endogenous WRN gene copies were knocked out by CRISPR-mediated editing using standard CRISPR methods. The resulting cell line, DLD1-WRN-KO, was used to assess potential off-target compound effects.

SW48, SNU-407 and DLD1-WRN-KO cells were cultured in growth medium composed of RPMI-1640 (Amimed Cat #1-41F22-1), 2 mM L-Glutamine (Amimed Cat #5-10K50), 10 mM HEPES (Gibco Cat #15630-056), 1 mM sodium pyruvate (Amimed Cat #5-60F00-H), 1× Penicillin-Streptomycin (Amimed Cat #4-01F00-H) and 10% fetal calf serum (Amimed Cat #2-01F30-G, Lot #LB11566P). HCT 116 cells were cultured in growth medium composed of McCoys 5A (Amimed catalog #1-18F01-1), 2 mM L-Glutamine (Amimed Cat #5-10K50), 1× Penicillin-Streptomycin (Amimed Cat #4-01F00-H) and 10% fetal calf serum (Amimed Cat #2-01F30-G, Lot #LB11566P). All cells were maintained at 37° C. in a humidified 5% $CO_2$ incubator.

Following filtration through a Steriflip-NY 20 μm filter (Millipore Cat #SCNY00020), trypsinized cells were seeded in 100 microliters growth medium at 2'000 (SW48) or 1'500 (SNU-407, DLD1-WRN-KO, HCT 116) cells/well into white, clear-bottom 96-well plates (Costar Cat #3903). Three replicate plates were prepared for each compound treatment condition. In addition, one plate (termed "day 0") was prepared to quantify the number of viable cells at the time of compound addition. Following overnight incubation at 37° C. in a humidified 5% $CO_2$ atmosphere, eight 3-fold serial dilutions of a given compound stock (obtained at a concentration of 10 mM in DMSO and stored at 4° C.) were dispensed directly into each of the triplicate assay plates using a HP 300D non-contact Digital Dispenser (TECAN). The final concentration of DMSO was normalized to 0.1% in all wells. 96 hours after compound addition, cellular ATP levels as a surrogate for cell viability was assessed following addition of 50 microliters CellTiterGlo (Promega Cat #G7573) reagent and luminescence quantification on a MPLEX multi-mode plate-reader (TECAN) following a 10 minute incubation at room temperature. The number of viable cells in the "day 0" plate were quantified identically on the day of compound addition.

For data analysis, the assay background signal that was determined in wells containing medium, but no cells, was subtracted from all other data points prior to further calculations. The extent of growth inhibition and potential cell kill was assessed by comparing the ATP levels (measured using CellTiterGlo, Promega) in compound-treated cells with those present at the time of compound addition. To this end, the following conditional concept was programmatically applied in HELIOS, an in-house software applying a multi-step decision tree to arrive at optimal concentration response curve fits (Gubler et al, SLAS DOI: 10.1177/2472555217752140) to calculate % growth (% G) for each compound-treated well: % G=(T−V0)/V0))*100 when T<V0, and % G=(T−V0)/(V−V0)))*100 when T≥V0, where V0 is the viability level at time of compound addition, while V and T represent vehicle-control and compound-treated viability levels, respectively, at the end of the compound incubation. 100%, 0% and −100% signify absence of growth inhibition, growth stasis, and complete cell kill, respectively. Compound concentrations leading to half-maximal growth inhibition (G150) and residual cell viability at the highest tested compound concentration (Data (cmax), expressed in percent) were routinely calculated. Data analysis can also be carried out using commercially available software designed to derive IC50 values using 4-parameter fits (e.g. GraphPad Prism, XL fit). The reported $GI_{50}$ values are the geometrical means of at least 2 independent replicates.

In Vivo Efficacy Demonstration for Compounds of the Invention

Experiments were performed in female Crl:NU(NCr)-Foxn1nu-Homozygous nude mice (Charles River). Animals were housed under Optimized Hygienic Conditions in Allentown XJ cages (IVC, max. 6 mice per cage) with food and water at libitum and a 12 h:12 h light:dark cycle. Animals were allowed to acclimatize for at least 1 week before being enrolled in the experimental design. The study described here was performed according to license 2275 approved by the Basel Cantonal Veterinary Office.

SW48 human colorectal cancer cells were obtained from ATCC. The cells were cultured in RPMI-1640 medium (BioConcept Ltd. Amimed, #1-41F01-1) supplemented with 10% FCS (Bio Concept #2-01F30-1), 2 mM L-glutamine (BioConcept Ltd. Amimed, #5-10K50-H), 1 mM sodium pyruvate (Bio Concept #5-60F00-H) and 10 mM HEPES (Bio Concept #5-31F00-H) at 37° C. in an atmosphere of 5% $CO_2$ in air. To establish SW48 xenografts cells were harvested and re-suspended in HBSS (Gibco, #14175) before injecting 100 μL containing 5 million cells subcutaneously in the right flank of animals which were anesthetized with isoflurane.

Tumour growth was monitored regularly post cell inoculation and animals were randomised into treatment groups (n=7) when tumor volume reached appropriate volume. During the treatment period, tumor volume was measured about twice a week. Tumor size, in $mm^3$, was calculated from: (L×W2×π/6). Where W=width and L=length of the tumor.

Depending on the target concentration, 50-200 mg of amorphous sodium salt of test compound (corrected by salt factor) were dissolved in 8 mL of an aqueous 10% w/v solution of 2-hydroxypropyl-beta-cyclodextrin (HPBCD). The pH was adjusted to pH 7.4 with 0.1 M HCl (~1 eq.) and the resulting solution filled up to a total volume of 10 mL with aqueous 10% HPBCD solution. In case of turbidity, the solution was filtered. The resulting solution formulation was used for in vivo studies.

Tumor bearing animals were enrolled into treatment groups (n=7) when their tumors reached an appropriate size to form groups with a mean tumor volume of 186 $mm^3$.

Animals were then treated with vehicle (10% Hydroxypropyl-beta-Cyclodextrine) or 240 mg/kg of a compound of the invention daily (QD) by oral gavage at 20 mL/kg.

Animals were weighed twice per week and examined frequently for overt signs of any adverse effects.

Tumor and body weight change data were analyzed statistically using GraphPad Prism 7.00 (GraphPad Software). If the variances in the data were normally distributed, the data were analyzed using one-way ANOVA with post hoc Dunnett's test for comparison of treatment versus control group. When applicable, results are presented as mean±SEM.

As a measure of efficacy the % T/C value is calculated at the end of the experiment according to:

$$(\Delta\text{tumor volume}^{treated}/\Delta\text{tumor volume}^{control})*100$$

Tumor regression was calculated according to:

$$-(\Delta\text{tumor volume}^{treated}/\text{tumor volume}^{treated\ at\ start})*100$$

Where Δtumor volumes represent the mean tumor volume on the evaluation day minus the mean tumor volume at the start of the experiment.

Figure 6B:
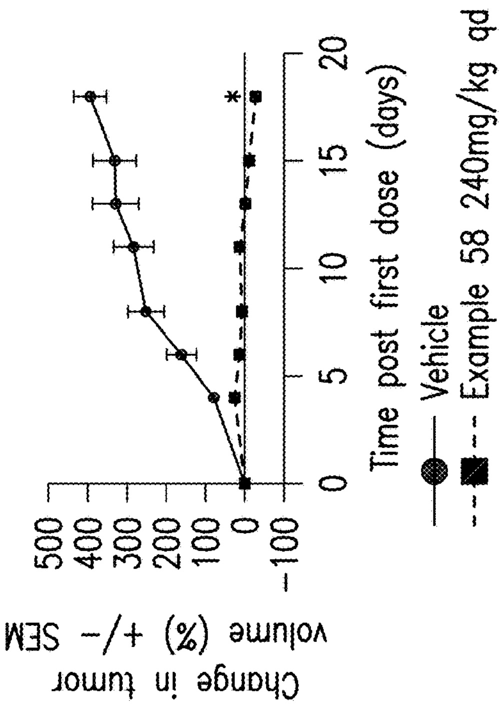
FIG. 6 shows efficacy and tolerability of Example 58 after once daily (qd) administration in female nude mice bearing SW48 xenografts
Figure 6A:
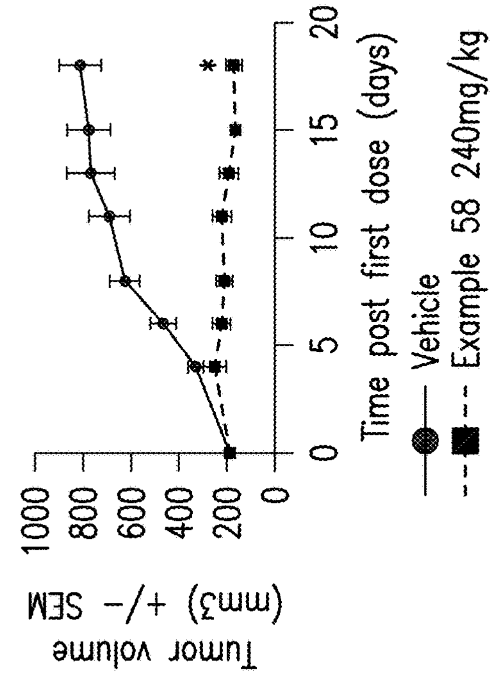
Figure 6C:
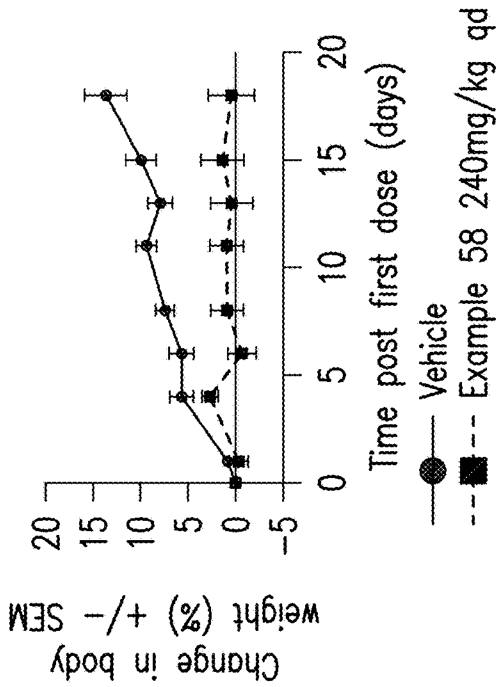
Figure 9:
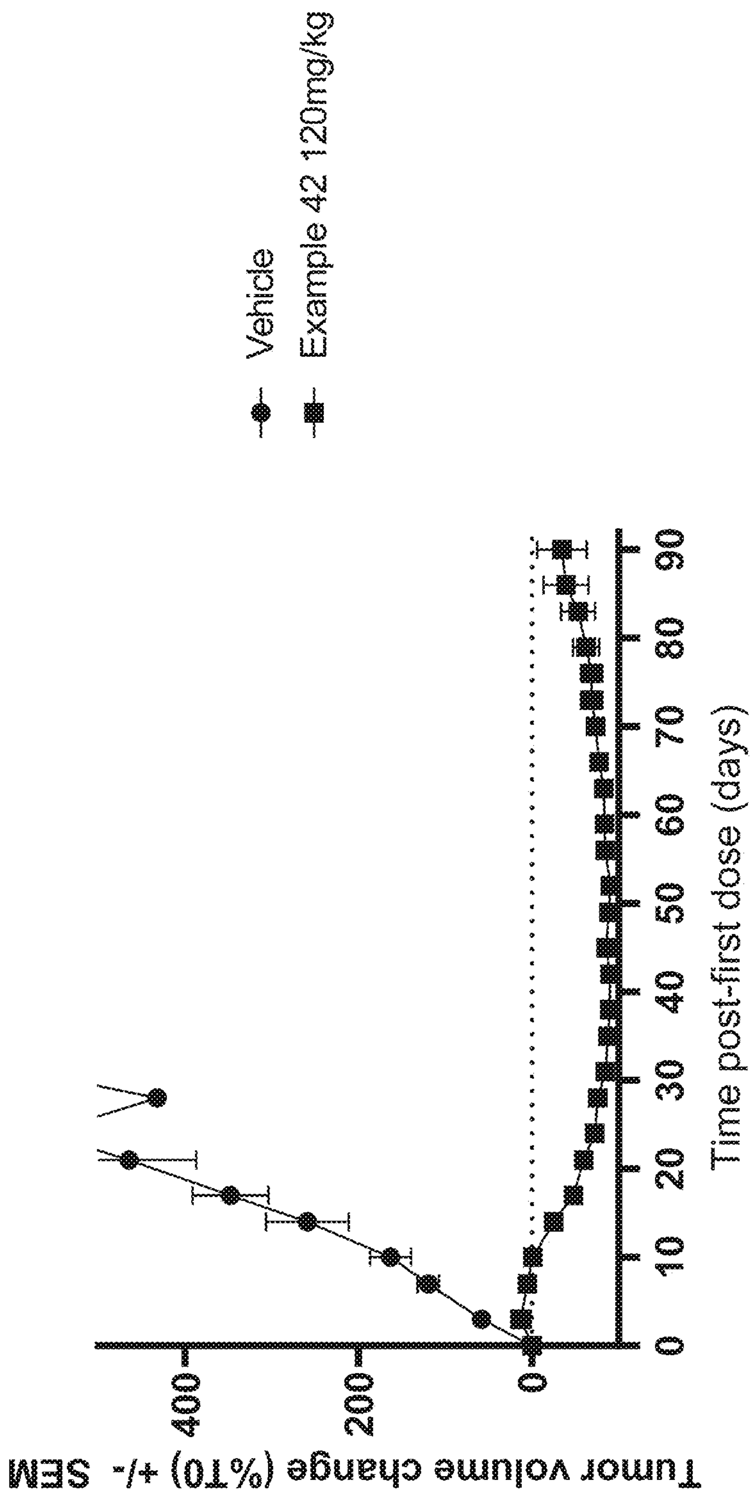
FIG. 9 shows efficacy of Example 42 after administration in female nude mice bearing SW48 xenografts
Figure 10:
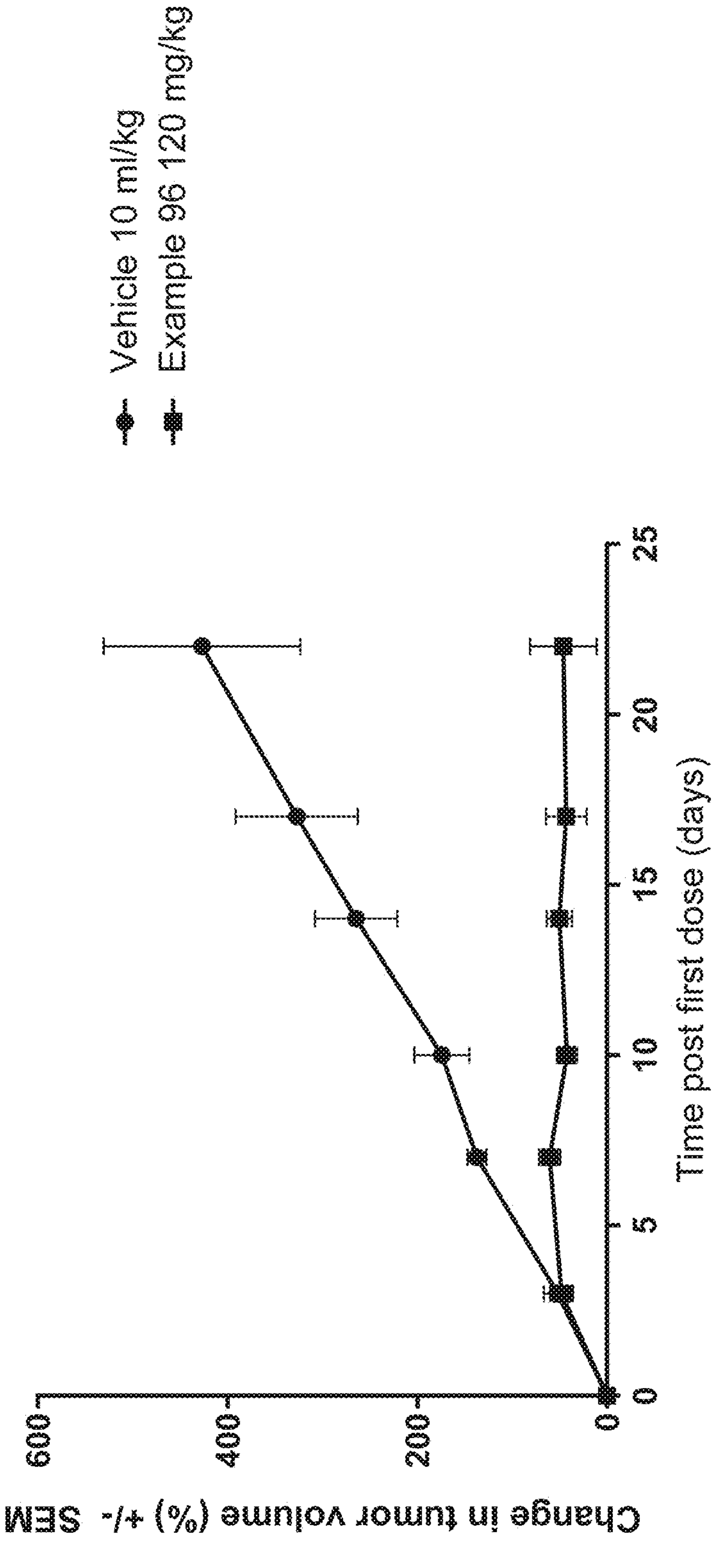
FIG. 10 shows efficacy of Example 96 after administration in female nude mice bearing SW48 xenografts
Figure 11:
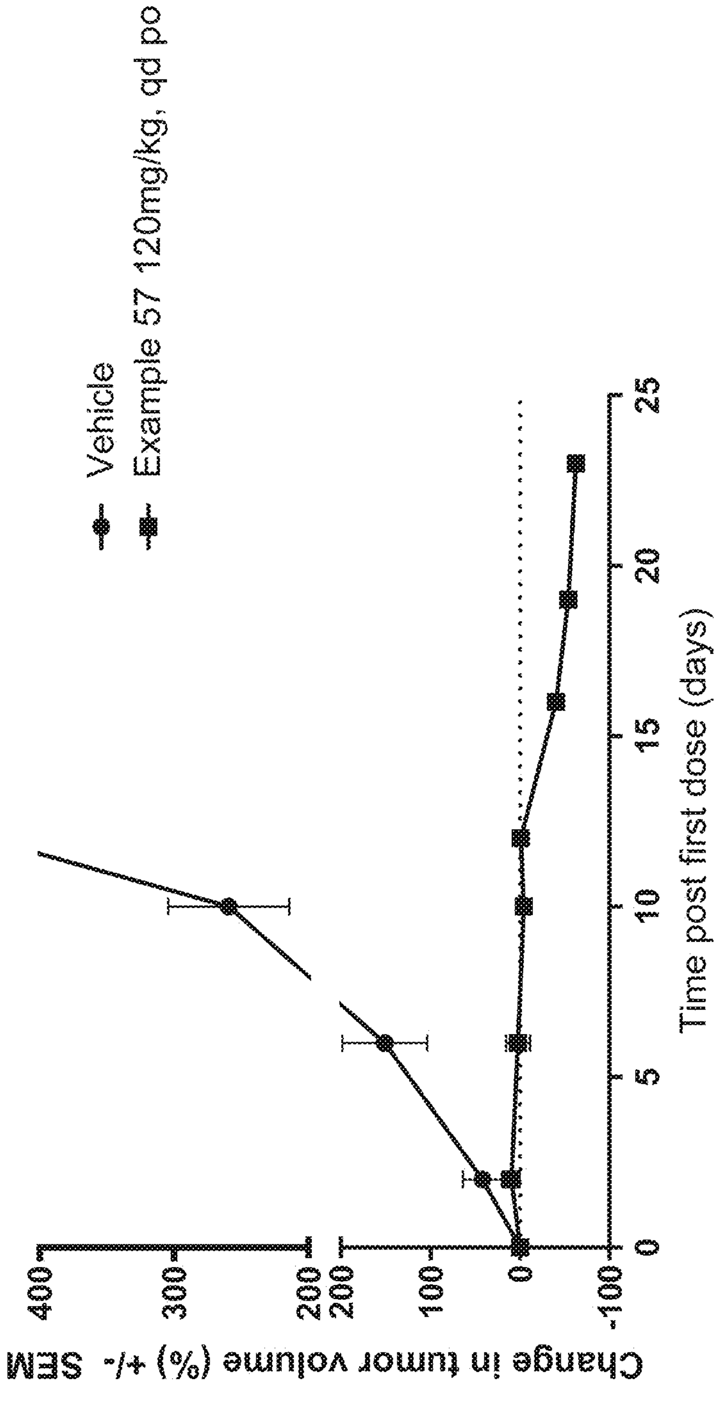
FIG. 11 shows efficacy of Example 57 after administration in female nude mice bearing SW48 xenografts.

Treatment was initiated with, for example, Example 58 in 10% Hydroxypropyl-beta-Cyclodextrine in water at 240 mg/kg using QD oral application when the average tumor volume was 186 $mm^3$ (n=7/group). The treatment period with Example 58 was 18 days after which overall efficacy and tolerability were evaluated based on tumor volume and body weight changes observed during the treatment period (FIG. 6). Example 58 dosed orally at 240 mg/kg qd induced an antitumor response against SW48 xenografts in nude mice (FIG. 6). The T/C % value on day 18 was −9 (p=<0.05 when compared with vehicle control, one way ANOVA with Dunnett's post hoc test). The mean tumor volume on day 18 in the 4/7 surviving animals showed a −26% regression. Based on body weight, QD dosing of 240 mg/kg of Example 58 was well tolerated (FIG. 6). Data for the compounds of Examples 42, 96 and 57 are presented in FIGS. 9, 10 and 11 respectively.

The following table shows the $IC_50$ data in the WRN ATPase assay and the $GI_{50}$ data for the proliferation assays using SW48 and DLD1-WRN-KO cell lines for compounds of the invention. For example, Example 1 is a 50 nM WRN ATPase inhibitor with a proliferation $GI_{50}$ of 50 nM in the SW48 and >10 micromolar in the DLD1 WRN-KO cell lines.

| Ex. | WRN ATPase Activity ($IC_{50}$) μM | Proliferation Assay SW48 ($GI_{50}$) μM | Proliferation Assay DLD1-WRN-KO ($GI_{50}$) μM | Ex. | WRN ATPase Activity ($IC_{50}$) μM | Proliferation Assay SW48 ($GI_{50}$) μM | Proliferation Assay DLD1-WRN-KO ($GI_{50}$) μM |
|---|---|---|---|---|---|---|---|
| 1 | 0.05 | 0.05 | >10 | 61 | 0.05 | 0.05 | >10 |
| 2 | 0.08 | 0.19 | >10 | 62 | 0.05 | 0.05 | >10 |
| 3 | 0.07 | 0.09 | >10 | 63 | 0.11 | 0.05 | >10 |
| 4 | 0.04 | 0.06 | >10 | 64 | 0.09 | 0.48 | >10 |
| 5 | 0.09 | 0.12 | >10 | 65 | 0.05 | 0.08 | 7.8 |
| 6 | 0.07 | 0.27 | >10 | 66 | 0.04 | 0.09 | >10 |
| 7 | 0.09 | 0.21 | >10 | 67 | 0.15 | 0.19 | >10 |
| 8 | 0.08 | 0.21 | >10 | 68 | 0.12 | 0.27 | >10 |
| 9 | 0.06 | 0.35 | >10 | 69 | 0.04 | 0.03 | 6.3 |
| 10 | 0.25 | 0.29 | 9.9 | 70 | 0.10 | 0.22 | >10 |
| 11 | 0.11 | 0.38 | >10 | 71 | 0.07 | 0.06 | >10 |
| 12 | 0.13 | 0.55 | >10 | 72 | 0.05 | 0.05 | >10 |
| 13 | 0.03 | 0.16 | 5.2 | 73 | 0.07 | 0.20 | >10 |
| 14 | 0.14 | 0.48 | >10 | 74 | 0.05 | 0.07 | >10 |
| 14a | 0.08 | 0.37 | >10 | 75 | 0.05 | 0.08 | >10 |
| 14b | 0.09 | 0.26 | >10 | | | | |
| 15 | 0.11 | 0.44 | >10 | 76 | 0.08 | 0.19 | >10 |
| 15a | 0.14 | 0.40 | >10 | 77 | 0.21 | 0.38 | >10 |
| 15b | 0.12 | 0.36 | >10 | 78 | 0.08 | 0.30 | >10 |

-continued

| Ex. | WRN ATPase Activity ($IC_{50}$) μM | Proliferation Assay SW48 ($GI_{50}$) μM | Proliferation Assay DLD1-WRN-KO ($GI_{50}$) μM | Ex. | WRN ATPase Activity ($IC_{50}$) μM | Proliferation Assay SW48 ($GI_{50}$) μM | Proliferation Assay DLD1-WRN-KO ($GI_{50}$) μM |
|---|---|---|---|---|---|---|---|
| 16 | 0.23 | 0.32 | >10 | 79 | 0.04 | 0.50 | >10 |
| 16a | 0.19 | 0.34 | >10 | 80 | 0.06 | 0.07 | >10 |
| 16b | 0.18 | 0.23 | >10 | 80a | 0.07 | 0.07 | >10 |
| 17 | 0.14 | 0.24 | >10 | 80b | 0.08 | 0.06 | >10 |
| 18 | 0.18 | 0.26 | >10 | 81a | 0.04 | 0.07 | >10 |
| 19 | 0.09 | 0.11 | 5 | 81b | 0.04 | 0.06 | >10 |
| 20 | 0.31 | 0.10 | >10 | 82 | 0.28 | 7.72 | >10 |
| 21 | 0.18 | 1.07 | >10 | 83 | 0.09 | 0.06 | >10 |
| 22 | 0.60 | 2.63 | >10 | 84 | 0.05 | 0.13 | >10 |
| 23 | 0.26 | 1.54 | >10 | 85 | 0.07 | 0.11 | >10 |
| 24a | 0.11 | 0.04 | >10 | 86 | 0.09 | 0.08 | >10 |
| 24b | 0.10 | 0.05 | >10 | 87 | 0.11 | 0.06 | >10 |
| 25a | 0.16 | 0.05 | >10 | 88 | 0.37 | 0.76 | >10 |
| 25b | 0.10 | 0.05 | >10 | 89 | 0.04 | 0.17 | >10 |
| 26 | 0.25 | 0.08 | >10 | 90 | 0.13 | 0.30 | >10 |
| 27 | 0.13 | 0.27 | >10 | 91 | 0.08 | 0.32 | >10 |
| 28 | 0.13 | 0.10 | >10 | 92 | 0.05 | 0.08 | >10 |
| 29 | 0.09 | 0.05 | >10 | 93 | 0.08 | 0.07 | >10 |
| 30 | 0.14 | 0.16 | >10 | 94 | 0.04 | 0.05 | >10 |
| 31 | 0.23 | 0.32 | >10 | 95 | 0.05 | 0.06 | >10 |
| 32 | 0.06 | 0.06 | 7.6 | 96 | 0.06 | 0.06 | >10 |
| 33 | 0.26 | 0.22 | >10 | 97 | 0.08 | 0.07 | >10 |
| 34 | 0.25 | 0.28 | >10 | 98 | 0.04 | 0.14 | >10 |
| 35 | 0.19 | 0.40 | >10 | 99 | 0.18 | 0.28 | >10 |
| 36 | 0.93 | 1.78 | >10 | 100 | 0.06 | 0.03 | >10 |
| 37 | 0.02 | 0.03 | >10 | 101 | 0.10 | 0.21 | >10 |
| 38 | 0.04 | 0.05 | >10 | 102 | 0.09 | 0.17 | >10 |
| 39 | 0.04 | 0.05 | >10 | 103 | 0.10 | 0.25 | >10 |
| 40 | 0.02 | 0.03 | >10 | 104 | 0.07 | 0.05 | >10 |
| 41 | 0.04 | 0.04 | >10 | 105 | 0.20 | 1.13 | >10 |
| 42 | 0.10 | 0.05 | >10 | 106 | 0.06 | 0.11 | >10 |
| 43 | 0.07 | 0.05 | >10 | 107 | 0.05 | 0.10 | >10 |
| 44 | 0.11 | 0.08 | >10 | 108 | 0.08 | 0.09 | >10 |
| 45 | 0.13 | 0.08 | >10 | 109 | 1.18 | 0.69 | >10 |
| 46 | 0.11 | 0.11 | >10 | 110 | 0.36 | 1.21 | >10 |
| 47 | 0.14 | 0.17 | >10 | 111 | 0.33 | 1.12 | >10 |
| 48 | 0.07 | 0.08 | >10 | 112 | 0.51 | 7.94 | >10 |
| 49 | 0.12 | 0.12 | >10 | 113 | 0.04 | 0.12 | >10 |
| 50 | 0.03 | 0.05 | >10 | 114 | 0.09 | 0.18 | >10 |
| 51 | 0.04 | 0.03 | >10 | 115 | 0.17 | 0.20 | >10 |
| 52 | 0.04 | 0.04 | >10 | 116 | 0.06 | 0.08 | 6.6 |
| 53 | 0.12 | 0.14 | >10 | 117 | 0.04 | 0.26 | >10 |
| 54 | 1.30 | 6.01 | >10 | 118 | 0.09 | 0.45 | >10 |
| 55 | 0.20 | 0.10 | >10 | 119 | 0.16 | 0.05 | >10 |
| 56 | 0.16 | 0.25 | >10 | 120 | 0.47 | 0.93 | >10 |
| 57 | 0.10 | 0.10 | >10 | 121 | 0.86 | 1.74 | >10 |
| 58 | 0.06 | 0.07 | >10 | 122 | 0.15 | 0.10 | >10 |
| 59 | 0.80 | | | 123 | 0.10 | 0.05 | >10 |
| 60 | 0.24 | 0.88 | >10 | 124 | 0.36 | 0.39 | >10 |
| 126 | 0.13 | | | 125 | 0.03 | 0.01 | >10 |
| 127 | 0.08 | 0.09 | >10 | 134 | 0.06 | 0.21 | >10 |
| 128 | 0.08 | 0.69 | >10 | 135 | 0.13 | 0.28 | >10 |
| 129 | 0.50 | 2.55 | >10 | 136 | 0.08 | 0.65 | >10 |
| 130 | 0.10 | 0.05 | >10 | 137 | 0.05 | 0.24 | 6.1 |
| 131 | 0.11 | 0.03 | >10 | | | | |
| 132 | 0.89 | 0.49 | >10 | | | | |
| 133 | 0.12 | 0.06 | >10 | | | | |

Data are geometric means with at least 2 duplicate determinations.

In another aspect, the invention provides a compound of formula (I), for use in the treatment of cancer, or as a research chemical such as a chemical probe, wherein part of the WRN inhibition activity is via a mechanism which is not assessed by the biochemical assay described above.

Method for Detecting Clonogenic Effects on Cellular Proliferation (CFA=Colony Formation Assay)

Figure 8:
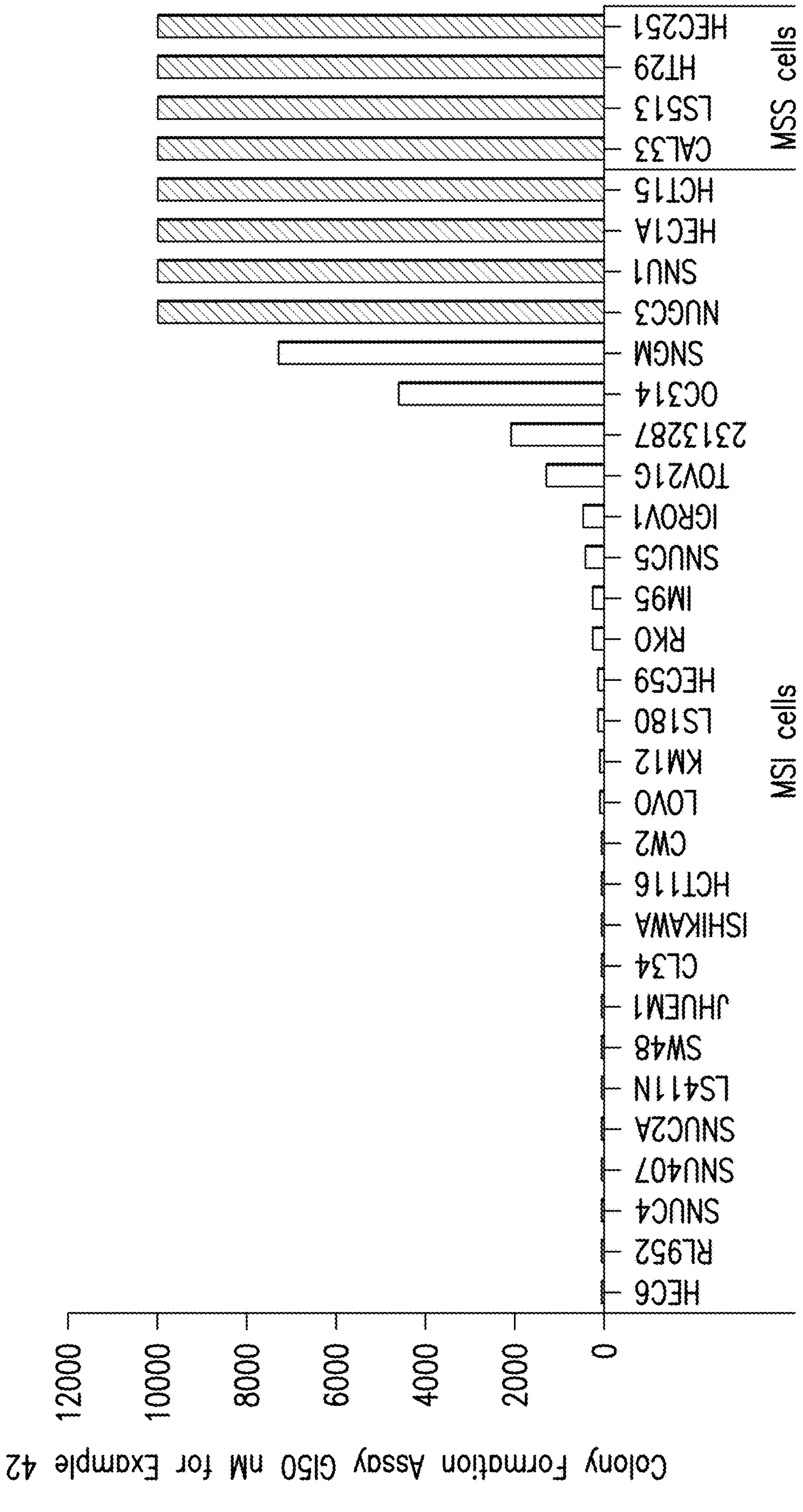
FIG. 8 shows the colony formation assay data for the compound of example 42, using MSI and MSS cells.

Cell lines were obtained from ATCC and media and culture conditions used as recommended by ATCC. All cells were maintained at 37° C. in a humidified 5% $CO_2$ incubator. Cells were seeded at 250-2,000 cells per well in a 12-well plate in 1 ml of media. The WRN inhibitor compound of example 42 was added with a starting concentration of 10 uM. Following overnight incubation at 37° C. in a humidified 5% $CO_2$ atmosphere, ten 3-fold serial dilutions of a given compound stock (obtained at a concentration of 10 mM in DMSO and stored at 4° C.) were dispensed directly into each assay plates using a HP 300D non-contact Digital Dispenser (TECAN). The final concentration of DMSO was normalized to 0.1% in all wells. Cells were left in the incubator for 8-20 days, with medium exchange every 3-4 days. After this time, 100 µl formaldehyde 37% was added directly in each test well and incubated for 15 minutes at room temperature. After rinsing twice with 5 ml of water, 0.5 ml of 0.05% methylene blue was added for 20 minutes at room temperature. Wells were rinsed three times with water and 1 ml of 3% HCl added to the plates and shaken until complete color dissolution. 200 µl of this solution was transferred in a 96 well plate and absorbance measured at 650 nM using microtiter plate reader (Synergy HT). Compound concentrations leading to half-maximal growth inhibition (G150) were calculated using XLfit using the Dose Response One Site model 201, with fit=(A+((B−A)/(1+((x/C)^D)))). For non-adherent cell lines, cellular ATP levels as a surrogate for cell viability were assessed following addition of 200 µl of CellTiterGlo (Promega Cat #G7573) reagent to the culture after removal of 600 µl. Luminescence quantification was performed on a Synergy HT plate-reader following a 15 min incubation at room temperature. Data were analyzed as for the methylene blue stain. Results are shown in FIG. 8. Further information regarding MSI-H and MSS is available in the following references:

Chan et Al., WRN helicase is a synthetic lethal target in microsatellite unstable cancers. *Nature.* 2019 April; 568 (7753):551-556. doi: 10.1038/s41586-019-1102-x. Epub 2019 Apr. 10. PMID: 30971823; PMCID: PMC6580861.

McDonald E. R. et al., Project DRIVE: A Compendium of Cancer Dependencies and Synthetic Lethal Relationships Uncovered by Large-Scale, Deep RNAi Screening. Cell 170(3):577-592 (2017)).

Preparation of Compounds

Compounds of the present invention can be prepared as described in the following Examples. The Examples are intended to illustrate the invention and are not to be construed as being limitations thereof.

Instrumentation

Microwave: All microwave reactions were conducted in a Biotage Initiator or an Anton Paar monowave 450, irradiating at 0-400 W from a magnetron at 2.45 GHz with Robot Eight/Robot Sixty/Robot twentyfour processing capacity, unless otherwise stated.

UPLC-MS Methods: Using Waters Acquity UPLC with Waters SQ detector, unless stated otherwise.

UPLC-MS 1:

| | |
|---|---|
| Column | CORTECS ™ C18+ 2.7 µm, |
| Column Dimension | 2.1 × 50 mm |
| Column Temperature | 80° C. |
| Eluents | A: water + 4.76% isopropanol + 0.05% FA + 3.75 mM AA<br>B: isopropanol + 0.05% FA |
| Flow Rate | 1.0 mL/min |
| Gradient | 1 to 50% B in 1.4 min; 50 to 98% B in 0.3 min |

UPLC-MS 2:

| | |
|---|---|
| Column | ACQUITY UPLC ® BEH C18 1.7 µm |
| Column Dimension | 2.1 × 100 mm |
| Column Temperature | 80° C. |
| Eluents | A: water + 4.76% isopropanol + 0.05% FA + 3.75 mM AA<br>B: isopropanol + 0.05% FA |
| Flow Rate | 0.4 mL/min |
| Gradient | 1 to 60% B in 8.4 min; 60 to 98% B in 1.0 min |

UPLC-MS 3:

| | |
|---|---|
| Column | ACQUITY UPLC ® BEH C18 1.7 µm |
| Column Dimension | 2.1 × 50 mm |
| Column Temperature | 80° C. |
| Eluents | A: water + 4.76% isopropanol + 0.05% FA + 3.75 mM AA<br>B: isopropanol + 0.05% FA |
| Flow Rate | 0.6 mL/min |
| Gradient | 1 to 98% B in 1.7 min |

UPLC-MS 4:

| | |
|---|---|
| Column | ACQUITY UPLC ® BEH C18 1.7 µm |
| Column Dimension | 2.1 × 50 mm |
| Column Temperature | 80° C. |
| Eluents | A: water + 0.05% FA + 3.75 mM AA<br>B: isopropanol + 0.05% FA |
| Flow Rate | 0.6/0.7 mL/min |
| Gradient | 5 to 98% B in 1.7 min |

UPLC-MS 5:

| | |
|---|---|
| Column | XBridge ® BEH ™ C18 2.5 µm |
| Column Dimension | 2.1 × 50 mm |
| Column Temperature | 80° C. |
| Eluents | A: water + 5 mM $NH_4OH$<br>B: acetonitrile + 5 mM $NH_4OH$ |
| Flow Rate | 1.0 mL/min |
| Gradient | 2 to 98% B in 1.4 min |

UPLC-MS 6:

| | |
|---|---|
| Column | Ascentis ® Express C18 2.7 µm |
| Column Dimension | 2.1 × 50 mm |
| Column Temperature | 80° C. |
| Eluents | A: water + 4.76% isopropanol + 0.05% FA + 3.75 mM AA<br>B: isopropanol + 0.05% FA |
| Flow Rate | 1.0 mL/min |
| Gradient | 1 to 50% B in 1.4 min; 50-98% B in 0.3 min |

UPLC-MS 7:

| | |
|---|---|
| Column | Acquity UPLC ® HSS T3 1.8 µm |
| Column Dimension | 2.1 × 50 mm |
| Column Temperature | 60° C. |
| Eluents | A: water + 0.05% formic acid + 3.75 mM ammonium acetate<br>B: acetonitrile + 0.04% FA |
| Flow Rate | 1.0 mL/min |
| Gradient | 2 to 98% B in 1.4 min |

UPLC-MS 8:

| | |
|---|---|
| Column | Acquity UPLC ® HSS T3 1.8 µm |
| Column Dimension | 2.1 × 50 mm |
| Column Temperature | 60° C. |
| Eluents | A: water + 0.05% formic acid + 3.75 mM ammonium acetate<br>B: acetonitrile + 0.04% FA |
| Flow Rate | 1.0 mL/min |
| Gradient | 5 to 98% B in 1.4 min |

UPLC-MS 9:

| | |
|---|---|
| Column | XBridge ® BEH ™ C18 2.5 μm |
| Column Dimension | 2.1 × 50 mm |
| Column Temperature | 80° C. |
| Eluents | A: water + 5 mM $NH_4OH$<br>B: acetonitrile + 5 mM $NH_4OH$ |
| Flow Rate | 1.0 mL/min |
| Gradient | 2 to 98% B in 9.4 min |

UPLC-MS 10:

| | |
|---|---|
| Column | CORTECS ™ C18+ 2.7 μm, |
| Column Dimension | 2.1 × 50 mm |
| Column Temperature | 80° C. |
| Eluents | A: water + 0.05% FA + 3.75 mM AA<br>B: isopropanol + 0.05% FA |
| Flow Rate | 1.0 mL/min |
| Gradient | concave from 1 to 98% B in 1.4 min |

UPLC-MS 11:

| | |
|---|---|
| Instrument | Shimadzu NEXERA UPLC PDA with Shimadzu LCMS 2020 as MSD |
| Column | Mercury MS Synergi C12 2.5 μm |
| Column Dimension | 20 × 4.0 mm |
| Column Temperature | 40° C. |
| Eluents | A: water + 0.1% FA<br>B: acetonitrile |
| Flow Rate | 2.0 mL/min |
| Gradient | Time/% B: 0.01/5, 0.5/5, 1.0/95, 1.5/95, 2.0/5, 3.0/5 |

UPLC-MS 12:

| | |
|---|---|
| Instrument | Agilent 1200 HPLC PDA with AB Sciex API2000 TQ as MSD |
| Column | Mercury MS Synergi C12 2.5 μm |
| Column Dimension | 20 × 4.0 mm |
| Column Temperature | 30° C. |
| Eluents | A: water + 0.1% FA<br>B: acetonitrile |
| Flow Rate | 2.0 mL/min |
| Gradient | Time/% B: 0.01/30, 0.5/30, 1.0/95, 2.4/95, 2.5/30, 3.0/30 |

UPLC-MS 13:

| | |
|---|---|
| Instrument | Agilent 1200 HPLC PDA with AB Sciex API3200 QTRAP as MSD |
| Column | Kinetex EVO C18 2.6 μm |
| Column Dimension | 50 × 4.6 mm |
| Column Temperature | 30° C. |
| Eluents | A: water + 0.1% FA<br>B: acetonitrile + 0.1% FA |
| Flow Rate | 1.5 mL/min |
| Gradient | Time/B: 0/20, 0.2/50, 1/95, 2.7/95, 2.8/20, 4/20 |

UPLC-MS 14:

| | |
|---|---|
| Column | Acquity UPLC ® HSS T3 1.8 μm |
| Column Dimension | 2.1 × 100 mm |
| Column Temperature | 60° C. |
| Eluents | A: water + 0.05% formic acid + 3.75 mM ammonium acetate<br>B: acetonitrile + 0.04% FA |

-continued

| | |
|---|---|
| Flow Rate | 1.0 mL/min |
| Gradient | 5 to 98% B in 9.4 min |

HPLC Methods:

HPLC 1:

| | |
|---|---|
| Instrument | Agilent 1100 series with PDA Detector |
| Column | Kinetex C-18, 5 μm |
| Column Dimension | 150 × 4.6 mm |
| Column Temperature | 40° C. |
| Eluents | A: water + 0.01% TFA<br>B: acetonitrile |
| Flow Rate | 1.0 mL/min |
| Gradient | Time/B: 0/30, 2/40, 5/90, 8/100, 10/100, 11/30, 12/30 |

HPLC 2:

| | |
|---|---|
| Instrument | Acquity Arc Waters UHPLC With PDA Dectector(2998 PDA) |
| Column | Kinetex EO, 2.6 μm |
| Column Dimension | 100 × 4.6 mm |
| Column Temperature | 40° C. |
| Eluents | A: water + 0.01% TFA<br>B: acetonitrile |
| Flow Rate | 1.0 mL/min |
| Gradient | Time/B: 0/5, 2/5, 6/70, 10/100, 13/100, 13.5/5, 15/5 |

HPLC 3:

| | |
|---|---|
| Instrument | Agilent 1260 HPLC |
| Column | Agilent Poroshell 120 C18, 2.7 μm |
| Column Dimension | 4.6 × 50 mm |
| Column Temperature | 40° C. |
| Eluents | A: water + 0.01% TFA<br>B: acetonitrile + 0.01% TFA |
| Flow Rate | 1.2 mL/min |
| Gradient | 0% B to 50% B in 5 min, hold 2 min |

HPLC 4:

| | |
|---|---|
| Instrument | Agilent 1260 |
| Column | Agilent Poroshell 120 EC-C18, 2.7 μm |
| Column Dimension | 4.6 × 50 mm |
| Column Temperature | 40° C. |
| Eluents | A: water + 0.1% TFA<br>B: acetonitrile + 0.1% TFA |
| Flow Rate | 1.2 mL/min |
| Gradient | 5% B to 95% B in 5 min, hold 2 min |

HPLC 5:

| | |
|---|---|
| Instrument | Agilent 1260 HPLC |
| Column | InertSustain C18, 5 μm |
| Column Dimension | 4.6 × 150 mm |
| Column Temperature | 30° C. |
| Eluents | A: water + 5 mmol $(NH_4)_2CO_3$<br>B: acetonitrile |
| Flow Rate | 1.0 mL/min |
| Gradient | 10% B to 90% B in 8 min, hold 2 min |

HPLC 6:

| | |
|---|---|
| Instrument | Agilent 1260 infinity series HPLC system with DAD/ELSD |
| Column | Atlantis dC18, 5 μm |
| Column Dimension | 4.6 × 250 mm |
| Column Temperature | 25° C. |
| Eluents | A: water + 0.1% TFA<br>B: acetonitrile |
| Flow Rate | 1.0 mL/min |
| Gradient | 10% B to 100% B in 15 min, hold 5 min |

Chiral HPLC Methods:

C-HPLC 1:

| | |
|---|---|
| Instrument: | Agilent 1260 Infinity II series with PDA Detector |
| Injection: | 3 μL |
| Mobile phase: | A: hexane B: 0.1% HCOOH in EtOH |
| Flow rate: | 20 mL/min |
| Column: | CELLULOSE 4 (150 × 4.6 mm, 5 μm) |
| Detection UV: | 210 nm |
| Gradient: | Isocratic: 50:50 |

C-HPLC 2:

| | |
|---|---|
| Instrument: | Agilent 1260 Infinity II series with PDA Detector |
| Injection: | 10 μL |
| Mobile phase: | A: hexane B: 0.1% HCOOH in EtOH |
| Flow rate: | 15 mL/min |
| Column: | CELLULOSE 4 (150 × 4.6 mm, 5 μm) |
| Detection UV: | 210 nm |
| Gradient: | Isocratic: 50:50 |

C-HPLC 3:

| | |
|---|---|
| Instrument: | Agilent 1260 Infinity II series with PDA Detector |
| Injection volume: | 8 μL |
| Mobile phase: | A: hexane B: 0.1% HCOOH in EtOH |
| Flow rate: | 1 mL/min |
| Column: | CELLULOSE 4 (150 × 4.6 mm, 5 μm) |
| Detection UV: | 210, or 254 nm |
| Gradient: | Isocratic: 50:50 |

C-HPLC 4:

| | |
|---|---|
| Instrument: | Agilent 1260 Infinity II series with PDA Detector |
| Injection volume: | 3 μL |
| Mobile phase: | A: hexane B: 0.1% HCOOH in EtOH |
| Flow rate: | 1 mL/min |
| Column: | CELLULOSE 4 (150 × 4.6 mm, 5 μm) |
| Detection UV: | 210, or 254 nm |
| Gradient: | Isocratic: 50:50 |

C-HPLC 5:

| | |
|---|---|
| Instrument: | Agilent 1260 Infinity II series with PDA Detector |
| Injection volume: | 2 μL |
| Mobile phase: | A: hexane B: 0.1% TFA in EtOH |
| Flow rate: | 1 mL/min |
| Column: | CELLULOSE 4 (150 × 4.6 mm, 5 μm) |
| Detection UV: | 210, or 254 nm |
| Gradient: | Isocratic: 50:50 |

C-HPLC 6:

| | |
|---|---|
| Instrument: | Agilent 1260 Infinity II series with PDA Detector |
| Injection volume: | 3 μL |
| Mobile phase: | A: hexane B: 0.1% TFA in EtOH |
| Flow rate: | 1 mL/min |
| Column: | CELLULOSE 4 (150 × 4.6 mm, 5 μm) |
| Detection UV: | 210, or 254 nm |
| Gradient: | Isocratic: 50:50 |

C-HPLC 7:

| | |
|---|---|
| Instrument: | Waters $UPC^2$ MS |
| Injection volume: | 5 μL |
| Mobile phase: | A: 25% (MeOH + 0.1% $NH_3$);<br>B: 75% $scCO_2$ isocractic |
| Flow rate: | 3 mL/min |
| Column: | Chiralpak IB-N 5 μm, 100 × 4.6 mm |
| Detection UV: | 190-400 nm |
| Oven Temperature: | 40° C. |

C-HPLC 8:

| | |
|---|---|
| Instrument: | Waters $UPC^2$ MS |
| Injection volume: | 5 μL |
| Mobile phase: | A: 35% (MeOH + 0.1% $NH_3$);<br>B: 65% $scCO_2$ isocratic |
| Flow rate: | 3 mL/min |
| Column: | Chiralpak IB-N 5 μm, 100 × 4.6 mm |
| Detection: | 190-400 nm |
| Oven Temperature: | 40° C. |

C-HPLC 9:

| | |
|---|---|
| Instrument: | Waters $UPC^2$ |
| Injection volume: | 1 μL |
| Mobile phase: | A: $CO_2$; B: MeOH + 0.05% DEA |
| Flow rate: | 2.4 mL/min |
| Column: | ChiralPak IC, 3 μm, 100 × 4.6 mm |
| Detection: | 220 nm |
| Column Temperature: | 35° C. |
| Back pressure: | 100 bar |

C-HPLC 10:

| | |
|---|---|
| Instrument: | Waters $UPC^2$-MS |
| Injection volume: | 5 μL |
| Mobile phase: | isocratic A = 35% (IPA + 0.1% $NH_3$)<br>B = 65% $scCO_2$ |
| Flow rate: | 3 mL/min |
| Column: | ChiralPak IB, 5 μm, 100 × 4.6 mm |
| Detection: | DAD 210-400 nm |
| Back pressure: | 1800 psi |

C-HPLC 11:

| | |
|---|---|
| Instrument: | Waters Acquity UPC |
| Injection volume: | 5 μL |
| Mobile phase: | A: 35% (MeOH + 0.05% $NH_3$);<br>B: 65% $scCO_2$ |
| Flow rate: | 3 mL/min |
| Column: | Chiralpak IB-N 5 μm, 100 × 4.6 mm |
| Detection UV: | 240 nm |
| Oven Temperature: | 40° C. |

C-HPLC 12:

| | |
|---|---|
| Instrument: | Waters Acquity UPC |
| Injection volume: | 5 μL |
| Mobile phase: | A: 35% (MeOH + 0.05% $NH_3$); B: 65% $scCO_2$ |
| Flow rate: | 3 mL/min |
| Column: | Chiralpak IB-N 5 μm, 100 × 4.6 mm |
| Detection UV: | 240 nm |
| Oven Temperature: | 40° C. |

C-HPLC 13:

| | |
|---|---|
| Instrument: | Waters $UPC^2$-MS |
| Injection volume: | 5 μL |
| Mobile phase: | isocratic A = 25% (MeOH + 0.05% $NH_3$) B = 75% $scCO_2$ |
| Flow rate: | 3 mL/min |
| Column: | ChiralPak IB, 5 μm, 100 × 4.6 mm |
| Detection: | DAD 210-400 nm |
| Back pressure: | 1800 psi |

Preparative Methods:

Column Chromatography:

Column chromatography was run on silica gel using prepacked columns, as detailed below, or using glass columns following standard flash chromatography methodology, unless otherwise stated.

| | |
|---|---|
| System 1 | Teledyne ISCO, CombiFlash Rf, CombiFlash Rf+ |
| System 2 | Biotage Isolera |
| Column | pre-packed RediSep Rf cartridges, or SNAP cartridges |
| Sample adsorption | onto Isolute, or on silica gel, or applied as solutions |

Supercritical Fluid Chromatography (SFC)

Purifications were achieved on a Waters Preparative SFC-100-MS system with ABSYS update, with a Waters 2998 Photodiode Array Detector and a Waters MS Single Quadrupole Detector.

SFC 1:

| | |
|---|---|
| Instrument: | WATERS SFC 100 with ABSYS update |
| Mobile phase: | A: $CO_2$, B: MeOH |
| Flow rate: | 150 mL/min MeOH + 30 mL/min $CO_2$, constant flow of 180 mL/min |
| Column: | 250 × 30 Reprospher PEI 100A 5 um |
| Temperature: | 50° C. |
| Back pressure: | 100 bar |
| Detection UV: | 210-400 nm |
| Gradient: | 18% B to 26% B in 6.86 min |

SFC 2:

| | |
|---|---|
| Instrument: | WATERS SFC 100 with ABSYS update |
| Mobile phase: | A: $CO_2$, B: MeOH |
| Flow rate: | 150 mL/min MeOH + 30 mL/min $CO_2$, constant flow of 180 mL/min |
| Column: | 100 × 30 Reprosil $NH_2$ 100A 3 μm |
| Temperature: | 50° C. |
| Back pressure: | 100 bar |
| Detection UV: | 210-400 nm |
| Gradient: | 34% B to 42% B in 2.8 min |

SFC 3:

| | |
|---|---|
| Instrument: | WATERS SFC 100 with ABSYS update |
| Mobile phase: | A: $CO_2$, B: MeOH |
| Flow rate: | 150 mL/min MeOH + 30 mL/min $CO_2$, constant flow of 180 mL/min |
| Column: | 100 × 30 Reprosil $NH_2$ 100A 3μpm |
| Temperature: | 50° C. |
| Back pressure: | 100 bar |
| Detection UV: | 210-400 nm |
| Gradient: | 21% B to 29% B in 2.8 min first run 25% B to 33% B in 2.8 min second run to improve the detection |

SFC 4:

| | |
|---|---|
| Instrument: | WATERS SFC 100 |
| Mobile phase: | A. CO2, B: MeOH |
| Flow rate: | 100 mL/min |
| Column: | 250 × 30 Reprospher PEI 100A 5 μm |
| Temperature: | 32° C. |
| Back pressure: | 120 bar |
| Detection UV: | 210-400 nm |
| Gradient: | 40% B to 55% B in 10.2 min |

SFC 5:

| | |
|---|---|
| Instrument: | WATERS SFC 100 |
| Mobile phase: | A: $CO_2$, B: MeOH |
| Flow rate: | 100 mL/min MeOH |
| Column: | 250 × 30 Reprospher PEI 100A 5 μm |
| Temperature: | 32° C. |
| Back pressure: | 120 bar |
| Detection UV: | 210-400 nm |
| Gradient: | 35% B to 45% B in 10.3 min |

SFC 6:

| | |
|---|---|
| Instrument: | WATERS SFC 100 with ABSYS update |
| Mobile phase: | A: $CO_2$, B: MeOH |
| Flow rate: | 150 mL/min MeOH + 30 mL/min $CO_2$, constant flow of 180 mL/min |
| Column: | 100 × 30 Reprosil $NH_2$ 100A 3 μm |
| Temperature: | 50° C. |
| Back pressure: | 100 bar |
| Detection UV: | 210-400 nm |
| Gradient: | 31% B to 39% B in 2.8 min |

SFC 6:

| | |
|---|---|
| Instrument: | WATERS SFC 100 with ABSYS update |
| Mobile phase: | A: $CO_2$, B: MeOH |
| Flow rate: | 150 mL/min MeOH + 30 mL/min $CO_2$, constant flow of 180 mL/min |
| Column: | 250 × 30 waters Torus 2-PIC 130A 5 μm |
| Temperature: | 50° C. |
| Back pressure: | 100 bar |
| Detection UV: | 210-400 nm |
| Gradient: | 26% B to 34% B in 5.48 min |

Reversed Phase HPLC:

RP-HPLC Basic 1:

| | |
|---|---|
| System | Gilson |
| Column | Waters X-Bridge Prep C18 OBD (100 mm × 30 mm), 5 μm |
| Eluents | A: water + 7.3 mM $NH_4OH$, B: acetonitrile |
| Flow rate | 40 mL/min |

RP-HPLC Basic 2:

| | |
|---|---|
| System | Agilent 1200 series, with single quad mass spectrometer |
| Column | XBRIDGE(150 mm × 20 mm), 5.0 μm |
| Eluents | A: 0.02% ammonia in water, B: acetonitrile |
| Flow rate | 20 mL/min |

RP-HPLC Acidic 1:

| | |
|---|---|
| System | Gilson |
| Column | Waters SunFire Prep C18 OBD (100 mm × 30 mm), 5 μm |
| Eluents | A: water + 0.1% TFA, B: acetonitrile |
| Flow rate | 40 mL/min |

RP-HPLC Acidic 2:

| | |
|---|---|
| System | Agilent 1200 series, with single quad mass spectrometer |
| Column | LUNA C18 (250 mm × 19 mm), 4.0 μm |
| Eluents | A: 0.1% HCOOH in water, B: acetonitrile |
| Flow rate | 20 mL/min |

RP-HPLC Acidic 3:

| | |
|---|---|
| System | Agilent 1200 series, with single quad mass spectrometer |
| Column | LUNA (250 mm × 21.2 mm), 5.0 μm |
| Eluents | A: 0.1% HCOOH in water, B: acetonitrile |
| Flow rate | 18 mL/ min |

RP-HPLC Acidic 4:

| | |
|---|---|
| System | Agilent 1200 series, with single quad mass spectrometer |
| Column | LUNA (250 mm × 21.2 mm), 5.0 μm |
| Eluents | A: 0.1% HCOOH in water, B: acetonitrile |
| Flow rate | 20 mL/min |

RP-HPLC Acidic 5:

| | |
|---|---|
| System | Agilent 1200 series, with single quad mass spectrometer |
| Column | LUNA Phenomenex (250 mm × 21.2 mm), 5.0 μm |
| Eluents | A: 0.1% HCOOH in water, B: acetonitrile |
| Flow rate | 18 mL/min |

RP-HPLC Acidic 6:

| | |
|---|---|
| System | Agilent 1200 series, with single quad mass spectrometer |
| Column | Atlantis (250 mm × 19 mm), 5.0 μm |
| Eluents | A: 0.1% HCOOH in water, B: acetonitrile:MeOH |
| Flow rate | 18 mL/min |

RP-HPLC Acidic 7:

| | |
|---|---|
| System | Agilent 1200 series, with single quad mass spectrometer |
| Column | LUNA C18 (250 mm × 21.2 mm), 5.0 μm |
| Eluents | A: 0.1% HCOOH in water, B: acetonitrile |
| Flow rate | 20 mL/min |

RP-HPLC Acidic 8:

-continued

| | |
|---|---|
| System | Agilent 1200 series, with single quad mass spectrometer |
| Column | Atlantis (250 mm × 19 mm), 5.0 μm |
| Eluents | A: 0.1% HCOOH in water, B: acetonitrile |
| Flow rate | 18 mL/min |

RP-HPLC Acidic 9:

| | |
|---|---|
| System | Agilent 1200 series, with single quad mass spectrometer |
| Column | Atlantis (250 mm × 21.2 mm), 5.0 μm |
| Eluents | A: 0.1% HCOOH in water, B: acetonitrile |
| Flow rate | 20 mL/min |

RP-HPLC Acidic 10:

| | |
|---|---|
| System | Agilent 1200 series, with single quad mass spectrometer |
| Column | Atlantis (250 mm × 21.2 mm), 5.0 μm |
| Eluents | A: 0.1% HCOOH in water, B: acetonitrile |
| Flow rate | 18 mL/min |

RP-HPLC Acidic 11:

| | |
|---|---|
| System | Agilent 1200 series, with single quad mass spectrometer |
| Column | LUNA OMEGA (250 mm × 21.2 mm), 5.0 μm |
| Eluents | A: 0.1% HCOOH in water, B: acetonitrile:MeOH (1:1) |
| Flow rate | 20 mL/min |

RP-HPLC Acidic 12:

| | |
|---|---|
| System | Agilent 1200 series, with single quad mass spectrometer |
| Column | LUNA C18 (250 mm × 21.2 mm), 5.0 μm |
| Eluents | A: 0.1% HCOOH in water, B: acetonitrile |
| Flow rate | 18 mL/min |

RP-HPLC Acidic 13:

| | |
|---|---|
| System | Gilson |
| Column | Nucleodur C18 (21 mm × 250 mm) |
| Eluents | A: water + 0.1% COOH, B: acetonitrile + 0.1% COOH |
| Flow rate | 40 mL/min |

RP-HPLC Acidic 14:

| | |
|---|---|
| System | Teledyne/Isco AccqPrep HP150 prep |
| Column | 50 × 100 Xbridge C18 (50 mm × 100 mm), 5 μm |
| Eluents | A: water + 0.1% TFA, B: acetonitrile |
| Flow rate | 100 mL/min |

RP-HPLC Neutral 1:

| | |
|---|---|
| System | Agilent 1200 series, with single quad mass spectrometer |
| Column | KINETEX (150 mm × 21.2 mm), 5 μm |
| Eluents | A: water, B: acetonitrile |
| Flow rate | 20 mL/min |

RP-HPLC Neutral 2:

| | |
|---|---|
| System | Agilent 1200 series, with single quad mass spectrometer |
| Column | ATLANTIS (250 mm × 21.2 mm), 5 μm |
| Eluents | A: water, B: acetonitrile |
| Flow rate | 17 mL/min |

RP-HPLC Neutral 3:

| | |
|---|---|
| System | Agilent 1200 series, with single quad mass spectrometer |
| Column | LUNA C18 (250 mm × 21.2 mm), 5 μm |
| Eluents | A: water, B: acetonitrile |
| Flow rate | 20 mL/min |

RP-HPLC Neutral 4:

| | |
|---|---|
| System | Agilent 1200 series, with single quad mass spectrometer |
| Column | LUNA Phenomenex (250 mm × 21.2 mm), 5 μm |
| Eluents | A: water, B: acetonitrile |
| Flow rate | 18 mL/min |

RP-HPLC Neutral 5:

| | |
|---|---|
| System | Agilent 1200 series, with single quad mass spectrometer |
| Column | LUNA (250 mm × 21.2 mm) |
| Eluents | A: water, B: acetonitrile |
| Flow rate | 20 mL/min |

Preparation of Compounds

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

The structures of all final products, intermediates and starting materials are confirmed by standard analytical spectroscopic characteristics, e.g., MS, IR or NMR. The absolute stereochemistry of certain isomers has been determined by analyses of X-ray crystal structures of complexes in which the respective compounds are bound to WRN or by small molecule X-ray crystal structures of a precursor of the final compound.

Amines synthetized via acidic deprotection of the Boc-precursor were often obtained as HCl or TFA salt. The corresponding free base can be isolated by partitioning between DCM and aq sat NaHCO3 as described for Intermediate Y.

General Conditions:

Mass spectra were acquired on LC-MS systems using electrospray, chemical and electron impact ionization methods with a range of instruments of the following configurations: Waters Acquity UPLC with Waters SQ detector, Shimadzu NEXERA UPLC PDA with Shimadzu LCMS 2020 as MSD, Agilent 1200 HPLC PDA with AB Sciex AP12000 TQ as MSD and Agilent 1200 HPLC PDA with AB Sciex AP13200 QTRAP as MSD. $[M+H]^+$ refers to the protonated molecular ion of the chemical species.

NMR spectra were run with Bruker Ultrashield™400 (400 MHz), Bruker Ultrashield™400 Plus (400 MHz), Bruker Ultrashield™600 (600 MHz) and Bruker Ascend™400 (400 MHz) spectrometers, all with and without tetramethylsilane as an internal standard. Chemical shifts (d-values) are reported in ppm downfield from tetramethylsilane, spectra splitting pattern are designated as singlet (s), doublet (d), triplet (t), multiplet, unresolved or more overlapping signals (m), broad signal (br). Solvents are given in parentheses.

Celite: Celite® (the Celite corporation)=filtering aid based on diatomaceous earth Phase separator: Biotage—Isolute phase separator—(Part number: 120-1906-D for 15 mL, Part number: 120-1908-F for 70 mL and Part number: 120-1909-J for 150 mL)

SiliaMetS® Thiol: SiliCYCLE thiol metal scavenger—(Part number: R51030B, Loading: 1.31 mmol/g Particle Size: 40-63 μm)

ISOLUTE® Si-Thiol: Biotage thiol metal scavenger—(Part number: 9180-0100, Loading: 1.3 mmol/g)

PL-BnSH MP-Resin: Agilent thiol metal scavenger—(Part number: PL3582-6689, 2.2 mmol/g 100A 150-1 kg)

ISOLUTE® Si-TMT: Biotage thiol metal scavenger—(Part number: 9538)

Smopex®-301: Alfa Aesar thiol metal scavenger (Part number: 45902)

PL-$HCO_3$ MP SPE cartridge (500 mg per 6 mL)—(Part number: PL3540-C603)

PL-$HCO_3$ MP SPE cartridge (100 mg per 6 mL)—(Part number: PL3540-A603)

Selected compounds were crystallized and further characterized. The experimental procedures are outlined in the examples, infra, and the instrument and method descriptions are outlined below:

| X-ray Powder Diffraction Instrument and Method, FIGS. 1 to 5 | |
|---|---|
| Instrument Model | Bruker D8 Discover new |
| Detector | VANTEC-500 |
| Radiation (Wavelength) | Cu (1.5418 Å) |
| X-ray generator power | 40 kV, 40 mA |
| Step size, resolution | Time/step 60 s, steps 2 |
| Scan range | 9° to 36° (2Theta value) |
| Scan time | 120 s |
| Temperature | Room temperature |
| Source slit | Optics-Goebel mirror-Cu, Microslit-10 height 1 mm, UBC-Collimator-G-10 width 1 mm |

Figure 7:
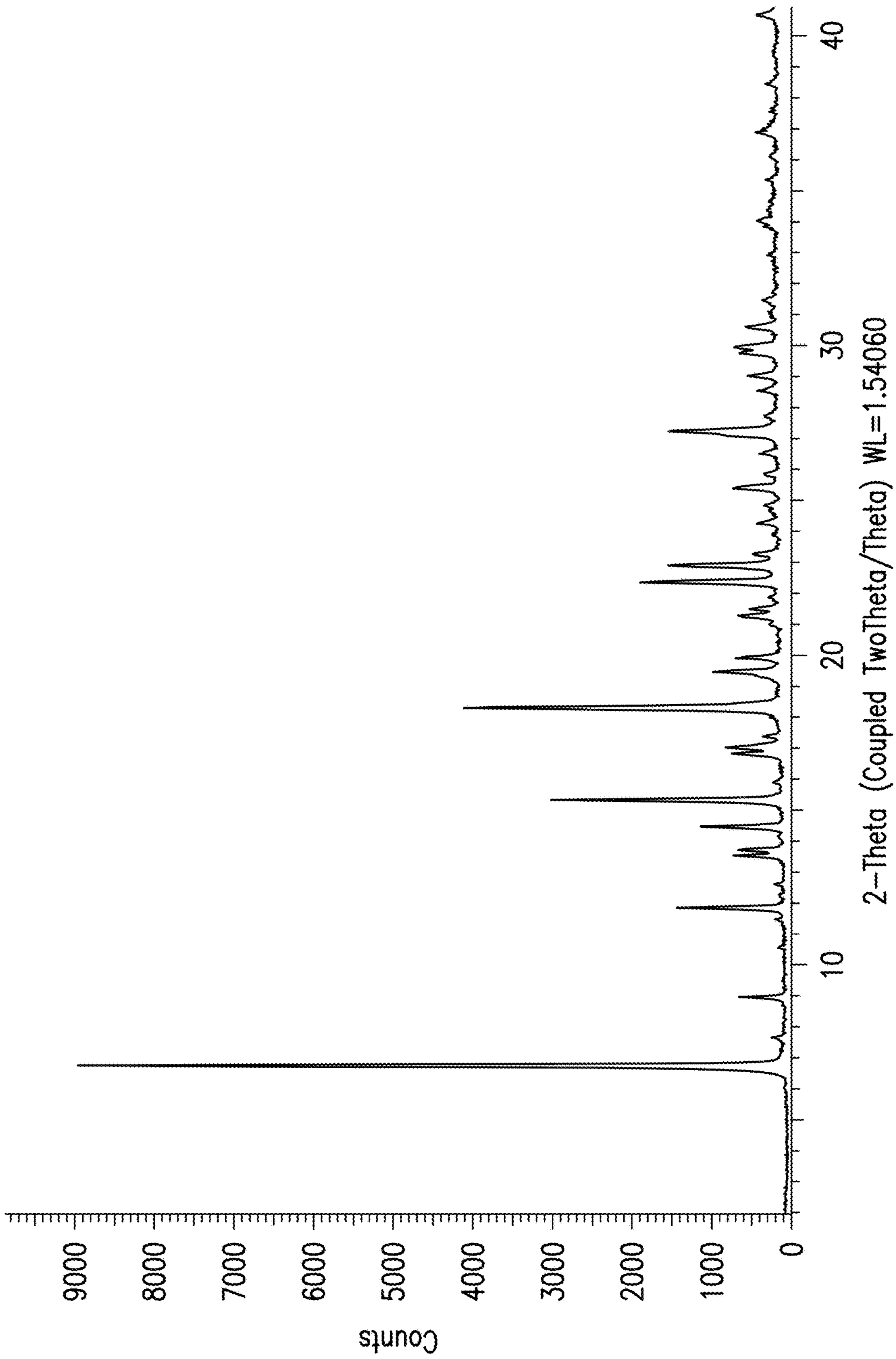
FIG. 7 shows a X-ray powder diffractogram for example 42.

| X-ray Powder Diffraction Instrument and Method, FIG. 7 | |
|---|---|
| Instrument Model | Bruker D8 Advance |
| Detector | LynxEye (1D mode), open angle: 2.948° |
| Radiation (Wavelength) | CuKα (0.15418 nm) |
| Monochromator | Ni-filter |
| X-ray generator power | 40 kV, 40 mA |
| Step size | 0.0164° (2theta) |
| Time per step | 0.3 s |
| Scan range | 2°-40° 2theta |
| Scan time | 768 s |
| Source slit | Primary fixed illuminated sample size: 10 mm, secondary: open angle: 2.2°, axial soller: 2.5° |

Sodium Salt Formation:

The compound was suspended in tert-butanol. NaOH 0.1 M (1 eq) was added. The mixture was stirred/sonicated at RT. If the suspension turned into a clear solution it was lyophilized. If the suspension was still turbid, water was added and the resulting solution was lyophilized. If no change happened, NaOH 0.1M up to 2 eq in total was added until a clear solution was observed, which was then lyophilized. If the NMR of the resulting solid still contained tert-butanol, the solid was dissolved in a small amount of water and lyophilized again. The final sodium salts were obtained as colourless powders. The amorphous state was confirmed by XRPD.

Synthetic Schemes

Typically, the compounds of formula (I) can be prepared according to the Schemes provided infra. The examples which outline specific synthetic routes, and the generic schemes below provide guidance to the synthetic chemist of ordinary skill in the art, who will readily appreciate that the solvent, concentration, reagent, protecting group, order of synthetic steps, time, temperature, and the like can be modified as necessary.

The schemes provided infra are intended to represent single diastereomers/enantiomers as well as their isomeric mixtures. Separation of diastereomers/enantiomers may be performed according to techniques described herein.

The invention includes the novel processes described herein, and further includes any variant of the present processes, in which an intermediate obtainable at any stage thereof is used as starting material and the remaining steps are carried out, or in which the starting materials are formed in situ under the reaction conditions, or in which the reaction components are used in the form of their salts or optically pure material. Compounds of the present invention and intermediates can also be converted into each other according to methods generally known to those skilled in the art. In another aspect, the invention provides novel intermediate compounds, as described herein.

Abbreviations

| Abbreviation | Description |
|---|---|
| AA | ammonium acetate |
| ACN | acetonitrile |
| AcOH | acetic acid |
| $AgBF_4$ | silver tetrafluoroborate |
| ATCC | American Type Culture Collection, Mannassas, Virginia |
| aq | aqueous |
| $BCl_3$ | boron trichloride |
| BINAP | 2,2'-bis(diphenylphosphino)-1,1'-binaphthyl |
| Boc | tert-butyloxycarbonyl |
| $Boc_2O$ | di-tert-butyl decarbonate |
| br | broad signal |
| brine | saturated aqueous sodium chloride |
| ° C. | degrees Celsius |
| $CaCl_2$ | calcium chloride |
| CO | carbon monoxide |
| $CO_2$ | carbon dioxide |
| CPhos | 2-dicyclohexylphosphino-2',6'-bis(N,N-dimethylamino)biphenyl |
| CPhos Pd G3 | [(2-dicyclohexylphosphino-2',6'-bis(N,N-dimethylamino)-1,1'-biphenyl)-2-(2'-amino-1,1'-biphenyl)] palladium(II) methanesulfonate |
| $Cs_2CO_3$ | caesium carbonate |
| DAST | diethylaminosulfur trifluoride |
| DCM | dichloromethane |
| DIBAL-H | diisobutylaluminium hydride |
| DIPEA | N,N-diisopropylethylamine |
| DMAP | 4-dimethylaminopyridine |
| DME | 1,2-dimethoxyethane |
| DMF | N,N-dimethylformamide |
| DMSO | dimethyl sulfoxide |
| DMSO-$d_6$ | hexadeuterodimethyl sulfoxide |
| dppf | 1,1'-bis(diphenylphosphino)ferrocene |
| EDC • HCl | 3-(ethyliminomethyleneamino)-N,N-dimethyl-propan-1-amine hydrochloride |

-continued

| Abbreviation | Description |
|---|---|
| EDCl | 3-(ethyliminomethyleneamino)-N,N-dimethyl-propan-1-amine |
| ee | enantiomeric excess |
| eq | equivalent |
| $Et_3N$ | triethylamine |
| $Et_2O$ | diethyl ether |
| EtOAc | ethylacetate |
| EtOH | ethanol |
| FA | formic acid |
| $H_2O$ | water |
| HATU | 1-[Bis(dimethylamino)methylene]-1H-1,2,3-triazolo[4,5-b]pyridinium 3-oxide hexafluorophosphate |
| HBr | hydrobromic acid |
| HCl | hydrochloric acid |
| HCOOH | formic acid |
| Hg | mercury |
| HI | hydroiodic acid |
| $HNO_3$ | nitric acid |
| HOAt | 3H-[1,2,3]triazolo[4,5-b]pyridin-3-ol |
| HOBt | benzotriazol-1-ol |
| HPLC | high-performance liquid chromatography |
| $H_3PO_4$ | phosphoric acid |
| HV | high vacuum |
| Hz, MHz, GHz | hertz, megahertz, gigahertz |
| IPA | isopropyl alcohol |
| IPAc | isopropyl acetate |
| J | coupling constant |
| $K_2CO_3$ | potassium carbonate |
| kg/g/mg | kilogram/gram/milligram |
| KHMDS | potassium bis(trimethylsilyl)amide |
| KI | potassium iodide |
| $KMnO_4$ | potassium permanganate |
| KOH | potassium hydroxide |
| $K_3PO_4$ | potassium phosphate |
| L/mL/µL | liter/milliliter/microliter |
| LC-MS | liquid chromatography and mass spectrometry |
| LDA | lithium diisopropylamide |
| LiCl | lithium chloride |
| M/mM | molar/millimolar |
| mbar | millibar |
| MCC pad | microcrystalline cellulose |
| MeOH | methanol |
| MeTHF | 2-methyloxolane/2-methyltetrahydrofuran |
| $MgSO_4$ | magnesium sulfate |
| min | minutes |
| mm/nm/µm | millimeter/nanometer/micrometer |
| µM/mM | micromolar/millimolar |
| µmol/mmol/mol | micromol/millimol/mol |
| MS | mass spectrometry |
| MW, mw | microwave |
| m/z | mass to charge ratio |
| N | normality |
| NaCl | sodium chloride |
| NaCN | sodium cyanide |
| NaH | sodium hydride |
| $NaHCO_3$ | sodium bicarbonate |
| $NaH_2PO_4$ | sodium dihydrogen phosphate |
| NaHSO4 | sodium bisulfate |
| NaOH | sodium hydroxide |
| $Na_2O_3S_2$ | sodium thiosulfate |
| NaOtBu | sodium 2-methylpropan-2-olate |
| $Na_2SO_4$ | sodium sulfate |
| NBS | N-bromosuccinimide |
| $NH_3$ | ammonia |
| $NH_4Cl$ | ammonium chloride |
| $NH_4OH$ | ammonium hydroxide |
| $(NH_4)_2CO_3$ | ammonium carbonate |
| NIS | N-iodosuccinimide |
| NMP | 1-methylpyrrolidin-2-one |
| NMR | nuclear magnetic resonance |
| $PdCl_2(PPh_3)_2$ | bis(triphenylphosphine)palladium(II) dichloride |
| $Pd(dppf)Cl_2$ | [1,1'-bis(diphenylphosphino)ferrocene] palladium(II) dichloride |
| $Pd(dppf)Cl_2$ • DCM | [1,1'-Bis(diphenylphosphino)ferrocene] palladium(II) dichloride, DCM adduct |
| $Pd(OAc)_2$ | 1palladium(II) acetate |
| $Pd(PPh_3)_4$ | tetrakis(triphenylphosphine)palladium(0) |

-continued

| Abbreviation | Description |
|---|---|
| PMa | pressure maximum allowable |
| $POCl_3$ | phosphoryl chloride |
| $PtO_2$ | platinum dioxide |
| PyAOP | (7-azabenzotriazol-1-yloxy)tripyrrolidinophosphonium hexafluorophosphate |
| QD | once daily (quaque die) |
| $R_f$ | retardation factor |
| RM or rm | reaction mixture |
| RP | reversed phase |
| RPM | revolutions per minute |
| Rt | retention time (if not indicated, in minutes) |
| RT | room temperature |
| RuPhos | 2-dicyclohexylphosphino-2',6'-diisopropoxybiphenyl |
| s, d, dd, t, m | singulet, doublet, doublet of doublets, triplet, multiplet |
| sat | saturated |
| $scCO_2$ | supercritical $CO_2$ |
| SEM | β-(trimethylsilyl)ethoxymethyl |

-continued

| Abbreviation | Description |
|---|---|
| SFC | supercritical fluid chromatography |
| $T_3P$ | propanephosphonic acid anhydride |
| TBAF | tetrabutylammonium fluoride |
| TBME | 2-methoxy-2-methylpropane |
| TFA | trifluoroacetic acid |
| THF | tetrahydrofuran |
| TLC | thin-layer chromatography |
| TMSOTf | trimethylsilyl trifluoromethanesulfonate |
| UPLC | ultra performance liquid chromatography |
| W | watt |
| XPhos Pd G2 | chloro(2-dicyclohexylphosphino-2',4',6'-triisopropyl-1,1'-biphenyl)[2-(2'-amino-1,1'-biphenyl)]palladium(II) |
| XPhos Pd G3 | (2-dicyclohexylphosphino-2',4',6'-triisopropyl-1,1'-biphenyl)[2-(2'-amino-1,1'-biphenyl)] palladium(II) methanesulfonate |
| XRPD | X-Ray Powder Diffraction |

Preparation of Final Compounds

Scheme 1 preparation of final compounds

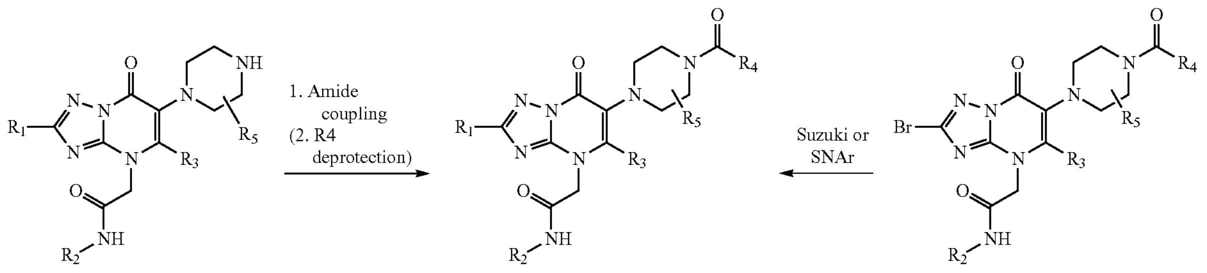

Example 1: 2-(6-(4-(4-chloro-3-hydroxypicolinoyl)piperazin-1-yl)-5-ethyl-2-morpholino-7-oxo-[1,2,4]triazolo[1,5-a]pyrimidin-4 (7H)-yl)-N-(2-chloro-4-(trifluoromethyl)phenyl)acetamide

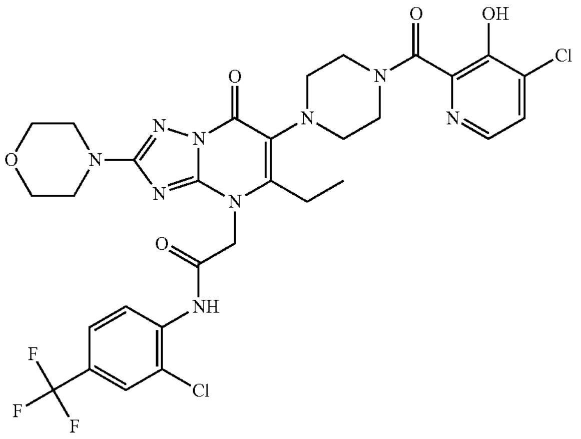 [SMILES: CCc1c(N2CCN(C(=O)c3nccc(Cl)c3O)CC2)c(=O)n2nc(N3CCOCC3)nc2n1CC(=O)Nc1ccc(C(F)(F)F)cc1Cl]

N-(2-chloro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide (Intermediate B) (630 mg, 1.11 mmol) was suspended in DMF (6 mL). 4-chloro-3-hydroxypicolinic acid (384 mg, 2.21 mmol), DIPEA (967 μL, 5.54 mmol), HOBt (299 mg, 2.21 mmol) and EDC·HCl (425 mg, 2.21 mmol) were added to the RM and it was stirred at RT for 12 hours. Water was added to the RM and the suspension was filtered. The resulting solid was purified by reverse phase preparative HPLC (RP-HPLC acidic 5: 20 to 30% B in 2 min, 30 to 60% B in 8 min) to give the title compound.

LC-MS: Rt=1.09 min; MS m/z $[M+H]^+$ 724.6/726.6, m/z $[M-H]^-$ 722.3/724.3; UPLC-MS 1

LC-MS: Rt=5.33 min; MS m/z $[M+H]^+$ 724.2/726.2, m/z $[M-H]^-$ 722.3/724.2; UPLC-MS 2

$^1H$ NMR (400 MHz, DMSO-$d_6$) δ 10.83 (s, br, 1H), 10.34 (s, 1H), 8.05 (m, 2H), 7.96 (d, J=2.1 Hz, 1H), 7.72 (dd, J=2.1 Hz, 8.8 Hz, 1H), 7.55 (d, J=5.1 Hz, 1H), 5.21 (s, 2H), 4.53 (m, 1H), 3.66 (m, 4H), 3.54 (m, 3H), 3.38 (m, 4H), 3.23 (m, 1H), 2.96 (m, 3H), 2.78 (m, 1H), 2.60 (m, 1H), 1.16 (t, J=7.3 Hz, 3H)

Example 2: N-(2-chloro-4-(trifluoromethyl)phenyl)-2-(5-ethyl-6-(4-(3-hydroxypicolinoyl)piperazin-1-yl)-2-morpholino-7-oxo-[1,2,4]triazolo[1,5-a]pyrimidin-4 (7H)-yl)acetamide

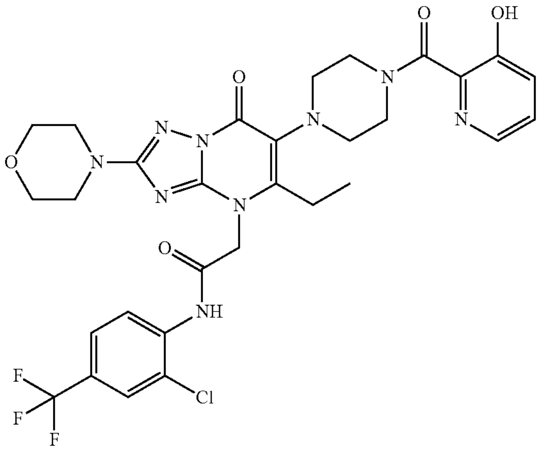 [SMILES: CCc1c(N2CCN(C(=O)c3ncccc3O)CC2)c(=O)n2nc(N3CCOCC3)nc2n1CC(=O)Nc1ccc(C(F)(F)F)cc1Cl]

N-(2-chloro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide (Intermediate B) (200 mg, 352 μmol) was suspended in DMF (5 mL). Perfluorophenyl 3-hydroxypicolinate (Intermediate CT) (215 mg, 703 μmol) and $Et_3N$ (97.0 μL, 703 μmol) were added and the RM was stirred at 70° C. for 3 hours. The RM was concentrated under reduced pressure. The crude product was first purified by column chromatography (Silica gel column: Silica 12 g, eluent DCM:MeOH 100:0 to 90:10). Then a second purification by reverse phase preparative HPLC (RP-HPLC acidic 9: 40 to 50% B in 2 min, 50 to 55% B in 10 min) afforded the title compound.

LC-MS: Rt=0.98 min; MS m/z $[M+H]^+$ 690.6/692.6, m/z $[M-H]^-$ 688.4/690.3; UPLC-MS 1

LC-MS: Rt=4.84 min; MS m/z $[M+H]^+$ 690.2/692.2 m/z $[M-H]^-$ 688.3/690.3; UPLC-MS 2

$^1H$ NMR (400 MHz, DMSO-$d_6$) δ 10.37 (s, br, 1H), 10.34 (s, br, 1H), 8.05 (m, 2H), 7.96 (d, J=2.1 Hz, 1H), 7.72 (dd, J=2.1 Hz, 8.7 Hz, 1H), 7.28 (m, 2H), 5.21 (s, 2H), 4.53 (m, 1H), 3.66 (m, 4H), 3.46 (m, 3H), 3.38 (m, 4H), 3.20 (m, 1H), 2.92 (m, 3H), 2.76 (m, 1H), 2.58 (m, 1H), 1.16 (t, J=7.5 Hz, 3H)

Example 3: N-(2-chloro-4-(trifluoromethyl)phenyl)-2-(5-ethyl-6-(4-(4-fluoro-3-hydroxypicolinoyl)piperazin-1-yl)-2-morpholino-7-oxo-[1,2,4]triazolo[1,5-a]pyrimidin-4 (7H)-yl)acetamide

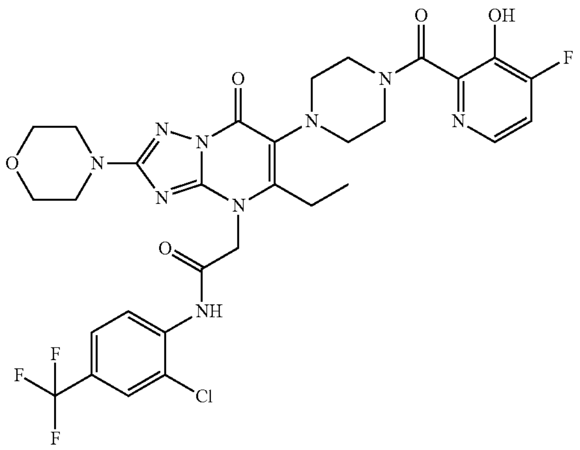 [SMILES: CCc1c(N2CCN(C(=O)c3nccc(F)c3O)CC2)c(=O)n2nc(N3CCOCC3)nc2n1CC(=O)Nc1ccc(C(F)(F)F)cc1Cl]

Step 1: 2-(6-(4-(3-(benzyloxy)-4-fluoropicolinoyl)piperazin-1-yl)-5-ethyl-2-morpholino-7-oxo-[1,2,4]triazolo[1,5-a]pyrimidin-4 (7H)-yl)-N-(2-chloro-4-(trifluoromethyl)phenyl)acetamide To N-(2-chloro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide·TFA (Intermediate B) (620 mg, 908 μmol) in DMF (3 mL) was added $Et_3N$ (503 μL, 3.63 mmol) followed by 3-(benzyloxy)-4-fluoropicolinic acid (Intermediate CU) (224 mg, 908 μmol), then HATU (380 mg, 999 μmol). The RM was stirred at RT for 30 minutes. The RM was diluted with water (5 mL) and the resulting suspension was stirred at RT for 90 minutes. The suspension was filtered. The cake was washed with water (20 mL) and dried under vacuum to give the title compound as an off-white solid.

LC-MS: Rt=1.21 min; MS m/z $[M+H]^+$ 798.5/800.5, m/z $[M-H]^-$ 796.5/798.5; UPLC-MS 1.

Step 2: N-(2-chloro-4-(trifluoromethyl)phenyl)-2-(5-ethyl-6-(4-(4-fluoro-3-hydroxypicolinoyl)piperazin-1-yl)-2-morpholino-7-oxo-[1,2,4]triazolo[1,5-a]pyrimidin-4 (7H)-yl)acetamide 2-(6-(4-(3-(benzyloxy)-4-fluoropicolinoyl)piperazin-1-yl)-5-ethyl-2-morpholino-7-oxo-[1,2,4]triazolo[1,5-a]pyrimidin-4 (7H)-yl)-N-(2-chloro-4-(trifluoromethyl)phenyl)acetamide (617 mg, 773 μmol) was dissolved in HBr (48% aq) (1.00 mL, 8.84 mmol) and stood at RT for 3 hours. Then it stood in a stoppered flask in the fridge over the weekend. The RM was allowed to warm to RT then heated at 35° C. with stirring for 140 minutes. The RM was neutralized to pH 6 by addition of 1M aq NaOH and extracted with DCM (2×30 mL). The combined organic layers were dried over $Na_2SO_4$, filtered and concentrated under reduced pressure. The crude product was purified in 2 portions by reverse phase preparative HPLC (RP-HPLC acidic 1: 30 to 50% B in 20 min with a plateau at 50% for 1 min and RP-HPLC acidic 1: 20 to 47% B in 20 min with a plateau at 20% for 1 min). The product containing fractions were combined and partitioned between DCM (30 mL) and aq sat $NaHCO_3$ (5 mL).

The organic layer was separated by filtration through a phase separator and concentrated under reduced pressure. The residue was recrystallized from MeOH/water to give the title compound as colourless crystals.

LC-MS: Rt=0.98 min; MS m/z $[M+H]^+$ 708.5/710.5, m/z $[M-H]^-$ 706.4/708.4; UPLC-MS 1

LC-MS: Rt=4.89 min; MS m/z $[M+H]^+$ 708.2/710.2, m/z $[M-H]^-$ 706.2/708.2; UPLC-MS 2

$^1$H NMR (400 MHz, DMSO-$d_6$) δ 10.72 (s, br, 1H), 10.33 (s, 1H), 8.08 (dd, J=5.3 Hz, 6.9 Hz, 1H), 8.04 (d, J=8.7 Hz, 1H), 7.96 (d, J=2.1 Hz, 1H), 7.72 (dd, J=2.2 Hz, 8.8 Hz, 1H), 7.35 (dd, J=5.3 Hz, 11.9 Hz, 1H), 5.21 (s, 2H), 4.52 (m, 1H), 3.66 (m, 4H), 3.45 (m, 3H), 3.38 (m, 4H), 3.21 (m, 1H), 2.94 (m, 3H), 2.77 (m, 1H), 2.59 (m, 1H), 1.16 (t, J=7.4 Hz, 3H)

Example 4: N-(5-chloro-2-methyl-4-(trifluoromethyl)phenyl)-2-(5-ethyl-6-(4-(3-hydroxypicolinoyl)piperazin-1-yl)-2-morpholino-7-oxo-[1,2,4]triazolo[1,5-a]pyrimidin-4 (7H)-yl)acetamide

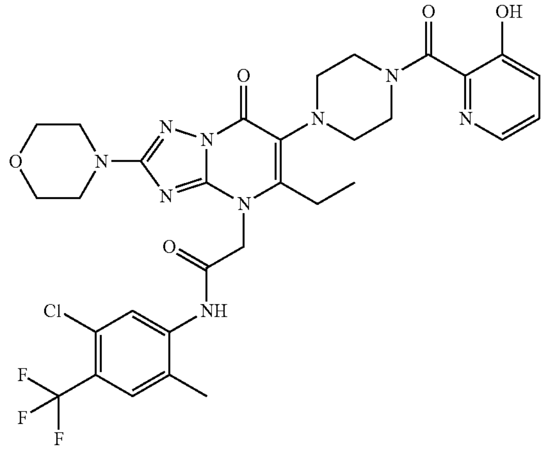 [SMILES: CCc1c(N2CCN(C(=O)c3ncccc3O)CC2)c(=O)n2nc(N3CCOCC3)nc2n1CC(=O)Nc1cc(Cl)c(C(F)(F)F)cc1C]

N-(5-chloro-2-methyl-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide (Intermediate C) (400 mg, 686 μmol) was suspended in DMF (5 mL). 3-hydroxypicolinic acid (191 mg, 1.37 mmol), DIPEA (599 μL, 3.43 mmol), HOBt (185 mg, 1.37 mmol) and EDC·HCl (263 mg, 1.37 mmol) were added to the RM and stirred at RT for 12 hours. Water was added to the RM and it was filtered. The solid was purified by reverse phase preparative HPLC (RP-HPLC neutral 5: 10 to 20% B in 2 min, 20 to 45% B in 10 min) to give the title compound.

LC-MS: Rt=1.00 min; MS m/z $[M+H]^+$ 704.1/706.2, m/z $[M-H]^-$ 702.2/704.2; UPLC-MS 1

LC-MS: Rt=5.01 min; MS m/z $[M+H]^+$ 704.2/706.1, m/z $[M-H]^-$ 702.3/704.3; UPLC-MS 2

$^1$H NMR (400 MHz, DMSO-$d_6$) δ 10.37 (s, br, 1H), 10.07 (s, 1H), 8.06 (m, 1H), 7.93 (s, 1H), 7.75 (s, 1H), 7.28 (m, 2H), 5.16 (s, 2H), 4.53 (m, 1H), 3.65 (m, 4H), 3.46 (m, 3H), 3.39 (m, 4H), 3.20 (m, 1H), 2.94 (m, 3H), 2.75 (m, 1H), 2.58 (m, 1H), 2.34 (s, 3H), 1.16 (t, J=7.1 Hz, 3H)

Example 5: 2-(5-ethyl-6-(4-(3-hydroxypicolinoyl)piperazin-1-yl)-2-morpholino-7-oxo-[1,2,4]triazolo[1,5-a]pyrimidin-4 (7H)-yl)-N-(5-fluoro-2-methyl-4-(trifluoromethyl)phenyl)acetamide

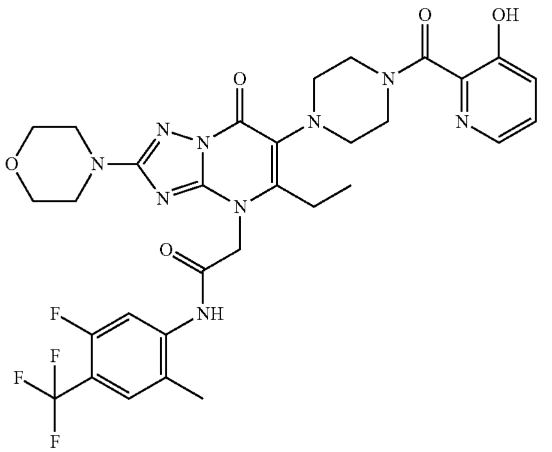 [SMILES: CCc1c(N2CCN(C(=O)c3ncccc3O)CC2)c(=O)n2nc(N3CCOCC3)nc2n1CC(=O)Nc1cc(F)c(C(F)(F)F)cc1C]

2-(5-Ethyl-2-morpholino-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide·HCl (Intermediate D) (230 mg, 381 μmol) and DIPEA (333 μL, 1.91 mmol) were dissolved in DCM (10 mL) and then 3-hydroxypicolinoyl chloride (Intermediate CV) (90.0 mg, 572 μmol) was added at 0° C. and stirred for 1 hour. 3-hydroxypicolinoyl chloride (Intermediate CV) (90.0 mg, 572 μmol) was added again at 0° C. and stirred for 1 hour. The RM was diluted with DCM and washed with water, aq $NaHCO_3$ solution (2×20 mL), again with water and brine, dried over $Na_2SO_4$, filtered and concentrated. The crude product was purified by reverse phase preparative HPLC (RP-HPLC acidic 7: 30 to 40% B in 2 min, 40 to 50% B in 9 min) to give the title compound as a pale brown solid.

LC-MS: Rt=0.96 min; MS m/z $[M+H]^+$ 688.2, m/z $[M-H]^-$ 686.3; UPLC-MS 1

LC-MS: Rt=4.81 min; MS m/z $[M+H]^+$ 688.2, m/z $[M-H]^-$ 686.3; UPLC-MS 2

$^1$H NMR (400 MHz, DMSO-$d_6$) δ 10.35 (s, broad, 1H), 10.06 (s, br, 1H), 8.05 (m, 1H), 7.77 (d, J=13.0 Hz, 1H), 7.66 (d, J=8.2 Hz, 1H), 7.28 (m, 2H), 5.18 (s, 2H), 4.53 (m, 1H), 3.66 (m, 4H), 3.46 (m, 3H), 3.38 (m, 4H), 3.20 (m, 1H), 2.92 (m, 3H), 2.76 (m, 1H), 2.58 (m, 1H), 2.33 (s, 3H), 1.15 (t, J=7.2 Hz, 3H)

Example 6: 2-(6-(4-(4-chloro-3-hydroxypicolinoyl)piperazin-1-yl)-5-ethyl-2-morpholino-7-oxo-[1,2,4]triazolo[1,5-a]pyrimidin-4 (7H)-yl)-N-(5-fluoro-2-methyl-4-(trifluoromethyl)phenyl)acetamide

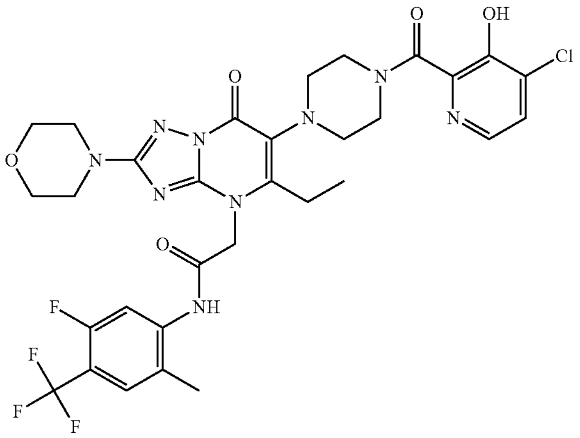 [SMILES: CCc1c(N2CCN(C(=O)c3nccc(Cl)c3O)CC2)c(=O)n2nc(N3CCOCC3)nc2n1CC(=O)Nc1cc(F)c(C(F)(F)F)cc1C]

2-(5-Ethyl-2-morpholino-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide (Intermediate D) (220 mg, 388 μmol) was suspended in DMF (5 mL). 4-chloro-3-hydroxypicolinic acid (101 mg, 582 μmol), DIPEA (339 μL, 1.94 mmol), HOBt (105 mg, 777 μmol) and EDC·HCl (149 mg, 777 μmol) were added to the RM and it was stirred at RT for 12 hours. Water was added to the RM and the precipitate was filtered off. The obtained solid was purified by reverse phase preparative HPLC (RP-HPLC acidic 5: 20 to 30% B in 2 min, 30 to 60% B in 8 min) to give the title compound.

LC-MS: Rt=1.07 min; MS m/z $[M+H]^+$ 722.3/724.3, m/z $[M-H]^-$ 720.3/722.3; UPLC-MS 1

LC-MS: Rt=5.32 min; MS m/z $[M+H]^+$ 722.2/724.2 m/z $[M-H]^-$ 720.2/722.2; UPLC-MS 2

$^1$H NMR (400 MHz, DMSO-$d_6$) δ 10.82 (s, br, 1H), 10.05 (s, 1H), 8.06 (d, J=5.1 Hz, 1H), 7.77 (d, J=12.8 Hz, 1H), 7.67 (d, J=8.1 Hz, 1H), 7.55 (d, J=4.8 Hz, 1H), 5.18 (s, 2H), 4.53 (m, 1H), 3.65 (m, 4H), 3.53 (m, 3H), 3.38 (m, 4H), 3.24 (m, 1H), 2.93 (m, 3H), 2.78 (m, 1H), 2.60 (m, 1H), 2.33 (s, 3H), 1.16 (t, J=7.1 Hz, 3H)

Example 7: N-(2-chloro-5-fluoro-4-(trifluoromethyl)phenyl)-2-(5-ethyl-6-(4-(3-hydroxypicolinoyl)piperazin-1-yl)-2-morpholino-7-oxo-[1,2,4]triazolo[1,5-a]pyrimidin-4 (7H)-yl)acetamide

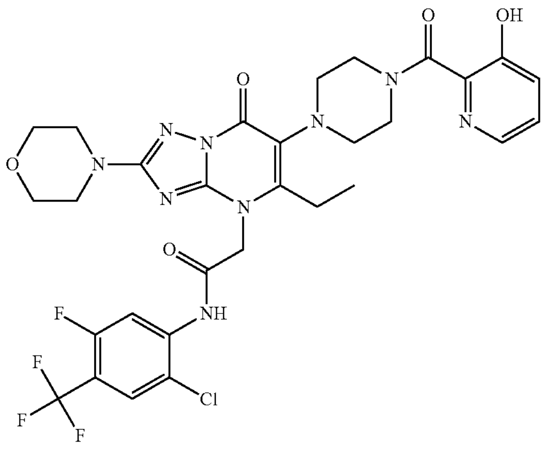 [SMILES: CCc1c(N2CCN(C(=O)c3ncccc3O)CC2)c(=O)n2nc(N3CCOCC3)nc2n1CC(=O)Nc1cc(F)c(C(F)(F)F)cc1Cl]

N-(2-chloro-5-fluoro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide·HCl (Intermediate E) (300 mg, 481 μmol) and DIPEA (420 μL, 2.41 mmol) were dissolved in DCM (15 mL) and then 3-hydroxypicolinoyl chloride (Intermediate CV) (152 mg, 962 μmol) was added at 0° C. and stirred for 2 hours. 3-hydroxypicolinoyl chloride (Intermediate CV) (152 mg, 962 μmol) was added again and continued stirring for 14 hours. The RM was diluted with DCM and washed with water, aq $NaHCO_3$ solution (2×20 mL), again with water and brine, dried over $Na_2SO_4$, filtered and concentrated. The crude product was purified by column chromatography (Silica gel column: Silica 12 g, eluent DCM:MeOH 100:0 to 99:1). The product containing fractions were concentrated, then further purified by reverse phase preparative HPLC (RP-HPLC acidic 7: 40 to 50% B in 2 min, 50 to 60% B in 8 min) to give the title compound as an off white solid.

LC-MS: Rt=1.01 min; MS m/z $[M+H]^+$ 708.4/710.4, m/z $[M-H]^-$ 706.4/708.4; UPLC-MS 1

LC-MS: Rt=5.11 min; MS m/z $[M+H]^+$ 708.2/710.1 m/z $[M-H]^-$ 706.2/708.2; UPLC-MS 2

$^1$H NMR (400 MHz, DMSO-$d_6$) δ 10.44 (s, 1H), 10.37 (s, 1H), 8.07 (m, 2H), 8.01 (d, J=7.3 Hz, 1H), 7.28 (m, 2H), 5.25 (s, 2H), 4.53 (m, 1H), 3.65 (m, 4H), 3.46 (m, 3H), 3.37 (m, 4H), 3.22 (m, 1H), 2.93 (m, 3H), 2.76 (m, 1H), 2.58 (m, 1H), 1.15 (t, J=7.4 Hz, 3H)

Example 8: 2-(5-ethyl-6-(4-(3-hydroxypicolinoyl)piperazin-1-yl)-2-morpholino-7-oxo-[1,2,4]triazolo[1,5-a]pyrimidin-4 (7H)-yl)-N-(2-methyl-4-(trifluoromethyl)phenyl)acetamide

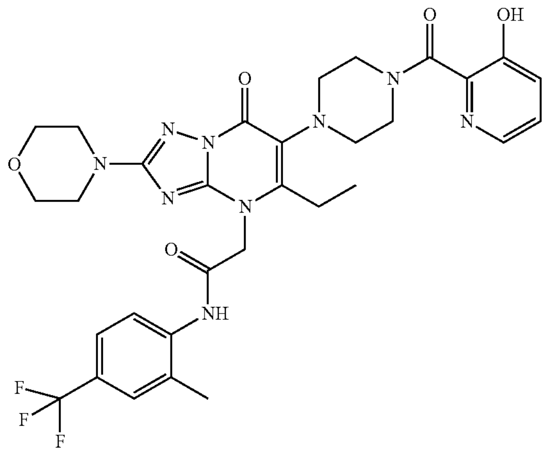 [SMILES: CCc1c(N2CCN(C(=O)c3ncccc3O)CC2)c(=O)n2nc(N3CCOCC3)nc2n1CC(=O)Nc1ccc(C(F)(F)F)cc1C]

To the stirred solution of 3-hydroxypicolinic acid (143 mg, 1.03 mmol) in DMF (2.5 mL) were added EDC·HCl (197 mg, 1.03 mmol) and HOBt (13.0 mg, 1.03 mmol) at RT. In another flask 2-(5-ethyl-2-morpholino-7-oxo-6-(piperazin-1-yl)-[1,2,4]triazolo[1,5-a]pyrimidin-4 (7H)-yl)-N-(2-methyl-4-(trifluoromethyl)phenyl)acetamide·HCl (Intermediate F) (300 mg, 513 μmol) in DMF (2.5 mL) was mixed with DIPEA (537 μL, 3.08 mmol) at RT. This solution was added to the first RM at RT and stirred for 12 hours. The RM was concentrated, water was added and it was extracted with EtOAc. The organic layer was washed with aq $NaHCO_3$ solution (2 times), dried over $Na_2SO_4$ and concentrated under reduced pressure. The crude product was purified by reverse phase preparative HPLC (RP-HPLC neutral 4: 30 to 40% B in 2 min, 40 to 50% B in 8 min) to give the title compound.

LC-MS: Rt=0.92 min; MS m/z $[M+H]^+$ 670.4, m/z $[M-H]^-$ 668.3; UPLC-MS 1

LC-MS: Rt=4.64 min; MS m/z $[M+H]^+$ 670.3, m/z $[M-H]^-$ 668.3; UPLC-MS 2

$^1$H NMR (400 MHz, DMSO-$d_6$) δ 10.40 (s, 1H, br), 9.98 (s, 1H), 8.05 (m, 1H), 7.70 (d, J=8.4 Hz, 1H), 7.62 (s, br, 1H), 7.53 (d, J=8.3 Hz, 1H), 7.28 (m, 2H), 5.14 (s, 2H), 4.53 (m, 1H), 3.66 (m, 4H), 3.46 (m, 3H), 3.39 (m, 4H), 3.20 (m, 1H), 2.95 (m, 3H), 2.76 (m, 1H), 2.58 (m, 1H), 2.33 (s, 3H), 1.16 (t, J=7.1 Hz, 3H)

Example 9: 2-(6-(4-(4-chloro-3-hydroxypicolinoyl)piperazin-1-yl)-5-ethyl-2-morpholino-7-oxo-[1,2,4]triazolo[1,5-a]pyrimidin-4 (7H)-yl)-N-(2-methyl-4-(trifluoromethyl)phenyl)acetamide

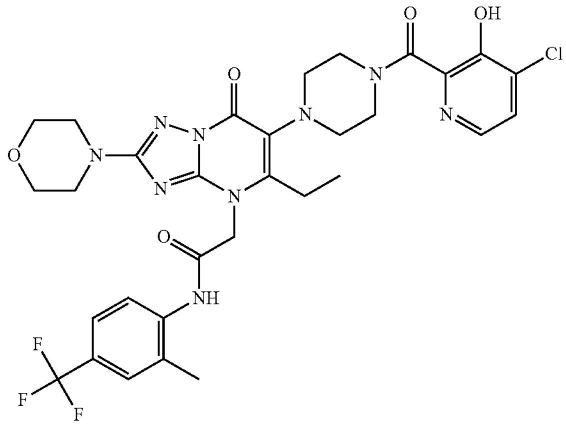 [SMILES: CCc1c(N2CCN(C(=O)c3nccc(Cl)c3O)CC2)c(=O)n2nc(N3CCOCC3)nc2n1CC(=O)Nc1ccc(C(F)(F)F)cc1C]

4-Chloro-3-hydroxypicolinic acid (120 mg, 692 μmol) was dissolved in DMF (3 mL) and then 2-(5-ethyl-2-morpholino-7-oxo-6-(piperazin-1-yl)-[1,2,4]triazolo[1,5-a]pyrimidin-4 (7H)-yl)-N-(2-methyl-4-(trifluoromethyl)phenyl)acetamide·HCl (Intermediate F) (270 mg, 462 μmol), EDC·HCl (177 mg, 923 μmol), DIPEA (403 μL, 2.31 mmol) and HOBt (125 mg, 923 μmol) were added at 0° C. and stirred at RT for 14 hours. The RM was diluted with water and extracted with 5% MeOH in DCM and washed with aq sat $NaHCO_3$ and brine. The combined organic layers were dried over $Na_2SO_4$ and concentrated under reduced pressure. The crude product was purified by reverse phase preparative HPLC (RP-HPLC acidic 7: 30 to 40% B in 2 min, 40 to 60% B in 8 min) to give the title compound.

LC-MS: Rt=1.02 min; MS m/z $[M+H]^+$ 704.2/706.2, m/z $[M-H]^-$ 702.2/704.2; UPLC-MS 1

LC-MS: Rt=5.05 min; MS m/z $[M+H]^+$ 704.2/706.2, m/z $[M-H]^-$ 702.3/704.2; UPLC-MS 2

$^1$H NMR (400 MHz, DMSO-$d_6$) δ 10.85 (s, br, 1H), 9.99 (s, 1H), 8.03 (d, J=5.1 Hz, 1H), 7.70 (d, J=8.4 Hz, 1H), 7.62 (s, br, 1H), 7.53 (m, 2H), 5.14 (s, 2H), 4.53 (m, 1H), 3.66 (m, 4H), 3.53 (m, 3H), 3.39 (m, 4H), 3.24 (m, 1H), 2.95 (m, 3H), 2.77 (m, 1H), 2.60 (m, 1H), 2.34 (s, 3H), 1.17 (t, J=7.1 Hz, 3H)

Example 10: N-(2-chloro-6-(trifluoromethyl)pyridin-3-yl)-2-(5-ethyl-6-(4-(3-hydroxypicolinoyl)piperazin-1-yl)-2-morpholino-7-oxo-[1,2,4]triazolo[1,5-a]pyrimidin-4 (7H)-yl)acetamide

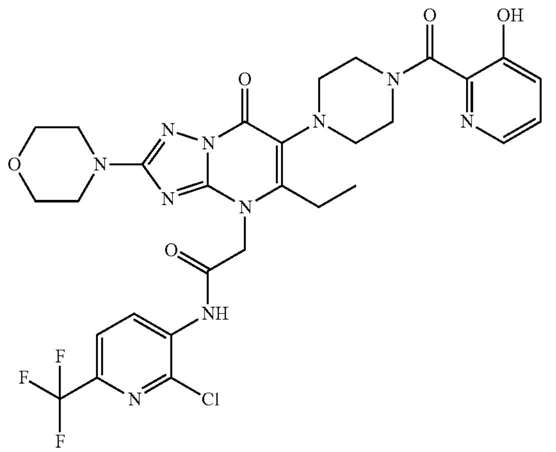 [SMILES: CCc1c(N2CCN(C(=O)c3ncccc3O)CC2)c(=O)n2nc(N3CCOCC3)nc2n1CC(=O)Nc1ccc(C(F)(F)F)nc1Cl]

N-(2-chloro-6-(trifluoromethyl)pyridin-3-yl)-2-(5-ethyl-2-morpholino-7-oxo-6-(piperazin-1-yl)-[1,2,4]triazolo[1,5-a]pyrimidin-4 (7H)-yl)acetamide (Intermediate G) (900 mg, 1.58 mmol) was suspended in DMF (5 mL). Perfluorophenyl 3-hydroxypicolinate (Intermediate CT) (964 mg, 3.16 mmol) and $Et_3N$ (438 μL, 3.16 mmol) were added and the RM was stirred at 70° C. for 3 hours. The RM was concentrated under reduced pressure. The crude product was purified by column chromatography (Silica gel column: Silica 24 g, eluent DCM:MeOH 100:0 to 99:1) and recrystallized using isopropanol to give the title compound.

LC-MS: Rt=0.85 min; MS m/z $[M+H]^+$ 691.4/693.4, m/z $[M-H]^-$ 689.5/691.5; UPLC-MS 1

$^1$H NMR (400 MHz, DMSO-$d_6$) δ 10.52 (s, 1H), 10.36 (s, 1H), 8.54 (d, J=8.3 Hz, 1H), 8.06 (m, 1H), 7.96 (d, J=8.5 Hz, 1H), 7.28 (m, 2H), 5.25 (s, 2H), 4.53 (m, 1H), 3.65 (m, 4H), 3.46 (m, 3H), 3.37 (m, 4H), 3.20 (m, 1H), 2.94 (m, 3H), 2.76 (m, 1H), 2.58 (m, 1H), 1.15 (t, J=7.1 Hz, 3H)

Example 11: 2-(5-ethyl-6-(4-(3-hydroxypicolinoyl)piperazin-1-yl)-2-morpholino-7-oxo-[1,2,4]triazolo[1,5-a]pyrimidin-4 (7H)-yl)-N-(2-fluoro-4-(trifluoromethyl)phenyl)acetamide

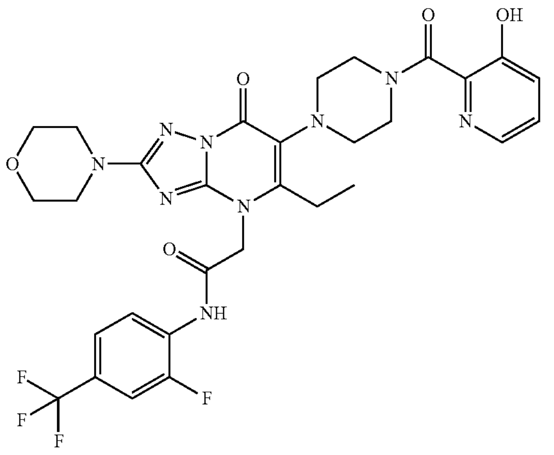 [SMILES: CCc1c(N2CCN(C(=O)c3ncccc3O)CC2)c(=O)n2nc(N3CCOCC3)nc2n1CC(=O)Nc1ccc(C(F)(F)F)cc1F]

To the stirred solution of 3-hydroxypicolinic acid (101 mg, 724 μmol), EDC·HCl (139 mg, 724 μmol) and HOBt (98.0 mg, 724 μmol) in DMF (3 mL) was added 2-(5-ethyl-2-morpholino-7-oxo-6-(piperazin-1-yl)-[1,2,4]triazolo[1,5-a]pyrimidin-4 (7H)-yl)-N-(2-fluoro-4-(trifluoromethyl)phenyl)acetamide (Intermediate H) (200 mg, 362 μmol) and then DIPEA (379 μL, 2.17 mmol) at RT. This RM was stirred at RT for 16 hours. The reaction was concentrated under reduced pressure and water was added. The resultant brown solid was filtered and dried under vacuum. The crude product was purified by reverse phase preparative HPLC (RP-HPLC neutral 1: 25 to 35% B in 2 min, 35 to 50% B in 9 min) to give the title compound.

LC-MS: Rt=0.95 min; MS m/z $[M+H]^+$ 674.6, m/z $[M-H]^-$ 672.4; UPLC-MS 1

LC-MS: Rt=4.68 min; MS m/z $[M+H]^+$ 674.2, m/z $[M-H]^-$ 672.3; UPLC-MS 2

$^1$H NMR (400 MHz, DMSO-$d_6$) δ 10.58 (s, br, 2H), 8.21 (m, 1H), 8.04 (m, 1H), 7.79 (d, J=10.9 Hz, 1H), 7.57 (d, J=8.7 Hz, 1H), 7.27 (m, 2H), 5.19 (s, 2H), 4.53 (m, 1H), 3.65 (m, 4H), 3.46 (m, 3H), 3.37 (m, 4H), 3.20 (m, 1H), 2.92 (m, 3H), 2.76 (m, 1H), 2.57 (m, 1H), 1.14 (t, J=7.2 Hz, 3H)

Example 12: N-(4-chloro-2-methyl-5-(trifluoromethyl)phenyl)-2-(5-ethyl-6-(4-(3-hydroxypicolinoyl)piperazin-1-yl)-2-morpholino-7-oxo-[1,2,4]triazolo[1,5-a]pyrimidin-4 (7H)-yl)acetamide

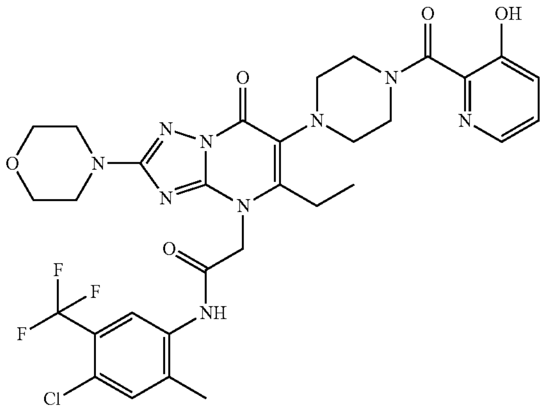 [SMILES: CCc1c(N2CCN(C(=O)c3ncccc3O)CC2)c(=O)n2nc(N3CCOCC3)nc2n1CC(=O)Nc1cc(C(F)(F)F)c(Cl)cc1C]

3-Hydroxypicolinic acid (84.0 mg, 605 μmol) was dissolved in DMF (8 mL) and then N-(4-chloro-2-methyl-5-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide·HCl (Intermediate I) (250 mg, 404 μmol), EDC·HCl (116 mg, 605 μmol), DIPEA (423 μL, 2.42 mmol) and HOBt (82.0 mg, 605 μmol) were added at 0° C. and stirred at RT for 16 hours. The RM was partially concentrated and diluted with water, extracted with EtOAc, washed with aq sat $NaHCO_3$ and brine and the combined organic layers were dried over $Na_2SO_4$, filtered and concentrated under reduced pressure. The crude product was sonicated in ACN and MeOH (1:1) (5 mL) and then filtered. The obtained solid was washed with EtOAc and pentane and dried to give the title compound as an off-white solid.

LC-MS: Rt=1.00 min; MS m/z $[M+H]^+$ 704.6/706.5, m/z $[M-H]^-$ 702.4/704.4; UPLC-MS 1

LC-MS: Rt=4.94 min; MS m/z $[M+H]^+$ 704.2/706.2, m/z $[M-H]^-$ 702.3/704.3; UPLC-MS 2

$^1$H NMR (400 MHz, DMSO-$d_6$) δ 10.41 (s, br, 1H), 10.07 (s, br, 1H), 8.04 (m, 1H), 7.94 (s, 1H), 7.66 (s, 1H), 7.27 (m, 2H), 5.12 (s, 2H), 4.53 (m, 1H), 3.65 (m, 4H), 3.46 (m, 3H), 3.39 (m, 4H), 3.20 (m, 1H), 2.94 (m, 3H), 2.75 (m, 1H), 2.58 (m, 1H), 2.33 (s, 3H), 1.16 (t, J=7.4 Hz, 3H)

Example 13: rac-N-(5-chloro-2-methyl-4-(trifluoromethyl)phenyl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide

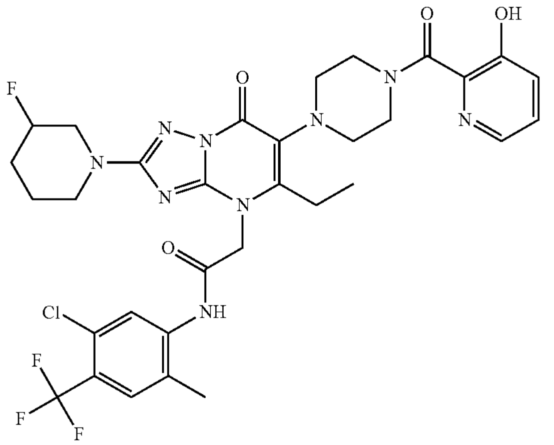 [SMILES: CCc1c(N2CCN(C(=O)c3ncccc3O)CC2)c(=O)n2nc(N3CCCC(F)C3)nc2n1CC(=O)Nc1cc(Cl)c(C(F)(F)F)cc1C]

Rac-N-(5-chloro-2-methyl-4-(trifluoromethyl)phenyl)-2-(5-ethyl-2-(3-fluoropiperidin-1-yl)-7-oxo-6-(piperazin-1-yl)-[1,2,4]triazolo[1,5-a]pyrimidin-4 (7H)-yl) acetamide·HCl (Intermediate K) (360 mg, 566 μmol), EDC·HCl (163 mg, 850 μmol), 3-hydroxypicolinic acid (118 mg, 850 μmol) and HOBt (115 mg, 850 μmol) were dissolved in DMF (5 mL) and then DIPEA (594 μL, 3.40 mmol) was added at 0° C. and stirred at RT for 16 hours. The RM was diluted with water and extracted with EtOAc and washed with aq sat $NaHCO_3$ and brine and the combined organic layers were dried over $Na_2SO_4$, filtered and concentrated under reduced pressure. The crude product was purified twice by column chromatography (2× Silica gel column: Silica 12 g, eluent DCM:MeOH 100:0 to 95:5) to give the title compound as an off white solid.

LC-MS: Rt=1.08 min; MS m/z $[M+H]^+$ 720.1/722.0 m/z $[M-H]^-$ 718.3/720.2; UPLC-MS 1

LC-MS: Rt=5.42 min; MS m/z $[M+H]^+$ 720.1/722.1, m/z $[M-H]^-$ 718.3/720.3; UPLC-MS 2

$^1$H NMR (400 MHz, DMSO-$d_6$) δ 10.38 (s, 1H), 10.08 (s, 1H), 8.06 (m, 1H), 7.92 (s, 1H), 7.76 (s, 1H), 7.29 (m, 2H), 5.15 (s, 2H), 4.75 (d, br, J, 47.5 Hz, 1H), 4.53 (m, 1H), 3.73 (m, 1H), 3.58 (m, 2H), 3.44 (m, 3H), 3.23 (m, 1H), 2.93 (m, 3H), 2.76 (m, 1H), 2.58 (m, 1H), 2.35 (s, 3H), 1.81 (m, 4H), 1.52 (m, 1H), 1.16 (t, J=7.2 Hz, 3H)

Example 14: rac-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

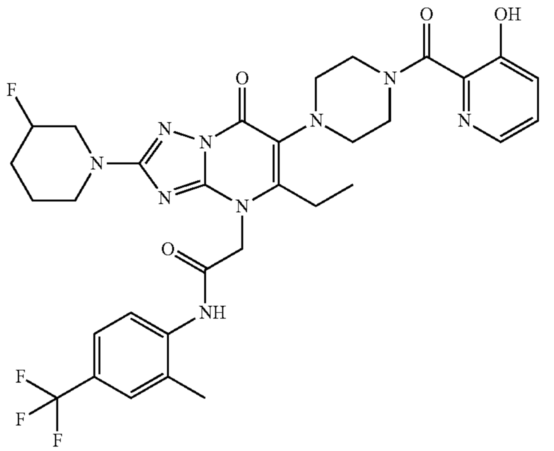 [SMILES: CCc1c(N2CCN(C(=O)c3ncccc3O)CC2)c(=O)n2nc(N3CCCC(F)C3)nc2n1CC(=O)Nc1ccc(C(F)(F)F)cc1C]

Rac-2-(5-ethyl-2-(3-fluoropiperidin-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide·HCl (Intermediate L) (300 mg, 499 μmol) was dissolved in DMF (4 mL). 3-hydroxypicolinic acid (174 mg, 1.25 mmol), EDC·HCl (239 mg, 1.25 mmol), HOBt (169 mg, 1.25 mmol) and DIPEA (436 μL, 2.50 mmol) were added at 0° C. and the RM was stirred at RT for 24 hours. The RM was diluted with water and extracted with 5% MeOH in DCM, washed with aq sat $NaHCO_3$, brine and the organic layer was dried and concentrated under reduced pressure. The crude product was purified by reverse phase preparative HPLC (RP-HPLC acidic 6: 40 to 50% B in 2 min, 50 to 70% B in 8 min) to give the title compound.

LC-MS: Rt=1.01 min; MS m/z $[M+H]^+$ 686.2, m/z $[M-H]^-$ 684.3; UPLC-MS 1

LC-MS: Rt=5.05 min; MS m/z $[M+H]^+$ 686.2, m/z $[M-H]^-$ 684.3; UPLC-MS 2

$^1$H NMR (400 MHz, DMSO-$d_6$) δ 10.32 (s, br, 1H), 9.99 (s, 1H), 8.06 (m, 1H), 7.69 (d, J=8.8 Hz, 1H), 7.62 (s, br, 1H), 7.53 (d, J=8.2 Hz, 1H), 7.28 (m, 2H), 5.13 (s, 2H), 4.75 (d, br, J=48.2 Hz, 1H), 4.53 (m, 1H), 3.72 (m, 1H), 3.58 (m, 2H), 3.43 (m, 3H), 3.21 (m, 2H), 2.93 (m, 3H), 2.75 (m, 1H), 2.58 (m, 1H), 2.34 (s, 3H), 1.82 (m, 3H), 1.53 (m, 1H), 1.16 (t, J=7.4 Hz, 3H)

Example 14a: (R)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide and Example 14b: (S)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

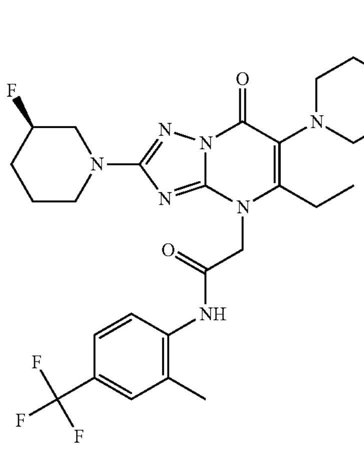

R-stereoisomer

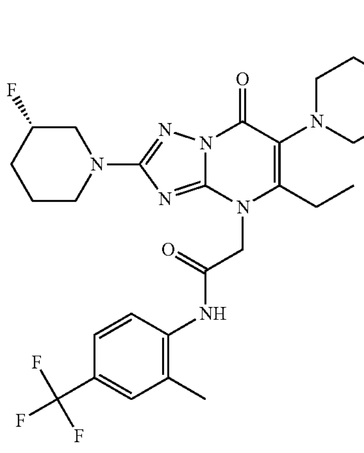

S-stereoisomer

Chiral separation of rac-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide: Preparative chiral HPLC (instrument: Agilent 1200 series, with single quad mass spectrometer; column: LUX CELLULOSE-4, 250 mm×21.2 mm; eluent: A=hexane, B=0.1% HCOOH in MeOH:EtOH 1:1; flow rate: 15.0 mL/min; detection: 210 nm; injection volume: 0.9 mL; Gradient: isocratic 70(A):30(B)).

Example 14a: The first eluting stereoisomer was stirred in $Et_2O$ (20 mL), filtered and the resultant solid was dried under vacuum to give the title compound.

Chiral HPLC (C-HPLC 3): Rt=6.17 min

LC-MS: Rt=1.01 min; MS m/z $[M+H]^+$ 686.2, m/z $[M-H]^-$ 684.3; UPLC-MS 1

LC-MS: Rt=5.05 min; MS m/z $[M+H]^+$ 686.2, m/z $[M-H]^-$ 684.3; UPLC-MS 2

$^1H$ NMR (400 MHz, DMSO-$d_6$) δ 10.36 (s, br, 1H), 10.00 (s, 1H), 8.05 (m, 1H), 7.69 (d, J=8.5 Hz, 1H), 7.62 (s, br, 1H), 7.53 (d, J=8.4 Hz, 1H), 7.28 (m, 2H), 5.13 (s, 2H), 4.85-4.65 (d, br, J=47.5 Hz, 1H), 4.53 (m, 1H), 3.72 (m, 1H), 3.65-3.35 (m, 6H), 3.20 (m, 1H), 2.94 (m, 3H), 2.75 (m, 1H), 2.57 (m, 1H), 2.34 (s, 3H), 1.81 (m, 3H), 1.52 (m, 1H), 1.16 (t, J=7.3 Hz, 3H)

Example 14b: The second eluting stereoisomer was purified by reverse phase preparative HPLC (RP-HPLC acidic 5: 20 to 30% B in 2 min, 30 to 60% B in 8 min) to give the title compound.

Chiral HPLC (C-HPLC 4): Rt=8.20 min

LC-MS: Rt=1.02 min; MS m/z $[M+H]^+$ 686.4, m/z $[M-H]^-$ 684.4; UPLC-MS 1

LC-MS: Rt=5.12 min; MS m/z $[M+H]^+$ 686.3, m/z $[M-H]^-$ 684.3; UPLC-MS 2

$^1H$ NMR (400 MHz, DMSO-$d_6$) δ 10.43 (s, br, 1H), 10.00 (s, 1H), 8.05 (m, 1H), 7.69 (d, J=8.5 Hz, 1H), 7.62 (s, br, 1H), 7.53 (d, J=8.5 Hz, 1H), 7.28 (m, 2H), 5.13 (s, 2H), 4.85-4.65 (d, br, J=47.7 Hz, 1H), 4.53 (m, 1H), 3.74 (m, 1H), 3.65-3.35 (m, 6H), 3.21 (m, 1H), 2.94 (m, 3H), 2.75 (m, 1H), 2.58 (m, 1H), 2.34 (s, 3H), 1.78 (m, 3H), 1.54 (m, 1H), 1.16 (t, J=7.4 Hz, 3H)

Example 15: rac-N-(2-chloro-4-(trifluoromethyl)phenyl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide

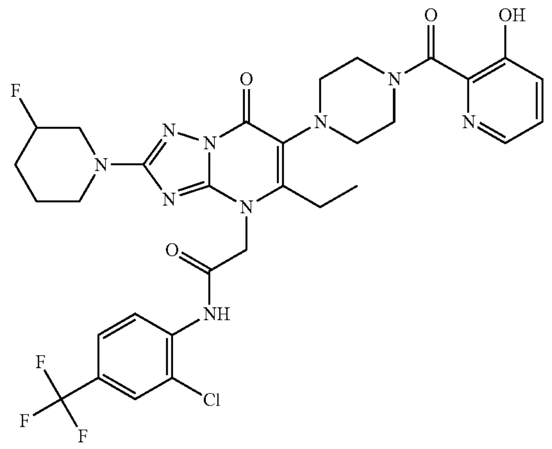

Rac-N-(2-chloro-4-(trifluoromethyl)phenyl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide (Intermediate M) (160 mg, 274 μmol) was suspended in DMF (2 mL) and 3-hydroxypicolinic acid (95.0 mg, 684 μmol), DIPEA (239 μL, 1.37 mmol), HOBt (92.0 mg, 684 μmol) and EDC·HCl (131 mg, 684 μmol) were added to the RM and it was stirred at RT for 12 hours. Water was added to the RM, the precipitate was filtered off and the obtained crude product was purified by reverse phase preparative HPLC (RP-HPLC neutral 2: 30 to 40% B in 2 min, 40 to 75% B in 9 min) to give the title compound.

LC-MS: Rt=1.06 min; MS m/z $[M+H]^+$ 706.3/708.2, m/z $[M-H]^-$ 704.3/706.4; UPLC-MS 1

LC-MS: Rt=5.34 min; MS m/z $[M+H]^+$ 706.2/708.1, m/z $[M-H]^-$ 704.3/706.3; UPLC-MS 2

$^1H$ NMR (400 MHz, DMSO-$d_6$) δ 10.36 (2s, 2H), 8.04 (m, 2H), 7.96 (s, br, 1H), 7.72 (d, J=8.7 Hz, 1H), 7.28 (m, 2H), 5.20 (s, 2H), 4.85-4.5 (d, br, J=48.6 Hz, 1H), 4.53 (m,

1H), 3.72 (m, 1H), 3.65-3.35 (m, 5H), 3.23 (m, 2H), 2.94 (m, 3H), 2.75 (m, 1H), 2.57 (m, 1H), 1.77 (m, 3H), 1.52 (m, 1H), 1.15 (t, J=7.2 Hz, 3H)

Example 15a: ((R)—N-(2-chloro-4-(trifluoromethyl) phenyl)-2-(5-ethyl-2-(3-fluoropiperidin-1-yl)-6-(4-(3-hydroxypicolinoyl)piperazin-1-yl)-7-oxo-[1,2,4] triazolo[1,5-a]pyrimidin-4 (7H)-yl)acetamide) or ((S)—N-(2-chloro-4-(trifluoromethyl)phenyl)-2-(5-ethyl-2-(3-fluoropiperidin-1-yl)-6-(4-(3-hydroxypicolinoyl)piperazin-1-yl)-7-oxo-[1,2,4]triazolo[1,5-a] pyrimidin-4 (7H)-yl)acetamide) and Example 15b: ((R)—N-(2-chloro-4-(trifluoromethyl)phenyl)-2-(5-ethyl-2-(3-fluoropiperidin-1-yl)-6-(4-(3-hydroxypicolinoyl)piperazin-1-yl)-7-oxo-[1,2,4]triazolo[1,5-a] pyrimidin-4 (7H)-yl)acetamide) or ((S)—N-(2-chloro-4-(trifluoromethyl)phenyl)-2-(5-ethyl-2-(3-fluoropiperidin-1-yl)-6-(4-(3-hydroxypicolinoyl) piperazin-1-yl)-7-oxo-[1,2,4]triazolo[1,5-a] pyrimidin-4 (7H)-yl)acetamide)

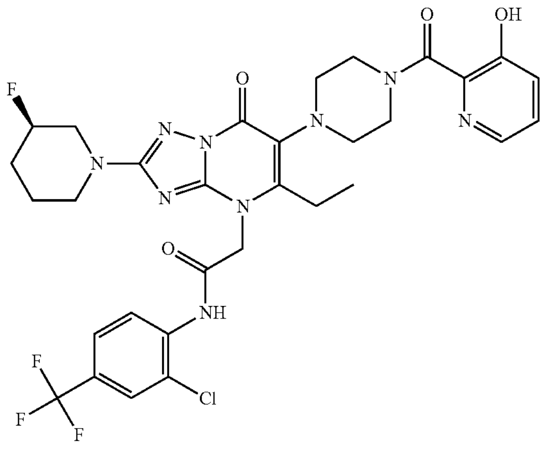

R-stereoisomer

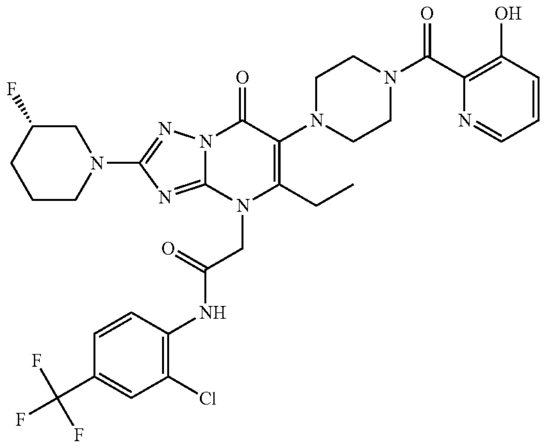 [SMILES: CCc1c(N2CCN(C(=O)c3ncccc3O)CC2)c(=O)n2nc(N3CCCC(F)C3)nc2n1CC(=O)Nc1ccc(C(F)(F)F)cc1Cl]

S-stereoisomer

Chiral separation of rac-N-(2-chloro-4-(trifluoromethyl) phenyl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide:

Preparative chiral HPLC (instrument: SEPIATEC SFC100; column: OVEN3 Chiralpak IB-N 250×30 mm 5 μm; eluent: A: 28% [MeOH+0.1% $NH_3$] B: 72% $scCO_2$; flow rate: 90.0 mL/min; detection: 236 nm; injection volume: 0.30 mL; Gradient: isocratic A: 28%, B: 72% $scCO_2$ Example 15a: The first eluting stereoisomer was concentrated under reduced pressure at 35° C. to give a white solid.

Chiral HPLC (C-HPLC 7): Rt=3.33 min, 99% ee

LC-MS: Rt=1.05 min; MS m/z $[M+H]^+$ 706.3/708.3, m/z $[M-H]^-$ 704.3/706.3; UPLC-MS 3

$^1H$ NMR (600 MHz, DMSO-$d_6$) δ 10.35 (2s, 2H), 8.05 (m, 1H), 8.03 (d, J=8.8 Hz, 1H), 7.96 (d, J=2.1 Hz, 1H), 7.71 (dd, J=2.2 Hz, 8.7 Hz, 1H), 7.28 (m, 2H), 5.20 (s, 2H), 4.80-4.65 (d, br, J=46.9 Hz, 1H), 4.53 (m, 1H), 3.72 (m, 1H), 3.65-3.35 (m, 5H), 3.29 (m, 1H), 3.19 (m, 1H), 2.93 (m, 3H), 2.75 (m, 1H), 2.58 (m, 1H), 1.95-1.7 (m, 3H), 1.52 (m, 1H), 1.15 (t, J=7.3 Hz, 3H)

Example 15b: The second eluting stereoisomer was concentrated under reduced pressure at 35° C. to give a beige solid.

Chiral HPLC (C-HPLC 7): Rt=3.89 min, 94% ee

LC-MS: Rt=1.05 min; MS m/z $[M+H]^+$ 706.3/708.3, m/z $[M-H]^-$ 704.3/706.2; UPLC-MS 3

$^1H$ NMR (600 MHz, DMSO-$d_6$) δ 10.35 (2s, 2H), 8.05 (m, 2H), 7.96 (d, J=2.1 Hz, 1H), 7.71 (dd, J=2.1 Hz, 8.8 Hz, 1H), 7.28 (m, 2H), 5.20 (s, 2H), 4.80-4.70 (d, br, J=47.8 Hz, 1H), 4.53 (m, 1H), 3.73 (m, 1H), 3.65-3.35 (m, 5H), 3.28 (m, 1H), 3.20 (m, 1H), 2.93 (m, 3H), 2.75 (m, 1H), 2.58 (m, 1H), 1.95-1.7 (m, 3H), 1.52 (m, 1H), 1.15 (t, J=7.3 Hz, 3H)

Example 16: rac-N-(2-chloro-6-(trifluoromethyl) pyridin-3-yl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide

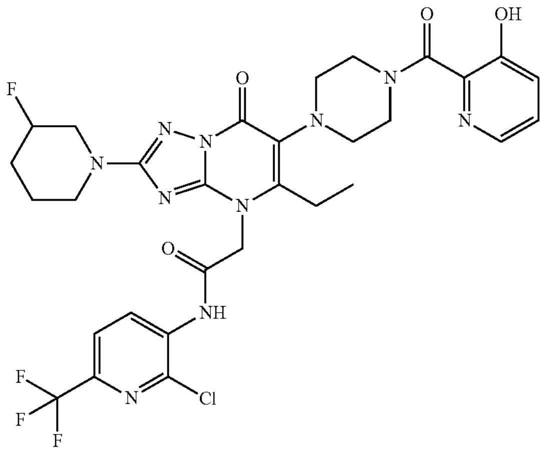 [SMILES: CCc1c(N2CCN(C(=O)c3ncccc3O)CC2)c(=O)n2nc(N3CCCC(F)C3)nc2n1CC(=O)Nc1ccc(C(F)(F)F)nc1Cl]

Rac-N-(2-chloro-6-(trifluoromethyl)pyridin-3-yl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide·HCl (Intermediate N) (100 mg, 161 μmol) and DIPEA (140 μL, 803 μmol) were dissolved in DCM (5 mL) and then 3-hydroxypicolinoyl chloride (Intermediate CV) (50.6 mg, 321 μmol) was added at 0° C. and stirred for 2 hours. The RM was diluted with DCM and washed with water and aq sat $NaHCO_3$ (2×20 mL), washed with water and brine. The organic layer was dried over $Na_2SO_4$, filtered and concentrated under reduced pressure. The crude product was purified by reverse phase preparative HPLC (RP-HPLC acidic 7: 30 to 40% B in 2 min, 40 to 50% B in 8 min) to give the title compound as a pale brown solid.

LC-MS: Rt=0.94 min; MS m/z $[M+H]^+$ 707.6/709.6, m/z $[M-H]^-$ 705.4/707.4; UPLC-MS 1

LC-MS: Rt=4.59 min; MS m/z $[M+H]^+$ 707.2/709.2, m/z $[M-H]^-$ 705.3/707.2; UPLC-MS 2

$^1$H NMR (400 MHz, DMSO-$d_6$) δ 10.54 (s, 1H), 10.37 (s, 1H), 8.54 (d, J=8.3 Hz, 1H), 8.06 (m, 1H), 7.96 (d, J=8.0 Hz, 1H), 7.28 (m, 2H), 5.25 (s, 2H), 4.85-4.65 (d, br, J=47.2 Hz, 1H), 4.53 (m, 1H), 3.73 (m, 1H), 3.60 (m, 1H), 3.46 (m, 4H), 3.23 (m, 2H), 2.94 (m, 3H), 2.75 (m, 1H), 2.57 (m, 1H), 1.79 (m, 3H), 1.52 (m, 1H), 1.15 (t, J=7.3 Hz, 3H)

Example 16a: (R)—N-(2-chloro-6-(trifluoromethyl)pyridin-3-yl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide and Example 16b: (S)—N-(2-chloro-6-(trifluoromethyl)pyridin-3-yl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide

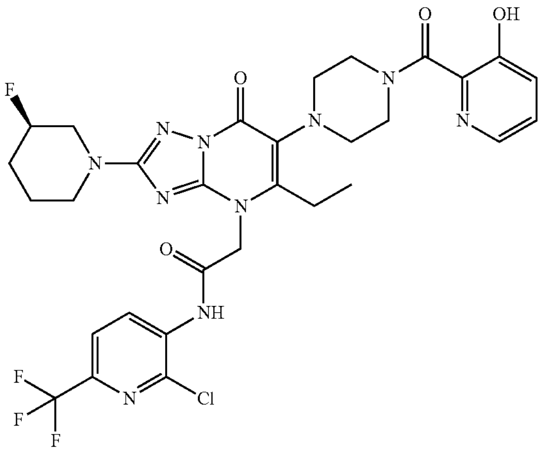

R-stereoisomer

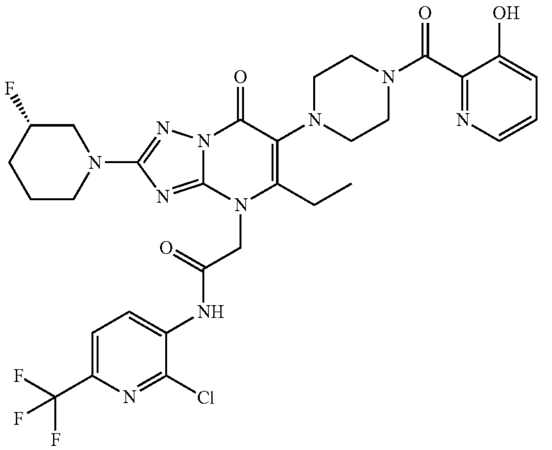

S-stereoisomer

Chiral separation of rac-N-(2-chloro-6-(trifluoromethyl)pyridin-3-yl)-2-(5-ethyl-2-(3-fluoropiperidin-1-yl)-6-(4-(3-hydroxypicolinoyl)piperazin-1-yl)-7-oxo-[1,2,4]triazolo[1,5-a]pyrimidin-4 (7H)-yl)acetamide:

Preparative chiral HPLC (instrument: Agilent 1200 series, with single quad mass spectrometer; column: CELLULOSE-4, 250 mm×21.2 mm; eluent: A=hexane, B=0.1% HCOOH in MeOH:EtOH 1:1; flow rate: 18.0 mL/min; detection: 210 nm; injection volume: 0.9 mL; Gradient: isocratic 70(A):30(B)). The chiral isomers which were separated and concentrated were taken, washed with n-hexane, decanted, dried and analysed.

Example 16a: First eluting stereoisomer, off white solid.

Chiral HPLC (C-HPLC 5): Rt=6.189 min

LC-MS: Rt=0.93 min; MS m/z $[M+H]^+$ 707.1/709.1, m/z $[M-H]^-$ 705.3/705.2; UPLC-MS 1

LC-MS: Rt=4.60 min; MS m/z $[M+H]^+$ 707.1/709.0, m/z $[M-H]^-$ 705.3/705.2; UPLC-MS 2

$^1$H NMR (400 MHz, DMSO-$d_6$) δ 10.63, (s, br, 2H), 8.53 (d, J=7.6 Hz, 1H), 8.05 (m, 1H), 7.89 (d, J=7.6 Hz, 1H), 7.28 (m, 2H), 5.19 (s, 2H), 4.85-4.65 (d, br, J=48.0 Hz, 1H), 4.53 (m, 1H), 3.71 (m, 1H), 3.65-3.15 (m, 7H), 2.93 (m, 3H), 2.75 (m, 1H), 2.58 (m, 1H), 1.81 (m, 3H), 1.52 (m, 1H), 1.15 (t, J=7.3 Hz, 3H)

Example 16b: Second eluting stereoisomer, off-white solid.

Chiral HPLC (C-HPLC 6): Rt=7.575 min

LC-MS: Rt=0.93 min; MS m/z $[M+H]^+$ 707.1/709.0, m/z $[M-H]^-$ 705.3/705.2; UPLC-MS 1

LC-MS: Rt=4.60 min; MS m/z $[M+H]^+$ 707.1/709.0, m/z $[M-H]^-$ 705.3/705.2; UPLC-MS 2

$^1$H NMR (400 MHz, DMSO-$d_6$) δ 10.43, (s, broad, 2H), 8.54 (d, J=8.2 Hz, 1H), 8.05 (m, 1H), 7.94 (d, J=8.2 Hz, 1H), 7.28 (m, 2H), 5.23 (s, 2H), 4.85-4.65 (d, br, J=48.3 Hz, 1H), 4.53 (m, 1H), 3.71 (m, 1H), 3.60 (m, 1H), 3.46 (m, 4H), 3.21 (m, 2H), 2.93 (m, 3H), 2.75 (m, 1H), 2.58 (m, 1H), 1.81 (m, 3H), 1.52 (m, 1H), 1.15 (t, J=7.3 Hz, 3H)

Example 17: 2-(5-ethyl-6-(4-(3-hydroxypicolinoyl)piperazin-1-yl)-7-oxo-2-(pyrrolidin-1-yl)-[1,2,4]triazolo[1,5-a]pyrimidin-4 (7H)-yl)-N-(2-methyl-4-(trifluoromethyl)phenyl)acetamide

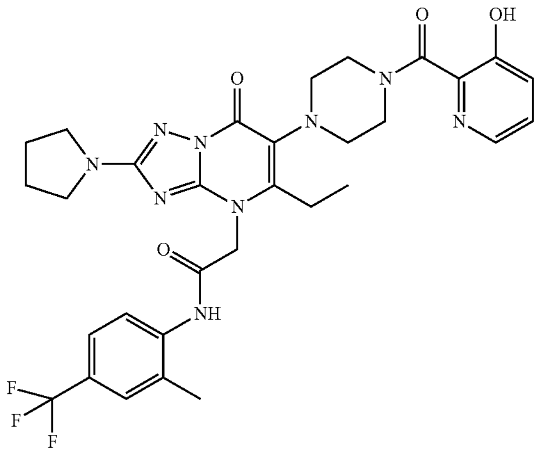 [SMILES: CCc1c(N2CCN(C(=O)c3ncccc3O)CC2)c(=O)n2nc(N3CCCC3)nc2n1CC(=O)Nc1ccc(C(F)(F)F)cc1C]

3-Hydroxypicolinic acid (183 mg, 1.32 mmol) was dissolved in DMF (10 mL) and then 2-(5-ethyl-7-oxo-6-(piperazin-1-yl)-2-(pyrrolidin-1-yl)-[1,2,4]triazolo[1,5-a]pyrimidin-4 (7H)-yl)-N-(2-methyl-4-(trifluoromethyl)phenyl)acetamide·HCl (Intermediate P) (500 mg, 879 μmol), EDC·HCl (337 mg, 1.76 mmol), DIPEA (767 μL, 4.39 mmol) and HOBt (237 mg, 1.76 mmol) were added at 0° C. and stirred at RT for 16 hours. The RM was diluted with water and extracted with 5% MeOH in DCM and washed with aq sat $NaHCO_3$ and brine and the combined organic layers were dried over $Na_2SO_4$, filtered and concentrated under reduced pressure. The crude product was purified twice by column chromatography (2× Silica gel column: Silica 12 g, eluent DCM:MeOH 100:0 to 98:2). The obtained solid was stirred with 5% ACN and MeOH in $Et_2O$ for 30 minutes, then sonicated for 10 minutes, filtered off, washed with n-pentane and dried to give the title compound as an off-white solid.

LC-MS: Rt=1.04 min; MS m/z $[M+H]^+$ 654.6, m/z $[M-H]^-$ 652.4; UPLC-MS 1

LC-MS: Rt=5.08 min; MS m/z $[M+H]^+$ 654.3, m/z $[M-H]^-$ 652.3; UPLC-MS 2

$^1H$ NMR (400 MHz, DMSO-$d_6$) δ 10.37 (s, 1H), 9.99 (s, 1H), 8.06 (m, 1H), 7.71 (d, J=8.4 Hz, 1H), 7.62 (m, 1H), 7.53 (d, J=8.4 Hz, 1H), 7.28 (m, 2H), 5.14 (s, 2H), 4.54 (m, 1H), 3.49 (m, 3H), 3.37 (m, 4H), 3.20 (m, 1H), 2.93 (m, 3H), 2.75 (m, 1H), 2.58 (m, 1H), 2.35 (s, 3H), 1.90 (m, 4H), 1.16 (t, J=7.1 Hz, 3H)

Example 18: N-(2-chloro-6-(trifluoromethyl)pyridin-3-yl)-2-(5-ethyl-6-(4-(3-hydroxypicolinoyl)piperazin-1-yl)-7-oxo-2-(pyrrolidin-1-yl)-[1,2,4]triazolo[1,5-a]pyrimidin-4 (7H)-yl)acetamide

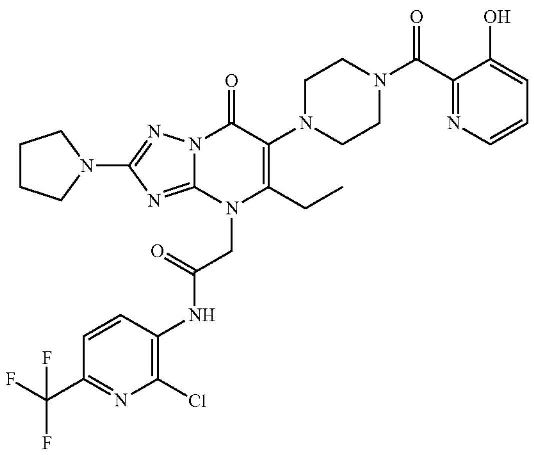 [SMILES: CCc1c(N2CCN(C(=O)c3ncccc3O)CC2)c(=O)n2nc(N3CCCC3)nc2n1CC(=O)Nc1ccc(C(F)(F)F)nc1Cl]

To the stirred solution of 3-hydroxypicolinic acid (166 mg, 1.19 mmol), EDC·HCl (228 mg, 1.19 mmol), HOBt (161 mg, 1.19 mmol) in DMF (3 mL) was added N-(2-chloro-6-(trifluoromethyl)pyridin-3-yl)-2-(5-ethyl-7-oxo-6-(piperazin-1-yl)-2-(pyrrolidin-1-yl)-[1,2,4]triazolo[1,5-a]pyrimidin-4 (7H)-yl)acetamide (Intermediate Q) (330 mg, 596 μmol) and DIPEA (624 μL, 3.57 mmol) and the RM was at RT for 16 hours. The RM was concentrated under reduced pressure and water was added. The resultant brown solid was filtered off and dried under vacuum. The crude product was purified by reverse phase preparative HPLC (RP-HPLC acidic 4: 35 to 40% B in 2 min, 40 to 45% B in 10 min) to give the title compound.

LC-MS: Rt=0.94 min; MS m/z $[M+H]^+$ 675.3/677.3, m/z $[M-H]^-$ 673.3/675.3; UPLC-MS 1

LC-MS: Rt=4.68 min; MS m/z $[M+H]^+$ 675.2/677.2, m/z $[M-H]^-$ 673.2/675.2; UPLC-MS 2

$^1H$ NMR (400 MHz, DMSO-$d_6$) δ 10.54 (s, br, 1H), 10.38 (s, br, 1H), 8.55 (d, J=8.4 Hz, 1H), 8.06 (m, 1H), 7.95 (d, J=8.4 Hz, 1H), 7.28 (m, 2H), 5.25 (s, 2H), 4.53 (m, 1H), 3.46 (m, 3H), 3.35 (m, 4H), 3.19 (m, 1H), 2.91 (m, 3H), 2.75 (m, 1H), 2.57 (m, 1H), 1.89 (m, 4H), 1.15 (t, 3H)

Example 19: N-(5-chloro-2-methyl-4-(trifluoromethyl)phenyl)-2-(5-ethyl-6-(4-(3-hydroxypicolinoyl)piperazin-1-yl)-7-oxo-2-(pyrrolidin-1-yl)-[1,2,4]triazolo[1,5-a]pyrimidin-4 (7H)-yl)acetamide

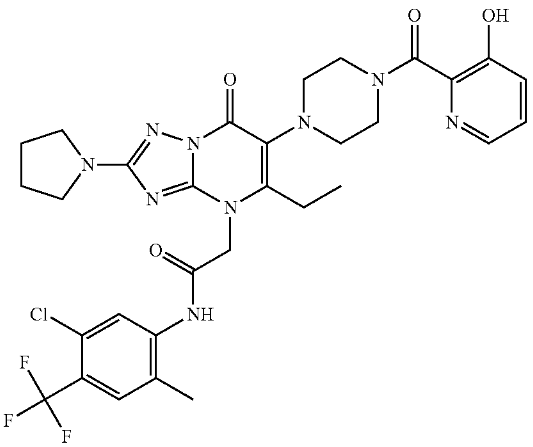 [SMILES: CCc1c(N2CCN(C(=O)c3ncccc3O)CC2)c(=O)n2nc(N3CCCC3)nc2n1CC(=O)Nc1cc(Cl)c(C(F)(F)F)cc1C]

To the stirred solution of N-(5-chloro-2-methyl-4-(trifluoromethyl)phenyl)-2-(5-ethyl-7-oxo-6-(piperazin-1-yl)-2-(pyrrolidin-1-yl)-[1,2,4]triazolo[1,5-a]pyrimidin-4 (7H)-yl)acetamide·HCl (Intermediate R) (150 mg, 249 μmol) in DCM (2 mL) was added 3-hydroxypicolinoyl chloride (Intermediate CV) (43.0 mg, 273 μmol) at 0° C., followed by dropwise addition of DIPEA (217 μL, 1.24 mmol). The RM was stirred at RT for 45 minutes. 3-Hydroxypicolinoyl chloride (Intermediate CV) (43.0 mg, 273 μmol) was added and the RM was stirred at RT for 12 hours. 3-Hydroxypicolinoyl chloride (Intermediate CV) (43.0 mg, 273 μmol) was added and the RM was stirred at RT for 16 hours. The RM was concentrated under reduced pressure.

The crude product was purified by reverse phase preparative HPLC (RP-HPLC neutral 3: 25 to 35% B in 2 min, 35 to 60% B in 8 min) to give the title compound.

LC-MS: Rt=1.11 min; MS m/z $[M+H]^+$ 688.7/690.6, m/z $[M-H]^-$ 686.4/688.3; UPLC-MS 1

LC-MS: Rt=5.52 min; MS m/z $[M+H]^+$ 688.2/690.2, m/z $[M-H]^-$ 686.3/688.3; UPLC-MS 2

$^1H$ NMR (400 MHz, DMSO-$d_6$) δ 10.37 (s, br, 1H), 10.08 (s, 1H), 8.06 (m, 1H), 7.95 (s, 1H), 7.75 (s, 1H), 7.28 (m, 2H), 5.17 (s, 2H), 4.53 (m, 1H), 3.46 (m, 3H), 3.36 (m, 4H), 3.20 (m, 1H), 2.93 (m, 3H), 2.75 (m, 1H), 2.58 (m, 1H), 2.35 (s, 3H), 1.90 (m, 4H), 1.15 (t, J=7.3 Hz, 3H)

Example 20: N-(2-chloro-6-(trifluoromethyl)pyridin-3-yl)-2-(2-(4-((2,2-difluoroethyl)(methyl)amino)piperidin-1-yl)-5-ethyl-6-(4-(3-hydroxypicolinoyl)piperazin-1-yl)-7-oxo-[1,2,4]triazolo[1,5-a]pyrimidin-4 (7H)-yl)acetamide

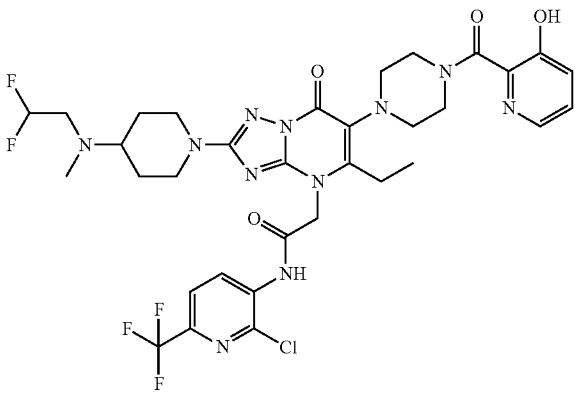 [SMILES: CCc1c(N2CCN(C(=O)c3ncccc3O)CC2)c(=O)n2nc(N3CCC(N(C)CC(F)F)CC3)nc2n1CC(=O)Nc1ccc(C(F)(F)F)nc1Cl]

To N-(2-chloro-6-(trifluoromethyl)pyridin-3-yl)-2-(2-(4-((2,2-difluoroethyl)(methyl)amino)piperidin-1-yl)-5-ethyl-7-oxo-6-(piperazin-1-yl)-[1,2,4]triazolo[1,5-a]pyrimidin-4 (7H)-yl)acetamide (Intermediate S) (310 mg, 309 μmol) in DCM (3 mL) at 5° C. was added 3-hydroxypicolinoyl chloride (Intermediate CV) (61.0 mg, 387 μmol) and the RM was stirred for 3 minutes. DIPEA (162 μL, 928 μmol) was added and the RM was allowed to warm to RT and stirred for 1 hour. Additional 3-hydroxypicolinoyl chloride (Intermediate CV) (61.0 mg, 387 μmol) and DIPEA (162 μL, 928 μmol) were added and the RM was further stirred at RT for 1 hour and 40 minutes.

The RM was partitioned between DCM (20 mL) and 5% aq $NaHCO_3$ (20 mL). The organic layer was separated by filtration through a phase separator. The aqueous layer was extracted with DCM (20 mL). The organic layers were combined and evaporated in vacuo to give a brown gum. The crude product was purified by reverse phase preparative HPLC (RP-HPLC acidic 1: 25 mL/min, 5 to 35% in 20 min with a plateau at 35% for 1 min). The product containing fractions were combined and basified with 5% aq $NaHCO_3$. Extracted with DCM (5×30 mL). The combined organic layers were filtered through a phase separator and evaporated in vacuo to give an off-white foam. Further purification by column chromatography (RediSep Column: Silica 4 g, eluent DCM:MeOH 100:0 to 94:6) afforded a colourless solid which was recrystallized from MeOH/water to give the title compound as a colourless powder.

LC-MS: Rt=0.73 min; MS m/z $[M+H]^+$ 782.4/784.3, m/z $[M-H]^-$ 780.5/782.5; UPLC-MS 1

$^1$H NMR (400 MHz, DMSO-$d_6$) δ 10.52 (s, 1H), 10.37 (s, 1H), 8.54 (d, J=8.2 Hz, 1H), 8.07 (m, 1H), 7.96 (d, J=8.6 Hz, 1H), 7.29 (m, 2H), 6.15-5.85 (m, br, 1H), 5.25 (s, 2H), 4.54 (m, 1H), 4.10 (m, 2H), 3.45 (m, 3H), 3.22 (m, 1H), 2.94 (m, 3H), 2.78 (m, 4H), 2.59 (m, 1H), 2.27 (s, 3H), 2.01 (m, 1H), 1.71 (m, 2H), 1.38 (m, 3H), 1.16 (t, J=7.4 Hz, 3H)

Example 21: 2-(2-(6-oxa-3-azabicyclo[3.1.1]heptan-3-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

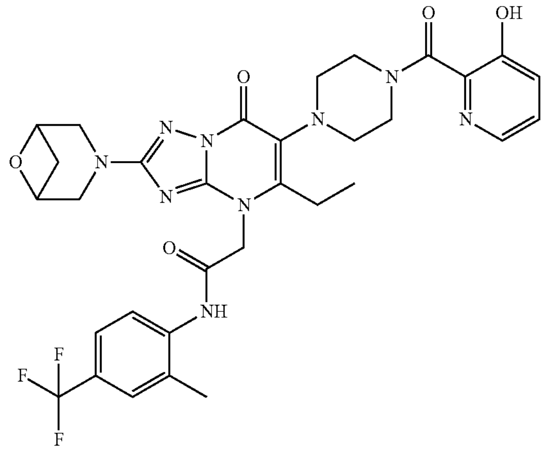 [SMILES: CCc1c(N2CCN(C(=O)c3ncccc3O)CC2)c(=O)n2nc(N3CC4CC(C3)O4)nc2n1CC(=O)Nc1ccc(C(F)(F)F)cc1C]

3-Hydroxypicolinic acid (141 mg, 992 μmol) was dissolved in DCM (5.5 mL) at RT under argon. 1-chloro-N,N,2-trimethylprop-1-en-1-amine (149 mg, 1.09 mmol) was added and the RM was stirred at RT for 1.25 hours. A solution of 2-(2-(6-oxa-3-azabicyclo[3.1.1]heptan-3-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate U) (278 mg, 496 μmol) in DCM (2.5 mL) and DIPEA (260 μL, 1.49 mmol) was added to the brown suspension. The resulting brown solution was stirred at RT for 3.5 hours. The RM was quenched with water (5 mL) and aq sat $NaHCO_3$ (5 mL). It was extracted 4 times with DCM (4×40 mL). The combined organic layers were washed twice with water, dried through a phase separator and concentrated under reduced pressure. The residue was adsorbed onto Isolute and purified by column chromatography (RediSep Column: Silica 24 g, eluent DCM:MeOH 100:0 to 90:10). The product containing fractions were combined and concentrated. The solid was submitted to SFC (SFC 5). The product containing fractions were combined and concentrated to give the title compound as an off-beige solid. A part of the solid was crystallized with MeOH (1.5 mL) and DCM (2 mL). The resulting solid was dried under HV to give the title compound.

LC-MS: Rt=0.97 min; MS m/z $[M+H]^+$ 682.4, m/z $[M-H]^-$ 680.3; UPLC-MS 3

$^1$H NMR (600 MHz, DMSO-$d_6$) δ 10.40 (s, 1H), 10.01 (s, 1H), 8.07 (m, 1H), 7.72 (d, J=8.1 Hz, 1H), 7.63 (s, br, 1H), 7.54 (d, J=8.3 Hz, 1H), 7.29 (m, 2H), 5.17 (s, 2H), 4.66 (m, 2H), 4.54 (m, 1H), 3.67 (d, J=12 Hz, 2H), 3.58 (d, J=11.8 Hz, 2H), 3.49 (m, 2H), 3.40 (m, 1H), 3.21 (m, 1H), 3.13 (m, 1H), 2.96 (m, 3H), 2.77 (m, 1H), 2.59 (m, 1H), 2.35 (s, 3H), 1.89 (m, 1H), 1.15 (t, J=7.6 Hz, 3H)

Example 22: 2-(2-(6-oxa-3-azabicyclo[3.1.1]heptan-3-yl)-6-(4-(3-hydroxypicolinoyl)piperazin-1-yl)-5-methyl-7-oxo-[1,2,4]triazolo[1,5-a]pyrimidin-4 (7H)-yl)-N-(2-fluoro-4-(trifluoromethyl)phenyl)acetamide

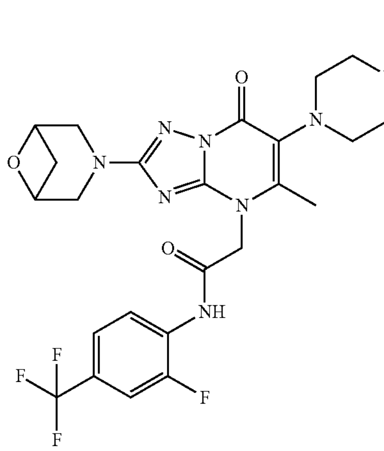

1-Chloro-N,N,2-trimethylprop-1-en-1-amine (141 mg, 1.06 mmol) was added to a solution of 3-hydroxypicolinic acid (134 mg, 961 μmol) in DCM (5 mL) under argon and the RM was stirred at RT for 2 hours, then 2-(2-(6-Oxa-3-azabicyclo[3.1.1]heptan-3-yl)-5-methyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide (Intermediate V) (441 mg, 481 μmol) dissolved in DCM (2.8 mL) was added, followed by DIPEA (420 μL, 2.40 mmol). The RM was stirred at RT for 2.2 hours. 0.5 equivalent of the above described activated 3-hydroxypicolinic acid solution was added again to the RM, followed by DIPEA (77.0 μL, 441 μmol). The RM was stirred at RT for 2 hours. The RM was quenched with water (6 mL) and aq sat $NaHCO_3$ (6 mL) was added. The mixture was extracted with DCM (4×40 mL). The organic layer was washed with aq sat $NaHCO_3$ and water, dried through a phase separator and concentrated under reduced pressure. The crude product was adsorbed onto Isolute and purified by column chromatography (RediSep Column: Silica 24 g, eluent DCM:MeOH 100:0 to 90:10). The product containing fractions were combined and concentrated under reduced pressure. The solid was further purified by reverse phase preparative HPLC (RP-HPLC acidic 1: 15 to 85% B in 20 min with a plateau at 85% for 1 min). The product containing fractions were combined and basified with a small amount of aq sat $NaHCO_3$. The ACN was removed under reduced pressure and the residue was extracted with DCM (3×40 mL). The combined organic layers were washed with water (10 mL), then dried through a phase separator and concentrated under reduced pressure to give the title compound as a beige solid.

LC-MS: Rt=0.93 min; MS m/z $[M+H]^+$ 672.4, m/z $[M-H]^-$ 670.4; UPLC-MS 3

$^1$H NMR (600 MHz, DMSO-$d_6$) δ 10.69 (s, br, 1H), 10.39 (s, br, 1H), 8.22 (t, J=8.1 Hz, 1H), 8.06 (t, J=3.1 Hz, 1H), 7.80 (dd, J=2.1 Hz, 10.9 Hz, 1H), 7.56 (dd, J=1.7 Hz, 8.4 Hz, 1H), 7.29 (m, 2H), 5.24 (s, 2H), 4.65 (m, 2H), 4.52 (m, 1H), 3.66 (m, 2H), 3.57 (m, 2H), 3.46 (m, 2H), 3.38 (m, 1H), 3.22 (m, 1H), 3.12 (m, 1H), 2.96 (m, 1H), 2.75 (m, 1H), 2.57 (m, 1H), 2.47 (s, 3H), 1.89 (m, 1H)

Example 23: 2-(2-((3R,4S)-3,4-difluoropyrrolidin-1-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

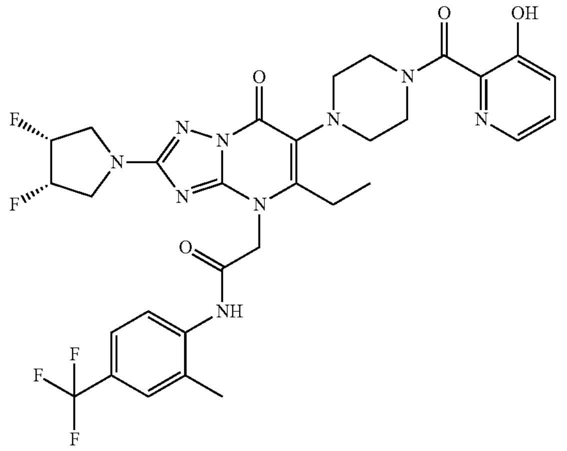 [SMILES: CCc1c(N2CCN(C(=O)c3ncccc3O)CC2)c(=O)n2nc(N3C[C@@H](F)[C@@H](F)C3)nc2n1CC(=O)Nc1ccc(C(F)(F)F)cc1C]

3-Hydroxypicolinic acid (152 mg, 1.07 mmol) was dissolved in DCM (6 mL) at RT under argon. 1-Chloro-N,N,2-trimethylprop-1-en-1-amine (161 mg, 1.18 mmol) was added and the RM was stirred at RT for 1.2 hours. A solution of 2-(2-((3R,4S)-3,4-difluoropyrrolidin-1-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate W) (430 mg, 537 μmol) in DCM (3.5 mL) and DIPEA (281 μL, 1.61 mmol) was added to the brown suspension. The resulting brown solution was stirred at RT for 1 hour. The RM was quenched with water (10 mL), aq sat $NaHCO_3$ (5 mL) and extracted with DCM (4×40 mL). The combined organic layers were washed twice with water, dried through a phase separator and concentrated under reduced pressure. The residue was adsorbed onto Isolute and purified by column chromatography (RediSep Column: Silica 40 g, eluent DCM:MeOH 100:0 to 90:10). The product containing fractions were combined and concentrated under reduced pressure to give the title compound. A part of the solid was crystallized from MeOH (1.5 mL) and DCM (2 mL). The resulting grey solid was suspended in $Et_2O$ and filtered, then dried under HV to give the title compound.

LC-MS: Rt=1.01 min; MS m/z $[M+H]^+$ 690.3, m/z $[M-H]^-$ 688.3; UPLC-MS 3

$^1$H NMR (600 MHz, DMSO-$d_6$) δ 10.39 (s, br, 1H), 10.01 (s, 1H), 8.06 (m, 1H), 7.72 (d, J=8.3 Hz, 1H), 7.64 (s, br, 1H), 7.54 (d, J=8.3 Hz, 1H), 7.29 (m, 2H), 5.45 (m, 1H), 5.36 (m, 1H), 5.16 (s, 2H), 4.54 (m, 1H), 3.81 (m, 2H), 3.57 (m, 2H), 3.47 (m, 2H), 3.39 (m, 1H), 3.21 (m, 1H), 2.95 (m, 3H), 2.76 (m, 1H), 2.58 (m, 1H), 2.36 (s, 3H), 1.16 (t, J=7.5 Hz, 3H)

Example 24a: ((R)-2-(6-(4-(4-chloro-3-hydroxypicolinoyl)piperazin-1-yl)-5-ethyl-2-(4-methoxycyclohex-1-en-1-yl)-7-oxo-[1,2,4]triazolo[1,5-a]pyrimidin-4 (7H)-yl)-N-(2-chloro-6-(trifluoromethyl)pyridin-3-yl)acetamide) or ((S)-2-(6-(4-(4-chloro-3-hydroxypicolinoyl)piperazin-1-yl)-5-ethyl-2-(4-methoxycyclohex-1-en-1-yl)-7-oxo-[1,2,4]triazolo[1,5-a]pyrimidin-4 (7H)-yl)-N-(2-chloro-6-(trifluoromethyl)pyridin-3-yl)acetamide) and Example 24b: ((R)-2-(6-(4-(4-chloro-3-hydroxypicolinoyl)piperazin-1-yl)-5-ethyl-2-(4-methoxycyclohex-1-en-1-yl)-7-oxo-[1,2,4]triazolo[1,5-a]pyrimidin-4 (7H)-yl)-N-(2-chloro-6-(trifluoromethyl)pyridin-3-yl)acetamide) or ((S)-2-(6-(4-(4-chloro-3-hydroxypicolinoyl)piperazin-1-yl)-5-ethyl-2-(4-methoxycyclohex-1-en-1-yl)-7-oxo-[1,2,4]triazolo[1,5-a]pyrimidin-4 (7H)-yl)-N-(2-chloro-6-(trifluoromethyl)pyridin-3-yl)acetamide)

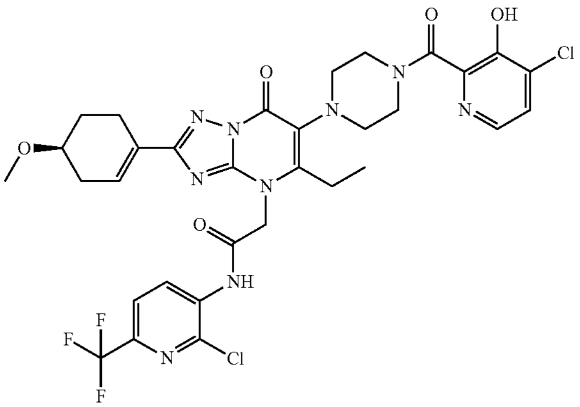

S-stereoisomer

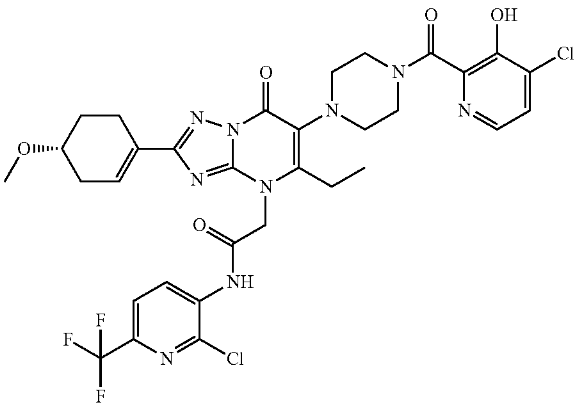

R-stereoisomer

To the stirred solution of N-(2-chloro-6-(trifluoromethyl)pyridin-3-yl)-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)acetamide (Intermediate Y) (300 mg, 504 μmol), 4-chloro-3-hydroxypicolinic acid (140 mg, 807 μmol), HOBt (136 mg, 1.01 mmol) and EDC·HCl (193 mg, 1.01 mmol) in DCM (20 mL) was added pyridine (122 μL, 1.51 mmol) at 0° C. The RM was stirred at RT for 16 hours. The RM was quenched with $NaHCO_3$ and extracted with DCM. The organic layer was dried over $Na_2SO_4$ and concentrated under reduced pressure. The crude product was purified by column chromatography (Silica gel column: Silica 4 g, eluent DCM:MeOH 100:0 to 98:2).

The residue was purified by preparative chiral HPLC (instrument: Agilent 1200 series, with single quad mass spectrometer; column: LUX CELLULOSE-4, 250 mm×21.1 mm, 5.0 μm; eluent: A=hexane, B=0.1% HCOOH in EtOH; flow rate: 15 mL/min; detection: 210 nm; injection volume: 0.9 mL; gradient: isocratic: 50(A):50(B)).

Example 24a: The product containing fractions were concentrated at 40° C. and washed with n-pentane (5×10 mL), decanted and dried to give the title compound as an off-white solid first eluting stereoisomer.

Chiral HPLC (C-HPLC 2): Rt=10.764 min

LC-MS: Rt=1.08 min; MS m/z $[M+H]^+$ 750.5/752.5, m/z $[M-H]^-$ 748.4/750.4; UPLC-MS 1

LC-MS: Rt=5.29 min; MS m/z $[M+H]^+$ 750.2/752.2, m/z $[M-H]^-$ 748.2/750.2; UPLC-MS 2

$^1H$ NMR (400 MHz, DMSO-$d_6$) δ 10.68 (s, br, 2H), 8.56 (d, J=8.1 Hz, 1H), 7.98 (d, J=5.6 Hz, 1H), 7.94 (d, J=8.1 Hz, 1H), 7.50 (d, J=5.1 Hz, 1H), 6.72 (m, 1H), 5.34 (s, 2H), 4.53 (m, 1H), 3.52 (m, 4H), 3.28 (m, 4H), 2.98 (m, 3H), 2.80 (m, 1H), 2.63 (m, 1H), 2.55 (m, 1H), 2.46 (m, 1H), 2.16 (m, 2H), 1.95 (m, 1H), 1.68 (m, 1H), 1.17 (t, J=7.3 Hz, 3H)

Example 24b: The product containing fractions were concentrated at 40° C. and washed with n-pentane (5×10 mL), decanted and dried to give the title compound as an off-white solid second eluting stereoisomer.

Chiral HPLC (C-HPLC 2): Rt=18.800 min

LC-MS: Rt=1.08 min; MS m/z $[M+H]^+$ 750.1/752.1, m/z $[M-H]^-$ 748.2/750.2; UPLC-MS 1

LC-MS: Rt=5.30 min; MS m/z $[M+H]^+$ 750.1/752.1, m/z $[M-H]^-$ 748.2/750.2; UPLC-MS 2

$^1H$ NMR (400 MHz, DMSO-$d_6$) δ 10.83 (s, br, 1H), 10.55 (s, br, 1H), 8.56 (d, J=8.2 Hz, 1H), 8.06 (d, J=5.3 Hz, 1H), 7.92 (d, J=8.2 Hz, 1H), 7.55 (d, J=5.3 Hz, 1H), 6.72 (m, 1H), 5.35 (s, 2H), 4.54 (m, 1H), 3.54 (m, 4H), 3.28 (m, 3H), 3.25 (m, 1H), 2.99 (m, 3H), 2.81 (m, 1H), 2.62 (m, 1H), 2.41 (m, 2H), 2.16 (m, 2H), 1.96 (m, 1H), 1.66 (m, 1H), 1.18 (t, J=7.3 Hz, 3H)

Example 25a: ((R)—N-(2-chloro-6-(trifluoromethyl)pyridin-3-yl)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)acetamide) or ((S)—N-(2-chloro-6-(trifluoromethyl)pyridin-3-yl)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)acetamide) and Example 25b: ((R)—N-(2-chloro-6-(trifluoromethyl)pyridin-3-yl)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)acetamide) or ((S)—N-(2-chloro-6-(trifluoromethyl)pyridin-3-yl)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)acetamide)

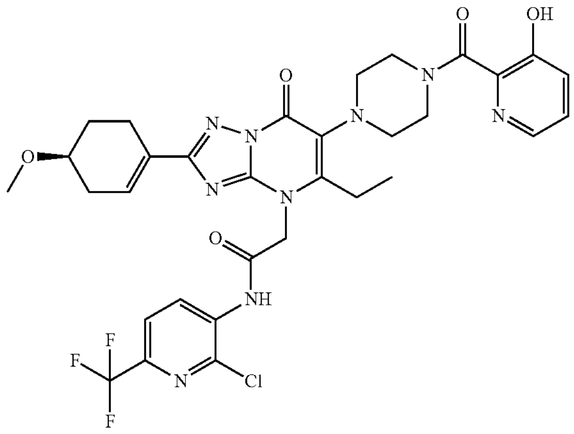

R-stereoisomer

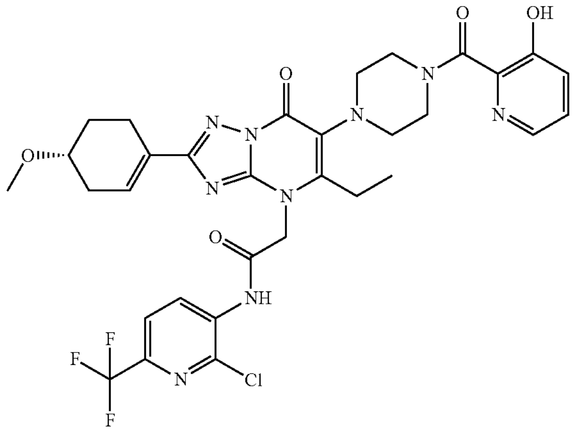

S-stereoisomer

N-(2-chloro-6-(trifluoromethyl)pyridin-3-yl)-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)acetamide·HCl (Intermediate Y) (120 mg, 190 μmol) and DIPEA (166 μL, 950 μmol) were dissolved in DCM (5 mL) and then 3-hydroxypicolinoyl chloride (Intermediate CV) (59.9 mg, 380 μmol) was added at 0° C. and stirred for 2 hours. 3-hydroxypicolinoyl chloride (Intermediate CV) (59.9 mg, 380 μmol) was added again and the reaction was continued under stirring for 12 hours. The RM was diluted with DCM and washed with water and aq $NaHCO_3$ (2×20 mL), washed with water and brine, dried over $Na_2SO_4$, filtered and concentrated. The crude product was combined with another experiment and purified by column chromatography (Silica gel column: Silica 4 g, eluent DCM:MeOH 100:0 to 99:1) then further purified by reverse phase preparative HPLC (RP-HPLC acidic 10: 40 to 50% B in 2 min, 50 to 60% B in 8 min) to give the title compound as an off-white solid.

The racemate was purified by preparative chiral HPLC (instrument: Agilent 1200 series, with single quad mass spectrometer; column: CELLULOSE-4, 250 mm×21.2 mm; eluent: A=hexane, B=0.1% HCOOH in MeOH:EtOH 1:1; flow rate: 20 mL/min; detection: 210 nm; injection volume: 0.9 mL; gradient: isocratic 60(A):40(B)).

Example 25a: First eluting stereoisomer, off-white solid.

Chiral HPLC (C-HPLC 1): Rt=10.070 min

LC-MS: Rt=0.98 min; MS m/z $[M+H]^+$ 716.5/718.6, m/z $[M-H]^-$ 714.3/716.3; UPLC-MS 1

LC-MS: Rt=4.76 min; MS m/z $[M+H]^+$ 716.2/718.2, m/z $[M-H]^-$ 714.2/716.2; UPLC-MS 2

$^1H$ NMR (400 MHz, DMSO-$d_6$) δ 10.46 (s, br, 2H), 8.56 (d, J=8.5 Hz, 1H), 8.05 (m, 1H), 7.90 (d, J=8.4 Hz, 1H), 7.28 (m, 2H), 6.72 (m, 1H), 5.30 (s, 2H), 4.54 (m, 1H), 3.47 (m, 4H), 3.27 (s, 3H), 3.21 (m, 1H), 2.96 (m, 3H), 2.79 (m, 1H), 2.59 (m, 3H), 2.43 (m, 1H), 2.14 (m, 1H), 1.95 (m, 1H), 1.67 (m, 1H), 1.17 (t, J=7.2 Hz, 3H)

Example 25b: Second eluting stereoisomer, off-white solid.

Chiral HPLC (C-HPLC 1): Rt=16.023 min

LC-MS: Rt=0.96 min; MS m/z $[M+H]^+$ 716.3/718.3, m/z $[M-H]^-$ 714.3/716.3; UPLC-MS 1

LC-MS: Rt=4.77 min; MS m/z $[M+H]^+$ 716.2/718.2, m/z $[M-H]^-$ 714.2/716.2; UPLC-MS 2

$^1H$ NMR (400 MHz, DMSO-$d_6$) δ 10.39 (s, br, 2H), 8.56 (d, J=8.0 Hz, 1H), 8.06 (m, 1H), 7.93 (d, J=8.1 Hz, 1H), 7.28 (m, 2H), 6.72 (m, 1H), 5.32 (s, 2H), 4.54 (m, 1H), 3.46 (m, 4H), 3.27 (s, 3H), 3.20 (m, 1H), 2.96 (m, 3H), 2.79 (m, 1H), 2.59 (m, 3H), 2.41 (m, 1H), 2.14 (m, 1H), 1.95 (m, 1H), 1.68 (m, 1H), 1.17 (t, J=7.1 Hz, 3H)

Example 26: rac-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(2-methyl-6-(trifluoromethyl)pyridin-3-yl)acetamide

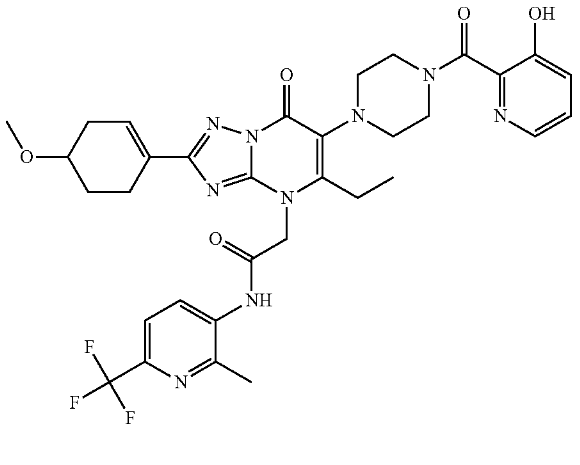 [SMILES: CCc1c(N2CCN(C(=O)c3ncccc3O)CC2)c(=O)n2nc(C3=CCC(OC)CC3)nc2n1CC(=O)Nc1ccc(C(F)(F)F)nc1C]

4-Chloro-3-hydroxypicolinic acid (118 mg, 851 μmol) was dissolved in DMF (5 mL) and then rac-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide·HCl (Intermediate Z) (260 mg, 425 μmol), EDC·HCl (163 mg, 851 μmol), DIPEA (372 μL, 2.13 mmol) and HOBt (115 mg, 851 μmol) were added at 0° C. and the RM was stirred at RT for 14 hours. The RM was diluted with water and extracted with 5% MeOH in DCM and washed with aq sat $NaHCO_3$, brine and the combined organic layers were dried over $Na_2SO_4$, filtered and concentrated under reduced pressure. The crude product was purified by reverse phase preparative HPLC (RP-HPLC acidic 5: 30 to 40% B in 2 min, 40 to 50% B in 8 min) to give the title compound.

LC-MS: Rt=0.90 min; MS m/z $[M+H]^+$ 696.3, m/z $[M-H]^-$ 694.3; UPLC-MS 1

LC-MS: Rt=4.38 min; MS m/z $[M+H]^+$ 696.3, m/z $[M-H]^-$ 694.4; UPLC-MS 2

$^1H$ NMR (400 MHz, DMSO-$d_6$) δ 10.26 (m, 2H), 8.19 (d, J=8.3 Hz, 1H), 8.06 (m, 1H), 7.72 (d, J=8.2 Hz, 1H), 7.28 (m, 2H), 6.72 (m, 1H), 5.27 (s, 2H), 4.54 (m, 1H), 3.47 (m, 4H), 3.28 (m, 4H), 2.98 (m, 3H), 2.80 (m, 1H), 2.57 (m, 6H), 2.15 (m, 1H), 1.96 (m, 1H), 1.68 (m, 1H), 1.19 (t, J=7.5 Hz, 3H)

Example 27: N-(2-chloro-6-(trifluoromethyl)pyridin-3-yl)-2-(2-(5,6-dihydro-1,4-dioxin-2-yl)-5-ethyl-6-(4-(3-hydroxypicolinoyl)piperazin-1-yl)-7-oxo-[1,2,4]triazolo[1,5-a]pyrimidin-4 (7H)-yl)acetamide

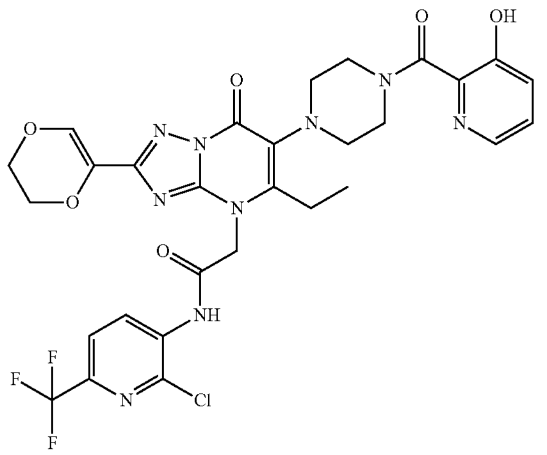 [SMILES: CCc1c(N2CCN(C(=O)c3ncccc3O)CC2)c(=O)n2nc(C3=COCCO3)nc2n1CC(=O)Nc1ccc(C(F)(F)F)nc1Cl]

N-(2-chloro-6-(trifluoromethyl)pyridin-3-yl)-2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)acetamide (Intermediate AA) (492 mg, 692 μmol) was dissolved in DCM (7 mL) at 0° C. under argon. 3-Hydroxypicolinoyl chloride (Intermediate CV) (163 mg, 1.04 mmol) was added to the suspension, followed by slow addition of DIPEA (483 μL, 2.77 mmol) and the solution was stirred at RT for 1.5 hours. 3-Hydroxypicolinoyl chloride (Intermediate CV) (25.0 mg, 159 μmol) and DIPEA (320 μL, 1.84 mmol) were added again and the RM was continued stirring at RT for 2.3 hours. The reaction was quenched by addition of water (5 mL) and aq sat $NaHCO_3$ (5 mL). Then it was extracted 4 times with DCM (4×40 mL). The organic layer was washed with water (5 mL), aq sat $NaHCO_3$ (5 mL) and water again (10 mL). The organic layer was dried through a phase separator and concentrated under reduced pressure. The residue was adsorbed onto Isolute and purified by column chromatography (RediSep Column: Silica 40 g Gold, eluent DCM:MeOH 100:0 to 90:10). The product containing fractions were combined and concentrated under reduced pressure. The resulting solid was purified by reverse phase preparative HPLC (RP-HPLC acidic 1: 15 to 85% in 20 min with a plateau at 85% for 1 min). The product containing fractions were combined, basified with aq sat $NaHCO_3$ (5 mL). The ACN was removed under reduced pressure. The aqueous layer was washed 4 times with DCM (4×35 mL). The combined organic layers were washed with water (10 mL), dried through a phase separator and concentrated under reduced pressure to give the title compound as a white solid.

LC-MS: Rt=0.87 min; MS m/z $[M+H]^+$ 690.3/692.3, m/z $[M-H]^-$ 688.1/690.1; UPLC-MS 1

Example 28: N-(2-chloro-6-(trifluoromethyl)pyridin-3-yl)-2-(2-(3,4-dihydro-2H-pyran-6-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

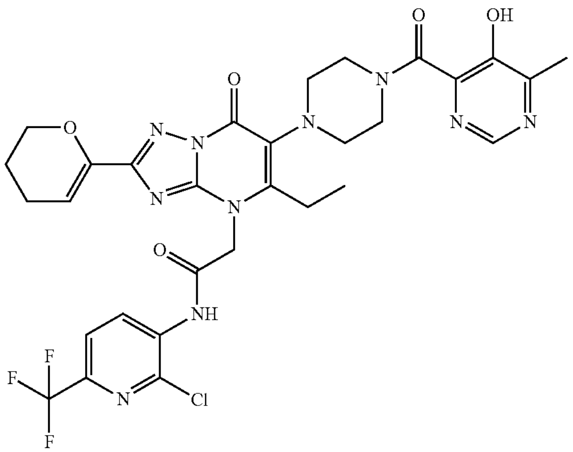 [SMILES: CCc1c(N2CCN(C(=O)c3ncnc(C)c3O)CC2)c(=O)n2nc(C3=CCCCO3)nc2n1CC(=O)Nc1ccc(C(F)(F)F)nc1Cl]

Step 1: N-(2-chloro-6-(trifluoromethyl)pyridin-3-yl)-2-(2-(3,4-dihydro-2H-pyran-6-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)acetamide To the stirred solution of 5-methoxy-6-methylpyrimidine-4-carboxylic acid (Intermediate CW) (133 mg, 794 μmol) in DCM (9 mL) at 0° C. were added EDC·HCl (203 mg, 1.06 mmol), pyridine (128 μL, 1.59 mmol) and HOBt (143 mg, 1.06 mmol) and the RM was stirred at 0° C. for 10 minutes, then was added N-(2-chloro-6-(trifluoromethyl)pyridin-3-yl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)acetamide (Intermediate AC) (300 mg, 529 μmol) and the RM was stirred at RT for 16 hours. The RM was diluted with DCM and washed with aq sat $NaHCO_3$, washed with water and the combined organic layers were dried over $Na_2SO_4$, concentrated and dried. The crude product was purified by column chromatography (Silica gel column: Silica 12 g, eluent DCM:MeOH 100:0 to 99:1) to give the title compound.

LC-MS: Rt=1.51 min; MS m/z $[M+H]^+$ 717.2/719.2; UPLC-MS 11

Step 2: N-(2-chloro-6-(trifluoromethyl)pyridin-3-yl)-2-(2-(3,4-dihydro-2H-pyran-6-yl)-5-ethyl-6-(4-(5-hydroxy-6-methylpyrimidine-4-carbonyl)piperazin-1-yl)-7-oxo-[1,2,4]triazolo[1,5-a]pyrimidin-4(7H)-yl)acetamide To the stirred solution of N-(2-chloro-6-(trifluoromethyl)pyridin-3-yl)-2-(2-(3,4-dihydro-2H-pyran-6-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl) acetamide (250 mg, 310 μmol) in DMF (3 mL) was added LiCl (132 mg, 3.10 mmol) and the RM was heated at 150° C. for 3 hours. LiCl (132 mg, 3.10 mmol) was added again and the RM was heated at 150° C. for 4 hours. The RM was quenched with water and extracted with 10% MeOH in DCM (3×50 mL) and dried over $Na_2SO_4$, filtered, concentrated and dried. The crude product was purified by column chromatography (Silica gel column: Silica 12 g, eluent DCM:MeOH 100:0 to 98:2). The residue was purified by reverse phase preparative HPLC (RP-HPLC acidic 4: 15 to 25% B in 2 min, 25 to 55% B in 7 min) and the product containing fractions were concentrated below 40° C. and dried to give the title compound as an off-white solid.

LC-MS: Rt=0.97 min; MS m/z $[M+H]^+$ 703.2/705.2, m/z $[M-H]^-$ 701.3/703.2; UPLC-MS 1

LC-MS: Rt=4.73 min; MS m/z $[M+H]^+$ 703.2/705.1, m/z $[M-H]^-$ 701.3/703.2; UPLC-MS 2

$^1$H NMR (400 MHz, DMSO-$d_6$) δ 10.52 (s, br, 1H), 10.25 (s, br, 1H), 8.57 (m, 2H), 7.95 (d, J=8.3 Hz, 1H), 5.86 (m, 1H), 5.35 (s, 2H), 4.52 (m, 1H), 4.10 (m, 2H), 3.49 (m, 3H), 3.25 (m, 1H), 2.99 (m, 3H), 2.81 (m, 1H), 2.64 (m, 1H), 2.44 (s, 3H), 2.17 (m, 2H), 1.84 (m, 2H), 1.18 (t, J=7.6 Hz, 3H)

Example 29: N-(2-chloro-6-(trifluoromethyl)pyridin-3-yl)-2-(2-(3,4-dihydro-2H-pyran-6-yl)-5-ethyl-6-(4-(3-hydroxypicolinoyl)piperazin-1-yl)-7-oxo-[1,2,4]triazolo[1,5-a]pyrimidin-4 (7H)-yl)acetamide

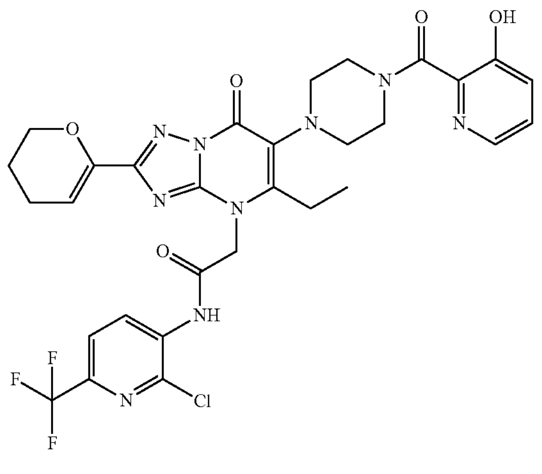 [SMILES: CCc1c(N2CCN(C(=O)c3ncccc3O)CC2)c(=O)n2nc(C3=CCCCO3)nc2n1CC(=O)Nc1ccc(C(F)(F)F)nc1Cl]

N-(2-chloro-6-(trifluoromethyl)pyridin-3-yl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)acetamide (Intermediate AC) (700 mg, 1.24 mmol) was suspended in DMF (12 mL), perfluorophenyl 3-hydroxypicolinate (Intermediate CT) (754 mg, 2.47 mmol) and $Et_3N$ (342 μL, 2.47 mmol) were added at RT and the RM was stirred at 80° C. for 16 hours. The RM was extracted three times with DCM. The combined organic layers were washed with brine, dried over $Na_2SO_4$ and concentrated under reduced pressure. The crude product was purified by column chromatography (Silica gel column: Silica 12 g, eluent hexane:EtOAc 100:0 to 60:40). The product containing fractions were concentrated and dried under HV to give the title compound.

LC-MS: Rt=0.94 min; MS m/z $[M+H]^+$ 688.5/690.5, m/z $[M-H]^-$ 686.2/688.2; UPLC-MS 1

LC-MS: Rt=4.58 min; MS m/z $[M+H]^+$ 688.2/690.2, m/z $[M-H]^-$ 686.2/688.2; UPLC-MS 2

$^1$H NMR (400 MHz, DMSO-$d_6$) δ 10.54 (s, 1H), 10.38 (s, 1H), 8.57 (d, J=8.5 Hz, 1H), 8.06 (m, 1H), 7.95 (d, J=8.5 Hz, 1H), 7.28 (m, 2H), 5.85 (m, 1H), 5.35 (s, 2H), 4.54 (m, 1H), 4.10 (m, 2H), 3.42 (m, 3H), 3.21 (m, 1H), 2.96 (m, 3H), 2.79 (m, 1H), 2.61 (m, 1H), 2.16 (m, 2H), 1.84 (m, 2H), 1.17 (t, J=7.3 Hz, 3H)

Example 30: 2-(6-(4-(4-chloro-3-hydroxypicolinoyl)piperazin-1-yl)-2-(3,4-dihydro-2H-pyran-6-yl)-5-ethyl-7-oxo-[1,2,4]triazolo[1,5-a]pyrimidin-4 (7H)-yl)-N-(2-chloro-6-(trifluoromethyl)pyridin-3-yl)acetamide

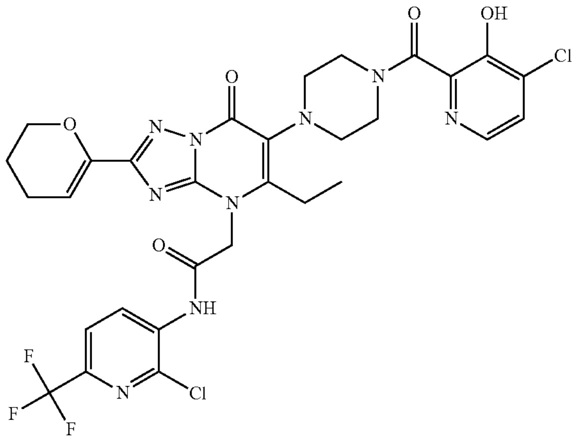 [SMILES: CCc1c(N2CCN(C(=O)c3nccc(Cl)c3O)CC2)c(=O)n2nc(C3=CCCCO3)nc2n1CC(=O)Nc1ccc(C(F)(F)F)nc1Cl]

To the stirred solution of 4-chloro-3-hydroxypicolinic acid (282 mg, 1.62 mmol) in DMF (5 mL) were added DIPEA (354 μL, 2.03 mmol) and PyAOP (635 mg, 1.22 mmol) at 0° C. After 10 minutes was added N-(2-chloro-6-(trifluoromethyl)pyridin-3-yl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)acetamide (Intermediate AC) (460 mg, 811 μmol) to the RM at 0° C. The RM was stirred at RT for 16 hours. Water was added and the mixture was extracted with EtOAc. The organic layer was dried over $Na_2SO_4$ and concentrated under reduced pressure. The crude product was purified by reverse phase preparative HPLC (RP-HPLC acidic 5: 20 to 30% B in 2 min, 30 to 60% B in 8 min) to give the title compound.

LC-MS: Rt=1.04 min; MS m/z $[M+H]^+$ 722.5/724.5/726.5, m/z $[M-H]^-$ 720.3/722.2/724.2; UPLC-MS 1

LC-MS: Rt=5.07 min; MS m/z $[M+H]^+$ 722.2/724.1/726.2, m/z $[M-H]^-$ 720.2/722.2/724.2; UPLC-MS 2

$^1$H NMR (400 MHz, DMSO-$d_6$) δ 10.83 (s, 1H), 10.55 (s, 1H), 8.58 (d, J=8.4 Hz, 1H), 8.07 (d, J=5.0 Hz, 1H), 7.96 (d, J=8.4 Hz, 1H), 7.56 (d, J=5.0 Hz, 1H), 5.86 (m, 1H), 5.36 (s, 2H), 4.54 (m, 1H), 4.10 (m, 2H), 3.54 (m, 3H), 3.24 (m,

1H), 2.98 (m, 3H), 2.81 (m, 1H), 2.65 (m, 1H), 2.16 (m, 2H), 1.84 (m, 2H), 1.18 (t, J=7.1 Hz, 3H)

Example 31: 2-(2-(3,4-dihydro-2H-pyran-6-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-6-(trifluoromethyl) pyridin-3-yl acetamide

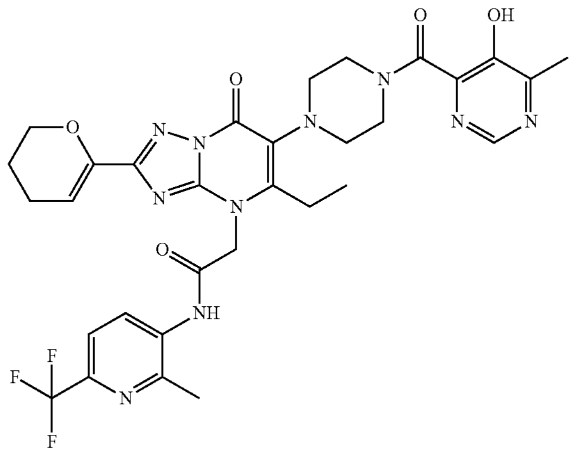 [SMILES: CCc1c(N2CCN(C(=O)c3ncnc(C)c3O)CC2)c(=O)n2nc(C3=CCCCO3)nc2n1CC(=O)Nc1ccc(C(F)(F)F)nc1C]

Step 1: 2-(2-(3,4-dihydro-2H-pyran-6-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(2-methyl-6-(trifluoromethyl)pyridin-3-yl)acetamide To the stirred solution of 2-(2-(3,4-dihydro-2H-pyran-6-yl)-5-ethyl-7-oxo-6-(piperazin-1-yl)-[1,2,4]triazolo[1,5-a] pyrimidin-4 (7H)-yl)-N-(2-methyl-6-(trifluoromethyl)pyridin-3-yl)acetamide (Intermediate AD) (600 mg, 1.10 mmol), 5-methoxy-6-methylpyrimidine-4-carboxylic acid (Intermediate CW) (222 mg, 1.32 mmol) and HATU (626 mg, 1.65 mmol) in DMF (15 mL) was added DIPEA (288 μL, 1.65 mmol) at 0° C. The RM was stirred at RT for 16 hours. The RM was concentrated under reduced pressure to give the title compound.

LC-MS: Rt=1.48 min; MS m/z $[M+H]^+$ 697.3; UPLC-MS 11

Step 2: 2-(2-(3,4-dihydro-2H-pyran-6-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-6-(trifluoromethyl)pyridin-3-yl)acetamide To the stirred solution of 2-(2-(3,4-dihydro-2H-pyran-6-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(2-methyl-6-(trifluoromethyl)pyridin-3-yl)acetamide (250 mg, 255 μmol) in DMF (2 mL) was added LiCl (108 mg, 2.55 mmol) and the RM was stirred at 200° C. for 1 hour in the MW. The RM was quenched with water and extracted with 10% MeOH in DCM (3×50 mL) and dried over $Na_2SO_4$, filtered, concentrated and dried. The crude product was purified by column chromatography (Silica gel column: Silica 12 g, eluent DCM:MeOH 100:0 to 98:2). The residue after the column chromatography was purified by reverse phase preparative HPLC (RP-HPLC acidic 10: 15 to 25% B in 2 min, 15 to 60% B in 10 min). The product containing fractions were concentrated to get 45 mg solid, which was combined with another batch, washed with 30% $Et_2O$ in n-hexane, decanted and dried to give the title compound as an off-white solid.

LC-MS: Rt=0.90 min; MS m/z $[M+H]^+$ 683.6, m/z $[M-H]^-$ 681.4; UPLC-MS 1

LC-MS: Rt=4.34 min; MS m/z $[M+H]^+$ 683.3, m/z $[M-H]^-$ 681.3; UPLC-MS 2

$^1$H NMR (400 MHz, DMSO-$d_6$) δ 10.22 (s, br, 2H), 8.57 (s, 1H), 8.20 (d, J=8.0 Hz, 1H), 7.73 (d, J=8.2 Hz, 1H), 5.86 (m, 1H), 5.27 (s, 2H), 4.52 (m, 1H), 4.10 (m, 2H), 3.50 (m, 3H), 3.27 (m, 1H), 2.99 (m, 3H), 2.81 (m, 1H), 2.65 (m, 1H), 2.58 (s, 3H), 2.44 (s, 3H), 2.18 (m, 2H), 1.85 (m, 2H), 1.19 (t, J=7.2 Hz, 3H)

Example 32: N-(2-chloro-4-(trifluoromethyl)phenyl)-2-(2-(3,4-dihydro-2H-pyran-6-yl)-5-ethyl-6-(4-(3-hydroxypicolinoyl)piperazin-1-yl)-7-oxo-[1,2,4] triazolo[1,5-a]pyrimidin-4 (7H)-yl)acetamide

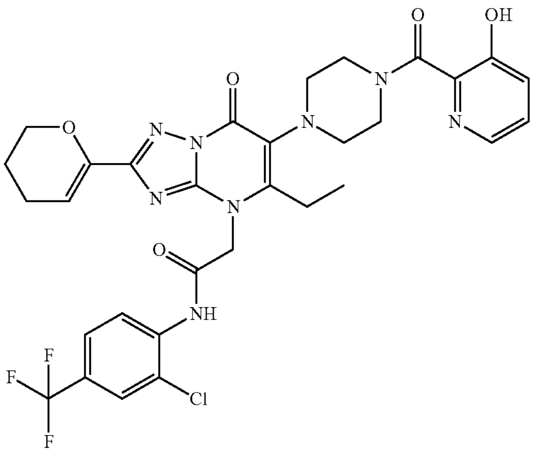 [SMILES: CCc1c(N2CCN(C(=O)c3ncccc3O)CC2)c(=O)n2nc(C3=CCCCO3)nc2n1CC(=O)Nc1ccc(C(F)(F)F)cc1Cl]

N-(2-chloro-4-(trifluoromethyl)phenyl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)acetamide (Intermediate AE) (590 mg with 80% purity, 833 μmol) was dissolved in DCM (10 mL) and 3-hydroxypicolinoyl chloride (Intermediate CV) (197 mg, 1.25 mmol) was added, followed by DIPEA (437 μL, 2.50 mmol). The RM was stirred at RT for 1.5 hours. 3-Hydroxypicolinoyl chloride (Intermediate CV) (36.0 mg, 228 μmol) was added. The RM was stirred at RT for 1 hour. DIPEA (1.00 mL, 5.73 mmol) was added. The RM was stirred at RT for 2 hours. 3-Hydroxypicolinoyl chloride (Intermediate CV) (116 mg, 736 μmol) was added. The RM was stirred at RT for 1 hour. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified in 5 portions by reverse phase preparative HPLC (5×RP-HPLC acidic 1: 5 to 100% B). All product containing fractions purer than 95% were combined, basified with aq sat $NaHCO_3$, extracted twice with DCM (2×15 mL), dried through a phase separator and concentrated under reduced pressure. The concentrated fractions were suspended in MeOH and sonicated for 1 minute.

Then it was filtered, the cake was washed with MeOH (500 µL) and dried under HV to give the title compound. All product containing fractions with the impurity at Rt=1.05 min were combined, basified with aq sat $NaHCO_3$, extracted twice with DCM (2×15 mL), dried through a phase separator and concentrated under reduced pressure. All product containing fractions with the impurity at Rt=1.13 min were combined, basified with aq sat $NaHCO_3$, extracted twice with DCM (2×15 mL), dried through a phase separator and concentrated under reduced pressure. Both impure fractions were combined and suspended in MeOH (10 mL). Then it was sonicated for 30 minutes and filtered. The cake was washed with a small amount of MeOH (10 mL) and dried under HV to give 90% pure product. The cake was suspended in MeOH (10 mL) and ACN (10 mL) and stirred at 40° C. for 2 hours. It was filtered, the cake was washed with MeOH (1 mL) and dried under HV to give the title compound.

Both pure fractions were dissolved in DCM (10 mL) and EtOH (10 mL) and left at RT for 5 days. The solid was filtered off and washed with a small amount of $Et_2O$. The cake was dried under HV to give the title compound.

LC-MS: Rt=1.08 min; MS m/z $[M+H]^+$ 687.2/689.2, m/z $[M-H]^-$ 685.4/687.5; UPLC-MS 1

$^1H$ NMR (400 MHz, DMSO-$d_6$) δ 10.38 (s, 1H), 10.33 (s, 1H), 8.07 (m, 2H), 7.96 (s, 1H), 7.71 (d, J=8.6 Hz, 1H), 7.29 (m, 2H), 5.87 (m, 1H), 5.31 (s, 2H), 4.55 (m, 1H), 4.10 (m, 2H), 3.43 (m, 3H), 3.23 (m, 1H), 2.97 (m, 3H), 2.80 (m, 1H), 2.62 (m, 1H), 2.17 (m, 2H), 1.84 (m, 2H), 1.18 (t, J=7.6 Hz, 3H)

Example 33: N-(4-chloro-6-(trifluoromethyl)pyridin-3-yl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)acetamide

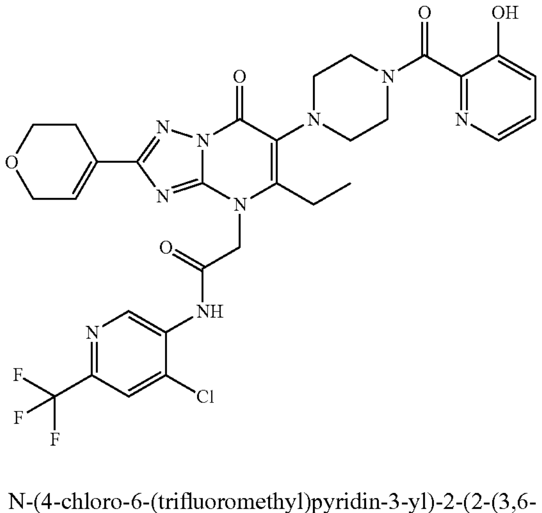

N-(4-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediates AG) (340 mg, 600 µmol) was suspended in DMF (10 mL) and perfluorophenyl 3-hydroxypicolinate (Intermediate CT) (366 mg, 1.20 mmol) and $Et_3N$ (166 µL, 1.20 mmol) were added and the RM was stirred at 70° C. for 3 hours. The crude product was purified by reverse phase preparative HPLC (RP-HPLC acidic 3: 10 to 20% B in 2 min, 20 to 60% B in 10 min) to give the title compound.

LC-MS: Rt=0.84 min; MS m/z $[M+H]^+$ 688.3/690.3, m/z $[M-H]^-$ 686.3/688.3; UPLC-MS 1

LC-MS: Rt=4.15 min; MS m/z $[M+H]^+$ 688.2/690.2, m/z $[M-H]^-$ 686.2/688.2; UPLC-MS 2

$^1H$ NMR (600 MHz, DMSO-$d_6$) δ 10.65 (s, 1H), 10.36 (s, 1H), 9.06 (s, 1H), 8.22 (s, 1H), 8.02 (m, 1H), 7.25 (m, 2H), 6.72 (m, 1H), 5.29 (s, 2H), 4.50 (m, 1H), 4.21 (m, 2H), 3.76 (m, 2H), 3.42 (m, 2H), 3.35 (m, 1H), 3.18 (m, 1H), 2.93 (m, 3H), 2.76 (m, 1H), 2.58 (m, 1H), 2.52 (m, 2H), 1.15 (t, J=7.6 Hz, 3H)

Example 34: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(4-methyl-6-(trifluoromethyl)pyridin-3-yl)acetamide

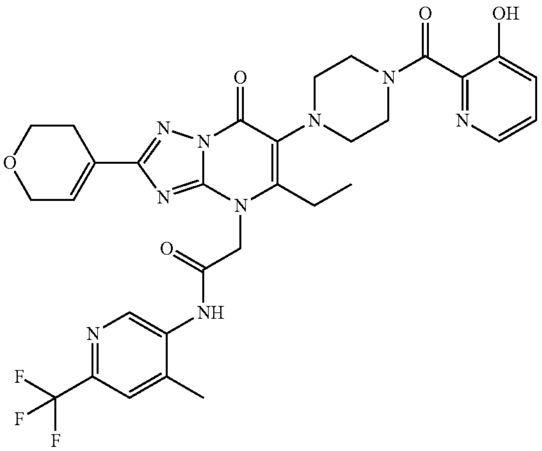 [SMILES: CCc1c(N2CCN(C(=O)c3ncccc3O)CC2)c(=O)n2nc(C3=CCOCC3)nc2n1CC(=O)Nc1cnc(C(F)(F)F)cc1C]

2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-methyl-6-(trifluoromethyl)pyridin-3-yl)acetamide (Intermediate AH) (450 mg, 823 µmol) was suspended in DMF (5 mL). Perfluorophenyl 3-hydroxypicolinate (Intermediate CT) (503 mg, 1.65 mmol) and $Et_3N$ (228 µL, 1.65 mmol) were added and the RM was stirred at 70° C. for 3 hours. The RM was concentrated under reduced pressure. The crude product was purified by reverse phase preparative HPLC (RP-HPLC acidic 11: 30 to 40% B in 2 min, 40 to 70% B in 10 min) to give the title compound.

LC-MS: Rt=0.77 min; MS m/z $[M+H]^+$ 668.3, m/z $[M-H]^-$ 666.3; UPLC-MS 1

LC-MS: Rt=3.79 min; MS m/z $[M+H]^+$ 668.3, m/z $[M-H]^-$ 666.3; UPLC-MS 2

$^1H$ NMR (400 MHz, DMSO-$d_6$) δ 10.36 (m, br, 2H), 8.78 (s, 1H), 8.05 (m, 1H), 7.85 (s, 1H), 7.28 (m, 2H), 6.83 (m, 1H), 5.25 (s, 2H), 4.55 (m, 1H), 4.26 (m, 2H), 3.81 (m, 2H), 3.45 (m, 3H), 3.22 (m, 1H), 3.00 (m, 3H), 2.80 (m, 1H), 2.62 (m, 1H), 2.50 (m, 2H), 2.38 (s, 3H), 1.20 (t, J=7.3 Hz, 3H)

Example 35: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-6-(trifluoromethyl)pyridin-3-yl)acetamide

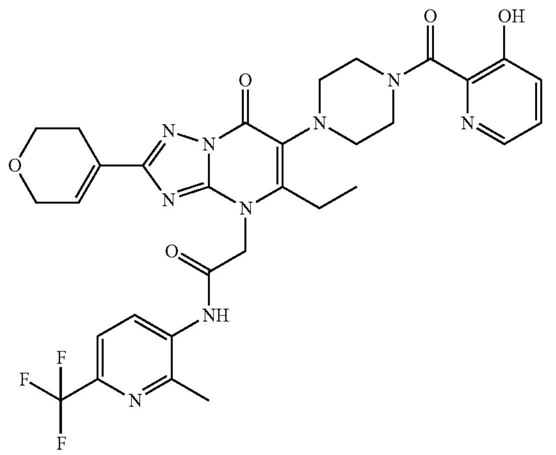 [SMILES: CCc1c(N2CCN(C(=O)c3ncccc3O)CC2)c(=O)n2nc(C3=CCOCC3)nc2n1CC(=O)Nc1ccc(C(F)(F)F)nc1C]

To a solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide·TFA (Intermediate AI) (400 mg, 606 μmol) in DMF (4 mL) was added $Et_3N$ (252 μL, 1.82 mmol), followed by dropwise addition of perfluorophenyl 3-hydroxypicolinate (Intermediate CT) (185 mg, 606 μmol) at 0° C. Then the RM was allowed to warm to RT and it was stirred at 80° C. for 14 hours. The crude product was concentrated under reduced pressure, extracted with water and purified by column chromatography (Silica gel column: Silica 12 g, eluent hexane:EtOAc 100:0 to 20:80). The product was recrystallized with ACN to give the title compound.

LC-MS: Rt=0.81 min; MS m/z $[M+H]^+$ 668.6, m/z $[M-H]^-$ 666.4; UPLC-MS 1

LC-MS: Rt=3.91 min; MS m/z $[M+H]^+$ 668.3, m/z $[M-H]^-$ 666.3; UPLC-MS 2

$^1$H NMR (400 MHz, DMSO-$d_6$) δ 10.38 (s, 1H), 10.23 (s, 1H), 8.19 (d, J=8.4 Hz, 1H), 8.06 (m, 1H), 7.73 (d, J=8.4 Hz, 1H), 7.28 (m, 2H), 6.82 (m, 1H), 5.28 (s, 2H), 4.55 (m, 1H), 4.26 (m, 2H), 3.80 (m, 2H), 3.44 (m, 3H), 3.22 (m, 1H), 2.97 (m, 3H), 2.80 (m, 1H), 2.62 (m, 1H), 2.57 (s, 3H), 2.52 (m, 2H), 1.19 (t, J=7.2 Hz, 3H)

Example 36: 2-(6-(4-(4-chloro-3-hydroxypicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-6-(trifluoromethyl)pyridin-3-yl)acetamide

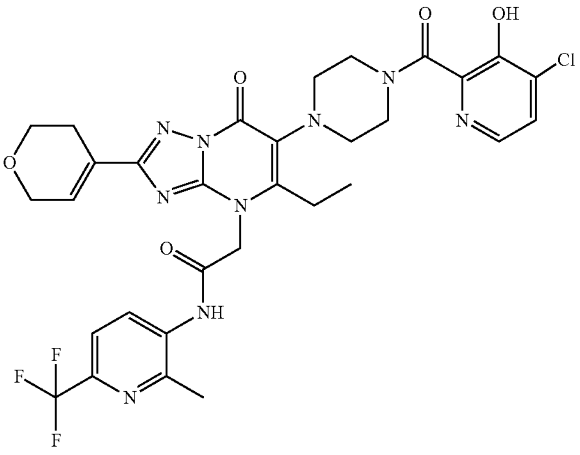 [SMILES: CCc1c(N2CCN(C(=O)c3nccc(Cl)c3O)CC2)c(=O)n2nc(C3=CCOCC3)nc2n1CC(=O)Nc1ccc(C(F)(F)F)nc1C]

To a solution of 4-chloro-3-hydroxypicolinic acid (423 mg, 2.44 mmol) in DCM (10 mL) were added DIPEA (500 μL, 2.86 mmol) and PyAOP (829 mg, 1.59 mmol). After the colour changed to dark brown, the RM was stirred for 10 minutes and then was added dropwise a solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide·TFA (Intermediate AI) (700 mg, 1.06 mmol) in DCM (10 mL) and DIPEA (500 μL, 2.86 mmol). The RM was stirred at RT for 18 hours. The RM was poured into aq sat $NaHCO_3$ and extracted several times with EtOAc. The combined organic layers were dried through a phase separator and concentrated. The crude product was purified by column chromatography (Silica gel column: Silica 12 g, eluent hexane:EtOAc 100:0 to 0:100). The product containing fractions were combined and concentrated under reduced pressure. Then washed with $Et_2O$. The solid was purified again by column chromatography (Silica gel column: Silica 12 g, eluent hexane:EtOAc 100:0 to 5:95) to give the title compound.

LC-MS: Rt=0.91 min; MS m/z $[M+H]^+$ 702.3/704.3, m/z $[M-H]^-$ 700.3/702.3; UPLC-MS 1

LC-MS: Rt=4.49 min; MS m/z $[M+H]^+$ 702.2/704.2, m/z $[M-H]^-$ 700.3/702.3; UPLC-MS 2

$^1$H NMR (400 MHz, DMSO-$d_6$) δ 10.83 (s, br, 1H), 10.22 (s, br, 1H), 8.19 (d, J=8.8 Hz, 1H), 8.06 (d, J=5.0 Hz, 1H), 7.73 (d, J=8.4 Hz, 1H), 7.55 (d, J=5.0 Hz, 1H), 6.82 (m, 1H), 5.28 (s, 2H), 4.54 (m, 1H), 4.26 (m, 2H), 3.80 (m, 2H), 3.50 (m, 3H), 3.15 (m, 1H), 3.00 (m, 3H), 2.81 (m, 1H), 2.65 (m, 1H), 2.57 (s, 3H), 2.48 (m, 2H), 1.19 (t, J=7.0 Hz, 3H)

Example 37: 2-(6-(4-(4-chloro-3-hydroxypicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(3-fluoro-2-methyl-4-(trifluoromethyl)phenyl)acetamide

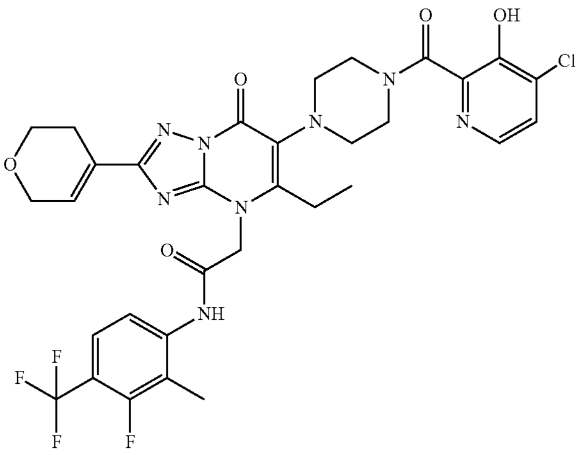 [SMILES: CCc1c(N2CCN(C(=O)c3nccc(Cl)c3O)CC2)c(=O)n2nc(C3=CCOCC3)nc2n1CC(=O)Nc1ccc(C(F)(F)F)c(F)c1C]

4-Chloro-3-hydroxypicolinic acid (233 mg, 1.34 mmol) was suspended in DCM (7 mL) and 1-chloro-N,N,2-trimethylprop-1-en-1-amine (190 μL, 1.44 mmol) was added. After 5 minutes most of the solid was dissolved. The light suspension was stirred at RT for 2.5 hours. The RM was cooled to 0° C. and 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide (Intermediate AJ) (431 mg, 765 μmol) was added, followed by DIPEA (601 μL, 3.44 mmol). The yellow solution turned into a black solution. The RM was stirred at RT for 20 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure and concentrated under reduced pressure. The crude product was purified by column chromatography (RediSep Column: Silica 40 g, eluent DCM:DCM/MeOH (8/2) 100:0 to 50:50). The product containing fractions were combined, concentrated under vacuum and dried under HV to afford a brown solid. Then it was purified in three portions by reverse phase preparative HPLC (RP-HPLC acidic 1: 20 to 75% B in 20 min with a plateau at 75% for 1 min, RP-HPLC acidic 1: 25 to 80% B in 20 min with a plateau at 80% for 1 min and RP-HPLC acidic 1: 40 to 80% B in 20 min with a plateau at 80% for 1 min). The product containing fractions were combined, basified with aq sat $NaHCO_3$, extracted twice with DCM (2×15 mL), dried through a phase separator and concentrated under reduced pressure. All impure fractions were combined, basified with aq sat $NaHCO_3$, extracted twice with DCM, dried through a phase separator and concentrated under reduced pressure. Then it was suspended in ACN (2 mL) and sonicated for 2 minutes, filtered, combined with the pure fractions and concentrated under reduced pressure to give the title compound. The solid was dissolved in EtOH (10 mL) and DCM (15 mL), filtered and left standing at RT for 3 days to crystallize. Then it was filtered and washed with $Et_2O$. The cake was dried under HV to give the title compound.

The sodium salt was prepared analogous to the general procedure.

LC-MS: Rt=1.11 min; MS m/z $[M+H]^+$ 719.4/721.4, m/z $[M-H]^-$ 717.5/719.5; UPLC-MS 1

$^1$H NMR (400 MHz, DMSO-$d_6$) δ 10.83 (s, 1H), 10.20 (s, 1H), 8.06 (d, J=5.1 Hz, 1H), 7.57 (m, 3H), 6.82 (m, 1H), 5.26 (s, 2H), 4.54 (m, 1H), 4.26 (m, 2H), 3.81 (m, 2H), 3.55 (m, 3H), 3.25 (m, 1H), 3.00 (m, 3H), 2.81 (m, 1H), 2.65 (m, 1H), 2.50 (m, 2H), 2.24 (s, 3H), 1.19 (t, J=7.4 Hz, 3H)

Example 38: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(3-fluoro-2-methyl-4-(trifluoromethyl)phenyl)acetamide

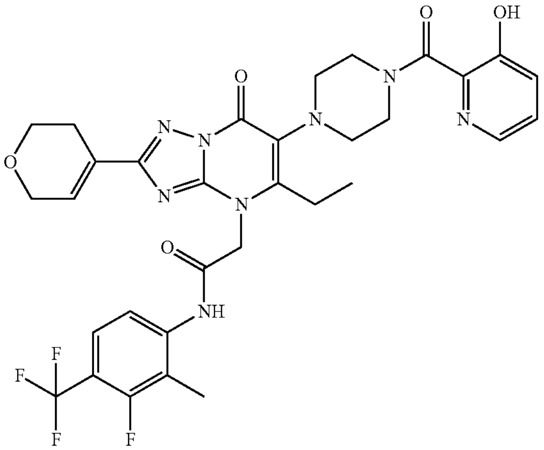 [SMILES: CCc1c(N2CCN(C(=O)c3ncccc3O)CC2)c(=O)n2nc(C3=CCOCC3)nc2n1CC(=O)Nc1ccc(C(F)(F)F)c(F)c1C]

2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide (Intermediate AJ) (504 mg, 894 μmol) and 3-hydroxypicolinoyl chloride (Intermediate CV) (254 mg, 1.61 mmol) were mixed in DCM (7 mL) and DIPEA (312 μL, 1.79 mmol) were added. The dark solution was stirred at RT for 1 hour. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure and concentrated under reduced pressure. The crude product was purified by column chromatography (RediSep Column: Silica 24 g, eluent DCM:DCM/MeOH (8/2) 100:0 to 35:65). The product containing fractions were combined, concentrated under vacuum and dried under HV to afford a white solid. The solid was dissolved in EtOH (5 mL) and DCM (15 mL) and left standing until it crystallized out to give the title compound.

LC-MS: Rt=1.02 min; MS m/z $[M+H]^+$ 685.3, m/z $[M-H]^-$ 683.4; UPLC-MS 1

$^1$H NMR (400 MHz, DMSO-$d_6$) δ 10.38 (s, 1H), 10.20 (s, 1H), 8.06 (m, 1H), 7.58 (m, 2H), 7.29 (m, 2H), 6.82 (m, 1H), 5.25 (s, 2H), 4.55 (m, 1H), 4.26 (m, 2H), 3.81 (m, 2H), 3.44 (m, 3H), 3.22 (m, 1H), 2.98 (m, 3H), 2.80 (m, 1H), 2.62 (m, 1H), 2.52 (m, 2H), 2.24 (s, 3H), 1.19 (t, J=7.3 Hz, 3H)

Example 39: 2-(6-(4-(4-chloro-3-hydroxypicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide

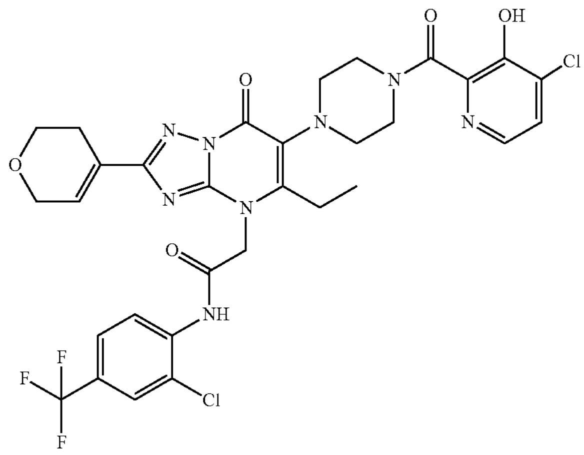 [SMILES: CCc1c(N2CCN(C(=O)c3nccc(Cl)c3O)CC2)c(=O)n2nc(C3=CCOCC3)nc2n1CC(=O)Nc1ccc(C(F)(F)F)cc1Cl]

The reaction was performed in 4 batches obtained as follows. 4-Chloro-3-hydroxypicolinic acid (400 mg, 2.31 mmol) was dissolved in DCM (36 mL) at RT under argon. 1-chloro-N,N,2-trimethylprop-1-en-1-amine (360 mg, 2.66 mmol) was added and the RM was stirred at RT for 2.5 hours. At 0° C. were added N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AK) (1.10 g, 1.58 mmol) and DIPEA (1.23 mL, 7.08 mmol). The resulting brown solution was stirred at RT for 1.3 hours. The combined RM from the 4 batches was quenched with water (40 mL) and aq sat $NaHCO_3$ (40 mL). It was extracted 4 times with DCM (4×200 mL). The combined organic layers were washed with water (50 mL) and brine (50 mL), dried through a phase separator and concentrated under reduced pressure. The residue was adsorbed onto Isolute and purified in 2 portions by column chromatography (RediSep Column: Silica 120 g Gold, eluent DCM:DCM/MeOH (1/1) 100:0 to 60:40) and (RediSep Column: Silica 120 g Gold, eluent DCM:DCM/MeOH (1/1) 100:0 to 90:10). The product containing fractions were combined and concentrated under reduced pressure to give the title compound as a beige solid.

LC-MS: Rt=1.13 min; MS m/z $[M+H]^+$ 721.4/723.4/725.4, m/z $[M-H]^-$ 719.5/721.5/723.5; UPLC-MS 1

$^1H$ NMR (400 MHz, DMSO-$d_6$) δ 10.83 (s, 1H), 10.35 (s, 1H), 8.06 (m, 2H), 7.96 (s, 1H), 7.71 (dd, J=2.1 Hz, 8.7 Hz, 1H), 7.55 (d, J=5.1 Hz, 1H), 6.83 (m, 1H), 5.32 (s, 2H), 4.54 (m, 1H), 4.25 (m, 2H), 3.80 (m, 2H), 3.53 (m, 3H), 3.26 (m, 1H), 2.99 (m, 3H), 2.82 (m, 1H), 2.65 (m, 1H), 2.52 (m, 2H), 1.19 (t, J=7.1 Hz, 3H)

Example 40: N-(2-chloro-4-(trifluoromethyl)phenyl)-2-(2-(3,6-dihydro-2H-pyran-4-yl)-5-ethyl-6-(4-(4-fluoro-3-hydroxypicolinoyl)piperazin-1-yl)-7-oxo-[1,2,4]triazolo[1,5-a]pyrimidin-4 (7H)-yl)acetamide

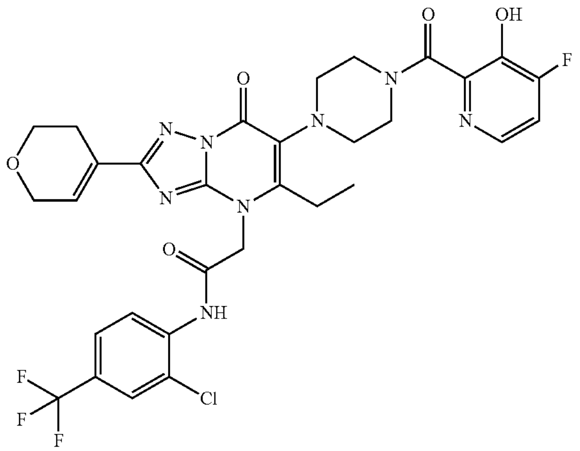 [SMILES: CCc1c(N2CCN(C(=O)c3nccc(F)c3O)CC2)c(=O)n2nc(C3=CCOCC3)nc2n1CC(=O)Nc1ccc(C(F)(F)F)cc1Cl]

Step 1: 2-(6-(4-(3-(benzyloxy)-4-fluoropicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide To a stirred solution of N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide·TFA (Intermediate AK) (300 mg, 441 μmol), 3-(benzyloxy)-4-fluoropicolinic acid (Intermediate CU) (115 mg, 463 μmol) and HATU (201 mg, 529 μmol) in DMF (10 mL) was added DIPEA (385 μL, 2.21 mmol) at RT and the RM was stirred at RT for 5 minutes. The RM was diluted with EtOAc/water, extracted twice with EtOAc and the combined organic extracts were dried over $Na_2SO_4$ and concentrated. The crude product was purified by column chromatography (RediSep Column: Silica 24 g, eluent DCM:DCM/MeOH (8/2) 100:0 to 50:50). The product containing fractions were combined and concentrated to afford a white foam.

LC-MS: Rt=1.23 min; MS m/z $[M+H]^+$ 795.3/797.3, m/z $[M-H]^-$ 793.4/795.4; UPLC-MS 1

Step 2: N-(2-chloro-4-(trifluoromethyl)phenyl)-2-(2-(3,6-dihydro-2H-pyran-4-yl)-5-ethyl-6-(4-(4-fluoro-3-hydroxypicolinoyl)piperazin-1-yl)-7-oxo-[1,2,4]triazolo[1,5-a]pyrimidin-4 (7H)-yl)acetamide To a stirred suspension of 2-(6-(4-(3-(benzyloxy)-4-fluoropicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (289 mg, 363 μmol) in DCM (10 mL) was added boron trichloride methyl sulfide complex (363 μL, 727 μmol) at RT and the RM was stirred at RT for 20 hours. The RM was quenched with MeOH. It was diluted in DCM/$NaHCO_3$, extracted twice with DCM and the combined organic extracts were washed with water and brine, dried over $Na_2SO_4$ and concentrated. The crude product was purified by column chromatography (RediSep Column: Silica 24 g, eluent DCM:

DCM/MeOH (8/2) 100:0 to 60:40). The product containing fractions were combined and concentrated to give an off-white solid. This solid was dissolved in EtOH (6 mL) at 50° C. and the RM was left at RT for 4 hours. A white solid was filtered to give the title compound.

The sodium salt was prepared analogous to the general procedure.

LC-MS: Rt=1.03 min; MS m/z $[M+H]^+$ 705.4/707.4, m/z $[M-H]^-$ 703.5/705.5; UPLC-MS 1

$^1$H NMR (400 MHz, DMSO-$d_6$) δ 10.80 (s, br, 1H), 10.36 (s, 1H), 8.06 (m, 2H), 7.96 (m, 1H), 7.71 (dd, J=2.1 Hz, 8.8 Hz, 1H), 7.34 (dd, J=5.3 Hz, 10.9 Hz, 1H), 6.83 (m, 1H), 5.31 (s, 2H), 4.54 (m, 1H), 4.25 (m, 2H), 3.80 (m, 2H), 3.46 (m, 3H), 3.23 (m, 1H), 2.98 (m, 3H), 2.80 (m, 1H), 2.63 (m, 1H), 2.51 (m, 2H), 1.18 (t, J=7.5 Hz, 3H)

Example 41: N-(2-chloro-4-(trifluoromethyl)phenyl)-2-(2-(3,6-dihydro-2H-pyran-4-yl)-5-ethyl-6-(4-(4-fluoro-3-hydroxy-6-methylpicolinoyl)piperazin-1-yl)-7-oxo-[1,2,4]triazolo[1,5-a]pyrimidin-4 (7H)-yl) acetamide

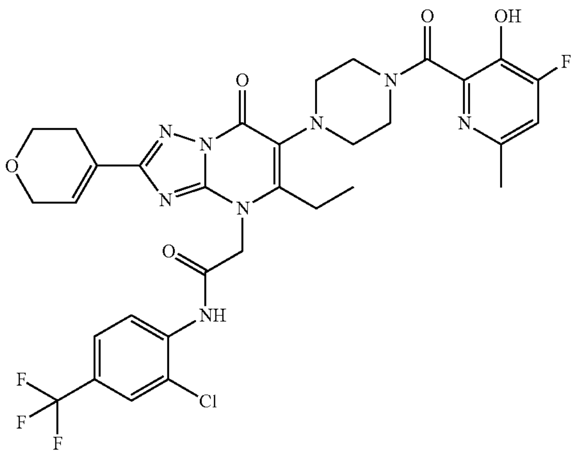 [SMILES: CCc1c(N2CCN(C(=O)c3nc(C)cc(F)c3O)CC2)c(=O)n2nc(C3=CCOCC3)nc2n1CC(=O)Nc1ccc(C(F)(F)F)cc1Cl]

Step 1: 2-(6-(4-(3-(benzyloxy)-4-fluoro-6-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl) acetamide N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AK) (227 mg, 334 μmol), 3-(benzyloxy)-4-fluoro-6-methylpicolinic acid (Intermediate CX) (110 mg, 371 μmol) and HATU (140 mg, 367 μmol) were suspended in DCM (5 mL) and cooled to 0° C. Then DIPEA (204 μL, 1.17 mmol) was added and the RM was stirred at RT for 2.5 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by reverse phase preparative HPLC (RP-HPLC basic 1: 5 to 95% B in 20 min with a plateau at 95% for 1 min). The product containing fractions were combined, basified with aq sat $NaHCO_3$, extracted twice with DCM, dried through a phase separator and concentrated under reduced pressure to give the title compound.

LC-MS: Rt=1.27 min; MS m/z $[M+H]^+$ 809.5/811.5, m/z $[M-H]^-$ 807.2/809.2; UPLC-MS 1

Step 2: N-(2-chloro-4-(trifluoromethyl)phenyl)-2-(2-(3,6-dihydro-2H-pyran-4-yl)-5-ethyl-6-(4-(4-fluoro-3-hydroxy-6-methylpicolinoyl)piperazin-1-yl)-7-oxo-[1,2,4]triazolo[1,5-a]pyrimidin-4 (7H)-yl) acetamide 2-(6-(4-(3-(Benzyloxy)-4-fluoro-6-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (242 mg, 292 μmol) was dissolved in DCM (5 mL) and TFA (5.00 mL, 64.9 mmol) was added and the RM was stirred at 60° C. overnight. After 1 night ca 50% conversion. The RM was continued stirring at 60° C. for one further night. The RM was concentrated under reduced pressure. The crude product was purified by reverse phase preparative ISCO (RediSep Column: C18 50 g Gold, eluent water+0.1% TFA:ACN 100:0 to 0:100). The product containing fractions were combined, basified with aq sat $NaHCO_3$, extracted twice with DCM, dried through a phase separator and concentrated under reduced pressure to give the title compound.

LC-MS: Rt=1.06 min; MS m/z $[M+H]^+$ 719.5/721.6, m/z $[M-H]^-$ 717.4/719.4; UPLC-MS 1

LC-MS: Rt=5.31 min; MS m/z $[M+H]^+$ 719.5/721.5, m/z $[M-H]^-$ 717.5/719.3; UPLC-MS 2

$^1$H NMR (400 MHz, DMSO-$d_6$) δ 10.35 (s, 2H), 8.05 (d, J=8.3 Hz, 1H), 7.96 (d, J=2.1 Hz, 1H), 7.71 (dd, J=2.1 Hz, 8.7 Hz, 1H), 7.22 (d, J=11.8 Hz, 1H), 6.83 (m, 1H), 5.31 (s, 2H), 4.52 (m, 1H), 4.25 (m, 2H), 3.80 (m, 2H), 3.47 (m, 3H), 3.22 (m, 1H), 2.98 (m, 3H), 2.80 (m, 1H), 2.64 (m, 1H), 2.51 (m, 2H), 2.39 (s, 3H), 1.18 (t, J=7.1 Hz, 3H)

Example 42: N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

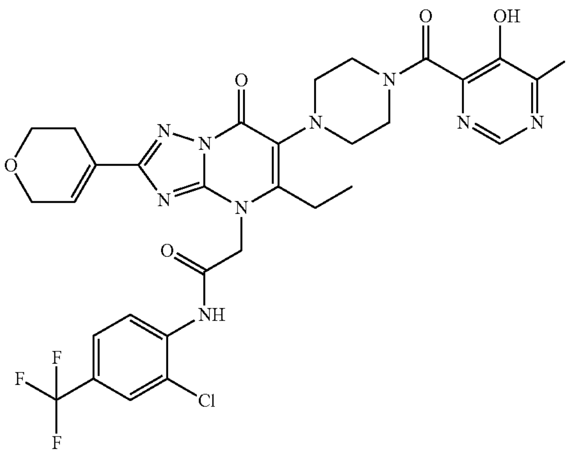 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Cl]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl) phenyl)acetamide To a stirred solution of N-(2-chloro-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide (Intermediate AK) (300 mg, 429 μmol), 5-(benzyloxy)-6-methylpyrimidine-4-carboxylic acid (Intermediate CY) (115 mg, 472 μmol) and HATU (245 mg, 644 μmol) in DMF (3 mL) was added DIPEA (375 μL, 2.15 mmol) at RT and the RM was stirred at RT for 15 minutes. The RM was diluted with EtOAc/water, extracted twice with EtOAc and the combined organic extracts were dried over $Na_2SO_4$ and concentrated. The crude product was purified by column chromatography (RediSep Column: Silica 24 g, eluent DCM:MeOH 100:0 to 90:10). The product containing fractions were combined and concentrated to give the title compound as a beige foam. The product was dissolved in EtOH, stirred at 60° C. over 18 hours, then cooled down to 0° C., filtered off and washed with EtOH to give the title compound as a white solid.

LC-MS: Rt=1.20 min; MS m/z $[M+H]^+$ 792.4/794.4, m/z $[M-H]^-$ 790.6/792.6; UPLC-MS 1

Step 2: N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl) acetamide To a stirred suspension of 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl) acetamide (266 mg, 312 μmol) in DCM (6 mL) was added boron trichloride methyl sulfide complex (312 μL, 625 μmol) at RT and the RM was stirred at RT for 14 hours. The RM was quenched with MeOH. Then it was diluted with DCM/water, extracted twice with DCM and the combined organic extracts were washed with water and brine, dried over $Na_2SO_4$ and concentrated. The crude product was purified by column chromatography (RediSep Column: Silica 24 g, eluent DCM:MeOH 100:0 to 93:07). The product containing fractions were combined and concentrated to give the title compound as an off-white solid. The product was dissolved in EtOH, stirred at 60° C. over 18h, then cooled down to 0° C., filtered off and washed with EtOH to give the title compound as a white solid characterized by the XRPD diffractogram in FIG. 1. The table Ex 42a below shows the most prominent peaks (deg 2theta) of the XRPD diffractogram of FIG. 1. The XRPD was repeated on a title compound sample as prepared by the procedure described in Ex 42 above, then purified by column chromatography (RediSep 150 g, eluent DCM:MeOH 100:0 to 90:10) followed by trituration in EtOH. The sample was characterized by the XPRD diffractogram in FIG. 7. The table Ex 42b below shows the most prominent peaks (deg 2theta) of the XRPD diffractogram of FIG. 7.

LC-MS: Rt=1.05 min; MS m/z $[M+H]^+$ 702.4/704.4, m/z $[M-H]^-$ 700.5/702.5; UPLC-MS 1

$^1$H NMR (600 MHz, DMSO-$d_6$) δ 10.40 (s, 1H), 10.20 (br s, 1H), 8.57 (s, 1H), 8.06 (d, J=8.5 Hz, 1H), 7.97 (d, J=2.0 Hz, 1H), 7.72 (dd, J=8.7 Hz, J=2.1 Hz, 1H), 6.83 (m, 1H), 5.32 (m, 2H), 4.52 (m, 1H), 4.25 (m, 2H), 3.80 (t, J=5.5 Hz,

2H), 3.50 (m, 3H), 3.25 (m, 1H), 2.99 (m, 3H), 2.81 (m, 1H), 2.63 (m, 1H), 2.51 (m, 2H), 2.44 (s, 3H), 1.18 (t, J=7.5 Hz, 3H).

The sodium salt was prepared analogous to the general procedure:

$^1$H NMR (400 MHz, DMSO-$d_6$) δ 10.36 (s, br, 2H), 8.55 (s, 1H), 8.05 (d, J=8.5 Hz, 1H), 7.96 (m, 1H), 7.71 (dd, J=2.1 Hz, 8.8 Hz, 1H), 6.83 (m, 1H), 5.32 (s, 2H), 4.52 (m, 1H), 4.25 (m, 2H), 3.80 (m, 2H), 3.48 (m, 3H), 3.25 (m, 1H), 2.99 (m, 3H), 2.81 (m, 1H), 2.64 (m, 1H), 2.52 (m, 2H), 2.43 (s, 3H), 1.18 (t, J=7.4 Hz, 3H).

Table Ex 42a

| Angle 2-Theta° | d Value Angstrom | Intensity |
|---|---|---|
| 11.85 | 7.46 | medium |
| 13.71 | 6.45 | medium |
| 14.46 | 6.12 | low |
| 15.33 | 5.78 | medium |
| 17.03 | 5.20 | medium |
| 18.33 | 4.84 | high |
| 19.98 | 4.44 | medium |
| 22.42 | 3.96 | medium |
| 22.95 | 3.87 | medium |
| 27.20 | 3.28 | low |

Table Ex42b

| Angle 2-Theta° | d Value Angstrom | Intensity |
|---|---|---|
| 6.78 | 13.033 | high |
| 8.97 | 9.846 | low |
| 11.88 | 7.446 | medium |
| 13.55 | 6.530 | low |
| 13.74 | 6.441 | low |
| 14.48 | 6.112 | medium |
| 15.34 | 5.771 | high |
| 16.83 | 5.264 | low |
| 17.03 | 5.203 | low |
| 18.30 | 4.843 | high |
| 19.49 | 4.550 | low |
| 19.94 | 4.449 | low |
| 21.28 | 4.172 | low |
| 21.51 | 4.127 | low |
| 22.38 | 3.970 | medium |
| 22.91 | 3.879 | medium |
| 23.27 | 3.819 | low |
| 25.41 | 3.502 | low |
| 27.26 | 3.269 | medium |
| 29.03 | 3.074 | low |
| 29.78 | 2.998 | low |
| 29.96 | 2.980 | low |

Example 43: N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide-2,2-d2

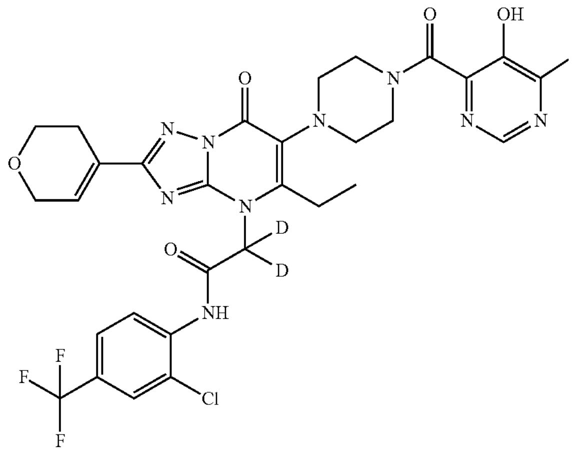 [SMILES: [2H]C([2H])(C(=O)Nc1ccc(C(F)(F)F)cc1Cl)n1c(CC)c(N2CCN(C(=O)c3ncnc(C)c3O)CC2)c(=O)n2nc(C3=CCOCC3)nc12]

A beige suspension of N-(2-chloro-4-(trifluoromethyl) phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide (Example 42) (70.0 mg, 100 μmol) and $K_2CO_3$ (13.8 mg, 100 μmol) in THF (997 μL)/DMSO-d6 (282 μL, 3.99 mmol)/D2O (180 μL, 9.97 mmol) was heated up to 65° C. and stirred for 45 minutes. A small amount of water was added to the RM, which was then extracted 3 times with EtOAc. The combined organic layers were washed once with brine, dried over $Na_2SO_4$, concentrated and dried under reduced pressure to give a beige solid. The aqueous layer showed still product in it. The aqueous layer was concentrated to remove THF, then it was extracted twice with DCM. The aqueous layer was diluted with aq sat $NaHCO_3$ then extracted three times with DCM. The combined organic layers were dried through a phase separator, concentrated and dried under vacuum to give the title compound.

LC-MS: Rt=1.04 min; MS m/z $[M+H]^+$ 704.5/706.5, m/z $[M-H]^-$ 702.2/704.2; UPLC-MS 1

$^1$H NMR (400 MHz, DMSO-$d_6$) δ 10.36 (s, 2H), 8.56 (s, 1H), 8.06 (d, J=8.4 Hz, 1H), 7.96 (d, J=2.1 Hz, 1H), 7.71 (dd, J=2.1 Hz, 8.8 Hz, 1H), 6.83 (m, 1H), 4.52 (m, 1H), 4.25 (m, 2H), 3.80 (m, 2H), 3.49 (m, 3H), 3.25 (m, 1H), 2.98 (m, 3H), 2.81 (m, 1H), 2.64 (m, 1H), 2.52 (m, 2H), 2.44 (s, 3H), 1.19 (t, J=7.2 Hz, 3H)

Example 44: N-(2-chloro-4-(trifluoromethyl)phenyl)-2-(2-(3,6-dihydro-2H-pyran-4-yl)-5-ethyl-6-(4-(5-hydroxypyrimidine-4-carbonyl)piperazin-1-yl)-7-oxo-[1,2,4]triazolo[1,5-a]pyrimidin-4 (7H)-yl) acetamide

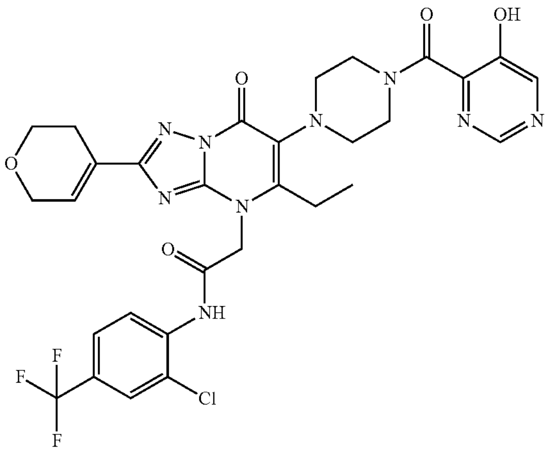 [SMILES: CCc1c(N2CCN(C(=O)c3ncncc3O)CC2)c(=O)n2nc(C3=CCOCC3)nc2n1CC(=O)Nc1ccc(C(F)(F)F)cc1Cl]

Step 1: N-(2-chloro-4-(trifluoromethyl)phenyl)-2-(2-(3,6-dihydro-2H-pyran-4-yl)-5-ethyl-6-(4-(5-methoxypyrimidine-4-carbonyl)piperazin-1-yl)-7-oxo-[1,2,4]triazolo[1,5-a]pyrimidin-4 (7H)-yl) acetamide N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AK) (508 mg, 727 μmol), 5-methoxypyrimidine-4-carboxylic acid (134 mg, 872 μmol) and HATU (427 mg, 1.09 mmol) were mixed in DMF (10 mL) at RT under argon. DIPEA (635 μL, 3.64 mmol) was added and the RM was stirred at RT for 2 hours. The reaction was quenched with water (10 mL). Aq sat $NaHCO_3$ (15 mL) was added and the mixture was extracted with EtOAc (3×70 mL). The organic layer was washed with water (20 mL) and brine (20 mL), dried over $Na_2SO_4$, filtered through a phase separator and concentrated under reduced pressure. The residue was adsorbed onto Isolute and purified by column chromatography (RediSep Column: Silica 40 g, eluent DCM:DCM/MeOH (8/2) 100:0 to 50:50). The product containing fractions were combined, concentrated, mixed with $Et_2O$, sonicated, filtered and dried under HV to give the title compound as a beige solid.

LC-MS: Rt=0.99 min; MS m/z $[M+H]^+$ 702.2/704.2, m/z $[M-H]^-$ 700.4/702.4; UPLC-MS 1

Step 2: N-(2-chloro-4-(trifluoromethyl)phenyl)-2-(2-(3,6-dihydro-2H-pyran-4-yl)-5-ethyl-6-(4-(5-hydroxypyrimidine-4-carbonyl)piperazin-1-yl)-7-oxo-[1,2,4]triazolo[1,5-a]pyrimidin-4 (7H)-yl)acetamide N-(2-chloro-4-(trifluoromethyl)phenyl)-2-(2-(3,6-dihydro-2H-pyran-4-yl)-5-ethyl-6-(4-(5-methoxypyrimidine-4-carbonyl)piperazin-1-yl)-7-oxo-[1,2,4]triazolo[1,5-a]pyrimidin-4 (7H)-yl)acetamide (178 mg, 254 μmol) was mixed with DMF (2 mL) and LiCl (43.0 mg, 1.01 mmol) was added and the RM was stirred at 150° C. for 18.3 hours. Then it was allowed to cool to RT. The reaction was diluted with water and aq sat $NaHCO_3$ (5 mL). It was extracted with EtOAc (3×20 mL). The organic layer was washed with water (5 mL) and brine (2×5 mL). The organic layer was washed again with EtOAc (3×20 mL). The combined organic layers were dried over $NaSO_4$, filtered through a phase separator and concentrated under reduced pressure. The residue was adsorbed onto Isolute and purified by column chromatography (RediSep Column: Silica 40 g, eluent DCM:DCM/MeOH (8/2) 100:0 to 35:65). The product containing fractions were combined and concentrated under reduced pressure. The solid was purified by reverse phase preparative HPLC (RP-HPLC basic 1: 15 to 65% B in 20 min with a plateau at 65% for 1 min). The product containing fractions were combined, the ACN was removed under reduced pressure and the residue was lyophilized to give the title compound as a beige solid.

LC-MS: Rt=0.98 min; MS m/z $[M+H]^+$ 688.3/690.3, m/z $[M-H]^-$ 686.3/688.3; UPLC-MS 1

$^1H$ NMR (400 MHz, DMSO-$d_6$) δ 10.75 (s, br, 1H), 10.35 (s, br, 1H), 8.70 (s, 1H), 8.44 (s, 1H), 8.05 (d, J=8.5 Hz, 1H), 7.96 (d, J=2.2 Hz, 1H), 7.71 (dd, J=2.1 Hz, 8.9 Hz, 1H), 6.83 (m, 1H), 5.31 (s, 2H), 4.51 (m, 1H), 4.25 (m, 2H), 3.80 (m, 2H), 3.47 (m, 3H), 3.23 (m, 1H), 2.97 (m, 3H), 2.81 (m, 1H), 2.63 (m, 1H), 2.50 (m, 2H), 1.18 (t, J=7.4 Hz, 3H)

Example 45: N-(2-chloro-6-(trifluoromethyl)pyridin-3-yl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)acetamide

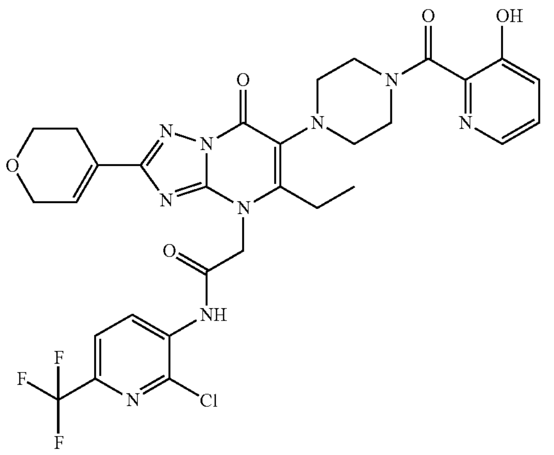 [SMILES: CCc1c(N2CCN(C(=O)c3ncccc3O)CC2)c(=O)n2nc(C3=CCOCC3)nc2n1CC(=O)Nc1ccc(C(F)(F)F)nc1Cl]

N-(2-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AL) (212 mg, 337 μmol) and 3-hydroxypicolinoyl chloride (Intermediate CV) (89.0 mg, 565 μmol) were dissolved in DCM (5 mL) and DIPEA (294 μL, 1.68 mmol) was added. The RM was stirred at RT for 30 minutes. 3-Hydroxypicolinoyl chloride (Intermediate CV) (89.0 mg, 565 μmol) was added again and the RM was continued stirring at RT for 1 hour. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 40 g, eluent DCM:DCM/MeOH (9/1) 100:0 to 60:40). The product containing fractions were combined, concentrated under vacuum and dried under HV to afford a beige solid. The crude product was purified by reverse phase preparative HPLC (RP-HPLC acidic 1: 20 to 80% B in 20 min with a plateau at 80% for 1 min). The product containing fractions were combined, basified with aq sat $NaHCO_3$, extracted twice with DCM (2×15 mL), dried through a phase separator and concentrated under reduced pressure. The product was dissolved in DCM (5 mL) and MeOH (2 mL) and left to stand at RT overnight. The resulting crystals were filtered off and washed with $Et_2O$ (4×3 mL). The cake was dried under HV to give the title compound as white crystals.

LC-MS: Rt=0.92 min; MS m/z $[M+H]^+$ 688.4/690.4, m/z $[M-H]^-$ 686.4/688.3; UPLC-MS 3

$^1H$ NMR (400 MHz, DMSO-$d_6$) δ 10.56 (s, 1H), 10.38 (s, 1H), 8.56 (d, J=8.0 Hz, 1H), 8.07 (m, 1H), 7.96 (d, J=8.0 Hz, 1H), 7.29 (m, 2H), 6.82 (m, 1H), 5.36 (s, 2H), 4.55 (m, 1H), 4.25 (m, 2H), 3.80 (m, 2H), 3.46 (m, 3H), 3.23 (m, 1H), 2.98 (m, 3H), 2.80 (m, 1H), 2.62 (m, 1H), 2.51 (m, 2H), 1.18 (t, J=7.3 Hz, 3H)

Example 46: 2-(6-(4-(4-chloro-3-hydroxypicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-6-(trifluoromethyl)pyridin-3-yl)acetamide

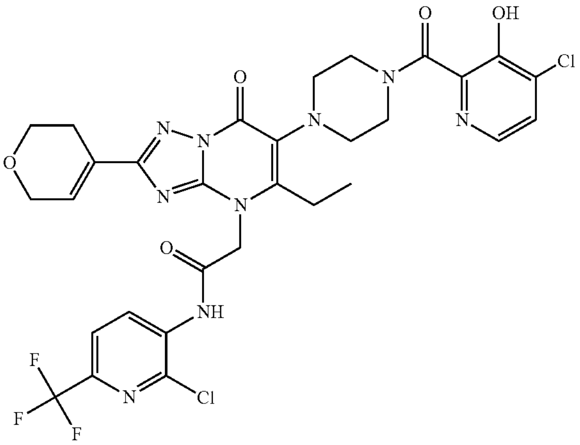 [SMILES: CCc1c(N2CCN(C(=O)c3nccc(Cl)c3O)CC2)c(=O)n2nc(C3=CCOCC3)nc2n1CC(=O)Nc1ccc(C(F)(F)F)nc1Cl]

4-Chloro-3-hydroxypicolinic acid (1.48 g, 8.54 mmol) was suspended in DCM (140 mL) and 1-chloro-N,N,2-trimethylprop-1-en-1-amine (1.29 mL, 9.73 mmol) was added. The red-brown solution turned into a yellow solution after 1 hour. The RM was stirred at RT for 2.5 hours. N-(2-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AL) (5.31 g, 8.43 mmol) and DIPEA (3.90 mL, 22.3 mmol) were dissolved in DCM (80 mL) and the prepared acid chloride solution was added dropwise during 1 hour. 5% aq $NaHCO_3$ and DCM were added. The aqueous layer was washed twice with DCM (2×100 mL). The combined organic layers were dried through a phase separator and concentrated under reduced pressure. The crude product was purified by column chromatography (RediSep Column: Silica 330 g, eluent DCM:MeOH 100:0 to 90:10). The product containing fractions were combined, concentrated and dried under HV. The residue was purified by reverse phase preparative ISCO (RediSep Column: C18 240 g, eluent water:ACN 100:0 to 0:100). The product containing fractions were combined, concentrated and dried under reduced pressure. The resulting solid was suspended at 55° C. in EtOH (25 mL), stirred overnight at 55° C., cooled to RT, stirred at 0° C. for 1 hour, filtered off, and dried under HV to give the title compound.

LC-MS: Rt=0.99 min; MS m/z $[M+H]^+$ 722.3/724.3/726.3, m/z $[M-H]^-$ 720.2/722.2/724.2; UPLC-MS 1

$^1$H NMR (400 MHz, DMSO-$d_6$) δ 10.79 (s, br, 1H), 10.59 (s, br, 1H), 8.57 (d, J=8.1 Hz, 1H), 8.05 (d, J=4.9 Hz, 1H), 7.95 (d, J=8.5 Hz, 1H), 7.54 (d, J=4.9 Hz, 1H), 6.82 (m, 1H), 5.36 (s, 2H), 4.54 (m, 1H), 4.25 (m, 2H), 3.80 (m, 2H), 3.53 (m, 3H), 3.23 (m, 1H), 2.99 (m, 3H), 2.81 (m, 1H), 2.66 (m, 1H), 2.51 (m, 2H), 1.18 (t, J=7.4 Hz, 3H)

Example 47: N-(2-chloro-6-(trifluoromethyl)pyridin-3-yl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

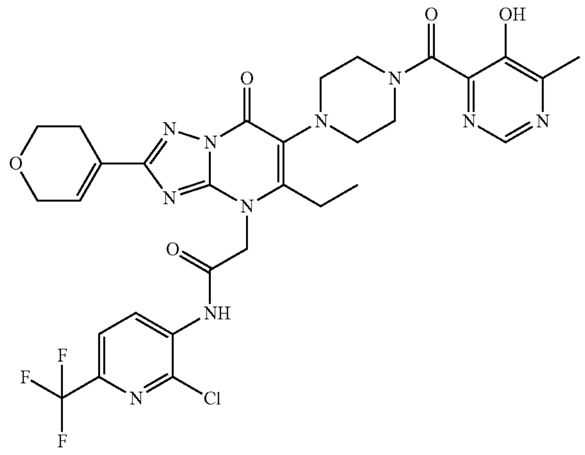

Step 1: N-(2-chloro-6-(trifluoromethyl)pyridin-3-yl)-2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)acetamide To the stirred solution of 5-methoxy-6-methylpyrimidine-4-carboxylic acid (Intermediate CW) (311 mg, 1.85 mmol) in DMF (10 mL) at RT were added EDC·HCl (355 mg, 1.85 mmol), HOBt (250 mg, 1.85 mmol) and pyridine (300 μL, 3.71 mmol). Then N-(2-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide (Intermediate AL) (700 mg, 1.24 mmol) was added and the RM was stirred at RT for 14 hours. Water (20 mL) was added to the RM and it was extracted with 10% MeOH in DCM (2×20 mL). The organic layer was washed with brine (20 mL), dried over $Na_2SO_4$, filtered and concentrated. The crude product was purified by column chromatography (Silica gel column: Silica 12 g, eluent DCM: MeOH 100:0 to 95:5) to give the title compound. The product was heated in EtOH:DCM (1:2) until fully dissolved. The solution was evaporated at RT until dry, then dried under vacuum to give the title compound as beige solid.

LC-MS: Rt=1.48 min; MS m/z $[M+H]^+$ 717.1/719.1; UPLC-MS 11

Step 2: N-(2-chloro-6-(trifluoromethyl)pyridin-3-yl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide To the stirred solution of N-(2-chloro-6-(trifluoromethyl) pyridin-3-yl)-2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl) acetamide (700 mg, 820 μmol) in DMF (10 mL) at RT, was added LiCl (348 mg, 8.20 mmol) and the RM was stirred at 140° C. for 14 hours. Water (20 mL) was added to the RM and it was extracted twice with DCM (2×20 mL). The organic layer was washed with brine (20 mL), dried over $Na_2SO_4$, filtered and concentrated. The crude product was purified by reverse phase preparative HPLC (RP-HPLC acidic 4: 30 to 40% B in 2 min, 40 to 55% B in 8 min) to give the title compound. The product was heated in 1:2 EtOH:DCM until fully dissolved. The solution was evaporated at RT until dry, then dried under vacuum to give the title compound as beige solid characterized by the XRPD diffractogram in FIG. 3. The table below shows the most prominent peaks (deg 2theta) of the XRPD diffractogram of FIG. 3. The sodium salt was prepared analogous to the general procedure.

LC-MS: Rt=0.92 min; MS m/z $[M+H]^+$ 703.4/705.4, m/z $[M-H]^-$ 701.5/703.5; UPLC-MS 1

$^1$H NMR (400 MHz, DMSO-$d_6$) δ 10.46 (s, br, 2H), 8.56 (m, 2H), 7.95 (d, J=8.4 Hz, 1H), 6.82 (m, 1H), 5.35 (s, 2H), 4.52 (m, 1H), 4.25 (m, 2H), 3.80 (m, 2H), 3.48 (m, 3H), 3.25 (m, 1H), 2.99 (m, 3H), 2.81 (m, 1H), 2.65 (m, 1H), 2.51 (m, 2H), 2.44 (s, 3H), 1.18 (t, J=7.7 Hz, 3H)

| Angle 2-Theta° | d Value Angstrom | Intensity |
|---|---|---|
| 9.45 | 9.35 | medium |
| 12.75 | 6.94 | high |
| 13.28 | 6.66 | medium |
| 21.69 | 4.09 | medium |
| 25.25 | 3.52 | high |
| 26.85 | 3.32 | medium |

Example 48: N-(2-chloro-6-(trifluoromethyl)pyridin-3-yl)-2-(2-(3,6-dihydro-2H-pyran-4-yl)-5-ethyl-6-(4-(4-fluoro-3-hydroxypicolinoyl)piperazin-1-yl)-7-oxo-[1,2,4]triazolo[1,5-a]pyrimidin-4 (7H)-yl) acetamide

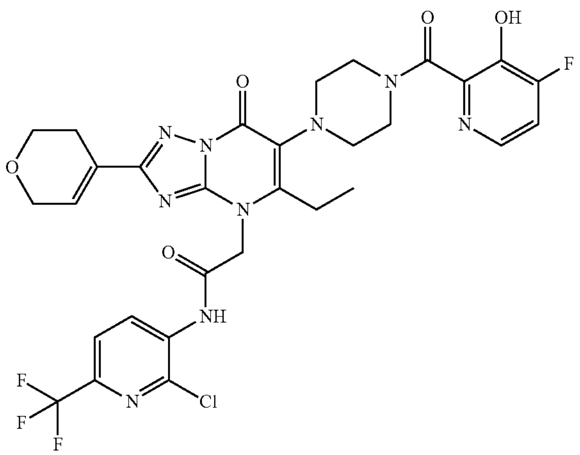 [SMILES: CCc1c(N2CCN(C(=O)c3nccc(F)c3O)CC2)c(=O)n2nc(C3=CCOCC3)nc2n1CC(=O)Nc1ccc(C(F)(F)F)nc1Cl]

Step 1: 2-(6-(4-(3-(benzyloxy)-4-fluoropicolinoyl) piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-6-(trifluoromethyl)pyridin-3-yl) acetamide To a stirred suspension of N-(2-chloro-6-(trifluoromethyl) pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AL) (445 mg, 785 μmol), 3-(benzyloxy)-4-fluoropicolinic acid (Intermediate CU) (204 mg, 824 μmol) and HATU (358 mg, 942 μmol) in DMF (10 mL) was added DIPEA (685 μL, 3.92 mmol) at RT and the RM was stirred at RT for 5 minutes. The RM was diluted in EtOAc/water, extracted twice with EtOAc and the combined organic extracts were washed with water and brine, dried over $Na_2SO_4$ and concentrated. The crude product was purified by column chromatography (RediSep Column: Silica 24 g, eluent DCM:DCM/MeOH (8/2) 100:0 to 50:50). The product containing fractions were combined and concentrated to give the title compound as a yellow foam.

LC-MS: Rt=1.14 min; MS m/z $[M+H]^+$ 796.5/798.5, m/z $[M-H]^-$ 794.5/796.5; UPLC-MS 1

Step 2: N-(2-chloro-6-(trifluoromethyl)pyridin-3-yl)-2-(2-(3,6-dihydro-2H-pyran-4-yl)-5-ethyl-6-(4-(4-fluoro-3-hydroxypicolinoyl)piperazin-1-yl)-7-oxo-[1,2,4]triazolo[1,5-a]pyrimidin-4 (7H)-yl) acetamide To a stirred suspension of 2-(6-(4-(3-(benzyloxy)-4-fluoropicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-6-(trifluoromethyl)pyridin-3-yl)acetamide (610 mg, 758 μmol) in DCM (1 mL) was added TFA (5.00 mL, 64.9 mmol) at 50° C. and the RM was stirred at 50° C. for 3 hours, then at 45° C. for 18 hours. The RM was diluted with DCM/$NaHCO_3$, extracted twice with DCM and the combined organic extracts were washed with brine, dried over $Na_2SO_4$ and concentrated. The crude product was purified by column chromatography (RediSep Column: Silica 40 g, eluent DCM:DCM/MeOH (8/2) 100:0 to 60:40). The product containing fractions were combined and concentrated. This solid was dissolved at 50° C. in EtOH (20 mL) and left at RT overnight. A white solid was filtered off to give the title compound as a white solid.

LC-MS: Rt=0.91 min; MS m/z $[M+H]^+$ 706.2/708.1, m/z $[M-H]^-$ 704.5/706.5; UPLC-MS 1

$^1$H NMR (400 MHz, DMSO-$d_6$) δ 10.65 (s, br, 2H), 8.56 (d, J=8.3 Hz, 1H), 8.07 (m, 1H), 7.95 (d, J=8.4 Hz, 1H), 7.35 (m, 1H), 6.82 (m, 1H), 5.35 (s, 2H), 4.54 (m, 1H), 4.25 (m, 2H), 3.80 (m, 2H), 3.45 (m, 3H), 3.23 (m, 1H), 2.97 (m, 3H), 2.80 (m, 1H), 2.62 (m, 1H), 2.50 (m, 2H), 1.18 (t, J=7.3 Hz, 3H)

Example 49: N-(2-chloro-6-(trifluoromethyl)pyridin-3-yl)-2-(2-(3,6-dihydro-2H-pyran-4-yl)-5-ethyl-6-(4-(4-fluoro-3-hydroxy-6-methylpicolinoyl)piperazin-1-yl)-7-oxo-[1,2,4]triazolo[1,5-a]pyrimidin-4 (7H)-yl)acetamide

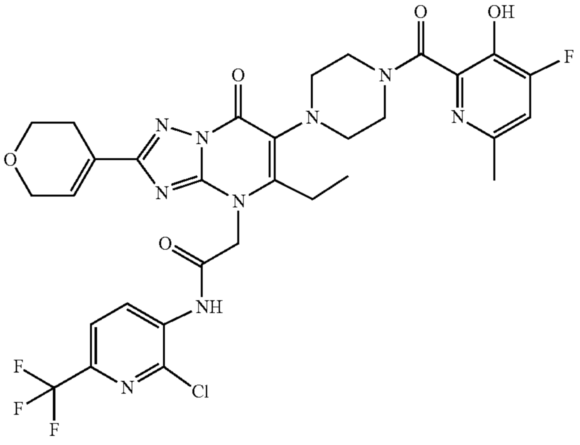 [SMILES: CCc1c(N2CCN(C(=O)c3nc(C)cc(F)c3O)CC2)c(=O)n2nc(C3=CCOCC3)nc2n1CC(=O)Nc1ccc(C(F)(F)F)nc1Cl]

Step 1: 2-(6-(4-(3-(benzyloxy)-4-fluoro-6-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-6-(trifluoromethyl)pyridin-3-yl)acetamide N-(2-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AL) (277 mg, 407 μmol), 3-(benzyloxy)-4-fluoro-6-methylpicolinic acid (Intermediate CX) (133 mg, 447 μmol) and HATU (170 mg, 447 μmol) were suspended in DCM (5 mL) and cooled to 0° C. Then DIPEA (249 μL, 1.42 mmol) was added and the RM was stirred at RT for 2 hours. Water (20 mL), aq sat $NaHCO_3$ (10 mL) and DCM (30 mL) were added. The aqueous layer was washed twice with DCM (2×20 mL). The combined organic layers were dried through a phase separator and concentrated under reduced pressure. The crude product was purified by reverse phase preparative ISCO (RediSep Column: C18 26 g, eluent water+0.1% TFA:ACN 90:10 to 0:100). The product containing fractions were combined, basified with aq sat $NaHCO_3$, extracted twice with DCM (2×15 mL), dried through a phase separator and concentrated under reduced pressure to give the title compound.

LC-MS: Rt=1.17 min; MS m/z $[M+H]^+$ 810.5/812.5, m/z $[M-H]^-$ 808.2/810.2; UPLC-MS 1

Step 2: N-(2-chloro-6-(trifluoromethyl)pyridin-3-yl)-2-(2-(3,6-dihydro-2H-pyran-4-yl)-5-ethyl-6-(4-(4-fluoro-3-hydroxy-6-methylpicolinoyl)piperazin-1-yl)-7-oxo-[1,2,4]triazolo[1,5-a]pyrimidin-4 (7H)-yl) acetamide 2-(6-(4-(3-(Benzyloxy)-4-fluoro-6-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-6-(trifluoromethyl)pyridin-3-yl)acetamide (244 mg, 289 μmol) was dissolved in DCM (5 mL) and TFA (5.00 mL, 64.9 mmol) was added. The RM was stirred at 50° C. for 2 days. The RM was concentrated under reduced pressure. The crude product was purified by reverse phase preparative ISCO (RediSep Column: C18 50 g Gold, eluent water+0.1% TFA:ACN 90:10 to 0:100). The product containing fractions were combined, basified with aq sat $NaHCO_3$, extracted twice with DCM (2×15 mL), dried through a phase separator and concentrated under reduced pressure to give the title compound.

LC-MS: Rt=0.93 min; MS m/z $[M+H]^+$ 720.6/722.5, m/z $[M-H]^-$ 718.4/720.3; UPLC-MS 1

$^1$H NMR (400 MHz, DMSO-$d_6$) δ 10.55 (s, 1H), 10.35 (s, 1H), 8.56 (d, J=7.9 Hz, 1H), 7.95 (d, J=8.5 Hz, 1H), 7.22 (d, J=11.6 Hz, 1H), 6.82 (m, 1H), 5.36 (s, 2H), 4.52 (m, 1H), 4.25 (m, 2H), 3.80 (m, 2H), 3.47 (m, 3H), 3.23 (m, 1H), 2.98 (m, 3H), 2.80 (m, 1H), 2.63 (m, 1H), 2.50 (m, 2H), 2.39 (s, 3H), 1.18 (t, J=7.2 Hz, 3H)

Example 50: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(5-fluoro-2-methyl-4-(trifluoromethyl)phenyl)acetamide

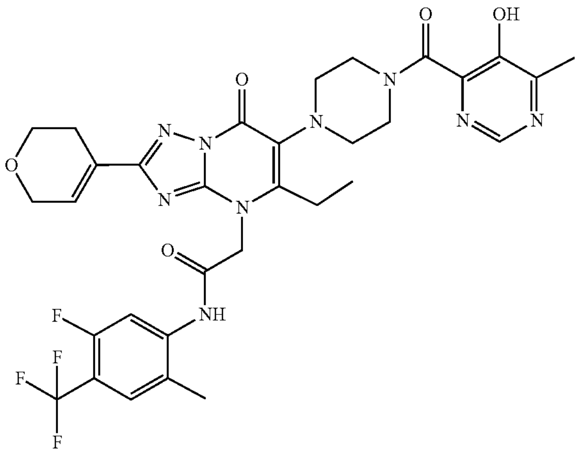 [SMILES: CCc1c(N2CCN(C(=O)c3ncnc(C)c3O)CC2)c(=O)n2nc(C3=CCOCC3)nc2n1CC(=O)Nc1cc(F)c(C(F)(F)F)cc1C]

Step 1: 2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(5-fluoro-2-methyl-4-(trifluoromethyl) phenyl)acetamide 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide (Intermediate AM) (700 mg, 1.24 mmol) was suspended in DMF (5 mL) and 5-methoxy-6-methylpyrimidine-4-carboxylic acid (Intermediate CW) (292 mg, 1.74 mmol) was added at 0° C. PyAOP (971 mg, 1.86 mmol) and DIPEA (651 μL, 3.73 mmol) were added and the RM was stirred at RT for 12 hours. The RM was concentrated under reduced pressure. Water was added and the mixture was filtered to give the title compound.

LC-MS: Rt=1.64 min; MS m/z $[M+H]^+$ 714.1; UPLC-MS 12

Step 2: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(5-fluoro-2-methyl-4-(trifluoromethyl) phenyl)acetamide 2-(2-(3,6-Dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(5-fluoro-2-methyl-4-(trifluoromethyl)phenyl)acetamide (800 mg, 953 μmol) was suspended in DMF (5 mL) and LiCl (182 mg, 4.29 mmol) was added. The reaction was stirred in the MW at 200° C. for 20 minutes. The reaction was concentrated under reduced pressure. The crude product was purified by reverse phase preparative HPLC (RP-HPLC acidic 2: 40 to 50% B in 2 min, 50 to 60% B in 9 min) to give the title compound.

The sodium salt was prepared analogous to the general procedure.

LC-MS: Rt=1.02 min; MS m/z $[M+H]^+$ 700.5, m/z $[M-H]^-$ 698.4; UPLC-MS 1

LC-MS: Rt=5.10 min; MS m/z $[M+H]^+$ 700.3, m/z $[M-H]^-$ 698.3; UPLC-MS 2

$^1$H NMR (400 MHz, DMSO-$d_6$) δ 10.22 (s, br, 1H), 10.06 (s, 1H), 8.57 (s, 1H), 7.78 (d, J=13 Hz, 1H), 7.67 (d, J=8.3 Hz, 1H), 6.81 (m, 1H), 5.29 (s, 2H), 4.52 (m, 1H), 4.25 (m, 2H), 3.80 (m, 2H), 3.49 (m, 3H), 3.27 (m, 1H), 2.99 (m, 3H), 2.82 (m, 1H), 2.65 (m, 1H), 2.52 (m, 2H), 2.44 (s, 3H), 2.35 (s, 3H), 1.19 (t, J=7.4 Hz, 3H)

Example 51: N-(2-chloro-4-(pentafluorosulfanyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

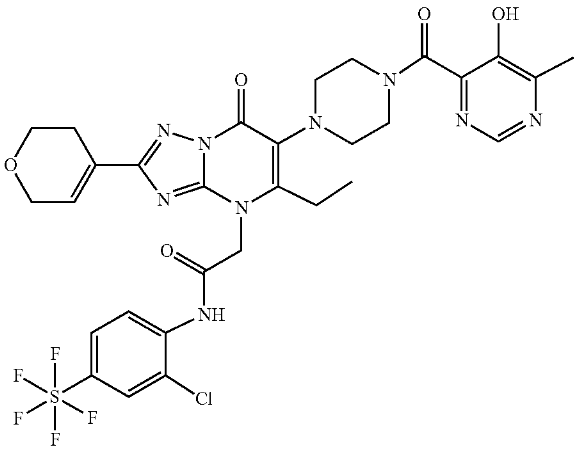 [SMILES: CCc1c(N2CCN(C(=O)c3ncnc(C)c3O)CC2)c(=O)n2nc(C3=CCOCC3)nc2n1CC(=O)Nc1ccc(S(F)(F)(F)(F)F)cc1Cl]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(pentafluorosulfanyl)phenyl)acetamide N-(2-chloro-4-(pentafluorosulfanyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AN) (296 mg, 360 μmol), 5-(benzyloxy)-6-methylpyrimidine-4-carboxylic acid (Intermediate CY) (97.0 mg, 396 μmol) and HATU (144 mg, 378 μmol) were mixed in DCM (5 mL) and DIPEA (189 μL, 1.08 mmol) was added. The suspension turned into a solution and was stirred at RT for 2 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by reverse phase preparative HPLC (RP-HPLC acidic 1: 10 to 90% B in 20 min with a plateau at 90% for 1 min). The product containing fractions were combined, basified with aq sat $NaHCO_3$, extracted twice with DCM, dried through a phase separator and concentrated under reduced pressure. The crude product was purified by column chromatography (RediSep Column: Silica 40 g, eluent DCM:DCM/MeOH (1/1) 100:0 to 0:100). The product containing fractions were combined, concentrated under vacuum and dried under HV to give the title compound.

LC-MS: Rt=1.25 min; MS m/z $[M+H]^+$ 850.5/852.5, m/z $[M-H]^-$ 848.5/850.5; UPLC-MS 1

Step 2: N-(2-chloro-4-(pentafluorosulfanyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(pentafluorosulfanyl)phenyl)acetamide (195 mg, 227 μmol) was dissolved in DCM (3 mL) and TFA (3.00 mL, 38.9 mmol) was added and the RM was stirred at 70° C. for 1 day. The RM was concentrated under reduced pressure. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 24 g, eluent DCM:DCM/MeOH (1/1) 100:0 to 90:10). The product containing fractions were combined and concentrated under reduced pressure. A part of the solid was dissolved in DCM:ACN (8:2), filtered and left standing at RT. The resulting crystals were filtered off, suspended in $Et_2O$, washed with a small amount of $Et_2O$ and dried under HV to give the title compound.

LC-MS: Rt=1.12 min; MS m/z $[M+H]^+$ 760.4/762.4, m/z $[M-H]^-$ 758.4/760.4; UPLC-MS 1

$^1H$ NMR (400 MHz, DMSO-$d_6$) δ 10.40 (s, 1H), 10.22 (s, 1H), 8.58 (s, 1H), 8.15 (d, J=2.7 Hz, 1H), 8.09 (d, J=9.3 Hz, 1H), 7.90 (dd, J=2.5 Hz, 9.2 Hz, 1H), 6.82 (m, 1H), 5.33 (s, 2H), 4.52 (m, 1H), 4.25 (m, 2H), 3.80 (m, 2H), 3.50 (m, 3H), 3.25 (m, 1H), 2.98 (m, 3H), 2.81 (m, 1H), 2.66 (m, 1H), 2.50 (m, 2H), 2.44 (s, 3H), 1.18 (t, J=7.4 Hz, 3H)

Example 52: N-(2-chloro-4-(pentafluorosulfanyl)phenyl)-2-(2-(3,6-dihydro-2H-pyran-4-yl)-5-ethyl-6-(4-(5-hydroxypyrimidine-4-carbonyl)piperazin-1-yl)-7-oxo-[1,2,4]triazolo[1,5-a]pyrimidin-4 (7H)-yl) acetamide

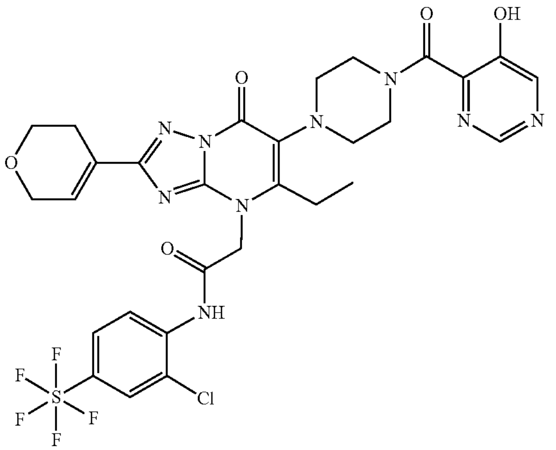 [SMILES: CCc1c(N2CCN(C(=O)c3ncncc3O)CC2)c(=O)n2nc(C3=CCOCC3)nc2n1CC(=O)Nc1ccc(S(F)(F)(F)(F)F)cc1Cl]

Step 1: N-(2-chloro-4-(pentafluorosulfanyl)phenyl)-2-(2-(3,6-dihydro-2H-pyran-4-yl)-5-ethyl-6-(4-(5-methoxypyrimidine-4-carbonyl)piperazin-1-yl)-7-oxo-[1,2,4]triazolo[1,5-a]pyrimidin-4 (7H)-yl) acetamide N-(2-chloro-4-(pentafluorosulfanyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AN) (256 mg, 312 μmol), 5-methoxypyrimidine-4-carboxylic acid (67.9 mg, 441 μmol) and HATU (160 mg, 421 μmol) were mixed in DCM (5 mL) and DIPEA (210 μL, 1.20 mmol) was added. The suspension turned into a solution and was stirred at RT for 2 hours. Then it was stored in the fridge overnight. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified in 2 portions by reverse phase preparative HPLC (RP-HPLC acidic 1: 5 to 95% B in 20 min with a plateau at 95% for 1 min and RP-HPLC acidic 1: 15 to 80% B in 20 min with a plateau at 80% for 1 min). The product containing fractions were combined, basified with aq sat $NaHCO_3$, extracted twice with DCM, dried through a phase separator and concentrated under reduced pressure. It was purified by column chromatography (RediSep Column: Silica 40 g, eluent DCM:DCM/MeOH (1/1) 100:0 to 90:10). The product containing fractions were combined, concentrated under vacuum and dried under HV to afford the title compound.

LC-MS: Rt=1.04 min; MS m/z $[M+H]^+$ 760.0/762.0, m/z $[M-H]^-$ 758.4/760.4; UPLC-MS 1

Step 2: N-(2-chloro-4-(pentafluorosulfanyl)phenyl)-2-(2-(3,6-dihydro-2H-pyran-4-yl)-5-ethyl-6-(4-(5-hydroxypyrimidine-4-carbonyl)piperazin-1-yl)-7-oxo-[1,2,4]triazolo[1,5-a]pyrimidin-4 (7H)-yl) acetamide N-(2-chloro-4-(pentafluorosulfanyl)phenyl)-2-(2-(3,6-dihydro-2H-pyran-4-yl)-5-ethyl-6-(4-(5-methoxypyrimidine- 4-carbonyl)piperazin-1-yl)-7-oxo-[1,2,4]triazolo[1,5-a]pyrimidin-4 (7H)-yl)acetamide (169 mg, 222 μmol) and LiCl (37.7 mg, 889 μmol) were mixed with DMF (2 mL) and stirred at 140° C. under sealed conditions for 1 day. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by reverse phase preparative HPLC (RP-HPLC acidic 1: 10 to 90% B in 20 min with a plateau at 90% for 1 min). The product containing fractions were combined, basified with aq sat $NaHCO_3$, extracted twice with DCM, dried through a phase separator and concentrated under reduced pressure. It was purified by column chromatography (RediSep Column: Silica 24 g, eluent DCM:DCM/MeOH (1/1) 100:0 to 75:25). The product containing fractions were combined, concentrated under vacuum and dried under HV to afford the title compound as a pale yellow solid.

LC-MS: Rt=1.02 min; MS m/z $[M+H]^+$ 746.4/748.4, m/z $[M-H]^-$ 744.4/746.3; UPLC-MS 1

LC-MS: Rt=5.20 min; MS m/z $[M+H]^+$ 746.1/748.1, m/z $[M-H]^-$ 744.2/746.2; UPLC-MS 2

$^1$H NMR (400 MHz, DMSO-$d_6$) δ 10.96 (s, br, 1H), 10.40 (s, br, 1H), 8.70 (s, 1H), 8.44 (s, 1H), 8.15 (d, J=2.6 Hz, 1H), 8.09 (d, J=9.2 Hz, 1H), 7.90 (dd, J=2.6 Hz, 9.2 Hz, 1H), 6.82 (m, 1H), 5.32 (s, 2H), 4.51 (m, 1H), 4.25 (m, 2H), 3.80 (m, 2H), 3.47 (m, 3H), 3.27 (m, 1H), 2.98 (m, 3H), 2.81 (m, 1H), 2.65 (m, 1H), 2.52 (m, 2H), 1.18 (t, J=7.6 Hz, 3H)

Example 53: N-(4-(difluoromethyl)-5-fluoro-2-methylphenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

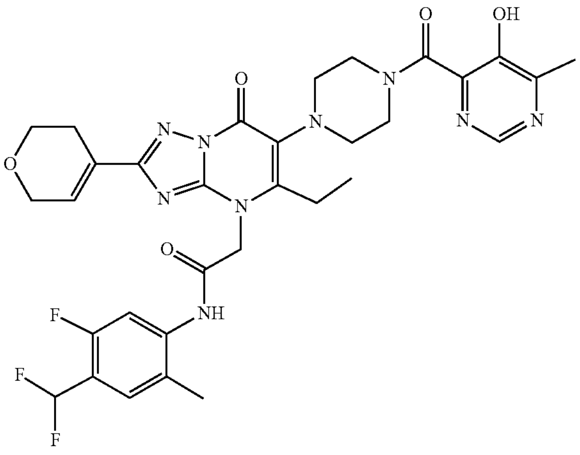 [SMILES: CCc1c(N2CCN(C(=O)c3ncnc(C)c3O)CC2)c(=O)n2nc(C3=CCOCC3)nc2n1CC(=O)Nc1cc(F)c(C(F)F)cc1C]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(4-(difluoromethyl)-5-fluoro-2-methylphenyl)acetamide To N-(4-(difluoromethyl)-5-fluoro-2-methylphenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AO) (880 mg, 1.61 mmol) and 5-(benzyloxy)-6-methylpyrimidine-4-carboxylic acid (Intermediate CY) (394 mg, 1.61 mmol) in DMF (12 mL) was added DIPEA (1.41 mL, 8.07 mmol) followed by HATU (675 mg, 1.77 mmol). The RM was stirred at RT for 15 minutes. The RM was diluted with water (50 mL) and EtOAc (50 mL) and the resulting precipitate was stirred at RT overnight. The brown solid was filtered and washed with water (10 mL). The solid was redissolved in DCM (70 mL), dried over $Na_2SO_4$, filtered and evaporated in vacuo to give the title compound as a brown solid—contains aldehyde side product LC-MS: Rt=1.08 min; MS m/z $[M+H]^+$ 772.6, m/z $[M-H]^-$ 770.4; UPLC-MS 1

Step 2: N-(4-(difluoromethyl)-5-fluoro-2-methylphenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide 2-(6-(4-(5-(Benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(4-(difluoromethyl)-5-fluoro-2-methylphenyl)acetamide (1.10 g, 1.43 mmol) was heated in TFA (5.00 mL, 64.9 mmol) at 50° C. for 1 hour. LCMS indicated minor peak for desired product at Rt=0.90 min $[M+H]^+$ 682/683. Significant hydrolysis of $CF_2H$ to aldehyde. The RM was evaporated in vacuo to give a brown oil. The crude product was redissolved in MeOH and purified in 3 portions by reverse phase preparative HPLC (RP-HPLC acidic 1: 20 to 48% B in 20 min with a plateau at 48% for 1 min and 2×RP-HPLC acidic 1: 25 to 46% B in 20 min with a plateau at 46% for 1 min). The impure fractions containing >2% aldehyde side-product were combined and the pH basified by addition of aq sat $NaHCO_3$, extracted with DCM (2×50 mL). The organic layers were combined, dried over $Na_2SO_4$, filtered and evaporated to give a pale brown solid. The brown solid was redissolved in MeOH and purified by reverse phase preparative HPLC (RP-HPLC basic 1: 20 to 50% B in 10 min with a plateau at 50% for 1 min). The pure product containing fractions were extracted with DCM (2×50 mL). The organic layers were combined, dried over $Na_2SO_4$, filtered and evaporated to give the title compound as a colourless solid.

LC-MS: Rt=0.89 min; MS m/z $[M+H]^+$ 682.2, m/z $[M-H]^-$ 680.4; UPLC-MS 1

$^1$H NMR (400 MHz, DMSO-$d_6$) δ 10.22 (s, br, 1H), 9.99 (s, 1H), 8.57 (s, 1H), 7.61 (d, J=12.2 Hz, 1H), 7.50 (d, J=8.1 Hz, 1H), 7.26-7.00 (t, br, J=54.9 Hz, 1H), 6.82 (m, 1H), 5.26 (s, 2H), 4.52 (m, 1H), 4.26 (m, 2H), 3.80 (m, 2H), 3.48 (m, 3H), 3.26 (m, 1H), 3.01 (m, 3H), 2.81 (m, 1H), 2.64 (m, 1H), 2.50 (m, 2H), 2.44 (s, 3H), 2.31 (s, 3H), 1.19 (t, J=7.1 Hz, 3H)

Example 54: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(5-fluoro-4-formyl-2-methylphenyl)acetamide Side product of Example 53.

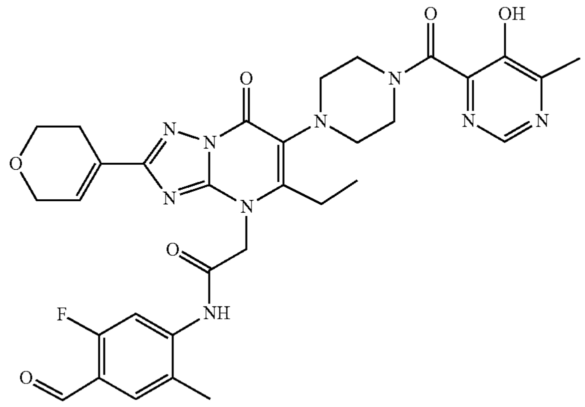 [SMILES: CCc1c(N2CCN(C(=O)c3ncnc(C)c3O)CC2)c(=O)n2nc(C3=CCOCC3)nc2n1CC(=O)Nc1cc(F)c(C=O)cc1C]

The fractions from the acidic RP Prep HPLC containing the aldehyde side-product >97% pure were combined and the pH basified by addition of aq sat $NaHCO_3$, then it was extracted with DCM (2×50 mL). The organic layers were combined, dried over $Na_2SO_4$, filtered and evaporated to give the title compound as a beige solid.

LC-MS: Rt=0.76 min; MS m/z $[M+H]^+$ 660.2, m/z $[M-H]^-$ 658.3; UPLC-MS 1

$^1$H NMR (400 MHz, DMSO-$d_6$) δ 10.23 (s, br, 1H), 10.10 (s, 1H), 10.04 (s, br, 1H), 8.55 (s, 1H), 7.78 (d, J=13.1 Hz, 1H), 7.71 (d, J=7.8 Hz, 1H), 6.81 (m, 1H), 5.32 (s, 2H), 4.52 (m, 1H), 4.25 (m, 2H), 3.80 (m, 2H), 3.50 (m, 3H), 3.25 (m, 1H), 2.98 (m, 3H), 2.82 (m, 1H), 2.65 (m, 1H), 2.50 (m, 2H), 2.43 (s, 3H), 2.36 (s, 3H), 1.18 (t, J=7.1 Hz, 3H)

Example 55: 2-(2-(3,4-dihydro-2H-pyran-6-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-6-(trifluoromethyl)pyridin-3-yl)acetamide

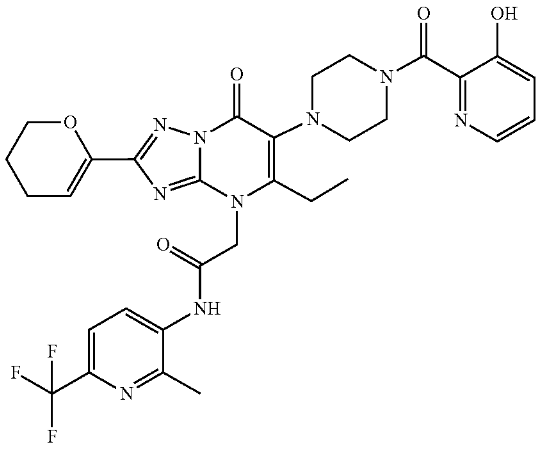 [SMILES: CCc1c(N2CCN(C(=O)c3ncccc3O)CC2)c(=O)n2nc(C3=CCCCO3)nc2n1CC(=O)Nc1ccc(C(F)(F)F)nc1C]

3-Hydroxypicolinic acid (170 mg, 1.20 mmol) was dissolved in DCM (6 mL) at RT under argon. 1-Chloro-N,N,2-trimethylprop-1-en-1-amine (180 mg, 1.32 mmol) was added and the RM was stirred at RT for 1.5 hours. A solution of 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide (Intermediate AD) (400 mg, 600 μmol) in DCM (4 mL) and DIPEA (524 μL, 3.00 mmol) was added. The resulting brown solution was stirred at RT for 2.3 hours. The RM was quenched with water (5 mL) and aq sat $NaHCO_3$ (5 mL). It was extracted with DCM (4×40 mL). The organic layers were combined, washed with aq sat $NaHCO_3$ and water, dried through a phase separator and concentrated under reduced pressure. The residue was adsorbed onto Isolute and purified by column chromatography (RediSep Column: Silica 24 g, eluent DCM:MeOH 100:0 to 90:10). The product containing fractions were combined and concentrated. The resulting beige solid was purified by SFC (SFC 6) to give the title compound.

LC-MS: Rt=0.94 min; MS m/z $[M+H]^+$ 668.4, m/z $[M-H]^-$ 666.2; UPLC-MS 3

$^1$H NMR (600 MHz, DMSO-$d_6$) δ 10.40 (s, 1H), 10.23 (s, 1H), 8.21 (d, J=8.4 Hz, 1H), 8.07 (m, 1H), 7.74 (d, J=8.4 Hz, 1H), 7.29 (m, 2H), 5.87 (m, 1H), 5.28 (s, 2H), 4.55 (m, 1H), 4.11 (m, 2H), 3.48 (m, 2H), 3.40 (m, 1H), 3.22 (m, 1H), 2.98 (m, 3H), 2.80 (m, 1H), 2.62 (m, 1H), 2.59 (s, 3H), 2.19 (m, 2H), 1.85 (m, 2H), 1.19 (t, J=7.4 Hz, 3H)

Example 56: 2-(6-(4-(4-chloro-3-hydroxypicolinoyl)piperazin-1-yl)-2-(3,4-dihydro-2H-pyran-6-yl)-5-ethyl-7-oxo-[1,2,4]triazolo[1,5-a]pyrimidin-4 (7H)-yl)-N-(2-methyl-6-(trifluoromethyl)pyridin-3-yl)acetamide

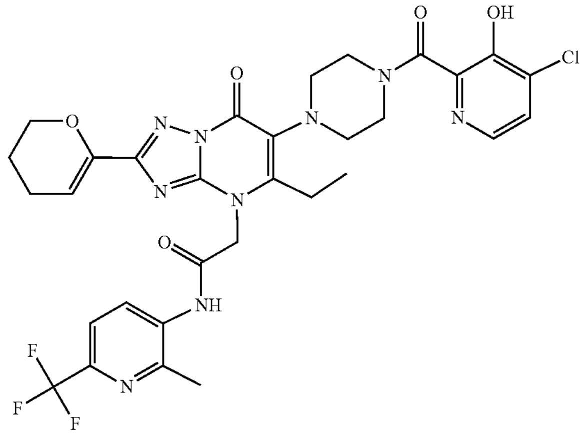 [SMILES: CCc1c(N2CCN(C(=O)c3nccc(Cl)c3O)CC2)c(=O)n2nc(C3=CCCCO3)nc2n1CC(=O)Nc1ccc(C(F)(F)F)nc1C]

To the stirred solution of 4-chloro-3-hydroxypicolinic acid (381 mg, 2.20 mmol) in DCM (20 mL) at RT, were added PyAOP (1.15 g, 2.20 mmol), DIPEA (575 μL, 3.29 mmol) and then 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide (Intermediate AD) (600 mg, 1.10 mmol), and the RM was stirred at RT for 14 hours. Water (20 mL) was added to the RM and it was extracted with 10% MeOH in DCM (2×20 mL). The organic layers were combined, washed with brine (20 mL), dried over $Na_2SO_4$ and concentrated. The crude product was purified by column chromatography (silica gel column: silica 12 g, eluent DCM:MeOH 100:0 to 93:7). Then it was further purified by reverse phase preparative HPLC (RP-HPLC acidic 8: 25 to 35% B in 2 min, 35 to 75% B in 10 min) to give after lyophilization the title compound as a white solid.

LC-MS: Rt=0.96 min; MS m/z $[M+H]^+$ 702.3, m/z $[M-H]^-$ 700.3; UPLC-MS 1

LC-MS: Rt=4.75 min; MS m/z $[M+H]^+$ 702.2, m/z $[M-H]^-$ 700.3; UPLC-MS 2

$^1$H NMR (400 MHz, DMSO-$d_6$) δ 10.8 (m, br, 1H), 10.23 (s, 1H), 8.21 (d, J=8.4 Hz, 1H), 8.03 (d, J=4.7 Hz, 1H), 7.73 (d, J=8.4 Hz, 1H), 7.54 (d, J=4.8 Hz, 1H), 5.86 (m, 1H), 5.28 (s, 2H), 4.54 (m, 1H), 4.10 (m, 2H), 3.52 (m, 3H), 3.24 (m, 1H), 2.99 (m, 3H), 2.81 (m, 1H), 2.64 (m, 1H), 2.58 (s, 3H), 2.18 (m, 2H), 1.84 (m, 2H), 1.19 (t, J=7.2 Hz, 3H)

Example 57: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide

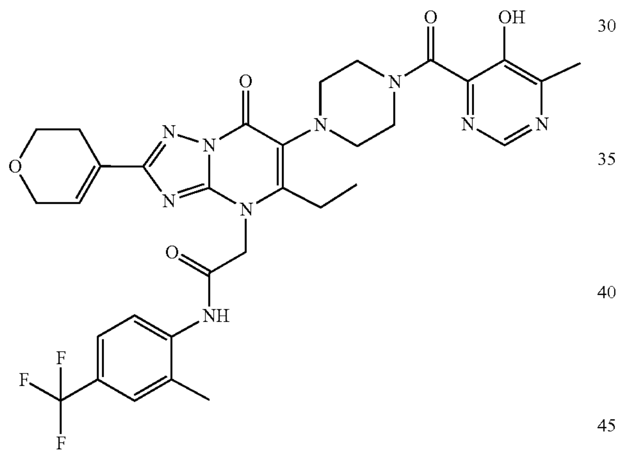

Step 1: 2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide To a stirred solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (8.30 g, 15.2 mmol), 5-methoxy-6-methylpyrimidine-4-carboxylic acid (Intermediate CW) (3.46 g, 19.8 mmol) and HATU (8.68 g, 22.8 mmol) in DMF (80 mL) was added DIPEA (13.3 mL, 76.0 mmol) at RT and the RM was stirred at RT for 15 minutes. The RM was diluted with EtOAc/water, extracted twice with EtOAc and the combined organic extracts were dried over $Na_2SO_4$ and concentrated. The crude product was purified by column chromatography (RediSep Column: Silica 120 g, eluent DCM:DCM/MeOH (8/2) 100:0 to 65:35). The product containing fractions were combined and concentrated to give the title compound as a beige foam. Trituration of the product in $Et_2O$ at 40° C. for 30 minutes afforded the title compound as a white solid.

LC-MS: Rt=1.02 min; MS m/z $[M+H]^+$ 696.3, m/z $[M-H]^-$ 694.5; UPLC-MS 1

Step 2: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide To a stirred solution of 2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide (8.46 g, 8.63 mmol) in DMF (80 mL) was added LiCl (1.46 g, 34.5 mmol) at RT and the RM was stirred at 210° C. for 12 minutes in the MW (split into 8 vials). The RM was diluted with EtOAc/water, the pH was adjusted to 2-3 with 1N HCl, and the mixture was extracted 3 times with EtOAc. The combined organic extracts were washed with brine, dried over $Na_2SO_4$ and concentrated. The crude product was purified by column chromatography (RediSep Column: Silica 120 g Gold, eluent DCM:DCM/MeOH (8/2) 100:0 to 70:30). The product containing fractions were combined and concentrated. The solid was triturated in $Et_2O$ for 30 minutes at 40° C. to give the title compound as a colorless solid characterized by the XRPD diffractogram in FIG. 4. The table below shows the most prominent peaks (deg 2theta) of the XRPD diffractogram of FIG. 4.

The sodium salt was prepared analogous to the general procedure.

LC-MS: Rt=1.00 min; MS m/z $[M+H]^+$ 682.5, m/z $[M-H]^-$ 680.6; UPLC-MS 1

$^1$H NMR (400 MHz, DMSO-$d_6$) δ 10.34 (s, br, 1H), 10.00 (s, 1H), 8.55 (s, 1H), 7.72 (d, J=8.5 Hz, 1H), 7.62 (m, 1H), 7.53 (d, J=8.8 Hz, 1H), 6.83 (m, 1H), 5.24 (s, 2H), 4.52 (m, 1H), 4.26 (m, 2H), 3.81 (m, 2H), 3.50 (m, 3H), 3.25 (m, 1H), 3.00 (m, 3H), 2.81 (m, 1H), 2.63 (m, 1H), 2.51 (m, 2H), 2.43 (s, 3H), 2.35 (s, 3H), 1.20 (t, J=7.4 Hz, 3H)

| Angle 2-Theta° | d Value Angstrom | Intensity |
|---|---|---|
| 11.81 | 7.49 | medium |
| 13.75 | 6.44 | medium |
| 14.45 | 6.13 | medium |
| 15.32 | 5.78 | medium |
| 17.04 | 5.20 | high |
| 17.40 | 5.09 | medium |
| 18.27 | 4.85 | medium |
| 19.95 | 4.45 | medium |
| 22.92 | 3.88 | medium |
| 27.13 | 3.28 | medium |

Example 58: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

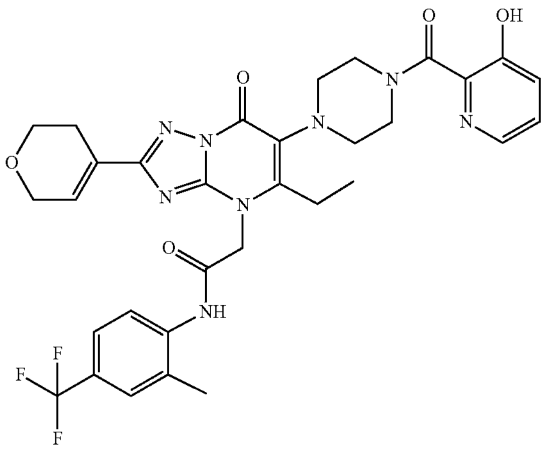 [SMILES: CCc1c(N2CCN(C(=O)c3ncccc3O)CC2)c(=O)n2nc(C3=CCOCC3)nc2n1CC(=O)Nc1ccc(C(F)(F)F)cc1C]

3-Hydroxypicolinic acid (110 mg, 778 μmol) was dissolved in DCM (5 mL) at RT under argon. 1-Chloro-N,N,2-trimethylprop-1-en-1-amine (113 μL, 856 μmol) was added and the RM was stirred at RT for 1.75 hours. A solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (312 mg, 389 μmol) in DCM (2 mL) and DIPEA (340 μL, 1.94 mmol) were added and the RM was stirred at RT for 2.5 hours. The RM was quenched with water (5 mL) and aq sat $NaHCO_3$ (5 mL) and extracted with DCM (4×20 mL). The combined organic layers were washed with aq sat $NaHCO_3$ (5 mL) and water, dried over a phase separator and concentrated under reduced pressure. The crude product was adsorbed onto Isolute and purified by column chromatography (RediSep Column: Silica 24 g, eluent DCM:MeOH 100:0 to 90:10). The product containing fractions were combined and concentrated under reduced pressure. The still impure product was purified in 2 portions by reverse phase preparative HPLC (RP-HPLC acidic 1: 10 to 90% B in 20 min and RP-HPLC acidic 1: 20 to 80% B in 20 min). The product containing fractions were combined, basified with aq sat $NaHCO_3$ and the ACN was removed under reduced pressure. The residue was extracted with DCM (3×10 mL), dried through a phase separator and concentrated under reduced pressure to give the title compound as a pale yellow solid.

The sodium salt was prepared analogous to the general procedure.

LC-MS: Rt=1.00 min; MS m/z $[M+H]^+$ 667.4, m/z $[M-H]^-$ 665.4; UPLC-MS 4

$^1$H NMR (400 MHz, DMSO-$d_6$) δ 10.39 (s, 1H), 10.01 (s, 1H), 8.06 (m, 1H), 7.72 (d, J=8.4 Hz, 1H), 7.63 (m, 1H), 7.53 (d, J=8.6 Hz, 1H), 7.29 (m, 2H), 6.83 (m, 1H), 5.24 (s, 2H), 4.55 (m, 1H), 4.26 (m, 2H), 3.81 (m, 2H), 3.44 (m, 3H), 3.22 (m, 1H), 2.99 (m, 3H), 2.80 (m, 1H), 2.62 (m, 1H), 2.54 (m, 2H), 2.35 (s, 3H), 1.20 (t, J=7.4 Hz, 3H)

Example 59: 2-(2-(3,4-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

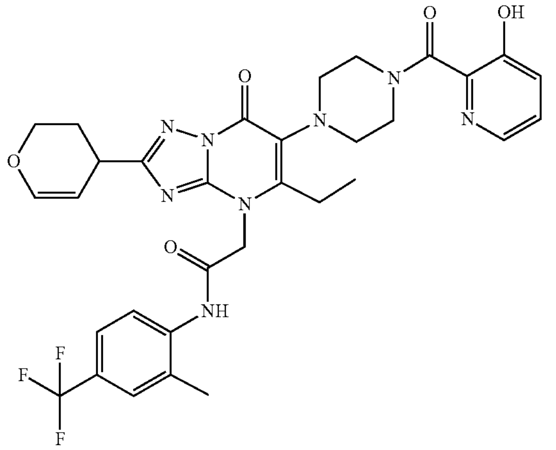 [SMILES: CCc1c(N2CCN(C(=O)c3ncccc3O)CC2)c(=O)n2nc(C3C=COCC3)nc2n1CC(=O)Nc1ccc(C(F)(F)F)cc1C]

2-(2-(3,6-Dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Example 58) (100 mg, 145 μmol) was suspended in DMF (500 μL). Sodium methanethiolate (100 mg, 1.43 mmol) was added and the RM was stirred at 120° C. for 40 minutes. The RM was allowed to cool to RT and it was partitioned between water (60 mL) and DCM/MeOH (3:1) (50 mL). The organic layer was separated, dried over $MgSO_4$, filtered and reduced in vacuo to give a solution of the crude product in DMF, which was purified in 2 portions by reverse phase preparative HPLC (RP-HPLC acidic 1: 30 to 55% B in 15 min with a plateau at 55% for 1 min and RP-HPLC acidic 1: 30 to 50% B in 15 min with a plateau at 50% for 1 min). The product containing fractions were basified with 5% aq $NaHCO_3$ and extracted with DCM (2×10 mL). The organics were eluted through a phase separator and evaporated in vacuo to give the title compound as a white solid.

LC-MS: Rt=1.02 min; MS m/z $[M+H]^+$ 667.5, m/z $[M-H]^-$ 665.5; UPLC-MS 1

LC-MS: Rt=3.02 min; MS m/z $[M+H]^+$ 667.4, m/z $[M-H]^-$ 665.3; UPLC-MS 9

$^1$H NMR (600 MHz, DMSO-$d_6$) δ 10.38 (s, br, 1H), 9.99 (s, 1H), 8.06 (m, 1H), 7.68 (d, J=8.2 Hz, 1H), 7.62 (m, 1H), 7.53 (d, J=8.2 Hz, 1H), 7.28 (m, 2H), 6.51 (m, 1H), 5.22 (s, 2H), 4.83 (m, 1H), 4.54 (m, 1H), 4.08 (m, 1H), 4.01 (m, 1H), 3.62 (m, 1H), 3.46 (m, 3H), 3.22 (m, 1H), 2.95 (m, 3H), 2.78 (m, 1H), 2.59 (m, 1H), 2.34 (s, 3H), 2.09 (m, 2H), 1.18 (t, J=7.5 Hz, 3H)

Example 60: 2-(5-ethyl-6-(4-(3-hydroxypicolinoyl) piperazin-1-yl)-7-oxo-2-(6-oxo-3,6-dihydro-2H-pyran-4-yl)-[1,2,4]triazolo[1,5-a]pyrimidin-4 (7H)-yl)-N-(2-methyl-4-(trifluoromethyl)phenyl) acetamide

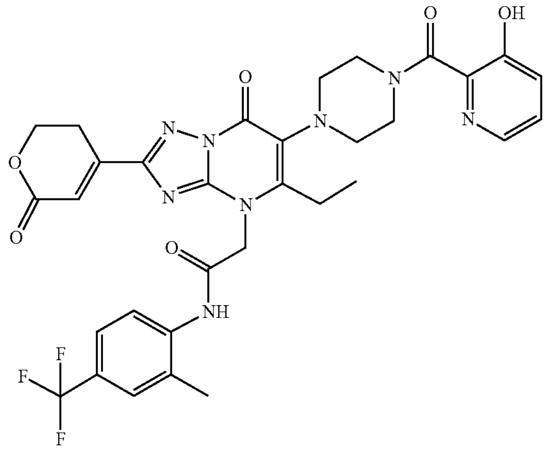 [SMILES: CCc1c(N2CCN(C(=O)c3ncccc3O)CC2)c(=O)n2nc(C3=CC(=O)OCC3)nc2n1CC(=O)Nc1ccc(C(F)(F)F)cc1C]

To a 3 L plastic Erlenmeyer covered with a breathable seal was added McIlvaine Puffer pH 4.5 (970 mL), 2-(2-(3,6-dihydro-2H-pyran-4-yl)-5-ethyl-6-(4-(3-hydroxypicolinoyl) piperazin-1-yl)-7-oxo-[1,2,4]triazolo[1,5-a]pyrimidin-4 (7H)-yl)-N-(2-methyl-4-(trifluoromethyl)phenyl)acetamide (Example 58) (100 mg, 150 μmol) dissolved in DMSO (5 mL), N-hydroxyphthalimide (163 mg, 1.00 mmol) dissolved in DMSO (5 mL) and laccase (3.00 g) (Supplier: Aldrich laccase from trametes versicolor 0.5 U/mg). The RM was stirred at 30° C. 150 RPM in an Infors HT Multitron Shaker. After 3 hours, the conversion stopped at 19% and laccase (1.00 g) was added. A decrease in the conversion was observed in the next 45 minutes and the reaction was quenched and extracted with EtOAc (1 L) and then EtOAc (500 mL). The organic layer was dried over $MgSO_4$ and concentrated to dryness. The crude product was dissolved in DMSO (4 mL) and purified by reverse phase preparative HPLC (RP-HPLC acidic 13: 0 to 70% B in 30 min with a plateau at 70% for 5 min). The target compound was dried and submitted to SFC (SFC 7) to give the title compound.

LC-MS: Rt=0.94 min; MS m/z $[M+H]^+$ 681.4, m/z $[M-H]^-$ 679.4; UPLC-MS 1

$^1$H NMR (600 MHz, DMSO-$d_6$) δ 10.08 (s, 1H), 8.05 (m, 1H), 7.70 (d, J=8.4 Hz, 1H), 7.63 (m, 1H), 7.53 (d, J=8.4 Hz, 1H), 7.28 (m, 2H), 6.66 (m, 1H), 5.29 (s, 2H), 4.52 (m, 3H), 3.46 (m, 3H), 3.23 (m, 1H), 3.03 (m, 2H), 2.97 (m, 3H), 2.81 (m, 1H), 2.63 (m, 1H), 2.36 (s, 3H), 1.20 (t, J=7.5 Hz, 3H)

Example 61: 2-(6-(4-(4-chloro-3-hydroxypicolinoyl) piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(trifluoromethyl)phenyl) acetamide

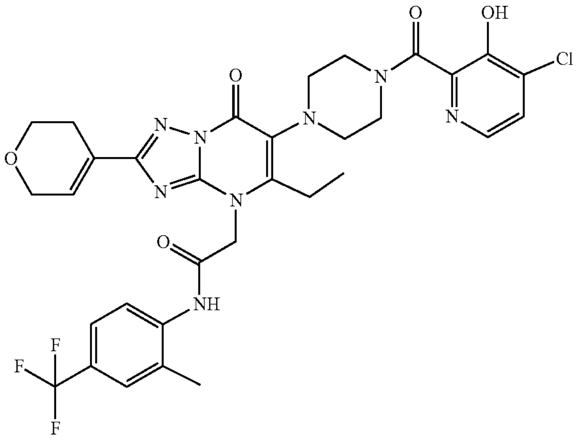 [SMILES: CCc1c(N2CCN(C(=O)c3nccc(Cl)c3O)CC2)c(=O)n2nc(C3=CCOCC3)nc2n1CC(=O)Nc1ccc(C(F)(F)F)cc1C]

4-Chloro-3-hydroxypicolinic acid (199 mg, 1.15 mmol) was dissolved in DCM (12 mL) at RT under argon. 1-Chloro-N,N,2-trimethylprop-1-en-1-amine (171 mg, 1.28 mmol) was added and the RM was stirred at RT for 2.5 hours. 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (250 mg, 458 μmol) and DIPEA (320 μL, 1.83 mmol) were added and the brown solution was stirred at RT for 1.25 hours. The RM was quenched with water (10 mL) and aq sat $NaHCO_3$ (10 mL). Then it was extracted with DCM (4×40 mL). The organic layers were combined and washed with water (10 mL), dried through a phase separator and concentrated under reduced pressure. The residue was adsorbed onto Isolute and purified by column chromatography (RediSep Column: Silica 24 g, eluent DCM:MeOH 100:0 to 80:20). The product containing fractions were combined, concentrated under reduced pressure and dried under HV to give the title compound as a beige solid. A part of the solid was dissolved in MeOH (2.5 mL) and DCM (2.5 mL) and crystallized on standing. The resulting solid was dried under HV to give the title compound.

LC-MS: Rt=1.09 min; MS m/z $[M+H]^+$ 701.5, m/z $[M-H]^-$ 699.3; UPLC-MS 1

$^1$H NMR (600 MHz, DMSO-$d_6$) δ 10.83 (s, 1H), 10.00 (s, 1H), 8.06 (d, J=5.0 Hz, 1H), 7.72 (d, J=8.4 Hz, 1H), 7.62 (m, 1H), 7.56 (d, J=5.1 Hz, 1H), 7.53 (d, J=8.2 Hz, 1H), 6.83 (m, 1H), 5.24 (s, 2H), 4.54 (m, 1H), 4.26 (m, 2H), 3.81 (m, 2H), 3.53 (m, 3H), 3.25 (m, 1H), 3.00 (m, 3H), 2.81 (m, 1H), 2.64 (m, 1H), 2.54 (m, 2H), 2.35 (s, 3H), 1.20 (t, J=7.5 Hz, 3H)

Example 62: 2-(2-(3,6-dihydro-2H-pyran-4-yl)-5-ethyl-6-(4-(4-fluoro-3-hydroxy-6-methylpicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

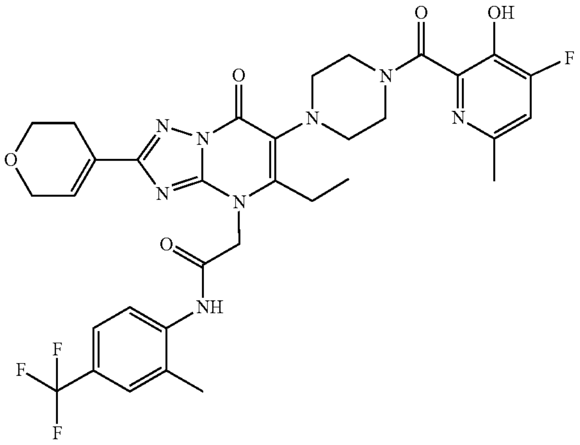 [SMILES: CCc1c(N2CCN(C(=O)c3nc(C)cc(F)c3O)CC2)c(=O)n2nc(C3=CCOCC3)nc2n1CC(=O)Nc1ccc(C(F)(F)F)cc1C]

Step 1: 2-(6-(4-(3-(benzyloxy)-4-fluoro-6-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(trifluoromethyl)phenyl)acetamide 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (285 mg, 522 μmol), 3-(benzyloxy)-4-fluoro-6-methylpicolinic acid (Intermediate CX) (171 mg, 575 μmol) and HATU (218 mg, 575 μmol) were suspended in DCM (5 mL) and cooled to 0° C. Then DIPEA (228 μL, 1.31 mmol) was added and the RM was stirred at RT for 2.5 hours. Water (20 mL), aq sat $NaHCO_3$ (10 mL) and DCM (30 mL) were added. The aqueous layer was washed with DCM (2×20 mL). The combined organic layers were dried through a phase separator and concentrated under reduced pressure. The crude product was purified in 2 portions by reverse phase preparative HPLC (2×RP-HPLC basic 1: 5 to 95% B in 20 min with a plateau at 95% for 1 min). The product containing fractions were combined, basified with aq sat $NaHCO_3$, extracted twice with DCM, dried through a phase separator and concentrated under reduced pressure to give the title compound.

LC-MS: Rt=1.23 min; MS m/z $[M+H]^+$ 789.6, m/z $[M-H]^-$ 787.3; UPLC-MS 1

Step 2: 2-(2-(3,6-dihydro-2H-pyran-4-yl)-5-ethyl-6-(4-(4-fluoro-3-hydroxy-6-methylpicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide 2-(6-(4-(3-(Benzyloxy)-4-fluoro-6-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(trifluoromethyl)phenyl)acetamide (156 mg, 178 μmol) was dissolved in DCM (5 mL) and TFA (5.00 mL, 64.9 mmol) was added and the RM was stirred at 60° C. overnight. The RM was concentrated under reduced pressure. The crude product was purified by reverse phase preparative ISCO (RediSep Column: C18 50 g Gold, eluent water+0.1% TFA:ACN 100:0 to 0:100). The product containing fractions were combined, basified with aq sat $NaHCO_3$, extracted twice with DCM, dried through a phase separator and concentrated under reduced pressure to give the title compound.

LC-MS: Rt=1.02 min; MS m/z $[M+H]^+$ 699.5, m/z $[M-H]^-$ 697.5; UPLC-MS 1

$^1H$ NMR (400 MHz, DMSO-$d_6$) δ 10.36 (s, 1H), 9.99 (s, 1H), 7.72 (d, J=8.4 Hz, 1H), 7.62 (m, 1H), 7.53 (d, J=8.6 Hz, 1H), 7.22 (d, J=11.6 Hz, 1H), 6.83 (m, 1H), 5.24 (s, 2H), 4.53 (m, 1H), 4.26 (m, 2H), 3.81 (m, 2H), 3.47 (m, 3H), 3.23 (m, 1H), 3.00 (m, 3H), 2.80 (m, 1H), 2.63 (m, 1H), 2.52 (m, 2H), 2.39 (s, 3H), 2.35 (s, 3H), 1.20 (t, J=7.4 Hz, 3H)

Example 63: 2-(2-(3,6-dihydro-2H-pyran-4-yl)-5-ethyl-6-(4-(4-fluoro-3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

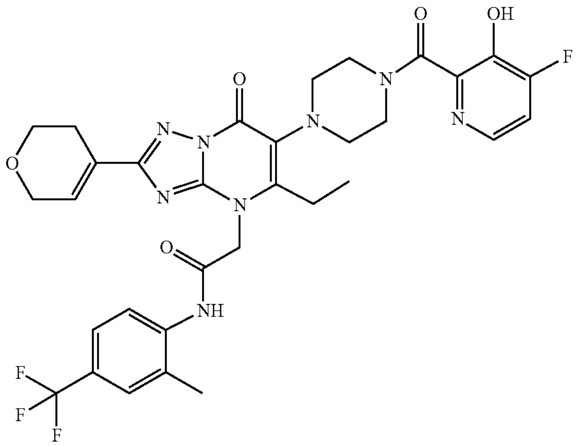 [SMILES: CCc1c(N2CCN(C(=O)c3nccc(F)c3O)CC2)c(=O)n2nc(C3=CCOCC3)nc2n1CC(=O)Nc1ccc(C(F)(F)F)cc1C]

Step 1: 2-(6-(4-(3-(benzyloxy)-4-fluoropicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(trifluoromethyl)phenyl)acetamide To a stirred solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (500 mg, 916 μmol), 3-(benzyloxy)-4-fluoropicolinic acid (Intermediate CU) (238 mg, 962 μmol) and HATU (418 mg, 1.10 mmol) in DMF (10 mL) was added DIPEA (800 μL, 4.58 mmol) at RT and the RM was stirred at RT for 10 minutes. The RM was diluted with EtOAc/water, extracted twice with EtOAc and the combined organic extracts were dried over $Na_2SO_4$ and concentrated. The crude product was purified by column chromatography (RediSep Column: Silica 24 g, eluent DCM:MeOH 100:0 to 40:60). The product containing fractions were combined and concentrated to give the title compound as a white foam.

LC-MS: Rt=1.20 min; MS m/z $[M+H]^+$ 775.3, m/z $[M-H]^-$ 773.5; UPLC-MS 1

Step 2: 2-(2-(3,6-dihydro-2H-pyran-4-yl)-5-ethyl-6-(4-(4-fluoro-3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide To a stirred suspension of 2-(6-(4-(3-(benzyloxy)-4-fluoropicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(trifluoromethyl)phenyl)acetamide (510 mg, 652 μmol) in DCM (10 mL) was added boron trichloride methyl sulfide complex (652 μL, 1.30 mmol) at RT and the RM was stirred at RT for 14 hours. The RM was quenched with MeOH. Then it was diluted with DCM/water, extracted twice with DCM and the combined organic extracts were washed with water and brine, dried over $Na_2SO_4$ and concentrated. The crude product was purified by column chromatography (RediSep Column: Silica 24 g, eluent DCM: MeOH 100:0 to 20:80). The product containing fractions were combined and concentrated. The resulting solid was purified by reverse phase preparative HPLC (RP-HPLC acidic 1: 15 to 75% B in 20 min with a plateau at 75% for 1 min). The combined fractions were basified with $NaHCO_3$, the ACN was evaporated and the resulting aqueous layer was extracted with DCM, the organic extract was washed with brine, dried over $Na_2SO_4$ and concentrated to give the title compound as a white solid.

The sodium salt was prepared analogous to the general procedure.

LC-MS: Rt=0.98 min; MS m/z $[M+H]^+$ 685.3, m/z $[M-H]^-$ 683.3; UPLC-MS 1

$^1H$ NMR (400 MHz, DMSO-$d_6$) δ 10.76 (s, br, 1H), 10.00 (s, 1H), 8.06 (m, 1H), 7.72 (d, J=8.4 Hz, 1H), 7.62 (m, 1H), 7.53 (d, J=8.6 Hz, 1H), 7.34 (m, 1H), 6.83 (m, 1H), 5.24 (s, 2H), 4.54 (m, 1H), 4.26 (m, 2H), 3.81 (m, 2H), 3.46 (m, 3H), 3.23 (m, 1H), 3.00 (m, 3H), 2.81 (m, 1H), 2.62 (m, 1H), 2.50 (m, 2H), 2.35 (s, 3H), 1.19 (t, J=7.4 Hz, 3H)

Example 64: 2-(2-(3,6-dihydro-2H-pyran-4-yl)-5-ethyl-6-(4-(5-hydroxypyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl) acetamide

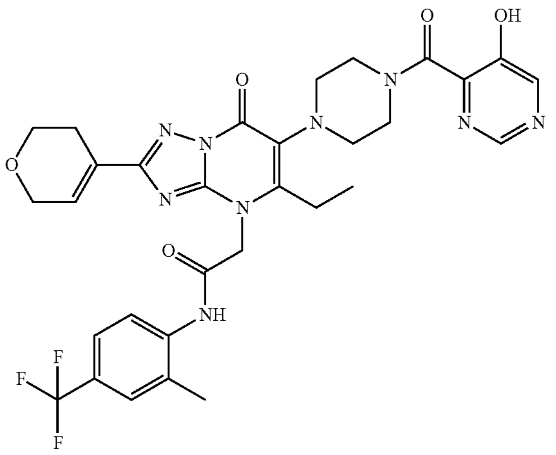 [SMILES: CCc1c(N2CCN(C(=O)c3ncncc3O)CC2)c(=O)n2nc(C3=CCOCC3)nc2n1CC(=O)Nc1ccc(C(F)(F)F)cc1C]

Step 1: 2-(2-(3,6-dihydro-2H-pyran-4-yl)-5-ethyl-6-(4-(5-methoxypyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide To a beige suspension of 5-methoxy-pyrimidine-4-carboxylic acid (83.0 mg, 522 μmol) in DCM (6 mL) was added 1-chloro-N,N,2-trimethyl-1-prop-1-en-1-amine (120 μL, 871 μmol). The RM was stirred at RT for 5 minutes. DIPEA (182 μL, 1.05 mmol) was added slowly, followed by 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (200 mg, 348 μmol). The RM became progressively a yellow to brown solution and was stirred at RT for 28 hours. There was still starting material left. To a beige suspension of 5-methoxy-pyrimidine-4-carboxylic acid (83.0 mg, 522 μmol) in DCM (6 mL) was added 1-chloro-N,N,2-trimethyl-1-prop-1-en-1-amine (120 μL, 871 μmol). The RM was stirred at RT for 5 minutes. DIPEA (182 μL, 1.05 mmol) was added, followed by the previous RM. The mixture was stirred at RT for 18 hours. There was still some starting material left, as detected by LCMS. To a beige suspension of 5-methoxy-pyrimidine-4-carboxylic acid (83.0 mg, 522 μmol) in DCM (6 mL) was added 1-chloro-N,N,2-trimethyl-1-prop-1-en-1-amine (120 μL, 871 μmol). The RM was stirred at RT for 30 minutes. DIPEA (182 μL, 1.05 mmol) was added slowly, followed by the previous RM. The resulting beige/light yellow RM was stirred at RT for 4 hours, diluted with DCM and washed with water. The aqueous layer was extracted twice with DCM. The combined organic layers were dried through a phase separator, concentrated and dried under reduced pressure to give a brown residue. The crude product was purified by column chromatography (RediSep Column: Silica 12 g, eluent DCM:DCM/MeOH (9/1) 100:0 to 50:50). The product containing fractions were combined, concentrated and dried under reduced pressure to give the title compound as a beige solid.

LC-MS: Rt=0.93 min; MS m/z $[M+H]^+$ 682.4, m/z $[M-H]^-$ 680.5; UPLC-MS 1

Step 2: 2-(2-(3,6-dihydro-2H-pyran-4-yl)-5-ethyl-6-(4-(5-hydroxypyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide To a light yellow solution of 2-(2-(3,6-dihydro-2H-pyran-4-yl)-5-ethyl-6-(4-(5-methoxypyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide (146 mg, 176 μmol) in DMF (1.8 mL) was added LiCl (22.3 mg, 527 μmol). The light yellow RM was heated to 145° C. and stirred for 2 hours. LiCl (22.3 mg, 527 μmol) was added, and the brown RM was heated to 145° C. and stirred for 21 hours. The dark brown RM was diluted with DCM and washed once with water. The aqueous layer was extracted four times with DCM and a small amount of MeOH. The combined organic layers were dried through a phase separator and concentrated to give the crude product as a solution in remaining DMF, which was purified by reverse phase preparative HPLC (RP-HPLC basic 1: 0 to 20% B in 27 min with a plateau at 20% for 1 min). The product containing fractions were combined, concentrated and lyophilized to give the title compound.

LC-MS: Rt=0.93 min; MS m/z $[M+H]^+$ 668.4, m/z $[M-H]^-$ 666.5; UPLC-MS 1

$^{1}$H NMR (600 MHz, DMSO-$d_6$) δ 10.01 (s, 1H), 8.60 (s, 1H), 8.37 (s, 1H), 7.71 (d, J=8.5 Hz, 1H), 7.62 (m, 1H), 7.53 (d, J=8.4 Hz, 1H), 6.83 (m, 1H), 5.24 (s, 2H), 4.51 (m, 1H), 4.26 (m, 2H), 3.80 (m, 2H), 3.47 (m, 3H), 3.25 (m, 1H), 2.99 (m, 3H), 2.80 (m, 1H), 2.62 (m, 1H), 2.50 (m, 2H), 2.35 (s, 3H), 1.19 (t, J=7.5 Hz, 3H)

Example 65: 2-(6-(4-(5-chloro-3-hydroxypicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(trifluoromethyl)phenyl)acetamide

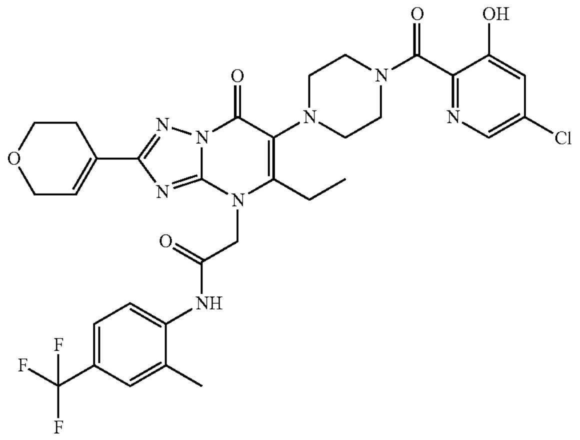 [SMILES: CCc1c(N2CCN(C(=O)c3ncc(Cl)cc3O)CC2)c(=O)n2nc(C3=CCOCC3)nc2n1CC(=O)Nc1ccc(C(F)(F)F)cc1C]

5-Chloro-3-hydroxypicolinic acid (300 mg, 1.73 mmol) was dissolved in DCM (5 mL) and 1-chloro-N,N,2-trimethylprop-1-en-1-amine (301 μL, 2.27 mmol) was added. The mixture was stirred at RT for 2 hours. Then 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (100 mg, 152 μmol) was added. The mixture was stirred at RT for 1 hour. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure. The crude product was purified by column chromatography (RediSep Column: Silica 40 g, eluent DCM: DCM/MeOH (9/1) 100:0 to 80:20). The product containing fractions were combined, concentrated and dried under reduced pressure to give impure product which was further purified by reverse phase preparative HPLC (RP-HPLC acidic 1: 5 to 100% B in 20 min). The product containing fractions were combined, basified with aq sat $NaHCO_3$, extracted twice with DCM, dried through a phase separator and concentrated under reduced pressure to give the title compound.

LC-MS: Rt=1.08 min; MS m/z $[M+H]^+$ 701.4, m/z $[M-H]^-$ 699.4; UPLC-MS 3

$^{1}$H NMR (400 MHz, DMSO-$d_6$) δ 10.97 (s, 1H), 10.00 (s, 1H), 8.13 (d, J=2.0 Hz, 1H), 7.72 (d, J=8.4 Hz, 1H), 7.63 (m, 1H), 7.53 (d, J=8.34 Hz, 1H), 7.37 (d, J=2.0 Hz, 1H), 6.83 (m, 1H), 5.24 (s, 2H), 4.53 (m, 1H), 4.27 (m, 2H), 3.81 (m, 2H), 3.44 (m, 3H), 3.22 (m, 1H), 2.99 (m, 3H), 2.80 (m, 1H), 2.61 (m, 1H), 2.51 (m, 2H), 2.35 (s, 3H), 1.20 (t, J=7.5 Hz, 3H)

Example 66: 2-(2-(3,6-dihydro-2H-pyran-4-yl)-5-ethyl-6-(4-(3-hydroxy-4-methylpicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

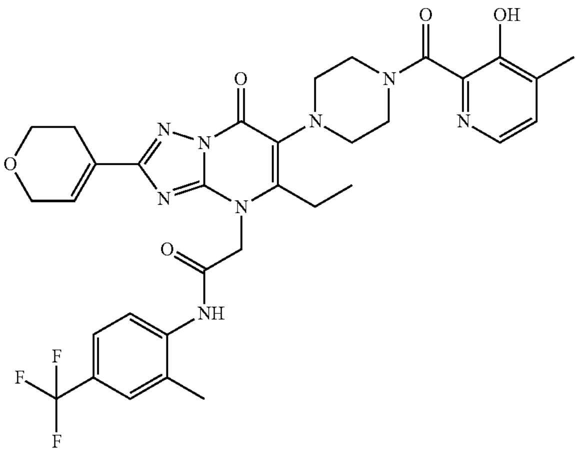

To a suspension of 3-hydroxy-4-methylpyridine-2-carboxylic acid·HCl (56.1 mg, 281 μmol) in DCM (3.1 mL) was added 1-chloro-N,N,2-trimethylprop-1-en-1-amine (60.0 μL, 435 μmol). The RM was stirred at RT for 55 minutes, and DIPEA (152 μL, 871 μmol) was added slowly, followed by 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (100 mg, 174 μmol). The RM was stirred at RT for 18.25 hours, diluted with DCM and washed with water. The aqueous layer was extracted twice with DCM. The combined organic layers were dried through a phase separator and concentrated under reduced pressure. The crude product was suspended in MeOH and filtered. The filtrate was concentrated under reduced pressure, and the residue was purified by reverse phase preparative HPLC (RP-HPLC acidic 1: 20 to 50% B in 20 min, with a plateau at 50% for 1 min). The product containing fractions were combined and concentrated to remove the ACN. The residue was basified with solid $NaHCO_3$, extracted twice with DCM, dried through a phase separator and concentrated under reduced pressure to give the title compound.

LC-MS: Rt=1.05 min; MS m/z $[M+H]^+$ 681.5, m/z $[M-H]^-$ 679.4; UPLC-MS 3

$^{1}$H NMR (600 MHz, DMSO-$d_6$) δ 10.39 (s, br, 1H), 10.02 (s, 1H), 7.98 (d, J=4.6 Hz, 1H), 7.72 (d, J=8.4 Hz, 1H), 7.62 (m, 1H), 7.53 (d, J=8.4 Hz, 1H), 7.25 (d, J=4.6 Hz, 1H), 6.83 (m, 1H), 5.25 (s, 2H), 4.57 (m, 1H), 4.26 (m, 2H), 4.10 (m, 1H), 3.81 (m, 2H), 3.51 (m, 2H), 3.29 (m 1H), 3.01 (m, 3H), 2.82 (m, 1H), 2.66 (m, 1H), 2.52 (m, 2H), 2.35 (s, 3H), 2.23 (s, 3H), 1.20 (t, J=7.5 Hz, 3H)

Example 67: 2-(2-(3,6-dihydro-2H-pyran-4-yl)-5-ethyl-6-(4-(3-hydroxy-4-(trifluoromethoxy)picolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

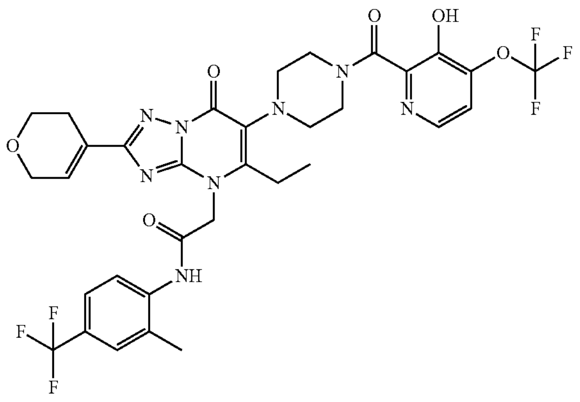 [SMILES: CCc1c(N2CCN(C(=O)c3nccc(OC(F)(F)F)c3O)CC2)c(=O)n2nc(C3=CCOCC3)nc2n1CC(=O)Nc1ccc(C(F)(F)F)cc1C]

Step 1: 2-(2-(3,6-dihydro-2H-pyran-4-yl)-5-ethyl-6-(4-(3-methoxy-4-(trifluoromethoxy)picolinoyl)piperazin-1-yl)-7-oxo-[1,2,4]triazolo[1,5-a]pyrimidin-4 (7H)-yl)-N-(2-methyl-4-(trifluoromethyl)phenyl) acetamide To a suspension of 3-methoxy-4-(trifluoromethoxy)picolinic acid (Intermediate CZ) (32.9 mg, 136 μmol) in DCM (1.9 mL) was added 1-chloro-N,N,2-trimethylprop-1-en-1-amine (39.0 μL, 283 μmol), and the RM was stirred at RT for 1 hour. DIPEA (59.3 μL, 340 μmol) was added slowly, followed by 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (65.0 mg, 113 μmol). The RM was stirred at RT for 3 hours, diluted with DCM and washed with water. The aqueous layer was extracted twice with DCM. The combined organic layers were dried through a phase separator and concentrated under reduced pressure. The crude product was purified by column chromatography (RediSep Column: Silica 4 g, eluent DCM:DCM/MeOH (8/2) 100:0 to 50:50). The product containing fractions were combined and concentrated under reduced pressure to give the title compound as a beige solid.

LC-MS: Rt=1.17 min; MS m/z $[M+H]^+$ 765.5, m/z $[M-H]^-$ 763.5; UPLC-MS 1

Step 2: 2-(2-(3,6-dihydro-2H-pyran-4-yl)-5-ethyl-6-(4-(3-hydroxy-4-(trifluoromethoxy)picolinoyl)piperazin-1-yl)-7-oxo-[1,2,4]triazolo[1,5-a]pyrimidin-4 (7H)-yl)-N-(2-methyl-4-(trifluoromethyl)phenyl) acetamide A RM of 2-(2-(3,6-dihydro-2H-pyran-4-yl)-5-ethyl-6-(4-(3-methoxy-4-(trifluoromethoxy)picolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (48.0 mg, 49.0 μmol) and LiCl (8.30 mg, 196 μmol) in DMF (490 μL) was submitted to MW irradiations (very high absorption) at 200° C. for 10 minutes. The RM was diluted with water and extracted three times with EtOAc. The combined organic layers were washed once with brine, dried over $Na_2SO_4$, concentrated and dried under HV. The residue was purified by reverse phase preparative HPLC (RP-HPLC basic 1: 5 to 70% B in 20 min, with a plateau at 70% for 1 min). The product containing fractions were combined and concentrated to remove the ACN, then it was lyophilized to give the title compound.

LC-MS: Rt=1.17 min; MS m/z $[M+H]^+$ 751.3, m/z $[M-H]^-$ 749.3; UPLC-MS 1

Example 68: 2-(2-(3,6-dihydro-2H-pyran-4-yl)-5-ethyl-6-(4-(5-hydroxy-2-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl) phenyl)acetamide

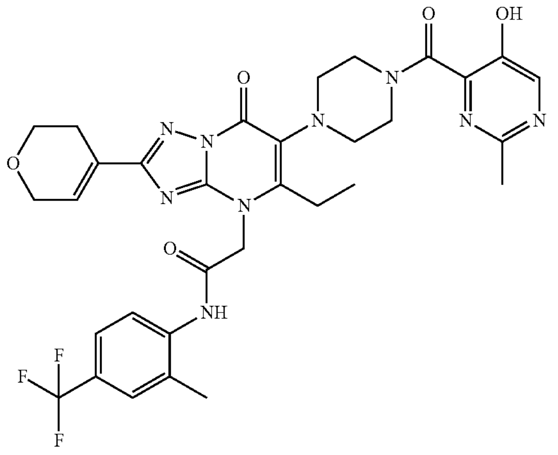 [SMILES: CCc1c(N2CCN(C(=O)c3nc(C)ncc3O)CC2)c(=O)n2nc(C3=CCOCC3)nc2n1CC(=O)Nc1ccc(C(F)(F)F)cc1C]

Step 1: 2-(2-(3,6-dihydro-2H-pyran-4-yl)-5-ethyl-6-(4-(5-methoxy-2-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl) acetamide To a brown suspension of 5-methoxy-2-methylpyrimidine-4-carboxylic acid (40.6 mg, 229 μmol) in DCM (3.1 mL) was added 1-chloro-N,N,2-trimethylprop-1-en-1-amine (35.4 μL, 257 μmol). The RM was stirred at RT for 30 minutes. DIPEA (96.0 μL, 550 μmol) was added slowly, followed by 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (100 mg, 174 μmol). The brown solution was stirred at RT for 20 hours. To a suspension of 5-methoxy-2-methylpyrimidine-4-carboxylic acid (40.6 mg, 229 μmol) in DCM (3.1 mL) was added 1-chloro-N,N,2-trimethylprop-1-en-1-amine (35.4 μL, 257 μmol). The RM was stirred at RT for 2.25 hours. DIPEA (96.0 μL, 550 μmol) was added slowly, followed by the previous RM. The RM was stirred at RT over the weekend. The RM was diluted with DCM and washed with water. The aqueous layer was extracted twice with DCM. The combined organic layers were dried through a phase separator and concentrated under reduced pressure. The aqueous layer still contained product so it was extracted twice with DCM and a small amount of MeOH. The combined organic layers were dried through a phase separator and concentrated under reduced pressure. The first crude product was purified by column chromatography (RediSep Column: Silica 4 g, eluent EtOAc:EtOAc/

EtOH (95/5) 100:0 to 0:100). The product containing fractions were combined and concentrated to give product. The second crude product was purified by column chromatography (RediSep Column: Silica 4 g, eluent EtOAc:EtOAc/EtOH (95/5) 100:0 to 0:100). The product containing fractions were combined and concentrated to give product. Both materials were combined to give the title compound.

LC-MS: Rt=0.97 min; MS m/z $[M+H]^+$ 696.5, m/z $[M-H]^-$ 694.4; UPLC-MS 3

Step 2: 2-(2-(3,6-dihydro-2H-pyran-4-yl)-5-ethyl-6-(4-(5-hydroxy-2-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl) acetamide To a light yellow solution of 2-(2-(3,6-dihydro-2H-pyran-4-yl)-5-ethyl-6-(4-(5-methoxy-2-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl) acetamide (28.0 mg, 38.0 μmol) in DMF (396 μL) was added LiCl (5.04 mg, 119 μmol). The RM was heated to 145° C. and stirred for 7.5 hours. LiCl (3.00 mg, 71.0 μmol) was added. The RM was heated to 145° C. and stirred for 15 hours. The RM was diluted with DCM and washed once with water. The aqueous layer was extracted once with DCM. The combined organic layers were dried through a phase separator, concentrated and dried under vacuum. The residue was purified by reverse phase preparative HPLC (RP-HPLC basic 1: 5 to 50% B in 20 min, with a plateau at 50% for 1 min). The product containing fraction was lyophilized to give the title compound.

LC-MS: Rt=0.58 min; MS m/z $[M+H]^+$ 682.5, m/z $[M-H]^-$ 680.4; UPLC-MS 5

$^1$H NMR (600 MHz, DMSO-$d_6$) δ 10.41 (s, br, 1H), 10.01 (s, 1H), 8.33 (s, 1H), 7.72 (d, J=8.4 Hz, 1H), 7.63 (m, 1H), 7.54 (d, J=8.1 Hz, 1H), 6.83 (m, 1H), 5.25 (s, 2H), 4.51 (m, 1H), 4.27 (m, 2H), 3.81 (m, 2H), 3.47 (m, 3H), 3.25 (m, 1H), 2.99 (m, 3H), 2.81 (m, 1H), 2.62 (m, 1H), 2.53 (s, 3H), 2.50 (m, 2H), 2.36 (s, 3H), 1.20 (t, J=7.5 Hz, 3H)

Example 69: N-(5-chloro-2-methyl-4-(trifluoromethyl)phenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl) acetamide

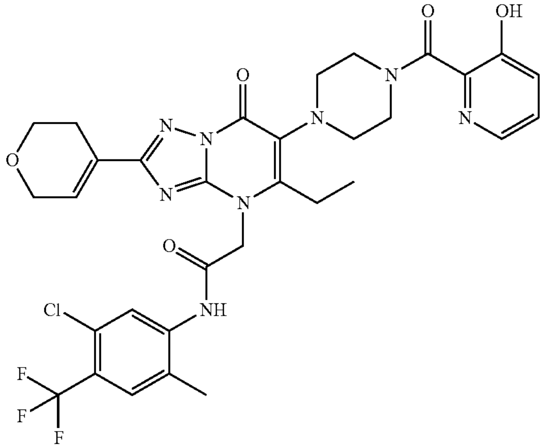 [SMILES: CCc1c(N2CCN(C(=O)c3ncccc3O)CC2)c(=O)n2nc(C3=CCOCC3)nc2n1CC(=O)Nc1cc(Cl)c(C(F)(F)F)cc1C]

N-(5-chloro-2-methyl-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AQ) (170 mg, 293 μmol) was suspended in DMF (5 mL) and 3-hydroxypicolinic acid (82.0 mg, 586 μmol), DIPEA (256 μL, 1.47 mmol), HOBt (79.0 mg, 586 μmol) and EDC·HCl (112 mg, 586 μmol) were added to the RM and it was stirred at RT for 12 hours. Water was added to the RM and it was filtered to obtain a solid crude product which was purified by reverse phase preparative HPLC (RP-HPLC basic 2: 15 to 25% B in 2 min, 25 to 60% B in 10 min) to give the title compound.

LC-MS: Rt=1.05 min; MS m/z $[M+H]^+$ 701.6, m/z $[M-H]^-$ 699.4; UPLC-MS 1

LC-MS: Rt=5.22 min; MS m/z $[M+H]^+$ 701.2, m/z $[M-H]^-$ 699.3; UPLC-MS 2

$^1$H NMR (400 MHz, DMSO-$d_6$) δ 10.40 (s, br, 1H), 10.11 (s, br, 1H), 8.06 (m, 1H), 7.96 (s, 1H), 7.75 (s, 1H), 7.28 (m, 2H), 6.82 (m, 1H), 5.27 (s, 2H), 4.55 (m, 1H), 4.25 (m, 2H), 3.81 (m, 2H), 3.44 (m, 3H), 3.22 (m, 1H), 2.98 (m, 3H), 2.80 (m, 1H), 2.62 (m, 1H), 2.50 (m, 2H), 2.35 (s, 3H), 1.18 (t, J=6.8 Hz, 3H)

Example 70: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(5-fluoro-2-methyl-6-(trifluoromethyl)pyridin-3-yl) acetamide

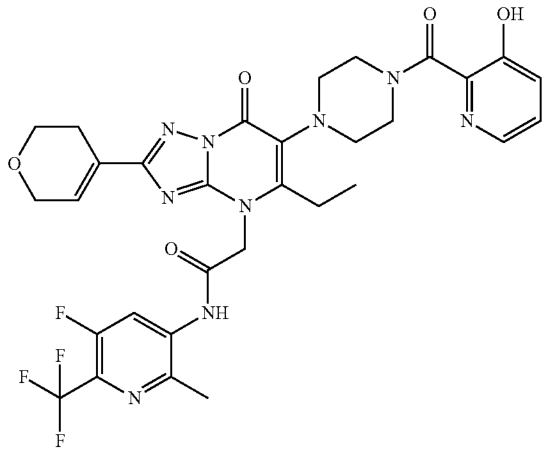

2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-6-(trifluoromethyl)pyridin-3-yl)acetamide (Intermediate AR) (1.40 g, 1.84 mmol) was dissolved in DCM (10 mL) and 3-hydroxypicolinoyl chloride (Intermediate CV) (520 mg, 3.30 mmol) was added, followed by DIPEA (1.60 mL, 9.18 mmol). The RM was stirred at RT for 2 hours. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure. The crude product was purified by column chromatography (RediSep Column: Silica 40 g, eluent DCM: DCM/MeOH (9/1) 100:0 to 30:70). The product containing fractions were combined, concentrated under vacuum and dried under HV to afford a grey solid which was purified by reverse phase preparative HPLC (RP-HPLC acidic 1: 5 to 95% B in 20 min). The product containing fractions were combined, basified with aq sat $NaHCO_3$, extracted twice with DCM, dried through a phase separator and concentrated under reduced pressure to give the title compound.

LC-MS: Rt=0.96 min; MS m/z $[M+H]^+$ 686.4, m/z $[M-H]^-$ 684.4; UPLC-MS 3

$^1$H NMR (400 MHz, DMSO-$d_6$) δ 10.38 (s, 1H), 10.33 (s, br, 1H), 8.31 (d, J=12.4 Hz, 1H), 8.07 (m, 1H), 7.29 (m, 2H), 6.82 (m, 1H), 5.33 (s, 2H), 4.55 (m, 1H), 4.26 (m, 2H), 3.81 (m, 2H), 3.46 (m, 3H), 3.23 (m, 1H), 2.97 (m, 3H), 2.80 (m, 1H), 2.62 (m, 1H), 2.59 (s, 3H), 2.51 (m, 2H), 1.19 (t, J=7.5 Hz, 3H)

Example 71: (R)-2-(2-(3,6-dihydro-2H-pyran-4-yl)-5-ethyl-6-(4-(3-hydroxypicolinoyl)-3-methylpiperazin-1-yl)-7-oxo-[1,2,4]triazolo[1,5-a]pyrimidin-4(7H)-yl)-N-(4-(trifluoromethyl)phenyl)acetamide

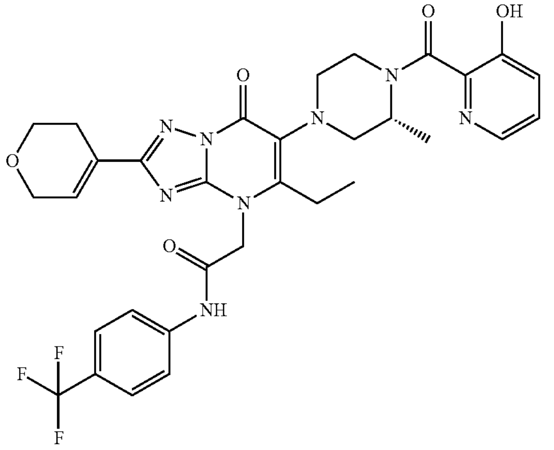 [SMILES: CCc1c(N2CCN(C(=O)c3ncccc3O)[C@H](C)C2)c(=O)n2nc(C3=CCOCC3)nc2n1CC(=O)Nc1ccc(C(F)(F)F)cc1]

3-Hydroxypicolinic acid (59.8 mg, 421 μmol) was dissolved in DCM (3.4 mL) at RT under argon. 1-Chloro-N,N,2-trimethylprop-1-en-1-amine (61.3 μL, 463 μmol) was added and the RM was stirred at RT for 1.5 hours. A solution of (R)-2-(2-(3,6-dihydro-2H-pyran-4-yl)-5-ethyl-6-(3-methylpiperazin-1-yl)-7-oxo-[1,2,4]triazolo[1,5-a]pyrimidin-4(7H)-yl)-N-(4-(trifluoromethyl)phenyl)acetamide (Intermediate BF) (174 mg, 210 μmol) in DCM (1 mL) and DIPEA (184 μL, 1.05 mmol) was added and the brown solution was stirred at RT for 24 hours. The RM was quenched with water (5 mL) and aq sat $NaHCO_3$ (5 mL) and then extracted with DCM (4×20 mL). The organic layers were combined, dried through a phase separator and concentrated under reduced pressure. The residue was adsorbed onto Isolute and purified by column chromatography (RediSep Column: Silica 40 g, eluent DCM:MeOH 100:0 to 90:10). The product containing fractions were combined and concentrated under reduced pressure. This material was purified by reverse phase preparative HPLC (RP-HPLC acidic 1: 10 to 90% B in 20 min). The product containing fractions were lyophilized. The resulting solid was dissolved in DCM/MeOH and filtered through a PL-$HCO_3$ MP SPE (100 mg per 6 mL) cartridge. The filtrate was concentrated and dried under HV to give the title compound as a colorless solid.

LC-MS: Rt=1.04 min; MS m/z $[M+H]^+$ 667.3, m/z $[M-H]^-$ 665.1; UPLC-MS 4

$^1$H NMR (400 MHz, DMSO-$d_6$) δ 10.87 (s, 1H), 10.34 (d, J=9.3 Hz, 1H), 8.07 (m, 1H), 7.79 (d, J=8.5 Hz, 2H), 7.71 (d, J=8.5 Hz, 2H), 7.29 (m, 2H), 6.80 (m, 1H), 5.21 (m, 2H), 4.81-4.40 (m, 1H), 4.24 (m, 2H), 3.80 (m, 2H), 3.68 (m, 2H), 3.43 (m, 1H), 3.16 (m, 2H), 2.92 (m, 1H), 2.81 (m, 1H), 2.63 (m, 1H), 2.55 (s, 2H), 1.39 (dd, J=6.5 Hz, 19.0 Hz, 3H), 1.20 (t, J=7.2 Hz, 3H)

Example 72: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(4-(trifluoromethyl)phenyl)acetamide

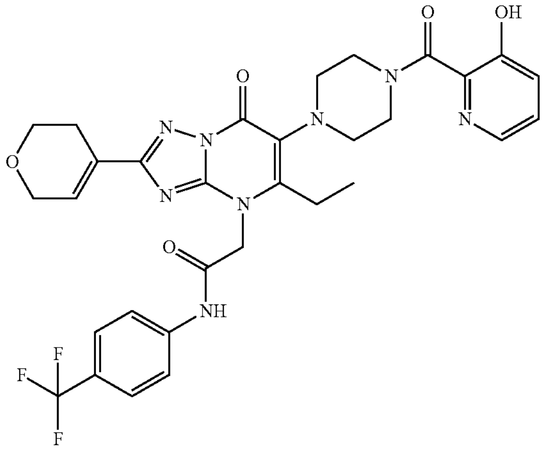 [SMILES: CCc1c(N2CCN(C(=O)c3ncccc3O)CC2)c(=O)n2nc(C3=CCOCC3)nc2n1CC(=O)Nc1ccc(C(F)(F)F)cc1]

3-Hydroxypicolinic acid (141 mg, 1.01 mmol) was dissolved in DCM (2 mL) and 1-chloro-N,N,2-trimethylprop-1-en-1-amine (221 μL, 1.67 mmol) was added. The RM was stirred at RT for 2 hours. Then 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide (Intermediate AS) (267 mg, 477 μmol) was added, followed by DIPEA (417 μL, 2.39 mmol). The RM was stirred at RT for 2 hours. Water, aq sat $NaHCO_3$ and DCM were added. The aqueous layer was extracted twice with DCM. The combined organic layers were dried through a phase separator and concentrated under reduced pressure. The crude product was purified by reverse phase preparative HPLC (RP-HPLC acidic 1: 20 to 65% B in 30 min). The product containing fractions were combined, basified with aq sat $NaHCO_3$, extracted twice with DCM, dried through a phase separator and concentrated under reduced pressure. The concentrated fractions were suspended in MeOH and sonicated. Then this material was filtered and the cake was washed three times with MeOH. The cake was purified by reverse phase preparative HPLC (RP-HPLC acidic 1: 27 to 45% B in 25 min). The product containing fractions were combined, basified with aq sat $NaHCO_3$, extracted twice with DCM, dried through a phase separator and concentrated under reduced pressure to give the title compound.

LC-MS: Rt=0.94 min; MS m/z $[M+H]^+$ 653.2, m/z $[M-H]^-$ 651.1; UPLC-MS 4

$^1$H NMR (400 MHz, DMSO-$d_6$) δ 10.85 (s, 1H), 10.38 (s, 1H), 8.07 (m, 1H), 7.78 (d, J=8.6 Hz, 2H), 7.70 (d, J=8.8 Hz, 2H), 7.29 (m, 2H), 6.80 (m, 1H), 5.20 (s, 2H), 4.56 (m, 1H), 4.24 (m, 2H), 3.80 (m, 2H), 3.47 (m, 3H), 3.23 (m, 1H), 2.98 (m, 3H), 2.81 (m, 1H), 2.63 (m, 1H), 2.51 (m, 2H), 1.18 (t, J=7.4 Hz, 3H)

Example 73: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(4-(trifluoromethyl)phenyl) acetamide

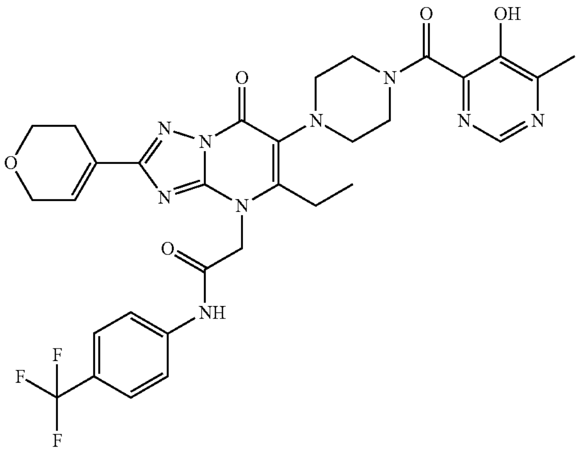 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1]

Step 1: 2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(4-(trifluoromethyl)phenyl)acetamide To a solution of 5-methoxy-6-methylpyrimidine-4-carboxylic acid (Intermediate CW) (74.1 mg, 423 μmol) in DMF (3 mL), was added HATU (161 mg, 423 μmol). The RM was stirred for 15 minutes and then 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-(trifluoromethyl) phenyl)acetamide (Intermediate AS) (150 mg, 282 μmol) was added, followed by DIPEA (148 μL, 847 μmol). The resulting RM was stirred at 30° C. for 16 hours. The RM was diluted with EtOAc and washed with water. The aqueous layer was extracted twice with EtOAc and twice with DCM. The organic layers were combined, dried through a phase separator and concentrated. The crude product was purified by column chromatography (RediSep Column: Silica 12 g, eluent DCM:MeOH 100:0 to 90:10). The product containing fractions were combined and concentrated under reduced pressure to give the title compound as a white solid.

LC-MS: Rt=1.02 min; MS m/z $[M+H]^+$ 682.3, m/z $[M-H]^-$ 680.2; UPLC-MS 3

Step 2: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(4-(trifluoromethyl)phenyl)acetamide A solution of 2-(2-(3,6-dihydro-2H-pyran-4-yl)-5-ethyl-6-(4-(5-methoxy-6-methylpyrimidine-4-carbonyl)piperazin-1-yl)-7-oxo-[1,2,4]triazolo[1,5-a]pyrimidin-4 (7H)-yl)-N-(4-(trifluoromethyl)phenyl)acetamide (70.0 mg, 103 μmol) in DMF (1 mL) under argon was cooled to −78° C. LiCl (43.5 mg, 1.03 mmol) was added portionwise. The RM was stirred at 125° C. for 26 hours. The RM was diluted with EtOAc and washed with water. The organic layer was dried through a phase separator and concentrated. The crude product was purified by reverse phase preparative HPLC (RP-HPLC basic 1: 5 to 50% B in 20 min with a plateau at 50% for 1 min). The product containing fractions were lyophilized, and the title compound was obtained as a colorless powder.

LC-MS: Rt=1.03 min; MS m/z $[M+H]^+$ 668.5, m/z $[M-H]^-$ 666.4; UPLC-MS 6

$^1H$ NMR (400 MHz, DMSO-$d_6$) δ 10.87 (s, 1H), 8.55 (s, 1H), 7.78 (d, J=8.6 Hz, 2H), 7.70 (d, J=8.8 Hz, 2H), 6.79 (m, 1H), 5.20 (s, 2H), 4.52 (m, 1H), 4.23 (m, 2H), 3.79 (m, 2H), 3.50 (m, 3H), 3.26 (m, 1H), 2.98 (m, 3H), 2.82 (m, 1H), 2.65 (m, 1H), 2.51 (m, 2H), 2.43 (s, 3H), 1.17 (t, J=7.4 Hz, 3H)

Example 74: 2-(2-(3,6-dihydro-2H-pyran-4-yl)-5-ethyl-6-(4-(3-hydroxy-6-methylpicolinoyl)piperazin-1-yl)-7-oxo-[1,2,4]triazolo[1,5-a]pyrimidin-4 (7H)-yl)-N-(4-(trifluoromethyl)phenyl)acetamide

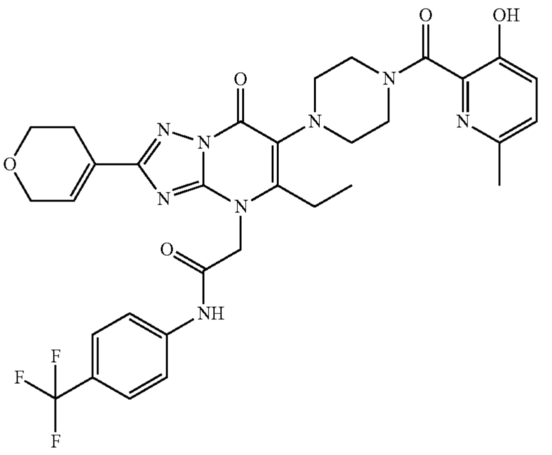 [SMILES: CCc1c(N2CCN(C(=O)c3nc(C)ccc3O)CC2)c(=O)n2nc(C3=CCOCC3)nc2n1CC(=O)Nc1ccc(C(F)(F)F)cc1]

3-Hydroxy-6-methylpicolinic acid (88.0 mg, 376 μmol) was suspended in DCM (4 mL) at RT. After cooling to 0° C., 1-chloro-N,N,2-trimethylprop-1-en-1-amine (62.0 μL, 470 μmol) was added dropwise. The RM was stirred at RT for 2 hours, then it was cooled to 0° C. again. DIPEA (164 μL, 941 μmol) was added. This solution was added dropwise at 0° C. to a solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide (Intermediate AS) (100 mg, 188 μmol) in DCM (4 mL). The RM was stirred at RT for 18 hours. The RM was diluted with DCM, washed with aq sat $NH_4Cl$, dried over $Na_2SO_4$, concentrated and dried. The crude product was purified by reverse phase preparative HPLC (RP-HPLC basic 1: 5 to 100% B in 20 min). The product containing fractions were combined, the ACN was removed and the residue was lyophilized to give the title compound as a foam.

LC-MS: Rt=1.05 min; MS m/z $[M+H]^+$ 667.2, m/z $[M-H]^-$ 665.1; UPLC-MS 4

$^1H$ NMR (400 MHz, DMSO-$d_6$) δ 10.88 (s, 1H), 10.09 (s, br, 1H), 7.78 (d, J=8.6 Hz, 2H), 7.71 (d, J=8.8 Hz, 2H), 7.19 (d, J=8.4 Hz, 1H), 7.13 (d, J=8.5 Hz, 1H), 6.79 (m, 1H), 5.20 (s, 2H), 4.53 (m, 1H), 4.24 (m, 2H), 3.79 (m, 2H), 3.47 (m, 3H), 3.22 (m, 1H), 2.96 (m, 3H), 2.80 (m, 1H), 2.63 (m, 1H), 2.50 (m, 2H), 2.37 (s, 3H), 1.17 (t, J=7.4 Hz, 3H)

Example 75: 2-(2-(3,6-dihydro-2H-pyran-4-yl)-5-ethyl-6-(4-(3-hydroxy-4-methylpicolinoyl)piperazin-1-yl)-7-oxo-[1,2,4]triazolo[1,5-a]pyrimidin-4 (7H)-yl)-N-(4-(trifluoromethyl)phenyl)acetamide

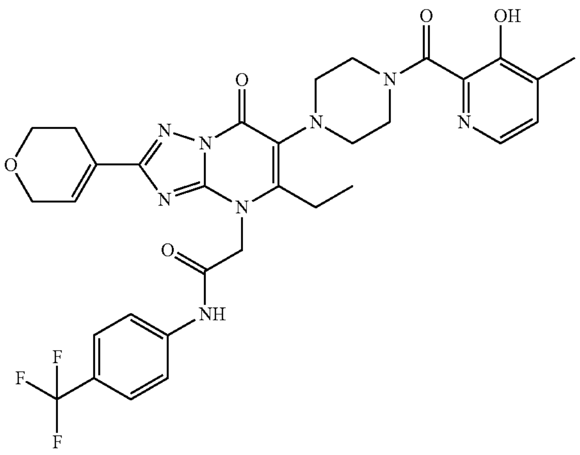 [SMILES: CCc1c(N2CCN(C(=O)c3nccc(C)c3O)CC2)c(=O)n2nc(C3=CCOCC3)nc2n1CC(=O)Nc1ccc(C(F)(F)F)cc1]

3-Hydroxy-4-methylpicolinic acid (74.9 mg, 395 μmol) was suspended in DCM (4 mL) at RT. After cooling to 0° C., 1-chloro-N,N,2-trimethylprop-1-en-1-amine (62.0 μL, 470 μmol) was added dropwise. The RM was stirred at RT for 2 hours, then it was cooled to 0° C. again. DIPEA (164 μL, 941 μmol) was added. This solution was added dropwise at 0° C. to a solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide (Intermediate AS) (100 mg, 188 μmol) in DCM (4 mL). The RM was stirred at RT for 18 hours. The RM was diluted with DCM, washed with aq sat $NH_4Cl$, dried over $Na_2SO_4$ and concentrated. The resulting solid was filtered off, washed with DCM and TBME and dried to give the title compound as a grey solid.

LC-MS: Rt=1.12 min; MS m/z $[M+H]^+$ 667.2, m/z $[M-H]^-$ 665.1; UPLC-MS 4

$^1$H NMR (400 MHz, DMSO-$d_6$) δ 10.88 (s, 1H), 10.37 (s, 1H), 8.00 (d, J=4.6 Hz, 1H), 7.78 (d, J=8.6 Hz, 2H), 7.71 (d, J=8.8 Hz, 2H), 7.26 (d, J=4.6 Hz, 1H), 6.79 (m, 1H), 5.20 (s, 2H), 4.58 (m, 1H), 4.24 (m, 2H), 4.08 (m, 1H), 3.79 (m, 2H), 3.52 (m, 2H), 3.30 (m, 1H), 2.99 (m, 3H), 2.80 (m, 1H), 2.67 (m, 1H), 2.51 (m, 2H), 2.24 (s, 3H), 1.18 (t, J=7.4 Hz, 3H)

Example 76: 2-(5-ethyl-6-(4-(3-hydroxypicolinoyl) piperazin-1-yl)-7-oxo-2-(pyridin-3-yl)-[1,2,4]triazolo[1,5-a]pyrimidin-4 (7H)-yl)-N-(2-methyl-4-(trifluoromethyl)phenyl)acetamide

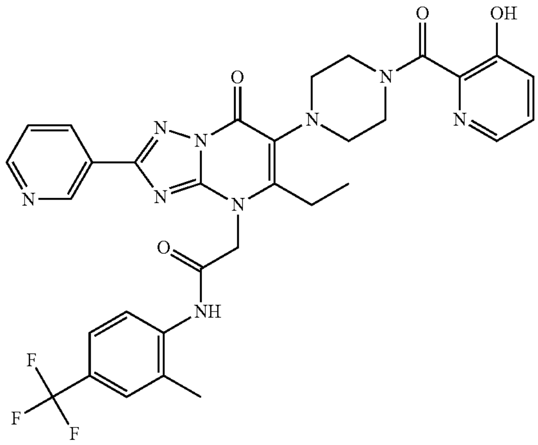 [SMILES: CCc1c(N2CCN(C(=O)c3ncccc3O)CC2)c(=O)n2nc(-c3cccnc3)nc2n1CC(=O)Nc1ccc(C(F)(F)F)cc1C]

To the stirred solution of 2-(5-ethyl-7-oxo-6-(piperazin-1-yl)-2-(pyridin-3-yl)-[1,2,4]triazolo[1,5-a]pyrimidin-4 (7H)-yl)-N-(2-methyl-4-(trifluoromethyl)phenyl)acetamide (Intermediate AT) (170 mg, 314 μmol) in DMF (2 mL), the mixture of 3-hydroxypicolinic acid (87.0 mg, 629 μmol), EDC·HCl (121 mg, 629 μmol), HOBt (85.0 mg, 629 μmol) and DIPEA (330 μL, 1.89 mmol) was added at RT. The RM was stirred at RT for 4 hours. The RM was concentrated under reduced pressure, water was added and the precipitate was filtered off and dried under reduced pressure. The crude product was purified by reverse phase preparative HPLC (RP-HPLC acidic 7: 30 to 40% B in 2 min, 40 to 60% B in 8 min) to give the title compound.

LC-MS: Rt=0.95 min; MS m/z $[M+H]^+$ 662.3, MS m/z $[M-H]^-$ 660.3; UPLC-MS 1

LC-MS: Rt=4.74 min; MS m/z $[M+H]^+$ 662.2, MS m/z $[M-H]^-$ 660.3; UPLC-MS 2

$^1$H NMR (600 MHz, DMSO-$d_6$) δ 10.38 (s, 1H), 10.05 (s, 1H), 9.22 (m, 1H), 8.67 (m, 1H), 8.39 (m, 1H), 8.03 (m, 1H), 7.68 (d, J=8.5 Hz, 1H), 7.59 (m, 1H), 7.54 (m, 1H), 7.49 (d, J=8.9 Hz, 1H), 7.25 (m, 2H), 5.30 (s, 2H), 4.52 (m, 1H), 3.46 (m, 2H), 3.37 (m, 1H), 3.20 (m, 1H), 2.96 (m, 3H), 2.79 (m, 1H), 2.61 (m, 1H), 2.33 (s, 3H), 1.18 (t, J=7.5 Hz, 3H)

Example 77: 2-(5-ethyl-6-(4-(3-hydroxypicolinoyl)piperazin-1-yl)-2-(6-methylpyridin-3-yl)-7-oxo-[1,2,4]triazolo[1,5-a]pyrimidin-4 (7H)-yl)-N-(2-methyl-4-(trifluoromethyl)phenyl)acetamide

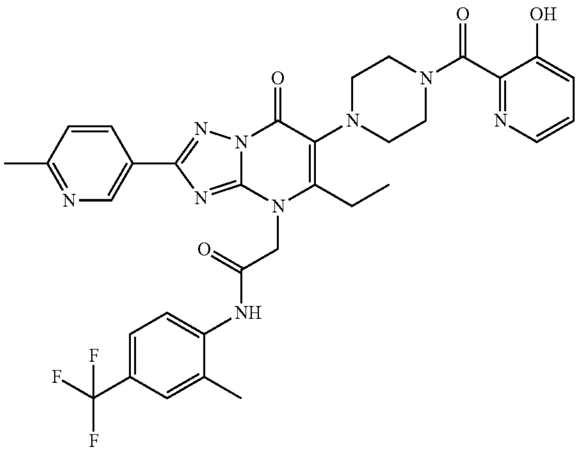 [SMILES: CCc1c(N2CCN(C(=O)c3ncccc3O)CC2)c(=O)n2nc(-c3ccc(C)nc3)nc2n1CC(=O)Nc1ccc(C(F)(F)F)cc1C]

To a solution of 2-(5-ethyl-2-(6-methylpyridin-3-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AU) (188 mg, 183 µmol) in DCM (1.2 mL) under argon at 0° C. was added 3-hydroxypicolinoyl chloride (Intermediate CV) (43.1 mg, 274 µmol). DIPEA (159 µL, 913 µmol) was then added dropwise. The resulting solution was stirred at 0° C. for 15 minutes, then at RT for 3.5 hours. 3-Hydroxypicolinoyl chloride (Intermediate CV) (43.1 mg, 274 µmol) was added to the RM at 0° C., and the RM was stirred at RT for 19 hours. Then DIPEA (159 µL, 913 µmol) was added, and the RM was stirred at RT for 3.5 hours. The RM was diluted with DCM and washed with water. The aqueous layer was extracted twice with DCM. The combined organic layers were dried through a phase separator and concentrated under reduced pressure. The crude product was purified by reverse phase preparative HPLC (RP-HPLC acidic 1: 8 to 38% B in 20 min with a plateau at 38% for 1 min). The product containing fractions were combined and concentrated to remove ACN and TFA. The resulting aqueous residue was basified with solid $NaHCO_3$. A precipitate was formed which was filtered off, washed with water until neutral and dried under reduced pressure to give the title compound as a colorless solid.

LC-MS: Rt=0.99 min; MS m/z $[M+H]^+$ 676.5, m/z $[M-H]^-$ 674.5; UPLC-MS 1

$^1$H NMR (400 MHz, DMSO-$d_6$) δ 10.49 (s, br, 1H), 10.08 (s, br, 1H), 9.14 (d, J=2.0 Hz, 1H), 8.32 (dd, J=2.2 Hz, 8.0 Hz, 1H), 8.06 (m, 1H), 7.72 (d, J=8.4 Hz, 1H), 7.63 (m, 1H), 7.53 (d, J=8.4 Hz, 1H), 7.44 (d, J=8.1 Hz, 1H), 7.29 (m, 2H), 5.33 (s, 2H), 4.57 (m, 1H), 3.48 (m, 3H), 3.23 (m, 1H), 3.03 (m, 3H), 2.83 (m, 1H), 2.67 (m, 1H), 2.55 (s, 3H), 2.38 (s, 3H), 1.23 (t, J=7.4 Hz, 3H)

Example 78: 2-(6-(4-(4-chloro-3-hydroxypicolinoyl)piperazin-1-yl)-2-(5,6-dihydro-1,4-dioxin-2-yl)-5-ethyl-7-oxo-[1,2,4]triazolo[1,5-a]pyrimidin-4 (7H)-yl)-N-(2-methyl-4-(trifluoromethyl)phenyl)acetamide

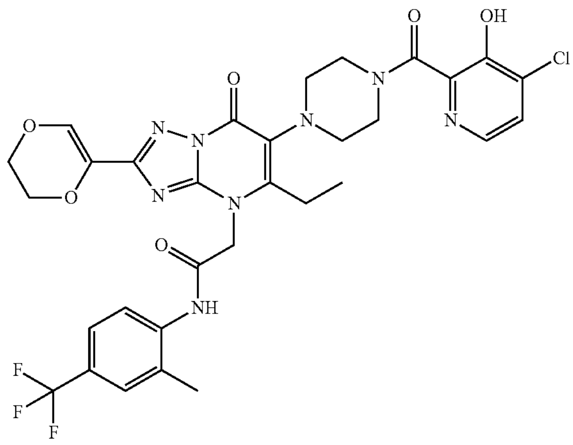 [SMILES: CCc1c(N2CCN(C(=O)c3nccc(Cl)c3O)CC2)c(=O)n2nc(C3=COCCO3)nc2n1CC(=O)Nc1ccc(C(F)(F)F)cc1C]

To the stirred solution of 4-chloro-3-hydroxypicolinic acid (86.0 mg, 493 µmol) in DMF (10 mL) at RT were added EDC·HCl (95.0 mg, 493 µmol), HOBt (66.6 mg, 493 µmol), pyridine (80.0 µL, 986 µmol) and then 2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AV) (180 mg, 329 µmol), and the RM was stirred at RT for 14 hours. Water (20 mL) was added to the RM and it was extracted with 10% MeOH in DCM (2×20 mL). The organic layers were washed with brine (20 mL), dried over $Na_2SO_4$ and concentrated. The crude product was purified by column chromatography (Silica gel column: Silica 40 g, eluent DCM:MeOH 100:0 to 94:6) to give the title compound.

LC-MS: Rt=1.04 min; MS m/z $[M+H]^+$ 703.6, m/z $[M-H]^-$ 701.3; UPLC-MS 1

LC-MS: Rt=5.06 min; MS m/z $[M+H]^+$ 703.2, m/z $[M-H]^-$ 701.3; UPLC-MS 2

$^1$H NMR (400 MHz, DMSO-$d_6$) δ 10.83 (s, br, 1H), 9.99 (s, 1H), 8.06 (d, J=5.0 Hz, 1H), 7.72 (d, J=8.4 Hz, 1H), 7.63 (m, 1H), 7.54 (m, 2H), 7.09 (s, 1H), 5.21 (s, 2H), 4.54 (m, 1H), 4.19 (m, 4H), 3.51 (m, 3H), 3.23 (m, 1H), 2.99 (m, 3H), 2.81 (m, 1H), 2.65 (m, 1H), 2.35 (s, 3H), 1.19 (t, J=7.4 Hz, 3H)

Example 79: 2-(6-(4-(4-chloro-3-hydroxypicolinoyl)piperazin-1-yl)-2-(5,6-dihydro-1,4-dioxin-2-yl)-5-ethyl-7-oxo-[1,2,4]triazolo[1,5-a]pyrimidin-4 (7H)-yl)-N-(3-fluoro-2-methyl-4-(trifluoromethyl)phenyl)acetamide

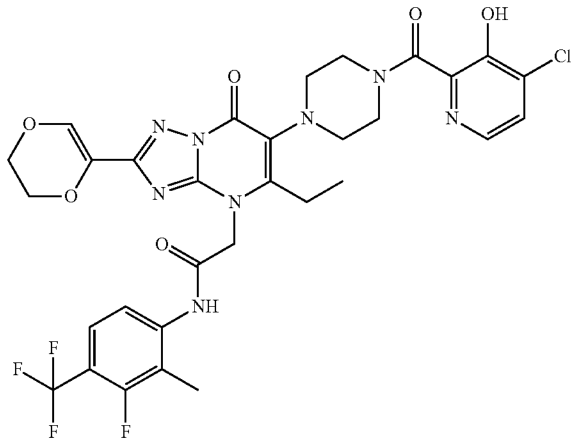 [SMILES: CCc1c(N2CCN(C(=O)c3nccc(Cl)c3O)CC2)c(=O)n2nc(C3=COCCO3)nc2n1CC(=O)Nc1ccc(C(F)(F)F)c(F)c1C]

4-Chloro-3-hydroxypicolinic acid (1.40 g, 8.06 mmol) was suspended in DCM (40 mL). Then 1-chloro-N,N,2-trimethylprop-1-en-1-amine (2.13 mL, 16.1 mmol) was added. The RM was stirred at RT for 45 minutes. 2-(2-(5,6-Dihydro-1,4-dioxin-2-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide (Intermediate AW) (1.22 g, 1.61 mmol) was added, followed by DIPEA (5.63 mL, 32.2 mmol). The RM was stirred at RT for 1 hour. Water (10 mL), aq sat $NaHCO_3$ (10 mL) and DCM (10 mL) were added. The aqueous layer was extracted twice with DCM (2×10 mL). The combined organic layers were dried through a phase separator and concentrated under reduced pressure. The crude product was purified by column chromatography (RediSep Column: Silica 80 g, eluent DCM:DCM/MeOH (9/1) 100:0 to 0:100). The product containing fractions were combined, concentrated under vacuum and dried under HV to give product which was not pure. This material was purified in 2 portions by reverse phase preparative HPLC (RP-HPLC acidic 1: 10 to 100% B in 20 min and RP-HPLC acidic 1: 15 to 100% in 20 min). The product containing fractions were combined, basified with aq sat $NaHCO_3$, extracted twice with DCM, dried through a phase separator and concentrated under reduced pressure to give the title compound.

LC-MS: Rt=1.07 min; MS m/z $[M+H]^+$ 721.3, m/z $[M-H]^-$ 719.4; UPLC-MS 1

$^1$H NMR (600 MHz, DMSO-$d_6$) δ 10.83 (s, 1H), 10.19 (s, 1H), 8.06 (d, J=5.0 Hz, 1H), 7.59 (m, 2H), 7.55 (d, J=5.0 Hz, 1H), 7.08 (s, 1H), 5.22 (s, 2H), 4.54 (m, 1H), 4.19 (m, 4H), 3.52 (m, 3H), 3.24 (m, 1H), 2.98 (m, 3H), 2.81 (m, 1H), 2.62 (m, 1H), 2.24 (s, 3H), 1.18 (t, J=7.5 Hz, 3H)

Example 80: rac-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(2-methyl-4-(trifluoromethyl)phenyl)acetamide

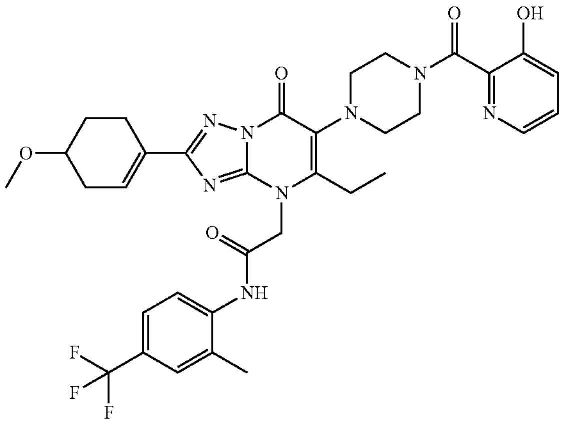 [SMILES: CCc1c(N2CCN(C(=O)c3ncccc3O)CC2)c(=O)n2nc(C3=CCC(OC)CC3)nc2n1CC(=O)Nc1ccc(C(F)(F)F)cc1C]

3-Hydroxypicolinic acid (51.3 mg, 369 μmol) was dissolved in DMF (2 mL) and then EDC·HCl (70.7 mg, 369 μmol), DIPEA (258 μL, 1.48 mmol), HOBt (49.8 mg, 369 μmol) and rac-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide·HCl (Intermediate AX) (150 mg, 246 μmol) were added at 0° C. and the RM was stirred at RT for 16 hours. The RM was diluted with water, extracted with EtOAc, washed with aq sat $NaHCO_3$ and brine and the combined organic layers were dried over $Na_2SO_4$, filtered and concentrated under reduced pressure. The crude product was purified by column chromatography (Silica gel column: Silica 12 g, eluent DCM:MeOH 100:0 to 95:5) to give the title compound as a fluffy white solid.

LC-MS: Rt=1.04 min; MS m/z $[M+H]^+$ 695.1, m/z $[M-H]^-$ 693.3; UPLC-MS 1

LC-MS: Rt=5.18 min; MS m/z $[M+H]^+$ 695.2, m/z $[M-H]^-$ 693.3; UPLC-MS 2

$^1$H NMR (400 MHz, DMSO-$d_6$) δ 10.38 (s, 1H), 9.99 (s, 1H), 8.06 (m, 1H), 7.72 (d, J=8.2 Hz, 1H), 7.62 (m, 1H), 7.53 (d, J=8.4 Hz, 1H), 7.28 (m, 2H), 6.73 (m, 1H), 5.23 (s, 2H), 4.54 (m, 1H), 3.45 (m, 4H), 3.28 (s, 3H), 3.22 (m, 1H), 2.97 (m, 3H), 2.79 (m, 1H), 2.60 (m, 3H), 2.35 (s, 3H), 2.33 (m, 1H), 2.15 (m, 1H), 1.95 (m, 1H), 1.67 (m, 1H), 1.19 (t, J=7.3 Hz, 3H)

Example 80a: ((R)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(2-methyl-4-(trifluoromethyl)phenyl) acetamide) or ((S)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(2-methyl-4-(trifluoromethyl)phenyl) acetamide) and Example 80b: ((R)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a] pyrimidin-4 (7H)-yl)-N-(2-methyl-4-(trifluoromethyl)phenyl)acetamide) or ((S)-2-(5-ethyl-6-(4-(3-hydroxypicolinoyl)piperazin-1-yl)-2-(4-methoxycyclohex-1-en-1-yl)-7-oxo-[1,2,4] triazolo[1,5-a]pyrimidin-4 (7H)-yl)-N-(2-methyl-4-(trifluoromethyl)phenyl)acetamide)

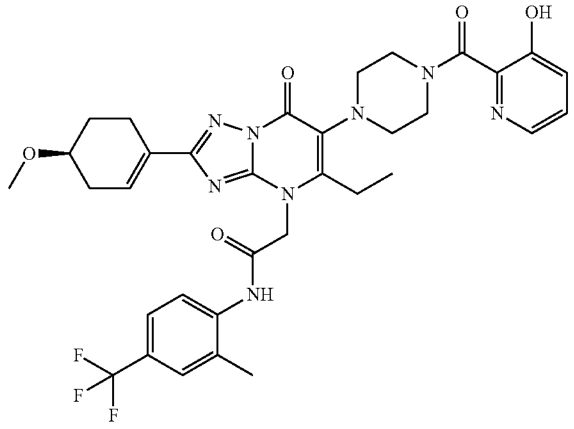

*S*-stereoisomer

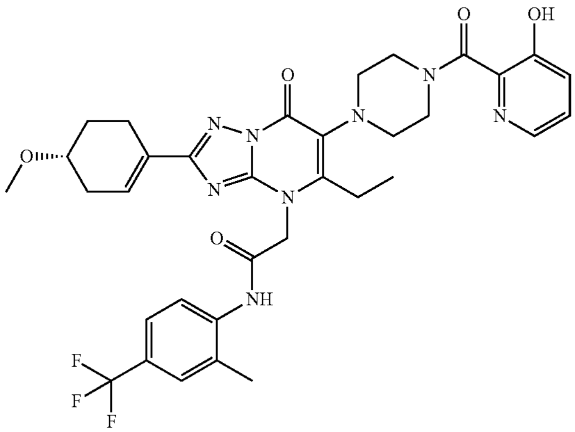

*R*-stereoisomer

Chiral separation of rac-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(2-methyl-4-(trifluoromethyl)phenyl)acetamide: Preparative chiral HPLC (instrument: Waters Prep SFC100 Mass directed; column: Chiralpak IB-N 250×30 mm 5 μm; eluent: A: 30% [MeOH+0.1% $NH_3$]; B: 70% $scCO_2$; flow rate: 80 mL/min; detection: 190-400 nm; injection volume: 1.2 mL; Gradient: isocratic: A(30):B(70) in 17 minutes).

Example 80a: First eluting stereoisomer, white solid.

Chiral HPLC (C-HPLC 8): Rt=2.19 min, 99.5% ee

LC-MS: Rt=1.04 min; MS m/z $[M+H]^+$ 695.5, m/z $[M-H]^-$ 693.5; UPLC-MS 1

LC-MS: Rt=5.16 min; MS m/z $[M+H]^+$ 695.3, m/z $[M-H]^-$ 693.3; UPLC-MS 2

$^1$H NMR (400 MHz, DMSO-$d_6$) δ 10.37 (s, br, 1H), 9.99 (s, 1H), 8.06 (m, 1H), 7.72 (d, J=8.4 Hz, 1H), 7.62 (m, 1H), 7.53 (d, J=8.4 Hz, 1H), 7.29 (m, 2H), 6.73 (m, 1H), 5.23 (s, 2H), 4.54 (m, 1H), 3.47 (m, 4H), 3.28 (s, 3H), 3.22 (m, 1H), 2.98 (m, 3H), 2.79 (m, 1H), 2.60 (m, 3H), 2.35 (s, 3H), 2.33 (m, 1H), 2.16 (m, 1H), 1.95 (m, 1H), 1.67 (m, 1H), 1.19 (t, J=7.4 Hz, 3H)

Example 80b: Second eluting stereoisomer, white solid. Chiral HPLC (C-HPLC 8): Rt=2.73 min, 98.5% ee LC-MS: Rt=1.04 min; MS m/z $[M+H]^+$ 695.5, m/z $[M-H]^-$ 693.5; UPLC-MS 1

LC-MS: Rt=5.16 min; MS m/z $[M+H]^+$ 695.3, m/z $[M-H]^-$ 693.3; UPLC-MS 2

$^1$H NMR (400 MHz, DMSO-$d_6$) δ 10.37 (s, br, 1H), 9.99 (s, 1H), 8.06 (m, 1H), 7.72 (d, J=8.4 Hz, 1H), 7.62 (m, 1H), 7.52 (d, J=8.1 Hz, 1H), 7.28 (m, 2H), 6.73 (m, 1H), 5.23 (s, 2H), 4.54 (m, 1H), 3.46 (m, 4H), 3.28 (s, 3H), 3.22 (m, 1H), 2.97 (m, 3H), 2.79 (m, 1H), 2.61 (m, 2H), 2.41 (m, 2H), 2.35 (s, 3H), 2.33 (m, 1H), 2.15 (m, 1H), 1.96 (m, 1H), 1.68 (m, 1H), 1.19 (t, J=7.4 Hz, 3H)

Example 81: rac-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(4-(trifluoromethyl)phenyl)acetamide

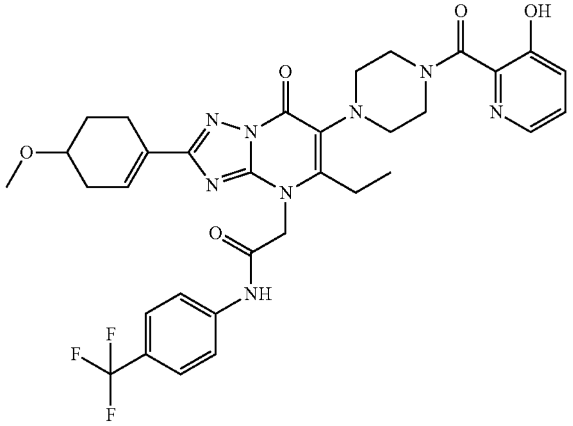 [SMILES: CCc1c(N2CCN(C(=O)c3ncccc3O)CC2)c(=O)n2nc(C3=CCC(OC)CC3)nc2n1CC(=O)Nc1ccc(C(F)(F)F)cc1]

3-Hydroxypicolinic acid (67.6 mg, 486 μmol) was dissolved in DCM (1 mL) and 1-chloro-N,N,2-trimethylprop-1-en-1-amine (113 μL, 851 μmol) was added. The RM was stirred at RT for 1 hour. Then rac-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(4-(trifluoromethyl) phenyl)acetamide (Intermediate AY) (200 mg, 243 μmol) and DIPEA (170 μL, 973 μmol) were added and the RM was stirred at RT for 3 hours. Water, aq sat $NaHCO_3$, brine and DCM were added. The aqueous layer was extracted twice with DCM. The combined organic layers were dried through a phase separator and concentrated under reduced pressure. The crude product was purified by reverse phase preparative HPLC (RP-HPLC acidic 1: 10 to 100% B in 30 min). The product containing fractions were combined, basified with aq sat $NaHCO_3$, extracted twice with DCM, dried through a phase separator and concentrated under reduced pressure.

The resulting solid was purified by reverse phase preparative HPLC (RP-HPLC acidic 1: 25 to 75% B in 20 min with a plateau at 75% for 1 min). The product containing fractions were combined, basified with aq sat $NaHCO_3$, extracted twice with DCM, dried through a phase separator and concentrated under reduced pressure to give the title compound.

LC-MS: Rt=0.97 min; MS m/z $[M+H]^+$ 681.4, m/z $[M-H]^-$ 679.5; UPLC-MS 4

Example 81a: ((R)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(4-(trifluoromethyl)phenyl)acetamide or ((S)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(4-(trifluoromethyl)phenyl)acetamide and Example 81 b: ((R)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(4-(trifluoromethyl)phenyl)acetamide or ((S)-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(4-(trifluoromethyl)phenyl)acetamide

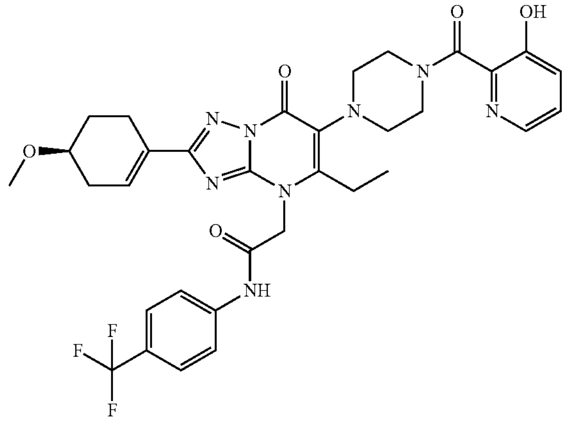

*R*-stereoisomer

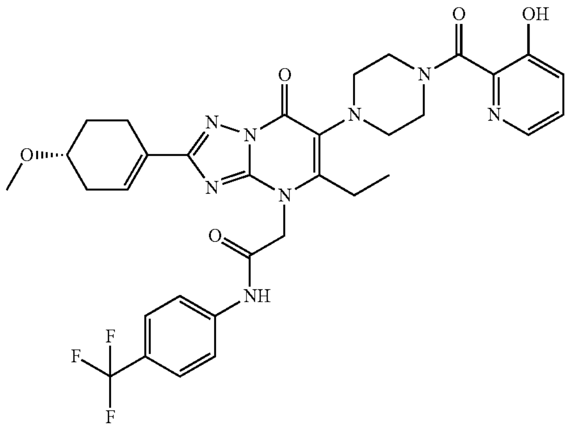

*S*-stereoisomer

Chiral separation of rac-2-(5-ethyl-6-(4-(3-hydroxypicolinoyl)piperazin-1-yl)-2-(4-methoxycyclohex-1-en-1-yl)-7-oxo-[1,2,4]triazolo[1,5-a]pyrimidin-4 (7H)-yl)-N-(4-(trifluoromethyl)phenyl)acetamide: Preparative chiral HPLC (instrument: Waters Prep SFC100 Mass directed; column: Chiralpak IBN 250×30 mm 5 μm; eluent: A: 35% [MeOH+0.1% $NH_3$]; B: 65% $scCO_2$; flow rate: 80 mL/min; detection: 190-400 nm; injection volume: 4 mL; gradient: isocratic: A(35):B(65) in 17 min). The peaks were dissolved in a large amount of DCM and MeOH and filtered through a PL-$HCO_3$ MP SPE cartridge (100 mg per 6 mL). The filtrate was concentrated under reduced pressure and dried under HV.

Example 81a: First eluting stereoisomer, beige solid.

Chiral HPLC (C-HPLC 8): Rt=2.51 min, 99% ee

LC-MS: Rt=1.04 min; MS m/z $[M+H]^+$ 681.4, m/z $[M-H]^-$ 679.4; UPLC-MS 4

LC-MS: Rt=5.23 min; MS m/z $[M+H]^+$ 681.3, m/z $[M-H]^-$ 679.3; UPLC-MS 2

$^1$H NMR (400 MHz, DMSO-$d_6$) δ 10.85 (s, 1H), 10.38 (s, 1H), 8.06 (m, 1H), 7.78 (d, J=8.4 Hz, 2H), 7.70 (d, J=8.6 Hz, 2H), 7.29 (m, 2H), 6.69 (m, 1H), 5.18 (s, 2H), 4.55 (m, 1H), 3.46 (m, 4H), 3.27 (s, 3H), 3.21 (m, 1H), 2.97 (m, 3H), 2.80 (m, 1H), 2.62 (m, 2H), 2.42 (m, 2H), 2.13 (m, 1H), 1.93 (m, 1H), 1.66 (m, 1H), 1.17 (t, J=7.2 Hz, 3H)

Example 81b: Second eluting stereoisomer, beige solid.

Chiral HPLC (C-HPLC 8): Rt=3.23 min, 95% ee

LC-MS: Rt=1.04 min; MS m/z $[M+H]^+$ 681.4, m/z $[M-H]^-$ 679.4; UPLC-MS 4

Example 82: 2-(4-(4-(2-((2-chloro-4-(trifluoromethyl)phenyl)amino)-2-oxoethyl)-5-ethyl-6-(4-(3-hydroxypicolinoyl)piperazin-1-yl)-7-oxo-4,7-dihydro-[1,2,4]triazolo[1,5-a]pyrimidin-2-yl)piperazin-1-yl)acetic acid

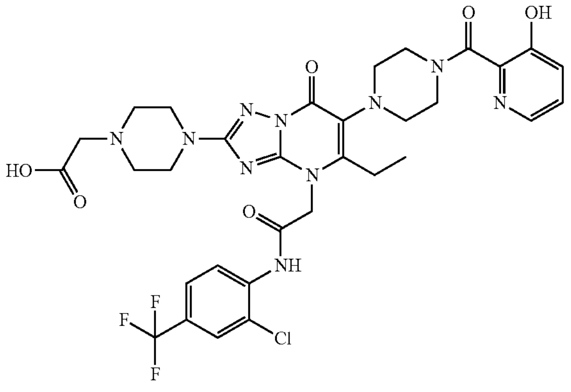 [SMILES: CCc1c(N2CCN(C(=O)c3ncccc3O)CC2)c(=O)n2nc(N3CCN(CC(=O)O)CC3)nc2n1CC(=O)Nc1ccc(C(F)(F)F)cc1Cl]

Step 1: ethyl 2-(4-(4-(2-((2-chloro-4-(trifluoromethyl)phenyl)amino)-2-oxoethyl)-5-ethyl-6-(4-(3-hydroxypicolinoyl)piperazin-1-yl)-7-oxo-4,7-dihydro-[1,2,4]triazolo[1,5-a]pyrimidin-2-yl)piperazin-1-yl)acetate Ethyl 2-(4-(4-(2-((2-chloro-4-(trifluoromethyl)phenyl)amino)-2-oxoethyl)-5-ethyl-7-oxo-6-(piperazin-1-yl)-4,7-dihydro-[1,2,4]triazolo[1,5-a]pyrimidin-2-yl)piperazin-1-yl)acetate (Intermediate AZ) (300 mg, 459 μmol) was dissolved in DCM (1 mL) and DIPEA (481 μL, 2.75 mmol) was added at 0° C., followed by 3-hydroxypicolinoyl chloride (Intermediate CV) (217 mg, 1.38 mmol). The RM was allowed to warm to RT and stirred at RT for 16 hours. The RM was concentrated under reduced pressure and washed with $Et_2O$ to give the title compound.

LC-MS: Rt=1.16 min; MS m/z $[M+H]^+$ 775.3; UPLC-MS 13

Step 2: 2-(4-(4-(2-((2-chloro-4-(trifluoromethyl) phenyl)amino)-2-oxoethyl)-5-ethyl-6-(4-(3-hydroxypicolinoyl)piperazin-1-yl)-7-oxo-4,7-dihydro-[1,2,4]triazolo[1,5-a]pyrimidin-2-yl)piperazin-1-yl) acetic acid Ethyl 2-(4-(4-(2-((2-chloro-4-(trifluoromethyl)phenyl) amino)-2-oxoethyl)-5-ethyl-6-(4-(3-hydroxypicolinoyl)piperazin-1-yl)-7-oxo-4,7-dihydro-[1,2,4]triazolo[1,5-a]pyrimidin-2-yl)piperazin-1-yl)acetate (300 mg, 387 μmol) was dissolved in EtOH (1 mL) and water (1 mL), and $LiOH·H_2O$ (48.7 mg, 1.16 mmol) was added and the RM was stirred at RT for 2 hours. The EtOH was removed under reduced pressure and the residue was acidified with citric acid and extracted with EtOAc. The crude product was purified by reverse phase preparative HPLC (RP-HPLC acidic 9: 25 to 35% B in 2 min, 35 to 45% B in 10 min) to give the title compound.

LC-MS: Rt=0.78 min; MS m/z $[M+H]^+$ 747.2, m/z $[M-H]^-$ 745.3; UPLC-MS 1

LC-MS: Rt=3.90 min; MS m/z $[M+H]^+$ 747.2, m/z $[M-H]^-$ 745.3; UPLC-MS 2

$^1H$ NMR (400 MHz, DMSO-$d_6$) δ 10.32 (s, br, 1H), 8.05 (m, 2H), 7.96 (m, 1H), 7.72 (d, J=8.6 Hz, 1H), 7.28 (m, 2H), 5.20 (s, 2H), 4.53 (m, 1H), 3.55-3.20 (m, 8H), 3.16 (s, 2H), 2.92 (m, 3H), 2.75 (m, 1H), 2.59 (m, 5H), 1.15 (t, J=7.4 Hz, 3H)

Example 83: 2-(2-(3,4-dihydro-2H-pyran-6-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

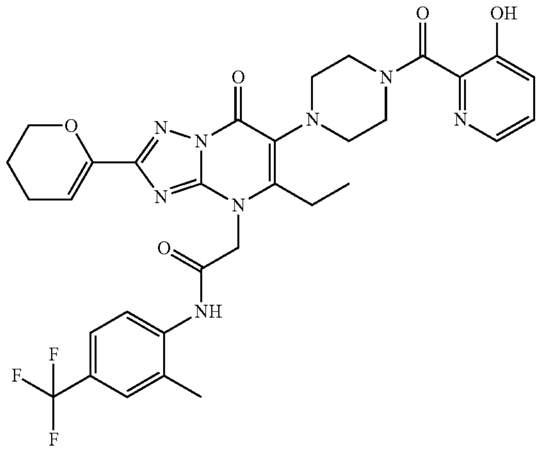 [SMILES: CCc1c(N2CCN(C(=O)c3ncccc3O)CC2)c(=O)n2nc(C3=CCCCO3)nc2n1CC(=O)Nc1ccc(C(F)(F)F)cc1C]

2-(2-(3,4-Dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate BA) (190 mg, 261 μmol) was dissolved in DCM (5 mL) at 0° C. under argon. 3-Hydroxypicolinoyl chloride (Intermediate CV) (61.7 mg, 392 μmol) was added, followed by slow addition of DIPEA (228 μL, 1.31 mmol) over 5 minutes at 0° C. The RM was stirred at 0° C. for 20 minutes, then at RT for 1.2 hours. 3-Hydroxypicolinoyl chloride (Intermediate CV) (26.0 mg, 165 μmol) and DIPEA (70.0 μL, 402 μmol) were added and the RM was stirred at RT for 1.5 hours. The RM was quenched with water (5 mL) and aq sat $NaHCO_3$ (5 mL), and it was extracted with DCM (4×50 mL). The combined organic layers were washed with aq sat $NaHCO_3$ and water, dried through a phase separator and concentrated under reduced pressure. The residue was adsorbed onto Isolute and purified by column chromatography (RediSep Column: Silica 24 g, eluent DCM:MeOH 100:0 to 90:10). The product containing fractions were combined and concentrated under reduced pressure. This material was adsorbed onto Isolute and purified by column chromatography (RediSep Column: Silica 24 g, eluent DCM:MeOH 100:0 to 95:5). The resulting solid was further purified by SFC (SFC 2). The product containing fractions were combined, concentrated under reduced pressure and dried under HV to give the title compound as a slightly yellow solid.

LC-MS: Rt=1.02 min; MS m/z $[M+H]^+$ 667.4, m/z $[M-H]^-$ 665.4; UPLC-MS 3

$^1H$ NMR (600 MHz, DMSO-$d_6$) δ 10.00 (s, br, 2H), 8.07 (m, 1H), 7.74 (d, J=8.4 Hz, 1H), 7.63 (m, 1H), 7.54 (d, J=8.3 Hz, 1H), 7.29 (m, 2H), 5.87 (m, 1H), 5.24 (s, 2H), 4.55 (m, 1H), 4.11 (m, 2H), 3.46 (m, 3H), 3.22 (m, 1H), 2.98 (m, 3H), 2.80 (m, 1H), 2.62 (m, 1H), 2.36 (s, 3H), 2.19 (m, 2H), 1.85 (m, 2H), 1.19 (t, J=7.4 Hz, 3H)

Example 84: 2-(2-(3,4-dihydro-2H-pyran-6-yl)-5-ethyl-6-(4-(3-hydroxypicolinoyl)piperazin-1-yl)-7-oxo-[1,2,4]triazolo[1,5-a]pyrimidin-4 (7H)-yl)-N-(4-(trifluoromethyl)phenyl)acetamide

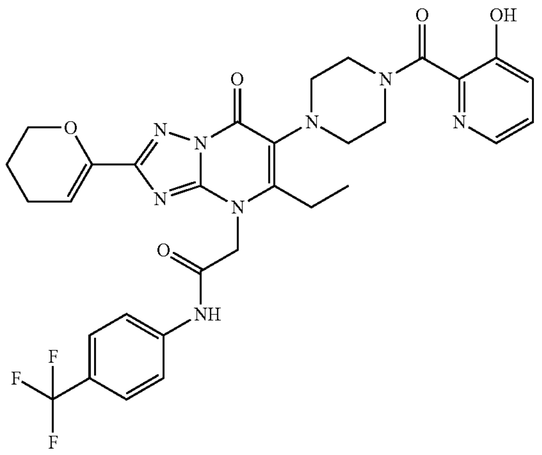 [SMILES: CCc1c(N2CCN(C(=O)c3ncccc3O)CC2)c(=O)n2nc(C3=CCCCO3)nc2n1CC(=O)Nc1ccc(C(F)(F)F)cc1]

3-Hydroxypicolinic acid (83.0 mg, 600 μmol) was dissolved in DCM (2 mL) and 1-chloro-N,N,2-trimethylprop-1-en-1-amine (139 μL, 1.05 mmol) was added. The RM was stirred at RT for 2 hours. Then 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide (Intermediate BB) (159 mg, 300 μmol) was added, followed by DIPEA (262 μL, 1.50 mmol). The RM was stirred at RT for 1 day. Water, aq sat $NaHCO_3$ and DCM were added. The aqueous layer was extracted twice with DCM. The combined organic layers were dried through a phase separator and concentrated under reduced pressure. The crude product was purified by reverse phase preparative HPLC (RP-HPLC acidic 1: 25 to 75% B in 30 min). The product containing fractions were combined, basified with aq sat $NaHCO_3$, extracted twice with DCM, dried through a phase separator and concentrated under reduced pressure. The resulting solid was purified by SFC (SFC 4) to give the title compound.

LC-MS: Rt=1.02 min; MS m/z $[M+H]^+$ 653.6, m/z $[M-H]^-$ 651.4; UPLC-MS 1

LC-MS: Rt=5.04 min; MS m/z $[M+H]^+$ 653.3, m/z $[M-H]^-$ 651.3; UPLC-MS 2

$^1$H NMR (400 MHz, DMSO-$d_6$) δ 10.85 (s, 1H), 10.38 (s, br, 1H), 8.06 (m, 1H), 7.78 (d, J=8.6 Hz, 2H), 7.70 (d, J=8.7 Hz, 2H), 7.29 (m, 2H), 5.83 (m, 1H), 5.18 (m, 2H), 4.55 (m, 1H), 4.08 (m, 2H), 3.44 (m, 3H), 3.24 (m, 1H), 2.98 (m, 3H), 2.80 (m, 1H), 2.62 (m, 1H), 2.16 (m, 2H), 1.83 (m, 2H), 1.16 (t, J=7.4 Hz, 3H)

Example 85: (S)-2-(6-(4-(4-chloro-3-hydroxypicolinoyl)piperazin-1-yl)-5-ethyl-2-(3-fluoropiperidin-1-yl)-7-oxo-[1,2,4]triazolo[1,5-a]pyrimidin-4 (7H)-yl)-N-(2-methyl-4-(trifluoromethyl)phenyl) acetamide

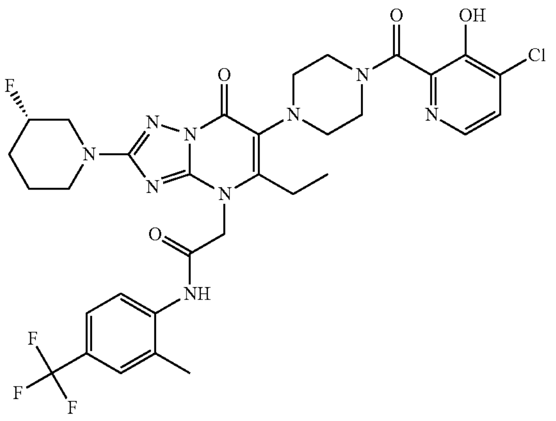 [SMILES: CCc1c(N2CCN(C(=O)c3nccc(Cl)c3O)CC2)c(=O)n2nc(N3CCC[C@H](F)C3)nc2n1CC(=O)Nc1ccc(C(F)(F)F)cc1C]

To the stirred solution of (S)-2-(5-ethyl-2-(3-fluoropiperidin-1-yl)-7-oxo-6-(piperazin-1-yl)-[1,2,4]triazolo[1,5-a]pyrimidin-4 (7H)-yl)-N-(2-methyl-4-(trifluoromethyl)phenyl) acetamide·HCl (Intermediate BC) (550 mg, 915 µmol) in DMF (6 mL) were added 4-chloro-3-hydroxypicolinic acid (318 mg, 1.83 mmol), EDC·HCl (351 mg, 1.83 mmol), HOBt (247 mg, 1.83 mmol) and DIPEA (959 µL, 5.49 mmol) at RT. The RM was stirred at RT for 16 hours. The RM was concentrated under reduced pressure, water was added and the precipitate was filtered off and dried under reduced pressure. The crude product was purified by reverse phase preparative HPLC (RP-HPLC acidic 4: 20 to 30% B in 2 min, 30 to 65% B in 8 min) to give the title compound.

LC-MS: Rt=1.11 min; MS m/z $[M+H]^+$ 720.3, m/z $[M-H]^-$ 718.3; UPLC-MS 1

LC-MS: Rt=5.52 min; MS m/z $[M+H]^+$ 720.2, m/z $[M-H]^-$ 718.2; UPLC-MS 2

$^1$H NMR (400 MHz, DMSO-$d_6$) δ 10.87 (s, br, 1H), 10.00 (s, 1H), 8.02 (m, 1H), 7.69 (d, J=8.4 Hz, 1H), 7.63 (m, 1H), 7.53 (m, 2H), 5.13 (s, 2H), 4.75 (m, 1H), 4.52 (m, 1H), 3.74 (m, 1H), 3.55 (m, 5H), 3.22 (m, 2H), 2.95 (m, 3H), 2.77 (m, 1H), 2.59 (m, 1H), 2.34 (s, 3H), 1.83 (m, 3H), 1.53 (m, 1H), 1.17 (d, J=7.1 Hz, 3H)

Example 86: (R)—N-(2-chloro-4-(trifluoromethyl) phenyl)-2-(2-(3,6-dihydro-2H-pyran-4-yl)-5-ethyl-6-(4-(5-hydroxy-6-methylpyrimidine-4-carbonyl)-3-methylpiperazin-1-yl)-7-oxo-[1,2,4]triazolo[1,5-a] pyrimidin-4 (7H)-yl)acetamide

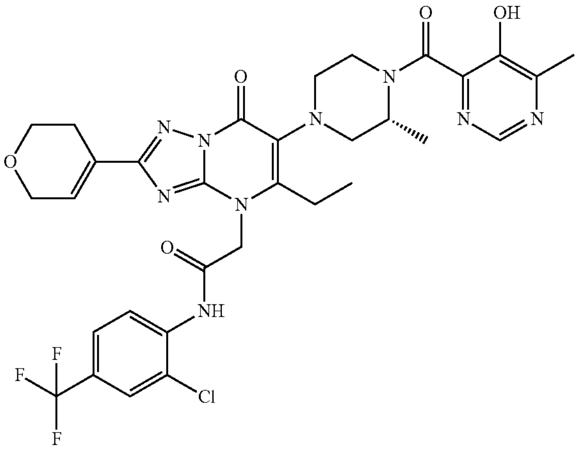 [SMILES: CCc1c(N2CCN(C(=O)c3ncnc(C)c3O)[C@H](C)C2)c(=O)n2nc(C3=CCOCC3)nc2n1CC(=O)Nc1ccc(C(F)(F)F)cc1Cl]

Step 1: (R)-2-(6-(4-(5-(benzyloxy)-6-methylpyrimidine-4-carbonyl)-3-methylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (R)—N-(2-chloro-4-(trifluoromethyl)phenyl)-2-(2-(3,6-dihydro-2H-pyran-4-yl)-5-ethyl-6-(3-methylpiperazin-1-yl)-7-oxo-[1,2,4]triazolo[1,5-a]pyrimidin-4 (7H)-yl)acetamide (Intermediate BE) (350 mg, 603 µmol), 5-(benzyloxy)-6-methylpyrimidine-4-carboxylic acid (Intermediate CY) (155 mg, 634 µmol) and HATU (241 mg, 634 µmol) were suspended in DCM (10 mL) and DMF (200 µL) and the mixture was cooled to 0° C. DIPEA (263 µL, 1.51 mmol) was added, and the suspension was stirred at 0° C. for 10 minutes and at RT for 30 minutes. Water (10 mL), aq sat $NaHCO_3$ (10 mL) and DCM (10 mL) were added. The aqueous layer was extracted with DCM (2×10 mL), and the organic layers were combined, dried through a phase separator and concentrated under reduced pressure. The crude product was purified by column chromatography (RediSep Column: Silica 24 g, eluent DCM:MeOH 100:0 to 75:25). The product containing fractions were combined, concentrated under vacuum and dried under HV to afford the title compound as a brown oil. The product was heated in water:MeOH (1:3) until fully dissolved and left to cool to RT. The suspension was filtered off and washed with MeOH, then dried to give the title compound as beige solid.

LC-MS: Rt=1.23 min; MS m/z $[M+H]^+$ 806.5, m/z $[M-H]^-$ 804.5; UPLC-MS 1

Step 2: (R)—N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)-3-methylpiperazin-1-yl)-7-oxo-[1,2,4]triazolo[1,5-a]pyrimidin-4 (7H)-yl)acetamide (R)-2-(6-(4-(5-(benzyloxy)-6-methylpyrimidine-4-carbonyl)-3-methylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (598 mg, 600 μmol) was dissolved in DCM (1 mL), and TFA (1.00 mL, 13.0 mmol) was added. The RM was stirred at 45° C. for 1 day. The RM was concentrated under reduced pressure, and water (10 mL), aq sat $NaHCO_3$ (10 mL) and DCM (10 mL) were added. The aqueous layer was extracted with DCM (2×10 mL). The combined organic layers were dried through a phase separator and concentrated under reduced pressure. The crude product was purified by column chromatography (RediSep Column: Silica 40 g, eluent DCM:MeOH 100:0 to 95:05). The product containing fractions were combined, concentrated under vacuum and dried under HV. This material was further purified in 2 portions by reverse phase preparative HPLC (RP-HPLC acidic 1: 20 to 80% B in 20 min with a plateau at 80% for 1 min and RP-HPLC acidic 1: 25 to 75% B in 20 min with a plateau at 75% for 1 min). All product containing fractions were combined, basified with aq sat $NaHCO_3$, extracted twice with DCM, dried through a phase separator and concentrated under reduced pressure. The concentrated fractions were suspended in MeOH, sonicated and filtered. The cake was dried under HV. This material was heated in water and MeOH (1:3) until fully dissolved and left to cool. The suspension was filtered off and washed with MeOH, then dried to give the title compound as beige solid characterized by the XRPD diffractogram in FIG. 2 The table below shows the most prominent peaks (deg 2theta) of the XRPD diffractogram of FIG. 2. The sodium salt was prepared analogous to the general procedure.

LC-MS: Rt=1.06 min; MS m/z $[M+H]^+$ 716.1, m/z $[M-H]^-$ 714.4; UPLC-MS 1

LC-MS: Rt=5.26 min; MS m/z $[M+H]^+$ 716.1, m/z $[M-H]^-$ 714.5; UPLC-MS 2

$^1$H NMR (400 MHz, DMSO-$d_6$) δ 10.35 (s, 1H), 10.15 (d, J=19.4 Hz, 1H), 8.57 (d, J=3.7 Hz, 1H), 8.06 (d, J=8.6 Hz, 1H), 7.96 (m, 1H), 7.71 (d, J=8.6 Hz, 1H), 6.83 (m, 1H), 5.32 (s, 2H), 4.82-4.36 (m, 1H), 4.25 (m, 2H), 3.80 (m, 2H), 3.71 (m, 2H), 3.50 (m, 1H), 3.16 (m, 2H), 2.92 (m, 1H), 2.81 (m, 1H), 2.66 (m, 1H), 2.50 (m, 2H), 2.44 (s, 3H), 1.40 (m, 3H), 1.20 (t, J=7.4 Hz, 3H)

| Angle 2-Theta° | d Value Angstrom | Intensity |
|---|---|---|
| 10.29 | 8.59 | high |
| 13.31 | 6.65 | medium |
| 14.01 | 6.32 | low |
| 15.26 | 5.80 | medium |
| 17.34 | 5.11 | medium |

Example 87: (S)—N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)-2-methylpiperazin-1-yl)-7-oxo-[1,2,4]triazolo[1,5-a]pyrimidin-4 (7H)-yl)acetamide

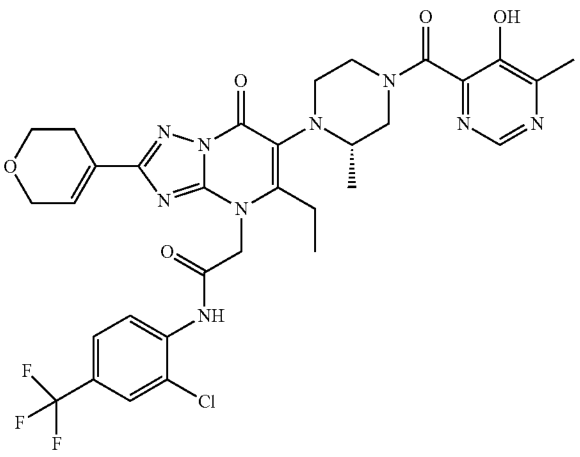 [SMILES: CCc1c(N2CCN(C(=O)c3ncnc(C)c3O)C[C@@H]2C)c(=O)n2nc(C3=CCOCC3)nc2n1CC(=O)Nc1ccc(C(F)(F)F)cc1Cl]

Step 1: (S)-2-(6-(4-(5-(benzyloxy)-6-methylpyrimidine-4-carbonyl)-2-methylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (S)—N-(2-chloro-4-(trifluoromethyl)phenyl)-2-(2-(3,6-dihydro-2H-pyran-4-yl)-5-ethyl-6-(2-methylpiperazin-1-yl)-7-oxo-[1,2,4]triazolo[1,5-a]pyrimidin-4 (7H)-yl)acetamide (Intermediate BH) (58.0 mg, 80.0 μmol) and 5-(benzyloxy)-6-methylpyrimidine-4-carboxylic acid (Intermediate CY) (19.5 mg, 80.0 μmol) were mixed in DMF (1 mL) at RT under argon. HATU (36.5 mg, 96.0 μmol) was added, followed by DIPEA (69.9 μL, 400 μmol). The RM was stirred at RT for 1.75 hours. Water (10 mL) was added and the RM was extracted with EtOAc (4×50 mL). The organic layers were combined, washed with water (2×10 mL) and brine (2×10 mL), dried trough a phase separator and concentrated under reduced pressure. The crude product was purified by column chromatography (RediSep Column: Silica 24 g, eluent DCM:DCM/MeOH (8/2) 100:0 to 60:40). The product containing fractions were combined and concentrated to give the title compound as a beige solid.

LC-MS: Rt=1.21 min; MS m/z $[M+H]^+$ 806.3, m/z $[M-H]^-$ 804.3; UPLC-MS 1

Step 2: (S)—N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)-2-methylpiperazin-1-yl)-7-oxo-[1,2,4]triazolo[1,5-a]pyrimidin-4 (7H)-yl)acetamide (S)-2-(6-(4-(5-(benzyloxy)-6-methylpyrimidine-4-carbonyl)-2-methylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (33.0 mg, 41.0 μmol) in TFA (1.00 mL, 13.0 mmol) was stirred at 50° C. for 3 hours and then at RT overnight. The RM was concentrated and dried under HV, water (10 mL) was added, and the residue was extracted with DCM (4×15 mL). The organic layers were washed with aq sat $NaHCO_3$ (5 mL) and brine (5 mL), dried through a phase separator and concentrated under reduced pressure. The crude product was adsorbed onto Isolute and purified by column chromatography (RediSep Column: Silica 12 g, eluent DCM:DCM/MeOH (8/2) 100:0 to 70:30). The product containing fractions were combined and concentrated under reduced pressure to give the title compound as a beige solid.

LC-MS: Rt=1.07 min; MS m/z $[M+H]^+$ 716.3, m/z $[M-H]^-$ 714.3; UPLC-MS 1

LC-MS: Rt=5.35 min; MS m/z $[M+H]^+$ 716.2, m/z $[M-H]^-$ 714.3; UPLC-MS 2

$^1$H NMR (400 MHz, DMSO-$d_6$) δ 10.35 (s, br, 2H), 8.55 (d, J=5.3 Hz, 1H), 8.05 (d, J=8.5 Hz, 1H), 7.96 (m, 1H), 7.71 (d, J=8.9 Hz, 1H), 6.83 (m, 1H), 5.30 (m, 2H), 4.50 (m, 1H), 4.25 (m, 2H), 3.80 (m, 2H), 3.62 (m, 1H), 3.45 (m, 2H), 2.98 (m, 1H), 2.81 (m, 3H), 2.61 (m, 1H), 2.50 (m, 2H), 2.43 (d, J=4.4 Hz, 3H), 1.24 (s, 3H), 1.17 (m, 3H)

Example 88: (R)—N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)-2-methylpiperazin-1-yl)-7-oxo-[1,2,4]triazolo[1,5-a]pyrimidin-4 (7H)-yl)acetamide

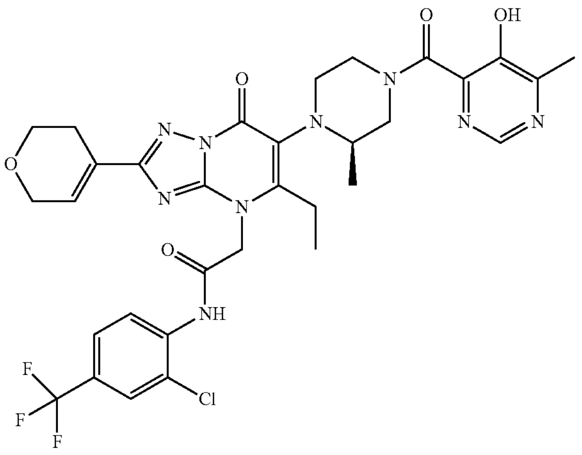 [SMILES: CCc1c(N2CCN(C(=O)c3ncnc(C)c3O)C[C@H]2C)c(=O)n2nc(C3=CCOCC3)nc2n1CC(=O)Nc1ccc(C(F)(F)F)cc1Cl]

Step 1: (R)-2-(6-(4-(5-(benzyloxy)-6-methylpyrimidine-4-carbonyl)-2-methylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (R)—N-(2-chloro-4-(trifluoromethyl)phenyl)-2-(2-(3,6-dihydro-2H-pyran-4-yl)-5-ethyl-6-(2-methylpiperazin-1-yl)-7-oxo-[1,2,4]triazolo[1,5-a]pyrimidin-4 (7H)-yl)acetamide (Intermediate BJ) (93.0 mg, 160 μmol) and 5-(benzyloxy)-6-methylpyrimidine-4-carboxylic acid (Intermediate CY) were mixed in DMF (2 mL) at RT under argon. HATU (75.0 mg, 192 μmol) and DIPEA (140 μL, 802 μmol) were added. The RM was stirred at RT for 40 minutes, then it was quenched with water (5 mL) and extracted with EtOAc (3×50 mL). The organic layers were washed with water (2×10 mL) and brine (2×10 mL), dried through a phase separator and concentrated under reduced pressure. The crude product was purified by reverse phase preparative HPLC (RP-HPLC acidic 1: 15 to 85% B in 20 min with a plateau at 85% for 1 min). The product containing fractions were combined and lyophilized to give the title compound as a white solid.

LC-MS: Rt=1.21 min; MS m/z $[M+H]^+$ 806.3, m/z $[M-H]^-$ 804.4; UPLC-MS 1

Step 2: (R)—N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)-2-methylpiperazin-1-yl)-7-oxo-[1,2,4]triazolo[1,5-a]pyrimidin-4 (7H)-yl)acetamide (R)-2-(6-(4-(5-(benzyloxy)-6-methylpyrimidine-4-carbonyl)-2-methylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (70.7 mg, 88.0 μmol) was mixed with TFA (2.00 mL, 26.0 mmol) and stirred at 50° C. for 2.75 hours. The RM was concentrated under reduced pressure, dried under HV and extracted with DCM (4×30 mL). The organic layers were washed with aq sat $NaHCO_3$ (15 mL) and brine (20 mL), dried through a phase separator and concentrated under reduced pressure. The crude product was adsorbed onto Isolute and purified by column chromatography (RediSep Column: Silica 12 g, eluent DCM:MeOH 100:0 to 80:20). The product containing fractions were combined and concentrated to give the title compound as a colorless solid.

LC-MS: Rt=1.07 min; MS m/z $[M+H]^+$ 716.3, m/z $[M-H]^-$ 714.3; UPLC-MS 1

LC-MS: Rt=5.33 min; MS m/z $[M+H]^+$ 716.2, m/z $[M-H]^-$ 714.2; UPLC-MS 2

$^1$H NMR (400 MHz, DMSO-$d_6$) δ 10.36 (s, 1H), 10.22 (d, J=12.6 Hz, 1H), 8.57 (d, J=4.5 Hz, 1H), 8.05 (d, J=8.6 Hz, 1H), 7.96 (m, 1H), 7.71 (d, J=8.1 Hz, 1H), 6.83 (m, 1H), 5.43-5.20 (m, 2H), 4.51 (m, 1H), 4.25 (m, 2H), 3.80 (m, 2H), 3.63 (m, 1H), 3.46 (m, 2H), 3.26 (m, 1H), 2.99 (m, 1H), 2.81 (m, 2H), 2.60 (m, 1H), 2.50 (m, 2H), 2.44 (d, J=4.1 Hz, 3H), 1.18 (m, 3H), 0.92-0.67 (m, 3H)

Example 89: (R)-2-(2-(3,6-dihydro-2H-pyran-4-yl)-6-(4-(3-hydroxypicolinoyl)-3-methylpiperazin-1-yl)-5-methyl-7-oxo-[1,2,4]triazolo[1,5-a]pyrimidin-4 (7H)-yl)-N-(4-(trifluoromethyl)phenyl)acetamide

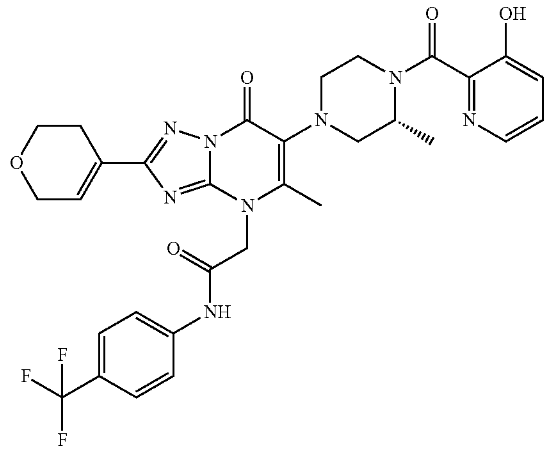 [SMILES: Cc1c(N2CCN(C(=O)c3ncccc3O)[C@H](C)C2)c(=O)n2nc(C3=CCOCC3)nc2n1CC(=O)Nc1ccc(C(F)(F)F)cc1]

To a suspension of 3-hydroxypicolinic acid (47.1 mg, 339 μmol) in DCM (3 mL) was added 1-chloro-N,N,2-trimethylprop-1-en-1-amine (49.0 μL, 373 μmol) and the RM was stirred at RT for 40 minutes. DIPEA (148 µL, 847 µmol) was added slowly, followed by (R)-2-(2-(3,6-dihydro-2H-pyran-4-yl)-5-methyl-6-(3-methylpiperazin-1-yl)-7-oxo-[1,2,4]triazolo[1,5-a]pyrimidin-4 (7H)-yl)-N-(4-(trifluoromethyl)phenyl)acetamide (Intermediate BL) (100 mg, 169 µmol). The RM was stirred at RT for 16.5 hours. To a suspension of 3-hydroxypicolinic acid (23.6 mg, 169 µmol) in DCM (2 mL) was added 1-chloro-N,N,2-trimethylprop-1-en-1-amine (25.0 µL, 187 µmol) and the RM was stirred at RT for 2 hours. The first RM was added dropwise and the resulting mixture was stirred at RT for 2.5 hours. DIPEA (74.0 µL, 424 µmol) was added slowly, and the RM was stirred at RT for 17 hours. The RM was concentrated to dryness, and the residue was purified by column chromatography (RediSep Column: Silica 4 g, eluent DCM:DCM/MeOH (9/1) 100:0 to 60:40). The product containing fractions were combined and concentrated under reduced pressure. This material was purified in 2 portions by reverse phase preparative HPLC (2×RP-HPLC acidic 1: 18 to 48% B in 20 min). The product containing fractions were combined, basified with solid $NaHCO_3$, sonicated and concentrated to remove the ACN/TFA. The residue was extracted twice with DCM and a small amount of MeOH. The combined organic layers were dried through a phase separator and concentrated under reduced pressure to give the title compound.

LC-MS: Rt=1.01 min; MS m/z $[M+H]^+$ 653.2, m/z $[M-H]^-$ 651.0; UPLC-MS 4

$^1H$ NMR (600 MHz, DMSO-$d_6$) δ 10.93 (s, 1H), 10.33 (s, br, 1H), 8.05 (m, 1H), 7.79 (d, J=8.0 Hz, 2H), 7.71 (d, J=7.9 Hz, 2H), 7.28 (m, 2H), 6.81 (m, 1H), 5.23 (s, 2H), 4.83-4.36 (m, 1H), 4.24 (m, 2H), 3.79 (m, 2H), 3.64 (m, 1H), 3.45 (m, 1H), 3.32 (m, 1H), 3.19 (m, 1H), 2.80 (m, 1H), 2.64 (m, 1H), 2.60 (s, 3H), 2.51 (m, 2H), 1.38 (m, 3H)

Example 90: 2-(2-(3,6-dihydro-2H-pyran-4-yl)-6-(4-(3-hydroxy-4-methylpicolinoyl)piperazin-1-yl)-5-methyl-7-oxo-[1,2,4]triazolo[1,5-a]pyrimidin-4 (7H)-yl)-N-(4-(trifluoromethyl)phenyl)acetamide

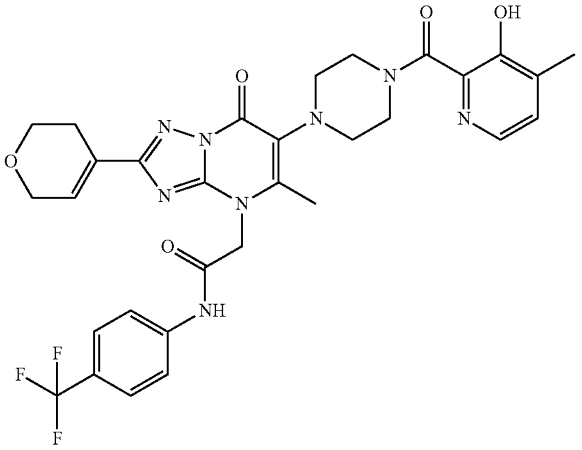 [SMILES: Cc1ccnc(C(=O)N2CCN(c3c(C)n(CC(=O)Nc4ccc(C(F)(F)F)cc4)c4nc(C5=CCOCC5)nn4c3=O)CC2)c1O]

3-Hydroxy-4-methylpicolinic acid (73.3 mg, 386 µmol) was suspended in DCM (4 mL) at RT. The mixture was cooled to 0° C. and 1-chloro-N,N,2-trimethylprop-1-en-1-amine (64.0 µL, 483 µmol) was added dropwise. The RM was stirred at RT for 2 hours, then it was cooled to 0° C. again. DIPEA (169 µL, 966 µmol) was added. This solution was added dropwise at 0° C. to a solution of 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide (Intermediate BN) (100 mg, 193 µmol) in DCM (4 mL). The RM was stirred at RT for 18 hours. The RM was diluted with DCM, washed with aq sat $NH_4Cl$, dried over $Na_2SO_4$, concentrated and dried. The crude product was purified by reverse phase preparative HPLC (RP-HPLC acidic 1: 5 to 100% B in 20 min). The product containing fractions were combined, the ACN was removed and the residue was lyophilized to give the title compound as a foam.

LC-MS: Rt=1.07 min; MS m/z $[M+H]^+$ 653.2, m/z $[M-H]^-$ 651.1; UPLC-MS 4

$^1H$ NMR (400 MHz, DMSO-$d_6$) δ 10.89 (s, 1H), 10.47 (s, br, 1H), 8.03 (d, J=4.7 Hz, 1H), 7.79 (d, J=8.6 Hz, 2H), 7.71 (d, J=8.8 Hz, 2H), 7.30 (d, J=4.8 Hz, 1H), 6.81 (m, 1H), 5.22 (s, 2H), 4.55 (m, 1H), 4.24 (m, 2H), 4.04 (m, 1H), 3.79 (m, 2H), 3.50 (m, 2H), 3.31 (m, 1H), 3.03 (m, 1H), 2.81 (m, 1H), 2.63 (m, 1H), 2.58 (s, 3H), 2.51 (m, 2H), 2.26 (s, 3H)

Example 91: 2-(2-(3,6-dihydro-2H-pyran-4-yl)-6-(4-(3-hydroxy-6-methylpicolinoyl)piperazin-1-yl)-5-methyl-7-oxo-[1,2,4]triazolo[1,5-a]pyrimidin-4 (7H)-yl)-N-(4-(trifluoromethyl)phenyl)acetamide

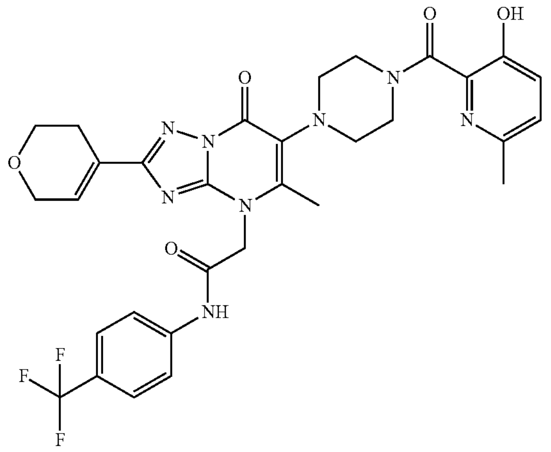 [SMILES: Cc1ccc(O)c(C(=O)N2CCN(c3c(C)n(CC(=O)Nc4ccc(C(F)(F)F)cc4)c4nc(C5=CCOCC5)nn4c3=O)CC2)n1]

3-Hydroxy-6-methylpicolinic acid (90.0 mg, 386 µmol) was suspended in DCM (4 mL) at RT. The mixture was cooled to 0° C. and 1-chloro-N,N,2-trimethylprop-1-en-1-amine (56.0 µL, 425 µmol) was added dropwise. The RM was stirred at RT for 2 hours, then it was cooled to 0° C. again. DIPEA (169 µL, 966 µmol) was added. This solution was added dropwise at 0° C. to a solution of 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide (Intermediate BN) (100 mg, 193 µmol) in DCM (4 mL). The RM was stirred at RT for 18 hours. The RM was diluted with DCM, and the organic phase was washed with aq sat $NH_4Cl$, dried over $Na_2SO_4$, concentrated and dried. The crude product was purified by reverse phase preparative HPLC (RP-HPLC acidic 1: 5 to 100% B in 20 min). The product containing fractions were combined, the ACN was removed and the residue was lyophilized to give the title compound.

LC-MS: Rt=1.02 min; MS m/z $[M+H]^+$ 653.2, m/z $[M-H]^-$ 651.1; UPLC-MS 4

$^1$H NMR (400 MHz, DMSO-$d_6$) δ 10.87 (s, 1H), 10.47 (s, br, 1H), 7.79 (d, J=8.6 Hz, 2H), 7.71 (d, J=8.8 Hz, 2H), 7.35 (d, J=8.5 Hz, 1H), 7.26 (d, J=8.5 Hz, 1H), 6.81 (m, 1H), 5.22 (s, 2H), 4.52 (m, 1H), 4.24 (m, 2H), 3.80 (m, 2H), 3.46 (m, 3H), 3.26 (m, 1H), 3.00 (m, 1H), 2.80 (m, 1H), 2.63 (m, 1H), 2.58 (s, 3H), 2.51 (m, 2H), 2.43 (s, 3H)

Example 92: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-fluoro-4-(trifluoromethyl)phenyl)acetamide

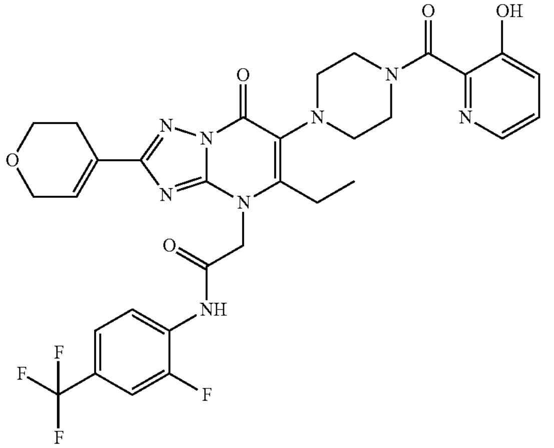

3-Hydroxypicolinic acid (114 mg, 801 μmol) was dissolved in DCM (5 mL) at RT under argon. 1-Chloro-N,N,2-trimethylprop-1-en-1-amine (118 mg, 881 μmol) was added and the RM was stirred at RT for 1.75 hours. A solution of 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide (Intermediate BP) (310 mg, 401 μmol) in DCM (2.2 mL) and DIPEA (350 μL, 2.00 mmol) was added. The brown solution was stirred at RT for 2.5 hours. The RM was quenched with water (5 mL) and aq sat $NaHCO_3$ (5 mL). Then it was extracted 4 times with DCM (4×20 mL). The organic layer was washed with water and aq sat $NaHCO_3$, dried through a phase separator and concentrated under reduced pressure. The residue was adsorbed onto Isolute and purified by column chromatography (RediSep Column: Silica 40 g, eluent DCM:MeOH 100:0 to 60:40). The product containing fractions were combined and concentrated under reduced pressure. The resulting solid was adsorbed onto Isolute and purified by column chromatography (RediSep Column: Silica 24 g, eluent DCM:MeOH 100:0 to 95:05). The crude product was further purified by SFC (SFC 3) gave the title compound as a white solid.

LC-MS: Rt=0.99 min; MS m/z $[M+H]^+$ 671.4, m/z $[M-H]^-$ 669.4; UPLC-MS 4

$^1$H NMR (600 MHz, DMSO-$d_6$) δ 10.70 (s, br, 1H), 10.40 (s, br, 1H), 8.23 (t, J=8.1 Hz, 1H), 8.07 (m, 1H), 7.81 (dd, J=2.1 Hz, 11.1 Hz, 1H), 7.57 (dd, J=2.0 Hz, 8.6 Hz, 1H), 7.29 (m, 2H), 6.81 (m, 1H), 5.30 (s, 2H), 4.55 (m, 1H), 4.25 (m, 2H), 3.80 (m, 2H), 3.48 (m, 2H), 3.40 (m, 1H), 3.22 (m, 1H), 2.97 (m, 3H), 2.80 (m, 1H), 2.63 (m, 1H), 2.51 (m, 2H), 1.17 (t, J=7.7 Hz, 3H)

Example 93: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(3-fluoro-2-methyl-4-(trifluoromethyl)phenyl)acetamide

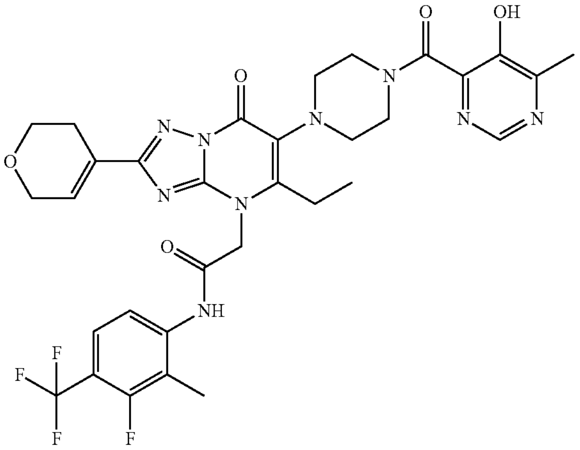 [SMILES: CCc1c(N2CCN(C(=O)c3ncnc(C)c3O)CC2)c(=O)n2nc(C3=CCOCC3)nc2n1CC(=O)Nc1ccc(C(F)(F)F)c(F)c1C]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(3-fluoro-2-methyl-4-(trifluoromethyl)phenyl)acetamide 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide (Intermediate AJ) (97.0 mg, 139 μmol) and 5-(benzyloxy)-6-methylpyrimidine-4-carboxylic acid (Intermediate CY) (59.0 mg, 242 μmol) were dissolved in DCM (10 mL) and HATU (82.6 mg, 218 μmol) was added, followed by DIPEA (111 μL, 695 μmol). The RM was stirred at RT for 45 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 12 g, eluent DCM:DCM/MeOH (1/1) 100:0 to 88:12) to afford the title compound.

LC-MS: Rt=1.18 min; MS m/z $[M+H]^+$ 790.4, m/z $[M-H]^-$ 788.4; UPLC-MS 1

Step 2: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(3-fluoro-2-methyl-4-(trifluoromethyl)phenyl)acetamide 2-(6-(4-(5-(Benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(3-fluoro-2-methyl-4-(trifluoromethyl)phenyl)acetamide (131 mg, 124 μmol) was dissolved in DCM (2 mL) and $BCl_3$ 2M in DCM (124 μL, 249 μmol) was added. The solution stayed a solution and was stirred at RT for 1 hour. The solution had turned into a suspension. The suspension was stirred at RT for 30 minutes. The RM was purged with argon and $BCl_3$ 2M in DCM (124 μL, 249 μmol) was added. The suspension was stirred at RT overnight. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified in 2 portions by column chromatography (RediSep Column: Silica 4 g, eluent DCM:DCM/MeOH (1/1) 100:0 to 90:10) and (RediSep Column: Silica 12 g, eluent DCM: DCM/MeOH (1/1) 100:0 to 90:10). The product containing fractions were combined, concentrated under vacuum and dried under HV to afford a yellow solid. The yellow solid was purified by reverse phase preparative HPLC (RP-HPLC basic 1: 5 to 95% B in 20 min with a plateau at 95% for 1 min). The product containing fractions were combined, basified with aq sat $NaHCO_3$, extracted twice with DCM, dried through a phase separator and concentrated under reduced pressure to give the title compound. The product was dissolved in DCM (5 mL) and EtOH (1 mL). The mixture was standing around for crystallization. The crystals were filtered and washed with a small amount of $Et_2O$. Then they were dried under HV to give the title compound as a colourless solid.

LC-MS: Rt=1.03 min; MS m/z $[M+H]^+$ 700.4, m/z $[M-H]^-$ 698.3; UPLC-MS 1

$^1H$ NMR (400 MHz, DMSO-$d_6$) δ 10.21 (m, 2H), 8.58 (s, 1H), 7.58 (m, 2H), 6.82 (m, 1H), 5.26 (s, 2H), 4.52 (m, 1H), 4.26 (m, 2H), 3.81 (m, 2H), 3.47 (m, 3H), 3.25 (m, 1H), 2.99 (m, 3H), 2.81 (m, 1H), 2.63 (m, 1H), 2.50 (m, 2H), 2.44 (s, 3H), 2.24 (s, 3H), 1.19 (t, J=7.5 Hz, 3H)

Example 94: 2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(5-fluoro-2-methyl-4-(trifluoromethyl)phenyl)acetamide

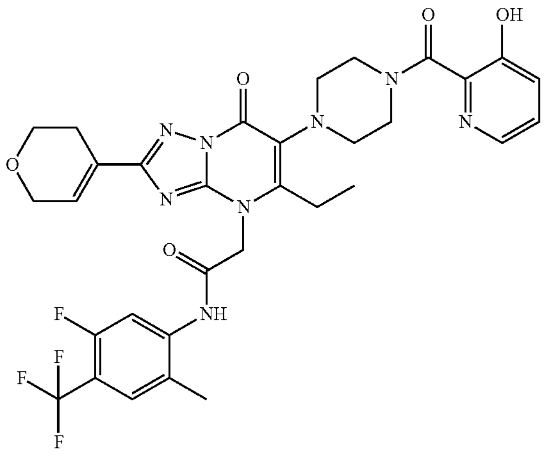 [SMILES: CCc1c(N2CCN(C(=O)c3ncccc3O)CC2)c(=O)n2nc(C3=CCOCC3)nc2n1CC(=O)Nc1cc(F)c(C(F)(F)F)cc1C]

2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide (Intermediate AM) (657 mg, 1.11 mmol) and 3-hydroxypicolinoyl chloride (Intermediate CV) (227 mg, 1.44 mmol) were dissolved in DCM (5 mL) and DIPEA (967 μL, 5.54 mmol) was added. The RM was stirred at RT for 30 minutes. 3-Hydroxypicolinoyl chloride (Intermediate CV) (227 mg, 1.44 mmol) and DIPEA (967 μL, 5.54 mmol) were added again and the RM was continued stirring at RT for 3.5 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was suspended in DCM and ACN and sonicated for 5 minutes. Then it was filtered. The cake was adsorbed onto Isolute and purified in 2 portions by column chromatography (RediSep Column: Silica 24 g, eluent DCM:DCM/MeOH (9/1) 100:0 to 0:100) and (RediSep Column: Silica 24 g, eluent DCM:DCM/MeOH (9/1) 100:0 to 60:40) to afford the title compound as a white solid.

LC-MS: Rt=1.03 min; MS m/z $[M+H]^+$ 685.3, m/z $[M-H]^-$ 683.2; UPLC-MS 3

$^1H$ NMR (400 MHz, DMSO-$d_6$) δ 10.47 (s, br, 1H), 10.07 (s, 1H), 8.08 (m, 1H), 7.79 (d, J=12.9 Hz, 1H), 7.67 (d, J=8.1 Hz, 1H), 7.32 (m, 2H), 6.82 (m, 1H), 5.29 (s, 2H), 4.55 (m, 1H), 4.26 (m, 2H), 3.81 (m, 2H), 3.46 (m, 3H), 3.23 (m, 1H), 2.97 (m, 3H), 2.81 (m, 1H), 2.63 (m, 1H), 2.53 (m, 2H), 2.35 (s, 3H), 1.19 (t, J=7.3 Hz, 3H)

Example 95: 2-(6-(4-(4-chloro-3-hydroxypicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(5-fluoro-2-methyl-4-(trifluoromethyl)phenyl)acetamide

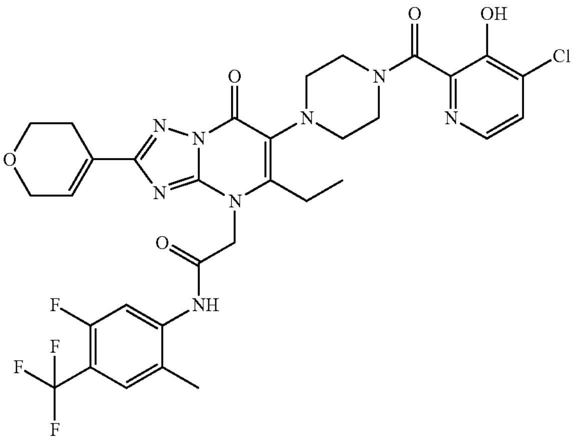 [SMILES: CCc1c(N2CCN(C(=O)c3nccc(Cl)c3O)CC2)c(=O)n2nc(C3=CCOCC3)nc2n1CC(=O)Nc1cc(F)c(C(F)(F)F)cc1C]

4-Chloro-3-hydroxypicolinic acid (148 mg, 852 μmol) was dissolved in DCM (8 mL) at RT under argon. 1-Chloro-N,N,2-trimethylprop-1-en-1-amine (127 mg, 954 μmol) was added and the RM was stirred at RT for 2 hours. 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide (Intermediate AM) (240 mg, 341 μmol) and DIPEA (238 μL, 1.36 mmol) were added. The RM was stirred at RT for 1.5 hours. The RM was quenched with water (10 mL) and aq sat $NaHCO_3$ (10 mL). Then it was extracted 4 times with DCM (4×50 mL). The organic layer was washed with water (10 mL), dried through a phase separator and concentrated under reduced pressure. The residue was adsorbed onto Isolute and purified by column chromatography (RediSep Column: Silica 24 g, eluent DCM:MeOH 100:0 to 75:25). The product containing fractions were combined and concentrated under reduced pressure. The residue was purified by column chromatography (RediSep Column: Silica 24 g, eluent DCM:MeOH 100:0 to 95:5). The product containing fractions were combined and concentrated under reduced pressure. The residue was purified by column chromatography (RediSep Column: Silica 24 g, eluent DCM:MeOH 100:0 to 95:5). The solid was purified by reverse phase preparative HPLC (RP-HPLC acidic 1: 30 to 70% B in 20 min with a plateau at 70% for 1 min). The product containing fractions were combined, basified with aq sat $NaHCO_3$ and the ACN was removed under reduced pressure. The aqueous layer was extracted 4 times with DCM (4×50 mL), dried through a phase separator and concentrated under reduced pressure to give the title compound as a beige solid.

LC-MS: Rt=1.12 min; MS m/z $[M+H]^+$ 719.3/721.3, m/z $[M-H]^-$ 717.2/719.2; UPLC-MS 1

$^1$H NMR (600 MHz, DMSO-$d_6$) δ 10.83 (s, 1H), 10.06 (s, 1H), 8.07 (d, J=5.1 Hz, 1H), 7.78 (d, J=13.1 Hz, 1H), 7.67 (d, J=8.2 Hz, 1H), 7.56 (d, J=5.4 Hz, 1H), 6.82 (m, 1H), 5.29 (s, 2H), 4.54 (m, 1H), 4.25 (m, 2H), 3.80 (m, 2H), 3.59 (m, 1H), 3.50 (m, 2H), 3.25 (m, 1H), 2.98 (m, 3H), 2.82 (m, 1H), 2.64 (m, 1H), 2.52 (m, 2H), 2.35 (s, 3H), 1.19 (d, J=7.2 Hz, 3H)

Example 96: N-(2-chloro-4-(trifluoromethyl)phenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)acetamide

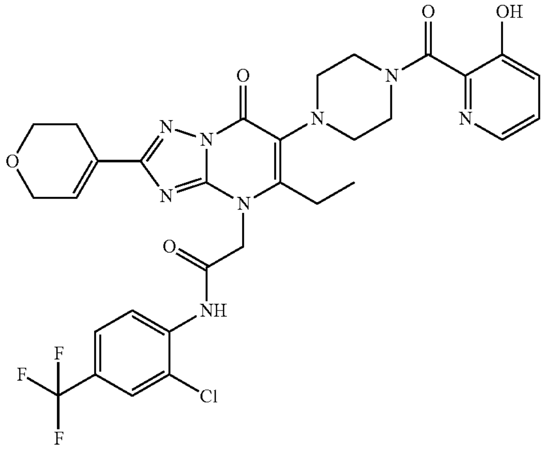

N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AK) (450 mg, 604 μmol) was dissolved in DCM (6 mL) at 0° C. under argon. 3-Hydroxypicolinoyl chloride (Intermediate CV) (119 mg, 755 μmol) was added, followed by slow addition of DIPEA (106 μL, 607 μmol). The RM was stirred at RT for 1.75 hours. 3-Hydroxypicolinoyl chloride (Intermediate CV) (125 mg, 793 μmol) and DIPEA (320 μL, 1.83 mmol) were added again and the RM was stirred at RT for 2.5 hours. 3-Hydroxypicolinoyl chloride (Intermediate CV) (150 mg, 952 μmol) and DIPEA (110 μL, 630 μmol) were added again. The RM was stirred at RT for 1 hour. 3-Hydroxypicolinoyl chloride (Intermediate CV) (110 mg, 698 μmol) was added again and the RM was stirred at RT for 2.25 hours. Then it was stored in the freezer overnight. The RM was quenched with water (10 mL) and aq sat $NaHCO_3$ (10 mL). Then it was extracted 4 times with DCM (4×40 mL). The organic layer was washed with water (10 mL), aq sat $NaHCO_3$ (10 mL) and water (15 mL), dried through a phase separator and concentrated under reduced pressure. The residue was adsorbed onto Isolute and purified by column chromatography (RediSep Column: Silica 24 g, eluent DCM:MeOH 100:0 to 75:25). The product containing fractions were combined and concentrated under reduced pressure. The resulting solid was purified in 2 equal portions by reverse phase preparative HPLC (2×RP-HPLC acidic 1: 10 to 60% B in 20 min with a plateau at 60% for 1 min). The product containing fractions were combined, basified with aq sat $NaHCO_3$ and the ACN was removed under reduced pressure. The aqueous layer was extracted 4 times with DCM (4×50 mL). The aqueous layer was extracted three times with EtOAc (3×60 mL). The combined organic layers were dried through a phase separator and concentrated under reduced pressure to give the title compound as a beige solid characterized by the XRPD diffractogram in FIG. 5. The table below shows the most prominent peaks (deg 2theta) of the XRPD diffractogram of FIG. 5.

The sodium salt was prepared analogous to the general procedure.

LC-MS: Rt=1.03 min; MS m/z $[M+H]^+$ 687.3/689.3, m/z $[M-H]^-$ 685.2/687.1; UPLC-MS 1

$^1$H NMR (600 MHz, DMSO-$d_6$) δ 10.38 (s, 1H), 10.36 (s, 1H), 8.06 (m, 2H), 7.96 (m, 1H), 7.71 (dd, J=1.9 Hz, 8.4 Hz, 1H), 7.29 (m, 2H), 6.83 (m, 1H), 5.31 (s, 2H), 4.55 (m, 1H), 4.25 (m, 2H), 3.80 (m, 2H), 3.46 (m, 3H), 3.22 (m, 1H), 2.97 (m, 3H), 2.80 (m, 1H), 2.62 (m, 1H), 2.52 (m, 2H), 1.18 (t, J=7.5 Hz, 3H)

| Angle 2-Theta° | d Value Angstrom | Intensity |
|---|---|---|
| 13.20 | 6.70 | medium |
| 14.78 | 5.99 | medium |
| 15.97 | 5.55 | medium |
| 16.91 | 5.24 | low |
| 19.95 | 4.45 | medium |
| 20.85 | 4.26 | medium |
| 24.43 | 3.64 | high |
| 25.47 | 3.49 | low |
| 31.06 | 2.88 | low |

Example 97: N-(2-chloro-4-(trifluoromethyl)phenyl)-2-(2-(3,6-dihydro-2H-pyran-4-yl)-5-ethyl-6-(4-(4-fluoro-3-hydroxy-5-methylpicolinoyl)piperazin-1-yl)-7-oxo-[1,2,4]triazolo[1,5-a]pyrimidin-4 (7H)-yl) acetamide

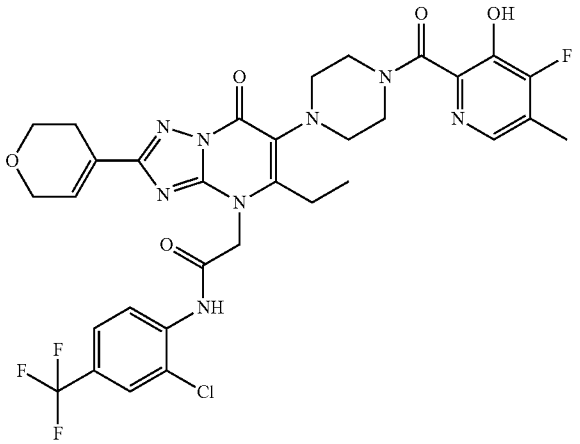 [SMILES: CCc1c(N2CCN(C(=O)c3ncc(C)c(F)c3O)CC2)c(=O)n2nc(C3=CCOCC3)nc2n1CC(=O)Nc1ccc(C(F)(F)F)cc1Cl]

Step 1: 2-(6-(4-(3-(benzyloxy)-4-fluoro-5-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl) acetamide To a beige suspension of N-(2-chloro-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide (Intermediate AK) (65.0 mg, 109 μmol) and 3-(benzyloxy)-4-fluoro-5-methylpicolinic acid (Intermediate DA) (30.0 mg, 109 μmol) in DMF (1 mL) were added DIPEA (95.0 μL, 546 μmol) and HATU (49.8 mg, 131 μmol). The yellow RM was stirred at RT for 20 minutes. The RM was diluted with water and extracted twice with DCM. The combined organic layers were dried through a phase separator and concentrated under reduced pressure. The crude product was purified by column chromatography (RediSep Column: Silica 4 g, eluent DCM:DCM/MeOH (8/2) 100:0 to 50:50). The product containing fractions were combined, concentrated under reduced pressure and dried under HV. The residue was purified by column chromatography (RediSep Column: Silica 4 g, eluent DCM:DCM/MeOH (8/2) 100:0 to 65:35) to give the title compound as a colourless solid.

LC-MS: Rt=1.28 min; MS m/z $[M+H]^+$ 809.4/811.4, m/z $[M-H]^-$ 807.1/809.1; UPLC-MS 1

Step 2: N-(2-chloro-4-(trifluoromethyl)phenyl)-2-(2-(3,6-dihydro-2H-pyran-4-yl)-5-ethyl-6-(4-(4-fluoro-3-hydroxy-5-methylpicolinoyl)piperazin-1-yl)-7-oxo-[1,2,4]triazolo[1,5-a]pyrimidin-4 (7H)-yl) acetamide A light yellow solution of 2-(6-(4-(3-(benzyloxy)-4-fluoro-5-methylpicolinoyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl) acetamide (59.0 mg, 69.0 μmol) in TFA (513 μL) was stirred at 50° C. for 3 hours, then at RT overnight. The RM was diluted with DCM and washed with aq sat $NaHCO_3$. The aqueous layer was extracted twice with DCM. The combined organic layers were dried through a phase separator and concentrated under reduced pressure. The residue was adsorbed onto Isolute and purified by column chromatography (RediSep Column: Silica 4 g, eluent DCM:DCM/MeOH (8/2) 100:0 to 65:35) to give the title compound as a beige solid.

LC-MS: Rt=1.09 min; MS m/z $[M+H]^+$ 719.2/721.2, m/z $[M-H]^-$ 717.3/719.3; UPLC-MS 1

$^1H$ NMR (400 MHz, DMSO-$d_6$) δ 10.65 (s, 1H), 10.35 (s, 1H), 8.05 (d, J=8.4 Hz, 1H), 7.99 (d, J=8.4 Hz, 1H), 7.96 (m, 1H), 7.71 (dd, J=2.2 Hz, 8.8 Hz, 1H), 6.83 (m, 1H), 5.31 (s, 2H), 4.53 (m, 1H), 4.25 (m, 2H), 3.80 (m, 2H), 3.49 (m, 3H), 3.24 (m, 1H), 2.99 (m, 3H), 2.80 (m, 1H), 2.62 (m, 1H), 2.50 (m, 2H), 2.24 (s, 3H), 1.19 (t, J=7.2 Hz, 3H)

Example 98: N-(2-chloro-4-(trifluoromethyl)phenyl)-2-(2-(3,6-dihydro-2H-pyran-4-yl)-5-ethyl-6-(4-(3-hydroxy-4-(trifluoromethoxy)picolinoyl)piperazin-1-yl)-7-oxo-[1,2,4]triazolo[1,5-a]pyrimidin-4 (7H)-yl)acetamide

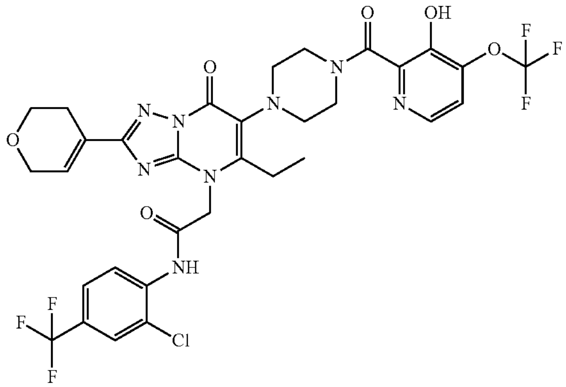

Step 1: N-(2-chloro-4-(trifluoromethyl)phenyl)-2-(2-(3,6-dihydro-2H-pyran-4-yl)-5-ethyl-6-(4-(3-methoxy-4-(trifluoromethoxy)picolinoyl)piperazin-1-yl)-7-oxo-[1,2,4]triazolo[1,5-a]pyrimidin-4 (7H)-yl)acetamide To a white suspension of 3-methoxy-4-(trifluoromethoxy) picolinic acid (Intermediate CZ) (43.6 mg, 180 μmol) in DCM (2.5 mL) was added 1-chloro-N,N,2-trimethylprop-1-en-1-amine (51.7 μL, 375 μmol). The white suspension was stirred for at RT for 1 hour. DIPEA (79.0 μL, 451 μmol) was added slowly, followed by N-(2-chloro-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide (Intermediate AK) (85.0 mg, 150 μmol). The light brown turbid RM was stirred at RT for 3 hours. The RM was diluted with DCM and washed with water. The aqueous layer was extracted with DCM. The combined organic layers were dried through a phase separator and concentrated under reduced pressure. The crude product was purified by column chromatography (RediSep Column: Silica 4 g, eluent DCM: DCM/MeOH (8/2) 100:0 to 70:30) to give the title compound as a yellow solid.

LC-MS: Rt=1.22 min; MS m/z $[M+H]^+$ 785.5/787.5, m/z $[M-H]^-$ 783.4/785.4; UPLC-MS 1

Step 2: N-(2-chloro-4-(trifluoromethyl)phenyl)-2-(2-(3,6-dihydro-2H-pyran-4-yl)-5-ethyl-6-(4-(3-hydroxy-4-(trifluoromethoxy)picolinoyl)piperazin-1-yl)-7-oxo-[1,2,4]triazolo[1,5-a]pyrimidin-4 (7H)-yl) acetamide A light yellow RM of N-(2-chloro-4-(trifluoromethyl) phenyl)-2-(2-(3,6-dihydro-2H-pyran-4-yl)-5-ethyl-6-(4-(3-methoxy-4-(trifluoromethoxy)picolinoyl)piperazin-1-yl)-7-oxo-[1,2,4]triazolo[1,5-a]pyrimidin-4 (7H)-yl)acetamide (78.0 mg, 94.0 μmol) and LiCl (16.9 mg, 397 μmol) in DMF (1 mL) was heated in the MW at 200° C. for 10 minutes. The dark brown RM was diluted with water and extracted twice with EtOAc and once with 10% MeOH in EtOAc. The combined organic layers were dried over $Na_2SO_4$, concentrated and dried under reduced pressure. The crude product was purified by reverse phase preparative HPLC (RP-HPLC basic 1: 5 to 70% B in 20 min with a plateau at 70% for 1 min) and lyophilized. The product was dissolved in EtOH/DCM (1:2) and left to stand in an open flask for 24 h. The resulting solid was filtered, washed with $Et_2O$ and dried under vacuum at 30° C. to give the title compound.

LC-MS: Rt=1.20 min; MS m/z $[M+H]^+$ 771.4/773.4, m/z $[M-H]^-$ 769.4/771.4; UPLC-MS 1

$^1$H NMR (400 MHz, DMSO-$d_6$) δ 11.0 (s, br, 1H), 10.35 (s, br, 1H), 8.15 (d, J=5.7 Hz, 1H), 8.05 (d, J=8.5 Hz, 1H), 7.96 (m, 1H), 7.71 (dd, J=2.0 Hz, 8.4 Hz, 1H), 7.43 (m, 1H), 6.83 (m, 1H), 5.31 (s, 2H), 4.54 (m, 1H), 4.25 (m, 2H), 3.80 (m, 2H), 3.48 (m, 3H), 3.25 (m, 1H), 3.00 (m, 3H), 2.81 (m, 1H), 2.66 (m, 1H), 2.50 (m, 2H), 1.19 (t, J=7.1 Hz, 3H)

Example 99: N-(2-chloro-5-fluoro-6-(trifluoromethyl)pyridin-3-yl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl) acetamide

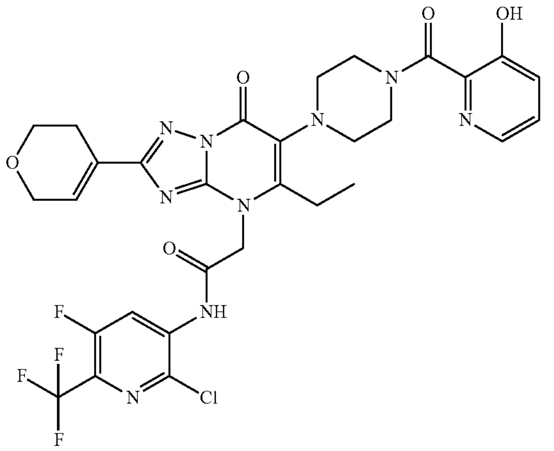 [SMILES: CCc1c(N2CCN(C(=O)c3ncccc3O)CC2)c(=O)n2nc(C3=CCOCC3)nc2n1CC(=O)Nc1cc(F)c(C(F)(F)F)nc1Cl]

N-(2-chloro-5-fluoro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BQ) (390 mg, 580 μmol) in DCM (7 mL) was cooled to 0° C. under argon, then 3-hydroxypicolinoyl chloride (Intermediate CV) (183 mg, 1.16 mmol) was added, followed by DIPEA (355 μL, 2.03 mmol). The RM was stirred at RT for 1.5 hours. The RM was quenched with 5% $NaHCO_3$-solution, extracted three times with DCM, the organic layer was dried through a phase separator and concentrated under reduced pressure. The crude product was purified by column chromatography (RediSep Column: Silica 80 g Gold, eluent DCM:MeOH 100:0 to 93:07) to give the title compound as a solid.

LC-MS: Rt=1.02 min; MS m/z $[M+H]^+$ 706.2/708.3, m/z $[M-H]^-$ 704.2/706.2; UPLC-MS 1

$^1$H NMR (400 MHz, DMSO-$d_6$) δ 10.69 (s, 1H), 10.38 (s, 1H), 8.62 (d, J=11.9 Hz, 1H), 8.06 (m, 1H), 7.29 (m, 2H), 6.81 (m, 1H), 5.40 (s, 2H), 4.55 (m, 1H), 4.24 (m, 2H), 3.80 (m, 2H), 3.45 (m, 3H), 3.22 (m, 1H), 2.97 (m, 3H), 2.79 (m, 1H), 2.62 (m, 1H), 2.52 (m, 2H), 1.17 (t, J=7.4 Hz, 3H)

Example 100: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(pentafluorosulfanyl)phenyl)acetamide

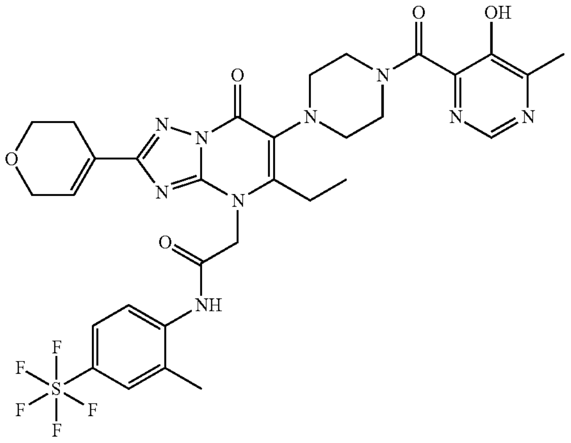 [SMILES: CCc1c(N2CCN(C(=O)c3ncnc(C)c3O)CC2)c(=O)n2nc(C3=CCOCC3)nc2n1CC(=O)Nc1ccc(S(F)(F)(F)(F)F)cc1C]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(pentafluorosulfanyl)phenyl)acetamide 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(pentafluorosulfanyl)phenyl)acetamide (Intermediate BR) (414 mg, 686 μmol), 5-(benzyloxy)-6-methylpyrimidine-4-carboxylic acid (Intermediate CY) (184 mg, 754 μmol) and HATU (417 mg, 1.10 mmol) were mixed in DCM (6 mL) and DIPEA (599 μL, 3.43 mmol) was added. The RM was stirred at RT for 1 hour. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 24 g, eluent DCM:DCM/MeOH (1/1) 100:0 to 72:28) to give the title compound.

LC-MS: Rt=1.22 min; MS m/z $[M+H]^+$ 830.5, m/z $[M-H]^-$ 828.5; UPLC-MS 1

Step 2: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(pentafluorosulfanyl)phenyl)acetamide 2-(6-(4-(5-(Benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-methyl-4-(pentafluorosulfanyl)phenyl)acetamide (641 mg, 649 μmol) was dissolved in DCM (15 mL) and TFA (1.00 mL, 13.0 mmol) was added. The RM was stirred at 45° C. for 1 day. No product was observed. TFA (2.00 mL, 26.0 mmol) was added, followed by DCM (2 mL) and the RM was stirred at 50° C. for 8 hours. Then it was allowed to cool to RT and stirred at RT for 4.5 days. Then TFA (1.00 mL, 13.0 mmol) was added and it was stirred at 65° C. for 1 day. The RM was concentrated under reduced pressure. The crude product was purified in 2 portions by reverse phase preparative HPLC (RP-HPLC acidic 1: 5 to 95% B in 20 min with a plateau at 95% for 1 min and RP-HPLC acidic 1: 5 to 95% B in 20 min with a plateau at 95% for 1 min). The product containing fractions were basified with aq sat $NaHCO_3$, extracted twice with DCM, dried through a phase separator and concentrated under reduced pressure. The residue was suspended in MeOH/ACN (1:1) and sonicated for 1 minute. Then it was filtered and dried under HV to give a solid. The solid was dissolved in DCM (5 mL) and EtOH (2 mL) and filtered. The filtrate crystallized over the weekend. The crystals were filtered, washed with $Et_2O$ and dried to give the title compound.

LC-MS: Rt=1.07 min; MS m/z $[M+H]^+$ 740.3, m/z $[M-H]^-$ 738.3; UPLC-MS 1

$^1$H NMR (400 MHz, DMSO-$d_6$) δ 10.22 (s, 1H), 10.03 (s, 1H), 8.58 (s, 1H), 7.75 (m, 3H), 6.82 (m, 1H), 5.25 (s, 2H), 4.52 (m, 1H), 4.26 (m, 2H), 3.81 (m, 2H), 3.49 (m, 3H), 3.26 (m, 1H), 2.99 (m, 3H), 2.81 (m, 1H), 2.64 (m, 1H), 2.51 (m, 2H), 2.44 (s, 3H), 2.37 (s, 3H), 1.19 (t, J=7.1 Hz, 3H)

Example 101: N-(2,4-dichlorophenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)acetamide

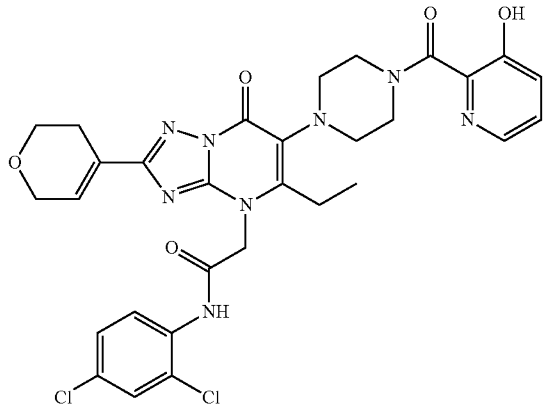 [SMILES: CCc1c(N2CCN(C(=O)c3ncccc3O)CC2)c(=O)n2nc(C3=CCOCC3)nc2n1CC(=O)Nc1ccc(Cl)cc1Cl]

To a brown solution of N-(2,4-dichlorophenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BS) (258 mg, 436 μmol) in DCM (3 mL) under argon at 0° C. was added 3-hydroxypicolinoyl chloride (Intermediate CV) (103 mg, 654 μmol). DIPEA (381 μL, 2.18 mmol) was added dropwise. The resulting brown RM was stirred at 0° C. for 5 hours. 3-Hydroxypicolinoyl chloride (Intermediate CV) (103 mg, 654 μmol) was added to the RM at 0° C., which was then stirred for 90.5 hours, allowing the temperature to slowly come back to RT. The RM was diluted with DCM and washed once with water. The aqueous layer was extracted once with DCM. The combined organic layers were dried through a phase separator, concentrated and dried under vacuum. The crude product was purified by column chromatography (RediSep Column: Silica 12 g, eluent DCM:DCM/MeOH (9/1) 100:0 to 60:40). The product containing fractions were combined, concentrated and dried under vacuum to give a beige solid. MeOH was added to the solid and sonicated. The resulting beige milky suspension was filtered. The cake was washed with MeOH and dried under vacuum to give the title compound as a white solid.

LC-MS: Rt=0.95 min; MS m/z $[M+H]^+$ 653.3/655.3/657.3, m/z $[M-H]^-$ 651.5/653.5/655.5; UPLC-MS 6

$^1$H NMR (600 MHz, DMSO-$d_6$) δ 10.52 (s, br, 1H), 10.21 (s, br, 1H), 8.05 (m, 1H), 7.71 (m, 2H), 7.41 (dd, J=2.4 Hz, 8.9 Hz, 1H), 7.27 (m, 2H), 6.83 (m, 1H), 5.24 (s, 2H), 4.53 (m, 1H), 4.26 (m, 2H), 3.80 (m, 2H), 3.45 (m, 3H), 3.22 (m, 1H), 2.96 (m, 3H), 2.79 (m, 1H), 2.60 (m, 1H), 2.50 (m, 2H), 1.18 (t, J=7.4 Hz, 3H)

Example 102: N-(5-chloro-2-methyl-6-(trifluoromethyl)pyridin-3-yl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)acetamide

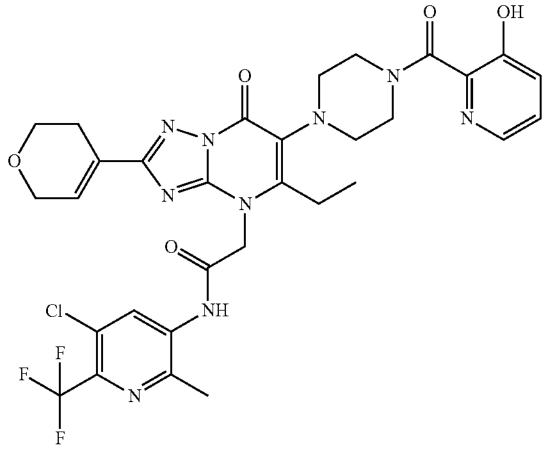 [SMILES: CCc1c(N2CCN(C(=O)c3ncccc3O)CC2)c(=O)n2nc(C3=CCOCC3)nc2n1CC(=O)Nc1cc(Cl)c(C(F)(F)F)nc1C]

3-Hydroxypicolinic acid (69.3 mg, 488 μmol) was dissolved in DCM (2.5 mL) at RT under argon. 1-chloro-N,N,2-trimethylprop-1-en-1-amine (71.7 mg, 537 μmol) was added and the RM was stirred at RT for 1.25 hours. A solution of N-(5-chloro-2-methyl-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BT) (175 mg, 244 μmol) in DCM (1.5 mL) and DIPEA (128 μL, 732 μmol) was added. The brown solution was stirred at RT for 1.75 hours. The RM was quenched with water (4 mL) and aq sat $NaHCO_3$ (4 mL). Then it was extracted 4 times with DCM (4×40 mL). The organic layer was washed with water (10 mL), dried through a phase separator and concentrated under reduced pressure. The crude product was purified by reverse phase preparative HPLC (RP-HPLC acidic 1: 15 to 85% in 20 min with a plateau at 85% for 1 min). The product containing fractions were combined and filtered through a PL-$HCO_3$ MP SPE cartridge (500 mg per 6 mL). The filtrate was lyophilized. Repurified by reverse phase preparative HPLC (RP-HPLC acidic 1: 20 to 80% in 20 min with a plateau at 80% for 1 min). The product containing fractions were combined and filtered through a PL-$HCO_3$ MP SPE cartridge (500 mg per 6 mL). The filtrate was lyophilized to give the title compound as a colourless solid.

LC-MS: Rt=0.99 min; MS m/z $[M+H]^+$ 702.4/704.4, m/z $[M-H]^-$ 700.4/702.4; UPLC-MS 3

$^{1}$H NMR (600 MHz, DMSO-$d_6$) δ 10.40 (s, br, 2H), 8.50 (s, 1H), 8.06 (m, 1H), 7.29 (m, 2H), 6.82 (m, 1H), 5.15 (s, br, 2H), 4.55 (m, 1H), 4.25 (m, 2H), 3.81 (m, 2H), 3.49 (m, 2H), 3.42 (m, 1H), 3.22 (m, 1H), 2.96 (m, 3H), 2.80 (m, 1H), 2.61 (m, 1H), 2.53 (m, 5H), 1.18 (t, J=7.6 Hz, 3H)

Example 103: N-(4-chloro-2-methyl-5-(trifluoromethyl)phenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl) acetamide

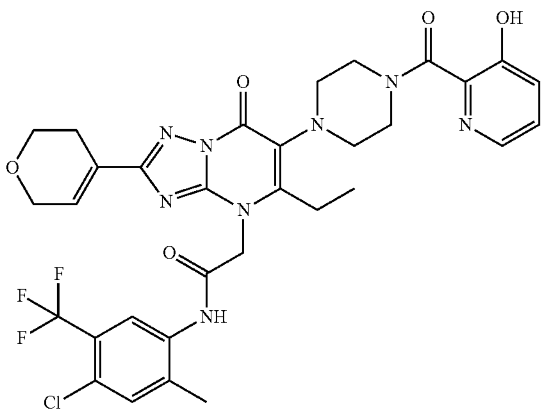 [SMILES: CCc1c(N2CCN(C(=O)c3ncccc3O)CC2)c(=O)n2nc(C3=CCOCC3)nc2n1CC(=O)Nc1cc(C(F)(F)F)c(Cl)cc1C]

N-(4-chloro-2-methyl-5-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BU) (214 mg, 280 μmol) was dissolved in DCM (2.8 mL) at RT under argon. 3-Hydroxypicolinoyl chloride (Intermediate CV) (66.3 mg, 421 μmol) was added, followed by DIPEA (147 μL, 841 μmol) and the RM was stirred at RT for 21 hours. 3-Hydroxypicolinoyl chloride (Intermediate CV) (40.0 mg, 254 μmol) and DIPEA (90.0 μL, 515 μmol) were added again and the RM was stirred at RT for 3 hours. The RM was quenched with water (4.00 mL) and aq sat $NaHCO_3$ (4 mL), then it was extracted with DCM (4×25 mL). The organic layer was washed with water (10 mL), dried through a phase separator, concentrated and dried under reduced pressure. The crude product was purified by reverse phase preparative HPLC (RP-HPLC acidic 1: 10 to 90% B in 20 min with a plateau at 90% for 1 min). The product containing fractions were combined, basified with aq sat $NaHCO_3$ and the ACN was removed under reduced pressure. The aqueous layer was washed three times with DCM. The organic layer was dried through a phase separator, concentrated and dried under reduced pressure to give a beige solid. The beige solid was dissolved in MeOH (1.5 mL) and DCM (2 mL) and filtered. The filtrate crystallized on standing at RT to give the title compound as a beige solid.

LC-MS: Rt=1.05 min; MS m/z $[M+H]^+$ 701.5/703.5, m/z $[M-H]^-$ 699.3/701.4; UPLC-MS 1

$^{1}$H NMR (600 MHz, DMSO-$d_6$) δ 10.38 (s, 1H), 10.07 (s, 1H), 8.06 (m, 1H), 7.96 (s, 1H), 7.66 (s, 1H), 7.28 (m, 2H), 6.82 (m, 1H), 5.22 (s, 2H), 4.54 (m, 1H), 4.25 (m, 2H), 3.81 (m, 2H), 3.46 (m, 3H), 3.22 (m, 1H), 2.98 (m, 3H), 2.80 (m, 1H), 2.63 (m, 1H), 2.50 (m, 2H), 2.34 (s, 3H), 1.19 (t, J=7.4 Hz, 3H)

Example 104: N-(5-chloro-4-ethyl-2-methylphenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl)acetamide

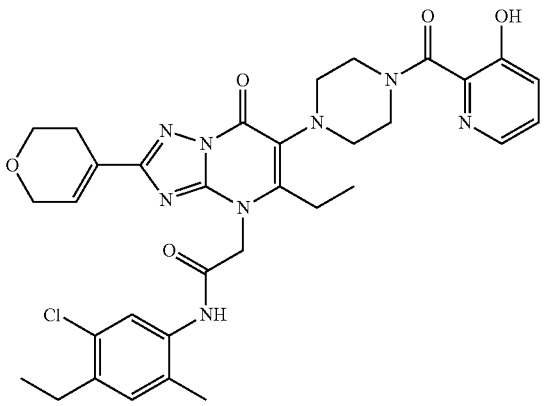 [SMILES: CCc1cc(C)c(NC(=O)Cn2c(CC)c(N3CCN(C(=O)c4ncccc4O)CC3)c(=O)n3nc(C4=CCOCC4)nc23)cc1Cl]

N-(5-chloro-4-ethyl-2-methylphenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BV) (383 mg, 702 μmol) was dissolved in DCM (5 mL). Then 3-hydroxypicolinoyl chloride (Intermediate CV) (221 mg, 1.40 mmol) was added, followed by DIPEA (490 μL, 2.81 mmol). The RM was stirred at RT for 1 hour. 3-hydroxypicolinoyl chloride (Intermediate CV) (1.50 g, 9.52 mmol) was added, followed by DIPEA (2.45 mL, 14.0 mmol). The RM was stirred at RT for 2 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 40 g, eluent DCM:DCM/MeOH (9/1) 100:0 to 50:50). The product containing fractions were combined, concentrated under vacuum and dried under HV. The residue was purified by reverse phase preparative HPLC (RP-HPLC acidic 1: 5 to 100% in 20 min). The product containing fractions were combined, basified with aq sat $NaHCO_3$, extracted twice with DCM, dried through a phase separator and concentrated under reduced pressure to give a white solid. The solid was crystallized from DMF (1 mL) to give the title compound as a colourless solid.

LC-MS: Rt=1.05 min; MS m/z $[M+H]^+$ 661.4/663.4, m/z $[M-H]^-$ 659.7/661.7; UPLC-MS 6

$^{1}$H NMR (400 MHz, DMSO-$d_6$) δ 10.39 (s, 1H), 9.84 (s, 1H), 8.07 (m, 1H), 7.48 (s, 1H), 7.29 (m, 2H), 7.21 (s, 1H), 6.84 (m, 1H), 5.18 (s, 2H), 4.55 (m, 1H), 4.27 (m, 2H), 3.82 (m, 2H), 3.45 (m, 3H), 3.23 (m, 1H), 2.99 (m, 3H), 2.80 (m, 1H), 2.62 (m, 3H), 2.55 (m, 2H), 2.22 (s, 3H), 1.19 (d, J=7.2 Hz, 3H), 1.14 (t, J=7.4 Hz, 3H)

Example 105: N-(4-chloro-2-methylphenyl)-2-(2-(3,6-dihydro-2H-pyran-4-yl)-6-(4-(3-hydroxypicolinoyl)piperazin-1-yl)-5-methyl-7-oxo-[1,2,4]triazolo[1,5-a]pyrimidin-4 (7H)-yl)acetamide

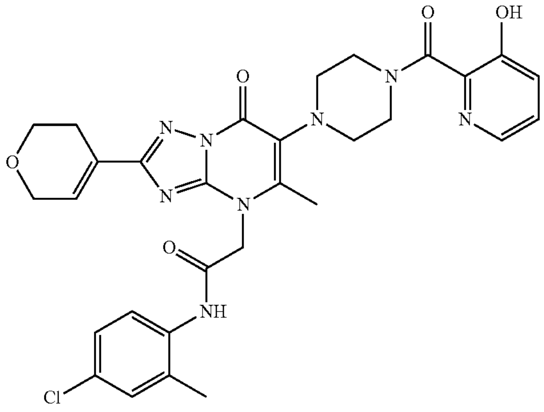 [SMILES: Cc1cc(Cl)ccc1NC(=O)Cn1c(C)c(N2CCN(C(=O)c3ncccc3O)CC2)c(=O)n2nc(C3=CCOCC3)nc12]

3-Hydroxypicolinic acid (205 mg, 1.47 mmol) was dissolved in DCM (10 mL) and 1-chloro-N,N,-trimethylprop-1-en-1-amine (260 μL, 1.97 mmol) was added. The mixture was stirred at RT for 1.5 hours. Then N-(4-chloro-2-methylphenyl)-2-(2-(3,6-dihydro-2H-pyran-4-yl)-5-methyl-7-oxo-6-(piperazin-1-yl)-[1,2,4]triazolo[1,5-a]pyrimidin-4 (7H)-yl)acetamide (Intermediate BW) (550 mg, 983 μmol) and DIPEA (687 μL, 3.93 mmol) were added and the mixture was stirred at RT for 20 hours. Water, aq sat $NaHCO_3$ and DCM were added.

The aqueous layer was washed twice with DCM. The combined organic layers were dried through a phase separator and concentrated under reduced pressure. The crude product was purified in 2 portions by reverse phase preparative HPLC (RP-HPLC acidic 1: 10 to 90% in 25 min and RP-HPLC acidic 1: 10 to 75% in 22 min). The product containing fractions were combined, basified with aq sat $NaHCO_3$, extracted twice with DCM, dried through a phase separator and concentrated under reduced pressure to give the title compound.

LC-MS: Rt=0.91 min; MS m/z $[M+H]^+$ 619.3/621.3, m/z $[M-H]^-$ 617.3/619.3; UPLC-MS 4

$^1H$ NMR (400 MHz, DMSO-$d_6$) δ 10.39 (s, 1H), 9.88 (s, 1H), 8.06 (m, 1H), 7.43 (d, J=8.5 Hz, 1H), 7.33 (d, J=2.3 Hz, 1H), 7.29 (m, 2H), 7.23 (dd, J=2.4 Hz, 8.7 Hz, 1H), 6.84 (m, 1H), 5.20 (s, 2H), 4.53 (m, 1H), 4.27 (m, 2H), 3.81 (m, 2H), 3.43 (m, 3H), 3.23 (m, 1H), 2.98 (m, 1H), 2.77 (m, 1H), 2.60 (m, 1H), 2.59 (s, 3H), 2.51 (m, 2H), 2.23 (s, 3H)

Example 106: N-(4-bromo-2-chlorophenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl) acetamide

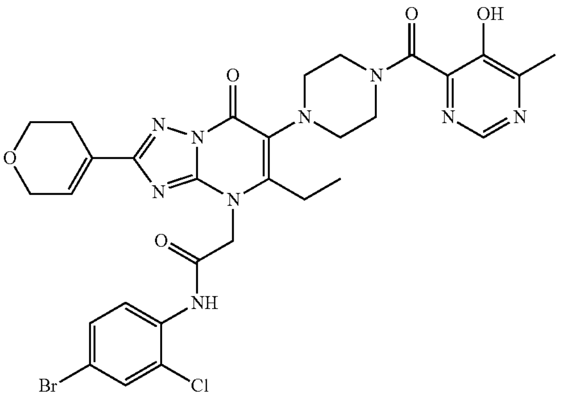 [SMILES: CCc1c(N2CCN(C(=O)c3ncnc(C)c3O)CC2)c(=O)n2nc(C3=CCOCC3)nc2n1CC(=O)Nc1ccc(Br)cc1Cl]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(4-bromo-2-chlorophenyl) acetamide N-(4-bromo-2-chlorophenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BX) (280 mg, 388 μmol) and 5-(benzyloxy)-6-methylpyrimidine-4-carboxylic acid (Intermediate CY) (95.0 mg, 388 μmol) were mixed in DMF (2.1 mL) at RT under argon. HATU (177 mg, 466 μmol) was added, followed by DIPEA (339 μL, 1.94 mmol) and the RM was stirred at RT for 1.75 hours. The RM was quenched with water (10 mL) and EtOAc (40 mL). Then it was extracted with EtOAc (3×50 mL), water (3×10 mL) and brine (2×10 mL). The organic layer was dried over $Na_2SO_4$, filtered and concentrated under reduced pressure. The crude product was mixed with EtOH, stirred at 40° C. and sonicated for 1 hour. The suspension was filtered, washed with a small amount of EtOH and dried under HV to give the title compound as a white solid LC-MS: Rt=1.14 min; MS m/z $[M+H]^+$ 802.3/804.3/806.3, m/z $[M-H]^-$ 800.3/802.3/804.3; UPLC-MS 1

Step 2: N-(4-bromo-2-chlorophenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide 2-(6-(4-(5-(Benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(4-bromo-2-chlorophenyl)acetamide (255 mg, 318 μmol) was dissolved in TFA (1.76 mL, 22.9 mmol) and the RM was stirred at 50° C. for 4.5 hours, then at RT overnight. The RM was concentrated under reduced pressure. The resulting foam was extracted with DCM (4×50 mL), aq sat $NaHCO_3$ (15 mL) and brine (15 mL). The organic layer was dried through a phase separator and concentrated under reduced pressure. The crude product was suspended in EtOH (4 mL)

and stirred at 45° C. for 6 hours, then it was sonicated. DCM was added until full dissolution and then DCM was carefully removed under reduced pressure. Concentration of the EtOH solution at 45° C. under reduced pressure was continued until a cloudiness was observed, then it was stirred at RT for 4 hours. The resulting suspension was filtered and dried to give the title compound as a beige solid.

LC-MS: Rt=0.98 min; MS m/z $[M+H]^+$ 712.2/714.2/716.2, m/z $[M-H]^-$ 710.2/712.2/714.2; UPLC-MS 1

LC-MS: Rt=4.86 min; MS m/z $[M+H]^+$ 712.1/714.1/716.1, m/z $[M-H]^-$ 710.1/712.2/714.2; UPLC-MS 2

$^1$H NMR (400 MHz, DMSO-$d_6$) δ 10.22 (s, br, 1H), 10.17 (s, 1H), 8.57 (s, 1H), 7.81 (m, 1H), 7.67 (d, J=8.5 Hz, 1H), 7.54 (dd, J=2.1 Hz, 8.8 Hz, 1H), 6.83 (m, 1H), 5.24 (s, 2H), 4.52 (m, 1H), 4.26 (m, 2H), 3.80 (m, 2H), 3.48 (m, 3H), 3.26 (m, 1H), 2.97 (m, 3H), 2.81 (m, 1H), 2.64 (m, 1H), 2.50 (m, 2H), 2.44 (s, 3H), 1.18 (t, J=7.1 Hz, 3H)

Example 107: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-fluoro-4-(trifluoromethyl)phenyl)acetamide

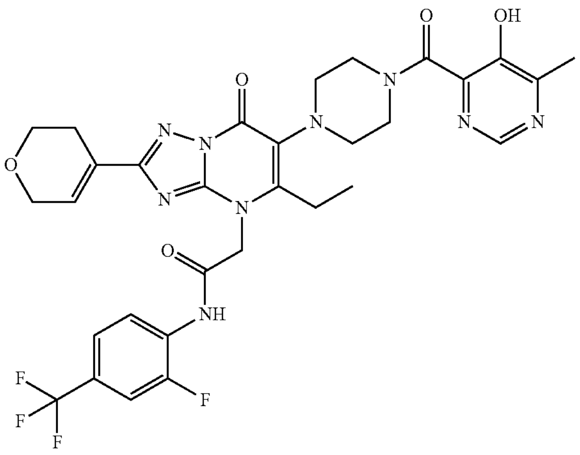 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1F]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-fluoro-4-(trifluoromethyl)phenyl)acetamide 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide (Intermediate BP) (268 mg, 439 μmol) and 5-(benzyloxy)-6-methylpyrimidine-4-carboxylic acid (Intermediate CY) (107 mg, 439 μmol) were mixed in DMF (2.4 mL) at RT under argon. HATU (200 mg, 527 μmol) was added, followed by DIPEA (383 μL, 2.20 mmol) and the RM was stirred at RT for 55 minutes. Water (10 mL) and EtOAc (40 mL) was added. Then it was extracted with EtOAc (3×40 mL), water (2×10 mL) and brine (2×10 mL). The organic layer was dried over $Na_2SO_4$ and concentrated under reduced pressure. The crude product was mixed with EtOH (4 mL) and stirred at 40° C. The beige suspension was filtered, washed with a small amount of cold EtOH and dried to give the title compound as a beige solid.

LC-MS: Rt=1.16 min; MS m/z $[M+H]^+$ 776.3, m/z $[M-H]^-$ 774.4; UPLC-MS 1

Step 2: 2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-fluoro-4-(trifluoromethyl)phenyl)acetamide 2-(6-(4-(5-(Benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-fluoro-4-(trifluoromethyl)phenyl)acetamide (199 mg, 257 μmol) was mixed with TFA (1.50 mL, 19.5 mmol) and the RM was stirred at 50° C. for 20 hours. The RM was concentrated under reduced pressure and dried under HV. The foam was extracted with DCM (4×40 mL), aq sat $NaHCO_3$ (10 mL) and brine (10 mL). The organic layer was dried through a phase separator and concentrated under reduced pressure. The crude product was suspended in EtOH (3 mL) and stirred at 60° C. for 16 hours. The suspension was filtered and dried under HV to give the title compound as a beige solid.

LC-MS: Rt=1.00 min; MS m/z $[M+H]^+$ 686.3, m/z $[M-H]^-$ 684.4; UPLC-MS 1

$^1$H NMR (400 MHz, DMSO-$d_6$) δ 10.67 (s, 1H), 10.22 (s, 1H), 8.58 (s, 1H), 8.22 (t, J=8.0 Hz, 1H), 7.79 (d, J=11.2 Hz, 1H), 7.56 (d, J=8.3 Hz, 1H), 6.80 (m, 1H), 5.30 (s, 2H), 4.52 (m, 1H), 4.24 (m, 2H), 3.79 (m, 2H), 3.50 (m, 3H), 3.25 (m, 1H), 2.97 (m, 3H), 2.82 (m, 1H), 2.64 (m, 1H), 2.50 (m, 2H), 2.44 (s, 3H), 1.18 (t, J=7.5 Hz, 3H)

Example 108: N-(2-bromo-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

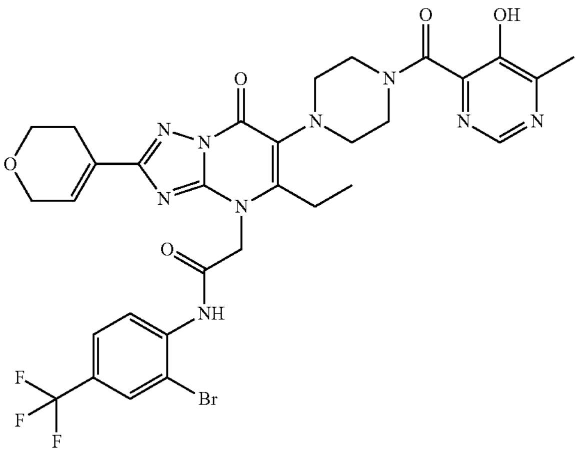 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Br]

Step 1: 2-(6-(4-(5-(benzyloxy)-6-methylpyrimidine-4-carbonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-bromo-4-(trifluoromethyl)phenyl)acetamide N-(2-bromo-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate BY) (280 mg, 358 μmol) and 5-(benzyloxy)-6-methylpyrimidine-4-carboxylic acid (Intermediate CY) (87.0 mg, 358 μmol) were mixed in DMF (2 mL) at RT under argon. HATU (163 mg, 429 μmol) was added, followed by DIPEA (312 μL, 1.79 mmol) and the RM was stirred at RT for 1.75 hours. Water (10 mL) and EtOAc (40 mL) were added. Then it was extracted with EtOAc (3×40 mL). The combined organic layers were washed with water (3×10 mL) and brine (2×10 mL), dried over $Na_2SO_4$ and concentrated under reduced pressure. The crude product was mixed with EtOH (4.00 mL) and stirred at 40° C. for 5 hours. The suspension was filtered, washed with a small amount of cold EtOH and dried under HV to give the title compound as a white solid.

LC-MS: Rt=1.19 min; MS m/z $[M+H]^+$ 836.4/838.5, m/z $[M-H]^-$ 834.1/836.0; UPLC-MS 1

Step 2: N-(2-bromo-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl) acetamide 2-(6-(4-(5-(Benzyloxy)-6-methylpyrimidine-4-carbonyl) piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-bromo-4-(trifluoromethyl)phenyl)acetamide (224 mg, 268 μmol) and TFA (1.50 mL, 19.5 mmol) were stirred at 50° C. for 17.5 hours. The RM was concentrated under reduced pressure and dried under HV. The foam was extracted with DCM (4×40 mL), aq sat $NaHCO_3$ (10 mL) and brine (10 mL). The organic layer was dried through a phase separator and concentrated under reduced pressure. The solid was suspended in EtOH (3 mL) and stirred at 45° C. for 6 hours. The suspension was filtered and dried under HV to give the title compound as a beige solid.

LC-MS: Rt=1.03 min; MS m/z $[M+H]^+$ 746.2/748.2, m/z $[M-H]^-$ 744.3/746.2; UPLC-MS 1

$^1H$ NMR (400 MHz, DMSO-$d_6$) δ 10.26 (s, 1H), 10.22 (s, 1H), 8.58 (s, 1H), 8.08 (s, 1H), 7.91 (d, J=8.3 Hz, 1H), 7.76 (d, J=8.3 Hz, 1H), 6.85 (m, 1H), 5.29 (s, 2H), 4.52 (m, 1H), 4.26 (m, 2H), 3.80 (m, 2H), 3.49 (m, 3H), 3.23 (m, 1H), 2.98 (m, 3H), 2.82 (m, 1H), 2.64 (m, 1H), 2.50 (m, 2H), 2.44 (s, 3H), 1.20 (t, J=7.6 Hz, 3H)

Example 109: 2-(5-ethyl-6-(4-(3-hydroxypicolinoyl) piperazin-1-yl)-7-oxo-2-(1,4,5,6-tetrahydropyridin-3-yl)-[1,2,4]triazolo[1,5-a]pyrimidin-4 (7H)-yl)-N-(2-methyl-4-(trifluoromethyl)phenyl)acetamide

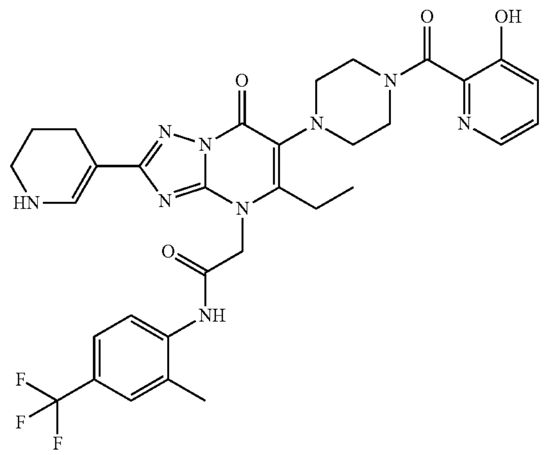 [SMILES: CCc1c(N2CCN(C(=O)c3ncccc3O)CC2)c(=O)n2nc(C3=CNCCC3)nc2n1CC(=O)Nc1ccc(C(F)(F)F)cc1C]

Step 1: Tert-butyl 5-(5-ethyl-6-(4-(3-hydroxypicolinoyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3,4-dihydropyridine-1 (2H)-carboxylate 2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (218 mg, 329 μmol), tert-butyl 6-(4,4,5,5-tetramethyl-1,3,2-dioxaborolan-2-yl)-3,4-dihydropyridine-1 (2H)-carboxylate (Intermediate DI) (152 mg, 493 μmol) and XPhos Pd G3 (13.9 mg, 16.0 μmol) were combined in a MW vial. 1,4-Dioxane (3 mL) and 1M aq $K_3PO_4$ (986 μL, 986 μmol) were added. The vial was capped, degassed and flushed with argon. The RM was stirred at 90° C. for 55 minutes. The RM was cooled to RT. The RM was diluted with DCM (8 mL) and water (2 mL). The biphasic mixture was stirred at RT for 1 minute then the organic layer was separated by filtering through a phase separator. Added SiliaMetS® Thiol and stirred at RT for 15 minutes. Filtered and the filtrate was concentrated under reduced pressure. The crude product was purified by reverse phase preparative HPLC (RP-HPLC acidic 1: 40 to 80% in 15 min with a plateau at 80% for 1 min). The product containing fractions were basified with 5% aq $NaHCO_3$ and extracted with DCM (2×10 mL). The organics were eluted through a phase separator and evaporated in vacuo to give the title compound as a pale yellow gum.

LC-MS: Rt=1.24 min; MS m/z $[M+H]^+$ 766.5, m/z $[M-H]^-$ 764.7; UPLC-MS 1

Step 2: 2-(5-ethyl-6-(4-(3-hydroxypicolinoyl)piperazin-1-yl)-7-oxo-2-(1,4,5,6-tetrahydropyridin-3-yl)-[1,2,4]triazolo[1,5-a]pyrimidin-4 (7H)-yl)-N-(2-methyl-4-(trifluoromethyl)phenyl)acetamide To tert-butyl 5-(5-ethyl-6-(4-(3-hydroxypicolinoyl)piperazin-1-yl)-4-(2-((2-methyl-4-(trifluoromethyl)phenyl) amino)-2-oxoethyl)-7-oxo-4,7-dihydro-[1,2,4]triazolo[1,5-a]pyrimidin-2-yl)-3,4-dihydropyridine-1 (2H)-carboxylate (60.0 mg, 78.0 μmol) in DCM (2 mL) was added 4N HCl in 1,4-dioxane (3 mL) and the suspension was briefly heated with a heat gun to reflux for a few seconds then allowed to stand for 15 minutes. The RM was concentrated under reduced pressure The crude product was purified by reverse phase preparative HPLC (RP-HPLC acidic 1: 20 to 55% B in 7 min with a plateau at 55% for 1 min). The product containing fraction was basified with 5% aq $NaHCO_3$ and extracted with DCM (20 mL). The organic layer was separated by filtration through a phase separator and evaporated in vacuo to give a yellow solid. It was recrystallized from EtOAc to give the title compound as a colourless solid.

LC-MS: Rt=0.96 min; MS m/z $[M+H]^+$ 666.5, m/z $[M-H]^-$ 664.4; UPLC-MS 1

$^1$H NMR (400 MHz, DMSO-$d_6$) δ 10.37 (s, 1H), 9.97 (s, 1H), 8.06 (m, 1H), 7.71 (d, J=8.1 Hz, 1H), 7.62 (m, 1H), 7.52 (dd, J=2.3 Hz, 8.5 Hz, 1H), 7.29 (m, 3H), 6.11 (m, 1H), 5.16 (s, 2H), 4.54 (m, 1H), 3.45 (m, 3H), 3.20 (m, 1H), 3.13 (m, 2H), 2.94 (m, 3H), 2.76 (m, 1H), 2.58 (m, 1H), 2.38 (m, 2H), 2.35 (s, 3H), 1.77 (m, 2H), 1.17 (t, J=7.1 Hz, 3H)

Example 110: 2-(5-ethyl-6-(4-(3-hydroxypicolinoyl) piperazin-1-yl)-7-oxo-2-(1,4,5,6-tetrahydropyridin-2-yl)-[1,2,4]triazolo[1,5-a]pyrimidin-4 (7H)-yl)-N-(2-methyl-4-(trifluoromethyl)phenyl)acetamide

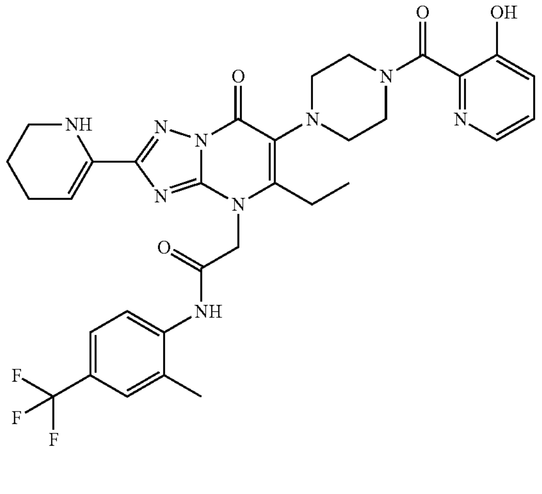 [SMILES: CCc1c(N2CCN(C(=O)c3ncccc3O)CC2)c(=O)n2nc(C3=CCCCN3)nc2n1CC(=O)Nc1ccc(C(F)(F)F)cc1C]

Step 1: Tert-butyl 6-(5-ethyl-6-(4-(3-hydroxypicolinoyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3,4-dihydropyridine-1 (2H)-carboxylate 2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (2.48 g, 3.74 mmol), tert-butyl 6-(4,4,5,5-tetramethyl-1,3,2-dioxaborolan-2-yl)-3,4-dihydropyridine-1 (2H)-carboxylate (Intermediate DI) (2.54 g, 8.22 mmol) and XPhos Pd G3 (158 mg, 187 μmol) were mixed in a MW vial. 1,4-Dioxane (30 mL) and 1M aq $K_3PO_4$ (11.2 mL, 11.2 mmol) were added. The vial was capped, degassed and flushed with argon. Then it was stirred at 90° C. for 3 days. The reaction was allowed to cool to RT. The RM was diluted with DCM (40 mL) and water (10 mL). The organic layer was separated by filtering through a phase separator. SiliaMetS® Thiol was added, the suspension was stirred at 35° C. for 30 minutes, filtered and the filtrate was concentrated in vacuo. The crude product was purified by column chromatography (RediSep Column: Silica 40 g, eluent DCM:MeOH 100:0 to 95:5) to give the title compound as a pale brown gum.

LC-MS: Rt=1.14 min; MS m/z $[M+H]^+$ 766.5, m/z $[M-H]^-$ 764.6; UPLC-MS 1

Step 2: 2-(5-ethyl-6-(4-(3-hydroxypicolinoyl)piperazin-1-yl)-7-oxo-2-(1,4,5,6-tetrahydropyridin-2-yl)-[1,2,4]triazolo[1,5-a]pyrimidin-4 (7H)-yl)-N-(2-methyl-4-(trifluoromethyl)phenyl)acetamide Tert-butyl 6-(5-ethyl-6-(4-(3-hydroxypicolinoyl)piperazin-1-yl)-4-(2-((2-methyl-4-(trifluoromethyl)phenyl) amino)-2-oxoethyl)-7-oxo-4,7-dihydro-[1,2,4]triazolo[1,5-a]pyrimidin-2-yl)-3,4-dihydropyridine-1 (2H)-carboxylate (1.20 g, 32% pure) was dissolved in DCM (5 mL) and 4M HCl in 1,4-dioxane (5 mL) was added. Immediately, an insoluble brown gum precipitated. Heated briefly to reflux with a heat gun then allowed to cool for 10 minutes. The RM was concentrated in vacuo and the brown residue was partitioned between DCM (70 mL) and 1M aq HCl (100 mL). The biphasic mixture was stirred vigorously for 10 minutes. The aqueous layer was separated, the pH adjusted to pH 5 by addition of solid KOH and extracted with DCM (2×50 mL). The combined DCM layers were eluted through a phase separator and concentrated in vacuo to give a pale brown foam. The crude product was purified by column chromatography (RediSep Column: Silica 12 g, eluent DCM:MeOH 100:0 to 97:03). The crude product was further purified by reverse phase preparative HPLC (RP-HPLC acidic 1: 5 to 40% in 15 min with a plateau at 40% for 1 min, 25 mL/min). The product containing fractions were basified with aq sat $NaHCO_3$ and extracted with DCM/MeOH (9/1, 2×30 mL). The combined extracts were eluted through a phase separator and concentrated under reduced pressure to give a colourless solid. Recrystallized from MeOH/water to give the title compound as colourless crystals.

LC-MS: Rt=0.80 min; MS m/z $[M+H]^+$ 666.4, m/z $[M-H]^-$ 664.5; UPLC-MS 1

$^1$H NMR (400 MHz, DMSO-$d_6$) δ 10.38 (s, 1H), 9.99 (s, 1H), 8.07 (m, 1H), 7.76 (m, 1H), 7.63 (m, 1H), 7.53 (m, 1H), 7.29 (m, 2H), 5.45 (m, 1H), 5.26 (d, J=23.7 Hz, 2H), 4.83 (m, 1H), 4.56 (m, 1H), 3.75 (m, 1H), 3.46 (m, 3H), 3.18 (m, 2H), 2.98 (m, 3H), 2.81 (m, 1H), 2.65 (m, 1H), 2.37 (d, J=3.3 Hz, 3H), 2.18 (m, 1H), 1.75 (m, 2H), 1.61 (m, 1H), 1.20 (t, J=7.4 Hz, 3H)

Example 111: rac-2-(5-ethyl-2-(5-fluoro-1,4,5,6-tetrahydropyridin-2-yl)-6-(4-(3-hydroxypicolinoyl) piperazin-1-yl)-7-oxo-[1,2,4]triazolo[1,5-a]pyrimidin-4 (7H)-yl)-N-(2-methyl-4-(trifluoromethyl) phenyl)acetamide

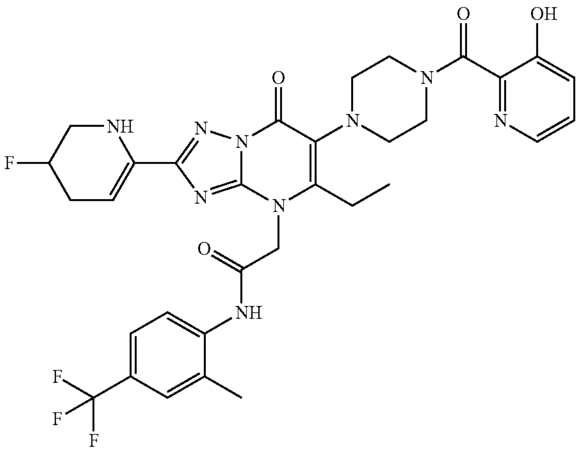 [SMILES: CCc1c(N2CCN(C(=O)c3ncccc3O)CC2)c(=O)n2nc(C3=CCC(F)CN3)nc2n1CC(=O)Nc1ccc(C(F)(F)F)cc1C]

Step 1: rac-tert-butyl 6-(5-ethyl-6-(4-(3-hydroxypicolinoyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3-fluoro-3,4-dihydropyridine-1 (2H)-carboxylate 2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (91.0 mg, 138 μmol) and XPhos Pd G3 (5.82 mg, 6.88 μmol) were combined in a MW vial, tert-butyl 3-fluoro-6-(4,4,5,5-tetramethyl-1,3,2-dioxaborolan-2-yl)-3,4-dihydropyridine-1 (2H)-carboxylate (Intermediate DJ) (45.0 mg, 138 μmol) in 1,4-dioxane (1 mL) and 1M aq $K_3PO_4$ (413 μL, 413 μmol) were added. The vial was capped, degassed, flushed with argon and stirred at 90° C. for 3 hours. The RM was allowed to cool to RT then diluted with DCM (8 mL) and water (2 mL). The biphasic mixture was stirred at RT for 1 minute then the organic layer was separated by filtering through a phase separator. SiliaMetS® Thiol was added and the mixture was stirred at RT for 20 minutes. The suspension was filtered and the filtrate was concentrated in vacuo. The crude product was purified by reverse phase preparative HPLC (RP-HPLC acidic 1: 25 to 60% B in 20 min with a plateau at 60% for 1 min). The product containing fractions were basified with 5% aq $NaHCO_3$ and extracted with DCM (2×10 mL). The organics were eluted through a phase separator and evaporated in vacuo to give the title compound as a colourless gum.

LC-MS: Rt=1.10 min; MS m/z $[M+H]^+$ 784.5, m/z $[M-H]^-$ 782.6; UPLC-MS 1

Step 2: rac-2-(5-ethyl-2-(5-fluoro-1,4,5,6-tetrahydropyridin-2-yl)-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl) acetamide To rac-tert-butyl 6-(5-ethyl-6-(4-(3-hydroxypicolinoyl) piperazin-1-yl)-4-(2-((2-methyl-4-(trifluoromethyl)phenyl) amino)-2-oxoethyl)-7-oxo-4,7-dihydro-[1,2,4]triazolo[1,5-a]pyrimidin-2-yl)-3-fluoro-3,4-dihydropyridine-1 (2H)-carboxylate in DCM (300 μL) was added TFA (200 μL) and the solution was briefly heated with a heat gun, then allowed to stand for 20 minutes. The RM was evaporated in vacuo, resuspended in 5% aq $NaHCO_3$ (5 mL) and extracted with DCM (2×5 mL). The organic layer was separated by filtration through a phase separator and evaporated in vacuo to give the title compound as a pale yellow solid.

LC-MS: Rt=0.94 min; MS m/z $[M+H]^+$ 684.5, m/z $[M-H]^-$ 682.5; UPLC-MS 1

Example 112: 2-(5-ethyl-6-(4-(3-hydroxypicolinoyl) piperazin-1-yl)-7-oxo-2-(1,2,3,6-tetrahydropyridin-4-yl)-[1,2,4]triazolo[1,5-a]pyrimidin-4 (7H)-yl)-N-(2-methyl-4-(trifluoromethyl)phenyl)acetamide

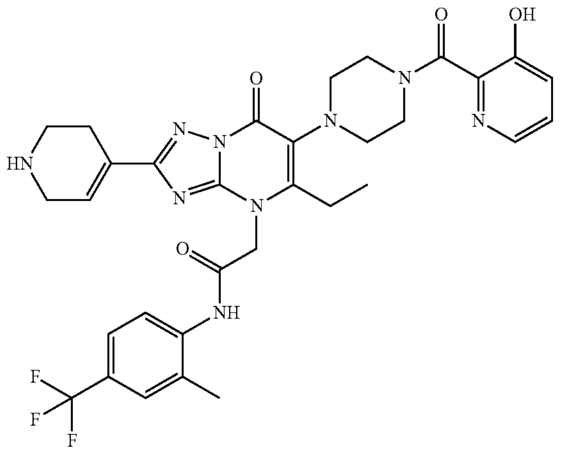 [SMILES: CCc1c(N2CCN(C(=O)c3ncccc3O)CC2)c(=O)n2nc(C3=CCNCC3)nc2n1CC(=O)Nc1ccc(C(F)(F)F)cc1C]

Step 1: tert-butyl 4-(5-ethyl-6-(4-(3-hydroxypicolinoyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3,6-dihydropyridine-1 (2H)-carboxylate 2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (1.42 g, 2.14 mmol), tert-butyl 4-(4,4,5,5-tetramethyl-1,3,2-dioxaborolan-2-yl)-3,6-dihydropyridine-1 (2H)-carboxylate (827 mg, 2.68 mmol) and XPhos Pd G3 (91.0 mg, 107 μmol) were mixed in a MW vial and the RM was purged with vacuum and argon several times. DMF (15 mL) and 1M aq $K_3PO_4$ (2.14 mL, 2.14 mmol) were added and the RM was stirred at 80° C. for 2.5 hours. The RM was diluted with DCM and 50% aq brine. Then it was washed three times with brine and dried through a phase separator. The residue was adsorbed onto Isolute and purified by column chromatography (RediSep Column: Silica 80 g, eluent EtOAc:MeOH 100:0 to 75:25). The product containing fractions were combined, concentrated and dried at HV to give the title compound.

LC-MS: Rt=1.23 min; MS m/z $[M+H]^+$ 766.5, m/z $[M-H]^-$ 764.3; UPLC-MS 1

Step 2: 2-(5-ethyl-6-(4-(3-hydroxypicolinoyl)piperazin-1-yl)-7-oxo-2-(1,2,3,6-tetrahydropyridin-4-yl)-[1,2,4]triazolo[1,5-a]pyrimidin-4 (7H)-yl)-N-(2-methyl-4-(trifluoromethyl)phenyl)acetamide Tert-butyl 4-(5-ethyl-6-(4-(3-hydroxypicolinoyl)piperazin-1-yl)-4-(2-((2-methyl-4-(trifluoromethyl)phenyl) amino)-2-oxoethyl)-7-oxo-4,7-dihydro-[1,2,4]triazolo[1,5-a]pyrimidin-2-yl)-3,6-dihydropyridine-1 (2H)-carboxylate (1.52 g, 1.79 mmol) was dissolved in DCM (20 mL) and TFA (2.75 mL, 35.7 mmol) was added. The RM was stirred at RT for 2 hours. Aq $NaHCO_3$ was added and the pH was adjusted to pH 10. Then it was extracted 5 times with DCM, dried through a phase separator and concentrated under reduced pressure to give the title compound.

LC-MS: Rt=0.71 min; MS m/z $[M+H]^+$ 666.6, m/z $[M-H]^-$ 664.3; UPLC-MS 1

$^1$H NMR (400 MHz, DMSO-$d_6$) δ 10.01 (s, 1H), 8.05 (m, 1H), 7.71 (d, J=8.5 Hz, 1H), 7.62 (m, 1H), 7.53 (dd, J=2.2 Hz, 8.6 Hz, 1H), 7.28 (m, 2H), 6.83 (m, 1H), 5.24 (s, 2H), 4.55 (m, 1H), 3.47 (m, 3H), 3.39 (m, 1H), 3.22 (m, 2H), 2.98 (m, 3H), 2.91 (m, 2H), 2.79 (m, 1H), 2.61 (m, 1H), 2.42 (m, 2H), 2.35 (s, 3H), 1.19 (t, J=7.4 Hz, 3H)

Example 113: 2-(2-(5,6-dihydro-1,4-dioxin-2-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

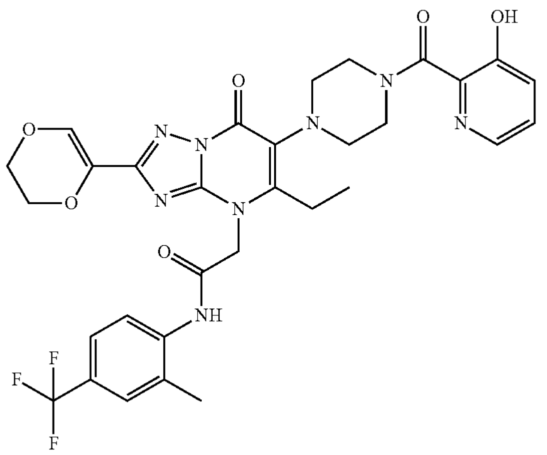

2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (200 mg, 301 μmol), 2-(5,6-dihydro-1,4-dioxin-2-yl)-4,4,5,5-tetramethyl-1,3,2-dioxaborolane (77.0 mg, 362 μmol), XPhos Pd G3 (12.8 mg, 15.0 μmol) and 1M aq $K_3PO_4$ (904 μL, 904 μmol) were mixed in 1,4-dioxane (5 mL). The RM was stirred at 80° C. for 30 minutes. Water (10 mL), aq sat $NaHCO_3$ (10 mL) and DCM (10 mL) were added. The aqueous layer was extracted with DCM (2×10 mL) then with EtOAc (4×10 mL). The combined organic layers were eluted through a phase separator and concentrated under reduced pressure. The crude product was dissolved in DCM and EtOAc and SiliaMetS® Thiol was added. The mixture was stirred at 40° C. for 1 hour filtered, and the cake was washed with DCM. The filtrate was concentrated under reduced pressure. The crude product was purified twice by reverse phase preparative HPLC (RP-HPLC acidic 1: 10 to 90% B in 20 min with a plateau at 90% for 1 min and RP-HPLC acidic 1: 40 to 70% B in 10 min with a plateau at 70% for 1 min). The product containing fractions were combined, basified with aq sat $NaHCO_3$, extracted twice with DCM, dried through a phase separator and concentrated under reduced pressure to give the title compound as a white solid. The solid was redissolved in DMF and concentrated under reduced pressure to give an oily residue which was redissolved in MeOH (1 mL) and left to stand at RT for 2 days. The resulting precipitate was filtered, washed twice with $Et_2O$ and dried under HV to give the title compound as a colourless solid.

LC-MS: Rt=0.95 min; MS m/z $[M+H]^+$ 669.5, m/z $[M-H]^-$ 667.5; UPLC-MS 1

$^1$H NMR (600 MHz, DMSO-$d_6$) δ 10.38 (s, 1H), 9.98 (s, 1H), 8.06 (m, 1H), 7.72 (d, J=8.3 Hz, 1H), 7.63 (m, 1H), 7.53 (dd, J=2.4 Hz, 8.6 Hz, 1H), 7.28 (m, 2H), 7.09 (s, 1H), 5.21 (s, 2H), 4.54 (m, 1H), 4.19 (m, 4H), 3.47 (m, 2H), 3.40 (m, 1H), 3.21 (m, 1H), 2.96 (m, 3H), 2.79 (m, 1H), 2.61 (m, 1H), 2.35 (s, 3H), 1.18 (t, J=7.3 Hz, 3H)

Example 114: 2-(2-(5,6-dihydro-2H-pyran-3-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

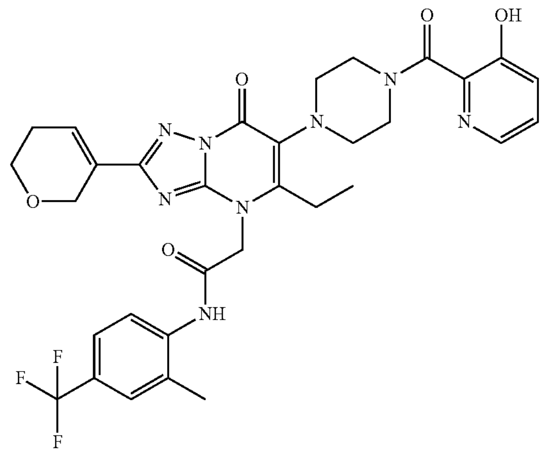 [SMILES: CCc1c(N2CCN(C(=O)c3ncccc3O)CC2)c(=O)n2nc(C3=CCCOC3)nc2n1CC(=O)Nc1ccc(C(F)(F)F)cc1C]

2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (168 mg, 254 μmol), XPhos Pd G3 (10.7 mg, 13.0 μmol), 2-(5,6-dihydro-2H-pyran-3-yl)-4,4,5,5-tetramethyl-1,3,2-dioxaborolane (64.0 mg, 305 μmol) were suspended in 1,4-dioxane (5 mL) and 1M aq $K_3PO_4$ (761 μL, 761 μmol) was added. The suspension was stirred at 80° C. for 2 days. Water (10 mL), aq sat $NaHCO_3$ (10 mL) and DCM (10 mL) were added. The aqueous layer was extracted with DCM (2×10 mL) and EtOAc (2×10 mL). The combined organic layers were eluted through a phase separator and concentrated under reduced pressure. The crude product was dissolved in DCM and EtOAc and SiliaMetS® Thiol was added. The mixture was stirred at 40° C. for 1 hour, filtered, and the cake was washed with DCM. The filtrate was concentrated under reduced pressure. The crude product was purified by column chromatography (RediSep Column: Silica 24 g, eluent DCM:DCM/MeOH (9/1) 100:0 to 60:40). The product containing fractions were combined, concentrated under vacuum and dried under HV. The residue was purified twice by reverse phase preparative HPLC (RP-HPLC acidic 1: 30 to 70% B in 20 min with a plateau at 70% for 1 min and RP-HPLC acidic 1: 40 to 60% B in 20 min with a plateau at 60% for 1 min). The product containing fractions were combined, basified with aq sat $NaHCO_3$, extracted twice with DCM, dried through a phase separator and concentrated under reduced pressure to give the title compound as a solid. The solid was dissolved in DCM/MeOH and left to stand at RT for 1 day. The resulting precipitate was dried under HV to give the title compound as a solid.

LC-MS: Rt=0.99 min; MS m/z $[M+H]^+$ 667.4, m/z $[M-H]^-$ 665.5; UPLC-MS 1

$^1$H NMR (400 MHz, DMSO-$d_6$) δ 10.37 (s, 1H), 10.00 (s, 1H), 8.06 (m, 1H), 7.72 (d, J=8.4 Hz, 1H), 7.63 (m, 1H), 7.53 (dd, J=2.1 Hz, 8.5 Hz, 1H), 7.28 (m, 2H), 6.91 (m, 1H), 5.24 (s, 2H), 4.54 (m, 1H), 4.45 (m, 2H), 3.76 (m, 2H), 3.45 (m, 3H), 3.22 (m, 1H), 2.97 (m, 3H), 2.79 (m, 1H), 2.61 (m, 1H), 2.36 (s, 3H), 2.33 (m, 2H), 1.19 (t, J=7.1 Hz, 3H)

Example 115: 2-(2-(1-(2,2-difluoroethyl)-1,2,3,6-tetrahydropyridin-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

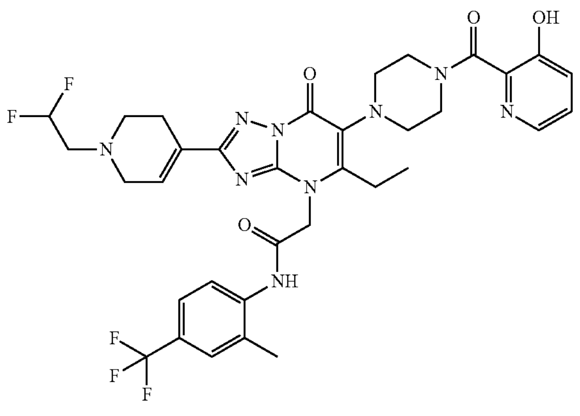 [SMILES: CCc1c(N2CCN(C(=O)c3ncccc3O)CC2)c(=O)n2nc(C3=CCN(CC(F)F)CC3)nc2n1CC(=O)Nc1ccc(C(F)(F)F)cc1C]

Step 1: tert-butyl 4-(5-ethyl-6-(4-(3-hydroxypicolinoyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3,6-dihydropyridine-1 (2H)-carboxylate 2-(2-Bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate BZ) (3.60 g, 4.88 mmol), tert-butyl 4-(4,4,5,5-tetramethyl-1,3,2-dioxaborolan-2-yl)-3,6-dihydropyridine-1 (2H)-carboxylate (1.89 g, 6.10 mmol) and XPhos Pd G3 (207 mg, 244 μmol) were mixed and purged with argon several times. DMF (40 mL) was added, followed by $K_3PO_4$ 1M in water (4.88 mL, 4.88 mmol). The RM was stirred at 80° C. for 4.5 hours. XPhos Pd G3 (207 mg, 244 μmol) was added again and the RM was stirred at 80° C. for 1.5 hours. $K_3PO_4$ 1M in water (14.7 mL, 14.7 mmol) was added and the RM was stirred at 80° C. overnight. The RM was diluted with DCM and 50% brine. Then it was washed three times with brine and dried through a phase separator. The residue was adsorbed onto Isolute and purified by column chromatography (RediSep Column: Silica 220 g, eluent EtOAc:MeOH 100:0 to 95:5) to give the title compound as a solid.

LC-MS: Rt=1.19 min; MS m/z $[M+H]^+$ 766.5, m/z $[M-H]^-$ 764.3; UPLC-MS 1

Step 2: 2-(5-ethyl-6-(4-(3-hydroxypicolinoyl)piperazin-1-yl)-7-oxo-2-(1,2,3,6-tetrahydropyridin-4-yl)-[1,2,4]triazolo[1,5-a]pyrimidin-4 (7H)-yl)-N-(2-methyl-4-(trifluoromethyl)phenyl)acetamide Tert-butyl 4-(5-ethyl-6-(4-(3-hydroxypicolinoyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3,6-dihydropyridine-1 (2H)-carboxylate (3.27 g, 3.71 mmol) was dissolved in DCM (40 mL) and TFA (5.72 mL, 74.3 mmol) was added. The RM was stirred at RT for 3 hours. The RM was quenched with aq $NaHCO_3$ and the pH adjusted to pH 10. Then it was extracted 5 times with DCM, dried through a phase separator and concentrated under reduced pressure. The crude product was purified by reverse phase preparative ISCO (RediSep Column: C18 240 g, eluent water:ACN 100:0 to 0:100). The product containing fractions were combined and lyophilized to give the title compound as a powder.

LC-MS: Rt=0.75 min; MS m/z $[M+H]^+$ 666.3, m/z $[M-H]^-$ 664.3; UPLC-MS 1

Step 3: 2-(2-(1-(2,2-difluoroethyl)-1,2,3,6-tetrahydropyridin-4-yl)-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide DIPEA (803 μL, 4.60 mmol) and 2,2-difluoroethan-1-ol (234 μL, 3.70 mmol) were dissolved in dry DMF (8 mL) and heated up to 40° C. Sulfuryl difluoride was bubbled through the RM for 2 mins, then the RM was purged with argon for 10 minutes. This RM was added dropwise to a solution of 2-(5-ethyl-6-(4-(3-hydroxypicolinoyl)piperazin-1-yl)-7-oxo-2-(1,2,3,6-tetrahydropyridin-4-yl)-[1,2,4]triazolo[1,5-a]pyrimidin-4 (7H)-yl)-N-(2-methyl-4-(trifluoromethyl)phenyl)acetamide (600 mg, 901 μmol) in DMF (8 mL) at 40° C. The RM was stirred at 40° C. for 2 hours. The residue was adsorbed onto Isolute and purified by reverse phase preparative ISCO (RediSep Column: C18 100 g Gold, eluent water:ACN 100:0 to 0:100). The product containing fractions were combined and concentrated under reduced pressure. The solid was further purified by reverse phase preparative ISCO (RediSep Column: C18 50 g Gold, eluent water:ACN 100:0 to 0:100) and lyophilized. The resulting solid was dissolved in EtOAc:EtOH (1:1) and stirred at 57° C. for 48 hours, then at RT over the weekend. Afterwards it was cooled in an ice bath and the solid was filtered off and dried under HV to give the title compound.

LC-MS: Rt=0.95 min; MS m/z $[M+H]^+$ 730.3, m/z $[M-H]^-$ 728.3; UPLC-MS 1

$^1$H NMR (400 MHz, DMSO-$d_6$) δ 10.37 (s, 1H), 9.99 (s, 1H), 8.06 (m, 1H), 7.71 (d, J=8.6 Hz, 1H), 7.62 (m, 1H), 7.53 (d, J=9.0 Hz, 1H), 7.28 (m, 2H), 6.75 (m, 1H), 6.35-6.00 (t, J=55.4 Hz, 1H), 5.23 (s, 1H), 4.54 (m, 1H), 3.44 (m, 4H), 3.22 (m, 2H), 3.05-2.75 (m, 11H), 2.61 (m, 1H), 2.35 (s, 3H), 1.19 (t, J=7.3 Hz, 3H)

Example 116: N-(2-chloro-5-fluoro-4-(trifluoromethyl)phenyl)-2-(2-(3,6-dihydro-2H-pyran-4-yl)-5-ethyl-6-(4-(3-hydroxypicolinoyl)piperazin-1-yl)-7-oxo-[1,2,4]triazolo[1,5-a]pyrimidin-4 (7H)-yl) acetamide

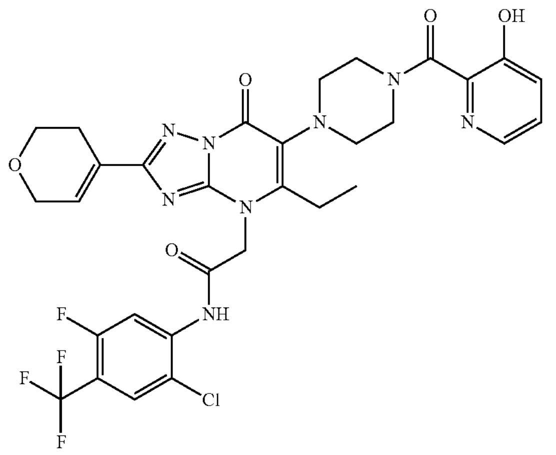 [SMILES: CCc1c(N2CCN(C(=O)c3ncccc3O)CC2)c(=O)n2nc(C3=CCOCC3)nc2n1CC(=O)Nc1cc(F)c(C(F)(F)F)cc1Cl]

N-(2-chloro-5-fluoro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate CA) (212 mg, 228 μmol) was dissolved in DCM (2 mL) and 3-hydroxypicolinoyl chloride (Intermediate CV) (64.0 mg, 406 μmol) was added, followed by DIPEA (120 μL, 685 μmol). The RM was stirred at RT for 15 minutes. Then DIPEA (200 μL, 1.15 mmol) was added and the RM was stirred at RT for 7 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 24 g, eluent DCM:DCM/MeOH (9/1) 100:0 to 60:40) to afford the title compound as a white solid.

LC-MS: Rt=1.08 min; MS m/z $[M+H]^+$ 705.4/707.4, m/z $[M-H]^-$ 703.5/705.4; UPLC-MS 1

$^1$H NMR (600 MHz, DMSO-$d_6$) δ 10.47 (s, 1H), 10.38 (s, 1H), 8.10 (d, J=12.6 Hz, 1H), 8.06 (dd, J=2.2 Hz, 5.8 Hz, 1H), 8.02 (d, J=7.1 Hz, 1H), 7.29 (m, 2H), 6.81 (m, 1H), 5.36 (s, 2H), 4.55 (m, 1H), 4.25 (m, 2H), 3.80 (m, 2H), 3.45 (m, 3H), 3.22 (m, 1H), 2.97 (m, 3H), 2.80 (m, 1H), 2.61 (m, 1H), 2.50 (m, 2H), 1.17 (t, J=7.5 Hz, 3H)

Example 117: 2-(2-(3,6-dihydro-2H-pyran-4-yl)-6-(4-(3-hydroxypicolinoyl)piperazin-1-yl)-5-methyl-7-oxo-[1,2,4]triazolo[1,5-a]pyrimidin-4 (7H)-yl)-N-(4-(trifluoromethyl)phenyl)acetamide

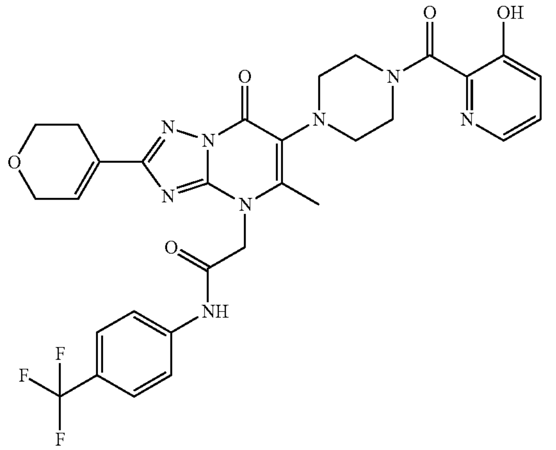 [SMILES: Cc1c(N2CCN(C(=O)c3ncccc3O)CC2)c(=O)n2nc(C3=CCOCC3)nc2n1CC(=O)Nc1ccc(C(F)(F)F)cc1]

3-Hydroxypicolinic acid (53.8 mg, 386 μmol) was mixed with DCM (4 mL) at RT. The mixture was cooled to 0° C. and 1-chloro-N,N,2-trimethylprop-1-en-1-amine (56.0 μL, 425 μmol) was added dropwise. The RM was stirred at RT for 2 hours, then it was cooled to 0° C. again. DIPEA (169 μL, 966 μmol) was added. This solution was added dropwise at 0° C. to a solution of 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide (Intermediate BN) (100 mg, 193 μmol) in DCM (4 mL). The RM was stirred at RT for 1 hour. The RM was diluted with DCM, washed with aq sat $NaHCO_3$, dried over $Na_2SO_4$, concentrated and dried. The crude product was purified by reverse phase preparative HPLC (RP-HPLC acidic 1: 5 to 100% B in 20 min). The product containing fractions were combined and the ACN was removed under reduced pressure. The aqueous residue was mixed with DCM, basified with $NaHCO_3$, dried over $Na_2SO_4$ and concentrated under reduced pressure to give the title compound as a solid.

LC-MS: Rt=0.96 min; MS m/z $[M+H]^+$ 639.2, m/z $[M-H]^-$ 637.1; UPLC-MS 8

$^1$H NMR (400 MHz, DMSO-$d_6$) δ 10.85 (s, 1H), 10.37 (s, 1H), 8.07 (m, 1H), 7.78 (d, J=8.6 Hz, 2H), 7.70 (d, J=8.6 Hz, 2H), 7.29 (m, 2H), 6.81 (m, 1H), 5.22 (s, 2H), 4.53 (m, 1H), 4.24 (m, 2H), 3.80 (m, 2H), 3.44 (m, 3H), 3.22 (m, 1H), 2.98 (m, 1H), 2.79 (m, 1H), 2.62 (m, 1H), 2.57 (s, 3H), 2.49 (m, 2H)

Example 118: N-(2-chloro-4-(trifluoromethyl)phenyl)-2-(2-(3,6-dihydro-2H-pyran-4-yl)-5-ethyl-6-((2S,5R)-4-(5-hydroxy-6-methylpyrimidine-4-carbonyl)-2,5-dimethylpiperazin-1-yl)-7-oxo-[1,2,4]triazolo[1,5-a]pyrimidin-4 (7H)-yl)acetamide

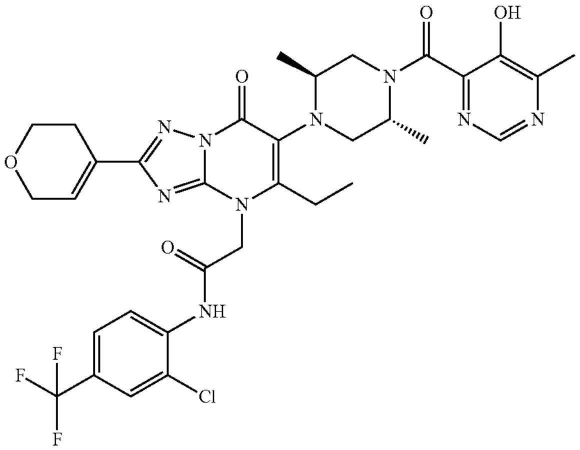 [SMILES: CCc1c(N2C[C@@H](C)N(C(=O)c3ncnc(C)c3O)C[C@@H]2C)c(=O)n2nc(C3=CCOCC3)nc2n1CC(=O)Nc1ccc(C(F)(F)F)cc1Cl]

Step 1: 2-(6-((2S,5R)-4-(5-(benzyloxy)-6-methylpyrimidine-4-carbonyl)-2,5-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide To a brown solution of N-(2-chloro-4-(trifluoromethyl)phenyl)-2-(2-(3,6-dihydro-2H-pyran-4-yl)-6-((2S,5R)-2,5-dimethylpiperazin-1-yl)-5-ethyl-7-oxo-[1,2,4]triazolo[1,5-a]pyrimidin-4 (7H)-yl)acetamide (Intermediate CC) (1.11 g, 1.28 mmol) and 5-(benzyloxy)-6-methylpyrimidine-4-carboxylic acid (Intermediate CY) (369 mg, 1.51 mmol) in DMF (14.4 mL) were added HATU (656 mg, 1.73 mmol) and DIPEA (754 μL, 4.32 mmol) at RT and the RM was stirred at RT for 45 minutes. The RM was quenched with water and extracted twice with EtOAc. The combined organic layers were washed three times with brine then dried over $MgSO_4$ cartridge and concentrated under vacuum. The crude product was purified by column chromatography (Silica gel column: Silica 40 g, eluent DCM:DCM/MeOH (8/2) 100:0 to 55:45) to give the title compound.

LC-MS: Rt=1.23 min; MS m/z $[M+H]^+$ 820.5/822.5, m/z $[M-H]^-$ 818.5/820.5; UPLC-MS 1

Step 2: N-(2-chloro-4-(trifluoromethyl)phenyl)-2-(2-(3,6-dihydro-2H-pyran-4-yl)-5-ethyl-6-((2S,5R)-4-(5-hydroxy-6-methylpyrimidine-4-carbonyl)-2,5-dimethylpiperazin-1-yl)-7-oxo-[1,2,4]triazolo[1,5-a]pyrimidin-4 (7H)-yl)acetamide 2-(6-((2S,5R)-4-(5-(benzyloxy)-6-methylpyrimidine-4-carbonyl)-2,5-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (1.09 g, 998 μmol) was dissolved in DCM (3 mL). TFA (3.08 mL, 39.9 mmol) was added. The brown solution was stirred at 45° C. for 18 hours. The RM was diluted with DCM, washed with water and aq sat $NaHCO_3$. The aqueous layer was extracted twice with DCM. The combined organic layers were dried through a phase separator and concentrated under reduced pressure. The crude product was adsorbed onto Isolute and purified by column chromatography (Silica gel column: Silica 40 g, eluent DCM:DCM/MeOH (8/2) 100:0 to 65:35). The product containing fractions were combined and concentrated under reduced pressure to give a light brown solid. The light brown solid was purified in 2 portions by reverse phase preparative HPLC (2×RP-HPLC acidic 14: 20 to 70% B in 20 min with a plateau at 70% for 3 min). The product containing fractions were combined, the ACN was removed and the residue was quenched with aq sat $NaHCO_3$, then extracted twice with DCM. The combined organic layers were dried through a phase separator and concentrated under reduced pressure to give the title compound as a beige solid.

LC-MS: Rt=1.11 min; MS m/z $[M+H]^+$ 730.2/732.2, m/z $[M-H]^-$ 728.3/730.3; UPLC-MS 1

$^1$H NMR (400 MHz, DMSO-$d_6$) δ 10.35 (s, 1H), 10.14 (s, br, 1H), 8.57 (m, 1H), 8.05 (m, 1H), 7.96 (m, 1H), 7.71 (m, 1H), 6.82 (m, 1H), 5.31 (m, 2H), 4.21 (m, 3H), 3.79 (m, 2H), 3.69 (m, 1H), 3.45 (m, 1H), 3.11 (m, 2H), 2.87 (m, 1H), 2.45 (m, 5H), 2.33 (m, 1H), 1.35 (m, 2H), 1.24 (m, 2H), 1.16 (m, 4H), 1.03 (m, 1H), 0.92 (m, 1H)

Example 119: N-(2-chloro-4-(trifluoromethyl)phenyl)-2-(2-(3,6-dihydro-2H-pyran-4-yl)-5-ethyl-6-((2R,3R)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide

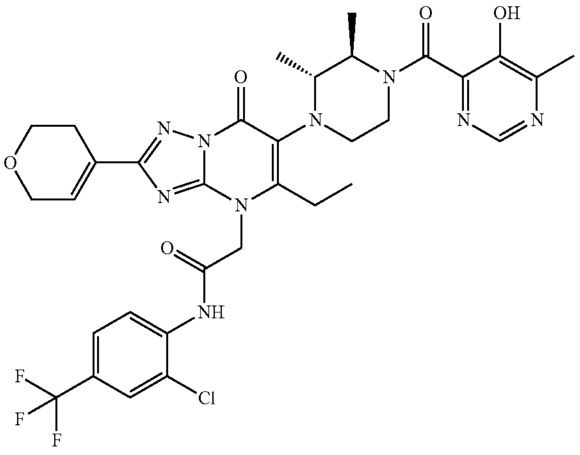 [SMILES: CCc1c(N2CCN(C(=O)c3ncnc(C)c3O)[C@H](C)[C@H]2C)c(=O)n2nc(C3=CCOCC3)nc2n1CC(=O)Nc1ccc(C(F)(F)F)cc1Cl]

Step 1: 2-(6-((2R,3R)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide To a stirred solution of N-(2-chloro-4-(trifluoromethyl)phenyl)-2-(2-(3,6-dihydro-2H-pyran-4-yl)-6-((2R,3R)-2,3-dimethylpiperazin-1-yl)-5-ethyl-7-oxo-[1,2,4]triazolo[1,5-a]pyrimidin-4 (7H)-yl)acetamide (Intermediate CI) (618 mg, 978 μmol), 5-(benzyloxy)-6-methylpyrimidine-4-carboxylic acid (Intermediate CY) (239 mg, 978 μmol) and HATU (446 mg, 1.17 mmol) in DMF (2 mL) was added DIPEA (854 μL, 4.89 mmol) at RT and the RM was stirred at RT for 10 minutes. The RM was diluted with EtOAc/water, extracted twice with EtOAc and the combined organic extracts were washed with brine, dried over $Na_2SO_4$ and concentrated. The crude product was purified by column chromatography (RediSep Column: Silica 40 g, eluent DCM:DCM/MeOH (8/2) 100:0 to 50:50) to give the title compound as a beige foam.

LC-MS: Rt=1.24 min; MS m/z $[M+H]^+$ 820.5/822.5, m/z $[M-H]^-$ 818.4/820.5; UPLC-MS 1

Step 2: N-(2-chloro-4-(trifluoromethyl)phenyl)-2-(2-(3,6-dihydro-2H-pyran-4-yl)-5-ethyl-6-((2R,3R)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide 2-(6-((2R,3R)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (858 mg, 889 μmol) in TFA (5.00 mL, 64.9 mmol) was stirred at 40° C. for 14 hours. The RM was diluted with DCM and $NaHCO_3$, extracted twice with DCM and the combined organic extracts were washed with brine, dried over $Na_2SO_4$ and concentrated. The crude product was purified by column chromatography (RediSep Column: Silica 40 g, eluent DCM:DCM/MeOH (8/2) 100:0 to 50:50) to give the title compound as a white solid.

LC-MS: Rt=1.12 min; MS m/z $[M+H]^+$ 730.1/732.1, m/z $[M-H]^-$ 728.3/730.2; UPLC-MS 1

LC-MS: Rt=5.50 min; MS m/z $[M+H]^+$ 730.1/732.1, m/z $[M-H]^-$ 728.3/730.2; UPLC-MS 2

$^1H$ NMR (400 MHz, DMSO-$d_6$) δ 10.36 (s, br, 1H), 10.17 (s, br, 1H), 8.56 (m, 1H), 8.06 (m, 1H), 7.96 (m, 1H), 7.71 (m, 1H), 6.82 (m, 1H), 5.34 (m, 2H), 4.60-4.35 (m, 1H), 4.25 (m, 2H), 4.09 (m, 1H), 3.80 (m, 2H), 3.38 (m, 1H), 3.13 (m, 3H), 2.88 (m, 2H), 2.58 (m, 1H), 2.51 (m, 2H), 2.44 (m, 3H), 1.48 (m, 2H), 1.22 (m, 5H), 1.08 (m, 1H)

Example 120: N-(2-chloro-4-(trifluoromethyl)phenyl)-2-(2-(3,6-dihydro-2H-pyran-4-yl)-5-ethyl-6-((2S,3S)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide

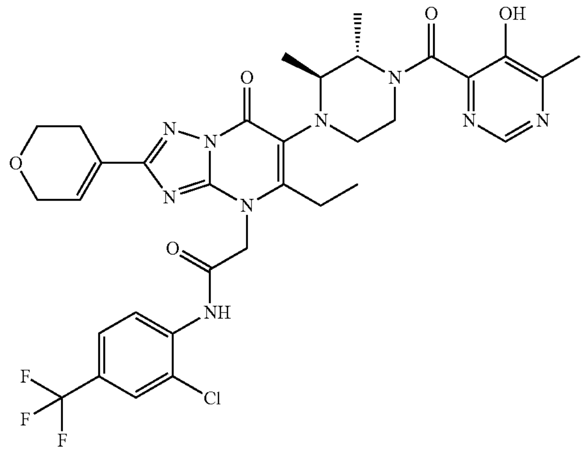 [SMILES: CCc1c(N2CCN(C(=O)c3ncnc(C)c3O)[C@@H](C)[C@@H]2C)c(=O)n2nc(C3=CCOCC3)nc2n1CC(=O)Nc1ccc(C(F)(F)F)cc1Cl]

Step 1: 2-(6-((2S,3S)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide To a stirred solution of N-(2-chloro-4-(trifluoromethyl)phenyl)-2-(2-(3,6-dihydro-2H-pyran-4-yl)-6-((2S,3S)-2,3-dimethylpiperazin-1-yl)-5-ethyl-7-oxo-[1,2,4]triazolo[1,5-a]pyrimidin-4 (7H)-yl)acetamide (Intermediate CJ) (50.0 mg, 84.0 μmol), 5-(benzyloxy)-6-methylpyrimidine-4-carboxylic acid (Intermediate CY) (20.6 mg, 84.0 μmol) and HATU (38.4 mg, 101 μmol) in DMF (1 mL) was added DIPEA (74.0 μL, 421 μmol) at RT and the RM was stirred at RT for 10 minutes. The RM was diluted with EtOAc/water, extracted twice with EtOAc and the combined organic extracts were washed with brine, dried over $Na_2SO_4$ and concentrated. The crude product was purified by column chromatography (RediSep Column: Silica 12 g, eluent DCM:DCM/MeOH (8/2) 100:0 to 50:50) to give the title compound as a white foam.

LC-MS: Rt=1.24 min; MS m/z $[M+H]^+$ 820.3/822.3, m/z $[M-H]^-$ 818.4/820.4; UPLC-MS 1

Step 2: N-(2-chloro-4-(trifluoromethyl)phenyl)-2-(2-(3,6-dihydro-2H-pyran-4-yl)-5-ethyl-6-((2S,3S)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide 2-(6-((2S,3S)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (57.0 mg, 63.0 μmol) in TFA (1.00 mL, 13.0 mmol) was stirred at 50° C. for 14 hours. The RM was diluted with DCM/water, extracted twice with DCM and the combined organic extracts were washed with brine, dried over $Na_2SO_4$ and concentrated. The crude product was purified by reverse phase preparative HPLC (RP-HPLC acidic 1: 5 to 95% B in 20 min with a plateau at 95% for 1 min). The product containing fractions were combined, basified with $NaHCO_3$, the ACN was removed and the resulting aqueous residue was extracted with DCM. The combined organic layers were washed with brine, dried over $Na_2SO_4$ and concentrated under reduced pressure to give the title compound as a white solid.

LC-MS: Rt=1.11 min; MS m/z $[M+H]^+$ 730.3/732.3, m/z $[M-H]^-$ 728.4/730.4; UPLC-MS 1

LC-MS: Rt=5.51 min; MS m/z $[M+H]^+$ 730.2/732.2, m/z $[M-H]^-$ 728.3/730.3; UPLC-MS 2

$^1H$ NMR (400 MHz, DMSO-$d_6$) δ 10.37 (s, br, 1H), 10.17 (s, br, 1H), 8.56 (m, 1H), 8.06 (m, 1H), 7.97 (m, 1H), 7.71 (m, 1H), 6.82 (m, 1H), 5.35 (m, 2H), 4.60-4.35 (m, 1H), 4.25 (m, 2H), 4.10 (m, 1H), 3.80 (m, 2H), 3.37 (m, 1H), 3.25-2.80 (m, 4H), 2.57 (m, 1H), 2.51 (m, 2H), 2.44 (m, 3H), 2.40 (m, 1H), 1.48 (m, 2H), 1.23 (m, 5H), 1.08 (m, 1H)

Example 121: N-(2-chloro-4-(trifluoromethyl)phenyl)-2-(2-(3,6-dihydro-2H-pyran-4-yl)-5-ethyl-6-((2R,3S)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((2S,3R)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide

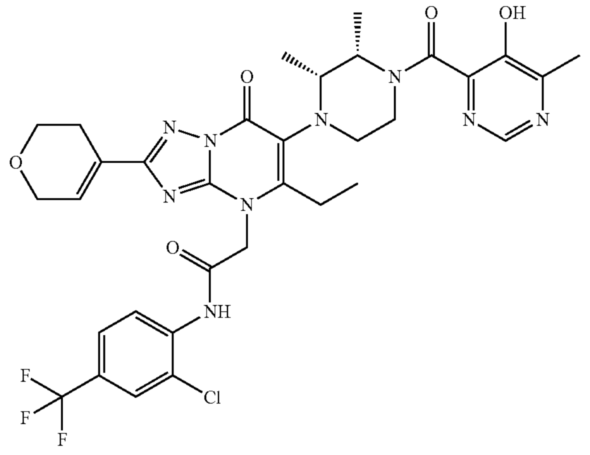

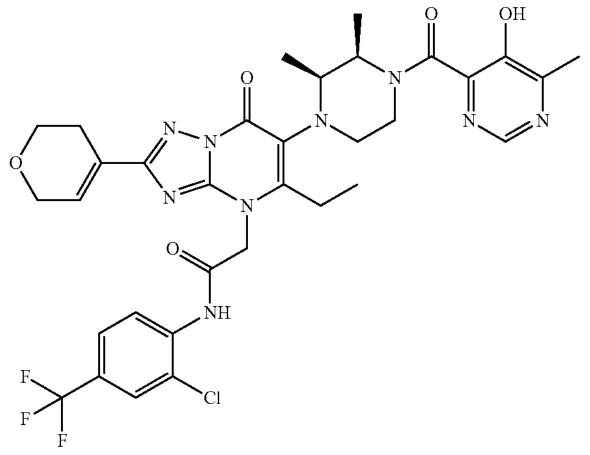

Step 1: 2-(6-((2R,3S)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((2S,3R)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide To a stirred solution of N-(2-chloro-4-(trifluoromethyl)phenyl)-2-(2-(3,6-dihydro-2H-pyran-4-yl)-6-((2R,3S)-2,3-dimethylpiperazin-1-yl)-5-ethyl-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-6-((2S,3R)-2,3-dimethylpiperazin-1-yl)-5-ethyl-7-oxo-[1,2,4]triazolo[1,5-a]pyrimidin-4 (7H)-yl)acetamide (Intermediate CK) (212 mg, 353 μmol), 5-(benzyloxy)-6-methylpyrimidine-4-carboxylic acid (Intermediate CY) (86.0 mg, 353 μmol) and HATU (161 mg, 424 μmol) in DMF (2 mL) was added DIPEA (309 μL, 1.77 mmol) at RT and the RM was stirred at RT for 5 minutes. The RM was diluted with EtOAc/water, extracted twice with EtOAc and the combined organic extracts were washed with brine, dried over $Na_2SO_4$ and concentrated. The crude product was purified by column chromatography (RediSep Column: Silica 24 g, eluent DCM:DCM/MeOH (8/2) 100:0 to 40:60) to give the title compound as a white foam.

LC-MS: Rt=1.25 min; MS m/z $[M+H]^+$ 820.4/822.4, m/z $[M-H]^-$ 818.4/820.4; UPLC-MS 1

Step 2: N-(2-chloro-4-(trifluoromethyl)phenyl)-2-(2-(3,6-dihydro-2H-pyran-4-yl)-5-ethyl-6-((2R,3S)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((2S,3R)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide 2-(6-((2R,3S)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((2S,3R)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (285 mg, 264 μmol) in TFA (1.00 mL, 13.0 mmol) was stirred at 40° C. for 20 hours. The RM was diluted with DCM and $NaHCO_3$, extracted twice with DCM and the combined organic extracts were washed with brine, dried over $Na_2SO_4$ and concentrated. The crude product was purified by column chromatography (RediSep Column: Silica 24 g, eluent DCM:DCM/MeOH (8/2) 100:0 to 50:50). The product containing fractions were combined and concentrated to give a yellow foam. The foam was triturated in ACN and a white solid was filtered. The solid was stirred overnight in 10% water in EtOH at 40° C. to afford the title compound as a white solid.

LC-MS: Rt=1.09 min; MS m/z $[M+H]^+$ 730.2/732.1, m/z $[M-H]^-$ 728.3/730.3; UPLC-MS 1

LC-MS: Rt=5.38 min; MS m/z $[M+H]^+$ 730.2/732.1, m/z $[M-H]^-$ 728.3/730.3; UPLC-MS 2

$^1H$ NMR (400 MHz, DMSO-$d_6$) δ 10.38 (s, br, 2H), 8.56 (d, J=5.4 Hz, 1H), 8.05 (d, J=8.4 Hz, 1H), 7.96 (d, J=2.1 Hz, 1H), 7.71 (dd, J=1.8 Hz, 8.7 Hz, 1H), 6.83 (m, 1H), 5.32 (m, 2H), 4.60-4.35 (m, 1H), 4.25 (m, 2H), 3.79 (m, 2H), 3.49 (m, 1H), 3.21 (m, 3H), 2.89 (m, 2H), 2.63 (m, 1H), 2.52 (m, 2H), 2.44 (m, 3H), 1.22 (m, 6H), 0.85-0.65 (m, 3H)

Example 122: N-(2-chloro-4-(trifluoromethyl)phenyl)-2-(2-(3,6-dihydro-2H-pyran-4-yl)-5-ethyl-6-((2S,3R)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((2R,3S)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide

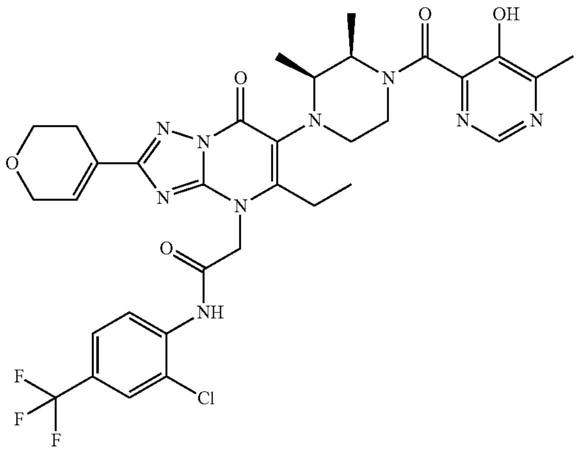

2S,3R-stereoisomer

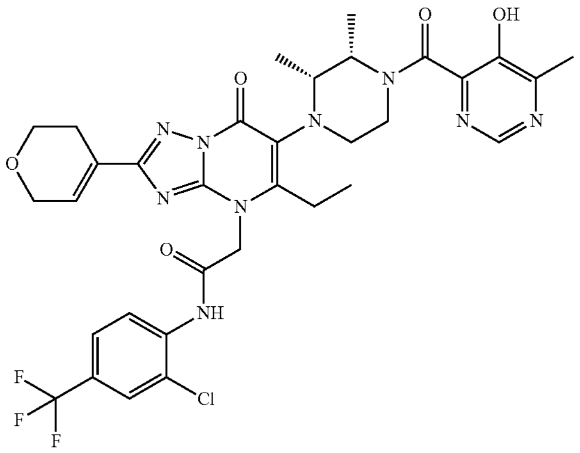

2R,3S-stereoisomer

Step 1: 2-(6-((2S,3R)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((2R,3S)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide To a stirred solution of N-(2-chloro-4-(trifluoromethyl)phenyl)-2-(2-(3,6-dihydro-2H-pyran-4-yl)-6-((2S,3R)-2,3-dimethylpiperazin-1-yl)-5-ethyl-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-6-((2R,3S)-2,3-dimethylpiperazin-1-yl)-5-ethyl-7-oxo-[1,2,4]triazolo[1,5-a]pyrimidin-4 (7H)-yl)acetamide (Intermediate CL) (212 mg, 343 μmol), 5-(benzyloxy)-6-methylpyrimidine-4-carboxylic acid (Intermediate CY) (84.0 mg, 343 μmol) and HATU (156 mg, 411 μmol) in DMF (2 mL) was added DIPEA (299 μL, 1.71 mmol) at RT and the RM was stirred at RT for 5 minutes. The RM was diluted with EtOAc/water, extracted twice with EtOAc and the combined organic extracts were washed with brine, dried over $Na_2SO_4$ and concentrated. The crude product was purified by column chromatography (RediSep Column: Silica 24 g, eluent DCM:DCM/MeOH (8/2) 100:0 to 40:60) to give a beige foam.

LC-MS: Rt=1.25 min; MS m/z $[M+H]^+$ 820.4/822.3, m/z $[M-H]^-$ 818.4/820.4; UPLC-MS 1

Step 2: N-(2-chloro-4-(trifluoromethyl)phenyl)-2-(2-(3,6-dihydro-2H-pyran-4-yl)-5-ethyl-6-((2S,3R)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((2R,3S)-4-(5-hydroxy-6-methylpyrimidine-4-carbonyl)-2,3-dimethylpiperazin-1-yl)-7-oxo-[1,2,4]triazolo[1,5-a]pyrimidin-4 (7H)-yl)acetamide 2-(6-((2S,3R)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((2R,3S)-4-(5-(benzyloxy)-6-methylpyrimidine-4-carbonyl)-2,3-dimethylpiperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (273 mg, 233 μmol) in TFA (1.00 mL, 13.0 mmol) was stirred at 40° C. for 14 hours. The RM was diluted with DCM and $NaHCO_3$, extracted twice with DCM and the combined organic extracts were washed with brine, dried over $Na_2SO_4$ and concentrated. The crude product was purified in 2 portions by reverse phase preparative HPLC (RP-HPLC acidic 1: 5 to 80% B in 25 min with a plateau at 80% for 1 min and RP-HPLC acidic 1: 30 to 70% B in 20 min with a plateau at 70% for 1 min). The product containing fractions were basified with $NaHCO_3$, the ACN was evaporated and the resulting aqueous residue was extracted with DCM, the organic extract was washed with brine, dried over $Na_2SO_4$ and concentrated to afford the title compound as a white solid.

LC-MS: Rt=1.10 min; MS m/z $[M+H]^+$ 730.3/732.3, m/z $[M-H]^-$ 728.4/730.4; UPLC-MS 1

LC-MS: Rt=5.47 min; MS m/z $[M+H]^+$ 730.3/732.3, m/z $[M-H]^-$ 728.3/730.3; UPLC-MS 2

$^1H$ NMR (400 MHz, DMSO-$d_6$) δ 10.37 (s, br, 1H), 10.20 (s, br, 1H), 8.55 (d, J=6.1 Hz, 1H), 8.04 (d, J=8.5 Hz, 1H), 7.96 (d, J=2.3 Hz, 1H), 7.71 (dd, J=1.9 Hz, 9.0 Hz, 1H), 6.83 (m, 1H), 5.32 (m, 2H), 4.65-4.30 (m, 1H), 4.25 (m, 2H), 3.79 (m, 2H), 3.46 (m, 2H), 3.20 (m, 2H), 2.89 (m, 2H), 2.63 (m, 1H), 2.51 (m, 2H), 2.44 (m, 3H), 1.22 (m, 6H), 0.85-0.65 (m, 3H)

Example 123: N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

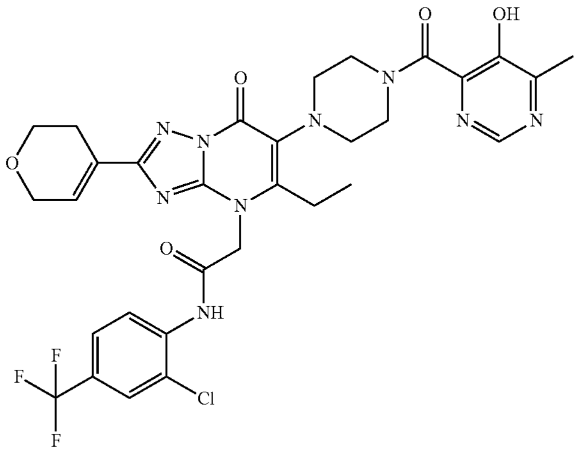 [SMILES: CCc1c(N2CCN(C(=O)c3ncnc(C)c3O)CC2)c(=O)n2nc(C3=CCOCC3)nc2n1CC(=O)Nc1ccc(C(F)(F)F)cc1Cl]

Under nitrogen was mixed 5-hydroxy-6-methylpyrimidine-4-carboxylic acid (Intermediate DB) (2.61 g, 17.0 mmol) in ACN (40 mL) as a suspension. A suspension of HOAt (192 mg, 1.41 mmol) in ACN was added, followed by EDCI (4.06 g, 21.2 mmol). The mixture was stirred at RT for 1 hour. N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide (Intermediate AK) (8.00 g, 14.1 mmol) and DIPEA (7.41 mL, 42.2 mmol) were added. The RM was stirred at RT for 1 hour, then it was treated with water (8 mL) and stirred for additional 8 hours. Diluted with THF (160 mL) and 20% $NaH_2PO_4$ solution (80 mL), the organic phase was isolated, and washed with brine. The organic layer was further diluted with THF (160 mL) and was dried over $MgSO_4$. The solid was removed by filtration and was concentrated under vacuum (to remove 25% of solvent). A solution of NaOtBu (1.49 g, 15.6 mmol) in THF was added dropwise, and the resulting suspension was filtered to give the title compound as a sodium salt.

LC-MS: Rt=1.05 min; MS m/z $[M+H]^+$ 702.4/704.4, m/z $[M-H]^-$ 700.5/702.5; UPLC-MS 1

$^1$H NMR (400 MHz, DMSO-$d_6$) δ 10.36 (s, br, 2H), 8.55 (s, 1H), 8.05 (d, J=8.5 Hz, 1H), 7.96 (m, 1H), 7.71 (dd, J=2.1 Hz, 8.8 Hz, 1H), 6.83 (m, 1H), 5.32 (s, 2H), 4.52 (m, 1H), 4.25 (m, 2H), 3.80 (m, 2H), 3.48 (m, 3H), 3.25 (m, 1H), 2.99 (m, 3H), 2.81 (m, 1H), 2.64 (m, 1H), 2.52 (m, 2H), 2.43 (s, 3H), 1.18 (t, J=7.4 Hz, 3H)

Example 124: N-(2-chloro-4-(trifluoromethyl)phenyl)-2-(2-(3,6-dihydro-2H-pyran-4-yl)-5-ethyl-6-((1R,6R)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide

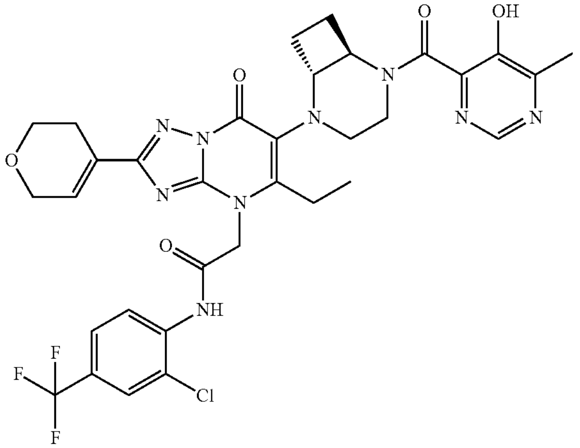

1R,6R

Step 1: 2-(6-((1R,6R)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide 2-(6-((1R,6R)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (Intermediate CP) (159 mg, 215 μmol) and 5-(benzyloxy)-6-methylpyrimidine-4-carboxylic acid (Intermediate CY) (55.1 mg, 226 μmol) were mixed in DMF (3 mL) at RT under argon. HATU (101 mg, 258 μmol) was added, followed by DIPEA (188 μL, 1.07 mmol). The RM was stirred at RT for 1.2 hours. The RM was quenched with water (5 mL), then extracted with EtOAc (3×60 mL), water (2×20 mL) and brine (2×20 mL). The combined organic layers were dried through a phase separator and concentrated under reduced pressure to give a brown oil. The crude product was adsorbed onto Isolute and purified by column chromatography (RediSep Column: Silica 40 g, eluent DCM:DCM/MeOH (8/2) 100:0 to 60:40) to give a beige solid. The impure fractions were concentrated under reduced pressure then adsorbed onto Isolute and purified by column chromatography (RediSep Column: Silica 24 g, eluent DCM:DCM/MeOH (8/2) 100:0 to 60:40). The product containing fractions were combined were combined with the solid obtained from the first purification to give the title compound as a beige solid.

LC-MS: Rt=1.22 min; MS m/z $[M+H]^+$ 818.5/820.5, m/z $[M-H]^-$ 816.5/818.5; UPLC-MS 1

Step 2: N-(2-chloro-4-(trifluoromethyl)phenyl)-2-(2-(3,6-dihydro-2H-pyran-4-yl)-5-ethyl-6-((1R,6R)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide 2-(6-((1R,6R)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (81.0 mg, 94.0 μmol) was mixed with TFA (2.17 mL, 28.2 mmol) and the RM was stirred at 50° C. for 2.5 hours, then it was concentrated under reduced pressure. The residue was dissolved in DCM and concentrated under reduced pressure. This was performed twice. The crude product was purified by reverse phase preparative HPLC (RP-HPLC acidic 1: 25 to 90% B in 20 min with a plateau at 90% for 1 min). The product containing fractions were combined, basified with aq sat $NaHCO_3$ (3 mL), the ACN was removed under reduced pressure and the residue was extracted with DCM (4×50 mL), dried through a phase separator and concentrated under reduced pressure to give the title compound as a beige solid.

Chiral HPLC (C-HPLC 11): Rt=2.65 min, 95% ee

LC-MS: Rt=1.13 min; MS m/z $[M+H]^+$ 728.5/730.5, m/z $[M-H]^-$ 726.4/728.4; UPLC-MS 1

LC-MS: Rt=5.52 min; MS m/z $[M+H]^+$ 728.2/730.3, m/z $[M-H]^-$ 726.3/728.3; UPLC-MS 2

$^1$H NMR (400 MHz, DMSO-$d_6$) δ 10.34 (m, 2H), 8.56 (s, 1H), 8.05 (d, J=8.6 Hz, 1H), 7.96 (d, J=1.9 Hz, 1H), 7.71 (dd, J=2.1 Hz, 8.5 Hz, 1H), 6.83 (m, 1H), 5.31 (s, 2H), 4.41 (m, 1H), 4.25 (m, 2H), 3.80 (m, 2H), 3.62 (m, 1H), 3.40 (m, 3H), 3.25 (m, 1H), 3.01 (m, 2H), 2.51 (m, 2H), 2.43 (m, 4H), 1.63 (m, 1H), 1.34 (m, 2H), 1.19 (t, J=7.2 Hz, 3H)

Example 125 N-(2-chloro-4-(trifluoromethyl)phenyl)-2-(2-(3,6-dihydro-2H-pyran-4-yl)-5-ethyl-6-((1S,6S)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide

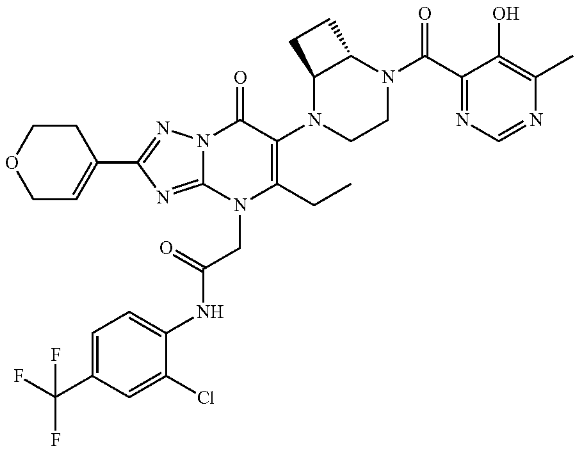

1S,6S

Step 1: 2-(6-((1S,6S)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide 2-(6-((1S,6S)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (Intermediate CQ) (143 mg, 184 μmol) and 5-(benzyloxy)-6-methylpyrimidine-4-carboxylic acid (Intermediate CY) (47.1 mg, 193 μmol) were mixed in DMF (2.5 mL) at RT under argon. HATU (86.0 mg, 220 μmol) was added, followed by DIPEA (160 μL, 918 μmol). The RM was stirred at RT for 45 minutes. The RM was quenched with water (5 mL), then extracted with EtOAc (3×60 mL), water (2×20 mL) and brine (2×15 mL). The combined organic layers were dried through a phase separator and concentrated under reduced pressure to give a bright brown solid. The crude product was adsorbed onto Isolute and purified by column chromatography (RediSep Column: Silica 40 g, eluent DCM:DCM/MeOH (8/2) 100:0 to 60:40) to give the title compound as a pale beige solid.

LC-MS: Rt=1.23 min; MS m/z $[M+H]^+$ 818.5/820.5, m/z $[M-H]^-$ 816.5/818.5; UPLC-MS 1

Step 2: N-(2-chloro-4-(trifluoromethyl)phenyl)-2-(2-(3,6-dihydro-2H-pyran-4-yl)-5-ethyl-6-((1S,6S)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide 2-(6-((1S,6S)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (100 mg, 122 μmol) was mixed with TFA (2.83 mL, 36.7 mmol) and the RM was stirred at 50° C. for 3 hours, then it was concentrated under reduced pressure. The crude product was purified by reverse phase preparative HPLC (RP-HPLC acidic 1: 20 to 90% B in 20 min with a plateau at 90% for 1 min). The product containing fractions were combined, basified with aq sat $NaHCO_3$ (3 mL), the ACN was removed under reduced pressure and the residue was extracted with DCM (4×40 mL), dried through a phase separator and concentrated under reduced pressure to give the title compound as a white solid. The product was dissolved in EtOAc and left to stand in a closed flask for 18 hours. The resulting solid was filtered, washed with EtOAc and dried at 60° C. under reduced pressure to give a colorless solid. The crystals were combined with the mother liquors and stirred in EtOAc at 50° C. for 18 hours. Filtered and dried at 60° C. under reduced pressure to give a colorless solid.

Chiral HPLC (C-HPLC 12): Rt=3.49 min, 95% ee

LC-MS: Rt=1.12 min; MS m/z $[M+H]^+$ 728.3/730.3, m/z $[M-H]^-$ 726.4/728.3; UPLC-MS 1

LC-MS: Rt=5.54 min; MS m/z $[M+H]^+$ 728.3/730.2, m/z $[M-H]^-$ 726.3/728.2; UPLC-MS 2

$^1$H NMR (400 MHz, DMSO-$d_6$) δ 10.34 (m, 2H), 8.56 (s, 1H), 8.05 (d, J=8.7 Hz, 1H), 7.96 (d, J=2.0 Hz, 1H), 7.71 (dd, J=2.3 Hz, 8.7 Hz, 1H), 6.83 (m, 1H), 5.31 (s, 2H), 4.41 (m, 1H), 4.25 (m, 2H), 3.80 (m, 2H), 3.64 (m, 1H), 3.40 (m, 3H), 3.25 (m, 1H), 3.01 (m, 2H), 2.51 (m, 2H), 2.43 (m, 4H), 1.63 (m, 1H), 1.34 (m, 2H), 1.19 (t, J=7.1 Hz, 3H)

Example 126: tert-butyl 4-(6-(4-(3-hydroxypicolinoyl)piperazin-1-yl)-5-methyl-7-oxo-4-(2-oxo-2-((4-(trifluoromethyl)phenyl)amino)ethyl)-4,7-dihydro-[1,2,4]triazolo[1,5-a]pyrimidin-2-yl)-3,6-dihydropyridine-1 (2H)-carboxylate

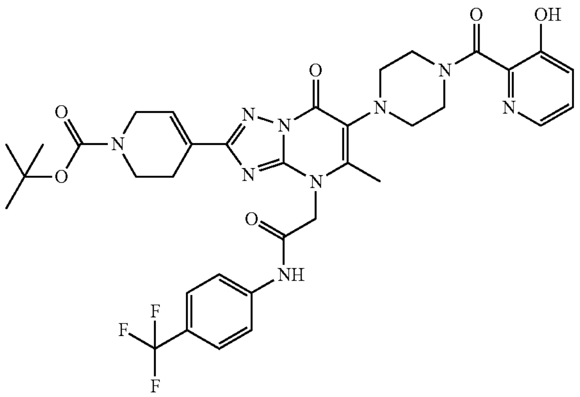 [SMILES: Cc1c(N2CCN(C(=O)c3ncccc3O)CC2)c(=O)n2nc(C3=CCN(C(=O)OC(C)(C)C)CC3)nc2n1CC(=O)Nc1ccc(C(F)(F)F)cc1]

3-Hydroxypicolinic acid (166 mg, 1.17 mmol) was dissolved in DCM (9.5 mL) at RT under argon. 1-Chloro-N,N,2-trimethylprop-1-en-1-amine (170 μL, 1.29 mmol) was added and the RM was stirred at RT for 1.5 hours. Tert-butyl 4-(5-methyl-7-oxo-4-(2-oxo-2-((4-(trifluoromethyl)phenyl)amino)ethyl)-6-(piperazin-1-yl)-4,7-dihydro-[1,2,4]triazolo[1,5-a]pyrimidin-2-yl)-3,6-dihydropyridine-1 (2H)-carboxylate (Intermediate CR) (380 mg, 585 μmol) was added, followed by DIPEA (511 μL, 2.93 mmol) and the RM was stirred at RT for 4 hours and quenched with water. Aq sat $NaHCO_3$ (10 mL) was added and the mixture was extracted with DCM (4×30 mL). The combined organic layers were dried through a phase separator and concentrated under reduced pressure to give a green-brown oil. The oil was adsorbed onto Isolute and purified by column chromatography (RediSep Column: Silica 24 g, eluent DCM:MeOH 100:0 to 70:30) to give the title compound as a beige solid.

LC-MS: Rt=1.09 min; MS m/z $[M+H]^+$ 738.3, m/z $[M-H]^-$ 736.1; UPLC-MS 4 Example 127: (S)—N-(2-chloro-4-(trifluoromethyl)phenyl)-2-(5-ethyl-2-(3-fluoro-3,4-dihydro-2H-pyran-6-yl)-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide

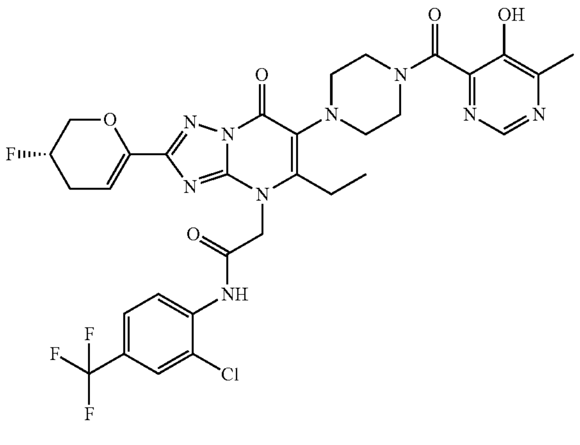 [SMILES: CCc1c(N2CCN(C(=O)c3ncnc(C)c3O)CC2)c(=O)n2nc(C3=CC[C@H](F)CO3)nc2n1CC(=O)Nc1ccc(C(F)(F)F)cc1Cl]

Step 1: (S)-2-(6-(4-(5-(benzyloxy)-6-methylpyrimidine-4-carbonyl)piperazin-1-yl)-5-ethyl-2-(3-fluoro-3,4-dihydro-2H-pyran-6-yl)-7-oxo-[1,2,4]triazolo[1,5-a]pyrimidin-4 (7H)-yl)-N-(2-chloro-4-(trifluoromethyl)phenyl)acetamide To a stirred solution of 5-(benzyloxy)-6-methylpyrimidine-4-carboxylic acid (Intermediate CY) (5.86 mg, 24.0 μmol) and HATU (10.0 mg, 26.0 μmol) in DMF (1 mL) was added DIPEA (21.0 μL, 120 μmol) at RT and the RM was stirred at RT for 10 minutes. Then a solution of (S)—N-(2-chloro-4-(trifluoromethyl)phenyl)-2-(5-ethyl-2-(3-fluoro-3,4-dihydro-2H-pyran-6-yl)-7-oxo-6-(piperazin-1-yl)-[1,2,4]triazolo[1,5-a]pyrimidin-4 (7H)-yl)acetamide (Intermediate CS) (14.0 mg, 24.0 μmol) in DMF (1 mL) was added dropwise at RT. The RM was stirred at RT for 1 hour. The RM was extracted with water (30 mL) and TBME (30 mL). The organic phase was washed with aq sat $NaHCO_3$ (30 mL) and brine (30 mL). The combined aqueous layers were extracted with TBME (2×30 mL). The combined organic phases were dried over anhydrous $Na_2SO_4$, filtered and concentrated in vacuo at 45° C. to give a yellow resin. The crude product was purified by column chromatography (Silica gel column: Silica 24 g SNAP cartridge (Biotage), eluent heptane:EtOAc 80:20 to 0:100, then DCM:DCM/MeOH (9/1) 100:0 to 0:100) to give the title compound as a yellow resin.

LC-MS: Rt=1.19 min; MS m/z $[M+H]^+$ 810.4/812.4, m/z $[M-H]^-$ 808.4/810.4; UPLC-MS 1

Step 2: (S)—N-(2-chloro-4-(trifluoromethyl)phenyl)-2-(5-ethyl-2-(3-fluoro-3,4-dihydro-2H-pyran-6-yl)-6-(4-(5-hydroxy-6-methylpyrimidine-4-carbonyl)piperazin-1-yl)-7-oxo-[1,2,4]triazolo[1,5-a]pyrimidin-4 (7H)-yl)acetamide (S)-2-(6-(4-(5-(benzyloxy)-6-methylpyrimidine-4-carbonyl)piperazin-1-yl)-5-ethyl-2-(3-fluoro-3,4-dihydro-2H-pyran-6-yl)-7-oxo-[1,2,4]triazolo[1,5-a]pyrimidin-4 (7H)-yl)-N-(2-chloro-4-(trifluoromethyl)phenyl)acetamide (11.4 mg, 11.0 μmol) in TFA (1 mL) was heated to 50° C. and stirred for 4 hours. The RM was diluted with DCM (5 mL) and evaporated under reduced pressure at 45° C. The residue was dissolved in DCM (3×5 mL) and evaporated again to give the crude product as TFA salt. This crude product was purified by reverse phase preparative HPLC (RP-HPLC basic 1: 5 to 100% B in 20 min). The product containing fractions were combined and concentrated under reduced pressure to give a yellow solid. The yellow solid was purified by reverse phase preparative HPLC (RP-HPLC basic 1: 5 to 70% B in 20 min with a plateau at 70% for 1 min) to give the title compound as a yellow resin.

LC-MS: Rt=1.03 min; MS m/z $[M+H]^+$ 720.4/722.4, m/z $[M-H]^-$ 718.3/720.3; UPLC-MS 1

$^1H$ NMR (600 MHz, DMSO-$d_6$) δ 10.36 (s, br, 1H), 8.73 (m, br, 1H), 8.47 (s, 1H), 8.09 (d, J=9.0 Hz, 1H), 7.97 (d, J=1.9 Hz, 1H), 7.71 (dd, J=2.1 Hz, 8.7 Hz, 1H), 5.83 (m, 1H), 5.31 (s, 2H), 5.14 (m, 1H), 4.53 (m, 1H), 4.35 (m, 1H), 4.03 (m, 1H), 3.49 (m, 4H), 3.24 (m, 1H), 2.98 (m, 3H), 2.81 (m, 1H), 2.62 (m, 1H), 2.41 (s, 3H), 2.35 (m, 1H), 1.18 (t, J=7.6 Hz, 3H)

Example 128: 2-(2-(3,6-dihydro-2H-pyran-4-yl)-5-ethyl-6-(4-(5-hydroxy-2-(4-methylpiperazin-1-yl)pyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide

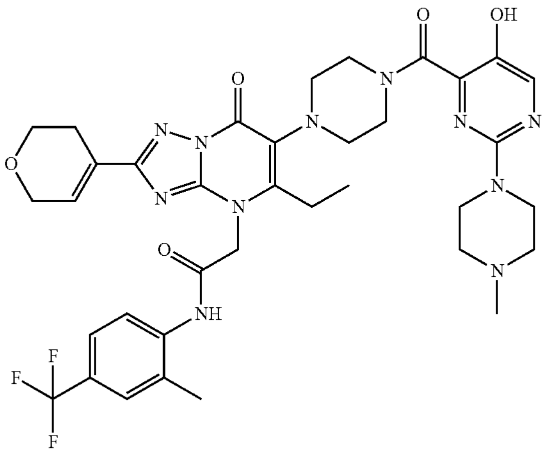 [SMILES: CCc1c(N2CCN(C(=O)c3nc(N4CCN(C)CC4)ncc3O)CC2)c(=O)n2nc(C3=CCOCC3)nc2n1CC(=O)Nc1ccc(C(F)(F)F)cc1C]

Step 1: 2-(2-(3,6-dihydro-2H-pyran-4-yl)-5-ethyl-6-(4-(5-hydroxy-2-(methylthio)pyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide

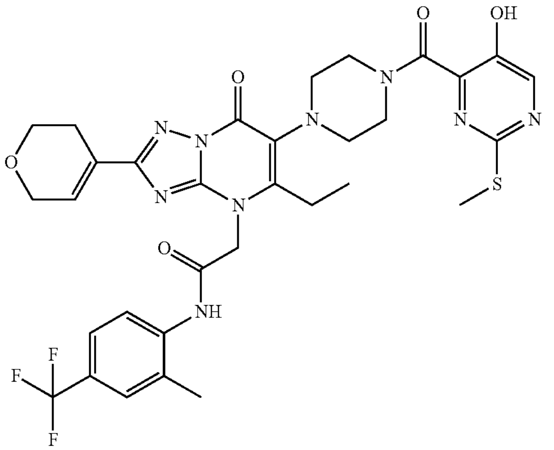 [SMILES: CCc1c(N2CCN(C(=O)c3nc(SC)ncc3O)CC2)c(=O)n2nc(C3=CCOCC3)nc2n1CC(=O)Nc1ccc(C(F)(F)F)cc1C]

The glass was flame dried in vacuo and backfilled with argon. Then the dry argon flushed flask was charged with 5-hydroxy-2-(methylthio)pyrimidine-4-carboxylic acid (194 mg, 767 μmol) and anhydrous THF (10.2 mL). The solution mixture was treated with pyridine (418 μL, 5.11 mmol) and cooled at 0° C. HOBT (237 mg, 1.53 mmol) was added prior to EDC·HCl (300 mg, 1.53 mmol) and the resulting mixture was stirred for 15 minutes. 2-(2-(3,6-Dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate AP) (300 mg, 511 μmol) was added. The bath was removed, and the resulting mixture was stirred at RT for 5 days. The reaction was quenched with aq 0.35% $NaHCO_3$ (30 mL). DCM (30 mL) was added. The organic layer was collected, and the aqueous layer was back-extracted with DCM (3×20 mL). The combined organic layers were washed with brine (60 mL), dried through a phase separator, and concentrated under reduced pressure to give a yellow oil (639 mg). The crude product was adsorbed onto Isolute and purified by column chromatography (Flash Pure ID HP silica cartridge 24 g, eluent DCM:DCM/MeOH (8/2) 100:0 to 70:30). The product containing fractions were combined and concentrated under reduced pressure to give the title compound as a white solid (203 mg, 98% pure, yield: 55%).

LC-MS: Rt=1.07 min; MS m/z $[M+H]^+$ 714.3, m/z $[M-H]^-$ 712.3; UPLC-MS 1

Step 2: 2-(2-(3,6-dihydro-2H-pyran-4-yl)-5-ethyl-6-(4-(5-hydroxy-2-(methylsulfinyl)pyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide

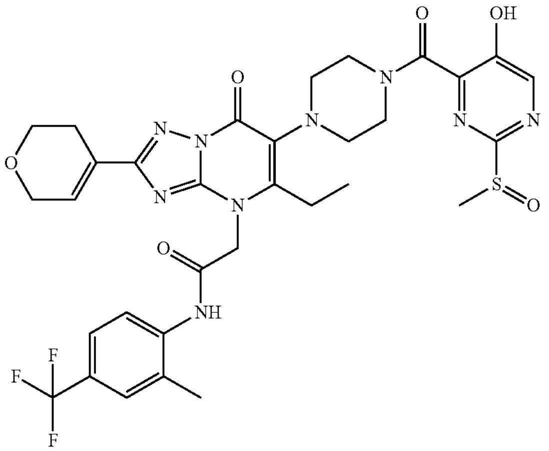 [SMILES: CCc1c(N2CCN(C(=O)c3nc(S(C)=O)ncc3O)CC2)c(=O)n2nc(C3=CCOCC3)nc2n1CC(=O)Nc1ccc(C(F)(F)F)cc1C]

A dry argon flushed flask was charged with 2-(2-(3,6-dihydro-2H-pyran-4-yl)-5-ethyl-6-(4-(5-hydroxy-2-(methylthio)pyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide (200 mg, 275 μmol) and anhydrous DCM (2.75 mL). The clear solution was cooled to 0-5° C. and m-chloroperbenzoic acid (61.5 mg, 275 μmol) was added. The RM was stirred under ice cooling for 1.75 hours. The RM was quenched with aq 0.35% $NaHCO_3$ (25 mL). DCM (15 mL) was added. The organic layer was collected, and the aqueous layer was back-extracted with DCM (3×15 mL). The combined organic layers were washed with brine (40 mL), dried through a phase separator, and concentrated under reduced pressure to give the title compound as a white powder (152 mg, 97% pure, yield: 74%).

LC-MS: Rt=0.89 min; MS m/z $[M+H]^+$ 730.3, m/z $[M-H]^-$ 728.3; UPLC-MS 1

Step 3: 2-(2-(3,6-dihydro-2H-pyran-4-yl)-5-ethyl-6-(4-(5-hydroxy-2-(4-methylpiperazin-1-yl)pyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide

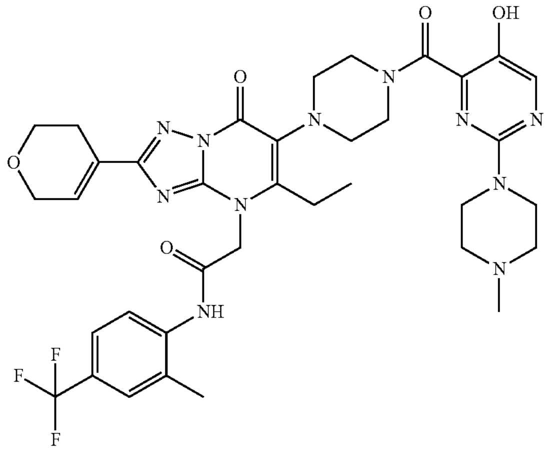 [SMILES: CCc1c(N2CCN(C(=O)c3nc(N4CCN(C)CC4)ncc3O)CC2)c(=O)n2nc(C3=CCOCC3)nc2n1CC(=O)Nc1ccc(C(F)(F)F)cc1C]

The vial was charged with 2-(2-(3,6-dihydro-2H-pyran-4-yl)-5-ethyl-6-(4-(5-hydroxy-2-(methylsulfinyl)pyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide (105 mg, 140 μmol), anhydrous NMP (1.4 mL) and 1-methylpiperazine (157 μL, 1.40 mmol). The reaction tube was sealed and irradiated at 200° C. for 1.5 hours. The RM was filtered and purified by reverse phase preparative HPLC (RP-HPLC acidic 1: 20 to 45% B in 15 min, RP-HPLC acidic 1: 20 to 40% B in 15 min with a plateau at 55% for 1 min). The product containing fractions were combined and lyophilized to give the title compound as a beige solid (4.10 mg, 98% pure, yield: 3%).

LC-MS: Rt=0.87 min; MS m/z $[M+H]^+$ 766.4, m/z $[M-H]^-$ 764.5; UPLC-MS 1

$^1$H NMR (400 MHz, DMSO-$d_6$) δ 10.02 (s, 1H), 9.80 (s, 1H), 8.20 (s, 1H), 7.71 (d, J=8.8 Hz, 1H), 7.63 (m, 1H), 7.53 (d, J=8.8 Hz, 1H), 6.83 (m, 1H), 5.25 (s, 2H), 4.49 (m, 3H), 4.26 (m, 2H), 3.81 (m, 2H), 3.44 (m, 5H), 3.26 (m, 3H), 3.00 (m, 5H), 2.82 (s, 3H), 2.79 (m, 1H), 2.65 (m, 1H), 2.53 (m, 2H), 2.35 (s, 3H), 1.20 (t, J=7.3 Hz, 3H)

Example 129: 2-(2-(3,6-dihydro-2H-pyran-4-yl)-6-(4-(3-hydroxypicolinoyl)piperazin-1-yl)-5-methyl-7-oxo-[1,2,4]triazolo[1,5-a]pyrimidin-4 (7H)-yl)-N-(2-methyl-6-(trifluoromethyl)pyridin-3-yl)acetamide

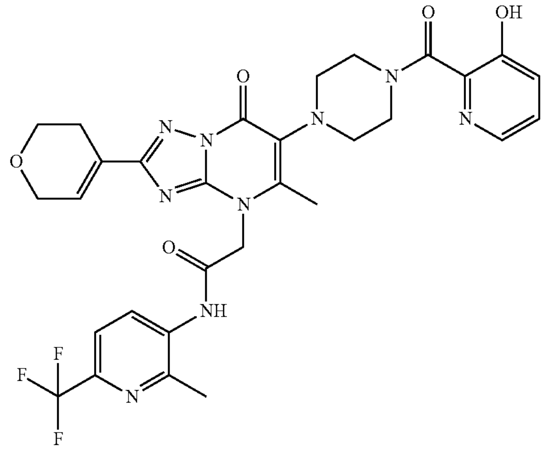 [SMILES: Cc1nc(C(F)(F)F)ccc1NC(=O)Cn1c(C)c(N2CCN(C(=O)c3ncccc3O)CC2)c(=O)n2nc(C3=CCOCC3)nc12]

2-(2-(3,6-Dihydro-2H-pyran-4-yl)-5-methyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide (Intermediate ES) (172 mg, 232 μmol) was dissolved in DCM (4 mL) at 0° C. under argon. 3-Hydroxypicolinoyl chloride (Intermediate CV) (54.8 mg, 348 μmol) was added slowly, followed by DIPEA (202 μL, 1.16 mmol). The RM was stirred at 0° C. for 20 minutes, the at RT for 1.5 hours. 3-Hydroxypicolinoyl chloride (Intermediate CV) (30.0 mg, 191 μmol) was added slowly, followed by DIPEA (100 μL, 574 μmol). The RM was stirred at RT for 30 minutes. Water (5 mL) and aq sat $NaHCO_3$ (5 mL) were added and the mixture was extracted with DCM (4×50 mL). The combined organic layers were washed with aq sat $NaHCO_3$ and water, dried through a phase separator and concentrated under reduced pressure. The crude product was purified by reverse phase preparative HPLC (RP-HPLC acidic 1: 15 to 85% B in 20 min with a plateau at 95% for 1 min). The product containing fractions were combined, basified with aq sat $NaHCO_3$, ACN was removed and the residue was extracted with DCM (4×25 mL). The combined organic layers were washed with water (10 mL), dried through a phase separator and concentrated under reduced pressure to give the title compound as a pale grey solid (99.1 mg, 100% pure, yield: 65%).

LC-MS: Rt=0.86 min; MS m/z $[M+H]^+$ 654.4, m/z $[M-H]^-$ 652.4; UPLC-MS 4

$^1$H NMR (600 MHz, DMSO-$d_6$) δ 10.39 (s, 1H), 10.25 (s, 1H), 8.23 (d, J=8.3 Hz, 1H), 8.07 (m, 1H), 7.74 (d, J=8.4 Hz, 1H), 7.29 (m, 2H), 6.84 (m, 1H), 5.31 (s, 2H), 4.53 (m, 1H), 4.27 (m, 2H), 3.81 (m, 2H), 3.45 (m, 2H), 3.39 (m, 1H), 3.24 (m, 1H), 2.98 (m, 1H), 2.78 (m, 1H), 2.62 (m, 1H), 2.60 (s, 3H), 2.58 (s, 3H), 2.54 (m, 2H)

Example 130: tert-butyl 4-(5-ethyl-6-(4-(5-hydroxy-6-methylpyrimidine-4-carbonyl)piperazin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-2-yl)-3,6-dihydropyridine-1 (2H)-carboxylate

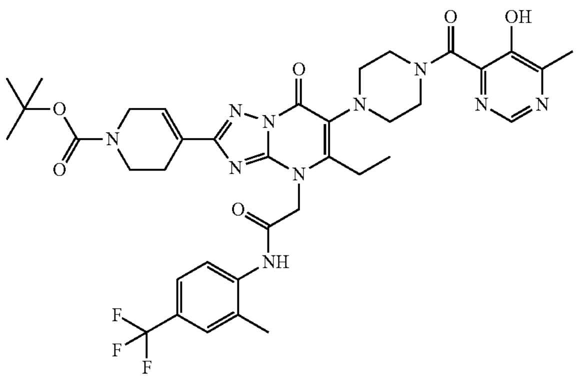 [SMILES: CCc1c(N2CCN(C(=O)c3ncnc(C)c3O)CC2)c(=O)n2nc(C3=CCN(C(=O)OC(C)(C)C)CC3)nc2n1CC(=O)Nc1ccc(C(F)(F)F)cc1C]

To a stirred solution of 2-(2-bromo-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide (Intermediate ET) (100 mg, 113 μmol), $K_3PO_4$ (72.3 mg, 340 μmol) and PdCl2(dppf)·DCM adduct (9.27 mg, 11.0 μmol) in 1,4-dioxane (4 mL) and water (2 mL) was added at RT tert-butyl 4-(4,4,5,5-tetramethyl-1,3,2-dioxaborolan-2-yl)-3,6-dihydropyridine-1 (2H)-carboxylate (52.6 mg, 170 μmol) and the RM was stirred at 80° C. for 15 minutes. The RM was diluted with EtOAc and water, extracted twice with EtOAc and the combined organic layers were washed with brine, dried over $Na_2SO_4$ and concentrated under reduced pressure. The crude product was first purified by column chromatography (RediSep Column: Silica 12 g, eluent DCM:DCM/MeOH (8/2) 100:0 to 40:60), then by reverse phase preparative HPLC (RP-HPLC basic 1: 15 to 95% B in 20 min). The product containing fractions were lyophilized to give the title compound as a white solid (62.0 mg, 98% pure, yield: 69%).

LC-MS: Rt=1.26 min; MS m/z $[M+H]^+$ 781.6; UPLC-MS 1

$^1H$ NMR (400 MHz, DMSO-$d_6$) δ 10.02 (m, 2H), 8.56 (s, 1H), 7.73 (d, J=8.2 Hz, 1H), 7.64 (m, 1H), 7.54 (d, J=8.5 Hz, 1H), 6.79 (m, 1H), 5.25 (s, 2H), 4.52 (m, 1H), 4.06 (m, 2H), 3.53 (m, 3H), 3.47 (m, 2H), 3.23 (m, 1H), 3.00 (m, 3H), 2.83 (m, 1H), 2.66 (m, 1H), 2.54 (m, 2H), 2.44 (s, 3H), 2.36 (s, 3H), 1.43 (s, 9H), 1.20 (t, J=7.2 Hz, 3H)

Example 131: N-(2-chloro-4-(trifluoromethyl)phenyl)-2-(2-(3,6-dihydro-2H-pyran-4-yl)-5-ethyl-6-((1S,6R)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((1R,6S)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide

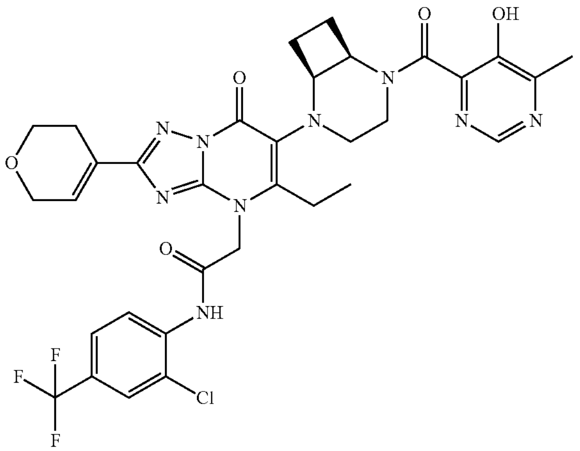

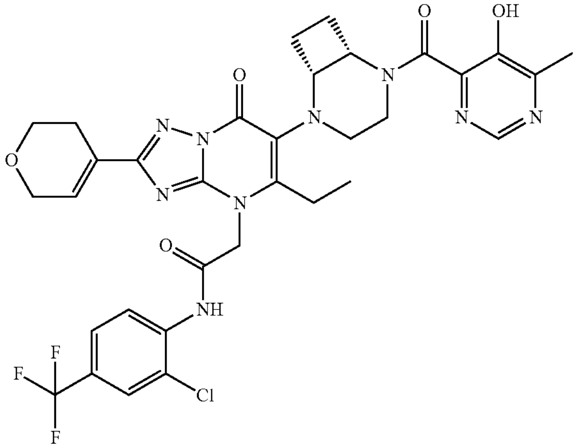

Step 1: 2-(6-((1R,6S)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide 2-(6-((1S,6R)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (Intermediate EX) (38.0 mg, 58.0 μmol), 5-(benzyloxy)-6-methylpyrimidine-4-carboxylic acid (Intermediate CY) (16.0 mg, 64.0 μmol) and HATU (26.0 mg, 69.0 μmol) were mixed in DMF (1 mL). DIPEA (20.0 μL, 120 μmol) was added and the RM was stirred at RT for 5 minutes. The RM was diluted with EtOAc and water, extracted twice with EtOAc and the combined organic layers were washed with brine, dried over $Na_2SO_4$ and concentrated under reduced pressure. The crude product was purified by column chromatography (RediSep Column: Silica 12 g, eluent DCM:DCM/MeOH (8/2) 100:0 to 50:50). The product containing fractions were combined and concentrated under reduced pressure to give the title compound as a white solid (25.0 mg, 94% pure, yield: 50%).

LC-MS: Rt=1.28 min; MS m/z $[M+H]^+$ 818.5/820.1, m/z $[M-H]^-$ 816.4/818.4; UPLC-MS 1

LC-MS: Rt=6.07 min; MS m/z $[M+H]^+$ 818.6/820.1, m/z $[M-H]^-$ 816.3/818.4; UPLC-MS 2

Step 2: N-(2-chloro-4-(trifluoromethyl)phenyl)-2-(2-(3,6-dihydro-2H-pyran-4-yl)-5-ethyl-6-((1S,6R)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((1R,6S)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide 2-(6-((1 S,6R)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (25.0 mg, 31.0 μmol) was mixed with TFA (500 μL, 6.00 mmol) and the RM was stirred at RT for 3 days. The RM was diluted with DCM and $NaHCO_3$, extracted twice with DCM and the combined organic layers were washed with brine, dried over $Na_2SO_4$, and concentrated under reduced pressure. The crude product was purified by reverse phase preparative HPLC (RP-HPLC acidic 1: 5 to 95% B in 20 min) to give the title compound as a white solid (14.0 mg, 100% pure, yield: 63%).

LC-MS: Rt=1.11 min; MS m/z $[M+H]^+$ 728.4/730.4, m/z $[M-H]^-$ 726.3/728.3; UPLC-MS 1

LC-MS: Rt=5.49 min; MS m/z $[M+H]^+$ 728.4/730.4, m/z $[M-H]^-$ 726.4/728.3; UPLC-MS 2

$^1H$ NMR (400 MHz, DMSO-$d_6$) b

Example 132: N-(2-chloro-4-(trifluoromethyl)phenyl)-2-(2-(3,6-dihydro-2H-pyran-4-yl)-5-ethyl-6-((1S,6R)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((1R,6S)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide

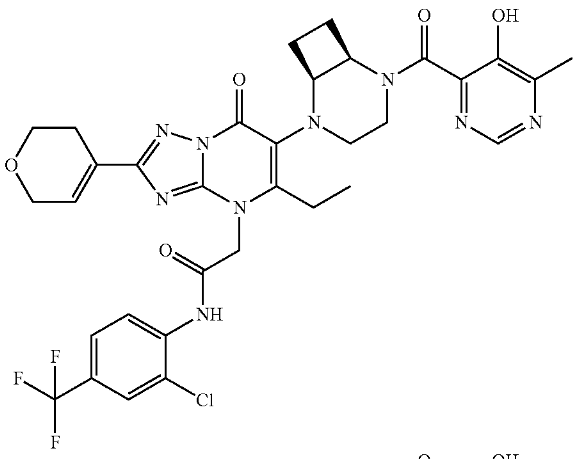

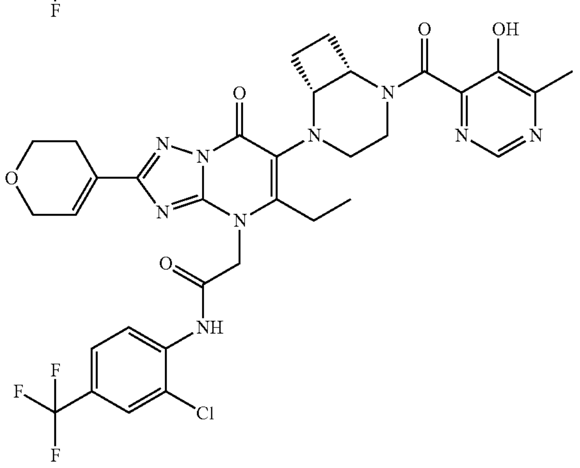

Step 1: 2-(6-((1S,6R)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide 2-(6-((1 S,6R)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (Intermediate EY) (38.0 mg, 64.0 μmol), 5-(benzyloxy)-6-methylpyrimidine-4-carboxylic acid (Intermediate CY) (17.0 mg, 71.0 μmol) and HATU (29.0 mg, 77.0 μmol) were mixed in DMF (1 mL). DIPEA (22.0 μL, 130 μmol) was added and the RM was stirred at RT for 5 minutes. The RM was diluted with EtOAc and water, extracted twice with EtOAc and the combined organic layers were washed with brine, dried over $Na_2SO_4$ and concentrated under reduced pressure. The crude product was purified by column chromatography (RediSep Column: Silica 12 g, eluent DCM:DCM/MeOH (8/2) 100:0 to 50:50). The product containing fractions were combined and concentrated under reduced pressure to give the title compound as a white solid (25.0 mg, 98% pure, yield: 47%).

LC-MS: Rt=1.27 min; MS m/z $[M+H]^+$ 818.5/820.5, m/z $[M-H]^-$ 816.5/818.6; UPLC-MS 1

LC-MS: Rt=6.14 min; MS m/z $[M+H]^+$ 818.4/820.4, m/z $[M-H]^-$ 816.4/818.4; UPLC-MS 2

Step 2: N-(2-chloro-4-(trifluoromethyl)phenyl)-2-(2-(3,6-dihydro-2H-pyran-4-yl)-5-ethyl-6-((1S,6R)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-5-ethyl-6-((1R,6S)-5-(5-hydroxy-6-methylpyrimidine-4-carbonyl)-2,5-diazabicyclo[4.2.0]octan-2-yl)-7-oxo-[1,2,4]triazolo[1,5-a]pyrimidin-4 (7H)-yl)acetamide 2-(6-((1S,6R)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-5-(5-(benzyloxy)-6-methylpyrimidine-4-carbonyl)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (25.0 mg, 31.0 μmol) was mixed with TFA (500 μL, 6.00 mmol) and the RM was stirred at RT for 3 days. The RM was diluted with DCM and $NaHCO_3$, extracted twice with DCM and the combined organic layers were washed with brine, dried over $Na_2SO_4$, and concentrated under reduced pressure. The crude product was purified by reverse phase preparative HPLC (RP-HPLC acidic 1: 5 to 95% B in 20 min) to give the title compound as a white solid (16.0 mg, 100% pure, yield: 72%).

LC-MS: Rt=1.13 min; MS m/z $[M+H]^+$ 728.5/730.5, m/z $[M-H]^-$ 726.5/728.5; UPLC-MS 1

LC-MS: Rt=5.50 min; MS m/z $[M+H]^+$ 728.4/730.4, m/z $[M-H]^-$ 726.4/728.4; UPLC-MS 2

$^1H$ NMR (600 MHz, DMSO-$d_6$) δ 10.4 (m, 2H), 8.56 (d, J=11.1 Hz, 1H), 8.04 (d, J=9.3 Hz, 1H), 7.6 (m, 1H), 7.71 (d, J=8.3 Hz, 1H), 6.83 (m, 1H), 5.45 (m, 1H), 5.23 (m, 1H), 4.95 (m, 1H), 4.36 (m, 1H), 4.24 (m, 2H), 4.13 (m, 1H), 3.99 (m, 1H), 3.79 (m, 2H), 3.57 (m, 1H), 2.89 (m, 1H), 2.71 (m, 3H), 2.50 (m, 2H), 2.44 (d, broad, J=13.6 Hz, 3H), 1.96 (m, 1H), 1.41 (m, 1H), 1.21 (m, 4H)

Example 133: N-(2-chloro-4-(trifluoromethyl)phenyl)-2-(2-(3,6-dihydro-2H-pyran-4-yl)-5-ethyl-6-(4-(5-hydroxy-6-methylpyrimidine-4-carbonyl)piperazin-1-yl-2,2,3,3,5,5,6,6-d8)-7-oxo-[1,2,4]triazolo[1,5-a]pyrimidin-4 (7H)-yl)acetamide

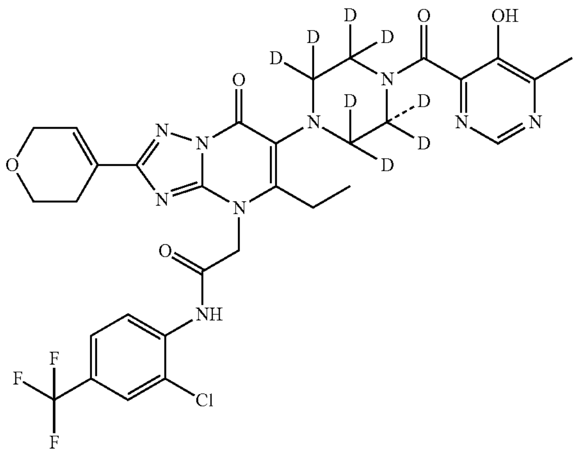

To 5-hydroxy-6-methylpyrimidine-4-carboxylic acid (102 mg, 665 μmol) in DCM (3 mL) was added 1-chloro-N,N,2-trimethylprop-1-en-1-amine (114 μL, 859 μmol). The RM was stirred at RT for 1 hour. N-(2-chloro-4-(trifluoromethyl)phenyl)-2-(2-(3,6-dihydro-2H-pyran-4-yl)-5-ethyl-7-oxo-6-(piperazin-1-yl-2,2,3,3,5,5,6,6-d8)-[1,2,4]triazolo[1,5-a]pyrimidin-4 (7H)-yl)acetamide (Intermediate EZ) (318 mg, 554 μmol) and DCM (1 mL) were added. The RM was stirred at RT for 30 minutes. DIPEA (290 μL, 1.66 mmol) was added dropwise and the mixture was continued stirring at RT for 2.5 hours. The RM was diluted with 0.5M HCl (1.6 mL) and DCM (5 mL). The biphasic mixture was stirred vigorously for 1 minute. The organic layer was separated. The aqueous layer was extracted with DCM (5 mL). The combined organic layers were dried through a phase separator and concentrated under reduced pressure. The crude product was purified in 2 portions by reverse phase preparative HPLC (RP-HPLC acidic 1: 20 to 75% B in 20 min), (RP-HPLC acidic 1: 25 to 54% B in 20 min). The product containing fractions were combined, basified to pH 8 with aq sat $NaHCO_3$, extracted with DCM (2×100 mL), dried over $Na_2SO_4$, and concentrated under reduced pressure to give the title compound as a colourless solid (174 mg, 99% pure, yield: 44%).

LC-MS: Rt=1.03 min; MS m/z $[M+H]^+$ 710.4/712.4, m/z $[M-H]^-$ 708.4/710.4; UPLC-MS 1

LC-MS: Rt=5.12 min; MS m/z $[M+H]^+$ 710.3/712.3, m/z $[M-H]^-$ 708.4/710.3; UPLC-MS 2

$^1H$ NMR (400 MHz, DMSO-$d_6$) δ 10.37 (m, 2H), 8.57 (s, 1H), 8.06 (d, J=8.5 Hz, 1H), 7.97 (m, 1H), 7.72 (dd, J=2.2 Hz, 9.2 Hz, 1H), 6.84 (m, 1H), 5.32 (s, 2H), 4.26 (m, 2H), 3.81 (m, 2H), 2.99 (m, 2H), 2.52 (m, 2H), 2.45 (s, 3H), 1.19 (t, J=7.4 Hz, 3H)

Example 134: 2-(5-cyclopropyl-2-(3,6-dihydro-2H-pyran-4-yl)-6-(4-(3-hydroxypicolinoyl)piperazin-1-yl)-7-oxo-[1,2,4]triazolo[1,5-a]pyrimidin-4 (7H)-yl)-N-(4-(trifluoromethyl)phenyl)acetamide

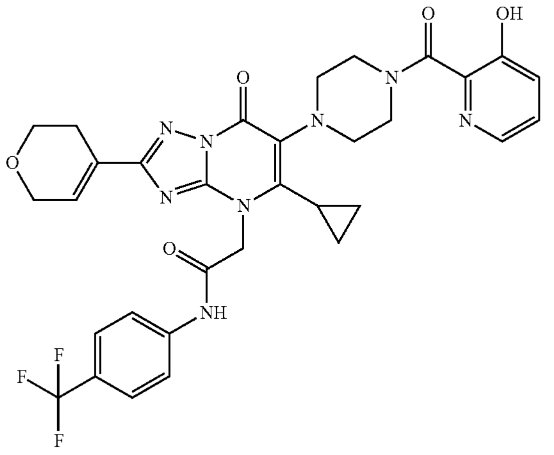 [SMILES: O=C(Cn1c(C2CC2)c(N2CCN(C(=O)c3ncccc3O)CC2)c(=O)n2nc(C3=CCOCC3)nc12)Nc1ccc(C(F)(F)F)cc1]

3-Hydroxypicolinic acid (49.1 mg, 353 μmol) was mixed with DCM (1.85 mL) at RT under argon. 1-Chloro-N,N,2-trimethylprop-1-en-1-amine (51.9 mg, 389 μmol) was added and the RM was stirred at RT for 1.75 hours. This suspension was added to a cooled suspension of 2-(5-cyclopropyl-2-(3,6-dihydro-2H-pyran-4-yl)-7-oxo-6-(piperazin-1-yl)-[1,2,4]triazolo[1,5-a]pyrimidin-4 (7H)-yl)-N-(4-(trifluoromethyl)phenyl)acetamide (Intermediate FA) (96.0 mg, 177 μmol) in DCM (1.5 mL) and DIPEA (154 μL, 883 μmol). The resulting brown solution was stirred at RT for 2.5 hours.

3-Hydroxypicolinic acid (32.4 mg, 233 μmol) was mixed with DCM (1.22 mL) at RT under argon. 1-Chloro-N,N,2-trimethylprop-1-en-1-amine (34.3 mg, 257 μmol) was added and the RM was stirred at RT for 1.75 hours. This solution was added to the previous solution, followed by DIPEA (105 μL, 602 μmol). The RM was stirred at RT for 1 hour. The RM was quenched with water (4 mL) and aq sat $NaHCO_3$ (3 mL), then it was extracted with DCM (4×20 mL). The organic layer was washed with aq sat $NaHCO_3$ and water. The organic layer was dried through a phase separator and concentrated under reduced pressure. The aqueous layer was extracted with EtOAc (3×40 mL). The organic layer was dried through a phase separator, combined with the first crude and concentrated under reduced pressure. The crude product (140 mg) was purified by reverse phase preparative HPLC (RP-HPLC acidic 1: 25 to 75% in 20 min). The product containing fractions were combined, basified with aq sat $NaHCO_3$ and ACN was removed under reduced pressure. The aqueous residue was extracted with DCM (4×30 mL) and water. The organic layer was dried through a phase separator and concentrated under reduced pressure to give the title compound as a white solid (13.7 mg). The impure product containing fractions were combined and purified again by reverse phase preparative HPLC (RP-HPLC acidic 1: 25 to 75% in 20 min). The product containing fractions were neutralized trough a PL-HCO3 MP SPE (500 mg per 6 mL) cartridge to give the title compound as a white solid (5.90 mg). Both batches were combined to give the title compound as a white solid (19.6 mg, 99% pure, yield: 17%).

LC-MS: Rt=0.99 min; MS m/z $[M+H]^+$ 665.4, m/z $[M-H]^-$ 663.4; UPLC-MS 3

$^1H$ NMR (600 MHz, DMSO-$d_6$) δ 10.86 (s, 1H), 10.39 (s, 1H), 8.07 (m, 1H), 7.78 (m, 2H), 7.71 (m, 2H), 7.30 (m, 2H), 6.80 (m, 1H), 5.35 (s, 2H), 4.40 (m, 1H), 4.24 (m, 2H), 3.80 (m, 2H), 3.42 (m, 3H), 3.25 (m, 1H), 3.10 (m, 1H), 2.87 (m, 1H), 2.71 (m, 1H), 2.58 (m, 2H), 1.76 (m, 1H), 1.24 (m, 4H)

Example 135: 2-(2-(3,6-dihydro-2H-pyran-4-yl)-5-(2-hydroxyethyl)-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl) acetamide

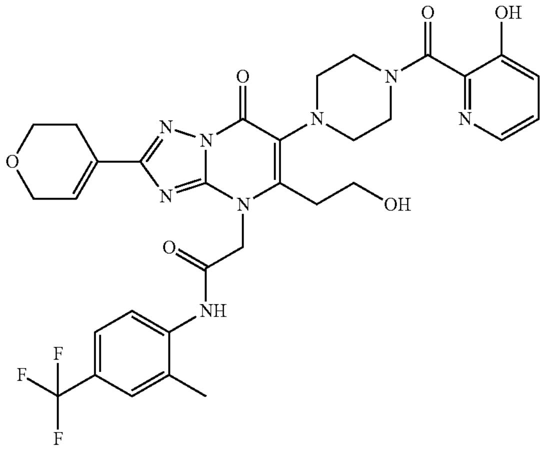 [SMILES: Cc1cc(C(F)(F)F)ccc1NC(=O)Cn1c(CCO)c(N2CCN(C(=O)c3ncccc3O)CC2)c(=O)n2nc(C3=CCOCC3)nc12]

2-(2-(3,6-dihydro-2H-pyran-4-yl)-5-(2-hydroxyethyl)-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate FB) (152 mg, 76.0 μmol) and 3-hydroxypicolinoyl chloride (Intermediate CV) (13.1 mg, 83.0 μmol) were dissolved in DCM (1 mL) and DIPEA (26.0 μL, 151 μmol) was added. The mixture was stirred at RT for 1 day. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure. The crude product was purified by column chromatography (RediSep Column: Silica 12 g, eluent DCM:DCM/MeOH (8/2) 100:0 to 60:40). The product containing fractions were combined, concentrated under vacuum, and purified by reverse phase preparative HPLC (RP-HPLC acidic 1: 5 to 100% B in 20 min). The product containing fractions were combined, basified with aq sat $NaHCO_3$, extracted twice with DCM, dried through a phase separator, and concentrated under reduced pressure to give the title compound (17.2 mg, 97% pure, yield: 32%).

LC-MS: Rt=0.92 min; MS m/z $[M+H]^+$ 683.5, m/z $[M-H]^-$ 681.5; UPLC-MS 1

$^1H$ NMR (400 MHz, DMSO-$d_6$) δ 10.37 (s, 1H), 10.01 (s, 1H), 8.06 (m, 1H), 7.73 (d, J=8.5 Hz, 1H), 7.62 (m, 1H), 7.53 (d, J=8.5 Hz, 1H), 7.28 (m, 2H), 6.84 (m, 1H), 5.34 (s, 2H), 5.02 (m, 1H), 4.53 (m, 1H), 4.26 (m, 2H), 3.81 (m, 2H), 3.73 (m, 2H), 3.44 (m, 3H), 3.20 (m, 3H), 2.95 (m, 1H), 2.81 (m, 1H), 2.64 (m, 1H), 2.51 (m, 2H), 2.35 (s, 3H)

Example 136: 2-(2-(3,6-dihydro-2H-pyran-4-yl)-6-(1-(3-hydroxypicolinoyl)piperidin-4-yl)-5-methyl-7-oxo-[1,2,4]triazolo[1,5-a]pyrimidin-4 (7H)-yl)-N-(4-(trifluoromethyl)phenyl)acetamide

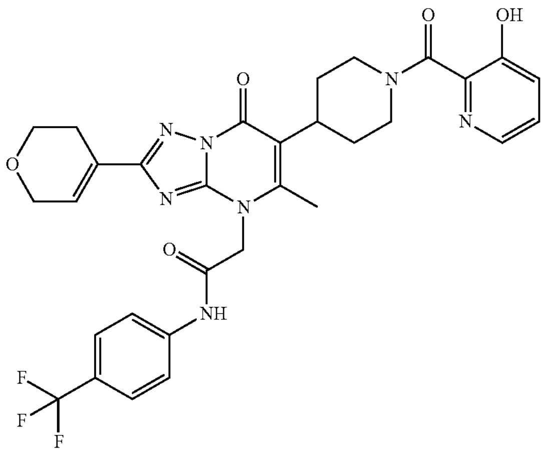 [SMILES: Cc1c(C2CCN(C(=O)c3ncccc3O)CC2)c(=O)n2nc(C3=CCOCC3)nc2n1CC(=O)Nc1ccc(C(F)(F)F)cc1]

3-Hydroxypicolinic acid (8.89 mg, 64.0 μmol) was mixed with thionyl chloride (6.91 mg, 58.0 μmol) at 80° C. for 1 hour. S02 gas evolution was detected. The RM was cooled down, dissolved with toluene, and evaporated to dryness. The residue was dissolved in DCM (1.16 mL) and DIPEA (40.6 μL, 232 μmol) was added, followed by 2-(2-(3,6-dihydro-2H-pyran-4-yl)-5-methyl-7-oxo-6-(piperidin-4-yl)-[1,2,4]triazolo[1,5-a]pyrimidin-4 (7H)-yl)-N-(4-(trifluoromethyl)phenyl)acetamide (Intermediate FC) (30.0 mg, 58.0 μmol). The RM was stirred at RT for 2 days. DCM was added and the RM was washed with aq sat $NaHCO_3$ and water. The organic layer was dried through a phase separator and concentrated under reduced pressure. The crude product was purified by column chromatography (Silica gel column, eluent DCM:MeOH 100:0 to 95:5), then by reverse phase preparative HPLC (RP-HPLC basic 1: 6 to 36% B in 20 min) to give the title compound (2.00 mg, 90% pure, yield: 5%).

LC-MS: Rt=0.95 min; MS m/z $[M+H]^+$ 638.2, m/z $[M-H]^-$ 636.2; UPLC-MS 4

LC-MS: Rt=4.55 min; MS m/z $[M+H]^+$ 638.2, m/z $[M-H]^-$ 636.2; UPLC-MS 14

$^1$H NMR (600 MHz, DMSO-$d_6$) δ 10.91 (m, 2H), 8.00 (m, 1H), 7.78 (d, J=8.4 Hz, 2H), 7.70 (d, J=8.6 Hz, 2H), 7.24 (m, 2H), 6.80 (m, 1H), 5.25 (s, 2H), 4.64 (m, 1H), 4.23 (m, 2H), 3.79 (m, 2H), 3.47 (m, 1H), 3.12 (m, 3H), 2.82 (m, 1H), 2.50 (m, 5H), 2.31 (m, 1H), 1.59 (m, 1H), 1.41 (m, 1H)

Example 137 N-(2-chloro-4-(trifluoromethyl)phenyl)-2-(2-(3,6-dihydro-2H-pyran-4-yl)-5-ethyl-6-(4-((3-hydroxypyridin-2-yl)sulfonyl)piperazin-1-yl)-7-oxo-[1,2,4]triazolo[1,5-a]pyrimidin-4 (7H)-yl) acetamide

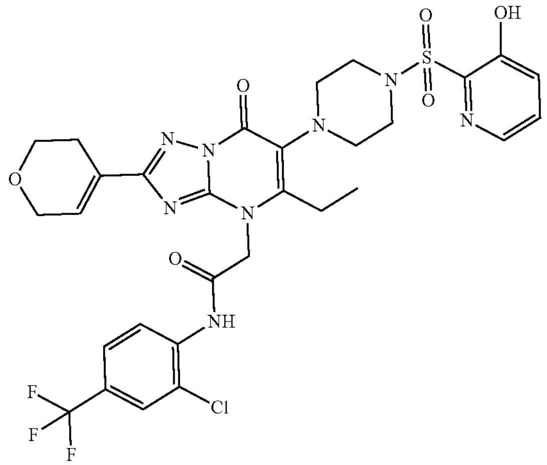 [SMILES: CCc1c(N2CCN(S(=O)(=O)c3ncccc3O)CC2)c(=O)n2nc(C3=CCOCC3)nc2n1CC(=O)Nc1ccc(C(F)(F)F)cc1Cl]

Step 1: 2-(6-(4-((3-(benzyloxy)pyridin-2-yl)sulfonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl) acetamide To a stirred solution of N-(2-chloro-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide (Intermediate AK) (71 mg, 125 μmol) was added triethylamine (35 μL, 250 mmol) followed by (3-(benzyloxy)pyridine-2-sulfonyl chloride (commercially available) (36 mg, 125 μmol) at RT and the RM was stirred at RT for 10 minutes. Diluted with water (1 ml) and DCM (5 ml) and stirred vigorously for 1 minute. The organic phase was separated by filtering through a phase separator and concentrated under reduced pressure to afford the title compound as a pale brown solid.

LC-MS: Rt=1.25 min; MS m/z $[M+H]^+$ 813.5/815.5, m/z $[M-H]^-$ 811.5/813.5; UPLC-MS 1

Step 2: N-(2-chloro-4-(trifluoromethyl)phenyl)-2-(2-(3,6-dihydro-2H-pyran-4-yl)-5-ethyl-6-(4-((3-hydroxypyridin-2-yl)sulfonyl)piperazin-1-yl)-7-oxo-[1,2,4]triazolo[1,5-a]pyrimidin-4 (7H)-yl)acetamide 2-(6-(4-((3-(benzyloxy)pyridin-2-yl)sulfonyl)piperazin-1-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide was mixed with TFA (2 ml) and stirred at 60° C. for 18 hours. The RM was concentrated under reduced pressure and purified by reverse phase preparative HPLC (RP-HPLC acidic 1: 20 to 60% B in 20 min). The product containing fractions were combined, basified with aq sat $NaHCO_3$ and the ACN was removed under reduced pressure. The residue was extracted with DCM (3×10 mL), dried over $Na_2SO_4$ and concentrated under reduced pressure to give the title compound as a colourless solid.

LC-MS: Rt=1.08 min; MS m/z $[M+H]^+$ 723.1/725.0, m/z $[M-H]^-$ 721.1/723.1; UPLC-MS 1

$^1$H NMR (400 MHz, DMSO-$d_6$) δ 10.97 (s, 1H), 10.37 (s, 1H), 8.14 (m, 1H), 8.06 (m, 1H), 7.98 (m, 1H), 7.72 (m, 1H), 7.51 (m, 2H), 6.83 (m, 1H), 5.32 (s, 2H), 4.27 (m, 2H), 3.79 (m, 3H), 3.56 (m, 2H), 3.19 (m, 3H), 2.94 (m, 2H), 2.74 (m, 2H), 1.17 (m, 3H)

Preparation of Intermediates

Scheme 2 general overview of intermediates of route I

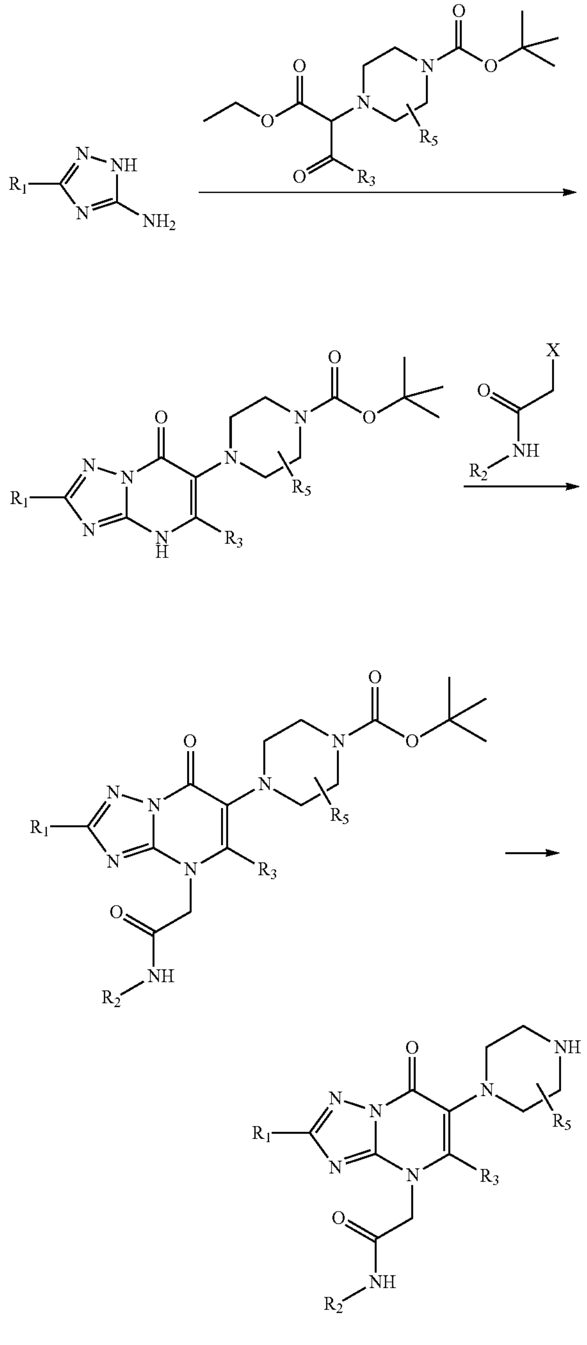

Intermediate A: tert-butyl 4-(5-ethyl-2-morpholino-7-oxo-4,7-dihydro-[1,2,4]triazolo[1,5-a]pyrimidin-6-yl)piperazine-1-carboxylate

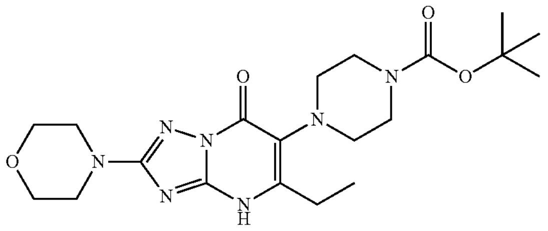 [SMILES: CCc1[nH]c2nc(N3CCOCC3)nn2c(=O)c1N1CCN(C(=O)OC(C)(C)C)CC1]

To the stirred solution of 3-morpholino-1H-1,2,4-triazol-5-amine (12.0 g, 71.0 mmol) in EtOH (100 mL), were added tert-butyl 4-(1-ethoxy-1,3-dioxopentan-2-yl)piperazine-1-carboxylate (Intermediate EJ) (34.9 g, 106 mmol) and $H_3PO_4$ (3.70 mL, 71.0 mmol) at RT. The RM was stirred at 110° C. for 48 hours. The RM was filtered to obtain a first portion of the product. To the filtrate were added $Boc_2O$ (16.5 mL, 71.0 mmol) and DIPEA (12.4 mL, 71.0 mmol) at 0° C. and the RM was stirred at RT for 16 hours. The RM was filtered to obtain a second portion of the product which was combined with the first portion to give the title compound.

LC-MS: Rt=1.43 min; MS m/z $[M+H]^+$ 434.2; UPLC-MS 11

Intermediate B: N-(2-chloro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl) acetamide Step 1: tert-butyl 4-(4-(2-((2-chloro-4-(trifluoromethyl)phenyl)amino)-2-oxoethyl)-5-ethyl-2-morpholino-7-oxo-4,7-dihydro-[1,2,4]triazolo[1,5-a] pyrimidin-6-yl)piperazine-1-carboxylate

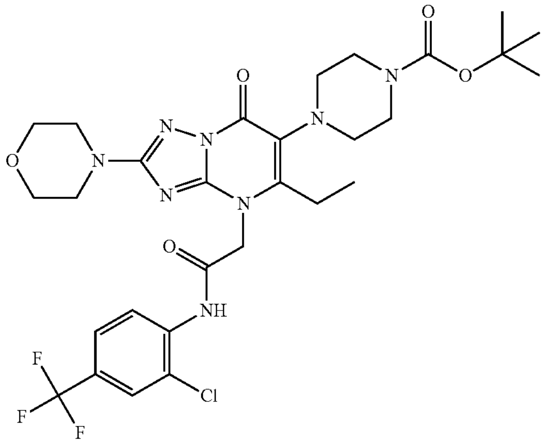 [SMILES: CCc1c(N2CCN(C(=O)OC(C)(C)C)CC2)c(=O)n2nc(N3CCOCC3)nc2n1CC(=O)Nc1ccc(C(F)(F)F)cc1Cl]

To tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (500 mg, 1.15 mmol) in DMF (4 mL) was added DIPEA (504 μL, 2.88 mmol) followed by N-(2-chloro-4-(trifluoromethyl)phenyl)-2-iodoacetamide (Intermediate DL) (440 mg, 1.21 mmol). The RM was stirred at RT for 24 hours. The RM was diluted with water (10 mL) and the resulting suspension was stirred at RT for 20 minutes, filtered and washed with water (10 mL) then dried under vacuum to give the title compound as an off-white solid.

LC-MS: Rt=1.30 min; MS m/z $[M-H]^-$ 667.5/669.5; UPLC-MS 1

Step 2: N-(2-chloro-4-(trifluoromethyl)phenyl)-2-(5-ethyl-2-morpholino-7-oxo-6-(piperazin-1-yl)-[1,2,4] triazolo[1,5-a]pyrimidin-4 (7H)-yl)acetamide

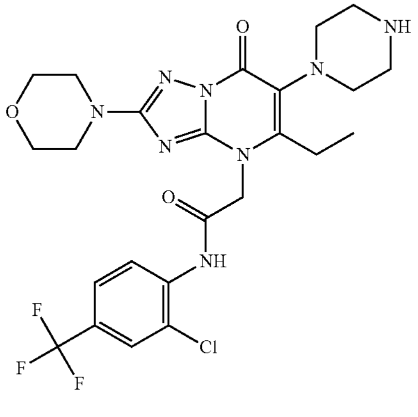 [SMILES: CCc1c(N2CCNCC2)c(=O)n2nc(N3CCOCC3)nc2n1CC(=O)Nc1ccc(C(F)(F)F)cc1Cl]

Tert-butyl 4-(4-(2-((2-chloro-4-(trifluoromethyl)phenyl) amino)-2-oxoethyl)-5-ethyl-2-morpholino-7-oxo-4,7-dihydro-[1,2,4]triazolo[1,5-a]pyrimidin-6-yl)piperazine-1-carboxylate (700 mg, 1.05 mmol) was dissolved in DCM (5 mL) and TFA (1.21 mL, 15.7 mmol) was added and the RM was stood at RT for 2 hours. The RM was evaporated in vacuo to give the desired product trifluoroacetate salt as a brown solid.

LC-MS: Rt=0.78 min; MS m/z $[M+H]^+$ 569.3/571.3, m/z $[M-H]^-$ 567.2/569.2; UPLC-MS 1 The free base of intermediate B can be prepared by partitioning the TFA salt between dichloromethane and saturated aqueous $NaHCO_3$, followed by separation and drying of the organic layer.

Intermediate C: N-(5-chloro-2-methyl-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide Step 1: tert-butyl 4-(4-(2-((5-chloro-2-methyl-4-(trifluoromethyl)phenyl)amino)-2-oxoethyl)-5-ethyl-2-morpholino-7-oxo-4,7-dihydro-[1,2,4]triazolo[1,5-a]pyrimidin-6-yl)piperazine-1-carboxylate

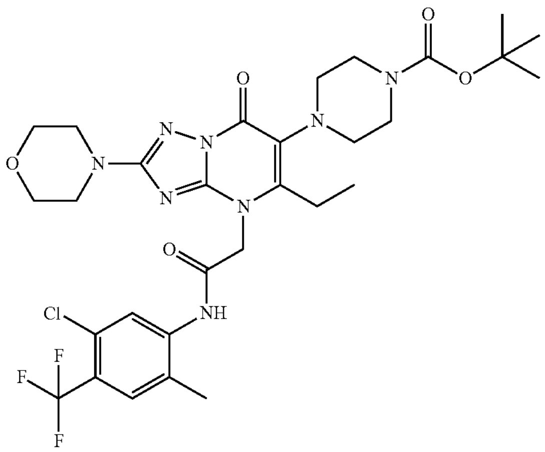 [SMILES: CCc1c(N2CCN(C(=O)OC(C)(C)C)CC2)c(=O)n2nc(N3CCOCC3)nc2n1CC(=O)Nc1cc(Cl)c(C(F)(F)F)cc1C]

To the stirred solution of tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (600 mg, 1.38 mmol) in DMF (4 mL) were added 2-bromo-N-(5-chloro-2-methyl-4-(trifluoromethyl)phenyl)acetamide (Intermediate DM) (550 mg, 1.66 mmol) and DIPEA (600 μL, 3.47 mmol) at 0° C. The RM was stirred at RT for 16 hours. The RM was concentrated under reduced pressure and ice was added to the remaining suspension, then it was filtered and dried under reduced pressure. The crude product was purified by column chromatography (Silica gel column: Silica 12 g, eluent DCM:MeOH 95:5 to 90:10). The product containing fractions were combined and concentrated under reduced pressure to give the title compound as a brown solid.

LC-MS: Rt=1.64 min; MS m/z $[M-H]^-$ 681.3/683.3; UPLC-MS 11

Step 2: N-(5-chloro-2-methyl-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide

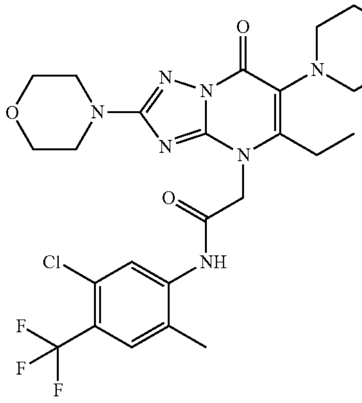

To tert-butyl 4-(4-(2-((5-chloro-2-methyl-4-(trifluoromethyl)phenyl)amino)-2-oxoethyl)-5-ethyl-2-morpholino-7-oxo-4,7-dihydro-[1,2,4]triazolo[1,5-a]pyrimidin-6-yl)piperazine-1-carboxylate (1.00 g, 1.46 mmol) was added TFA (10.0 mL, 130 mmol) and DCM (10 mL) at 0° C. The RM was stirred at 40° C. for 14 hours. The RM was concentrated under reduced pressure to give the title compound.

LC-MS: Rt=1.36 min; MS m/z $[M+H]^+$ 583.2/585.2; UPLC-MS 11

Intermediate D: 2-(5-ethyl-2-morpholino-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide Step 1: tert-butyl 4-(5-ethyl-4-(2-((5-fluoro-2-methyl-4-(trifluoromethyl)phenyl)amino)-2-oxoethyl)-2-morpholino-7-oxo-4,7-dihydro-[1,2,4]triazolo[1,5-a]pyrimidin-6-yl)piperazine-1-carboxylate

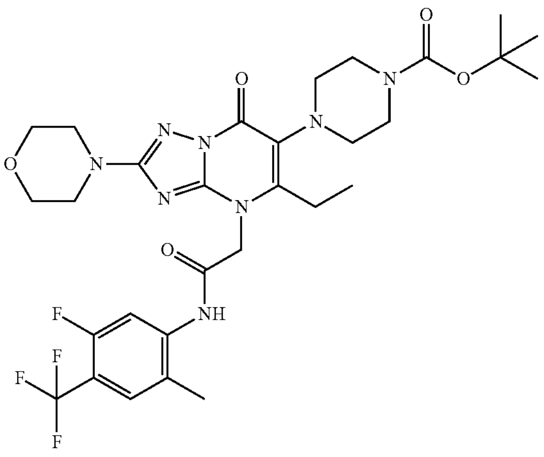 [SMILES: CCc1c(N2CCN(C(=O)OC(C)(C)C)CC2)c(=O)n2nc(N3CCOCC3)nc2n1CC(=O)Nc1cc(F)c(C(F)(F)F)cc1C]

Tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (350 mg, 807 μmol) was suspended in DMF (4 mL). 2-Bromo-N-(5-fluoro-2-methyl-4-(trifluoromethyl)phenyl)acetamide (Intermediate DN) (254 mg, 807 μmol) and DIPEA (423 μL, 2.42 mmol) were added at 0° C. and the RM was stirred at RT for 12 hours. The RM was cooled to 0° C., water was added and the precipitate was filtered, washed with hexane and dried under reduced pressure. The crude product was purified by column chromatography (Silica gel column: Silica 12 g, eluent DCM: MeOH 100:0 to 98:2). The product containing fractions were combined, concentrated and dried under HV to give the title compound as an off-white solid.

LC-MS: Rt=1.63 min; MS m/z $[M+H]^+$ 667.3; UPLC-MS 11

Step 2: 2-(5-ethyl-2-morpholino-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide

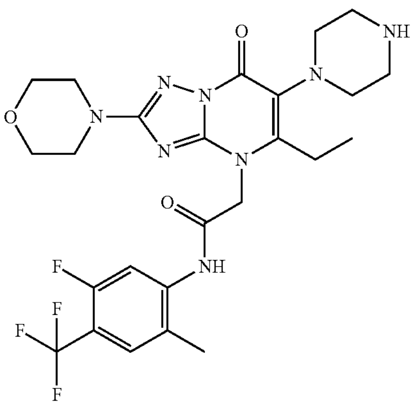 [SMILES: CCc1c(N2CCNCC2)c(=O)n2nc(N3CCOCC3)nc2n1CC(=O)Nc1cc(F)c(C(F)(F)F)cc1C]

To the solution of tert-butyl 4-(5-ethyl-4-(2-((5-fluoro-2-methyl-4-(trifluoromethyl)phenyl)amino)-2-oxoethyl)-2-morpholino-7-oxo-4,7-dihydro-[1,2,4]triazolo[1,5-a]pyrimidin-6-yl)piperazine-1-carboxylate (300 mg, 449 μmol) in 1,4-dioxane (10 mL) was added HCl 4M in 1,4-dioxane (10.0 mL, 40.0 mmol) at 0° C. and the RM was stirred at RT for 16 hours. The RM was concentrated under reduced pressure and washed with $Et_2O$ (2×10 mL) and dried under reduced pressure to give the HCl salt of the title compound as an off-white solid.

LC-MS: Rt=1.35 min; MS m/z $[M+H]^+$ 567.3; UPLC-MS 11 Intermediate E: N-(2-chloro-5-fluoro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide Step 1: tert-butyl 4-(4-(2-((2-chloro-5-fluoro-4-(trifluoromethyl)phenyl)amino)-2-oxoethyl)-5-ethyl-2-morpholino-7-oxo-4,7-dihydro-[1,2,4]triazolo[1,5-a]pyrimidin-6-yl)piperazine-1-carboxylate

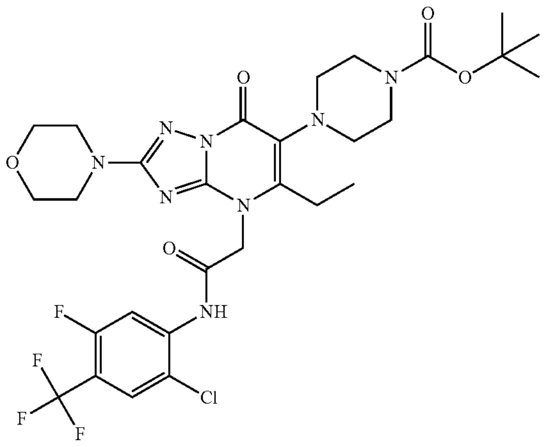

Tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (400 mg, 920 μmol) was suspended in DMF (5 mL). 2-Bromo-N-(2-chloro-5-fluoro-4-(trifluoromethyl)phenyl)acetamide (Intermediate DO) (463 mg, 1.38 mmol) and DIPEA (403 μL, 2.31 mmol) were added at 0° C. and the RM was stirred at RT for 14 hours. The RM was cooled to 0° C., water was added and the precipitate was filtered off, washed with hexane and dried under reduced pressure. The crude product was purified by column chromatography (Silica gel column: Silica 12 g, eluent DCM:MeOH 100:0 to 98:2). The product containing fractions were combined, concentrated under reduced pressure and dried under HV to give the title compound.

LC-MS: Rt=1.67 min; MS m/z $[M+H]^+$ 687.3/689.3; UPLC-MS 11

Step 2: N-(2-chloro-5-fluoro-4-(trifluoromethyl)phenyl)-2-(5-ethyl-2-morpholino-7-oxo-6-(piperazin-1-yl)-[1,2,4]triazolo[1,5-a]pyrimidin-4 (7H)-yl)acetamide

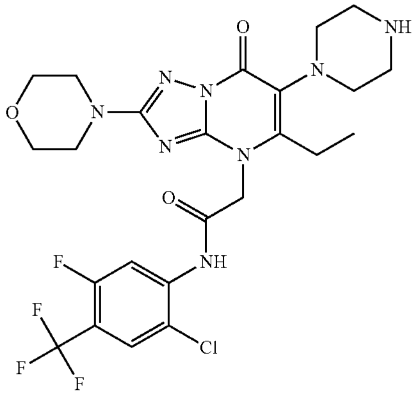 [SMILES: CCc1c(N2CCNCC2)c(=O)n2nc(N3CCOCC3)nc2n1CC(=O)Nc1cc(F)c(C(F)(F)F)cc1Cl]

To the solution of tert-butyl 4-(4-(2-((2-chloro-5-fluoro-4-(trifluoromethyl)phenyl)amino)-2-oxoethyl)-5-ethyl-2-morpholino-7-oxo-4,7-dihydro-[1,2,4]triazolo[1,5-a]pyrimidin-6-yl)piperazine-1-carboxylate (400 mg, 582 μmol) in DCM (5 mL) was added HCl 4M in 1,4-dioxane (10.0 mL, 40.0 mmol) at 0° C. and the reaction mixture was stirred at RT for 16 hours. The RM was concentrated under reduced pressure, washed with $Et_2O$ (2×10 mL) and dried under HV to give the title compound as an off-white solid, as the HCl salt.

LC-MS: Rt=1.34 min; MS m/z $[M+H]^+$ 587.2/589.2; UPLC-MS 11

Intermediate F: 2-(5-ethyl-2-morpholino-7-oxo-6-(piperazin-1-yl)-[1,2,4]triazolo[1,5-a]pyrimidin-4 (7H)-yl)-N-(2-methyl-4-(trifluoromethyl)phenyl) acetamide Step 1: tert-butyl 4-(5-ethyl-4-(2-((2-methyl-4-(trifluoromethyl)phenyl)amino)-2-oxoethyl)-2-morpholino-7-oxo-4,7-dihydro-[1,2,4]triazolo[1,5-a]pyrimidin-6-yl)piperazine-1-carboxylate

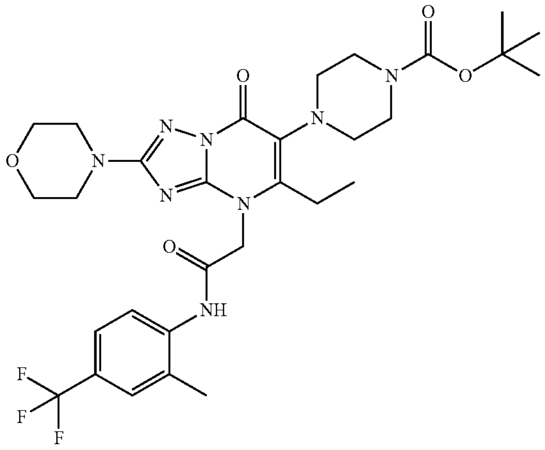

To the stirred solution of tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (500 mg, 1.15 mmol) in DMF (5 mL) were added 2-bromo-N-(2-methyl-4-(trifluoromethyl)phenyl)acetamide (Intermediate DP) (410 mg, 1.38 mmol) and DIPEA (504 μL, 2.88 mmol). The RM was stirred at RT for 16 hours. The RM was concentrated under reduced pressure, water was added and the RM was extracted with DCM. The combined organic layers were dried over $Na_2SO_4$, concentrated and dried under reduced pressure. The crude product was purified by column chromatography (Silica gel column: Silica 12 g, eluent DCM:MeOH 95:5 to 90:10). The product containing fractions were combined and concentrated under reduced pressure to give the title compound as a brown sticky liquid.

LC-MS: Rt=1.65 min; MS m/z $[M+H]^+$ 649.3; UPLC-MS 11

Step 2: 2-(5-ethyl-2-morpholino-7-oxo-6-(piperazin-1-yl)-[1,2,4]triazolo[1,5-a]pyrimidin-4 (7H)-yl)-N-(2-methyl-4-(trifluoromethyl)phenyl)acetamide

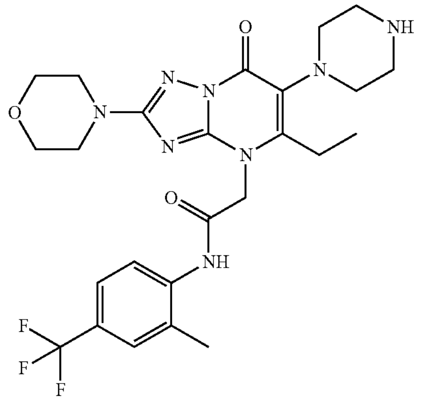 [SMILES: CCc1c(N2CCNCC2)c(=O)n2nc(N3CCOCC3)nc2n1CC(=O)Nc1ccc(C(F)(F)F)cc1C]

To the stirred solution of tert-butyl 4-(5-ethyl-4-(2-((2-methyl-4-(trifluoromethyl)phenyl)amino)-2-oxoethyl)-2-morpholino-7-oxo-4,7-dihydro-[1,2,4]triazolo[1,5-a]pyrimidin-6-yl)piperazine-1-carboxylate (500 mg, 771 μmol) in 1,4-dioxane (15 mL) was added HCl 4M in 1,4-dioxane (7.50 mL, 30.0 mmol) at 0° C. The RM was stirred at RT for 12 hours. The RM was concentrated, washed three times with a mixture of pentane and $Et_2O$ (1:1) and dried under reduced pressure to give the title compound, as the HCl salt.

LC-MS: Rt=1.35 min; MS m/z $[M+H]^+$ 549.2; UPLC-MS 11

Intermediate G: N-(2-chloro-6-(trifluoromethyl)pyridin-3-yl)-2-(5-ethyl-2-morpholino-7-oxo-6-(piperazin-1-yl)-[1,2,4]triazolo[1,5-a]pyrimidin-4 (7H)-yl)acetamide Step 1: tert-butyl 4-(4-(2-((2-chloro-6-(trifluoromethyl)pyridin-3-yl)amino)-2-oxoethyl)-5-ethyl-2-morpholino-7-oxo-4,7-dihydro-[1,2,4]triazolo[1,5-a]pyrimidin-6-yl)piperazine-1-carboxylate

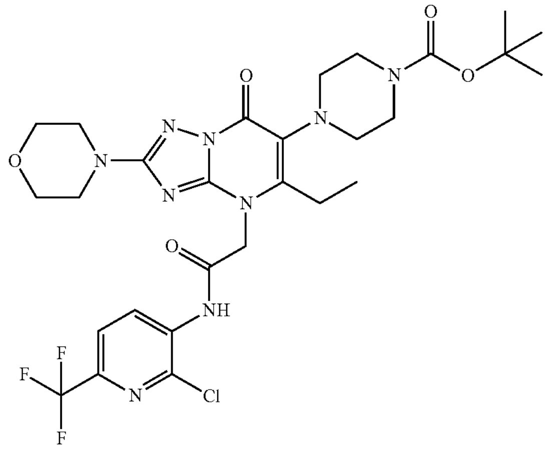 [SMILES: CCc1c(N2CCN(C(=O)OC(C)(C)C)CC2)c(=O)n2nc(N3CCOCC3)nc2n1CC(=O)Nc1ccc(C(F)(F)F)nc1Cl]

Tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (950 mg, 2.19 mmol) was suspended in DMF (5 mL). 2-Bromo-N-(2-chloro-6-(trifluoromethyl)pyridin-3-yl)acetamide (Intermediate DQ) (626 mg, 1.97 mmol) and DIPEA (957 μL, 5.48 mmol) were added at 0° C. and the RM was stirred at RT for 12 hours. Water was added and the precipitate was filtered off, washed with $Et_2O$ and dried under HV to give the title compound.

LC-MS: Rt=1.81 min; MS m/z $[M+H]^+$ 670.0/672.0; UPLC-MS 12

Step 2: N-(2-chloro-6-(trifluoromethyl)pyridin-3-yl)-2-(5-ethyl-2-morpholino-7-oxo-6-(piperazin-1-yl)-[1,2,4]triazolo[1,5-a]pyrimidin-4 (7H)-yl)acetamide

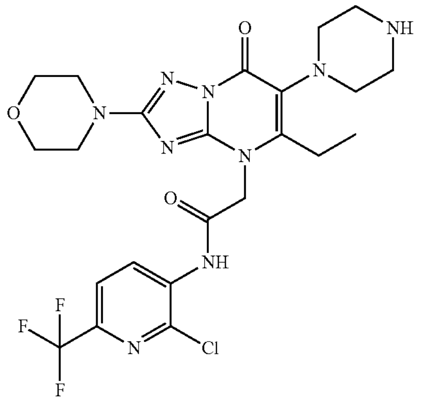

Tert-butyl 4-(4-(2-((2-chloro-6-(trifluoromethyl)pyridin-3-yl)amino)-2-oxoethyl)-5-ethyl-2-morpholino-7-oxo-4,7-dihydro-[1,2,4]triazolo[1,5-a]pyrimidin-6-yl)piperazine-1-carboxylate (1.10 g, 1.36 mmol) was suspended in 1,4-dioxane (10 mL) and HCl 4M in 1,4-dioxane (10.0 mL, 40.0 mmol) was added at 0° C. and the RM was stirred at RT for 12 hours. The RM was concentrated under reduced pressure to give the title compound, as the HCl salt.

LC-MS: Rt=1.35 min; MS m/z $[M+H]^+$ 570.2/572.2; UPLC-MS 11

Intermediate H: 2-(5-ethyl-2-morpholino-7-oxo-6-(piperazin-1-yl)-[1,2,4]triazolo[1,5-a]pyrimidin-4(7H)-yl)-N-(2-fluoro-4-(trifluoromethyl)phenyl)acetamide Step 1: tert-butyl 4-(5-ethyl-4-(2-((2-fluoro-4-(trifluoromethyl)phenyl)amino)-2-oxoethyl)-2-morpholino-7-oxo-4,7-dihydro-[1,2,4]triazolo[1,5-a]pyrimidin-6-yl)piperazine-1-carboxylate

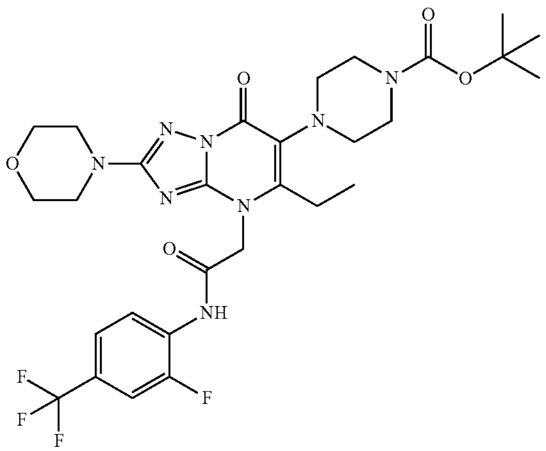 [SMILES: CCc1c(N2CCN(C(=O)OC(C)(C)C)CC2)c(=O)n2nc(N3CCOCC3)nc2n1CC(=O)Nc1ccc(C(F)(F)F)cc1F]

To the stirred solution of tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (800 mg, 1.85 mmol) in DMF (6 mL) were added 2-bromo-N-(2-fluoro-4-(trifluoromethyl)phenyl)acetamide (Intermediate DR) (665 mg, 2.22 mmol) and DIPEA (806 μL, 4.61 mmol) at 0° C. and the RM was stirred at RT for 16 hours. The RM was concentrated under reduced pressure, ice cold water was added and the precipitate was filtered off and dried under reduced pressure. The crude product was purified by column chromatography (Silica gel column: Silica 24 g, eluent DCM:MeOH 100:0 to 90:10). The product containing fractions were combined, concentrated under reduced pressure and dried under HV to give the title compound as a brown solid.

LC-MS: Rt=1.60 min; MS m/z $[M-H]^-$ 651.3; UPLC-MS 11

Step 2: 2-(5-ethyl-2-morpholino-7-oxo-6-(piperazin-1-yl)-[1,2,4]triazolo[1,5-a]pyrimidin-4(7H)-yl)-N-(2-fluoro-4-(trifluoromethyl)phenyl)acetamide

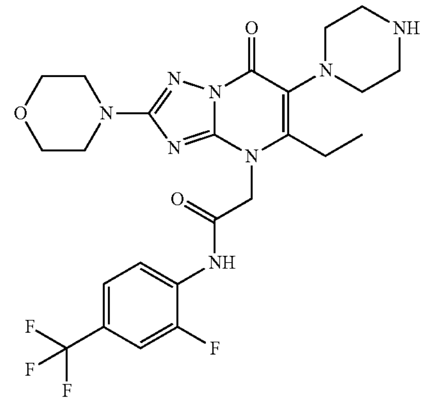

To the stirred solution of tert-butyl 4-(5-ethyl-4-(2-((2-fluoro-4-(trifluoromethyl)phenyl)amino)-2-oxoethyl)-2-morpholino-7-oxo-4,7-dihydro-[1,2,4]triazolo[1,5-a]pyrimidin-6-yl)piperazine-1-carboxylate (500 mg, 766 μmol) in DCM (10 mL) was added HCl 4M in 1,4-dioxane (2.00 mL, 8.00 mmol) at 0° C. and the RM was stirred at RT for 6 hours. The RM was concentrated under reduced pressure to give the title compound, as the HCl salt.

LC-MS: Rt=1.32 min; MS m/z $[M+H]^+$ 553.3; UPLC-MS 11

Intermediate I: N-(4-chloro-2-methyl-5-(trifluoromethyl)phenyl)-2-(5-ethyl-2-morpholino-7-oxo-6-(piperazin-1-yl)-[1,2,4]triazolo[1,5-a]pyrimidin-4(7H)-yl)acetamide Step 1: tert-butyl 4-(4-(2-((4-chloro-2-methyl-5-(trifluoromethyl)phenyl)amino)-2-oxoethyl)-5-ethyl-2-morpholino-7-oxo-4,7-dihydro-[1,2,4]triazolo[1,5-a]pyrimidin-6-yl)piperazine-1-carboxylate

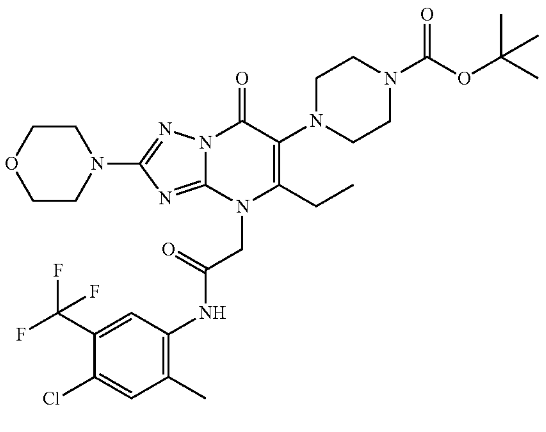 [SMILES: CCc1c(N2CCN(C(=O)OC(C)(C)C)CC2)c(=O)n2nc(N3CCOCC3)nc2n1CC(=O)Nc1cc(C(F)(F)F)c(Cl)cc1C]

Tert-butyl 4-(5-ethyl-2-morpholino-7-oxo-4,7-dihydro-[1,2,4]triazolo[1,5-a]pyrimidin-6-yl)piperazine-1-carboxylate (Intermediate A) (600 mg, 1.38 mmol) was suspended in DMF (10 mL). 2-Bromo-N-(4-chloro-2-methyl-5-(trifluoromethyl)phenyl)acetamide (Intermediate DS) (503 mg, 1.52 mmol) and DIPEA (604 μL, 3.46 mmol) were added at 0° C. and the RM was stirred at RT for 12 hours. The RM was cooled to 0° C., water was added, the precipitate was filtered off, washed with hexane and dried under reduced pressure. The crude product was purified twice by column chromatography (Silica gel column: Silica 12 g, eluent DCM:MeOH 100:0 to 98:2). The product containing fractions were combined, concentrated and dried under HV to give the title compound as an off-white solid.

LC-MS: Rt=1.64 min; MS m/z $[M+H]^+$ 683.2/685.2; UPLC-MS 11

Step 2: N-(4-chloro-2-methyl-5-(trifluoromethyl)phenyl)-2-(5-ethyl-2-morpholino-7-oxo-6-(piperazin-1-yl)-[1,2,4]triazolo[1,5-a]pyrimidin-4 (7H)-yl) acetamide

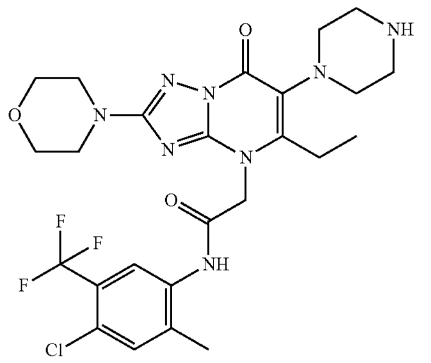 [SMILES: CCc1c(N2CCNCC2)c(=O)n2nc(N3CCOCC3)nc2n1CC(=O)Nc1cc(C(F)(F)F)c(Cl)cc1C]

To the solution of tert-butyl 4-(4-(2-((4-chloro-2-methyl-5-(trifluoromethyl)phenyl)amino)-2-oxoethyl)-5-ethyl-2-morpholino-7-oxo-4,7-dihydro-[1,2,4]triazolo[1,5-a]pyrimidin-6-yl)piperazine-1-carboxylate (700 mg, 799 μmol) in 1,4-dioxane (10 mL) was added HCl 4M in 1,4-dioxane (10.0 mL, 40.0 mmol) at 0° C. and the RM was stirred at RT for 16 hours. The RM was concentrated under reduced pressure, washed with $Et_2O$ (2×10 mL) and dried under reduced pressure to give the title compound as a HCl salt.

LC-MS: Rt=1.08 min; MS m/z $[M+H]^+$ 583.1/585.1; UPLC-MS 13

Intermediate J: rac-tert-butyl 4-(5-ethyl-2-(3-fluoropiperidin-1-yl)-7-oxo-4,7-dihydro-[1,2,4]triazolo[1,5-a]pyrimidin-6-yl)piperazine-1-carboxylate Step 1: rac-3-(3-fluorocyclohexyl)-1H-1,2,4-triazol-5-amine

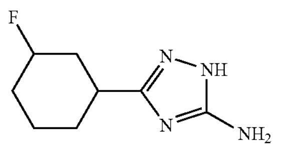

The rac-3-fluoropiperidine·HCl (4.90 g, 35.1 mmol) was suspended in ACN (250 mL), then dimethyl cyanocarbonimidodithioate (5.20 g, 35.6 mmol) and DIPEA (6.25 mL, 35.8 mmol) were added and the RM was heated at 80° C. for 14 hours. Hydrazine hydrate (1.74 mL, 35.8 mmol) was added to the RM which was stirred at 80° C. for 14 hours. The RM was concentrated, water was added and it was extracted with 10% MeOH in DCM. The combined organic layers were dried over $Na_2SO_4$, filtered and concentrated under reduced pressure to give the title compound.

LC-MS: Rt=0.24 min; MS m/z $[M+H]^+$ 185.1; UPLC-MS 11

Step 2: rac-tert-butyl 4-(5-ethyl-2-(3-fluoropiperidin-1-yl)-7-oxo-4,7-dihydro-[1,2,4]triazolo[1,5-a]pyrimidin-6-yl)piperazine-1-carboxylate

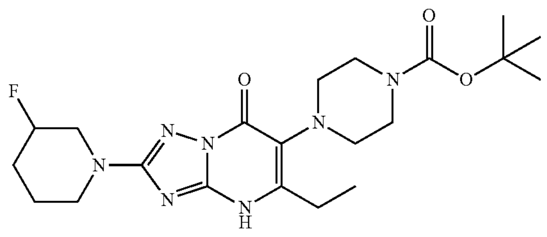 [SMILES: CCc1[nH]c2nc(N3CCCC(F)C3)nn2c(=O)c1N1CCN(C(=O)OC(C)(C)C)CC1]

To the stirred solution of rac-3-(3-fluorocyclohexyl)-1H-1,2,4-triazol-5-amine (2.10 g, 11.3 mmol) in EtOH (30.0 mL) were added tert-butyl 4-(1-ethoxy-1,3-dioxopentan-2-yl)piperazine-1-carboxylate (Intermediate EJ) (5.59 g, 17.0 mmol) and $H_3PO_4$ (1.33 g, 13.6 mmol) at RT. The RM was stirred at 90° C. for 18 hours. $Boc_2O$ (3.95 mL, 17.0 mmol) and DIPEA (4.95 mL, 28.3 mmol) were added at 0° C. and the RM was stirred at RT for 20 hours. The RM was cooled to RT, the suspension was filtered and washed with EtOH. The filtrate was concentrated under reduced pressure and the residue was purified by column chromatography (Silica gel column: Silica 24 g, eluent DCM:MeOH 100:0 to 98:2) to get the title compound.

LC-MS: Rt=1.50 min; MS m/z $[M+H]^+$ 450.3; UPLC-MS 11

Intermediate K: rac-N-(5-chloro-2-methyl-4-(trifluoromethyl)phenyl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide Step 1: rac-tert-butyl 4-(4-(2-((5-chloro-2-methyl-4-(trifluoromethyl)phenyl)amino)-2-oxoethyl)-5-ethyl-2-(3-fluoropiperidin-1-yl)-7-oxo-4,7-dihydro-[1,2,4]triazolo[1,5-a]pyrimidin-6-yl)piperazine-1-carboxylate

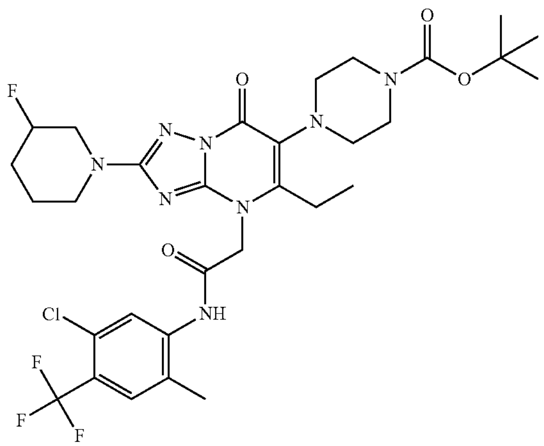 [SMILES: CCc1c(N2CCN(C(=O)OC(C)(C)C)CC2)c(=O)n2nc(N3CCCC(F)C3)nc2n1CC(=O)Nc1cc(Cl)c(C(F)(F)F)cc1C]

Rac-tert-butyl 4-(5-ethyl-2-(3-fluoropiperidin-1-yl)-7-oxo-4,7-dihydro-[1,2,4]triazolo[1,5-a]pyrimidin-6-yl)piperazine-1-carboxylate (Intermediate J) (150 mg, 334 μmol) was suspended in DMF (2 mL). 2-Bromo-N-(5-chloro-2-methyl-4-(trifluoromethyl)phenyl)acetamide (Intermediate DM) (88.0 mg, 267 μmol) and DIPEA (117 μL, 667 μmol) were added at 0° C. and the RM was stirred at RT for 12 hours. The RM was cooled to 0° C., water was added and the precipitate was filtered off, washed with hexane and dried under reduced pressure. The crude product was combined with another batch and purified twice by column chromatography (2× Silica gel column: Silica 12 g, eluent DCM: MeOH 100:0 to 98:2). The product containing fractions were combined, concentrated and dried under HV to give the title compound as an off-white solid.

LC-MS: Rt=1.68 min; MS m/z $[M-H]^-$ 697.2/699.2; UPLC-MS 11

Step 2: rac-N-(5-chloro-2-methyl-4-(trifluoromethyl)phenyl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide

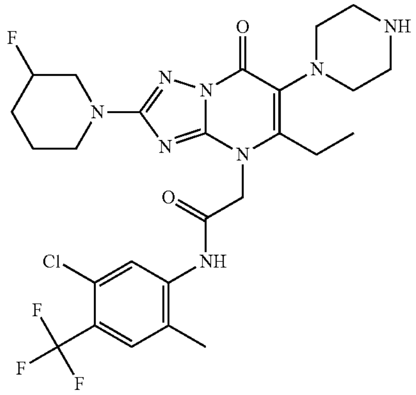 [SMILES: CCc1c(N2CCNCC2)c(=O)n2nc(N3CCCC(F)C3)nc2n1CC(=O)Nc1cc(Cl)c(C(F)(F)F)cc1C]

To the solution of rac-tert-butyl 4-(4-(2-((5-chloro-2-methyl-4-(trifluoromethyl)phenyl)amino)-2-oxoethyl)-5-ethyl-2-(3-fluoropiperidin-1-yl)-7-oxo-4,7-dihydro-[1,2,4]triazolo[1,5-a]pyrimidin-6-yl)piperazine-1-carboxylate (410 mg, 516 μmol) in 1,4-dioxane (10 mL) was added HCl 4M in 1,4-dioxane (10.0 mL, 4.00 mmol) at 0° C. and the RM was stirred at RT for 16 hours. The RM was concentrated under reduced pressure, washed with $Et_2O$ (2×10 mL) and dried under HV to give the title compound as a HCl salt.

LC-MS: Rt=1.37 min; MS m/z $[M+H]^+$ 599.3/601.3; UPLC-MS 11

Intermediate L: rac-2-(5-ethyl-2-(3-fluoropiperidin-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: rac-tert-butyl 4-(5-ethyl-2-(3-fluoropiperidin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

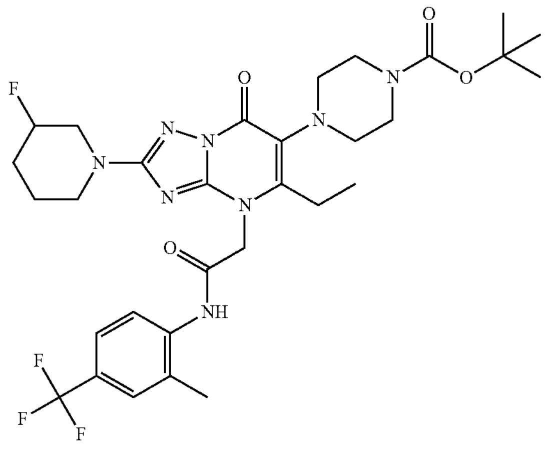 [SMILES: CCc1c(N2CCN(C(=O)OC(C)(C)C)CC2)c(=O)n2nc(N3CCCC(F)C3)nc2n1CC(=O)Nc1ccc(C(F)(F)F)cc1C]

Rac-tert-butyl 4-(5-ethyl-2-(3-fluoropiperidin-1-yl)-7-oxo-4,7-dihydro-[1,2,4]triazolo[1,5-a]pyrimidin-6-yl)piperazine-1-carboxylate (Intermediate J) (500 mg, 1.11 mmol) was suspended in DMF (10 mL). 2-bromo-N-(2-methyl-4-(trifluoromethyl)phenyl)acetamide (Intermediate DP) (329 mg, 1.11 mmol) and DIPEA (486 μL, 2.78 mmol) were added at 0° C. and the RM was stirred at RT for 12 hours. The RM was cooled to 0° C., water was added and the precipitate was filtered off, washed with hexane and dried under reduced pressure. The crude product was purified by column chromatography (Silica gel column: Silica 24 g, eluent DCM:MeOH 100:0 to 95:5). The product containing fractions were combined, concentrated down and dried under HV to give the title compound.

LC-MS: Rt=1.64 min; MS m/z $[M+H]^+$ 665.3; UPLC-MS 11

Step 2: rac-2-(5-ethyl-2-(3-fluoropiperidin-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide

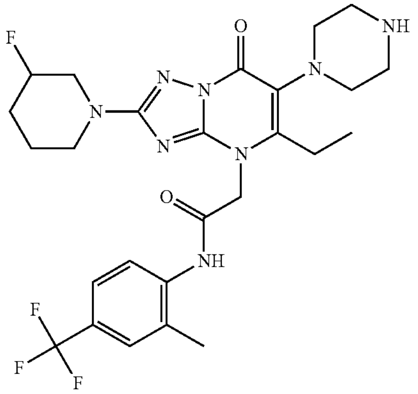 [SMILES: CCc1c(N2CCNCC2)c(=O)n2nc(N3CCCC(F)C3)nc2n1CC(=O)Nc1ccc(C(F)(F)F)cc1C]

The solution of rac-tert-butyl 4-(5-ethyl-2-(3-fluoropiperidin-1-yl)-4-(2-((2-methyl-4-(trifluoromethyl)phenyl) amino)-2-oxoethyl)-7-oxo-4,7-dihydro-[1,2,4]triazolo[1,5-a]pyrimidin-6-yl)piperazine-1-carboxylate (350 mg, 527 μmol) in 1,4-dioxane (10 mL) was added HCl 4M in 1,4-dioxane (1.32 mL, 5.27 mmol) and the RM was stirred at RT for 16 hours. The RM was concentrated under reduced pressure. The resulting solid was triturated with $Et_2O$ to give the title compound, as the HCl salt.

LC-MS: Rt=1.37 min; MS m/z $[M+H]^+$ 565.3; UPLC-MS 11

Intermediate M: rac-N-(2-chloro-4-(trifluoromethyl) phenyl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide Step 1: rac-tert-butyl 4-(4-(2-((2-chloro-4-(trifluoromethyl)phenyl)amino)-2-oxoethyl)-5-ethyl-2-(3-fluoropiperidin-1-yl)-7-oxo-4,7-dihydro-[1,2,4]triazolo[1,5-a]pyrimidin-6-yl)piperazine-1-carboxylate

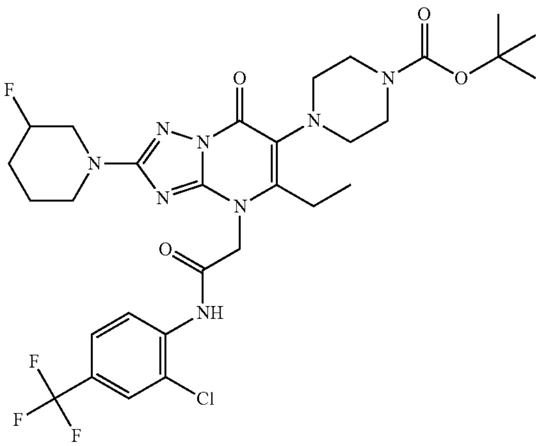 [SMILES: CCc1c(N2CCN(C(=O)OC(C)(C)C)CC2)c(=O)n2nc(N3CCCC(F)C3)nc2n1CC(=O)Nc1ccc(C(F)(F)F)cc1Cl]

Rac-tert-butyl 4-(5-ethyl-2-(3-fluoropiperidin-1-yl)-7-oxo-4,7-dihydro-[1,2,4]triazolo[1,5-a]pyrimidin-6-yl)piperazine-1-carboxylate (Intermediate J) (400 mg, 890 μmol) was suspended in DMF (2 mL). 2-Bromo-N-(2-chloro-4-(trifluoromethyl)phenyl)acetamide (Intermediate DT) (225 mg, 710 μmol) and DIPEA (311 μL, 1.78 mmol) were added at 0° C. and the RM was stirred at RT for 12 hours. Water was added, the precipitate was filtered off and dried under reduced pressure. The crude product was purified by column chromatography (Silica gel column: Silica 12 g, eluent DCM:MeOH 100:0 to 98:2). The product containing fractions were combined, concentrated and dried under reduced pressure to give the title compound.

LC-MS: Rt=1.67 min; MS m/z $[M-H]^-$ 683.3/685.3; UPLC-MS 11

Step 2: rac-N-(2-chloro-4-(trifluoromethyl)phenyl)-2-(5-ethyl-2-(3-fluoropiperidin-1-yl)-7-oxo-6-(piperazin-1-yl)-[1,2,4]triazolo[1,5-a]pyrimidin-4 (7H)-yl) acetamide

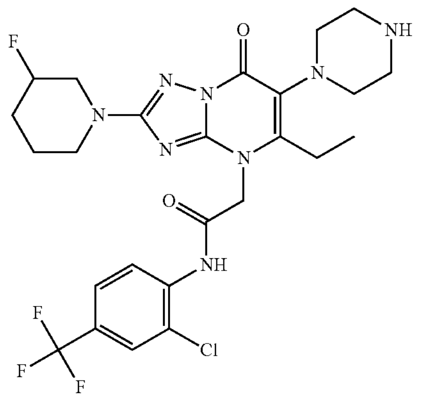

Rac-tert-butyl 4-(4-(2-((2-chloro-4-(trifluoromethyl)phenyl)amino)-2-oxoethyl)-5-ethyl-2-(3-fluoropiperidin-1-yl)-7-oxo-4,7-dihydro-[1,2,4]triazolo[1,5-a]pyrimidin-6-yl)piperazine-1-carboxylate (200 mg, 292 μmol) was suspended in DCM (5 mL) and HCl 4M in 1,4-dioxane (3.00 mL, 99.0 mmol) was added at 0° C. and the RM was stirred at RT for 2 hours. The RM was concentrated under reduced pressure to give the title compound, as the HCl salt.

LC-MS: Rt=1.38 min; MS m/z $[M+H]^+$ 585.2/587.2; UPLC-MS 11

Intermediate N: rac-N-(2-chloro-6-(trifluoromethyl) pyridin-3-yl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide Step 1: rac-tert-butyl 4-(4-(2-((2-chloro-6-(trifluoromethyl)pyridin-3-yl)amino)-2-oxoethyl)-5-ethyl-2-(3-fluoropiperidin-1-yl)-7-oxo-4,7-dihydro-[1,2,4] triazolo[1,5-a]pyrimidin-6-yl)piperazine-1-carboxylate

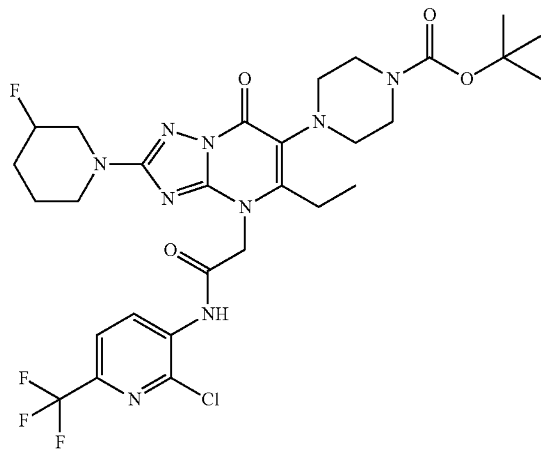 [SMILES: CCc1c(N2CCN(C(=O)OC(C)(C)C)CC2)c(=O)n2nc(N3CCCC(F)C3)nc2n1CC(=O)Nc1ccc(C(F)(F)F)nc1Cl]

Rac-tert-butyl 4-(5-ethyl-2-(3-fluoropiperidin-1-yl)-7-oxo-4,7-dihydro-[1,2,4]triazolo[1,5-a]pyrimidin-6-yl)piperazine-1-carboxylate (Intermediate J) (500 mg, 1.11 mmol) was suspended in DMF (10 mL). 2-Bromo-N-(2-chloro-6-(trifluoromethyl)pyridin-3-yl)acetamide (Intermediate DQ) (353 mg, 1.11 mmol) and DIPEA (389 μL, 2.23 mmol) were added at 0° C. and the RM was stirred at RT for 12 hours. The RM was cooled to 0° C., water was added and the precipitate was filtered off, washed with hexane and dried under reduced pressure. The crude product was purified by column chromatography (Silica gel column: Silica 12 g, eluent DCM:MeOH 100:0 to 98:2). The product containing fractions were combined, concentrated under reduced pressure and dried under HV to give the title compound.

LC-MS: Rt=1.62 min; MS m/z $[M-H]^-$ 684.2/686.2; UPLC-MS 11

Step 2: rac-N-(2-chloro-6-(trifluoromethyl)pyridin-3-yl)-2-(5-ethyl-2-(3-fluoropiperidin-1-yl)-7-oxo-6-(piperazin-1-yl)-[1,2,4]triazolo[1,5-a]pyrimidin-4 (7H)-yl)acetamide

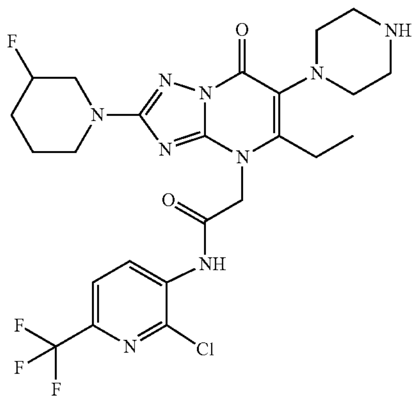 [SMILES: CCc1c(N2CCNCC2)c(=O)n2nc(N3CCCC(F)C3)nc2n1CC(=O)Nc1ccc(C(F)(F)F)nc1Cl]

To the solution of rac-tert-butyl 4-(4-(2-((2-chloro-6-(trifluoromethyl)pyridin-3-yl)amino)-2-oxoethyl)-5-ethyl-2-(3-fluoropiperidin-1-yl)-7-oxo-4,7-dihydro-[1,2,4]triazolo [1,5-a]pyrimidin-6-yl)piperazine-1-carboxylate (100 mg, 109 μmol) was dissolved in 1,4-dioxane (5 mL) and HCl 4M in 1,4-dioxane (5.00 mL, 20.0 mmol) was added at 0° C. and the RM was stirred at RT for 16 hours. The RM was concentrated under reduced pressure, washed with $Et_2O$ (2×10 mL) and dried under HV to give the title compound as a HCl salt as an off-white solid.

LC-MS: Rt=0.53 min; MS m/z $[M+H]^+$ 586.4/588.4; UPLC-MS 12

Intermediate 0: tert-butyl 4-(5-ethyl-7-oxo-2-(pyrrolidin-1-yl)-4,7-dihydro-[1,2,4]triazolo[1,5-a]pyrimidin-6-yl)piperazine-1-carboxylate

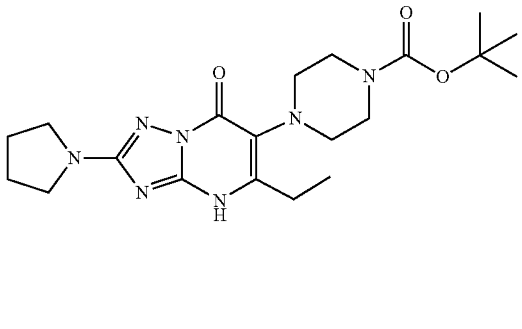 [SMILES: CCc1[nH]c2nc(N3CCCC3)nn2c(=O)c1N1CCN(C(=O)OC(C)(C)C)CC1]

To the stirred solution of 5-(pyrrolidin-1-yl)-4H-1,2,4-triazol-3-amine (1.00 g, 6.53 mmol) in EtOH (30.0 mL) were added tert-butyl 4-(1-methoxy-1,3-dioxopentan-2-yl) piperazine-1-carboxylate (Intermediate EH) (3.08 g, 9.79 mmol) and $H_3PO_4$ (340 μL, 6.53 mmol) at RT. The RM was stirred at 90° C. for 64 hours. $Boc_2O$ (1.51 mL, 6.53 mmol) and DIPEA (2.85 mL, 16.3 mmol) were added at 0° C. and RM was stirred at RT for 16 hours. The RM was filtered and the obtained solid was dried under reduced pressure to give the title compound as a white solid.

LC-MS: Rt=1.63 min; MS m/z $[M+H]^+$ 418.2; UPLC-MS 13

Intermediate P: 2-(5-ethyl-7-oxo-6-(piperazin-1-yl)-2-(pyrrolidin-1-yl)-[1,2,4]triazolo[1,5-a]pyrimidin-4 (7H)-yl)-N-(2-methyl-4-(trifluoromethyl)phenyl) acetamide Step 1: tert-butyl 4-(5-ethyl-4-(2-((2-methyl-4-(trifluoromethyl)phenyl)amino)-2-oxoethyl)-7-oxo-2-(pyrrolidin-1-yl)-4,7-dihydro-[1,2,4]triazolo[1,5-a] pyrimidin-6-yl)piperazine-1-carboxylate

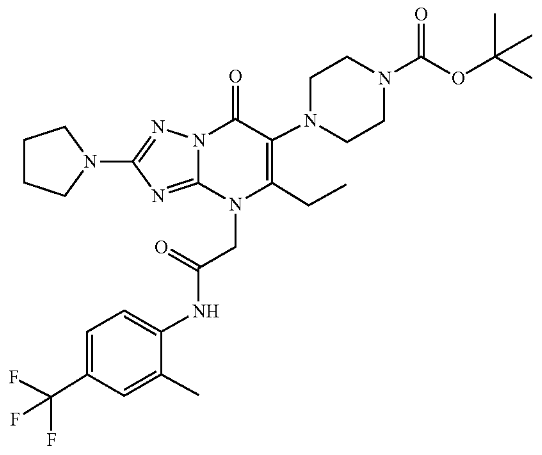 [SMILES: CCc1c(N2CCN(C(=O)OC(C)(C)C)CC2)c(=O)n2nc(N3CCCC3)nc2n1CC(=O)Nc1ccc(C(F)(F)F)cc1C]

Tert-butyl 4-(5-ethyl-7-oxo-2-(pyrrolidin-1-yl)-4,7-dihydro-[1,2,4]triazolo[1,5-a]pyrimidin-6-yl)piperazine-1-carboxylate (Intermediate 0) was suspended in DMF (10 mL). 2-bromo-N-(2-methyl-4-(trifluoromethyl)phenyl)acetamide (Intermediate DP) (468 mg, 1.58 mmol) and DIPEA (627 μL, 3.59 mmol) were added at 0° C. and the RM was stirred at RT for 12 hours. The RM was cooled to 0° C., water was added and the precipitate was filtered off, washed with hexane and dried under reduced pressure. The crude product was purified twice by column chromatography (Silica gel column: Silica 12 g, eluent DCM:MeOH 100:0 to 98:2). The product containing fractions were combined, concentrated and dried under HV to give the title compound as an off-white solid.

LC-MS: Rt=1.64 min; MS m/z $[M+H]^+$ 633.3; UPLC-MS 11

Step 2: 2-(5-ethyl-7-oxo-6-(piperazin-1-yl)-2-(pyrrolidin-1-yl)-[1,2,4]triazolo[1,5-a]pyrimidin-4 (7H)-yl)-N-(2-methyl-4-(trifluoromethyl)phenyl)acetamide

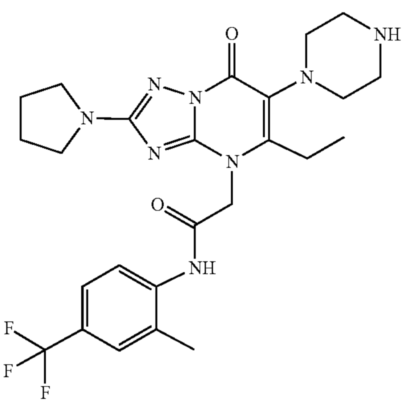 [SMILES: CCc1c(N2CCNCC2)c(=O)n2nc(N3CCCC3)nc2n1CC(=O)Nc1ccc(C(F)(F)F)cc1C]

To the solution of tert-butyl 4-(5-ethyl-4-(2-((2-methyl-4-(trifluoromethyl)phenyl)amino)-2-oxoethyl)-7-oxo-2-(pyrrolidin-1-yl)-4,7-dihydro-[1,2,4]triazolo[1,5-a]pyrimidin-6-yl)piperazine-1-carboxylate (750 mg, 759 μmol) in 1,4-dioxane (10 mL) was added HCl 4M in 1,4-dioxane (10.0 mL, 40.0 mmol) at 0° C. and the RM was stirred at RT for 16 hours. The RM was concentrated under reduced pressure, washed with $Et_2O$ (2×10 mL) and dried under HV to give the title compound, as the HCl salt.

LC-MS: Rt=1.34 min; MS m/z $[M+H]^+$ 533.3; UPLC-MS 11

Intermediate Q: N-(2-chloro-6-(trifluoromethyl) pyridin-3-yl)-2-(5-ethyl-7-oxo-6-(piperazin-1-yl)-2-(pyrrolidin-1-yl)-[1,2,4]triazolo[1,5-a]pyrimidin-4 (7H)-yl)acetamide Step 1: tert-butyl 4-(4-(2-((2-chloro-6-(trifluoromethyl)pyridin-3-yl)amino)-2-oxoethyl)-5-ethyl-7-oxo-2-(pyrrolidin-1-yl)-4,7-dihydro-[1,2,4]triazolo [1,5-a]pyrimidin-6-yl)piperazine-1-carboxylate

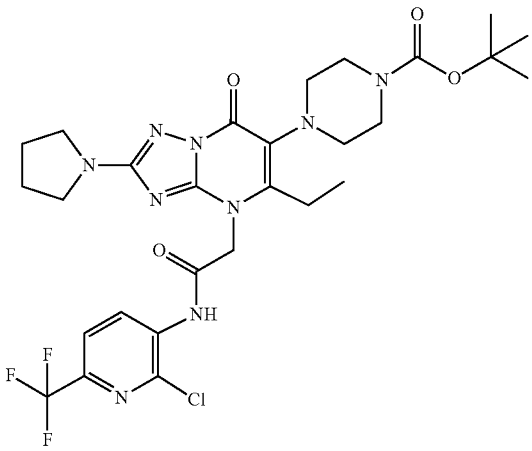 [SMILES: CCc1c(N2CCN(C(=O)OC(C)(C)C)CC2)c(=O)n2nc(N3CCCC3)nc2n1CC(=O)Nc1ccc(C(F)(F)F)nc1Cl]

To the stirred solution of tert-butyl 4-(5-ethyl-7-oxo-2-(pyrrolidin-1-yl)-4,7-dihydro-[1,2,4]triazolo[1,5-a]pyrimidin-6-yl)piperazine-1-carboxylate (Intermediate O) (700 mg, 1.68 mmol) in DMF (10 mL) were added 2-bromo-N-(2-chloro-6-(trifluoromethyl)pyridin-3-yl)acetamide (Intermediate DQ) (479 mg, 1.51 mmol) and DIPEA (732 μL, 4.19 mmol) at 0° C. and the RM was stirred at RT for 16 hours. The RM was concentrated under reduced pressure ice cold water was added and the precipitate was filtered off and dried under reduced pressure. The crude product was purified by column chromatography (Silica gel column: Silica 24 g, eluent DCM:MeOH 100:0 to 90:10). The product containing fractions were combined, concentrated and dried under HV to give the title compound as a brown solid.

LC-MS: Rt=1.64 min; MS m/z $[M+H]^+$ 654.2/656.2; UPLC-MS 11

Step 2: N-(2-chloro-6-(trifluoromethyl)pyridin-3-yl)-2-(5-ethyl-7-oxo-6-(piperazin-1-yl)-2-(pyrrolidin-1-yl)-[1,2,4]triazolo[1,5-a]pyrimidin-4 (7H)-yl) acetamide

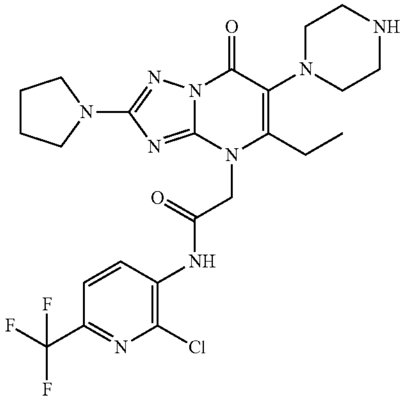 [SMILES: CCc1c(N2CCNCC2)c(=O)n2nc(N3CCCC3)nc2n1CC(=O)Nc1ccc(C(F)(F)F)nc1Cl]

To the stirred solution of tert-butyl 4-(4-(2-((2-chloro-6-(trifluoromethyl)pyridin-3-yl)amino)-2-oxoethyl)-5-ethyl-7-oxo-2-(pyrrolidin-1-yl)-4,7-dihydro-[1,2,4]triazolo[1,5-a]pyrimidin-6-yl)piperazine-1-carboxylate (500 mg, 680 μmol) in DCM (10 mL) was added HCl 4M in 1,4-dioxane (5.00 mL, 20.0 mmol) at 0° C. and the RM was stirred at RT for 16 hours. The RM was concentrated under reduced pressure to give the title compound, as the HCl salt.

LC-MS: Rt=1.37 min; MS m/z $[M+H]^+$ 554.2/556.2; UPLC-MS 11

Intermediate R: N-(5-chloro-2-methyl-4-(trifluoromethyl)phenyl)-2-(5-ethyl-7-oxo-6-(piperazin-1-yl)-2-(pyrrolidin-1-yl)-[1,2,4]triazolo[1,5-a]pyrimidin-4 (7H)-yl)acetamide Step 1: tert-butyl 4-(4-(2-((5-chloro-2-methyl-4-(trifluoromethyl)phenyl)amino)-2-oxoethyl)-5-ethyl-7-oxo-2-(pyrrolidin-1-yl)-4,7-dihydro-[1,2,4]triazolo[1,5-a]pyrimidin-6-yl)piperazine-1-carboxylate

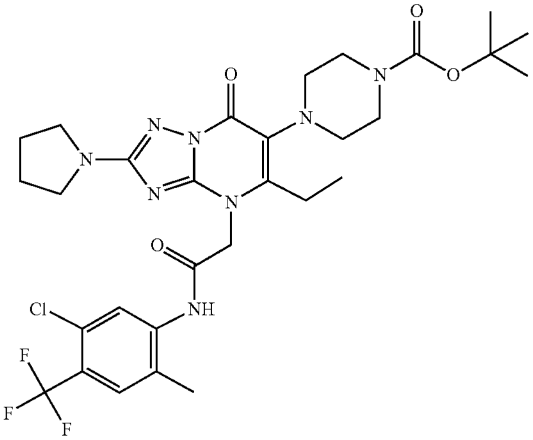 [SMILES: CCc1c(N2CCN(C(=O)OC(C)(C)C)CC2)c(=O)n2nc(N3CCCC3)nc2n1CC(=O)Nc1cc(Cl)c(C(F)(F)F)cc1C]

To the stirred solution of tert-butyl 4-(5-ethyl-7-oxo-2-(pyrrolidin-1-yl)-4,7-dihydro-[1,2,4]triazolo[1,5-a]pyrimidin-6-yl)piperazine-1-carboxylate (Intermediate O) (450 mg, 1.08 mmol) in DMF (5 mL) were added 2-bromo-N-(5-chloro-2-methyl-4-(trifluoromethyl)phenyl)acetamide (Intermediate DM) (356 mg, 1.08 mmol) and DIPEA (471 μL, 2.69 mmol) at 0° C. and the RM was stirred at RT for 16 hours. The RM was concentrated under reduced pressure, ice cold water was added, the precipitate was filtered off and dried under reduced pressure. The crude product was purified by column chromatography (Silica gel column: Silica 24 g, eluent DCM:MeOH 100:0 to 90:10). The product containing fractions were combined, concentrated and dried to give the title compound as a brown solid.

LC-MS: Rt=1.67 min; MS m/z $[M+H]^+$ 667.3/669.3; UPLC-MS 11

Step 2: N-(5-chloro-2-methyl-4-(trifluoromethyl)phenyl)-2-(5-ethyl-7-oxo-6-(piperazin-1-yl)-2-(pyrrolidin-1-yl)-[1,2,4]triazolo[1,5-a]pyrimidin-4 (7H)-yl)acetamide

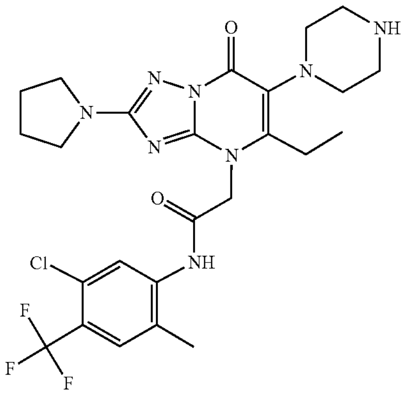 [SMILES: CCc1c(N2CCNCC2)c(=O)n2nc(N3CCCC3)nc2n1CC(=O)Nc1cc(Cl)c(C(F)(F)F)cc1C]

To the stirred solution of tert-butyl 4-(4-(2-((5-chloro-2-methyl-4-(trifluoromethyl)phenyl)amino)-2-oxoethyl)-5-ethyl-7-oxo-2-(pyrrolidin-1-yl)-4,7-dihydro-[1,2,4]triazolo[1,5-a]pyrimidin-6-yl)piperazine-1-carboxylate (200 mg, 300 μmol) in DCM (5 mL) was added HCl 4M in 1,4-dioxane (2.00 mL, 8.00 mmol) at 0° C. and the RM was stirred at RT for 2 hours. The RM was concentrated under reduced pressure to give the title compound, as the HCl salt.

LC-MS: Rt=1.38 min; MS m/z $[M+H]^+$ 567.2/569.2; UPLC-MS 11

Intermediate S: N-(2-chloro-6-(trifluoromethyl)pyridin-3-yl)-2-(2-(4-((2,2-difluoroethyl)(methyl)amino)piperidin-1-yl)-5-ethyl-7-oxo-6-(piperazin-1-yl)-[1,2,4]triazolo[1,5-a]pyrimidin-4 (7H)-yl)acetamide Step 1: 1-(5-amino-1H-1,2,4-triazol-3-yl)-N-(2,2-difluoroethyl)-N-methylpiperidin-4-amine

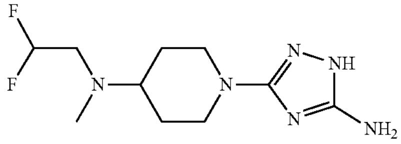 [SMILES: CN(CC(F)F)C1CCN(c2n[nH]c(N)n2)CC1]

To N-(2,2-difluoroethyl)-N-methylpiperidin-4-amine (998 mg, 3.97 mmol) in ACN (10 mL) was added DIPEA (1.46 mL, 8.34 mmol) and the RM was stirred at RT for 5 minutes. Then dimethyl cyanocarbonimidodithioate (581 mg, 3.97 mmol) was added and the RM was heated at 85° C. for 21 hours. Hydrazine hydrate (328 μL, 6.76 mmol) was added and the RM was continued heating at 85° C. for 21 hours. Further hydrazine hydrate (85.0 μL, 1.75 mmol) was added and the RM was continued heating at 100° C. for 4 hours. Then it was allowed to cool to RT with stirring. The resulting suspension was filtered and the solid was washed with ACN (10 mL) and dried under vacuum to give the title compound as a colourless solid.

LC-MS: Rt=0.12 min; MS m/z $[M+H]^+$ 261.3; UPLC-MS 1

Step 2: tert-butyl 4-(2-(4-((2,2-difluoroethyl)(methyl)amino)piperidin-1-yl)-5-ethyl-7-oxo-4,7-dihydro-[1,2,4]triazolo[1,5-a]pyrimidin-6-yl)piperazine-1-carboxylate

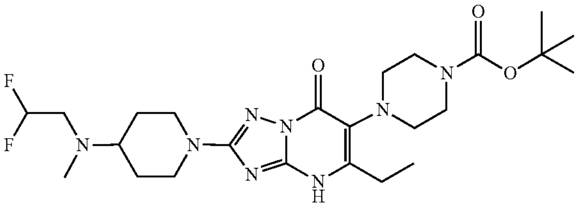 [SMILES: CCc1[nH]c2nc(N3CCC(N(C)CC(F)F)CC3)nn2c(=O)c1N1CCN(C(=O)OC(C)(C)C)CC1]

To 1-(5-amino-1H-1,2,4-triazol-3-yl)-N-(2,2-difluoroethyl)-N-methylpiperidin-4-amine (510 mg, 1.96 mmol) in EtOH (10 mL) was added $H_3PO_4$ (384 mg, 3.92 mmol) and the RM was stirred at RT for 3 minutes. Tert-butyl 4-(1-methoxy-1,3-dioxopentan-2-yl)piperazine-1-carboxylate (Intermediate EH) (678 mg, 2.16 mmol) was added and the RM was heated at 85° C. for 18 hours. While still warm, the orange solution was decanted from the residual solid and evaporated in vacuo to give an orange gum which was partitioned between DCM/MeOH (9/1, 30 mL) and 5% aq $NaHCO_3$ (20 mL). The organic layer was separated and the aqueous layer was extracted with DCM (2×20 mL). The combined organic layers were dried through a phase separator and concentrated under reduced pressure to give an orange gum. The crude product was purified in 2 portions by column chromatography (2× RediSep Column: Silica 12 g, eluent DCM:MeOH 100:0 to 92:08). The product containing fractions were combined, concentrated and dried under HV to give the title compound as a dark pink solid.

LC-MS: Rt=0.76 min; MS m/z $[M+H]^+$ 525.4/526.4, m/z $[M-H]^-$ 523.5/524.5; UPLC-MS 1

Step 3: tert-butyl 4-(4-(2-((2-chloro-6-(trifluoromethyl)pyridin-3-yl)amino)-2-oxoethyl)-2-(4-((2,2-difluoroethyl)(methyl)amino)piperidin-1-yl)-5-ethyl-7-oxo-4,7-dihydro-[1,2,4]triazolo[1,5-a]pyrimidin-6-yl)piperazine-1-carboxylate

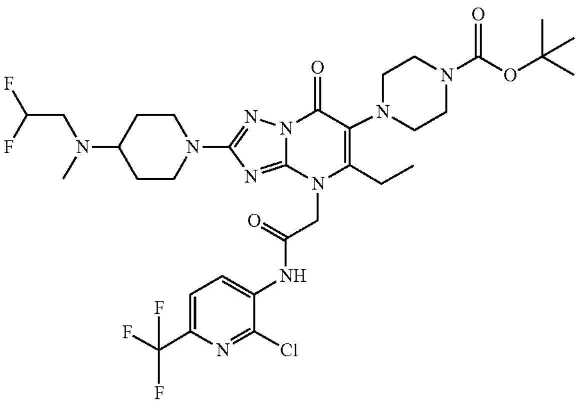 [SMILES: CCc1c(N2CCN(C(=O)OC(C)(C)C)CC2)c(=O)n2nc(N3CCC(N(C)CC(F)F)CC3)nc2n1CC(=O)Nc1ccc(C(F)(F)F)nc1Cl]

To tert-butyl 4-(2-(4-((2,2-difluoroethyl)(methyl)amino)piperidin-1-yl)-5-ethyl-7-oxo-4,7-dihydro-[1,2,4]triazolo[1,5-a]pyrimidin-6-yl)piperazine-1-carboxylate (162 mg, 309 μmol) in DMF (2 mL) was added DIPEA (81.0 μL, 463

μmol), followed by N-(2-chloro-6-(trifluoromethyl)pyridin-3-yl)-2-iodoacetamide (Intermediate DU) (124 mg, 340 μmol). The RM was heated at 50° C. for 2 hours.

LC-MS: Rt=1.11 min; MS m/z $[M-H]^-$ 759.3/761.3; UPLC-MS 1

Step 4: N-(2-chloro-6-(trifluoromethyl)pyridin-3-yl)-2-(2-(4-((2,2-difluoroethyl)(methyl)amino)piperidin-1-yl)-5-ethyl-7-oxo-6-(piperazin-1-yl)-[1,2,4]triazolo[1,5-a]pyrimidin-4 (7H)-yl)acetamide

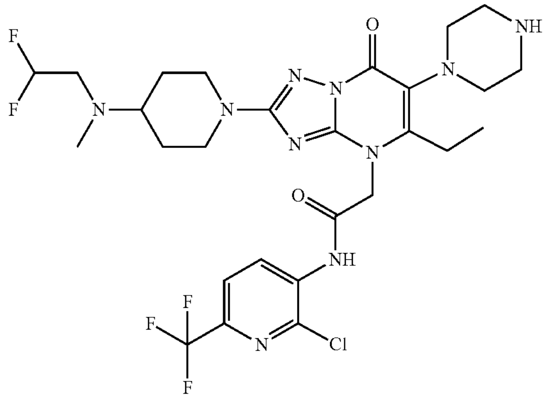 [SMILES: CCc1c(N2CCNCC2)c(=O)n2nc(N3CCC(N(C)CC(F)F)CC3)nc2n1CC(=O)Nc1ccc(C(F)(F)F)nc1Cl]

The RM from step 3 was allowed to cool to RT then TFA (357 μL, 4.63 mmol) was added and the RM was heated at 55° C. for 1 hour, then at 100° C. for 70 minutes. The RM was concentrated under reduced pressure to give a solution of desired product in DMF (1 mL). The solution was partitioned between DCM (20 mL) and 5% aq $NaHCO_3$ (15 mL). The organic layer was separated, dried through a phase separator and concentrated under reduced pressure to give the title compound as a brown gum.

LC-MS: Rt=0.48 min; MS m/z $[M+H]^+$ 661.5/663.4, m/z $[M-H]^-$ 659.5/661.4; UPLC-MS 1

Intermediate T: tert-butyl 4-(2-(6-oxa-3-azabicyclo[3.1.1]heptan-3-yl)-5-ethyl-7-oxo-4,7-dihydro-[1,2,4]triazolo[1,5-a]pyrimidin-6-yl)piperazine-1-carboxylate Step 1: 3-(6-oxa-3-azabicyclo[3.1.1]heptan-3-yl)-1H-1,2,4-triazol-5-amine

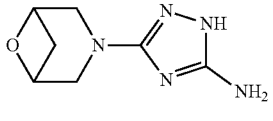 [SMILES: Nc1nc(N2CC3CC(C2)O3)n[nH]1]

6-Oxa-3-azabicyclo[3.1.1]heptane·HCl (1.25 g, 9.22 mmol) was dissolved in ACN (16 mL) and $Et_3N$ (1.34 mL, 9.68 mmol). Dimethyl cyanocarbonimidodithioate (1.50 g, 9.22 mmol) was added and the RM was stirred at reflux for 19.75 hours. 6-Oxa-3-azabicyclo[3.1.1]heptane·HCl (160 mg, 1.18 mmol) dissolved in ACN (500 μL) and $Et_3N$ (170 μL, 1.23 mmol) was added and the RM was stirred at reflux for 20 hours, then it was cooled to 0° C. Hydrazine hydrate (508 mg, 10.1 mmol) was added dropwise to the thick suspension within 1 minute. The suspension was stirred at reflux for 7 hours. Hydrazine hydrate (320 mg, 6.36 mmol) was added again and the RM was continued stirring at reflux for 20 hours. The RM was cooled to RT and concentrated under reduced pressure. The residue was taken up in EtOAc and concentrated to give the title compound as a beige solid.

LC-MS: Rt=0.25 min; MS m/z $[M+H]^+$ 182.1; UPLC-MS 4

Step 2: tert-butyl 4-(2-(6-oxa-3-azabicyclo[3.1.1]heptan-3-yl)-5-ethyl-7-oxo-4,7-dihydro-[1,2,4]triazolo[1,5-a]pyrimidin-6-yl)piperazine-1-carboxylate

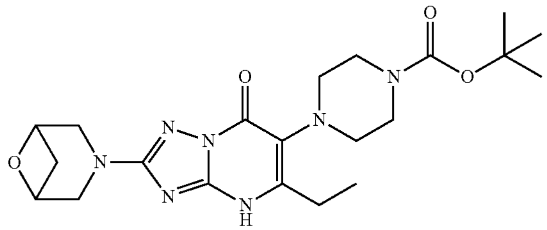 [SMILES: CCc1[nH]c2nc(N3CC4CC(C3)O4)nn2c(=O)c1N1CCN(C(=O)OC(C)(C)C)CC1]

3-(6-Oxa-3-azabicyclo[3.1.1]heptan-3-yl)-1H-1,2,4-triazol-5-amine (1.25 g, 4.35 mmol) and tert-butyl 4-(1-methoxy-1,3-dioxopentan-2-yl)piperazine-1-carboxylate (Intermediate EH) (1.64 g, 5.22 mmol) were dissolved in EtOH (12 mL) and $H_3PO_4$ (526 mg, 4.56 mmol) was added. The RM was stirred at 90° C. for 6.5 hours, then at RT overnight. Tert-butyl 4-(1-methoxy-1,3-dioxopentan-2-yl)piperazine-1-carboxylate (Intermediate EH) (350 mg, 1.11 mmol) was added again and the RM was stirred at 90° C. for 4 hours. The red solution was cooled to RT and DIPEA (2.28 mL, 13.0 mmol) was added, followed by $Boc_2O$ (426 mL, 1.83 mmol). The RM was stirred at RT for 1 hour and was quenched with water. The solvent was removed under reduced pressure and the aqueous layer was extracted with EtOAc (3×60 mL), aq sat $NaHCO_3$ (2×20 mL) and brine (2×20 mL). The combined organic layers were dried through a phase separator and concentrated under reduced pressure. The residue was adsorbed onto Isolute and purified by column chromatography (RediSep Column: Silica 40 g, eluent DCM:MeOH 100:0 to 85:15). The product containing fractions were combined, concentrated and dried under HV to give the title compound as an orange solid.

LC-MS: Rt=0.94 min; MS m/z $[M+H]^+$ 446.2, m/z $[M-H]^-$ 444.2; UPLC-MS 3

Intermediate U: 2-(2-(6-oxa-3-azabicyclo[3.1.1]heptan-3-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-(6-oxa-3-azabicyclo[3.1.1]heptan-3-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

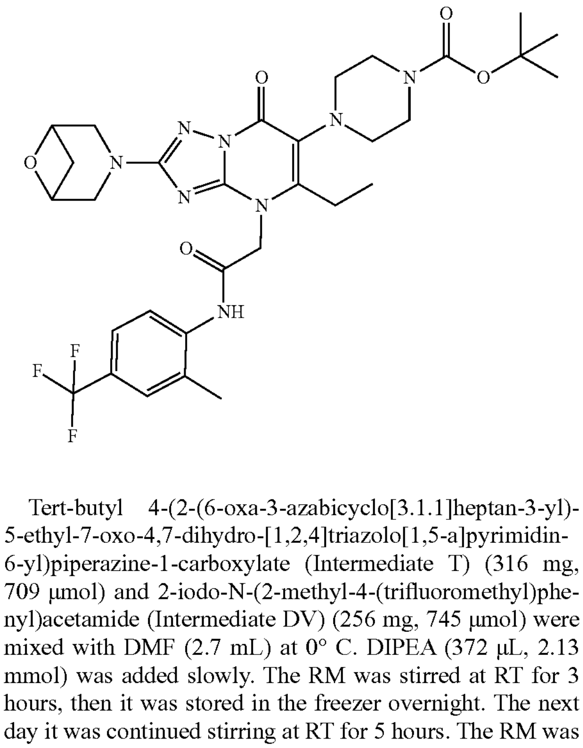

Tert-butyl 4-(2-(6-oxa-3-azabicyclo[3.1.1]heptan-3-yl)-5-ethyl-7-oxo-4,7-dihydro-[1,2,4]triazolo[1,5-a]pyrimidin-6-yl)piperazine-1-carboxylate (Intermediate T) (316 mg, 709 μmol) and 2-iodo-N-(2-methyl-4-(trifluoromethyl)phenyl)acetamide (Intermediate DV) (256 mg, 745 μmol) were mixed with DMF (2.7 mL) at 0° C. DIPEA (372 μL, 2.13 mmol) was added slowly. The RM was stirred at RT for 3 hours, then it was stored in the freezer overnight. The next day it was continued stirring at RT for 5 hours. The RM was quenched with water (5 mL) and stirred at RT. The suspension was filtered and washed with water to give the title compound as a bright brown solid.

LC-MS: Rt=1.17 min; MS m/z $[M+H]^+$ 661.3, m/z $[M-H]^-$ 659.2; UPLC-MS 3

Step 2: 2-(2-(6-oxa-3-azabicyclo[3.1.1]heptan-3-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide

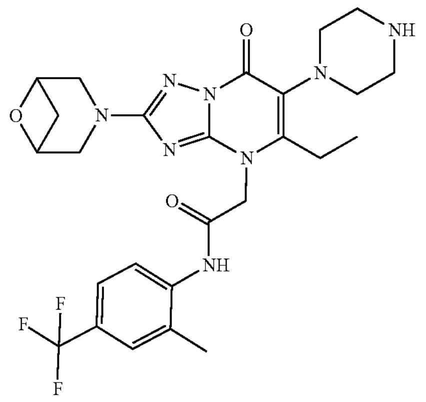 [SMILES: CCc1c(N2CCNCC2)c(=O)n2nc(N3CC4CC(C3)O4)nc2n1CC(=O)Nc1ccc(C(F)(F)F)cc1C]

Tert-butyl 4-(2-(6-oxa-3-azabicyclo[3.1.1]heptan-3-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (426 mg, 645 μmol) was dissolved in DCM (4.4 mL) and TFA (745 μL, 9.67 mmol) was added. The RM was stirred at RT for 25 minutes, then it was cooled with dry ice and $Et_3N$ (1.79 mL, 12.9 mmol) was added. The RM was concentrated under reduced pressure. The residue was adsorbed onto Isolute and purified by column chromatography (RediSep Column: Silica 40 g, eluent DCM:MeOH 100:0 to 75:25). The product containing fractions were combined, concentrated under reduced pressure and dried under HV to give the title compound as a bright brown solid.

LC-MS: Rt=0.81 min; MS m/z $[M+H]^+$ 561.5, m/z $[M-H]^-$ 559.3; UPLC-MS 3

Intermediate V: 2-(2-(6-oxa-3-azabicyclo[3.1.1]heptan-3-yl)-5-methyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide Step 1: tert-butyl 4-(2-(6-oxa-3-azabicyclo[3.1.1]heptan-3-yl)-5-methyl-7-oxo-4,7-dihydro-[1,2,4]triazolo[1,5-a]pyrimidin-6-yl)piperazine-1-carboxylate

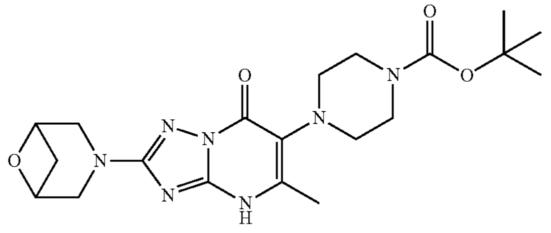 [SMILES: Cc1[nH]c2nc(N3CC4CC(C3)O4)nn2c(=O)c1N1CCN(C(=O)OC(C)(C)C)CC1]

3-(6-Oxa-3-azabicyclo[3.1.1]heptan-3-yl)-1H-1,2,4-triazol-5-amine (Intermediate T step 1) (1.25 g, 4.35 mmol) and tert-butyl 4-(1-ethoxy-1,3-dioxobutan-2-yl)piperazine-1-carboxylate (Intermediate EP) (1.64 g, 5.22 mmol) were mixed in EtOH (12 mL). $H_3PO_4$ 85% (526 mg, 4.56 mmol)

was added and the RM was stirred at 90° C. for 3 hours, then it was cooled to RT. The RM was diluted with water and the resulting suspension was filtered. The cake was discarded. The filtrate was concentrated under reduced pressure. The residue was extracted three times with EtOAc (3×80 mL), once with aq sat $NaHCO_3$ (25 mL) and once with brine (25 mL). The combined organic layers were dried through a phase separator and concentrated under reduced pressure to give crude product. The aqueous layer still contained product so it was concentrated under reduced pressure. The solid residue was suspended in EtOAc and filtered. The cake still contained product so it was suspended in DCM/MeOH and filtered. The filtrates were combined and concentrated under reduced pressure. The residue was combined with the crude product to give the title compound as a brown solid foam.

LC-MS: Rt=0.87 min; MS m/z $[M+H]^+$ 432.4, m/z $[M-H]^-$ 430.4; UPLC-MS 3

Step 2: tert-butyl 4-(2-(6-oxa-3-azabicyclo[3.1.1]heptan-3-yl)-4-(2-((2-fluoro-4-(trifluoromethyl)phenyl)amino)-2-oxoethyl)-5-methyl-7-oxo-4,7-dihydro-[1,2,4]triazolo[1,5-a]pyrimidin-6-yl)piperazine-1-carboxylate

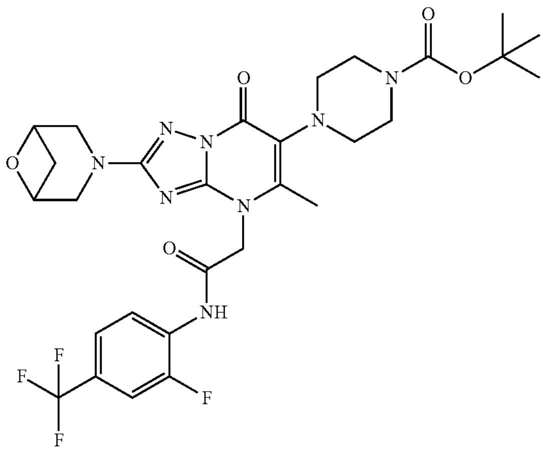 [SMILES: Cc1c(N2CCN(C(=O)OC(C)(C)C)CC2)c(=O)n2nc(N3CC4CC(C3)O4)nc2n1CC(=O)Nc1ccc(C(F)(F)F)cc1F]

Tert-butyl 4-(2-(6-oxa-3-azabicyclo[3.1.1]heptan-3-yl)-5-methyl-7-oxo-4,7-dihydro-[1,2,4]triazolo[1,5-a]pyrimidin-6-yl)piperazine-1-carboxylate (399 mg, 786 μmol) and 2-bromo-N-(2-fluoro-4-(trifluoromethyl)phenyl)acetamide (Intermediate DR) (259 mg, 865 μmol) were mixed in DMF (3 mL) at RT. DIPEA (412 μL, 2.36 mmol) was added slowly. The suspension was stirred at RT for 1.5 hours. Water (10 mL) was added and the mixture was continued stirring at RT. The suspension was filtered and washed with water. The crude product was adsorbed onto Isolute and purified by column chromatography (RediSep Column: Silica 40 g, eluent DCM:MeOH 100:0 to 90:10). The product containing fractions were combined and concentrated to give the title compound as a pale beige solid.

LC-MS: Rt=1.12 min; MS m/z $[M+H]^+$ 651.4, m/z $[M-H]^-$ 649.4; UPLC-MS 3

Step 3: 2-(2-(6-oxa-3-azabicyclo[3.1.1]heptan-3-yl)-5-methyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide

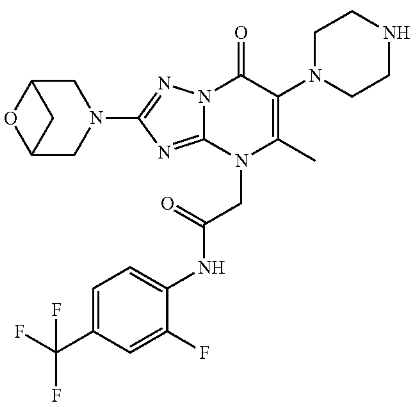 [SMILES: Cc1c(N2CCNCC2)c(=O)n2nc(N3CC4CC(C3)O4)nc2n1CC(=O)Nc1ccc(C(F)(F)F)cc1F]

Tert-butyl 4-(2-(6-oxa-3-azabicyclo[3.1.1]heptan-3-yl)-4-(2-((2-fluoro-4-(trifluoromethyl)phenyl)amino)-2-oxoethyl)-5-methyl-7-oxo-4,7-dihydro-[1,2,4]triazolo[1,5-a]pyrimidin-6-yl)piperazine-1-carboxylate (353 mg, 543 μmol) was dissolved in DCM (3.7 mL) and TFA (836 μL, 10.9 mmol) was added. The RM was stirred at RT for 1 hour. The RM was concentrated under reduced pressure, dissolved and concentrated twice in DCM and toluene. Then it was dried under HV to give the title compound as a beige solid foam.

LC-MS: Rt=0.79 min; MS m/z $[M+H]^+$ 551.3, m/z $[M-H]^-$ 549.3; UPLC-MS 3

Intermediate W: 2-(2-((3R,4S)-3,4-difluoropyrrolidin-1-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: 3-((3R,4S)-3,4-difluoropyrrolidin-1-yl)-1H-1,2,4-triazol-5-amine

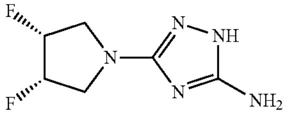

(3S,4R)-3,4-difluoropyrrolidine·HCl (1.50 g, 10.5 mmol) was dissolved in ACN (18 mL) and $Et_3N$ (1.52 mL, 11.0 mmol). Dimethyl cyanocarbonimidodithioate (2.01 g, 12.9 mmol) was added and the RM was stirred at reflux for 2.5 hours. (3S,4R)-3,4-difluoropyrrolidine·HCl (310 mg, 2.16 mmol) and $Et_3N$ (170 μL, 1.23 mmol) were added again and the RM was stirred at reflux for 18.5 hours. The RM was cooled to 0° C. and hydrazine hydrate (710 mg, 14.2 mmol) was added within 1 minute to the suspension. The RM was stirred at reflux for 23.5 hours. The suspension turned into a solution. Hydrazine hydrate (500 mg, 10.0 mmol) was added and the RM was stirred at 88° C. for 3 hours. The RM was cooled to 0° C. and the suspension was filtered and washed with cold EtOH. The obtained solid was dried under HV to give the title compound as a beige solid.

LC-MS: Rt=0.29 min; MS m/z $[M+H]^+$ 190.2, m/z $[M-H]^-$ 188.1; UPLC-MS 3

Step 2: tert-butyl 4-(2-((3R,4S)-3,4-difluoropyrrolidin-1-yl)-5-ethyl-7-oxo-4,7-dihydro-[1,2,4]triazolo[1,5-a]pyrimidin-6-yl)piperazine-1-carboxylate

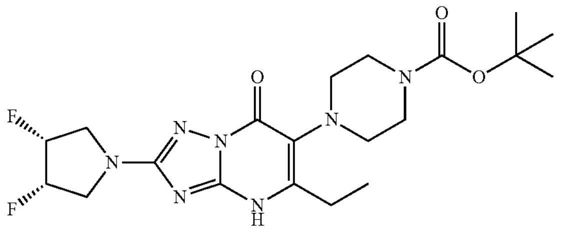 [SMILES: CCc1[nH]c2nc(N3C[C@@H](F)[C@@H](F)C3)nn2c(=O)c1N1CCN(C(=O)OC(C)(C)C)CC1]

3-((3R,4S)-3,4-difluoropyrrolidin-1-yl)-1H-1,2,4-triazol-5-amine (1.25 g, 6.61 mmol) and tert-butyl 4-(1-methoxy-1,3-dioxopentan-2-yl)piperazine-1-carboxylate (Intermediate EH) (2.29 g, 7.27 mmol) were dissolved in EtOH (10 mL) and $H_3PO_4$ (85%) (800 mg, 6.94 mmol) was added slowly. Additional EtOH (10 mL) was added and RM was stirred at 90° C. for 21 hours. Tert-butyl 4-(1-methoxy-1,3-dioxopentan-2-yl)piperazine-1-carboxylate (Intermediate EH) (700 mg, 2.22 mmol) was added and the mixture was continued stirring at 90° C. for 24 hours. Tert-butyl 4-(1-methoxy-1,3-dioxopentan-2-yl)piperazine-1-carboxylate (Intermediate EH) (500 mg, 1.59 mmol) was added and the RM was continued stirring at 90° C. for 7 hours. The RM was allowed to cool to RT then DIPEA (3.46 mL, 19.8 mmol) and $Boc_2O$ (600 mg, 2.75 mmol) were added and the RM was stirred at RT for 2 hours. Then water was added and the organic solvent was evaporated under reduced pressure. The aqueous layer was extracted with EtOAc (3×60 mL), aq sat $NaHCO_3$ (2×20 mL) and brine (2×20 mL). The combined organic layers were dried through a phase separator and concentrated under reduced pressure. The aqueous layer still contained product so it was concentrated under reduced pressure. The residue was suspended several times in DCM and a small amount of MeOH and filtered. The residue was combined with the concentrated organic layer. It was dissolved in DCM and concentrated to ⅓ of the volume. Then it was standing around at RT overnight, the resulting suspension was filtered and washed with a small amount of DCM to obtain product as a solid. The filtrate was adsorbed onto Isolute and purified by column chromatography (RediSep Column: Silica 40 g, eluent DCM:MeOH 100:0 to 90:10). The product containing fractions were combined, concentrated, combined with the cake and dried under HV to give the title compound as a yellow solid.

LC-MS: Rt=0.95 min; MS m/z $[M+H]^+$ 454.4, m/z $[M-H]^-$ 452.4; UPLC-MS 3

Step 3: tert-butyl 4-(2-((3R,4S)-3,4-difluoropyrrolidin-1-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

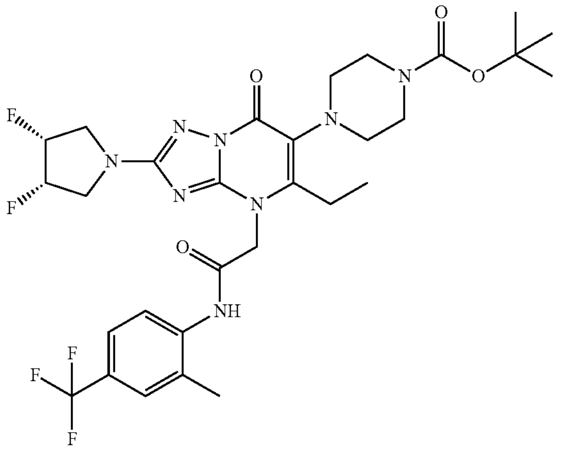 [SMILES: CCc1c(N2CCN(C(=O)OC(C)(C)C)CC2)c(=O)n2nc(N3C[C@@H](F)[C@@H](F)C3)nc2n1CC(=O)Nc1ccc(C(F)(F)F)cc1C]

Tert-butyl 4-(2-((3R,4S)-3,4-difluoropyrrolidin-1-yl)-5-ethyl-7-oxo-4,7-dihydro-[1,2,4]triazolo[1,5-a]pyrimidin-6-yl)piperazine-1-carboxylate (600 mg, 1.32 mmol) and 2-iodo-N-(2-methyl-4-(trifluoromethyl)phenyl)acetamide (Intermediate DV) (499 mg, 1.46 mmol) were dissolved in DMF (6 mL) and DIPEA (693 μL, 3.97 mmol) was added. The RM was stirred at 30° C. for 2 hours, then at 40° C. for 4 hours. 2-Iodo-N-(2-methyl-4-(trifluoromethyl)phenyl)acetamide (Intermediate DV) (35.0 mg, 102 μmol) was added again and the RM was stirred at 40° C. for 2.75 hours, then it was cooled to RT overnight. 2-Iodo-N-(2-methyl-4-(trifluoromethyl)phenyl)acetamide (Intermediate DV) (60.0 mg, 176 μmol) was added again and the RM was stirred at 40° C. for 1.5 hours. The RM was quenched with water and stirred at RT. The resulting suspension was filtered off and washed with a small amount of water. The crude product was adsorbed onto Isolute and purified by column chromatography (RediSep Column: Silica 40 g, eluent DCM:MeOH 100:0 to 90:10). The product containing fractions were combined, concentrated and dried under HV to give the title compound as a pale beige solid.

LC-MS: Rt=1.20 min; MS m/z $[M+H]^+$ 669.4, m/z $[M-H]^-$ 667.4; UPLC-MS 3

Step 4: 2-(2-((3R,4S)-3,4-difluoropyrrolidin-1-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide

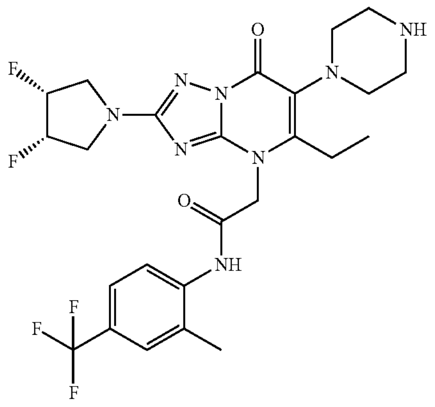 [SMILES: CCc1c(N2CCNCC2)c(=O)n2nc(N3C[C@@H](F)[C@@H](F)C3)nc2n1CC(=O)Nc1ccc(C(F)(F)F)cc1C]

Tert-butyl 4-(2-((3R,4S)-3,4-difluoropyrrolidin-1-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (410 mg, 613 μmol) was dissolved in DCM (4.1 mL) and TFA (709 μL, 9.20 mmol) was added and the RM was stirred at RT for 2 hours. The RM was concentrated under reduced pressure. The residue was dissolved three times in DCM and a small amount of toluene and concentrated under reduced pressure again. Then it was dried under HV to give the title compound as a bright brown solid.

LC-MS: Rt=0.85 min; MS m/z $[M+H]^+$ 569.4, m/z $[M-H]^-$ 567.3; UPLC-MS 3

Scheme 3 general overview of intermediates of route II

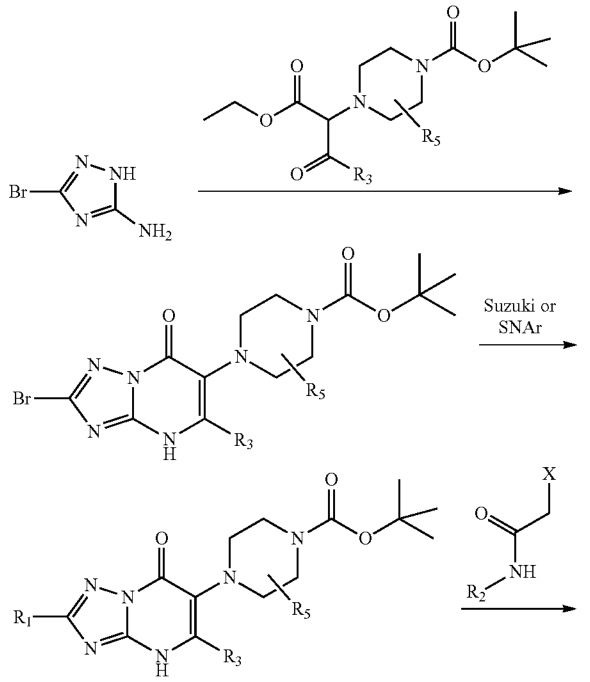

-continued

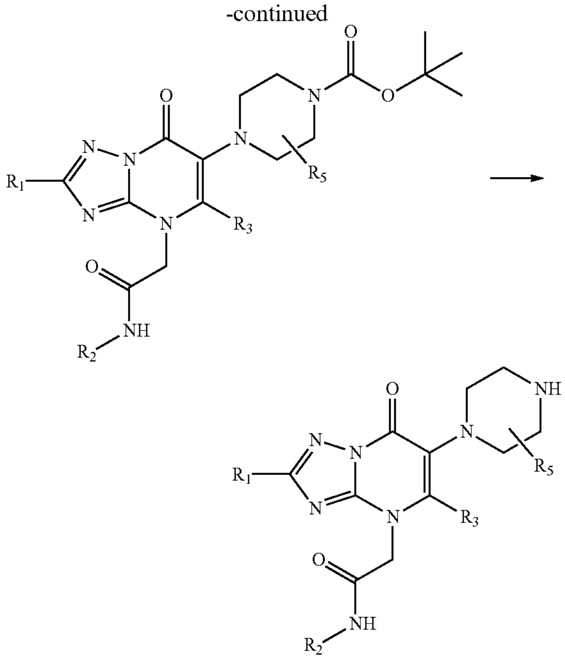

Intermediate X: tert-butyl 4-(2-bromo-5-ethyl-7-oxo-4,7-dihydro-[1,2,4]triazolo[1,5-a]pyrimidin-6-yl)piperazine-1-carboxylate

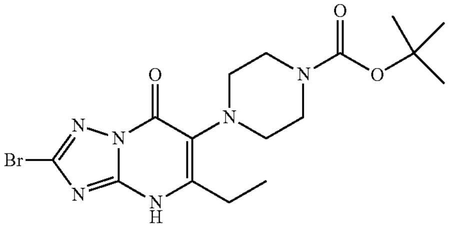 [SMILES: CCc1[nH]c2nc(Br)nn2c(=O)c1N1CCN(C(=O)OC(C)(C)C)CC1]

3-Bromo-1H-1,2,4-triazol-5-amine (Intermediate ER) (82.6 g, 507 mmol) and tert-butyl 4-(1-methoxy-1,3-dioxopentan-2-yl)piperazine-1-carboxylate (Intermediate EH) (175 g, 557 mmol) were mixed in EtOH (465 mL). $H_3PO_4$ (49.7 g, 507 mmol) was added. The mixture was stirred at 80° C. for 12 hours under nitrogen. The mixture was concentrated in vacuo to remove EtOH, then quenched by addition of aq sat $NaHCO_3$ (1 L), and extracted with DCM (3×1 L). The combined organic layers were washed with brine (3×1 L), dried over $Na_2SO_4$, filtered and concentrated under reduced pressure to give a residue. The residue was purified by column chromatography (Silica column, eluent DCM:MeOH 1:0 to 10:1). The product containing fractions were combined and concentrated under reduced pressure to give the title compound as a yellow solid.

LC-MS: Rt=0.91 min; MS m/z $[M+H-Boc]^+$ 327.1/329.1, m/z $[M+H]^+$ 427.2/429.2, m/z $[M-H]^-$ 425.2/427.2; UPLC-MS 1

LC-MS: Rt=4.53 min; MS m/z $[M+H-Boc]^+$ 327.1/329.1, m/z $[M-H]^-$ 425.2/427.2; UPLC-MS 2

$^1H$ NMR (400 MHz, DMSO-$d_6$) δ 13.27 (s, 1H), 3.91 (m, 2H), 3.31 (m, 2H), 2.88 (m, 2H), 2.75 (m, 2H), 2.61 (m, 2H), 1.42 (s, 9H), 1.17 (t, J=7.4 Hz, 3H)

Intermediate Y: N-(2-chloro-6-(trifluoromethyl)pyridin-3-yl)-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)acetamide Step 1: tert-butyl 4-(5-ethyl-2-(4-methoxycyclohex-1-en-1-yl)-7-oxo-4,7-dihydro-[1,2,4]triazolo[1,5-a]pyrimidin-6-yl)piperazine-1-carboxylate

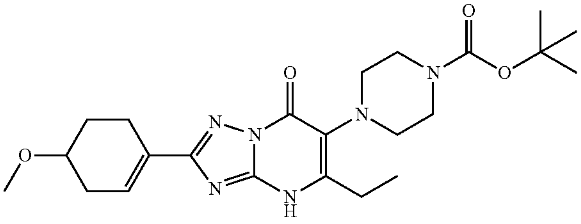 [SMILES: CCc1[nH]c2nc(C3=CCC(OC)CC3)nn2c(=O)c1N1CCN(C(=O)OC(C)(C)C)CC1]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (1.40 g, 3.28 mmol) was suspended in DMF/Water (9:1) (20 mL). Rac-2-(4-methoxycyclohex-1-en-1-yl)-4,4,5,5-tetramethyl-1,3,2-dioxaborolane (Intermediate DH) (1.56 g, 6.55 mmol) and $K_3PO_4$ (2.09 g, 9.83 mmol) were added and the RM was degassed for 15 minutes with argon, then Pd(dppf)$Cl_2$·DCM (134 mg, 164 μmol) was added and the RM was stirred at 100° C. for 16 hours. The RM was extracted three times with DCM. The organic layer was washed with brine, dried over $Na_2SO_4$ and concentrated under reduced pressure. The crude product was purified by column chromatography (Silica gel column: Silica 40 g, eluent DCM:MeOH 100:0 to 98:2). The product containing fractions were combined and concentrated under reduced pressure to give the title compound.

LC-MS: Rt=2.15 min; MS m/z $[M+H]^+$ 459.3; UPLC-MS 13

Step 2: tert-butyl 4-(4-(2-((2-chloro-6-(trifluoromethyl)pyridin-3-yl)amino)-2-oxoethyl)-5-ethyl-2-(4-methoxycyclohex-1-en-1-yl)-7-oxo-4,7-dihydro-[1,2,4]triazolo[1,5-a]pyrimidin-6-yl)piperazine-1-carboxylate

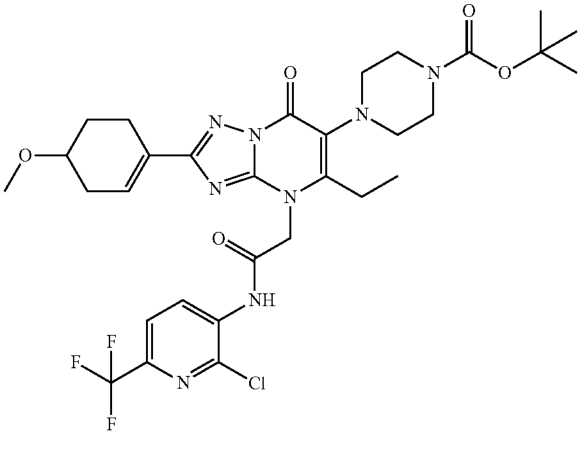 [SMILES: CCc1c(N2CCN(C(=O)OC(C)(C)C)CC2)c(=O)n2nc(C3=CCC(OC)CC3)nc2n1CC(=O)Nc1ccc(C(F)(F)F)nc1Cl]

Tert-butyl 4-(5-ethyl-2-(4-methoxycyclohex-1-en-1-yl)-7-oxo-4,7-dihydro-[1,2,4]triazolo[1,5-a]pyrimidin-6-yl)piperazine-1-carboxylate (1.20 g, 2.54 mmol) and 2-bromo-N-(2-chloro-6-(trifluoromethyl)pyridin-3-yl)acetamide (Intermediate DQ) (645 mg, 2.03 mmol) were suspended in DMF (8 mL) at 0° C. and DIPEA (1.33 mL, 7.62 mmol) was added dropwise. The RM was stirred at RT for 14 hours. The RM was concentrated, extracted with 10% MeOH in DCM, dried over $Na_2SO_4$ and concentrated under reduced pressure. The crude product was purified by column chromatography (Silica gel column: Silica 12 g, eluent DCM:MeOH 100:0 to 98:2). The product containing fractions were combined and concentrated to give the title compound.

LC-MS: Rt=2.41 min; MS m/z $[M+H]^+$ 695.7/697.7; UPLC-MS 13

Step 3: N-(2-chloro-6-(trifluoromethyl)pyridin-3-yl)-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)acetamide

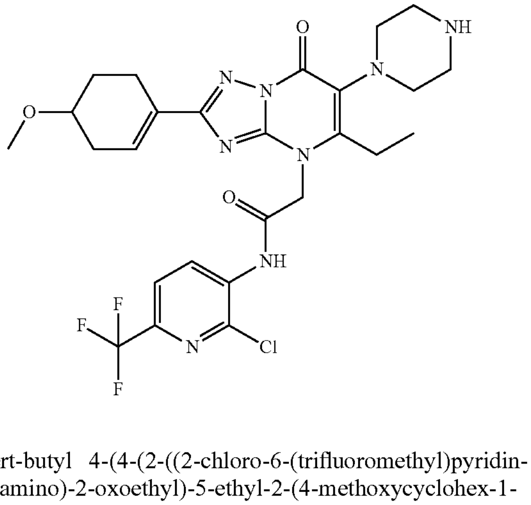

Tert-butyl 4-(4-(2-((2-chloro-6-(trifluoromethyl)pyridin-3-yl)amino)-2-oxoethyl)-5-ethyl-2-(4-methoxycyclohex-1-en-1-yl)-7-oxo-4,7-dihydro-[1,2,4]triazolo[1,5-a]pyrimidin-6-yl)piperazine-1-carboxylate (400 mg, 529 μmol) was suspended in DCM (15 mL) and TFA (8.00 mL, 104 mmol) was added at 0° C. The RM was stirred at RT for 16 hours. The RM was quenched with $NaHCO_3$ and extracted with DCM. The organic layer was dried over $Na_2SO_4$ and concentrated under reduced pressure. The solid was triturated with $Et_2O$ to give the title compound.

LC-MS: Rt=0.51 min; MS m/z $[M+H]^+$ 595.1/597.1; UPLC-MS 12

Intermediate Z: rac-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide Step 1: rac-tert-butyl 4-(5-ethyl-2-(4-methoxycyclohex-1-en-1-yl)-7-oxo-4,7-dihydro-[1,2,4]triazolo[1,5-a]pyrimidin-6-yl)piperazine-1-carboxylate

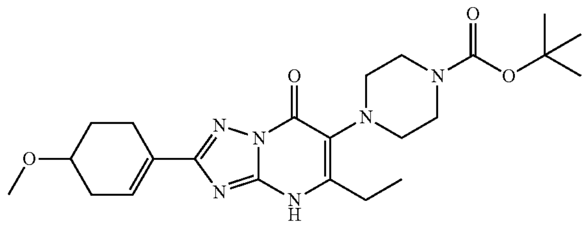 [SMILES: CCc1[nH]c2nc(C3=CCC(OC)CC3)nn2c(=O)c1N1CCN(C(=O)OC(C)(C)C)CC1]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (1.00 g, 2.34 mmol) was suspended in DMF/Water (9:1) (15 mL). Rac-2-(4-methoxycyclohex-1-en-1-yl)-4,4,5,5-tetramethyl-1,3,2-dioxaborolane (Intermediate DH) (1.12 g, 4.68 mmol) and $K_3PO_4$ (1.49 g, 7.02 mmol) were added and the RM was degassed for 15 minutes with argon, then XPhos Pd G2 (92.0 mg, 117 μmol) was added and the RM was stirred at 110° C. for 12 hours. The RM was concentrated, ice cold water was added and the precipitate was filtered off, washed with $Et_2O$ and dried under reduced pressure. The crude product was purified by column chromatography (Silica gel column: Silica 40 g, eluent DCM:MeOH 100:0 to 97:3). The product containing fractions were combined and concentrated under reduced pressure to give the title compound.

LC-MS: Rt=1.48 min; MS m/z $[M+H]^+$ 459.2; UPLC-MS 11

Step 2: rac-tert-butyl 4-(5-ethyl-2-(4-methoxycyclohex-1-en-1-yl)-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

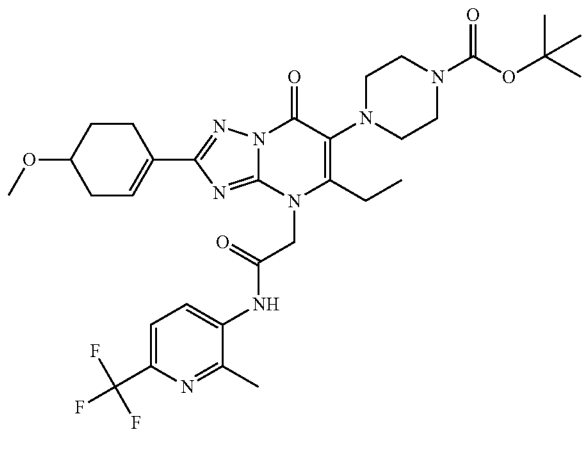 [SMILES: CCc1c(N2CCN(C(=O)OC(C)(C)C)CC2)c(=O)n2nc(C3=CCC(OC)CC3)nc2n1CC(=O)Nc1ccc(C(F)(F)F)nc1C]

To the solution of rac-tert-butyl 4-(5-ethyl-2-(4-methoxycyclohex-1-en-1-yl)-7-oxo-4,7-dihydro-[1,2,4]triazolo[1,5-a]pyrimidin-6-yl)piperazine-1-carboxylate (400 mg, 872 μmol) in DMF (8 mL) were added 2-bromo-N-(2-methyl-6-(trifluoromethyl)pyridin-3-yl)acetamide (Intermediate DW) (311 mg, 1.05 mmol) and DIPEA (457 μL, 2.62 mmol) and the RM was stirred at RT for 16 hours. The RM was diluted with water and extracted with 5% MeOH in DCM, washed with brine, dried over $Na_2SO_4$ and concentrated. The crude product was purified by column chromatography (Silica gel column: Silica 24 g, eluent DCM:MeOH 100:0 to 98:2). The product containing fractions were combined, concentrated and dried under HV to give the title compound.

LC-MS: Rt=2.33 min; MS m/z $[M+H]^+$ 675.2; UPLC-MS 13

Step 3: rac-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide

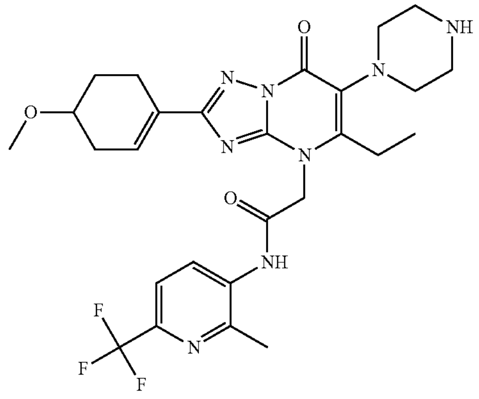 [SMILES: CCc1c(N2CCNCC2)c(=O)n2nc(C3=CCC(OC)CC3)nc2n1CC(=O)Nc1ccc(C(F)(F)F)nc1C]

To the solution of rac-tert-butyl 4-(5-ethyl-2-(4-methoxycyclohex-1-en-1-yl)-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (400 mg, 414 μmol) in DCM (5 mL) was added 1,4-dioxane 4M in HCl (10.0 mL, 40.0 mmol) at 0° C. and the RM was stirred at RT for 12 hours. The RM was concentrated under reduced pressure, washed with $Et_2O$ (2×10 mL) and dried under HV to give the title compound as a HCl salt as an off-white solid.

LC-MS: Rt=1.31 min; MS m/z $[M+H]^+$ 575.3; UPLC-MS 11

Intermediate AA: N-(2-chloro-6-(trifluoromethyl)pyridin-3-yl)-2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)acetamide Step 1: tert-butyl 4-(2-(5,6-dihydro-1,4-dioxin-2-yl)-5-ethyl-7-oxo-4,7-dihydro-[1,2,4]triazolo[1,5-a]pyrimidin-6-yl)piperazine-1-carboxylate

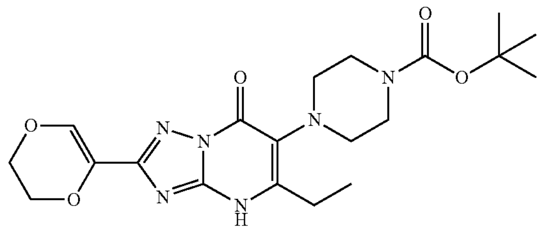 [SMILES: CCc1[nH]c2nc(C3=COCCO3)nn2c(=O)c1N1CCN(C(=O)OC(C)(C)C)CC1]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (600 mg, 1.40 mmol), 2-(5,6-dihydro-1,4-dioxin-2-yl)-4,4,5,5-tetramethyl-1,3,2-dioxaborolane (357 mg, 1.69 mmol) and XPhos Pd G3 (59.4 mg, 70.0 μmol) were mixed, evaporated and purged with argon several times. 1,4-Dioxane (10 mL) and $K_3PO_4$ 1M in water (4.21 mL, 4.21 mmol) were added and the RM was stirred at 80° C. for 4.75 hours. 2-(5,6-dihydro-1,4-dioxin-2-yl)-4,4,5,5-tetramethyl-1,3,2-dioxaborolane (90.0 mg, 425 μmol) was added and the mixture was continued stirring at 80° C. for 1.5 hours. 2-(5,6-dihydro-1,4-dioxin-2-yl)-4,4,5,5-tetramethyl-1,3,2-dioxaborolane (110 mg, 519 μmol) and XPhos Pd G3 (15.0 mg, 17.7 μmol) were added and the RM was stirred at 80° C. for 45 minutes. Then it was stirred at RT overnight. 2-(5,6-dihydro-1,4-dioxin-2-yl)-4,4,5,5-tetramethyl-1,3,2-dioxaborolane (60.0 mg, 283 μmol) was added and the RM was stirred at 80° C. for 2.5 hours. The RM was cooled to RT and water (5 mL) and aq sat $NaHCO_3$ (5 mL) were added. The RM was extracted with EtOAc (3×40 mL). The organic layer was washed with water (10 mL), dried through a phase separator and concentrated under reduced pressure. The aqueous layer was washed with DCM (4×40 mL) and with brine, then 4 times with 10% MeOH in DCM. The organic layer was dried through a phase separator and concentrated under reduced pressure. The organic layers were combined and ISOLUTE® Si-Thiol (1.50 g) was added. The mixture was stirred at 35° C. for 30 minutes. The suspension was filtered and washed with DCM and MeOH, the filtrate was concentrated under reduced pressure. The crude product was dissolved in DCM (15 mL) and sonicated for 2 minutes. The suspension was filtered, washed with a small amount of DCM and dried to give the title compound as a white solid.

LC-MS: Rt=0.88 min; MS m/z $[M+H]^+$ 433.4, m/z $[M-H]^-$ 431.4; UPLC-MS 1

Step 2: tert-butyl 4-(4-(2-((2-chloro-6-(trifluoromethyl)pyridin-3-yl)amino)-2-oxoethyl)-2-(5,6-dihydro-1,4-dioxin-2-yl)-5-ethyl-7-oxo-4,7-dihydro-[1,2,4]triazolo[1,5-a]pyrimidin-6-yl)piperazine-1-carboxylate

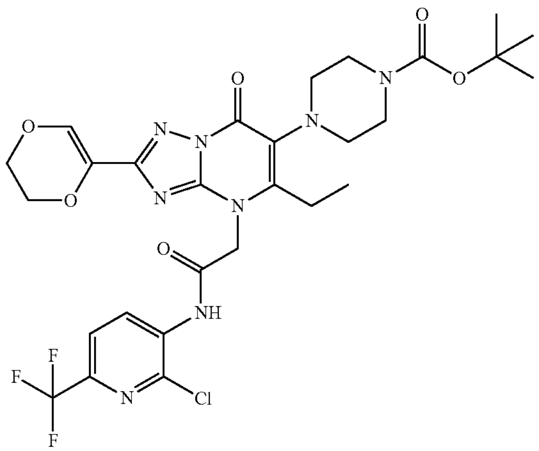 [SMILES: CCc1c(N2CCN(C(=O)OC(C)(C)C)CC2)c(=O)n2nc(C3=COCCO3)nc2n1CC(=O)Nc1ccc(C(F)(F)F)nc1Cl]

Tert-butyl 4-(2-(5,6-dihydro-1,4-dioxin-2-yl)-5-ethyl-7-oxo-4,7-dihydro-[1,2,4]triazolo[1,5-a]pyrimidin-6-yl)piperazine-1-carboxylate (756 mg, 1.40 mmol) and N-(2-chloro-6-(trifluoromethyl)pyridin-3-yl)-2-iodoacetamide (Intermediate DU) (510 mg, 1.40 mmol) were mixed with DMF (6.1 mL) at RT. DIPEA (733 μL, 4.20 mmol) was added and the RM was stirred at RT for 2.75 hours. The RM was stored in the fridge overnight. The next morning it was stirred at RT for 21 hours. The RM was quenched with water (25 mL) and the mixture was stirred at RT. The suspension was filtered, washed with water and the cake was dried. The filtrate was extracted with DCM (4×40 mL). The organic layer was dried through a phase separator and concentrated under reduced pressure. The resulting solid was combined with the cake. The crude product was adsorbed onto Isolute and purified by column chromatography (RediSep Column: Silica 24 g, eluent DCM:MeOH 100:0 to 85:15). The product containing fractions were combined, concentrated and dried under HV to give the title compound as a beige solid.

LC-MS: Rt=1.18 min; MS m/z $[M+H-Boc]^+$ 569.3/571.3, m/z $[M-H]^-$ 667.2/669.1; UPLC-MS 1

Step 3: N-(2-chloro-6-(trifluoromethyl)pyridin-3-yl)-2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)acetamide

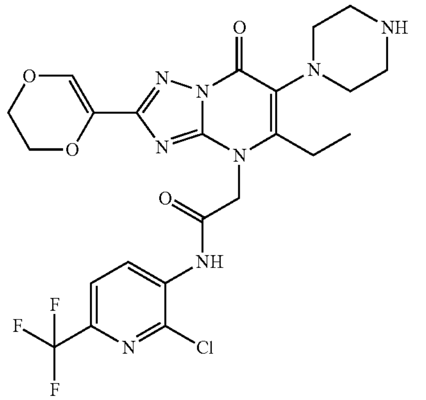 [SMILES: CCc1c(N2CCNCC2)c(=O)n2nc(C3=COCCO3)nc2n1CC(=O)Nc1ccc(C(F)(F)F)nc1Cl]

Tert-butyl 4-(4-(2-((2-chloro-6-(trifluoromethyl)pyridin-3-yl)amino)-2-oxoethyl)-2-(5,6-dihydro-1,4-dioxin-2-yl)-5-ethyl-7-oxo-4,7-dihydro-[1,2,4]triazolo[1,5-a]pyrimidin-6-yl)piperazine-1-carboxylate (462 mg, 380 μmol) was dissolved in DCM (5 mL). TFA (798 μL, 10.4 mmol) was added and the RM was stirred at RT for 1.5 hours. Then it was concentrated under reduced pressure. The residue was dissolved in DCM and a small amount of toluene and concentrated under reduced pressure. This was performed three times. The residue was dried under HV to give the title compound as a beige solid.

LC-MS: Rt=0.64 min; MS m/z $[M+H]^+$ 569.3/571.3, m/z $[M-H]^-$ 567.1/569.1; UPLC-MS 1

Intermediate AB: tert-butyl 4-(2-(3,4-dihydro-2H-pyran-6-yl)-5-ethyl-7-oxo-4,7-dihydro-[1,2,4]triazolo[1,5-a]pyrimidin-6yl)piperazine-1-carboxylate

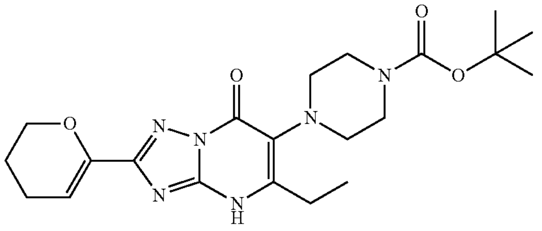 [SMILES: CCc1[nH]c2nc(C3=CCCCO3)nn2c(=O)c1N1CCN(C(=O)OC(C)(C)C)CC1]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (5.00 g, 11.7 mmol) was suspended in DMF/water (9:1) (50 mL). 2-(3,4-dihydro-2H-pyran-6-yl)-4,4,5,5-tetramethyl-1,3,2-dioxaborolane (3.69 g, 17.6 mmol) and $K_3PO_4$ (7.45 g, 35.1 mmol) were added and the RM was degassed with argon for 15 minutes. Pd(dppf)$Cl_2$·DCM (478 mg, 585 μmol) was added and the RM was stirred at 100° C. for 12 hours. The RM was diluted with DCM and washed with water. The organic layer was dried over $Na_2SO_4$ and concentrated under reduced pressure. The insoluble solid was filtered and washed with n-hexane and $Et_2O$ and dried. The solid was dissolved in 10% MeOH in DCM and washed with water and brine. The organic layer was concentrated under reduced pressure. The crude product was purified twice by column chromatography (2× Silica gel column: Silica 40 g, eluent DCM:MeOH 100:0 to 95:5). The product containing fractions were combined, concentrated under reduced pressure and dried to give the title compound.

LC-MS: Rt=2.12 min; MS m/z $[M+H]^+$ 431.1; UPLC-MS 13

Intermediate AC: N-(2-chloro-6-(trifluoromethyl)pyridin-3-yl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-6-(trifluoromethyl)pyridin-3-yl)amino)-2-oxoethyl)-2-(3,4-dihydro-2H-pyran-6-yl)-5-ethyl-7-oxo-4,7-dihydro-[1,2,4]triazolo[1,5-a]pyrimidin-6-yl)piperazine-1-carboxylate

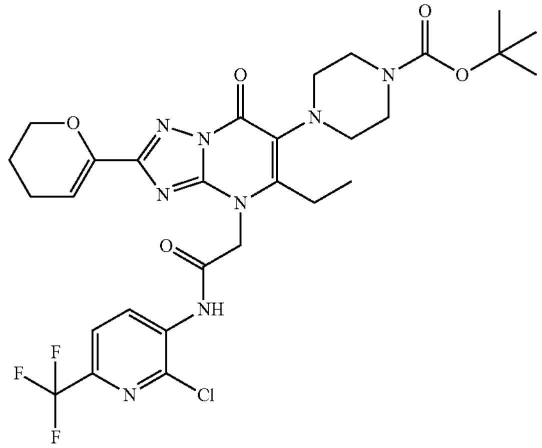

To the stirred solution of tert-butyl 4-(2-(3,4-dihydro-2H-pyran-6-yl)-5-ethyl-7-oxo-4,7-dihydro-[1,2,4]triazolo[1,5-a]pyrimidin-6-yl)piperazine-1-carboxylate (Intermediate AB) (630 mg, 1.46 mmol) in DMF (10 mL) were added 2-bromo-N-(2-chloro-6-(trifluoromethyl)pyridin-3-yl)acetamide (Intermediate DQ) (441 mg, 1.39 mmol) and DIPEA (1.02 mL, 5.85 mmol) at 0° C. The RM was stirred at RT for 16 hours. The RM was concentrated, ice cold water was added, the precipitate was filtered off and dried under HV. The crude product was purified by column chromatography (Silica gel column: Silica 12 g, eluent DCM:MeOH 100:0 to 90:10). The product containing fractions were combined and concentrated to give the title compound as a brown solid.

LC-MS: Rt=1.65 min; MS m/z $[M+H]^+$ 667.2/669.2; UPLC-MS 11

Step 2: N-(2-chloro-6-(trifluoromethyl)pyridin-3-yl)-2-(2-(3,4-dihydro-2H-pyran-6-yl)-5-ethyl-7-oxo-6-(piperazin-1-yl)-[1,2,4]triazolo[1,5-a]pyrimidin-4(7H)-yl)acetamide

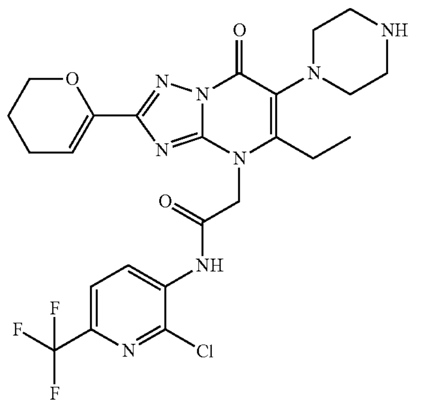 [SMILES: CCc1c(N2CCNCC2)c(=O)n2nc(C3=CCCCO3)nc2n1CC(=O)Nc1ccc(C(F)(F)F)nc1Cl]

Tert-butyl 4-(4-(2-((2-chloro-6-(trifluoromethyl)pyridin-3-yl)amino)-2-oxoethyl)-2-(3,4-dihydro-2H-pyran-6-yl)-5-ethyl-7-oxo-4,7-dihydro-[1,2,4]triazolo[1,5-a]pyrimidin-6-yl)piperazine-1-carboxylate (650 mg, 818 μmol) was suspended in DCM (10 mL). $Et_3N$ (567 μL, 4.09 mmol) and TMSOTf (887 μL, 4.91 mmol) were added at RT and the RM was stirred at 0° C. to RT for 4 hours. The RM was concentrated under reduced pressure to give the title compound.

LC-MS: Rt=1.34 min; MS m/z $[M+H]^+$ 567.2/569.2; UPLC-MS 11

Intermediate AD: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide Step 1: tert-butyl 4-(2-(3,4-dihydro-2H-pyran-6-yl)-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

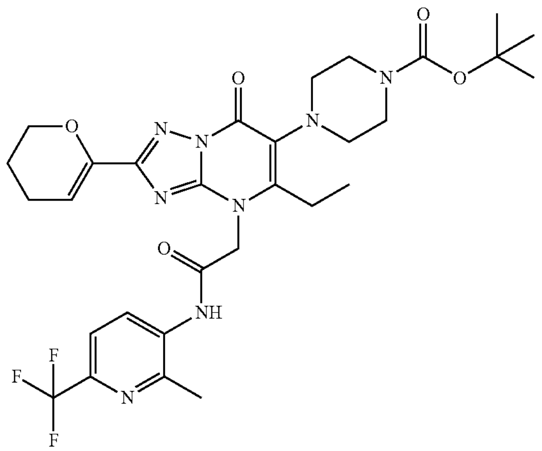

Tert-butyl 4-(2-(3,4-dihydro-2H-pyran-6-yl)-5-ethyl-7-oxo-4,7-dihydro-[1,2,4]triazolo[1,5-a]pyrimidin-6-yl)piperazine-1-carboxylate (Intermediate AB) (2.00 g, 4.65 mmol) was dissolved in DMF (20 mL) and 2-bromo-N-(2-methyl-6-(trifluoromethyl)pyridin-3-yl)acetamide (Intermediate DW) (1.38 g, 4.65 mmol) and DIPEA (2.43 mL, 13.9 mmol) were added and the RM was stirred at RT for 16 hours. The RM was diluted with water, extracted with 5% MeOH in DCM, washed with brine, dried over $Na_2SO_4$ and concentrated under reduced pressure. The crude product was purified by column chromatography (Silica gel column: Silica 40 g, eluent DCM:MeOH 100:0 to 98:2). The product containing fractions were combined, concentrated and dried. The still impure product was purified again by column chromatography (Silica gel column: Silica 40 g, eluent DCM:MeOH 100:0 to 98:2). The product containing fractions were combined, concentrated and dried to give the title compound.

LC-MS: Rt=1.6 min; MS m/z $[M-H]^-$ 645.3; UPLC-MS 11

Step 2: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide

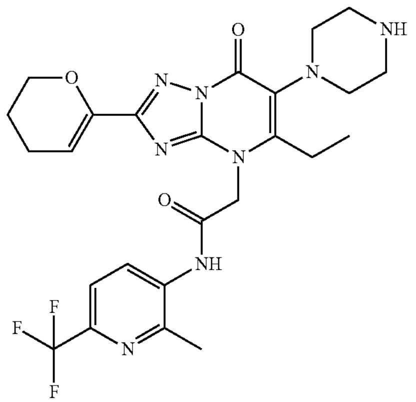 [SMILES: CCc1c(N2CCNCC2)c(=O)n2nc(C3=CCCCO3)nc2n1CC(=O)Nc1ccc(C(F)(F)F)nc1C]

To the stirred solution of tert-butyl 4-(2-(3,4-dihydro-2H-pyran-6-yl)-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (1.00 g, 1.44 mmol) in DCM (20 mL) at 0° C. were added $Et_3N$ (1.20 mL, 8.63 mmol) and TMSOTf (1.56 mL, 8.63 mol) and the RM was stirred at 0° C. for 4 hours, then at RT for 16 hours. The RM was concentrated and ice cold water was added. The mixture was stirred for 30 minutes. The precipitate was filtered off, washed with water (5 mL) and n-pentane and dried under HV to give the title compound.

LC-MS: Rt=1.34 min; MS m/z $[M+H]^+$ 547.3; UPLC-MS 11

Intermediate AE: N-(2-chloro-4-(trifluoromethyl) phenyl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-4-(trifluoromethyl)phenyl)amino)-2-oxoethyl)-2-(3,4-dihydro-2H-pyran-6-yl)-5-ethyl-7-oxo-4,7-dihydro-[1,2,4]triazolo[1,5-a]pyrimidin-6-yl)piperazine-1-carboxylate

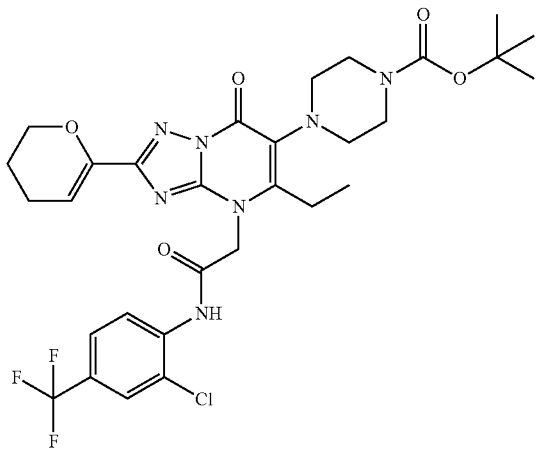

Tert-butyl 4-(2-(3,4-dihydro-2H-pyran-6-yl)-5-ethyl-7-oxo-4,7-dihydro-[1,2,4]triazolo[1,5-a]pyrimidin-6-yl)piperazine-1-carboxylate (Intermediate AB) (5.05 g, 6.92 mmol) and N-(2-chloro-4-(trifluoromethyl)phenyl)-2-iodo-acetamide (Intermediate DL) (1.85 g, 5.09 mmol) were mixed in 1,4-dioxane (20 mL) and DIPEA (2.42 mL, 13.8 mmol) was added. The RM was stirred at 80° C. for 30 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 80 g, eluent DCM:DCM/MeOH (1/1) 100:0 to 70:30). The product containing fractions were combined, concentrated under reduced pressure and dried under HV to afford a brown oil. It was purified by column chromatography again (RediSep Column: Silica 40 g, eluent DCM:DCM/MeOH (8/2) 100:0 to 45:55). The product containing fractions were combined, concentrated under vacuum and dried under HV to afford the title compound as a brown oil.

LC-MS: Rt=1.36 min; MS m/z $[M-H]^-$ 664.5/666.5; UPLC-MS 1

Step 2: N-(2-chloro-4-(trifluoromethyl)phenyl)-2-(2-(3,4-dihydro-2H-pyran-6-yl)-5-ethyl-7-oxo-6-(piperazin-1-yl)-[1,2,4]triazolo[1,5-a]pyrimidin-4 (7H)-yl) acetamide

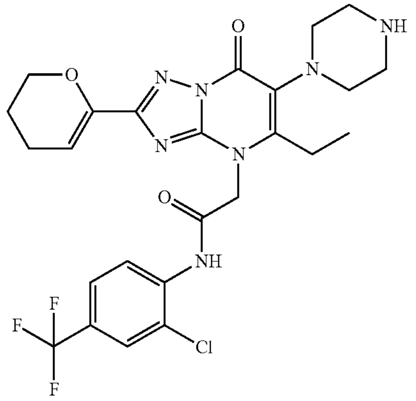 [SMILES: CCc1c(N2CCNCC2)c(=O)n2nc(C3=CCCCO3)nc2n1CC(=O)Nc1ccc(C(F)(F)F)cc1Cl]

Tert-butyl 4-(4-(2-((2-chloro-4-(trifluoromethyl)phenyl) amino)-2-oxoethyl)-2-(3,4-dihydro-2H-pyran-6-yl)-5-ethyl-7-oxo-4,7-dihydro-[1,2,4]triazolo[1,5-a]pyrimidin-6-yl)piperazine-1-carboxylate (763 mg, 882 μmol) was dissolved in DCM (5 mL) and TFA (1.00 mL, 13.0 mmol) was added. The mixture was stirred at 40° C. for 1 hour. The mixture was concentrated under reduced pressure. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was suspended in $Et_2O$ and sonicated for 5 minutes. Then it was filtered. The cake was washed with $Et_2O$ and dried under HV to give the title compound.

LC-MS: Rt=0.87 min; MS m/z $[M+H]^+$ 566.3/568.3, m/z $[M-H]^-$ 564.4/566.4; UPLC-MS 1

Intermediate AF: tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

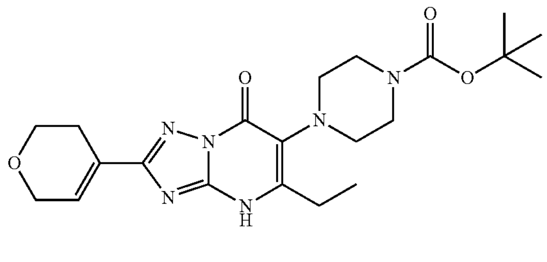 [SMILES: CCc1[nH]c2nc(C3=CCOCC3)nn2c(=O)c1N1CCN(C(=O)OC(C)(C)C)CC1]

To the stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (15.0 g, 35.1 mmol) in 1,4-dioxane (150 mL) and water (50 mL) was added 2-(3,6-dihydro-2H-pyran-4-yl)-4,4,5,5-tetramethyl-1,3,2-dioxaborolane (11.1 g, 52.7 mmol) and $Na_2CO_3$ (7.44 g, 70.2 mmol). The RM was degassed with nitrogen for 15 minutes. $Pd(dppf)Cl_2 \cdot DCM$ (1.43 g, 1.76 mmol) was added and the RM was stirred at 100° C. for 14 hours. Water (300 mL) was added and the RM was extracted with 10% MeOH in DCM (2×500 mL). The organic layer was washed with brine (300 mL), dried over $Na_2SO_4$ and concentrated under reduced pressure. The crude product was purified by column chromatography (Silica gel column: Silica 40 g, eluent DCM:MeOH 100:0 to 97:3). The product containing fractions were combined, concentrated under vacuum and dried under HV to give the title compound.

LC-MS: Rt=0.96 min; MS m/z $[M+H]^+$ 431.4, m/z $[M-H]^-$ 429.3; UPLC-MS 3

$^1H$ NMR (400 MHz, DMSO-$d_6$) δ 13.00 (s, br, 1H), 6.81 (m, 1H), 4.28 (m, 2H), 3.92 (m, 2H), 3.82 (m, 2H), 3.37 (m, 2H), 2.89 (m, 2H), 2.76 (m, 2H), 2.62 (m, 2H), 2.51 (m, 2H), 1.43 (s, 9H), 1.19 (t, J=7.3 Hz, 3H)

Intermediate AG: N-(4-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((4-chloro-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

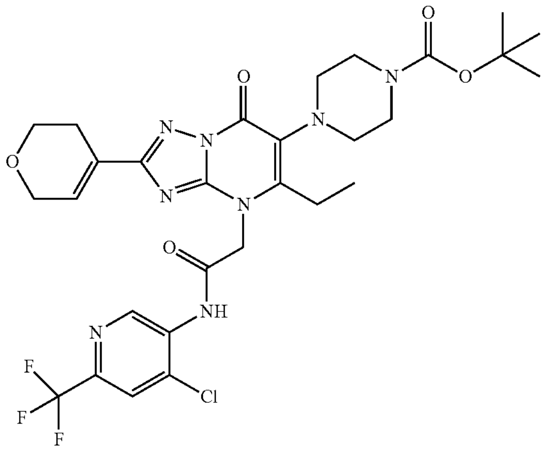

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (610 mg, 1.42 mmol) was suspended in DMF (5 mL). 2-Chloro-N-(4-chloro-6-(trifluoromethyl)pyridin-3-yl)acetamide (Intermediate DX) (348 mg, 1.28 mmol) and DIPEA (619 μL, 3.54 mmol) were added at 0° C. and stirred at 70° C. for 24 hours. Water was added and the solid was filtered. Then it was washed with $Et_2O$ and dried. The crude product was purified by column chromatography (Silica gel column: Silica 24 g, eluent DCM:MeOH 100:0 to 99:1). The product containing fractions were combined, concentrated and dried to give the title compound.

LC-MS: Rt=2.33 min, MS m/z $[M+H]^+$ 667.3/669.3; UPLC-MS 13

Step 2: N-(4-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

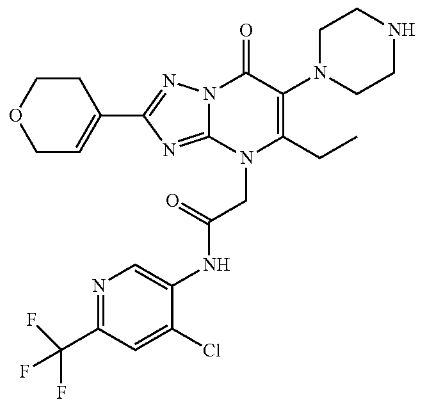 [SMILES: CCc1c(N2CCNCC2)c(=O)n2nc(C3=CCOCC3)nc2n1CC(=O)Nc1cnc(C(F)(F)F)cc1Cl]

Tert-butyl 4-(4-(2-((4-chloro-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (500 mg, 750 μmol) was suspended in DCM (10 mL) and TFA (5.00 mL, 64.9 mmol) was added at 0° C. The RM was stirred at RT for 12 hours. The RM was concentrated under reduced pressure to give the title compound.

LC-MS: Rt=1.34 min, MS m/z $[M+H]^+$ 567.2/569.2; UPLC-MS 11

Intermediate AH: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-methyl-6-(trifluoromethyl)pyridin-3-yl)acetamide Step 1: tert-butyl 4-(2-(3,6-dihydro-2H-pyran-4-yl)-5-ethyl-4-(2-((4-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

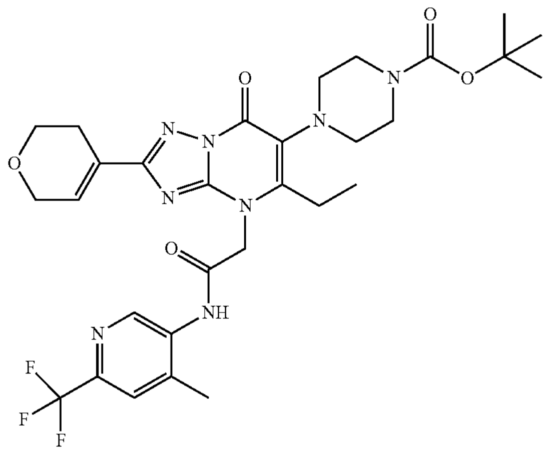 [SMILES: CCc1c(N2CCN(C(=O)OC(C)(C)C)CC2)c(=O)n2nc(C3=CCOCC3)nc2n1CC(=O)Nc1cnc(C(F)(F)F)cc1C]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (400 mg, 929 µmol) was suspended in DMF (5 mL). 2-Bromo-N-(4-methyl-6-(trifluoromethyl)pyridin-3-yl)acetamide (Intermediate DY) (248 mg, 836 µmol) and DIPEA (406 µL, 2.32 mmol) were added at 0° C. and the RM was stirred at RT for 12 hours. Water was added and the solid was filtered. Then it was washed with $Et_2O$ and dried to give the title compound.

LC-MS: Rt=1.55 min, MS m/z $[M+H-Boc]^+$ 547.2; UPLC-MS 11

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-methyl-6-(trifluoromethyl)pyridin-3-yl)acetamide

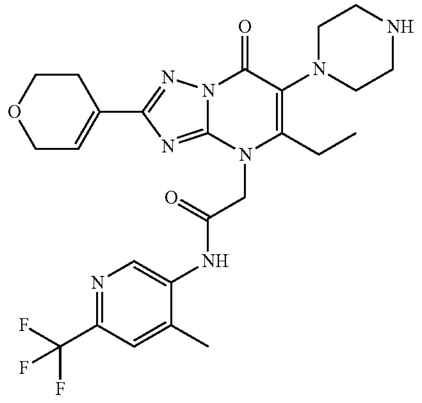 [SMILES: CCc1c(N2CCNCC2)c(=O)n2nc(C3=CCOCC3)nc2n1CC(=O)Nc1cnc(C(F)(F)F)cc1C]

Tert-butyl 4-(2-(3,6-dihydro-2H-pyran-4-yl)-5-ethyl-4-(2-((4-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (450 mg, 70% pure, 487 µmol) was suspended in DCM (10 mL) and TFA (5.00 mL, 64.9 mmol) was added at 0° C. The RM was stirred at RT for 12 hours. The RM was concentrated under reduced pressure to give the title compound.

LC-MS: Rt=0.72 min, MS m/z $[M+H]^+$ 547.3; UPLC-MS 13

Intermediate AI: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide Step 1: tert-butyl 4-(2-(3,6-dihydro-2H-pyran-4-yl)-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

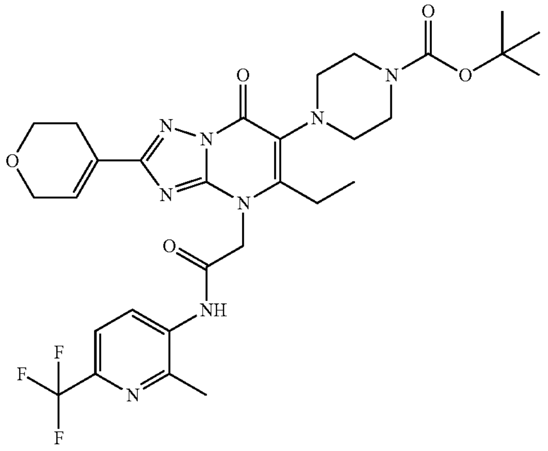 [SMILES: CCc1c(N2CCN(C(=O)OC(C)(C)C)CC2)c(=O)n2nc(C3=CCOCC3)nc2n1CC(=O)Nc1ccc(C(F)(F)F)nc1C]

To a solution of tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (3.00 g, 6.97 mmol) in DMF (30 mL) was added DIPEA (3.65 mL, 20.9 mmol) and 2-bromo-N-(2-methyl-6-(trifluoromethyl)pyridin-3-yl)acetamide (Intermediate DW) (1.66 g, 5.57 mmol) at 0° C., then allowed to warm to RT and stirred at RT for 18 hours. The RM was quenched with water and acidified with HCl. Then it was extracted with DCM, dried over $Na_2SO_4$ and concentrated under reduced pressure. The crude product was purified by column chromatography (Silica gel column: Silica 40 g, eluent hexane:EtOAc 100:0 to 40:60). The product containing fractions were combined, concentrated and washed with $Et_2O$ to give the title compound.

LC-MS: Rt=1.59 min; MS m/z $[M-H]^-$ 645.3; UPLC-MS 13

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide

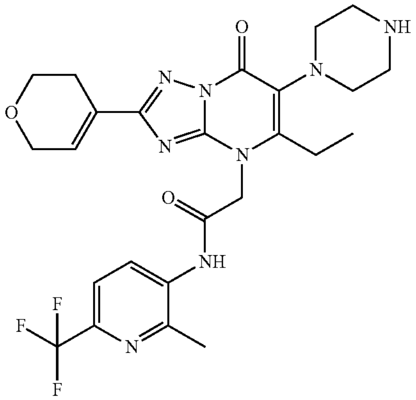 [SMILES: CCc1c(N2CCNCC2)c(=O)n2nc(C3=CCOCC3)nc2n1CC(=O)Nc1ccc(C(F)(F)F)nc1C]

Tert-butyl 4-(2-(3,6-dihydro-2H-pyran-4-yl)-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (2.50 g, 3.75 mmol) was taken in DCM (25 mL) and TFA (8.00 mL, 104 mmol) was added. The RM was stirred at RT for 2 hours. The crude product was concentrated under reduced pressure, washed with $Et_2O$ and dried under HV to give the title compound, as the TFA salt.

LC-MS: Rt=0.45 min, MS m/z $[M+H]^+$ 547.6; UPLC-MS 13

Intermediate AJ: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide Step 1: tert-butyl 4-(2-(3,6-dihydro-2H-pyran-4-yl)-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

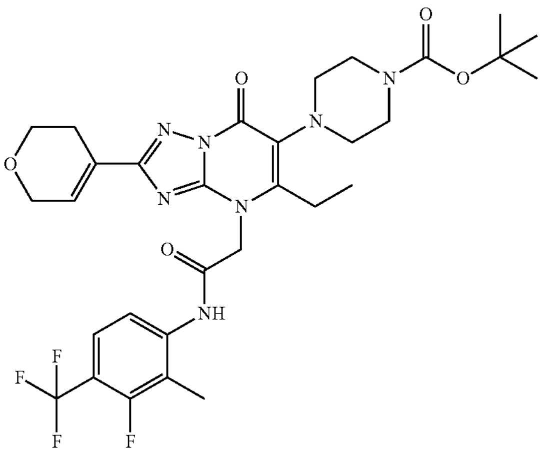 [SMILES: CCc1c(N2CCN(C(=O)OC(C)(C)C)CC2)c(=O)n2nc(C3=CCOCC3)nc2n1CC(=O)Nc1ccc(C(F)(F)F)c(F)c1C]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (2.00 g, 4.55 mmol) and N-(3-fluoro-2-methyl-4-(trifluoromethyl)phenyl)-2-iodoacetamide (Intermediate DZ) (2.26 g, 4.82 mmol) were mixed in 1,4-dioxane (20 mL) and DIPEA (1.59 mL, 9.11 mmol) was added. The mixture was stirred at 70° C. for 1.5 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 80 g, eluent DCM:DCM/MeOH (8/2) 100:0 to 65:35). The product containing fractions were combined, concentrated under vacuum and dried under HV to afford the title compound.

LC-MS: Rt=1.30 min; MS m/z $[M+H-Boc]^+$ 564.2, m/z $[M-H]^-$ 662.5; UPLC-MS 1

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide

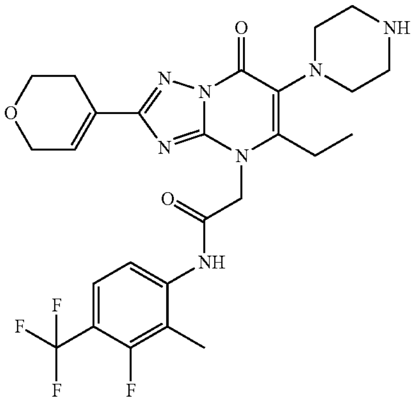 [SMILES: CCc1c(N2CCNCC2)c(=O)n2nc(C3=CCOCC3)nc2n1CC(=O)Nc1ccc(C(F)(F)F)c(F)c1C]

Tert-butyl 4-(2-(3,6-dihydro-2H-pyran-4-yl)-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (2.18 g, 3.02 mmol) was dissolved in DCM (15 mL) and TFA (1.00 mL, 13.0 mmol) was added. The RM was stirred at 40° C. for 3 hours. About 50% conversion was observed. The RM was concentrated under reduced pressure to store it over the weekend, then it was restarted with DCM (15 mL) and TFA (1.00 mL, 13.0 mmol). The RM was stirred at 40° C. for 3 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=0.81 min; MS m/z $[M+H]^+$ 564.2, m/z $[M-H]^-$ 562.4; UPLC-MS 1

Intermediate AK: N-(2-chloro-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

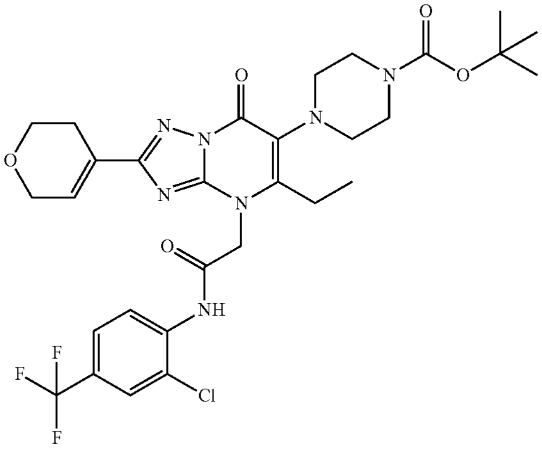 [SMILES: CCc1c(N2CCN(C(=O)OC(C)(C)C)CC2)c(=O)n2nc(C3=CCOCC3)nc2n1CC(=O)Nc1ccc(C(F)(F)F)cc1Cl]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (6.50 g, 15.1 mmol) and N-(2-chloro-4-(trifluoromethyl)phenyl)-2-iodo-acetamide (Intermediate DL) (6.04 g, 16.6 mmol) were mixed in DMF (72 mL) at 0° C. DIPEA (7.91 mL, 45.3 mmol) was added and the RM was stirred at 45° C. for 3.5 hours. The RM was cooled to RT. Water (70 mL) was added and the suspension was stirred at RT overnight. The suspension was sonicated for 25 minutes and filtered. The cake was washed with a small amount of water and dried. The filtrate was filtered again. The second filtrate was extracted with EtOAc (2×400 mL), washed with brine (2×50 mL), dried through a phase separator and concentrated under reduced pressure. The 2 cakes were adsorbed onto Isolute and purified by column chromatography (RediSep Column: Silica 220 g, eluent DCM:DCM/MeOH (1/1) 100:0 to 80:20). The pure product containing fractions were combined and concentrated under reduced pressure. The beige solid foam was dissolved in $Et_2O$ and the resulting crystals were sonicated. The suspension was left standing overnight, filtered, washed with a small amount of $Et_2O$ and dried under HV to give cake 1 as a white solid. The impure fractions were combined and concentrated under reduced pressure. Then they were combined with the concentrated organic layer from the extraction and purified by column chromatography again (RediSep Column: Silica 120 g Gold, eluent DCM:DCM/MeOH (1/1) 100:0 to 85:15). The product containing fractions were combined, concentrated under reduced pressure and dried under HV. The beige solid foam was crystallized out of $Et_2O$ to give cake 2 as a white solid. Cake 1 and cake 2 were combined to give the title compound.

LC-MS: Rt=1.33 min; MS m/z $[M+H-Boc]^+$566.0/568.0, m/z $[M+H]^+$ 666.0/668.0, m/z $[M-H]^-$ 664.1/666.1; UPLC-MS 1

Step 2: N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide

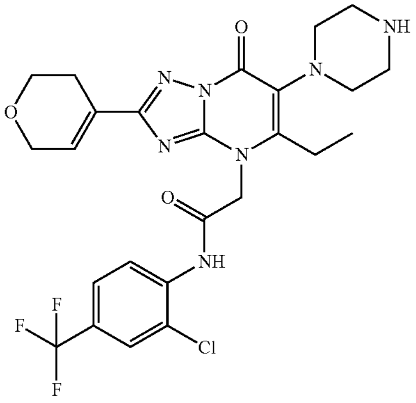 [SMILES: CCc1c(N2CCNCC2)c(=O)n2nc(C3=CCOCC3)nc2n1CC(=O)Nc1ccc(C(F)(F)F)cc1Cl]

Tert-butyl 4-(4-(2-((2-chloro-4-(trifluoromethyl)phenyl) amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (6.41 g, 9.62 mmol) was dissolved in DCM (70 mL) and TFA (11.1 mL, 144 mmol) was added. The RM was stirred at RT for 1 hour. The RM was concentrated under reduced pressure. The residue was dissolved in DCM and concentrated under reduced pressure again. This was performed three times. The resulting oil was dried under HV to result in a pale rose solid foam. The foam was suspended in $Et_2O$ and sonicated. The suspension was filtered, washed with $Et_2O$ and dried under HV to give the title compound as a white solid.

LC-MS: Rt=0.78 min; MS m/z $[M+H]^+$ 566.4/568.4, m/z $[M-H]^-$ 564.2/566.2; UPLC-MS 1

Intermediate AL: N-(2-chloro-6-(trifluoromethyl) pyridin-3-yl)-2-(2-(3,6-dihydro-2H-pyran-4-yl)-5-ethyl-7-oxo-6-(piperazin-1-yl)-[1,2,4]triazolo[1,5-a] pyrimidin-4 (7H)-yl)acetamide Step 1: tert-butyl 4-(4-(2-((2-chloro-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

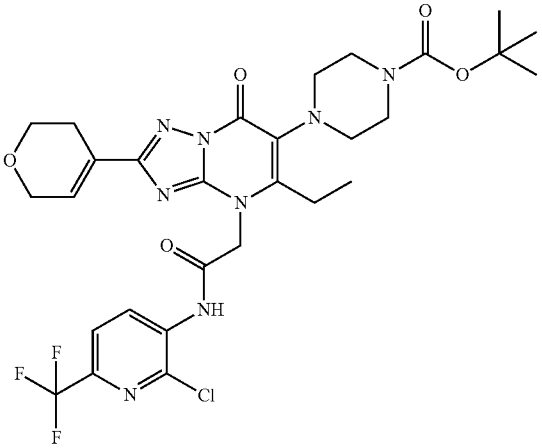

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (344 mg, 719 μmol) and N-(2-chloro-6-(trifluoromethyl)pyridin-3-yl)-2-iodoacetamide (Intermediate DU) (365 mg, 791 μmol) were mixed in 1,4-dioxane (5 mL) and DIPEA (314 μL, 1.78 mmol) was added. The mixture was stirred at 80° C. for 4.5 hours. After stirring at RT for 2 days, it was stirred at 80° C. for 6 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 24 g, eluent DCM:DCM/MeOH (9/1) 100:0 to 50:50). The product containing fractions were combined, concentrated under vacuum and dried under HV to afford the title compound as a brown solid.

LC-MS: Rt=1.14 min; MS m/z $[M+H-Boc]^+$ 567.5/569.4, m/z $[M-H]^-$ 665.3/667.3; UPLC-MS 3

Step 2: N-(2-chloro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

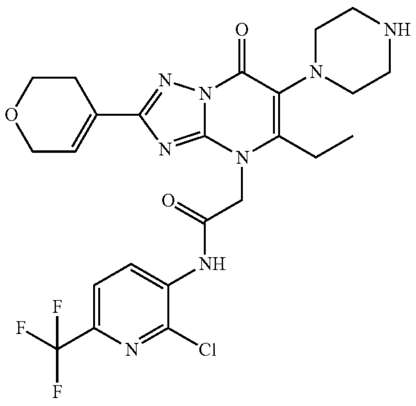 [SMILES: CCc1c(N2CCNCC2)c(=O)n2nc(C3=CCOCC3)nc2n1CC(=O)Nc1ccc(C(F)(F)F)nc1Cl]

Tert-butyl 4-(4-(2-((2-chloro-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (342 mg, 513 μmol) was dissolved in DCM (5 mL) and TFA (1.00 mL, 13.0 mmol) was added. The RM was stirred at 40° C. for 20 minutes. The RM was concentrated under reduced pressure. The crude product was purified in 2 portions by reverse phase preparative HPLC (2×RP-HPLC acidic 1: 20 to 55% B in 10 min with a plateau at 55% for 1 min). The product containing fractions were combined, basified with aq sat $NaHCO_3$, extracted twice with DCM, dried through a phase separator and concentrated under reduced pressure to give the title compound.

LC-MS: Rt=0.78 min; MS m/z $[M+H]^+$ 567.3/569.3, m/z $[M-H]^-$ 565.1/567.1; UPLC-MS 3

Intermediate AM: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide Step 1: tert-butyl 4-(2-(3,6-dihydro-2H-pyran-4-yl)-5-ethyl-4-(2-((5-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

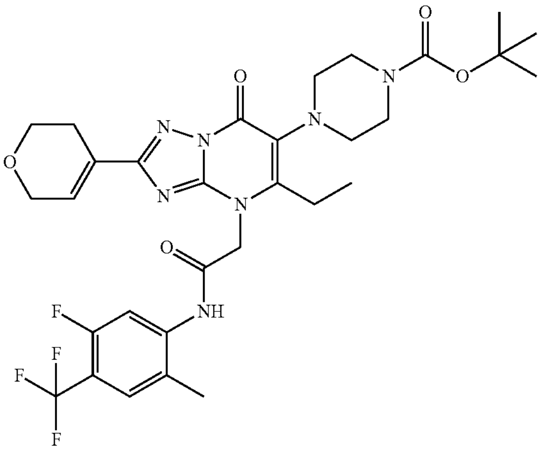 [SMILES: CCc1c(N2CCN(C(=O)OC(C)(C)C)CC2)c(=O)n2nc(C3=CCOCC3)nc2n1CC(=O)Nc1cc(F)c(C(F)(F)F)cc1C]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (800 mg, 1.86 mmol) was suspended in DMF (5 mL). 2-Bromo-N-(5-fluoro-2-methyl-4-(trifluoromethyl)phenyl)acetamide (Intermediate DN) (700 mg, 2.23 mmol) and DIPEA (974 μL, 5.57 mmol) were added at 0° C. and the RM was stirred at RT for 12 hours. Water was added and the solid was filtered and dried to give the title compound.

LC-MS: Rt=1.65 min; MS m/z $[M+H]^+$ 664.2; UPLC-MS 11

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide

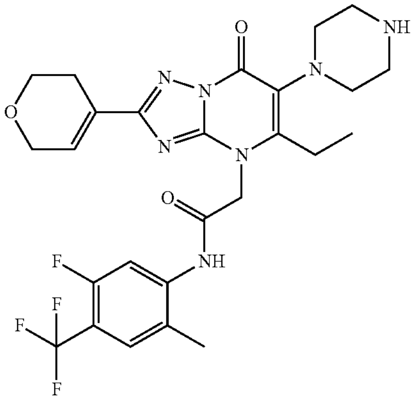 [SMILES: CCc1c(N2CCNCC2)c(=O)n2nc(C3=CCOCC3)nc2n1CC(=O)Nc1cc(F)c(C(F)(F)F)cc1C]

Tert-butyl 4-(2-(3,6-dihydro-2H-pyran-4-yl)-5-ethyl-4-(2-((5-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (800 mg, 1.00 mmol) was suspended in DCM (2 mL) and TFA (2.00 mL, 26.0 mmol) was added at 0° C. The RM was stirred at RT for 12 hours. The RM was concentrated under reduced pressure to give the title compound.

LC-MS: Rt=1.34 min, MS m/z $[M+H]^+$ 564.2; UPLC-MS 11

Intermediate AN: N-(2-chloro-4-(pentafluorosulfanyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-4-(pentafluorosulfanyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

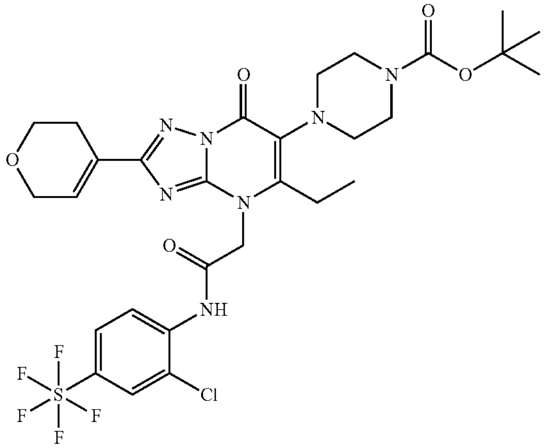 [SMILES: CCc1c(N2CCN(C(=O)OC(C)(C)C)CC2)c(=O)n2nc(C3=CCOCC3)nc2n1CC(=O)Nc1ccc(S(F)(F)(F)(F)F)cc1Cl]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (625 mg, 1.45 mmol) and 2-chloro-N-(2-chloro-4-(pentafluorosulfanyl)phenyl)acetamide (Intermediate EA) (527 mg, 1.60 mmol) were mixed in 1,4-dioxane (10 mL) and DMF (5 mL). Then DIPEA (634 μL, 3.63 mmol) was added and the RM was stirred at 80° C. for 3 days. Then it was stirred at 110° C. for 3 days. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 40 g, eluent DCM:DCM/MeOH (1/1) 100:0 to 65:35). The product containing fractions were combined, concentrated under reduced pressure and dried under HV. The resulting impure product was purified in 5 portions by reverse phase preparative HPLC (5×RP-HPLC acidic 1: 5 to 95% B in 20 min with a plateau at 95% for 1 min). The product containing fractions were combined, basified with aq sat $NaHCO_3$, extracted twice with DCM, dried through a phase separator and concentrated under reduced pressure to give the title compound.

LC-MS: Rt=1.39 min; MS m/z $[M+H-Boc]^+$ 624.4/626.4, m/z $[M-H]^-$ 722.5/724.5; UPLC-MS 1

Step 2: N-(2-chloro-4-(pentafluorosulfanyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

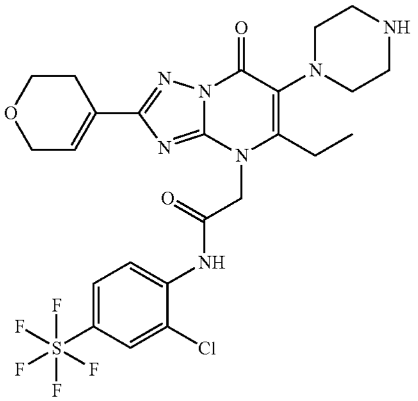 [SMILES: CCc1c(N2CCNCC2)c(=O)n2nc(C3=CCOCC3)nc2n1CC(=O)Nc1ccc(S(F)(F)(F)(F)F)cc1Cl]

Tert-butyl 4-(4-(2-((2-chloro-4-(pentafluorosulfanyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (600 mg, 81% pure, 671 μmol) was dissolved in DCM (10 mL) and TFA (2.00 mL, 26.0 mmol) was added. The RM was stirred at 40° C. for 1 hour. The RM was concentrated under reduced pressure. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=0.90 min; MS m/z $[M+H]^+$ 624.3/626.2, m/z $[M-H]^-$ 622.4/624.3; UPLC-MS 1

Intermediate AO: N-(4-(difluoromethyl)-5-fluoro-2-methylphenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(2-(3,6-dihydro-2H-pyran-4-yl)-5-ethyl-4-(2-((5-fluoro-4-formyl-2-methylphenyl)amino)-2-oxoethyl)-7-oxo-4,7-dihydro-[1,2,4]triazolo[1,5-a]pyrimidin-6-yl)piperazine-1-carboxylate

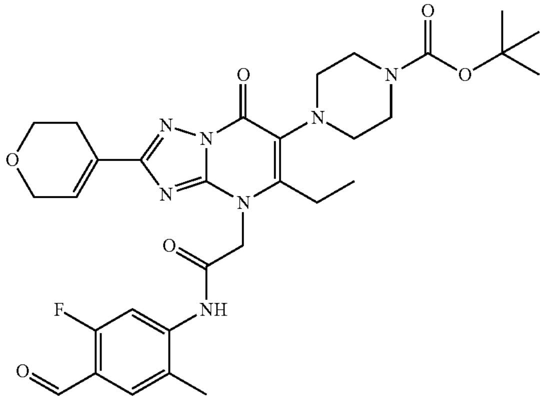 [SMILES: CCc1c(N2CCN(C(=O)OC(C)(C)C)CC2)c(=O)n2nc(C3=CCOCC3)nc2n1CC(=O)Nc1cc(F)c(C=O)cc1C]

To the stirred solution of tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (3.00 g, 6.97 mmol) in DMF (30 mL) at 0° C. were added 2-bromo-N-(5-fluoro-4-formyl-2-methylphenyl)acetamide (Intermediate EB) (1.91 g, 6.97 mmol) and DIPEA (3.65 mL, 20.9 mmol) and the RM was stirred at RT for 12 hours. Water (50 mL) was added and the RM was extracted with DCM (2×50 mL). The organic layer was washed with brine (50 mL), dried over $Na_2SO_4$ and concentrated under reduced pressure. The crude product was purified by column chromatography (Silica gel column: Silica 12 g, eluent DCM:MeOH 100:0 to 98:2). The product containing fractions were combined and concentrated to give the title compound.

LC-MS: Rt=1.73 min, MS m/z $[M+H-Boc]^+$ 524.0; UPLC-MS 12

Step 2: tert-butyl 4-(4-(2-((4-(difluoromethyl)-5-fluoro-2-methylphenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

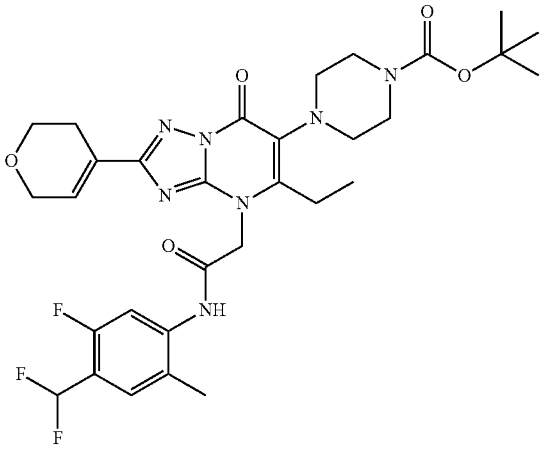 [SMILES: CCc1c(N2CCN(C(=O)OC(C)(C)C)CC2)c(=O)n2nc(C3=CCOCC3)nc2n1CC(=O)Nc1cc(F)c(C(F)F)cc1C]

To tert-butyl 4-(2-(3,6-dihydro-2H-pyran-4-yl)-5-ethyl-4-(2-((5-fluoro-4-formyl-2-methylphenyl)amino)-2-oxoethyl)-7-oxo-4,7-dihydro-[1,2,4]triazolo[1,5-a]pyrimidin-6-yl)piperazine-1-carboxylate (1.34 g, 2.15 mmol) in DCM (20 mL) at −78° C. was added DAST (1.14 mL, 8.59 mmol). The RM was stirred at −78° C. for 30 minutes. Then removed from cooling bath and allowed to warm for 40 minutes. Continued stirring at RT for 1.3 hours. The RM was cooled to 0° C. and carefully quenched by addition of aq sat $NaHCO_3$ (30 mL). Stirred the biphasic mixture at RT for 20 minutes. The organic layer was separated by filtration through a phase separator and evaporated in vacuo to give a brown oil. The crude product was purified by column chromatography (RediSep Column: Silica 40 g, eluent DCM:MeOH 100:0 to 50:50). The product containing fractions were combined and concentrated to give the title compound as a pale brown solid—contains aldehyde as major side-product LC-MS: Rt=1.19 min; MS m/z $[M+H-Boc]^+$ 546.5, m/z $[M-H]^-$ 644.3; UPLC-MS 1

Step 3: N-(4-(difluoromethyl)-5-fluoro-2-methylphenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

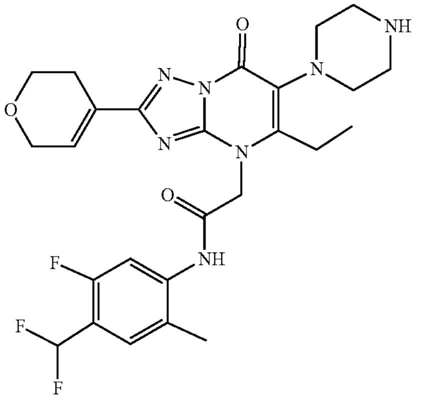 [SMILES: CCc1c(N2CCNCC2)c(=O)n2nc(C3=CCOCC3)nc2n1CC(=O)Nc1cc(F)c(C(F)F)cc1C]

To tert-butyl 4-(4-(2-((4-(difluoromethyl)-5-fluoro-2-methylphenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (1.25 g, 1.94 mmol) in DCM (5 mL) was added TFA (750 μL, 9.73 mmol) and the RM was stirred at RT for 1 hour. The RM was evaporated in vacuo. The residue was partitioned between DCM (50 mL) and aq sat $NaHCO_3$ (20 mL). The organic layer was filtered through a phase separator and evaporated in vacuo to give the title compound as a brown solid—contains aldehyde side-product.

LC-MS: Rt=0.64 min; MS m/z $[M+H]^+$ 546.3, m/z $[M-H]^-$ 544.2; UPLC-MS 1

Scheme 4 general overview of compounds of route III

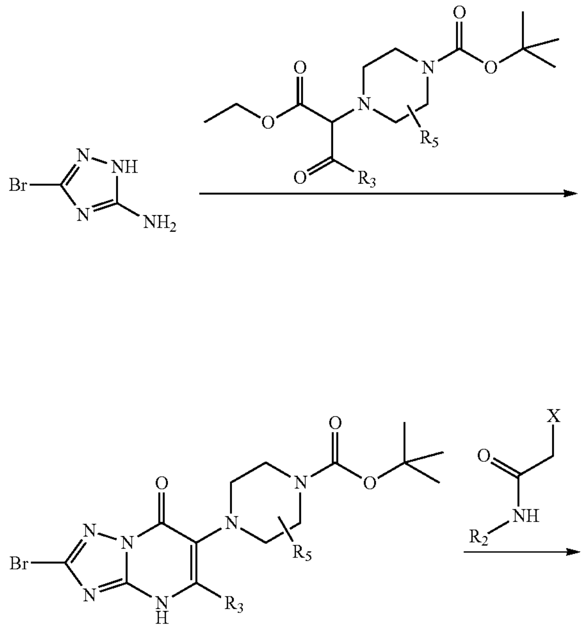

-continued

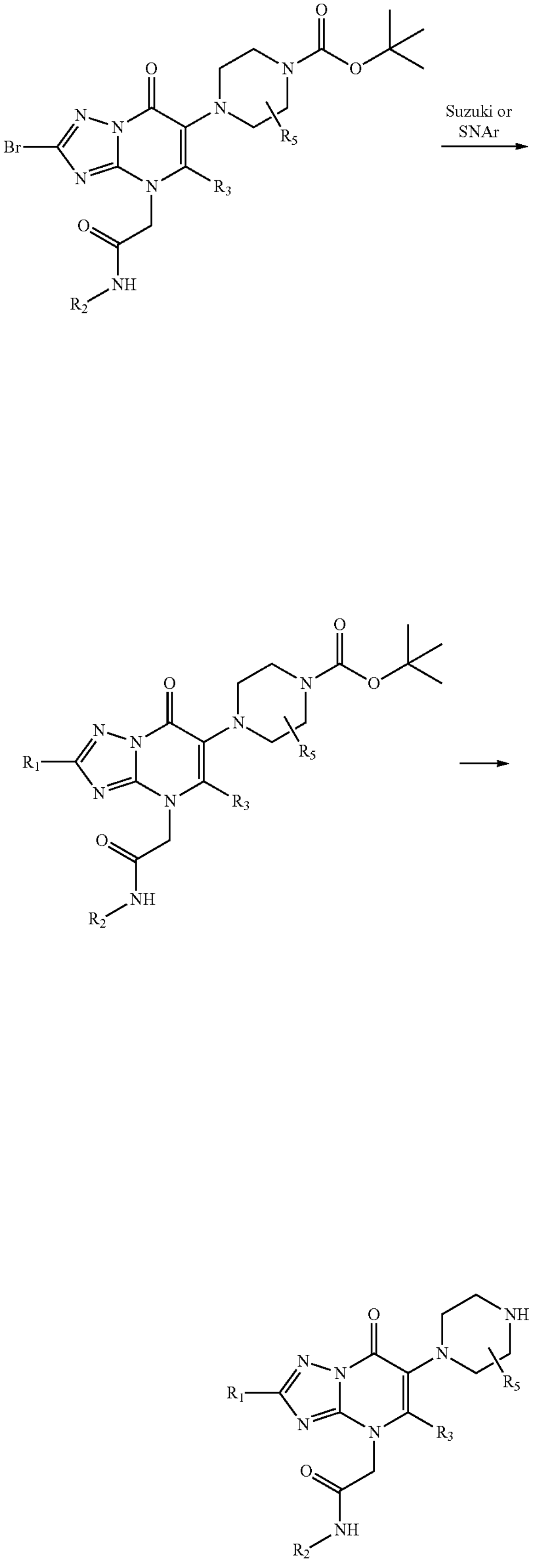

Intermediate AD: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide Step 1: tert-butyl 4-(2-bromo-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

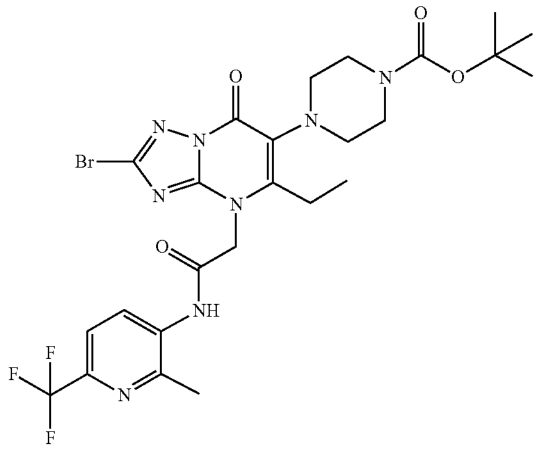 [SMILES: CCc1c(N2CCN(C(=O)OC(C)(C)C)CC2)c(=O)n2nc(Br)nc2n1CC(=O)Nc1ccc(C(F)(F)F)nc1C]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (355 mg, 831 μmol) and 2-iodo-N-(2-methyl-6-(trifluoromethyl)pyridin-3-yl)acetamide (Intermediate EC) (370 mg, 914 μmol) were mixed in DMF (3.2 mL). DIPEA (435 μL, 2.49 mmol) was added and the RM was stirred at 30° C. for 2 hours, then at 40° C. for 4.75 hours, then at RT overnight. Water (5 mL) was added and stirring was continued at RT for 1 hour. The suspension was filtered and washed with a small amount of water to give the title compound as a redbrown solid foam.

LC-MS: Rt=1.11 min; MS m/z $[M+H-Boc]^+$ 543.2, m/z $[M-H]^-$ 641.3; UPLC-MS 3

Step 2: tert-butyl 4-(2-(3,4-dihydro-2H-pyran-6-yl)-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

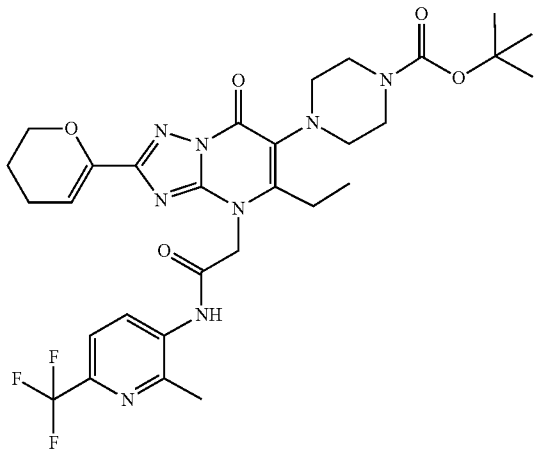 [SMILES: CCc1c(N2CCN(C(=O)OC(C)(C)C)CC2)c(=O)n2nc(C3=CCCCO3)nc2n1CC(=O)Nc1ccc(C(F)(F)F)nc1C]

Tert-butyl 4-(2-bromo-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (413 mg, 642 μmol), 2-(3,4-dihydro-2H-pyran-6-yl)-4,4,5,5-tetramethyl-1,3,2-dioxaborolane (202 mg, 963 μmol) and XPhos Pd G3 (27.7 mg, 32.0 μmol) were degassed and purged with argon several times. 1,4-Dioxane (3 mL) was added, followed by $K_3PO_4$ 1M in water (1.93 mL, 1.93 mmol) and the RM was stirred at 90° C. for 1.3 hours. The RM was concentrated under reduced pressure. The aqueous residue was extracted with EtOAc (3×50 mL), and the organic phases were washed with water (2×10 mL) and brine (10 mL). The organic layer was dried through a phase separator. ISOLUTE® Si-Thiol (550 mg) was added and the mixture was stirred for 20 minutes. The suspension was filtered and the filtrate was concentrated under reduced pressure. The crude product was adsorbed onto Isolute and purified by column chromatography (RediSep Column: Silica 40 g, eluent DCM:MeOH 100:0 to 90:10). The product containing fractions were combined and concentrated under reduced pressure to give the title compound as a grey-brown solid.

LC-MS: Rt=1.11 min; MS m/z $[M+H-Boc]^+$547.3, m/z $[M-H]^-$ 645.5; UPLC-MS 3

Step 3: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide

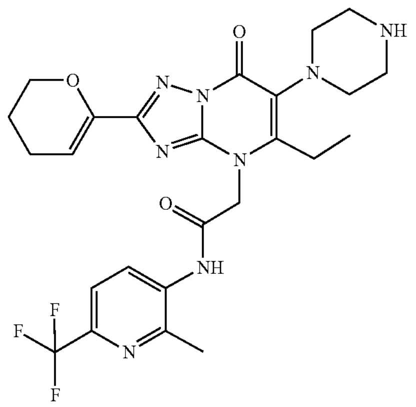 [SMILES: CCc1c(N2CCNCC2)c(=O)n2nc(C3=CCCCO3)nc2n1CC(=O)Nc1ccc(C(F)(F)F)nc1C]

Tert-butyl 4-(2-(3,4-dihydro-2H-pyran-6-yl)-5-ethyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (414 mg, 608 μmol) was dissolved in DCM (4 mL) and TFA (937 μL, 12.2 mmol) was added and the RM was stirred at RT for 1.3 hours. The RM was concentrated under reduced pressure. Then it was dissolved in DCM and concentrated under reduced pressure again. This was performed three times. The resulting material was dried under HV to give the title compound as a brown solid.

LC-MS: Rt=0.83 min; MS m/z $[M+H]^+$ 547.4, m/z $[M-H]^-$ 545.4; UPLC-MS 3

Intermediate AP: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

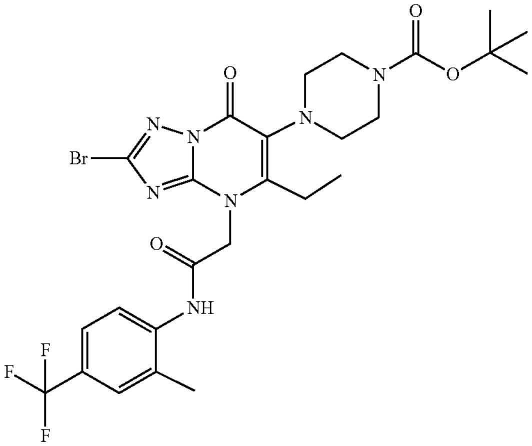 [SMILES: CCc1c(N2CCN(C(=O)OC(C)(C)C)CC2)c(=O)n2nc(Br)nc2n1CC(=O)Nc1ccc(C(F)(F)F)cc1C]

To a stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (15.0 g, 33.3 mmol) and 2-iodo-N-(2-methyl-4-(trifluoromethyl)phenyl)acetamide (Intermediate DV) (13.2 g, 38.4 mmol) in 1,4-dioxane (200 mL) was added DIPEA (17.5 mL, 100 mmol) at RT and the RM was stirred at 80° C. for 15 minutes. The RM was concentrated under reduced pressure. The crude product was diluted with EtOAc and water, extracted once with EtOAc and the organic layer was washed with brine, dried over $Na_2SO_4$ and concentrated under reduced pressure. The crude product was purified by column chromatography (eluent heptane:EtOAc 70:30 to 0:100). The product containing fractions were combined, concentrated and triturated in $Et_2O$ to give the title compound as a white solid.

LC-MS: Rt=1.31 min; MS m/z $[M+H-Boc]^+$542.2, m/z $[M-H]^-$ 640.5; UPLC-MS 1

Step 2: tert-butyl 4-(2-(3,6-dihydro-2H-pyran-4-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

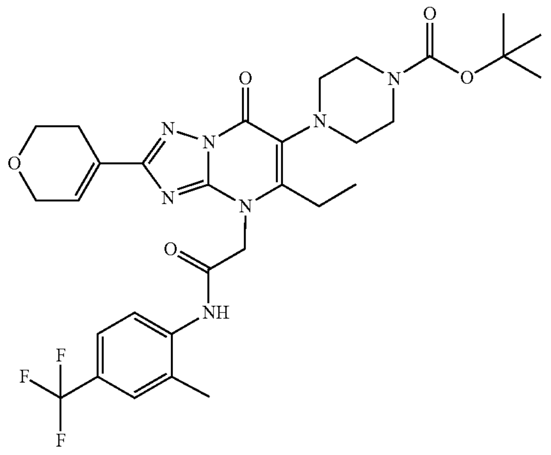 [SMILES: CCc1c(N2CCN(C(=O)OC(C)(C)C)CC2)c(=O)n2nc(C3=CCOCC3)nc2n1CC(=O)Nc1ccc(C(F)(F)F)cc1C]

To a stirred solution of tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (11.2 g, 17.4 mmol), $K_3PO_4$ (11.1 g, 52.2 mmol) and XPhos Pd G3 (736 mg, 870 μmol) in 1,4-dioxane (100 mL) and water (50 mL) was added dropwise at 80° C. a solution of 2-(3,6-dihydro-2H-pyran-4-yl)-4,4,5,5-tetramethyl-1,3,2-dioxaborolane (4.75 g, 22.6 mmol) in 1,4-dioxane (50 mL) and the RM was stirred at 80° C. for 30 minutes. The RM was diluted with DCM and water, extracted twice with DCM and the combined organic extracts were washed with brine, dried over $Na_2SO_4$, concentrated under reduced pressure and triturated in $Et_2O$ to give the title compound as a white solid.

LC-MS: Rt=1.26 min; MS m/z $[M+H-Boc]^+$546.4, m/z $[M-H]^-$ 644.3; UPLC-MS 1

Step 3: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide

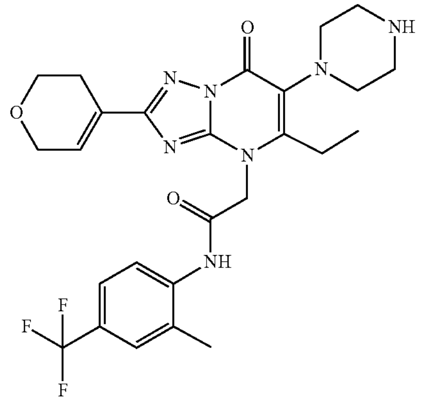 [SMILES: CCc1c(N2CCNCC2)c(=O)n2nc(C3=CCOCC3)nc2n1CC(=O)Nc1ccc(C(F)(F)F)cc1C]

HCl 4N in 1,4-dioxane (30.0 mL, 120 mmoL) was added to tert-butyl 4-(2-(3,6-dihydro-2H-pyran-4-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (9.83 g, 15.2 mmol) and the RM was stirred at 0° C. for 2 hours. The RM was diluted with DCM and $NaHCO_3$, extracted three times with 10% MeOH in DCM and the combined organic layers were dried over $Na_2SO_4$, concentrated under reduced pressure and dried to give the title compound as a white solid.

LC-MS: Rt=0.75 min; MS m/z $[M+H]^+$ 546.3, m/z $[M-H]^-$ 544.4; UPLC-MS 1

Intermediate AQ: N-(5-chloro-2-methyl-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(2-bromo-4-(2-((5-chloro-2-methyl-4-(trifluoromethyl)phenyl)amino)-2-oxoethyl)-5-ethyl-7-oxo-4,7-dihydro-[1,2,4]triazolo[1,5-a]pyrimidin-6-yl)piperazine-1-carboxylate

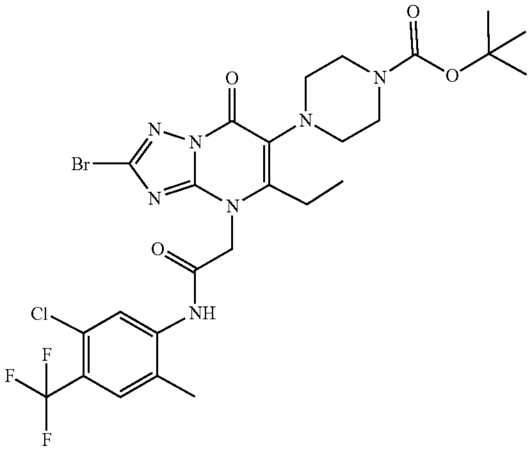 [SMILES: CCc1c(N2CCN(C(=O)OC(C)(C)C)CC2)c(=O)n2nc(Br)nc2n1CC(=O)Nc1cc(Cl)c(C(F)(F)F)cc1C]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (300 mg, 702 μmol) was suspended in DMF (3 mL) and 2-bromo-N-(5-chloro-2-methyl-4-(trifluoromethyl)phenyl)acetamide (Intermediate DM) (278 mg, 842 μmol) and DIPEA (368 μL, 2.11 mmol) were added at 0° C. The RM was stirred at RT for 12 hours. Water was added and the precipitate was filtered off to give the title compound.

LC-MS: Rt=1.68 min; MS m/z $[M+H]^+$ 676.1; UPLC-MS 11

Step 2: tert-butyl 4-(4-(2-((5-chloro-2-methyl-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

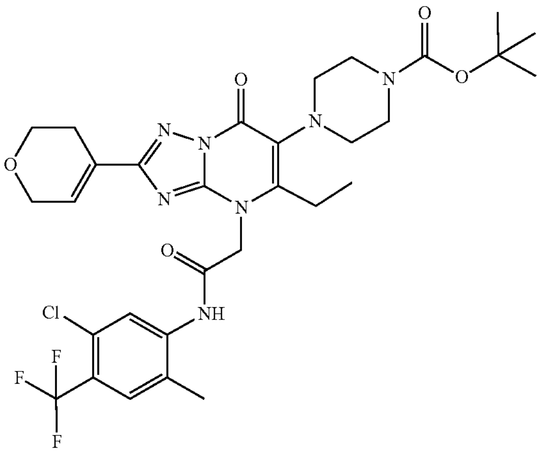 [SMILES: CCc1c(N2CCN(C(=O)OC(C)(C)C)CC2)c(=O)n2nc(C3=CCOCC3)nc2n1CC(=O)Nc1cc(Cl)c(C(F)(F)F)cc1C]

Tert-butyl 4-(2-bromo-4-(2-((5-chloro-2-methyl-4-(trifluoromethyl)phenyl)amino)-2-oxoethyl)-5-ethyl-7-oxo-4,7-dihydro-[1,2,4]triazolo[1,5-a]pyrimidin-6-yl)piperazine-1-carboxylate (400 mg, 479 μmol) was suspended in 1,4-dioxane (5 mL). 2-(3,6-Dihydro-2H-pyran-4-yl)-4,4,5,5-tetramethyl-1,3,2-dioxaborolane (201 mg, 957 μmol) and 0.6M aq $Na_2CO_3$ (2 mL) were added and the RM was degassed for 10 minutes with argon. $PdCl_2(PPh_3)_2$ (33.6 mg, 48.0 μmol) was added and the RM was stirred at 90° C. for 12 hours. The RM was concentrated under reduced pressure, and the crude product was purified by column chromatography (Silica gel column: Silica 12 g, eluent DCM:MeOH 100:0 to 97:3). The product containing fractions were combined, concentrated and dried under HV to give the title compound.

LC-MS: Rt=1.66 min; MS m/z $[M+H]^+$ 680.2; UPLC-MS 11

Step 3: N-(5-chloro-2-methyl-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

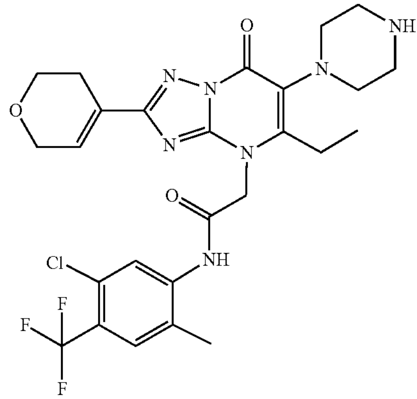 [SMILES: CCc1c(N2CCNCC2)c(=O)n2nc(C3=CCOCC3)nc2n1CC(=O)Nc1cc(Cl)c(C(F)(F)F)cc1C]

Tert-butyl 4-(4-(2-((5-chloro-2-methyl-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (200 mg, 232 μmol) was suspended in DCM (5 mL). TFA (500 μL, 6.49 mmol) was added and the RM was stirred at 40° C. for 3 hours. The RM was concentrated under reduced pressure to give the title compound.

LC-MS: Rt=1.37 min; MS m/z $[M+H]^+$ 580.2; UPLC-MS 11

Intermediate AR: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-6-(trifluoromethyl)pyridin-3-yl)acetamide Step 1: tert-butyl 4-(2-bromo-5-ethyl-4-(2-((5-fluoro-2-methyl-6-(trifluoromethyl)pyridin-3-yl) amino)-2-oxoethyl)-7-oxo-4,7-dihydro-[1,2,4]triazolo[1,5-a]pyrimidin-6-yl)piperazine-1-carboxylate

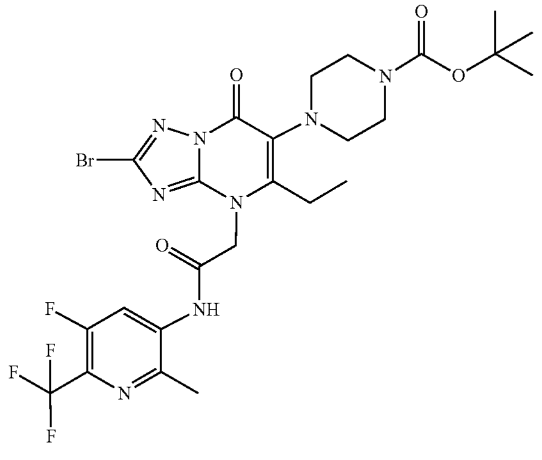 [SMILES: CCc1c(N2CCN(C(=O)OC(C)(C)C)CC2)c(=O)n2nc(Br)nc2n1CC(=O)Nc1cc(F)c(C(F)(F)F)nc1C]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (663 mg, 1.55 mmol) and N-(5-fluoro-2-methyl-6-(trifluoromethyl)pyridin-3-yl)-2-iodoacetamide (Intermediate ED) (638 mg, 1.41 mmol) were mixed in 1,4-dioxane (5 mL) and DIPEA (616 μL, 3.52 mmol) was added. The mixture was stirred at 80° C. for 1.5 hours. Water (10 mL), aq sat $NaHCO_3$ (10 mL) and DCM (10 mL) were added. The aqueous layer was extracted twice with DCM (2×10 mL). The combined organic layers were dried through a phase separator and concentrated under reduced pressure. The crude product was dissolved in DCM and MeOH and SiliaMetS® Thiol was added. The mixture was stirred at 40° C. for 1 hour and then filtered. The cake was washed with DCM. The filtrate was concentrated under reduced pressure to give the title compound.

LC-MS: Rt=1.17 min; MS m/z $[M+H-Boc]^+$ 561.3, m/z $[M-H]^-$ 659.3; UPLC-MS 3

Step 2: tert-butyl 4-(2-(3,6-dihydro-2H-pyran-4-yl)-5-ethyl-4-(2-((5-fluoro-2-methyl-6-(trifluoromethyl) pyridin-3-yl)amino)-2-oxoethyl)-7-oxo-4,7-dihydro-[1,2,4]triazolo[1,5-a]pyrimidin-6-yl)piperazine-1-carboxylate

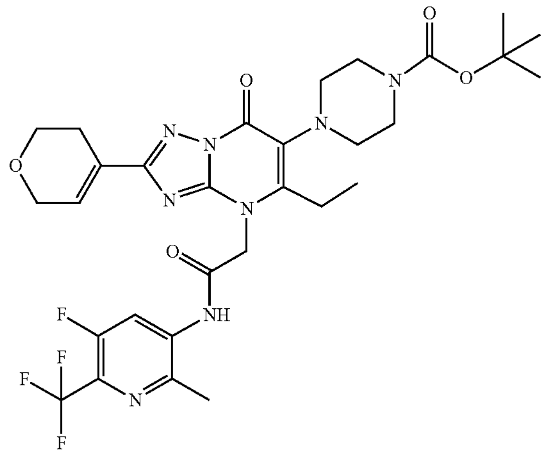 [SMILES: CCc1c(N2CCN(C(=O)OC(C)(C)C)CC2)c(=O)n2nc(C3=CCOCC3)nc2n1CC(=O)Nc1cc(F)c(C(F)(F)F)nc1C]

Tert-butyl 4-(2-bromo-5-ethyl-4-(2-((5-fluoro-2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (1.60 g, 1.45 mmol), 2-(3,6-dihydro-2H-pyran-4-yl)-4,4,5,5-tetramethyl-1,3,2-dioxaborolane (468 mg, 2.23 mmol) and XPhos Pd G3 (61.0 mg, 73.0 μmol) were mixed in 1,4-dioxane (5 mL) and $K_3PO_4$ 1 M in water (4.35 mL, 4.35 mmol) was added. The mixture was stirred at 80° C. for 2.5 hours. Water (10 mL), aq sat $NaHCO_3$ (10 mL) and DCM (10 mL) were added. The aqueous layer was extracted with DCM (2×10 mL). The combined organic layers were dried through a phase separator and concentrated under reduced pressure to give the title compound.

LC-MS: Rt=1.15 min; MS m/z $[M+H-Boc]^+$ 565.4, m/z $[M-H]^-$ 663.4; UPLC-MS 3

Step 3: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-6-(trifluoromethyl)pyridin-3-yl)acetamide

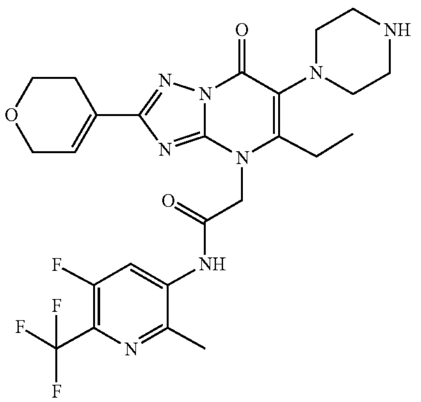 [SMILES: CCc1c(N2CCNCC2)c(=O)n2nc(C3=CCOCC3)nc2n1CC(=O)Nc1cc(F)c(C(F)(F)F)nc1C]

Tert-butyl 4-(2-(3,6-dihydro-2H-pyran-4-yl)-5-ethyl-4-(2-((5-fluoro-2-methyl-6-(trifluoromethyl)pyridin-3-yl) amino)-2-oxoethyl)-7-oxo-4,7-dihydro-[1,2,4]triazolo[1,5-a]pyrimidin-6-yl)piperazine-1-carboxylate (1.31 g, 1.58 mmol) was dissolved in DCM (5 mL) and TFA (1.00 mL, 13.0 mmol) was added. The mixture was stirred at 40° C. for 20 minutes and then concentrated under reduced pressure. Water (10 mL), aq sat $NaHCO_3$ (10 mL) and EtOAc (10 mL) were added. The aqueous layer was extracted with EtOAc (2×10 mL). The combined organic layers were dried through a phase separator and concentrated under reduced pressure to give the title compound.

LC-MS: Rt=0.84 min; MS m/z $[M+H]^+$ 565.3, m/z $[M-H]^-$ 563.1; UPLC-MS 3

Intermediate AS: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide Step 1: tert-butyl 4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

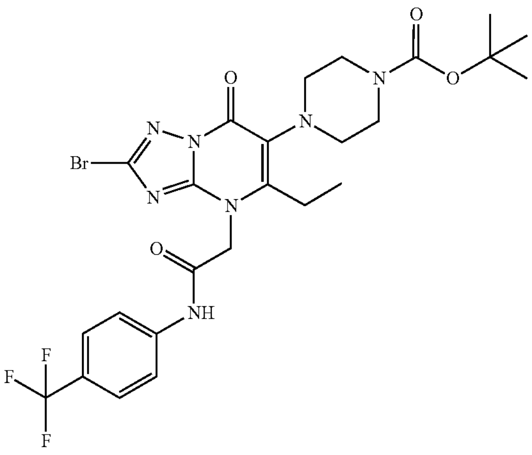 [SMILES: CCc1c(N2CCN(C(=O)OC(C)(C)C)CC2)c(=O)n2nc(Br)nc2n1CC(=O)Nc1ccc(C(F)(F)F)cc1]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (4.11 g, 8.37 mmol) and 2-bromo-N-(4-(trifluoromethyl)phenyl)acetamide (2.36 g, 8.37 mmol) were dissolved in 1,4-dioxane (40 mL) and DIPEA (3.65 mL, 20.9 mmol) was added. The mixture was stirred at 80° C. for 4.5 hours. Water, aq sat $NaHCO_3$ and DCM were added, and the aqueous layer was extracted twice with DCM. The combined organic layers were dried through a phase separator and concentrated under reduced pressure. The crude product was purified by column chromatography (RediSep Column: Silica 120 g, eluent DCM:DCM/MeOH (9/1) 100:0 to 0:100). The product containing fractions were combined and concentrated under reduced pressure. This material was purified by reverse phase preparative HPLC (RP-HPLC acidic 1: 20 to 80% B in 25 min with a plateau at 80% for 1 min). The product containing fractions were combined, basified with aq sat $NaHCO_3$, extracted twice with DCM, dried through a phase separator and concentrated under reduced pressure to give the title compound.

LC-MS: Rt=1.22 min; MS m/z $[M+H\text{-}Boc]^+$528.1, m/z $[M-H]^-$ 626.0; UPLC-MS 4

Step 2: tert-butyl 4-(2-(3,6-dihydro-2H-pyran-4-yl)-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

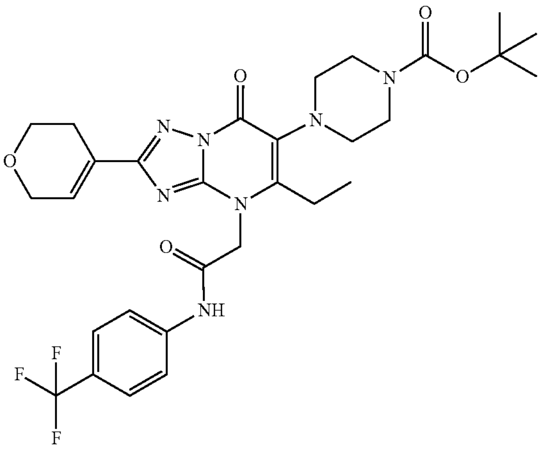 [SMILES: CCc1c(N2CCN(C(=O)OC(C)(C)C)CC2)c(=O)n2nc(C3=CCOCC3)nc2n1CC(=O)Nc1ccc(C(F)(F)F)cc1]

Tert-butyl 4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (255 mg, 406 μmol), 2-(3,6-dihydro-2H-pyran-4-yl)-4,4,5,5-tetramethyl-1,3,2-dioxaborolane (128 mg, 609 μmol) and XPhos Pd G3 (3.43 mg, 4.06 μmol) were mixed in 1,4-dioxane (4 mL). Then $K_3PO_4$ 1M in water (2.03 mL, 2.03 mmol) was added. The mixture was stirred at 80° C. for 4.5 hours. Water, aq sat $NaHCO_3$ and DCM were added, and the aqueous layer was extracted twice with DCM. The combined organic layers were dried through a phase separator. SiliaMetS® Thiol was added and the mixture was stirred at 40° C. for 2 hours. This mixture was filtered, and the solids were washed with DCM. The filtrate was concentrated under reduced pressure, and the crude product was purified by column chromatography (RediSep Column: Silica 12 g, eluent DCM:DCM/MeOH (9/1) 100:0 to 0:100). The product containing fractions were combined, concentrated and dried under HV to give the title compound.

LC-MS: Rt=1.14 min; MS m/z $[M+H]^+$ 632.3, m/z $[M-H]^-$ 630.1; UPLC-MS 4

Step 3: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide

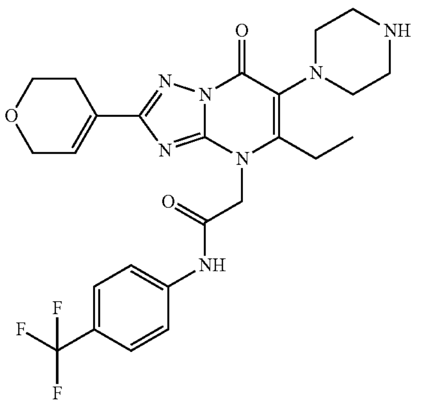

Tert-butyl 4-(2-(3,6-dihydro-2H-pyran-4-yl)-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (290 mg, 436 μmol) was dissolved in DCM (2 mL) and TFA (168 μL, 2.18 mmol) was added. The mixture was stirred at RT for 1 hour. Water, aq sat $NaHCO_3$ and DCM were added, and the aqueous layer was extracted with DCM twice. The combined organic layers were dried through a phase separator and concentrated under reduced pressure to give the title compound.

LC-MS: Rt=0.79 min; MS m/z $[M+H]^+$ 532.2, m/z $[M-H]^-$ 530.0; UPLC-MS 4

Intermediate AT: 2-(5-ethyl-7-oxo-6-(piperazin-1-yl)-2-(pyridin-3-yl)-[1,2,4]triazolo[1,5-a]pyrimidin-4 (7H)-yl)-N-(2-methyl-4-(trifluoromethyl)phenyl) acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

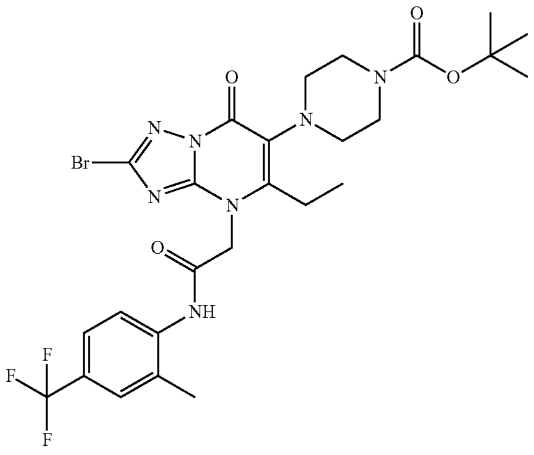 [SMILES: CCc1c(N2CCN(C(=O)OC(C)(C)C)CC2)c(=O)n2nc(Br)nc2n1CC(=O)Nc1ccc(C(F)(F)F)cc1C]

To the stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (2.50 g, 5.85 mmol) in DMF (20 mL) were added 2-bromo-N-(2-methyl-4-(trifluoromethyl)phenyl)acetamide (Intermediate DP) (2.08 g, 7.02 mmol) and DIPEA (2.55 mL, 14.6 mmol) at 0° C. The RM was stirred at RT for 16 hours. The RM was concentrated and ice cold water was added. The precipitate was filtered off and dried under HV. The crude product was purified by column chromatography (Silica gel column: Silica 40 g, eluent DCM:MeOH 100:0 to 90:10). The product containing fractions were combined, concentrated and dried under HV to give the title compound.

LC-MS: Rt=1.64 min; MS m/z $[M+H]^+$ 642.2; UPLC-MS 11

Step 2: tert-butyl 4-(5-ethyl-4-(2-((2-methyl-4-(trifluoromethyl)phenyl)amino)-2-oxoethyl)-7-oxo-2-(pyridin-3-yl)-4,7-dihydro-[1,2,4]triazolo[1,5-a]pyrimidin-6-yl)piperazine-1-carboxylate

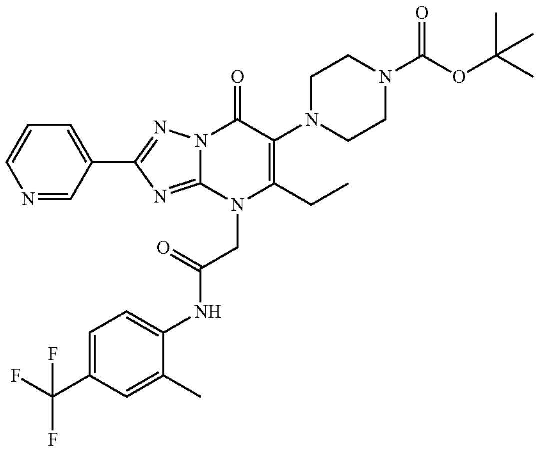 [SMILES: CCc1c(N2CCN(C(=O)OC(C)(C)C)CC2)c(=O)n2nc(-c3cccnc3)nc2n1CC(=O)Nc1ccc(C(F)(F)F)cc1C]

To the stirred solution of tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (400 mg, 623 μmol) in 1,4-dioxane (3 mL) were added 2-(3,6-dihydro-2H-pyran-4-yl)-4,4,5,5-tetramethyl-1,3,2-dioxaborolane (153 mg, 1.25 mmol) and $K_3PO_4$ (1.87 mL, 1.87 mmol) at RT, and the mixture was degassed for 2 minutes. XPhos Pd G3 (26.3 mg, 31.0 μmol) was added and the RM was degassed for 5 minutes, then it was stirred at 110° C. in the MW for 2 hours. The RM was concentrated and ice cold water was added. The solid was filtered and dried under HV. The solid was dissolved in a small amount of 10% MeOH in DCM, filtered and dried. Smopex®-301 (350 mg) and DCM (50 mL) were added and the mixture was stirred at RT for 16 hours. The suspension was filtered and the filtrate was concentrated under reduced pressure to give the title compound.

LC-MS: Rt=1.58 min; MS m/z $[M+H]^+$ 641.3; UPLC-MS 11

Step 3: 2-(5-ethyl-7-oxo-6-(piperazin-1-yl)-2-(pyridin-3-yl)-[1,2,4]triazolo[1,5-a]pyrimidin-4 (7H)-yl)-N-(2-methyl-4-(trifluoromethyl)phenyl)acetamide

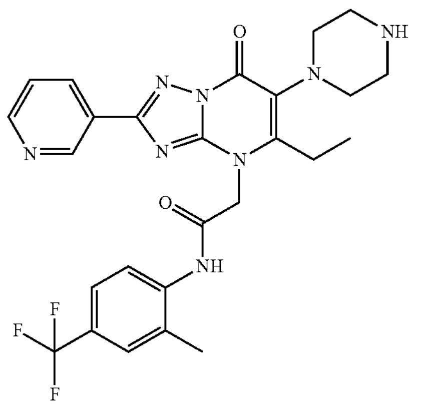 [SMILES: CCc1c(N2CCNCC2)c(=O)n2nc(-c3cccnc3)nc2n1CC(=O)Nc1ccc(C(F)(F)F)cc1C]

To the stirred solution of tert-butyl 4-(5-ethyl-4-(2-((2-methyl-4-(trifluoromethyl)phenyl)amino)-2-oxoethyl)-7-oxo-2-(pyridin-3-yl)-4,7-dihydro-[1,2,4]triazolo[1,5-a]pyrimidin-6-yl)piperazine-1-carboxylate (200 mg, 231 μmol) in DCM (10 mL) was added HCl 4M in 1,4-dioxane (4.00 mL, 16.0 mmol) at 0° C. The RM was stirred at RT for 6 hours. The RM was concentrated under reduced pressure to give the title compound.

LC-MS: Rt=1.31 min; MS m/z $[M+H]^+$ 541.3; UPLC-MS 11

Intermediate AU: 2-(5-ethyl-2-(6-methylpyridin-3-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

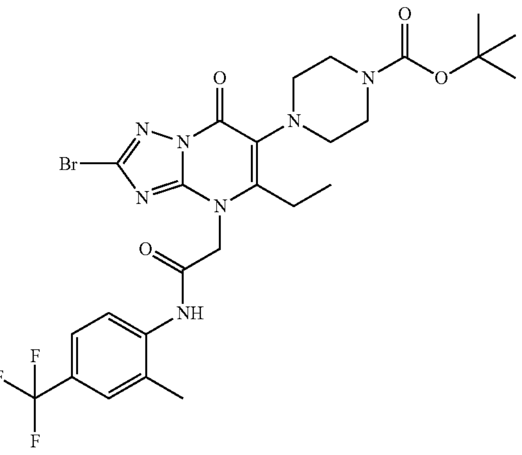

To the stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (16.9 g, 37.6 mmol) and 2-iodo-N-(2-methyl-4-(trifluoromethyl)phenyl)acetamide (Intermediate DV) (15.5 g, 45.1 mmol) in 1,4-dioxane (200 mL) was added DIPEA (19.7 mL, 113 mmol) at RT and the RM was stirred at 80° C. for 4 hours. The RM was concentrated, diluted with EtOAc and water, and extracted once with EtOAc. The organic layer was washed with brine, dried over $Na_2SO_4$ and concentrated under reduced pressure. The crude product was purified by column chromatography (RediSep Column: Silica 120 g, eluent heptane:EtOAc 70:30 to 5:95). The product containing fractions were combined, concentrated, triturated in $Et_2O$ and dried under HV to give the title compound.

LC-MS: Rt=1.33 min; MS m/z $[M+H-Boc]^+$ 542.2, m/z $[M-H]^-$ 640.3; UPLC-MS 6

Step 2: tert-butyl 4-(5-ethyl-4-(2-((2-methyl-4-(trifluoromethyl)phenyl)amino)-2-oxoethyl)-2-(6-methylpyridin-3-yl)-7-oxo-4,7-dihydro-[1,2,4]triazolo[1,5-a]pyrimidin-6-yl)piperazine-1-carboxylate

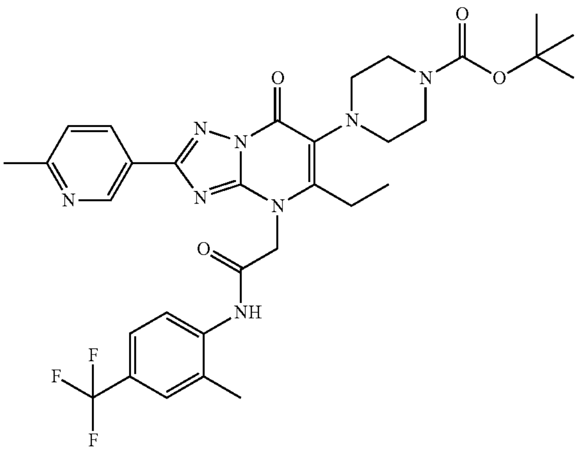 [SMILES: CCc1c(N2CCN(C(=O)OC(C)(C)C)CC2)c(=O)n2nc(-c3ccc(C)nc3)nc2n1CC(=O)Nc1ccc(C(F)(F)F)cc1C]

Tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (200 mg, 296 μmol), (6-methylpyridin-3-yl)boronic acid (51.2 mg, 355 μmol), $Na_2CO_3$ (62.7 mg, 591 μmol), mesylate[(di(1-adamantyl)-n-butylphosphine)-2-(2-amino-1,1-biphenyl)]palladium(II) (22.7 mg, 30.0 μmol), 1,4-dioxane (657 μL) and water (329 μL) were mixed. The RM was degassed and purged with argon several times and then stirred at 120° C. for 1 hour under MW irradiation (normal absorption). (6-Methylpyridin-3-yl)boronic acid (51.2 mg, 355 μmol), $Na_2CO_3$ (62.7 mg, 591 μmol) and mesylate[(di(1-adamantyl)-n-butylphosphine)-2-(2-amino-1,1-biphenyl)]palladium(II) (22.7 mg, 30.0 μmol) were added to the RM, which was then stirred at 120° C. for 30 minutes under MW irradiation (normal absorption). The RM was diluted with THF (4 mL) and 5N aq $NH_4Cl$ (8 mL). The organic layer was collected and the aq layer was extracted 4 times with EtOAc. The combined organic layers were dried over $Na_2SO_4$ and concentrated. The residue was dissolved in DCM. PL-BnSH MP-Resin (59.9 mg, 148 μmol) was added and the resulting suspension was stirred at RT for 1 hour, then filtered. The filtrate was concentrated and dried under vacuum. The crude product was purified by column chromatography (RediSep Column: Silica 12 g, eluent DCM:

DCM/MeOH (9/1) 100:0 to 50:50). The product containing fractions were combined, concentrated and dried under HV to give the title compound.

LC-MS: Rt=1.29 min; MS m/z $[M+H]^+$ 655.5, m/z $[M-H]^-$ 653.5; UPLC-MS 1

Step 3: 2-(5-ethyl-2-(6-methylpyridin-3-yl)-7-oxo-6-(piperazin-1-yl)-[1,2,4]triazolo[1,5-a]pyrimidin-4 (7H)-yl)-N-(2-methyl-4-(trifluoromethyl)phenyl acetamide

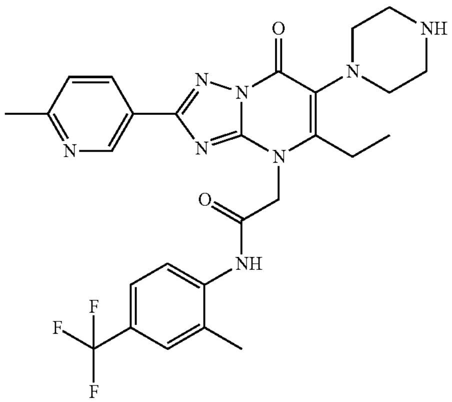 [SMILES: CCc1c(N2CCNCC2)c(=O)n2nc(-c3ccc(C)nc3)nc2n1CC(=O)Nc1ccc(C(F)(F)F)cc1C]

To a suspension of tert-butyl 4-(5-ethyl-4-(2-((2-methyl-4-(trifluoromethyl)phenyl)amino)-2-oxoethyl)-2-(6-methylpyridin-3-yl)-7-oxo-4,7-dihydro-[1,2,4]triazolo[1,5-a]pyrimidin-6-yl)piperazine-1-carboxylate (127 mg, 184 μmol) in DCM (500 μL) was added TFA (500 μL, 6.49 mmol). The solution was stirred at RT for 40 minutes. The RM was concentrated and dried under HV to give the title compound as a brown foam.

LC-MS: Rt=0.74 min; MS m/z $[M+H]^+$ 555.3, m/z $[M-H]^-$ 553.4; UPLC-MS 1

Intermediate AV: 2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

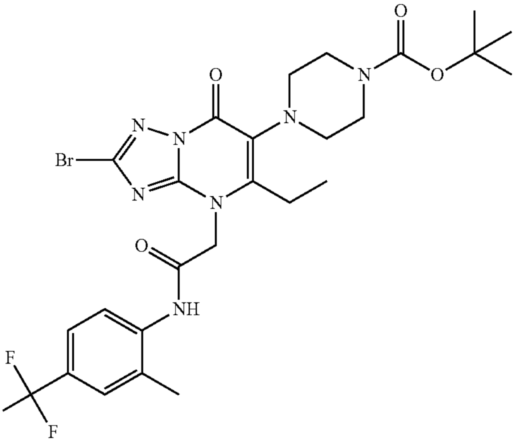

To the stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (3.00 g, 7.02 mmol) in DMF (20 mL) were added 2-bromo-N-(2-methyl-4-(trifluoromethyl)phenyl)acetamide (Intermediate DP) (3.12 g, 10.5 mmol) and DIPEA (3.68 mL, 21.1 mmol) at 0° C. and the RM was stirred at RT for 14 hours. The RM was diluted with water and extracted with 5% MeOH in DCM. The combined organic layers were washed with aq sat $NaHCO_3$ and brine, dried over $Na_2SO_4$ and concentrated under reduced pressure to give the title compound.

LC-MS: Rt=1.64 min; MS m/z $[M+H]^+$ 642.1; UPLC-MS 11

Step 2: tert-butyl 4-(2-(5,6-dihydro-1,4-dioxin-2-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

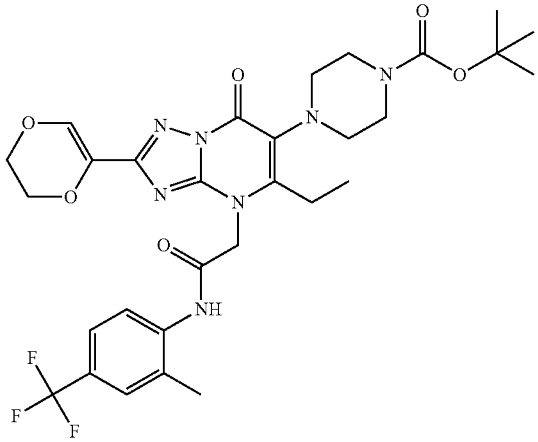 [SMILES: CCc1c(N2CCN(C(=O)OC(C)(C)C)CC2)c(=O)n2nc(C3=COCCO3)nc2n1CC(=O)Nc1ccc(C(F)(F)F)cc1C]

To a stirred solution of tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (400 mg, 623 μmol) in 1,4-dioxane (10 mL) and water (3 mL) were added 2-(5,6-dihydro-1,4-dioxin-2-yl)-4,4,5,5-tetramethyl-1,3,2-dioxaborolane (238 mg, 1.12 mmol) and $K_3PO_4$ (264 mg, 1.25 mmol). The RM was degassed with nitrogen for 15 minutes, then XPhos Pd G2 (24.5 mg, 31.0 μmol) was added and the RM was stirred at 100° C. for 2 hours. Water (20 mL) was added and the mixture was extracted with EtOAc (2×20 mL). The combined organic layers were washed with brine (20 mL), dried over $Na_2SO_4$ and concentrated under reduced pressure. The crude product was purified by column chromatography (Silica gel column: Silica 12 g, eluent DCM: MeOH 100:0 to 99:1). The product containing fractions were combined, concentrated and dried under HV to give the title compound.

LC-MS: Rt=1.84 min; MS m/z $[M+H]^+$ 648.2; UPLC-MS 12

Step 3: 2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide

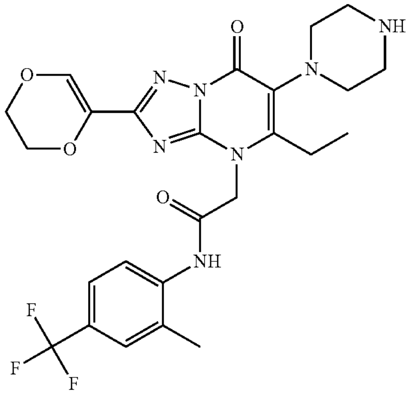 [SMILES: CCc1c(N2CCNCC2)c(=O)n2nc(C3=COCCO3)nc2n1CC(=O)Nc1ccc(C(F)(F)F)cc1C]

To the stirred solution of tert-butyl 4-(2-(5,6-dihydro-1,4-dioxin-2-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (260 mg, 393 μmol) in $Et_2O$ (10 mL) was added HCl 2M in $Et_2O$ (10.0 mL, 20.0 mmol) and the RM was stirred at RT for 6 hours. The RM was concentrated under reduced pressure and washed with $Et_2O$ to give the title compound.

LC-MS: Rt=1.91 min; MS m/z $[M+H]^+$ 548.5; UPLC-MS 13

Intermediate AW: 2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide Step 1: tert-butyl 4-(2-bromo-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

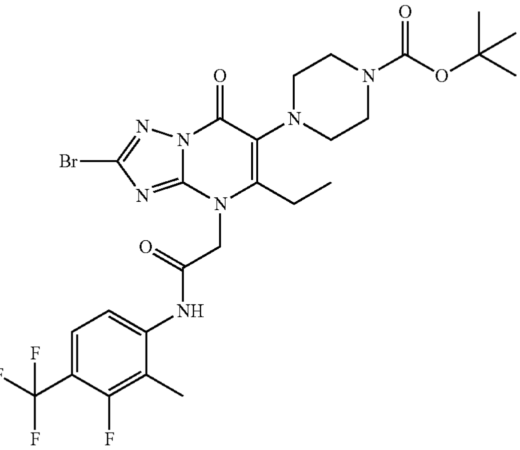

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (555 mg, 1.30 mmol) and 2-chloro-N-(3-fluoro-2-methyl-4-(trifluoromethyl)phenyl)acetamide (Intermediate EE) (403 mg, 1.30 mmol) were mixed in 1,4-dioxane (5 mL) and DIPEA (454 μL, 2.60 mmol) was added. The mixture was stirred at 80° C. for 5 hours, overnight at RT and then again at 80° C. for 8 hours. Water (10 mL), aq sat $NaHCO_3$ (10 mL) and DCM (10 mL) were added. The aqueous layer was extracted with DCM (2×10 mL), and the combined organic layers were dried through a phase separator and concentrated under reduced pressure. The crude product was purified in 2 portions by reverse phase preparative HPLC (2×RP-HPLC acidic 1: 5 to 100% in 20 min). The product containing fractions were combined, basified with aq sat $NaHCO_3$, extracted twice with DCM, dried through a phase separator and concentrated under reduced pressure to give the title compound as a beige solid.

LC-MS: Rt=1.34 min; MS m/z $[M+H-Boc]^+$ 560.2, m/z $[M-H]^-$ 658.3; UPLC-MS 1

Step 2: tert-butyl 4-(2-(5,6-dihydro-1,4-dioxin-2-yl)-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

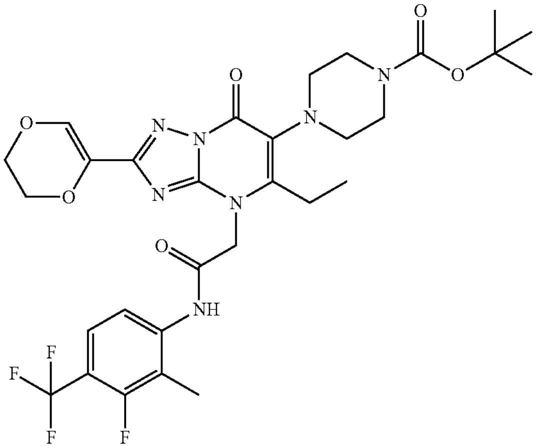 [SMILES: CCc1c(N2CCN(C(=O)OC(C)(C)C)CC2)c(=O)n2nc(C3=COCCO3)nc2n1CC(=O)Nc1ccc(C(F)(F)F)c(F)c1C]

Tert-butyl 4-(2-bromo-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (650 mg, 846 μmol), 2-(5,6-dihydro-1,4-dioxin-2-yl)-4,4,5,5-tetramethyl-1,3,2-dioxaborolane (197 mg, 931 μmol) and XPhos Pd G3 (35.8 mg, 42.0 μmol) were mixed in 1,4-dioxane (5 mL) and $K_3PO_4$ 1M in water (2.54 mL, 2.54 mmol) was added. The mixture was stirred at 80° C. for 1 hour. Water (10 mL), aq sat $NaHCO_3$ (10 mL) and DCM (10 mL) were added. The aqueous layer was extracted with DCM (2×10 mL), and the combined organic layers were dried through a phase separator and concentrated under reduced pressure. The crude product was dissolved in DCM and MeOH and SiliaMetS® Thiol was added. The mixture was stirred at 40° C. for 1 hour. Then it was filtered, and the cake was washed with DCM. The filtrate was concentrated under reduced pressure to give the title compound.

LC-MS: Rt=1.26 min; MS m/z $[M+H-Boc]^+$ 566.3, m/z $[M-H]^-$ 664.2; UPLC-MS 1

Step 3: 2-(2-(5,6-dihydro-1,4-dioxin-2-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide

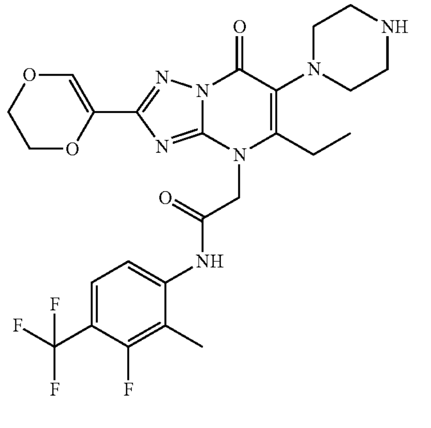 [SMILES: CCc1c(N2CCNCC2)c(=O)n2nc(C3=COCCO3)nc2n1CC(=O)Nc1ccc(C(F)(F)F)c(F)c1C]

Tert-butyl 4-(2-(5,6-dihydro-1,4-dioxin-2-yl)-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (831 mg, 986 μmol) was dissolved in DCM (5 mL) and TFA (500 μL, 6.49 mmol) was added. The mixture was stirred at 40° C. for 3 hours, concentrated under reduced pressure, and the crude product was purified in 2 portions by reverse phase preparative HPLC (2×RP-HPLC acidic 1: 5 to 100% in 20 min). The product containing fractions were combined, basified with aq sat $NaHCO_3$, extracted twice with DCM, dried through a phase separator and concentrated under reduced pressure to give the title compound.

LC-MS: Rt=0.79 min; MS m/z $[M+H]^+$ 566.4, m/z $[M-H]^-$ 564.2; UPLC-MS 1

Intermediate AX: 2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

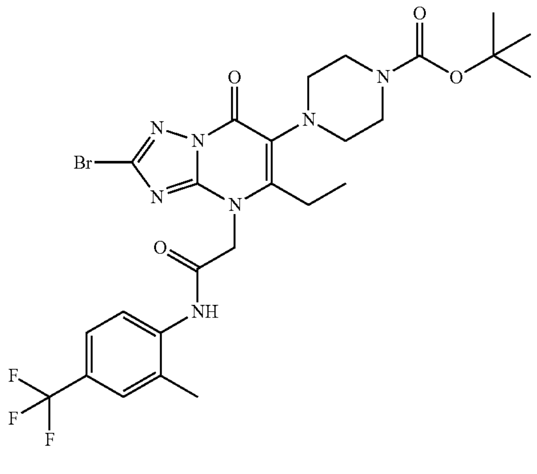 [SMILES: CCc1c(N2CCN(C(=O)OC(C)(C)C)CC2)c(=O)n2nc(Br)nc2n1CC(=O)Nc1ccc(C(F)(F)F)cc1C]

See Intermediate AT Step 1.

Step 2: tert-butyl 4-(5-ethyl-2-(4-methoxycyclohex-1-en-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

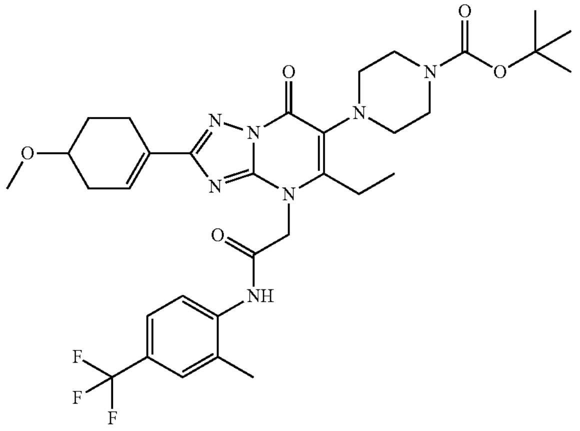 [SMILES: CCc1c(N2CCN(C(=O)OC(C)(C)C)CC2)c(=O)n2nc(C3=CCC(OC)CC3)nc2n1CC(=O)Nc1ccc(C(F)(F)F)cc1C]

Tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (550 mg, 856 μmol) was suspended in 1,4-dioxane (15 mL). Rac-2-(4-methoxycyclohex-1-en-1-yl)-4,4,5,5-tetramethyl-1,3,2-dioxaborolane (Intermediate DH) (408 mg, 1.71 mmol), XPhos Pd G3 (36.2 mg, 43.0 μmol) and $K_3PO_4$ 1M in water (856 μL, 856 μmol) were added and the RM was stirred at 80° C. for 48 hours. The RM was concentrated under reduced pressure, ice cold water was added and it was extracted with 5% MeOH in DCM, washed with brine, dried over $Na_2SO_4$ and concentrated under reduced pressure. The crude product was purified by column chromatography (Silica gel column: Silica 12 g, eluent DCM:MeOH 100:0 to 95:5). The product containing fractions were combined, concentrated and dried under HV to give the title compound.

LC-MS: Rt=1.65 min; MS m/z $[M+H]^+$ 674.3; UPLC-MS 11

Step 3: rac-2-(5-ethyl-2-(4-methoxycyclohex-1-en-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide

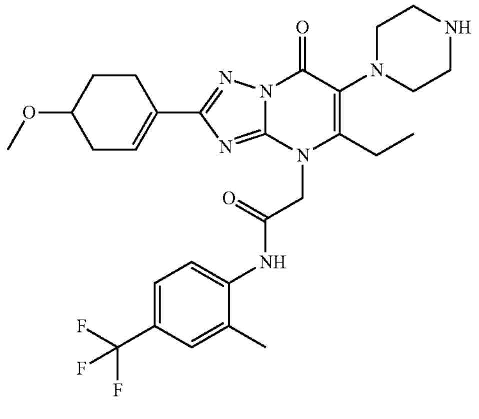 [SMILES: CCc1c(N2CCNCC2)c(=O)n2nc(C3=CCC(OC)CC3)nc2n1CC(=O)Nc1ccc(C(F)(F)F)cc1C]

To the solution of rac-tert-butyl 4-(5-ethyl-2-(4-methoxy-cyclohex-1-en-1-yl)-4-(2-((2-methyl-4-(trifluoromethyl) phenyl)amino)-2-oxoethyl)-7-oxo-4,7-dihydro-[1,2,4]tri-azolo[1,5-a]pyrimidin-6-yl)piperazine-1-carboxylate (180 mg, 246 μmol) in 1,4-dioxane (10 mL) was added HCl 4M in 1,4-dioxane (10.0 mL, 40.0 mmol) at 0° C. and the RM was stirred at RT for 16 hours. The RM was concentrated under reduced pressure, washed with $Et_2O$ (2×10 mL) and dried under HV to give the title compound, as the HCl salt.

LC-MS: Rt=1.36 min; MS m/z $[M+H]^+$ 574.3; UPLC-MS 11

Intermediate AY: 2-(5-ethyl-2-(4-methoxycyclohex-1-en-1-yl)-7-oxo-6-(piperazin-1-yl)-[1,2,4]triazolo [1,5-a]pyrimidin-4 (7H)-yl)-N-(4-(trifluoromethyl) phenyl)acetamide Step 1: tert-butyl 4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

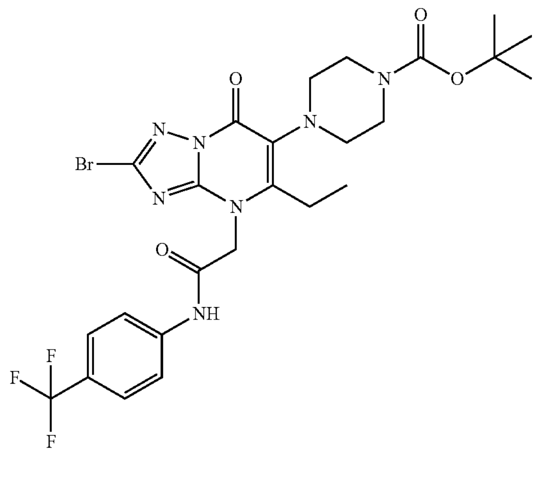 [SMILES: CCc1c(N2CCN(C(=O)OC(C)(C)C)CC2)c(=O)n2nc(Br)nc2n1CC(=O)Nc1ccc(C(F)(F)F)cc1]

Tert-butyl 4-(2-bromo-5-ethyl-7-oxo-4,7-dihydro-[1,2,4] triazolo[1,5-a]pyrimidin-6-yl)piperazine-1-carboxylate (Intermediate X) (320 mg, 748 μmol) was dissolved in 1,4-dioxane (2 mL) and 2-bromo-N-(4-(trifluoromethyl)phenyl) acetamide (226 mg, 800 μmol) was added, followed by DIPEA (314 μL, 1.80 mmol). The mixture was stirred at 80° C. for 5 hours. Water, aq sat $NaHCO_3$ and DCM were added. The aqueous layer was extracted twice with DCM. The combined organic layers were dried through a phase separator and concentrated under reduced pressure to give the title compound.

LC-MS: Rt=1.24 min; MS m/z $[M-H]^-$ 626.0; UPLC-MS 7

Step 2: rac-tert-butyl 4-(5-ethyl-2-(4-methoxycyclo-hex-1-en-1-yl)-7-oxo-4-(2-oxo-2-((4-(trifluorom-ethyl)phenyl)amino)ethyl)-4,7-dihydro-[1,2,4]tri-azolo[1,5-a]pyrimidin-6-yl)piperazine-1-carboxylate

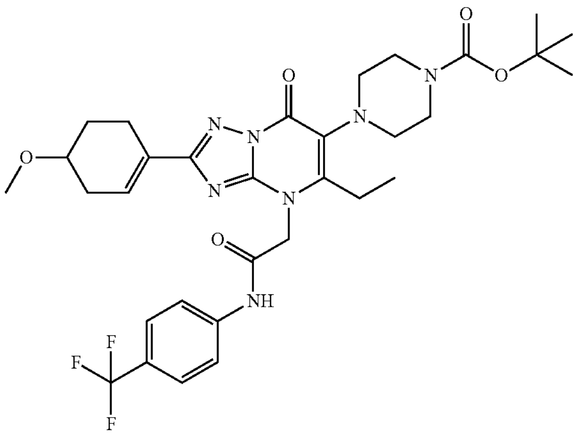 [SMILES: CCc1c(N2CCN(C(=O)OC(C)(C)C)CC2)c(=O)n2nc(C3=CCC(OC)CC3)nc2n1CC(=O)Nc1ccc(C(F)(F)F)cc1]

Tert-butyl 4-(2-bromo-5-ethyl-7-oxo-4-(2-oxo-2-((4-(tri-fluoromethyl)phenyl)amino)ethyl)-4,7-dihydro-[1,2,4]tri-azolo[1,5-a]pyrimidin-6-yl)piperazine-1-carboxylate (991 mg, 1.06 mmol) was dissolved in 1,4-dioxane (5 mL) and rac-2-(4-methoxycyclohex-1-en-1-yl)-4,4,5,5-tetramethyl-1,3,2-dioxaborolane (Intermediate DH) (252 mg, 1.06 mmol) was added, followed by XPhos Pd G3 (14.5 mg, 17.0 μmol) and $K_3PO_4$ 1M in water (2.00 mL, 2.00 mmol). The mixture was stirred at 80° C. for 3 hours. Water, aq sat $NaHCO_3$ and DCM were added. The aqueous layer was extracted twice with DCM. The combined organic layers were dried through a phase separator and concentrated under reduced pressure. The crude product was purified by column chromatography (RediSep Column: Silica 40 g, eluent DCM:DCM/MeOH (9/1) 100:0 to 0:100). The product containing fractions were combined, concentrated and dried under HV to give the title compound.

LC-MS: Rt=1.27 min; MS m/z $[M+H]^+$ 660.3, m/z $[M-H]^-$ 658.2; UPLC-MS 7

Step 3: rac-2-(5-ethyl-2-(4-methoxycyclohex-1-en-1-yl)-7-oxo-6-(piperazin-1-yl)-[1,2,4]triazolo[1,5-a] pyrimidin-4 (7H)-yl)-N-(4-(trifluoromethyl)phenyl) acetamide

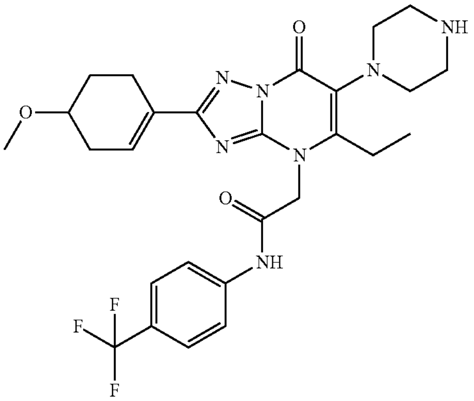 [SMILES: CCc1c(N2CCNCC2)c(=O)n2nc(C3=CCC(OC)CC3)nc2n1CC(=O)Nc1ccc(C(F)(F)F)cc1]

Rac-tert-butyl 4-(5-ethyl-2-(4-methoxycyclohex-1-en-1-yl)-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (575 mg, 636 μmol) was dissolved in DCM (5 mL) and TFA (490 μL, 6.36 mmol) was added. The mixture was stirred at RT for 1.5 hours and then concentrated under reduced pressure. Water, aq sat $NaHCO_3$ and DCM were added, and the aqueous layer was washed twice with DCM. The combined organic layers were dried through a phase separator and concentrated under reduced pressure to give the title compound.

LC-MS: Rt=0.80 min; MS m/z $[M+H]^+$ 560.3, m/z $[M-H]^-$ 558.1; UPLC-MS 4

Intermediate AZ: ethyl 2-(4-(4-(2-((2-chloro-4-(trifluoromethyl)phenyl)amino)-2-oxoethyl)-5-ethyl-7-oxo-6-(piperazin-1-yl)-4,7-dihydro-[1,2,4]triazolo[1,5-a]pyrimidin-2-yl)piperazin-1-yl)acetate Step 1: tert-butyl 4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)piperazine-1-carboxylate

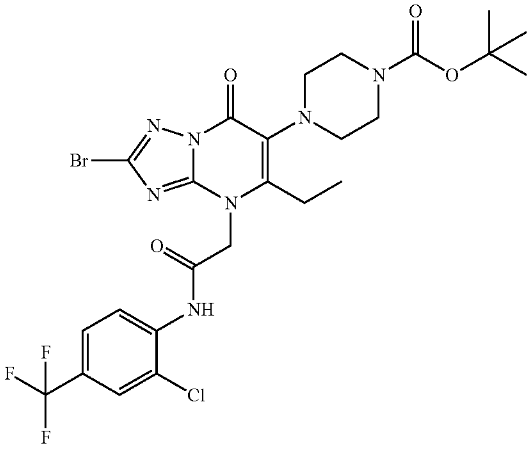

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (500 mg, 1.17 mmol) was dissolved in DMF (1 mL) and DIPEA (613 μL, 3.51 mmol) was added at 0° C. 2-Bromo-N-(2-chloro-4-(trifluoromethyl)phenyl)acetamide (Intermediate DT) (556 mg, 1.76 mmol) was added and the RM was stirred at RT for 16 hours. The RM was diluted with water and extracted with EtOAc. The crude product was purified by column chromatography (Silica gel column: Silica 4 g, eluent hexane:EtOAc 100:0 to 90:10). The product containing fractions were combined and concentrated to give the title compound.

LC-MS: Rt=1.67 min; MS m/z $[M+H]^+$ 662.1; UPLC-MS 11

Step 2: tert-butyl 4-(4-(2-((2-chloro-4-(trifluoromethyl)phenyl)amino)-2-oxoethyl)-2-(4-(2-ethoxy-2-oxoethyl)piperazin-1-yl)-5-ethyl-7-oxo-4,7-dihydro-[1,2,4]triazolo[1,5-a]pyrimidin-6-yl)piperazine-1-carboxylate

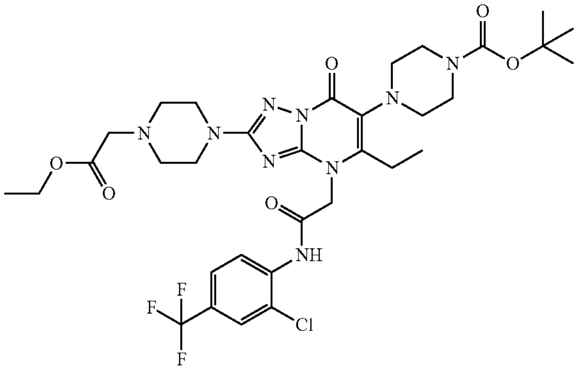 [SMILES: CCOC(=O)CN1CCN(c2nc3n(CC(=O)Nc4ccc(C(F)(F)F)cc4Cl)c(CC)c(N4CCN(C(=O)OC(C)(C)C)CC4)c(=O)n3n2)CC1]

Tert-butyl 4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)piperazine-1-carboxylate (450 mg, 645 μmol) was dissolved in DMSO (2 mL) and DMF (2 mL). Ethyl 2-(piperazin-1-yl)acetate (Intermediate DC) (333 mg, 1.94 mmol) and KOAc (380 mg, 3.87 mmol) were added and the RM was stirred at 120° C. for 16 hours. The RM was diluted with water and the precipitate was filtered off and washed with 10% EtOAc in hexane to give the title compound.

LC-MS: Rt=1.60 min; MS m/z $[M+H]^+$ 754.5; UPLC-MS 12

Step 3: ethyl 2-(4-(4-(2-((2-chloro-4-(trifluoromethyl)phenyl)amino)-2-oxoethyl)-5-ethyl-7-oxo-6-(piperazin-1-yl)-4,7-dihydro-[1,2,4]triazolo[1,5-a]pyrimidin-2-yl)piperazin-1-yl)acetate

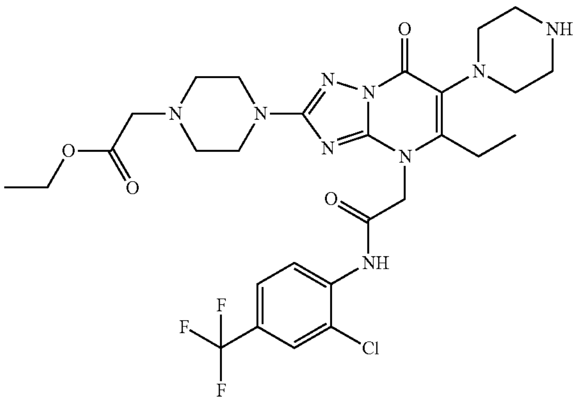 [SMILES: CCOC(=O)CN1CCN(c2nc3n(CC(=O)Nc4ccc(C(F)(F)F)cc4Cl)c(CC)c(N4CCNCC4)c(=O)n3n2)CC1]

Tert-butyl 4-(4-(2-((2-chloro-4-(trifluoromethyl)phenyl)amino)-2-oxoethyl)-2-(4-(2-ethoxy-2-oxoethyl)piperazin-1-yl)-5-ethyl-7-oxo-4,7-dihydro-[1,2,4]triazolo[1,5-a]pyrimidin-6-yl)piperazine-1-carboxylate (400 mg, 530 μmol) was dissolved in 1,4-dioxane (5 mL) and HCl 4N in 1,4-dioxane (20.0 mL, 80.0 mmol) was added and the RM was stirred at RT for 2 hours. The RM was concentrated under reduced pressure and washed with $Et_2O$ to get the title compound.

LC-MS: Rt=1.28 min; m/z $[M-H]^-$ 652.2 UPLC-MS 11

Intermediate BA: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

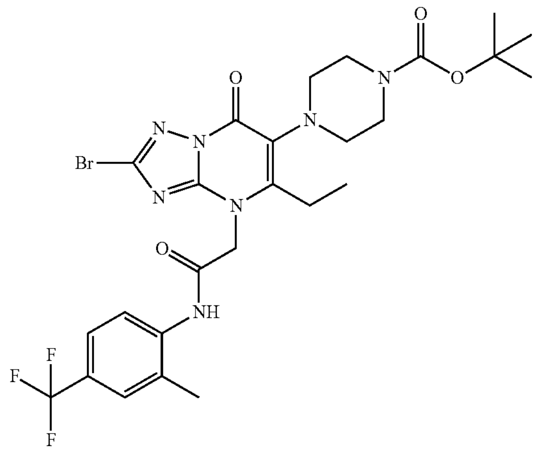 [SMILES: CCc1c(N2CCN(C(=O)OC(C)(C)C)CC2)c(=O)n2nc(Br)nc2n1CC(=O)Nc1ccc(C(F)(F)F)cc1C]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (300 mg, 702 μmol), 2-iodo-N-(2-methyl-4-(trifluoromethyl)phenyl)acetamide (Intermediate DV) (301 mg, 878 μmol) and DIPEA (368 μL, 2.11 mmol) were dissolved in DMF (1.75 mL) and the RM was stirred at 50° C. for 6.5 hours. 2-iodo-N-(2-methyl-4-(trifluoromethyl)phenyl)acetamide (Intermediate DV) (50.0 mg, 146 μmol) was added and the RM was stirred at 50° C. for 16 hours. 2-Iodo-N-(2-methyl-4-(trifluoromethyl)phenyl)acetamide (Intermediate DV) (50.0 mg, 146 μmol) was added and the RM was stirred at 50° C. for 7.5 hours. Water was added and the mixture was extracted with EtOAc (3×20 mL). The combined organic layers were washed with water and brine, dried through a phase separator and concentrated under reduced pressure. The crude product was adsorbed onto Isolute and purified by column chromatography (RediSep Column: Silica 40 g, eluent DCM:MeOH 100:0 to 95:05). The product containing fractions were combined and concentrated to give the title compound as a pale brown solid.

LC-MS: Rt=1.19 min; MS m/z $[M+H-Boc]^+$542.2, m/z $[M-H]^-$ 640.3; UPLC-MS 4

Step 2: tert-butyl 4-(2-(3,4-dihydro-2H-pyran-6-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

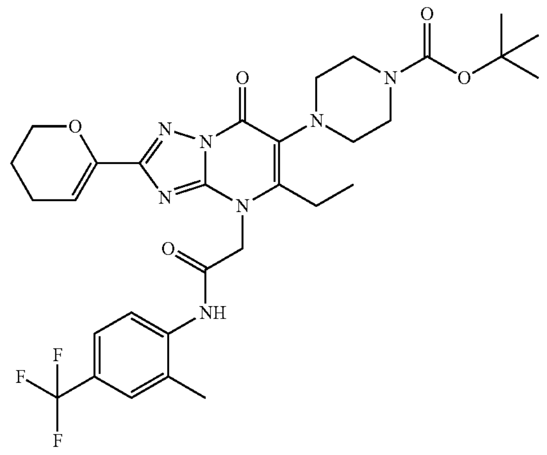 [SMILES: CCc1c(N2CCN(C(=O)OC(C)(C)C)CC2)c(=O)n2nc(C3=CCCCO3)nc2n1CC(=O)Nc1ccc(C(F)(F)F)cc1C]

Tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (452 mg, 704 μmol), 2-(3,4-dihydro-2H-pyran-6-yl)-4,4,5,5-tetramethyl-1,3,2-dioxaborolane (222 mg, 1.06 mmol) and XPhos Pd G3 (30.4 mg, 35.0 μmol) were mixed and degassed and purged with argon several times. 1,4-Dioxane (3.7 mL) and $K_3PO_4$ 1M in water (2.11 mL, 2.11 mmol) were added and the RM was stirred at 90° C. for 2 hours. The RM was concentrated under reduced pressure, and the residue was extracted with EtOAc (3×50 mL). The organic layers were washed with water (2×10 mL) and brine (10 mL), dried through a phase separator and concentrated under reduced pressure. The residue was dissolved in DCM and MeOH and ISOLUTE® Si-Thiol (2.50 g) was added. The mixture was stirred for 45 minutes, then it was filtered and washed with DCM and MeOH. The filtrate was concentrated, and the crude product was adsorbed onto Isolute and purified by column chromatography (RediSep Column: Silica 40 g, eluent DCM:MeOH 100:0 to 95:05). The product containing fractions were combined and concentrated to give the title compound as a pale brown solid.

LC-MS: Rt=1.18 min; MS m/z $[M+H]^+$ 646.5, m/z $[M-H]^-$ 644.4; UPLC-MS 4

Step 3: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide

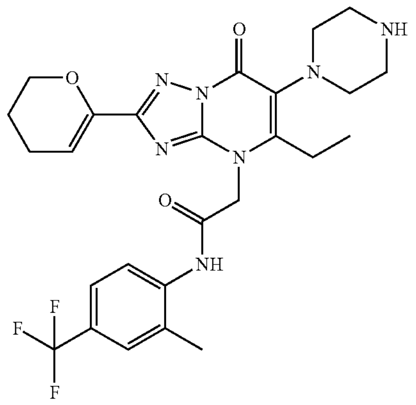 [SMILES: CCc1c(N2CCNCC2)c(=O)n2nc(C3=CCCCO3)nc2n1CC(=O)Nc1ccc(C(F)(F)F)cc1C]

Tert-butyl 4-(2-(3,4-dihydro-2H-pyran-6-yl)-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (326 mg, 505 μmol) was dissolved in DCM (3.4 mL) and TFA (778 μL, 10.1 mmol) was added and the RM was stirred at RT for 1.3 hours. The RM was concentrated under reduced pressure. The residue was dissolved in DCM and toluene and was concentrated under reduced pressure (two times). The residue was dried under HV to give the title compound as a pale brown solid.

LC-MS: Rt=0.92 min; MS m/z $[M+H]^+$ 546.2, m/z $[M-H]^-$ 544.1; UPLC-MS 3

Intermediate BB: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide Step 1: tert-butyl 4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

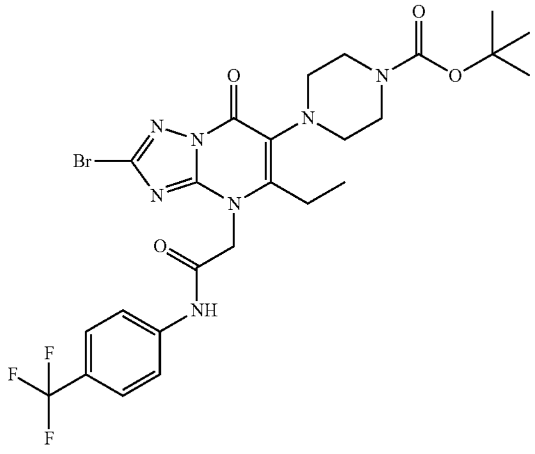 [SMILES: CCc1c(N2CCN(C(=O)OC(C)(C)C)CC2)c(=O)n2nc(Br)nc2n1CC(=O)Nc1ccc(C(F)(F)F)cc1]

See Intermediate AS Step 1.

Step 2: tert-butyl 4-(2-(3,4-dihydro-2H-pyran-6-yl)-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

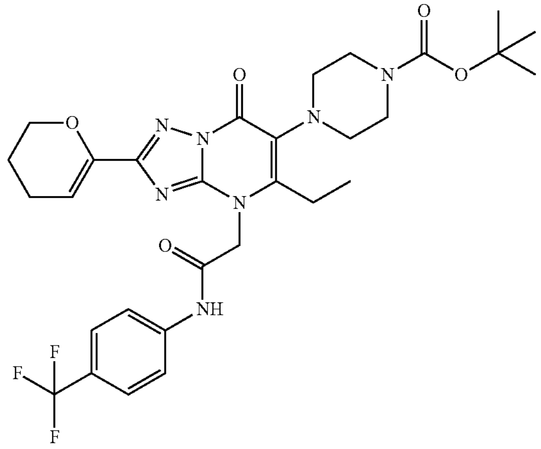 [SMILES: CCc1c(N2CCN(C(=O)OC(C)(C)C)CC2)c(=O)n2nc(C3=CCCCO3)nc2n1CC(=O)Nc1ccc(C(F)(F)F)cc1]

Tert-butyl 4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (245 mg, 390 μmol), 2-(3,4-dihydro-2H-pyran-6-yl)-4,4,5,5-tetramethyl-1,3,2-dioxaborolane (123 mg, 585 μmol) and XPhos Pd G3 (3.30 mg, 3.90 μmol) were dissolved in 1,4-dioxane (2 mL). Then $K_3PO_4$ 1M in water (1.95 mL, 1.95 mmol) was added. The mixture was stirred at 80° C. for 15.5 hours. Water, aq sat $NaHCO_3$ and DCM were added. The aqueous layer was extracted twice with DCM. The combined organic layers were dried through a phase separator and concentrated under reduced pressure. The crude product was purified by column chromatography (RediSep Column: Silica 12 g, eluent DCM:DCM/MeOH (9/1) 100:0 to 60:40). The product containing fractions were combined and concentrated to give the title compound.

LC-MS: Rt=1.17 min; MS m/z $[M+H]^+$ 632.3, m/z $[M-H]^-$ 630.1; UPLC-MS 4

Step 3: 2-(2-(3,4-dihydro-2H-pyran-6-yl)-5-ethyl-7-oxo-6-(piperazin-1-yl)-[1,2,4]triazolo[1,5-a]pyrimidin-4 (7H)-yl)-N-(4-(trifluoromethyl)phenyl)acetamide

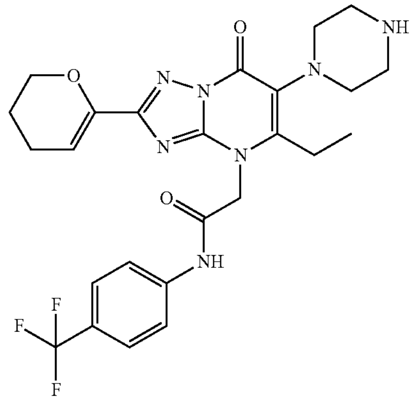 [SMILES: CCc1c(N2CCNCC2)c(=O)n2nc(C3=CCCCO3)nc2n1CC(=O)Nc1ccc(C(F)(F)F)cc1]

Tert-butyl 4-(2-(3,4-dihydro-2H-pyran-6-yl)-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (185 mg, 284 μmol) was dissolved in DCM (2 mL) and TFA (500 μL, 6.49 mmol) was added. The mixture was stirred at RT for 1 hour. Water, aq sat $NaHCO_3$ and DCM were added. The aqueous layer was extracted twice with DCM. The combined organic layers were dried through a phase separator and concentrated under reduced pressure. As the crude product still contained tert-butyl 4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate, the Suzuki reaction was restarted using conditions of step 2 (see above). Water, aq sat $NaHCO_3$ and DCM were added to the crude product, and the aqueous layer was extracted twice with DCM. The combined organic layers were mixed with SiliaMetS® Thiol and stirred at 40° C. for 2 hours. Then it was filtered, dried through a phase separator and concentrated under reduced pressure to give the title compound.

LC-MS: Rt=0.83 min; MS m/z $[M+H]^+$ 532.2, m/z $[M-H]^-$ 530.3; UPLC-MS 4

Intermediate BC: (S)-2-(5-ethyl-2-(3-fluoropiperidin-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

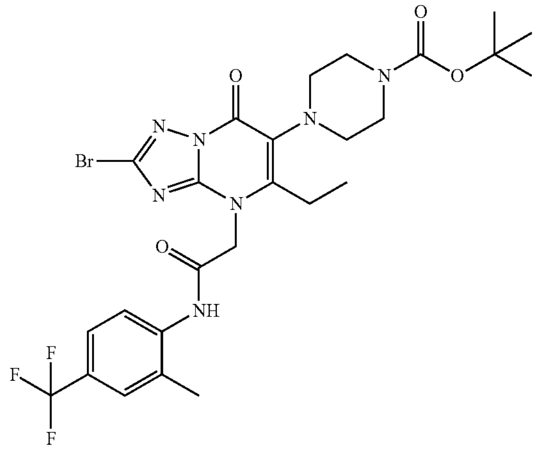

To a stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (1.00 g, 2.34 mmol) in DMF (1 mL) were added 2-bromo-N-(2-methyl-4-(trifluoromethyl)phenyl)acetamide (Intermediate DP) (970 mg, 3.28 mmol) and DIPEA (1.02 mL, 5.85 mmol) at 0° C. The RM was stirred at RT for 16 hours. The RM was concentrated, ice cold water was added and the precipitate was filtered off and dried under HV. The crude product was purified by column chromatography (Silica gel column: Silica 24 g, eluent DCM:MeOH 100:0 to 90:10). The product containing fractions were combined, concentrated and dried under HV to get the title compound as a brown solid.

LC-MS: Rt=1.64 min; MS m/z $[M+H]^+$ 642.1; UPLC-MS 11

Step 2: tert-butyl (S)-4-(5-ethyl-2-(3-fluoropiperidin-1-yl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

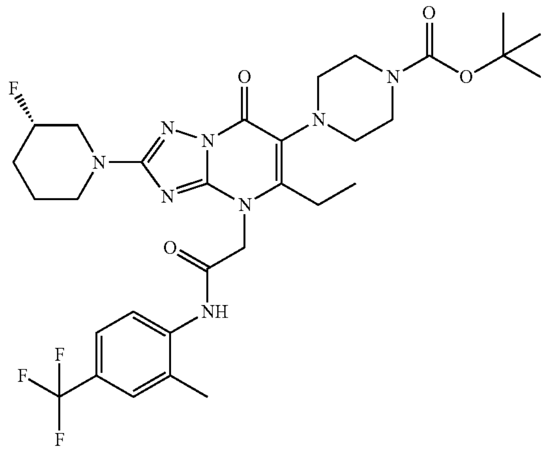 [SMILES: CCc1c(N2CCN(C(=O)OC(C)(C)C)CC2)c(=O)n2nc(N3CCC[C@H](F)C3)nc2n1CC(=O)Nc1ccc(C(F)(F)F)cc1C]

To a stirred solution of tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (400 mg, 535 μmol) in DMSO (4 mL) were added (S)-3-fluoropiperidine·HCl (374 mg, 2.68 mmol) and KOAc (315 mg, 3.21 mmol) at 0° C. The RM was stirred at 120° C. for 16 hours. (S)-3-fluoropiperidine·HCl (110 mg, 623 μmol) was added and the RM was stirred at 120° C. for 16 hours. Ice cold water was added and the resultant solid was collected and dried under HV. The crude product was purified by column chromatography (Silica gel column: Silica 24 g, eluent DCM:MeOH 100:0 to 90:10). The product containing fractions were combined and concentrated under reduced pressure to give the title compound as a brown solid.

LC-MS: Rt=1.64 min; MS m/z $[M+H]^+$ 665.3; UPLC-MS 11

Step 3: (S)-2-(5-ethyl-2-(3-fluoropiperidin-1-yl)-7-oxo-6-(piperazin-1-yl)-[1,2,4]triazolo[1,5-a]pyrimidin-4 (7H)-yl)-N-(2-methyl-4-(trifluoromethyl)phenyl)acetamide

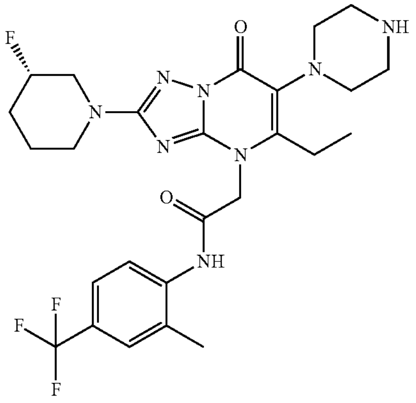 [SMILES: CCc1c(N2CCNCC2)c(=O)n2nc(N3CCC[C@H](F)C3)nc2n1CC(=O)Nc1ccc(C(F)(F)F)cc1C]

To the stirred solution of tert-butyl (S)-4-(5-ethyl-2-(3-fluoropiperidin-1-yl)-4-(2-((2-methyl-4-(trifluoromethyl) phenyl)amino)-2-oxoethyl)-7-oxo-4,7-dihydro-[1,2,4]triazolo[1,5-a]pyrimidin-6-yl)piperazine-1-carboxylate (120 mg, 181 μmol) in DCM (10 mL) was added HCl 4M in 1,4-dioxane (1.00 mL, 4.00 mmol) at 0° C. The RM was stirred at RT for 16 hours and then concentrated under reduced pressure. $Et_2O$ (10 mL) was added, decanted and the precipitate was dried under HV to give the title compound, as the HCl salt.

LC-MS: Rt=1.36 min; MS m/z $[M+H]^+$ 565.3; UPLC-MS 11

Intermediate BD: tert-butyl (R)-4-(2-bromo-5-ethyl-7-oxo-4,7-dihydro-[1,2,4]triazolo[1,5-a]pyrimidin-6-yl)-2-methylpiperazine-1-carboxylate

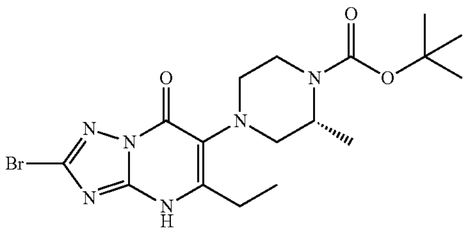 [SMILES: CCc1[nH]c2nc(Br)nn2c(=O)c1N1CCN(C(=O)OC(C)(C)C)[C@H](C)C1]

Tert-butyl (2R)-4-(1-ethoxy-1,3-dioxopentan-2-yl)-2-methylpiperazine-1-carboxylate (Intermediate EK) (16.8 g, 48.1 mmol) was dissolved in EtOH (45 mL) and 3-bromo-1H-1,2,4-triazol-5-amine (Intermediate ER) (7.50 g, 43.7 mmol) was added, followed by $H_3PO_4$ (5.29 g, 45.9 mmol). The RM was stirred at 90° C. for 44 hours. DIPEA (22.9 mL, 131 mmol) and $Boc_2O$ (5.08 mL, 21.9 mmol) were added. The RM was stirred at RT for 1.5 hours. The reaction was quenched with water, diluted with EtOAc and concentrated under reduced pressure. The residue was extracted with EtOAc (3×500 mL), and the organic layers were washed with water (2×50 mL) and brine (2×50 mL), dried through a phase separator and concentrated under reduced pressure. This material was suspended in $Et_2O$ (1 L) and stirred at reflux for 20 minutes. The suspension was filtered, and the mother liquor was concentrated under reduced pressure. This material was mixed with hexane (2×600 mL), stirred at 40° C., and then filtered. The cake was dissolved in DCM and MeOH, concentrated again and adsorbed onto Isolute and purified twice by column chromatography (RediSep Column: Silica 120 g, eluent DCM:MeOH 100:0 to 85:15) and (RediSep Column: Silica 80 g, eluent DCM:MeOH 100:0 to 85:15). The product containing fractions were combined and concentrated under reduced pressure to give the title compound as a beige solid.

LC-MS: Rt=0.94 min; MS m/z $[M+H-Boc]^+$341.1, m/z $[M-H]^-$ 439.3; UPLC-MS 4

$^1H$ NMR (400 MHz, DMSO-$d_6$) δ 13.27 (s, 1H), 4.19 (m, 1H), 3.76 (m, 1H), 3.52 (m, 1H), 3.37 (m, 1H), 3.10 (m, 1H), 2.86 (m, 1H), 2.71 (m, 3H), 1.44 (s, 9H), 1.26 (m, 3H), 1.21 (t, J=7.5 Hz, 3H)

Intermediate BE: (R)—N-(2-chloro-4-(trifluoromethyl)phenyl)-2-(2-(3,6-dihydro-2H-pyran-4-yl)-5-ethyl-6-(3-methylpiperazin-1-yl)-7-oxo-[1,2,4]triazolo[1,5-a]pyrimidin-4 (7H)-yl)acetamide Step 1: tert-butyl (R)-4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)-2-methylpiperazine-1-carboxylate

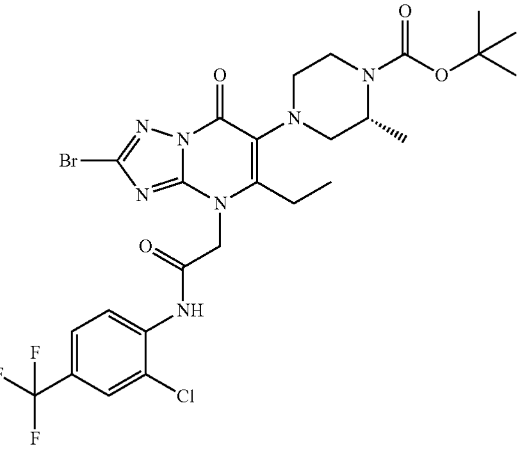

To a solution of tert-butyl (R)-4-(2-bromo-5-ethyl-7-oxo-4,7-dihydro-[1,2,4]triazolo[1,5-a]pyrimidin-6-yl)-2-methylpiperazine-1-carboxylate (Intermediate BD) (4.07 g, 9.21 mmol) and N-(2-chloro-4-(trifluoromethyl)phenyl)-2-iodoacetamide (Intermediate DL) (3.68 g, 10.1 mmol) in DMF (61 mL) was added DIPEA (4.83 mL, 27.6 mmol). The RM was stirred at 50° C. for 2.5 hours, then allowed to cool to 30° C., and water was added slowly. The aqueous mixture was extracted twice with EtOAc. The combined organic layers were washed 3 times with brine, dried through a phase separator and concentrated under reduced pressure. The crude product was adsorbed onto Isolute and purified by column chromatography (RediSep Column: Silica 120 g, eluent heptane:EtOAc 100:0 to 0:100). The product containing fractions were combined, concentrated and dried under HV to give the title compound as an orange-brown solid.

LC-MS: Rt=1.40 min; MS m/z $[M+H-Boc]^+$ 576.2, m/z $[M-H]^-$ 674.4; UPLC-MS 1

Step 2: tert-butyl (R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2-methylpiperazine-1-carboxylate

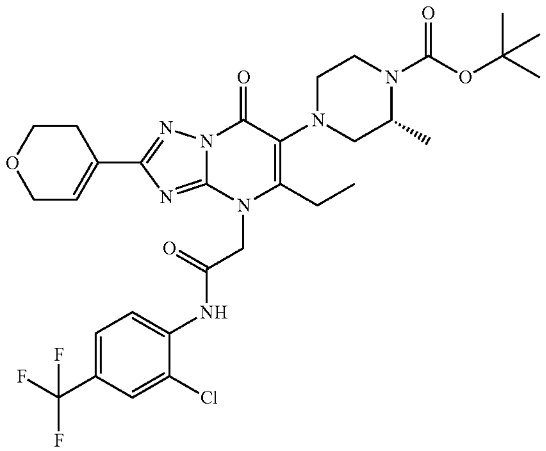 [SMILES: CCc1c(N2CCN(C(=O)OC(C)(C)C)[C@H](C)C2)c(=O)n2nc(C3=CCOCC3)nc2n1CC(=O)Nc1ccc(C(F)(F)F)cc1Cl]

To a stirred solution of tert-butyl (R)-4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)-2-methylpiperazine-1-carboxylate (5.93 g, 7.71 mmol), $K_3PO_4$ (5.58 g, 26.3 mmol) and Pd(dppf)$Cl_2$·DCM (358 mg, 438 μmol) in 1,4-dioxane (44 mL) and water (15 mL) was added at 80° C. a solution of 2-(3,6-dihydro-2H-pyran-4-yl)-4,4,5,5-tetramethyl-1,3,2-dioxaborolane (2.39 g, 11.4 mmol) in 1,4-dioxane (15 mL) dropwise over 5 minutes and the RM was stirred at 80° C. for 1 hour. The RM was concentrated and diluted with EtOAc and water. The aqueous layer was extracted twice with EtOAc, and the combined organic phases were washed three times with brine, dried through a phase separator and concentrated under reduced pressure. The residue was suspended in EtOAc, sonicated until a fine suspension was formed and then filtered. The cake was washed with a small amount of EtOAc. The filtrate was concentrated under reduced pressure. The residue was suspended in a small amount of EtOAc, sonicated until a fine suspension was formed and then filtered. The cake was washed with a small amount of EtOAc. Both cakes were combined and triturated in $Et_2O$, sonicated and then filtered. The cake was washed with a small amount of $Et_2O$ then dried under vacuum to give product. The EtOAc and $Et_2O$ filtrates were combined and concentrated to dryness. The residue was adsorbed onto Isolute and purified by column chromatography (RediSep Column: Silica 80 g, eluent heptane:EtOAc 100:0 to 0:100). The product containing fractions were combined and concentrated to give product. Both product samples were combined to give the title compound as a light brown solid.

LC-MS: Rt=1.36 min; MS m/z $[M+H-Boc]^+$ 580.3, m/z $[M-H]^-$ 678.5; UPLC-MS 1

Step 3: (R)—N-(2-chloro-4-(trifluoromethyl)phenyl)-2-(2-(3,6-dihydro-2H-pyran-4-yl)-5-ethyl-6-(3-methylpiperazin-1-yl)-7-oxo-[1,2,4]triazolo[1,5-a]pyrimidin-4 (7H)-yl)acetamide

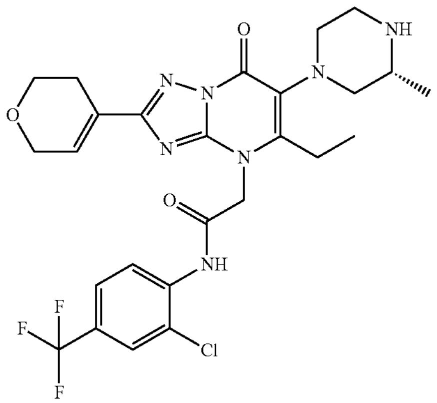 [SMILES: CCc1c(N2CCN[C@H](C)C2)c(=O)n2nc(C3=CCOCC3)nc2n1CC(=O)Nc1ccc(C(F)(F)F)cc1Cl]

A solution of tert-butyl (R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2-methylpiperazine-1-carboxylate (4.08 g, 5.70 mmol) in HCl 4N in 1,4-dioxane (42.8 mL, 171 mmol) was stirred at RT for 45 minutes. The RM was quenched slowly with aq sat $NaHCO_3$, then 10% MeOH in DCM was added. The biphasic mixture was stirred at RT overnight. Both phases were separated, and the aqueous layer was concentrated and extracted twice with 10% MeOH in DCM. The combined organic layers were dried through a phase separator, concentrated and dried under HV to give the title compound as a beige solid.

LC-MS: Rt=0.88 min; MS m/z $[M+H]^+$ 580.3, m/z $[M-H]^-$ 578.4; UPLC-MS 1

Intermediate BF: (R)-2-(2-(3,6-dihydro-2H-pyran-4-yl)-5-ethyl-6-(3-methylpiperazin-1-yl)-7-oxo-[1,2,4]triazolo[1,5-a]pyrimidin-4 (7H)-yl)-N-(4-(trifluoromethyl)phenyl)acetamide Step 1: tert-butyl (R)-4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate

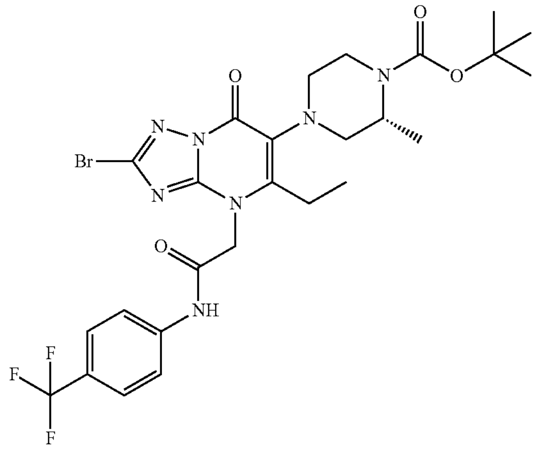 [SMILES: CCc1c(N2CCN(C(=O)OC(C)(C)C)[C@H](C)C2)c(=O)n2nc(Br)nc2n1CC(=O)Nc1ccc(C(F)(F)F)cc1]

Tert-butyl (R)-4-(2-bromo-5-ethyl-7-oxo-4,7-dihydro-[1,2,4]triazolo[1,5-a]pyrimidin-6-yl)-2-methylpiperazine-1-carboxylate (Intermediate BD) (2.50 g, 5.66 mmol) and 2-bromo-N-(4-(trifluoromethyl)phenyl)acetamide (2.02 g, 6.80 mmol) were dissolved in DMF (15 mL). DIPEA (2.97 mL, 17.0 mmol) was added and the RM was stirred at 85° C. for 4.75 hours, then allowed to cool to RT. The RM was slowly added dropwise to ice-water (40 mL). The product precipitated, the water was decanted and the residue was extracted with EtOAc (3×80 mL). The organic layers were washed with water (2×20 mL) and brine (2×20 mL), dried through a phase separator and concentrated under reduced pressure. The crude product was adsorbed onto Isolute and purified by column chromatography (RediSep Column: Silica 120 g, eluent DCM:MeOH 100:0 to 85:15). The product containing fractions were combined and concentrated under reduced pressure to give the title compound as a brown solid foam.

LC-MS: Rt=1.16 min; MS m/z $[M+H-Boc]^+$ 542.1, m/z $[M-H]^-$ 640.2; UPLC-MS 4

Step 2: tert-butyl (R)-4-(2-(3,6-dihydro-2H-pyran-4-yl)-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate

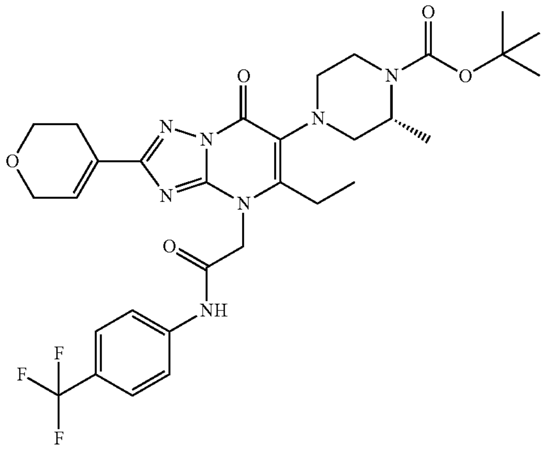 [SMILES: CCc1c(N2CCN(C(=O)OC(C)(C)C)[C@H](C)C2)c(=O)n2nc(C3=CCOCC3)nc2n1CC(=O)Nc1ccc(C(F)(F)F)cc1]

Tert-butyl (R)-4-(2-bromo-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate (3.82 g, 4.16 mmol), 2-(3,6-dihydro-2H-pyran-4-yl)-4,4,5,5-tetramethyl-1,3,2-dioxaborolane (1.31 g, 6.25 mmol) and XPhos Pd G3 (176 mg, 208 µmol) were purged with argon. 1,4-Dioxane (20 mL) and $K_3PO_4$ 1M in water (12.5 mL, 12.5 mmol) were added and the RM was stirred at 90° C. for 3.5 hours. The RM was allowed to cool to RT and stirred at RT overnight. DMF was removed, and the aqueous residue was extracted with EtOAc (3×50 mL). The organic layers were washed with water (2×10 mL) and brine (2×5 mL), dried through a phase separator and concentrated under reduced pressure. The residue was dissolved in DCM and MeOH. ISOLUTE® Si-Thiol (3.20 g) was added and the suspension was stirred for 30 minutes. The suspension was filtered and washed with DCM and MeOH. The filtrate was concentrated under reduced pressure. The crude product was adsorbed onto Isolute and purified by column chromatography (RediSep Column: Silica 120 g, eluent DCM:MeOH 100:0 to 85:15). The product containing fractions were combined and concentrated under reduced pressure. The solid was dissolved in $Et_2O$ and hexane was added. The $Et_2O$ was removed under reduced pressure. The precipitate was filtered off, the cake was mixed with hot hexane and filtered. The beige solid was adsorbed onto Isolute and purified by column chromatography (RediSep Column: Silica 120 g, eluent DCM:MeOH 100:0 to 90:10). The product containing fractions were combined and concentrated under reduced pressure. The solid was dissolved in $Et_2O$ and hexane was added. $Et_2O$ was removed under reduced pressure. The resulting suspension was filtered, the cake was washed with hexane and dried under HV to give the title compound.

LC-MS: Rt=1.20 min; MS m/z $[M+H-Boc]^+$ 546.3, m/z $[M-H]^-$ 644.4; UPLC-MS 4

Step 3: (R)-2-(2-(3,6-dihydro-2H-pyran-4-yl)-5-ethyl-6-(3-methylpiperazin-1-yl)-7-oxo-[1,2,4]triazolo[1,5-a]pyrimidin-4 (7H)-yl)-N-(4-(trifluoromethyl)phenyl)acetamide

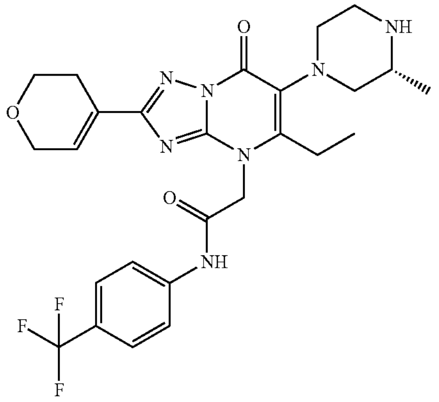 [SMILES: CCc1c(N2CCN[C@H](C)C2)c(=O)n2nc(C3=CCOCC3)nc2n1CC(=O)Nc1ccc(C(F)(F)F)cc1]

Tert-butyl (R)-4-(2-(3,6-dihydro-2H-pyran-4-yl)-5-ethyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate (150 mg, 232 µmol) was dissolved in DCM (1 mL) and TFA (358 µL, 4.65 mmol) was added. The RM was stirred at RT for 2.3 hours. The RM was concentrated under reduced pressure. DCM and toluene were added and removed under reduced pressure. The residue was dried under HV to give the title compound as brown foam.

LC-MS: Rt=0.88 min; MS m/z $[M+H]^+$ 546.2, m/z $[M-H]^-$ 544.0; UPLC-MS 4

Intermediate BG: tert-butyl (S)-4-(2-bromo-5-ethyl-7-oxo-4,7-dihydro-[1,2,4]triazolo[1,5-a]pyrimidin-6-yl)-3-methylpiperazine-1-carboxylate

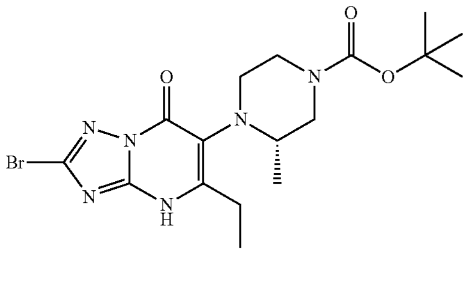 [SMILES: CCc1[nH]c2nc(Br)nn2c(=O)c1N1CCN(C(=O)OC(C)(C)C)C[C@@H]1C]

Tert-butyl (3S)-4-(1-ethoxy-1,3-dioxopentan-2-yl)-3-methylpiperazine-1-carboxylate (Intermediate EL) (1.32 g, 3.85 mmol) was dissolved in EtOH (5 mL) and 3-bromo-1H-1,2,4-triazol-5-amine (Intermediate ER) (600 mg, 3.50 mmol) was added, followed by $H_3PO_4$ (444 mg, 3.85 mmol). The RM was stirred at 85° C. for 22.5 hours, then it was allowed to cool to RT. After 30 minutes at RT the RM was quenched with water, diluted with EtOAc and concentrated under reduced pressure. The residue was extracted with EtOAc (3×60 mL), and the organic layers were washed with water (3×10 mL) and brine (2×10 mL), dried through a phase separator and concentrated under reduced pressure. The crude product was adsorbed onto Isolute and purified by column chromatography (RediSep Column: Silica 80 g, eluent DCM:DCM/MeOH (8/2) 100:0 to 0:100. The product containing fractions were combined and concentrated under reduced pressure to give the title compound as an orange oil.

LC-MS: Rt=0.98 min; MS m/z $[M+H]^+$ 441.3, m/z $[M-H]^-$ 439.1; UPLC-MS 1

Intermediate BH: (S)—N-(2-chloro-4-(trifluoromethyl)phenyl)-2-(2-(3,6-dihydro-2H-pyran-4-yl)-5-ethyl-6-(2-methylpiperazin-1-yl)-7-oxo-[1,2,4]triazolo[1,5-a]pyrimidin-4 (7H)-yl)acetamide Step 1: tert-butyl (S)-4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)-3-methylpiperazine-1-carboxylate

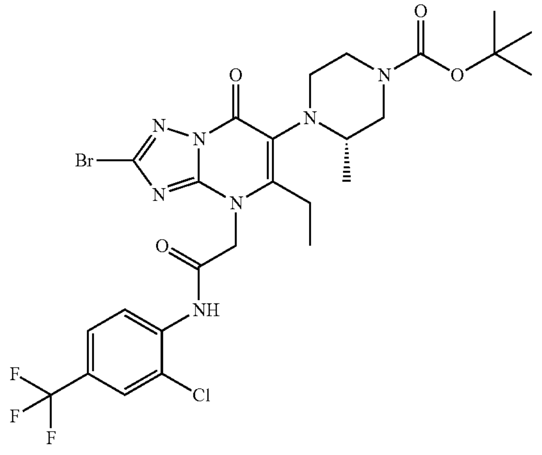 [SMILES: CCc1c(N2CCN(C(=O)OC(C)(C)C)C[C@@H]2C)c(=O)n2nc(Br)nc2n1CC(=O)Nc1ccc(C(F)(F)F)cc1Cl]

Tert-butyl (S)-4-(2-bromo-5-ethyl-7-oxo-4,7-dihydro-[1,2,4]triazolo[1,5-a]pyrimidin-6-yl)-3-methylpiperazine-1-carboxylate (Intermediate BG) (236 mg, 417 μmol) and N-(2-chloro-4-(trifluoromethyl)phenyl)-2-iodoacetamide (Intermediate DL) (185 mg, 459 μmol) were dissolved in DMF (2.5 mL). DIPEA (219 μL, 1.25 mmol) was added and the RM was stirred at 65° C. for 2.5 hours. The RM was cooled to RT and water (5 mL) was added dropwise. The RM was extracted with EtOAc (3×40 mL), and the organic layers were washed with water (2×10 mL) and brine (2×10 mL), dried through a phase separator and concentrated under reduced pressure. The crude product was dissolved in $Et_2O$ and heptane was added. The $Et_2O$ was evaporated and the suspension was filtered and washed with heptane. The cake was mixed with $Et_2O$ again and heptane was added. $Et_2O$ was removed and the suspension was filtered to give the title compound as a brown solid.

LC-MS: Rt=1.38 min; MS m/z $[M+H-Boc]^+$ 576.1, m/z $[M-H]^-$ 674.2; UPLC-MS 1

Step 2: tert-butyl (S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-3-methylpiperazine-1-carboxylate

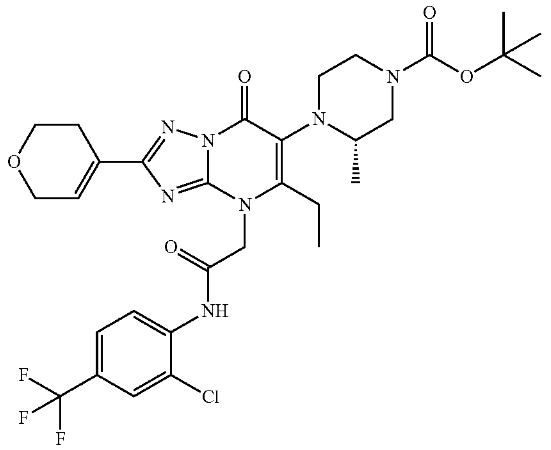 [SMILES: CCc1c(N2CCN(C(=O)OC(C)(C)C)C[C@@H]2C)c(=O)n2nc(C3=CCOCC3)nc2n1CC(=O)Nc1ccc(C(F)(F)F)cc1Cl]

Tert-butyl (S)-4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)-3-methylpiperazine-1-carboxylate (130 mg, 192 μmol), $K_3PO_4$ (122 mg, 576 μmol) and Pd(dppf)$Cl_2$·DCM (7.84 mg, 9.60 μmol) were mixed under argon, then degassed and purged with argon several times. 1,4-Dioxane (3.2 mL) and water (1.6 mL) were added, followed by 2-(3,6-dihydro-2H-pyran-4-yl)-4,4,5,5-tetramethyl-1,3,2-dioxaborolane (60.5 mg, 288 μmol). The RM was stirred at 80° C. for 1 hour. Pd(dppf)$Cl_2$·DCM was added and the RM was stirred at 80° C. for 2 hours. Pd(dppf)$Cl_2$·DCM (5.00 mg, 6.12 μmol), $K_3PO_4$ (30.0 mg, 142 μmol) and 2-(3,6-dihydro-2H-pyran-4-yl)-4,4,5,5-tetramethyl-1,3,2-dioxaborolane (20.0 mg, 95.2 μmol) were added and the RM was stirred at 80° C. for 30 minutes. The RM was cooled to RT and extracted with EtOAc (3×40 mL). The organic layers were washed with water (2×15 mL) and brine (15 mL), dried through a phase separator and concentrated under reduced pressure. The crude product was adsorbed onto Isolute and purified by column chromatography (RediSep Column: Silica 40 g, eluent heptane:EtOAc 100:0 to 20:80). The product containing fractions were combined and concentrated to give the title compound as a white solid.

LC-MS: Rt=1.34 min; MS m/z $[M+H-Boc]^+$580.3, m/z $[M-H]^-$ 678.3; UPLC-MS 1

Step 3: (S)—N-(2-chloro-4-(trifluoromethyl)phenyl)-2-(2-(3,6-dihydro-2H-pyran-4-yl)-5-ethyl-6-(2-methylpiperazin-1-yl)-7-oxo-[1,2,4]triazolo[1,5-a]pyrimidin-4 (7H)-yl)acetamide

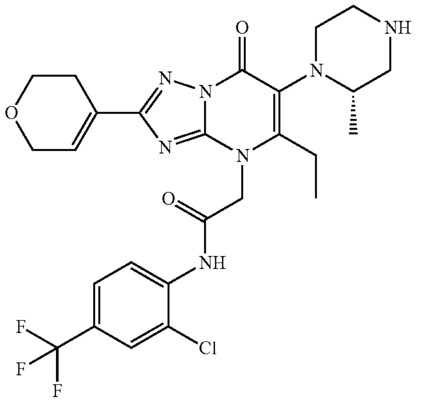 [SMILES: CCc1c(N2CCNC[C@@H]2C)c(=O)n2nc(C3=CCOCC3)nc2n1CC(=O)Nc1ccc(C(F)(F)F)cc1Cl]

Tert-butyl (S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-3-methylpiperazine-1-carboxylate (53.7 mg, 79.0 μmol) was dissolved in DCM (600 μL) and TFA (122 μL, 1.58 mmol) was added. The RM was stirred at RT for 1 hour and then concentrated under reduced pressure. DCM was added and removed twice. The residue was dried under HV to give the title compound as a brown solid.

LC-MS: Rt=0.76 min; MS m/z $[M+H]^+$ 580.3, m/z $[M-H]^-$ 578.2; UPLC-MS 1

Intermediate BI: tert-butyl (R)-4-(2-bromo-5-ethyl-7-oxo-4,7-dihydro-[1,2,4]triazolo[1,5-a]pyrimidin-6-yl)-3-methylpiperazine-1-carboxylate

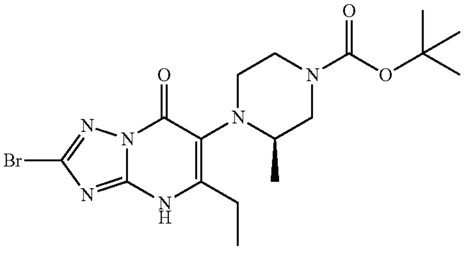 [SMILES: CCc1[nH]c2nc(Br)nn2c(=O)c1N1CCN(C(=O)OC(C)(C)C)C[C@H]1C]

Tert-butyl (3R)-4-(1-ethoxy-1,3-dioxopentan-2-yl)-3-methylpiperazine-1-carboxylate (Intermediate EM) (1.60 g, 4.66 mmol) was dissolved in EtOH (7 mL). 3-bromo-1H-1,2,4-triazol-5-amine (Intermediate ER) (800 mg, 4.66 mmol) and $H_3PO_4$ (564 mg, 4.90 mmol) were added and the RM was stirred at 85° C. for 23.5 hours. The RM was cooled to RT. DIPEA (2.44 mL, 14.0 mmol) and $Boc_2O$ (509 mg, 2.33 mmol) were added and the RM was stirred at RT for 2 hours. The RM was quenched with a small amount of water, EtOH was removed under reduced pressure, and the residue was extracted with EtOAc (3×60 mL). The organic layers were washed with water (2×30 mL) and brine (2×25 mL), dried through a phase separator and concentrated under reduced pressure. The crude product was adsorbed onto Isolute and purified by column chromatography (RediSep Column: Silica 120 g, eluent DCM:DCM/MeOH (8/2) 100:0 to 70:30). The product containing fractions were combined and concentrated under reduced pressure. This material was adsorbed onto Isolute and purified by column chromatography (RediSep Column: Silica 80 g, eluent heptane:EtOAc 100:0 to 25:75). The product containing fractions were combined and concentrated under reduced pressure to give the title compound as a pale yellow solid.

LC-MS: Rt=0.97 min; MS m/z $[M+H]^+$ 441.2, m/z $[M-H]^-$ 439.2; UPLC-MS 1

Intermediate BJ: (R)—N-(2-chloro-4-(trifluoromethyl)phenyl)-2-(2-(3,6-dihydro-2H-pyran-4-yl)-5-ethyl-6-(2-methylpiperazin-1-yl)-7-oxo-[1,2,4]triazolo[1,5-a]pyrimidin-4 (7H)-yl)acetamide Step 1: tert-butyl (R)-4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)-3-methylpiperazine-1-carboxylate

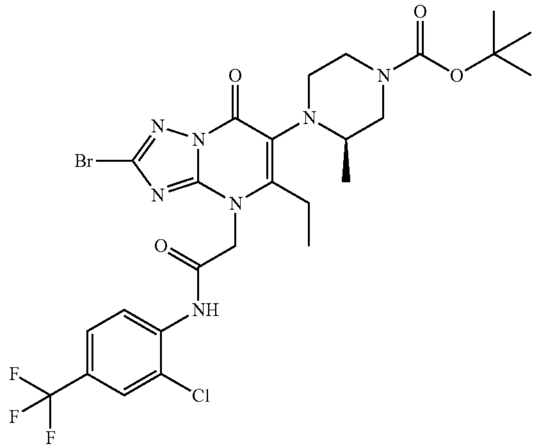 [SMILES: CCc1c(N2CCN(C(=O)OC(C)(C)C)C[C@H]2C)c(=O)n2nc(Br)nc2n1CC(=O)Nc1ccc(C(F)(F)F)cc1Cl]

Tert-butyl (R)-4-(2-bromo-5-ethyl-7-oxo-4,7-dihydro-[1,2,4]triazolo[1,5-a]pyrimidin-6-yl)-3-methylpiperazine-1-carboxylate (Intermediate BI) (191 mg, 433 μmol) and N-(2-chloro-4-(trifluoromethyl)phenyl)-2-iodoacetamide (Intermediate DL) (182 mg, 476 μmol) were dissolved in 1,4-dioxane (2.5 mL). DIPEA (227 μL, 1.30 mmol) was added and the RM was stirred at 80° C. for 3.5 hours. The RM was cooled to RT, quenched with water (5 mL) and extracted with EtOAc (3×40 mL). The organic layers were washed with water (2×10 mL) and brine (2×10 mL), dried through a phase separator and concentrated under reduced pressure. The crude product was adsorbed onto Isolute and purified by column chromatography (RediSep Column: Silica 40 g, eluent heptane:EtOAc 100:0 to 45:55). The product containing fractions were combined and concentrated under reduced pressure to give the title compound as a pale yellow solid.

LC-MS: Rt=1.38 min; MS m/z $[M+H-Boc]^+$576.1, m/z $[M-H]^-$ 674.2; UPLC-MS 1

Step 2: tert-butyl (R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-3-methylpiperazine-1-carboxylate

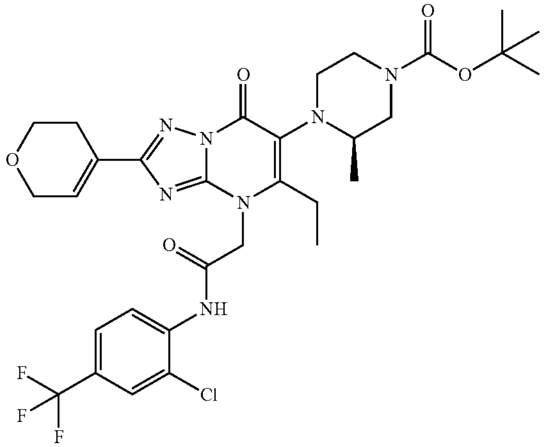 [SMILES: CCc1c(N2CCN(C(=O)OC(C)(C)C)C[C@H]2C)c(=O)n2nc(C3=CCOCC3)nc2n1CC(=O)Nc1ccc(C(F)(F)F)cc1Cl]

Tert-butyl (R)-4-(2-bromo-4-(2-((2-chloro-4-(trifluoromethyl)phenyl)amino)-2-oxoethyl)-5-ethyl-7-oxo-4,7-dihydro-[1,2,4]triazolo[1,5-a]pyrimidin-6-yl)-3-methylpiperazine-1-carboxylate (183 mg, 270 μmol), $K_3PO_4$ (115 mg, 541 μmol), Pd(dppf)$Cl_2$·DCM (22.1 mg, 27.0 μmol) and 2-(3,6-dihydro-2H-pyran-4-yl)-4,4,5,5-tetramethyl-1,3,2-dioxaborolane (85.0 mg, 406 μmol) were mixed under argon. The mixture was degassed and purged with argon several times. 1,4-Dioxane (4.5 mL) and water (2.25 mL) were added and the RM was stirred at 80° C. for 6 hours. The RM was cooled to RT and extracted with EtOAc (3×40 mL). The organic layers were washed with water (2×10 mL) and brine (2×10 mL) and dried through a phase separator. The aqueous layers were extracted with EtOAc (2×40 mL), and the organic layers were dried through a phase separator. The combined organic layers were concentrated under reduced pressure. To this mixture were added $K_3PO_4$ (172 mg, 812 μmol) and Pd(dppf)$Cl_2$·DCM (22.1 mg, 27.0 μmol) at RT under argon. The mixture was degassed and purged with argon several times. 1,4-Dioxane (4.5 mL) and water (2.25 mL) were added, followed by 2-(3,6-dihydro-2H-pyran-4-yl)-4,4,5,5-tetramethyl-1,3,2-dioxaborolane (85.0 mg, 406 μmol). The RM was stirred at 80° C. for 1.25 hours, then cooled to RT and extracted with EtOAc (3×40 mL). The organic layers were washed with water (2×10 mL) and brine (2×10 mL), dried through a phase separator and concentrated under reduced pressure to one third of volume. ISOLUTE® Si-Thiol (300 mg) was added and the mixture was stirred for 45 minutes. The suspension was filtered and concentrated under reduced pressure. The crude product was adsorbed onto Isolute and purified by column chromatography (RediSep Column: Silica 24 g, eluent heptane:EtOAc 100:0 to 0:100). The product containing fractions were combined and concentrated under reduced pressure to give the title compound as a colorless solid.

LC-MS: Rt=1.35 min; MS m/z $[M+H-Boc]^+$ 580.6, m/z $[M-H]^-$ 678.4; UPLC-MS 1

Step 3: (R)—N-(2-chloro-4-(trifluoromethyl)phenyl)-2-(2-(3,6-dihydro-2H-pyran-4-yl)-5-ethyl-6-(2-methylpiperazin-1-yl)-7-oxo-[1,2,4]triazolo[1,5-a]pyrimidin-4 (7H)-yl)acetamide

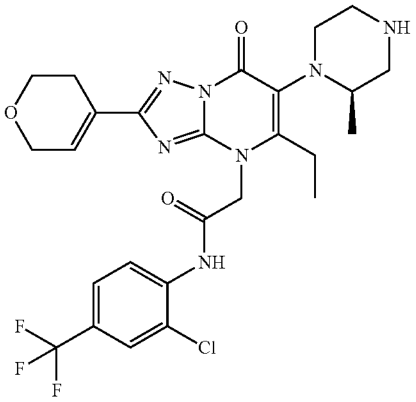 [SMILES: CCc1c(N2CCNC[C@H]2C)c(=O)n2nc(C3=CCOCC3)nc2n1CC(=O)Nc1ccc(C(F)(F)F)cc1Cl]

Tert-butyl (R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-3-methylpiperazine-1-carboxylate (108 mg, 159 μmol) was dissolved in DCM (1.1 mL) and TFA (245 μL, 3.18 mmol) was added. The RM was stirred at RT for 1 hour, then it was concentrated under reduced pressure. The residue was dissolved in DCM and concentrated under reduced pressure again. This was performed twice, then it was dried under HV. The residue was extracted with DCM (3×40 mL) and the organic layers were washed with aq sat $NaHCO_3$ (15 mL), dried through a phase separator and concentrated under reduced pressure to give the title compound as a beige solid.

LC-MS: Rt=0.75 min; MS m/z $[M+H]^+$ 580.3, m/z $[M-H]^-$ 578.2; UPLC-MS 1

Intermediate BK: tert-butyl (R)-4-(2-bromo-5-methyl-7-oxo-4,7-dihydro-[1,2,4]triazolo[1,5-a]pyrimidin-6-yl)-2-methylpiperazine-1-carboxylate

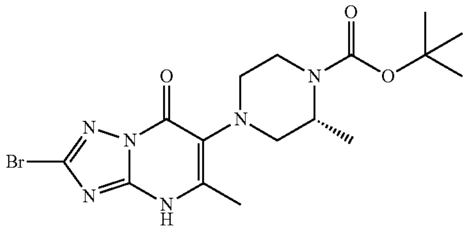 [SMILES: Cc1[nH]c2nc(Br)nn2c(=O)c1N1CCN(C(=O)OC(C)(C)C)[C@H](C)C1]

A solution of 3-bromo-1H-1,2,4-triazol-5-amine (Intermediate ER) (1.49 g, 9.14 mmol) and tert-butyl (2R)-4-(1-ethoxy-1,3-dioxobutan-2-yl)-2-methylpiperazine-1-carboxylate (Intermediate EO) (3.18 g, 8.71 mmol) in AcOH (5.23 mL, 91.0 mmol) was stirred at 110° C. for 4 hours. The RM was allowed to cool to RT and stand overnight. Water was added and the resulting suspension was stirred at RT for 30 minutes and then concentrated and dried under vacuum. The crude product was dissolved in DCM and washed with water, insoluble parts between the two phases were collected and dried under vacuum, and the aqueous layer was extracted twice with DCM. The combined organic layers were dried through a phase separator, concentrated under reduced pressure and dried. This crude product was purified by column chromatography (RediSep Column: Silica 24 g, eluent DCM:DCM/MeOH (9/1) 100:0 to 0:100). The product containing fractions were combined and concentrated to give the title compound.

LC-MS: Rt=0.94 min; MS m/z $[M+H]^+$ 427.1, m/z $[M-H]^-$ 425.1; UPLC-MS 8 The aqueous layer from above extraction contained debocylated product and was concentrated and dried under vacuum to give an orange-brown solid. Together with the collected insoluble parts, this material (3.00 g, 7.79 mmol) was suspended in EtOH (20 mL). DIPEA (4.32 mL, 24.7 mmol) and $Boc_2O$ (1.91 mL, 8.24 mmol) were added. The RM was stirred at RT for 50 minutes and concentrated, and the residue was dissolved in DCM and washed with water. The aqueous layer was extracted twice with DCM. The combined organic layers were dried through a phase separator, concentrated under reduced pressure and dried. This material was purified by column chromatography (RediSep Column: Silica 120 g, eluent DCM:DCM/MeOH (9/1) 100:0 to 0:100). The product containing fractions were combined and concentrated under reduced pressure to give the title compound.

LC-MS: Rt=0.94 min; MS m/z $[M+H]^+$ 427.2, m/z $[M-H]^-$ 425.1; UPLC-MS 8

Intermediate BL: (R)-2-(2-(3,6-dihydro-2H-pyran-4-yl)-5-methyl-6-(3-methylpiperazin-1-yl)-7-oxo-[1,2,4]triazolo[1,5-a]pyrimidin-4 (7H)-yl)-N-(4-(trifluoromethyl)phenyl)acetamide Step 1: tert-butyl (R)-4-(2-bromo-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate

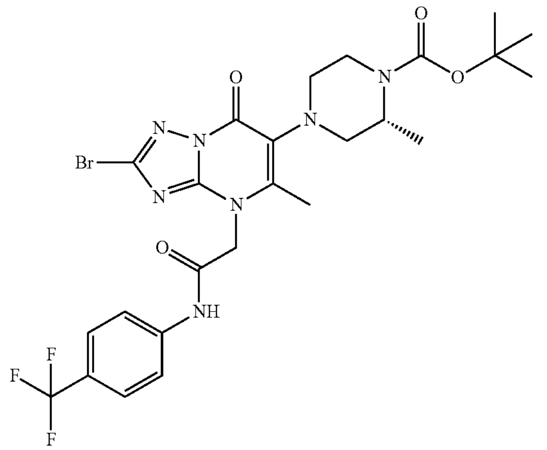 [SMILES: Cc1c(N2CCN(C(=O)OC(C)(C)C)[C@H](C)C2)c(=O)n2nc(Br)nc2n1CC(=O)Nc1ccc(C(F)(F)F)cc1]

A solution of tert-butyl (R)-4-(2-bromo-5-methyl-7-oxo-4,7-dihydro-[1,2,4]triazolo[1,5-a]pyrimidin-6-yl)-2-methylpiperazine-1-carboxylate (Intermediate BK) (1.29 g, 2.71 mmol) in DMF (12 mL) was cooled to 0° C., and DIPEA (1.39 mL, 7.96 mmol) was added. After 1 hour stirring at 0° C. 2-bromo-N-(4-(trifluoromethyl)phenyl)acetamide (914 mg, 2.92 mmol) was added. After 10 minutes, the ice bath was removed and the mixture was stirred at RT for 20.5 hours. Water (60 mL) was added, and the mixture was extracted once with DCM and once with DCM and a small amount of MeOH. The organic layers were combined, dried through a phase separator and concentrated under reduced pressure to give a dark brown oil. The crude product was purified by column chromatography (RediSep Column: Silica 80 g, eluent heptane:EtOAc 100:0 to 0:100), and the product containing fractions were combined to give the title compound.

LC-MS: Rt=1.24 min; MS m/z $[M+H]^+$ 628.1, m/z $[M-H]^-$ 626.0; UPLC-MS 8

Step 2: tert-butyl (R)-4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate

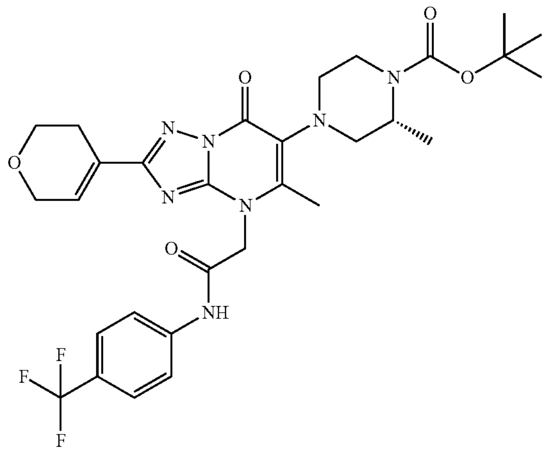 [SMILES: Cc1c(N2CCN(C(=O)OC(C)(C)C)[C@H](C)C2)c(=O)n2nc(C3=CCOCC3)nc2n1CC(=O)Nc1ccc(C(F)(F)F)cc1]

Tert-butyl (R)-4-(2-bromo-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate (845 mg, 1.16 mmol), 3,6-dihydro-2H-pyran-4-boronic acid pinacol ester (304 mg, 1.45 mmol) and XPhos Pd G3 (48.9 mg, 58.0 μmol) were introduced into a MW vial, which was then degassed and purged with argon several times. DMF (7.7 mL) and $K_3PO_4$ 1M in water (2.31 mL, 2.31 mmol) were added. The resulting mixture was stirred at 60° C. for 7.25 hours. The RM was diluted with DCM and washed twice with aq sat $NaHCO_3$. The combined aqueous layer was extracted four times with DCM. The organic layers were combined, dried through a phase separator and concentrated under reduced pressure, and the crude product was purified by column chromatography (RediSep Column: Silica 40 g, eluent heptane:EtOAc 100:0 to 0:100). The product containing fractions were combined, concentrated and dried under HV. This material was dissolved in DCM and PL-BnSH MP-Resin (101 mg, 250 μmol) was added. The suspension was stirred at 37° C. for 1 hour and then filtered. The filtrate was concentrated and dried under vacuum to give the title compound as a beige foam.

LC-MS: Rt=1.22 min; MS m/z $[M+H]^+$ 632.3, m/z $[M-H]^-$ 630.1; UPLC-MS 8

Step 3: (R)-2-(2-(3,6-dihydro-2H-pyran-4-yl)-5-methyl-6-(3-methylpiperazin-1-yl)-7-oxo-[1,2,4]triazolo[1,5-a]pyrimidin-4 (7H)-yl)-N-(4-(trifluoromethyl)phenyl)acetamide

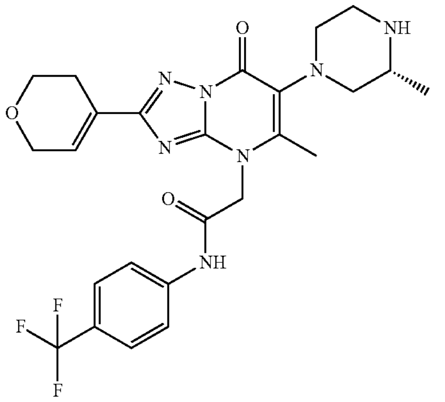 [SMILES: Cc1c(N2CCN[C@H](C)C2)c(=O)n2nc(C3=CCOCC3)nc2n1CC(=O)Nc1ccc(C(F)(F)F)cc1]

To a solution of tert-butyl (R)-4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)-2-methylpiperazine-1-carboxylate (693 mg, 1.04 mmol) in DCM (1.6 mL) was added TFA (1.61 mL, 20.9 mmol). The RM was stirred at RT for 2 hours. The RM was concentrated to dryness, and the crude product was dissolved in DCM/MeOH (1:1) and split into three portions. Those were filtered through PL-$HCO_3$ MP SPE cartridges (500 mg per 6 mL), prewashed with DCM/MeOH (1:1). The cartridges were washed with DCM/MeOH (1:1), and the filtrates were combined, concentrated and dried under vacuum. This material was dissolved in DCM/MeOH (1:1), split into two portions and filtered through prewashed PL-$HCO_3$ MP SPE cartridges (500 mg per 6 mL). The cartridges were washed with DCM/MeOH (1:1), and the filtrates were combined, concentrated and dried under vacuum to give the title compound as a light brown foam.

LC-MS: Rt=0.77 min; MS m/z $[M+H]^+$ 532.3, m/z $[M-H]^-$ 530.3; UPLC-MS 4

Intermediate BM: tert-butyl 4-(2-bromo-5-methyl-7-oxo-4,7-dihydro-[1,2,4]triazolo[1,5-a]pyrimidin-6-yl)piperazine-1-carboxylate

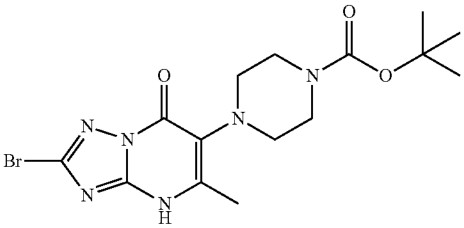 [SMILES: Cc1[nH]c2nc(Br)nn2c(=O)c1N1CCN(C(=O)OC(C)(C)C)CC1]

3-Bromo-1H-1,2,4-triazol-5-amine (Intermediate ER) (4.00 g, 24.5 mmol), tert-butyl 4-(1-ethoxy-1,3-dioxobutan-2-yl)piperazine-1-carboxylate (Intermediate EP) (8.49 g, 27.0 mmol) and $H_3PO_4$ (2.97 g, 25.8 mmol) were mixed in EtOH (25 mL) and stirred at reflux for 18 hours. The RM was cooled to RT, DIPEA (12.9 mL, 73.6 mmol) and $Boc_2O$ (1.71 mL, 7.36 mmol) were added, and the RM was stirred at RT for 1 hour. The RM was quenched with aq $NH_4Cl$, diluted with DCM, extracted twice with DCM, dried over $Na_2SO_4$, concentrated and dried. The crude product was crystallized from DCM and TBME to give the title compound.

LC-MS: Rt=0.87 min; MS m/z $[M+H]^+$ 413.1, m/z $[M-H]^-$ 411.0; UPLC-MS 4

Intermediate BN: 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide Step 1: tert-butyl 4-(2-bromo-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

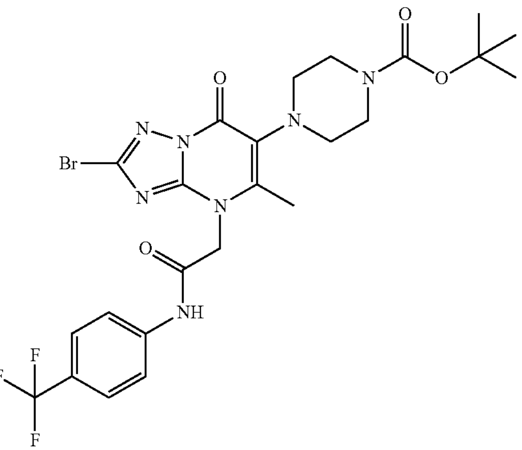

Tert-butyl 4-(2-bromo-5-methyl-7-oxo-4,7-dihydro-[1,2,4]triazolo[1,5-a]pyrimidin-6-yl)piperazine-1-carboxylate (Intermediate BM) (7.38 g, 17.9 mmol), 2-bromo-N-(4-(trifluoromethyl)phenyl)acetamide (6.04 g, 21.4 mmol) and DIPEA (9.36 mL, 53.6 mmol) were dissolved in DMF (50 mL) and the RM was stirred at 80° C. for 2 hours. The RM was cooled to RT, diluted with DCM, and the organic phase was extracted with aq sat $NaHCO_3$ and brine, dried over $Na_2SO_4$ and concentrated under reduced pressure. The crude product was purified by column chromatography (eluent heptane:EtOAc/MeOH (9/1) 100:0 to 30:70). The product containing fractions were combined and concentrated under reduced pressure and then crystallized from TBME to give the title compound.

LC-MS: Rt=1.15 min; MS m/z $[M+H]^+$ 614.0, m/z $[M-H]^-$ 612.0; UPLC-MS 4

Step 2: tert-butyl 4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

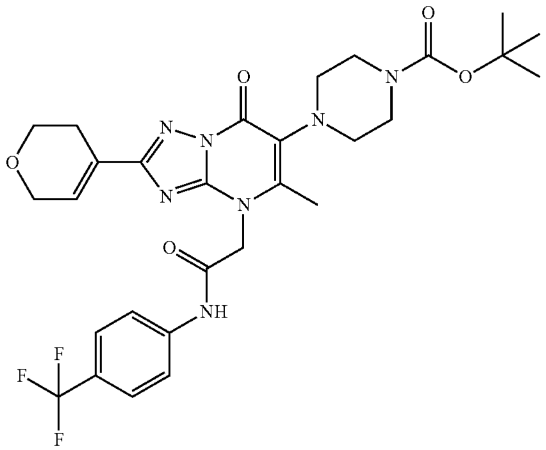 [SMILES: Cc1c(N2CCN(C(=O)OC(C)(C)C)CC2)c(=O)n2nc(C3=CCOCC3)nc2n1CC(=O)Nc1ccc(C(F)(F)F)cc1]

Tert-butyl 4-(2-bromo-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (7.70 g, 12.5 mmol), 2-(3,6-dihydro-2H-pyran-4-yl)-4,4,5,5-tetramethyl-1,3,2-dioxaborolane (3.95 g, 18.8 mmol), $K_3PO_4$ 1.5N (20.9 mL, 31.3 mmol) and XPhos Pd G3 (1.06 g, 1.25 mmol) were dissolved in 1,4-dioxane (50 mL). The RM was stirred at 90° C. for 1 hour and after cooling diluted with EtOAc. The organic phase was washed with aq sat $NaHCO_3$ and brine, dried over $Na_2SO_4$ and concentrated under reduced pressure. This material was dissolved in DCM/MeOH (1:1) and ISOLUTE® Si-Thiol (258 mg) was added. After stirring for 30 minutes, the mixture was filtered and concentrated. The crude product was crystallized from DCM and TBME to give the title compound.

LC-MS: Rt=1.13 min; MS m/z $[M+H]^+$ 618.2, m/z $[M-H]^-$ 616.1; UPLC-MS 4

Step 3: 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide

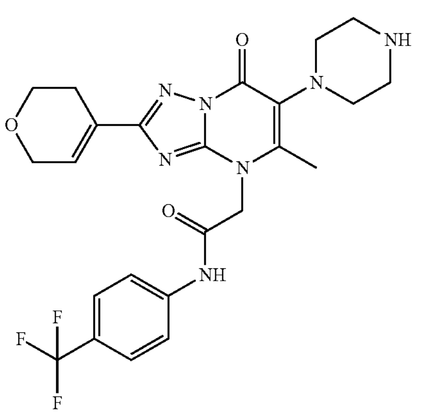 [SMILES: Cc1c(N2CCNCC2)c(=O)n2nc(C3=CCOCC3)nc2n1CC(=O)Nc1ccc(C(F)(F)F)cc1]

Tert-butyl 4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (5.95 g, 9.63 mmol) was dissolved in DCM (50 mL) and TFA (22.3 mL, 289 mmol) was added. The RM was stirred at RT for 1 hour and then concentrated under reduced pressure. Toluene was added and removed again, and this procedure was repeated. The residue was dissolved in EtOAc and washed with aq sat $NaHCO_3$ and brine. During the extraction the product crystallized, and the solids were collected and dried to give the title compound.

LC-MS: Rt=0.84 min; MS m/z $[M+H]^+$ 518.2, m/z $[M-H]^-$ 516.0; UPLC-MS 4

Scheme 5 general overview of intermediates of route IV

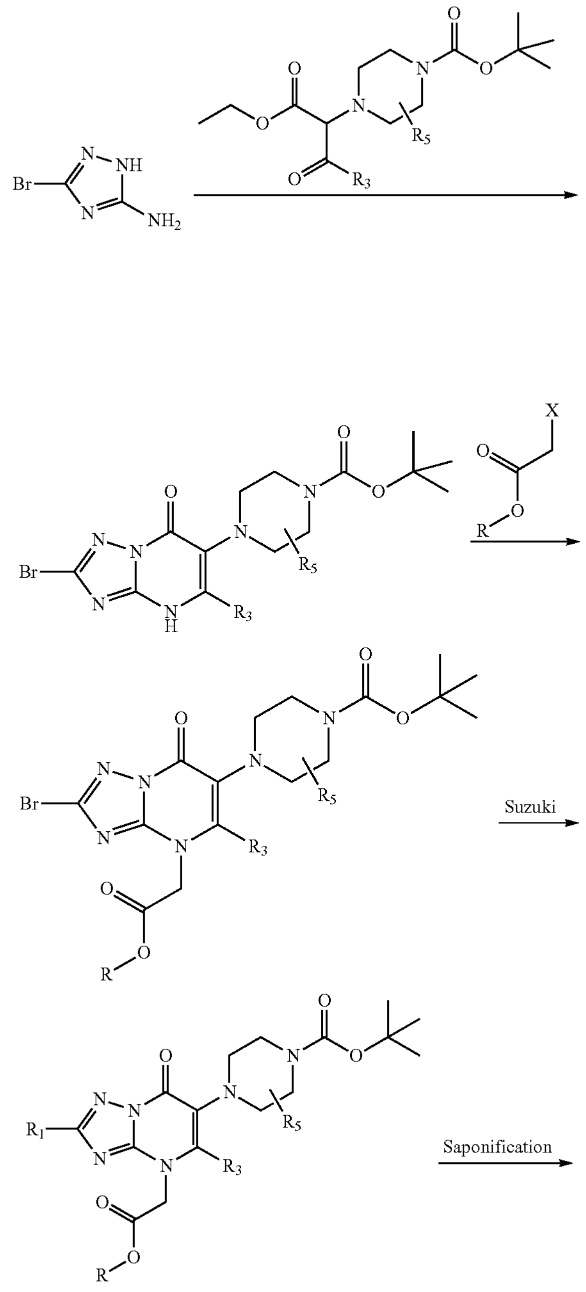

-continued

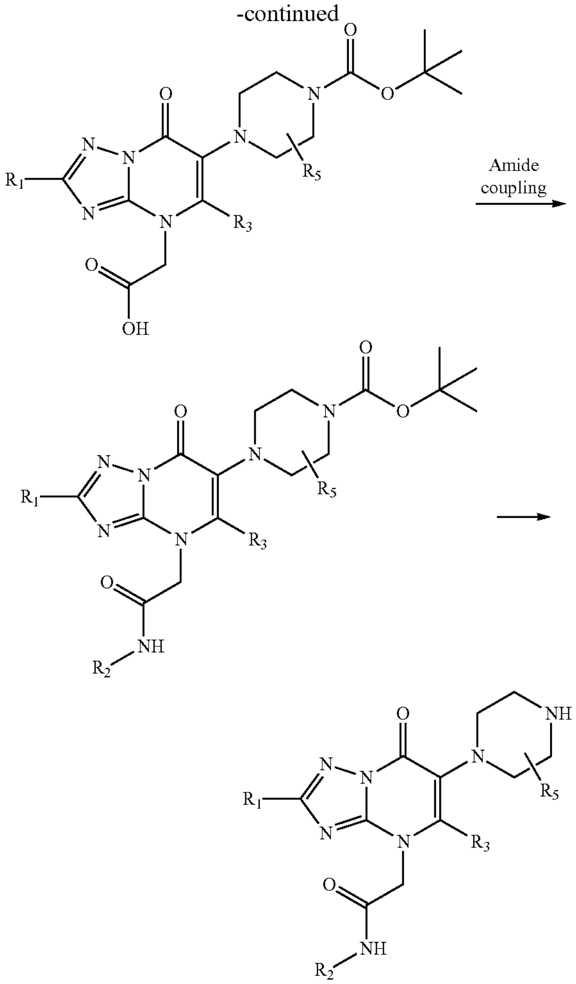

Intermediate BO: 2-(6-(4-(tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl) acetic acid Step 1: tert-butyl 4-(2-bromo-4-(2-(tert-butoxy)-2-oxoethyl)-5-ethyl-7-oxo-4,7-dihydro-[1,2,4]triazolo [1,5-a]pyrimidin-6-yl)piperazine-1-carboxylate

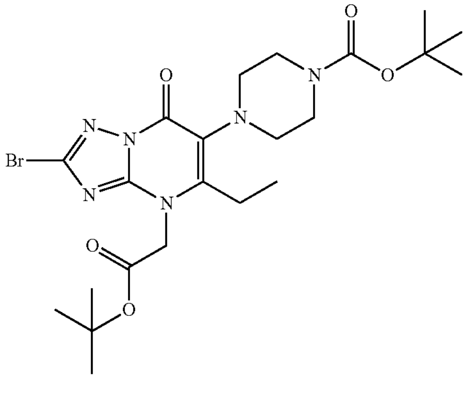 [SMILES: CCc1c(N2CCN(C(=O)OC(C)(C)C)CC2)c(=O)n2nc(Br)nc2n1CC(=O)OC(C)(C)C]

Tert-butyl 4-(2-bromo-5-ethyl-7-oxo-4,7-dihydro-[1,2,4] triazolo[1,5-a]pyrimidin-6-yl)piperazine-1-carboxylate (Intermediate X) (23.0 g, 30.7 mmol) was dissolved in 1,4-dioxane (20 mL) and tert-butyl 2-bromoacetate (6.79 mL, 46.0 mmol) was added, followed by DIPEA (16.1 mL, 92.0 mmol). The mixture was stirred at 80° C. for 3 hours. Water, aq sat $NaHCO_3$ and DCM were added. The aqueous layer was extracted twice with DCM. The combined organic layers were dried through a phase separator and concentrated under reduced pressure. The crude product was suspended in $Et_2O$ and sonicated for 5 minutes and filtered. The cake was washed twice with $Et_2O$ and dried under HV to give the title compound. The filtrate was purified by column chromatography (RediSep Column: Silica 330 g, eluent DCM:DCM/MeOH (9/1) 100:0 to 80:20. The product containing fractions were combined, concentrated under vacuum and dried under HV and combined with the previously isolated crop to give the title compound.

LC-MS: Rt=1.13 min; MS m/z $[M+H-Boc]^+$ 441.2/443.2, m/z $[M-H]^-$ 539.2/541.2; UPLC-MS 3

Step 2: tert-butyl 4-(4-(2-(tert-butoxy)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

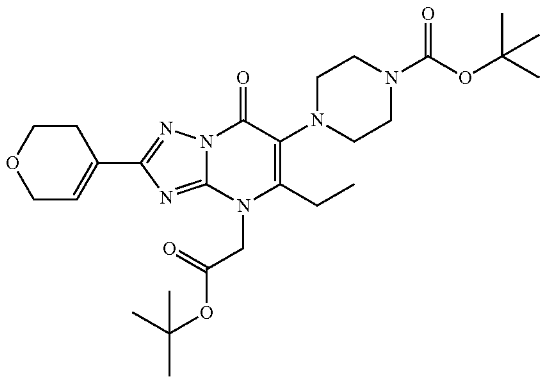 [SMILES: CCc1c(N2CCN(C(=O)OC(C)(C)C)CC2)c(=O)n2nc(C3=CCOCC3)nc2n1CC(=O)OC(C)(C)C]

Tert-butyl 4-(2-bromo-4-(2-(tert-butoxy)-2-oxoethyl)-5-ethyl-7-oxo-4,7-dihydro-[1,2,4]triazolo[1,5-a]pyrimidin-6-yl)piperazine-1-carboxylate (9.12 g, 16.8 mmol), 2-(3,6-dihydro-2H-pyran-4-yl)-4,4,5,5-tetramethyl-1,3,2-dioxaborolane (4.86 g, 23.1 mmol) and XPhos Pd G3 (590 mg, 697 μmol) were mixed in 1,4-dioxane (50 mL) and $K_3PO_4$ (50.5 mL, 50.5 mmol) was added. The mixture was stirred at 80° C. for 1 hour. Water, aq sat $NaHCO_3$ and DCM were added. The aqueous layer was washed twice with DCM. The combined organic layers were dried through a phase separator and concentrated under reduced pressure. The crude product was dissolved in DCM and SiliaMetS® Thiol was added. The mixture was stirred at RT for 1 hour then filtered. The cake was washed with DCM. The filtrate was concentrated under reduced pressure to give the title compound.

LC-MS: Rt=1.10 min; MS m/z $[M+H-Boc]^+$ 445.3, UPLC-MS 3

Step 3: 2-(6-(4-(tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid

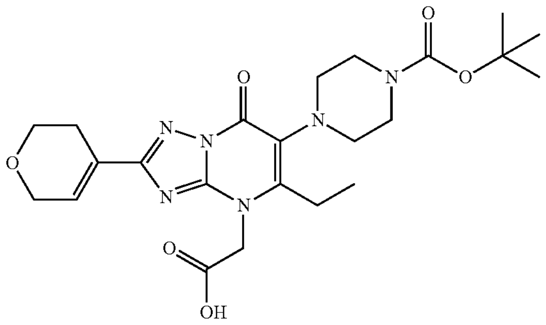 [SMILES: CCc1c(N2CCN(C(=O)OC(C)(C)C)CC2)c(=O)n2nc(C3=CCOCC3)nc2n1CC(=O)O]

Tert-butyl 4-(4-(2-(tert-butoxy)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (11.0 g, 17.8 mmol) was suspended in MeOH (50 mL) and NaOH 1M in water (26.7 mL, 26.7 mmol) was added. The suspension was stirred at RT for 1 day. Water, aq 1M HCl and DCM were added. The aqueous layer was extracted twice with DCM. The combined organic layers were dried through a phase separator and concentrated under reduced pressure. The crude product was suspended in $Et_2O$, sonicated and filtered to give the title compound as a solid.

LC-MS: Rt=0.84 min; MS m/z $[M+H-Boc]^+$389.3, m/z $[M-H]^-$ 487.4; UPLC-MS 3

Intermediate BP: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide Step 1: tert-butyl 4-(2-(3,6-dihydro-2H-pyran-4-yl)-5-ethyl-4-(2-((2-fluoro-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

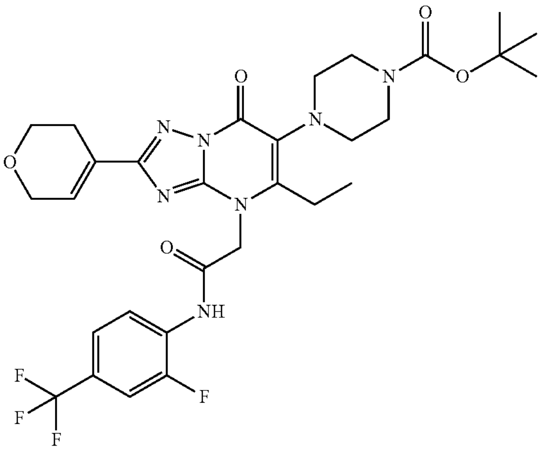 [SMILES: CCc1c(N2CCN(C(=O)OC(C)(C)C)CC2)c(=O)n2nc(C3=CCOCC3)nc2n1CC(=O)Nc1ccc(C(F)(F)F)cc1F]

2-(6-(4-(tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (420 mg, 860 μmol) and 2-fluoro-4-(trifluoromethyl)aniline (157 mg, 860 μmol) were mixed with EtOAc (6 mL). $Et_3N$ (596 μL, 4.30 mmol) and $T_3P$ 50% in EtOAc (1.02 mL, 1.72 mmol) were added and the RM was stirred at RT for 1 hour. The RM was extracted with EtOAc (3×40 mL), water (2×15 mL) and brine (15 mL). The organic layer was separated, filtered through a phase separator and concentrated under reduced pressure. The crude product was adsorbed onto Isolute and purified by column chromatography (RediSep Column: Silica 40 g, eluent DCM:DCM/MeOH (8/2) 100:0 to 95:5). The product containing fractions were combined and concentrated to give the title compound as a pale yellow solid.

LC-MS: Rt=1.18 min; MS m/z $[M+H-Boc]^+$ 550.3, m/z $[M-H]^-$ 648.4; UPLC-MS 4

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide

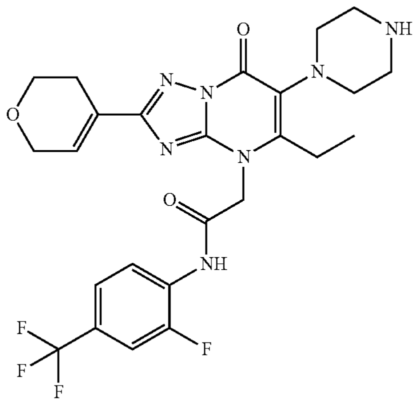 [SMILES: CCc1c(N2CCNCC2)c(=O)n2nc(C3=CCOCC3)nc2n1CC(=O)Nc1ccc(C(F)(F)F)cc1F]

Tert-butyl 4-(2-(3,6-dihydro-2H-pyran-4-yl)-5-ethyl-4-(2-((2-fluoro-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (346 mg, 533 μmol) was dissolved in DCM (3.6 mL) and TFA (821 μL, 10.7 mmol) was added. The RM was stirred at RT for 1 hour, concentrated under reduced pressure. Residual TFA was removed under reduced pressure by azeotroping with DCM and toluene to give the title compound as a bright brown foam as the trifluoroacetate salt.

LC-MS: Rt=0.86 min; MS m/z $[M+H]^+$ 550.3, m/z $[M-H]^-$ 548.3; UPLC-MS 4

Intermediate AJ: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide Step 1: tert-butyl 4-(2-(3,6-dihydro-2H-pyran-4-yl)-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

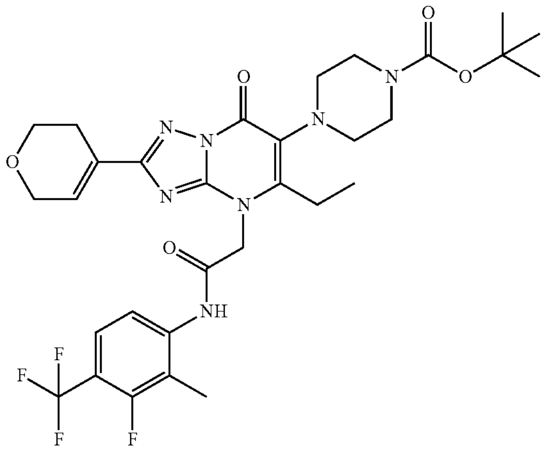 [SMILES: CCc1c(N2CCN(C(=O)OC(C)(C)C)CC2)c(=O)n2nc(C3=CCOCC3)nc2n1CC(=O)Nc1ccc(C(F)(F)F)c(F)c1C]

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (150 mg, 307 μmol) and 3-fluoro-2-methyl-4-(trifluoromethyl)aniline (65.0 mg, 337 μmol) was dissolved in DCM (8 mL). $Et_3N$ (170 μL, 1.23 mmol) was added followed by $T_3P$ 50% in EtOAc (366 μL, 615 μmol). The yellow solution was stirred at RT for 5 days. $T_3P$ 50% in EtOAc (2.00 mL, 3.36 mmol) and $Et_3N$ (2.00 mL, 14.4 mmol) were added and the mixture was stirred at RT for 15 minutes. Water (10 mL), aq sat $NaHCO_3$ (10 mL) and DCM (10 mL) were added. The aqueous layer was extracted twice with DCM (2×10 mL). The combined organic layers was dried through a phase separator and concentrated under reduced pressure to give the title compound.

LC-MS: Rt=1.29 min; MS m/z $[M+H-Boc]^+$ 564.4, m/z $[M-H]^-$ 662.3; UPLC-MS 1

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(3-fluoro-2-methyl-4-(trifluoromethyl)phenyl)acetamide

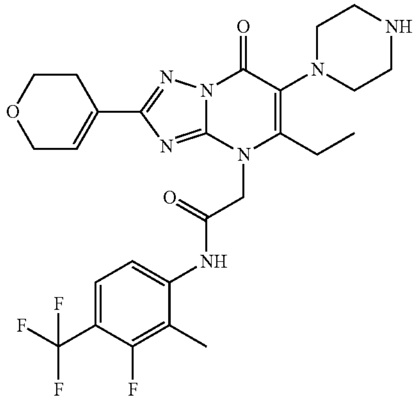 [SMILES: CCc1c(N2CCNCC2)c(=O)n2nc(C3=CCOCC3)nc2n1CC(=O)Nc1ccc(C(F)(F)F)c(F)c1C]

Tert-butyl 4-(2-(3,6-dihydro-2H-pyran-4-yl)-5-ethyl-4-(2-((3-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (335 mg, 242 μmol) was dissolved in DCM (10 mL) and TFA (1.00 mL, 13.0 mmol) was added. The mixture was stirred at 40° C. for 30 minutes. The mixture was concentrated under reduced pressure. The crude product was purified in 2 portions by reverse phase preparative HPLC (2×RP-HPLC acidic 1: 5 to 95% B in 20 min with a plateau at 95% for 1 min). The product containing fractions were combined, basified with aq sat $NaHCO_3$, extracted twice with DCM, dried through a phase separator and concentrated under reduced pressure to give the title compound.

LC-MS: Rt=0.83 min; MS m/z $[M+H]^+$ 564.2, m/z $[M-H]^-$ 562.3; UPLC-MS 1

Intermediate AM: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide Step 1: tert-butyl 4-(2-(3,6-dihydro-2H-pyran-4-yl)-5-ethyl-4-(2-((5-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

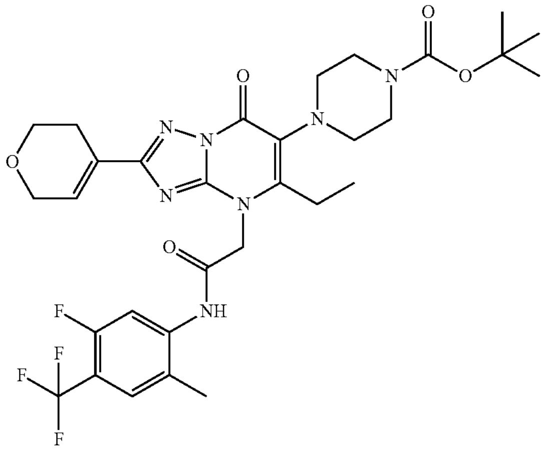

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (800 mg, 1.64 mmol) and 5-fluoro-2-methyl-4-(trifluoromethyl)aniline (Intermediate DD) (396 mg, 2.05 mmol) were mixed in DCM (5 mL). Then $Et_3N$ (908 μL, 6.55 mmol) was added, followed by $T_3P$ 50% in EtOAc (1.00 mL, 3.36 mmol). The mixture was stirred at RT for 2 hours. $T_3P$ 50% in EtOAc (1.00 mL, 3.36 mmol) was added and the mixture was stirred at RT for 1 hour. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was suspended in DCM and sonicated for 2 minutes and filtered. The cake was washed with a small amount of DCM (2 mL) and dried under HV to give a solid as a first crop of the title compound. The filtrate was purified by column chromatography (RediSep Column: Silica 40 g, eluent DCM:DCM/MeOH (9/1) 100:0 to 50:50). The product containing fractions were combined, concentrated under vacuum, combined with the first crop of the title compound and dried under HV to afford the title compound as a beige solid.

LC-MS: Rt=1.22 min; MS m/z $[M+H]^+$ 664.4, m/z $[M-H]^-$ 662.3; UPLC-MS 3

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(5-fluoro-2-methyl-4-(trifluoromethyl)phenyl)acetamide

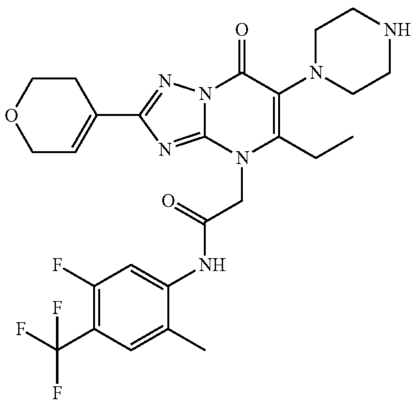

Tert-butyl 4-(2-(3,6-dihydro-2H-pyran-4-yl)-5-ethyl-4-(2-((5-fluoro-2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (520 mg, 760 μmol) was dissolved in DCM (5 mL) and TFA (1.00 mL, 13.0 mmol) was added. The mixture was stirred at 40° C. for 30 minutes. The mixture was concentrated under reduced pressure. The crude product was purified in 2 portions by reverse phase preparative HPLC (2×RP-HPLC acidic 1: 20 to 50% B in 10 min with a plateau at 50% for 1 min). The product containing fractions were combined, basified with aq sat $NaHCO_3$, extracted twice with DCM, dried through a phase separator and concentrated under reduced pressure to give the title compound.

LC-MS: Rt=0.89 min; MS m/z $[M+H]^+$ 564.3, m/z $[M-H]^-$ 562.1; UPLC-MS 3

Intermediate AK: N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

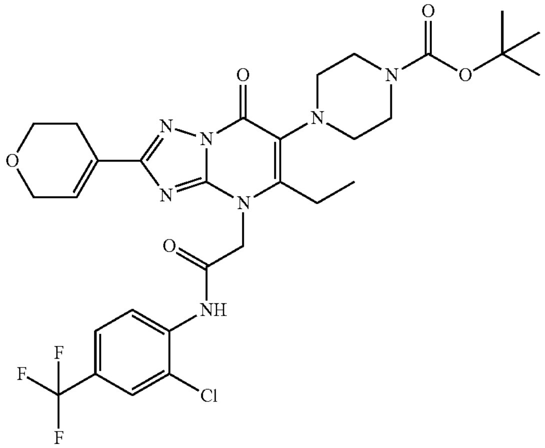

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (4.20 g, 8.60 mmol) was dissolved in EtOAc (50 mL) and $Et_3N$ (4.77 mL, 34.4 mmol). 2-Chloro-4-(trifluoromethyl)aniline (1.68 g, 8.60 mmol) and $T_3P$ 50% in DMF (10.2 mL, 17.2 mmol) were added and the RM was stirred at RT for 1 hour. The RM was adsorbed onto Isolute and purified by column chromatography (RediSep Column: Silica 120 g, eluent cyclohexane:EtOAc 100:0 to 20:80). The product containing fractions were combined and concentrated to give the title compound.

LC-MS: Rt=1.35 min; MS m/z $[M+H-Boc]^+$ 566.3/568.3, m/z $[M-H]^-$ 664.4/666.4; UPLC-MS 1

Step 2: N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

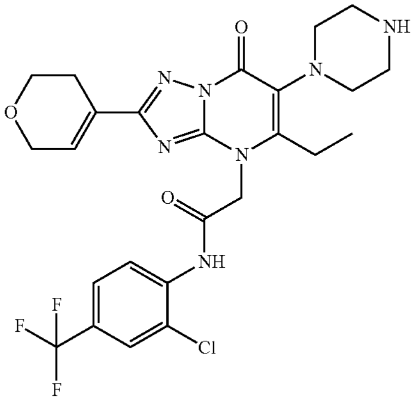

To a solution of tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (4.82 g, 7.24 mmol) in DCM (50 mL) was added TFA (8.36 mL, 109 mmol) and the RM was stirred at RT for 2 hours. The RM was concentrated under reduced pressure. DCM was added and the mixture was extracted with aq $NaHCO_3$, adjusted to pH 10, extracted three times with DCM, dried through a phase separator and concentrated under reduced pressure to give the title compound.

LC-MS: Rt=0.79 min; MS m/z $[M+H]^+$ 566.3/568.3, m/z $[M-H]^-$ 564.4/566.4; UPLC-MS 1

Intermediate BQ: N-(2-chloro-5-fluoro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-5-fluoro-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

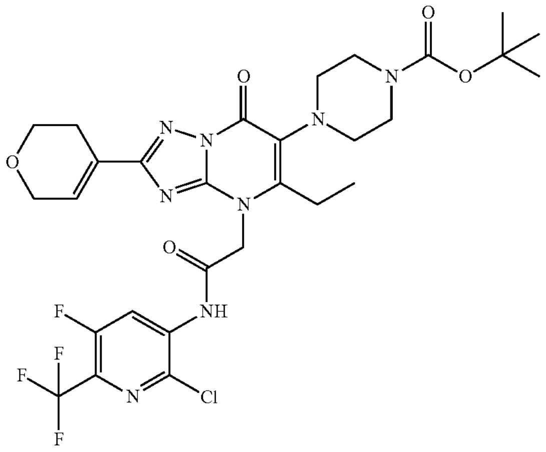

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (500 mg, 1.02 mmol) was dissolved in DCM (10 mL) and $Et_3N$ (851 µL, 6.14 mmol). 2-Chloro-5-fluoro-6-(trifluoromethyl)pyridin-3-amine (Intermediate DE) (263 mg, 1.13 mmol) and $T_3P$ 50% in DMF (1.22 mL, 2.05 mmol) were added and the RM was stirred at RT for 2 hours. The RM was adsorbed onto Isolute and purified by column chromatography (RediSep Column: Silica 80 g, eluent cyclohexane:EtOAc 100:0 to 0:100). The product containing fractions were combined and concentrated to give the title compound.

LC-MS: Rt=1.34 min; MS m/z $[M+H]^+$ 685.3/687.3, m/z $[M-H]^-$ 683.3/685.3; UPLC-MS 1

Step 2: N-(2-chloro-5-fluoro-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

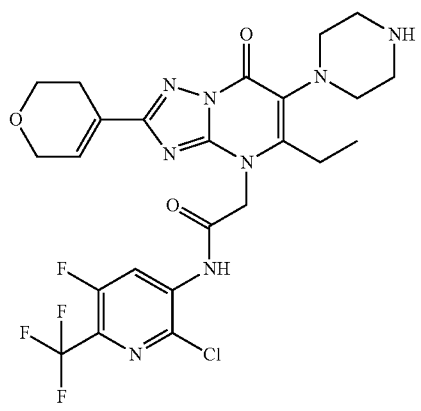

Tert-butyl 4-(4-(2-((2-chloro-5-fluoro-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (470 mg, 617 µmol) was dissolved in DCM (10 mL) and TFA (951 µL, 12.4 mmol) was added. The RM was stirred at RT over the weekend. The RM was adjusted to pH 10 by aq $NaHCO_3$, extracted twice with DCM, dried through a phase separator and concentrated under reduced pressure to give the title compound.

LC-MS: Rt=0.76 min; MS m/z $[M+H]^+$ 585.2/587.2, m/z $[M-H]^-$ 583.3/585.2; UPLC-MS 1

Intermediate BR: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(pentafluorosulfanyl)phenyl)acetamide Step 1: tert-butyl 4-(2-(3,6-dihydro-2H-pyran-4-yl)-5-ethyl-4-(2-((2-methyl-4-(pentafluorosulfanyl)phenyl)amino)-2-oxoethyl)-7-oxo-4,7-dihydro-[1,2,4]triazolo[1,5-a]pyrimidin-6-yl)piperazine-1-carboxylate

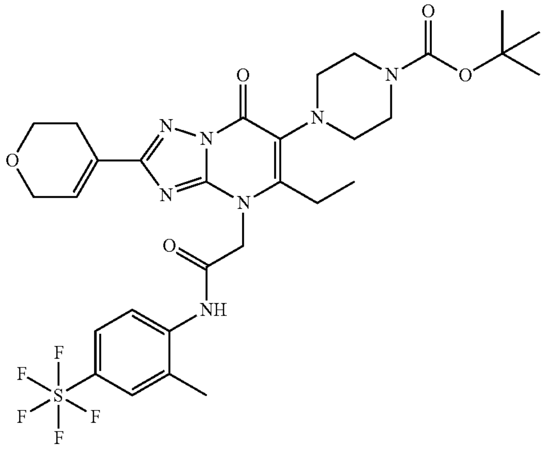 [SMILES: CCc1c(N2CCN(C(=O)OC(C)(C)C)CC2)c(=O)n2nc(C3=CCOCC3)nc2n1CC(=O)Nc1ccc(S(F)(F)(F)(F)F)cc1C]

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (413 mg, 845 µmol) and 2-methyl-4-(pentafluorosulfanyl)aniline (Intermediate DF) (249 mg, 930 µmol) were mixed in DCM (10 mL). $Et_3N$ (703 µL, 5.07 mmol) was added to the suspension and it turned into an orange solution, then $T_3P$ 50% in EtOAc (1.51 mL, 2.54 mmol) was added and the mixture was stirred at RT for 1.5 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=1.32 min; MS m/z $[M+H\text{-}Boc]^+$ 604.4, m/z $[M-H]^-$ 702.5; UPLC-MS 1

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-methyl-4-(pentafluorosulfanyl)phenyl)acetamide

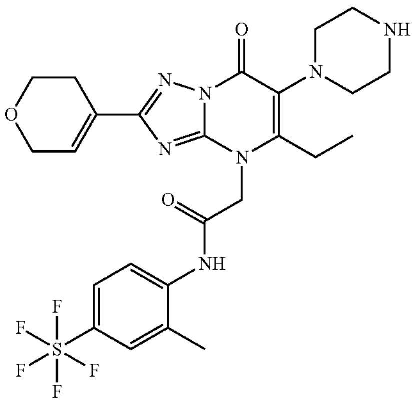

Tert-butyl 4-(2-(3,6-dihydro-2H-pyran-4-yl)-5-ethyl-4-(2-((2-methyl-4-(pentafluorosulfanyl)phenyl)amino)-2-oxoethyl)-7-oxo-4,7-dihydro-[1,2,4]triazolo[1,5-a]pyrimidin-6-yl)piperazine-1-carboxylate (748 mg, 913 µmol) was dissolved in DCM (5 mL) and TFA (500 µL, 6.49 mmol) was added. The mixture was stirred at 40° C. for 4 hours, then at RT overnight. The mixture was concentrated under reduced pressure. The crude product was purified by reverse phase preparative ISCO (RediSep Column: C18 130 g, eluent water+0.1% TFA:ACN 100:0 to 0:100). The product containing fractions were combined, basified with aq sat $NaHCO_3$, extracted twice with DCM, dried through a phase separator and concentrated under reduced pressure to give the title compound.

LC-MS: Rt=0.89 min; MS m/z $[M+H]^+$ 604.3, m/z $[M-H]^-$ 602.2; UPLC-MS 1

Intermediate BS: N-(2,4-dichlorophenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2,4-dichlorophenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

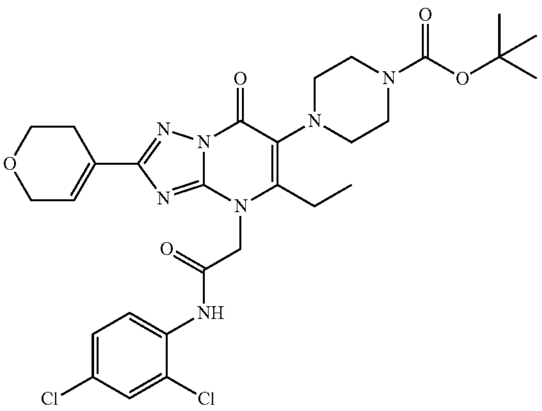

To a solution of 2-(6-(4-(tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (200 mg, 409 µmol) and 2,4-dichloroaniline (73.7 mg, 450 µmol) in DMF (2 mL) were added $Et_3N$ (170 µL, 1.23 mmol) and $T_3P$ 50% in DMF (487 µL, 819 µmol). The resulting brown solution was stirred at RT for 18 hours. The brown RM was diluted with DCM and extracted once with water. The aqueous layer was extracted twice with DCM and twice with DCM/MeOH. The combined organic layers were dried through a phase separator, concentrated under reduced pressure and dried. The crude product was purified by column chromatography (RediSep Column: Silica 12 g, eluent DCM:DCM/MeOH (9/1) 100:0 to 60:40). The product containing fractions were combined and concentrated under reduced pressure to give the title compound.

LC-MS: Rt=1.29 min; MS m/z $[M+H\text{-}Boc]^+$532.2/534.2, m/z $[M-H]^-$ 630.5/632.5; UPLC-MS 6

Step 2: N-(2,4-dichlorophenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

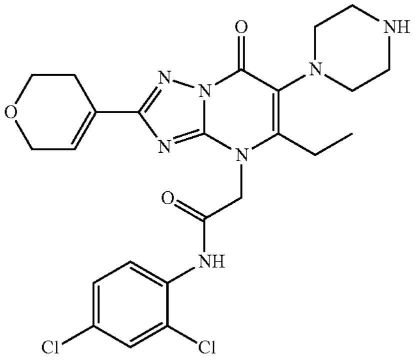

To a solution of tert-butyl 4-(4-(2-((2,4-dichlorophenyl) amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (220 mg, 313 μmol) in DCM (536 μL) was added TFA (536 μL, 6.96 mmol). The brown solution was stirred at RT for 70 minutes. The RM was concentrated under reduced pressure and dried under vacuum to give the title compound as the trifluoroacetate salt.

LC-MS: Rt=0.79 min; MS m/z $[M+H]^+$ 532.3/534.3, m/z $[M-H]^-$ 530.3/532.3; UPLC-MS 3

Intermediate BT: N-(5-chloro-2-methyl-6-(trifluoromethyl)pyridin-3-yl)-2-(2-(3,6-dihydro-2H-pyran-4-yl)-5-ethyl-7-oxo-6-(piperazin-1-yl)-[1,2,4]triazolo [1,5-a]pyrimidin-4 (7H)-yl)acetamide Step 1: tert-butyl 4-(4-(2-((5-chloro-2-methyl-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl) piperazine-1-carboxylate

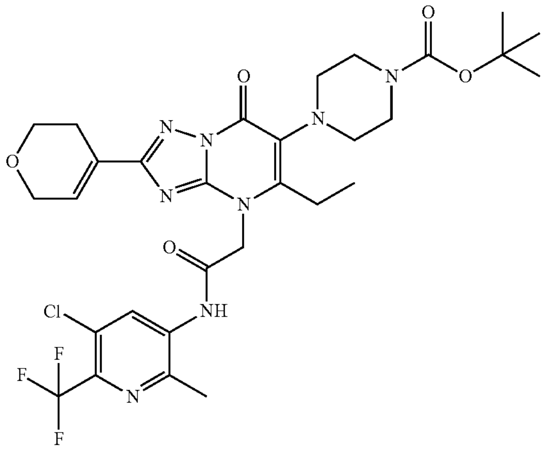

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a] pyrimidin-4 (7H)-yl)acetic acid (Intermediate BO) (300 mg, 614 μmol) and 5-chloro-2-methyl-6-(trifluoromethyl)pyridin-3-amine (Intermediate DG) (136 mg, 645 μmol) were mixed in EtOAc (4.2 mL). $Et_3N$ (340 μL, 2.46 mmol) and $T_3P$ 50% in EtOAc (731 μL, 1.23 mmol) were added and the RM was stirred at RT for 2.5 hours. The RM was quenched with water (5 mL) and it was extracted with EtOAc (3×50 mL), water (10 mL) and brine (10 mL). The organic layer was dried through a phase separator and concentrated under reduced pressure. The crude product was adsorbed onto Isolute and purified by column chromatography (RediSep Column: Silica 40 g, eluent DCM:MeOH 100:0 to 95:5). The product containing fractions were combined and concentrated to give the title compound as a beige solid.

LC-MS: Rt=1.17 min; MS m/z $[M+H-Boc]^+$581.4/583.4, m/z $[M-H]^-$ 679.3/681.3; UPLC-MS 3

Step 2: N-(5-chloro-2-methyl-6-(trifluoromethyl) pyridin-3-yl)-2-(2-(3,6-dihydro-2H-pyran-4-yl)-5-ethyl-7-oxo-6-(piperazin-1-yl)-[1,2,4]triazolo[1,5-a] pyrimidin-4 (7H)-yl)acetamide

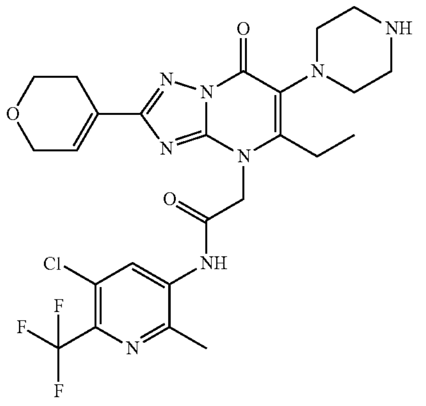

Tert-butyl 4-(4-(2-((5-chloro-2-methyl-6-(trifluoromethyl)pyridin-3-yl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (336 mg, 493 μmol) was dissolved in DCM (3.3 mL) and TFA (570 μL, 7.40 mmol) was added. The RM was stirred at RT for 1.25 hours, then it was concentrated under reduced pressure. Traces of TFA were removed by azeotroping with DCM and toluene to give the title compound trifluoroacetate salt as a pale brown solid.

LC-MS: Rt=0.88 min; MS m/z $[M+H]^+$ 581.4/583.4, m/z $[M-H]^-$ 579.3/581.2; UPLC-MS 3

Intermediate BU: N-(4-chloro-2-methyl-5-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((4-chloro-2-methyl-5-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

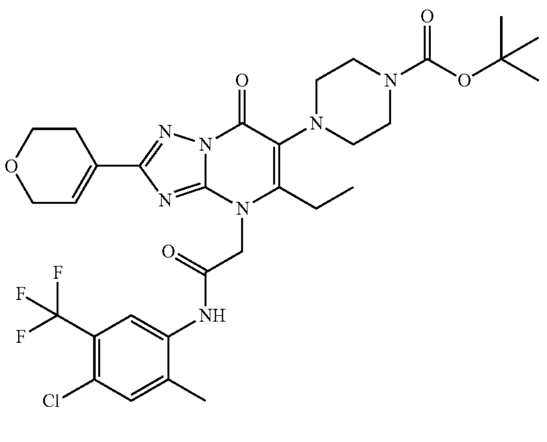 [SMILES: CCc1c(N2CCN(C(=O)OC(C)(C)C)CC2)c(=O)n2nc(C3=CCOCC3)nc2n1CC(=O)Nc1cc(C(F)(F)F)c(Cl)cc1C]

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (200 mg, 409 μmol) and 4-chloro-2-methyl-5-(trifluoromethyl)aniline (90.0 mg, 430 μmol) were mixed in EtOAc (2.7 mL). $Et_3N$ (227 μL, 1.64 mmol) and $T_3P$ 50% in EtOAc (487 μL, 819 μmol) were added. The RM was stirred at RT for 1.25 hours, then it was quenched with water (5 mL). The RM was extracted with EtOAc (3×30 mL) then DCM (3×25 ml). The combined organic layers were washed sequentially with aq sat $NaHCO_3$ (5 mL), water (10 mL) and brine (2×5 mL). The organic layer was dried through a phase separator and concentrated under reduced pressure. The crude product was purified by reverse phase preparative HPLC (RP-HPLC acidic 1: 30 to 90% B in 20 min with a plateau at 90% for 1 min). The product containing fractions were combined and lyophilized to give the title compound as a white solid.

LC-MS: Rt=1.18 min; MS m/z $[M+H-Boc]^+$ 580.3/582.3, m/z $[M-H]^-$ 678.3/680.3; UPLC-MS 3

Step 2: N-(4-chloro-2-methyl-5-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

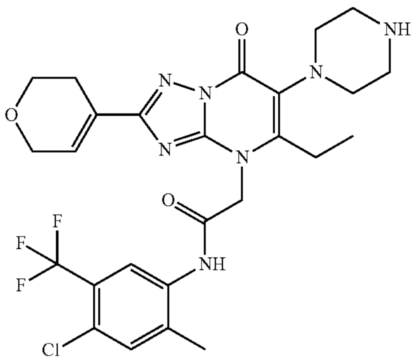 [SMILES: CCc1c(N2CCNCC2)c(=O)n2nc(C3=CCOCC3)nc2n1CC(=O)Nc1cc(C(F)(F)F)c(Cl)cc1C]

Tert-butyl 4-(4-(2-((4-chloro-2-methyl-5-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (192 mg, 282 μmol) was dissolved in DCM (2 mL) and TFA (326 μL, 4.23 mmol) was added. The RM was stirred at RT for 1.25 hours, then it was concentrated under reduced pressure. Traces of TFA were removed by azeotroping with DCM and toluene then it was dried under HV to give the title compound trifluoroacetate salt as a beige solid.

LC-MS: Rt=0.79 min; MS m/z $[M+H]^+$ 580.3/582.2, m/z $[M-H]^-$ 578.5/580.5; UPLC-MS 6

The free base of intermediate BU can be prepared by partitioning the TFA salt between dichloromethane and saturated aqueous $NaHCO_3$, followed by separation and drying of the organic layer.

Intermediate BV: N-(5-chloro-4-ethyl-2-methylphenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((4-bromo-5-chloro-2-methylphenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

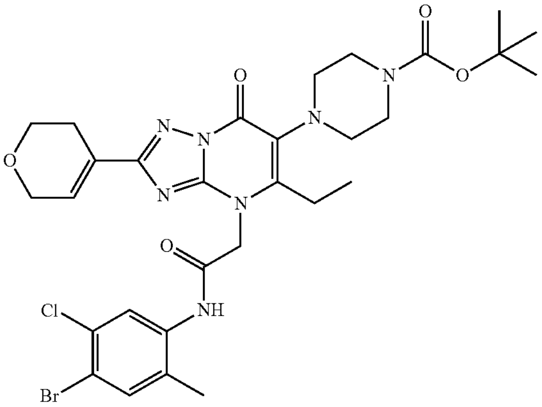 [SMILES: CCc1c(N2CCN(C(=O)OC(C)(C)C)CC2)c(=O)n2nc(C3=CCOCC3)nc2n1CC(=O)Nc1cc(Cl)c(Br)cc1C]

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (1.00 g, 2.05 mmol) and 4-bromo-5-chloro-2-methylaniline (515 mg, 2.34 mmol) were suspended in EtOAc (10 mL). Then $Et_3N$ (1.14 mL, 8.79 mmol) was added, followed by $T_3P$ 50% in EtOAc (2.44 mL, 4.09 mmol). The suspension became a solution and it was stirred at RT for 1 hour. Water (10 mL), aq sat $NaHCO_3$ (10 mL) and EtOAc (10 mL) were added. The aqueous layer was extracted with EtOAc (2×10 mL). The combined organic layers were dried through a phase separator and concentrated under reduced pressure. The crude product was suspended in DCM and $Et_2O$. The mixture was sonicated for 2 minutes and filtered. The cake was washed with DCM and $Et_2O$. The cake was dried under HV to give cake 1. The filtrate was concentrated under reduced pressure. The residue was suspended in MeOH and sonicated for 2 minutes and filtered. The cake was washed with $Et_2O$. The cake was dried under HV to give cake 2. The filtrate was purified by column chromatography (RediSep Column: Silica 40 g, eluent DCM:DCM/MeOH (9/1) 100:0 to 80:20). The product containing fractions were combined, concentrated under vacuum and dried under HV to afford a yellow solid. The yellow solid was purified by reverse phase preparative HPLC (RP-HPLC acidic 1: 5 to 100% B in 20 min). The product containing fractions were combined, basified with aq sat $NaHCO_3$, extracted twice with DCM, dried through a phase separator, concentrated under reduced pressure and combined with the cake 1 and cake 2 to give the title compound.

LC-MS: Rt=1.19 min; MS m/z $[M+H-Boc]^+$590.3/592.3/594.3, m/z $[M-H]^-$ 688.4/690.3/692.4; UPLC-MS 3

Step 2: tert-butyl 4-(4-(2-((5-chloro-4-ethyl-2-methylphenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

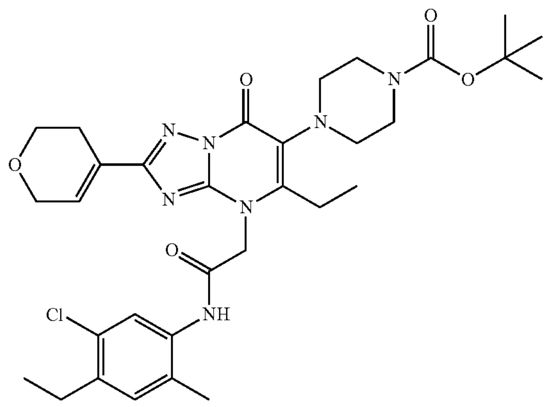 [SMILES: CCc1cc(C)c(NC(=O)Cn2c(CC)c(N3CCN(C(=O)OC(C)(C)C)CC3)c(=O)n3nc(C4=CCOCC4)nc23)cc1Cl]

Tert-butyl 4-(4-(2-((4-bromo-5-chloro-2-methylphenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (908 mg, 1.25 mmol), potassium ethyltrifluoroborate (305 mg, 2.25 mmol), $Pd(OAc)_2$ (14.0 mg, 62.0 μmol), $Cs_2CO_3$ (1.22 g, 3.74 mmol) and RuPhos (58.2 mg, 125 μmol) were mixed in toluene (9.3 mL) and water (3.1 mL) and stirred at 100° C. for 6 hours. Then it was allowed to cool to RT overnight. Water (10 mL), aq sat $NaHCO_3$ (10 mL) and DCM (10 mL) were added. The aqueous layer was extracted with DCM (2×10 mL). The combined organic layers were dried through a phase separator and concentrated under reduced pressure. The crude product was dissolved in DCM and MeOH and SiliaMetS® Thiol was added. The mixture was stirred at 40° C. for 1 hour and filtered. The cake was washed with DCM. The filtrate was concentrated under reduced pressure. The crude product was purified by column chromatography (RediSep Column: Silica 40 g, eluent DCM:DCM/MeOH (9/1) 100:0 to 80:20). The product containing fractions were combined, concentrated under vacuum and dried under HV to afford a pale beige solid, which was further purified by SFC (SFC 1). The product containing fractions were combined and concentrated to give the title compound.

LC-MS: Rt=1.20 min; MS m/z $[M+H-Boc]^+$540.4/542.4, m/z $[M-H]^-$ 638.4/640.4; UPLC-MS 3

Step 3: N-(5-chloro-4-ethyl-2-methylphenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide

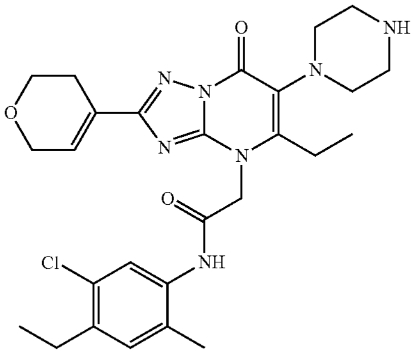 [SMILES: CCc1cc(C)c(NC(=O)Cn2c(CC)c(N3CCNCC3)c(=O)n3nc(C4=CCOCC4)nc23)cc1Cl]

Tert-butyl 4-(4-(2-((5-chloro-4-ethyl-2-methylphenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (510 mg, 797 μmol) was dissolved in DCM (5 mL) and TFA (300 μL, 3.89 mmol) was added. The mixture was stirred at 40° C. for 6 hours, left to stand at RT for 18 hours, then reheated to 40° C. and stirred for a further 6 hours. The mixture was concentrated under reduced pressure. Water (20 mL), aq sat $NaHCO_3$ (20 mL) and DCM (20 mL) were added. The aqueous layer was extracted with DCM (2×20 mL). The combined organic layers were dried through a phase separator and concentrated under reduced pressure to give the title compound.

LC-MS: Rt=0.89 min; MS m/z $[M+H]^+$ 540.4/542.4, m/z $[M-H]^-$ 538.3/540.3; UPLC-MS 3

Intermediate BW: N-(4-chloro-2-methylphenyl)-2-(2-(3,6-dihydro-2H-pyran-4-yl)-5-methyl-7-oxo-6-(piperazin-1-yl)-[1,2,4]triazolo[1,5-a]pyrimidin-4 (7H)-yl)acetamide Step 1: tert-butyl 4-(2-bromo-4-(2-(tert-butoxy)-2-oxoethyl)-5-methyl-7-oxo-4,7-dihydro-[1,2,4]triazolo[1,5-a]pyrimidin-6-yl)piperazine-1-carboxylate

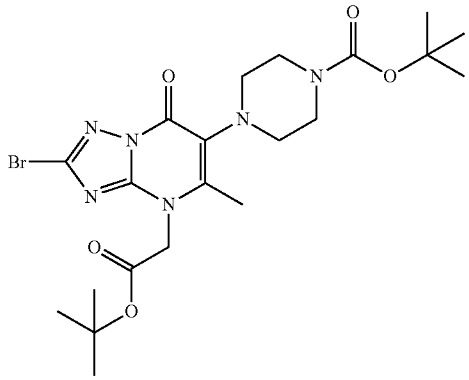 [SMILES: Cc1c(N2CCN(C(=O)OC(C)(C)C)CC2)c(=O)n2nc(Br)nc2n1CC(=O)OC(C)(C)C]

Tert-butyl 4-(2-bromo-5-methyl-7-oxo-4,7-dihydro-[1,2,4]triazolo[1,5-a]pyrimidin-6-yl)piperazine-1-carboxylate (Intermediate BM) (15.0 g, 36.3 mmol) was mixed with DMF (60.5 mL). Tert-butyl 2-bromoacetate (7.59 g, 38.1 mmol) and $K_2CO_3$ (10.0 g, 72.6 mmol) were added. The RM was stirred at 65° C. for 3.3 hours, then it was cooled to RT. Water (80 mL) was added and the suspension was stirred at RT for 30 minutes. The RM was cooled with an ice bath and continued stirring for 2 hours. The suspension was filtered and washed with water. The cake was dried under HV to give the title compound as a beige solid.

LC-MS: Rt=1.13 min; MS m/z $[M+H]^+$ 527.1/529.1, m/z $[M-H]^-$ 525.0/527.0; UPLC-MS 4

Step 2: tert-butyl 4-(4-(2-(tert-butoxy)-2-oxoethyl)-2-(3,6-dihydro-2H-pyran-4-yl)-5-methyl-7-oxo-4,7-dihydro-[1,2,4]triazolo[1,5-a]pyrimidin-6-yl)piperazine-1-carboxylate

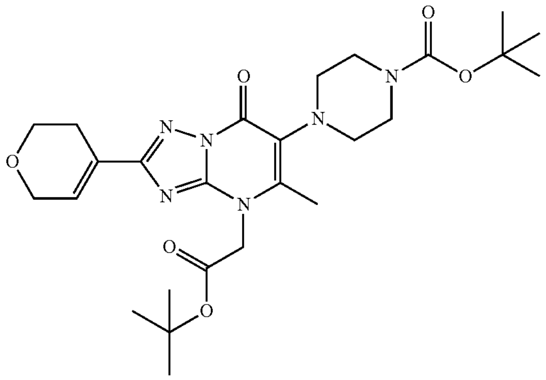 [SMILES: Cc1c(N2CCN(C(=O)OC(C)(C)C)CC2)c(=O)n2nc(C3=CCOCC3)nc2n1CC(=O)OC(C)(C)C]

Tert-butyl 4-(2-bromo-4-(2-(tert-butoxy)-2-oxoethyl)-5-methyl-7-oxo-4,7-dihydro-[1,2,4]triazolo[1,5-a]pyrimidin-6-yl)piperazine-1-carboxylate (2.00 g, 3.79 mmol), 2-(3,6-dihydro-2H-pyran-4-yl)-4,4,5,5-tetramethyl-1,3,2-dioxaborolane (2.00 g, 9.52 mmol) and XPhos Pd G3 (160 mg, 190 μmol) were mixed in 1,4-dioxane (10 mL) and $K_3PO_4$ 1M in water (9.48 mL, 9.48 mmol) was added. The mixture was stirred at 80° C. for 1 hour. Water, aq sat $NaHCO_3$ and DCM were added. The aqueous layer were extracted twice with DCM. The combined organic layers were dried through a phase separator and concentrated under reduced pressure. The crude product was dissolved in DCM and SiliaMetS® Thiol was added. The mixture was stirred at 40° C. for 1 hour and filtered. The cake was washed with DCM. The filtrate was concentrated under reduced pressure. The crude product was purified by column chromatography (RediSep Column: Silica 80 g, eluent DCM:DCM/MeOH (9/1) 100:0 to 50:50). The product containing fractions were combined and concentrated to give the title compound as a yellow oil.

LC-MS: Rt=1.10 min; MS m/z $[M+H]^+$ 531.3; UPLC-MS 4

Step 3: 2-(6-(4-(tert-butoxycarbonyl)piperazin-1-yl)-2-(3,6-dihydro-2H-pyran-4-yl)-5-methyl-7-oxo-[1,2,4]triazolo[1,5-a]pyrimidin-4 (7H)-yl)acetic acid

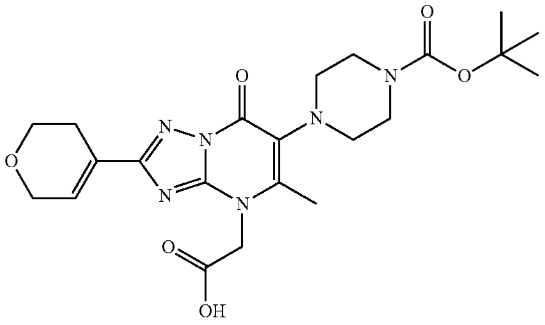 [SMILES: Cc1c(N2CCN(C(=O)OC(C)(C)C)CC2)c(=O)n2nc(C3=CCOCC3)nc2n1CC(=O)O]

Tert-butyl 4-(4-(2-(tert-butoxy)-2-oxoethyl)-2-(3,6-dihydro-2H-pyran-4-yl)-5-methyl-7-oxo-4,7-dihydro-[1,2,4]triazolo[1,5-a]pyrimidin-6-yl)piperazine-1-carboxylate (1.98 g, 3.62 mmol) was dissolved in THF (15 mL) and NaOH 1M in water (5.43 mL, 5.43 mmol) was added. The mixture was stirred at RT for 27 hours. Water and DCM were added. The aqueous layer was washed twice with DCM. The combined organic layers were dried through a phase separator and concentrated under reduced pressure. Then 1M HCl was added to the aqueous layer and it was extracted three times with DCM. The combined organic layers were dried through a phase separator and concentrated under reduced pressure to give the title compound.

LC-MS: Rt=0.79 min; MS m/z $[M+H-Boc]^+$ 375.3, m/z $[M-H]^-$ 473.4; UPLC-MS 3

Step 4: tert-butyl 4-(4-(2-((4-chloro-2-methylphenyl)amino)-2-oxoethyl)-2-(3,6-dihydro-2H-pyran-4-yl)-5-methyl-7-oxo-4,7-dihydro-[1,2,4]triazolo[1,5-a]pyrimidin-6-yl)piperazine-1-carboxylate

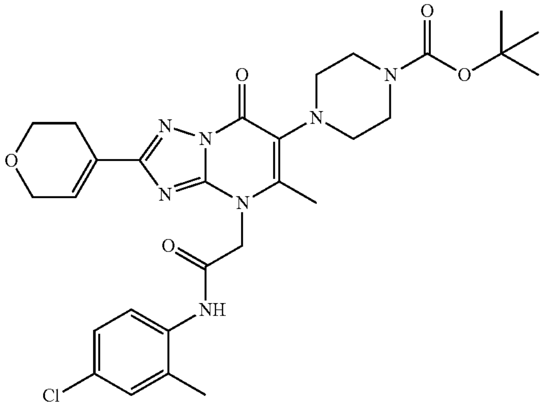 [SMILES: Cc1cc(Cl)ccc1NC(=O)Cn1c(C)c(N2CCN(C(=O)OC(C)(C)C)CC2)c(=O)n2nc(C3=CCOCC3)nc12]

2-(6-(4-(Tert-butoxycarbonyl)piperazin-1-yl)-2-(3,6-dihydro-2H-pyran-4-yl)-5-methyl-7-oxo-[1,2,4]triazolo[1,5-a]pyrimidin-4 (7H)-yl)acetic acid (550 mg, 1.16 mmol) and 4-chloro-2-methylaniline (181 mg, 1.28 mmol) were suspended in EtOAc (5 mL). Then $T_3P$ 50% in EtOAc (2.76 mL, 4.64 mmol) was added, followed by $Et_3N$ (964 μL, 6.95 mmol). The yellow solution was stirred at RT for 30 minutes. Water, aq sat $NaHCO_3$ and EtOAc were added. The aqueous layer were extracted twice with EtOAc. The combined organic layers was dried through a phase separator and concentrated under reduced pressure to give the title compound.

LC-MS: Rt=1.11 min; MS m/z $[M+H-Boc]^+$498.3/500.3, m/z $[M-H]^-$ 596.4/598.3; UPLC-MS 4

Step 5: N-(4-chloro-2-methylphenyl)-2-(2-(3,6-dihydro-2H-pyran-4-yl)-5-methyl-7-oxo-6-(piperazin-1-yl)-[1,2,4]triazolo[1,5-a]pyrimidin-4 (7H)-yl)acetamide

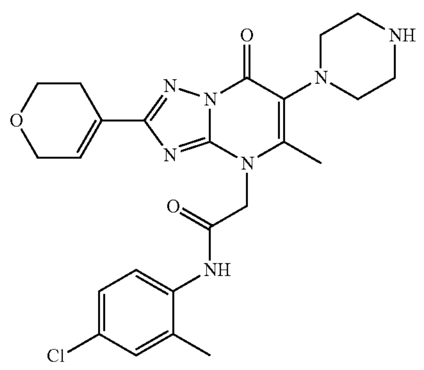 [SMILES: Cc1cc(Cl)ccc1NC(=O)Cn1c(C)c(N2CCNCC2)c(=O)n2nc(C3=CCOCC3)nc12]

Tert-butyl 4-(4-(2-((4-chloro-2-methylphenyl)amino)-2-oxoethyl)-2-(3,6-dihydro-2H-pyran-4-yl)-5-methyl-7-oxo-4,7-dihydro-[1,2,4]triazolo[1,5-a]pyrimidin-6-yl)piperazine-1-carboxylate (1.02 g, 1.51 mmol) was suspended in DCM (5 mL) and TFA (1.00 mL, 13.0 mmol) was added. The mixture was stirred at RT for 24 hours. Water, aq sat $NaHCO_3$ and DCM were added. The aqueous layer was extracted twice with DCM. The combined organic layers were dried through a phase separator and concentrated under reduced pressure. The crude product was dissolved in MeOH and DMF then stood at RT in an open flask for 3 hours. The resulting precipitate was filtered. The cake was washed with MeOH and dried under HV to give the title compound. The filtrate was concentrated under reduced pressure to give the title compound.

LC-MS: Rt=0.78 min; MS m/z $[M+H]^+$ 498.3/500.3, m/z $[M-H]^-$ 496.3/498.3; UPLC-MS 4

Scheme 6 general overview of intermediates of route V

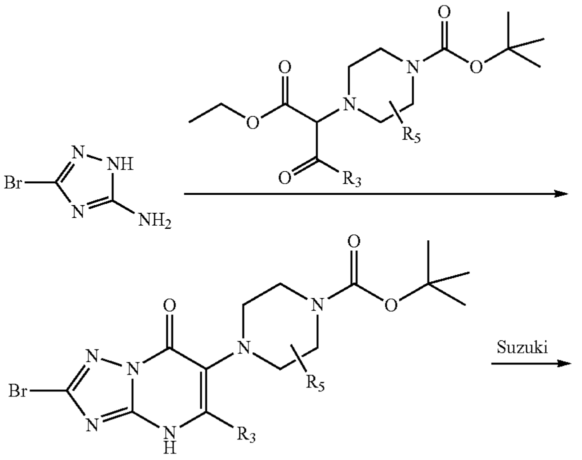

-continued

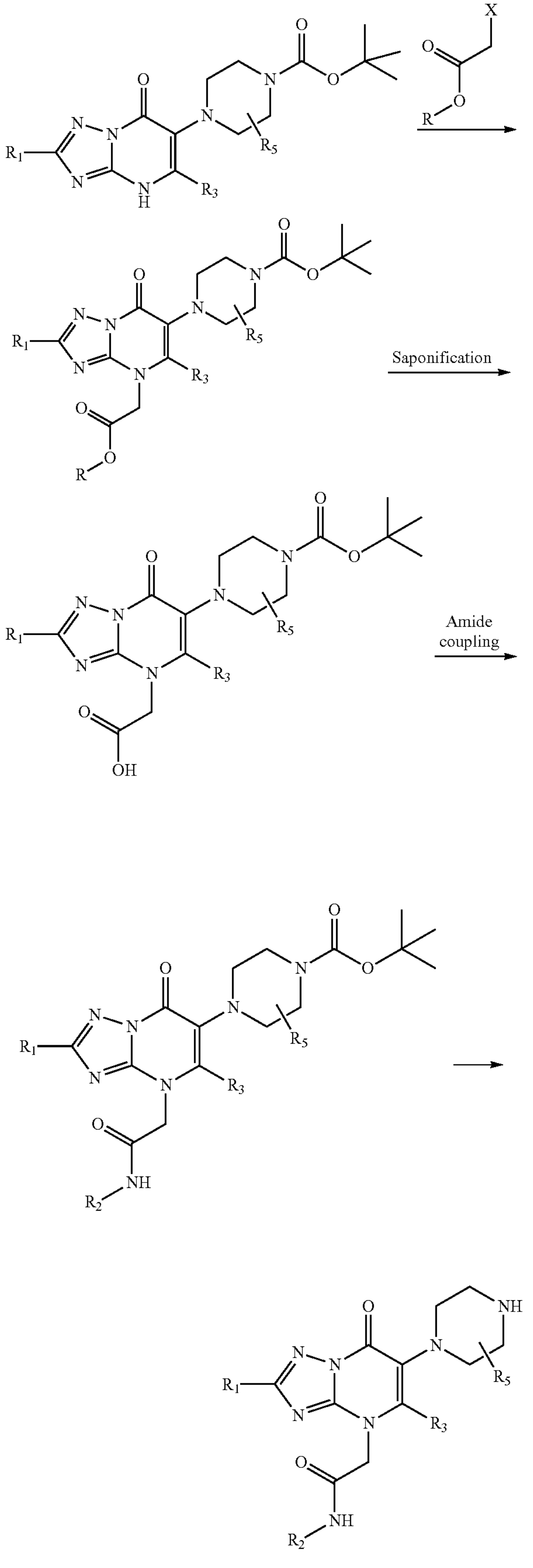

Intermediate BO: 2-(6-(4-(tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl) acetic acid Step 1: tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

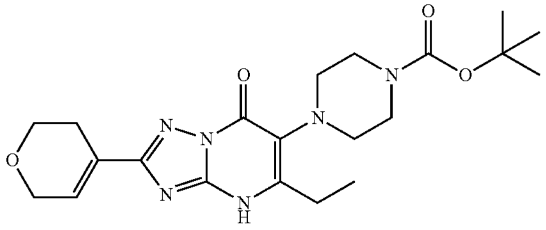 [SMILES: CCc1[nH]c2nc(C3=CCOCC3)nn2c(=O)c1N1CCN(C(=O)OC(C)(C)C)CC1]

See Intermediate AF.

Step 2: tert-butyl 4-(4-(2-(tert-butoxy)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

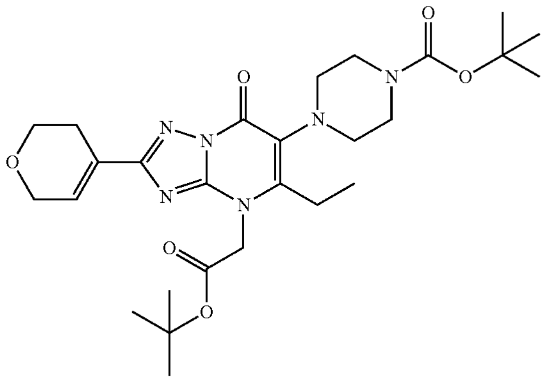 [SMILES: CCc1c(N2CCN(C(=O)OC(C)(C)C)CC2)c(=O)n2nc(C3=CCOCC3)nc2n1CC(=O)OC(C)(C)C]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (3.00 g, 6.97 mol) and tert-butyl 2-bromoacetate (1.46 g, 7.32 mmol) were mixed in DMF (20 mL) under argon. DIPEA (3.65 mL, 20.9 mmol) was added and the RM was stirred at 55° C. for 4.5 hours. Water (50 mL) was added and the RM was stirred at RT overnight. The suspension was sonicated for 10 minutes, filtered and washed with water. The cake was dried under HV, mixed with $Et_2O$ and sonicated for 5 minutes. The suspension was stirred at reflux, filtered and the solid washed with $Et_2O$. A second crop of solid precipitates from the filtrate which was filtered. Both cakes were combined to give the title compound as a beige solid.

LC-MS: Rt=1.16 min; MS m/z $[M+H-Boc]^+$ 445.4, UPLC-MS 1

Step 3: 2-(6-(4-(tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid

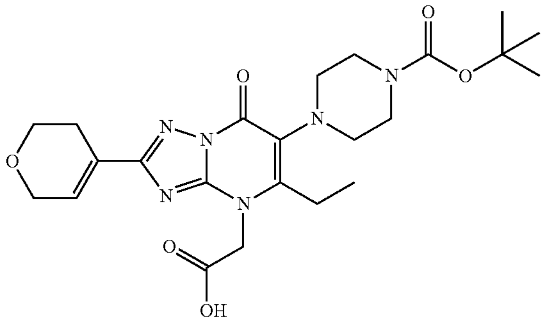 [SMILES: CCc1c(N2CCN(C(=O)OC(C)(C)C)CC2)c(=O)n2nc(C3=CCOCC3)nc2n1CC(=O)O]

Tert-butyl 4-(4-(2-(tert-butoxy)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (2.75 g, 5.00 mmol) was dissolved in THF (50 mL) and MeOH (20 mL). 1M NaOH (7.50 mL, 7.50 mmol) was added and the RM was stirred at RT for 18.5 hours. The solvent was removed, water was added and the RM was extracted with $Et_2O$ (3×70 mL) and water (3×15 mL). The aqueous layer was cooled to 0° C. and 4M HCl (1.87 mL, 7.50 mmol) was added until pH 3. The resulting suspension was extracted with EtOAc (3×200 mL) and twice with brine, then twice with EtOAc. The combined organic layers were eluted through a phase separator and concentrated under reduced pressure to give the title compound as a bright brown solid.

LC-MS: Rt=0.76 min; MS m/z $[M+H-Boc]^+$ 389.5, m/z $[M-H]^-$ 487.2; UPLC-MS 1

Intermediate BX: N-(4-bromo-2-chlorophenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl) acetamide Step 1: tert-butyl 4-(4-(2-((4-bromo-2-chlorophenyl) amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

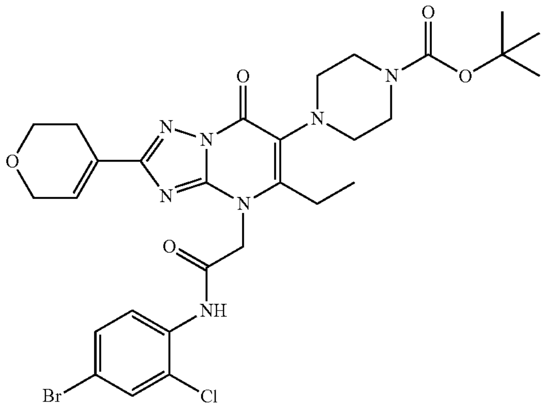 [SMILES: CCc1c(N2CCN(C(=O)OC(C)(C)C)CC2)c(=O)n2nc(C3=CCOCC3)nc2n1CC(=O)Nc1ccc(Br)cc1Cl]

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (250 mg, 512 μmol) and 4-bromo-2-chloroaniline (107 mg, 512 μmol) were mixed with EtOAc (3.6 mL). $Et_3N$ (355 μL, 2.56 mmol) and $T_3P$ 50% in DMF (609 μL, 1.02 mmol) were added and the RM was stirred at RT for 3 hours. The RM was extracted with EtOAc (3×40 mL), water (2×15 mL) and brine (2×10 mL). The combined organic layers were eluted through a phase separator and concentrated under reduced pressure. The crude product was adsorbed onto Isolute and purified by column chromatography (RediSep Column: Silica 40 g, eluent DCM:DCM/MeOH (8/2) 100:0 to 80:20). The product containing fractions were combined and concentrated to give the title compound as a white solid.

LC-MS: Rt=1.27 min; MS m/z $[M+H-Boc]^+$ 576.2/578.2/580.2, m/z $[M-H]^-$ 674.3/676.3/678.3; UPLC-MS 1

Step 2: N-(4-bromo-2-chlorophenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

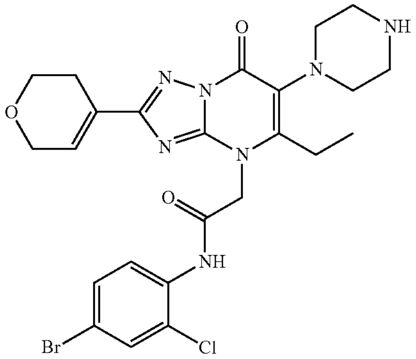 [SMILES: CCc1c(N2CCNCC2)c(=O)n2nc(C3=CCOCC3)nc2n1CC(=O)Nc1ccc(Br)cc1Cl]

Tert-butyl 4-(4-(2-((4-bromo-2-chlorophenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (265 mg, 391 μmol) was dissolved in DCM (2.6 mL) and TFA (603 μL, 7.83 mmol) was added. The RM was stirred at RT for 1 hour, concentrated under reduced pressure. Residual TFA was removed by azeotoping with DCM under reduced pressure to give the title compound trifluoroacetate salt as a white solid.

LC-MS: Rt=0.69 min; MS m/z $[M+H]^+$ 576.1/578.1/580.2, m/z $[M-H]^-$ 574.1/576.1/578.1; UPLC-MS 1

Intermediate BP: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide Step 1: tert-butyl 4-(2-(3,6-dihydro-2H-pyran-4-yl)-5-ethyl-4-(2-((2-fluoro-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

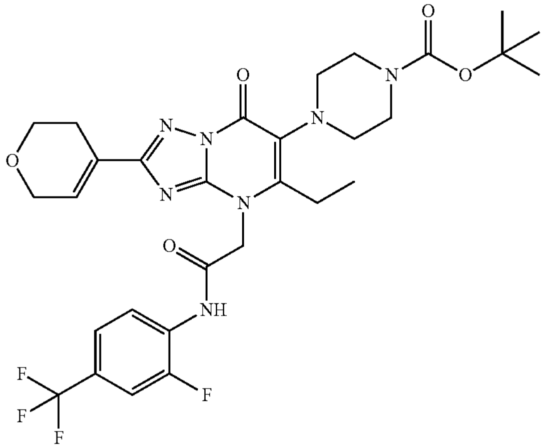 [SMILES: CCc1c(N2CCN(C(=O)OC(C)(C)C)CC2)c(=O)n2nc(C3=CCOCC3)nc2n1CC(=O)Nc1ccc(C(F)(F)F)cc1F]

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (250 mg, 512 μmol) and 2-fluoro-4-(trifluoromethyl)aniline (94.0 mg, 512 μmol) were mixed with EtOAc (3.6 mL). $Et_3N$ (355 μL, 2.56 mmol) and $T_3P$ 50% in DMF (609 μL, 1.02 mmol) were added and the RM was stirred at RT for 2.5 hours. The RM was extracted with EtOAc (3×40 mL), water (2×15 mL) and brine (2×10 mL). The combined organic layers were eluted through a phase separator and concentrated under reduced pressure. The crude product was adsorbed onto Isolute and purified by column chromatography (RediSep Column: Silica 40 g, eluent DCM:DCM/MeOH (8/2) 100:0 to 70:30). The product containing fractions were combined and concentrated to give the title compound as a white solid.

LC-MS: Rt=1.28 min; MS m/z $[M+H-Boc]^+$ 550.3, m/z $[M-H]^-$ 648.3; UPLC-MS 1

Step 2: 2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)-N-(2-fluoro-4-(trifluoromethyl)phenyl)acetamide

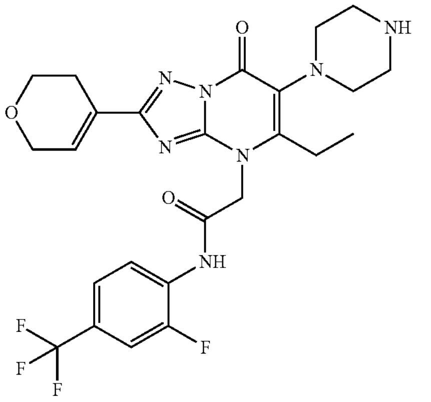 [SMILES: CCc1c(N2CCNCC2)c(=O)n2nc(C3=CCOCC3)nc2n1CC(=O)Nc1ccc(C(F)(F)F)cc1F]

Tert-butyl 4-(2-(3,6-dihydro-2H-pyran-4-yl)-5-ethyl-4-(2-((2-fluoro-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (237 mg, 365 μmol) was dissolved in DCM (2.5 mL) and TFA (562 μL, 7.30 mmol) was added. The RM was stirred at RT for 1 hour, concentrated under reduced pressure. Residual TFA was removed by azeotroping with DCM twice under reduced pressure to give the title compound trifluoroacetate salt as a beige foam.

LC-MS: Rt=0.76 min; MS m/z $[M+H]^+$ 550.3, m/z $[M-H]^-$ 548.3; UPLC-MS 1

Intermediate BY: N-(2-bromo-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-bromo-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

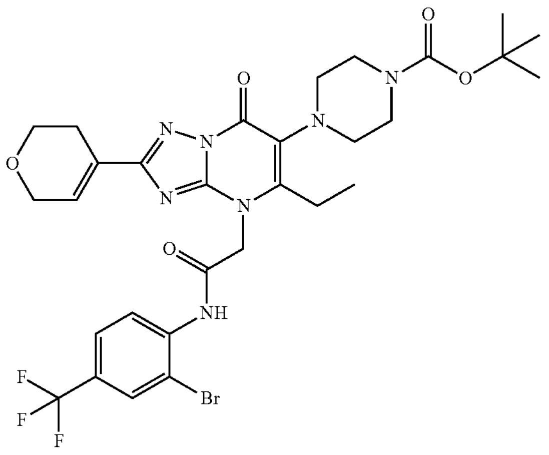

2-(6-(4-(Tert-butoxycarbonyl)piperazin-1-yl)-2-(3,6-dihydro-2H-pyran-4-yl)-5-ethyl-7-oxo-[1,2,4]triazolo[1,5-a]pyrimidin-4 (7H)-yl)acetic acid (Intermediate BO) (250 mg, 512 μmol) and 2-bromo-4-(trifluoromethyl)aniline (123 mg, 512 μmol) were mixed in EtOAc (3.6 mL). $Et_3N$ (355 μL, 2.56 mmol) and $T_3P$ 50% in DMF (609 μL, 1.02 mmol) were added and the RM was stirred at RT for 1.5 hours. The RM was extracted with EtOAc (3×40 mL), water (2×15 mL) and brine (2×10 mL). The organic layers were eluted through a phase separator and concentrated under reduced pressure. The crude product was placed onto Isolute and purified by column chromatography (RediSep Column: Silica 40 g, eluent DCM:DCM/MeOH (8/2) 100:0 to 70:30). The product containing fractions were combined and concentrated to give the title compound as a white solid.

LC-MS: Rt=1.31 min; MS m/z $[M+H-Boc]^+$ 610.2/612.2, m/z $[M-H]^-$ 708.3/710.3; UPLC-MS 1

Step 2: N-(2-bromo-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

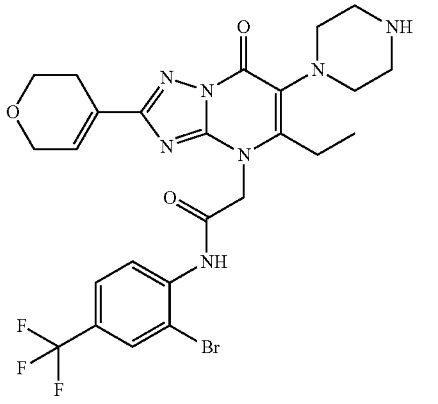

Tert-butyl 4-(4-(2-((2-bromo-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (258 mg, 363 μmol) was dissolved in DCM (2.5 mL) and TFA (559 μL, 7.26 mmol) was added. The RM was stirred at RT for 1 hour, then it was concentrated under reduced pressure. Residual TFA was removed by azeotroping with DCM under reduced pressure to give the title compound trifluoroacetate salt as a beige foam.

LC-MS: Rt=0.78 min; MS m/z $[M+H]^+$ 610.3/612.3, m/z $[M-H]^-$ 608.0/610.0; UPLC-MS 1

Scheme 7 general overview of compounds of route VI

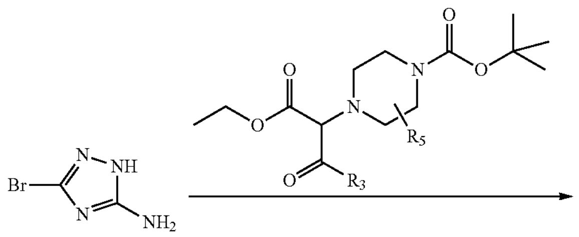

-continued

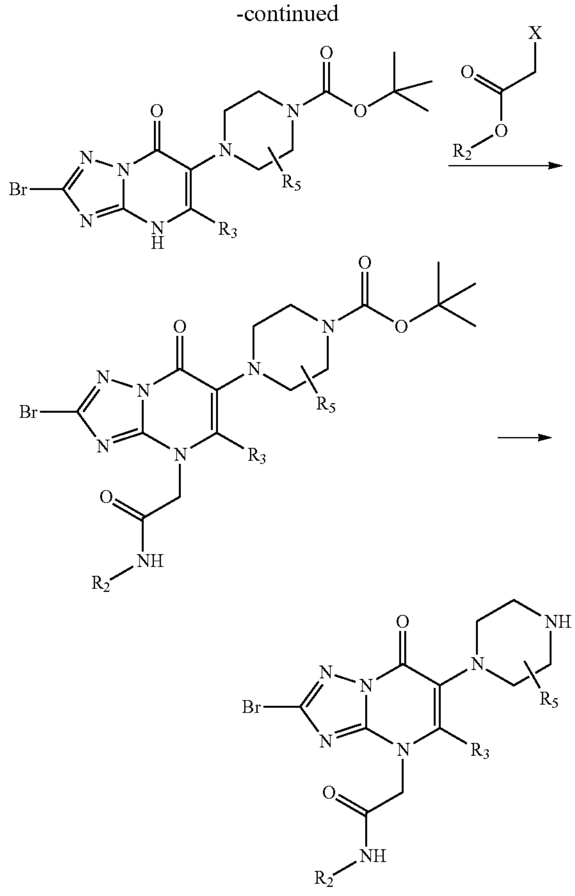

Intermediate BZ: 2-(2-bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide Step 1: tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

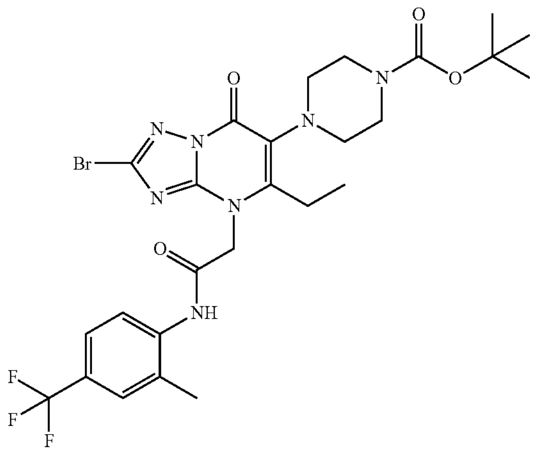 [SMILES: CCc1c(N2CCN(C(=O)OC(C)(C)C)CC2)c(=O)n2nc(Br)nc2n1CC(=O)Nc1ccc(C(F)(F)F)cc1C]

To a stirred solution of tert-butyl 4-(2-bromo-5-ethyl-7-oxo-4,7-dihydro-[1,2,4]triazolo[1,5-a]pyrimidin-6-yl)piperazine-1-carboxylate (Intermediate X) (16.9 g, 37.6 mmol) and 2-iodo-N-(2-methyl-4-(trifluoromethyl)phenyl)acetamide (Intermediate DV) (15.5 g, 45.1 mmol) in 1,4-dioxane (200 mL) was added DIPEA (19.7 mL, 113 mmol) at RT and the RM was stirred at 80° C. for 4 hours. The RM was concentrated, diluted with EtOAc/water, extracted once with EtOAc and the organic layer was washed with brine, dried over $Na_2SO_4$ and concentrated under reduced pressure. The crude product was purified by column chromatography (RediSep Column: Silica 120 g, eluent heptane:EtOAc 70:30 to 5:95). The product containing fractions were combined, triturated with $Et_2O$ and dried under HV to give the title compound as a white solid.

LC-MS: Rt=1.33 min; MS m/z $[M+H-Boc]^+$ 542.2/544.2, m/z $[M-H]^-$ 640.3/642.2; UPLC-MS 6

Step 2: 2-(2-bromo-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide

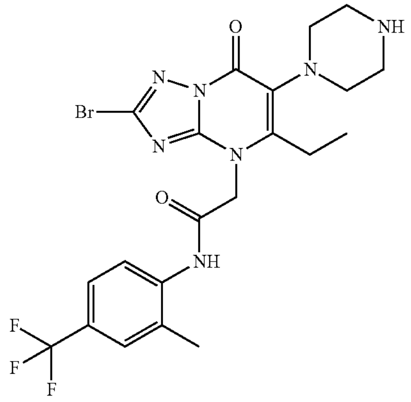 [SMILES: CCc1c(N2CCNCC2)c(=O)n2nc(Br)nc2n1CC(=O)Nc1ccc(C(F)(F)F)cc1C]

To a stirred solution of tert-butyl 4-(2-bromo-5-ethyl-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (2.00 g, 3.11 mmol) in DCM (20 mL) was added TFA (10.0 mL, 130 mmol) at RT and the RM was stirred at RT for 5 minutes. The RM was diluted with DCM and $NaHCO_3$ and extracted 4 times with 10% MeOH in DCM. The organic layer was dried over $Na_2SO_4$, concentrated and dried under HV to give the title compound as a beige foam.

LC-MS: Rt=0.74 min; MS m/z $[M+H]^+$ 542.1/544.1, m/z $[M-H]^-$ 540.4/542.4; UPLC-MS 6

Step 3: 2-(2-bromo-5-ethyl-6-(4-(3-hydroxypicolinoyl)piperazin-1-yl)-7-oxo-[1,2,4]triazolo[1,5-a]pyrimidin-4 (7H)-yl)-N-(2-methyl-4-(trifluoromethyl)phenyl)acetamide

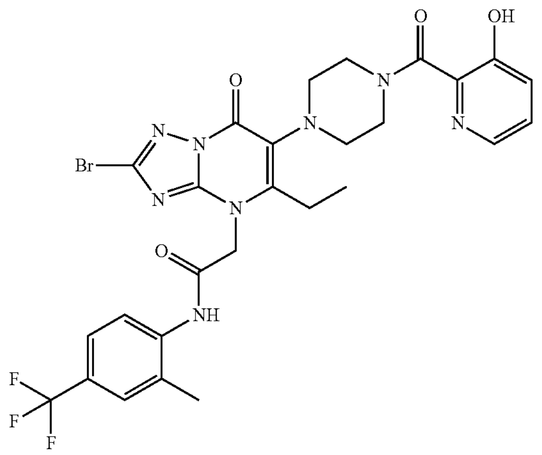 [SMILES: CCc1c(N2CCN(C(=O)c3ncccc3O)CC2)c(=O)n2nc(Br)nc2n1CC(=O)Nc1ccc(C(F)(F)F)cc1C]

To a stirred solution of 2-(2-bromo-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (1.00 g, 1.75 mmol) in DCM (20 mL) was added DIPEA (2.14 mL, 12.3 mmol), then 3-hydroxypicolinoyl chloride (Intermediate CV) (1.10 g, 7.01 mmol) in 4 portions at RT and the RM was stirred at RT for 1.5 hours. The RM was diluted with DCM and water and extracted twice with DCM. The combined organic layers were washed with brine, dried over $Na_2SO_4$, and concentrated. The crude product was purified by column chromatography (RediSep Column: Silica 40 g, eluent DCM:MeOH 100:0 to 50:50). The product containing fractions were combined and concentrated to afford the title compound as an off-white solid.

LC-MS: Rt=1.01 min; MS m/z $[M+H]^+$ 663.2/665.2, m/z $[M-H]^-$ 661.4/663.4; UPLC-MS 6

Scheme 8 general overview of compounds of route VII

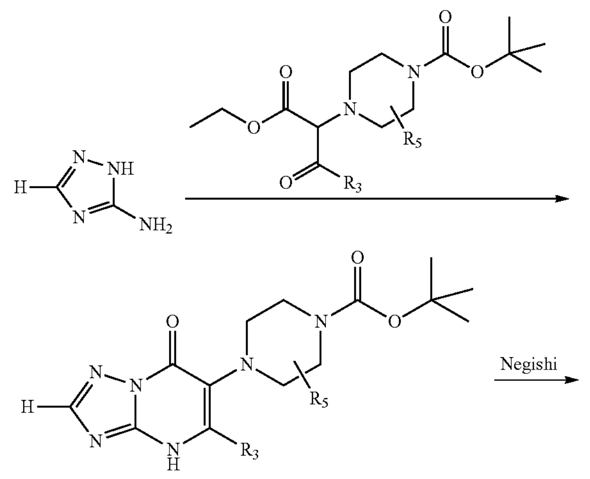

-continued

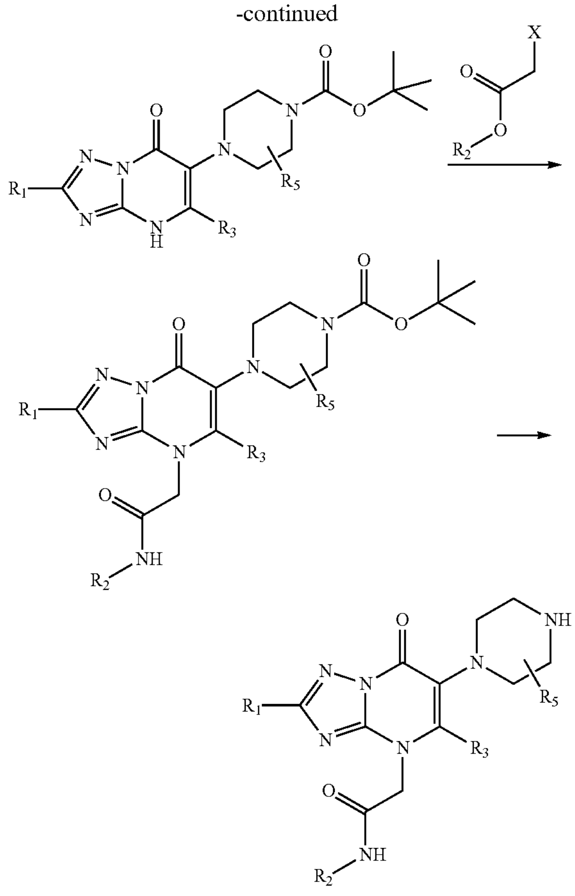

Intermediate CA: N-(2-chloro-5-fluoro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(5-ethyl-7-oxo-4,7-dihydro-[1,2,4]triazolo[1,5-a]pyrimidin-6-yl)piperazine-1-carboxylate

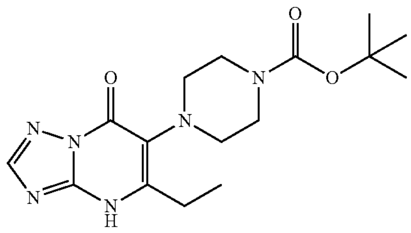 [SMILES: CCc1[nH]c2ncnn2c(=O)c1N1CCN(C(=O)OC(C)(C)C)CC1]

4H-1,2,4-triazol-3-amine (5.00 g, 59.5 mmol), tert-butyl 4-(1-methoxy-1,3-dioxopentan-2-yl)piperazine-1-carboxylate (Intermediate EH) (20.6 g, 65.4 mmol) and $H_3PO_4$ (4.21 mL, 62.4 mmol) were mixed in EtOH (50 mL). The RM was stirred at reflux for 18 hours. $H_3PO_4$ (1.00 mL, 14.8 mmol) was added and the RM was stirred at reflux for 18 hours. The RM was concentrated under reduced pressure. AcOH (20 mL) was added and the RM was stirred at 90° C. for 20 hours. The RM was concentrated under reduced pressure twice with toluene. THF was added, followed by DIPEA (31.2 mL, 178 mmol) and the RM was cooled to 0° C. $Boc_2O$ (20.7 mL, 89.0 mmol) was added and the RM was stirred for 7 hours. EtOAc was added and the mixture was washed with citric acid and brine, dried over $Na_2SO_4$ and concentrated under reduced pressure. The crude product was purified by column chromatography (RediSep Column: Silica 120 g, eluent DCM:MeOH 100:0 to 90:10). The product containing fractions were combined and concentrated under reduced pressure. The product was crystallized from DCM and TBME to give the title compound.

LC-MS: Rt=0.93 min; MS m/z $[M+H]^+$ 349.2, m/z $[M-H]^-$ 347.1; UPLC-MS 3

Step 2: tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Int AF)

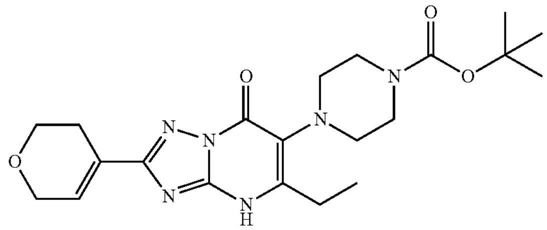 [SMILES: CCc1[nH]c2nc(C3=CCOCC3)nn2c(=O)c1N1CCN(C(=O)OC(C)(C)C)CC1]

The flask was flame-dried under reduced pressure and backfilled with nitrogen. The dry nitrogen flushed flask was charged with tert-butyl 4-(5-ethyl-7-oxo-4,7-dihydro-[1,2,4]triazolo[1,5-a]pyrimidin-6-yl)piperazine-1-carboxylate (6.50 g, 18.5 mmol) and anhydrous THF (18.5 mL). To the white suspension was added zinc chloro 2,2,6,6-tetramethylpiperidide lithium chloride complex solution (45.1 mL, 59.1 mmol) with dropwise 1.5 mL/min. The RM was stirred at RT for 2 hours. 4-bromo-3,6-dihydro-2H-pyran (6.02 mL, 55.4 mmol), VPhos (958 mg, 1.85 mmol) and CPhos Pd G3 (1.57 g, 1.85 mmol) were added. The RM was stirred at RT for 85.5 hours. The reaction was quenched with aq. 5N $NH_4Cl$ (100 mL). EtOAc (100 mL) was added and the organic layer was collected. The aqueous layer was extracted with EtOAc (3×60 mL). The organic layers were combined, washed with 0.35% aq. $NaHCO_3$ (150 mL), brine (150 mL) and dried through a phase separator. To the filtrates was added ISOLUTE® Si-TMT (57.7 g, 27.7 mmol) and the suspension was stirred at 40° C. for 1 hour. The mixture was filtered over a pad of celite. The filtrate was concentrated under reduced pressure. The crude product was adsorbed onto Isolute and purified by column chromatography (Reveleris® HP silica cartridge 220 g, eluent DCM:MeOH 100:0 to 95:5). The product containing fractions were combined and concentrated under reduced pressure. The residue was suspended in $Et_2O$ and filtered. The cake was dried under HV to give the title compound as a white powder. The filtrate was concentrated under reduced pressure, adsorbed onto Isolute and purified again by column chromatography (Reveleris® HP silica cartridge 120 g, eluent DCM:MeOH 100:0 to 95:5). The product containing fractions were combined and concentrated under reduced pressure to give a further crop of the title compound as a beige solid.

LC-MS: Rt=1.01 min; MS m/z $[M+H]^+$ 431.3, m/z $[M-H]^-$ 429.2; UPLC-MS 3

Step 3: tert-butyl 4-(4-(2-((2-chloro-5-fluoro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

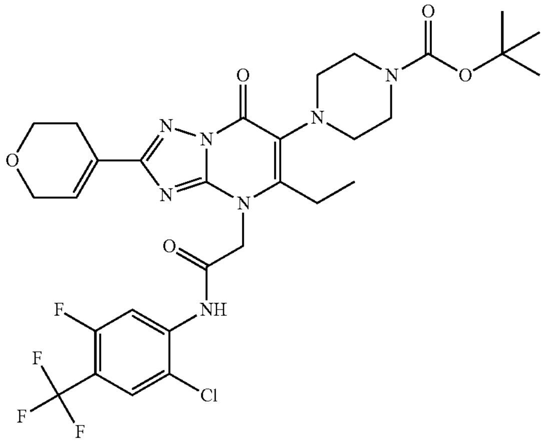 [SMILES: CCc1c(N2CCN(C(=O)OC(C)(C)C)CC2)c(=O)n2nc(C3=CCOCC3)nc2n1CC(=O)Nc1cc(F)c(C(F)(F)F)cc1Cl]

Tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (200 mg, 465 μmol) and 2-chloro-N-(2-chloro-5-fluoro-4-(trifluoromethyl)phenyl)acetamide (Intermediate EF) (150 mg, 517 μmol) were mixed in 1,4-dioxane (1 mL) and DMF (1 mL). Then DIPEA (203 μL, 1.16 mmol) was added. The dark solution was stirred at 80° C. for 1 day. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was dissolved in MeOH and filtered. The filtrate was allowed to stand in an open flask for 2 days. The resulting solid was suspended in $Et_2O$ (2 mL), sonicated, filtered and the cake was washed twice with $Et_2O$. The cake was dried under HV to give the title compound.

LC-MS: Rt=1.37 min; MS m/z $[M+H-Boc]^+$584.3/586.3, m/z $[M-H]^-$ 682.3/684.3; UPLC-MS 1

Step 4: N-(2-chloro-5-fluoro-4-(trifluoromethyl) phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

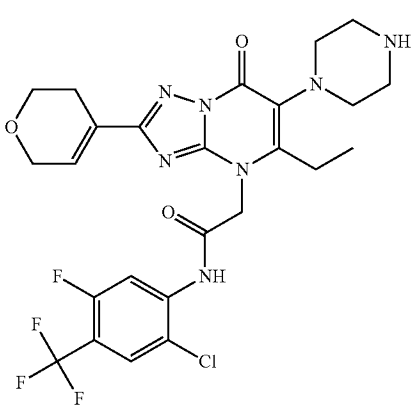

Tert-butyl 4-(4-(2-((2-chloro-5-fluoro-4-(trifluoromethyl) phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (165 mg, 229 μmol) was dissolved in DCM (2 mL) and TFA (100 μL, 1.30 mmol) was added. The mixture was stirred at 40° C. for 2 hours, then at RT overnight and then again at 40° C. for 2 hours. The mixture was concentrated under reduced pressure and dried under HV to give the title compound trifluoroacetate salt.

LC-MS: Rt=0.85 min; MS m/z $[M+H]^+$ 584.3/586.3, m/z $[M-H]^-$ 582.3/584.4; UPLC-MS 1

Intermediate CB: tert-butyl 4-(2-(3,6-dihydro-2H-pyran-4-yl)-5-methyl-7-oxo-4,7-dihydro-[1,2,4]triazolo[1,5-a]pyrimidin-6-yl)piperazine-1-carboxylate Step 1: tert-butyl 4-(5-methyl-7-oxo-4,7-dihydro-[1,2,4]triazolo[1,5-a]pyrimidin-6-yl)piperazine-1-carboxylate

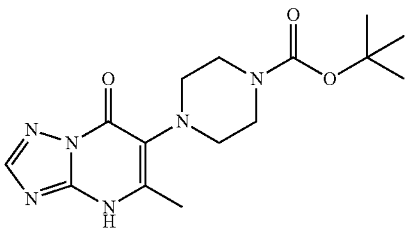 [SMILES: Cc1[nH]c2ncnn2c(=O)c1N1CCN(C(=O)OC(C)(C)C)CC1]

4H-1,2,4-triazol-3-amine (13.6 g, 162 mmol) and tert-butyl 4-(1-ethoxy-1,3-dioxobutan-2-yl)piperazine-1-carboxylate (Intermediate EP) (50.9 g, 162 mmol) were heated in AcOH (139 mL, 2.43 mol) at 100° C. for 70 minutes. The majority of the AcOH was removed in vacuo. The mixture was diluted with EtOH (100 mL) and heated at 88° C. for 18 hours. The mixture was allowed to cool to RT and filtered. The solid was washed with EtOH (120 mL) and dried in vacuo at 50° C. overnight to give the title compound as an off-white solid.

LC-MS: Rt=0.79 min; MS m/z $[M+H]^+$ 335.5, m/z $[M-H]^-$ 333.4; UPLC-MS 8

Step 2: tert-butyl 4-(2-(3,6-dihydro-2H-pyran-4-yl)-5-methyl-7-oxo-4,7-dihydro-[1,2,4]triazolo[1,5-a]pyrimidin-6-yl)piperazine-1-carboxylate

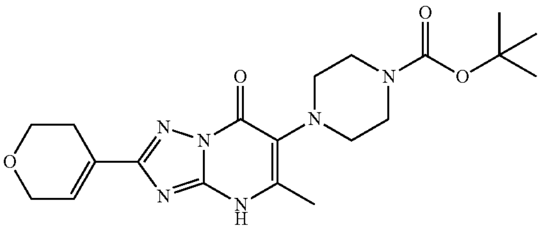 [SMILES: Cc1[nH]c2nc(C3=CCOCC3)nn2c(=O)c1N1CCN(C(=O)OC(C)(C)C)CC1]

A flask was flame-dried under reduced pressure and backfilled with argon. Tert-butyl 4-(5-methyl-7-oxo-4,7-dihydro-[1,2,4]triazolo[1,5-a]pyrimidin-6-yl)piperazine-1-carboxylate (5.00 g, 14.7 mmol) was suspended in anhydrous THF (14.7 mL). To the white suspension was added at RT zinc chloro 2,2,6,6-tetramethylpiperidide lithium chloride complex solution (35.9 mL, 32.2 mmol) with dropwise 1 mL/min. The RM was stirred for 1.5 hours. Then it was stored in the freezer under argon overnight. The next morning it was stirred at RT for 4 hours. 4-bromo-3,6-dihydro-2H-pyran (3.18 mL, 29.3 mmol), CPhos (392 mg, 879 μmol) and CPhos Pd G3 (746 mg, 879 μmol) were introduced under argon. The RM was stirred at RT for 68.5 hours. The reaction was partitioned between THF (100 mL) and aq. $NH_4Cl$ 5N (100 mL). The aqueous layer was back-extracted with EtOAc (3×50 mL). The organic layers were combined, washed with aq. 10% $Na_2S_2O_3$ (150 mL), brine (150 mL) and dried through a phase separator. The solvent was collected and treated with ISOLUTE® Si-TMT (36.6 g, 17.6 mmol). The suspension was stirred at 40° C. for 1 hour and was filtered off over a pad of celite. Removal of volatiles under pressure. The residue was adsorbed onto Isolute and purified by column chromatography (FlashPure® EcoFlex silica cartridge 330 g, eluent DCM:MeOH 100:0 to 95:5). The product containing fractions were combined and concentrated to give the title compound as an off-white solid.

LC-MS: Rt=0.89 min; MS m/z $[M+H]^+$ 417.3, m/z $[M-H]^-$ 415.2; UPLC-MS 8

Intermediate BN: 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide Step 1: tert-butyl 4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

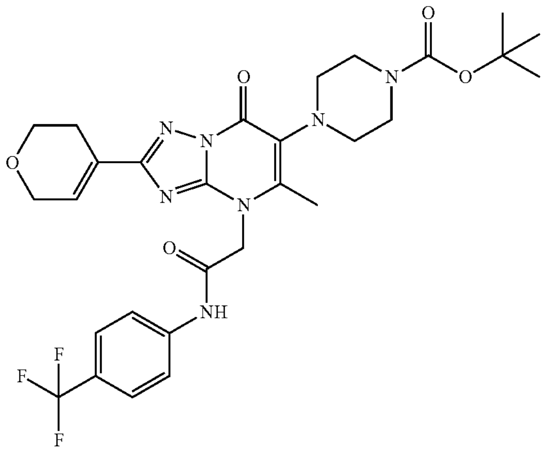

Tert-butyl 4-(2-(3,6-dihydro-2H-pyran-4-yl)-5-methyl-7-oxo-4,7-dihydro-[1,2,4]triazolo[1,5-a]pyrimidin-6-yl)piperazine-1-carboxylate (Intermediate CB) (500 mg, 1.20 mmol) 2-bromo-N-(4-(trifluoromethyl)phenyl)acetamide (406 mg, 1.44 mmol) and $K_2CO_3$ (232 mg, 1.68 mmol) were mixed in DMF (5 mL). The RM was stirred at 80° C. for 30 minutes. 2-Bromo-N-(4-(trifluoromethyl)phenyl)acetamide (40.6 mg, 144 μmol) was added again and the RM was stirred at 80° C. for 30 minutes. The RM was diluted with EtOAc, washed with aq sat $NaHCO_3$ and brine, dried over $Na_2SO_4$ and concentrated under reduced pressure. The crude product was crystallized from TBME, then dried under HV to give the title compound.

LC-MS: Rt=1.19 min; MS m/z $[M+H]^+$ 618.3, m/z $[M-H]^-$ 616.2; UPLC-MS 8

Step 2: 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(4-(trifluoromethyl)phenyl)acetamide

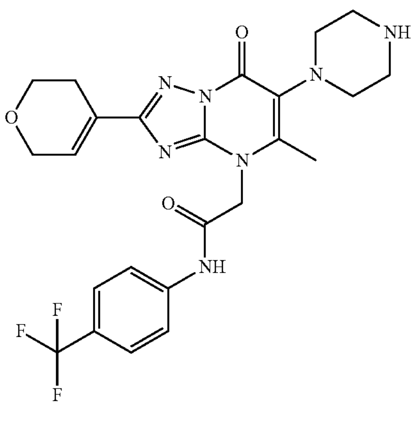 [SMILES: Cc1c(N2CCNCC2)c(=O)n2nc(C3=CCOCC3)nc2n1CC(=O)Nc1ccc(C(F)(F)F)cc1]

Tert-butyl 4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (600 mg, 971 μmol) was dissolved in DCM (5 mL). TFA (2.25 mL, 29.1 mmol) was added and the RM was stirred at RT for 1 hour. The RM was concentrated under reduced pressure, dissolved twice in toluene and concentrated under reduced pressure again. The residue was dissolved in EtOAc, washed with aq sat $NaHCO_3$ and brine, dried over $Na_2SO_4$ and concentrated under reduced pressure to give the title compound.

LC-MS: Rt=0.74 min; MS m/z $[M+H]^+$ 518.2, m/z $[M-H]^-$ 516.1; UPLC-MS 8

Scheme 9 general overview of compounds of route VIII

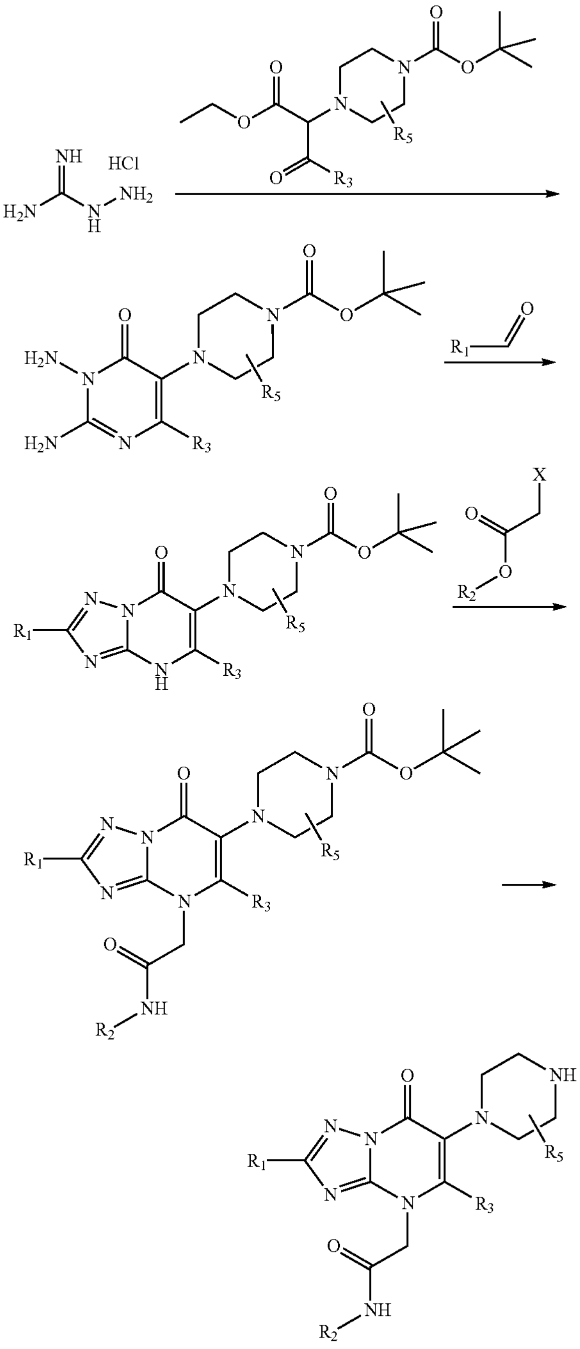

Intermediate CC: N-(2-chloro-4-(trifluoromethyl) phenyl)-2-(2-(3,6-dihydro-2H-pyran-4-yl)-6-((2S, 5R)-2,5-dimethylpiperazin-1-yl)-5-ethyl-7-oxo-[1,2, 4]triazolo[1,5-a]pyrimidin-4 (7H)-yl)acetamide Step 1: tert-butyl (2R,5S)-4-(3-amino-6-ethyl-2-imino-4-oxo-1,2,3,4-tetrahydropyrimidin-5-yl)-2,5-dimethylpiperazine-1-carboxylate

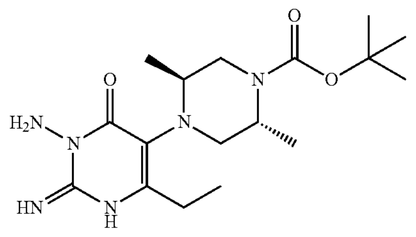 [SMILES: CCc1[nH]c(=N)n(N)c(=O)c1N1C[C@@H](C)N(C(=O)OC(C)(C)C)C[C@@H]1C]

To a beige suspension of hydrazinecarboximidamide hydrochloride (2.95 g, 26.7 mmol) in EtOH (44.4 mL) was added tetrabutylammonium hydroxide (18.3 mL, 28.0 mmol) at RT. The yellow turbid solution was stirred at 50° C. for 2.75 hours. Tert-butyl (2R,5S)-4-(1-ethoxy-1,3-dioxopentan-2-yl)-2,5-dimethylpiperazine-1-carboxylate (Intermediate EN) (5.00 g, 13.3 mmol) was added and the RM was stirred at 80° C. for 17.5 hours. The EtOH was removed under vacuum. Water was added to the brown oily residue, which was then stirred for 1 hour. Extracted three times with EtOAc. The combined organic layers were dried over $Na_2SO_4$, concentrated and dried under vacuum to give a dark brown oily residue. The crude product was purified by column chromatography (Silica gel column: Silica 120 g, eluent DCM:DCM/MeOH (8/2) 100:0 to 60:40). The product containing fractions were combined and concentrated to give the title compound as a beige foam.

LC-MS: Rt=0.88 min; MS m/z $[M+H]^+$ 367.4, m/z $[M-H]^-$ 365.4; UPLC-MS 1

Step 2: tert-butyl (2R,5S)-4-(2-(3,6-dihydro-2H-pyran-4-yl)-5-ethyl-7-oxo-4,7-dihydro-[1,2,4]triazolo[1,5-a]pyrimidin-6-yl)-2,5-dimethylpiperazine-1-carboxylate

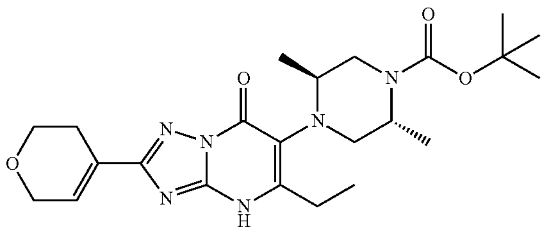 [SMILES: CCc1[nH]c2nc(C3=CCOCC3)nn2c(=O)c1N1C[C@@H](C)N(C(=O)OC(C)(C)C)C[C@@H]1C]

To a solution of tert-butyl (2R,5S)-4-(3-amino-6-ethyl-2-imino-4-oxo-1,2,3,4-tetrahydropyrimidin-5-yl)-2,5-dimethylpiperazine-1-carboxylate (1.55 g, 3.98 mmol) in NMP (4.42 mL) was added 3,6-dihydro-2H-pyran-4-carbaldehyde (Intermediate DK) (535 mg, 4.77 mmol) then iron(III) chloride (645 mg, 3.98 mmol). The dark brown mixture was stirred at 50° C. for 18.5 hours. 3,6-dihydro-2H-pyran-4-carbaldehyde (Intermediate DK) (150 mg, 1.34 mmol) was added to the dark brown RM, which was then stirred at 50° C. for 5 hours.

The RM was cooled down to RT. Water was added. The mixture was stirred at RT overnight.

No clean suspension obtained. It was extracted three times with DCM. The combined organic layers were dried through a phase separator and concentrated under reduced pressure to give the title compound as a brown liquid.

LC-MS: Rt=1.01 min; MS m/z $[M+H]^+$ 459.6, m/z $[M-H]^-$ 457.4; UPLC-MS 1

Step 3: tert-butyl (2R,5S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-dimethylpiperazine-1-carboxylate

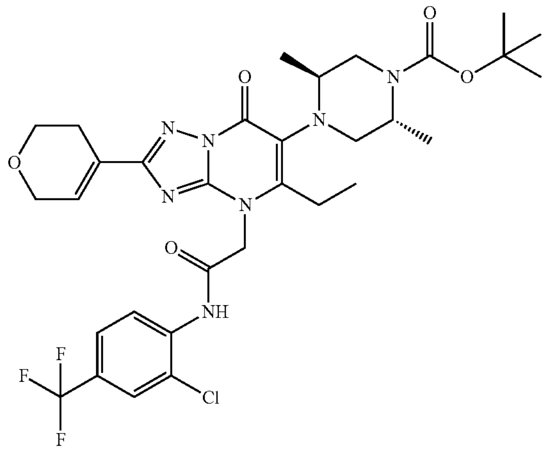 [SMILES: CCc1c(N2C[C@@H](C)N(C(=O)OC(C)(C)C)C[C@@H]2C)c(=O)n2nc(C3=CCOCC3)nc2n1CC(=O)Nc1ccc(C(F)(F)F)cc1Cl]

To a dark brown solution of tert-butyl (2R,5S)-4-(2-(3,6-dihydro-2H-pyran-4-yl)-5-ethyl-7-oxo-4,7-dihydro-[1,2,4]triazolo[1,5-a]pyrimidin-6-yl)-2,5-dimethylpiperazine-1-carboxylate (6.06 g, 3.96 mmol) in 1,4-dioxane (26.4 mL) were added N-(2-chloro-4-(trifluoromethyl)phenyl)-2-iodoacetamide (Intermediate DL) (1.60 g, 3.96 mmol), then DIPEA (900 μL, 5.15 mmol). The dark brown solution was stirred at 50° C. for 5.25 hours. The dark brown mixture was cooled down to RT. Water and EtOAc were added. The biphasic mixture was vigorously stirred for 30 minutes. Both phases were separated. The aqueous layer was extracted twice with EtOAc. The combined organic layers were dried through a phase separator and concentrated under reduced pressure to give a dark brown residue. The crude product was purified by column chromatography (Silica gel column: Silica 80 g, eluent heptane:EtOAc 100:0 to 0:100). The product containing fractions were combined and concentrated under reduced pressure to give the title compound as a light brown solid.

LC-MS: Rt=1.38 min; MS m/z $[M+H]^+$ 694.3/696.3, m/z $[M-H]^-$ 692.3/694.3; UPLC-MS 1

Step 4: N-(2-chloro-4-(trifluoromethyl)phenyl)-2-(2-(3,6-dihydro-2H-pyran-4-yl)-6-((2S,5R)-2,5-dimethylpiperazin-1-yl)-5-ethyl-7-oxo-[1,2,4]triazolo[1,5-a]pyrimidin-4 (7H)-yl)acetamide

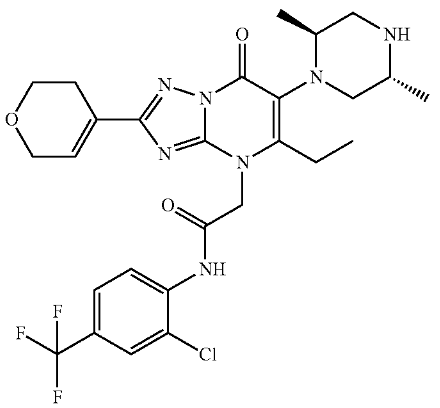 [SMILES: CCc1c(N2C[C@@H](C)NC[C@@H]2C)c(=O)n2nc(C3=CCOCC3)nc2n1CC(=O)Nc1ccc(C(F)(F)F)cc1Cl]

A light brown solution of tert-butyl (2R,5S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-dimethylpiperazine-1-carboxylate (934 mg, 1.28 mmol) in 4N HCl in 1,4-dioxane (6.39 mL, 25.6 mmol) was stirred at RT for 1 hour. The RM was dissolved in DCM and washed once with aq sat $NaHCO_3$. The aqueous layer was extracted once with DCM. Presence of beige solids at the bottom of the aqueous phase. The aqueous layer was extracted twice with DCM/MeOH (95/5). The aqueous layer was filtered to give a beige solid and the filtrate extracted once more with DCM. The filtered beige solids were dissolved in DCM/MeOH. The turbid solution was combined with the previous organic phases. They were dried through a phase separator, concentrated and dried under vacuum to give the title compound hydrochloride salt.

LC-MS: Rt=0.82 min; MS m/z $[M+H]^+$ 594.4/596.4, m/z $[M-H]^-$ 592.4/594.4; UPLC-MS 1

Intermediate CD: tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate Step 1: tert-butyl 4-(3-amino-6-ethyl-2-imino-4-oxo-1,2,3,4-tetrahydropyrimidin-5-yl)-2,3-dimethylpiperazine-1-carboxylate

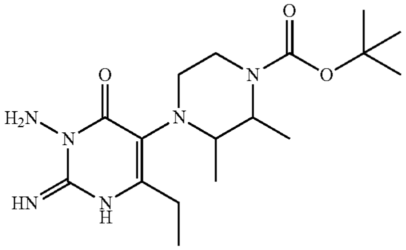 [SMILES: CCc1[nH]c(=N)n(N)c(=O)c1N1CCN(C(=O)OC(C)(C)C)C(C)C1C]

To a stirred solution of hydrazinecarboximidamide·HCl (13.6 g, 123 mmol) in EtOH (250 mL) was added tetrabutylammonium hydroxide (100 mL, 153 mmol) at RT. The RM was stirred at 55° C. for 30 minutes. Tert-butyl 4-(1-methoxy-1,3-dioxopentan-2-yl)-2,3-dimethylpiperazine-1-carboxylate (Intermediate EQ) (21.0 g, 61.3 mmol) was added and the RM was stirred at 90° C. for 16 hours. The RM was concentrated. The residue was dissolved in DCM/water, extracted twice with DCM and the combined organic extracts were dried over $Na_2SO_4$ and concentrated. The crude product was purified by column chromatography (Silica gel column: Silica 220 g, eluent DCM:DCM/MeOH (8/2) 100:0 to 50:50). The product containing fractions were combined and concentrated under reduced pressure to give the title compound as an oil.

LC-MS: Rt=0.87/0.91 min; MS m/z $[M+H]^+$ 367.3; UPLC-MS 1

Step 2: tert-butyl 4-(2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate

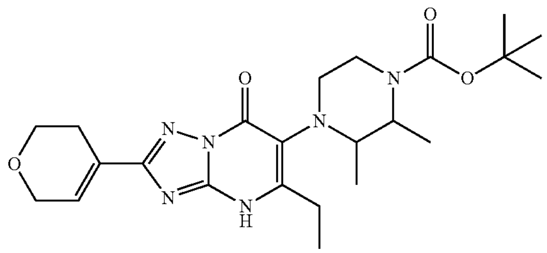 [SMILES: CCc1[nH]c2nc(C3=CCOCC3)nn2c(=O)c1N1CCN(C(=O)OC(C)(C)C)C(C)C1C]

To a stirred solution of tert-butyl 4-(3-amino-6-ethyl-2-imino-4-oxo-1,2,3,4-tetrahydropyrimidin-5-yl)-2,3-dimethylpiperazine-1-carboxylate (5.00 g, 12.3 mmol) and 3,6-dihydro-2H-pyran-4-carbaldehyde (Intermediate DK) (1.62 g, 14.7 mmol) in NMP (10 mL) was added iron(III) chloride (3.98 g, 24.6 mmol) at RT and the RM was stirred at 55° C. for 40 hours. The RM was diluted with DCM/water, filtered through celite, the filtrate was extracted twice with DCM and the combined organic extracts were dried over $Na_2SO_4$ and concentrated to give the title compound as a brown oil.

LC-MS: Rt=0.99 min; MS m/z $[M+H]^+$ 459.4, m/z $[M-H]^-$ 457.4; UPLC-MS 1

Step 3: tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate

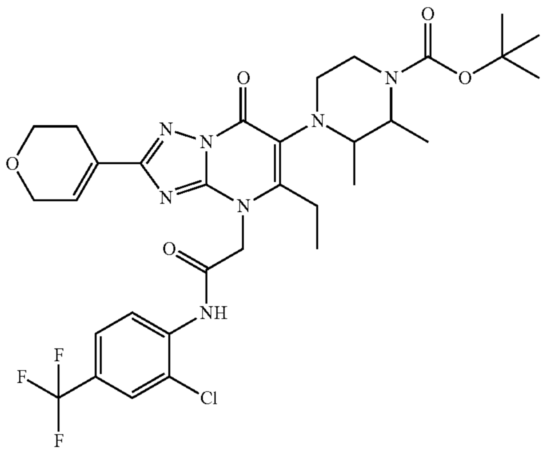 [SMILES: CCc1c(N2CCN(C(=O)OC(C)(C)C)C(C)C2C)c(=O)n2nc(C3=CCOCC3)nc2n1CC(=O)Nc1ccc(C(F)(F)F)cc1Cl]

To a stirred solution of tert-butyl 4-(2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate (9.00 g, 12.6 mmol) and N-(2-chloro-4-(trifluoromethyl)phenyl)-2-iodoacetamide (Intermediate DL) (5.02 g, 13.8 mmol) in 1,4-dioxane (100 mL) was added DIPEA (2.85 mL, 16.3 mmol) at RT and the RM was stirred at 45° C. for 14 hours. The RM was diluted with EtOAc/water, extracted twice with EtOAc and the combined organic extracts were washed with water and brine, dried over $Na_2SO_4$ and concentrated. The crude product was purified by column chromatography (Silica gel column: Silica 80 g, eluent heptane: EtOAc 100:0 to 0:100). The product containing fractions were combined and concentrated under reduced pressure to give the title compound as a beige solid.

LC-MS: Rt=1.36 min; MS m/z $[M+H]^+$ 694.4/696.4, m/z $[M-H]^-$ 692.5/694.5; UPLC-MS 1

Chiral separation of tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate: The compound was dissolved in 80 mL MeOH/DCM.

Preparative chiral SFC (instrument: MG II; column: ChiralPak IC, 250×30 mm I.D., 5 μm; eluent: A=$CO_2$, B=MeOH+0.1% $NH_4OH$; flow rate: 50.0 mL/min; detection: 220 nm; column temperature: 38° C.; back pressure: 100 bar; injection volume: 2 mL; Gradient: 0 to 35% B Intermediate CE: tert-butyl (2S,3R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate or tert-butyl (2R,3S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate

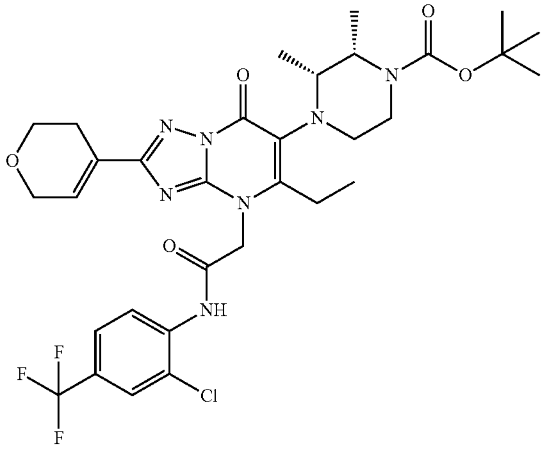

(2S,3R)

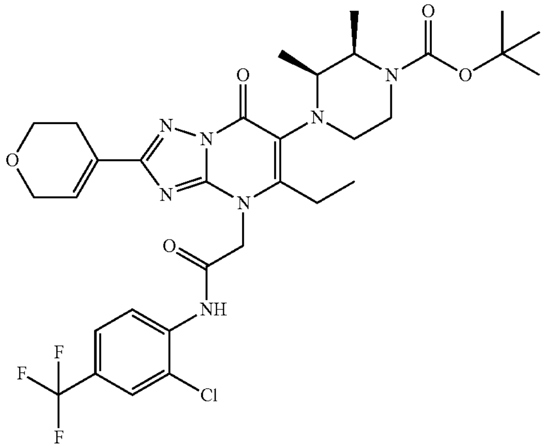

(2R,3S)

First Eluting Stereoisomer

Chiral HPLC (C-HPLC 9): Rt=1.649 min, 100% ee

LC-MS: Rt=1.38 min; MS m/z $[M+H]^+$ 694.6/696.6, m/z $[M-H]^-$ 692.4/694.4; UPLC-MS 1

Intermediate CF: tert-butyl (2S,3S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate

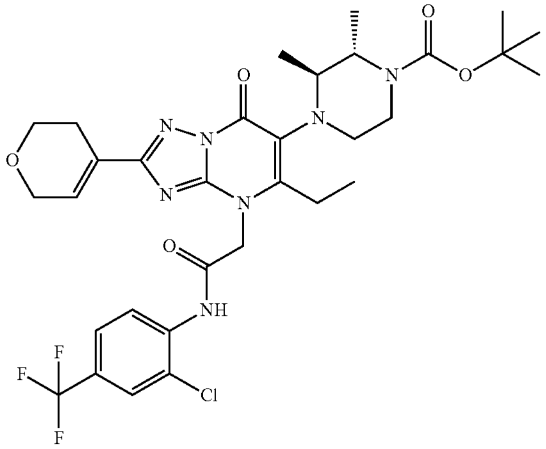

(2S,3S)

Second Eluting Stereoisomer

Chiral HPLC (C-HPLC 9): Rt=1.909 min, 99.8% ee

LC-MS: Rt=1.36 min; MS m/z $[M+H]^+$ 694.5/696.5, m/z $[M-H]^-$ 692.5/694.5; UPLC-MS 1

Intermediate CG: tert-butyl (2R,3S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate or tert-butyl (2S,3R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate

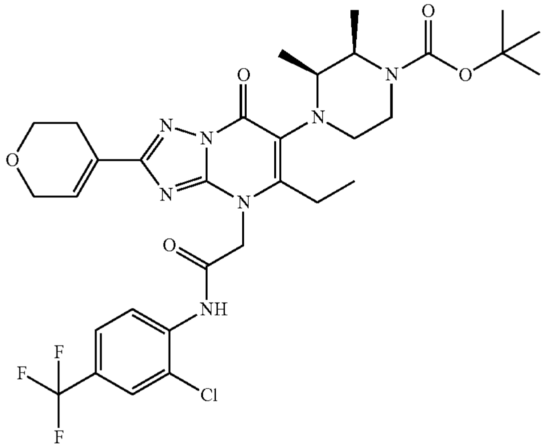

(2R,3S)

-continued

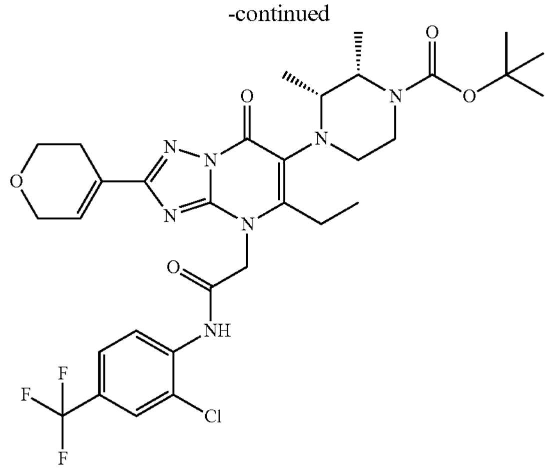

(2S,3R)

Third Eluting Stereoisomer

Chiral HPLC (C-HPLC 9): Rt=2.505 min, 99.8% ee

LC-MS: Rt=1.36 min; MS m/z $[M+H]^+$ 694.5/696.5, m/z $[M-H]^-$ 692.5/694.5; UPLC-MS 1

Intermediate CH: tert-butyl (2R,3R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate

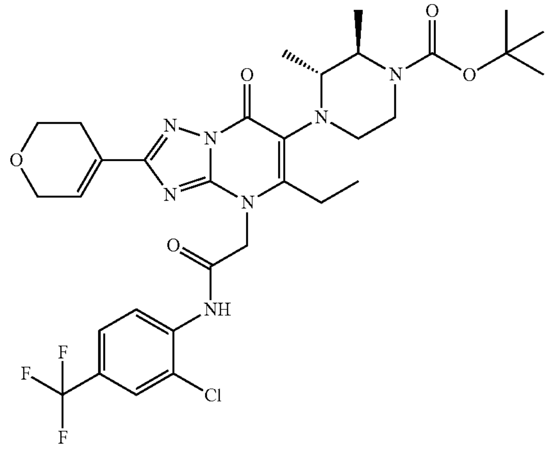

(2R,3R)

Fourth Eluting Stereoisomer

Chiral HPLC (C-HPLC 9): Rt=3.202 min, 100% ee

LC-MS: Rt=1.38 min; MS m/z $[M+H]^+$ 694.3/696.3, m/z $[M-H]^-$ 692.3/694.3; UPLC-MS 1

Intermediate CI: N-(2-chloro-4-(trifluoromethyl) phenyl)-2-(2-(3,6-dihydro-2H-pyran-4-yl)-6-((2R, 3R)-2,3-dimethylpiperazin-1-yl)-5-ethyl-7-oxo-[1,2, 4]triazolo[1,5-a]pyrimidin-4 (7H)-yl)acetamide

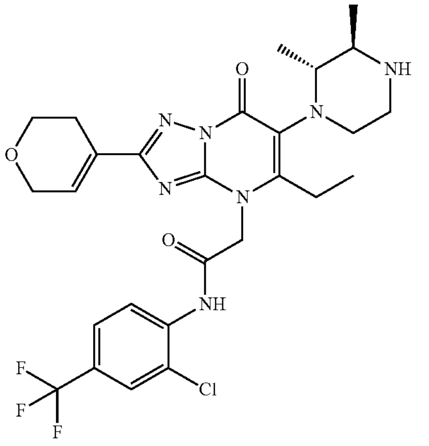

(2R,3R)

HCl 4N in 1,4-dioxane (3.00 mL, 12.0 mmol) was added to tert-butyl (2R,3R)-4-(4-(2-((2-chloro-4-(trifluoromethyl) phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate (Intermediate CH) (717 mg, 950 μmol) at RT and the RM was stirred at RT for 30 minutes. The RM was diluted with DCM/$NaHCO_3$, extracted twice with DCM and the combined organic extracts were washed with brine, dried over $Na_2SO_4$ and concentrated to give the title compound as a white solid.

LC-MS: Rt=0.85 min; MS m/z $[M+H]^+$ 594.4/596.4, m/z $[M-H]^-$ 592.4/594.5; UPLC-MS 1

Intermediate CJ: N-(2-chloro-4-(trifluoromethyl) phenyl)-2-(2-(3,6-dihydro-2H-pyran-4-yl)-6-((2S, 3S)-2,3-dimethylpiperazin-1-yl)-5-ethyl-7-oxo-[1,2, 4]triazolo[1,5-a]pyrimidin-4 (7H)-yl)acetamide

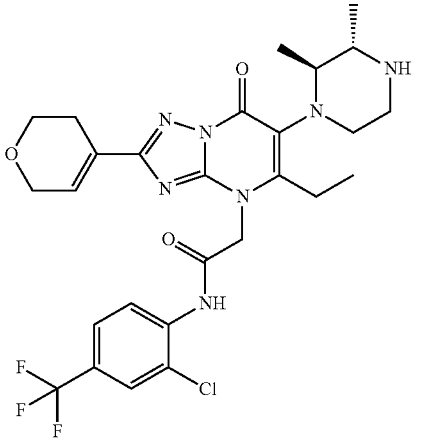

(2S,3S)

HCl 4N in 1,4-dioxane (21.3 μL, 85.0 μmol) was added to tert-butyl (2S,3S)-4-(4-(2-((2-chloro-4-(trifluoromethyl) phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate (Intermediate CF) (59.0 mg, 85.0 μmol) at RT and the RM was stirred at RT for 5 minutes. The RM was diluted with DCM/$NaHCO_3$, extracted twice with DCM and the combined organic extracts were washed with brine, dried over $Na_2SO_4$ and concentrated to give the title compound as a white solid.

LC-MS: Rt=0.80 min; MS m/z $[M+H]^+$ 594.6/596.6, m/z $[M-H]^-$ 592.2/594.3; UPLC-MS 1

Intermediate CK: N-(2-chloro-4-(trifluoromethyl) phenyl)-2-(2-(3,6-dihydro-2H-pyran-4-yl)-6-((2R, 3S)-2,3-dimethylpiperazin-1-yl)-5-ethyl-7-oxo-[1,2, 4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-6-((2S,3R)-2,3-dimethylpiperazin-1-yl)-5-ethyl-7-oxo-[1,2,4]triazolo[1,5-a]pyrimidin-4 (7H)-yl)acetamide

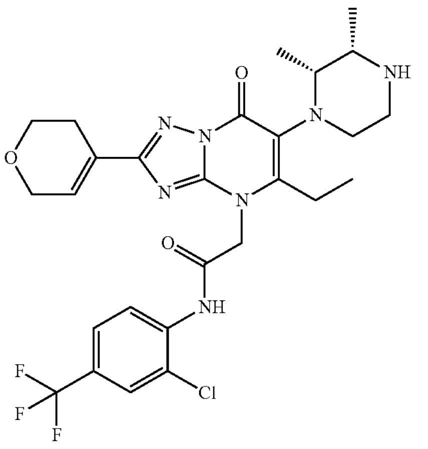

2R,3S-stereoisomer

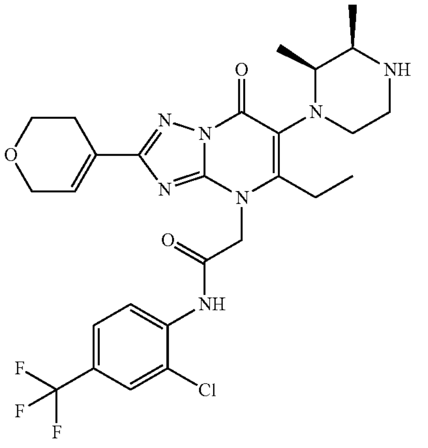

2S,3R-stereoisomer

HCl 4N in 1,4-dioxane (1.00 mL, 4.00 mmol) was added to tert-butyl (2S,3R)-4-(4-(2-((2-chloro-4-(trifluoromethyl) phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate or tert-butyl (2R,3S)-4-(4-(2-((2-chloro-4-(trifluoromethyl)phenyl) amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2, 3-dimethylpiperazine-1-carboxylate (Intermediate CE) (248 mg, 357 μmol) at RT and reactants were stirred at RT for 1 hour. The RM was diluted with DCM/$NaHCO_3$, extracted twice with DCM and the combined organic extracts were washed with brine, dried over $Na_2SO_4$ and concentrated to give the title compound as a white solid.

LC-MS: Rt=0.81 min; MS m/z $[M+H]^+$ 594.5/596.5, m/z $[M-H]^-$ 592.3/594.3; UPLC-MS 1

Intermediate CL: N-(2-chloro-4-(trifluoromethyl)phenyl)-2-(2-(3,6-dihydro-2H-pyran-4-yl)-6-((2S,3R)-2,3-dimethylpiperazin-1-yl)-5-ethyl-7-oxo-[1,2,4]triazolo[1,5-a]pyrimidin-4 (7H)-yl)acetamide or N-(2-chloro-4-(trifluoromethyl)phenyl)-2-(2-(3,6-dihydro-2H-pyran-4-yl)-6-((2R,3S)-2,3-dimethylpiperazin-1-yl)-5-ethyl-7-oxo-[1,2,4]triazolo[1,5-a]pyrimidin-4 (7H)-yl)acetamide

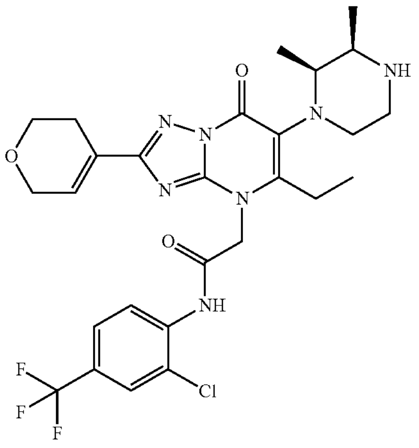

2S,3R-stereoisomer

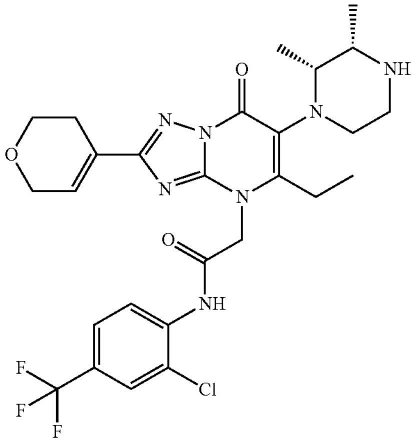

2R,3S-stereoisomer

HCl 4N in 1,4-dioxane (1.00 mL, 4.00 mmol) was added to tert-butyl (2R,3S)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate or tert-butyl (2S,3R)-4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,3-dimethylpiperazine-1-carboxylate (Intermediate CG) (258 mg, 357 μmol) at RT and reactants were stirred at RT for 15 minutes. The RM was diluted with DCM/$NaHCO_3$, extracted twice with DCM and the combined organic extracts were washed with brine, dried over $Na_2SO_4$ and concentrated to give the title compound as a reddish solid.

LC-MS: Rt=0.79 min; MS m/z $[M+H]^+$ 594.3/596.2, m/z $[M-H]^-$ 592.2/594.3; UPLC-MS 1

Intermediate AF: tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate Step 1: tert-butyl 4-(3-amino-6-ethyl-2-imino-4-oxo-1,2,3,4-tetrahydropyrimidin-5-yl)piperazine-1-carboxylate

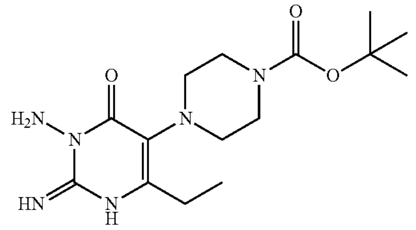 [SMILES: CCc1[nH]c(=N)n(N)c(=O)c1N1CCN(C(=O)OC(C)(C)C)CC1]

Hydrazinecarboximidamide·HCl (35.0 g, 317 mmol) was mixed with EtOH (400 mL), followed by aqueous tetrabutylammonium hydroxide solution, 40 wt % in water (206 g, 318 mmol). The mixture was stirred at 55° C. for 80 minutes. Tert-butyl 4-(1-methoxy-1,3-dioxopentan-2-yl)piperazine-1-carboxylate (Intermediate EH) (50.0 g, 159 mmol) was added. The mixture was stirred at reflux for 6 hours, and then it was cooled to RT. The solvent was removed under vacuum until % of the solvent volume remained. The resulting suspension was stirred for 1-2 hours, then filtered. The cake was dried under vacuum to give the title compound as a white solid.

MS m/z $[M+H]^+$ 339.2

Step 2: tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

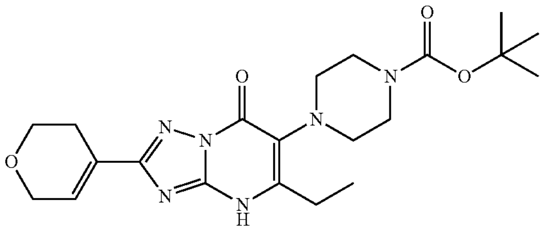 [SMILES: CCc1[nH]c2nc(C3=CCOCC3)nn2c(=O)c1N1CCN(C(=O)OC(C)(C)C)CC1]

A solution of 3,6-dihydro-2H-pyran-4-carbaldehyde (Intermediate DK) (20.0 g, 178 mmol) in NMP and tert-butyl 4-(3-amino-6-ethyl-2-imino-4-oxo-1,2,3,4-tetrahydropyrimidin-5-yl)piperazine-1-carboxylate (52.9 g, 149 mmol) in NMP (400 mL), followed by $FeCl_3$ (48 g, 297 mmol). The dark solution was heated to 50° C. open to air and stirred for 48 hours. The dark RM was cooled to RT. Water (1.2 L) was added slowly (exothermic). The suspension was filtered and washed with water (400 mL). The resulting wet cake was added to acetone (400 mL), stirred at RT for 4 hours. The suspension was filtered and washed with acetone (100 mL). The cake was added to EtOH (400 mL) and heated to 70° C., stirred for 4 hours. Then the mixture was cooled to RT, filtered and washed with EtOH (100 mL) to give the title compound as brown solid.

MS m/z $[M+H]^+$ 430.2

Intermediate AK: N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide Step 1: tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate

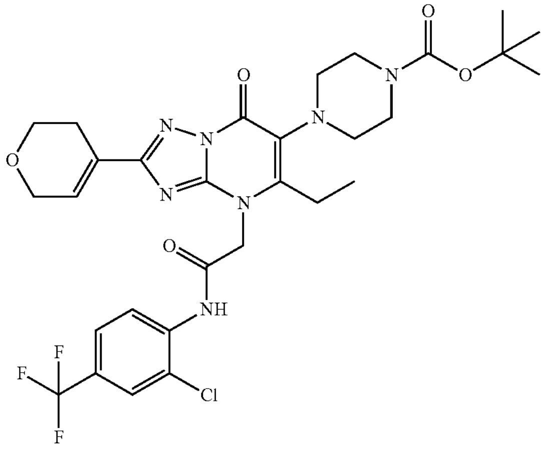 [SMILES: CCc1c(N2CCN(C(=O)OC(C)(C)C)CC2)c(=O)n2nc(C3=CCOCC3)nc2n1CC(=O)Nc1ccc(C(F)(F)F)cc1Cl]

A solution of tert-butyl 4-(2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (Intermediate AF) (50.0 g, 116 mmol), 2-chloro-N-(2-chloro-4-(trifluoromethyl)phenyl)acetamide (Intermediate DL step 1) (56.9 g, 209 mmol), DIPEA (60.9 mL, 348 mmol) in NMP (500 mL) was stirred at 50° C. for 16 hours. Water (1.5 L) was added to the RM and it was stirred for 1.5 hours, filtered and washed with water (600 mL). The resulting brown solid was added to EtOH (500 mL), stirred at RT for 4 hours, then it was filtered and washed with EtOH (150 mL). The cake was added to THF (1 L) and heated to 65° C., heptane (1 L) was added and it was stirred for 30 minutes.

Then the mixture was cooled to RT. The suspension was filtered and washed with heptane (100 mL). The wet cake was dried to give the title compound as a grey solid.

MS m/z $[M+H]^+$ 666.4

Step 2: N-(2-chloro-4-(trifluoromethyl)phenyl)-2-(2-(3,6-dihydro-2H-pyran-4-yl)-5-ethyl-7-oxo-6-(piperazin-1-yl)-[1,2,4]triazolo[1,5-a]pyrimidin-4 (7H)-yl)acetamide

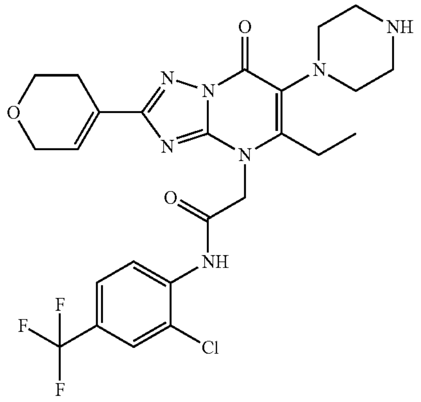 [SMILES: CCc1c(N2CCNCC2)c(=O)n2nc(C3=CCOCC3)nc2n1CC(=O)Nc1ccc(C(F)(F)F)cc1Cl]

Tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (3.10 g, 3.96 mmol) was mixed with DCM (225 mL) and HCl 2M in EtOAc (135 mL, 270 mmol). The suspension was stirred at RT for 6 hours. Then added DCM (305 mL) and HCl 2M in EtOAc (185 mL, 370 mmol), followed by solid tert-butyl 4-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)piperazine-1-carboxylate (57.4 g, 73.2 mmol). The RM was stirred at RT for 6 hours. The suspension was filtered and rinsed twice with premixed DCM:EtOAc (1:1, 220 mL). The cake was collected and dried under vacuum at RT for 4 hours. The dry cake was mixed with a premixed solution of $Et_3N$ (16.1 mL, 116 mmol) in ACN:water (1:1, 640 mL). The suspension was stirred at RT for 1 hour. Then water (1.6 L) was added over 2 hours, then stirred for 6 hours. The suspension was filtered and rinsed twice with ACN:water (1:4, 270 mL). The wet cake was dried under vacuum at 55° C. for 6 hours to give the title compound as a light brown solid.

MS m/z $[M+H]^+$ 566.2

Scheme 10 general overview of intermediates of route IX

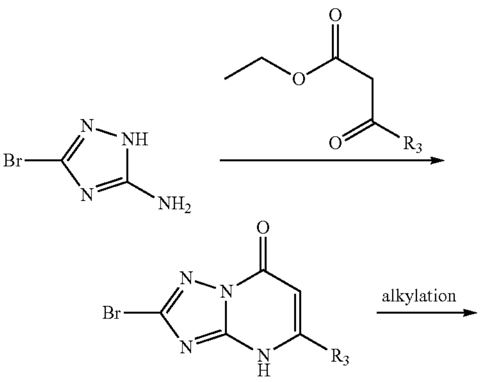

-continued

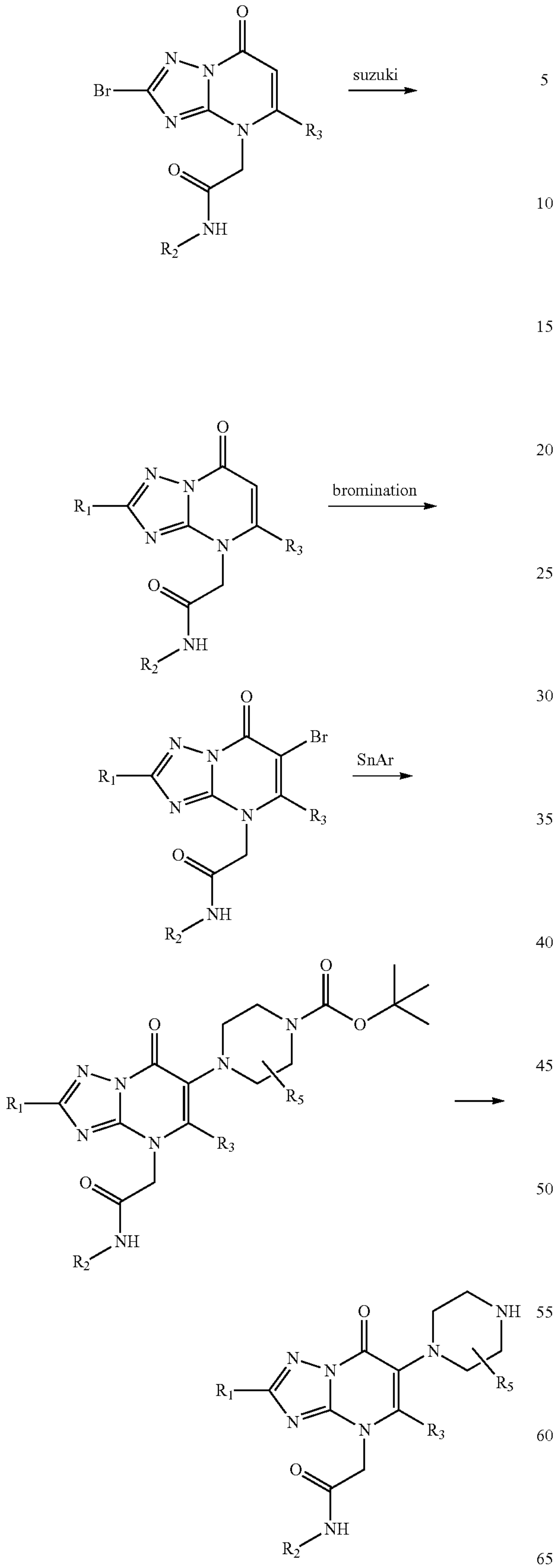

Intermediate CM: tert-butyl 5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate Step 1: 2-bromo-5-ethyl-[1,2,4]triazolo[1,5-a]pyrimidin-7 (4H)-one

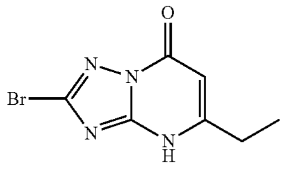

3-Bromo-1H-1,2,4-triazol-5-amine (Intermediate ER) (20.0 g, 123 mmol) and ethyl 3-oxopentanoate (22.1 g, 153 mmol) were mixed in AcOH (70 mL) and stirred at 80° C. for 19 hours. The RM was cooled to RT, then it was stirred at 0° C. for 1 hour. The resulting suspension was filtered and washed with a small amount of EtOH. The obtained solid was dried under HV to give the title compound as a white solid. The filtrate was concentrated and crystallized from EtOH to afford a second batch of product, which was dried under HV to give the title compound as a beige solid.

LC-MS: Rt=0.23 min; MS m/z $[M+H]^+$ 243.0/245.0, m/z $[M-H]^-$ 241.1/243.1; UPLC-MS 1

Step 2: 2-(2-bromo-5-ethyl-7-oxo-[1,2,4]triazolo[1,5-a]pyrimidin-4 (7H)-yl)-N-(2-chloro-4-(trifluoromethyl)phenyl)acetamide

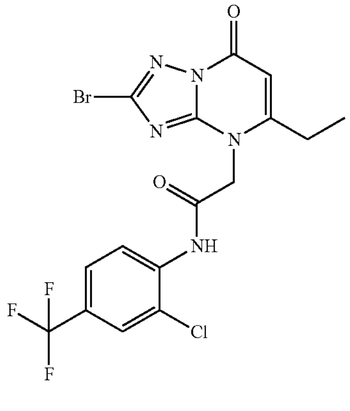 [SMILES: CCc1cc(=O)n2nc(Br)nc2n1CC(=O)Nc1ccc(C(F)(F)F)cc1Cl]

2-Bromo-5-ethyl-[1,2,4]triazolo[1,5-a]pyrimidin-7 (4H)-one (7.00 g, 28.8 mmol) and, N-(2-chloro-4-(trifluoromethyl)phenyl)-2-iodoacetamide (Intermediate DL) (11.8 g, 31.7 mmol) were mixed in 1,4-dioxane (170 mL) at RT under argon. DIPEA (15.1 mL, 86.0 mmol) was added and the RM was stirred at 80° C. for 4.25 hours. The RM was cooled to RT and extracted with EtOAc (3×300 mL), water (2×75 mL) and brine (2×75 mL). The aqueous layer was a suspension, which was filtered. The solid was dissolved in DCM/MeOH and combined with the organic layer. The combined organic layers were dried through a phase separator and concentrated under reduced pressure. The resulting bright brown solid was suspended in $Et_2O$ and sonicated for 30 minutes, then it was stirred at reflux for 3 hours. The suspension was filtered, washed with $Et_2O$ and dried under HV to give the title compound as a beige solid.

LC-MS: Rt=0.99 min; MS m/z $[M+H]^+$ 478.1/480.1/482.1, m/z $[M-H]^-$ 476.1/478.1/480.1; UPLC-MS 1

Step 3: N-(2-chloro-4-(trifluoromethyl)phenyl)-2-(2-(3,6-dihydro-2H-pyran-4-yl)-5-ethyl-7-oxo-[1,2,4]triazolo[1,5-a]pyrimidin-4 (7H)-yl)acetamide

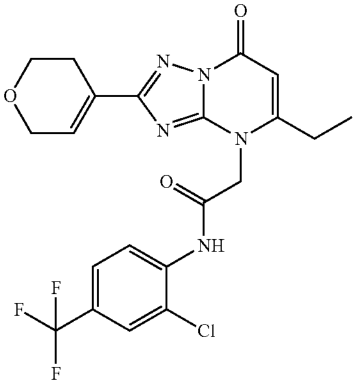 [SMILES: CCc1cc(=O)n2nc(C3=CCOCC3)nc2n1CC(=O)Nc1ccc(C(F)(F)F)cc1Cl]

2-(2-Bromo-5-ethyl-7-oxo-[1,2,4]triazolo[1,5-a]pyrimidin-4 (7H)-yl)-N-(2-chloro-4-(trifluoromethyl)phenyl)acetamide (14.0 g, 29.2 mmol), $K_3PO_4$ (18.6 g, 88.0 mmol) and $Pd(dppf)Cl_2 \cdot DCM$ (1.19 g, 1.46 mmol) were mixed at RT, evacuated and purged with argon several times. 1,4-Dioxane (300 mL) and water (150 mL) were added and the RM was evacuated and purged with argon several times. 2-(3,6-Dihydro-2H-pyran-4-yl)-4,4,5,5-tetramethyl-1,3,2-dioxaborolane (7.99 g, 38.0 mmol) was added and the RM was stirred at 80° C. for 1 hour. The RM was concentrated under reduced pressure. The residue was extracted with 10% MeOH in DCM (4×400 mL) and water (2×150 mL). The combined organic layers were dried through a phase separator and the filtrate was concentrated to half volume under reduced pressure. ISOLUTE® Si-Thiol (15.0 g) was added and the suspension was stirred for 30 minutes, the solid was filtered and washed sequentially with DCM/MeOH, 1,4-dioxane, warm MeOH and warm EtOH. The filtrates were concentrated under reduced pressure to give 2 batches of the title compound as a white solid and as a brown solid.

LC-MS: Rt=0.96 min; MS m/z $[M+H]^+$ 482.2/484.2, m/z $[M-H]^-$ 480.3/482.3; UPLC-MS 1

Step 4: 2-(6-bromo-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl) acetamide

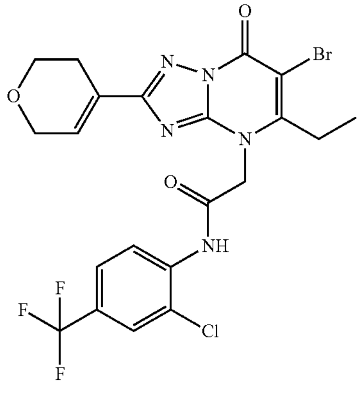 [SMILES: CCc1c(Br)c(=O)n2nc(C3=CCOCC3)nc2n1CC(=O)Nc1ccc(C(F)(F)F)cc1Cl]

N-(2-chloro-4-(trifluoromethyl)phenyl)-2-(2-(3,6-dihydro-2H-pyran-4-yl)-5-ethyl-7-oxo-[1,2,4]triazolo[1,5-a]pyrimidin-4 (7H)-yl)acetamide (1.20 g, 2.49 mmol) and NBS (488 mg, 2.74 mmol) were suspended in ACN (50 mL) and the RM was stirred at RT for 19.5 hours.

The RM was quenched with water and extracted with DCM (3×150 mL). The organic layer was dried through a phase separator and concentrated under reduced pressure. The crude product was adsorbed onto Isolute and purified by column chromatography (RediSep Column: Silica 40 g, eluent DCM:DCM/MeOH (8/2) 100:0 to 50:50). The product containing fractions were combined, concentrated and dried under HV to give a beige solid. The beige solid was adsorbed onto Isolute and purified by column chromatography (RediSep Column: Silica 40 g, eluent heptane:EtOAc 100:0 to 0:100, then DCM:DCM/MeOH (8/2) 50:50 to 0:100). The product containing fractions were combined, concentrated and dried under HV to give the title compound as a pale beige solid.

LC-MS: Rt=1.07 min; MS m/z $[M+H]^+$ 560.1/562.1/564.0, m/z $[M-H]^-$ 558.1/560.1/562.0; UPLC-MS 1

Step 5: tert-butyl 5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate

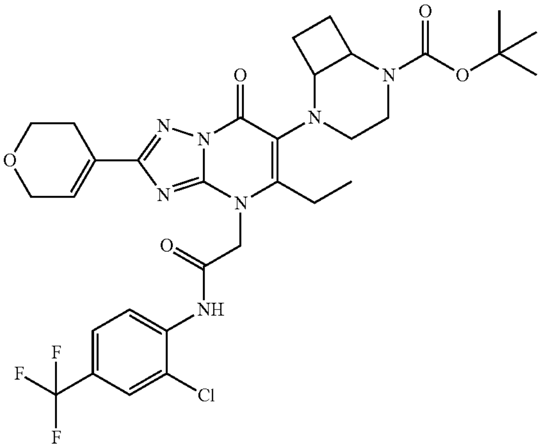 [SMILES: CCc1c(N2CCN(C(=O)OC(C)(C)C)C3CCC32)c(=O)n2nc(C3=CCOCC3)nc2n1CC(=O)Nc1ccc(C(F)(F)F)cc1Cl]

2-(6-Bromo-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (400 mg, 713 μmol), tert-butyl 2,5-diazabicyclo[4.2.0]octane-2-carboxylate (1.51 g, 7.13 mmol) and $AgBF_4$ (140 mg, 713 μmol) were mixed in DMSO (6 mL) and the RM was stirred at 120° C. in a sealed MW vial for 23 hours. The RM was cooled to RT. The RM was extracted with DCM (4×60 mL), aq $NaHCO_3$ (2×30 mL) and brine (30 mL). The organic layer was dried through a phase separator and concentrated under reduced pressure to give a brown oil. The crude product was adsorbed onto Isolute and purified by column chromatography (RediSep Column: Silica 40 g, eluent heptane:EtOAc 100:0 to 0:100). The product containing fractions were combined, concentrated and dried under HV to give a bright beige solid.

Chiral separation of rac-tert-butyl 5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate: Preparative chiral SFC (instrument: Sepiatec Prep SFC100; column: OVEN3 Chiralpak IB-N 250×30 mm, 5 μm; eluent: A: 35% [IPA+0.1% $NH_3$] B:65% scCO2; flow rate: 80.0 mL/min; detection: 210 nm; back pressure: 120 bar; injection volume: 1 mL; Gradient: isocratic)

Intermediate CN: tert-butyl (1R,6R)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate

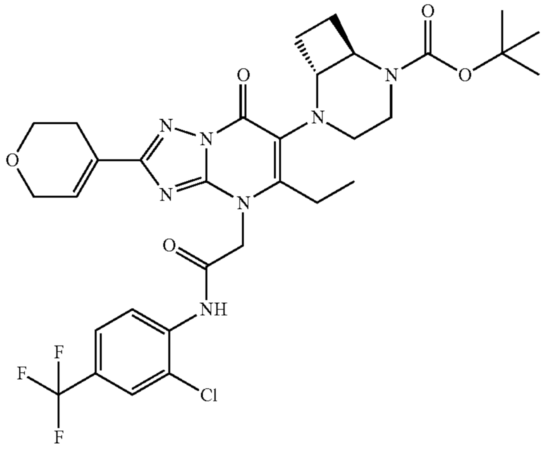 [SMILES: CCc1c(N2CCN(C(=O)OC(C)(C)C)[C@@H]3CC[C@H]32)c(=O)n2nc(C3=CCOCC3)nc2n1CC(=O)Nc1ccc(C(F)(F)F)cc1Cl]

First Eluting Stereoisomer

Chiral HPLC (C-HPLC 10): Rt=2.1 min, 97% ee

LC-MS: Rt=1.38 min; MS m/z $[M+H]^+$ 692.3/694.3, m/z $[M-H]^-$ 690.4/692.4; UPLC-MS 1

Intermediate CO: tert-butyl (1S,6S)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate

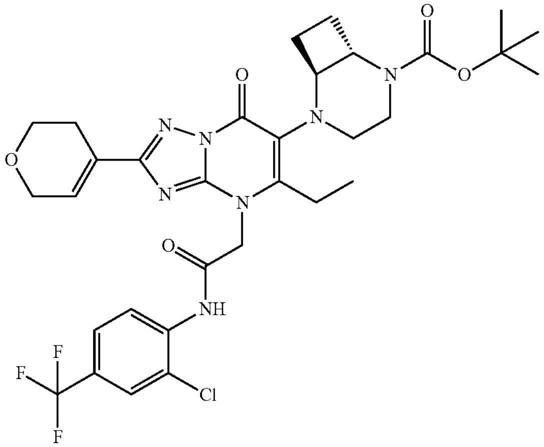

1S,6S

Second Eluting Stereoisomer

Chiral HPLC (C-HPLC 10): Rt=2.6 min, 95% ee

LC-MS: Rt=1.38 min; MS m/z $[M+H]^+$ 692.3/694.2, m/z $[M-H]^-$ 690.3/692.3; UPLC-MS 1

Intermediate CP: 2-(6-((1R,6R)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide

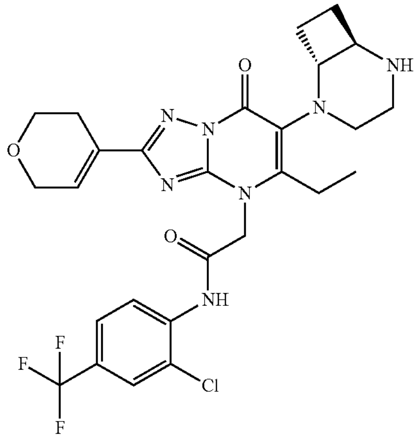

1R,6R

Tert-butyl (1R,6R)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate (Intermediate CN) (first eluting stereoisomer—150 mg, 217 μmol) was dissolved in DCM (3.1 mL) at RT. TFA (334 μL, 4.33 mmol) was added and the RM was stirred at RT for 2 hours. The RM was concentrated under reduced pressure and dried under HV to give the title compound trifluoroacetate salt as a bright brown solid.

LC-MS: Rt=0.78 min; MS m/z $[M+H]^+$ 592.3/594.3, m/z $[M-H]^-$ 590.2/592.2; UPLC-MS 1

Intermediate CQ: 2-(6-((1S,6S)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide

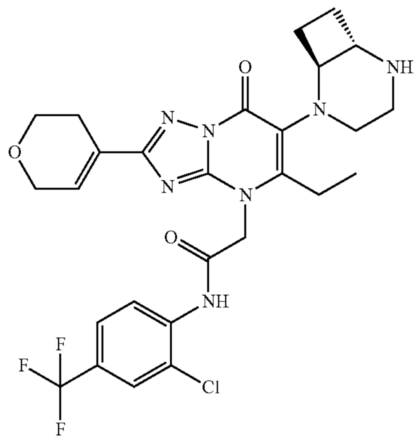

1S,6S

Tert-butyl (1S,6S)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate (Intermediate CO) (second eluting stereoisomer—128 mg, 185 μmol) was dissolved in DCM (2.6 mL) at RT. TFA (285 μL, 3.70 mmol) was added and the RM was stirred at RT for 1.25 hours. The RM was concentrated under reduced pressure and dried under HV to give the title compound trifluoroacetate salt as a bright brown solid.

LC-MS: Rt=0.79 min; MS m/z $[M+H]^+$ 592.3/594.2, m/z $[M-H]^-$ 590.3/592.2; UPLC-MS 1

Scheme 11 general overview of intermediates of route X

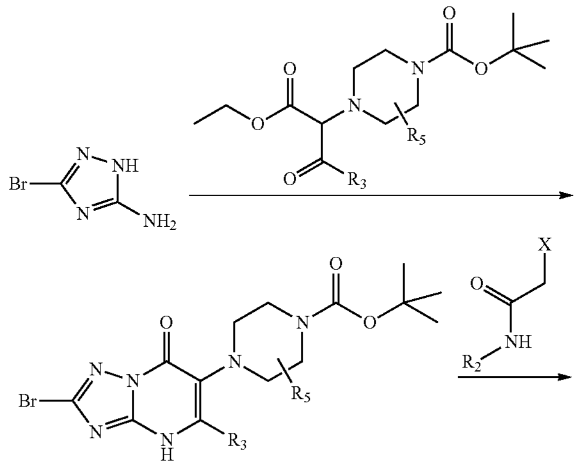

-continued

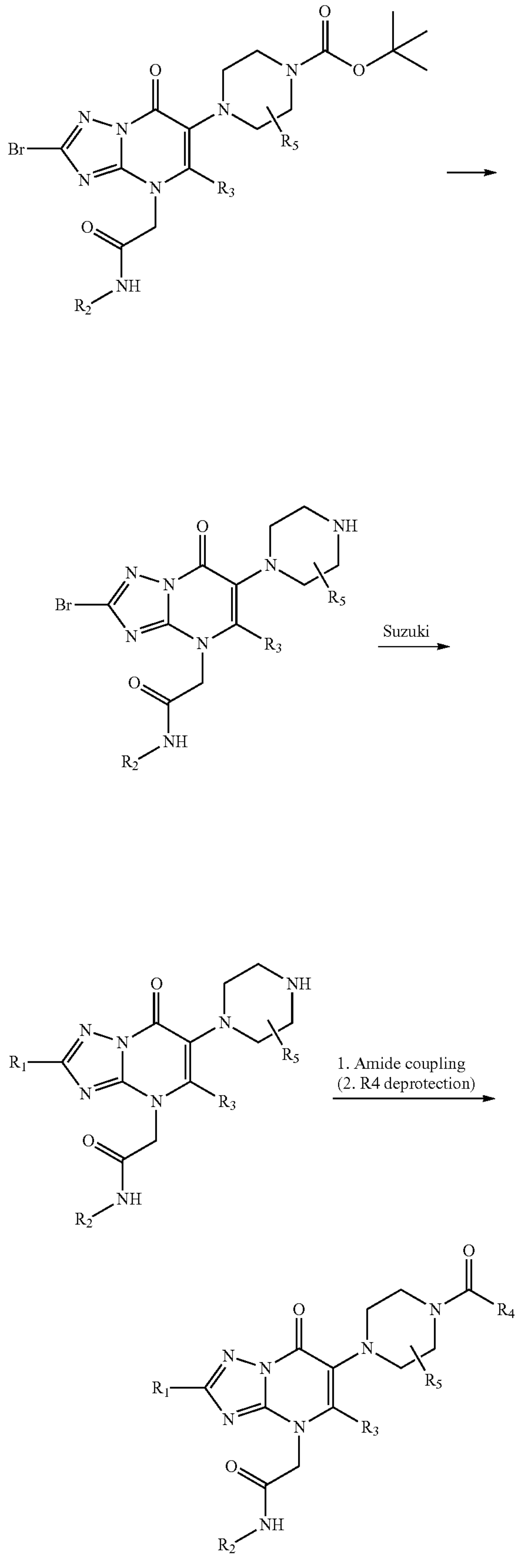

Intermediate CR: tert-butyl 4-(5-methyl-7-oxo-4-(2-oxo-2-((4-(trifluoromethyl)phenyl)amino)ethyl)-6-(piperazin-1-yl)-4,7-dihydro-[1,2,4]triazolo[1,5-a]pyrimidin-2-yl)-3,6-dihydropyridine-1 (2H)-carboxylate Step 1: tert-butyl 4-(2-bromo-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate

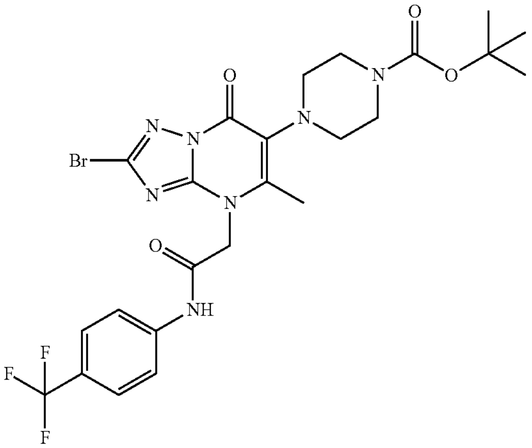 [SMILES: Cc1c(N2CCN(C(=O)OC(C)(C)C)CC2)c(=O)n2nc(Br)nc2n1CC(=O)Nc1ccc(C(F)(F)F)cc1]

Tert-butyl 4-(2-bromo-5-methyl-7-oxo-4,7-dihydro-[1,2,4]triazolo[1,5-a]pyrimidin-6-yl)piperazine-1-carboxylate (Intermediate BM) (4.00 g, 9.68 mmol) and 2-bromo-N-(4-(trifluoromethyl)phenyl)acetamide (3.28 g, 11.6 mmol) were mixed with DMF (25 mL) at RT. DIPEA (5.07 mL, 29.0 mmol) was added and the RM was stirred at 85° C. for 2.3 hours. The RM was cooled to RT and water (50 mL) was added slowly. The suspension was stirred at RT. Then it was cooled to 0° C. and filtered. The cake was washed with water and dried to give the title compound.

LC-MS: Rt=1.24 min; MS m/z $[M+H\text{-}Boc]^+$ 514.1/516.1, m/z $[M-H]^-$ 612.2/614.2; UPLC-MS 8

Step 2: 2-(2-bromo-5-methyl-7-oxo-6-(piperazin-1-yl)-[1,2,4]triazolo[1,5-a]pyrimidin-4 (7H)-yl)-N-(4-(trifluoromethyl)phenyl)acetamide

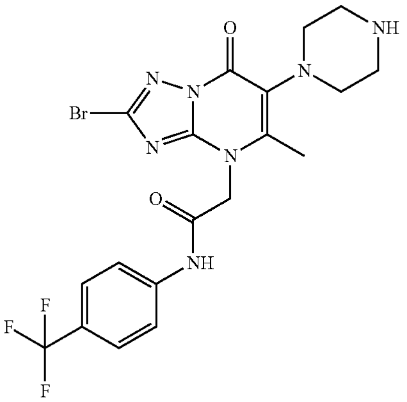 [SMILES: Cc1c(N2CCNCC2)c(=O)n2nc(Br)nc2n1CC(=O)Nc1ccc(C(F)(F)F)cc1]

Tert-butyl 4-(2-bromo-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperazine-1-carboxylate (5.67 g, 9.23 mmol) was mixed with DCM (25 mL). TFA (14.2 mL, 185 mmol) was added and the RM was stirred at RT for 40 minutes. The RM was concentrated under reduced pressure, redissolved in DCM and concentrated under reduced pressure again. This was performed three times. The resulting oil was dried under HV, extracted three times with EtOAc, once with aq sat $NaHCO_3$ and twice with brine. The combined organic layers were dried through a phase separator and concentrated under reduced pressure. The resulting brown solid was suspended in $Et_2O$ and sonicated. Then it was filtered and washed with $Et_2O$ to give the title compound as a bright brown solid.

LC-MS: Rt=0.78 min; MS m/z $[M+H]^+$ 514.1/516.1, m/z $[M-H]^-$ 512.0/514.0; UPLC-MS 8

Step 3: tert-butyl 4-(5-methyl-7-oxo-4-(2-oxo-2-((4-(trifluoromethyl)phenyl)amino)ethyl)-6-(piperazin-1-yl)-4,7-dihydro-[1,2,4]triazolo[1,5-a]pyrimidin-2-yl)-3,6-dihydropyridine-1 (2H)-carboxylate

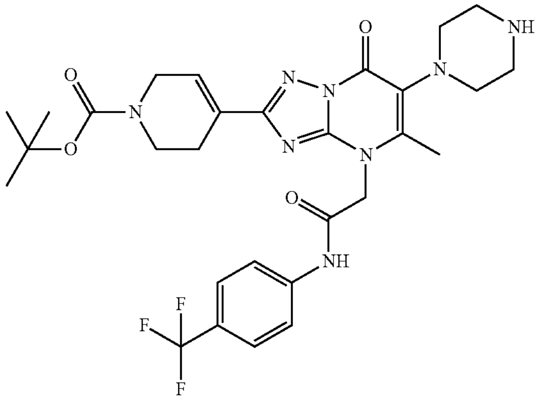 [SMILES: Cc1c(N2CCNCC2)c(=O)n2nc(C3=CCN(C(=O)OC(C)(C)C)CC3)nc2n1CC(=O)Nc1ccc(C(F)(F)F)cc1]

2-(2-Bromo-5-methyl-7-oxo-6-(piperazin-1-yl)-[1,2,4]triazolo[1,5-a]pyrimidin-4 (7H)-yl)-N-(4-(trifluoromethyl)phenyl)acetamide (500 mg, 924 μmol), tert-butyl 4-(4,4,5,5-tetramethyl-1,3,2-dioxaborolan-2-yl)-3,6-dihydropyridine-1 (2H)-carboxylate (376 mg, 1.15 mmol), XPhos Pd G3 (39.1 mg, 46.0 μmol), 1,4-dioxane (4.2 mL) and $K_3PO_4$ 1M in water (2.77 mL, 2.77 mmol) were mixed. The RM was vacuumed and purged with argon several times. Then it was stirred at 90° C. for 1.5 hours. The RM was cooled to RT and the 1,4-dioxane was removed under reduced pressure. The residue was extracted with EtOAc (3×50 mL), water (2×10 mL) and brine (2×5 mL). The organic layer was dried through a phase separator and concentrated under reduced pressure. The residue was dissolved in DCM/MeOH and ISOLUTE® Si-Thiol (750 mg) was added. The suspension was stirred for 20 minutes, then it was filtered and the cake was washed with DCM and MeOH. The filtrate was concentrated under reduced pressure. The residue was suspended in $Et_2O$, sonicated and filtered. The solid was dried under HV to give the title compound as a beige solid. LC-MS: Rt=0.99 min; MS m/z $[M+H]^+$ 617.3, m/z $[M-H]^-$ 615.2; UPLC-MS 4

Scheme 12 general overview of intermediates of route XI
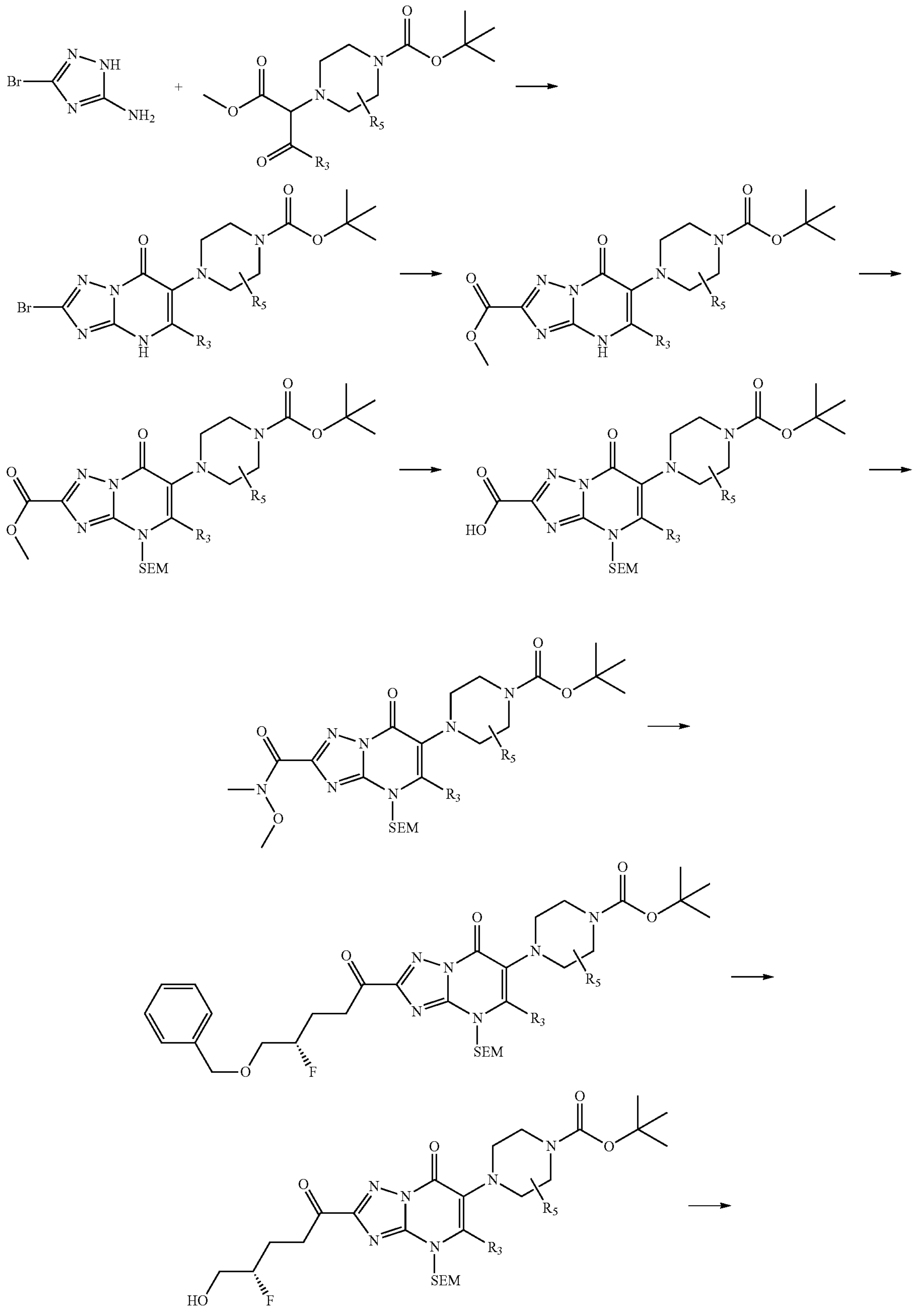

-continued

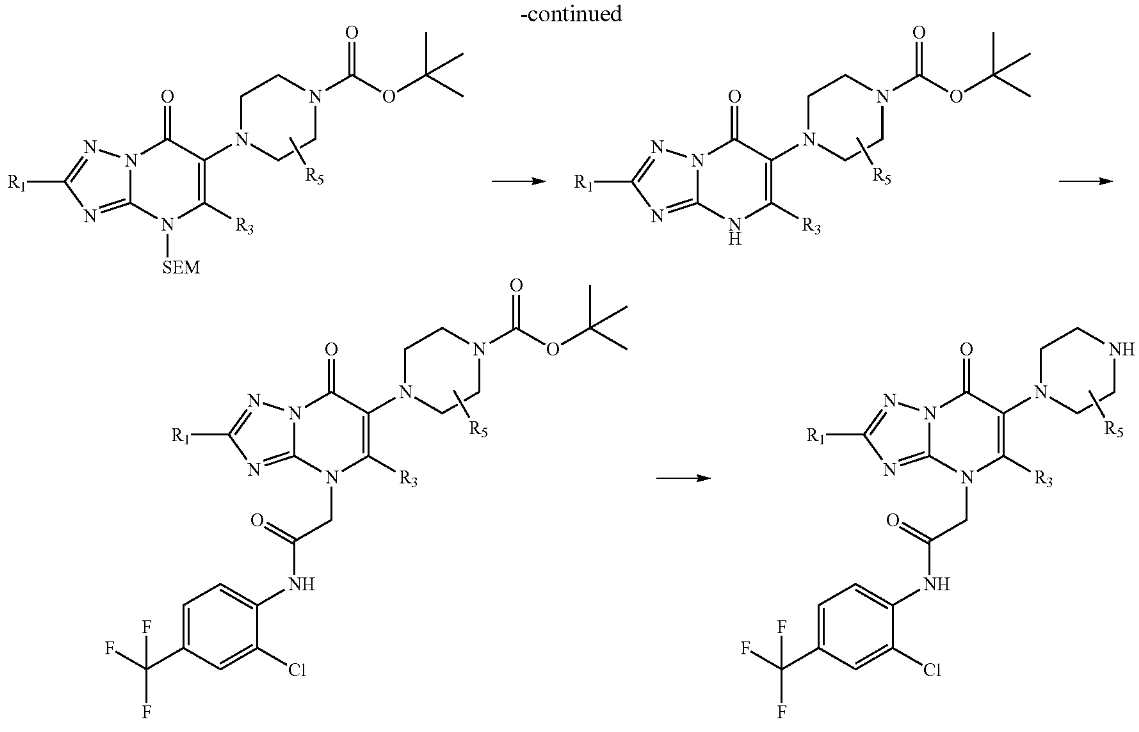

Intermediate CS: (S)—N-(2-chloro-4-(trifluoromethyl)phenyl)-2-(5-ethyl-2-(3-fluoro-3,4-dihydro-2H-pyran-6-yl)-7-oxo-6-(piperazin-1-yl)-[1,2,4]triazolo[1,5-a]pyrimidin-4 (7H)-yl)acetamide Step 1: methyl 6-(4-(tert-butoxycarbonyl)piperazin-1-yl)-5-ethyl-7-oxo-4,7-dihydro-[1,2,4]triazolo[1,5-a]pyrimidine-2-carboxylate

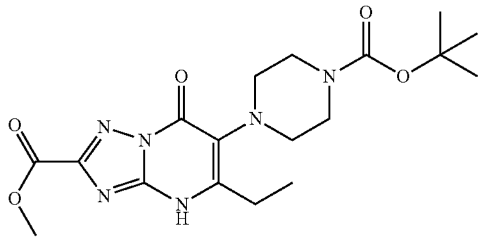 [SMILES: CCc1[nH]c2nc(C(=O)OC)nn2c(=O)c1N1CCN(C(=O)OC(C)(C)C)CC1]

Tert-butyl 4-(2-bromo-5-ethyl-7-oxo-4,7-dihydro-[1,2,4]triazolo[1,5-a]pyrimidin-6-yl)piperazine-1-carboxylate (Intermediate X) (6.00 g, 14.0 mmol), Pd(dppf)$Cl_2$·DCM (573 mg, 702 μmol), 1,1'-ferrocenediyl-bis(diphenylphosphin (389 mg, 702 μmol) and MeOH (140 mL) were mixed. Then $Et_3N$ (3.91 mL, 28.1 mmol) was added. The RM was set under CO gas (15 bar) and stirred at 100° C. for 22 hours. The red yellow fine suspension was filtered. The orange filter cake was washed with DCM and the filtrate was concentrated under reduced pressure. The crude product was purified by column chromatography (Silica gel column: Silica 120 g, eluent DCM:MeOH 100:0 to 90:10). The product containing fractions were combined and concentrated under reduced pressure (no separation). The crude product was purified by column chromatography (Silica gel column: Silica 120 g, eluent TBME:MeOH 100:0 to 60:40). The product containing fractions were combined and concentrated under reduced pressure to give the title compound.

LC-MS: Rt=0.84 min; MS m/z $[M+H]^+$ 407.5, m/z $[M-H]^-$ 405.5; UPLC-MS 1

Step 2: methyl 6-(4-(tert-butoxycarbonyl)piperazin-1-yl)-5-ethyl-7-oxo-4-((2-(trimethylsilyl)ethoxy)methyl)-4,7-dihydro-[1,2,4]triazolo[1,5-a]pyrimidine-2-carboxylate

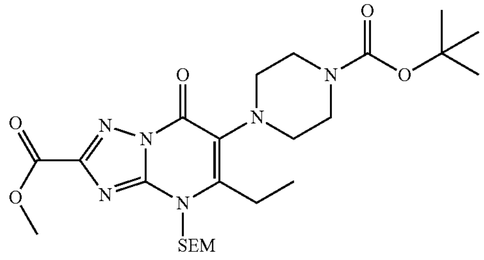 [SMILES: CCc1c(N2CCN(C(=O)OC(C)(C)C)CC2)c(=O)n2nc(C(=O)OC)nc2n1COCC[Si](C)(C)C]

A 300 mL 4 neck reaction flask with mechanical stirrer, internal thermometer, dropping funnel and nitrogen inlet was charged with methyl 6-(4-(tert-butoxycarbonyl)piperazin-1-yl)-5-ethyl-7-oxo-4,7-dihydro-[1,2,4]triazolo[1,5-a]pyrimidine-2-carboxylate (7.08 g, 13.2 mmol) (first as a solid the rest was added with the solvent). THF (100 mL) and DMF (20 mL) were added and the brown suspension was cooled in an ice bath under nitrogen. After 10 minutes sodium hydride (980 mg, 24.5 mmol) was added in portions. After another 30 minutes in the ice bath a solution of (2-(chloromethoxy)ethyl)trimethylsilane (4.34 mL, 24.5 mmol) in THF (20 mL) was added within 5 minutes. The ice bath was removed and the mixture was stirred at RT for 2 hours. The RM was cooled in an ice bath and stirred overnight. Additional sodium hydride (490 mg, 12.3 mmol) was added at RT and the RM was stirred for 4.5 hours. (2-(chloromethoxy)ethyl)trimethylsilane (2.17 mL, 12.3 mmol) was added and the RM was stirred for 40 minutes. The RM was slowly poured into an aq solution of water/ice (1:1) containing citric acid (9.67 g, 50.3 mmol). TBME (200 mL) was added and the phases were separated. A fine purple slurry remained between the phases that was poured into the aqueous phase, which was extracted with TBME (3×200 mL). The combined organic phases were washed with brine (100 mL) and dried over $MgSO_4$ and concentrated under reduced pressure to give a purple, viscous oil. The crude product was purified by column chromatography (Silica gel column: Silica 120 g, eluent heptane:EtOAc). The product containing fractions were combined and concentrated under reduced pressure to give the title compound as an isomeric mixture (SEM group also attached to 5-membered ring) as a white foam.

LC-MS: Rt=1.37/1.49 min; MS m/z $[M+H]^+$ 537.3; UPLC-MS 1

Step 3: 6-(4-(tert-butoxycarbonyl)piperazin-1-yl)-5-ethyl-7-oxo-4-((2-(trimethylsilyl)ethoxy)methyl)-4,7-dihydro-[1,2,4]triazolo[1,5-a]pyrimidine-2-carboxylic acid

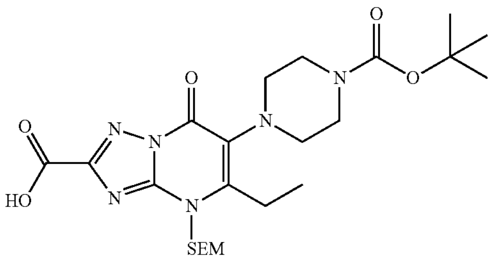 [SMILES: CCc1c(N2CCN(C(=O)OC(C)(C)C)CC2)c(=O)n2nc(C(=O)O)nc2n1COCC[Si](C)(C)C]

Methyl 6-(4-(tert-butoxycarbonyl)piperazin-1-yl)-5-ethyl-7-oxo-4-((2-(trimethylsilyl)ethoxy)methyl)-4,7-dihydro-[1,2,4]triazolo[1,5-a]pyrimidine-2-carboxylate (3.34 g, 6.09 mmol) was dissolved in THF (1.5 mL) and cooled in an ice bath. After 10 minutes, a solution of sodium hydroxide (375 mg, 9.37 mmol) in water (1.5 mL) was added. The mixture was stirred in the ice bath for 1.2 hours. The ice bath was removed and the RM was stirred at RT for 2 hours. Addition of a solution of sodium hydroxide (621 mg, 15.5 mmol) in water (2 mL). The RM was stirred at RT for 3.75 hours. Addition of HCl 1M (25.0 mL, 25.0 mmol) until pH=7. The solvent was evaporated at 40° C. in vacuo, a gum was formed that was dissolved in EtOAc (50 mL). After phase separation the aqueous phase was extracted with EtOAc (3×20 mL). The combined organic phases were dried over $MgSO_4$, filtered and concentrated under reduced pressure to give an isomeric mixture of the title compound as a white powder.

LC-MS: Rt=1.18/1.22 min; MS m/z $[M+H]^+$ 523.3, m/z $[M-H]^-$ 521.4; UPLC-MS 1

Step 4: tert-butyl 4-(5-ethyl-2-(methoxy(methyl)carbamoyl)-7-oxo-4-((2-(trimethylsilyl)ethoxy)methyl)-4,7-dihydro-[1,2,4]triazolo[1,5-a]pyrimidin-6-yl)piperazine-1-carboxylate

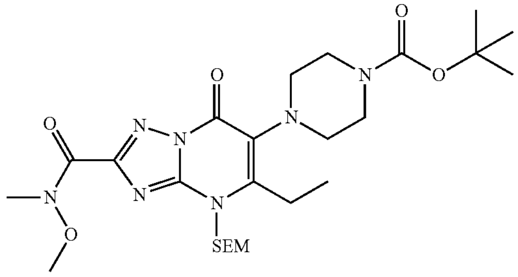 [SMILES: CCc1c(N2CCN(C(=O)OC(C)(C)C)CC2)c(=O)n2nc(C(=O)N(C)OC)nc2n1COCC[Si](C)(C)C]

A solution of 6-(4-(tert-butoxycarbonyl)piperazin-1-yl)-5-ethyl-7-oxo-4-((2-(trimethylsilyl)ethoxy)methyl)-4,7-dihydro-[1,2,4]triazolo[1,5-a]pyrimidine-2-carboxylic acid (2.93 g, 5.61 mmol), $Et_3N$ (1.88 mL, 13.5 mmol) and N,O-dimethylhydroxylamine hydrochloride (1.09 g, 11.2 mmol) in dry DCM (50 mL) was cooled in an ice bath for 10 minutes, then slowly $T_3P$ 50% in EtOAc (4.28 g, 6.73 mmol) was added. The ice bath was removed and the RM was stirred at RT for 3.5 hours. The RM was cooled in an ice bath and quenched with sat. $NaHCO_3$ (40 mL). After phase separation, the aqueous phase was extracted with DCM (2×10 mL). The combined DCM phases were washed with aqueous citric acid followed by brine. The organic phase was dried over $MgSO_4$, filtered and concentrated to give a pale brown foam. The crude product was purified by column chromatography (Silica gel column: Silica 120 g, eluent heptane:EtOAc 70:30 to 0:100). The product containing fractions were combined and concentrated under reduced pressure to give the title compound as an isomeric mixture.

LC-MS: Rt=1.34/1.49 min; MS m/z $[M+H]^+$ 566.5/567.5; UPLC-MS 1

Step 5: tert-butyl (S)-4-(2-(5-(benzyloxy)-4-fluoropentanoyl)-5-ethyl-7-oxo-4-((2-(trimethylsilyl)ethoxy)methyl)-4,7-dihydro-[1,2,4]triazolo[1,5-a]pyrimidin-6-yl)piperazine-1-carboxylate

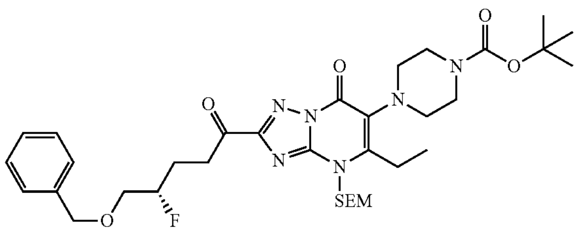 [SMILES: CCc1c(N2CCN(C(=O)OC(C)(C)C)CC2)c(=O)n2nc(C(=O)CC[C@H](F)COCc3ccccc3)nc2n1COCC[Si](C)(C)C]

(S)-((2-fluoro-4-iodobutoxy)methyl)benzene (Intermediate EG) (380 mg, 1.23 mmol) and tert-butyl 4-(5-ethyl-2-(methoxy(methyl)carbamoyl)-7-oxo-4-((2-(trimethylsilyl)ethoxy)methyl)-4,7-dihydro-[1,2,4]triazolo[1,5-a]pyrimidin-6-yl)piperazine-1-carboxylate (250 mg, 411 μmol) was dissolved in THF (19 mL) and pentane (19 mL). The colorless clear RM was cooled in a liquid nitrogen/EtOH bath to ca −100° C. Then tert-butyllithium 1.7M in pentane (1.45 mL, 2.47 mmol) was added dropwise within 10 minutes (using a syringe pump with a steel cannula which is immersed in the solution 145 μL/min). The RM was stirred at ca −100° C. for 60 minutes. The −100° C. cold RM was poured rapidly into a vigorously stirred mixture of 10% citric acid solution (50 mL) and TBME (50 mL) and stirred for 5 minutes. The phases were separated. The organic phase was extracted once with brine (50 mL). The aqueous phases was extracted with TBME (2×25 mL). The combined organic phases were dried over anhydrous $Na_2SO_4$, filtered and concentrated in vacuo at 45° C. to give a yellow resin. The crude product was purified by column chromatography (Silica gel column: Silica 40 g, eluent heptane:EtOAc 90:10 to 0:100). The product containing fractions were combined and concentrated under reduced pressure to give the title compound as a colourless resin.

LC-MS: Rt=1.62 min; MS m/z $[M+H-Boc]^+$ 587.5, m/z $[M+H]^+$ 687.6; UPLC-MS 1

Step 6: tert-butyl (S)-4-(5-ethyl-2-(4-fluoro-5-hydroxypentanoyl)-7-oxo-4-((2-(trimethylsilyl)ethoxy)methyl)-4,7-dihydro-[1,2,4]triazolo[1,5-a]pyrimidin-6-yl)piperazine-1-carboxylate

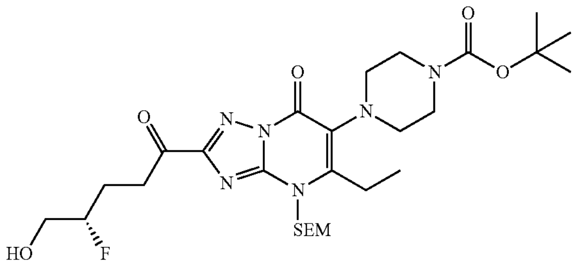 [SMILES: CCc1c(N2CCN(C(=O)OC(C)(C)C)CC2)c(=O)n2nc(C(=O)CC[C@H](F)CO)nc2n1COCC[Si](C)(C)C]

To a colorless solution of tert-butyl (S)-4-(2-(5-(benzyloxy)-4-fluoropentanoyl)-5-ethyl-7-oxo-4-((2-(trimethylsilyl)ethoxy)methyl)-4,7-dihydro-[1,2,4]triazolo[1,5-a]pyrimidin-6-yl)piperazine-1-carboxylate (170 mg, 247 μmol) in MeOH (8 mL) was added 10% palladium on carbon (26.3 mg, 25.0 μmol). The RM was hydrogenated at RT for 45 minutes. To the RM was added further palladium on carbon 10% (52.7 mg, 49.0 μmol) and hydrogenated at RT overnight. The RM was filtered through a syringe-filter, washed with MeOH and concentrated in vacuo at 45° C. to give the title compound as colourless resin.

LC-MS: Rt=1.34 min; MS m/z $[M+H-Boc]^+$ 497.4; UPLC-MS 1

Step 7: tert-butyl (S)-4-(5-ethyl-2-(3-fluoro-3,4-dihydro-2H-pyran-6-yl)-7-oxo-4-((2-(trimethylsilyl)ethoxy)methyl)-4,7-dihydro-[1,2,4]triazolo[1,5-a]pyrimidin-6-yl)piperazine-1-carboxylate

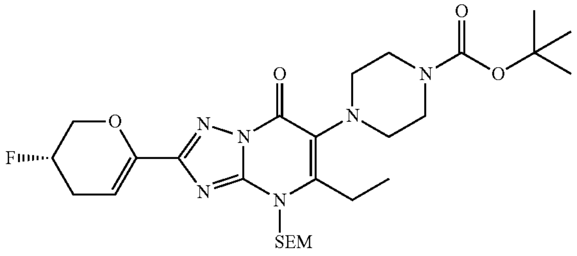 [SMILES: CCc1c(N2CCN(C(=O)OC(C)(C)C)CC2)c(=O)n2nc(C3=CC[C@H](F)CO3)nc2n1COCC[Si](C)(C)C]

To a solution of tert-butyl (S)-4-(5-ethyl-2-(4-fluoro-5-hydroxypentanoyl)-7-oxo-4-((2-(trimethylsilyl)ethoxy)methyl)-4,7-dihydro-[1,2,4]triazolo[1,5-a]pyrimidin-6-yl)piperazine-1-carboxylate (127 mg, 160 μmol) in toluene (6 mL), p-toluenesulfonic acid monohydrate (27.3 mg, 144 μmol) and Molecular sieves 3A (800 mg, 160 μmol) were added. The RM was heated to 45° C. and stirred for 20 hours. The RM was extracted with a pH 6.0 buffer (20 mL) and DCM (30 mL). The aqueous phase was extracted with DCM (3×20 mL). The combined organic phases were dried over anhydrous $Na_2SO_4$, filtered and concentrated in vacuo at 45° C. to give a pale yellow resin. The crude product was purified by column chromatography (Silica gel column: Silica 40 g, eluent DCM:DCM/MeOH (9/1) 100:0 to 20:80). The product containing fractions were combined and concentrated under reduced pressure to give the title compound as a colourless resin as well as 2 batches of tert-butyl (S)-4-(5-ethyl-2-(3-fluoro-3,4-dihydro-2H-pyran-6-yl)-7-oxo-4,7-dihydro-[1,2,4]triazolo[1,5-a]pyrimidin-6-yl)piperazine-1-carboxylate.

LC-MS: Rt=1.43 min; MS m/z $[M+H]^+$ 479.4; UPLC-MS 1

Step 8: tert-butyl (S)-4-(5-ethyl-2-(3-fluoro-3,4-dihydro-2H-pyran-6-yl)-7-oxo-4,7-dihydro-[1,2,4]triazolo[1,5-a]pyrimidin-6-yl)piperazine-1-carboxylate

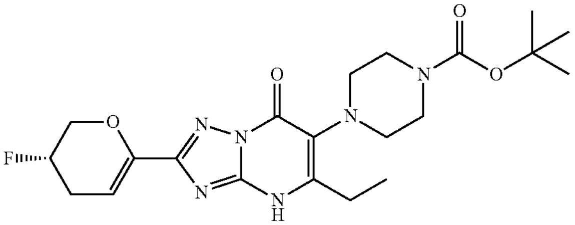 [SMILES: CCc1[nH]c2nc(C3=CC[C@H](F)CO3)nn2c(=O)c1N1CCN(C(=O)OC(C)(C)C)CC1]

To a colorless solution of tert-butyl (S)-4-(5-ethyl-2-(3-fluoro-3,4-dihydro-2H-pyran-6-yl)-7-oxo-4-((2-(trimethylsilyl)ethoxy)methyl)-4,7-dihydro-[1,2,4]triazolo[1,5-a]pyrimidin-6-yl)piperazine-1-carboxylate (19.0 mg, 18.0 μmol) in THF (1 mL) was added tetrabutylammonium fluoride 1 M in THF (90.0 μL, 90.0 μmol). The RM was heated to 40° C. and stirred overnight. The RM was evaporated in vacuo at 45° C. to give a pale brown oil. The crude product was purified by column chromatography (Silica gel column: Silica 40 g, eluent heptane:EtOAc 80:20 to 0:100, then DCM:DCM/MeOH (9/1) 100:0 to 0:100). The product containing fractions were combined and concentrated under reduced pressure to give the title compound as a white solid.

LC-MS: Rt=0.88 min; MS m/z $[M+H]^+$ 449.6, m/z $[M-H]^-$ 447.5; UPLC-MS 1

Step 9: tert-butyl (S)-4-(4-(2-((2-chloro-4-(trifluoromethyl)phenyl)amino)-2-oxoethyl)-5-ethyl-2-(3-fluoro-3,4-dihydro-2H-pyran-6-yl)-7-oxo-4,7-dihydro-[1,2,4]triazolo[1,5-a]pyrimidin-6-yl) piperazine-1-carboxylate

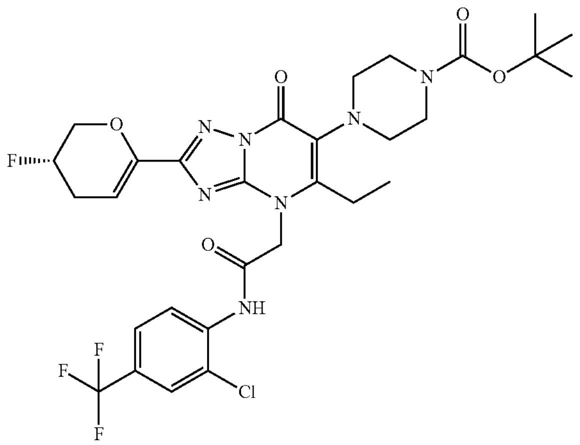 [SMILES: CCc1c(N2CCN(C(=O)OC(C)(C)C)CC2)c(=O)n2nc(C3=CC[C@H](F)CO3)nc2n1CC(=O)Nc1ccc(C(F)(F)F)cc1Cl]

To a pale yellow solution of tert-butyl (S)-4-(5-ethyl-2-(3-fluoro-3,4-dihydro-2H-pyran-6-yl)-7-oxo-4,7-dihydro-[1,2,4]triazolo[1,5-a]pyrimidin-6-yl)piperazine-1-carboxylate (35.0 mg, 78.0 μmol) and N-(2-chloro-4-(trifluoromethyl)phenyl)-2-iodoacetamide (Intermediate DL) (31.2 mg, 86.0 μmol) in 1,4-dioxane (5 mL) was added DIPEA (41.0 μL, 234 μmol). The RM was heated to 80° C. and stirred for 11 hours, then it was left to stand at RT overnight. DIPEA (41.0 μL, 234 μmol) was added again and the RM was stirred at 80° C. for 6 hours. The RM was concentrated in vacuo at 45° C. to give a pale brown resin (103 mg). The crude product was purified by column chromatography (Silica gel column: 40 g SNAP cartridge (Biotage), eluent heptane:EtOAc 80:20 to 0:100). The product containing fractions were combined and concentrated under reduced pressure to give the title compound as a pale brown residue.

LC-MS: Rt=1.31 min; MS m/z $[M+H-Boc]^+$ 584.3/586.3, m/z $[M-H]^-$ 682.4/684.4; UPLC-MS 1

Step 10: (S)—N-(2-chloro-4-(trifluoromethyl)phenyl)-2-(5-ethyl-2-(3-fluoro-3,4-dihydro-2H-pyran-6-yl)-7-oxo-6-(piperazin-1-yl)-[1,2,4]triazolo[1,5-a] pyrimidin-4 (7H)-yl)acetamide

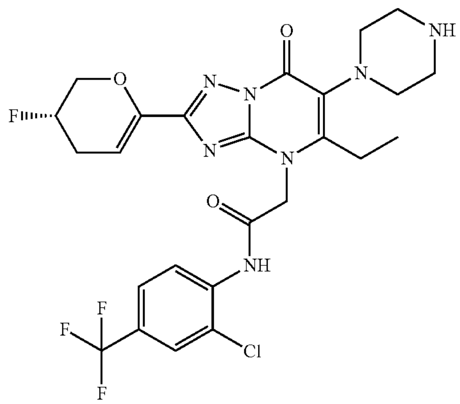 [SMILES: CCc1c(N2CCNCC2)c(=O)n2nc(C3=CC[C@H](F)CO3)nc2n1CC(=O)Nc1ccc(C(F)(F)F)cc1Cl]

To a solution of tert-butyl (S)-4-(4-(2-((2-chloro-4-(trifluoromethyl)phenyl)amino)-2-oxoethyl)-5-ethyl-2-(3-fluoro-3,4-dihydro-2H-pyran-6-yl)-7-oxo-4,7-dihydro-[1,2,4]triazolo[1,5-a]pyrimidin-6-yl)piperazine-1-carboxylate (42.0 mg, 53.4 μmol) in DCM (250 μL), TFA (247 μL, 3.21 mmol) was added and the RM was stirred at RT for 1 hour. The RM was concentrated in vacuo at 45° C. The residue was evaporated three times with DCM to give a yellow resin. The residue was diluted with DCM (10 mL) and extracted once with aq sat $NaHCO_3$ (10 mL). The aqueous phase was extracted with DCM (3×10 mL). The combined organic phases were dried over anhydrous $Na_2SO_4$, filtered and concentrated in vacuo at 45° C. to give a pale yellow resin. The crude product was purified by column chromatography (Silica gel column: 40 g SNAP cartridge (Biotage), eluent DCM:DCM/MeOH/$NH_3$ (85/15/1) 100:0 to 0:100). The product containing fractions were combined and concentrated under reduced pressure to give a colourless resin. The crude product was purified by column chromatography (Silica gel column: 24 g SNAP cartridge (Biotage), eluent DCM:DCM/MeOH/$NH_3$ (85/15/1) 100:0 to 0:100). The product containing fractions were combined and concentrated under reduced pressure to give the title compound as a pale yellow solid.

LC-MS: Rt=0.78 min; MS m/z $[M+H]^+$ 584.3/586.3, m/z $[M-H]^-$ 582.3/584.3; UPLC-MS 1

Preparation of Early Intermediates

Intermediate CT: perfluorophenyl 3-hydroxypicolinate

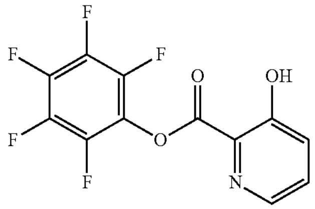 [SMILES: O=C(Oc1c(F)c(F)c(F)c(F)c1F)c1ncccc1O]

3-Hydroxypicolinic acid (8.00 g, 57.5 mmol) was suspended in DCM (50 mL). 2,3,4,5,6-pentafluorophenol (9.53 g, 51.8 mmol) and diisopropylmethanediimine (10.8 mL, 69.0 mmol) were added. The RM was stirred at RT for 12 hours, concentrated under reduced pressure and the crude product was purified by column chromatography (Silica gel column: Silica 40 g, eluent hexane:EtOAc 100:0 to 95:5). The product containing fractions were combined and concentrated under reduced pressure to give the title compound.

HPLC: Rt=5.97 min; HPLC 1

Intermediate CU: 3-(benzyloxy)-4-fluoropicolinic acid

Step 1: 2-chloro-4-fluoro-3-((4-methoxybenzyl)oxy)pyridine

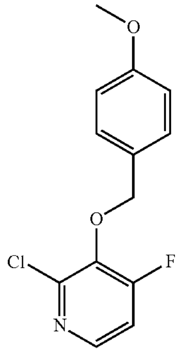 [SMILES: COc1ccc(COc2c(F)ccnc2Cl)cc1]

2-Chloro-4-fluoropyridin-3-ol (3.00 g, 19.3 mml) and $K_2CO_3$ (4.00 g, 29.0 mmol) were dissolved in DMF (55 mL). The RM was flushed with argon, 1-(chloromethyl)-4-methoxybenzene (2.15 mL, 21.3 mmol) was added and the RM was stirred at 60° C. for 4 hours. EtOAc (100 mL) was added and it was washed with water (2×50 mL) and brine (50 mL), dried over $Na_2SO_4$, filtered and evaporated. The crude product was purified by column chromatography (RediSep Column: Silica 80 g, eluent heptane/EtOAc 100:0 to 75:25). The product containing fractions were combined, concentrated under reduced pressure and dried under HV to give the title compound.

LC-MS: Rt=1.08 min; MS m/z $[M+H]^+$ 268.0/270.0; UPLC-MS 1

Step 2: methyl 4-fluoro-3-hydroxypicolinate

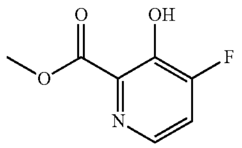

To a stirred and degassed solution of 2-chloro-4-fluoro-3-((4-methoxybenzyl)oxy)pyridine (3.44 g, 12.8 mmol) in $Et_3N$ (3.58 mL, 25.7 mmol) and MeOH (50 mL) was added $Pd(dppf)Cl_2 \cdot DCM$ (524 mg, 642 μmol) and the RM was stirred at 50° C. under 10 bars of CO until completion. The RM was filtered through celite and concentrated under reduced pressure. The crude product was purified by column chromatography (RediSep Column: Silica 40 g, eluent heptane:EtOAc 100:0 to 0:100). The product containing fractions were combined and concentrated under reduced pressure to give the title compound as a white solid.

LC-MS: Rt=0.37 min; MS m/z $[M+H]^+$ 172.1; UPLC-MS 1

Step 3: methyl 3-(benzyloxy)-4-fluoropicolinate

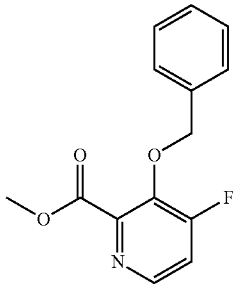 [SMILES: COC(=O)c1nccc(F)c1OCc1ccccc1]

To a stirred solution of methyl 4-fluoro-3-hydroxypicolinate (500 mg, 2.92 mmol) in DMF (5 mL) were added $K_2CO_3$ (606 mg, 4.38 mmol) and (bromomethyl)benzene (382 μL, 3.21 mmol) and reactants were stirred at RT for 14 hours. The RM was diluted with EtOAc/water, extracted with EtOAc and the organic layer was washed with water and brine, dried over $Na_2SO_4$ and concentrated under reduced pressure. The crude product was purified by column chromatography (RediSep Column: Silica 24 g, eluent heptane:EtOAc 100:0 to 50:50). The product containing fractions were combined and concentrated under reduced pressure to afford the title compound as a yellow oil.

LC-MS: Rt=0.89 min; MS m/z $[M+H]^+$ 262.0; UPLC-MS 1

Step 4: 3-(benzyloxy)-4-fluoropicolinic acid

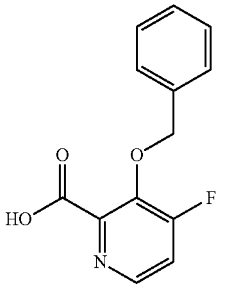 [SMILES: O=C(O)c1nccc(F)c1OCc1ccccc1]

To a stirred solution of methyl 3-(benzyloxy)-4-fluoropicolinate (750 mg, 2.87 mmol) in THF (5 mL) and MeOH (5 mL) was added NaOH 2N in water (5.00 mL, 10.0 mmol) at RT and the RM was stirred at RT for 30 minutes. THF and MeOH were removed under reduced pressure, then the resulting aqueous residue was acidified to pH 3 with 2N HCl and extracted three times with DCM. The combined organic layers were dried over $Na_2SO_4$ and concentrated under reduced pressure to give the title compound as a white solid.

LC-MS: Rt=0.58 min; MS m/z $[M+H]^+$ 248.1, m/z $[M-H]^-$ 246.1; UPLC-MS 1

Intermediate CV: 3-hydroxypicolinoyl chloride

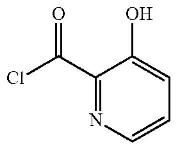

3-Hydroxypicolinic acid (12.0 g, 82.0 mmol) and sulfurous dichloride (121 mL, 1.64 mol) were mixed under argon at RT. The flask was equipped with a condenser and a drying tube ($CaCl_2$) and the suspension was stirred at RT for 5 days. Then it was filtered and the cake was washed several times with TBME. The solid was dried at 30° C. under HV and stored under argon.

Intermediate CW: 5-methoxy-6-methylpyrimidine-4-carboxylic acid

Step 1: 4-chloro-5-methoxy-6-methylpyrimidine

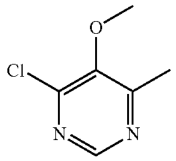

4,6-Dichloro-5-methoxypyrimidine (75.0 g, 419 mmol), methylboronic acid (26.4 g, 441 mmol) and $K_3PO_4$ (222 g, 1.05 mol), Pd(dppf)$Cl_2$·DCM (20.1 g, 24.6 mmol) were suspended in DME (300 mL). The RM was flushed with argon three times. The RM was heated at 85° C. for 18 hours. The RM was filtered through celite and the solution was concentrated under reduced pressure. The residue was dissolved in EtOAc (500 mL) and washed with aq sat $NaHCO_3$ (3×800 mL). The organic layer was collected, concentrated under reduced pressure and dried. The crude product was purified by column chromatography (silica column 60 mm×475 mm×50 mm, eluent heptane:EtOAc 50:1 to 20:1) to give the title compound as a solid.

HPLC: Rt=2.93 min; HPLC 4

Step 2: methyl 5-methoxy-6-methylpyrimidine-4-carboxylate

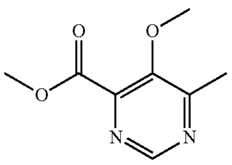

4-Chloro-5-methoxy-6-methylpyrimidine (24.0 g, 129 mmol), Pd(dppf)$Cl_2$·DCM (6.27 g, 7.68 mmol) and $Et_3N$ (35.5 mL, 256 mmol) were dissolved in DCM (600 mL). The RM was purged with CO for 3 times. The RM was heated at 60° C. under CO (0.3 PMa) for 18 hours. The RM was filtered through celite and the solution was concentrated under reduced pressure. The residue was purified by column chromatography (silica column 60 mm×475 mm×50 mm, eluent heptane:EtOAc 50: 1 to 30:1) to give the title compound as a solid.

HPLC: Rt=2.55 min; HPLC 4

Step 3: 5-methoxy-6-methylpyrimidine-4-carboxylic acid

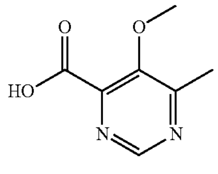

To a solution of methyl 5-methoxy-6-methylpyrimidine-4-carboxylate (15.0 g, 76.0 mmol) in THF (140 mL) and water (70 mL) was added LiOH·$H_2O$ (3.50 g, 83.0 mmol). The RM was stirred at RT for 16 hours. The RM was concentrated under reduced pressure to give the title compound as a lithium salt.

HPLC: Rt=2.10 min, HPLC 3

Intermediate CX: 3-(benzyloxy)-4-fluoro-6-methylpicolinic acid

Step 1: 2-bromo-6-methyl-4-nitropyridin-3-ol

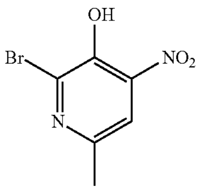

2-Bromo-6-methylpyridin-3-ol (15.0 g, 80.0 mmol) was mixed with $H_2SO_4$ (44.8 mL, 798 mmol) at 0° C. $HNO_3$ (66%) (6.03 mL, 88.0 mmol) was added dropwise within 12 minutes. The orange solution was stirred at 0° C. for 1 hour, then at RT for 3 hours. $HNO_3$ (66%) (1.10 mL, 16.0 mmol) was added and the reaction was stirred at RT for 3 hours. The RM was poured while vigorous stirring onto ice. The mixture was extracted with EtOAc (3×600 mL). The organic layer was washed with water (2×75 mL) and brine (2×75 mL), dried over $Na_2SO_4$, filtered and concentrated under reduced pressure. The residue was adsorbed onto Isolute and purified by column chromatography (RediSep Column: Silica 40 g, eluent DCM:DCM/MeOH (8/2) 100:0 to 0:100). The product containing fractions were combined and concentrated under reduced pressure to give the title compound as a yellow solid.

LC-MS: Rt=0.53 min; MS m/z $[M-H]^-$ 231.0/233.0; LC-MS 1

Step 2: 3-(benzyloxy)-2-bromo-6-methyl-4-nitropyridine

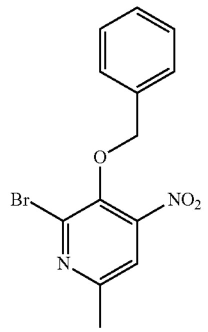 [SMILES: Cc1cc([N+](=O)[O-])c(OCc2ccccc2)c(Br)n1]

2-Bromo-6-methyl-4-nitropyridin-3-ol (10.4 g, 44.5 mmol) and $K_2CO_3$ (18.5 g, 134 mmol) were dissolved in DMF (110 mL) at RT under argon. (bromomethyl)benzene (11.7 g, 66.8 mmol) was added and the RM was stirred at 45° C. for 17 hours. The RM was cooled to RT, filtered and the cake was washed with ACN. The filtrate was concentrated under reduced pressure, the residue was adsorbed onto Isolute and purified by column chromatography (RediSep Column: Silica 220 g, eluent DCM). The product containing fractions were combined and concentrated under reduced pressure to give the title compound as an orange oil.

LC-MS: Rt=1.25 min; MS m/z $[M+H]^+$ 323.1/325.1; LC-MS 1

Step 3: 3-(benzyloxy)-2-bromo-4-fluoro-6-methylpyridine

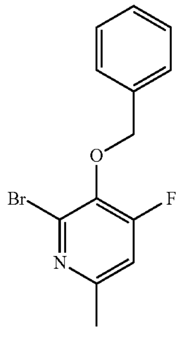 [SMILES: Cc1cc(F)c(OCc2ccccc2)c(Br)n1]

3-(Benzyloxy)-2-bromo-6-methyl-4-nitropyridine (9.30 g, 28.8 mmol) was dissolved in DMF (150 mL). The flask was vacuumed and purged with argon several times. TBAF 1M in THF (58.0 mL, 58.0 mmol) was added and the RM was stirred at RT for 45 minutes. TBAF 1M in THF (20.0 mL, 20.0 mmol) was added and the RM was stirred at RT for 1.75 hours. The RM was quenched with water (250 mL) and extracted with EtOAC (3×400 mL). The organic layer was washed with water (200 mL) and brine (2×150 mL), dried over $Na_2SO_4$ and filtered. The filtrate was concentrated under reduced pressure. The crude product was purified by column chromatography (RediSep Column: Silica 220 g, eluent DCM). The product containing fractions were combined and concentrated under reduced pressure. The residue was purified by column chromatography (RediSep Column: Silica 120 g, eluent DCM). The product containing fractions were combined and concentrated under reduced pressure to give the title compound as a beige solid.

LC-MS: Rt=1.23 min; MS m/z $[M+H]^+$ 296.1/298.1; LC-MS 1

Step 4: ethyl 3-(benzyloxy)-4-fluoro-6-methylpicolinate

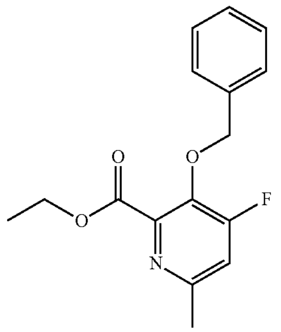 [SMILES: CCOC(=O)c1nc(C)cc(F)c1OCc1ccccc1]

A solution of 3-(benzyloxy)-2-bromo-4-fluoro-6-methylpyridine (4.93 g, 16.7 mmol), Pd(dppf)$Cl_2$·DCM (680 mg, 832 μmol) and $Et_3N$ (7.03 mL, 49.9 mmol) in EtOH (520 mL) was stirred at 80° C. under 18 bar of CO for 20 hours. SiliaMetS® Thiol was added, the mixture was stirred at 40° C. for 1 hour, filtered and the cake was washed with DCM. The filtrate was concentrated under reduced pressure, the crude product was suspended in DCM, filtered, washed with $Et_2O$ and purified by column chromatography (RediSep Column: Silica 120 g, eluent DCM:DCM/MeOH (1/1) 100:0 to 0:100). The product containing fractions were combined and concentrated under reduced pressure and further purified by reverse phase preparative HPLC (RP-HPLC acidic 1: 5 to 95% B in 20 min with a plateau at 95% for 1 min). The product containing fractions were combined, basified with aq sat $NaHCO_3$, extracted twice with DCM, dried through a phase separator and concentrated under reduced pressure to give the title compound.

LC-MS: Rt=1.06 min; MS m/z $[M+H]^+$ 290.3; LC-MS 1

Step 5: 3-(benzyloxy)-4-fluoro-6-methylpicolinic acid

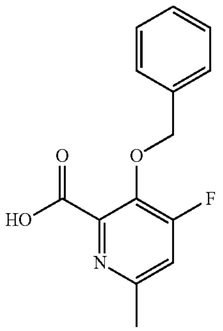 [SMILES: Cc1cc(F)c(OCc2ccccc2)c(C(=O)O)n1]

Ethyl 3-(benzyloxy)-4-fluoro-6-methylpicolinate (2.05 g, 5.95 mmol) was dissolved in 1,4-dioxane (5 mL) and NaOH 1M in water (12.0 mL, 12.0 mmol) was added and was stirred at 50° C. for 45 minutes. The RM was concentrated under reduced pressure and the residue was mixed with water (30 mL), aq 1M HCl (25 mL) and DCM (30 mL). The aqueous layer was washed with DCM (3×20 mL). The combined organic layers were dried through a phase separator and concentrated under reduced pressure to give the title compound.

LC-MS: Rt=0.56 min; MS m/z $[M+H]^+$ 262.2, m/z $[M-H]^-$ 260.1; UPLC-MS 1

Intermediate CY: 5-(benzyloxy)-6-methylpyrimidine-4-carboxylic acid

Step 1: 5-(benzyloxy)-4,6-dichloropyrimidine

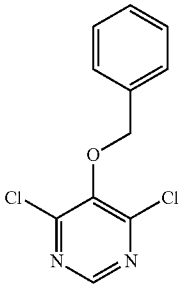 [SMILES: Clc1ncnc(Cl)c1OCc1ccccc1]

To a stirred solution of 4,6-dichloropyrimidin-5-ol (29.5 g, 179 mmol) in DMF (100 mL) was added $K_2CO_3$ (32.1 g, 232 mmol) then (bromomethyl)benzene (23.4 mL, 197 mmol) at RT and the RM was stirred at RT for 3 hours. The RM was diluted with EtOAc/water, extracted once with EtOAc and the organic layer was washed with brine, dried over $Na_2SO_4$ and concentrated under reduced pressure. The crude product was purified by column chromatography (RediSep Column: Silica 330 g, eluent heptane:EtOAc 100:0 to 87:13). The product containing fractions were combined and concentrated under reduced pressure to afford the title compound as a white solid.

LC-MS: Rt=1.18 min; no mass observed; UPLC-MS 1

Step 2: 5-(benzyloxy)-4-chloro-6-methylpyrimidine

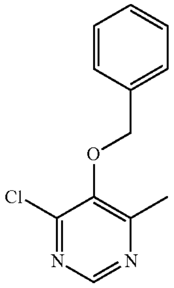 [SMILES: Cc1ncnc(Cl)c1OCc1ccccc1]

To a stirred solution of 5-(benzyloxy)-4,6-dichloropyrimidine (32.5 g, 127 mmol), $K_3PO_4$ (81.0 g, 382 mmol) and Pd(dppf)$Cl_2$·DCM (5.20 g, 6.36 mmol) in toluene (350 mL) and water (100 mL) was added methyl boronic acid (9.17 g, 153 mmol) in 1,4-dioxane (45 mL) at 105° C. and the reaction was stirred at 105° C. for 18 hours. Methyl boronic acid (9.17 g, 153 mmol) was added again and the RM was stirred at 105° C. for 8 hours. Methyl boronic acid (9.17 g, 153 mmol) was added again and the RM was stirred at 105° C. for 4 hours. The RM was diluted with EtOAc/water, extracted twice with EtOAc and the combined organic layers were washed with water and brine, dried over $Na_2SO_4$ and concentrated under reduced pressure. The crude product was purified by column chromatography (RediSep Column: Silica 330 g, eluent heptane:EtOAc 100:0 to 77:23). The product containing fractions were combined and concentrated under reduced pressure to give the title compound as a yellow oil.

LC-MS: Rt=1.03 min; MS m/z $[M+H]^+$ 235.2/237.2; UPLC-MS 1

Step 3: methyl 5-(benzyloxy)-6-methylpyrimidine-4-carboxylate

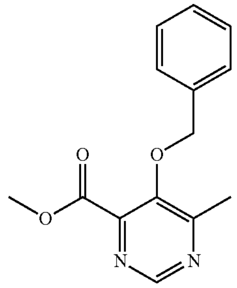 [SMILES: COC(=O)c1ncnc(C)c1OCc1ccccc1]

A solution of 5-(benzyloxy)-4-chloro-6-methylpyrimidine (25.9 g, 110 mmol), Pd(dppf)$Cl_2$·DCM (4.51 g, 5.52 mmol) and $Et_3N$ (30.8 mL, 221 mmol) in MeOH (25 mL) was stirred at 50° C. under 10 bar of CO for 40 hours. The RM was filtered through celite and concentrated under reduced pressure. The residue was triturated with DCM and the solid was filtered off. The filtrate was purified by column chromatography (eluent heptane:EtOAc 100:0 to 60:40). The product containing fractions were combined and concentrated under reduced pressure to give the title compound as a white solid.

LC-MS: Rt=0.81 min; MS m/z $[M+H]^+$ 259.1; UPLC-MS 1

Step 4: 5-(benzyloxy)-6-methylpyrimidine-4-carboxylic acid

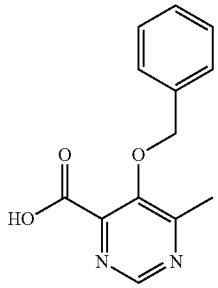 [SMILES: Cc1ncnc(C(=O)O)c1OCc1ccccc1]

To a stirred solution of methyl 5-(benzyloxy)-6-methylpyrimidine-4-carboxylate (22.9 g, 88.0 mmol) in THF (100 mL) and MeOH (100 mL) was added NaOH 2N in water (100 mL, 200 mmol) at RT and the RM was stirred at RT for 5 minutes. THF and MeOH were removed under reduced pressure, then the resulting aqueous residue was acidified to pH 3 with 2N HCl and the mixture was filtered to give the title compound as a white solid.

LC-MS: Rt=0.43 min; MS m/z $[M+H]^+$ 245.2, m/z $[M-H]^-$ 243.1; UPLC-MS 1

Intermediate CZ: 3-methoxy-4-(trifluoromethoxy)picolinic acid

Step 1: 4-(bromodifluoromethoxy)-2-chloro-3-methoxypyridine

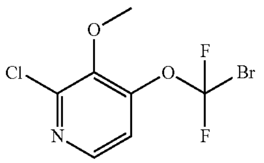

The flask was flame-dried in vacuo and backfilled with argon. The dry argon flushed flask was charged with NaH (1.05 g, 39.3 mmol). The content was suspended in anhydrous DMF (45 mL) and 2-chloro-3-methoxypyridin-4-ol (3.00 g, 17.9 mmol) was introduced portionwise. Then the RM was heated up to 60° C. for 1 hour, cooled to RT and left to stir for another 1 hour. The RM was cooled to 0° C. and a solution of dibromodifluoromethane (6.01 mL, 62.5 mmol) in anhydrous DMF (20 mL) was added dropwise with 0.8 mL/min. Then the bath was removed and the resulting RM was stirred at RT for 1.75 hours. The reaction was heated to 60° C. and stirred at 60° C. for 14.25 hours. The reaction was partitioned between water (190 mL) and EtOAc (70 mL). The organic layer was collected and the aqueous layer was back-extracted with EtOAc (3×70 mL). The organic layers were combined, washed with brine (210 mL) and dried through a phase separator. The mixture was concentrated under reduced pressure. The residue was adsorbed onto Isolute and purified by column chromatography (Buchi® FlashPure ID HP silica cartridge 220 g, eluent heptane: EtOAc 100:0 to 85:15). The product containing fractions were combined and concentrated under reduced pressure to give the title compound as a colourless oil.

LC-MS: Rt=1.10 min; MS m/z $[M+H]^+$ 288.0/290.0/292.0; UPLC-MS 1

Step 2: 2-chloro-3-methoxy-4-(trifluoromethoxy)pyridine

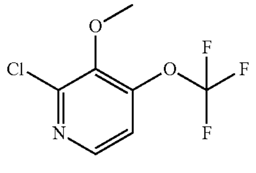

The flask was flame-dried in vacuo and backfilled with argon. The dry argon flushed flask was charged with 4-(bromodifluoromethoxy)-2-chloro-3-methoxypyridine (890 mg, 3.02 mmol) and anhydrous DCM (30 mL). To the colorless solution was added portionwise silver tetrafluoroborate (2.48 g, 12.1 mmol). The RM was stirred at RT for 17.5 hours. The RM was filtered over a pad of celite. To the filtrates were added water (100 mL). The organic layer was collected and the aqueous layer was back-extracted with DCM (3×30 mL). The organic layers were combined, washed with brine (120 mL) and dried through a phase separator. The filtrate was concentrated under reduced pressure. The residue was adsorbed onto Isolute and purified by column chromatography (Buchi® FlashPure ID HP silica cartridge 25 g, eluent heptane:EtOAc 100:0 to 85:15). The product containing fractions were combined and concentrated under reduced pressure to give the title compound as a colourless oil.

LC-MS: Rt=1.02 min; MS m/z $[M+H]^+$ 228.1/230.1; UPLC-MS 1

Step 3: ethyl 3-methoxy-4-(trifluoromethoxy)picolinate

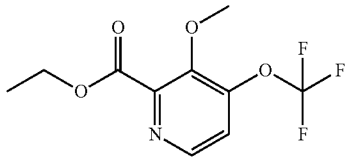 [SMILES: CCOC(=O)c1nccc(OC(F)(F)F)c1OC]

The reactor was charged with 2-chloro-3-methoxy-4-(trifluoromethoxy)pyridine (440 mg, 1.90 mmol), Pd(dppf)$Cl_2$·DCM (77.0 mg, 95.0 μmol), $Et_3N$ (800 μL, 5.68 mmol) and anhydrous EtOH (10 mL). The autoclave was subjected to three cycles of evacuation-backfilling with argon. Subsequently it was filled with 15 bar of CO at RT and then heated up to 80° C. for 15 hours. ISOLUTE® Si-TMT (1.93 g, 947 μmol) was introduced and the suspension was stirred for 1 hour at 40° C. The RM was filtered over a pad of Celite. The filtrate was concentrated under reduced pressure. The residue was adsorbed onto Isolute and purified by column chromatography (Buchi® FlashPure ID HP silica cartridge 40 g, eluent heptane:EtOAc 100:0 to 75:25). The product containing fractions were combined and concentrated under reduced pressure to give the title compound as a colourless oil.

LC-MS: Rt=0.90 min; MS m/z $[M+H]^+$ 266.1; UPLC-MS 1

Step 4: 3-methoxy-4-(trifluoromethoxy)picolinic acid

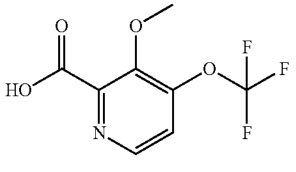 [SMILES: COc1c(OC(F)(F)F)ccnc1C(=O)O]

Ethyl 3-methoxy-4-(trifluoromethoxy)picolinate (355 mg, 1.31 mmol) was dissolved in 1,4-dioxane (8.75 mL) and the clear colorless solution was treated with NaOH 1 M in water (1.44 mL, 1.44 mmol). The resulting RM was stirred at RT for 14.75 hours. The reaction was partitioned between water (15 mL) and $Et_2O$ (25 mL). The organic layer was discarded. The aqueous layer was collected and frozen in a mixture of acetone/dry ice. After freeze drying under high pressure the title compound was afforded as a sodium salt.

LC-MS: Rt=0.43 min; MS m/z $[M+H]^+$ 238.1, m/z $[M-H]^-$ 236.1; UPLC-MS 1

Intermediate DA: 3-(benzyloxy)-4-fluoro-5-methylpicolinic acid

Step 1: 2-bromo-5-methyl-4-nitropyridin-3-ol

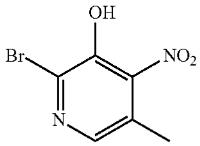

2-Bromo-5-methylpyridin-3-ol (1.50 g, 7.58 mmol) was suspended in sulfuric acid (8.42 mL). The resulting dark brown suspension was cooled at 0° C. and then $HNO_3$ (66%) (729 μL, 10.6 mmol) was introduced. The resulting RM was left to react at 0° C. for 30.75 hours. $HNO_3$ (66%) (104 mL, 1.52 mmol) was added, then it was stirred for 45 hours. The RM was poured into ice. The resulting mixture was partitioned between water (50 mL) and EtOAc (100 mL). The organic layer was collected and the aqueous layer was back-extracted with EtOAc (3×40 mL). The organic layers were combined, washed with brine (50 mL) and dried through a phase separator. The filtrate was concentrated under reduced pressure. The residue was adsorbed onto Isolute and purified by column chromatography (Redisep® HP silica cartridge 120 g, eluent heptane:EtOAc 100:0 to 55:45). The product containing fractions were combined and concentrated under reduced pressure to give the title compound as a yellow solid.

LC-MS: Rt=0.46 min; MS m/z $[M-H]^-$ 231.0/233.0; UPLC-MS 1

Step 2: 3-(benzyloxy)-2-bromo-5-methyl-4-nitropyridine

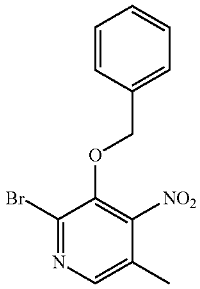 [SMILES: Cc1cnc(Br)c(OCc2ccccc2)c1[N+](=O)[O-]]

The flask was flame-dried in vacuo and backfilled with argon. The dry argon flushed flask was charged with 2-bromo-5-methyl-4-nitropyridin-3-ol (422 mg, 1.78 mmol) and $K_2CO_3$ (743 mg, 5.32 mmol). The contents were suspended in anhydrous DMF (5.92 mL) and the resulting RM was treated with (bromomethyl)benzene (280 μL, 2.31 mmol). The RM was stirred at RT for 22.5 hours. The reaction was partitioned between water (40 mL) and EtOAc (30 mL). The organic layer was collected and the aqueous layer was back-extracted with EtOAc (3×20 mL). The organic layers were combined, washed with brine (40 mL) and dried through a phase separator. The filtrate was concentrated under reduced pressure. The residue was adsorbed onto Isolute and purified by column chromatography (Buchi®FlashPure ID HP silica cartridge 40 g, eluent heptane:EtOAc 100:0 to 90:10). The product containing fractions were combined and concentrated under reduced pressure to give the title compound as a white solid.

LC-MS: Rt=1.26 min; MS m/z $[M+H]^+$ 323.2/325.2, m/z $[M-H]^-$ 321.1/323.1; UPLC-MS 1

Step 3: 3-(benzyloxy)-2-bromo-4-fluoro-5-methylpyridine

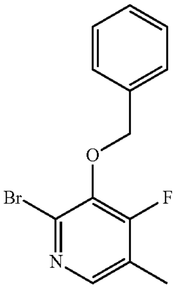

The flask was flame-dried in vacuo and backfilled with argon. The dry argon flushed vial was charged with 3-(benzyloxy)-2-bromo-5-methyl-4-nitropyridine (539 mg, 1.64 mmol) and anhydrous DMF (5.45 mL). To the clear stirred solution was added TBAF 1M in THF (2.45 mL, 2.45 mmol) and the resulting RM was stirred at RT for 7.5 hours. TBAF 1M in THF (490 μL, 490 μmol) was introduced. The RM was stirred at RT for 14.75 hours. The reaction was partitioned between water (30 mL) and EtOAc (25 mL). The organic layer was collected and the aqueous layer was back-extracted with EtOAc (3×20 mL). The organic layers were combined, washed with brine (40 mL) and dried through a phase separator. The filtrate was concentrated under reduced pressure. The residue was adsorbed onto Isolute and purified by column chromatography (Buchi® FlashPure ID HP silica cartridge 40 g, eluent heptane:DCM/MeOH (8/2) 100:0 to 90:10). The product containing fractions were combined and concentrated under reduced pressure to give the title compound as a colourless oil.

LC-MS: Rt=1.27 min; MS m/z $[M+H]^+$ 296.2/298.1, m/z $[M-H]^-$ 294.0/295.9; UPLC-MS 1

Step 4: ethyl 3-(benzyloxy)-4-fluoro-5-methylpicolinate

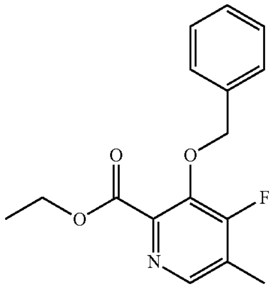 [SMILES: CCOC(=O)c1ncc(C)c(F)c1OCc1ccccc1]

The reactor was charged with 3-(benzyloxy)-2-bromo-4-fluoro-5-methylpyridine (160 mg, 351 μmol), Pd(dppf)$Cl_2$·DCM (14.3 mg, 18.0 μmol), $Et_3N$ (148 μL, 1.05 mmol) and anhydrous EtOH (10 mL). The autoclave was subjected to three cycles of evacuation-backfilling with argon. Subsequently it was filled with 15 bar of CO at RT and then heated at 80° C. for 18 hours. The RM was treated with ISOLUTE® Si-TMT (358 mg, 176 μmol). The suspension was stirred for 1 hour at 40° C. and filtered over a pad of celite. The mixture was concentrated under reduced pressure. The residue was adsorbed onto Isolute and purified by column chromatography (Buchi® FlashPure ID HP silica cartridge 12 g, eluent heptane:EtOAc 100:0 to 75:25). The product containing fractions were combined and concentrated under reduced pressure to give the title compound as a colourless oil.

LC-MS: Rt=1.06 min; MS m/z $[M+H]^+$ 290.2; UPLC-MS 1

Rebenzylation:

A dry argon flushed flask was charged with ethyl 3-(benzyloxy)-4-fluoro-5-methylpicolinate (38.0 mg, 131 μmol) and $K_2CO_3$ (22.0 mg, 158 μmol). The contents were suspended in anhydrous DMF (438 μL) and the resulting mixture was treated with (bromomethyl)benzene (17.5 μL, 144 μmol). The RM was stirred at RT for 1.75 hours. The reaction was partitioned between water (10 mL) and EtOAc (5 mL). The organic layer was collected and the aqueous layer was back-extracted three times with EtOAc. The organic layers were combined, washed with brine (25 mL) and dried through a phase separator. The filtrate was concentrated under reduced pressure and dried under HV to give the title compound as a colorless oil.

LC-MS: Rt=1.06 min; MS m/z $[M+H]^+$ 290.2; UPLC-MS 1

Step 5: 3-(benzyloxy)-4-fluoro-5-methylpicolinic acid

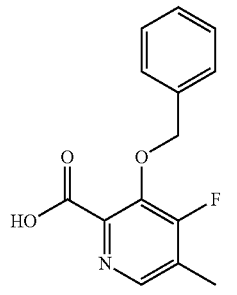 [SMILES: Cc1cnc(C(=O)O)c(OCc2ccccc2)c1F]

To a colorless solution of ethyl 3-(benzyloxy)-4-fluoro-5-methylpicolinate (40.0 mg, 131 μmol) dissolved in 1,4-dioxane (876 μL) was added NaOH 1M in water (144 μL, 144 μmol). The resulting light yellow solution was stirred at RT for 2.75 hours. The light yellow solution was diluted with water and extracted with $Et_2O$ (25 mL). The organic layer was discarded. The aqueous layer was frozen and lyophilized to give the title compound as a white solid.

LC-MS: Rt=0.68 min; MS m/z $[M+H]^+$ 262.2, m/z $[M-H]^-$ 260.2; UPLC-MS 1

Intermediate DB: 5-hydroxy-6-methylpyrimidine-4-carboxylic acid

Step 1: 4-chloro-5-methoxy-6-methylpyrimidine

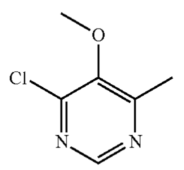

4,6-Dichloro-5-methoxypyrimidine (50.0 g, 279 mmol) was dissolved in THF (400 mL) under nitrogen and cooled to 5° C. Methylmagnesium chloride 3M (102 mL, 307 mmol) was added dropwise. The RM was stirred at 5° C. for 1 hour, then it was quenched by addition of HCl 1N (250 mL) and extracted twice with TBME (2×250 mL). The combined organic layers were washed with brine (250 mL) and concentrated under reduced pressure. The residue was treated with MeOH to give the title compound in solution.

$^1H$ NMR (400 MHz, DMSO-$d_6$) δ 8.66 (s, 1H), 3.86 (s, 3H), 2.50 (s, 3H)

Step 2: methyl 5-methoxy-6-methylpyrimidine-4-carboxylate

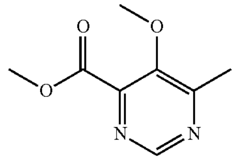

To a solution of 4-chloro-5-methoxy-6-methylpyrimidine (70.0 g, 441 mmol) in MeOH (350 mL) were added Pd(dppf)$Cl_2$·DCM (21.6 g, 26.5 mmol) and $Et_3N$ (122 mL, 883 mmol). Then the mixture was stirred at 60° C. for 16 hours under CO atmosphere (0.3-0.5 MPa). After cooling to RT the solids were collected by filtration and washed with MeOH. After the filtrate was concentrated under reduced pressure, IPAc (350 mL) and water (350 mL) were added. The organic phase and aqueous phase were separated, then the aqueous phase was extracted by IPAc (350 mL). After concentration, the residue was purified by column chromatography (silica glass column, eluent heptane:EtOAc 10:1, isocratic). The product containing fractions were combined and concentrated under reduced pressure to give the title compound as an oil.

$^1H$ NMR (400 MHz, DMSO-$d_6$) δ 8.85 (s, 1H), 3.93 (s, 3H), 3.84 (s, 3H), 1.17 (s 3H).

Step 3: 5-hydroxy-6-methylpyrimidine-4-carboxylic acid

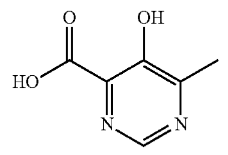

Methyl 5-methoxy-6-methylpyrimidine-4-carboxylate (22.0 g, 116 mmol) was dissolved in HBr (≥40% in water) (94.0 mL, 696 mmol). The reaction was heated and stirred at 40° C. for 10 hours. The solution was treated with HI (≥57% in water) (92.0 mL, 696 mmol) and stirred for further 6 hours. The pH was adjusted to 3-4 with NaOH (50% in water) at 0-20° C. The mixture was filtered to receive a yellow solid. The crude product was taken into water (150 mL) and HCl (37% in water) (44.0 mL, 536 mmol) was added. The suspension was heated at 60° C. for 2 hours, then it was filtered. The obtained solid was dried under vacuum to give the title compound as a white solid.

$^1$H NMR (400 MHz, DMSO-$d_6$) δ 11.71 (s, 2H), 8.66 (s, 1H), 2.47 (s, 3H).

Intermediate DC: ethyl 2-(piperazin-1-yl)acetate

Step 1: tert-butyl 4-(2-ethoxy-2-oxoethyl)piperazine-1-carboxylate

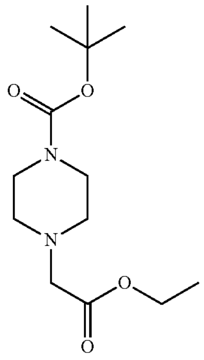 [SMILES: CCOC(=O)CN1CCN(C(=O)OC(C)(C)C)CC1]

Tert-butyl piperazine-1-carboxylate (1.00 g, 5.37 mmol) was taken in ACN (10 mL) and ethyl 2-bromoacetate (1.35 g, 8.05 mmol) and $K_2CO_3$ (2.23 g, 16.1 mmol) were added and the RM was stirred at RT for 16 hours. The RM was diluted with water and extracted with EtOAc. The crude product was purified by column chromatography (Silica gel column: Silica 12 g, eluent hexane:EtOAc 95:5 to 90:10). The product containing fractions were combined and concentrated under reduced pressure to give the title compound.

LC-MS: Rt=1.19 min; MS m/z $[M+H]^+$ 273.3; UPLC-MS 13

Step 2: ethyl 2-(piperazin-1-yl)acetate

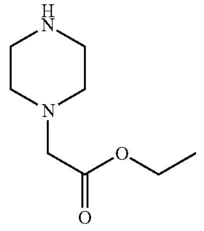

Tert-butyl 4-(2-ethoxy-2-oxoethyl)piperazine-1-carboxylate (500 mg, 1.45 mmol) was taken in 1,4-dioxane (1 mL) and HCl 4N in 1,4-dioxane (10.0 mL, 40.0 mmol) was added and the RM was stirred at RT for 1 hour. The RM was concentrated under reduced pressure and washed with $Et_2O$ to give the title compound.

LC-MS: Rt=0.15 min; MS m/z $[M+H]^+$ 173.1; UPLC-MS 12

Intermediate DD: 5-fluoro-2-methyl-4-(trifluoromethyl)aniline

Step 1: 5-fluoro-2-iodo-4-(trifluoromethyl)aniline

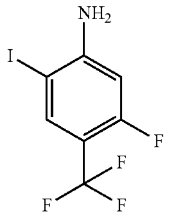 [SMILES: Nc1cc(F)c(C(F)(F)F)cc1I]

3-Fluoro-4-(trifluoromethyl)aniline (2.00 g, 11.2 mmol) was dissolved in DMF (10 mL) and cooled to 0° C. Then NIS (3.52 g, 15.6 mmol) was added and the mixture was stirred at 0° C. for 1.25 hours. Water, aq sat $NaHCO_3$ and DCM were added. The aqueous layer was washed twice with DCM. The combined organic layers were dried through a phase separator and concentrated under reduced pressure. The crude product was purified by column chromatography (RediSep Column: Silica 80 g, eluent DCM:DCM/MeOH (9/1) 100:0 to 0:100). The product containing fractions were combined, concentrated under vacuum and dried under HV. The resulting product was further purified in 3 portions by reverse phase preparative HPLC (RP-HPLC acidic 1: 20 to 80% B in 20 min and 2×RP-HPLC acidic 1: 25 to 85% B in 20 min). The product containing fractions were combined, basified with aq sat $NaHCO_3$, extracted twice with DCM, dried through a phase separator and concentrated under reduced pressure to give the title compound.

LC-MS: Rt=1.14 min; MS m/z $[M-H]^-$ 303.9; UPLC-MS 4

Step 2: 5-fluoro-2-methyl-4-(trifluoromethyl)aniline

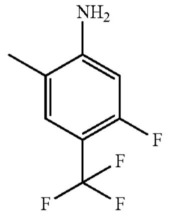

5-Fluoro-2-iodo-4-(trifluoromethyl)aniline (1.67 g, 5.48 mmol) was dissolved in 1,4-dioxane (10 mL) and 2,4,6-trimethyl-1,3,5,2,4,6-trioxatriborinane (2.50 mL, 17.9 mmol), $Pd(PPh_3)_4$ (290 mg, 251 μmol) and $K_2CO_3$ (3.50 g, 25.3 mmol) were added. The mixture was degassed and flushed with argon and stirred at 80° C. for 4 hours. The RM was filtered, the filter cake was washed with 1,4-dioxane and the filtrate was concentrated under reduced pressure. Water, aq sat $NaHCO_3$ and DCM were added to the filtrate and the aqueous layer was washed twice with DCM. The combined organic layers were dried through a phase separator and concentrated under reduced pressure. In addition water, aq sat $NaHCO_3$ and DCM were added to the previous filter cake. The aqueous layer was washed twice with DCM, the combined organic layers were dried through a phase separator and concentrated under reduced pressure. The crude product obtained from the filtrate was purified by reverse phase preparative HPLC (RP-HPLC acidic 1: 10 to 90% B in 25 min). The crude product obtained from the filter cake was purified in 5 portions by reverse phase preparative HPLC (5×RP-HPLC acidic 1: 30 to 90% B in 25 min). The product containing fractions were all combined, basified with aq sat $NaHCO_3$, extracted twice with DCM, dried through a phase separator and concentrated under reduced pressure to give the title compound.

LC-MS: Rt=1.06 min; no mass observed; UPLC-MS 4

Intermediate DE: 2-chloro-5-fluoro-6-(trifluoromethyl)pyridin-3-amine

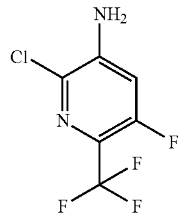 [SMILES: Nc1cc(F)c(C(F)(F)F)nc1Cl]

2-Chloro-5-fluoropyridin-3-amine (1.00 g, 6.82 mmol) and bis(((trifluoromethyl)sulfinyl)oxy)zinc (4.52 g, 13.7 mmol) were mixed in DCM (11 mL) and water (3.8 mL). Then 2-hydroperoxy-2-methylpropane (2.83 mL, 20.5 mmol) was added and the RM was stirred at RT overnight. Water and 5% aq $NaHCO_3$ was added. The mixture was extracted 3 times with DCM, the organic phase was filtered through Celite, dried through a phase separator and concentrated under reduced pressure. The crude product was purified by column chromatography (RediSep Column: Silica 40 g, eluent cyclohexane:EtOAc 100:0 to 50:50). The product containing fractions were combined and concentrated under reduced pressure to give the title compound.

LC-MS: Rt=0.88 min; MS m/z $[M+H]^+$ 215.1/217.1, m/z $[M-H]^-$ 213.1/215.1; UPLC-MS 1

Intermediate DF: 2-methyl-4-(pentafluorosulfanyl)aniline

Step 1: 2-bromo-4-(pentafluorosulfanyl)aniline

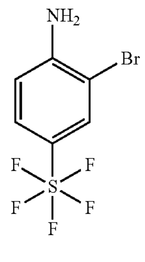

4-(Pentafluorosulfanyl)aniline (135 mg, 614 μmol) was dissolved in DCM (4 mL) and cooled to 0° C. Then 1,3-dibromo-5,5-dimethylimidazolidine-2,4-dione (90.3 mg, 316 μmol) was added. The mixture was stirred at 0° C. for 15 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=1.19 min; no mass observed; UPLC-MS 1

Step 2: 2-methyl-4-(pentafluorosulfanyl)aniline

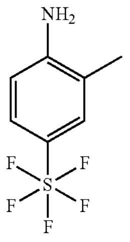

2-Bromo-4-(pentafluorosulfanyl)aniline (1.40 g, 4.37 mmol) was mixed with $Pd(PPh_3)_4$ (257 mg, 222 μmol), $K_2CO_3$ (2.72 g, 19.7 mmol) and suspended in 1,4-dioxane (40 mL) Then 2,4,6-trimethyl-1,3,5,2,4,6-trioxatriborinane (1.83 mL, 13.1 mmol) was added and the mixture was stirred at 80° C. for 5.5 hours, then at RT overnight. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by reverse phase preparative ISCO (RediSep Column: C18 130 g, eluent water+0.1% TFA: ACN 100:0 to 0:100). The product containing fractions were combined, concentrated under reduced pressure and lyophilized overnight to give the title compound as a yellow oil.

LC-MS: Rt=1.05 min; no mass observed; UPLC-MS 1

Intermediate DG: 5-chloro-2-methyl-6-(trifluoromethyl)pyridin-3-amine

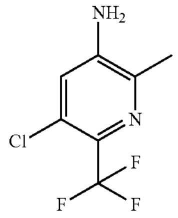

5-Chloro-2-methylpyridin-3-amine (500 mg, 3.44 mmol) and bis(((trifluoromethyl)sulfinyl)oxy)zinc (2.73 g, 8.25 mmol) were mixed in $CHCl_3$ (10 mL) and water (3.33 mL). 2-Hydroperoxy-2-methylpropane 70% in water (1.43 mL, 10.3 mmol) was added and the RM was stirred at 55° C. for 23 hours. The RM was cooled to RT and diluted with water (10 mL). The organic layer was washed with water (10 mL), dried through a phase separator and concentrated under reduced pressure. The crude product was adsorbed onto Isolute and purified by column chromatography (RediSep Column: Silica 80 g, eluent DCM:MeOH 100:0 to 85:15).

The product containing fractions were combined and concentrated under reduced pressure to give the title compound.

LC-MS: Rt=0.95 min; MS m/z $[M+H]^+$ 211.1/213.1, m/z $[M-H]^-$ 209.0/211.1; UPLC-MS 3

Intermediate DH: rac-2-(4-methoxycyclohex-1-en-1-yl)-4,4,5,5-tetramethyl-1,3,2-dioxaborolane Step 1: rac-4-methoxycyclohex-1-en-1-yl trifluoromethanesulfonate

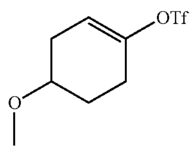

To the stirred solution of rac-4-methoxycyclohexan-1-one (5.00 g, 39.0 mmol) in dry THF (50 mL) was added LDA (39.0 mL, 78.0 mmol) dropwise at −78° C. The RM was stirred at −78° C. for 30 minutes and then 1,1,1-trifluoro-N-phenyl-N-((trifluoromethyl)sulfonyl)methanesulfonamide (20.9 g, 58.5 mmol) in dry THF (50 mL) was added. The RM was stirred at −78° C. for 30 minutes, then at RT for 3 hours. The RM was quenched with aq sat $NH_4Cl$ and extracted three times with EtOAc. The combined organic layers were washed with water, dried over $Na_2SO_4$, filtered and concentrated under reduced pressure. The crude product was purified by column chromatography (Silica gel column: Silica 24 g, eluent hexane:EtOAc 100:0 to 99:1). The product containing fractions were combined, concentrated under reduced pressure and dried under HV to give the title compound.

Step 2: rac-2-(4-methoxycyclohex-1-en-1-yl)-4,4,5,5-tetramethyl-1,3,2-dioxaborolane

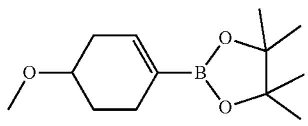

To the stirred solution of rac-4-methoxycyclohex-1-en-1-yl trifluoromethanesulfonate (4.50 g, 17.3 mmol) in 1,4-dioxane (30 mL) were added 4,4,4',4',5,5,5',5'-octamethyl-2,2'-bi(1,3,2-dioxaborolane) (6.59 g, 25.9 mmol) and KOAc (5.09 g, 51.9 mmol). The RM was degassed with argon for 30 minutes. Pd(dppf)$Cl_2$·DCM (706 mg, 865 μmol) was added and the RM was degassed with argon for 15 minutes. The RM was stirred at 90° C. for 16 hours. The RM was poured onto ice water and extracted twice with EtOAc. The organic layer was dried over $Na_2SO_4$ and concentrated under reduced pressure. The crude product was purified by column chromatography (Silica gel column: Silica 24 g, eluent hexane:EtOAc 100:0 to 99:1). The product containing fractions were combined, concentrated under reduced pressure and dried under HV to give the title compound as a colorless oil.

Intermediate DI: tert-butyl 6-(4,4,5,5-tetramethyl-1,3,2-dioxaborolan-2-yl)-3,4-dihydropyridine-1 (2H)-carboxylate Step 1: tert-butyl 6-(((trifluoromethyl)sulfonyl)oxy)-3,4-dihydropyridine-1 (2H)-carboxylate

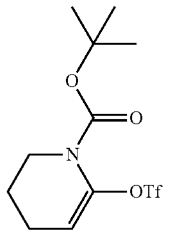 [SMILES: CC(C)(C)OC(=O)N1CCCC=C1OS(=O)(=O)C(F)(F)F]

To NaHMDS 1M in THF (47.4 mL, 47.4 mmol) in THF (400 mL) at −78° C. under nitrogen, was added tert-butyl 2-oxopiperidine-1-carboxylate (9.44 g, 47.4 mmol) in THF (50 mL) over 10 minutes. The resulting mixture was stirred at −78° C. for 45 minutes. Then 1,1,1-trifluoro-N-phenyl-N-((trifluoromethyl)sulfonyl)methanesulfonamide (16.9 g, 47.4 mmol) in THF (40 mL) was added over 10 minutes and stirred for 1 hour. The RM was allowed to warm slowly to RT overnight, then it was stirred at RT for 24 hours. The RM was partitioned between TBME (400 mL) and NaOH 0.1M (200 mL). The organic layer was separated, washed with brine (100 mL), dried over $Na_2SO_4$, filtered and evaporated in vacuo. The crude product was purified by column chromatography (RediSep Column: Silica 220 g, eluent heptane: EtOAc:$NH_3$ 90:10:1 to 85:15:1). The product containing fractions were combined and concentrated under reduced pressure to give the title compound.

$^1$H NMR (400 MHz, DMSO-$d_6$) δ 5.54 (t, J=3.8 Hz, 1H), 3.49 (m, 2H), 2.24 (m, 2H), 1.67 (m, 2H), 1.44 (s, 9H)

Step 2: tert-butyl 6-(4,4,5,5-tetramethyl-1,3,2-dioxaborolan-2-yl)-3,4-dihydropyridine-1 (2H)-carboxylate

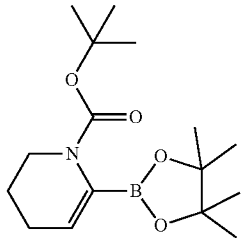 [SMILES: CC(C)(C)OC(=O)N1CCCC=C1B1OC(C)(C)C(C)(C)O1]

To BISPIN (9.79 g, 38.5 mmol), $PdCl_2(PPh_3)_2$ (966 mg, 1.38 mmol), triphenylphosphane (722 mg, 2.75 mmol) and $K_2CO_3$ (7.13 g, 51.6 mmol) was added tert-butyl 6-(((trifluoromethyl)sulfonyl)oxy)-3,4-dihydropyridine-1 (2H)-carboxylate (11.4 g, 34.4 mmol) in 1,4-dioxane (150 mL). The RM was degassed, flushed with argon and heated at 90° C. for 3 hours then at 70° C. overnight. After cooling to RT the mixture was diluted with TBME (200 mL) and washed with water (100 mL). The organic phase was dried over $Na_2SO_4$, filtered and concentrated under reduced pressure. The crude product was purified by column chromatography (eluent heptane:EtOAc 5:1). The product containing fractions were combined and concentrated under reduced pressure to give 2 batches of the title compound as pale brown oils.

LC-MS: Rt=1.20 min; no mass observed, UPLC-MS: 1

Intermediate DJ: tert-butyl 3-fluoro-6-(4,4,5,5-tetramethyl-1,3,2-dioxaborolan-2-yl)-3,4-dihydropyridine-1 (2H)-carboxylate Step 1: tert-butyl 5-fluoro-2-oxopiperidine-1-carboxylate

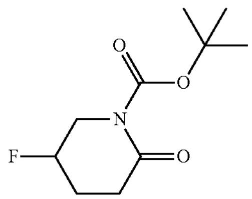

5-Fluoropiperidin-2-one (513 mg, 4.38 mmol), di-tert-butyl dicarbonate (2.03 mL, 8.76 mmol) and DMAP (53.5 mg, 438 μmol) were stirred in ACN (25 mL) and THF (10 mL) at RT for 3 days. The RM was concentrated under reduced pressure. The crude product was adsorbed onto Isolute and purified by column chromatography (RediSep Column: Silica 12g, eluent heptane:EtOAc 100:0 to 40:60). Fractions containing TLC $R_f$ 0.44 (heptane:EtOAc, 1:1, $KMnO_4$ visualization) were combined and evaporated in vacuo to give the title compound as a pale yellow oil.

$^1H$ NMR (600 MHz, DMSO-$d_6$) δ 5.14 (m, 1H), 3.98 (m, 1H), 3.67 (m, 1H), 2.41 (m, 2H), 2.17 (m, 1H), 1.96 (m, 1H), 1.44 (s, 9H)

Step 2: tert-butyl 3-fluoro-6-(((trifluoromethyl)sulfonyl)oxy)-3,4-dihydropyridine-1 (2H)-carboxylate

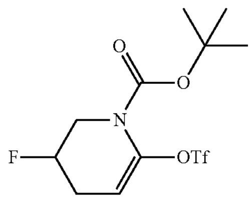 [SMILES: CC(C)(C)OC(=O)N1CC(F)CC=C1OS(=O)(=O)C(F)(F)F]

To KHMDS 0.5M in toluene (2.39 mL, 1.20 mmol) in THF (10 mL) at −78° C. under nitrogen was added dropwise a solution of tert-butyl 5-fluoro-2-oxopiperidine-1-carboxylate (208 mg, 957 μmol) in THF (2 mL). The RM was allowed to stir at −78° C. for 1.75 hours. Then added dropwise bis(trifluoromethanesulfonyl)aniline (428 mg, 1.20 mmol) in THF (2 mL) and stirred at −78° C. for 10 minutes. The RM was allowed to warm to RT and stirred for 1 hour at RT. NaOH 1M (15 mL) was added and the mixture was extracted with $Et_2O$ (2×30 mL). The organic layers were combined, washed with brine (10 mL), dried over $MgSO_4$ and $K_2CO_3$, filtered and evaporated in vacuo to give a yellow oil (540 mg). The crude product was purified by column chromatography (RediSep Column: Silica 12 g, eluent heptane:EtOAc:$NH_3$ 95:5:0.1 to 0:100:1). The product containing fractions were combined and concentrated under reduced pressure to give the title compound as a yellow oil.

LC-MS: Rt=1.20 min; MS m/z $[M-H]^-$ 348.0; UPLC-MS 1

Step 3: tert-butyl 3-fluoro-6-(4,4,5,5-tetramethyl-1,3,2-dioxaborolan-2-yl)-3,4-dihydropyridine-1 (2H)-carboxylate

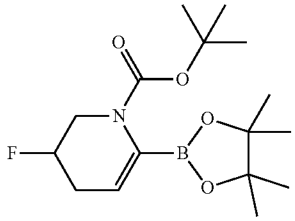 [SMILES: CC(C)(C)OC(=O)N1CC(F)CC=C1B1OC(C)(C)C(C)(C)O1]

To BISPIN (83.0 mg, 326 μmol), $PdCl_2(PPh_3)_2$ (7.64 mg, 10.9 μmol), triphenylphosphane (5.71 mg, 22.0 μmol) and $K_2CO_3$ (56.4 mg, 408 μmol) was added tert-butyl 3-fluoro-6-(((trifluoromethyl)sulfonyl)oxy)-3,4-dihydropyridine-1 (2H)-carboxylate (95.0 mg, 272 μmol) in 1,4-dioxane (1.5 mL). The RM was flushed with argon and heated at 70° C. for 18 hours. The RM was partitioned between DCM (8 mL) and water (3 mL). The organic layer was dried through a phase separator and concentrated under reduced pressure to give the title compound as a dark brown oil.

Intermediate DK: 3,6-dihydro-2H-pyran-4-carbaldehyde

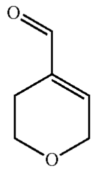

According to ref. Org. Lett. 2014, 16, 4142-4145.

To a mixture of tetrahydro-4H-pyran-4-one (30.0 g, 300 mmol) and water (300 mL), was added NaCN (15.4 g, 315 mmol) at 5° C. followed by $NaHSO_4$ until a pH=4-5 was reached. The reaction was stirred at 10° C. for 1 hour, then NaCl (17.5 g, 300 mmol) was added at 25° C. followed by 2-MeTHF. The organic layers were separated and the aqueous layer was extracted twice with 2-MeTHF. The combined organic layers were washed with brine, dried over $Na_2SO_4$, concentrated under reduced pressure and switched the solvent to toluene (300 mL) to give 4-hydroxytetrahydro-2H-pyran-4-carbonitrile. Pyridine (48.5 mL, 599 mmol) was added at 65° C., followed by a slow addition of $POCl_3$ (27.9 mL, 300 mmol). The RM was stirred at 65° C. for 1 hour, then it was cooled to RT and water was added. The layers were separated, and the aqueous layer was extracted twice with toluene. The combined organic layers were washed with brine, dried over $Na_2SO_4$ and concentrated under reduced pressure to give 3,6-dihydro-2H-pyran-4-carbonitrile. The residue was mixed with toluene (300 mL) and DIBAL-H (46.9 g, 330 mmol) was added at −10° C. The reaction was stirred at −10° C. for 1 hour, then HCl 4M was added. The two layers were separated, and the aqueous layer was extracted twice with DCM. The combined organic layers were washed with brine and dried over $Na_2SO_4$. The organic solution was then concentrated under reduced pressure to give the title compound as solution in toluene (not stable when concentrated).

$^1$H NMR (400 MHz, DMSO-$d_6$) δ 9.46 (s, 1H), 7.05 (m, 1H), 4.33 (m, 2H), 3.69 (m, 2H), 2.16 (m, 2H).

Intermediate DK: 3,6-dihydro-2H-pyran-4-carbaldehyde

Step 1: methyl tetrahydro-2H-pyran-4-carboxylate

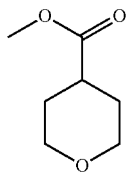

According to ref. WO2013/66729, 2013, A1

Into a solution of oxane-4-carboxylic acid (50.0 mg, 380 μmol) in MeOH (10 mL) was added thionyl chloride (46.0 mg, 390 μmol) dropwise with stirring at RT. The resulting solution was stirred at RT for 3 hours. The RM was concentrated under reduced pressure to give the title compound, which was used directly for next step without further purification (brown oil).

$^1$H NMR (400 MHz, DMSO-$d_6$) δ 3.81 (m, 2H), 3.62 (s, 3H), 3.34 (m, 2H), 2.59 (m, 1H), 1.74 (m, 2H), 1.56 (m, 2H).

Step 2: methyl 4-iodotetrahydro-2H-pyran-4-carboxylate

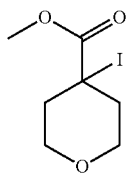

To a solution of DIPEA (528 mL, 3.03 mol) in THF (3.5 L) was added dropwise n-BuLi 2M in hexane (1.52 L, 3.03 mmol) at −10° C.~−5° C. The RM was stirred at −10° C.~−5° C. for 30 minutes. Methyl tetrahydro-2H-pyran-4-carboxylate (370 g, 2.43 mol) in THF (700 mL) was added dropwise into the RM at −70° C. The RM was stirred for at −70° C. for 1 hour. 12 (1.23 g, 4.85 mol) in THF (2.4 L) was added dropwise into the RM at −70° C. The RM was stirred for at −70° C. for 1 hour. The mixture was added dropwise into HCl 1N (1.5 L) and TBME (1.5 L) and it was stirred for 30 minutes. The organic was washed with aq 30% $Na_2O_3S_2$ (1.8 L) and brine (700 mL). The organic layer was concentrated under reduced pressure to give the title compound.

Step 3: methyl 3,6-dihydro-2H-pyran-4-carboxylate

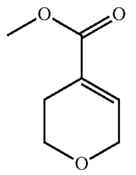

To a solution of methyl 4-iodotetrahydro-2H-pyran-4-carboxylate (500 g, 1.61 mol) in TBME (10 L) was added dropwise DBU (486 mL, 3.22 mol) at RT. The RM was stirred for at RT 2 hours, then it was filtered and to the filtrate was added HCl 9% (1.7 L). The mixture was stirred for 30 minutes. The pH of the organic was adjusted to 7 by washing with brine (2×1.5 L). The combined aqueous phase was extracted with TBME (1.5 L). After concentration, the residue was purified by distillation collects 55° C. of distillate to give the title compound.

$^1$H NMR (400 MHz, DMSO-$d_6$) δ 6.92 (m, 1H), 4.21 (m, 2H), 3.69 (m, 5H), 2.25 (m, 2H).

Step 4: (3,6-dihydro-2H-pyran-4-yl)methanol

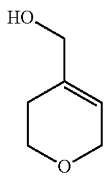

Methyl 3,6-dihydro-2H-pyran-4-carboxylate (50.0 g, 288 mmol) was mixed in THF (900 mL) under nitrogen. The solution was cooled to −10° C., followed by addition of DIBAL-H 1 M in hexane (721 mL, 721 mmol) dropwise. The RM was stirred at 0° C. for 2 hours, then it was quenched by addition of 3N Rochelle's salt solution (700 mL) and MeOH (117 mL). The biphasic solution was stirred for 16 hours, and the organic phase was isolated. The aqueous phase was extracted with DCM:MeOH 10:1 (5×200 mL) and the combined organic phases were concentrated under reduced pressure to give the title compound as a liquid.

$^1$H NMR (400 MHz, DMSO-$d_6$) δ 5.61 (m, 1H), 4.74 (m, 1H), 4.02 (m, 2H), 3.82 (m, 2H), 3.67 (m, 2H), 1.97 (m, 2H).

Step 5: 3,6-dihydro-2H-pyran-4-carbaldehyde

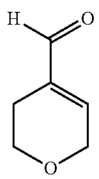

To a solution of DMP (122 g, 288 mol) in IPAc (600 mL) under nitrogen was added dropwise (3,6-dihydro-2H-pyran-4-yl)methanol (36.0 g, 262 mmol) at 0° C. The RM was stirred at RT for 3 minutes. The suspension was filtered and washed with IPAc (36 mL). The pH of the filtrate was adjusted to 8 by washing with 10% $Na_2CO_3$ (500 mL). The aqueous phase was extracted with IPAc (2×150 mL). The combined organic phase was concentrated under reduced pressure to ½ volume to give the title compound as a solution in IPAc.

$^1H$ NMR (400 MHz, DMSO-$d_6$) δ 9.46 (s, 1H), 7.05 (m, 1H), 4.33 (m, 2H), 3.69 (m, 2H), 2.16 (m, 2H).

Intermediate DL: N-(2-chloro-4-(trifluoromethyl)phenyl)-2-iodoacetamide

Step 1: 2-chloro-N-(2-chloro-4-(trifluoromethyl)phenyl)acetamide

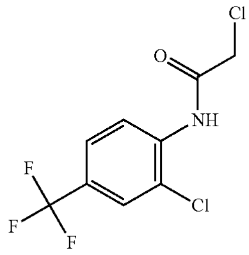 [SMILES: O=C(CCl)Nc1ccc(C(F)(F)F)cc1Cl]

2-Chloro-4-(trifluoromethyl)aniline (18.5 g, 95.0 mmol) was dissolved in DCM (180 mL) at 0° C. A solution of 2-chloroacetyl chloride (10.7 g, 95.0 mmol) in DCM (40 mL) was added dropwise over 15 minutes. After 30 minutes at 0° C. the RM was warmed to RT. The white suspension was stirred at RT overnight. The suspension was filtered and washed with DCM. The filtrate was concentrated under reduced pressure and dried under HV to give the title compound as a white solid.

LC-MS: Rt=1.14 min; MS m/z $[M-H]^-$ 270.1/272.1/274.0; UPLC-MS 1

Step 2: N-(2-chloro-4-(trifluoromethyl)phenyl)-2-iodoacetamide

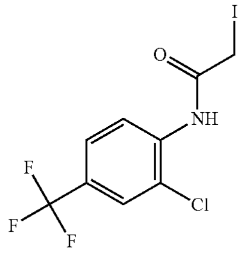 [SMILES: O=C(CI)Nc1ccc(C(F)(F)F)cc1Cl]

2-Chloro-N-(2-chloro-4-(trifluoromethyl)phenyl)acetamide (15.8 g, 58.2 mmol) was dissolved in acetone (215 mL), KI (10.6 g, 64.0 mmol) was added and the RM was stirred at reflux for 2.25 hours. The RM was cooled to RT and the suspension was filtered. The cake was washed with acetone and DCM. The filtrate was concentrated under reduced pressure and dried under HV to give the title compound.

LC-MS: Rt=1.13 min; MS m/z $[M-H]^-$ 362.0/364.0; UPLC-MS 1

Intermediate DM: 2-bromo-N-(5-chloro-2-methyl-4-(trifluoromethyl)phenyl)acetamide Step 1: 5-chloro-2-methyl-4-(trifluoromethyl)aniline

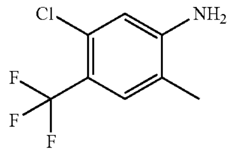

2-Bromo-5-chloro-4-(trifluoromethyl)aniline (2.70 g, 9.84 mol) was suspended in 1,4-dioxane (30 mL) and methylboronic acid (883 mg, 14.8 mol) and $K_2CO_3$ (3.40 g, 24.6 mmol) were added. The RM was degassed with argon for 15 minutes and Pd(dppf)$Cl_2$·DCM (402 mg, 492 μmol) was added and the RM was stirred at 80° C. for 16 hours. The RM was filtered through Celite and washed with 1,4-dioxane. The filtrate was concentrated under reduced pressure. The crude product was purified by column chromatography (Silica gel column: Silica 12 g, eluent hexane: EtOAc 100:0 to 90:10). The product containing fractions were combined and concentrated under reduced pressure to give the title compound.

LC-MS: Rt=1.56 min; MS m/z $[M+H]^+$ 210.1/212.1; UPLC-MS 11

Step 2: 2-bromo-N-(5-chloro-2-methyl-4-(trifluoromethyl)phenyl)acetamide

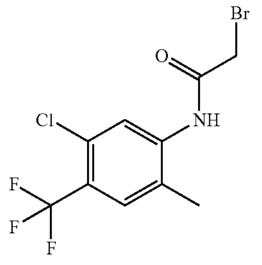 [SMILES: Cc1cc(C(F)(F)F)c(Cl)cc1NC(=O)CBr]

5-Chloro-2-methyl-4-(trifluoromethyl)aniline (1.50 g, 6.94 mmol) was suspended in DCM (20 mL) was mixed at 0° C. with 2-bromoacetyl bromide (665 μL, 7.64 mmol) and DMAP (848 mg, 6.94 mmol) and the RM was stirred at RT for 12 hours. The RM was diluted with DCM and washed with water. The organic layer was dried over $Na_2SO_4$ and concentrated under reduced pressure, washed with $Et_2O$ and dried under HV to give the title compound.

LC-MS: Rt=1.58 min; MS m/z $[M+H]^+$ 330.0/332.0/334.0; UPLC-MS 11

Intermediate DN: 2-bromo-N-(5-fluoro-2-methyl-4-(trifluoromethyl)phenyl)acetamide Step 1: 2-bromo-5-fluoro-4-(trifluoromethyl)aniline

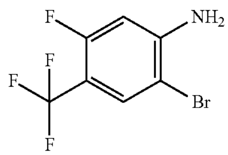 [SMILES: Nc1cc(F)c(C(F)(F)F)cc1Br]

To a stirred solution of 1-bromo-4-fluoro-2-nitro-5-(trifluoromethyl)benzene (5.00 g, 17.4 mmol) in EtOH (50 mL) and AcOH (50 mL) was added Fe dust (2.91 g, 52.1 mmol) and the RM was stirred at 80° C. for 2 hours. The solvents were evaporated and NaOH 5N was added. The mixture was extracted with EtOAc, the organic layer was dried and concentrated under reduced pressure to give the title compound.

LC-MS: Rt=1.58 min; no mass observed; UPLC-MS 11

Step 2: 5-fluoro-2-methyl-4-(trifluoromethyl)aniline

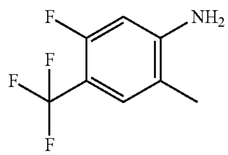

2-Bromo-5-fluoro-4-(trifluoromethyl)aniline (1.90 g, 7.22 mmol) was dissolved in 1,4-dioxane (50 mL) and degassed using argon. Then methylboronic acid (1.08 g, 18.0 mmol), $K_2CO_3$ (2.99 g, 21.7 mmol) and Pd(dppf)$Cl_2$·DCM (589 mg, 722 μmol) were added and the RM was stirred at 80° C. for 12 hours. The RM was filtered through Celite. The filtrate was concentrated under reduced pressure. The crude product was purified by column chromatography (Silica gel column: Silica 24 g, eluent hexane:EtOAc 100:0 to 95:5). The product containing fractions were combined, concentrated under reduced pressure and dried under HV to give the title compound.

LC-MS: Rt=1.55 min; no mass observed; UPLC-MS 11

Step 3: 2-bromo-N-(5-fluoro-2-methyl-4-(trifluoromethyl)phenyl)acetamide

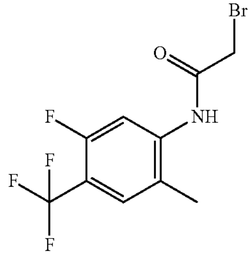 [SMILES: Cc1cc(C(F)(F)F)c(F)cc1NC(=O)CBr]

5-Fluoro-2-methyl-4-(trifluoromethyl)aniline (670 mg, 3.33 mmol) was suspended in DCM (10 mL) and DMAP (407 mg, 3.33 mmol) was added at 0° C. The RM was stirred at 0° C. for 10 minutes, then 2-bromoacetyl bromide (348 μL, 4.00 mmol) was added. The RM was stirred at RT for 12 hours. Water was added to the RM. The organic layer was dried over $Na_2SO_4$ and concentrated under reduced pressure to give the title compound.

LC-MS: Rt=1.45 min; MS m/z $[M+H]^+$ 314.0/316.0; UPLC-MS 13

Intermediate DO: 2-bromo-N-(2-chloro-5-fluoro-4-(trifluoromethyl)phenyl)acetamide

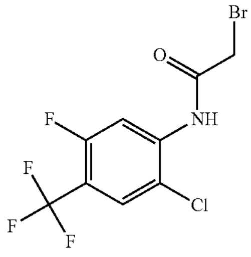 [SMILES: O=C(CBr)Nc1cc(F)c(C(F)(F)F)cc1Cl]

2-Chloro-5-fluoro-4-(trifluoromethyl)aniline (400 mg, 1.87 mmol) was suspended in DCM (5 mL). 2-Bromoacetyl bromide (179 μL, 2.06 mmol) and DMAP (229 mg, 1.87 mmol) were added at 0° C. and the RM was stirred at RT for 12 hours. The RM was cooled to 0° C., water was added and the suspension was filtered. The cake was washed with hexane and dried under reduced pressure. The crude product was purified by column chromatography (Silica gel column: Silica 12 g, eluent DCM:MeOH 100:0 to 98:2). The product containing fractions were combined and concentrated under reduced pressure to give the title compound.

LC-MS: Rt=2.28 min; MS m/z $[M+H]^+$ 333.9/335.9/337.9; UPLC-MS 13

Intermediate DP: 2-bromo-N-(2-methyl-4-(trifluoromethyl)phenyl)acetamide

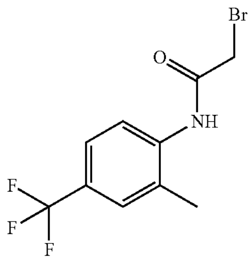

To 2-methyl-4-(trifluoromethyl)aniline (5.00 g, 28.5 mmol) in DCM (100 mL) was added dropwise 2-bromoacetyl bromide (3.73 mL, 42.8 mmol) at 0° C., followed by DIPEA (15.0 mL, 86.0 mmol) and the resulting black solution was stirred at RT for 30 minutes. 2-Bromoacetyl bromide (1.87 mL, 21.4 mmol) was added to the reaction and it was stirred for 1 hour. The RM was diluted with DCM (100 mL) and water (100 mL). The biphasic mixture was given in a separating funnel and shaken for 1 minute. The organic layer was dried over $Na_2SO_4$ and concentrated to give a black solution. The black solution was purified by column chromatography (eluent heptane:EtOAc 100:0 to 50:50). The product containing fractions were combined and concentrated under reduced pressure to give the title compound as a brown solid.

LC-MS: Rt=1.04 min; MS m/z $[M-H]^-$ 293.9/295.9; UPLC-MS 4

Intermediate DQ: 2-bromo-N-(2-chloro-6-(trifluoromethyl)pyridin-3-yl)acetamide

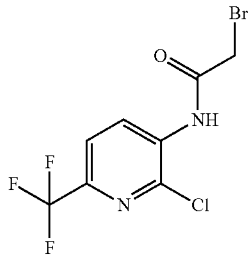 [SMILES: O=C(CBr)Nc1ccc(C(F)(F)F)nc1Cl]

2-Chloro-6-(trifluoromethyl)pyridin-3-amine (10.0 g, 50.9 mmol) was suspended in DCM (150 mL) and DMAP (6.22 g, 50.9 mmol) was added at 0° C. The RM was stirred at 0° C. for 10 minutes, then 2-bromoacetyl bromide (5.32 mL, 61.1 mmol) was added and the RM was stirred at RT for 12 hours. The RM was diluted with DCM, washed with water and the organic layer was dried over $Na_2SO_4$ and concentrated under reduced pressure. The crude product was purified by column chromatography (Silica gel column: Silica 40 g, eluent hexane:EtOAc 100:0 to 90:10). The product containing fractions were combined, concentrated under reduced pressure and dried under HV to give the title compound.

LC-MS: Rt=1.52 min; MS m/z $[M+H]^+$ 316.9/318.9/320.9; UPLC-MS 12

Intermediate DR: 2-bromo-N-(2-fluoro-4-(trifluoromethyl)phenyl)acetamide

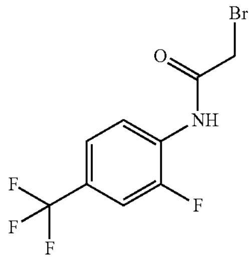 [SMILES: O=C(CBr)Nc1ccc(C(F)(F)F)cc1F]

To the stirred solution of 2-fluoro-4-(trifluoromethyl)aniline (4.00 g, 22.3 mmol) in DCM (20 mL) were added 2-bromoacetyl bromide (2.14 mL, 24.6 mmol) and DMAP (2.73 g, 22.3 mmol) at 0° C. The RM was stirred at RT for 16 hours. The RM was concentrated under reduced pressure. Water was added and it was extracted with 5% MeOH in DCM. It was washed twice with HCl 1N and the combined organic layers were dried over $Na_2SO_4$, filtered and concentrated under reduced pressure to give the title compound.

HPLC: Rt=7.705 min; HPLC 2

Intermediate DS: 2-bromo-N-(4-chloro-2-methyl-5-(trifluoromethyl)phenyl)acetamide

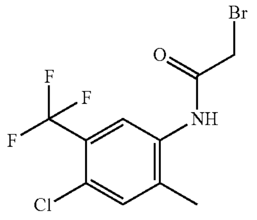 [SMILES: Cc1cc(Cl)c(C(F)(F)F)cc1NC(=O)CBr]

4-Chloro-2-methyl-5-(trifluoromethyl)aniline (1.00 g, 4.77 mmol) was suspended in DCM (20 mL), 2-bromoacetyl bromide (457 μL, 5.25 mmol) and DMAP (583 mg, 4.77 mmol) were added at 0° C. and the RM was stirred at RT for 12 hours. The RM was diluted with DCM and washed with water. The organic layer was dried over $Na_2SO_4$, concentrated under reduced pressure, washed with $Et_2O$ and dried to give the title compound as a white solid.

LC-MS: Rt=1.56 min; MS m/z $[M+H]^+$ 329.8/331.9/333.9; UPLC-MS 11

Intermediate DT: 2-bromo-N-(2-chloro-4-(trifluoromethyl)phenyl)acetamide

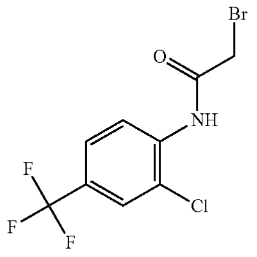 [SMILES: O=C(CBr)Nc1ccc(C(F)(F)F)cc1Cl]

2-Chloro-4-(trifluoromethyl)aniline (3.00 g, 15.3 mmol) was suspended in DCM (30 mL) and DMAP (1.87 g, 15.3 mmol) was added at 0° C. and stirred for 10 minutes. 2-Bromoacetyl bromide (3.72 g, 18.4 mmol) was added and the RM was stirred at RT for 12 hours. The organic layer was washed with HCl 1N. The layers were separated and the organic layer was dried over $Na_2SO_4$ and concentrated under reduced pressure to give the title compound.

LC-MS: Rt=1.59 min; MS m/z $[M+H]^+$ 316.0/318.0/320.0; UPLC-MS 11

Intermediate DU: N-(2-chloro-6-(trifluoromethyl)pyridin-3-yl)-2-iodoacetamide

Step 1: 2-chloro-N-(2-chloro-6-(trifluoromethyl)pyridin-3-yl)acetamide

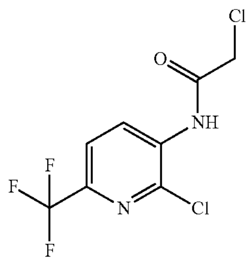 [SMILES: O=C(CCl)Nc1ccc(C(F)(F)F)nc1Cl]

2-Chloro-6-(trifluoromethyl)pyridin-3-amine (3.70 g, 18.8 mmol) was dissolved in DCM (20 mL) and 2-chloroacetyl chloride (1.80 mL, 22.6 mmol) was added to the yellow solution, followed by $Et_3N$ (6.52 mL, 47.1 mmol). The RM turned immediately into a dark solution. The RM was stirred at RT for 1.5 hours. Water (30 mL) and DCM (30 mL) were added. The aqueous layer was washed twice with DCM (2×30 mL). The combined organic layers were dried through a phase separator and concentrated under reduced pressure. The crude product was purified by column chromatography (RediSep Column: Silica 120 g, eluent DCM: DCM/MeOH (9/1) 100:0 to 90:10). The product containing fractions were combined, concentrated under reduced pressure and dried under HV to afford the title compound as an orange solid.

LC-MS: Rt=0.98 min; MS m/z $[M-H]^-$ 271.1/273.1/275.1; UPLC-MS 3

Step 2: N-(2-chloro-6-(trifluoromethyl)pyridin-3-yl)-2-iodoacetamide

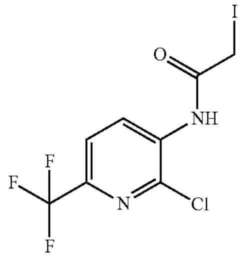 [SMILES: O=C(CI)Nc1ccc(C(F)(F)F)nc1Cl]

2-Chloro-N-(2-chloro-6-(trifluoromethyl)pyridin-3-yl)acetamide (5.46 g, 16.0 mmol) and KI (6.50 g, 39.2 mmol) were suspended in ACN (50 mL) and stirred at 82° C. for 45 minutes. The RM was cooled to RT and filtered. The cake was washed with ACN (3×50 mL). The filtrate was concentrated under reduced pressure. The crude product was dissolved in a small amount of DCM and purified by column chromatography (RediSep Column: Silica 120 g, eluent DCM. The product containing fractions were combined, concentrated under reduced pressure and dried under HV to afford the title compound as a pale beige solid.

LC-MS: Rt=0.98 min; MS m/z $[M-H]^-$ 362.9/364.9; UPLC-MS 3

Intermediate DV: 2-iodo-N-(2-methyl-4-(trifluoromethyl)phenyl)acetamide

Step 1: 2-chloro-N-(2-methyl-4-(trifluoromethyl)phenyl)acetamide

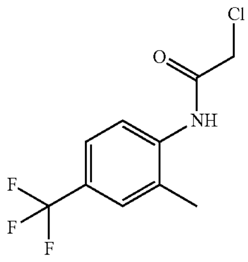 [SMILES: Cc1cc(C(F)(F)F)ccc1NC(=O)CCl]

2-Methyl-4-(trifluoromethyl)aniline (10.0 g, 56.0 mmol) was dissolved in DCM (93 mL) at 0° C. Then 2-chloroacetyl chloride (4.72 mL, 58.7 mmol) was added, followed by $Et_3N$ (17.1 mL, 123 mmol) (violet solution). After 30 minutes was the RM warmed to RT and it was stirred at RT for 1.2 hours. The RM was extracted with DCM (3×200 mL) and with water (2×60 mL). The organic layer was dried through a phase separator and concentrated under reduced pressure. The crude product was suspended in a small amount of DCM and filtered. The cake was washed with a small amount of DCM and $Et_2O$. The cake was dried under reduced pressure overnight. The filtrate was concentrated under reduced pressure. The residue was adsorbed onto Isolute and purified by column chromatography (RediSep Column: Silica 80 g, eluent heptane:EtOAc 50:50 to 0:100. The product containing fractions were combined and concentrated under reduced pressure and combined with the cake to give the title compound.

LC-MS: Rt=1.01 min; MS m/z $[M-H]^-$ 250.1/252.1; UPLC-MS 4

Step 2: 2-iodo-N-(2-methyl-4-(trifluoromethyl)phenyl)acetamide

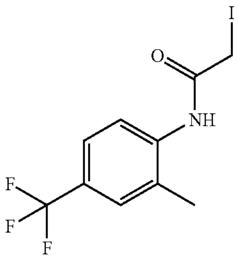 [SMILES: Cc1cc(C(F)(F)F)ccc1NC(=O)CI]

2-Chloro-N-(2-methyl-4-(trifluoromethyl)phenyl)acetamide (11.8 g, 46.8 mmol) was dissolved in acetone (173 mL) and KI (10.1 g, 60.9 mmol) was added. The RM was stirred at reflux for 2.5 hours. The RM was cooled to RT and the suspension was filtered. The cake was washed with acetone and DCM. The filtrate was concentrated under reduced pressure to give a beige solid. The solid was suspended in DCM and filtered to give the title compound as beige solid.

LC-MS: Rt=1.04 min; MS m/z $[M-H]^-$ 342.0; UPLC-MS 4

Intermediate DW: 2-bromo-N-(2-methyl-6-(trifluoromethyl)pyridin-3-yl)acetamide

Step 1: 2-methyl-6-(trifluoromethyl)pyridin-3-amine

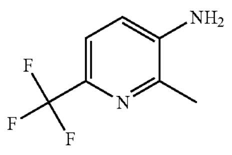

To the stirred solution of 2-chloro-6-(trifluoromethyl)pyridin-3-amine (5.00 g, 25.4 mmol) in 1,4-dioxane (50 mL) and water (10 mL) were added methylboronic acid (2.28 g, 38.2 mmol) and $K_2CO_3$ (7.03 g, 50.9 mmol) at RT and degassed with nitrogen for 15 minutes. Pd(dppf)$Cl_2$ (1.04 g, 1.27 mmol) was added and the RM was stirred at 100° C. for 12 hours. Water (20 mL) was added and the mixture was extracted with EtOAc (2×20 mL). The organic layer was washed with brine (20 mL), dried over $Na_2SO_4$ and concentrated under reduced pressure. The crude product was purified by column chromatography (Silica gel column: Silica 12 g, eluent hexane:EtOAc 100:0 to 75:25). The product containing fractions were concentrated under reduced pressure and dried under HV to give the title compound.

LC-MS: Rt=0.47 min; MS m/z $[M+H]^+$ 177.2; UPLC-MS 12

Step 2: 2-bromo-N-(2-methyl-6-(trifluoromethyl)pyridin-3-yl)acetamide

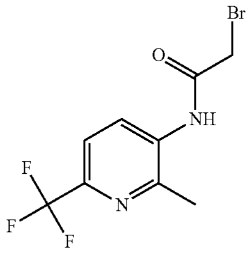 [SMILES: Cc1nc(C(F)(F)F)ccc1NC(=O)CBr]

To the stirred solution of 2-methyl-6-(trifluoromethyl)pyridin-3-amine (2.40 g, 13.5 mmol) in DCM (30 mL) were added 2-bromoacetyl bromide (2.99 g, 14.8 mmol) and DMAP (1.65 g, 13.5 mmol) and the RM was stirred at RT for 4 hours. Water (20 mL) was added to the RM and it was extracted with EtOAC (2×20 mL). The organic layer was dried over $Na_2SO_4$ and concentrated under reduced pressure. The crude product was purified by column chromatography (Silica gel column: Silica 12 g, eluent hexane:EtOAc 100:0 to 75:25). The product containing fractions were concentrated under reduced pressure and dried under HV to give the title compound.

LC-MS: Rt=1.29 min; MS m/z $[M+H]^+$ 297.0/299.0; UPLC-MS 13

Intermediate DX: 2-chloro-N-(4-chloro-6-(trifluoromethyl)pyridin-3-yl)acetamide

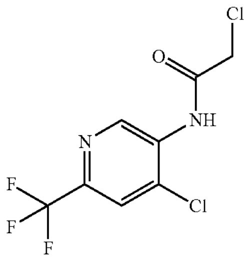 [SMILES: O=C(CCl)Nc1cnc(C(F)(F)F)cc1Cl]

4-Chloro-6-(trifluoromethyl)pyridin-3-amine (300 mg, 1.53 mmol) was suspended in ACN (10 mL). $K_2CO_3$ (211 mg, 1.53 mmol) and 2-chloroacetyl chloride (146 μL, 1.83 mmol) were added at 0° C. and the RM was stirred at 70° C. for 12 hours. Water was added and the organic layer was dried over $Na_2SO_4$ and concentrated under reduced pressure to give the title compound.

LC-MS: Rt=1.49 min; MS m/z $[M+H]^+$ 273.1/275.1/277.1; UPLC-MS 11

Intermediate DY: 2-bromo-N-(4-methyl-6-(trifluoromethyl)pyridin-3-yl)acetamide

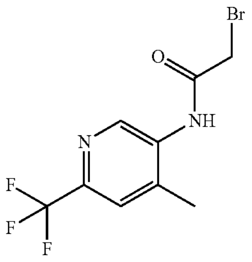 [SMILES: Cc1cc(C(F)(F)F)ncc1NC(=O)CBr]

4-Methyl-6-(trifluoromethyl)pyridin-3-amine (210 mg, 1.19 mmol) was suspended in DCM (3 mL) and DMAP (146 mg, 1.19 mmol) was added at 0° C. and the RM was stirred for 10 minutes. 2-bromoacetyl bromide (125 μL, 1.43 mmol) was added and the RM was stirred at RT for 12 hours. Water was added. The organic layer was washed with water, dried over $Na_2SO_4$ and concentrated under reduced pressure to give the title compound.

LC-MS: Rt=1.73 min; MS m/z $[M+H]^+$ 297.2/299.2; UPLC-MS 13

Intermediate DZ: N-(3-fluoro-2-methyl-4-(trifluoromethyl)phenyl)-2-iodoacetamide Step 1: 2-chloro-N-(3-fluoro-2-methyl-4-(trifluoromethyl)phenyl)acetamide

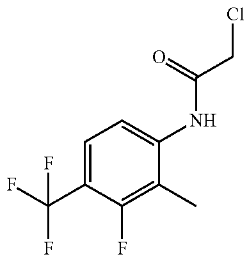 [SMILES: Cc1c(NC(=O)CCl)ccc(C(F)(F)F)c1F]

3-Fluoro-2-methyl-4-(trifluoromethyl)aniline (1.19 g, 6.14 mmol) was dissolved in DCM (25 mL) and 2-chloroacetyl chloride (538 μL, 6.75 mmol) was added at 0° C., followed by $Et_3N$ (1.70 mL, 12.3 mmol) and stirred at RT for 15 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound. The crude product still contained ca 34% of starting material.

LC-MS: Rt=1.00 min; MS m/z $[M-H]^-$ 268.1/270.1; UPLC-MS 1

LC-MS: Rt=4.98 min; MS m/z $[M-H]^-$ 268.1/270.0; UPLC-MS 2

Step 2: N-(3-fluoro-2-methyl-4-(trifluoromethyl)phenyl)-2-iodoacetamide

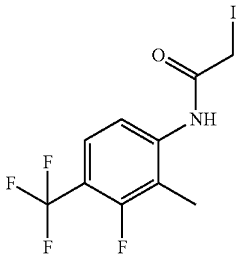 [SMILES: Cc1c(NC(=O)CI)ccc(C(F)(F)F)c1F]

2-Chloro-N-(3-fluoro-2-methyl-4-(trifluoromethyl)phenyl)acetamide (1.30 g, 4.82 mmol) were mixed in acetone (20 mL) and KI (880 mg, 5.30 mmol) was added. The RM was stirred at 60° C. for 30 minutes. The reaction was stopped and filtered. The cake was washed several times with acetone. The filtrate was concentrated under reduced pressure. As shown in the LCMS in the step before the reaction contains ca 34% aniline. For that reason the concentrated filtrate was dissolved in DCM (10 mL) and 2-chloroacetyl chloride (258 μL, 3.24 mmol) was added, followed by $Et_3N$ (898 μL, 6.48 mmol). The RM was stirred at RT for 20 minutes. LCMS showed a small amount of aniline left. Water (10 mL), aq sat $NaHCO_3$ (10 mL) and DCM (10 mL) were added. The aqueous layer was washed twice with DCM (2×100 mL). The combined organic layers were dried through a phase separator and concentrated under reduced pressure. The crude product from step 2 was restarted with KI (550 mg, 3.31 mmol) in acetone (10 mL) at 60° C. for 1 hour. The reaction was stopped and filtered. The cake was washed several times with acetone. The filtrate was concentrated under reduced pressure to give the title compound.

LC-MS: Rt=1.05 min; MS m/z $[M-H]^-$ 360.1; UPLC-MS 1

Intermediate EA: 2-chloro-N-(2-chloro-4-(pentafluorosulfanyl)phenyl)acetamide

Step 1: 2-chloro-4-(pentafluorosulfanyl)aniline

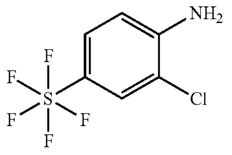 [SMILES: Nc1ccc(S(F)(F)(F)(F)F)cc1Cl]

4-(Pentafluorosulfanyl)aniline (2.00 g, 9.13 mmol) and NCS (1.28 g, 9.58 mmol) were diluted in DMF (18 mL) and the resulting RM was then stirred at 80° C. for 1 hour. The reaction was stopped and cooled down. The RM was adsorbed onto Isolute and purified by column chromatography (RediSep Column: Silica 80 g, eluent cyclohexane: cyclohexane/TBME (1/1) 100:0 to 40:60). The product containing fractions were combined and evaporated to dryness to give the title compound as beige, slightly pink crystals.

LC-MS: Rt=0.98 min; no mass observed; UPLC-MS 7

Step 2: 2-chloro-N-(2-chloro-4-(pentafluorosulfanyl)phenyl)acetamide

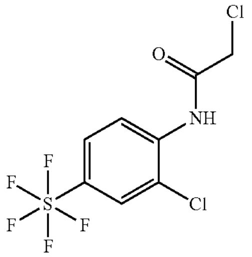 [SMILES: O=C(CCl)Nc1ccc(S(F)(F)(F)(F)F)cc1Cl]

2-Chloro-4-(pentafluorosulfanyl)aniline (404 mg, 1.59 mmol) was dissolved in DCM (5 mL) and 2-chloroacetyl chloride (152 μL, 1.91 mmol) was added, followed by $Et_3N$ (551 μL, 3.98 mmol). The RM was stirred at RT for 3 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified by column chromatography (RediSep Column: Silica 24 g, eluent DCM:DCM/MeOH (1/1) 100:0 to 70:30). The product containing fractions were combined, concentrated under reduced pressure and dried under HV to afford the title compound as a beige solid.

LC-MS: Rt=1.22 min; MS m/z $[M-H]^-$ 328.0/330.0/332.0; UPLC-MS 1

Intermediate EB: 2-bromo-N-(5-fluoro-4-formyl-2-methylphenyl)acetamide

Step 1: tert-butyl (5-fluoro-4-formyl-2-methylphenyl)carbamate

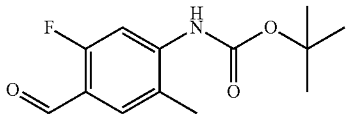 [SMILES: Cc1cc(C=O)c(F)cc1NC(=O)OC(C)(C)C]

To the stirred solution of 4-bromo-2-fluoro-5-methylbenzaldehyde (3.50 g, 16.1 mmol) in toluene (70 mL) were added tert-butyl carbamate (3.78 g, 32.3 mmol) and $Cs_2CO_3$ (10.5 g, 32.3 mmol). The RM was degassed with nitrogen for 15 minutes. BINAP (502 mg, 806 μmol) and $Pd(OAc)_2$ (181 mg, 806 μmol) were added and the RM was stirred at 100° C. for 14 hours. Water (50 mL) was added and it was extracted with DCM (2×50 mL). The organic layer was washed with brine (20 mL), dried over $Na_2SO_4$ and concentrated under reduced pressure. The crude product was purified by column chromatography (Silica gel column: Silica 12 g, eluent DCM:MeOH 100:0 to 99:1). The product containing fractions were combined and concentrated under reduced pressure to give the title compound.

LC-MS: Rt=1.7 min; MS m/z $[M+H]^+$ 254.1; UPLC-MS 12

Step 2: 4-amino-2-fluoro-5-methylbenzaldehyde

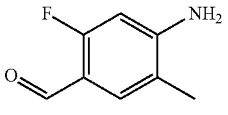

To the stirred solution of tert-butyl (5-fluoro-4-formyl-2-methylphenyl)carbamate (3.20 g, 12.5 mmol) in $Et_2O$ (15 mL) was added HCl 2M in $Et_2O$ (30.0 mL, 60.0 mmol) and the RM was stirred at RT for 4 hours. The RM was concentrated under reduced pressure and washed with $Et_2O$ to give the title compound.

LC-MS: Rt=0.81 min; MS m/z $[M+H]^+$ 154.3; UPLC-MS 13

Step 3: 2-bromo-N-(5-fluoro-4-formyl-2-methylphenyl)acetamide

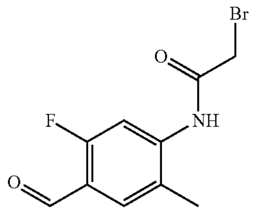

To the stirred solution of 4-amino-2-fluoro-5-methylbenzaldehyde (1.90 g, 11.4 mmol) in DCM (30 mL) at 0° C. were added 2-bromoacetyl bromide (2.30 g, 11.4 mmol) and DMAP (1.39 g, 11.4 mmol) and the RM was stirred at RT for 4 hours. Water (20 mL) was added and the RM was extracted with EtOAc (2×20 mL). The organic layer was washed with brine (20 mL), dried over $Na_2SO_4$ and concentrated under reduced pressure. The crude product was purified by column chromatography (Silica gel column: Silica 40 g, eluent hexane:EtOAc 100:0 to 70:30). The product containing fractions were combined and concentrated to give the title compound.

LC-MS: Rt=1.42 min; MS m/z $[M+H]^+$ 274.1/276.1; UPLC-MS 13

Intermediate EC: 2-iodo-N-(2-methyl-6-(trifluoromethyl)pyridin-3-yl)acetamide

Step 1: 2-chloro-N-(2-methyl-6-(trifluoromethyl)pyridin-3-yl)acetamide

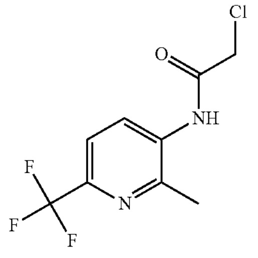 [SMILES: Cc1nc(C(F)(F)F)ccc1NC(=O)CCl]

2-Methyl-6-(trifluoromethyl)pyridin-3-amine (2.00 g, 11.4 mmol) was dissolved in DCM (19 mL). At 0° C. 2-chloroacetyl chloride (958 μL, 11.9 mmol) was added. The solution turned into a white suspension. $Et_3N$ (3.46 mL, 25.0 mmol) was added. The white suspension turned into a brown solution, which was stirred at 0° C. for 25 minutes. Then it was allowed to warm to RT. After 1.2 hours 2-chloroacetyl chloride (300 mg, 2.63 mmol) was added and the RM was stirred at RT for 17.5 hours. 2-Chloroacetyl chloride (200 mg, 1.75 mmol) was added again and the RM was continued stirring at RT for 1.5 hours. The RM was extracted with DCM (3×80 mL) and water (2×10 mL). The combined organic layers were dried through a phase separator and concentrated under reduced pressure. The residue was adsorbed onto Isolute and purified by column chromatography (RediSep Column: Silica 40 g, eluent DCM:MeOH 100:0 to 80:20). All product containing fractions were combined to give the title compound as a white solid.

LC-MS: Rt=0.83 min; MS m/z $[M+H]^+$ 253.1/255.1, m/z $[M-H]^-$ 251.1/253.1; UPLC-MS 3

Step 2: 2-iodo-N-(2-methyl-6-(trifluoromethyl)pyridin-3-yl)acetamide

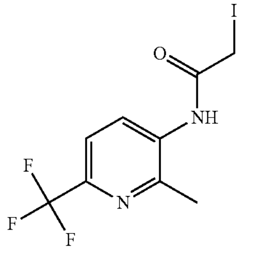 [SMILES: Cc1nc(C(F)(F)F)ccc1NC(=O)CI]

2-Chloro-N-(2-methyl-6-(trifluoromethyl)pyridin-3-yl) acetamide (2.28 g, 7.94 mmol) was dissolved in acetone (30 mL). KI (1.71 g, 10.3 mmol) was added to the pale brown solution and the RM was stirred at reflux for 1.3 hours. The RM was cooled to RT and the suspension was filtered. The cake was washed with acetone (2×20 mL). The filtrate was concentrated under reduced pressure to give a beige solid, which was suspended in DCM (20 mL) and filtered. The cake was washed with DCM (3×20 mL) and the filtrate was concentrated under reduced pressure to give the title compound as a slight yellow solid.

LC-MS: Rt=0.88 min; MS m/z $[M+H]^+$ 345.0, m/z $[M-H]^-$ 342.9; UPLC-MS 3

Intermediate ED: N-(5-fluoro-2-methyl-6-(trifluoromethyl)pyridin-3-yl)-2-iodoacetamide Step 1: 5-fluoro-2-methyl-6-(trifluoromethyl)pyridin-3-amine

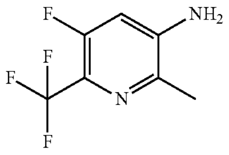

5-Fluoro-2-methylpyridin-3-amine·HCl (533 mg, 3.28 mmol) and bis(((trifluoromethyl)sulfinyl)oxy)zinc (2.58 g, 7.78 mmol) were mixed in DCM (5 mL) and water (1.7 mL). Then 2-hydroperoxy-2-methylpropane (1.36 mL, 9.83 mmol) was added. The mixture was stirred at RT for 5 hours. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure. The crude product was purified in 3 portions by reverse phase preparative HPLC (3×RP-HPLC acidic 1: 5 to 100% B in 20 min). The product containing fractions were combined, basified with aq sat $NaHCO_3$, extracted twice with DCM, dried through a phase separator and concentrated under reduced pressure to give the title compound.

LC-MS: Rt=0.89 min; MS m/z $[M+H]^+$ 195.1, m/z $[M-H]^-$ 193.0; UPLC-MS 3

Step 2: 2-chloro-N-(5-fluoro-2-methyl-6-(trifluoromethyl)pyridin-3-yl)acetamide

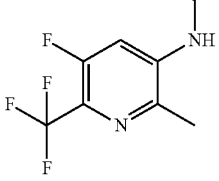

5-Fluoro-2-methyl-6-(trifluoromethyl)pyridin-3-amine (436 mg, 2.25 mmol) was dissolved in DCM (3 mL) and 2-chloroacetyl chloride (232 µL, 2.91 mmol) was added dropwise, followed by $Et_3N$ (685 µL, 4.94 mmol). The RM was stirred at RT for 15 minutes. 2-Chloroacetyl chloride (100 µL, 1.26 mmol) was added. The RM was stirred at RT for 15 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=0.98 min; MS m/z $[M+H]^+$ 271.2/273.1, m/z $[M-H]^-$ 269.0/271.0; UPLC-MS 3

Step 3: N-(5-fluoro-2-methyl-6-(trifluoromethyl)pyridin-3-yl)-2-iodoacetamide

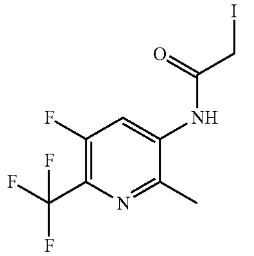 [SMILES: Cc1nc(C(F)(F)F)c(F)cc1NC(=O)CI]

2-Chloro-N-(5-fluoro-2-methyl-6-(trifluoromethyl)pyridin-3-yl)acetamide (771 mg, 2.71 mmol) and KI (899 mg, 5.41 mmol) were suspended in ACN (15 mL) and stirred at 82° C. for 30 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=1.04 min; MS m/z $[M+H]^+$ 363.0, m/z $[M-H]^-$ 360.9; UPLC-MS 3

Intermediate EE: 2-chloro-N-(3-fluoro-2-methyl-4-(trifluoromethyl)phenyl)acetamide

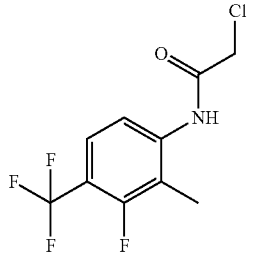 [SMILES: Cc1c(NC(=O)CCl)ccc(C(F)(F)F)c1F]

3-Fluoro-2-methyl-4-(trifluoromethyl)aniline (295 mg, 1.53 mmol) was dissolved in DCM (5 mL) and 2-chloroacetyl chloride (122 µL, 1.53 mmol) was added, followed by $Et_3N$ (423 µL, 3.05 mmol). The RM was stirred at RT for 1 hour. 2-Chloroacetyl chloride (122 µL, 1.53 mmol) was added, followed by $Et_3N$ (423 µL, 3.05 mmol). The RM was stirred at RT for 1 hour. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=1.01 min; MS m/z $[M-H]^-$ 268.2/270.1; UPLC-MS 1

Intermediate EF: 2-chloro-N-(2-chloro-5-fluoro-4-(trifluoromethyl)phenyl)acetamide

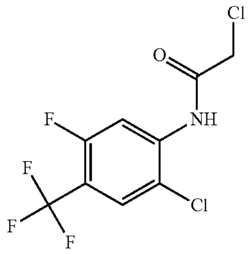 [SMILES: O=C(CCl)Nc1cc(F)c(C(F)(F)F)cc1Cl]

2-Chloro-5-fluoro-4-(trifluoromethyl)aniline (205 mg, 960 μmol) was dissolved in DCM (2 mL) and 2-chloroacetyl chloride (80.0 μL, 1.01 mmol) was added, followed by $Et_3N$ (400 μL, 2.89 mmol). The RM turned from a colorless solution to a brown solution. The RM was stirred at RT for 30 minutes. 2-Chloroacetyl chloride (120 μL, 1.51 mmol) was added and the RM was stirred at RT for 30 minutes. Water (10 mL), aq sat $NaHCO_3$ (10 mL) and DCM (10 mL) were added. The aqueous layer was washed twice with DCM (2×10 mL). The combined organic layers were dried through a phase separator and concentrated under reduced pressure to give the title compound.

LC-MS: Rt=1.22 min; MS m/z $[M-H]^-$ 288.0/290.0/292.0; UPLC-MS 1

Intermediate EG: (S)-((2-fluoro-4-iodobutoxy)methyl)benzene

Step 1: (R)-1-(benzyloxy)pent-4-en-2-ol

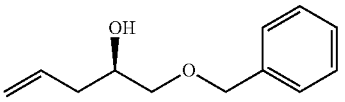

To a colorless solution of (R)-2-((benzyloxy)methyl)oxirane (9.29 mL, 59.7 mmol) in THF (200 mL) was added CuBr-DMS complex (12.5 g, 59.7 mmol). The brown fine suspension was cooled to −45° C. Then vinylmagnesium bromide 1M in THF (209 mL, 209 mmol) was added dropwise within 30 minutes at −45° C. to −35° C. After the addition the dark brown suspension was stirred at −45° C. for 20 minutes. The RM was allowed to warm to RT and stirred for 1 hr. The brown RM was warmed to −15° C. and quenched with aq sat $NH_4Cl$ (500 mL) and stirred at 0° C. for 30 minutes. The RM was filtered over celite, washed with TBME (5×200 mL) and the blue biphasic filtrate was extracted. The organic phase was extracted twice with brine (2×300 mL). The aqueous layers were washed twice with TBME (2×300 mL). The combined organic phases were dried over $Na_2SO_4$, filtered and concentrated under reduced pressure at 45° C. to give the title compound as a yellow oil.

LC-MS: Rt=0.90 min; no mass observed; UPLC-MS 1

Step 2: (S)-(((2-fluoropent-4-en-1-yl)oxy)methyl)benzene

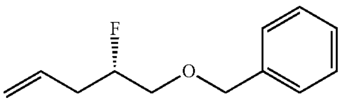

To a pale yellow solution of (R)-1-(benzyloxy)pent-4-en-2-ol (12.0 g, 62.4 mmol) in benzotrifluoride 547948 (180 mL) were added DIPEA (164 mL, 936 mmol) and triethylamine trihydrofluoride (61.0 ml, 374 mmol) at RT. A slight exotherm increased the internal temperature to a maximum of 29° C. 1,1,2,2,3,3,4,4,4-Nonafluorobutane-1-sulfonyl fluoride (11.2 mL, 62.4 mmol) was added at 25° C. (exothermic: internal temperature was slowly increased to a maximum of 36° C.). The clear yellow brown RM was stirred at RT for 1 hour (outside temperature was set to 20° C.). 1,1,2,2,3,3,4,4,4-Nonafluorobutane-1-sulfonyl fluoride (11.2 mL, 62.4 mmol) was added to the pale brown RM at RT (slightly exothermic). The clear pale brown RM was stirred at RT for 1 hour and 1,1,2,2,3,3,4,4,4-nonafluorobutane-1-sulfonyl fluoride (11.2 mL, 62.4 mmol) was added. The clear pale brown RM was stirred at RT for 1 hour. 1,1,2,2,3,3,4,4,4-Nonafluorobutane-1-sulfonyl fluoride (11.2 mL, 62.4 mmol) was added. The clear pale brown RM was stirred at RT overnight. The RM was poured into ice-cold HCl 2N (600 mL) and stirred for about 10 minutes. Then the phases were separated and the organic phase was extracted successively with ice-cold HCl 2N (500 mL), aq sat $NaHCO_3$ (400 mL) and water (400 mL). The aqueous layer was washed twice with TBME (2×300 mL). The combined organic phases were dried over $Na_2SO_4$, filtered and the filtrate was evaporated in vacuo at 50° C. to give crude product as a brown resin (24.5 g). The crude product was purified by column chromatography (Biotage Safer Silica D 60 μm cartridge: 350 g, eluent heptane:EtOAc 100:0 to 60:40). The product containing fractions were combined and concentrated under reduced pressure to give the title compound as a yellow oil.

LC-MS: Rt=1.31 min; no mass observed; UPLC-MS 1

Step 3: (S)-4-(benzyloxy)-3-fluorobutan-1-ol

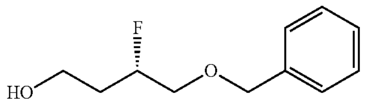 [SMILES: OCC[C@H](F)COCc1ccccc1]

A pale yellow solution of (S)-(((2-fluoropent-4-en-1-yl)oxy)methyl)benzene (11.5 g, 59.2 mmol) was dissolved in DCM (400 mL) and MeOH (100 mL). The pale yellow solution was cooled in a dry ice/acetone-bath to −74° C. internal temperature. Adjust oxygen to purge the lines (5 minutes). Then ozone generator was switched on (200 L/hour $O_2$, and 100% power). (slightly exothermic; internal temperature was slowly increased to a maximum of −68° C.). After about 13 minutes the RM was blue. Performance of the ozone generator adjusted to zero. During the flushing of the generator and the apparatus with argon, sodium borohydride (4.03 g, 107 mmol) was added portionwise within about 3 minutes to the RM (slightly exothermic;

internal temperature was slowly increased to a maximum of −69° C.). The RM decolorized from blue to colorless. After 5 minutes the cooling bath was removed and the RM was allowed to warm to RT (ca 45 minutes). The RM was stirred at RT for 1 hour. The RM was poured onto ice cold HCl 0.5N (500 mL) and stirred for 5 minutes. Then the phases were separated. The organic phase was extracted once with aq sat $NaHCO_3$ (500 mL). The aqueous layer was washed twice with DCM (2×200 mL). The combined organic phases were dried over $Na_2SO_4$, filtered and the solvent was removed in vacuo at 45° C. to give the title compound as a colorless slightly cloudy oil.

LC-MS: Rt=0.67 min; MS m/z $[M+H]^+$ 199.1, m/z $[M-H]^-$ 197.9; UPLC-MS 1

Step 4: (S)-((2-fluoro-4-iodobutoxy)methyl)benzene

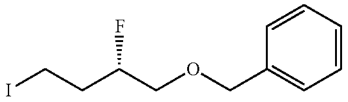 [SMILES: F[C@@H](CCI)COCc1ccccc1]

To a colorless solution of (S)-4-(benzyloxy)-3-fluorobutan-1-ol (10.0 g, 50.4 mmol) in THF (230 mL) were added triphenylphosphane (19.9 g, 76.0 mmol) and 1H-imidazole (6.87 g, 101 mmol). The colorless solution was cooled in an ice/MeOH bath to −10° C. Then $I_2$ (18.6 g, 73.1 mmol) was added (strong exotherm, temperature rose to 5° C.). The brown RM was stirred at 0° C. for 2 hours. After 30 minutes a fine yellow suspension was formed. The RM was poured onto ice cold aq sat $NH_4Cl$ (500 mL) and TBME (500 mL) and stirred for 5 minutes. Then the phases were separated. The organic phase was extracted once with aq sat $NaHCO_3$ (500 mL) and brine (500 mL). The aqueous layer was washed twice with TBME (2×300 mL). The combined organic phases were dried over $Na_2SO_4$, filtered and concentrated under reduced pressure at 45° C. until the triphenylphosphane oxide began to crystallize. Then heptane (250 mL) was added slowly. The rest of TBME and THF was evaporated. The yellow suspension was stirred at 10° C. for 30 minutes. The precipitated crystals were filtered off and the solid was washed with heptane. The cake was discarded. The filtrate was concentrated under reduced pressure at 45° C. to give a yellow oil (16.2 g) The crude product was purified by column chromatography (Biotage Sfaer Silica D 60 μm cartridge: 350 g, eluent heptane:DCM 100:0 to 50:50). The product containing fractions were combined. The impure fractions were purified by column chromatography (Biotage Sfaer Silica D 60 μm; 350 g, eluent heptane: DCM 100:0 to 50:50). The product containing fractions were combined with the ones from the first purification and concentrated under reduced pressure to give the title compound as a pale yellow oil.

LC-MS: Rt=1.33 min; no mass observed; UPLC-MS 1

Intermediate EH: tert-butyl 4-(1-methoxy-1,3-dioxopentan-2-yl)piperazine-1-carboxylate Step 1: methyl 2-chloro-3-oxopentanoate

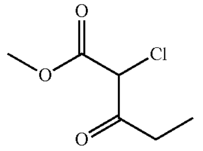

To a solution of methyl 3-oxopentanoate (10.4 kg, 80.0 mol) in DCM (67 L) was added $SO_2Cl_2$ (14.0 kg, 104 mol) at RT over 2.5 hours. The reaction was allowed to warm to RT and stirred for 16 hours. The RM was concentrated under reduced pressure and the residue was dissolved in DCM (20 L) and washed with water (10 L), brine (10 L), dried over $Na_2SO_4$ and filtered. The filtrate was concentrated under reduced pressure to give the title compound as a light yellow liquid.

$^1H$ NMR (400 MHz, $CDCl_3$-d) δ 4.65 (s, 1H), 3.68 (s, 3H), 2.59 (m, 2H), 0.96 (t, 3H)

Step 2: tert-butyl 4-(1-methoxy-1,3-dioxopentan-2-yl)piperazine-1-carboxylate

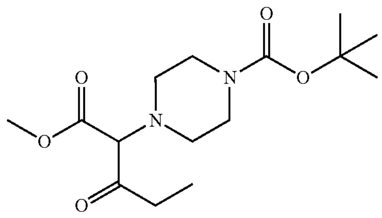 [SMILES: CCC(=O)C(C(=O)OC)N1CCN(C(=O)OC(C)(C)C)CC1]

To a solution of methyl 2-chloro-3-oxopentanoate (12.1 kg, 53.7 mol) in dry ACN (53 L) was added $Et_3N$ (22.3 L, 161 mol) over 1.5 hours, followed by dropwise addition of tert-butyl piperazine-1-carboxylate (10.0 kg, 53.7 mol) in ACN (50 L) over 2.5 hours. The reaction was stirred at 60° C. for 16 hours. The RM was filtered and washed with EtOAc (10 L). The filtrate was then concentrated under reduced pressure and the residue was dissolved in EtOAc (45 L) and washed with water (45 L), dried over $Na_2SO_4$ and filtered. The filtrate was concentrated under reduced pressure and the residue was purified by column chromatography (Silica column 150 mm×800 mm×70 mm, eluent heptane:EtOAc 100:0 to 90:10) to give the title compound.

HPLC: Rt=3.681/5.513 min; HPLC 4

Intermediate EI: ethyl 2-bromo-3-oxopentanoate

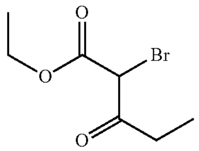

Ethyl 3-oxopentanoate (10.0 g, 65.9 mmol) was dissolved in DCM (100 mL), NBS (12.3 g, 69.2 mmol) was added, followed by TsOH·$H_2O$ (2.53 g, 13.2 mmol). The RM was stirred at RT for 2.5 hours. The RM was filtered through Hyflo and washed with DCM. The filtrate was extracted with water (3×50 mL). The organic layer was washed with DCM (3×200 mL). The combined organic layers were dried through a phase separator and concentrated under reduced pressure to give the title compound as a colourless liquid.

LC-MS: Rt=0.90 min; MS m/z $[M-H]^-$ 221.1/223.1; UPLC-MS 8

Intermediate EJ: tert-butyl 4-(1-ethoxy-1,3-dioxopentan-2-yl)piperazine-1-carboxylate

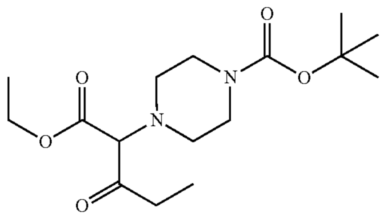

Ethyl 2-bromo-3-oxopentanoate (Intermediate EI) (2.87 g, 7.97 mmol), tert-butyl piperazine-1-carboxylate (8.20 g, 44.0 mmol) and $K_2CO_3$ (6.61 g, 47.8 mmol) were mixed in ACN (50 mL). The suspension was stirred at RT for 30 minutes. The RM was filtered. The cake was washed with ACN. The filtrate was concentrated under reduced pressure. The crude product was purified by column chromatography (RediSep Column: Silica 80 g, eluent DCM:DCM/MeOH (9/1) 100:0 to 0:100). The product containing fractions were combined, concentrated under reduced pressure and dried under HV to give the title compound.

LC-MS: Rt=1.11/1.38 min; MS m/z $[M+H]^+$ 329.3, m/z $[M-H]^-$ 327.2; UPLC-MS 8

Intermediate EK: tert-butyl (2R)-4-(1-ethoxy-1,3-dioxopentan-2-yl)-2-methylpiperazine-1-carboxylate

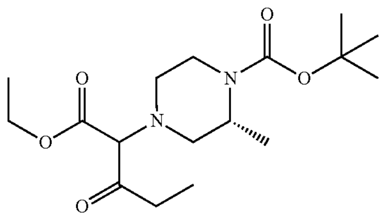 [SMILES: CCOC(=O)C(C(=O)CC)N1CCN(C(=O)OC(C)(C)C)[C@H](C)C1]

Ethyl 2-bromo-3-oxopentanoate (Intermediate EI) (15.6 g, 62.9 mmol) and tert-butyl (R)-2-methylpiperazine-1-carboxylate (13.2 g, 66.1 mmol) were mixed in ACN (250 mL) and $K_2CO_3$ (17.4 g, 126 mmol) was added. The reaction was stirred at RT for 4.5 hours. The suspension was filtered and the cake was washed with ACN. The filtrate was concentrated under reduced pressure. The yellow oil was extracted with DCM (4×200 mL) and water (2×150 mL). The organic layer was dried through a phase separator and concentrated under reduced pressure. The residue was adsorbed onto Isolute and purified by column chromatography (RediSep Column: Silica 330 g, eluent heptane:EtOAc 100:0 to 75:25)

The product containing fractions were combined and concentrated under reduced pressure to get the title compound as a colourless oil.

LC-MS: Rt=1.20/1.42 min; MS m/z $[M+H]^+$ 343.3, m/z $[M-H]^-$ 341.1; UPLC-MS 8

Intermediate EL: tert-butyl (3S)-4-(1-ethoxy-1,3-dioxopentan-2-yl)-3-methylpiperazine-1-carboxylate

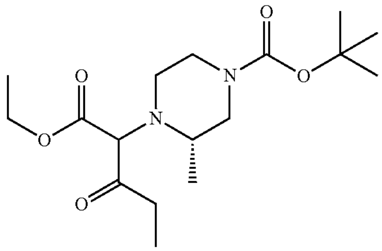 [SMILES: CCOC(=O)C(C(=O)CC)N1CCN(C(=O)OC(C)(C)C)C[C@@H]1C]

Ethyl 2-bromo-3-oxopentanoate (Intermediate EI) (5.00 g, 22.4 mmol) and tert-butyl (S)-3-methylpiperazine-1-carboxylate (4.71 g, 23.5 mmol) were mixed in ACN (100 mL) and $K_2CO_3$ (6.20 g, 44.8 mmol) was added. The RM was stirred at RT for 3.25 hours. Then it was filtered through Hyflo, washed with ACN and concentrated under reduced pressure. The orange oil was extracted with DCM (4×100 mL) and water (3×50 mL). The organic layer was dried through a phase separator and concentrated under reduced pressure. The crude product was adsorbed onto Isolute and purified by column chromatography (RediSep Column: Silica 120 g, eluent heptane:EtOAc 100:0 to 0:100). The product containing fractions were combined and concentrated under reduced pressure to give the title compound as a pale yellow liquid.

LC-MS: Rt=1.14/1.45 min; MS m/z $[M+H]^+$ 343.3, UPLC-MS 1

Intermediate EM: tert-butyl (3R)-4-(1-ethoxy-1,3-dioxopentan-2-yl)-3-methylpiperazine-1-carboxylate

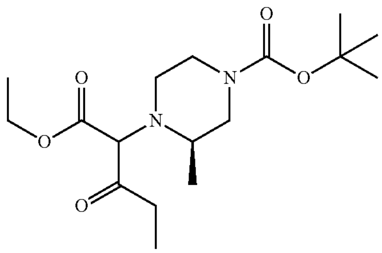 [SMILES: CCOC(=O)C(C(=O)CC)N1CCN(C(=O)OC(C)(C)C)C[C@H]1C]

Ethyl 2-bromo-3-oxopentanoate (Intermediate EI) (5.00 g, 22.4 mmol) and tert-butyl (R)-3-methylpiperazine-1-carboxylate (4.71 g, 23.5 mmol) were mixed in ACN (100 mL). $K_2CO_3$ (6.20 g, 44.8 mmol) was added and the RM was stirred at RT for 3.3 hours. The suspension was filtered through Hyflo and washed with ACN. The filtrate was concentrated under reduced pressure. The residue was extracted with DCM (4×100 mL) and water (3×50 mL). The organic layer was dried through a phase separator and concentrated under reduced pressure. The crude product was adsorbed onto Isolute and purified by column chromatography (RediSep Column: Silica 120 g, eluent heptane: EtOAc 100:0 to 0:100). The product containing fractions were combined and concentrated under reduced pressure to give the title compound as a pale yellow liquid.

LC-MS: Rt=1.14/1.45 min; MS m/z $[M+H]^+$ 343.4, UPLC-MS 1

Intermediate EN: tert-butyl (2R,5S)-4-(1-ethoxy-1,3-dioxopentan-2-yl)-2,5-dimethylpiperazine-1-carboxylate

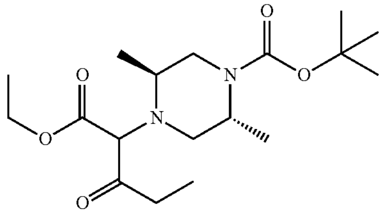 [SMILES: CCOC(=O)C(C(=O)CC)N1C[C@@H](C)N(C(=O)OC(C)(C)C)C[C@@H]1C]

A beige suspension of tert-butyl (2R,5S)-2,5-dimethylpiperazine-1-carboxylate (24.0 g, 106 mmol), ethyl 2-bromo-3-oxopentanoate (Intermediate EI) (25.0 g, 106 mmol) and $K_2CO_3$ (22.1 g, 160 mmol) in ACN (266 mL) was stirred at RT for 8.25 hours. The RM was filtered. The cake was washed with ACN and discarded. The filtrate was diluted with DCM and washed once with water. The aqueous layer was extracted twice with DCM. The combined organic phases were dried through a phase separator, concentrated under reduced pressure and dried under vacuum (40° C.) to give a brown oil. The crude product was adsorbed onto Isolute and purified in 2 portions by column chromatography (RediSep Column: Silica 330 g, eluent heptane:EtOAc 100:0 to 30:70) and (RediSep Column: Silica 330 g, eluent heptane:EtOAc 100:0 to 20:80). The product containing fractions were combined and concentrated under reduced pressure to give the title compound.

LC-MS: Rt=1.20/1.49 min; MS m/z $[M+H]^+$ 357.1, m/z $[M+H]^+$ 355.4; UPLC-MS 1

Intermediate EO: tert-butyl (2R)-4-(1-ethoxy-1,3-dioxobutan-2-yl)-2-methylpiperazine-1-carboxylate

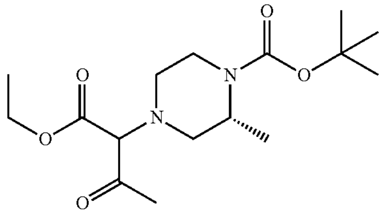 [SMILES: CCOC(=O)C(C(C)=O)N1CCN(C(=O)OC(C)(C)C)[C@H](C)C1]

To a colorless solution of tert-butyl (R)-2-methylpiperazine-1-carboxylate (10.0 g, 50.0 mmol) in toluene (100 mL) was added ethyl 2-chloro-3-oxobutanoate (8.73 mL, 60.0 mmol). The resulting yellow solution was stirred at 100° C. for 3.25 hours. The RM was concentrated under reduced pressure and dried under vacuum (40° C.) to give a brown residue. The crude product was adsorbed onto Isolute and purified by column chromatography (RediSep Column: Silica 220 g, eluent heptane:EtOAc 100:0 to 10:90). The product containing fractions were combined and concentrated under reduced pressure to give the title compound as a yellow oil.

LC-MS: Rt=1.12/1.35 min; MS m/z $[M+H]^+$ 329.2, m/z $[M+H]^+$ 327.1; UPLC-MS 8

Intermediate EP: tert-butyl 4-(1-ethoxy-1,3-dioxobutan-2-yl)piperazine-1-carboxylate

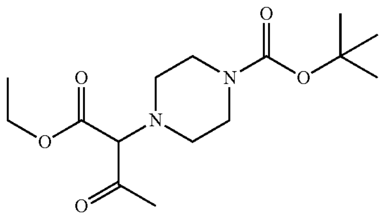 [SMILES: CCOC(=O)C(C(C)=O)N1CCN(C(=O)OC(C)(C)C)CC1]

To a stirred solution of tert-butyl piperazine-1-carboxylate (150 g, 805 mmoL) in ACN (1.5 L) at RT was added $K_2CO_3$ (223 g, 1.61 mol) and the RM was stirred for 15 minutes. Then ethyl 2-chloro-3-oxobutanoate (112 mL, 809 mmol) was added slowly at the same temperature. The resulting RM was stirred at RT for 16 hours. The RM was filtered through celite pad. The celite pad was washed with EtOAc (2 L). The combined organic layers were concentrated under reduced pressure to get crude residue. The residue was dissolved in EtOAc (3 L) and then washed with ice cold water, brine, dried over $Na_2SO_4$ and concentrated under reduced pressure to get crude product as pale brown liquid. The crude product was purified by column chromatography (silica gel, 60-120 mesh, eluent petroleum ether: EtOAc 100:0 to 85:15). The pure product containing fractions were combined and concentrated under reduced pressure to give the title compound as a liquid. The impure fractions were combined and concentrated under reduced pressure. Then they were purified again by column chromatography (silica gel, 60-120 mesh, eluent petroleum ether: EtOAc 100:0 to 85:15). The pure product containing fractions were combined and concentrated under reduced pressure to give the title compound as a liquid. Both liquids were mixed, dissolved in DCM and concentrated under reduced pressure to get the title compound as a brown liquid. The liquid was again dissolved in DCM, concentrated under reduced pressure. The process was repeated three times and then dried under vacuum to give the title compound as a brown liquid.

HPLC: Rt=11.763 min; HPLC 6

Intermediate EQ: tert-butyl 4-(1-methoxy-1,3-dioxopentan-2-yl)-2,3-dimethylpiperazine-1-carboxylate

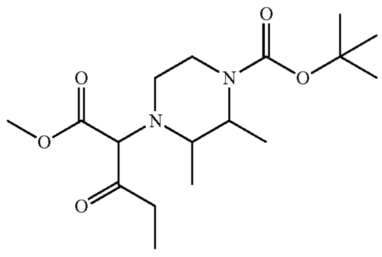 [SMILES: CCC(=O)C(C(=O)OC)N1CCN(C(=O)OC(C)(C)C)C(C)C1C]

To a stirred solution of tert-butyl 2,3-dimethylpiperazine-1-carboxylate (26.0 g, 121 mmol) in ACN (250 mL) were added $K_2CO_3$ (25.2 g, 182 mmol) and ethyl 2-bromo-3-oxopentanoate (Intermediate EI) (27.1 g, 121 mmol) at RT and the RM was stirred at RT for 16 hours. The RM was diluted with EtOAc/water, extracted once with EtOAc and the organic extract was washed with water and brine, dried over $Na_2SO_4$ and concentrated under reduced pressure to give the title compound as a yellow oil.

LC-MS: Rt=1.21/1.51 min; MS m/z $[M+H]^+$ 357.6; UPLC-MS 1

Intermediate ER: 3-bromo-1H-1,2,4-triazol-5-amine

Step 1: 3,5-dibromo-1-(methoxymethyl)-1H-1,2,4-triazole

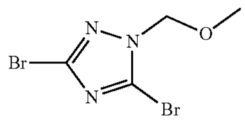

To a solution of NaH (846 g, 21.2 mol, 60%) in DMF (12 L) was added 3,5-dibromo-1H-1,2,4-triazole (4.00 kg, 17.6 mol) at 10° C. The resulting solution was stirred at 10° C. for 1 hour. This was followed by the addition of chloro (methoxy)methane (1.70 kg, 21.2 mol) dropwise at 20° C. The mixture was stirred at RT overnight. The reaction was quenched with $H_2O$ (20 L). The resulting solution was extracted with TBME (2×7 L). The combined organic layers were washed with 10% NaCl (2×7 L), dried over $Na_2SO_4$ and concentrated under reduced pressure at 40° C. The residue was triturated with heptane (3 L) to give the title compound as a white solid.

HPLC: Rt=3.042 min; HPLC 4

Step 2: 3-bromo-1-(methoxymethyl)-1H-1,2,4-triazol-5-amine

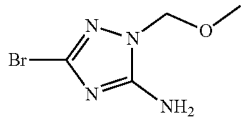

3,5-Dibromo-1-(methoxymethyl)-1H-1,2,4-triazole (800 g, 2.78 mol) was dissolved in 25% $NH_3H_2O$ (2.89 L, 16.3 mol) and MeOH (80 mL) at RT. The mixture was stirred at 120° C. for 18 hours. The mixture was cooled to 5-10° C., the solids were collected by filtration and washed with water (200 mL). The cake was dried under vacuum at 60° C. to give the title compound as a white solid.

HPLC: Rt=1.701 min; HPLC 4

Step 3: 3-bromo-1H-1,2,4-triazol-5-amine

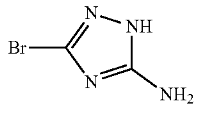

To a solution of 3-bromo-1-(methoxymethyl)-1H-1,2,4-triazol-5-amine (329 g, 1.45 mol) in MeOH (1.5 L) was added HBr (4.39 kg, 21.7 mol) at RT. The mixture was stirred at 100° C. for 18 hours. The mixture was adjusted to pH=7.0-7.5 with 10% NaOH at 20-30° C. and extracted with EtOAc (10×3 L). The combined organic phase was dried over $Na_2SO_4$ and concentrated under reduced pressure at 50° C. to give the title compound as a white solid.

HPLC: Rt=0.702 min; HPLC 4

HPLC: Rt=1.902 min; HPLC 5

Intermediate ER: 3-bromo-1H-1,2,4-triazol-5-amine

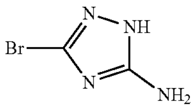

To a solution of 1H-1,2,4-triazole-3,5-diamine (300 g, 3.03 mol) in $HBr/H_2O$ (2.4 L) was added dropwise $NaNO_2$ (313 g, 4.54 mol) in water (782 mL) at 0° C. over 1.5 hours. The reaction was allowed to warm to RT and stirred for 1 hour. The reaction was stirred at 100° C. and for 16 hours. The RM was cooled to RT, filtered and the pH of the mixture (66 batches combined) was adjusted to 4 by addition of 10% NaOH. The mixture was extracted with EtOAc (2×55 L), dried over $Na_2SO_4$ and filtered. The organic phase was concentrated under reduced pressure to give the title compound. The pH of the aqueous phase was adjusted to 7-7.5 by 10% NaOH. Then it was extracted with EtOAc (10×35 L), dried over $Na_2SO_4$ and filtered. The organic phase was concentrated under reduced pressure to give the title compound.

HPLC: Rt=1.933 min; HPLC 5

Scheme 5 general overview of intermediates of route IV

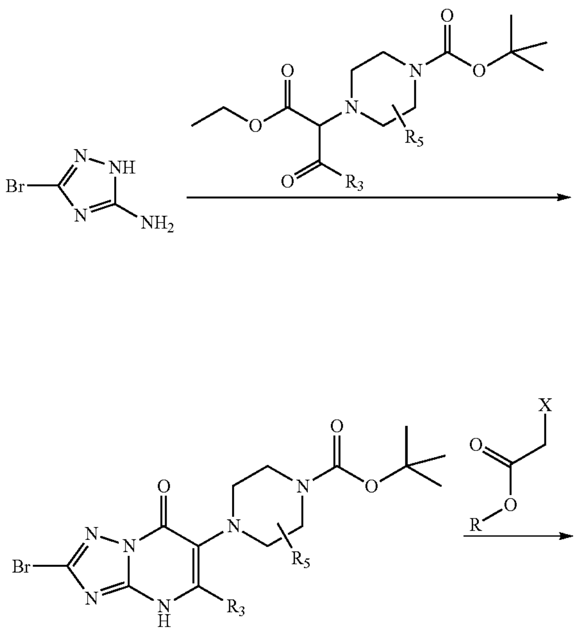

-continued

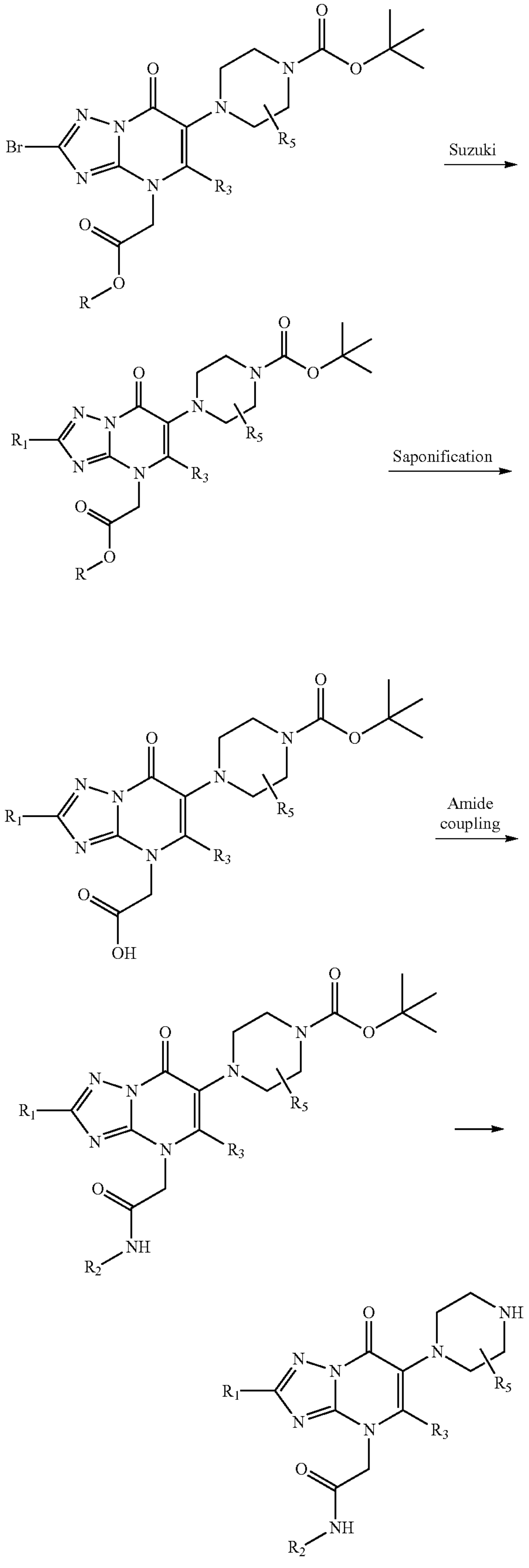

Intermediate ES: 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(2-methyl-6-(trifluoromethyl)pyridin-3-yl)acetamide Step 1: tert-butyl 4-(2-(3,6-dihydro-2H-pyran-4-yl)-5-methyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate

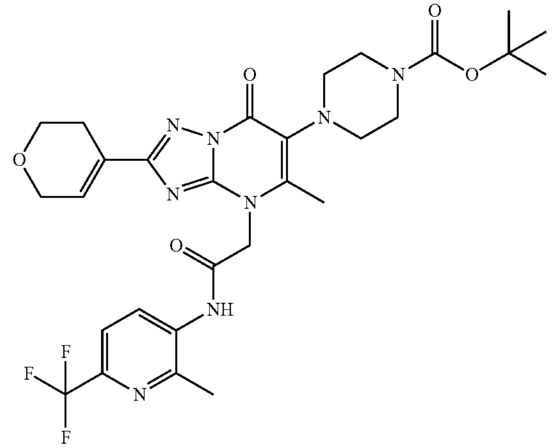 [SMILES: Cc1nc(C(F)(F)F)ccc1NC(=O)Cn1c(C)c(N2CCN(C(=O)OC(C)(C)C)CC2)c(=O)n2nc(C3=CCOCC3)nc12]

2-(6-(4-(Tert-butoxycarbonyl)piperazin-1-yl)-2-(3,6-dihydro-2H-pyran-4-yl)-5-methyl-7-oxo-[1,2,4]triazolo[1,5-a]pyrimidin-4 (7H)-yl)acetic acid (Intermediate BW—step 3) (120 mg, 253 μmol) and 2-methyl-6-(trifluoromethyl) pyridin-3-amine (46.8 mg, 266 μmol) were mixed in EtOAc (1.7 mL). Et3N (175 μL, 1.26 mmol) and $T_3P$ 50% in DMF (301 μL, 506 μmol) were added. The RM was stirred at RT for 30 minutes. Water (5 mL) was added, and the RM was extracted with EtOAc (4×20 mL), water (2×5 mL) and brine (5 mL). The organic layer was dried through a phase separator and concentrated under reduced pressure to give the title compound as a beige solid (172 mg, 93% pure, yield: 100%).

LC-MS: Rt=1.01 min; MS m/z $[M-H]^-$ 250.1/252.1; UPLC-MS 4

Step 2: 2-(2-(3,6-dihydro-2H-pyran-4-yl)-5-methyl-7-oxo-6-(piperazin-1-yl)-[1,2,4]triazolo[1,5-a]pyrimidin-4 (7H)-yl)-N-(2-methyl-6-(trifluoromethyl) pyridin-3-yl)acetamide

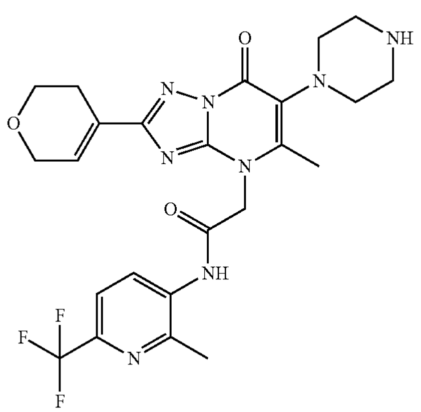

Tert-butyl 4-(2-(3,6-dihydro-2H-pyran-4-yl)-5-methyl-4-(2-((2-methyl-6-(trifluoromethyl)pyridin-3-yl)amino)-2-oxoethyl)-7-oxo-4,7-dihydro-[1,2,4]triazolo[1,5-a]pyrimidin-6-yl)piperazine-1-carboxylate (172 mg, 253 μmol) was mixed with DCM (1.7 mL). TFA (390 μL, 5.06 mmol) was added and the RM was stirred at RT for 1 hour. The RM was concentrated under reduced pressure. DCM and toluene was added and the mixture was concentrated again. This was performed twice. The residue was dried under HV to give the title compound as a beige solid (187 mg, 72% pure, yield: 100%).

LC-MS: Rt=0.72 min; MS m/z $[M+H]^+$ 533.3, m/z $[M-H]^-$ 531.3; UPLC-MS 4

Scheme 7 general overview of compounds of route VI

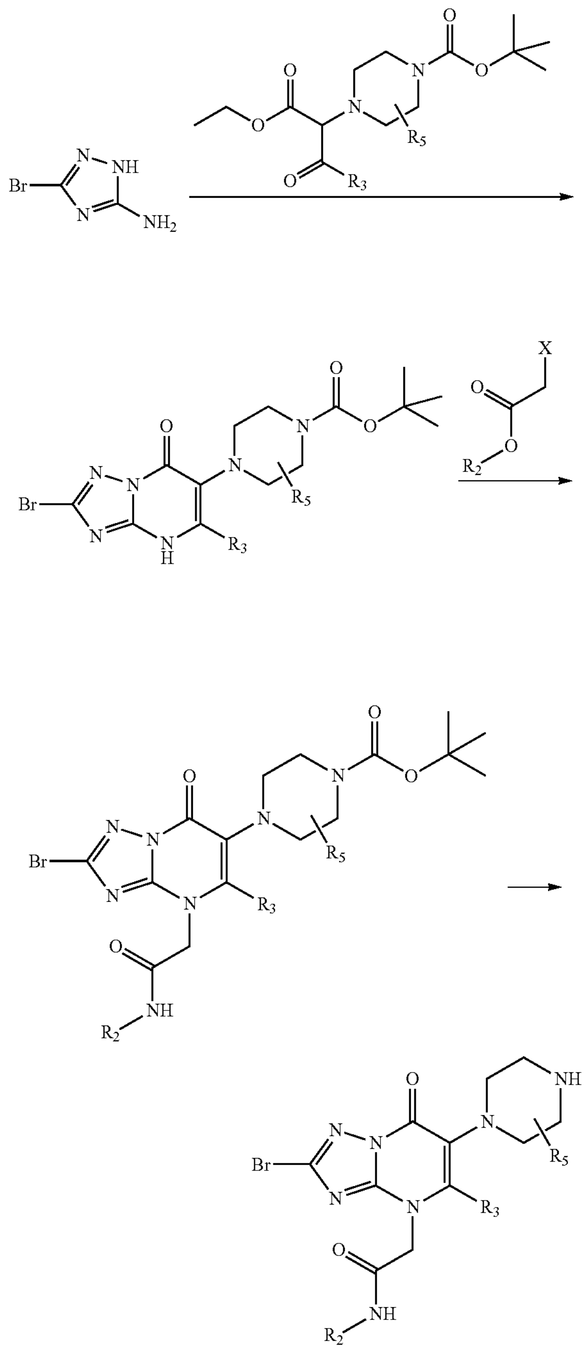

Intermediate ET: 2-(2-bromo-5-ethyl-6-(4-(5-hydroxy-6-methylpyrimidine-4-carbonyl)piperazin-1-yl)-7-oxo-[1,2,4]triazolo[1,5-a]pyrimidin-4 (7H)-yl)-N-(2-methyl-4-(trifluoromethyl)phenyl)acetamide

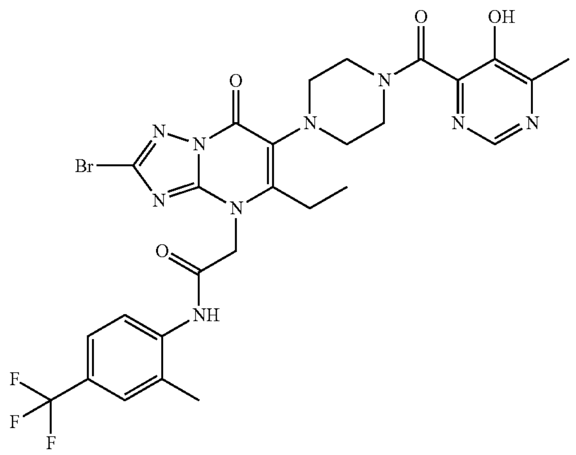 [SMILES: CCc1c(N2CCN(C(=O)c3ncnc(C)c3O)CC2)c(=O)n2nc(Br)nc2n1CC(=O)Nc1ccc(C(F)(F)F)cc1C]

To a stirred solution of 5-hydroxy-6-methylpyrimidine-4-carboxylic acid (Intermediate DB) (102 mg, 664 μmol) in DCM (10 mL) was added 1-chloro-N,N,2-trimethylprop-1-en-1-amine (113 μL, 857 μmol) and the RM was stirred at RT for 30 minutes. Then 2-(2-bromo-5-ethyl-7-oxo-6-(piperazin-1-yl)-[1,2,4]triazolo[1,5-a]pyrimidin-4 (7H)-yl)-N-(2-methyl-4-(trifluoromethyl)phenyl)acetamide (Intermediate BZ—step 2) (300 mg, 553 μmol) was added and the RM was stirred at RT for 30 minutes. DIPEA (290 μL, 1.66 mmol) in DCM (2 mL) was added dropwise and the RM was stirred at RT for 1 hour. The RM was diluted with DCM and water, extracted twice with DCM and the combined organic layers were washed with water, dried over $Na_2SO_4$ and concentrated under reduced pressure. The crude product was purified by column chromatography (RediSep Column: Silica 24 g, eluent DCM:DCM/MeOH (8/2) 100:0 to 50:50). The product containing fractions were combined and concentrated to give the title compound (100 mg, 77% pure, yield: 21%).

LC-MS: Rt=1.06 min; MS m/z $[M+H]^+$ 678.4/680.4; UPLC-MS 1

Scheme 10 general overview of intermediates of route IX

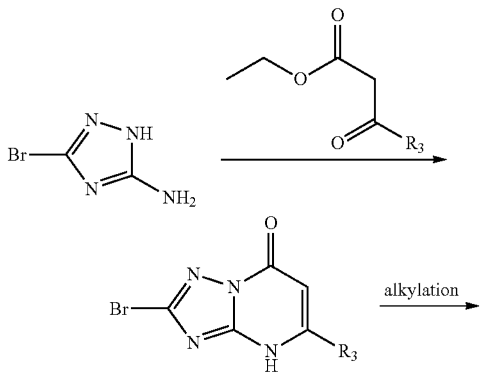

-continued

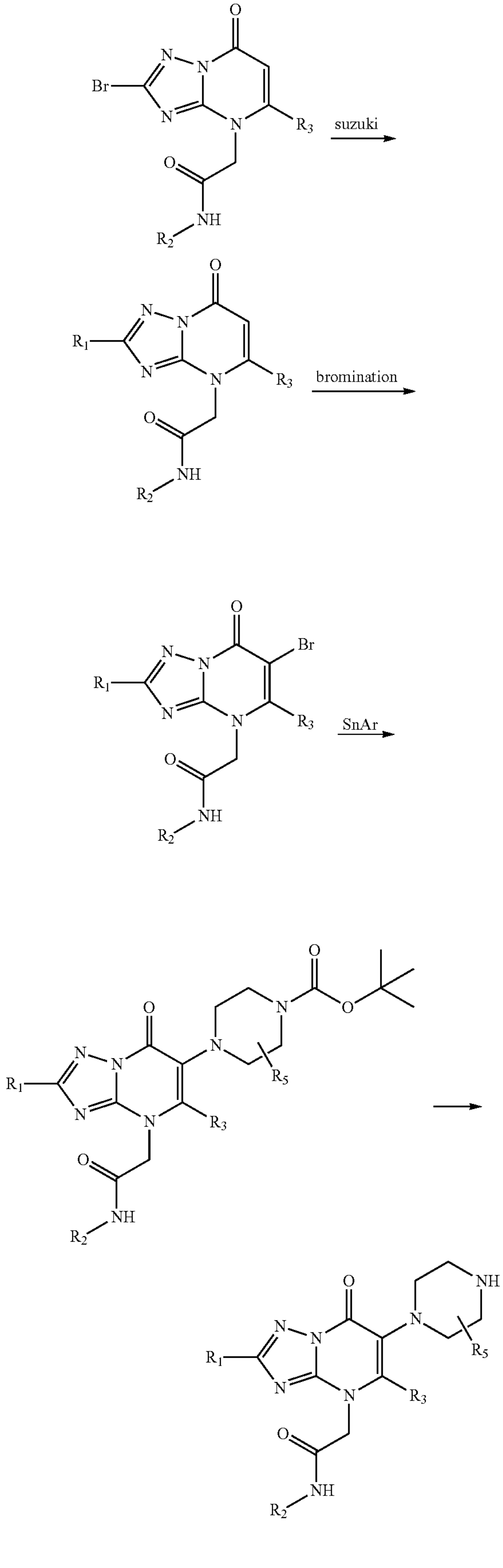

Intermediate EU: rac-tert-butyl 5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate

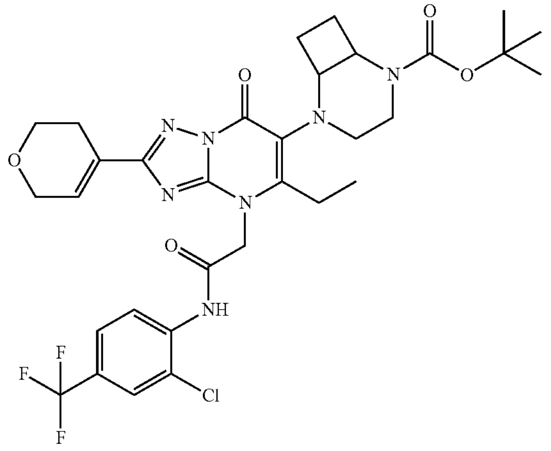 [SMILES: CCc1c(N2CCN(C(=O)OC(C)(C)C)C3CCC32)c(=O)n2nc(C3=CCOCC3)nc2n1CC(=O)Nc1ccc(C(F)(F)F)cc1Cl]

Chiral separation of rac-tert-butyl 5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate (Intermediate CM-Step 5) (88.0 mg): Preparative chiral HPLC (instrument: SEPIATEC SFC100; column: OVEN3 Chiralpak IB-N 250×30 mm 5 μm; eluent: A: 25% [MeOH+0.05% $NH_3$] B: 75% $scCO_2$; flow rate: 80.0 mL/min; detection: 240 nm; injection volume: 1.5 mL; Gradient: isocratic A: 25%, B: 75% $scCO_2$ Intermediate EV: tert-butyl (1R,6S)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate or tert-butyl (1S,6R)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate

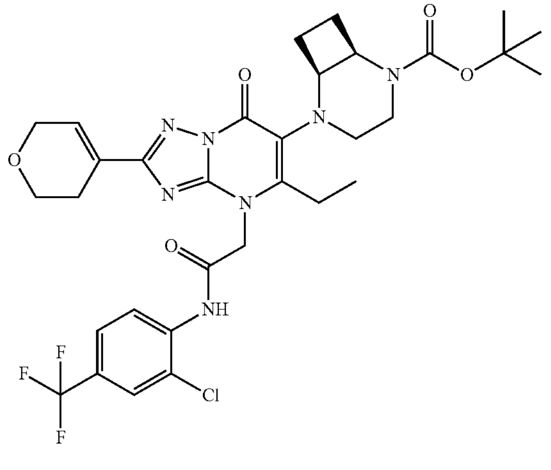

-continued

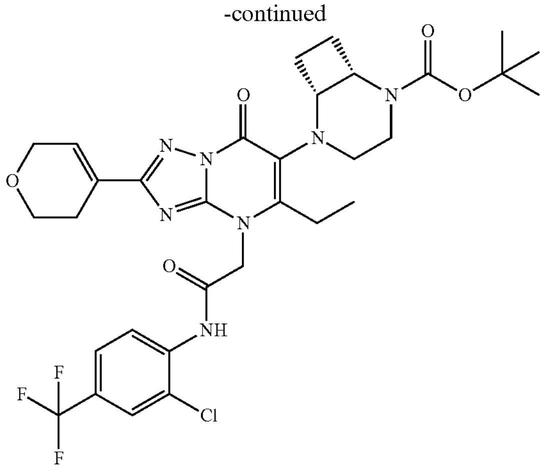

First eluting stereoisomer, white solid (40.0 mg, 100% pure, yield: 45%)

Chiral HPLC (C-HPLC 13): Rt=1.44 min, 99.5% ee

LC-MS: Rt=1.37 min; MS m/z $[M+H\text{-}Boc]^+$ 592.5/594.5, m/z $[M-H]^-$ 690.5/692.4; UPLC-MS 1

LC-MS: Rt=6.80 min; MS m/z $[M+H\text{-}Boc]^+$ 592.3/594.3, m/z $[M-H]^-$ 690.4/692.4; UPLC-MS 2

Intermediate EW: tert-butyl (1R,6S)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate or tert-butyl (1S,6R)-5-(4-(2-((2-chloro-4-(trifluoromethyl)phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate

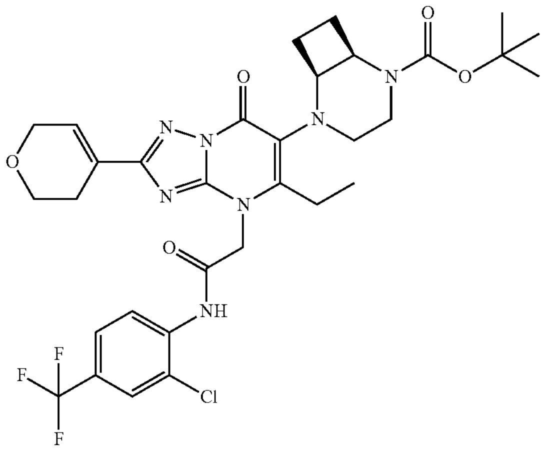

-continued

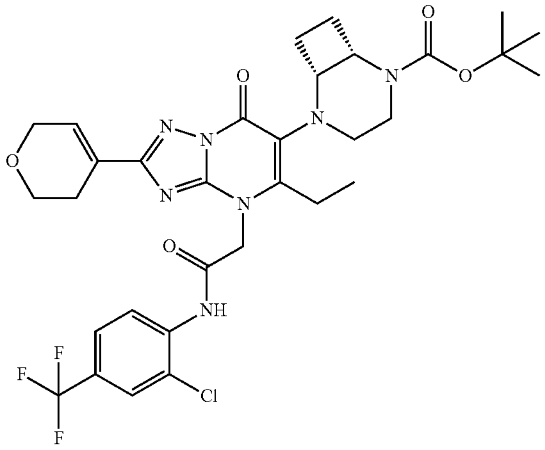

Second eluting stereoisomer, white solid (40.0 mg, 100% pure, yield: 45%)

Chiral HPLC (C-HPLC 13): Rt=2.05 min, 99.5% ee

LC-MS: Rt=1.37 min; MS m/z $[M+H\text{-}Boc]^+$592.5/594.5, m/z $[M-H]^-$ 690.4/692.4; UPLC-MS 1

LC-MS: Rt=6.77 min; MS m/z $[M+H\text{-}Boc]^+$592.3/594.3, m/z $[M-H]^-$ 690.4/692.3; UPLC-MS 2

Intermediate EX: 2-(6-((1S,6R)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide

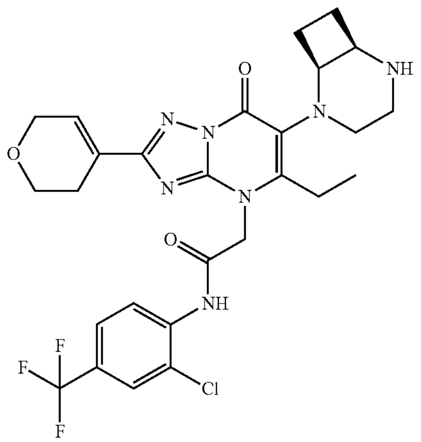

-continued

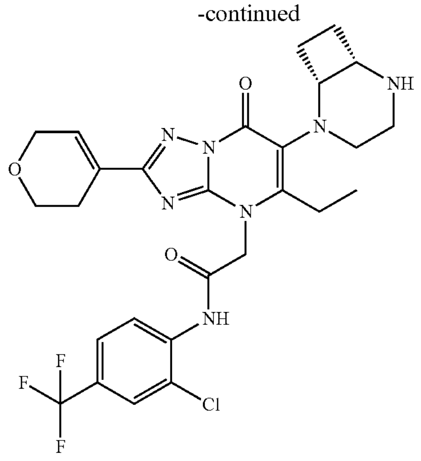

Tert-butyl (1S,6R)-5-(4-(2-((2-chloro-4-(trifluoromethyl) phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate or tert-butyl (1R,6S)-5-(4-(2-((2-chloro-4-(trifluoromethyl)phenyl) amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate (Intermediate EV) (first eluting stereoisomer—40.0 mg, 58.0 μmol) was mixed with HCl 4N in 1,4-dioxane (1.00 mL, 4.00 mmol) and the RM was stirred at RT for 1 hour. The RM was diluted with 10% MeOH in DCM and $NaHCO_3$, extracted twice with DCM and the combined organic layers were dried over $Na_2SO_4$ and concentrated under reduced pressure to give the title compound as a white foam (38.0 mg, 90% pure, yield: 100%).

LC-MS: Rt=0.80 min; MS m/z $[M+H]^+$ 592.5/594.5, m/z $[M-H]^-$ 590.3/592.4; UPLC-MS 1

Intermediate EY: 2-(6-((1S,6R)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide or 2-(6-((1R,6S)-2,5-diazabicyclo[4.2.0]octan-2-yl)-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide

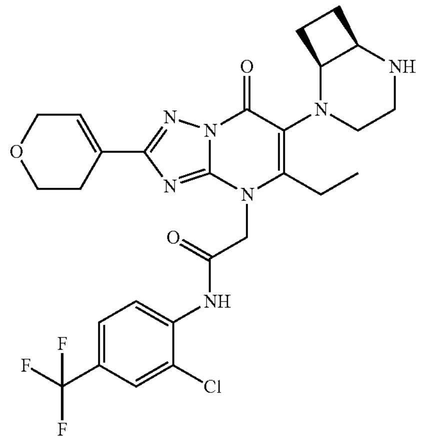

-continued

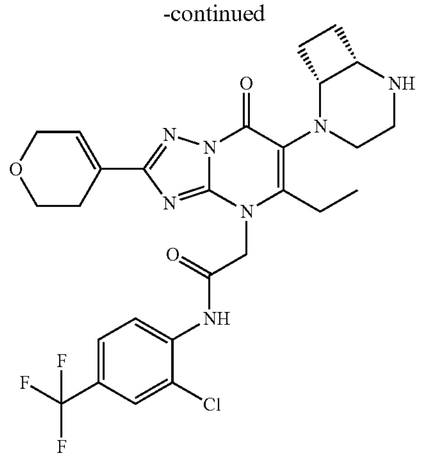

Tert-butyl (1S,6R)-5-(4-(2-((2-chloro-4-(trifluoromethyl) phenyl)amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate or tert-butyl (1R,6S)-5-(4-(2-((2-chloro-4-(trifluoromethyl)phenyl) amino)-2-oxoethyl)-2-(3,6-dihydro-2H-pyran-4-yl)-5-ethyl-7-oxo-4,7-dihydro-[1,2,4]triazolo[1,5-a]pyrimidin-6-yl)-2,5-diazabicyclo[4.2.0]octane-2-carboxylate (Intermediate EW) (second eluting stereoisomer—40.0 mg, 58.0 μmol) was mixed with HCl 4N in 1,4-dioxane (1.00 mL, 4.00 mmol) and the RM was stirred at RT for 1 hour. The RM was diluted with 10% MeOH in DCM and $NaHCO_3$, extracted twice with DCM and the combined organic layers were dried over $Na_2SO_4$ and concentrated under reduced pressure to give the title compound as a white foam (37.0 mg, 90% pure, yield: 97%).

LC-MS: Rt=0.79 min; MS m/z $[M+H]^+$ 592.3/594.3, m/z $[M-H]^-$ 590.3/592.3; UPLC-MS 1

Intermediate EZ: N-(2-chloro-4-(trifluoromethyl) phenyl)-2-(2-(3,6-dihydro-2H-pyran-4-yl)-5-ethyl-7-oxo-6-(piperazin-1-yl-2,2,3,3,5,5,6,6-d8)-[1,2,4]triazolo[1,5-a]pyrimidin-4 (7H)-yl)acetamide

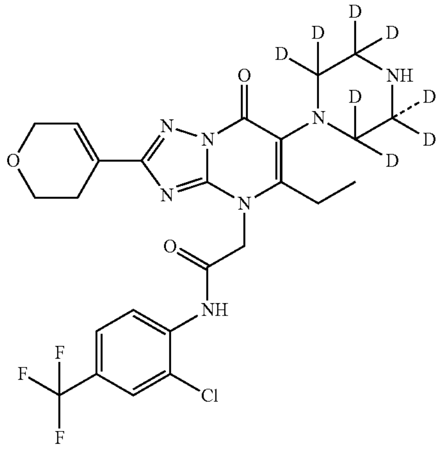

2-(6-Bromo-2-(3,6-dihydro-2H-pyran-4-yl)-5-ethyl-7-oxo-[1,2,4]triazolo[1,5-a]pyrimidin-4 (7H)-yl)-N-(2-chloro-4-(trifluoromethyl)phenyl)acetamide (Intermediate CM—step 4) (500 mg, 892 μmol) and piperazine-2,2,3,3,5, 5,6,6-d8 (403 mg, 4.28 mmol) were mixed in DMSO (300 μL). The RM was stirred at 120° C. in a capped vial for 1.75 hours. The RM was diluted with water (3 mL) and the suspension was stirred at RT for 1 hour. The beige solid was filtered off and redissolved in DCM (20 mL). Then it was filtered through a phase separator and concentrated under reduced pressure to ca 4 mL. The crude product was purified by column chromatography (RediSep Column: Silica 24 g, eluent DCM:MeOH 100:0 to 80:20). The product containing fractions were combined, concentrated, and dried under HV to give the title compound as a cream colored solid (318 mg, 89% pure, yield: 55%).

LC-MS: Rt=0.77 min; MS m/z $[M+H]^+$ 574.4/576.4, m/z $[M-H]^-$ 572.3/574.3; UPLC-MS 1

LC-MS: Rt=3.90 min; MS m/z $[M+H]^+$ 574.3/576.3, m/z $[M-H]^-$ 572.3/574.2; UPLC-MS 2

Intermediate FA: 2-(5-cyclopropyl-2-(3,6-dihydro-2H-pyran-4-yl)-7-oxo-6-(piperazin-1-yl)-[1,2,4]triazolo[1,5-a]pyrimidin-4 (7H)-yl)-N-(4-(trifluoromethyl)phenyl)acetamide Step 1: 2-bromo-5-cyclopropyl-[1,2,4]triazolo[1,5-a]pyrimidin-7 (4H)-one

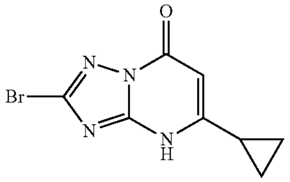 [SMILES: O=c1cc(C2CC2)[nH]c2nc(Br)nn12]

5-Bromo-4H-1,2,4-triazol-3-amine (5.00 g, 29.1 mmol) and ethyl 3-cyclopropyl-3-oxopropanoate (6.83 g, 43.7 mmol) were mixed in 1-butanol (40 mL). $H_3PO_4$ (8.40 g, 72.9 mmol) was added and the RM was stirred at 100° C. for 20 hours. Ethyl 3-cyclopropyl-3-oxopropanoate (1.00 g, 6.40 mmol) was added and the RM was stirred at 100° C. for 22.5 hours. Ethyl 3-cyclopropyl-3-oxopropanoate (1.00 g, 6.40 mmol) was added and the RM was stirred at 100° C. for 23.5 hours. The RM was cooled to RT and the yellow suspension was filtered. The cake was washed with a small amount of EtOH and the filtrate was concentrated under reduced pressure. The cake was washed with hot EtOH and the filtrate was concentrated under reduced pressure. The cake and the filtrate contained product, so both were combined again and concentrated under reduced pressure. The resulting oil was stood at RT over the weekend. A solid crystallized out which was filtered off and washed with $Et_2O$ to give a white solid (2.62 g). The crude product was adsorbed onto Isolute and purified by column chromatography (Silica gel column: Silica 40 g, eluent DCM:MeOH 100:0 to 85:15). The product containing fractions were combined and concentrated under reduced pressure to give the title compound as a white solid (923 mg, 99% pure, yield: 12%). The mother liquid was concentrated, adsorbed onto Isolute and purified by column chromatography (Silica gel column: Silica 120 g, eluent DCM:MeOH 100:0 to 85:15). The product containing fractions were combined and concentrated under reduced pressure to give the title compound as a beige solid (1.14 g, 99% pure, yield: 15%).

Total: 2.06 g, 99% pure, yield: 27%).

LC-MS: Rt=0.50 min; MS m/z $[M+H]^+$ 255.0/257.0, m/z $[M-H]^-$ 252.9/254.9; UPLC-MS 4

Step 2: 2-(2-bromo-5-cyclopropyl-7-oxo-[1,2,4]triazolo[1,5-a]pyrimidin-4 (7H)-yl)-N-(4-(trifluoromethyl)phenyl)acetamide

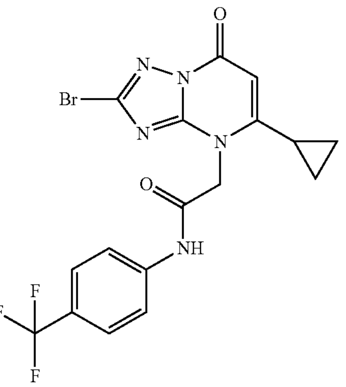

2-Bromo-5-cyclopropyl-[1,2,4]triazolo[1,5-a]pyrimidin-7 (4H)-one (1.19 g, 4.67 mmol) and 2-bromo-N-(4-(trifluoromethyl)phenyl)acetamide (1.73 g, 5.84 mmol) were mixed in DMF (12 mL). DIPEA (2.50 mL, 14.0 mmol) was added and the RM was stirred at 65° C. for 6 hours, then at RT overnight. Water was added and the RM was continued stirring at RT. A resin collapsed. The suspension was filtered and the cake was washed with water. The cake (1.78 g) was suspended in DCM and MeOH and filtered off. Then it was washed and dried under Hv to give the title compound as a beige solid (829 mg, 85% pure, yield: 33%).

LC-MS: Rt=1.03 min; MS m/z $[M+H]^+$ 456.1/458.1, m/z $[M-H]^-$ 453.9/455.9; UPLC-MS 4

Step 3: 2-(5-cyclopropyl-2-(3,6-dihydro-2H-pyran-4-yl)-7-oxo-[1,2,4]triazolo[1,5-a]pyrimidin-4 (7H)-yl)-N-(4-(trifluoromethyl)phenyl)acetamide

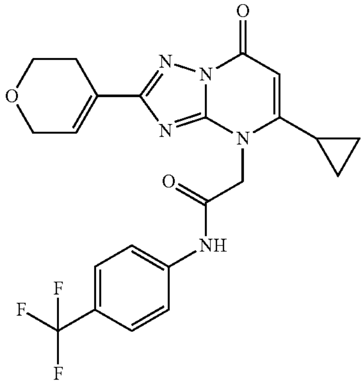 [SMILES: O=C(Cn1c(C2CC2)cc(=O)n2nc(C3=CCOCC3)nc12)Nc1ccc(C(F)(F)F)cc1]

2-(2-Bromo-5-cyclopropyl-7-oxo-[1,2,4]triazolo[1,5-a]pyrimidin-4 (7H)-yl)-N-(4-(trifluoromethyl)phenyl)acetamide (1.34 g, 2.94 mmol), 2-(3,6-dihydro-2H-pyran-4-yl)-4,4,5,5-tetramethyl-1,3,2-dioxaborolane (926 mg, 4.41 mmol) and Pd X-Phos G3 (124 mg, 147 μmol) were mixed in dioxane (15 mL) and 1M $K_3PO_4$ in water (8.81 mL, 8.81 mmol) was added. The RM was vacuumed and backfilled with argon several times, then it was stirred at 90° C. for 1.5 hours. The RM was cooled to RT. The RM was extracted with EtOAc (3×70 mL) and water (2×20 mL). The organic layer was dried through a phase separator and concentrated under reduced pressure. The aqueous layer was a suspension which was filtered. The aqueous layer was extracted three times with DCM, dried through a phase separator and concentrated under reduced pressure. All organics were combined with the cake and were suspended in hot EtOH (500 mL). Then it was filtered, and the cake was dissolved in warm ACN and Si-Thiol (2.00 g) was added. The mixture was stirred at 45° C. for 5 minutes, then it was filtered. The filtrate was concentrated under reduced pressure to give the title compound as a grey solid (650 mg, 99% pure, yield: 48%). The mother liquor was mixed with Si-Thiol (2.00 g) and stirred at 45° C. for 5 minutes, then it was filtered. The filtrate was concentrated under reduced pressure to give the title compound as a bright brown solid (610 mg, 79% pure, yield: 36%).

Total: 1.26 g, 89% pure, yield: 84%.

LC-MS: Rt=0.98 min; MS m/z $[M+H]^+$ 460.3, m/z $[M-H]^-$ 458.3; UPLC-MS 4

Step 4: 2-(6-bromo-5-cyclopropyl-2-(3,6-dihydro-2H-pyran-4-yl)-7-oxo-[1,2,4]triazolo[1,5-a]pyrimidin-4 (7H)-yl)-N-(4-(trifluoromethyl)phenyl)acetamide

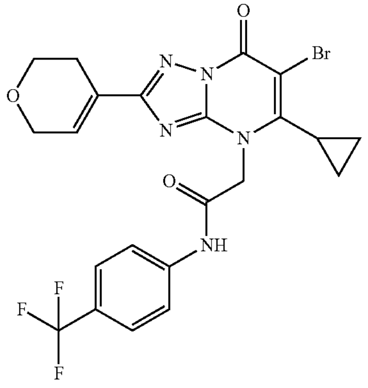 [SMILES: O=C(Cn1c(C2CC2)c(Br)c(=O)n2nc(C3=CCOCC3)nc12)Nc1ccc(C(F)(F)F)cc1]

2-(5-Cyclopropyl-2-(3,6-dihydro-2H-pyran-4-yl)-7-oxo-[1,2,4]triazolo[1,5-a]pyrimidin-4 (7H)-yl)-N-(4-(trifluoromethyl)phenyl)acetamide (610 mg, 1.33 mmol) and NBS (295 mg, 1.66 mmol) were mixed in DMF (28 mL). The RM was stirred at 60° C. for 5.5 hours, then it was stood at RT over the weekend. NBS (125 mg, 703 μmol) was added and the RM was stirred at 60° C. for 5 hours. NBS (50 mg, 281 μmol) was added and the RM was stirred at 60° C. for 1.5 hours. Then it was cooled to RT and stood at RT overnight. The RM was diluted with DCM and aq sat $NaHCO_3$. Most of the DMF was removed under reduced pressure. The solid residue was extracted with EtOAc (3×40 mL), water (2×20 mL) and brine (25 mL). The organic layer was dried through a phase separator and concentrated under reduced pressure. The brown solid residue was mixed with hexane and the suspension was filtered. The cake was mixed again with hexane and filtered again. The cake was dried under HV to give the title compound as a bright brown solid (508 mg, 74% pure, yield: 53%).

LC-MS: Rt=1.04 min; MS m/z $[M+H]^+$ 538.1/540.1, m/z $[M-H]^-$ 536.2/538.2; UPLC-MS 4

Step 5: 2-(5-cyclopropyl-2-(3,6-dihydro-2H-pyran-4-yl)-7-oxo-6-(piperazin-1-yl)-[1,2,4]triazolo[1,5-a]pyrimidin-4 (7H)-yl)-N-(4-(trifluoromethyl)phenyl)acetamide

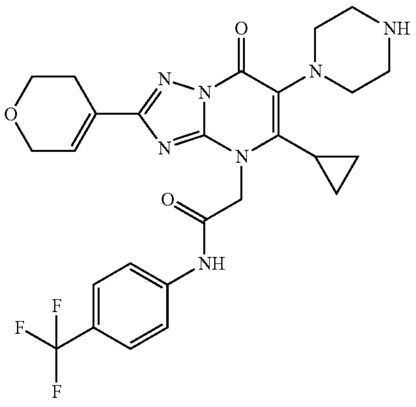 [SMILES: O=C(Cn1c(C2CC2)c(N2CCNCC2)c(=O)n2nc(C3=CCOCC3)nc12)Nc1ccc(C(F)(F)F)cc1]

2-(6-bromo-5-cyclopropyl-2-(3,6-dihydro-2H-pyran-4-yl)-7-oxo-[1,2,4]triazolo[1,5-a]pyrimidin-4 (7H)-yl)-N-(4-(trifluoromethyl)phenyl)acetamide (548 mg, 743 μmol) and piperazine (2.50 g, 29.0 mmol) were mixed with DMSO (5 mL) and the RM was stirred at 140° C. under argon for 5 hours. The RM was cooled to RT and stood at RT overnight, then it was combined with another batch. The RM was extracted with EtOAc (3×80 mL), aq sat $NaHCO_3$ (2×30 mL) and water (2×30 mL). The organic layer was washed with 1N HCl (4×25 mL) and water (2×20 mL). The organic layer was concentrated a bit and extracted twice with 1N HCl. The combined aqueous layers were basified with solid $NaHCO_3$ and extracted three times with EtOAc. The organic layer was dried through a phase separator and concentrated under reduced pressure. The solid residue was suspended in DCM and MeOH and filtered. The cake was washed well with DCM and the filtrate was concentrated down to give a bright brown solid (254 mg). The crude product was adsorbed onto Isolute and purified by column chromatography (Silica gel column: Silica 24 g, eluent DCM:MeOH/$Et_3N$ (95/5) 90:10 to 50:50). The product containing fractions were combined and concentrated under reduced pressure to give the title compound as a solid (97.0 mg, 87% pure, yield: 21%).

LC-MS: Rt=0.86 min; MS m/z $[M+H]^+$ 544.3, m/z $[M-H]^-$ 542.3; UPLC-MS 3

Scheme 13 general overview of intermediates of route XII
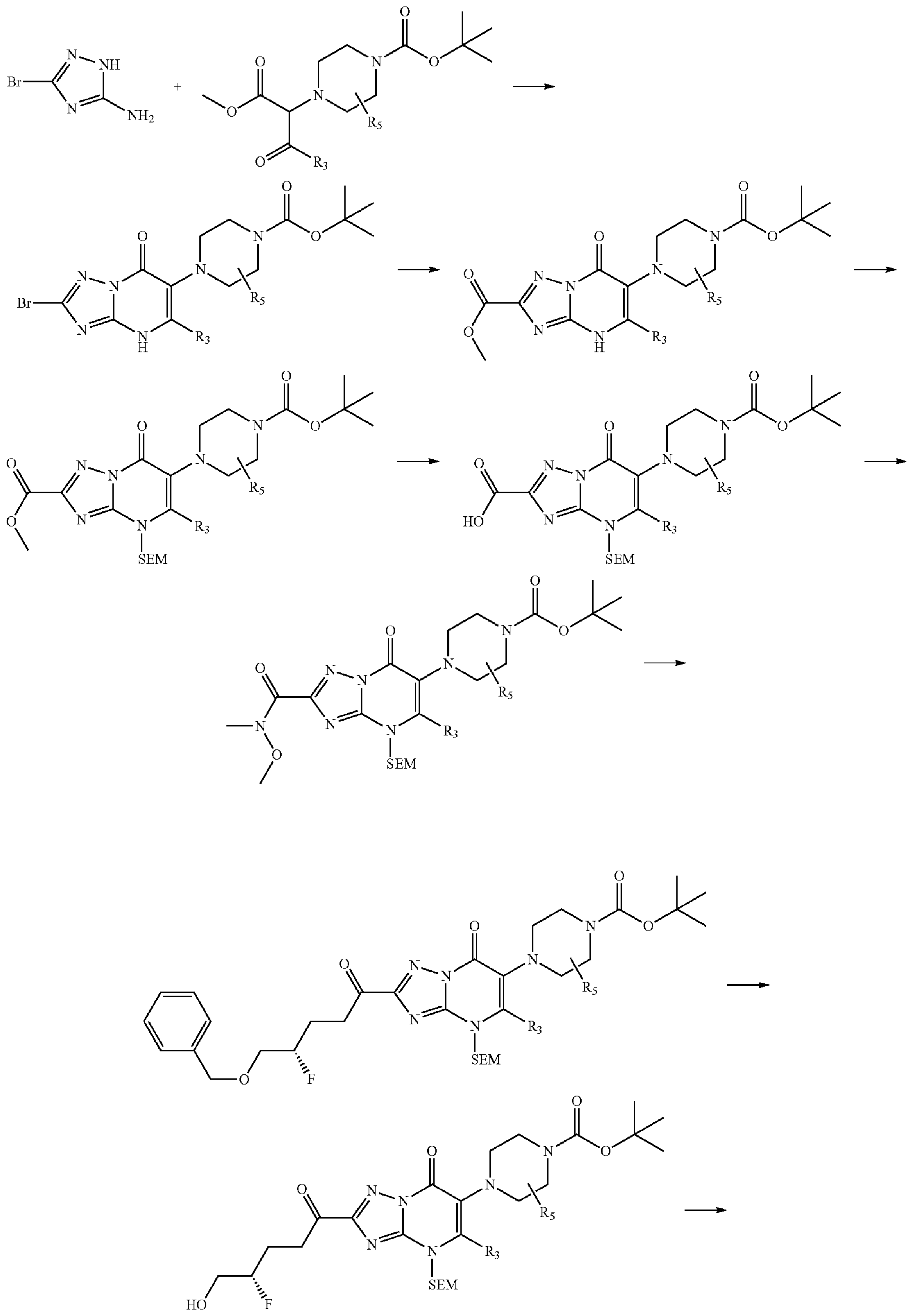

-continued

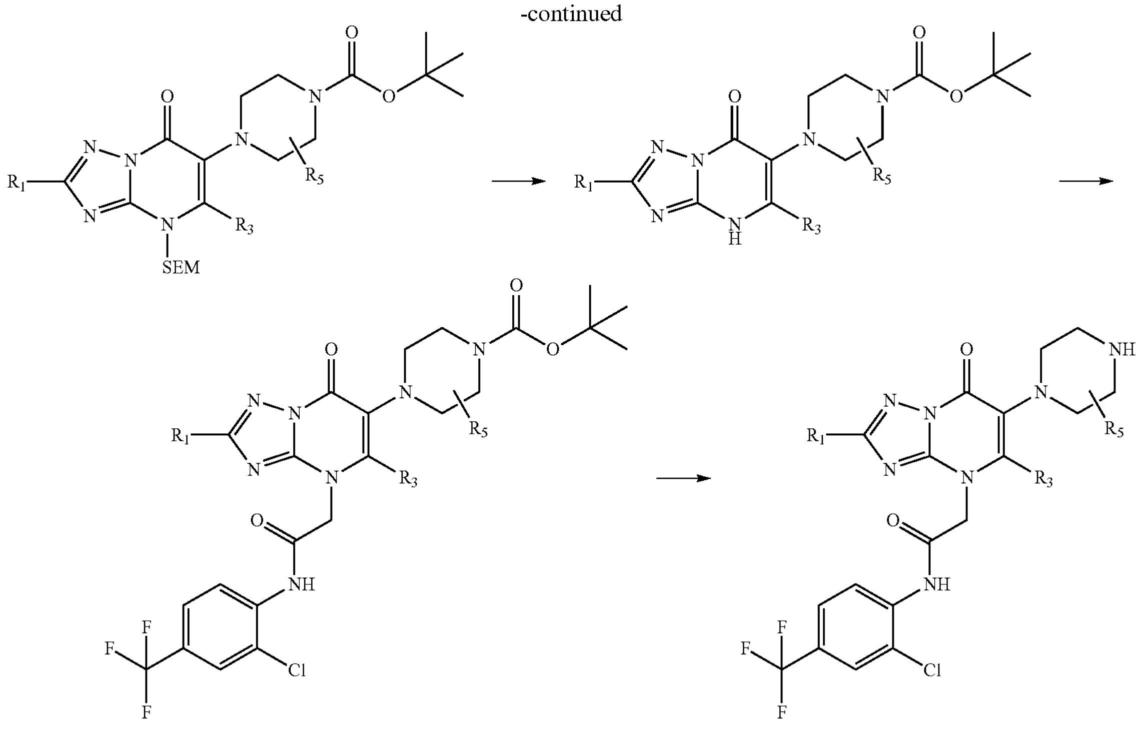

Intermediate FB: 2-(2-(3,6-dihydro-2H-pyran-4-yl)-5-(2-hydroxyethyl)-7-oxo-6-(piperazin-1-yl)-[1,2,4]triazolo[1,5-a]pyrimidin-4(7H)-yl)-N-(2-methyl-4-(trifluoromethyl)phenyl)acetamide Step 1: tert-butyl 4-(2-bromo-5-methyl-7-oxo-4-((2-(trimethylsilyl)ethoxy)methyl)-4,7-dihydro-[1,2,4]triazolo[1,5-a]pyrimidin-6-yl)piperazine-1-carboxylate

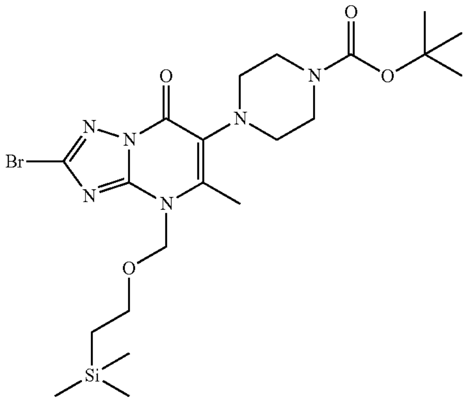 [SMILES: Cc1c(N2CCN(C(=O)OC(C)(C)C)CC2)c(=O)n2nc(Br)nc2n1COCC[Si](C)(C)C]

A yellow solution of tert-butyl 4-(2-bromo-5-methyl-7-oxo-4,7-dihydro-[1,2,4]triazolo[1,5-a]pyrimidin-6-yl)piperazine-1-carboxylate (Intermediate BM) (1.00 g, 2.42 mmol) in THF (10 mL) and DMF (2 mL) was cooled in an ice bath to 0° C. Then NaH 60% in mineral oil (116 mg, 2.90 mmol) was added carefully portionwise, gas evolution was observed. The RM was stirred at 0° C. for 30 minutes. Then (2-(chloromethoxy)ethyl)trimethylsilane (498 μL, 2.81 mmol) was added dropwise. The cooling bath was removed and the RM was allowed to warm to RT and stirred for 1 day. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure to give the title compound (3.50 g, 38% pure, quantitative).

LC-MS: Rt=1.46 min; MS m/z $[M+H]^+$ 443.3/445.3, m/z $[M-H]^-$ 411.3/413.2; UPLC-MS 1

Step 2: 2-(2-bromo-6-(4-(tert-butoxycarbonyl)piperazin-1-yl)-7-oxo-4-((2-(trimethylsilyl)ethoxy)methyl)-4,7-dihydro-[1,2,4]triazolo[1,5-a]pyrimidin-5-yl)acetic acid

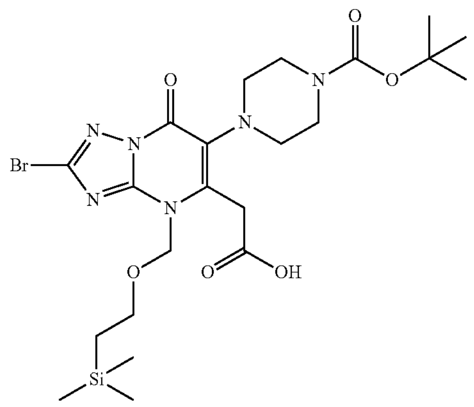 [SMILES: CC(C)(C)OC(=O)N1CCN(c2c(CC(=O)O)n(COCC[Si](C)(C)C)c3nc(Br)nn3c2=O)CC1]

Tert-butyl 4-(2-bromo-5-methyl-7-oxo-4-((2-(trimethylsilyl)ethoxy)methyl)-4,7-dihydro-[1,2,4]triazolo[1,5-a]pyrimidin-6-yl)piperazine-1-carboxylate (245 mg, 311 μmol) was dissolved in THF (3 mL) and NaHMDS 1M in THF (373 μL, 373 μmol) was added dropwise. The RM was stirred at −78° C. for 1.5 hours. Then $CO_2$ (collected from dry ice) was bubbled in. The reaction was stirred at −78° C. for 20 minutes. Water (10 mL), aq 1M HCl (10 mL) and DCM (10 mL) were added. The aqueous layer was washed with DCM (2×10 mL). The combined organic layers were dried through a phase separator and concentrated under reduced pressure to give the title compound (1.91 g, 60% pure, yield: 80%).

LC-MS: Rt=1.31 min; MS m/z $[M+H-Boc]^+$ 487.2/489.2; UPLC-MS 1

Step 3: tert-butyl 4-(2-bromo-5-(2-methoxy-2-oxoethyl)-7-oxo-4-((2-(trimethylsilyl)ethoxy)methyl)-4,7-dihydro-[1,2,4]triazolo[1,5-a]pyrimidin-6-yl)piperazine-1-carboxylate

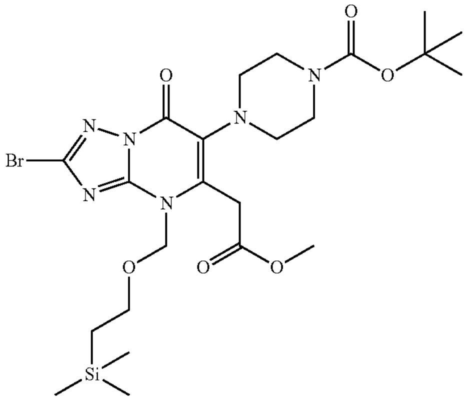 [SMILES: COC(=O)Cc1c(N2CCN(C(=O)OC(C)(C)C)CC2)c(=O)n2nc(Br)nc2n1COCC[Si](C)(C)C]

2-(2-Bromo-6-(4-(tert-butoxycarbonyl)piperazin-1-yl)-7-oxo-4-((2-(trimethylsilyl)ethoxy)methyl)-4,7-dihydro-[1,2,4]triazolo[1,5-a]pyrimidin-5-yl)acetic acid (1.90 g, 2.01 mmol) was dissolved in THF (10 mL) and MeOH (2 mL) and cooled to 0° C. Then (diazomethyl)trimethylsilane 2M in $Et_2O$ (1.10 mL, 2.21 mmol) was added dropwise. The reaction was stirred at RT for 30 minutes. Water (50 mL), aq sat $NaHCO_3$ (50 mL) and DCM (50 mL) were added. The aqueous layer was washed with DCM (2×50 mL). The combined organic layers were dried through a phase separator and concentrated under reduced pressure to give the title compound (1.86 g, 67% pure, quantitative).

LC-MS: Rt=1.40 min; MS m/z $[M+H-Boc]^+$501.3/503.3, m/z $[M-H]^-$ 599.1/601.1; UPLC-MS 1

Step 4: tert-butyl 4-(2-bromo-5-(2-methoxy-2-oxoethyl)-7-oxo-4,7-dihydro-[1,2,4]triazolo[1,5-a]pyrimidin-6-yl)piperazine-1-carboxylate

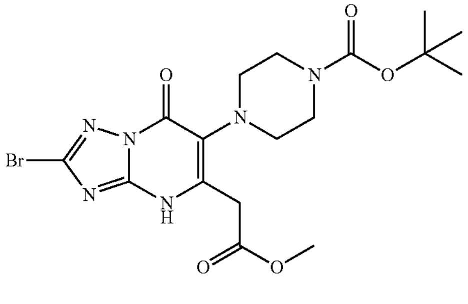 [SMILES: COC(=O)Cc1[nH]c2nc(Br)nn2c(=O)c1N1CCN(C(=O)OC(C)(C)C)CC1]

Tert-butyl 4-(2-bromo-5-(2-methoxy-2-oxoethyl)-7-oxo-4-((2-(trimethylsilyl)ethoxy)methyl)-4,7-dihydro-[1,2,4]triazolo[1,5-a]pyrimidin-6-yl)piperazine-1-carboxylate (1.36 g, 1.99 mmol) was dissolved in DCM (5 mL) and TFA (3.00 mL, 13.0 mmol) was added. The mixture was stirred at 40° C. for 2 hours. The RM was concentrated under reduced pressure. The residue was suspended in DCM (5 mL) and DIPEA (696 μL, 3.99 mmol) was added, followed by $Boc_2O$ (463 μL, 1.99 mmol). The mixture was stirred at RT for 1 hour. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure and concentrated under reduced pressure to give the title compound (400 mg, 35% pure, yield: 15%).

LC-MS: Rt=0.81 min; MS m/z $[M+H]^+$ 471.2/473.2, m/z $[M-H]^-$ 469.2/471.2; UPLC-MS 1

Step 5: tert-butyl 4-(2-bromo-5-(2-hydroxyethyl)-7-oxo-4,7-dihydro-[1,2,4]triazolo[1,5-a]pyrimidin-6-yl)piperazine-1-carboxylate

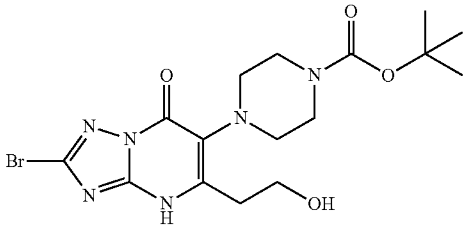 [SMILES: CC(C)(C)OC(=O)N1CCN(c2c(CCO)[nH]c3nc(Br)nn3c2=O)CC1]

Tert-butyl 4-(2-bromo-5-(2-methoxy-2-oxoethyl)-7-oxo-4,7-dihydro-[1,2,4]triazolo[1,5-a]pyrimidin-6-yl)piperazine-1-carboxylate (100 mg, 74.0 μmol) was dissolved in THF (1 mL) and $LiAlH_4$ (111 μL, 223 μmol) was added, the mixture was stirred at RT for 10 minutes. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure to give the title compound (208 mg, 44% pure, yield: 70%).

LC-MS: Rt=0.76 min; MS m/z $[M+H]^+$ 443.1/445.1, m/z $[M-H]^-$ 441.3/443.1; UPLC-MS 1

Step 6: tert-butyl 4-(2-bromo-5-(2-hydroxyethyl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

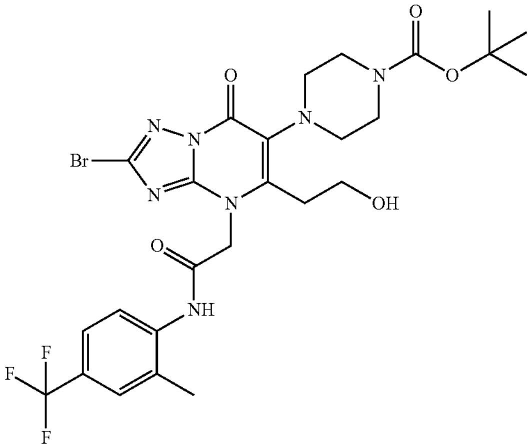 [SMILES: Cc1cc(C(F)(F)F)ccc1NC(=O)Cn1c(CCO)c(N2CCN(C(=O)OC(C)(C)C)CC2)c(=O)n2nc(Br)nc12]

Tert-butyl 4-(2-bromo-5-(2-hydroxyethyl)-7-oxo-4,7-dihydro-[1,2,4]triazolo[1,5-a]pyrimidin-6-yl)piperazine-1-carboxylate (208 mg, 206 μmol) and 2-bromo-N-(2-methyl-4-(trifluoromethyl)phenyl)acetamide (Intermediate DP) (67.2 mg, 227 μmol) were mixed in dioxane (2 mL) and DIPEA (72.0 μL, 413 μmol) was added. The mixture was stirred at 80° C. for 3 hours. Then at 50° C. for 2 hours and then at 80° C. overnight. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure. The crude product was purified by reverse phase preparative HPLC (RP-HPLC acidic 1: 5 to 100% B in 20 min). The product containing fractions were combined, basified with aq sat $NaHCO_3$, extracted twice with DCM, dried through a phase separator and concentrated under reduced pressure to give the title compound (45.4 mg, 82% pure, yield: 27%).

LC-MS: Rt=1.23 min; MS m/z $[M+H-Boc]^+$ 558.2/560.2, m/z $[M-H]^-$ 656.5/658.5; UPLC-MS 1

Step 7: tert-butyl 4-(2-(3,6-dihydro-2H-pyran-4-yl)-5-(2-hydroxyethyl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate

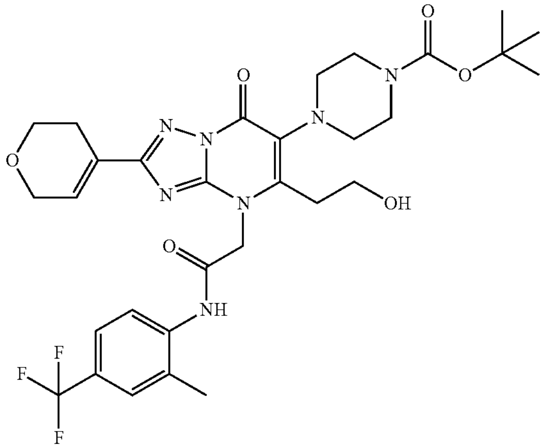 [SMILES: Cc1cc(C(F)(F)F)ccc1NC(=O)Cn1c(CCO)c(N2CCN(C(=O)OC(C)(C)C)CC2)c(=O)n2nc(C3=CCOCC3)nc12]

Tert-butyl 4-(2-bromo-5-(2-hydroxyethyl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (264 mg, 388 μmol), 2-(3,6-dihydro-2H-pyran-4-yl)-4,4,5,5-tetramethyl-1,3,2-dioxaborolane (136 mg, 647 μmol) and Pd X-Phos G3 (16.4 mg, 19.0 μmol) were mixed in dioxane (2 mL) and $K_3PO_4$ 1M in water (1.16 mL, 1.16 mmol) was added. The mixture was stirred at 80° C. for 20 minutes. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure. The crude product was redissolved in DCM and MeOH and SiliaMetS® Thiol was added. The mixture was stirred at 40° C. for 1 hour. Then it was filtered. The cake was washed with DCM. The filtrate was concentrated under reduced pressure to give the title compound (905 mg, 86% pure).

LC-MS: Rt=1.20 min; MS m/z $[M+H]^+$ 662.3, m/z $[M-H]^-$ 660.5; UPLC-MS 1

Step 8: 2-(2-(3,6-dihydro-2H-pyran-4-yl)-5-(2-hydroxyethyl)-7-oxo-6-(piperazin-1-yl)-[1,2,4]triazolo[1,5-a]pyrimidin-4 (7H)-yl)-N-(2-methyl-4-(trifluoromethyl)phenyl)acetamide

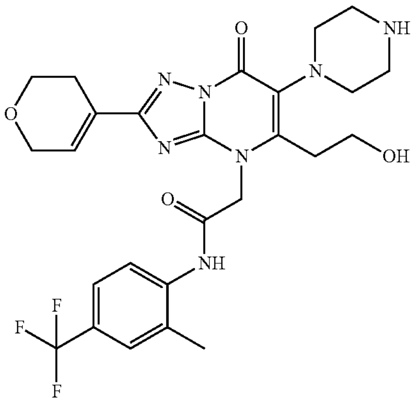 [SMILES: Cc1cc(C(F)(F)F)ccc1NC(=O)Cn1c(CCO)c(N2CCNCC2)c(=O)n2nc(C3=CCOCC3)nc12]

Tert-butyl 4-(2-(3,6-dihydro-2H-pyran-4-yl)-5-(2-hydroxyethyl)-4-(2-((2-methyl-4-(trifluoromethyl)phenyl)amino)-2-oxoethyl)-7-oxo-4,7-dihydro-[1,2,4]triazolo[1,5-a]pyrimidin-6-yl)piperazine-1-carboxylate (925 mg, 318 μmol) was dissolved in DCM (5 mL) and TFA (1.00 mL, 13.0 mmol) was added. The mixture was stirred at 40° C. for 3 hours. The product seems not to be stable under acidic conditions at 40° C. so the reaction was stopped. Water (10 mL), aq sat $NaHCO_3$ (10 mL) and DCM (10 mL) were added. The aqueous layer was washed with DCM (2×10 mL). The combined organic layers were dried through a phase separator and concentrated under reduced pressure to give the title compound (168 mg, 28% pure, yield: 26%).

LC-MS: Rt=1.20 min; MS m/z $[M+H]^+$ 562.2, m/z $[M-H]^-$ 560.4; UPLC-MS 1

Scheme 14 general overview of intermediates of route XIII

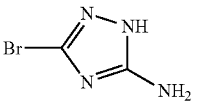

+

-continued
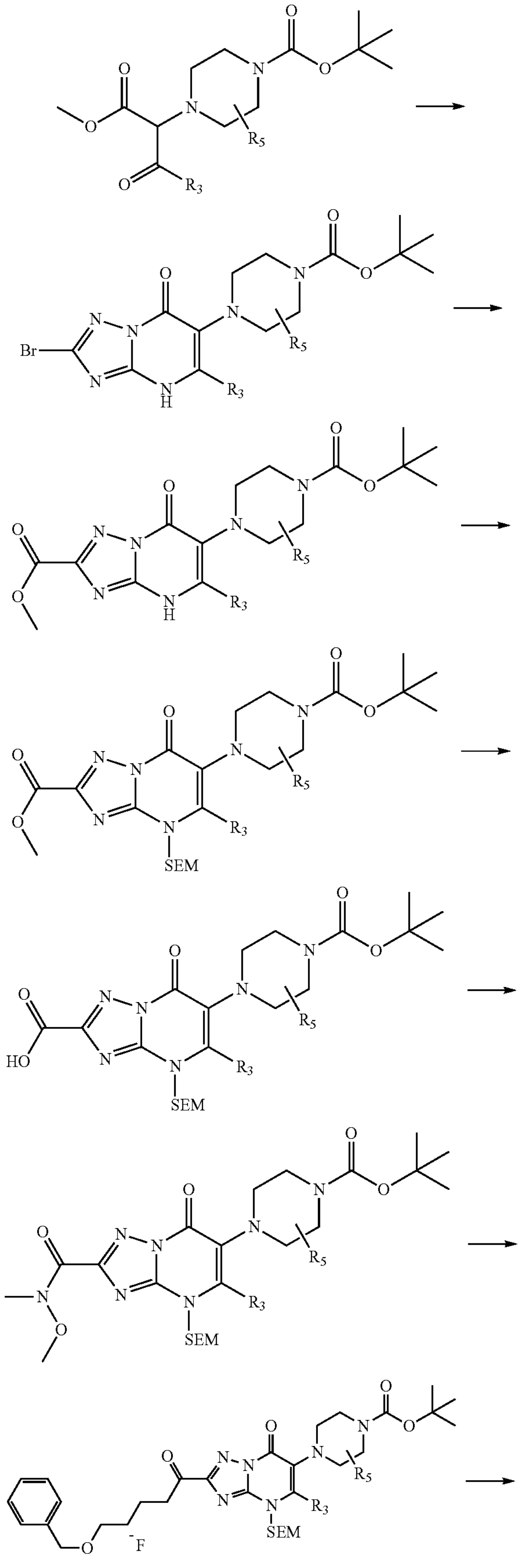
-continued
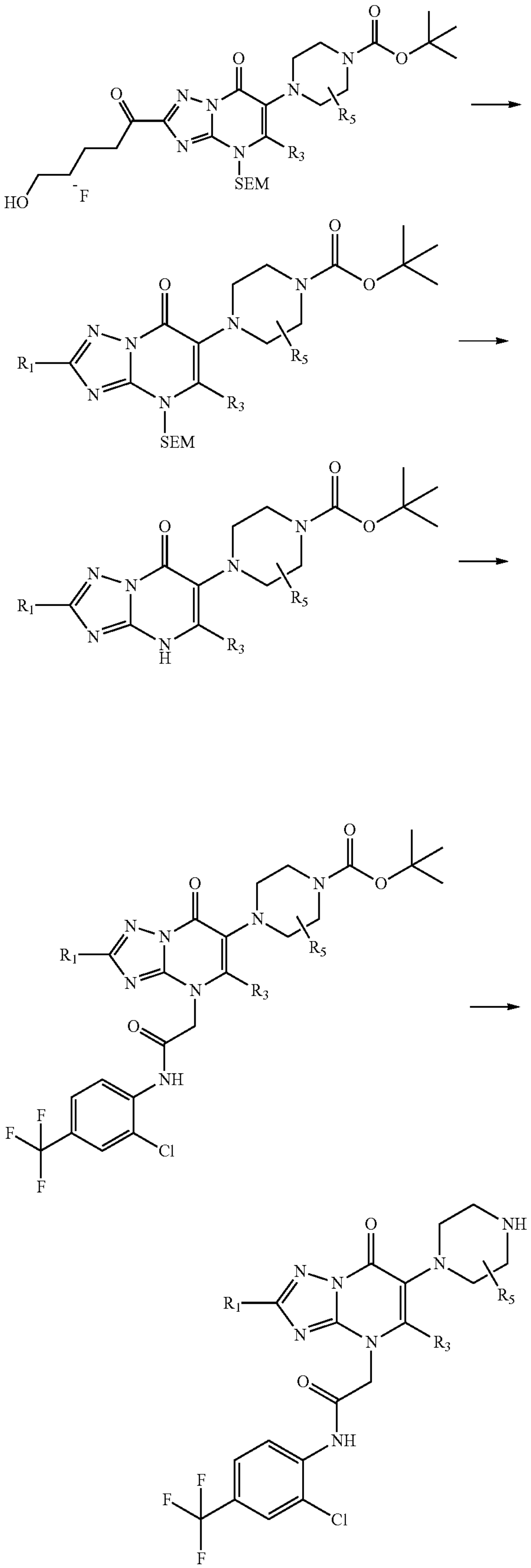

Intermediate FC: 2-(2-(3,6-dihydro-2H-pyran-4-yl)-5-methyl-7-oxo-6-(piperidin-4-yl)-[1,2,4]triazolo[1,5-a]pyrimidin-4 (7H)-yl)-N-(4-(trifluoromethyl) phenyl)acetamide Step 1: 2-bromo-5-methyl-[1,2,4]triazolo[1,5-a] pyrimidin-7 (4H)-one

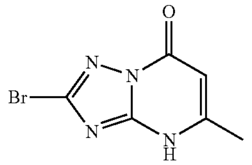

To a solution of 3-bromo-1H-1,2,4-triazol-5-amine (Intermediate ER) (60.0 g, 60.6 mmol) in AcOH (380 mL) was added ethyl 3-oxobutanoate (86.6 g, 66.6 mmol). The RM was stirred at 80° C. overnight. The mixture was filtrate and washed with AcOH (160 mL). The wet filter cake was dried to give the title compound (80.0 g, 80%).

Step 2: 2-bromo-6-iodo-5-methyl-[1,2,4]triazolo[1,5-a]pyrimidin-7 (4H)-one

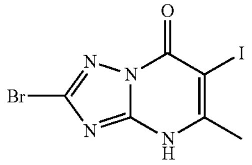

2-Bromo-5-methyl-[1,2,4]triazolo[1,5-a]pyrimidin-7 (4H)-one (2.00 g, 8.73 μmol) was added in a flame dried flask under nitrogen. Acetic acid (29.1 mL) was added, followed by NIS (2.16 g, 9.61 mmol). The RM was stirred at 60° C. for 1 hour. The RM was cooled to RT. The solid was filtered off and washed 3 times with EtOH. The solid was dried under Hv to give the title compound (2.76 g, 95% pure, yield: 89%).

LC-MS: Rt=0.56 min; MS m/z $[M+H]^+$ 354.9/356.9, m/z $[M-H]^-$ 353.0/355.0; UPLC-MS 8

Step 3: tert-butyl 4-(2-bromo-5-methyl-7-oxo-4,7-dihydro-[1,2,4]triazolo[1,5-a]pyrimidin-6-yl)-3,6-dihydropyridine-1 (2H)-carboxylate

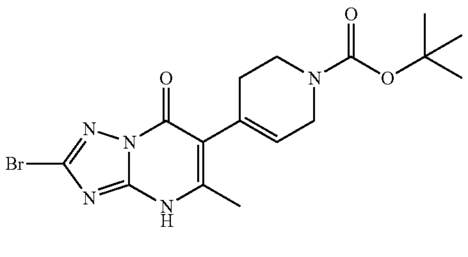 [SMILES: Cc1[nH]c2nc(Br)nn2c(=O)c1C1=CCN(C(=O)OC(C)(C)C)CC1]

Palladium G3-Tricyclohexylphosphine, [(Tricyclohexylphosphine)-2-(2-aminobiphenyl)]palladium(II) methanesulfonate (183 mg, 282 μmol) was purged with nitrogen. A solution of 2-bromo-6-iodo-5-methyl-[1,2,4]triazolo[1,5-a] pyrimidin-7 (4H)-one (1.00 g, 2.82 mmol) and tert-butyl 4-(4,4,5,5-tetramethyl-1,3,2-dioxaborolan-2-yl)-3,6-dihydropyridine-1 (2H)-carboxylate (894 mg, 2.89 mmol) in n-butanol (100 μL) was added, followed by $K_3PO_4$ 1.5M in water (5.63 mL, 8.45 mmol). The RM was stirred at 70° C. for 1 hour. Tert-butyl 4-(4,4,5,5-tetramethyl-1,3,2-dioxaborolan-2-yl)-3,6-dihydropyridine-1 (2H)-carboxylate (50.0 mg, 162 μmol) was added and the RM was stirred at 70° C. overnight. N-butanol was removed under reduced pressure. EtOAc was added and the mixture was washed with $NH_4Cl$. The organic layer was dried through a phase separator. ISOLUTE® Si-TMT (6.50 g, 2.82 mmol) was added and the mixture was stirred at 40° C. for 1 hour. The solid was filtered off and washed with EtOAc. The filtrate was concentrated under reduced pressure. The crude product was purified by column chromatography (Silica gel column: Silica 40 g, eluent DCM:DCM/MeOH (8/2) 100:0 to 50:50) to give the title compound as a white powder (734 mg, 90% pure, yield: 57%).

LC-MS: Rt=0.86 min; MS m/z $[M-H]^-$ 408.2/410.2; UPLC-MS 14

Step 4: tert-butyl 4-(2-bromo-5-methyl-7-oxo-4,7-dihydro-[1,2,4]triazolo[1,5-a]pyrimidin-6-yl)piperidine-1-carboxylate

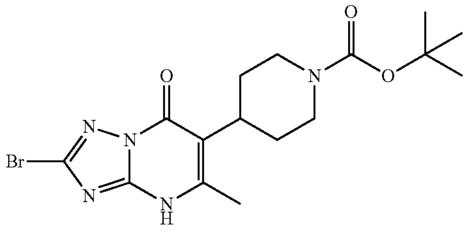

To a solution of tert-butyl 4-(2-bromo-5-methyl-7-oxo-4,7-dihydro-[1,2,4]triazolo[1,5-a]pyrimidin-6-yl)-3,6-dihydropyridine-1 (2H)-carboxylate (734 mg, 1.79 mmol) in MeOH (10 mL) was added $PtO_2$ (40.6 mg, 179 μmol) under N2 atmosphere. The flask was purged with hydrogen for 2 minutes. The RM was stirred at RT for 2 hours. $PtO_2$ (66.0 mg, 291 μmol) was added and the RM was stirred at RT for 2 hours. $PtO_2$ (103 mg, 454 μmol) was added and the RM was stirred at RT overnight. $PtO_2$ (122 mg, 543 μmol) was added and the RM was stirred at RT. The RM was filtered through a pad of celite. The crude product was purified by column chromatography (Silica gel column: Silica 12 g, eluent DCM:DCM/MeOH (8/2) 100:0 to 50:50) to give the title compound (580 mg, 80% pure, yield: 63%).

LC-MS: Rt=0.89 min; MS m/z $[M+H]^+$ 412.2/414.2, m/z $[M-H]^-$ 410.3/412.3; UPLC-MS 8

Step 5: tert-butyl 4-(2-(3,6-dihydro-2H-pyran-4-yl)-5-methyl-7-oxo-4,7-dihydro-[1,2,4]triazolo[1,5-a]pyrimidin-6-yl)piperidine-1-carboxylate

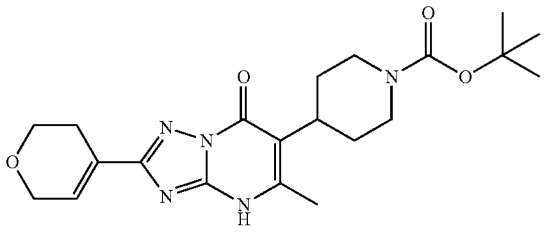

Tert-butyl 4-(2-bromo-5-methyl-7-oxo-4,7-dihydro-[1,2,4]triazolo[1,5-a]pyrimidin-6-yl)piperidine-1-carboxylate (580 mg, 1.41 mmol), 2-(3,6-dihydro-2H-pyran-4-yl)-4,4,5,5-tetramethyl-1,3,2-dioxaborolane (443 mg, 2.11 mmol) and X-Phos Pd G3 (71.4 mg, 84.0 μmol) were mixed. Under N2 atmosphere were added DMF (1.4 mL) and $K_3PO_4$ 1M in water (2.81 mL, 1.82 mmol). The RM was stirred at 80° C. for 1 hour. X-Phos Pd G3 (10.0 mg, 11.8 μmol) and 2-(3,6-dihydro-2H-pyran-4-yl)-4,4,5,5-tetramethyl-1,3,2-dioxaborolane (60.0 mg, 286 μmol) were added and the RM was stirred for 3 hours to give the title compound as RM.

LC-MS: Rt=1.25 min; MS m/z $[M+H]^+$ 416.3, m/z $[M-H]^-$ 414.4; UPLC-MS 8

Step 6: tert-butyl 4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperidine-1-carboxylate

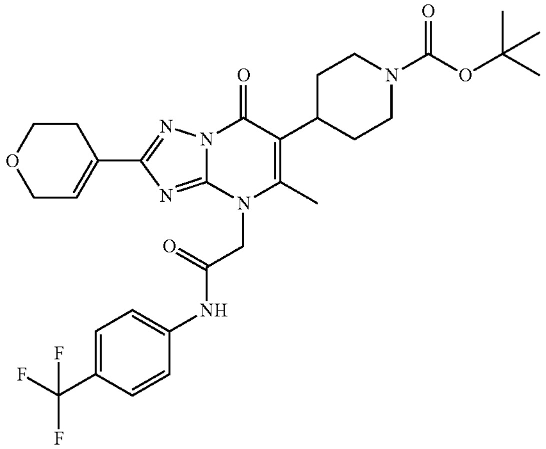

To the RM containing tert-butyl 4-(2-(3,6-dihydro-2H-pyran-4-yl)-5-methyl-7-oxo-4,7-dihydro-[1,2,4]triazolo[1,5-a]pyrimidin-6-yl)piperidine-1-carboxylate was added 2-bromo-N-(4-(trifluoromethyl)phenyl)acetamide (397 mg, 1.41 mmol). The RM was stirred at 80° C. for 40 minutes. 2-Bromo-N-(4-(trifluoromethyl)phenyl)acetamide (88.0 mg, 313 μmol) was added and the RM was stirred at 80° C. for 30 minutes. Most of the DMF was removed under reduced pressure. EtOAc was added and the mixture was washed with $NaHCO_3$. The organic layer was dried through a phase separator and concentrated under reduced pressure. The mixture was treated with Si TMT. The solvent was removed, the residue was adsorbed onto Isolute and purified by column chromatography (Silica gel column: Silica 24 g, eluent DCM:DCM/MeOH (8/2) 100:0 to 70:30), then in 5 portions by reverse phase preparative HPLC (5×RP-HPLC acidic 1: 20 to 95% B in 20 min), to give the title compound (185 mg, 60% pure, yield: 18%).

LC-MS: Rt=1.18 min; MS m/z $[M+H]^+$ 617.4, m/z $[M-H]^-$ 615.5; UPLC-MS 8

Step 7: 2-(2-(3,6-dihydro-2H-pyran-4-yl)-5-methyl-7-oxo-6-(piperidin-4-yl)-[1,2,4]triazolo[1,5-a]pyrimidin-4 (7H)-yl)-N-(4-(trifluoromethyl)phenyl) acetamide

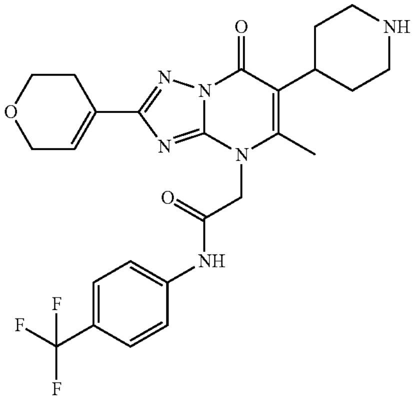

To tert-butyl 4-(2-(3,6-dihydro-2H-pyran-4-yl)-5-methyl-7-oxo-4-(2-oxo-2-((4-(trifluoromethyl)phenyl)amino)ethyl)-4,7-dihydro-[1,2,4]triazolo[1,5-a]pyrimidin-6-yl)piperidine-1-carboxylate (145 mg, 198 μmol) was added TFA (306 μL, 3.97 mmol) in DCM (2 mL). The RM was stirred at RT for 1 hour. DCM was added and the crude product was washed with NaOH solution. The aqueous layer was washed with EtOAc. The organic layer was dried through a phase separator and concentrated under reduced pressure to give the title compound (130 mg, 79% pure, quantitative).

LC-MS: Rt=0.74 min; MS m/z $[M+H]^+$ 517.3, m/z $[M-H]^-$ 515.4; UPLC-MS 8

Synthetic Schemes for the Compounds of Formulae 1b, 1c, 1d, 1e and 1f

Processes are provided to make to compounds of formulae 1b, 1c, 1d, 1e and 1f. Unless otherwise stated, the groups of the process schemes are as defined in the embodiments and preferences herein. The syntheses can be modified to make variants under formula (I), according to procedures known to the skilled chemist.

Scheme XI

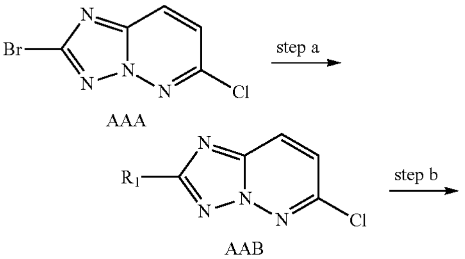

AAA

AAB

-continued

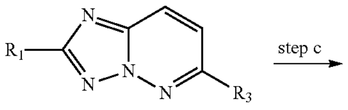

AAC

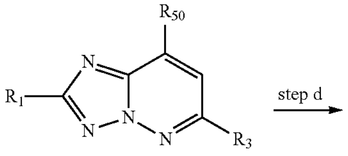

AAD

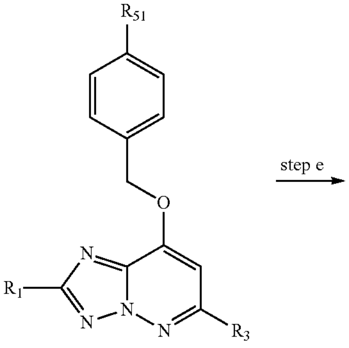

AAE

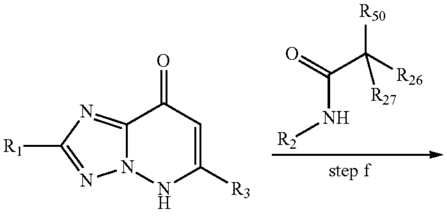

AAF

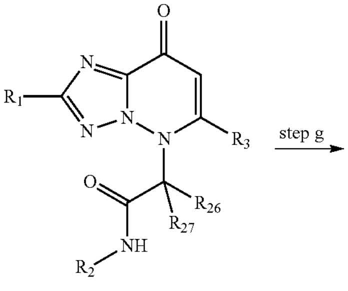

AAG

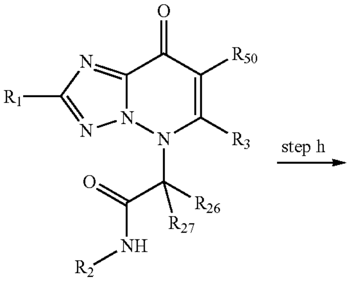

AAH

-continued

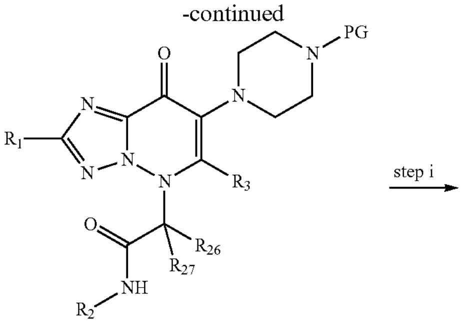

AAI

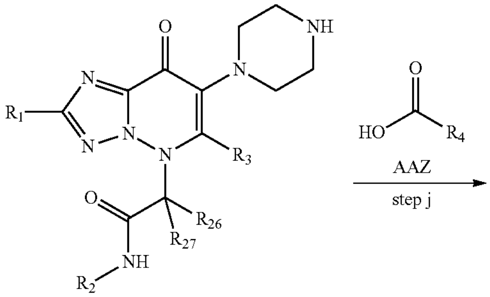

AAJ

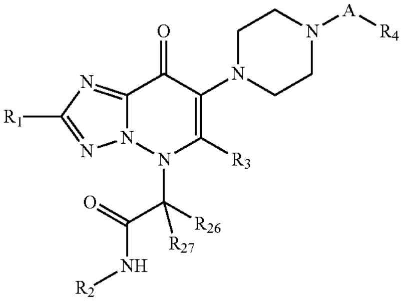

AAK

A process is provided for preparing a compound of formula AAK (Scheme XI) comprising steps a, b, c, d, e, f, g, h, i, and j. It is understood that the order of process steps a, b, c, d, e, f, g, h, i and j may be changed to optimize the synthesis as necessary. The compound of formula AAK can be obtained via coupling reaction step j by reacting compound of formula AAJ with compound AAZ wherein $R_4$ is defined above. The coupling reaction can be an amide formation. The coupling reaction step can be carried out with for example HATU ((1-[Bis(dimethylamino)methylene]-1H-1,2,3-triazolo[4,5-b]pyridinium 3-oxide hexafluorophosphate) or alternatively Ghosez reagent (1-Chloro-N, N,2-trimethylpropenylamine), preferably in a one or two step procedure. Alternatively, further alternative amide coupling methods are known in the art. For examples of amide bond formations, see Mantalbetti, C. A. G. N and Falque, V., Amide bond formation and peptide coupling, Tetrahedron, 2005, 61(46), pp 10827-10852 and references cited therein.

Compound of formula AAJ can be prepared comprising step i of deprotecting PG from the compound of formula AAI, wherein PG represents a suitable protecting group, preferably a BOC group, and wherein the other substituents are as defined above. There are many known ways of deprotecting BOC groups. The deprotection step can be carried out with for example TFA or HCl in a solvent for example dichloromethane or dioxane.

Compound of formula AAI can be prepared comprising step h starting from a compound of formula AAH wherein $R_{50}$ represents halo, particularly bromo and wherein PG represents a suitable protecting group for example a BOC group and the other substituents are as defined above. Step h can be a nucleophilic aromatic substitution reaction and can be carried out by combining compound of formula AAH with an amine for example tert-butyl piperazine-1-carboxylate or alternatively piperazine. A stoichiometric excess of the amine can be used, preferably between 2 and 50 mole equivalents in an organic solvent for example DMSO or NMP. The reaction is preferably stirred at a temperature of approximately 80-140° C. and can be carried out in a capped tube. An alternative method for step h can use Buchwald-Hartwig conditions using a amine for example tert-butyl piperazine-1-carboxylate, a ligand such as Brettphos or RuPhos or RuPhos hybrid with a palladium catalyst such as RuPhos Pd G1, RuPhos Pd G4 or [PdCl(allyl)]2 in the presence of a base such as K2CO3 or Cs2CO3 or tert-BuONa in an organic solvent such as dioxane or THF. The reaction is preferably stirred at a temperature of approximately 80-120° C. The reaction is preferably carried out under an inert gas such as nitrogen or argon. Alternatively, further alternative Buchwald-Hartwig coupling methods are known in the art, for examples of methods, see B. T. Ingoglia et al Biaryl monophosphine ligands in palladium-catalyzed C—N coupling: An updated User's guide, Tetrahedron, 2019, 75(32), pp 4199-4211 and references cited therein.

Compound of formula AAH can be prepared comprising step g wherein compound of formula AAG, wherein the substituents are defined as herein, is halogenated. Step g can be carried out using a halogenating reagent such as N-bromosuccinimide or N-iodosuccinimide in a solvent for example DMF or acetonitrile. The reaction is preferably stirred at a temperature of approximately 20-80° C.

Compound of formula AAG can be prepared comprising step f wherein compound of formula AAF, wherein the substituents are defined as herein, is alkylated by reacting compound of formula AAY wherein $R_{50}$ represents halo, particularly bromo, iodo or chloro and the other substituents are defined as above. Step f can be carried out in the presence of a base such as $K_2CO_3$ or N,N-diisopropylethylamine in a solvent for example DMF or dioxane. The reaction is preferably stirred at a temperature of approximately 20-80° C.

Compound of formula AAF can be prepared comprising step e starting from compound of formula AAE wherein $R_5$, represents H or methoxy and the other substituents are as defined above. Many methods of cleaving benzyl or para-methoxybenzyl groups are known in the art. Step e can be carried out in the presence of an acid such as TFA or HCl or HBr, preferably in stoichiometric excess in a solvent such as dichloromethane or dioxane and is preferably stirred at a temperature of approximately 20-80° C. An alternative method for step e can use hydrogenation conditions in the presence of a hydrogen atmosphere and a catalyst such as Pd/C or palladium hydroxide/C. The reaction is preferably stirred at a temperature of approximately 20-50° C. in an organic solvent such as ethanol or methanol.

Compound of formula AAE can be prepared comprising step d starting from compound of formula AAD wherein $R_{50}$ represents halo, particularly bromo and the other substituents are as defined above. Step d comprises reacting 2-10 mol equivalents of an alcohol for example benzyl alcohol or para-methoxybenzyl alcohol with 2-5 mol equivalents of a base such as sodium hydride in an organic solvent such as THF or dioxane with stirring at a temperature of approximately 20-40° C., preferably 20° C. for approximately 10-60 minutes. A compound of formula AAD is then added and stirring is continued at a temperature of approximately 20-100° C., preferably 20-60° C. The reaction is preferably carried out under an inert gas such as nitrogen or argon. An example method is described in WO2021/222522, 2021, A1 page 574.

Compound of formula AAD wherein $R_{50}$ represents halo, particularly bromo or iodo, and the other substituents are as defined herein, can be prepared comprising step c starting from compound of formula AAC. Step c comprises reacting a compound of formula AAC with a base such as LiTMP (lithium tetramethylpiperidide) or LDA (lithium diisopropylamide) with stirring in a solvent such as THF at a temperature of approximately −78° C. to 20° C. under an inert gas such as nitrogen or argon. After stirring for an appropriate time, approximately 30 minutes to 3 hours, a halogenating reagent such as bromine or iodine is then added at a temperature of approximately −78° C. to 20° C. and stirring is continued. Other suitable halogenating agents are known in the art.

Compound of formula AAC wherein $R_1$ and $R_3$ are as defined above can be prepared comprising step b starting from compound of formula AAB. Step b can be a Suzuki or Negishi or Stille or Kumada cross-coupling reaction and comprises reacting a compound of formula AAB with $R_3$n-MX wherein $R_3$ is as defined above, n is 1, 2, 3 or 4 and MX represents for example $B(OH)_2$, BPin (Pin represents boronic acid pinacol ester) BF3K, B(MIDA), Sn, Zn, Mg-Halo. Example Negishi cross-coupling conditions comprise reacting compound of formula AAD with an alkyl zincate for example dimethylzinc or diethylzinc, preferably in stoichiometric excess for example 2-10 mol equivalents, in the presence of a catalyst such as PdCl2(dppf) or Pd(PPh3)4 in a suitable solvent such as THF at a temperature of approximately 20-120° C., preferably 20-80° C. under an inert gas such as nitrogen or argon.

Compound of formula AAB wherein $R_1$ is as defined above can be prepared comprising step a from compound AAA. Step a can be a Suzuki or Negishi or Stille or Kumada cross-coupling reaction and comprises reacting a compound of formula AAA with R1n-MX wherein $R_1$ is as defined above, n is 1, 2, 3 or 4 and MX represents for example $B(OH)_2$, BPin (Pin represents boronic acid pinacol ester) $BF_3K$, Sn, Zn, Mg-Halo. Example Suzuki cross-coupling conditions comprise reacting compound of formula AAA with $R_1$-BPin in the presence of a catalyst such as $PdCl_2$(dppf) or $Pd(PPh_3)_4$ and a base such as $K_3PO_4$ or potassium carbonate in a suitable solvent mixture such as DMF, THF or dioxane or water at a temperature of approximately 20-120° C., preferably 20-80° C. under an inert gas such as nitrogen or argon. An example method is described in CN112707908 A page 32.

Compound of formula AAA can be prepared according to the method described in CN112707908 A page 31.

Scheme XII

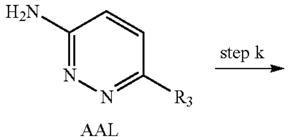

AAL

-continued

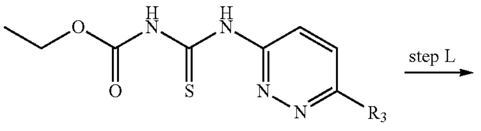

AAM

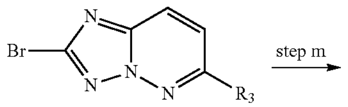

AAN

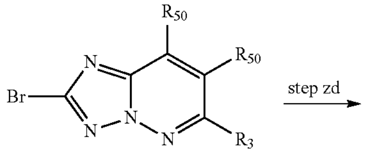

AAO

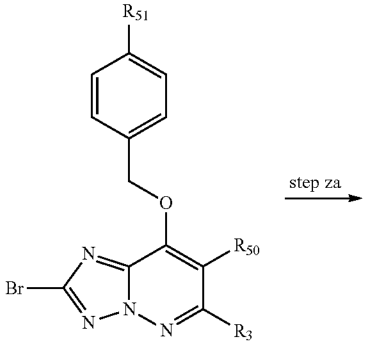

AAP

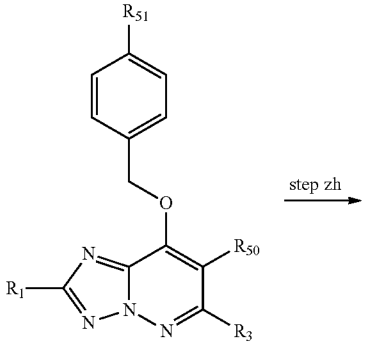

AAQ

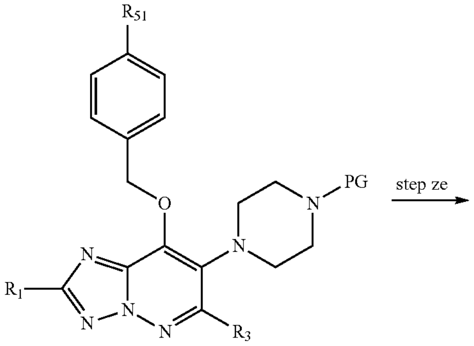

AAR

-continued

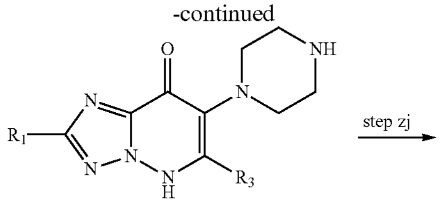

AAS

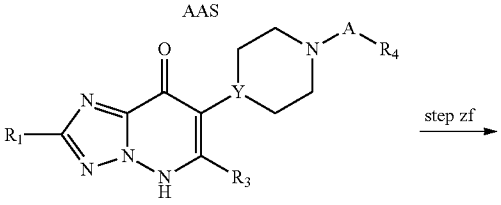

AAT

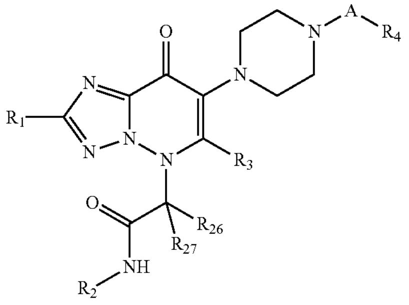

AAK

Alternatively compound of formula AAK can be prepared according to the route shown in Scheme XII comprising steps k, L, m, zd, za, zh, ze, zj and zf. Methods comprising steps zd, za, zh, ze, zj and zf to prepare compounds of formulas AAP, AAQ, AAR, AAS and AAT can be performed using analogous conditions as those described above for steps d, a, h, e, j and f for Scheme XI. It is understood that the order of process steps k, L, m, zd, za, zh, ze, zj and zf may be changed to optimize the synthesis as necessary.

Compound of formula AAO wherein $R_{50}$ represents halo, particularly bromo or chloro, and the other substituents are as defined above, can be prepared comprising step m starting from compound of formula AAN. Step m comprises reacting a compound of formula AAN with a halogenating agent such as $PCl_5$ or $PBr_3$ in stoichiometric excess for example 2-10 mol equivalents in a sealed tube at a temperature of approximately 200-270° C., preferably 250-270° C. for approximately 1-10 hours. An example method is described in *J. Org. Chem., Vol.* 39, No. 15, 1974, page 2146.

Compound of formula AAN wherein $R_3$ is as defined above, can be prepared comprising step L starting from compound of formula AAM. Step L comprises reacting a compound of formula AAM with hydroxylamine in the presence of a base such as triethylamine and a solvent such as ethanol or methanol at a temperature of approximately 60-100° C. The product of this reaction is then reacted with tert-butyl nitrite in the presence of $CuBr_2$ in a solvent such as acetonitrile at a temperature of approximately 20-50° C. An example method is described in CN 112707908 A page 31.

Compound of formula AAM wherein $R_3$ is as defined above, can be prepared comprising step k starting from AAL. Step k comprises reacting a compound of formula AAL with ethoxycarbonyl isothiocyanate in a solvent such as dichloromethane at a temperature of approximately 0-20° C. for 2-18 hours.

Compound of formula AAL wherein $R_3$ is as defined above are commercially available, or methods for their preparation are known in the art.

Scheme XIII

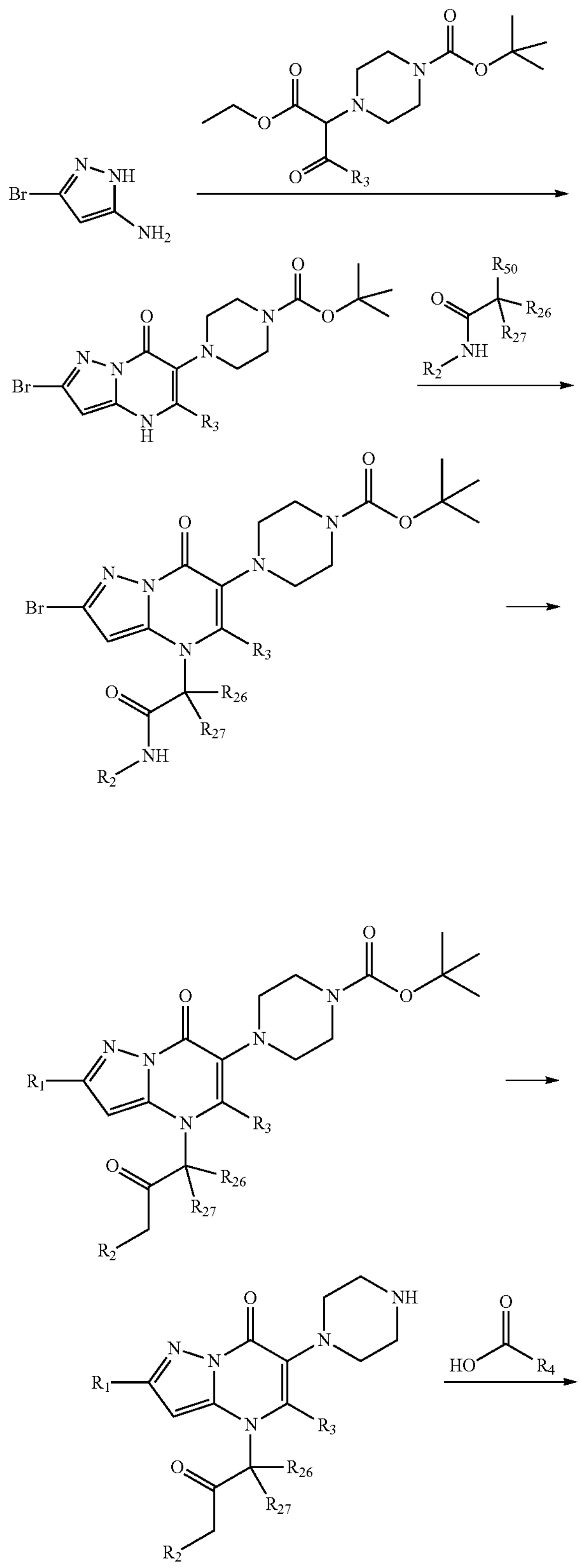

-continued

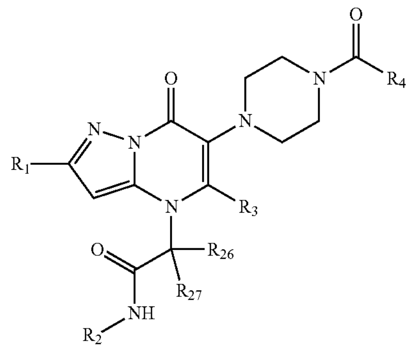

Compound of formula 1d can be prepared according to the example route shown in Scheme XIII using analogous methods to those described herein. Analogous methods to chemists skilled in the art can be adapted accordingly. It is understood that the order of process steps shown in Scheme XIII may change to optimize the synthesis as necessary.

Scheme XIV

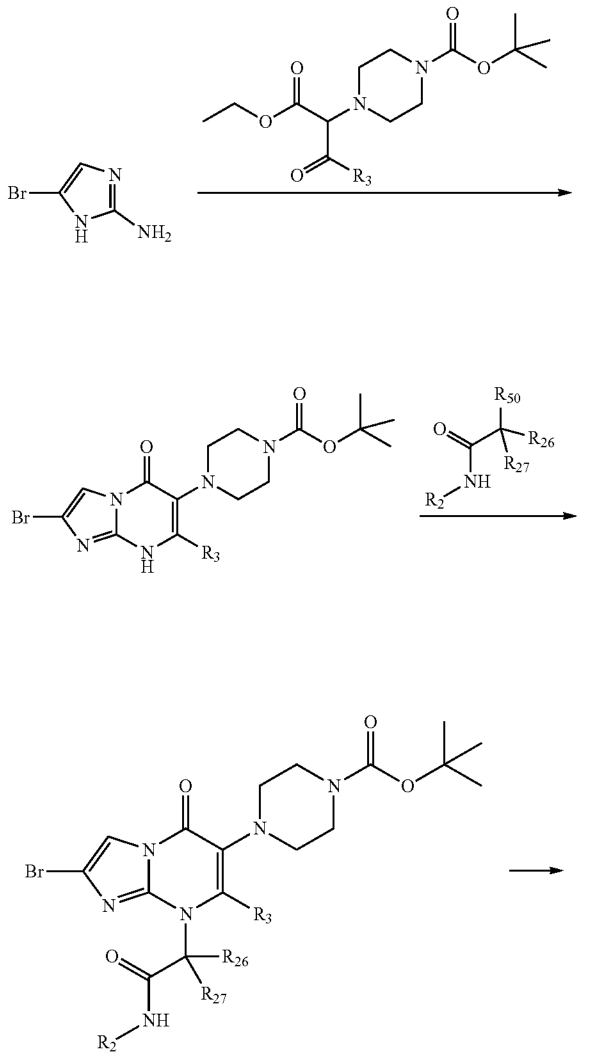

-continued

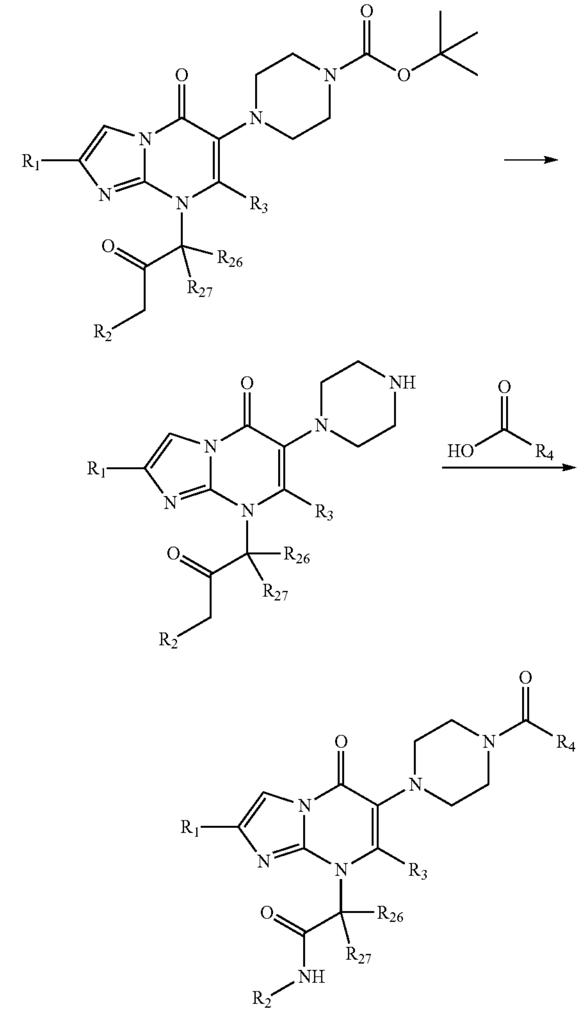

Compound of formula 1e can be prepared according to the example route shown in Scheme XIV using analogous methods to those described herein. Analogous methods to chemists skilled in the art can be adapted accordingly. It is understood that the order of process steps shown in Scheme XIV may change to optimize the synthesis as necessary.

Scheme XV

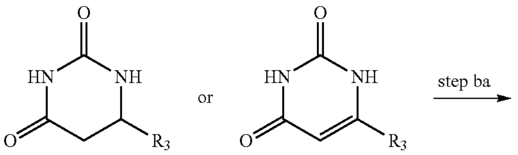

BBA BBAA

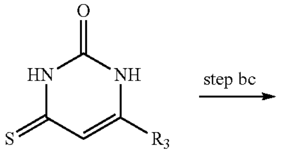

BBB

-continued

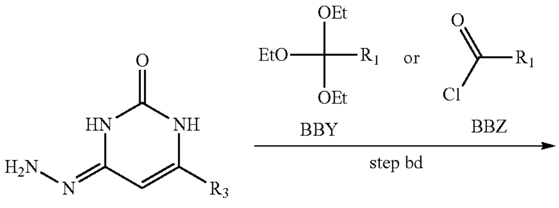

BBC

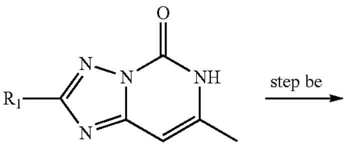

BBD

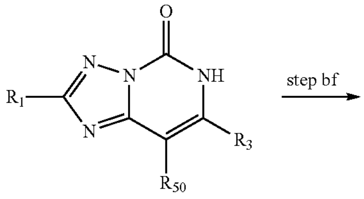

BBE

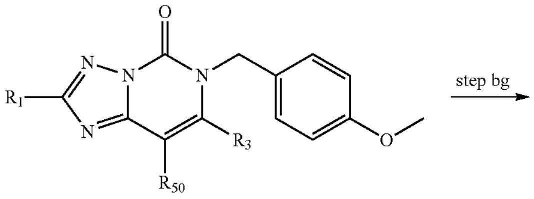

BBF

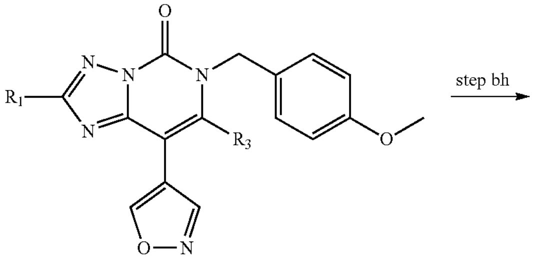

BBG

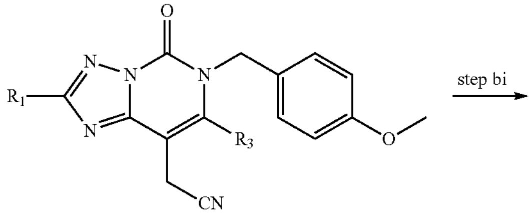

BBH

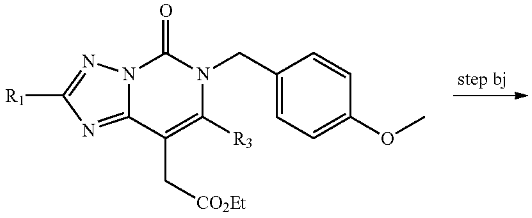

BBI

-continued

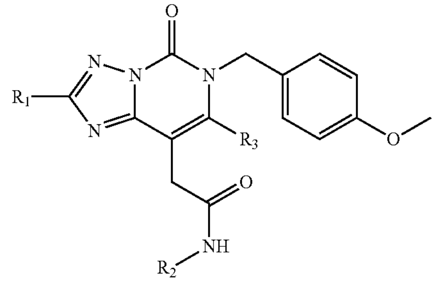

BBJ

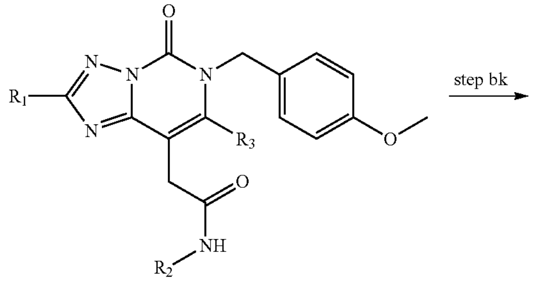

BBJ

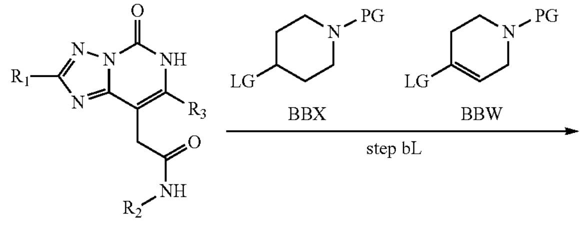

BBK

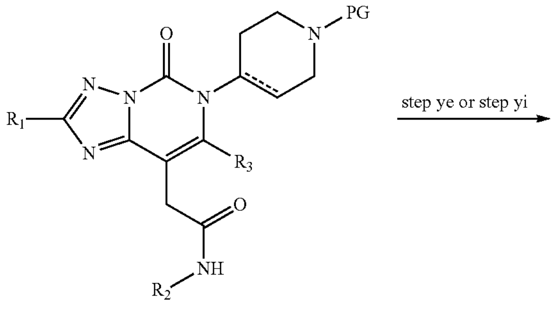

BBL

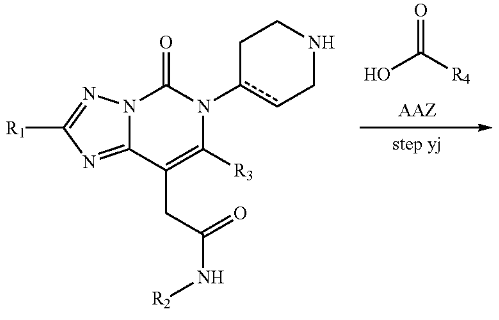

BBM

-continued

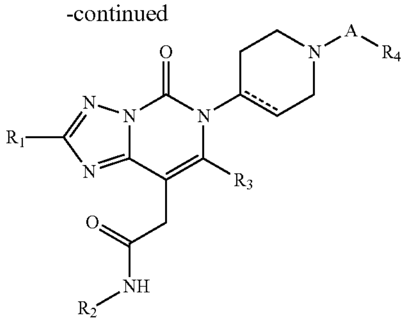

BBN

A process for preparing compound of formula BBN (Scheme XV) comprising steps ba, bc, bd, be, bf, bg, bh, bj, bk, bL, bm, ye or yi and yj. It is understood that the order of process ba, bc, bd, be, bf, bg, bh, bj, bk, bL, bm, ye or yi and yj may change to optimize the synthesis as necessary. The compound of formula BBN can be obtained via coupling reaction step yj by reacting compound of formula BBM wherein the substituents are as defined above with compound AAZ wherein $R_4$ is as defined above using analogous methods to those described herein.

Compound of formula BBM wherein the substituents are as defined above can be prepared deprotecting compound of formula BBL wherein PG represents a suitable protecting group such as BOC or para-methoxybenzyl or benzyl and the other substituents are as defined above comprising step ye or step yi using analogous methods to those described for step e or step i for Scheme XI.

Compound of formula BBL can be prepared comprising step bL starting from compound BBK wherein the substituents are as defined above with either compound BBX or compound BBW wherein PG is as defined above and LG is represented by halo, particularly iodo or bromo or OH or OMs (methanesulfonate) or OTs (p-toluenesulfonate) or OTf (trifluoromethanesulfonate) or B(OH)2, BPin (Pin represents boronic acid pinacol ester) BF3K. Step bL can be performed by combining compound of formula BBK with compound BBX in the presence of a base such as sodium hydride or K2CO3 or DBU or NaOtBu or phosphazene base P2-Et. A stoichiometric excess BBX can be used, preferably between 2 and 50 mole equivalents in an organic solvent for example DMF or NMP. The reaction is preferably stirred at a temperature of approximately 80-150° C. and can be carried out in a capped tube. An alternative method for step bL can use Ullmann-type reaction. Example Ullmann-type cross-coupling conditions comprise reacting compound of formula BBK with compound BBW in the presence of a catalyst such as copper(I)iodide, a ligand such as N-(2-cyanophenyl)pyridine-2-carboxamide or 4,7-dimethoxy-1,10-phenanthroline or N1,N2-dibenzylethane-1,2-diamine and a base such as K3PO4 or K2CO3 in a suitable solvent mixture such as DMSO or DMF at an approximate temperature of 80-150° C. A stoichiometric excess BBX can be used, preferably between 2 and 50 mole equivalents. An alternative method for step bL can comprise reacting compound of formula BBK with compound BBW using Buchwald-Hartwig conditions using for example using an analogous method to those described for step h (Scheme XI). The product of the reaction between the compound of formula BBK and the compound of formula BBW can optionally be hydrogenated using methods known in the art, to give a compound of formula BBL wherein the piperidine ring is saturated. Alternative cross-coupling conditions are known in the art, for examples of methods, see De Meijere et al. Metal-Catalyzed Cross-Coupling Reactions, Wiley, 2014 and references cited therein.

Compound of formula BBK can be prepared comprising step bk starting from compound of formula BBJ and the substituents are as defined above. Step bk comprises reacting a compound of formula BBJ with a stoichiometric excess of L-methionine for example 3 to 5 mol equivalents in a solvent such as methanesulfonic acid at approximate temperature of 20-80° C.

Compound of formula BBJ can be prepared comprising step bj starting from compound of formula BBI wherein the substituents are as defined above. Step bj comprises reacting a compound of formula BBI with a stoichiometric excess of R2-NH2 wherein $R_2$ is as defined above for example 3 to 5 mol equivalents in the presence of a stoichiometric excess of trimethylaluminium for example 3-5 mol equivalents in a solvent such as toluene at approximate temperature of 20-80° C.

Compound of formula BBI can be prepared comprising step bi starting from compound of formula BBH wherein the substituents are as defined above. Step bj comprises reacting a compound of formula BBH with a stoichiometric excess of gaseous hydrogen chloride for example 20-100 mol equivalents in ethanol at approximate temperature of 20-100° C. preferably in a sealed tube.

Compound of formula BBH can be prepared comprising step bh starting from compound of formula BBG wherein the substituents are as defined above. Step bh comprises reacting a compound of formula BBH with a stoichiometric excess of potassium fluoride for example 3 to 5 mol equivalents in water in the presence of an additional solvent such as DMF or methanol at an approximate temperature of 20-100° C. preferably 60-100° C.

Compound of formula BBG can be prepared comprising step bg starting from compound of formula BBF wherein $R_{50}$ is represented by halo, particularly iodo or bromo and the other substituents are as defined above. Step bg comprises reacting a compound of formula BBF with 4-(4,4,5,5-tetramethyl-1,3,2-dioxaborolan-2-yl)isoxazole in the presence of a catalyst such as XPhos Pd G3 and a base such as potassium carbonate in a suitable solvent such as DMF at a temperature of approximately 20-120° C., preferably 60-100° C. under an inert gas such as nitrogen or argon.

Compound of formula BBF can be prepared comprising step bf starting from compound of formula BBE wherein the substituents are as defined above. Step bf comprises reacting a compound of formula BBE with a base such as sodium hydride at an approximate temperature of 0-20° C. in a solvent such as DMF for approximately 5 to 30 minutes under an inert gas such as nitrogen or argon. 1-(bromomethyl)-4-methoxybenzene is then added and the reaction is stirred at a temperature of approximately 0-20° C.

Compound of formula BBE can be prepared comprising step be wherein compound of formula BBD wherein the substituents are defined as above is halogenated. Step be can be carried out using a halogenating reagent such as N-bromosuccinimide or N-iodosuccinimide in a solvent for example DMF or acetonitrile. The reaction is preferably stirred at a temperature of approximately 20-80° C.

Compound of formula BBD can be prepared comprising step bd starting from compound of formula BBC wherein the substituents are as defined above. Step bd comprises reacting a compound of formula BBC with a compound of formula BBY wherein R1 is defined as above in a solvent such as DMF or toluene or dioxane at a temperature of approximately 80-150° C. An alternative method for step bd can comprise reacting compound of formula BBC with a compound of formula BBZ wherein R1 is defined as above in a solvent such as dichloroethane or DMF or toluene or dioxane at a temperature of approximately 0-20° C. A base such as triethylamine may be added. The reaction is then stirred at an approximate temperature of 80-150° C.

Compound of formula BBC can be prepared comprising step bc starting from compound of formula BBB wherein the substituents are defined as above. Step bc comprises reacting a compound of formula BBB with a stoichiometric excess of hydrazine hydrate for example 2 to 5 mol equivalents in a solvent such as ethanol. The reaction is preferably stirred at a temperature of approximately 60-100° C.

Compound of formula BBB can be prepared comprising step ba starting from compound of formula BBA or BBAA wherein the substituents are defined as above. Compound of formula BBA or BBAA are commercially available, or methods for their preparation are known in the art. Step ba comprises reacting a compound of formula BBA or BBAA with P2S5 or lawessons reagent in a solvent such as dioxane or pyridine. The reaction is preferably stirred at a temperature of approximately 80-120° C.

Scheme XVI

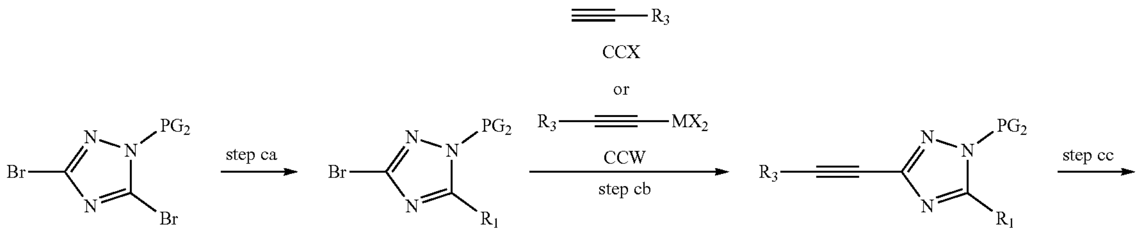

CCA CCB CCC

-continued
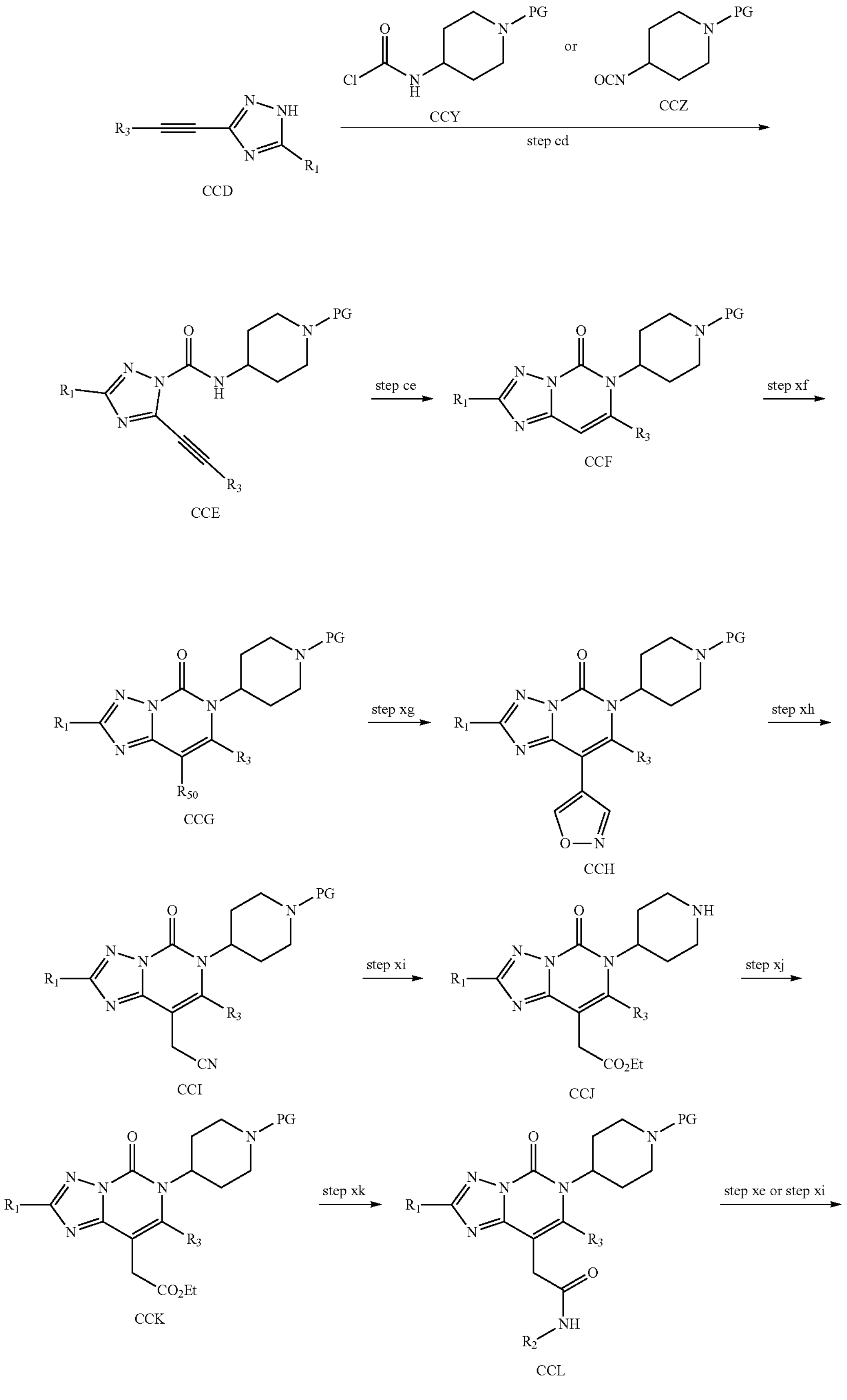

-continued

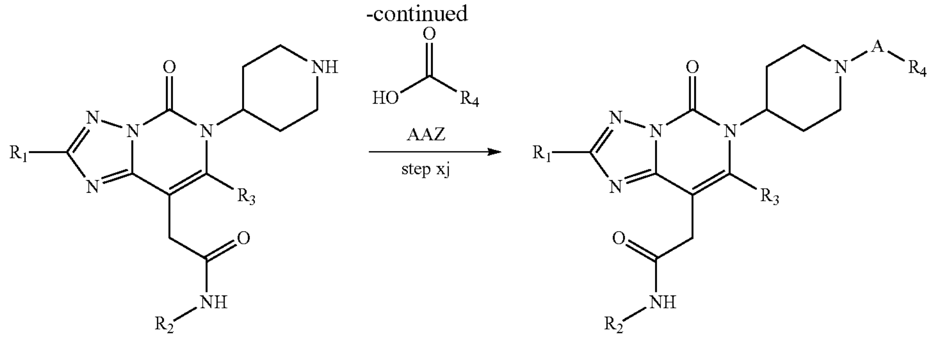

CCM CCN

Compound of formula CCN can be prepared according to the route shown in Scheme XVI comprising steps ca, cb, cc, cd, ce, cf, xg, xh, xi, xj, xk, xe or xi and xj. It is understood that the order of process ca, cb, cc, cd, ce, cf, xg, xh, xi, xj, xk, xe or xi and xj may change to optimize the synthesis as necessary. Methods comprising steps xg, xh, xi, xj, xk, xe or xi and xj to prepare compounds of formulas CCG, CCH, CCI, CCJ, CCL, CCM and CCN can be performed using analogous conditions as those described above for steps bf, bg, bh, bi, e, i and j for Scheme XI and Scheme XV.

Compound of formula CCK can be prepared comprising step xj starting from compound of formula CCJ wherein the substituents are defined as above. Step xj comprises reacting a compound of formula CCJ with di-tert-butyl dicarbonate or para-methoxybenzyl bromide or benzyl bromide in the presence of a base such as triethylamine in a solvent such as dichloromethane or dioxane at a temperature of approximately 0-20° C.

Compound of formula CCF wherein PG represents a suitable protecting group such as BOC or para-methoxybenzyl or benzyl and the other substituents are as defined above can be prepared comprising step ce starting from compound of formula CCE wherein substituents are as defined above. Step ce comprises reacting a compound of formula CCE with Echavarren's gold(I) catalyst in a solvent such as THF at a temperature of approximately 60-140° C., preferably 80-120° C. in a sealed tube. An example method is described in *Org. Lett.* 2013, 15, 11, 2616-2619. An alternative method of preparing compound of formula CCF comprises reacting compound of formula CCE with a base such as sodium hydride in a solvent such as DMF or THF or dioxane at a temperature of approximately 60-140° C., preferably 80-120° C. under an inert gas such as nitrogen or argon in a sealed tube.

Compound of formula CCE can be prepared comprising step cd starting from compound CCD wherein the substituents are defined as above. Step cd comprises reacting a compound of formula CCD with compound of formula CCY or CCZ wherein PG represents a suitable protecting group such as BOC or para-methoxybenzyl or benzyl in the presence of a base such as triethylamine or N-ethyl-N,N-diisopropylamine in a solvent such as THF or dioxane or DMF at a temperature of approximately 20-140° C. preferably 60-120° C. Compound of formula CCY or CCZ are commercially available, or methods for their preparation are known in the art.

Compound of formula CCD can be prepared comprising step cc starting from compound CCC wherein PG2 represents a protecting group such as MOM (methoxymethyl) or SEM (trimethylsilyl)ethoxymethyl) and the other substituents are as defined above. Step cc comprises reacting a compound of formula CCC with an acid such as HCl or TFA in a solvent such as dioxane or dichloromethane at a temperature of approximately 0-80° C. preferably 20-60° C. Alternative methods for deprotection of SEM or MOM groups are known in the art.

Compound of formula CCC can be prepared comprising step cb starting from compound of formula CCB wherein the substituents are as defined above. Step cb can be a Sonogashira reaction reacting a compound of formula CCB with a compound of formula CCX wherein $R_3$ is as defined above in the presence of a catalyst such as $Pd(PPh_3)_4$ and a copper catalyst such as copper(I) iodide and a base such as triethylamine or lithium carbonate in a solvent such as dioxane or DMF or acetonitrile THF at a temperature of approximately 20-120° C., preferably 80-120° C. under an inert gas such as nitrogen or argon. Step cb can alternatively be a Suzuki or Stille cross-coupling reaction and comprises reacting a compound of formula CCB with a compound of formula CCW wherein MX2 represents $B(OH)_2$, BPin (Pin represents boronic acid pinacol ester) $BF_3K$, B(MIDA), tributyltin and $R_3$ is as defined above. Methods for Sonogashira, Suzuki or Stille reactions are known in the art. for examples of methods, see Molnar et al. Palladium-Catalyzed Coupling Reactions, Wiley, 2013 and references cited therein.

Compound of formula CCB can be prepared comprising step ca starting from compound of formula CCA wherein the substituents are defined as above. Step a can be a Suzuki cross-coupling reaction and comprises reacting a compound of formula CCA with $R_{1n}$-MX wherein R1 is as defined above, n is 1, 2, 3 or 4 and MX represents for example $B(OH)_2$, BPin (Pin represents boronic acid pinacol ester) $BF_3K$. Example Suzuki cross-coupling conditions comprise reacting compound of formula CCA with $R_1$-BPin in the presence of a catalyst such as $PdCl_2(dppf)$ or $Pd(PPh_3)_4$ and a base such as $K_3PO_4$ or potassium carbonate in a suitable solvent mixture such as DMF, THF or dioxane or water at a temperature of approximately 20-120° C., preferably 60-120° C. under an inert gas such as nitrogen or argon. Compound of formula CCA are commercially available, or methods for their preparation are known in the art.

Scheme XVII
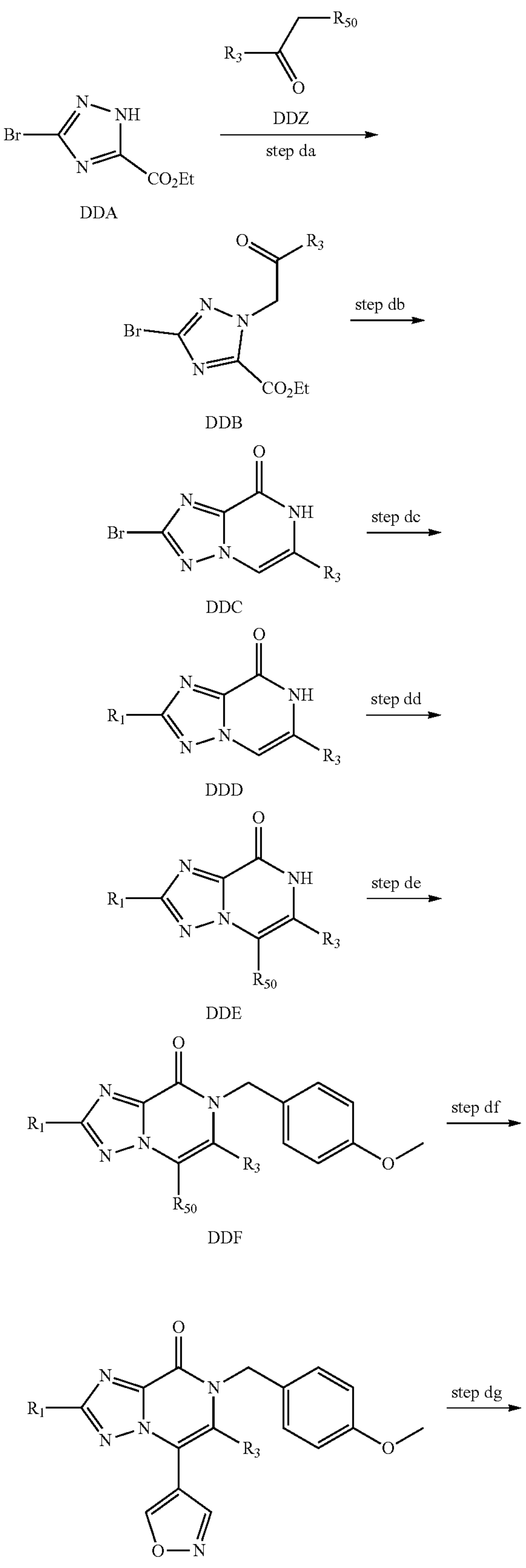
DDA, DDB, DDC, DDD, DDE, DDF, DDG
-continued
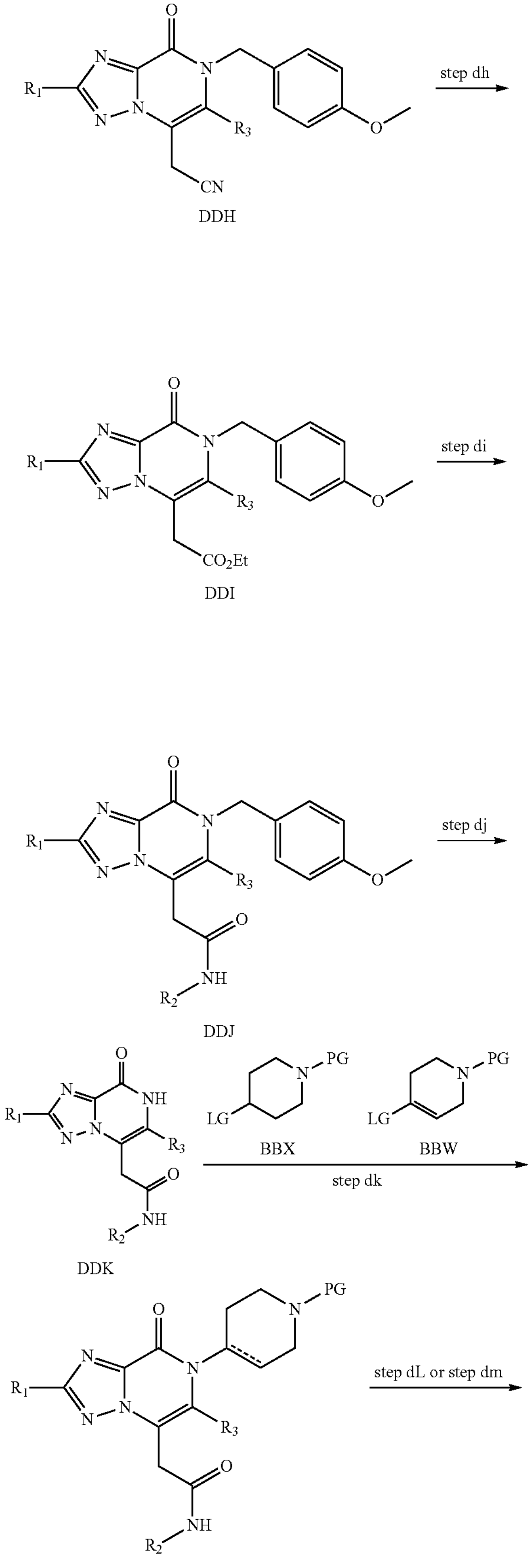
DDH, DDI, DDJ, DDK, DDL -continued

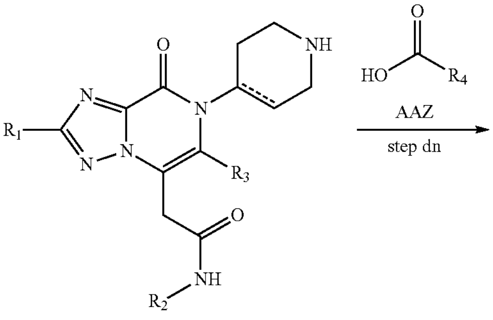

DDM

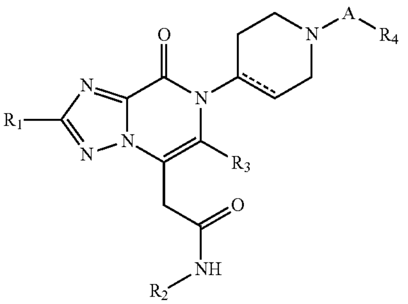

DDN

Compound of formula DDN can be prepared according to the route shown in Scheme XVII comprising steps da, db, dc, dd, de, df, dg, dh, di, dj, dk, dL or dM and dn. It is understood that the order of process da, db, dc, dd, de, df, dg, dh, di, dj, dk, dL or dM and dn may change to optimize the synthesis as necessary. Methods comprising steps de, df, dg, dh, di, dj, dk, dL, dM and dn to prepare compounds of formulas DDF, DDG, DDH, DDI, DDJ, DDK, DDL, DDM and DDN can be performed using analogous conditions as those described herein, including optional hydrogenation steps, for example step dk.

Compound of formula DDE wherein $R_{50}$ represents halo particularly bromo or iodo and the other substituents are as defined above can be prepared comprising step dd starting from compound of formula DDD wherein the substituents are as defined above. Step dd can be carried out using a halogenating reagent such as N-bromosuccinimide or N-iodosuccinimide in a solvent for example DMF or acetonitrile or acetic acid. The reaction is preferably stirred at a temperature of approximately 20-110° C.

Compound of formula DDD wherein the substituents are as defined above can be prepared comprising step dc starting from compound of formula DDC wherein the substituents are as defined above. Step dc can be performed using analogous conditions as those described above for step a for Scheme XI.

Compound of formula DDC wherein the substituents are as defined above can be prepared comprising step db starting from compound of formula DDB wherein the substituents are as defined above. Step db comprises reacting compound of formula DDB with a stoichiometric excess of an ammonium salt such as ammonium acetate for example 3 to 100 mol equivalents particularly 10 to 20 mol equivalents in a solvent such as acetic acid at an approximate temperature of 60-130° C., preferably 80-120° C.

Compound of formula DDB wherein the substituents are as defined above can be prepared comprising step da starting from compound of formula DDA. Step da comprises reacting compound of formula DDA with compound of formula DDZ wherein $R_{50}$ represents halo particularly chloro or bromo and the other the substituents are as defined above in the presence of a base such as potassium carbonate in a solvent such as acetone or acetonitrile at an approximate temperature of 0-50° C., preferably 0-20° C. Compound of formula DDZ are commercially available, or methods for their preparation are known in the art.

"Protecting Group":

In the methods describe above, functional groups which are present in the starting materials and are not intended to take part in the reaction, are present in protected form if necessary, and protecting groups that are present are cleaved, whereby said starting compounds may also exist in the form of salts provided that a salt-forming group is present and a reaction in salt form is possible. In additional process steps, carried out as desired, functional groups of the starting compounds which should not take part in the reaction may be present in unprotected form or may be protected for example by one or more protecting groups. The protecting groups are then wholly or partly removed according to one of the known methods. Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

Intermediates and final products can be worked up and/or purified according to standard methods, e.g. using chromatographic methods, distribution methods, (re-) crystallization, and the like.

The following applies in general to all processes mentioned herein before and hereinafter. All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein above.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

Sulfonimidamides, and their synthesis, are described in Chem. Eur. J. 2017, 23, 15189-15193 DOI:10.1002/chem.201703272.

SEQUENCE LISTING

```
Sequence total quantity: 12
SEQ ID NO: 1           moltype = DNA  length = 9674
FEATURE                Location/Qualifiers
misc_feature           1..9674
                       note = Description of Artificial Sequence: Synthetic
                        polynucleotide
source                 1..9674
                       mol_type = other DNA
                       organism = synthetic construct
SEQUENCE: 1
aaccatctcg caaataaata agtattttac tgttttcgta acagttttgt aataaaaaaa  60
cctataaata ttccggatta ttcataccgt cccaccatcg ggcgccatgg cttctcacca  120
ccatcaccat caccatcatc atcacgctca gcacgacgag gctgtggaca acaagttcaa  180
caaggagcag cagaacgctt tctacgagat cctgcacctc cctaacctga acgaggagca  240
gcgtaacgct ttcatccagt ccctgaagga cgacccttct cagtctgcta acctgctggc  300
tgaggctaag aagctgaacg acgctcaggc tcctaaggtg gacaacaagt tcaacaagga  360
gcagcagaac gctttctacg agatcctgca cctccctaac ctgaacgagg agcagcgtaa  420
cgctttcatc cagtccctga aggacgaccc ttctcagtct gctaacctgc tggctgaggc  480
taagaagctg aacgacgctc aggctcctaa ggtggacgct aacggtggcg gcggttccgg  540
cggtggtggc tctctcgagg ttctgttcca gggtccgaat gaaggcgagg aagatgatga  600
caaagacttc ctgtggccag ctccaaacga agaacaggtg acttgtctca agatgtactt  660
cggtcatagc agcttcaaac cagtgcagtg gaaagttatc cacagcgttc ttgaagaacg  720
tcgtgataat gtggctgtga tggctactgg ctatggtaag agcctgtgtt tccagtaccc  780
gccagtttac gttggtaaga tcggtctggt gattagcccg ctgatctctc tgatggaaga  840
ccaggtgctg caacttaaga tgagcaacat cccggcttgt ttcctgggtt ctgcacaaag  900
cgagaacgtg ctcaccgata tcaagctggg taagtaccgt atcgtgtacg tgacgccaga  960
atactgtagc ggcaacatgg gtcttctgca acagctcgaa gctgatattg gcatcaccct  1020
cattgcagtg gacgaagctc actgtatcag cgagtggggt catgatttcc gcgactcttt  1080
ccgtaaactg ggttctctga agactgcact tccgatggtt ccaattgtgg cactgaccgc  1140
aactgcttct agctctattc gtgaagacat cgttcgttgc ctgaacctcc gtaacccaca  1200
aattacctgc accggctttg accgtccgaa cctgtacctg gaggttcgtc gtaagaccgg  1260
taatatcctt caggacctgc aaccattcct ggttaagacc agcagccact gggagttcga  1320
aggtccgact atcatctact gcccaagccg taagatgacc cagcaggtta ctggtgaact  1380
gcgtaaactg aacctgagct gtggcactta ccacgcaggc atgtctttct ctacccgtaa  1440
agacatccat catcgtttcg tgcgtgatga aatccagtgc gttatcgcta ccattgcatt  1500
cggcatgggt atcaacaaag ctgacatccg tcaagtgatt cactacggtg caccgaaaga  1560
catggaaagc tactaccagg aaatcggccg tgcaggtcgt gatggtctgc aaagctcttg  1620
tcatgtgctg tgggcaccag cagatattaa cctgaaccgt cacctgctga ctgaaattcg  1680
taacgagaaa ttccgtctgt acaaactgaa gatgatggcg aagatggaga aatacctgca  1740
tagctcccgt tgtcgtcgtc aaatcattct gagccatttc gaggataaac aggtgcagaa  1800
agcttctctg ggtatcatgg gcactgagaa gtgctgcgat aactgtcgta gccgtcttga  1860
tcactgctac agcatggacg atagcgaaga cacttcttgg gatttcggtc cacaagcatt  1920
caaactgctg agcgcagttg atatcctggg tgagaaattc ggcatcggcc tcccaatcct  1980
gtttctgcgc ggttctaact ctcagcgtct tgctgatcaa taccgtcgtc actctctgtt  2040
cggcactggt aaagaccaga ccgaatcttg gtggaaagca ttcagccgtc aacttatcac  2100
cgaaggcttt ctggtggaag tgtctcgtta caacaagttc atgaagatct gcgcactgac  2160
taagaaaggt cgtaactggc tgcacaaggc aaataccgag tctcagtctc ttatccttca  2220
ggctaacgaa gaactgtgcc cgaagaagct tctgctgcca tcttctaaga ccgtgagctc  2280
tggtactaaa gagcattgct acaaccaggt gccggttgaa ctgtctaccg agaagaagtc  2340
caacctggag aagctgtact cctacaaacc gtgcgacaag atctcctccg gttctaatat  2400
cagcaagaag tccatcatgg tgcagtctcc ggagaaagct tacagcagct ctcagccagt  2460
tatctctgca caggaacagg aaactcagat tgtgctgtac ggtaaactgg tggaagcacg  2520
tcagaaacac gctaacaaga tggacgtgcc gccagcaatt cttgcaacca acaagattct  2580
ggtggacatg gctaagatgc gcccaactac tgttgagaac gtgaaacgta tcgacggtgt  2640
tagcgaaggt aaagctgcaa tgctggcacc actgcttgaa gttatcaagc atttctgcca  2700
gaccaactct gttcagaccg acctgttctc ttctaccaaa ccataatggt accgaattcg  2760
cggccgcaga gctcgctctg gtgccacgcg gtagttccgc ttggagccac ccgcagttcg  2820
aaaagtaagt gattaacctc aggttataca tatattttga atttaattaa ttatacatat  2880
attttatatt atttttgtct tttattatcg aggggccgtt gttggtgtgg ggttttgcat  2940
```

-continued

```
agaaataaca atgggagttg gcgacgttgc tgcgccaaca ccacctccct tccctccttt  3000
catcatgtat ctgtagataa aataaaatat taaacctaaa aacaagaccg cgcctatcaa  3060
caaaatgata ggcattaact tgccgctgac gctgtcacta acgttggacg atttgccgac  3120
taaaccttca tcgcccagta accaatctag gtagctgagc gcatgcaagc tgatccgggt  3180
tattagtaca tttattaagc gctagattct gtgcgttgtt gatttacaga caattgttgt  3240
acgtatttta ataattcatt aaatttataa tctttagggt ggtatgttag agcgaaaatc  3300
aaatgatttt cagcgtcttt atatctgaat ttaaatatta aatcctcaat agatttgtaa  3360
aataggtttc gattagtttc aaacaagggt tgtttttccg aaccgatggc tggactatct  3420
aatggatttt cgctcaacgc cacaaaactt gccaaatctt gtagcagcaa tctagctttg  3480
tcgatattcg tttgtgtttt gttttgtaat aaaggttcga cgtcgttcaa aatattatgc  3540
gcttttgtat ttctttcatc actgtcgtta gtgtacaatt gactcgacgt aaacacgtta  3600
aatagagctt ggacatattt aacatcgggc gtgttagctt tattaggccg attatcgtcg  3660
tcgtcccaac cctcgtcgtt agaagttgct tccgaagacg attttgccat agccacacga  3720
cgcctattaa ttgtgtcggc taacacgtcc gcgatcaaat ttgtagttga gctttttgga  3780
attatttctg attgcgggcg tttttgggcg ggtttcaatc taactgtgcc cgattttaat  3840
tcagacaaca cgttagaaag cgatggtgca ggcggtggta acatttcaga cggcaaatct  3900
actaatggcg gcggtggtgg agctgatgat aaatctacca tcggtggagg cgcaggcggg  3960
gctggcggcg gaggcggagg cggaggtggt ggcggtgatg cagacggcgg tttaggctca  4020
aatgtctctt taggcaacac agtcggcacc tcaactattg tactggtttc gggcgccgtt  4080
tttggtttga ccggtctaag acgagtgcga tttttttcgt ttctaatagc ttccaacaat  4140
tgttgtctgt cgtctaaagg tgcagcgggt tgaggttccg tcggcattgg tggagcgggc  4200
ggcaattcag acatcgatgg tggtggtggt ggtggaggcg ctggaatgtt aggcacggga  4260
gaaggtggtg gcggcggtgc cgccggtata atttgttctg gtttagtttg ttcgcgcacg  4320
attgtgggca ccggcgcagg cgccgctggc tgcacaacgg aaggtcgtct gcttcgaggc  4380
agcgcttggg gtggtggcaa ttcaatatta taattggaat acaaatcgta aaaatctgct  4440
ataagcattg taatttcgct atcgtttacc gtgccgatat ttaacaaccg ctcaatgtaa  4500
gcaattgtat tgtaaagaga ttgtctcaag ctcggatcga tcccgcacgc cgataacaag  4560
ccttttcatt tttactacag cattgtagtg gcgagacact tcgctgtcgt cgaggtttaa  4620
acgcttcctc gctcactgac tcgctgcgct cggtcgttcg gctgcggcga gcggtatcag  4680
ctcactcaaa ggcggtaata cggttatcca cagaatcagg ggataacgca ggaaagaaca  4740
tgtgagcaaa aggccagcaa aaggccagga accgtaaaaa ggccgcgttg ctggcgtttt  4800
tccataggct ccgcccccct gacgagcatc acaaaaatcg acgctcaagt cagaggtggc  4860
gaaacccgac aggactataa agataccagg cgtttccccc tggaagctcc ctcgtgcgct  4920
ctcctgttcc gaccctgccg cttaccggat acctgtccgc ctttctccct tcgggaagcg  4980
tggcgctttc tcatagctca cgctgtaggt atctcagttc ggtgtaggtc gttcgctcca  5040
agctgggctg tgtgcacgaa ccccccgttc agcccgaccg ctgcgcctta tccggtaact  5100
atcgtcttga gtccaacccg gtaagacacg acttatcgcc actggcagca gccactggta  5160
acaggattag cagagcgagg tatgtaggcg gtgctacaga gttcttgaag tggtggccta  5220
actacggcta cactagaagg acagtatttg gtatctgcgc tctgctgaag ccagttacct  5280
tcggaaaaag agttggtagc tcttgatccg gcaaacaaac caccgctggt agcggtggtt  5340
tttttgtttg caagcagcag attacgcgca gaaaaaaagg atctcaagaa gatcctttga  5400
tcttttctac ggggtctgac gctcagtgga acgaaaactc acgttaaggg attttggtca  5460
tgagattatc aaaaaggatc ttcacctaga tccttttaaa ttaaaaatga agttttaaat  5520
caatctaaag tatatatgag taaacttggt ctgacagtta ccaatgctta atcagtgagg  5580
cacctatctc agcgatctgt ctatttcgtt catccatagt tgcctgactc cccgtcgtgt  5640
agataactac gatacgggag ggcttaccat ctggccccag tgctgcaatg ataccgcgag  5700
acccacgctc accggctcca gatttatcag caataaacca gccagccgga agggccgagc  5760
gcagaagtgg tcctgcaact ttatccgcct ccatccagtc tattaattgt tgccgggaag  5820
ctagagtaag tagttcgcca gttaatagtt tgcgcaacgt tgttgccatt gctacaggca  5880
tcgtggtgtc acgctcgtcg tttggtatgg cttcattcag ctccggttcc caacgatcaa  5940
ggcgagttac atgatccccc atgttgtgca aaaaagcggt tagctccttc ggtcctccga  6000
tcgttgtcag aagtaagttg gccgcagtgt tatcactcat ggttatggca gcactgcata  6060
attctcttac tgtcatgcca tccgtaagat gcttttctgt gactggtgag tactcaacca  6120
agtcattctg agaatagtgt atgcggcgac cgagttgctc ttgcccggcg tcaatacggg  6180
ataataccgc gccacatagc agaactttaa aagtgctcat cattggaaaa cgttcttcgg  6240
ggcgaaaact ctcaaggatc ttaccgctgt tgagatccag ttcgatgtaa cccactcgtg  6300
cacccaactg atcttcagca tcttttactt tcaccagcgt ttctgggtga gcaaaaacag  6360
gaaggcaaaa tgccgcaaaa aagggaataa gggcgacacg gaaatgttga atactcatac  6420
tcttcctttt tcaatattat tgaagcattt atcagggtta ttgtctcatg agcggataca  6480
tatttgaatg tatttagaaa aataaacaaa taggggttcc gcgcacattt ccccgaaaag  6540
tgccacctga cgcgccctgt agcggcgcat taagcgcggc gggtgtggtg gttacgcgca  6600
gcgtgaccgc tacacttgcc agcgccctag cgcccgctcc tttcgctttc ttcccttcct  6660
ttctcgccac gttcgccggc tttccccgtc aagctctaaa tcgggggctc cctttagggt  6720
tccgatttag tgctttacgg cacctcgacc ccaaaaaact tgattagggt gatggttcac  6780
gtagtgggcc atcgccctga tagacggttt ttcgcccttt gacgttggag tccacgttct  6840
ttaatagtgg actcttgttc caaactggaa caacactcaa ccctatctcg gtctattctt  6900
ttgatttata agggattttg ccgatttcgg cctattggtt aaaaaatgag ctgatttaac  6960
aaaaatttaa cgcgaatttt aacaaaatat taacgtttac aatttcccat tcgccattca  7020
ggctgcgcaa ctgttgggaa gggcgatcgg tgcgggcctc ttcgctatta cgccaggaac  7080
ggctccgccc actattaatg aaattaaaaa ttccaatttt aaaaaacgca gcaagagaaa  7140
catttgtatg aaagaatgcg tagaaggaaa gaaaaatgtc gtcgacatgc tgaacaacaa  7200
gattaatatg cctccgtgta taaaaaaaat attgaacgat ttgaaagaaa acaatgtacc  7260
gcgcggcggt atgtacagga agaggtttat actaaactgt tacattgcaa acgtggtttc  7320
gtgtgccaag tgtgaaaacc gatgtttaat caaggctctg acgcatttct acaaccacga  7380
ctccaagtgt gtgggtgaag tcatgcatct tttaatcaaa tcccaagatg tgtataaacc  7440
accaaactgc caaaaaatga aaactgtcga caagctctgt ccgtttgctg gcaactgcaa  7500
gggtctcaat cctatttgta attattgaat aataaaacaa ttataaatgc taaatttgtt  7560
ttttattaac gatacaaacc aaacgcaaca agaacatttg tagtattatc tataattgaa  7620
aacgcgtagt tataatcgct gaggtaatat ttaaaatcat tttcaaatga ttcacagtta  7680
```

-continued

```
atttgcgaca atataatttt attttcacat aaactagacg ccttgtcgtc ttcttcttcg  7740
tattccttct ctttttcatt tttctcttca taaaaattaa catagttatt atcgtatcca  7800
tatatgtatc tatcgtatag agtaaatttt ttgttgtcat aaatatatat gtctttttta  7860
atggggtgta tagtaccgct gcgcatagtt tttctgtaat ttacaacagt gctattttct  7920
ggtagttctt cggagtgtgt tgctttaatt attaaattta tataatcaat gaatttggga  7980
tcgtcggttt tgtacaatat gttgccggca tagtacgcag cttcttctag ttcaattaca  8040
ccattttta gcagcaccgg attaacataa ctttccaaaa tgttgtacga accgttaaac  8100
aaaaacagtt cacctccctt ttctatacta ttgtctgcga gcagttgttt gttgttaaaa  8160
ataacagcca ttgtaataag acgcacaaac taatatcaca aactggaaat gtctatcaat  8220
atatagttgc tgatcagatc tacccgtagt ggctatggca gggcttgccg ccccgacgtt  8280
ggctgcgagc cctgggcctt cacccgaact tgggggttgg ggtggggaaa aggaagaaac  8340
gcgggcgtat tggtcccaat ggggtctcgg tggggtatcg acagagtgcc agccctggga  8400
ccgaaccccg cgtttatgaa caaacgaccc aacacccgtg cgttttattc tgtcttttta  8460
ttgccgtcat agcgcgggtt ccttccggta ttgtctcctt ccgtgtttca gttagcctcc  8520
cccatctccc ggtaccgcat gctatgcatc ggccgcttta cttgtacagc tcgtccatgc  8580
cgagagtgat cccggcggcg gtcacgaact ccagcaggac catgtgatcg cgcttctcgt  8640
tggggtcttt gctcagggcg gactgggtgc tcaggtagtg gttgtcgggc agcagcacgg  8700
ggccgtcgcc gatgggggtg ttctgctggt agtggtcggc gagctgcacg ctgccgtcct  8760
cgatgttgtg gcggatcttg aagttcacct tgatgccgtt cttctgcttg tcggccatga  8820
tatagacgtt gtggctgttg tagttgtact ccagcttgtg ccccaggatg ttgccgtcct  8880
ccttgaagtc gatgcccttc agctcgatgc ggttcaccag ggtgtcgccc tcgaacttca  8940
cctcggcgcg ggtcttgtag ttgccgtcgt ccttgaagaa gatggtgcgc tcctggacgt  9000
agccttcggg catggcggac ttgaagaagt cgtgctgctt catgtggtcg gggtagcggc  9060
tgaagcactg cacgccgtag gtcagggtgg tcacgagggt gggccagggc acgggcagct  9120
tgccggtggt gcagatgaac ttcagggtca gcttgccgta ggtggcatcg ccctcgccct  9180
cgccggacac gctgaacttg tggccgttta cgtcgccgtc cagctcgacc aggatgggca  9240
ccaccccggt gaacagctcc tcgcccttgc tcaccatcgt cgagatcccg ggcgtttaaa  9300
ttgtgtaatt tatgtagctg taatttttac cttattaata ttttttacgc tttgcattcg  9360
acgactgaac tcccaaatat atgtttaact cgtcttggtc gtttgaattt ttgttgctgt  9420
gtttcctaat attttccatc accttaaata tgttattgta atcctcaatg ttgaacttgc  9480
aattggacac ggcatagttt tccatagtcg tgtaaaacat ggtattggct gcattgtaat  9540
acatccgact gagcgggtac ggatctatgt gtttgagcag cctgttcaaa aactctgcat  9600
cgtcgcaaaa cggaatttgg tacccgggcg tatactccgg aatattaata gatcatggag  9660
ataattaaaa tgat                                                    9674

SEQ ID NO: 2           moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 2
tttttttttt tttttttttt ttccaagtaa aacgacggcc agtgc                45

SEQ ID NO: 3           moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 3
QVQLQESGPG LVKPSETLSL TCTVSGFSLT SYGVHWIRQP PGKGLEWIGV IYADGSTNYN  60
PSLKSRVTIS KDTSKNQVSL KLSSVTAADT AVYYCARAYG NYWYIDVWGQ GTTVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP PVAGGPSVFL  240
FPPKPKDTLM ISRTPEVTCV VVAVSQEDPE VQFNWYVDGV EVHNAKTKPR EEQFNSTYRV  300
VSVLTVVHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSKLTV DKSRWQEGNV  420
FSCSVMHEAL HNHYTQKSLS LSLGK                                      445

SEQ ID NO: 4           moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 4
DIVMTQSPDS LAVSLGERAT INCKSSESVS NDVAWYQQKP GQPPKLLINY AFHRFTGVPD  60
RFSGSGYGTD FTLTISSLQA EDVAVYYCHQ AYSSPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 5           moltype = AA  length = 118
```

-continued

```
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 5
QVQLQESGPG LVKPSETLSL TCTVSGFSLT SYGVHWIRQP PGKGLEWIGV IYADGSTNYN  60
PSLKSRVTIS KDTSKNQVSL KLSSVTAADT AVYYCARAYG NYWYIDVWGQ GTTVTVSS    118

SEQ ID NO: 6           moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 6
DIVMTQSPDS LAVSLGERAT INCKSSESVS NDVAWYQQKP GQPPKLLINY AFHRFTGVPD  60
RFSGSGYGTD FTLTISSLQA EDVAVYYCHQ AYSSPYTFGQ GTKLEIK                107

SEQ ID NO: 7           moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 7
GFSLTSYGVH                                                         10

SEQ ID NO: 8           moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 8
VIYADGSTNY NPSLKS                                                  16

SEQ ID NO: 9           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 9
ARAYGNYWYI DV                                                      12

SEQ ID NO: 10          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 10
KSSESVSNDV A                                                       11

SEQ ID NO: 11          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 11
YAFHRFT                                                            7
```

-continued

```
SEQ ID NO: 12           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 12
HQAYSSPYT                                                    9
```

The invention claimed is:

1. A compound, or a salt thereof, of formula A or formula B:

A

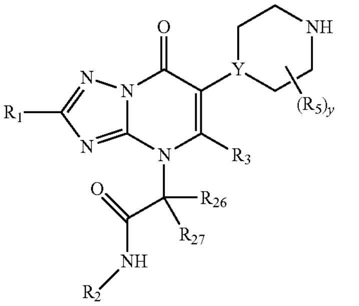

B

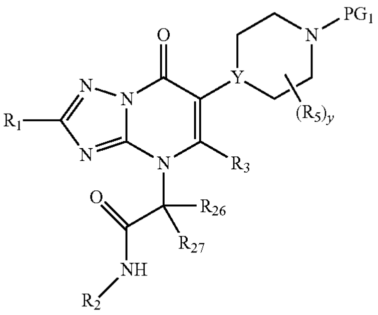

wherein $R_1$ is selected from:

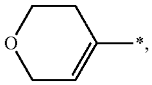,
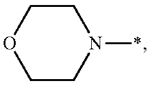,
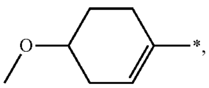,
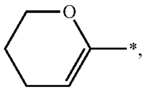,
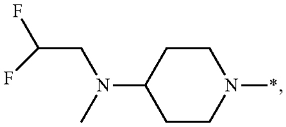,
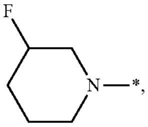,
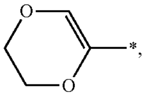,
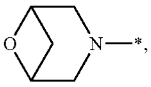,
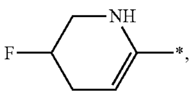, -continued

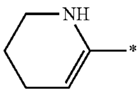,
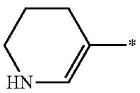,
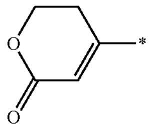,
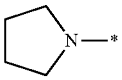,
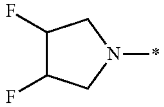,
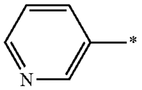,
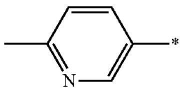,
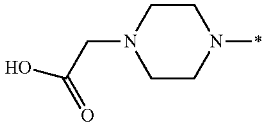,
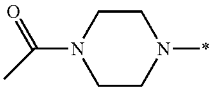,
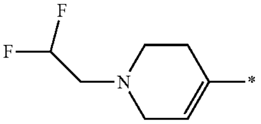,
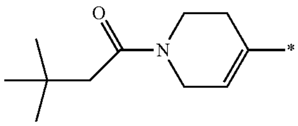,
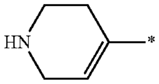,
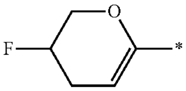,
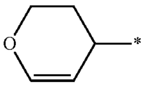 and
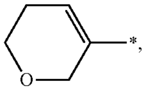, $R_2$ is selected from:

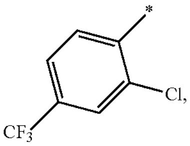
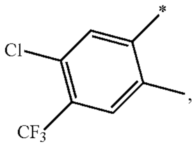,
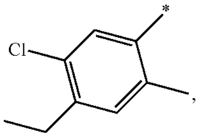,
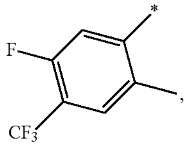,
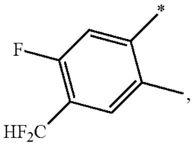,
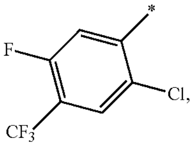

-continued

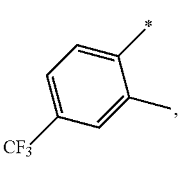 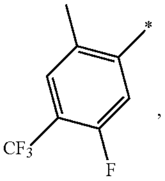

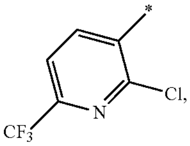 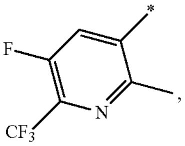

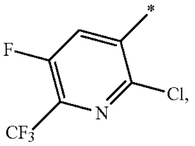 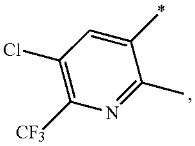

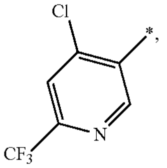 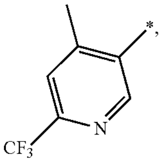 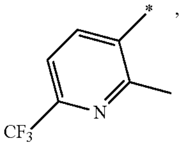

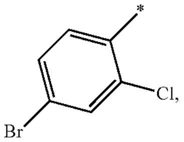 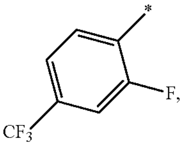

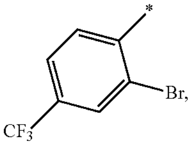 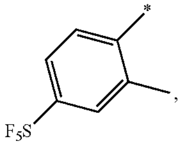

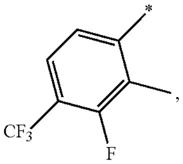 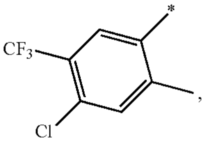

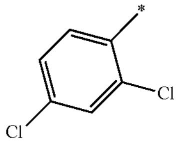 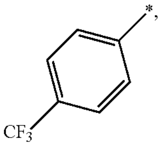

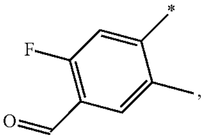 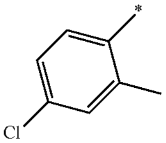 and

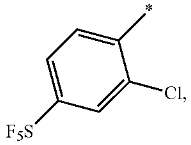

$R_3$ is ($C_1$-$C_2$)alkyl unsubstituted or substituted by 1, 2 or 3 substituents independently selected from halo and OH, $R_{26}$ is $CH_3$ or H, $R_{27}$ is H, $R_5$ is $CH_3$, or alternatively, two $R_5$ groups on adjacent carbon atoms join, along with the carbon atoms to which they are attached, to form a fused cyclobutyl ring, y is 0, 1, or 2, Y is N or CH, and $PG_1$ is a protecting group.

2. The compound of claim 1, or a salt thereof, which is:

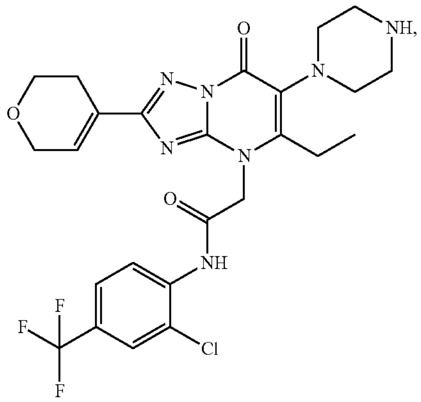 [SMILES: CCc1c(N2CCNCC2)c(=O)n2nc(C3=CCOCC3)nc2n1CC(=O)Nc1ccc(C(F)(F)F)cc1Cl]

or a salt thereof.

3. The compound of claim 1, or a salt thereof, wherein $PG_1$ is BOC.

4. The compound of claim 3, or a salt thereof, which is:

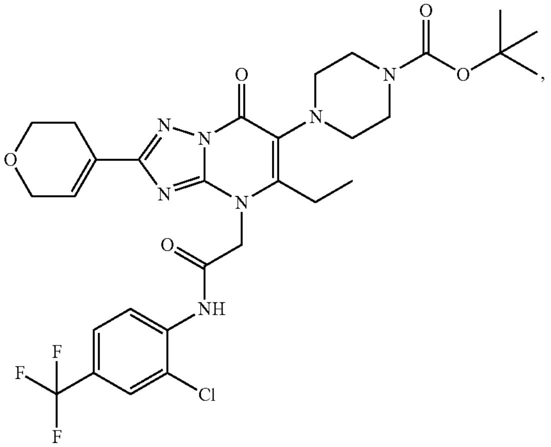 [SMILES: CCc1c(N2CCN(C(=O)OC(C)(C)C)CC2)c(=O)n2nc(C3=CCOCC3)nc2n1CC(=O)Nc1ccc(C(F)(F)F)cc1Cl]

or a salt thereof.

5. The compound of claim 1, or a salt thereof, wherein $R_1$ is

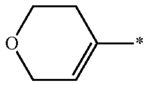 or 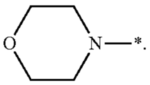

6. The compound of claim 1, or a salt thereof, wherein $R_1$ is

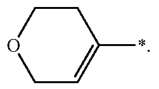

7. The compound of claim 1, or a salt thereof, wherein $R_2$ is

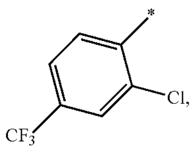

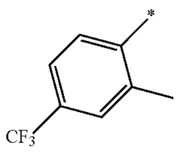

or

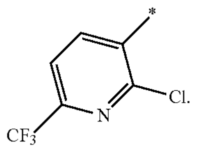

8. The compound of claim 1, or a salt thereof, wherein $R_2$ is

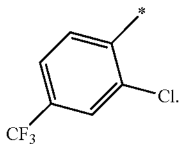 [SMILES: *c1ccc(C(F)(F)F)cc1Cl]

9. The compound of claim 1, or a salt thereof, wherein $R_3$ is $(C_1$-$C_2)$alkyl.

10. The compound of claim 1, or a salt thereof, wherein $R_3$ is $—CH_2CH_3$.

11. The compound of claim 1, or a salt thereof, wherein $R_{26}$ is H.

12. The compound of claim 1, or a salt thereof, wherein $R_5$ is $CH_3$.

13. The compound of claim 1, or a salt thereof, wherein two $R_5$ groups on adjacent carbon atoms join, along with the carbon atoms to which they are attached, to form a fused cyclobutyl ring.

14. The compound of claim 1, or a salt thereof, wherein y is 0.

15. The compound of claim 1, or a salt thereof, wherein Y is N.

16. The compound of claim 1, or a salt thereof, wherein $PG_1$ is BOC, para-methoxybenzyl, or benzyl.

* * * * *